US012404266B2

(12) United States Patent
Allasia et al.

(10) Patent No.: US 12,404,266 B2
(45) Date of Patent: *Sep. 2, 2025

(54) HETEROCYCLE DERIVATIVES FOR TREATING TRPM3 MEDIATED DISORDERS

(71) Applicant: Katholieke Universiteit Leuven, Leuven (BE)

(72) Inventors: Sara Allasia, Leuven (BE); Philippe Arzel, Ghent (BE); Patrick Chaltin, Zétrud-Lemay (BE); Amuri Kilonda, Boutersem (BE); Arnaud Marchand, Bierbeek (BE); Jean-Christophe Vanherck, Leuven (BE); Thomas Voets, Kessel-Lo (BE); Joris Vriens, Wakkerzeel (BE); Melanie Reich, Aachen (DE); André Welbers, Cologne (DE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/250,795

(22) PCT Filed: Nov. 24, 2021

(86) PCT No.: PCT/EP2021/082865
§ 371 (c)(1),
(2) Date: Apr. 27, 2023

(87) PCT Pub. No.: WO2022/112352
PCT Pub. Date: Jun. 2, 2022

(65) Prior Publication Data
US 2024/0051949 A1    Feb. 15, 2024

(30) Foreign Application Priority Data

Nov. 24, 2020 (EP) .................................. 20209574

(51) Int. Cl.
C07D 405/12  (2006.01)
C07D 401/14  (2006.01)
C07D 405/14  (2006.01)
C07D 407/12  (2006.01)
C07D 413/12  (2006.01)
C07D 417/12  (2006.01)
C07D 417/14  (2006.01)
C07D 471/04  (2006.01)

(52) U.S. Cl.
CPC .......... *C07D 405/12* (2013.01); *C07D 401/14* (2013.01); *C07D 405/14* (2013.01); *C07D 407/12* (2013.01); *C07D 413/12* (2013.01); *C07D 417/12* (2013.01); *C07D 417/14* (2013.01); *C07D 471/04* (2013.01)

(58) Field of Classification Search
CPC .. C07D 405/12; C07D 405/14; C07D 401/14; C07D 417/12; C07D 417/14; C07D 417/04; C07D 471/04
USPC ....................................................... 514/469
See application file for complete search history.

(56) References Cited

U.S. PATENT DOCUMENTS 12,209,081 B2 * 1/2025 Chaltin ................ C07D 417/12

FOREIGN PATENT DOCUMENTS

WO    2018/104479 A1    6/2018

OTHER PUBLICATIONS

May H. Abdel Aziz et al. "Allosteric Regulators of Thrombin. Monosulfated Benzofuran Dimers Selectively Interact with Arg173 of Exosite 2 to Induce Inhibition", Journal of Medicinal Chemistry, Jul. 25, 2012, vol. 55, No. 15, pp. 6888-6897, XP055777824.
Preetpal Singh Sidhu et al. "Supporting Information to Rational Design of Potent, Small, Synthetic Allosteric Inhibitors of Thrombin", Journal of Medicinal Chemistry, Jun. 29, 2011, pp. S1-S12, XP002792324.
Isabelle Straub et al. "Flavanones That Selectively Inhibit TRPM3 Attenuate Thermal Nociception In Vivo", Molecular Pharmacology, Nov. 7, 2013, vol. 84, No. 5, pp. 736-750, XP055777082.
International Search Report dated Feb. 4, 2022 issued for the corresponding application PCT/EP2021/082865 (4 pages).
Written Opinion dated Feb. 4, 2022 issued for the corresponding application PCT/EP2021/082865 (5 pages).
International Preliminary Report on Patentability dated May 30, 2023 issued for the corresponding application PCT/EP2021/082865 (7 pages).

* cited by examiner

*Primary Examiner* — Kahsay Habte

(57) ABSTRACT

The invention relates to compounds that are useful for the prevention or treatment of TRPM3 mediated disorders, more in particular disorders selected from pain and inflammatory hypersensitivity. The invention also relates to a method for the prevention or treatment of said TRPM3 mediated disorders.

13 Claims, No Drawings

HETEROCYCLE DERIVATIVES FOR TREATING TRPM3 MEDIATED DISORDERS

FIELD OF THE INVENTION

The invention relates to compounds that are useful for the prevention or treatment of TRPM3 mediated disorders, more in particular disorders selected from pain and inflammatory hypersensitivity. The invention also relates to a method for the prevention or treatment of said TRPM3 mediated disorders.

BACKGROUND OF THE INVENTION

The TRP superfamily consists of proteins with six transmembrane domains (6TM) that assemble as homo- or heterotetramers to form cation-permeable ion channels. The name TRP originates from the *Drosophila* trp (transient receptor potential) mutant, which is characterized by a transient receptor potential in the fly photoreceptors in the response to sustained light. In the last 15 years, trp-related channels have been identified in yeast, worms, insects, fish and mammals, including 27 TRPs in humans. Based on sequence homology, TRP channels can be divided into seven subfamilies: TRPC, TRPV, TRPM, TRPA, TRPP, TRPML and TRPN.

Members of the TRP superfamily are expressed in probably all mammalian organs and cell types, and in recent years great progress has been made in the understanding of their physiological role. The tailored selectivity of certain TRP channels enables them to play key roles in the cellular uptake and/or transepithelial transport of $Ca^{2+}$, $Mg^{2+}$ and trace metal ions. Moreover, the sensitivity of TRP channels to a broad array of chemical and physical stimuli, allows them to function as dedicated biological sensors involved in processes ranging from vision to taste, and tactile sensation. In particular, several members of the TRP superfamily exhibit a very high sensitivity to temperature. These so-called thermoTRPs are highly expressed in sensory neurons and/or skin keratinocytes, where they act as primary thermosensors for the detection of innocuous and noxious (painful) temperatures.

It is becoming increasingly clear that TRP channel dysfunction is directly involved in the etiology of various inherited and acquired diseases. Indeed, both loss-of-function and gain-of-function mutations in the TRP channel genes have been identified as the direct cause of inherited diseases, including brachyolmia, hypomagnesemia with secondary hypocalcemia, polycystic kidney disease, mucolipidosis type IV and familial focal segmental glomerulosclerosis. Moreover, TRP channel function/dysfunction has been directly linked to a wide range of pathological conditions, including chronic pain, hypertension, cancer and neurodegenerative disorders.

TRPM3 (Transient receptor potential melastatin 3) represents a promising pharmacological target. TRPM3 is expressed in a large subset of small-diameter sensory neurons from dorsal root and trigeminal ganglia, and is involved in heat sensing. The neurosteroid pregnenolone sulfate is a potent known activator of TRPM3 (Wagner et al., 2008). The neurosteroid pregnenolone sulfate evoked pain in wild type mice but not in knock-out TRPM3 mice. It was also recently shown that CFA induced inflammation and inflammatory pain are eliminated in TRPM3 knock-out mice. Therefore, TRPM3 antagonists could be used as analgesic drugs to counteract pain, such as inflammatory pain (Vriens J. et al. Neuron, May 2011).

A few TRPM3 antagonists are known, but none of them points towards the compounds of the current invention (Straub I et al. Mol Pharmacol, November 2013). For instance, Liquiritigenin, a postulated TRPM3 blocker has been described to decrease mechanical and cold hyperalgesia in a rat pain model (Chen L et al. Scientific reports, July 2014). There is still a great medical need for novel, alternative and/or better therapeutics for the prevention or treatment of TRPM3 mediated disorders, more in particular for pain such as inflammatory pain. Therapeutics with good potency on a certain type of pain, low level or no side-effects (such as no possibilities for addiction as with opiates, no toxicity) and/or good or better pharmacokinetic or -dynamic properties are highly needed.

The invention provides a class of novel compounds which are antagonists of TRPM3 and can be used as modulators of TRPM3 mediated disorders.

SUMMARY OF THE INVENTION

The invention provides benzofuran derivatives and pharmaceutical compositions comprising such benzofuran derivatives. The invention also provides benzofuran derivatives for use as a medicament, more in particular for use in the prevention and/or treatment of TRPM3 mediated disorders, especially for use in the prevention and/or treatment of pain and/or inflammatory hypersensitivity; and/or for counteracting pain and/or inflammatory hypersensitivity.

The invention also provides the use of benzofuran derivatives for the manufacture of pharmaceutical compositions or medicaments for the prevention and/or treatment of TRPM3 mediated disorders, especially for the prevention and/or treatment of pain and/or inflammatory hypersensitivity; and/or for counteracting pain and/or inflammatory hypersensitivity.

The invention also provides a method for the prevention or treatment of a TRPM3 mediated disorder by administering the benzofuran derivatives according to the invention to a subject in need thereof. More in particular, the invention relates to such method for the prevention and/or treatment of pain and/or inflammatory hypersensitivity; and/or for counteracting pain and/or inflammatory hypersensitivity.

The invention further provides a method for the preparation of the benzofuran derivatives of the invention, comprising the steps of:
 reacting a benzoquinone with a suitable $3-ketoester or an enamine derivative to obtain 5-hydroxybenzofuran-3-carboxylate ester derivatives,
 substituting previously obtained 5-hydroxybenzofuran-3-carboxylate ester derivatives with suitable derivatives bearing a leaving group or alcohol derivatives under Mistunobu conditions to obtain 5-O-substituted-benzofuran-3-carboxylate ester derivatives
 converting the previously obtained 5-O-substituted-benzofuran-3-carboxylate ester derivatives in carboxylic acid to obtain the desired benzofuran derivatives of the invention, and
 coupling the previously obtained 5-O-substituted-benzofuran-3-carboxylic acid derivatives with a suitable amine to obtain the desired amide derivatives of the invention.

DETAILED DESCRIPTION OF THE INVENTION

The invention will be further described and in some instances with respect to particular embodiments, but the invention is not limited thereto.

The first aspect of the invention is the provision of a compound of formula (I), a stereo-isomeric form, a physiologically acceptable salt, solvate and/or polymorph thereof

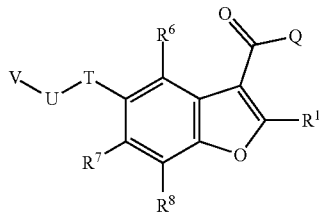

(I)

preferably for use in the treatment of pain;
wherein
$R^1$ represents —F, —Cl, —Br, —I, —CN, —$R^W$, —$OR^W$, —OC(=O)$R^W$, —$NR^WR^X$, —$NR^WC$(=O)$R^X$, —$SR^W$, —S(=O)$R^W$, —S(=O)$_2R^W$, —C(=O)$R^W$, —C(=O)$OR^W$, or —C(=O)$NR^WR^X$;
Q represents —$OR^2$ or —$NR^3R^4$;
$R^2$ represents —$R^Y$;
$R^3$ represents —OH or —$R^Y$;
$R^4$ represents —$R^Y$ or —S(=O)$_2R^Y$;
or $R^3$ and $R^4$ together form a 4, 5, 6, 7 or 8 membered heterocycle containing 1 to 3 heteroatoms selected from N, O and S, saturated or unsaturated, unsubstituted or mono- or polysubstituted;
T represents —O— and U represents —$CR^5R^{5'}$—; or T represents —$CR^5R^{5'}$— and U represents —O—;
$R^5$ and $R^{5'}$ independently of one another represent —$R^Y$;
$R^6$, $R^7$ and $R^8$ independently of one another represent —F, —Cl, —Br, —I, —CN, —$NO_2$, —$SF_5$, —$R^W$, —$OR^W$, —OC(=O)$R^W$, —$NR^WR^X$, —$NR^WC$(=O)$R^X$, —$SR^W$, —S(=O)$R^W$, —S(=O)$_2R^W$, —C(=O)$R^W$, —C(=O)$OR^W$, or —C(=O)$NR^WR^X$;
V represents 3-14-membered heterocycloalkyl, saturated or unsaturated; or 5-14-membered heteroaryl; in each case unsubstituted, mono- or polysubstituted with substituents independently of one another selected from —F, —Cl, —Br, —I, —CN, —NO, —$NO_2$, =O, =S, —$SF_5$, —$R^Y$, —$OR^Y$, —OC(=O)$R^Y$, —$NR^YR^Z$, —$NR^YC$(=O)$R^Z$, —$SR^Y$, —S(=O)$R^Y$, —S(=O)$_2R^Y$, —C(=O)$R^Y$, —C(=O)$OR^Y$, or —C(=O)$NR^YR^Z$;
wherein
$R^W$ and $R^X$ independently of one another in each case independently represent
—H;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted; or
3-14-membered heterocycloalkyl, saturated or unsaturated, unsubstituted, mono- or polysubstituted; wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;

$R^Y$ and $R^Z$ independently of one another in each case independently represent
—H;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or poly substituted;
3-14-membered heterocycloalkyl, saturated or unsaturated, unsubstituted, mono- or polysubstituted; wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;
6-14-membered aryl, unsubstituted, mono- or polysubstituted; wherein said 6-14-membered aryl is optionally connected through —$C_1$-$C_6$-alkylene- or —$C_1$-$C_6$-heteroalkylene-, in each case saturated or unsaturated, unsubstituted, mono- or polysubstituted; or
5-14-membered heteroaryl, unsubstituted, mono- or polysubstituted; wherein said 5-14-membered heteroaryl is optionally connected through —$C_1$-$C_6$-alkylene- or —$C_1$-$C_6$-heteroalkylene-, in each case saturated or unsaturated, unsubstituted, mono- or poly substituted;
or $R^Y$ and $R^Z$ together form a 4, 5, 6, 7 or 8 membered heterocycle containing 1 to 3 heteroatoms selected from N, O and S, saturated or unsaturated, unsubstituted or mono- or polysubstituted;
and wherein "mono- or polysubstituted" in each case independently means substituted with one or more, e.g. 1, 2, 3, 4, or more substituents independently of one another selected from —F, —Cl, —Br, —I, —CN, —$C_{1-6}$-alkyl, —$CF_3$, —$CF_2H$, —$CFH_2$, —$CF_2Cl$, —$CFCl_2$, —$C_{1-6}$-alkylene-$CF_3$, —$C_{1-6}$-alkylene-$CF_2H$, —$C_{1-6}$-alkylene-$CFH_2$, —$C_{1-6}$-alkylene-O—$CF_3$, —$C_{1-6}$-alkylene-O—$CF_2H$, —$C_{1-6}$-alkylene-O—$CFH_2$, —$C_{1-6}$-alkylene-NH—$C_{1-6}$-alkylene-$CF_3$, —$C_{1-6}$-alkylene-N($C_{1-6}$-alkyl)-$C_{1-6}$-alkylene-$CF_3$, —C(=O)—$C_{1-6}$-alkyl, —$C_{1-6}$-alkylene-C(=O)—$C_{1-6}$-alkyl, —C(=O)OH, —$C_{1-6}$-alkylene-C(=O)—OH, —C(=O)—O$C_{1-6}$-alkyl, —$C_{1-6}$-alkylene-C(=O)—O$C_{1-6}$-alkyl, —C(=O)O—$C_{1-6}$-alkylene-$CF_3$, —C(=O)—$NH_2$, —$C_{1-6}$-alkylene-C(=O)—$NH_2$, —C(=O)—NH($C_{1-6}$-alkyl), —$C_{1-6}$-alkylene-C(=O)—NH($C_{1-6}$-alkyl), —C(=O)—N($C_{1-6}$-alkyl)$_2$, —$C_{1-6}$-alkylene-C(=O)—N($C_{1-6}$-alkyl)$_2$, —C(=O)—NH(OH), —$C_{1-6}$-alkylene-C(=O)—NH(OH), —OH, —$C_{1-6}$-alkylene-OH, =O, —$OCF_3$, —$OCF_2H$, —$OCFH_2$, —$OCF_2Cl$, —$OCFCl_2$, —O—$C_{1-6}$-alkyl, —$C_{1-6}$-alkylene-O—$C_{1-6}$-alkyl, —O—$C_{1-6}$-alkylene-O—$C_{1-6}$-alkyl, —O—$C_{1-6}$-alkylene-$NH_2$, —O—$C_{1-6}$-alkylene-NH—$C_{1-6}$-alkyl, —O—$C_{1-6}$-alkylene-N($C_{1-6}$-alkyl)$_2$, —O—C(=O)—$C_{1-6}$-alkyl, —$C_{1-6}$-alkylene-O—C(=O)—$C_{1-6}$-alkyl, —O—C(=O)—O—$C_{1-6}$-alkyl, —$C_{1-6}$-alkylene-O—C(=O)—O—$C_{1-6}$-alkyl, —O—C(=O)—NH($C_{1-6}$-alkyl), —$C_{1-6}$-alkylene-O—C(=O)—NH($C_{1-6}$-alkyl), —O—C(=O)—N($C_{1-6}$-alkyl)$_2$, —$C_{1-6}$-alkylene-O—C(=O)—N($C_{1-6}$-alkyl)$_2$, —O—S(=O)$_2$—$NH_2$, —$C_{1-6}$-alkylene-O—S(=O)$_2$—$NH_2$, —O—S(=O)$_2$—NH($C_{1-6}$-alkyl), —$C_{1-6}$-alkylene-O—S(=O)$_2$—NH($C_{1-6}$-alkyl), —O—S(=O)$_2$—N($C_{1-6}$-alkyl)$_2$, —C$_{1-6}$-alkylene-O—S(═O)$_2$—N(C$_{1-6}$-alkyl)$_2$, —NH$_2$, —NO, —NO$_2$, —C$_{1-6}$-alkylene-NH$_2$, —NH(C$_{1-6}$-alkyl), —N(3-14-membered cycloalkyl)(C$_{1-6}$-alkyl), —N(C$_{1-6}$-alkyl)-C$_{1-6}$-alkylene-OH, —N(H)—C$_{1-6}$-alkylene-OH, —C$_{1-6}$-alkylene-NH(C$_{1-6}$-alkyl), —N(C$_{1-6}$-alkyl)$_2$, —C$_{1-6}$-alkylene-N(C$_{1-6}$-alkyl)$_2$, —NH—C(═O)—C$_{1-6}$-alkyl, —C$_{1-6}$-alkylene-NH—C(═O)—C$_{1-6}$-alkyl, —NH—C(═O)—O—C$_{1-6}$-alkyl, —C$_{1-6}$-alkylene-NH—C(═O)—O—C$_{1-6}$-alkyl, —NH—C(═O)—NH$_2$, —C$_{1-6}$-alkylene-NH—C(═O)—NH$_2$, —NH—C(═O)—NH(C$_{1-6}$-alkyl), —C$_{1-6}$-alkylene-NH—C(═O)—NH(C$_{1-6}$-alkyl), —NH—C(═O)—N(C$_{1-6}$-alkyl)$_2$, —C$_{1-6}$-alkylene-NH—C(═O)—N(C$_{1-6}$-alkyl)$_2$, —N(C$_{1-6}$-alkyl)-C(═O)—C$_{1-6}$-alkyl, —C$_{1-6}$-alkylene-N(C$_{1-6}$-alkyl)-C(═O)—C$_{1-6}$-alkyl, —N(C$_{1-6}$-alkyl)-C(═O)—O—C$_{1-6}$-alkyl, —C$_{1-6}$-alkylene-N(C$_{1-6}$-alkyl)-C(═O)—O—C$_{1-6}$-alkyl, —N(C$_{1-6}$-alkyl)-C(═O)—NH$_2$, —C$_{1-6}$-alkylene-N(C$_{1-6}$-alkyl)-C(═O)—NH$_2$, —N(C$_{1-6}$-alkyl)-C(═O)—NH(C$_{1-6}$-alkyl), —C$_{1-6}$-alkylene-N(C$_{1-6}$-alkyl)-C(═O)—NH(C$_{1-6}$-alkyl), —N(C$_{1-6}$-alkyl)-C(═O)—N(C$_{1-6}$-alkyl)$_2$, —C$_{1-6}$-alkylene-N(C$_{1-6}$-alkyl)-C(═O)—N(C$_{1-6}$-alkyl)$_2$, —NH—S(═O)$_2$OH, —C$_{1-6}$-alkylene-NH—S(═O)$_2$OH, —NH—S(═O)$_2$—C$_{1-6}$-alkyl, —C$_{1-6}$-alkylene-NH—S(═O)$_2$—C$_{1-6}$-alkyl, —NH—S(═O)$_2$—O—C$_{1-6}$-alkyl, —C$_{1-6}$-alkylene-NH—S(═O)$_2$—O—C$_{1-6}$-alkyl, —NH—S(═O)$_2$—NH$_2$, —C$_{1-6}$-alkylene-NH—S(═O)$_2$—NH$_2$, —NH—S(═O)$_2$—NH(C$_{1-6}$-alkyl), —C$_{1-6}$-alkylene-NH—S(═O)$_2$—NH(C$_{1-6}$-alkyl), —NH—S(═O)$_2$N(C$_{1-6}$-alkyl)$_2$, —C$_{1-6}$-alkylene-NH—S(═O)$_2$N(C$_{1-6}$-alkyl)$_2$, —N(C$_{1-6}$-alkyl)-S(═O)$_2$—OH, —C$_{1-6}$-alkylene-N(C$_{1-6}$-alkyl)-S(═O)$_2$—OH, —N(C$_{1-6}$-alkyl)-S(═O)$_2$—C$_{1-6}$-alkyl, —C$_{1-6}$-alkylene-N(C$_{1-6}$-alkyl)-S(═O)$_2$—C$_{1-6}$-alkyl, —N(C$_{1-6}$-alkyl)-S(═O)$_2$—O—C$_{1-6}$-alkyl, —C$_{1-6}$-alkylene-N(C$_{1-6}$-alkyl)-S(═O)$_2$—O—C$_{1-6}$-alkyl, —N(C$_{1-6}$-alkyl)-S(═O)$_2$—NH$_2$, —C$_{1-6}$-alkylene-N(C$_{1-6}$-alkyl)-S(═O)$_2$—NH$_2$, —N(C$_{1-6}$-alkyl)-S(═O)$_2$—NH(C$_{1-6}$-alkyl), —C$_{1-6}$-alkylene-N(C$_{1-6}$-alkyl)-S(═O)$_2$—NH(C$_{1-6}$-alkyl), —N(C$_{1-6}$-alkyl)-S(═O)$_2$—N(C$_{1-6}$-alkyl)$_2$, —C$_{1-6}$-alkylene-N(C$_{1-6}$-alkyl)-S(═O)$_2$—N(C$_{1-6}$-alkyl)$_2$, —SH, ═S, —SF$_5$, —SCF$_3$, —SCF$_2$H, —SCFH$_2$, —S—C$_{1-6}$-alkyl, —C$_{1-6}$-alkylene-S—C$_{1-6}$-alkyl, —S(═O)—C$_{1-6}$-alkyl, —C$_{1-6}$-alkylene-S(═O)—C$_{1-6}$-alkyl, —S(═O)$_2$—C$_{1-6}$-alkyl, —C$_{1-6}$-alkylene-S(═O)$_2$—C$_{1-6}$-alkyl, —S(═O)$_2$—OH, —C$_{1-6}$-alkylene-S(═O)$_2$—OH, —S(═O)$_2$—O—C$_{1-6}$-alkyl, —C$_{1-6}$-alkylene-S(═O)$_2$—O—C$_{1-6}$-alkyl, —S(═O)$_2$—NH$_2$, —C$_{1-6}$-alkylene-S(═O)$_2$—NH$_2$, —S(═O)$_2$—NH(C$_{1-6}$-alkyl), —C$_{1-6}$-alkylene-S(═O)$_2$—NH(C$_{1-6}$-alkyl), —S(═O)$_2$—N(C$_{1-6}$-alkyl)$_2$, —C$_{1-6}$-alkylene-S(═O)$_2$—N(C$_{1-6}$-alkyl)$_2$, 3-14-membered cycloalkyl, —C$_{1-6}$-alkylene-(3-14-membered cycloalkyl), 3 to 14-membered heterocycloalkyl, —C$_{1-6}$-alkylene-(3 to 14-membered heterocycloalkyl), -phenyl, —C$_{1-6}$-alkylene-phenyl, 5 to 14-membered heteroaryl, —C$_{1-6}$-alkylene-(5 to 14-membered heteroaryl), —O-(3-14-membered cycloalkyl), —O-(3 to 14-membered heterocycloalkyl), —O-phenyl, —O-(5 to 14-membered heteroaryl), —C(═O)-(3-14-membered cycloalkyl), —C(═O)-(3 to 14-membered heterocycloalkyl), —C(═O)-phenyl, —C(═O)-(5 to 14-membered heteroaryl), —S(═O)$_2$-(3-14-membered cycloalkyl), —S(═O)$_2$-(3 to 14-membered heterocycloalkyl), —S(═O)$_2$-phenyl, —S(═O)$_2$-(5 to 14-membered heteroaryl).

In preferred embodiments of the benzofuran derivative according to the invention (a-1) Q represents —OR$^2$; and R$^1$ represents —CH$_2$F, —CHF$_2$, or —CF$_3$; and/or (a-2) Q represents —OR$^2$; and at least one of R$^5$ and R$^{5'}$ does not represent —H; and/or (a-3) Q represents —OR$^2$; and R$^6$ does not represent —H; and/or (a-4) Q represents —OR$^2$; and R$^8$ does not represent —H; or (b-1) Q represents —NR$^3$R$^4$; with the proviso that the following compounds and their salts are excluded

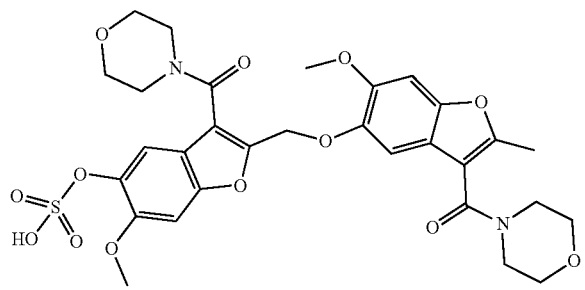

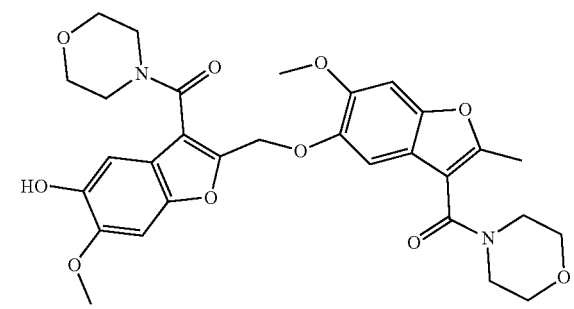

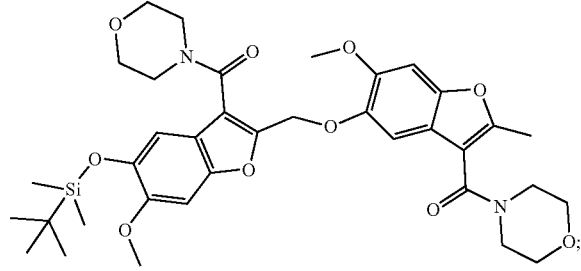

and/or (b-2) Q represents —NR$^3$R$^4$; and R$^1$ represents —CH$_2$F, —CHF$_2$, —CF$_3$, —CN, -propyl or -cyclopropyl; and/or (b-3) Q represents —NR$^3$R$^4$; and at least one of R$^5$ and R$^{5'}$ does not represent —H; and/or (b-4) Q represents —NR$^3$R$^4$; and R$^3$ represents —H.

In a preferred embodiment of the benzofuran derivative according to the invention T represents —O— and U represents —CR$^5$R$^{5'}$—. According to this embodiment, the benzofuran derivative according to the invention is a compound of formula (II), a stereo-isomeric form, a physiologically acceptable salt, solvate and/or polymorph thereof.

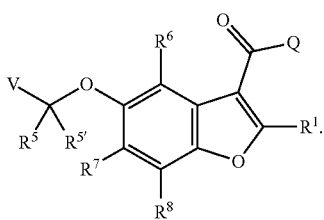

(II)

In another preferred embodiment of the benzofuran derivative according to the invention T represents —CR$^5$R$^{5'}$— and U represents —O—.

In a preferred embodiment of the benzofuran derivative according to the invention Q represents —NR$^3$R$^4$.

In another preferred embodiment of the benzofuran derivative according to the invention Q represents —OR$^2$.

In a preferred embodiment of the benzofuran derivative according to the invention V represents 5-14-membered heteroaryl, unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 5-14-membered heteroaryl within the definition of V is not benzofuran, unsubstituted, mono- or polysubstituted.

Preferably, the 5-14-membered heteroaryl within the definition of V is selected from benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and [1,2,4]triazolo[4,3-a]pyrimidine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 5-14-membered heteroaryl within the definition of V is selected from the group consisting of furane, thiophene, imdidazole, pyrazole, oxazole, isoxazole, thiazole, triazole, pyridine, isoquinoline, benzothiazole, pyridazine, pyrimidine, imidazopyridine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 5-14-membered heteroaryl within the definition of V is selected from the group consisting of furan-2-yl, furan-3-yl, thiophen-2-yl, thiophen-3-yl, pyrazol-5-yl, oxazol-5-yl, isoxazol-4-yl, thiazol-2-yl, thiazol-5-yl, 1,2,4-triazol-3-yl, 1,2,3-triazol-4-yl, pyridin-2-yl, pyridin-3-yl, pyridin-4-yl, isoquinolin-1-yl, isoquinolin-5-yl, benzo[d]thiazol-2-yl, pyridazin-3-yl, pyrimidin-5-yl, and imidazo[1,2-a]pyridin-6-yl; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

In another preferred embodiment of the benzofuran derivative according to the invention V represents 3-14-membered heterocycloalkyl, saturated or unsaturated, unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 3-14-membered heterocycloalkyl within the definition of V is selected from azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofurane, tetrahydropyrane, tetrahydrothiopyrane, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 3-14-membered heterocycloalkyl within the definition of V is tetrahydropyrane or pyrrolidine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

Preferably, the 3-14-membered heterocycloalkyl within the definition of V is tetrahydropyran-4-yl or pyrrolidin-3-yl; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

In a preferred embodiment of the benzofuran derivative according to the invention V is unsubstituted, mono- or polysubstituted with substituents independently of one another selected from
- —F, —Cl, —Br, —I, —CN, —C(=O)OH, —NH$_2$, —NO$_2$, —OH, =O, —SF$_5$;
- —C$_{1-6}$-alkyl, saturated or unsaturated, unsubstituted, mono- or polysubstituted;
- —C(=O)O—C$_{1-6}$-alkyl, saturated or unsaturated, unsubstituted, mono- or polysubstituted;
- —NHC$_{1-6}$-alkyl, saturated or unsaturated, unsubstituted, mono- or polysubstituted;
- —N(C$_{1-6}$-alkyl)$_2$, saturated or unsaturated, unsubstituted, mono- or poly substituted;
- —O—C$_{1-6}$-alkyl, saturated or unsaturated, unsubstituted, mono- or polysubstituted;

—S(=O)₂—C₁₋₆-alkyl, saturated or unsaturated, unsubstituted, mono- or polysubstituted;

3-14-membered cycloalkyl, saturated or unsaturated, unsubstituted, mono- or polysubstituted; wherein said 3-14-membered cycloalkyl is optionally connected through —C₁-C₆-alkylene- or —C₁-C₆-heteroalkylene-, in each case saturated or unsaturated, unsubstituted, mono- or polysubstituted; or 3-14-membered heterocycloalkyl, saturated or unsaturated, unsubstituted, mono- or polysubstituted; wherein said 3-14-membered heterocycloalkyl is optionally connected through —C₁-C₆-alkylene- or —C₁-C₆-heteroalkylene-, in each case saturated or unsaturated, unsubstituted, mono- or polysubstituted.

Preferably, V is unsubstituted, mono- or polysubstituted with substituents independently of one another selected from —OH, —F, —Cl, —Br, —I, —SH, —CF₃, —CHF₂, —CH₂F, —OCF₃, —OCHF₂, —OCH₂F, SF₅, —CN, —NO₂, —C(=O)OH, —NH₂, or —N(CH₃)₂;

—C₁₋₆-alkyl, saturated or unsaturated, unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O)OH, —NH₂, C(=O)CHF₂, and —C(=O)NH₂;

—C₁₋₆-heteroalkyl, saturated or unsaturated, unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O)OH, —NH₂, C(=O)CHF₂, and —C(=O)NH₂;

—OC₁₋₆-alkyl, unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O) OH, —NH₂, C(=O)CHF₂, and —C(=O)NH₂;

—O(C=O)C₁₋₆-alkyl, unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O) OH, —NH₂, C(=O)CHF₂, and —C(=O)NH₂;

—C(=O)OC₁₋₆-alkyl, unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O) OH, —NH₂, C(=O)CHF₂, and —C(=O)NH₂;

3-14-membered cycloalkyl selected from the group consisting of cyclopropyl, cyclobutyl, cyclopentyl, cyclohexyl and cycloheptyl; in each case unsubstituted, mono- or polysubstituted with substituents independently of one another selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O)OH, —NH₂, C(=O)CHF₂, and —C(=O)NH₂;

3-14-membered heterocycloalkyl selected from the group consisting of azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro-[3.3]heptane, 2-oxaspiro[3.3]heptane, 7-azaspiro[3.5]nonane, 8-azabicyclo[3.2.1]octane, 9-azabicyclo-[3.3.1]nonane, hexahydro-1H-pyrrolizine, hexahydrocyclopenta[c]pyrrole, octahydrocyclopenta[c]pyrrole, and octahydropyrrolo[1,2-a]pyrazin, in each case unsubstituted, mono- or polysubstituted with substituents independently of one another, selected from the group consisting of —F, —Cl, —Br, —I, —C₁₋₆-alkyl, C₂₋₆-alkenyl, —C₂₋₆-alkynyl, —OH, =O, —SH, =S, —CN, —CF₃, —CHF₂, —CH₂F, —OCF₃, —OCHF₂, —OCH₂F, SF₅, —NO₂, —C(=O)OH, —NH₂, C(=O)CHF₂, and —C(=O)NH₂.

Preferably, V is unsubstituted, mono- or polysubstituted with substituents independently of one another selected from —F, —Cl, —CN, —OH, =O, —C₁₋₆-alkyl, —CHF₂, —CF₃, —C₁₋₆-alkylene-NH₂, —C₁₋₆-alkylene-NHC(=O) O—C₁₋₆-alkyl, —C₁₋₆-alkylene-OH, —C₁₋₆-alkylene-NHC (=O)—O—C₁₋₆-alkyl, —C(=O)O—C₁₋₆-alkyl, —N(C₁₋₆-alkyl)₂, —OC₁₋₆-alkyl, —OCF₃, —O—C₁₋₆-alkylene-N (C₁₋₆-alkyl)₂, —S(=O)₂—C₁₋₆-alkyl, -azetidine, —C₁₋₆-alkylene-O-tetrahydropyran, or -piperazine substituted with —C₁₋₆-alkyl.

In a preferred embodiments of the benzofuran derivative according to the invention V is (i) unsubstituted;

(ii) monosubstituted;

(iii) disubstituted;

(iv) trisubstituted; or (v) tetrasubstituted.

In a preferred embodiments of the benzofuran derivative according to the invention V is (i) unsubstituted;

(ii) monosubstituted; or (iii) disubstituted.

In preferred embodiments, V represents a 3-14-membered heterocycloalkyl (preferably 5-membered heterocycloalkyl), saturated or unsaturated; or 5-14-membered heteroaryl (preferably 5-membered heteroaryl); in each case unsubstituted, mono- or polysubstituted; preferably a residue selected from the group consisting of:

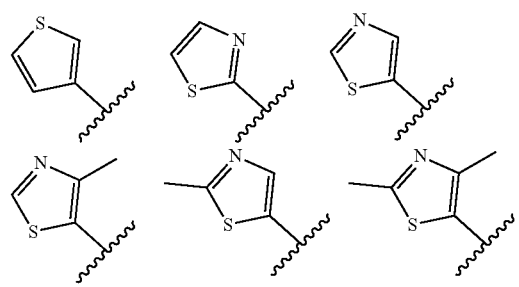

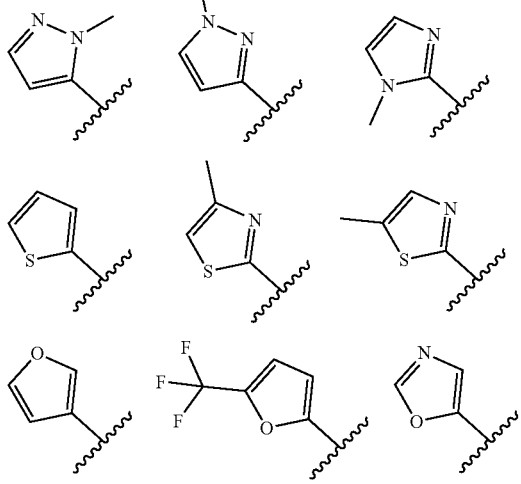

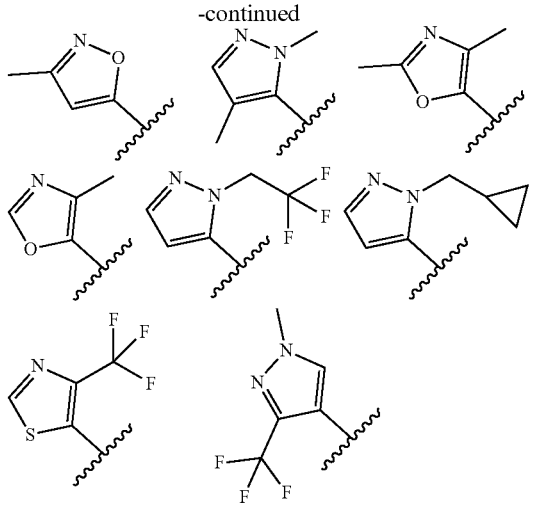

In a preferred embodiment, V represents -oxetanyl, unsubstituted, mono- or polysubstituted; preferably

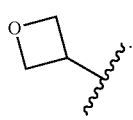

In preferred embodiments, V represents a residue according to general formula (E)

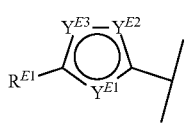

(E)

wherein
$Y^{E1}$ represents —N═, —NR$^{E2}$—, S, O, or —CR$^{E3}$═;
$Y^{E2}$ represents —N═, —NR$^{E3}$—, S, O, or —CR$^{E4}$═;
and $Y^{E3}$ represent —N═, —NR$^{E4}$—, S, O, or —CR$^{E5}$═; with the proviso that at least one of $Y^{E1}$ $Y^{E2}$ and $Y^{E3}$ is not —CR$^{E3}$═, —CR$^{E4}$═, and —CR$^{E5}$═, respectively. In another preferred embodiment, V represents a residue according to general formula (E) wherein $Y^{E1}$ represents —N═, —NR$^{E2}$—, S, or —CR$^{E3}$═; $Y^{E2}$ represents —N═, —NR$^{E3}$—, S, or —CR$^{E4}$═; and $Y^{E3}$ represent —N═, —NR$^{E4}$—, S, or —CR$^{E5}$═; with the proviso that at least one of $Y^{E1}$, $Y^{E2}$, and $Y^{E3}$ is not —CR$^{E3}$═, —CR$^{E4}$═, and —CR$^{E5}$═, respectively.

$R^{E1}$, $R^{E2}$, $R^{E3}$ and $R^{E4}$ independently of one another represent —H, —CH$_3$, —CH$_2$-cyclopropyl, —CH$_2$CF$_3$, —CH$_2$CHF$_2$ or —CF$_3$; more in particular $R^{E1}$, $R^{E2}$, $R^{E3}$ and $R^{E4}$ independently of one another represent —H, —CH$_3$, or —CF$_3$; preferably with the proviso that only one of $R^{E1}$, $R^{E2}$, $R^{E3}$ and $R^{E4}$ represents a residue that is not —H.

In preferred embodiments, V represents 2-pyridine, unsubstituted, mono- or polysubstituted. In preferred embodiments, V represents a residue selected from the group consisting of:

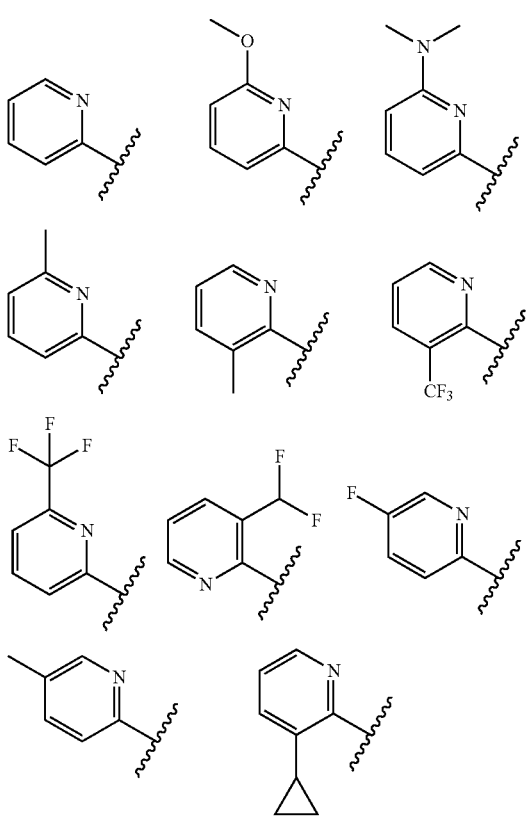

In preferred embodiments, V represents 3-pyridine, unsubstituted, mono- or polysubstituted. In preferred embodiments, V represents a residue selected from the group consisting of:

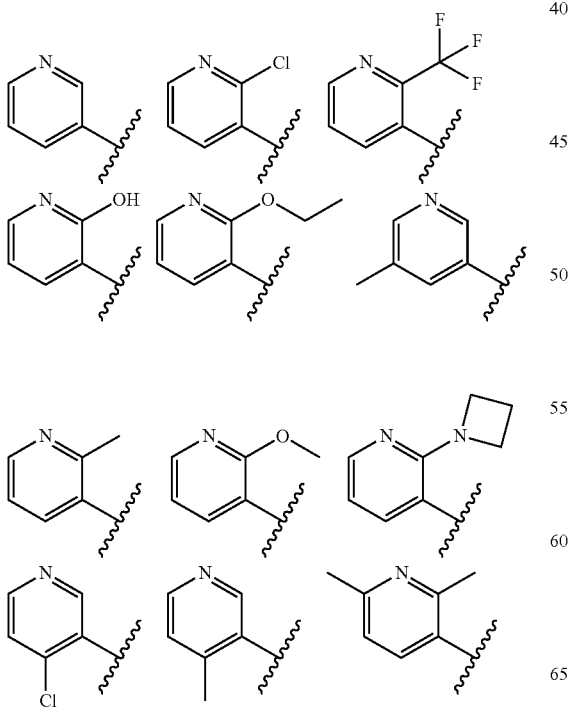

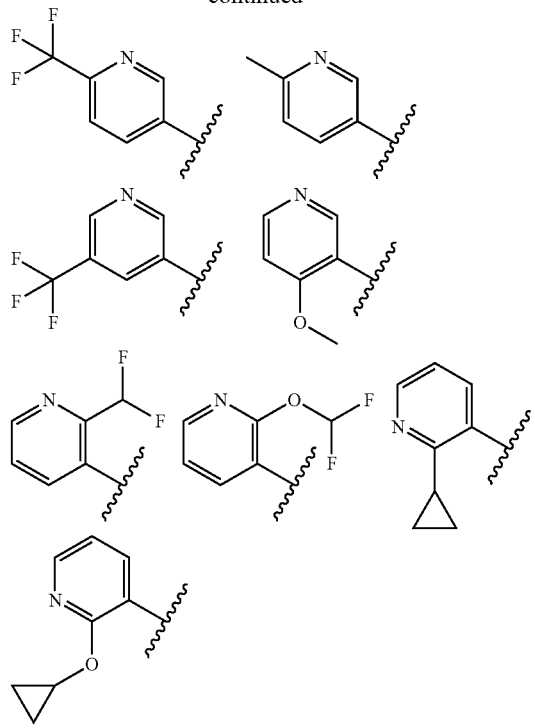

In preferred embodiments, V represents 4-pyridine, unsubstituted, mono- or polysubstituted. In preferred embodiments, V represents a residue selected from the group consisting of:

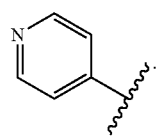 [SMILES: *c1ccncc1]

In preferred embodiments, V represents a residue selected from the group consisting of:

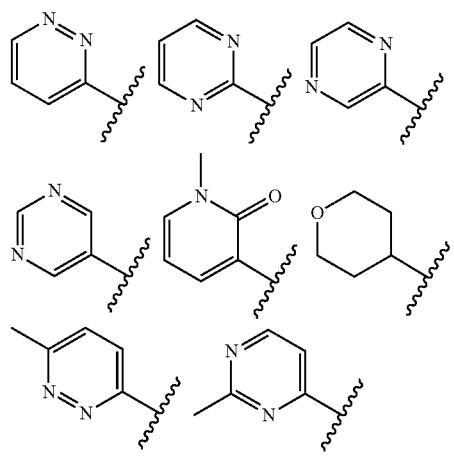

In preferred embodiments, V represents a bicyclic heteroaryl, unsubstituted, mono- or polysubstituted, preferably selected from the group consisting of:

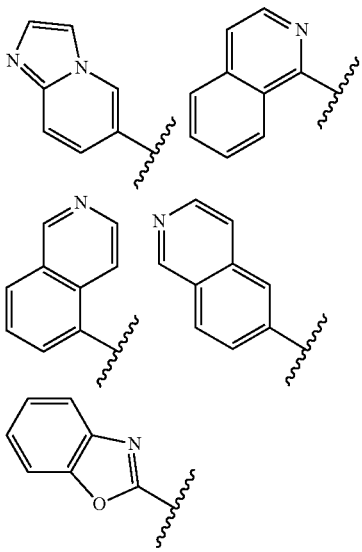

In preferred embodiments, V represents a residue according to general formula (F')

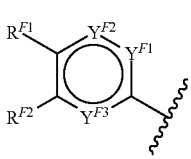

(F')

wherein
$Y^{F1}$ represents —N= or —CR$^{F4}$=; and $Y^{F2}$ represents —N= or —CR$^{F5}$=; and $Y^{F3}$ represents —N= or —CR$^{F3}$=; with the proviso that at least one of $Y^{F1}$ and $Y^{F2}$ is not —CR$^{F4}$= and —CR$^{F5}$=, respectively;
$R^{F1}$, $R^{F2}$, $R^{F3}$, $R^{F4}$, and $R^{F5}$ independently of one another represent —H, —CH$_3$, —CF$_3$, —OH, —OCH$_3$, —OCH$_2$CH$_3$, —Cl, or -azetidinyl; preferably with the proviso that only one of $R^{F1}$, $R^{F2}$, $R^{F3}$, $R^{F4}$, and $R^{F5}$ represents a residue that is not —H.

In another preferred embodiment, V represents a residue according to general formula (F)

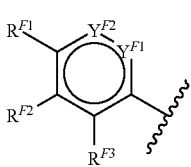

(F)

wherein
$Y^{F1}$ represents —N= or —CR$^{F4}$=; and $Y^{F2}$ represents —N= or —CR$^{F5}$=; with the proviso that at least one of $Y^{F1}$ and $Y^{F2}$ is not —CR$^{F4}$= and —CR$^{F5}$=, respectively;
$R^{F1}$, $R^{F2}$, $R^{F3}$, $R^{F4}$, and $R^{F5}$ independently of one another represent —H, —CH$_3$, —CF$_3$, —OH, —OCH$_3$, —OCH$_2$CH$_3$, —Cl, or -azetidinyl; preferably with the proviso that only one of $R^{F1}$, $R^{F2}$, $R^{F3}$, $R^{F4}$, and $R^{F5}$ represents a residue that is not —H.

In preferred embodiments, V represents a residue according to general formula (G) or (H)

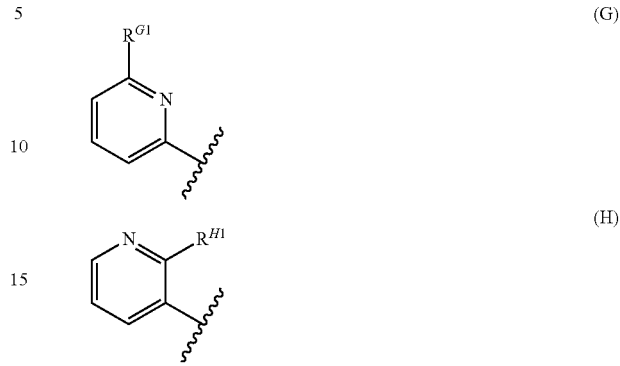

wherein $R^{G1}$ and $R^{H1}$ are selected from the group consisting of —H, —CH$_3$, —CF$_3$, —OH, —OCH$_3$, —OCH$_2$CH$_3$, —Cl, azetidinyl, -cyclopropyl, —O-cyclopropyl, and —CHF$_2$; or wherein $R^{G1}$ and $R^{H1}$ are selected from the group consisting of —H, —CH$_3$, —CF$_3$, —OH, —OCH$_3$, —OCH$_2$CH$_3$, —Cl, and azetidinyl.

In other preferred embodiments, V represents a residue according to general formula (G') or (H')

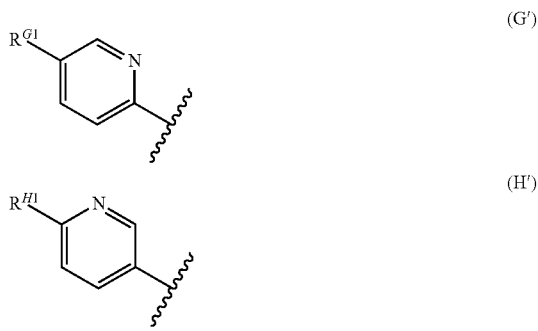

wherein $R^{G1}$ and $R^{H1}$ are selected from the group consisting of —H, —CH$_3$, —CF$_3$, —OH, —OCH$_3$, —OCH$_2$CH$_3$, —Cl, azetidinyl, -cyclopropyl, —O-cyclopropyl, and —CHF$_2$; or wherein $R^{G1}$ and $R^{H1}$ are selected from the group consisting of —H, —CH$_3$, —CF$_3$, —OH, —OCH$_3$, —OCH$_2$CH$_3$, —Cl, and azetidinyl;

In a preferred embodiment of the benzofuran derivative according to the invention $R^1$ represents
- —H, —F, —Cl, —Br, —I, —CN;
- —C$_{1-6}$-alkyl, saturated or unsaturated, unsubstituted, mono- or polysubstituted; —O—C$_{1-6}$-alkyl, saturated or unsaturated, unsubstituted, mono- or polysubstituted;
- —C(=O)C$_{1-6}$-alkyl, saturated or unsaturated, unsubstituted, mono- or polysubstituted;
- —C(=O)OC$_{1-6}$-alkyl, saturated or unsaturated, unsubstituted, mono- or polysubstituted;
- —C(=O)NHC$_{1-6}$-alkyl, saturated or unsaturated, unsubstituted, mono- or polysubstituted;
- —C(=O)N(C$_{1-6}$-alkyl)$_2$, saturated or unsaturated, unsubstituted, mono- or polysubstituted;

—S(=O)C$_{1-6}$-alkyl, saturated or unsaturated, unsubstituted, mono- or polysubstituted;

—S(=O)$_2$—C$_{1-6}$-alkyl, saturated or unsaturated, unsubstituted, mono- or polysubstituted;

—C$_1$-C$_6$-heteroalkyl, saturated or unsaturated, unsubstituted, mono- or polysubstituted; or 3-14-membered cycloalkyl, saturated or unsaturated, unsubstituted, mono- or polysubstituted; wherein said 3-14-membered cycloalkyl is optionally connected through —C$_1$-C$_6$-alkylene- or —C$_1$-C$_6$-heteroalkylene-, in each case saturated or unsaturated, unsubstituted, mono- or polysubstituted.

Preferably, R$^1$ represents —H, —F, —Cl, —Br, —I, —C$_{1-6}$-alkyl, —O—C$_{1-6}$-alkyl, —C$_{1-6}$-alkylene-O—C$_{1-6}$-alkyl, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, —C$_{1-6}$-alkylene-N(C$_{1-6}$-alkyl)-C$_1$-6-alkylene-CF$_3$, —C(=O)C$_{1-6}$-alkyl, —C(=O)OC$_{1-6}$-alkyl, —C(=O)NH$_2$, —C(=O)NHC$_{1-6}$-alkyl, —C(=O)N(C$_{1-6}$-alkyl)$_2$, —S(=O)—C$_{1-6}$-alkyl, —S(=O)$_2$—C$_{1-6}$-alkyl, —O—C$_{1-6}$-alkyl, -cyclopropyl unsubstituted, cyclobutyl unsubstituted, cyclopentyl unsubstituted or cyclohexyl unsubstituted.

Preferably, R$^1$ represents —H, —C$_{1-6}$-alkyl, —C$_{1-6}$-alkylene-O—C$_{1-6}$-alkyl, —CH$_2$F, —CHF$_2$, —CF$_3$, -cyclopentyl, unsubstituted, or -cyclopropyl. Preferably, R$^1$ represents —H, —C$_{1-6}$-alkyl, —C$_{1-6}$-alkylene-O—C$_{1-6}$-alkyl, —CH$_2$F, —CHF$_2$, —CF$_3$, -cyclopentyl, or unsubstituted. Preferably, R$^1$ represents —CH$_3$.

Preferably, R$^1$ represents —CH$_2$F, —CHF$_2$, —CH$_3$, or -cyclopropyl. Preferably, R$^1$ represents —CH$_2$F, —CHF$_2$, or —CH$_3$. Preferably, R$^1$ represents —C(=O)NH$_2$, or —CHF$_2$.

Preferably, R$^1$ represents —H, —C$_{1-3}$-alkyl, —CF$_3$, —CF$_2$H, —CFH$_2$, —CF$_2$Cl, —CFCl$_2$, —C$_{1-3}$-alkylene-CF$_3$, —C$_{1-3}$-alkylene-CF$_2$H, —C$_{1-3}$-alkylene-CFH$_2$, or -cyclopropyl; preferably, R$^1$ represents —H, —C$_{1-3}$-alkyl, —CF$_3$, —CF$_2$H, —CFH$_2$, —CF$_2$Cl, —CFCl$_2$, —C$_{1-3}$-alkylene-CF$_3$, —C$_{1-3}$-alkylene-CF$_2$H, or —C$_{1-3}$-alkylene-CFH$_2$; more preferably —CH$_3$.

In a preferred embodiment of the benzofuran derivative according to the invention R$^2$ represents

—H;

—C$_1$-C$_6$-alkyl, saturated or unsaturated, unsubstituted, mono- or polysubstituted;

—C$_1$-C$_6$-heteroalkyl, saturated or unsaturated, unsubstituted, mono- or polysubstituted;

3-14-membered cycloalkyl, saturated or unsaturated, unsubstituted, mono- or polysubstituted; wherein said 3-14-membered cycloalkyl is optionally connected through —C$_1$-C$_6$-alkylene- or —C$_1$-C$_6$-heteroalkylene-, in each case saturated or unsaturated, unsubstituted, mono- or polysubstituted; or 3-14-membered heterocycloalkyl, saturated or unsaturated, unsubstituted, mono- or polysubstituted; wherein said 3-14-membered heterocycloalkyl is optionally connected through —C$_1$-C$_6$-alkylene- or —C$_1$-C$_6$-heteroalkylene-, in each case saturated or unsaturated, unsubstituted, mono- or polysubstituted.

Preferably, R$^2$ represents —H, —C$_{1-6}$-alkyl, —C$_{1-6}$-alkylene-O—C$_{1-6}$-alkyl, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, or —C$_{1-6}$-alkylene-N(C$_{1-6}$-alkyl)-C$_{1-6}$-alkylene-CF$_3$.

Preferably, R$^2$ represents —H or —C$_{1-6}$-alkyl.

In a preferred embodiment of the benzofuran derivative according to the invention R$^3$ represents

—H;

—OH;

—C$_1$-C$_6$-alkyl, saturated or unsaturated, unsubstituted, mono- or polysubstituted; or —C$_1$-C$_6$-heteroalkyl, saturated or unsaturated, unsubstituted, mono- or polysubstituted.

Preferably, R$^3$ represents —H, —OH, —C$_{1-6}$-alkyl, —C$_{1-6}$-alkylene-OH, —C$_{1-6}$-alkylene-O—C$_{1-6}$-alkyl, —C$_{1-6}$-alkylene-NH$_2$, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, or —C$_{1-6}$-alkylene-N(C$_{1-6}$-alkyl)-C$_{1-6}$-alkylene-CF$_3$.

Preferably, R$^3$ represents —H, —OH, or —C$_{1-6}$-alkyl, saturated, unsubstituted or monosubstituted with —OH.

Preferably, R$^3$ represents —H.

Preferably, R$^3$ represents —H and R$^4$ represents a residue other than —H.

In a preferred embodiment of the benzofuran derivative according to the invention R$^4$ represents

—H;

—S(=O)C$_{1-6}$-alkyl, saturated or unsaturated, unsubstituted, mono- or polysubstituted;

—S(=O)$_2$—C$_{1-6}$-alkyl, saturated or unsaturated, unsubstituted, mono- or polysubstituted;

—C$_1$-C$_6$-alkyl, saturated or unsaturated, unsubstituted, mono- or polysubstituted;

—C$_1$-C$_6$-heteroalkyl, saturated or unsaturated, unsubstituted, mono- or polysubstituted;

3-14-membered cycloalkyl, saturated or unsaturated, unsubstituted, mono- or polysubstituted; wherein said 3-14-membered cycloalkyl is optionally connected through —C$_1$-C$_6$-alkylene- or —C$_1$-C$_6$-heteroalkylene-, in each case saturated or unsaturated, unsubstituted, mono- or poly substituted;

3-14-membered heterocycloalkyl, saturated or unsaturated, unsubstituted, mono- or polysubstituted; wherein said 3-14-membered heterocycloalkyl is optionally connected through —C$_1$-C$_6$-alkylene- or —C$_1$-C$_6$-heteroalkylene-, in each case saturated or unsaturated, unsubstituted, mono- or polysubstituted;

6-14-membered aryl, unsubstituted, mono- or polysubstituted; wherein said 6-14-membered aryl is optionally connected through —C$_1$-C$_6$-alkylene- or —C$_1$-C$_6$-heteroalkylene-, in each case saturated or unsaturated, unsubstituted, mono- or polysubstituted; or 5-14-membered heteroaryl, unsubstituted, mono- or polysubstituted; wherein said 5-14-membered heteroaryl is optionally connected through —C$_1$-C$_6$-alkylene- or —C$_1$-C$_6$-heteroalkylene-, in each case saturated or unsaturated, unsubstituted, mono- or poly substituted.

Preferably, R$^4$ represents

—S(=O)$_2$C$_{1-6}$-alkyl, saturated or unsaturated, unsubstituted, mono- or polysubstituted with substituents independently of one another selected from the group consisting of —F, —Cl, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

—S(=O)$_2$(3-14-membered cycloalkyl), wherein said 3-14-membered cycloalkyl is selected from the group consisting of cyclopropyl, cyclobutyl, cyclopentyl, cyclohexyl, and cycloheptyl, in each case saturated or unsaturated, unsubstituted, mono- or polysubstituted with substituents independently of one another selected from the group consisting of —F, —Cl, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

—C$_{1-6}$-alkyl, saturated or unsaturated, unsubstituted, mono- or polysubstituted with substituents independently of one another selected from the group consisting of —F, —Cl, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

3-14-membered cycloalkyl or —C$_{1-6}$-alkylene-(3-14-membered cycloalkyl), wherein —C$_{1-6}$-alkylene- is unsubstituted or monosubstituted with —OH, wherein said 3-14-membered cycloalkyl is selected from the group consisting of cyclopropyl, cyclobutyl, cyclopentyl, cyclohexyl, and cycloheptyl, in each case saturated or unsaturated, in each case unsubstituted, mono- or polysubstituted with substituents independently of one another selected from the group consisting of —F, —Cl, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

3-14-membered heterocycloalkyl or —C$_{1-6}$-alkylene-(3-14-membered heterocycloalkyl), wherein —C$_{1-6}$-alkylene- is unsubstituted or monosubstituted with —OH, wherein said 3-14-membered heterocycloalkyl in each case is selected from the group consisting of azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin; in each case unsubstituted, mono- or polysubstituted with substituents independently of one another selected from the group consisting of —F, —Cl, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

-phenyl unsubstituted, mono- or polysubstituted with substituents independently of one another selected from the group consisting of —F, —Cl, —CN, —C$_{1-6}$-alkyl, —C$_{1-6}$-alkylene-CF$_3$, —OH, =O, —OC$_{1-6}$-alkyl, —C$_{1-6}$-alkylene-OH, —C$_{1-6}$-alkylene-O—C$_{1-6}$-alkyl, —NH$_2$, —NHC$_{1-6}$-alkyl, —N(C$_{1-6}$-alkyl)$_2$, —NHC(=O)O—C$_{1-6}$-alkyl, —N(C$_{1-6}$-alkyl)C(=O)O—C$_{1-6}$-alkyl, —C$_{1-6}$-alkylene-NHC(=O)O—C$_{1-6}$-alkyl, —C$_{1-6}$-alkylene-NH$_2$, —C$_{1-6}$-alkylene-NH—C$_{1-6}$-alkyl, —C$_{1-6}$-alkylene-N(C$_{1-6}$-alkyl)$_2$, —C$_{1-6}$-alkylene-NH—C$_{1-6}$-alkylene-CF$_3$, —C(=O)—C$_{1-6}$-alkyl, —C(=O)OH, —C(=O)O—C$_{1-6}$-alkyl, —C(=O)O—C$_{1-6}$-alkylene-CF$_3$, —C(=O)NH$_2$, —C(=O)NH(C$_{1-6}$-alkyl), —C(=O)N(C$_{1-6}$-alkyl)$_2$, —S(=O)$_2$C$_{1-6}$-alkyl, -phenyl, —C$_{1-6}$-alkylene-phenyl, 3-14-membered heterocycloalkyl, saturated or unsaturated, unsubstituted; and 5-14-membered heteroaryl, unsubstituted;

5-14-membered heteroaryl or —C$_{1-6}$-alkylene-(5-14-membered heteroaryl), wherein —C$_{1-6}$-alkylene- is unsubstituted or monosubstituted with —OH, wherein said 5-14-membered heteroaryl in each case is selected from the group consisting of benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and [1,2,4]triazolo[4,3-a]pyrimidine; in each case unsubstituted, mono- or polysubstituted with substituents independently of one another selected from the group consisting of —F, —Cl, —CN, —$C_{1-6}$-alkyl, —$C_{1-6}$-alkylene-CF$_3$, —OH, =O, —O$C_{1-6}$-alkyl, —$C_{1-6}$-alkylene-OH, —$C_{1-6}$-alkylene-O—$C_{1-6}$-alkyl, —NH$_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-NH$_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-CF$_3$, —C(=O)—$C_{1-6}$-alkyl, —C(=O)OH, —C(=O)O—$C_{1-6}$-alkyl, —C(=O)O—$C_{1-6}$-alkylene-CF$_3$, —C(=O)NH$_2$, —C(=O)NH($C_{1-6}$-alkyl), —C(=O)N($C_{1-6}$-alkyl)$_2$, —S(=O)$_2 C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted.

Preferably, R$^4$ represents
—H;
—S(=O)$_2 C_{1-6}$-alkyl, saturated, unsubstituted, monosubstituted or polysubstituted with —F;
—S(=O)$_2$(3-14-membered cycloalkyl), saturated, unsubstituted;
—$C_{1-6}$-alkyl, saturated, monosubstituted or disubstituted with substituents independently of one another selected from the group consisting of —OH, =O, —NH$_2$, —NH$C_{1-6}$-alkyl, —N($C_{1-6}$-alkyl)$_2$, —O$C_{1-6}$-alkyl, —$C_{1-6}$-alkylene-NH$_2$, —$C_{1-6}$-alkylene-NH—$C_{1-6}$-alkyl, —C(=O)NH$_2$, —C(=O)—NH—$C_{1-3}$-alkyl, —C(=O)—N($C_{1-3}$-alkyl)$_2$, -phenyl unsubstituted;
3-14-membered cycloalkyl or —$C_{1-6}$-alkylene-(3-14-membered cycloalkyl), wherein —$C_{1-6}$-alkylene- is unsubstituted or monosubstituted with —OH, wherein said 3-14-membered cycloalkyl is saturated, unsubstituted, monosubstituted or disubstituted with substituents independently of one another selected from the group consisting of —$C_{1-6}$-alkyl, —$C_{1-6}$-alkylene-NH$_2$, —$C_{1-6}$-alkylene-NH—$C_{1-6}$-alkylene-CF$_3$, —$C_{1-6}$-alkylene-OH, —$C_{1-6}$-alkylene-NHC(=O)O—$C_{1-6}$-alkyl, —OH, —O$C_{1-6}$-alkyl, —NH$_2$, —N($C_{1-6}$-alkyl)$_2$, —NHC(=O)O—$C_{1-6}$-alkyl;
3-14-membered heterocycloalkyl or —$C_{1-6}$-alkylene-(3-14-membered heterocycloalkyl), wherein —$C_{1-6}$-alkylene- is unsubstituted or monosubstituted with —OH, wherein said 3-14-membered heterocycloalkyl in each case is selected from azetane, 1,4-oxazepane, pyrrolidine, piperidine, azepane, diazepane, tetrahydrofuran, tetrahydropyran, oxetane, morpholine, piperazine, hexahydrocyclopenta[c]pyrrole, octahydrocyclopenta[c]pyrrole, octahydropyrrolo[1,2-a]pyrazin, 8-azabicyclo[3.2.1]octane, 9-azabicyclo[3.3.1]nonane, quinuclidine, hexahydro-1H-pyrrolizine, 2-oxaspiro[3.3]heptane, 2-azaspiro[3.3]heptane, 7-azaspiro[3.5]nonane, 1,1-dioxothiacyclohexane, in each case unsubstituted, mono- or polysubstituted with substituents independently of one another selected from the group consisting of —F, —OH, =O, —$C_{1-6}$-alkyl, —$C_{1-6}$-alkylene-CF$_3$, —$C_{1-6}$-alkylene-OH, —$C_{1-6}$-alkylene-O—$C_{1-6}$-alkyl, —NH$_2$, —N($C_{1-6}$-alkyl)$_2$, —$C_{1-6}$-alkylene-NH$_2$, —$C_{1-6}$-alkylene-N($C_{1-6}$-alkyl)$_2$, —C(=O)—$C_{1-6}$-alkyl, —C(=O)OH, —C(=O)O—$C_{1-6}$-alkyl, —C(=O)O—$C_{1-6}$-alkylene-CF$_3$, —C(=O)NH$_2$, —C(=O)NH($C_{1-6}$-alkyl), —S(=O)$_2 C_{1-6}$-alkyl, oxetanyl, pyrimidinyl, —$C_{1-6}$-alkylene-phenyl;
-phenyl unsubstituted;
5-14-membered heteroaryl or —$C_{1-6}$-alkylene-(5-14-membered heteroaryl), wherein —$C_{1-6}$-alkylene- is unsubstituted or monosubstituted with —OH, wherein said 5-14-membered heteroaryl in each case is selected from the group consisting of pyridine, pyridazine, pyrazine, pyrazole, isoxazole, triazole, and [1,2,4]triazolo[4,3-a]pyrimidine, in each case unsubstituted, monosubstituted or disubstituted with substituents independently of one another selected from the group consisting of —$C_{1-6}$-alkyl, —OH.

In a preferred embodiment of the benzofuran derivative according to the invention R$^3$ and R$^4$ together form a 5- or 6-membered heterocycle containing 1 or 2 heteroatoms selected from N, O and S, saturated or unsaturated, unsubstituted or mono- or polysubstituted.

Preferably, R$^3$ and R$^4$ together form a heterocycle selected from the group consisting of pyrrolidine, piperidine, morpholine, and piperazine, in each case unsubstituted, mono- or polysubstituted with substituents independently of one another selected from the group consisting of —F, —$C_{1-6}$-alkyl, —NH$_2$, —NHCH$_3$, —N(CH$_3$)$_2$, —C(=O)NH—$C_{1-6}$-alkyl, —C(=O)N($C_{1-6}$-alkyl)$_2$, —C(=O)O—$C_{1-6}$-alkyl, —NHC(=O)O—$C_{1-6}$-alkyl, -pyridyl unsubstituted, and 1,2,4-oxadiazole unsubstituted or monosubstituted with —$C_{1-6}$-alkyl. In a preferred embodiment, R$^3$ and R$^4$ together do not form morpholine unsubstituted, mono- or polysubstituted.

Preferably, R$^3$ and R$^4$ together form a
pyrrolidine ring, unsubstituted or monosubstituted with —N(CH$_3$)$_2$;
piperidine ring, unsubstituted or monosubstituted with a substituent selected from the group consisting of —$C_{1-6}$-alkyl, —NH$_2$, —N(CH$_3$)$_2$, —C(=O)NH—$C_{1-6}$-alkyl, —C(=O)O—$C_{1-6}$-alkyl, —NHC(=O)O—$C_{1-6}$-alkyl, and 1,2,4-oxadiazole unsubstituted or monosubstituted with —$C_{1-6}$-alkyl;
morpholine ring, unsubstituted; or
piperazine ring, unsubstituted or N-substituted with a substituent selected from the group consisting of —$C_{1-6}$-alkyl and -pyridyl unsubstituted.

In a preferred embodiment, R$^3$ and R$^4$ both do not represent —H. In preferred embodiments, R$^3$ and R$^4$ together with the nitrogen atom to which they are attached form a residue selected from the group consisting of:

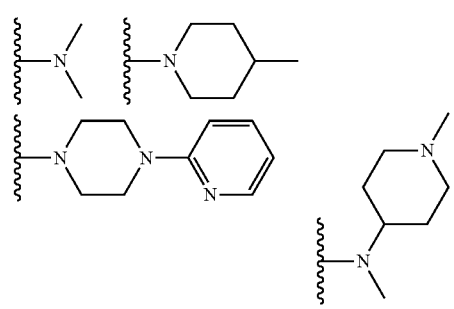

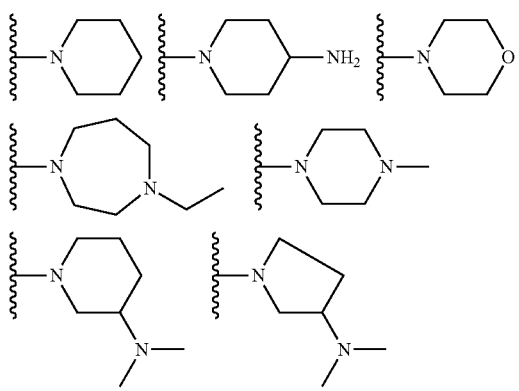

In other preferred embodiments R³ represents —H and R⁴ does not represent —H.

In preferred embodiments, R³ represents —H and R⁴ represent C₁-C₆-alkyl saturated or unsaturated, unsubstituted, mono- or polysubstituted. In preferred embodiments, R³ represents —H and R⁴ represents a residue selected from the group consisting of:

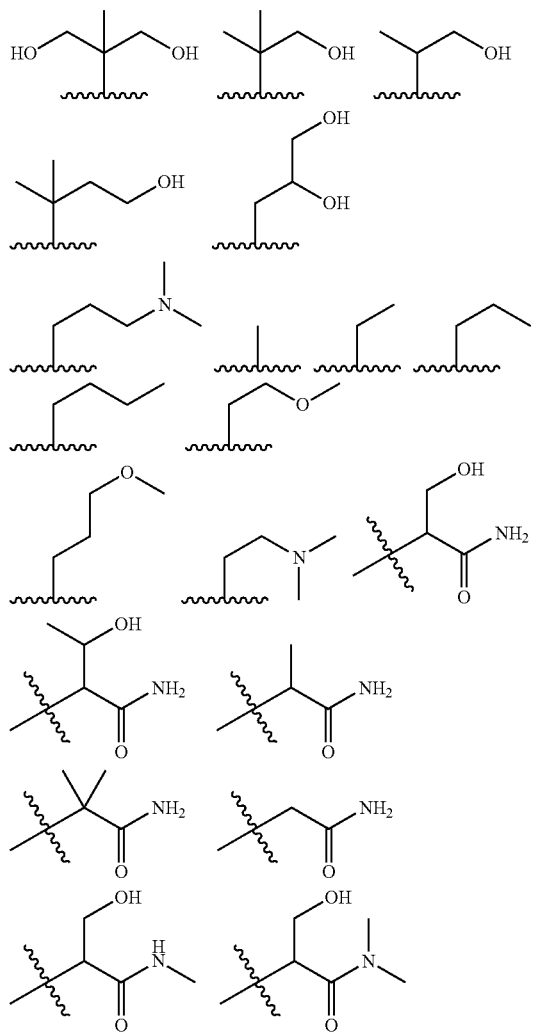

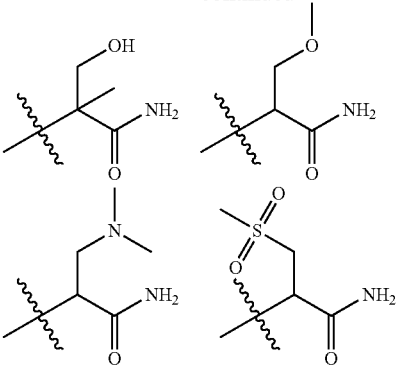

In preferred embodiments, R³ represents —H and R⁴ represents a residue —CR'R''—(CH₂)$_m$—OH, wherein m is an integer of from 1 to 6, preferably from 1 to 3; and wherein R' and R'' independently of one another represent —H, —C$_{1-3}$-alkyl, —CF₃, —CF₂H, —CFH₂, —C$_{1-3}$-alkylene-CF₃, —C$_{1-3}$-alkylene-CF₂H, —C$_{1-3}$-alkylene-CFH₂, —C$_{1-3}$-alkylene-O—C$_{1-3}$-alkyl, —C$_{1-3}$-alkylene-OH, —C(=O)—NH₂, or C(=O)—NH—C$_{1-3}$-alkyl; preferably —H, —CH₃, —C$_{1-3}$-alkylene-OH, —C(=O)—NH₂, or C(=O)—NH—C$_{1-3}$-alkyl. In a preferred embodiment, at least R' or R'' does not represent —H. In a preferred embodiment, neither R' nor R'' represents —H.

In other preferred embodiments, R³ represents —H and R⁴ represents a 3-14-membered cycloalkyl, saturated or unsaturated, unsubstituted, mono- or polysubstituted; or a 3-14-membered heterocycloalkyl, saturated or unsaturated, unsubstituted, mono- or poly substituted.

In preferred embodiments, R³ represents —H and R⁴ represents a 3-membered cycloalkyl, saturated or unsaturated, unsubstituted, mono- or polysubstituted; or a 3-membered heterocycloalkyl, saturated or unsaturated, unsubstituted, mono- or polysubstituted. In preferred embodiments, R³ represents —H and R⁴ represents a residue selected from the group consisting of:

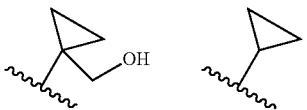

In preferred embodiments, R³ represents —H and R⁴ represents a 3-14-membered cycloalkyl (preferably a 4-membered cycloalkyl), saturated or unsaturated, unsubstituted, mono- or polysubstituted; or a 3-14-membered heterocycloalkyl (preferably a 4-membered heterocycloalkyl), saturated or unsaturated, unsubstituted, mono- or polysubstituted. In preferred embodiments, R³ represents —H and R⁴ represents a residue selected from the group consisting of:

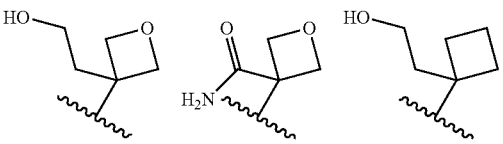

-continued

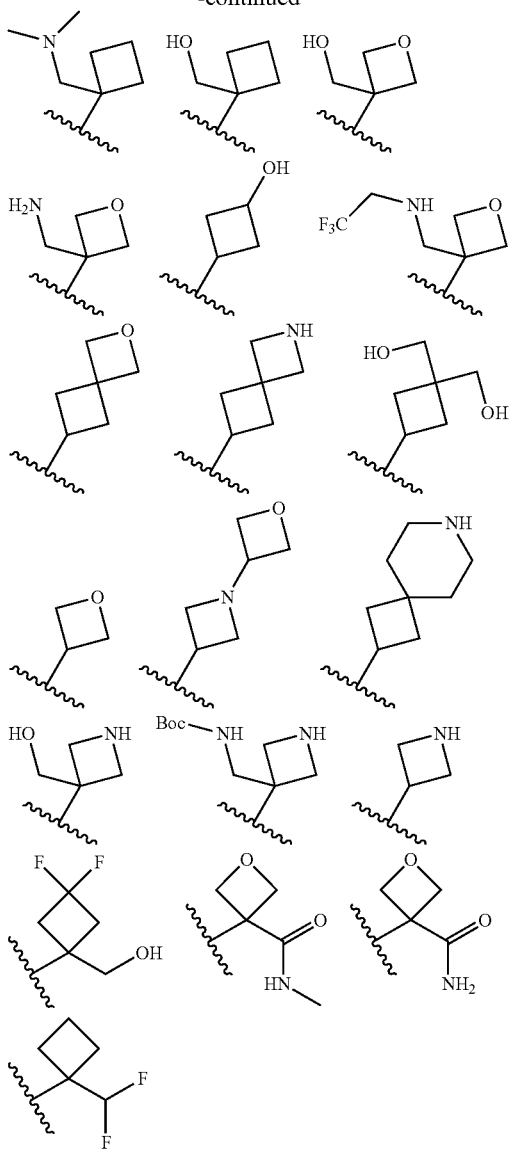

In preferred embodiments, R³ represents —H and R⁴ represents a residue according to general formula (A),

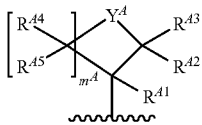

wherein
m^A is 0 or 1;
Y^A is selected from —O—, —NR^{46}— and —CR^{47}R^{48}—; and
R^{41}, R^{42}, R^{43}, R^{44}, R^{45}, R^{46}, R^{47}, and R^{48} independently of one another represent —H, F, —$C_{1-3}$-alkyl, —$C_{1-3}$-alkylene-OH, —$C_{1-3}$-alkylene-NH₂, —$C_{1-3}$-alkylene-NH($C_{1-3}$-alkyl), —$C_{1-3}$-alkylene-N($C_{1-3}$-alkyl)₂, —$C_{1-3}$-alkylene-NH($C_{1-3}$-alkylene-CF₃), —$C_{1-3}$-alkylene-C(=O)NH₂, —$C_{1-3}$-alkylene-NH—C(=O) $OC_{1-4}$-alkyl, —C(=O)NH₂, —C(=O)—NH—$C_{1-3}$-alkyl, —C(=O)—N($C_{1-3}$-alkyl)₂, -3-oxetanyl, or —CHF₂; preferably, R^{41}, R^{42}, R^{43}, R^{44}, R^{45}, R^{46}, R^{47}, and R^{48} independently of one another represent —H, F, —$C_{1-3}$-alkyl, —$C_{1-3}$-alkylene-OH, —$C_{1-3}$-alkylene-NH₂, —$C_{1-3}$-alkylene-NH($C_{1-3}$-alkyl), —$C_{1-3}$-alkylene-N($C_{1-3}$-alkyl)₂, —$C_{1-3}$-alkylene-NH($C_{1-3}$-alkylene-CF₃), —$C_{1-3}$-alkylene-C(=O)NH₂, —$C_{1-3}$-alkylene-NH—C(=O)$OC_{1-4}$-alkyl, —C(=O)NH₂, —C(=O)—NH—$C_{1-3}$-alkyl, —C(=O)—N($C_{1-3}$-alkyl)₂, or -3-oxetanyl; or R^{47} and R^{48} together with the carbon atom to which they are attached form a ring and represent —CH₂OCH₂—, —CH₂OCH₂CH₂— or —CH₂CH₂OCH₂CH₂—, —CH₂NHCH₂—, —CH₂NHCH₂CH₂— or —CH₂CH₂NHCH₂CH₂—.

In preferred embodiments, R³ represents —H and R⁴ represents a residue according to general formula (A) as defined above, wherein
m^A is 0 or 1;
Y^A is selected from —O— and —CR^{47}R^{48}—; and
R^{41}, R^{42}, R^{43}, R^{44}, R^{45}, R^{47}, and R^{48} independently of one another represent —H, —$C_{1-3}$-alkylene-OH, —$C_{1-3}$-alkylene-N($C_{1-3}$-alkyl)₂, —C(=O)NH₂, or —CHF₂; preferably R^{41}, R^{42}, R^{43}, R^{44}, R^{45}, R^{47}, and R^{48} independently of one another represent —H, —$C_{1-3}$-alkylene-OH, —$C_{1-3}$-alkylene-N($C_{1-3}$-alkyl)₂, or —C(=O)NH₂; preferably with the proviso that only one of R^{41}, R^{42}, R^{43}, R^{44}, R^{45}, R^{47}, and R^{48} represents a residue that is not —H.

In preferred embodiments, R³ represents —H and R⁴ represents a residue according to general formula (A) as defined above, wherein
m^A is 0 or 1;
Y^A is selected from —O— and —CR^{47}R^{48}—; and
R^{41} represents —$C_{1-3}$-alkylene-OH, —$C_{1-3}$-alkylene-N($C_{1-3}$-alkyl)₂, —C(=O)NH₂, or —CHF₂; preferably R^{41} represents —$C_{1-3}$-alkylene-OH, —$C_{1-3}$-alkylene-N($C_{1-3}$-alkyl)₂, or —C(=O)NH₂; and
R^{41}, R^{42}, R^{43}, R^{41}, R^{45}, R^{47}, and R^{48} represent —H.

In preferred embodiments, R³ represents —H and R⁴ represents a 3-14-membered cycloalkyl (preferably a 5-membered cycloalkyl), saturated or unsaturated, unsubstituted, mono- or polysubstituted; or a 3-14-membered heterocycloalkyl (preferably a 5-membered heterocycloalkyl), saturated or unsaturated, unsubstituted, mono- or polysubstituted; or a 5-14-membered heteroaryl (preferably a 5-membered heteroaryl), unsubstituted, mono- or polysubstituted. In preferred embodiments, R³ represents —H and R⁴ represents a residue selected from the group consisting of:

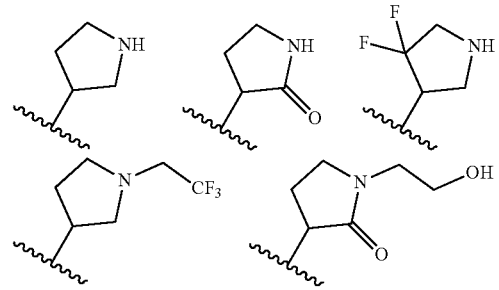

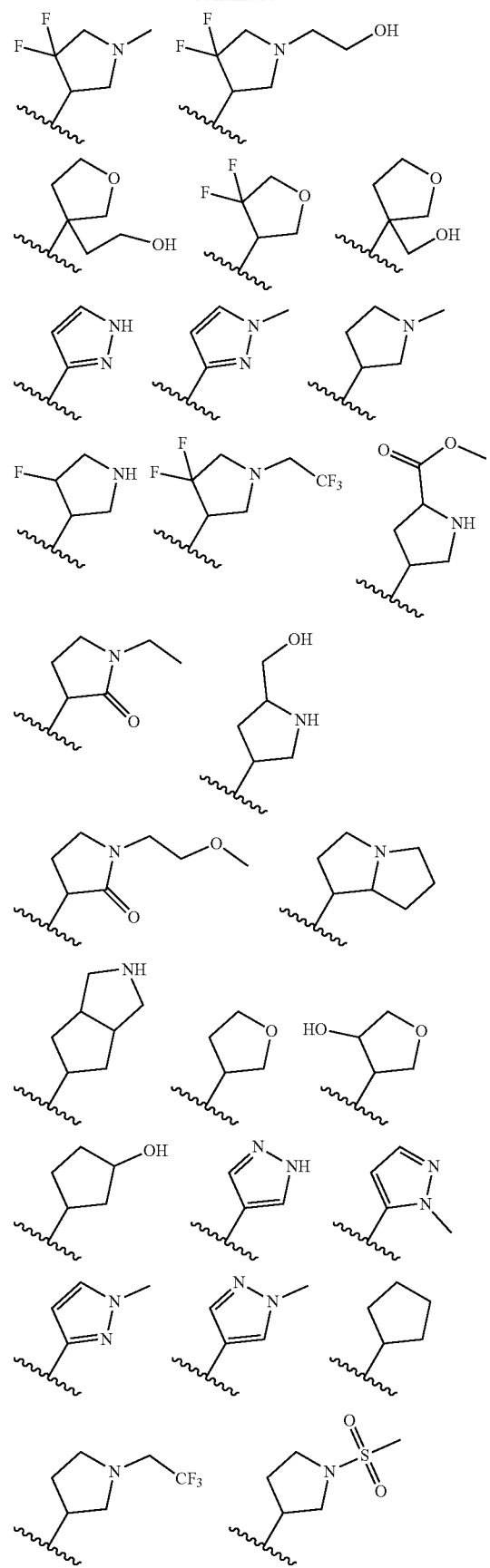
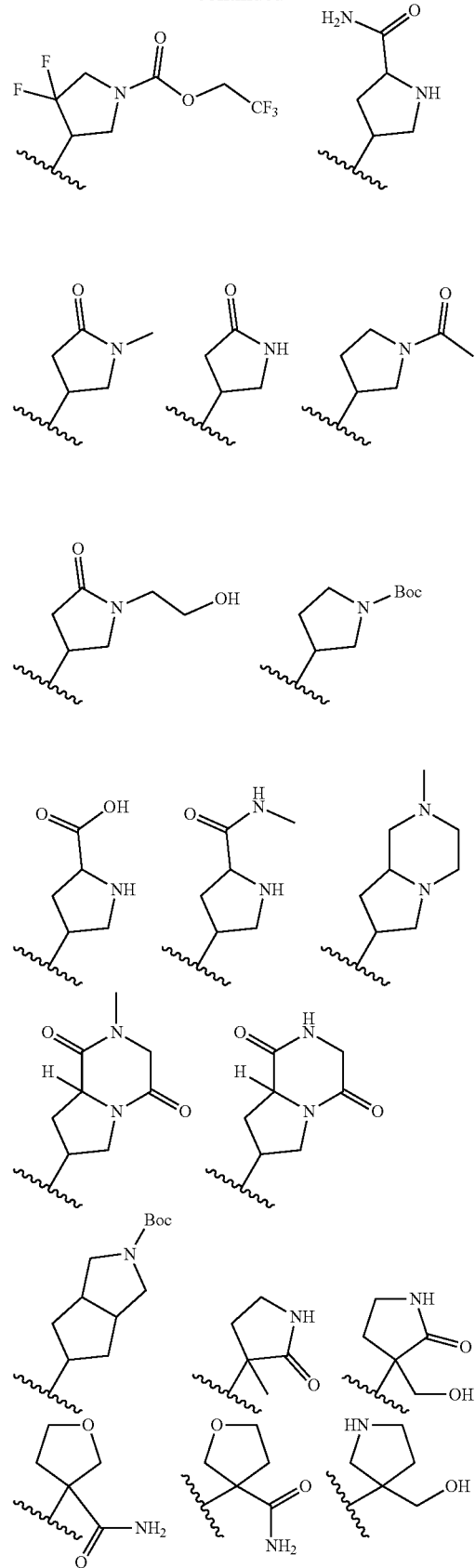

In preferred embodiments, $R^3$ represents —H and $R^4$ represents a residue according to general formula (B),

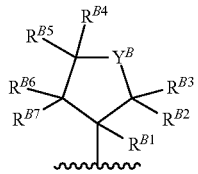
(B)

wherein $Y^B$ is selected from —O—, —NR$^{B8}$— and —CR$^{B9}$R$^{B10}$—; and $R^{B1}$, $R^{B2}$, $R^{B3}$, $R^{B4}$, $R^{B5}$, $R^{B6}$, $R^{B7}$, $R^{B8}$, $R^{B9}$ and $R^{B10}$ independently of one another represent —H, —F, —OH, —C$_{1-3}$-alkyl, —C$_{1-3}$-alkylene-OH, —C$_{1-3}$-alkylene-O—C$_{1-3}$-alkyl, —C$_{1-3}$-alkylene-CF$_3$, —C$_{1-3}$-alkylene-CO$_2$H, —C$_{1-3}$-alkylene-C(=O)O—C$_{1-3}$-alkyl, —C(=O)NH$_2$, —C(=O)NH—C$_{1-3}$-alkyl, or —C(=O)N(C$_{1-3}$-alkyl)$_2$; or $R^{B2}$ and $R^{B3}$ together represent =O; or $R^{B4}$ and $R^{B5}$ together represent =O.

In preferred embodiments, $R^3$ represents —H and $R^4$ represents a residue according to general formula (B) as defined above, wherein $Y^B$ is selected from —O— and —NR$^{B8}$—; and $R^{B1}$, $R^{B2}$, $R^{B3}$, $R^{B4}$, $R^{B5}$, $R^{B6}$, $R^{B7}$, $R^{B8}$ independently of one another represent —H, —F, —C$_{1-3}$-alkyl, —C$_{1-3}$-alkylene-OH, —C$_{1-3}$-alkylene-CF$_3$ or —C(=O)NH$_2$; or $R^{B2}$ and $R^{B3}$ together represent =O; or $R^{B4}$ and $R^{B5}$ together represent =O; preferably with the proviso that only 1, 2 or 3 of $R^{A1}$, $R^{A2}$, $R^{A3}$, $R^{A4}$, $R^{A5}$, $R^{A7}$, and $R^{A8}$ represent a residue that is not —H; preferably with the proviso that at least one of $R^{A1}$, $R^{A2}$, $R^{A3}$, $R^{A4}$, $R^{A5}$, $R^{A7}$, and $R^{A8}$ represent a residue that is not —H.

In preferred embodiments, $R^3$ represents —H and $R^4$ represents a 3-14-membered cycloalkyl (preferably a 6-membered cycloalkyl), saturated or unsaturated, unsubstituted, mono- or polysubstituted; or a 3-14-membered heterocycloalkyl (preferably a 6-membered heterocycloalkyl), saturated or unsaturated, unsubstituted, mono- or polysubstituted; or a 6-14-membered aryl (preferably a 6-membered aryl), unsubstituted, mono- or polysubstituted; or a 5-14-membered heteroaryl (preferably a 6-membered heteroaryl), unsubstituted, mono- or polysubstituted. In preferred embodiments, $R^3$ represents —H and $R^4$ represents a residue selected from the group consisting of:

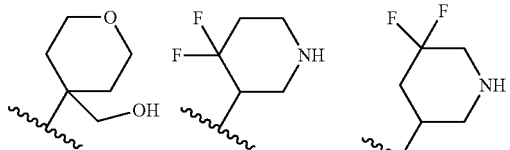

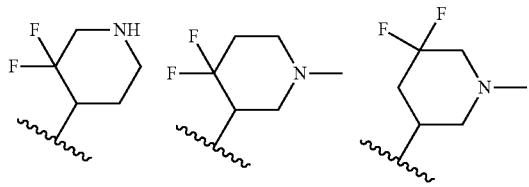

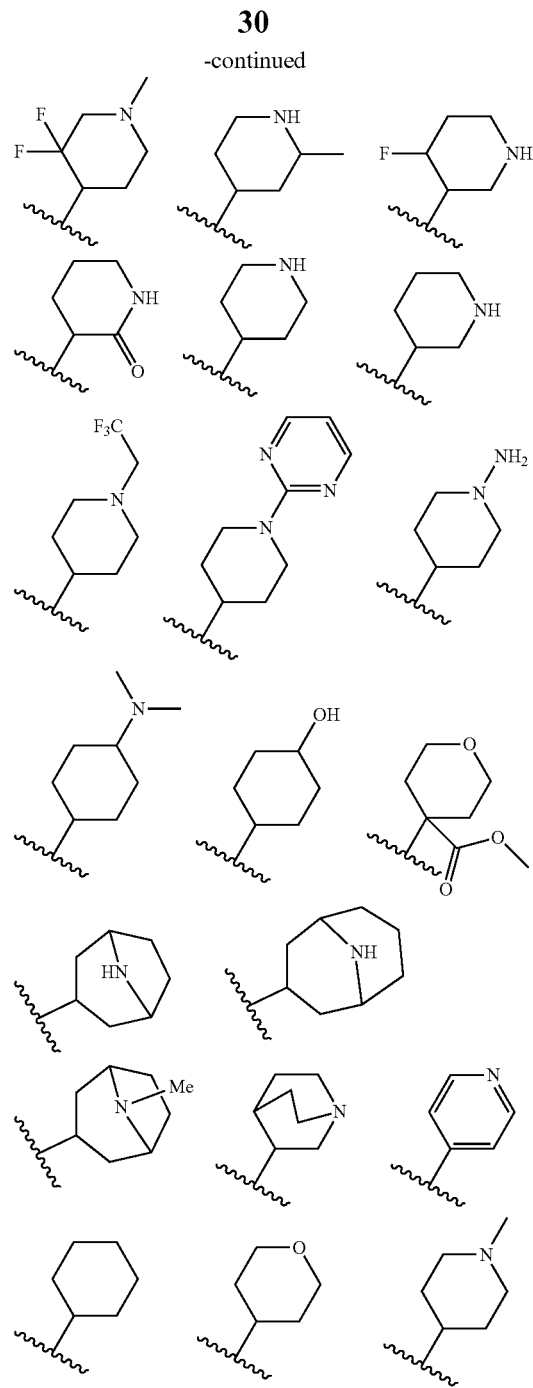

-continued

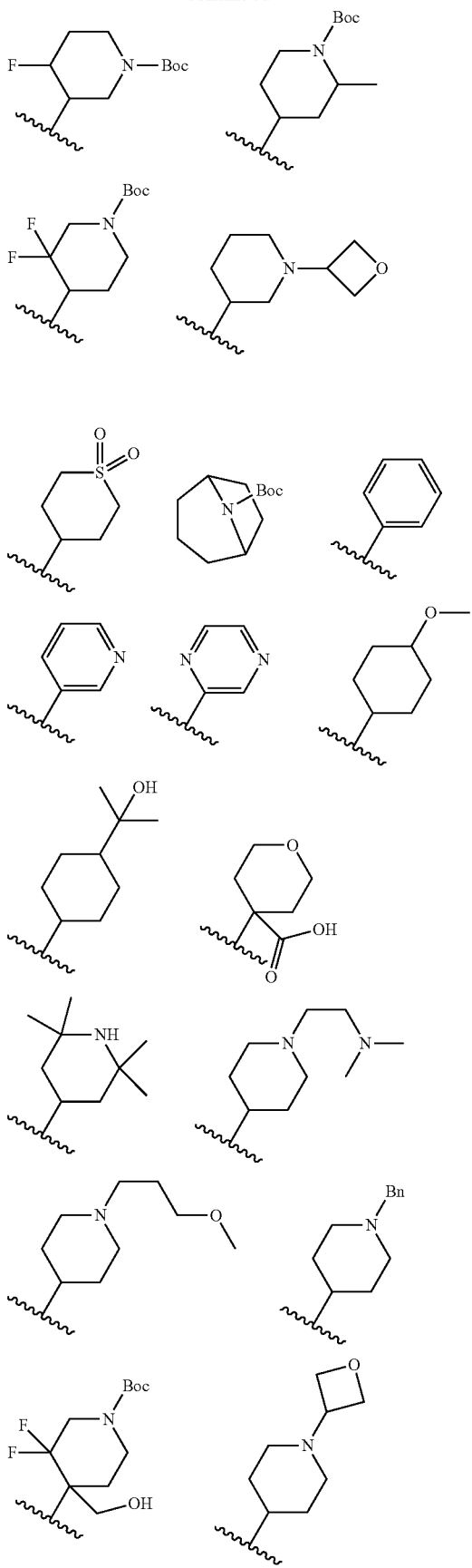

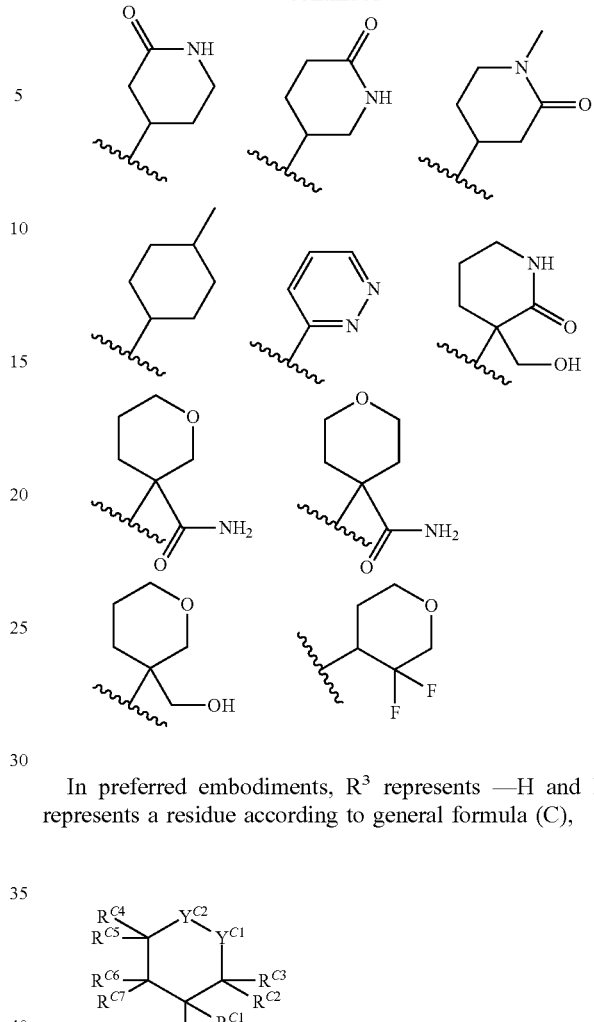

In preferred embodiments, R³ represents —H and R⁴ represents a residue according to general formula (C),

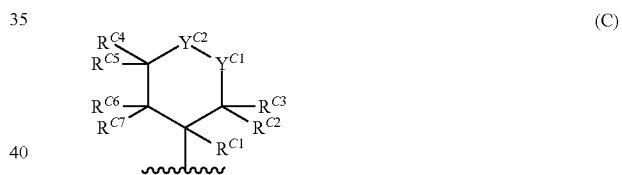

wherein
Y$^{C1}$ is selected from —O—, —S(=O)$_2$—, —NR$^{C8}$— and —CR$^{C9}$R$^{C10}$— and Y$^{C2}$ represents —CR$^{C11}$R$^{C12}$—, or Y$^{C1}$ represents —CR$^{C9}$R$^{C10}$— and Y$^{C2}$ is selected from —O—, —S(=O)$_2$—, and —NR$^{C8}$—;
R$^{C1}$, R$^{C2}$, R$^{C3}$, R$^{C4}$, R$^{C5}$, R$^{C6}$, R$^{C7}$, R$^{C8}$, R$^{C9}$, R$^{C10}$, R$^{C11}$ and R$^{C12}$ independently of one another represent —H, —F, —OH, —C(=O)OC$_{1-3}$-alkyl, —NH$_2$, —NH(C$_{1-3}$-alkyl), —N(C$_{1-3}$-alkyl)$_2$, —C$_{1-3}$-alkyl, —C$_{1-3}$-alkylene-OH, —C$_{1-3}$-alkylene-, —C(=O)NH$_2$, —C(=O)NH—C$_{1-3}$-alkyl, or —C(=O)N(C$_{1-3}$-alkyl)$_2$: or R$^{C2}$ and R$^{C3}$ together represent =O; or R$^{C4}$ and R$^{C5}$ together represent =O; or R$^{C9}$ and R$^{C10}$ together represent =O; or R$^{C11}$ and R$^{C12}$ together represent =O.

In preferred embodiments, R³ represents —H and R⁴ represents a residue according to general formula (C) as defined above, wherein
Y$^{C1}$ is selected from —O— or —NR$^{C8}$— and Y$^{C2}$ represents —CR$^{C11}$R$^{C12}$—, or Y$^{C1}$ represents —CR$^{C9}$R$^{C10}$— and Y$^{C2}$ is selected from —O—, and —NR$^{C8}$—;
R$^{C1}$, R$^{C2}$, R$^{C3}$, R$^{C4}$, R$^{C5}$, R$^{C6}$, R$^{C7}$, R$^{C8}$, R$^{C9}$, R$^{C10}$, R$^{C11}$ and R$^{C12}$ independently of one another represent —H, —F, —C$_{1-3}$-alkyl, —C$_{1-3}$-alkylene-OH, or —C(=O)NH$_2$; preferably with the proviso that only 1, 2 or 3 of R$^{C1}$, R$^{C2}$, R$^{C3}$, R$^{C4}$, R$^{C5}$, R$^{C6}$, R$^{C7}$, R$^{C8}$, R$^{C9}$, R$^{C10}$, R$^{C11}$ and R$^{C12}$ represent a residue that is not —H; preferably with the proviso that at least one of R$^{C1}$, R$^{C2}$, R$^{C3}$, R$^{C4}$, R$^{C5}$, R$^{C6}$, R$^{C7}$, R$^{C8}$, R$^{C9}$, R$^{C10}$, R$^{C11}$ and R$^{C12}$ represent a residue that is not —H.

In preferred embodiments, R$^3$ represents —H and R$^4$ represents a 7-membered cycloalkyl, saturated or unsaturated, unsubstituted, mono- or polysubstituted; or a 7-membered heterocycloalkyl, saturated or unsaturated, unsubstituted, mono- or polysubstituted. In preferred embodiments, R$^3$ represents —H and R$^4$ represents a residue:

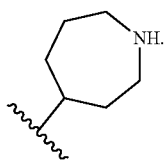 [SMILES: *C1CCCNCC1]

In preferred embodiments, R$^3$ represents —H and R$^4$ represents a 3-14-membered cycloalkyl (preferably a 4, 5 or 6-membered cycloalkyl), saturated or unsaturated, unsubstituted, mono- or polysubstituted; wherein said 3-14-membered cycloalkyl is connected through —C$_1$-C$_6$-alkylene-, saturated or unsaturated, unsubstituted, mono- or polysubstituted; or a 3-14-membered heterocycloalkyl (preferably a 4, 5 or 6-membered heterocycloalkyl), saturated or unsaturated, unsubstituted, mono- or polysubstituted; wherein said 3-14-membered heterocycloalkyl is connected through —C$_1$-C$_6$-alkylene-, saturated or unsaturated, unsubstituted, mono- or polysubstituted; or a 6-14-membered aryl (preferably a 6-membered aryl), unsubstituted, mono- or polysubstituted; wherein said 36-14-membered aryl is connected through —C$_1$-C$_6$-alkylene-, saturated or unsaturated, unsubstituted, mono- or polysubstituted; or a 5-14-membered heteroaryl (preferably a 5 or 6-membered heteroaryl), unsubstituted, mono- or polysubstituted; wherein said 5-14-membered heteroaryl is connected through —C$_1$-C$_6$-alkylene-, saturated or unsaturated, unsubstituted, mono- or polysubstituted. In preferred embodiments, R$^3$ represents —H and R$^4$ represents a residue selected from the group consisting of:

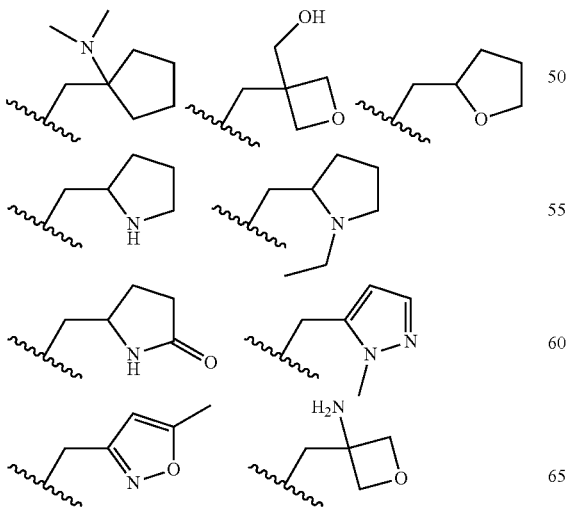

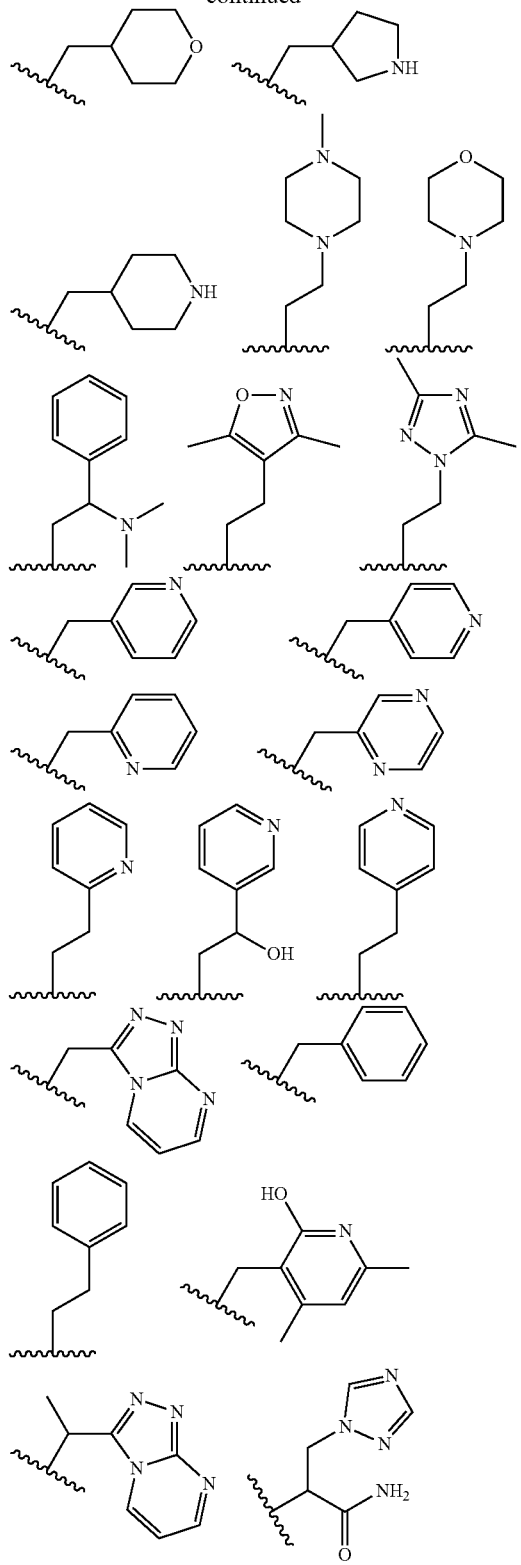

In preferred embodiments, R$^3$ represents —H and R$^4$ represents a 5-membered heterocycloalkyl, saturated or unsaturated, unsubstituted, mono- or polysubstituted; wherein said 5-membered heterocycloalkyl is connected through —C$_1$-C$_6$-alkylene-, saturated or unsaturated, unsubstituted, mono- or polysubstituted; or a 5-membered heteroaryl, unsubstituted, mono- or polysubstituted; wherein said 5-membered heteroaryl is connected through —$C_1$-$C_6$-alkylene-, saturated or unsaturated, unsubstituted, mono- or poly substituted.

In preferred embodiments, $R^3$ represents —H and $R^4$ represents a residue selected from the group consisting of:

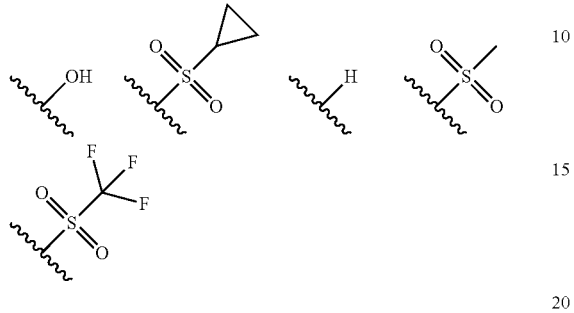

In preferred embodiments, $R^3$ represents —H and $R^4$ represents (i) a residue —CR'R"—$(CH_2)_m$—OH, wherein m is an integer of from 1 to 6, preferably from 1 to 3; and wherein R' and R" independently of one another represent —H, —$C_{1-3}$-alkyl, —$CF_3$, —$CF_2H$, —$CFH_2$, —$C_{1-3}$-alkylene-$CF_3$, —$C_{1-3}$-alkylene-$CF_2H$, —$C_{1-3}$-alkylene-$CFH_2$, —$C_{1-3}$-alkylene-O—$C_{1-3}$-alkyl, or —$C_{1-3}$-alkylene-OH; preferably —H, —$CH_3$, or —$C_{1-3}$-alkylene-OH. In a preferred embodiment, at least R' or R" does not represent —H. In a preferred embodiment, neither R' nor R" represents —H; or (ii) a residue according to general formula (D),

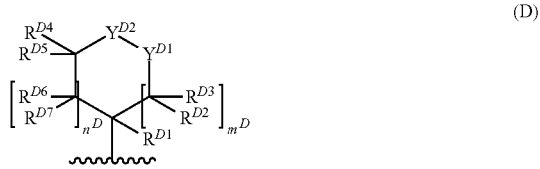

(D)

wherein $m^D$ and $n^D$ independently of one another are 0, 1, 2, or 3; preferably with the proviso that $m^D + n^D \leq 3$;

$Y^{D1}$ is selected from —O—, —S($=$O)$_2$—, —S($=$O)($=$NH)—, —NR$^{D8}$— and —CR$^{D9}$R$^{D10}$— and $Y^{D2}$ represents —CR$^{D11}$R$^{D12}$—;

or $Y^{D1}$ is selected from —O—, —S($=$O)$_2$—, —NR$^{D8}$— and —CR$^{D9}$R$^{D10}$— and $Y^{D2}$ represents —CR$^{D11}$R$^{D12}$—; or $Y^{D1}$ represents —CR$^{D9}$R$^{D10}$— and $Y^{D2}$ is selected from —O—, —S($=$O)$_2$—, and —NR$^{D8}$—;

$R^{D1}$, $R^{D2}$, $R^{D3}$, $R^{D4}$, $R^{D5}$, $R^{D6}$, $R^{D7}$, $R^{D8}$, $R^{D9}$, $R^{D10}$, $R^{D11}$ and $R^{D12}$ independently of one another represent —H, —F, —OH, —$C_{1-3}$-alkylene-OH, —C($=$O)NH$_2$, —$C_{1-3}$-alkylene-C(O)NH$_2$, —C($=$O)O—$C_{1-3}$-alkyl, —NH$_2$, —$C_{1-3}$-alkylene-NH$_2$, —NH($C_{1-3}$-alkyl), —N($C_{1-3}$-alkyl)$_2$, —NH($C_{1-3}$-alkylene-CF$_3$), —$C_{1-3}$-alkylene-OCH$_3$, —$C_{1-3}$-alkyl, —$C_{1-3}$-alkylene-CF$_3$; or $R^{D2}$ and $R^{D3}$ together represent $=$O; or $R^{D4}$ and $R^{D5}$ together represent $=$O; or $R^{D9}$ and $R^{D10}$ together represent $=$O; or $R^{D11}$ and $R^{D12}$ together represent $=$O;

preferably wherein $m^D$ and $n^D$ independently of one another are 0, 1, 2 or 3; preferably with the proviso that $m^D + n^D \leq 3$.

$Y^{D1}$ is selected from —O—, —NR$^{D8}$— and —CR$^{D9}$R$^{D10}$— and $Y^{D2}$ represents —CR$^{D11}$R$^{D12}$—; or $Y^{D1}$ represents —CR$^{D9}$R$^{D10}$— and $Y^{D2}$ is selected from —O— and —NR$^{D8}$—;

$R^{D1}$, $R^{D2}$, $R^{D3}$, $R^{D4}$, $R^{D5}$, $R^{D6}$, $R^{D7}$, $R^{D8}$, $R^{D9}$, $R^{D10}$, $R^{D11}$ and $R^{D12}$ independently of one another represent —H, —F, —OH, —$C_{1-3}$-alkylene-OH, —C($=$O)NH$_2$, —CH$_2$NH$_2$, —CH$_2$N(CH$_3$)$_2$, —NHCH$_2$CF$_3$, —CH$_3$, or —CH$_2$CF$_3$; or $R^{D2}$ and $R^{D3}$ together represent $=$O; or $R^{D4}$ and $R^{D5}$ together represent $=$O; or $R^{D9}$ and $R^{D10}$ together represent $=$O; or $R^{D11}$ and $R^{D12}$ together represent $=$O;

preferably with the proviso that only 1, 2 or 3 of $R^{D1}$, $R^{D2}$, $R^{D3}$, $R^{D4}$, $R^{D5}$, $R^{D6}$, $R^{D7}$, $R^{D8}$, $R^{D9}$, $R^{D10}$, $R^{D11}$ and $R^{D12}$ represent a residue that is not —H; preferably with the proviso that at least one of $R^{D1}$, $R^{D2}$, $R^{D3}$, $R^{D4}$, $R^{D5}$, $R^{D6}$, $R^{D7}$, $R^{D8}$, $R^{D9}$, $R^{D10}$, $R^{D11}$ and $R^{D12}$ represent a residue that is not —H.

In a preferred embodiment of the benzofuran derivative according to the invention $R^5$ and $R^{5'}$ independently of one another represent

—H;

—$C_1$-$C_6$-alkyl, saturated or unsaturated, unsubstituted, mono- or polysubstituted;

—$C_1$-$C_6$-heteroalkyl, saturated or unsaturated, unsubstituted, mono- or polysubstituted;

3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or poly substituted.

Preferably, $R^5$ and $R^{5'}$ independently of one another represent —H, —$C_1$-$C_6$-alkyl, or —$C_1$-$C_6$-alkylene-N($C_1$-$C_6$-alkyl)$_2$.

In a preferred embodiment of the benzofuran derivative according to the invention, at least one of $R^5$ and $R^{5'}$ is not —H.

In a preferred embodiment of the benzofuran derivative according to the invention, $R^5$ and $R^{5'}$ are both —H.

In preferred embodiments, T represents —O— and U represents —CR$^5$R$^{5'}$— and the resultant moiety —O—CR$^5$R$^{5'}$— represents a residue selected from the group consisting of:

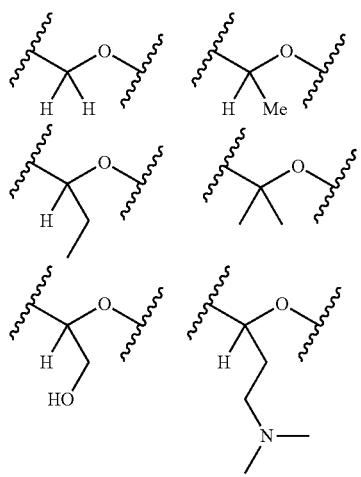

In preferred embodiments, T represents —CR$^5$R$^{5'}$— and U represents —O— and the resultant moiety —CR$^5$R$^{5'}$—O— represents a residue:

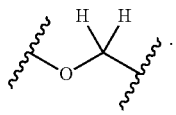 [SMILES: *CO*]

In preferred embodiments, R$^5$ represents —H and R$^{5'}$ represents a residue selected from the group consisting of —H, —C$_{1-3}$-alkyl, —CF$_3$, —CF$_2$H, —CFH$_2$, —C$_{1-3}$-alkylene-CF$_3$, —C$_{1-3}$-alkylene-CF$_2$H, —C$_{1-3}$-alkylene-CFH$_2$, and —C$_{1-3}$-alkylene-OH; preferably —H or C$_{1-3}$-alkyl.

In a preferred embodiment of the benzofuran derivative according to the invention R$^6$, R$^7$ and R$^8$ independently of one another represent

- —H;
- —F, —Cl, —Br, —I, —OH, —SH, —SF$_5$, —CN, —NO$_2$, —C(=O)OH, —NH$_2$;
- —C$_{1-6}$-alkyl, saturated or unsaturated, unsubstituted, mono- or polysubstituted;
- —O—C$_{1-6}$-alkyl, saturated or unsaturated, unsubstituted, mono- or polysubstituted;
- —NHC$_{1-6}$-alkyl, saturated or unsaturated, unsubstituted, mono- or polysubstituted;
- —N(C$_{1-6}$-alkyl)$_2$, saturated or unsaturated, unsubstituted, mono- or poly substituted;
- —C(=O)OC$_{1-6}$-alkyl, saturated or unsaturated, unsubstituted, mono- or polysubstituted;
- —OC(=O)C$_{1-6}$-alkyl, saturated or unsaturated, unsubstituted, mono- or polysubstituted;
- —C$_{1-6}$-heteroalkyl, saturated or unsaturated, unsubstituted, mono- or poly substituted.

Preferably, R$^6$, R$^7$ and R$^8$ independently of one another represent

- —H, —F, —Cl, —Br, —I, —OH, —SH, —SF$_5$, —CN, —NO$_2$, —C(=O)OH, —NH$_2$,
- —C$_{1-6}$-alkyl, —CF$_3$, —CHF$_2$, —CH$_2$F,
- —O—C$_{1-6}$-alkyl, —OCF$_3$, —OCHF$_2$, —OCH$_2$F,
- —NHC$_{1-6}$-alkyl unsubstituted or substituted with one or more substituents independently of one another selected from —OH, =O, —F, —Cl, —Br, —I, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, and —C(=O)NH$_2$;
- —N(C$_{1-6}$-alkyl)$_2$ unsubstituted or substituted with one or more substituents independently of one another selected from —OH, =O, —F, —Cl, —Br, —I, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, and —C(=O)NH$_2$;
- —C(=O)OC$_{1-6}$-alkyl unsubstituted or substituted with one or more substituents independently of one another selected from —OH, =O, —F, —Cl, —Br, —I, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, and —C(=O)NH$_2$; or
- —OC(=O)C$_{1-6}$-alkyl unsubstituted or substituted with one or more substituents independently of one another selected from —OH, =O, —F, —Cl, —Br, —I, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, and —C(=O)NH$_2$; or
- —C$_{1-6}$-heteroalkyl unsubstituted or substituted with one or more substituents independently of one another selected from —OH, =O, —F, —Cl, —Br, —I, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, and —C(=O)NH$_2$.

In preferred embodiments, R$^6$, R$^7$ and R$^8$ independently of one another represents a residue selected from the group consisting of —H, —F, —Cl, —Br, —I, —CN, C$_{1-3}$-alkyl, —CF$_3$, —CF$_2$H, and —CFH$_2$; preferably —H or —F.

In a preferred embodiment of the benzofuran derivative according to the invention R$^6$ represents —H, —F, —Cl, —CN, or —C$_1$-C$_6$-alkyl.

In a preferred embodiment of the benzofuran derivative according to the invention, R$^6$ does not represent —H.

In preferred embodiments, R$^6$ represents a residue selected from the group consisting of —H, —F, —Cl, —CN or —CH$_3$; preferably —H, —F, —CN or —CH$_3$.

In a preferred embodiment of the benzofuran derivative according to the invention R$^7$ represents —H, —F, —Cl, —CN, or —C$_1$-C$_6$-alkyl.

In a preferred embodiment of the benzofuran derivative according to the invention R$^7$ does not represent —H.

In preferred embodiments, especially when Q represents —NR$^3$R$^4$, R$^7$ represents a residue selected from the group consisting of —H, —F, —Cl, —CN or CH$_3$; preferably —H, —F, —C$_1$ or —CH$_3$.

In preferred embodiments, especially when Q represents —OR$^2$, R$^7$ represents a residue selected from the group consisting of —H or

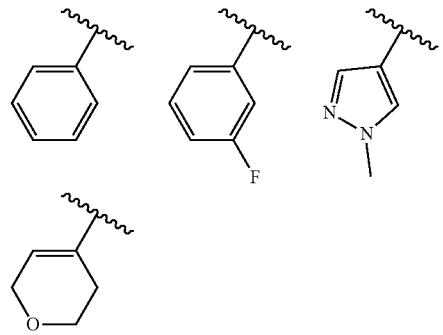

In a preferred embodiment of the benzofuran derivative according to the invention R$^8$ represents —H, —F, —Cl, —CN, or —C$_1$-C$_6$-alkyl.

In a preferred embodiment of the benzofuran derivative according to the invention R$^8$ does not represent —H.

In preferred embodiments, R$^8$ represents a residue selected from the group consisting of —H, —F, —Cl, —CN or CH$_3$; preferably —F.

In a preferred embodiments of the benzofuran derivative according to the invention (i) R$^6$, R$^7$ and R$^8$ each represent —H; or (ii) two of R$^6$, R$^7$ and R$^8$ represent —H and the other of R$^6$, R$^7$ and R$^8$ represents —F, —Cl, —CN, or —CH$_3$; or (iii) one of R$^6$, R$^7$ and R$^8$ represents —H and the other of R$^6$, R$^7$ and R$^8$ independently of one another represent —F, —Cl, —CN, or —CH$_3$.

In a particularly preferred embodiment, the compound is according to general formula (I), wherein $R^1$ represents —$CH_3$; and/or $R^6$, $R^7$ and $R^5$ each represent —H; and/or T represents —O—; and/or U represents —$CH_2$—; and/or V represents thiazolyl, pyridyl, or pyrazolyl; wherein said thiazolyl, pyridyl, and pyrazolyl each independently from one another can be unsubstituted, monosubstituted or disubstituted with a substituent selected from the group consisting of —$CH_3$; —F; —$CH_2CHF_2$; and —$CF_3$; and/or Q represents $NR^3R^4$; and/or $R^3$ represents H; and/or $R^4$ represents

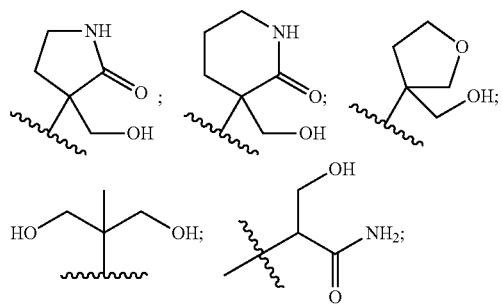

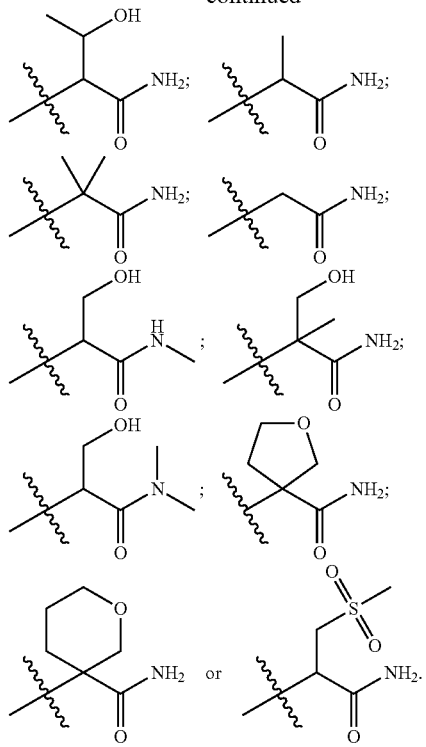

In preferred embodiments of the invention, the benzofuran derivative is selected from the group consisting of:

| | |
|---|---|
| cpd 001 | 5-(furan-3-ylmethoxy)-2-methylbenzofuran-3-carboxylic acid |
| cpd 002 | 2-methyl-5-(oxazol-5-ylmethoxy)benzofuran-3-carboxylic acid |
| cpd 003 | 2-methyl-5-(pyrrolidin-3-ylmethoxy)benzofuran-3-carboxylic acid |
| cpd 004 | 2-methyl-5-(pyridin-4-ylmethoxy)benzofuran-3-carboxylic acid |
| cpd 005 | 2-methyl-5-(pyridin-2-ylmethoxy)benzofuran-3-carboxylic acid |
| cpd 006 | 2-methyl-5-(pyridin-3-ylmethoxy)benzofuran-3-carboxylic acid |
| cpd 007 | 2-methyl-5-(pyridazin-3-ylmethoxy)benzofuran-3-carboxylic acid |
| cpd 008 | 2-methyl-5-((1-methyl-1H-pyrazol-5-yl)methoxy)benzofuran-3-carboxylic acid |
| cpd 009 | 2-methyl-5-((1-methyl-1H-pyrazol-3-yl)methoxy)benzofuran-3-carboxylic acid |
| cpd 010 | 2-methyl-5-((1-methyl-1H-pyrazol-4-yl)methoxy)benzofuran-3-carboxylic acid |
| cpd 011 | 2-methyl-5-(thiophen-3-ylmethoxy)benzofuran-3-carboxylic acid |
| cpd 012 | 2-methyl-5-(thiophen-2-ylmethoxy)benzofuran-3-carboxylic acid |
| cpd 013 | 2-methyl-5-(thiazol-2-ylmethoxy)benzofuran-3-carboxylic acid |
| cpd 014 | 2-methyl-5-(thiazol-5-ylmethoxy)benzofuran-3-carboxylic acid |
| cpd 015 | 2-methyl-5-((tetrahydro-2H-pyran-4-yl)methoxy)benzofuran-3-carboxylic acid |
| cpd 016 | 5-((3,5-dimethylisoxazol-4-yl)methoxy)-2-methylbenzofuran-3-carboxylic acid |
| cpd 017 | 5-(benzo[d]thiazol-2-ylmethoxy)-2-methylbenzofuran-3-carboxylic acid |
| cpd 018 | 2-methyl-5-((5-(trifluoromethyl)furan-2-yl)methoxy)benzofuran-3-carboxylic acid |
| cpd 019 | 5-((1-(tert-butoxycarbonyl)pyrrolidin-3-yl)methoxy)-2-methylbenzofuran-3-carboxylic acid |
| cpd 020 | (S)-2-methyl-5-(oxazol-5-ylmethoxy)-N-(pyrrolidin-3-yl)benzofuran-3-carboxamide |
| cpd 021 | (S)-2-methyl-5-(pyridin-4-ylmethoxy)-N-(pyrrolidin-3-yl)benzofuran-3-carboxamide |
| cpd 022 | (S)-2-methyl-5-(pyridin-3-ylmethoxy)-N-(pyrrolidin-3-yl)benzofuran-3-carboxamide |
| cpd 023 | (S)-2-methyl-5-((1-methyl-1H-pyrazol-3-yl)methoxy)-N-(pyrrolidin-3-yl)benzofuran-3-carboxamide |
| cpd 024 | (S)-2-methyl-N-(pyrrolidin-3-yl)-5-(thiazol-5-ylmethoxy)benzofuran-3-carboxamide |
| cpd 025 | (S)-2-methyl-N-(pyrrolidin-3-yl)-5-(thiazol-2-ylmethoxy)benzofuran-3-carboxamide |
| cpd 026 | 2-methyl-N-(2-oxopyrrolidin-3-yl)-5-(pyridin-2-ylmethoxy)benzofuran-3-carboxamide |
| cpd 027 | 2-methyl-N-(2-oxopyrrolidin-3-yl)-5-(pyridin-3-ylmethoxy)benzofuran-3-carboxamide |
| cpd 028 | (S)-2-methyl-5-((5-methylpyridin-3-yl)methoxy)-N-(pyrrolidin-3-yl)benzofuran-3-carboxamide |
| cpd 029 | (S)-2-methyl-5-((6-methylpyridin-2-yl)methoxy)-N-(pyrrolidin-3-yl)benzofuran-3-carboxamide |
| cpd 030 | 2-methyl-N-(2-oxopyrrolidin-3-yl)-5-(pyridazin-3-ylmethoxy)benzofuran-3-carboxamide |
| cpd 031 | 2-methyl-N-(2-oxopyrrolidin-3-yl)-5-(pyrazin-2-ylmethoxy)benzofuran-3-carboxamide |
| cpd 032 | 2-methyl-N-(2-oxopyrrolidin-3-yl)-5-(pyrimidin-5-ylmethoxy)benzofuran-3-carboxamide |
| cpd 033 | 2-methyl-5-((6-methylpyridin-3-yl)methoxy)-N-(tetrahydrofuran-3-yl)benzofuran-3-carboxamide |
| cpd 034 | 2-methyl-5-((4-methylpyridin-3-yl)methoxy)-N-(tetrahydrofuran-3-yl)benzofuran-3-carboxamide |
| cpd 035 | 2-methyl-N-(2-oxopyrrolidin-3-yl)-5-(thiophen-3-ylmethoxy)benzofuran-3-carboxamide |
| cpd 036 | 2-methyl-N-(2-oxopyrrolidin-3-yl)-5-(thiazol-2-ylmethoxy)benzofuran-3-carboxamide |
| cpd 037 | 2-methyl-5-((4-methylpyridin-3-yl)methoxy)-N-(2-oxopyrrolidin-3-yl)benzofuran-3-carboxamide |
| cpd 038 | 2-methyl-5-((5-methylpyridin-3-yl)methoxy)-N-(2-oxopyrrolidin-3-yl)benzofuran-3-carboxamide |
| cpd 039 | 2-methyl-N-(1-methylpiperidin-4-yl)-5-(pyridin-2-ylmethoxy)benzofuran-3-carboxamide |
| cpd 040 | 5-((4-methoxypyridin-3-yl)methoxy)-2-methyl-N-(tetrahydrofuran-3-yl)benzofuran-3-carboxamide |

| | -continued |
|---|---|
| cpd 041 | 2-methyl-N-(1-methylpiperidin-4-yl)-5-(thiophen-2-ylmethoxy)benzofuran-3-carboxamide |
| cpd 042 | 2-methyl-5-((4-methylthiazol-5-yl)methoxy)-N-(2-oxopyrrolidin-3-yl)benzofuran-3-carboxamide |
| cpd 043 | 2-methyl-5-((4-methylthiazol-2-yl)methoxy)-N-(2-oxopyrrolidin-3-yl)benzofuran-3-carboxamide |
| cpd 044 | 5-((2,6-dimethylpyridin-3-yl)methoxy)-2-methyl-N-(2-oxopyrrolidin-3-yl)benzofuran-3-carboxamide |
| cpd 045 | 2-methyl-N-(1-methylpiperidin-4-yl)-5-(1-(pyridin-4-yl)ethoxy)benzofuran-3-carboxamide |
| cpd 046 | 5-((2-methoxypyridin-3-yl)methoxy)-2-methyl-N-(2-oxopyrrolidin-3-yl)benzofuran-3-carboxamide |
| cpd 047 | N-(4-(hydroxymethyl)tetrahydro-2H-pyran-4-yl)-2-methyl-5-(pyridin-2-ylmethoxy)benzofuran-3-carboxamide |
| cpd 048 | N-(3,3-difluoropiperidin-4-yl)-2-methyl-5-(pyridin-2-ylmethoxy)benzofuran-3-carboxamide |
| cpd 049 | N-(4-(hydroxymethyl)tetrahydro-2H-pyran-4-yl)-2-methyl-5-(thiazol-2-ylmethoxy)benzofuran-3-carboxamide |
| cpd 050 | N-(3,3-difluoropiperidin-4-yl)-2-methyl-5-(thiazol-2-ylmethoxy)benzofuran-3-carboxamide |
| cpd 051 | 5-((2-methoxypyridin-3-yl)methoxy)-2-methyl-N-(1-methylpiperidin-4-yl)benzofuran-3-carboxamide |
| cpd 052 | N-(4-(hydroxymethyl)tetrahydro-2H-pyran-4-yl)-2-methyl-5-((4-methylpyridin-3-yl)methoxy)-benzofuran-3-carboxamide |
| cpd 053 | N-(3,3-difluoropiperidin-4-yl)-2-methyl-5-((3-methylpyridin-2-yl)methoxy)benzofuran-3-carboxamide |
| cpd 054 | N-(4-(hydroxymethyl)tetrahydro-2H-pyran-4-yl)-2-methyl-5-((4-methylthiazol-5-yl)methoxy)-benzofuran-3-carboxamide |
| cpd 055 | (S)-2-methyl-N-(pyrrolidin-3-yl)-5-((5-(trifluoromethyl)pyridin-3-yl)methoxy)benzofuran-3-carboxamide |
| cpd 056 | N-(3,3-difluoropiperidin-4-yl)-2-methyl-5-((4-methylthiazol-5-yl)methoxy)benzofuran-3-carboxamide |
| cpd 057 | 2-methyl-N-(tetrahydrofuran-3-yl)-5-((4-(trifluoromethyl)thiazol-2-yl)methoxy)benzofuran-3-carboxamide |
| cpd 058 | N-(4-(hydroxymethyl)tetrahydro-2H-pyran-4-yl)-5-((2-methoxypyridin-3-yl)methoxy)-2-methyl-benzofuran-3-carboxamide |
| cpd 059 | 5-(isoquinolin-1-ylmethoxy)-2-methyl-N-(1-methylpiperidin-4-yl)benzofuran-3-carboxamide |
| cpd 060 | 5-(isoquinolin-5-ylmethoxy)-2-methyl-N-(1-methylpiperidin-4-yl)benzofuran-3-carboxamide |
| cpd 061 | 5-(isoquinolin-6-ylmethoxy)-2-methyl-N-(1-methylpiperidin-4-yl)benzofuran-3-carboxamide |
| cpd 062 | N-(3,3-difluoropiperidin-4-yl)-5-((2-methoxypyridin-3-yl)methoxy)-2-methylbenzofuran-3-carboxamide |
| cpd 063 | N-(3,3-difluoropiperidin-4-yl)-5-((6-methoxypyridin-2-yl)methoxy)-2-methylbenzofuran-3-carboxamide |
| cpd 064 | 2-methyl-N-(2-oxopyrrolidin-3-yl)-5-((2-(trifluoromethyl)pyridin-3-yl)methoxy)benzofuran-3-carboxamide |
| cpd 065 | 2-methyl-N-(2-oxopyrrolidin-3-yl)-5-((6-(trifluoromethyl)pyridin-2-yl)methoxy)benzofuran-3-carboxamide |
| cpd 066 | 2-methyl-N-(2-oxopyrrolidin-3-yl)-5-((6-(trifluoromethyl)pyridin-3-yl)methoxy)benzofuran-3-carboxamide |
| cpd 067 | 5-((2-chloropyridin-3-yl)methoxy)-N-(3,3-difluoropiperidin-4-yl)-2-methylbenzofuran-3-carboxamide |
| cpd 068 | 5-((4-chloropyridin-3-yl)methoxy)-N-(3,3-difluoropiperidin-4-yl)-2-methylbenzofuran-3-carboxamide |
| cpd 069 | 2-methyl-N-(1-methylpiperidin-4-yl)-5-((5-(trifluoromethyl)furan-2-yl)methoxy)benzofuran-3-carboxamide |
| cpd 070 | N-(3,3-difluoropiperidin-4-yl)-5-(imidazo[1,2-a]pyridin-6-ylmethoxy)-2-methylbenzofuran-3-carboxamide |
| cpd 071 | N-(3,3-difluoropiperidin-4-yl)-5-((6-(dimethylamino)pyridin-2-yl)methoxy)-2-methylbenzofuran-3-carboxamide |
| cpd 072 | N-(4-(hydroxymethyl)tetrahydro-2H-pyran-4-yl)-2-methyl-5-((2-(trifluoromethyl)pyridin-3-yl)-methoxy)benzofuran-3-carboxamide |
| cpd 073 | tert-butyl (S)-3-(2-methyl-5-((5-methylpyridin-3-yl)methoxy)benzofuran-3-carboxamido)pyrrolidine-1-carboxylate |
| cpd 074 | N-(3,3-difluoropiperidin-4-yl)-2-methyl-5-((2-(trifluoromethyl)pyridin-3-yl)methoxy)benzofuran-3-carboxamide |
| cpd 075 | N-(3,3-difluoropiperidin-4-yl)-2-methyl-5-((5-(trifluoromethyl)pyridin-3-yl)methoxy)benzofuran-3-carboxamide |
| cpd 076 | N-(3,3-difluoropiperidin-4-yl)-2-methyl-5-((3-(trifluoromethyl)pyridin-2-yl)methoxy)benzofuran-3-carboxamide |
| cpd 077 | tert-butyl (S)-3-(2-methyl-5-((5-(trifluoromethyl)pyridin-3-yl)methoxy)benzofuran-3-carboxamido)pyrrolidine-1-carboxylate |
| cpd 078 | tert-butyl 4-(5-((6-(dimethylamino)pyridin-2-yl)methoxy)-2-methylbenzofuran-3-carboxamido)-3,3-difluoropiperidine-1-carboxylate |
| cpd 079 | tert-butyl 3-(((3-(ethoxycarbonyl)-2-methylbenzofuran-5-yl)oxy)methyl)pyrrolidine-1-carboxylate |
| cpd 080 | tert-butyl (R)-3-(2-methyl-5-(oxazol-5-ylmethoxy)benzofuran-3-carboxamido)pyrrolidine-1-carboxylate |
| cpd 081 | tert-butyl (R)-3-(2-methyl-5-(pyridin-4-ylmethoxy)benzofuran-3-carboxamido)pyrrolidine-1-carboxylate |
| cpd 082 | tert-butyl (R)-3-(2-methyl-5-(pyridin-3-ylmethoxy)benzofuran-3-carboxamido)pyrrolidine-1-carboxylate |
| cpd 083 | tert-butyl (R)-3-(2-methyl-5-((1-methyl-1H-pyrazol-3-yl)methoxy)benzofuran-3-carboxamido)-pyrrolidine-1-carboxylate |
| cpd 084 | tert-butyl (R)-3-(2-methyl-5-(thiazol-5-ylmethoxy)benzofuran-3-carboxamido)pyrrolidine-1-carboxylate |
| cpd 085 | tert-butyl (R)-3-(2-methyl-5-(thiazol-2-ylmethoxy)benzofuran-3-carboxamido)pyrrolidine-1-carboxylate |
| cpd 086 | tert-butyl (R)-3-(2-methyl-5-((6-methylpyridin-2-yl)methoxy)benzofuran-3-carboxamido)-pyrrolidine-1-carboxylate |
| cpd 087 | tert-butyl 3,3-difluoro-4-(2-methyl-5-(thiazol-2-ylmethoxy)benzofuran-3-carboxamido)piperidine-1-carboxylate |
| cpd 088 | tert-butyl 3,3-difluoro-4-(2-methyl-5-((3-methylpyridin-2-yl)methoxy)benzofuran-3-carboxamido)piperidine-1-carboxylate |

-continued

| | |
|---|---|
| cpd 089 | tert-butyl 3,3-difluoro-4-(5-((2-methoxypyridin-3-yl)methoxy)-2-methylbenzofuran-3-carboxamido)piperidine-1-carboxylate |
| cpd 090 | tert-butyl 3,3-difluoro-4-(2-methyl-5-((4-methylthiazol-5-yl)methoxy)benzofuran-3-carboxamido)piperidine-1-carboxylate |
| cpd 091 | tert-butyl 3,3-difluoro-4-(5-((6-methoxypyridin-2-yl)methoxy)-2-methylbenzofuran-3-carboxamido)piperidine-1-carboxylate |
| cpd 092 | tert-butyl 4-(5-((2-chloropyridin-3-yl)methoxy)-2-methylbenzofuran-3-carboxamido)-3,3-difluoro-piperidine-1-carboxylate |
| cpd 093 | tert-butyl 4-(5-((4-chloropyridin-3-yl)methoxy)-2-methylbenzofuran-3-carboxamido)-3,3-difluoro-piperidine-1-carboxylate |
| cpd 094 | tert-butyl 3,3-difluoro-4-(5-(imidazo[1,2-a]pyridin-6-ylmethoxy)-2-methylbenzofuran-3-carboxamido)piperidine-1-carboxylate |
| cpd 095 | tert-butyl 3,3-difluoro-4-(2-methyl-5-((5-(trifluoromethyl)pyridin-3-yl)methoxy)benzofuran-3-carboxamido)piperidine-1-carboxylate |
| cpd 096 | tert-butyl 3,3-difluoro-4-(2-methyl-5-((3-(trifluoromethyl)pyridin-2-yl)methoxy)benzofuran-3-carboxamido)piperidine-1-carboxylate |
| cpd 097 | tert-butyl 3,3-difluoro-4-(2-methyl-5-(pyridin-2-ylmethoxy)benzofuran-3-carboxamido)piperidine-1-carboxylate |
| cpd 098 | tert-butyl 3,3-difluoro-4-(2-methyl-5-((2-(trifluoromethyl)pyridin-3-yl)methoxy)benzofuran-3-carboxamido)piperidine-1-carboxylate |
| cpd 099 | 2-methyl-5-((4-methylpyridin-3-yl)methoxy)benzofuran-3-carboxylic acid |
| cpd 100 | 5-((2-methoxypyridin-3-yl)methoxy)-2-methylbenzofuran-3-carboxylic acid |
| cpd 101 | 2-methyl-5-((2-(trifluoromethyl)pyridin-3-yl)methoxy)benzofuran-3-carboxylic acid |
| cpd 102 | 2-methyl-5-((4-methylthiazol-5-yl)methoxy)benzofuran-3-carboxylic acid |
| cpd 103 | N-(4,4-difluoropiperidin-3-yl)-2-methyl-5-((4-methylthiazol-5-yl)methoxy)benzofuran-3-carboxamide |
| cpd 104 | N-(1-hydroxy-2-methylpropan-2-yl)-2-methyl-5-((4-methylthiazol-5-yl)methoxy)benzofuran-3-carboxamide |
| cpd 105 | N-(4,4-difluoropyrrolidin-3-yl)-2-methyl-5-((2-(trifluoromethyl)pyridin-3-yl)methoxy)benzofuran-3-carboxamide |
| cpd 106 | N-(4,4-difluoropyrrolidin-3-yl)-2-methyl-5-((4-methylthiazol-5-yl)methoxy)benzofuran-3-carboxamide |
| cpd 107 | N-(1-(hydroxymethyl)cyclobutyl)-2-methyl-5-((4-methylthiazol-5-yl)methoxy)benzofuran-3-carboxamide |
| cpd 108 | N-(1-((dimethylamino)methyl)cyclobutyl)-2-methyl-5-((4-methylthiazol-5-yl)methoxy)benzofuran-3-carboxamide |
| cpd 109 | N-(1-hydroxy-2-methylpropan-2-yl)-2-methyl-5-((2-(trifluoromethyl)pyridin-3-yl)methoxy)benzofuran-3-carboxamide |
| cpd 110 | N-(3,3-difluoro-1-methylpiperidin-4-yl)-2-methyl-5-((4-methylthiazol-5-yl)methoxy)benzofuran-3-carboxamide |
| cpd 111 | N-(4,4-difluoropiperidin-3-yl)-2-methyl-5-((2-(trifluoromethyl)pyridin-3-yl)methoxy)benzofuran-3-carboxamide |
| cpd 112 | N-(3,3-difluoropiperidin-4-yl)-4-fluoro-2-methyl-5-((2-(trifluoromethyl)pyridin-3-yl)methoxy)-benzofuran-3-carboxamide |
| cpd 113 | N-(3,3-difluoropiperidin-4-yl)-6-fluoro-2-methyl-5-((2-(trifluoromethyl)pyridin-3-yl)methoxy)-benzofuran-3-carboxamide |
| cpd 114 | N-(1-(2-hydroxyethyl)cyclobutyl)-2-methyl-5-((4-methylthiazol-5-yl)methoxy)benzofuran-3-carboxamide |
| cpd 115 | N-(5,5-difluoropiperidin-3-yl)-2-methyl-5-((4-methylthiazol-5-yl)methoxy)benzofuran-3-carboxamide |
| cpd 116 | 2-methyl-5-((4-methylthiazol-5-yl)methoxy)-N-(1-(2,2,2-trifluoroethyl)pyrrolidin-3-yl)benzofuran-3-carboxamide |
| cpd 117 | N-(1-(hydroxymethyl)cyclobutyl)-2-methyl-5-((2-(trifluoromethyl)pyridin-3-yl)methoxy)benzofuran-3-carboxamide |
| cpd 118 | N-(4,4-difluoro-1-methylpiperidin-3-yl)-2-methyl-5-((4-methylthiazol-5-yl)methoxy)benzofuran-3-carboxamide |
| cpd 119 | N-(3-carbamoyloxetan-3-yl)-2-methyl-5-((4-methylthiazol-5-yl)methoxy)benzofuran-3-carboxamide |
| cpd 120 | N-(1-(2-hydroxyethyl)-2-oxopyrrolidin-3-yl)-2-methyl-5-((2-(trifluoromethyl)pyridin-3-yl)-methoxy)benzofuran-3-carboxamide |
| cpd 121 | N-(3-(2-hydroxyethyl)tetrahydrofuran-3-yl)-2-methyl-5-((4-methylthiazol-5-yl)methoxy)benzofuran-3-carboxamide |
| cpd 122 | 7-fluoro-N-(4-(hydroxymethyl)tetrahydro-2H-pyran-4-yl)-2-methyl-5-((4-methylthiazol-5-yl)-methoxy)benzofuran-3-carboxamide |
| cpd 123 | N-(4,4-difluoro-1-methylpyrrolidin-3-yl)-2-methyl-5-((4-methylthiazol-5-yl)methoxy)benzofuran-3-carboxamide |
| cpd 124 | N-(4,4-difluoro-1-methylpyrrolidin-3-yl)-2-methyl-5-((2-(trifluoromethyl)pyridin-3-yl)methoxy)-benzofuran-3-carboxamide |
| cpd 125 | N-(5,5-difluoropiperidin-3-yl)-2-methyl-5-((2-(trifluoromethyl)pyridin-3-yl)methoxy)benzofuran-3-carboxamide |
| cpd 126 | N-(3-(2-hydroxyethyl)tetrahydrofuran-3-yl)-2-methyl-5-((2-(trifluoromethyl)pyridin-3-yl)-methoxy)benzofuran-3-carboxamide |
| cpd 127 | N-(1-(2-hydroxyethyl)cyclobutyl)-2-methyl-5-((2-(trifluoromethyl)pyridin-3-yl)methoxy)-benzofuran-3-carboxamide |
| cpd 128 | N-(3-(2-hydroxyethyl)oxetan-3-yl)-2-methyl-5-((4-methylthiazol-5-yl)methoxy)benzofuran-3-carboxamide |
| cpd 129 | N-(3-(2-hydroxyethyl)oxetan-3-yl)-2-methyl-5-((2-(trifluoromethyl)pyridin-3-yl)methoxy)-benzofuran-3-carboxamide |
| cpd 130 | N-(3,3-difluoro-1-methylpiperidin-4-yl)-2-methyl-5-((2-(trifluoromethyl)pyridin-3-yl)methoxy)-benzofuran-3-carboxamide |

-continued

| | |
|---|---|
| cpd 131 | N-(4,4-difluoro-1-methylpiperidin-3-yl)-2-methyl-5-((2-(trifluoromethyl)pyridin-3-yl)methoxy)-benzofuran-3-carboxamide |
| cpd 132 | N-(3-(hydroxymethyl)tetrahydrofuran-3-yl)-2-methyl-5-((4-methylthiazol-5-yl)methoxy)-benzofuran-3-carboxamide |
| cpd 133 | N-(3-(hydroxymethyl)oxetan-3-yl)-2-methyl-5-((2-(trifluoromethyl)pyridin-3-yl)methoxy)-benzofuran-3-carboxamide |
| cpd 134 | N-(4,4-difluoro-1-(2-hydroxyethyl)pyrrolidin-3-yl)-2-methyl-5-((2-(trifluoromethyl)pyridin-3-yl)methoxy)benzofuran-3-carboxamide |
| cpd 135 | N-(3-(hydroxymethyl)tetrahydrofuran-3-yl)-2-methyl-5-((2-(trifluoromethyl)pyridin-3-yl)-methoxy)benzofuran-3-carboxamide |
| cpd 136 | N-(1-(aminomethyl)cyclobutyl)-2-methyl-5-((2-(trifluoromethyl)pyridin-3-yl)methoxy)-benzofuran-3-carboxamide |
| cpd 137 | N-(1-(aminomethyl)cyclobutyl)-2-methyl-5-((4-methylthiazol-5-yl)methoxy)benzofuran-3-carboxamide |
| cpd 138 | 2-methyl-N-(1H-pyrazol-3-yl)-5-((2-(trifluoromethyl)pyridin-3-yl)methoxy)benzofuran-3-carboxamide |
| cpd 139 | N-(1-(hydroxymethyl)cyclopropyl)-2-methyl-5-((4-methylthiazol-5-yl)methoxy)benzofuran-3-carboxamide |
| cpd 140 | N-(1-((dimethylamino)methyl)cyclobutyl)-2-methyl-5-((2-(trifluoromethyl)pyridin-3-yl)methoxy)-benzofuran-3-carboxamide |
| cpd 141 | N-(5,5-difluoro-1-methylpiperidin-3-yl)-2-methyl-5-((2-(trifluoromethyl)pyridin-3-yl)methoxy)-benzofuran-3-carboxamide |
| cpd 142 | N-(3-(hydroxymethyl)oxetan-3-yl)-2-methyl-5-((4-methylthiazol-5-yl)methoxy)benzofuran-3-carboxamide |
| cpd 143 | 2-methyl-N-(1-methyl-1H-pyrazol-4-yl)-5-((2-(trifluoromethyl)pyridin-3-yl)methoxy)benzofuran-3-carboxamide |
| cpd 144 | 2-methyl-5-((4-methylthiazol-5-yl)methoxy)-N-(1H-pyrazol-3-yl)benzofuran-3-carboxamide |
| cpd 145 | 2-methyl-5-((4-methylthiazol-5-yl)methoxy)-N-(1-(((2,2,2-trifluoroethyl)amino)methyl)cyclo-butyl)benzofuran-3-carboxamide |
| cpd 146 | 2-methyl-N-(1-methyl-1H-pyrazol-3-yl)-5-((2-(trifluoromethyl)pyridin-3-yl)methoxy)benzofuran-3-carboxamide |
| cpd 147 | N-(4-hydroxytetrahydrofuran-3-yl)-2-methyl-5-((2-(trifluoromethyl)pyridin-3-yl)methoxy)-benzofuran-3-carboxamide |
| cpd 148 | 2-methyl-N-(tetrahydrofuran-3-yl)-5-((2-(trifluoromethyl)pyridin-3-yl)methoxy)benzofuran-3-carboxamide |
| cpd 149 | 2-methyl-N-(1-(2,2,2-trifluoroethyl)pyrrolidin-3-yl)-5-((2-(trifluoromethyl)pyridin-3-yl)-methoxy)benzofuran-3-carboxamide |
| cpd 150 | 2-methyl-5-((4-methylthiazol-5-yl)methoxy)-N-(1H-pyrazol-4-yl)benzofuran-3-carboxamide |
| cpd 151 | N-(4,4-difluoro-1-(2-hydroxyethyl)pyrrolidin-3-yl)-2-methyl-5-((4-methylthiazol-5-yl)methoxy)-benzofuran-3-carboxamide |
| cpd 152 | 2-methyl-N-(1-methyl-1H-pyrazol-4-yl)-5-((4-methylthiazol-5-yl)methoxy)benzofuran-3-carboxamide |
| cpd 153 | 2-methyl-N-(1-(((2,2,2-trifluoroethyl)amino)methyl)cyclobutyl)-5-((2-(trifluoromethyl)pyridin-3-yl)methoxy)benzofuran-3-carboxamide |
| cpd 154 | 2-methyl-N-(1-methyl-1H-pyrazol-5-yl)-5-((2-(trifluoromethyl)pyridin-3-yl)methoxy)benzofuran-3-carboxamide |
| cpd 155 | N-(4,4-difluoro-1-(2,2,2-trifluoroethyl)pyrrolidin-3-yl)-2-methyl-5-((4-methylthiazol-5-yl)-methoxy)benzofuran-3-carboxamide |
| cpd 156 | 2-methyl-5-((4-methylthiazol-5-yl)methoxy)-N-(2-oxaspiro[3.3]heptan-6-yl)benzofuran-3-carboxamide |
| cpd 157 | N-(4,4-difluoro-1-(2,2,2-trifluoroethyl)pyrrolidin-3-yl)-2-methyl-5-((2-(trifluoromethyl)pyridin-3-yl)methoxy)benzofuran-3-carboxamide |
| cpd 158 | 2-methyl-N-(1H-pyrazol-4-yl)-5-((2-(trifluoromethyl)pyridin-3-yl)methoxy)benzofuran-3-carboxamide |
| cpd 159 | 2-methyl-5-((4-methylthiazol-5-yl)methoxy)-N-(tetrahydrofuran-3-yl)benzofuran-3-carboxamide |
| cpd 160 | N-(1-(2-hydroxyethyl)-2-oxopyrrolidin-3-yl)-2-methyl-5-((4-methylthiazol-5-yl)methoxy)benzofuran-3-carboxamide |
| cpd 161 | 2-methyl-N-(1-methyl-1H-pyrazol-3-yl)-5-((4-methylthiazol-5-yl)methoxy)benzofuran-3-carboxamide |
| cpd 162 | N-(4-hydroxytetrahydrofuran-3-yl)-2-methyl-5-((4-methylthiazol-5-yl)methoxy)benzofuran-3-carboxamide |
| cpd 163 | N-(5,5-difluoro-1-methylpiperidin-3-yl)-2-methyl-5-((4-methylthiazol-5-yl)methoxy)benzofuran-3-carboxamide |
| cpd 164 | N-(1-(2-hydroxyethyl)-2-oxopyrrolidin-3-yl)-2-methyl-5-((2-methylpyridin-3-yl)methoxy)benzofuran-3-carboxamide |
| cpd 165 | 6-chloro-N-(3,3-difluoropiperidin-4-yl)-2-methyl-5-((2-(trifluoromethyl)pyridin-3-yl)methoxy)-benzofuran-3-carboxamide |
| cpd 166 | 2-methyl-5-((4-methylthiazol-5-yl)methoxy)-N-(1-(2,2,2-trifluoroethyl)piperidin-4-yl)benzofuran-3-carboxamide |
| cpd 167 | 2-methyl-N-(2-oxaspiro[3.3]heptan-6-yl)-5-((2-(trifluoromethyl)pyridin-3-yl)methoxy)benzofuran-3-carboxamide |
| cpd 168 | 2-methyl-N-(1-(2,2,2-trifluoroethyl)piperidin-4-yl)-5-((2-(trifluoromethyl)pyridin-3-yl)methoxy)-benzofuran-3-carboxamide |
| cpd 169 | N-(1-(2-methoxyethyl)-2-oxopyrrolidin-3-yl)-2-methyl-5-((4-methylthiazol-5-yl)methoxy)benzofuran-3-carboxamide |
| cpd 170 | (3-aminotetrahydrofuran-3-yl)methyl 2-methyl-5-((2-(trifluoromethyl)pyridin-3-yl)methoxy)-benzofuran-3-carboxylate |
| cpd 171 | 2-methyl-N-(1-methyl-1H-pyrazol-5-yl)-5-((4-methylthiazol-5-yl)methoxy)benzofuran-3-carboxamide |
| cpd 172 | 2,2,2-trifluoroethyl 3,3-difluoro-4-(2-methyl-5-((4-methylthiazol-5-yl)methoxy)benzofuran-3-carboxamido)pyrrolidine-1-carboxylate |
| cpd 173 | 2-methyl-N-(2-azaspiro[3.3]heptan-6-yl)-5-((2-(trifluoromethyl)pyridin-3-yl)methoxy)benzofuran-3-carboxamide |
| cpd 174 | 6-chloro-N-(4-(hydroxymethyl)tetrahydro-2H-pyran-4-yl)-2-methyl-5-((4-methylthiazol-5-yl)-methoxy)benzofuran-3-carboxamide |

-continued

| | |
|---|---|
| cpd 175 | 2,2,2-trifluoroethyl (R)-3,3-difluoro-4-(2-methyl-5-((2-(trifluoromethyl)pyridin-3-yl)methoxy)-benzofuran-3-carboxamido)pyrrolidine-1-carboxylate |
| cpd 176 | N-(3,3-difluoropiperidin-4-yl)-7-fluoro-2-methyl-5-((2-(trifluoromethyl)pyridin-3-yl)methoxy)-benzofuran-3-carboxamide |
| cpd 177 | 4-fluoro-N-(4-(hydroxymethyl)tetrahydro-2H-pyran-4-yl)-2-methyl-5-((4-methylthiazol-5-yl)-methoxy)benzofuran-3-carboxamide |
| cpd 178 | (3-amino-1H-pyrazol-1-yl)(2-methyl-5-((2-(trifluoromethyl)pyridin-3-yl)methoxy)benzofuran-3-yl)methanone |
| cpd 179 | N-(3,3-difluoropiperidin-4-yl)-2,6-dimethyl-5-((2-(trifluoromethyl)pyridin-3-yl)methoxy)benzofuran-3-carboxamide |
| cpd 180 | N-(1-(2-hydroxyethyl)-5-oxopyrrolidin-3-yl)-2-methyl-5-((4-methylthiazol-5-yl)methoxy)benzofuran-3-carboxamide |
| cpd 181 | (4-amino-1H-pyrazol-1-yl)(2-methyl-5-((2-(trifluoromethyl)pyridin-3-yl)methoxy)benzofuran-3-yl)methanone |
| cpd 182 | 6-fluoro-N-(4-(hydroxymethyl)tetrahydro-2H-pyran-4-yl)-2-methyl-5-((4-methylthiazol-5-yl)-methoxy)benzofuran-3-carboxamide |
| cpd 183 | N-(3,3-difluoropiperidin-4-yl)-2,7-dimethyl-5-((2-(trifluoromethyl)pyridin-3-yl)methoxy)-benzofuran-3-carboxamide |
| cpd 184 | 7-chloro-N-(3,3-difluoropiperidin-4-yl)-2-methyl-5-((2-(trifluoromethyl)pyridin-3-yl)methoxy)-benzofuran-3-carboxamide |
| cpd 185 | N-(4-(hydroxymethyl)tetrahydro-2H-pyran-4-yl)-2,6-dimethyl-5-((4-methylthiazol-5-yl)methoxy)-benzofuran-3-carboxamide |
| cpd 186 | N-(4-(hydroxymethyl)tetrahydro-2H-pyran-4-yl)-2,7-dimethyl-5-((4-methylthiazol-5-yl)methoxy)-benzofuran-3-carboxamide |
| cpd 187 | 7-chloro-N-(4-(hydroxymethyl)tetrahydro-2H-pyran-4-yl)-2-methyl-5-((4-methylthiazol-5-yl)-methoxy)benzofuran-3-carboxamide |
| cpd 188 | 7-cyano-N-(4-(hydroxymethyl)tetrahydro-2H-pyran-4-yl)-2-methyl-5-((4-methylthiazol-5-yl)-methoxy)benzofuran-3-carboxamide |
| cpd 189 | N-((3-aminooxetan-3-yl)methyl)-2-methyl-5-((2-(trifluoromethyl)pyridin-3-yl)methoxy)-benzofuran-3-carboxamide |
| cpd 190 | 2-methyl-5-((4-methylthiazol-5-yl)methoxy)-N-(2-azaspiro[3.3]heptan-6-yl)benzofuran-3-carboxamide |
| cpd 191 | 4-cyano-N-(3,3-difluoropiperidin-4-yl)-2-methyl-5-((2-(trifluoromethyl)pyridin-3-yl)methoxy)-benzofuran-3-carboxamide |
| cpd 192 | (3-amino-1H-pyrazol-1-yl)(2-methyl-5-((4-methylthiazol-5-yl)methoxy)benzofuran-3-yl)-methanone |
| cpd 193 | 4-cyano-N-(4-(hydroxymethyl)tetrahydro-2H-pyran-4-yl)-2-methyl-5-((4-methylthiazol-5-yl)-methoxy)benzofuran-3-carboxamide |
| cpd 194 | 6-cyano-N-(4-(hydroxymethyl)tetrahydro-2H-pyran-4-yl)-2-methyl-5-((4-methylthiazol-5-yl)-methoxy)benzofuran-3-carboxamide |
| cpd 195 | 6-cyano-N-(3,3-difluoropiperidin-4-yl)-2-methyl-5-((2-(trifluoromethyl)pyridin-3-yl)methoxy)-benzofuran-3-carboxamide |
| cpd 196 | 7-cyano-N-(3,3-difluoropiperidin-4-yl)-2-methyl-5-((2-(trifluoromethyl)pyridin-3-yl)methoxy)-benzofuran-3-carboxamide |
| cpd 197 | 2-(difluoromethyl)-N-(4-(hydroxymethyl)tetrahydro-2H-pyran-4-yl)-5-((4-methylthiazol-5-yl)-methoxy)benzofuran-3-carboxamide |
| cpd 198 | 2-(difluoromethyl)-N-(1-(2-hydroxyethyl)-2-oxopyrrolidin-3-yl)-5-((4-methylthiazol-5-yl)-methoxy)benzofuran-3-carboxamide |
| cpd 199 | 2-(difluoromethyl)-N-(3,3-difluoropiperidin-4-yl)-5-((2-(trifluoromethyl)pyridin-3-yl)methoxy)-benzofuran-3-carboxamide |
| cpd 200 | N-(1-(hydroxymethyl)cyclopropyl)-2-methyl-5-((2-(trifluoromethyl)pyridin-3-yl)methoxy)-benzofuran-3-carboxamide |
| cpd 201 | N-(3-(hydroxymethyl)azetidin-3-yl)-2-methyl-5-((4-methylthiazol-5-yl)methoxy)benzofuran-3-carboxamide |
| cpd 202 | N-(3-(hydroxymethyl)azetidin-3-yl)-2-methyl-5-((2-(trifluoromethyl)pyridin-3-yl)methoxy)-benzofuran-3-carboxamide |
| cpd 203 | N-(4,4-difluorotetrahydrofuran-3-yl)-2-methyl-5-((4-methylthiazol-5-yl)methoxy)benzofuran-3-carboxamide |
| cpd 204 | N-(4-(hydroxymethyl)tetrahydro-2H-pyran-4-yl)-2-methyl-5-((1-methyl-1H-imidazol-2-yl)-methoxy)benzofuran-3-carboxamide |
| cpd 205 | N-(3,3-difluoropiperidin-4-yl)-2-methyl-5-((1-methyl-1H-imidazol-2-yl)methoxy)benzofuran-3-carboxamide |
| cpd 206 | 5-((2-ethoxypyridin-3-yl)methoxy)-N-(4-(hydroxymethyl)tetrahydro-2H-pyran-4-yl)-2-methyl-benzofuran-3-carboxamide |
| cpd 207 | N-(3,3-difluoropiperidin-4-yl)-5-((2-ethoxypyridin-3-yl)methoxy)-2-methylbenzofuran-3-carboxamide |
| Cpd 208 | 2-methyl-5-((2-methylthiazol-5-yl)methoxy)benzofuran-3-carboxylic acid |
| Cpd 209 | 2-methyl-5-((2-(trifluoromethyl)thiazol-5-yl)methoxy)benzofuran-3-carboxylic acid |
| Cpd 210 | 2-methyl-5-((2-methyl-4-(trifluoromethyl)thiazol-5-yl)methoxy)benzofuran-3-carboxylic acid |
| Cpd 211 | 2-methyl-5-((2-methyloxazol-5-yl)methoxy)benzofuran-3-carboxylic acid |
| Cpd 212 | 2-methyl-5-((2-methylthiazol-4-yl)methoxy)benzofuran-3-carboxylic acid |
| Cpd 213 | 2-methyl-5-((3-(trifluoromethyl)-1H-pyrazol-4-yl)methoxy)benzofuran-3-carboxylic acid |
| Cpd 214 | 2-methyl-5-((4-methylpyridin-3-yl)methoxy)benzofuran-3-carboxylic acid |
| Cpd 215 | 2-methyl-5-((5-methylisoxazol-3-yl)methoxy)benzofuran-3-carboxylic acid |
| Cpd 216 | 2-methyl-5-((5-methylthiazol-4-yl)methoxy)benzofuran-3-carboxylic acid |
| Cpd 217 | 2-methyl-5-((6-methylpyridin-3-yl)methoxy)benzofuran-3-carboxylic acid |
| Cpd 218 | 2-methyl-5-(oxetan-3-ylmethoxy)benzofuran-3-carboxylic acid |
| Cpd 219 | 2-methyl-5-(pyrimidin-4-ylmethoxy)benzofuran-3-carboxylic acid |
| Cpd 220 | 5-((1-(2,2-difluoroethyl)-1H-pyrazol-5-yl)methoxy)-2-methylbenzofuran-3-carboxylic acid |
| Cpd 221 | 5-((2-(difluoromethoxy)pyridin-3-yl)methoxy)-2-methylbenzofuran-3-carboxylic acid |

| | -continued |
|---|---|
| Cpd 222 | 5-((2-(dimethylamino)pyridin-3-yl)methoxy)-2-methylbenzofuran-3-carboxylic acid |
| Cpd 223 | 5-((2,4-dimethylthiazol-5-yl)methoxy)-2-methylbenzofuran-3-carboxylic acid |
| Cpd 224 | 5-((2,5-dimethylthiazol-4-yl)methoxy)-2-methylbenzofuran-3-carboxylic acid |
| Cpd 225 | 5-((2-aminopyridin-3-yl)methoxy)-2-methylbenzofuran-3-carboxylic acid |
| Cpd 226 | 5-((3-(difluoromethyl)pyridin-2-yl)methoxy)-2-methylbenzofuran-3-carboxylic acid |
| Cpd 227 | 5-((6-methoxypyridin-3-yl)methoxy)-2-methylbenzofuran-3-carboxylic acid |
| Cpd 228 | 5-((4-fluoro-1-methyl-1H-pyrazol-5-yl)methoxy)-2-methylbenzofuran-3-carboxylic acid |
| Cpd 229 | 2-(difluoromethyl)-5-((4-methylthiazol-5-yl)methoxy)benzofuran-3-carboxylic acid |
| Cpd 230 | 2-(difluoromethyl)-5-((2-methoxypyridin-3-yl)methoxy)benzofuran-3-carboxylic acid |
| Cpd 231 | 2-cyclopropyl-5-((2-(trifluoromethyl)pyridin-3-yl)methoxy)benzofuran-3-carboxylic acid |
| Cpd 232 | 2-methyl-5-((4-methylthiazol-5-yl)methoxy)benzofuran-3-carboxamide |
| Cpd 233 | 4-fluoro-2-methyl-5-((4-methylthiazol-5-yl)methoxy)benzofuran-3-carboxylic acid |
| Cpd 234 | 4-fluoro-5-((2-methoxypyridin-3-yl)methoxy)-2-methylbenzofuran-3-carboxylic acid |
| Cpd 235 | 5-((1-(2,2-difluoroethyl)-1H-imidazol-2-yl)methoxy)-2-methylbenzofuran-3-carboxylic acid |
| Cpd 236 | 5-((2-(azetidin-1-yl)pyridin-3-yl)methoxy)-2-methylbenzofuran-3-carboxylic acid |
| Cpd 237 | 5-((2-(difluoromethyl)pyridin-3-yl)methoxy)-2-methylbenzofuran-3-carboxylic acid |
| Cpd 238 | 5-((2-cyanopyridin-3-yl)methoxy)-2-methylbenzofuran-3-carboxylic acid |
| Cpd 239 | 5-((2-ethoxypyridin-3-yl)methoxy)-2-methylbenzofuran-3-carboxylic acid |
| Cpd 240 | 5-((3-fluoropyridin-2-yl)methoxy)-2-methylbenzofuran-3-carboxylic acid |
| Cpd 241 | 5-((5-(2-hydroxyethoxy)pyridin-2-yl)methoxy)-2-methylbenzofuran-3-carboxylic acid |
| Cpd 242 | 5-((5-fluoropyridin-2-yl)methoxy)-2-methylbenzofuran-3-carboxylic acid |
| Cpd 243 | 6-fluoro-2-methyl-5-((4-methylthiazol-5-yl)methoxy)benzofuran-3-carboxylic acid |
| Cpd 244 | 6-fluoro-5-((2-methoxypyridin-3-yl)methoxy)-2-methylbenzofuran-3-carboxylic acid |
| Cpd 245 | 7-fluoro-2-methyl-5-((4-methylthiazol-5-yl)methoxy)benzofuran-3-carboxylic acid |
| Cpd 246 | 7-fluoro-5-((2-methoxypyridin-3-yl)methoxy)-2-methylbenzofuran-3-carboxylic acid |
| Cpd 247 | 2-methyl-5-((2-methylpyridin-3-yl)methoxy)benzofuran-3-carboxylic acid |
| Cpd 248 | 2-methyl-5-(1-(2-(trifluoromethyl)thiazol-5-yl)ethoxy)benzofuran-3-carboxylic acid |
| Cpd 249 | 2-methyl-5-((1-methyl-1H-imidazol-2-yl)methoxy)benzofuran-3-carboxylic acid |
| Cpd 250 | 2-methyl-5-((1-methyl-2-oxo-1,2-dihydropyridin-3-yl)methoxy)benzofuran-3-carboxylic acid |
| Cpd 251 | 2,4-dimethyl-5-((2-(trifluoromethyl)pyridin-3-yl)methoxy)benzofuran-3-carboxylic acid |
| Cpd 252 | 2-methyl-5-(((2-(trifluoromethyl)pyridin-3-yl)oxy)methyl)benzofuran-3-carboxylic acid |
| Cpd 253 | 2-methyl-5-((1-methyl-1H-1,2,3-triazol-4-yl)methoxy)benzofuran-3-carboxylic acid |
| Cpd 254 | 2-methyl-5-((1-methyl-1H-1,2,3-triazol-5-yl)methoxy)benzofuran-3-carboxylic acid |
| Cpd 255 | 2-methyl-5-((1-methyl-1H-1,2,4-triazol-3-yl)methoxy)benzofuran-3-carboxylic acid |
| Cpd 256 | 2-methyl-5-((1-methyl-6-oxo-1,6-dihydropyridin-2-yl)methoxy)benzofuran-3-carboxylic acid |
| Cpd 257 | 2-methyl-5-((2-methylpyrimidin-4-yl)methoxy)benzofuran-3-carboxylic acid |
| Cpd 258 | 2-methyl-5-((3-methyloxetan-3-yl)methoxy)benzofuran-3-carboxylic acid |
| Cpd 259 | 2-methyl-5-((4-methyloxazol-2-yl)methoxy)benzofuran-3-carboxylic acid |
| Cpd 260 | 2-methyl-5-((4-methylthiazol-2-yl)methoxy)benzofuran-3-carboxylic acid |
| Cpd 261 | 2-methyl-5-((5-methylpyrazin-2-yl)methoxy)benzofuran-3-carboxylic acid |
| Cpd 262 | 2-methyl-5-((5-methylthiazol-2-yl)methoxy)benzofuran-3-carboxylic acid |
| Cpd 263 | 2-methyl-5-((6-methylpyridazin-3-yl)methoxy)benzofuran-3-carboxylic acid |
| Cpd 264 | 2-methyl-5-(pyrimidin-2-ylmethoxy)benzofuran-3-carboxylic acid |
| Cpd 265 | 2-cyclopropyl-5-((4-methylthiazol-5-yl)methoxy)benzofuran-3-carboxylic acid |
| Cpd 266 | 5-((6-methoxypyridin-2-yl)methoxy)-2-methylbenzofuran-3-carboxylic acid |
| Cpd 267 | 5-(imidazo[1,2-a]pyridin-6-ylmethoxy)-2-methylbenzofuran-3-carboxylic acid |
| Cpd 268 | 2-methyl-5-(1-(4-methylthiazol-5-yl)ethoxy)benzofuran-3-carboxylic acid |
| Cpd 269 | 5-((2-methoxypyridin-4-yl)methoxy)-2-methylbenzofuran-3-carboxylic acid |
| Cpd 270 | (2-methyl-5-((4-methylthiazol-5-yl)methoxy)benzofuran-3-carbonyl)serine |
| Cpd 271 | (R)-N-(1-amino-1-oxopropan-2-yl)-2-methyl-5-((4-methylthiazol-5-yl)methoxy)benzofuran-3-carboxamide |
| Cpd 272 | (R)-N-(1-amino-3-(methylsulfonyl)-1-oxopropan-2-yl)-2-methyl-5-((4-methylthiazol-5-yl)methoxy)benzofuran-3-carboxamide |
| Cpd 273 | (R)-N-(1-amino-3-methyl-1-oxobutan-2-yl)-2-methyl-5-((4-methylthiazol-5-yl)methoxy)benzofuran-3-carboxamide |
| Cpd 274 | (R)-N-(1-hydroxy-3-(methylsulfonyl)propan-2-yl)-2-methyl-5-((2-methylthiazol-5-yl)methoxy)benzofuran-3-carboxamide |
| Cpd 275 | (R)-N-(1-hydroxy-3-(methylsulfonyl)propan-2-yl)-2-methyl-5-((4-methylthiazol-5-yl)methoxy)benzofuran-3-carboxamide |
| Cpd 276 | (R)-N-(3-hydroxy-1-(methylamino)-1-oxopropan-2-yl)-2-methyl-5-((4-methylthiazol-5-yl)methoxy)benzofuran-3-carboxamide |
| Cpd 277 | (S)-N-(1-(3,3-difluoropyrrolidin-1-yl)-3-hydroxy-1-oxopropan-2-yl)-2-methyl-5-((2-methylthiazol-5-yl)methoxy)benzofuran-3-carboxamide |
| Cpd 278 | (S)-N-(1-(dimethylamino)-3-hydroxy-1-oxopropan-2-yl)-2-methyl-5-((2-methylthiazol-5-yl)methoxy)benzofuran-3-carboxamide |
| Cpd 279 | (S)-N-(1-amino-1-oxopropan-2-yl)-2-methyl-5-((4-methylthiazol-5-yl)methoxy)benzofuran-3-carboxamide |
| Cpd 280 | (S)-N-(1-amino-3-hydroxy-1-oxopropan-2-yl)-2-methyl-5-((2-(trifluoromethyl)pyridin-3-yl)methoxy)benzofuran-3-carboxamide |
| Cpd 281 | (S)-N-(1-amino-3-hydroxy-1-oxopropan-2-yl)-2-methyl-5-((2-(trifluoromethyl)thiazol-5-yl)methoxy)benzofuran-3-carboxamide |
| Cpd 282 | (S)-N-(1-amino-3-hydroxy-1-oxopropan-2-yl)-2-methyl-5-((2-methyl-4-(trifluoromethyl)thiazol-5-yl)methoxy)benzofuran-3-carboxamide |
| Cpd 283 | (S)-N-(1-amino-3-hydroxy-1-oxopropan-2-yl)-2-methyl-5-((2-methyloxazol-5-yl)methoxy)benzofuran-3-carboxamide |
| Cpd 284 | (S)-N-(1-amino-3-hydroxy-1-oxopropan-2-yl)-2-methyl-5-((2-methylpyridin-3-yl)methoxy)benzofuran-3-carboxamide |
| Cpd 285 | (S)-N-(1-amino-3-hydroxy-1-oxopropan-2-yl)-2-methyl-5-((2-methylthiazol-4-yl)methoxy)benzofuran-3-carboxamide |

-continued

| | |
|---|---|
| Cpd 286 | (S)-N-(1-amino-3-hydroxy-1-oxopropan-2-yl)-2-methyl-5-((3-(trifluoromethyl)-1H-pyrazol-4-yl)methoxy)benzofuran-3-carboxamide |
| Cpd 287 | (S)-N-(1-amino-3-hydroxy-1-oxopropan-2-yl)-2-methyl-5-((4-methylpyridin-3-yl)methoxy)benzofuran-3-carboxamide |
| Cpd 288 | (S)-N-(1-amino-3-hydroxy-1-oxopropan-2-yl)-2-methyl-5-((4-methylthiazol-5-yl)methoxy)benzofuran-3-carboxamide |
| Cpd 289 | (S)-N-(1-amino-3-hydroxy-1-oxopropan-2-yl)-2-methyl-5-((5-methylisoxazol-3-yl)methoxy)benzofuran-3-carboxamide |
| Cpd 290 | (S)-N-(1-amino-3-hydroxy-1-oxopropan-2-yl)-2-methyl-5-((5-methylthiazol-4-yl)methoxy)benzofuran-3-carboxamide |
| Cpd 291 | (S)-N-(1-amino-3-hydroxy-1-oxopropan-2-yl)-2-methyl-5-((6-methylpyridin-3-yl)methoxy)benzofuran-3-carboxamide |
| Cpd 292 | (S)-N-(1-amino-3-hydroxy-1-oxopropan-2-yl)-2-methyl-5-(oxetan-3-ylmethoxy)benzofuran-3-carboxamide |
| Cpd 293 | (S)-N-(1-amino-3-hydroxy-1-oxopropan-2-yl)-2-methyl-5-(pyridazin-3-ylmethoxy)benzofuran-3-carboxamide |
| Cpd 294 | (S)-N-(1-amino-3-hydroxy-1-oxopropan-2-yl)-2-methyl-5-(pyrimidin-4-ylmethoxy)benzofuran-3-carboxamide |
| Cpd 295 | (S)-N-(1-amino-3-hydroxy-1-oxopropan-2-yl)-5-((1-(2,2-difluoroethyl)-1H-pyrazol-5-yl)methoxy)-2-methylbenzofuran-3-carboxamide |
| Cpd 296 | (S)-N-(1-amino-3-hydroxy-1-oxopropan-2-yl)-5-((2-(difluoromethoxy)pyridin-3-yl)methoxy)-2-methylbenzofuran-3-carboxamide |
| Cpd 297 | (S)-N-(1-amino-3-hydroxy-1-oxopropan-2-yl)-5-((2-(dimethylamino)pyridin-3-yl)methoxy)-2-methylbenzofuran-3-carboxamide |
| Cpd 298 | (S)-N-(1-amino-3-hydroxy-1-oxopropan-2-yl)-5-((2,4-dimethylthiazol-5-yl)methoxy)-2-methylbenzofuran-3-carboxamide |
| Cpd 299 | (S)-N-(1-amino-3-hydroxy-1-oxopropan-2-yl)-5-((2,5-dimethylthiazol-4-yl)methoxy)-2-methylbenzofuran-3-carboxamide |
| Cpd 300 | (S)-N-(1-amino-3-hydroxy-1-oxopropan-2-yl)-5-((2-aminopyridin-3-yl)methoxy)-2-methylbenzofuran-3-carboxamide |
| Cpd 301 | (S)-N-(1-amino-3-hydroxy-1-oxopropan-2-yl)-5-((3-(difluoromethyl)pyridin-2-yl)methoxy)-2-methylbenzofuran-3-carboxamide |
| Cpd 302 | (S)-N-(1-amino-3-hydroxy-1-oxopropan-2-yl)-5-((4-fluoro-1-methyl-1H-pyrazol-5-yl)methoxy)-2-methylbenzofuran-3-carboxamide |
| Cpd 303 | (S)-N-(1-amino-3-methoxy-1-oxopropan-2-yl)-2-methyl-5-((2-methylthiazol-5-yl)methoxy)benzofuran-3-carboxamide |
| Cpd 304 | (S)-N-(1-amino-3-methyl-1-oxobutan-2-yl)-2-methyl-5-((4-methylthiazol-5-yl)methoxy)benzofuran-3-carboxamide |
| Cpd 305 | (S)-N-(3-hydroxy-1-(methylamino)-1-oxopropan-2-yl)-2-methyl-5-((2-methylthiazol-5-yl)methoxy)benzofuran-3-carboxamide |
| Cpd 306 | (S)-N-(3-hydroxy-1-(methylamino)-1-oxopropan-2-yl)-2-methyl-5-((4-methylthiazol-5-yl)methoxy)benzofuran-3-carboxamide |
| Cpd 307 | (S)-N-(3-hydroxy-1-oxo-1-(pyrrolidin-1-yl)propan-2-yl)-2-methyl-5-((2-methylthiazol-5-yl)methoxy)benzofuran-3-carboxamide |
| Cpd 308 | 2-(difluoromethyl)-N-(1-(hydroxymethyl)cyclopropyl)-5-((4-methylthiazol-5-yl)methoxy)benzofuran-3-carboxamide |
| Cpd 309 | 2-(difluoromethyl)-N-(3-(hydroxymethyl)oxetan-3-yl)-5-((4-methylthiazol-5-yl)methoxy)benzofuran-3-carboxamide |
| Cpd 310 | 2-(difluoromethyl)-N-(3,3-difluoropiperidin-4-yl)-5-((4-methylthiazol-5-yl)methoxy)benzofuran-3-carboxamide |
| Cpd 311 | 2-(difluoromethyl)-N-(4-(hydroxymethyl)tetrahydro-2H-pyran-4-yl)-5-((2-hydroxypyridin-3-yl)methoxy)benzofuran-3-carboxamide |
| Cpd 312 | 2-(difluoromethyl)-N-(4-(hydroxymethyl)tetrahydro-2H-pyran-4-yl)-5-((2-methoxypyridin-3-yl)methoxy)benzofuran-3-carboxamide |
| Cpd 313 | 2-cyclopropyl-N-(3,3-difluoropiperidin-4-yl)-5-((2-(trifluoromethyl)pyridin-3-yl)methoxy)benzofuran-3-carboxamide |
| Cpd 314 | 2-cyclopropyl-N-(4-(hydroxymethyl)tetrahydro-2H-pyran-4-yl)-5-((4-methylthiazol-5-yl)methoxy)benzofuran-3-carboxamide |
| Cpd 315 | 2-methyl-5-((4-methylthiazol-5-yl)methoxy)-N-(1-(oxazol-2-yl)ethyl)benzofuran-3-carboxamide |
| Cpd 316 | 2-methyl-5-((4-methylthiazol-5-yl)methoxy)-N-(1,1,1-trifluoro-3-hydroxypropan-2-yl)benzofuran-3-carboxamide |
| Cpd 317 | 2-methyl-5-((4-methylthiazol-5-yl)methoxy)-N-(5-oxo-1,4-oxazepan-6-yl)benzofuran-3-carboxamide |
| Cpd 318 | 2-methyl-N-(1-(methylcarbamoyl)cyclobutyl)-5-((2-methylthiazol-5-yl)methoxy)benzofuran-3-carboxamide |
| Cpd 319 | 2-methyl-N-(1-(methylcarbamoyl)cyclobutyl)-5-((4-methylthiazol-5-yl)methoxy)benzofuran-3-carboxamide |
| Cpd 320 | 2-methyl-N-(1-(methylcarbamoyl)cyclobutyl)-5-(pyridin-2-ylmethoxy)benzofuran-3-carboxamide |
| Cpd 321 | 2-methyl-N-(2-(methylamino)-2-oxoethyl)-5-((4-methylthiazol-5-yl)methoxy)benzofuran-3-carboxamide |
| Cpd 322 | 2-methyl-N-(2-(methylsulfonamido)ethyl)-5-((4-methylthiazol-5-yl)methoxy)benzofuran-3-carboxamide |
| Cpd 323 | 2-methyl-N-(2-(methylsulfonyl)ethyl)-5-((4-methylthiazol-5-yl)methoxy)benzofuran-3-carboxamide |
| Cpd 324 | 2-methyl-N-(3-(methylcarbamoyl)oxetan-3-yl)-5-((4-methylthiazol-5-yl)methoxy)benzofuran-3-carboxamide |
| Cpd 325 | 3-(((3-((4-(hydroxymethyl)tetrahydro-2H-pyran-4-yl)carbamoyl)-2-methylbenzofuran-5-yl)oxy)methyl)picolinamide |

| | -continued |
|---|---|
| Cpd 326 | 4-fluoro-N-(1-(2-hydroxyethyl)-2-oxopyrrolidin-3-yl)-2-methyl-5-((4-methylthiazol-5-yl)methoxy)benzofuran-3-carboxamide |
| Cpd 327 | 4-fluoro-N-(1-(hydroxymethyl)cyclopropyl)-2-methyl-5-((4-methylthiazol-5-yl)methoxy)benzofuran-3-carboxamide |
| Cpd 328 | 4-fluoro-N-(3-(hydroxymethyl)oxetan-3-yl)-2-methyl-5-((4-methylthiazol-5-yl)methoxy)benzofuran-3-carboxamide |
| Cpd 329 | 4-fluoro-N-(4-(hydroxymethyl)tetrahydro-2H-pyran-4-yl)-5-((2-hydroxypyridin-3-yl)methoxy)-2-methylbenzofuran-3-carboxamide |
| Cpd 330 | 4-fluoro-N-(4-(hydroxymethyl)tetrahydro-2H-pyran-4-yl)-5-((2-methoxypyridin-3-yl)methoxy)-2-methylbenzofuran-3-carboxamide |
| Cpd 331 | 5-((1-(2,2-difluoroethyl)-1H-imidazol-2-yl)methoxy)-N-(4-(hydroxymethyl)tetrahydro-2H-pyran-4-yl)-2-methylbenzofuran-3-carboxamide |
| Cpd 332 | 5-((1-(2,2-difluoroethyl)-1H-pyrazol-5-yl)methoxy)-N-(3-(hydroxymethyl)-2-oxopiperidin-3-yl)-2-methylbenzofuran-3-carboxamide |
| Cpd 333 | 5-((1-(2,2-difluoroethyl)-1H-pyrazol-5-yl)methoxy)-N-(3-(hydroxymethyl)-2-oxopyrrolidin-3-yl)-2-methylbenzofuran-3-carboxamide |
| Cpd 334 | 5-((1-(2,2-difluoroethyl)-1H-pyrazol-5-yl)methoxy)-N-(4-(hydroxymethyl)tetrahydro-2H-pyran-4-yl)-2-methylbenzofuran-3-carboxamide |
| Cpd 335 | 5-((2-(azetidin-1-yl)pyridin-3-yl)methoxy)-N-(1-(2-hydroxyethyl)-2-oxopyrrolidin-3-yl)-2-methylbenzofuran-3-carboxamide |
| Cpd 336 | 5-((2-(azetidin-1-yl)pyridin-3-yl)methoxy)-N-(3,3-difluoropiperidin-4-yl)-2-methylbenzofuran-3-carboxamide |
| Cpd 337 | 5-((2-(azetidin-1-yl)pyridin-3-yl)methoxy)-N-(4-(hydroxymethyl)tetrahydro-2H-pyran-4-yl)-2-methylbenzofuran-3-carboxamide |
| Cpd 338 | 5-((2-(difluoromethoxy)pyridin-3-yl)methoxy)-N-(3,3-difluoropiperidin-4-yl)-2-methylbenzofuran-3-carboxamide |
| Cpd 339 | 5-((2-(difluoromethoxy)pyridin-3-yl)methoxy)-N-(4-(hydroxymethyl)tetrahydro-2H-pyran-4-yl)-2-methylbenzofuran-3-carboxamide |
| Cpd 340 | 5-((2-(difluoromethyl)pyridin-3-yl)methoxy)-N-(1-(2-hydroxyethyl)-2-oxopyrrolidin-3-yl)-2-methylbenzofuran-3-carboxamide |
| Cpd 341 | 5-((2-(difluoromethyl)pyridin-3-yl)methoxy)-N-(3-(hydroxymethyl)oxetan-3-yl)-2-methylbenzofuran-3-carboxamide |
| Cpd 342 | 5-((2-(difluoromethyl)pyridin-3-yl)methoxy)-N-(3,3-difluoropiperidin-4-yl)-2-methylbenzofuran-3-carboxamide |
| Cpd 343 | 5-((2-(difluoromethyl)pyridin-3-yl)methoxy)-N-(4-(hydroxymethyl)tetrahydro-2H-pyran-4-yl)-2-methylbenzofuran-3-carboxamide |
| Cpd 344 | 5-((2-(dimethylamino)pyridin-3-yl)methoxy)-N-(4-(hydroxymethyl)tetrahydro-2H-pyran-4-yl)-2-methylbenzofuran-3-carboxamide |
| Cpd 345 | 5-((2,4-dimethylthiazol-5-yl)methoxy)-N-(4-(hydroxymethyl)tetrahydro-2H-pyran-4-yl)-2-methylbenzofuran-3-carboxamide |
| Cpd 346 | 5-((2-aminopyridin-3-yl)methoxy)-N-(4-(hydroxymethyl)tetrahydro-2H-pyran-4-yl)-2-methylbenzofuran-3-carboxamide |
| Cpd 347 | 5-((2-cyanopyridin-3-yl)methoxy)-N-(4-(hydroxymethyl)tetrahydro-2H-pyran-4-yl)-2-methylbenzofuran-3-carboxamide |
| Cpd 348 | 5-((2-ethoxypyridin-3-yl)methoxy)-N-(1-(2-hydroxyethyl)-2-oxopyrrolidin-3-yl)-2-methylbenzofuran-3-carboxamide |
| Cpd 349 | 5-((2-hydroxypyridin-3-yl)methoxy)-N-(cis-4-hydroxytetrahydrofuran-3-yl)-2-methylbenzofuran-3-carboxamide |
| Cpd 350 | 5-((2-hydroxypyridin-3-yl)methoxy)-N-(trans-4-hydroxytetrahydrofuran-3-yl)-2-methylbenzofuran-3-carboxamide |
| Cpd 351 | 5-((3-(difluoromethyl)pyridin-2-yl)methoxy)-N-(4-(hydroxymethyl)tetrahydro-2H-pyran-4-yl)-2-methylbenzofuran-3-carboxamide |
| Cpd 352 | 5-((3-fluoropyridin-2-yl)methoxy)-N-(4-(hydroxymethyl)tetrahydro-2H-pyran-4-yl)-2-methylbenzofuran-3-carboxamide |
| Cpd 355 | 5-((4-fluoro-1-methyl-1H-pyrazol-5-yl)methoxy)-N-(3-(hydroxymethyl)-2-oxopiperidin-3-yl)-2-methylbenzofuran-3-carboxamide |
| Cpd 356 | 5-((4-fluoro-1-methyl-1H-pyrazol-5-yl)methoxy)-N-(3-(hydroxymethyl)-2-oxopyrrolidin-3-yl)-2-methylbenzofuran-3-carboxamide |
| Cpd 357 | 5-((4-fluoro-1-methyl-1H-pyrazol-5-yl)methoxy)-N-(4-(hydroxymethyl)tetrahydro-2H-pyran-4-yl)-2-methylbenzofuran-3-carboxamide |
| Cpd 358 | 5-((5-(2-hydroxyethoxy)pyridin-2-yl)methoxy)-N-(4-(hydroxymethyl)tetrahydro-2H-pyran-4-yl)-2-methylbenzofuran-3-carboxamide |
| Cpd 359 | 5-((5-fluoropyridin-2-yl)methoxy)-N-(4-(hydroxymethyl)tetrahydro-2H-pyran-4-yl)-2-methylbenzofuran-3-carboxamide |
| Cpd 360 | 6-fluoro-N-(1-(2-hydroxyethyl)-2-oxopyrrolidin-3-yl)-2-methyl-5-((4-methylthiazol-5-yl)methoxy)benzofuran-3-carboxamide |
| Cpd 361 | 6-fluoro-N-(1-(hydroxymethyl)cyclopropyl)-2-methyl-5-((4-methylthiazol-5-yl)methoxy)benzofuran-3-carboxamide |
| Cpd 362 | 6-fluoro-N-(3-(hydroxymethyl)oxetan-3-yl)-2-methyl-5-((4-methylthiazol-5-yl)methoxy)benzofuran-3-carboxamide |
| Cpd 363 | 6-fluoro-N-(4-(hydroxymethyl)tetrahydro-2H-pyran-4-yl)-5-((2-hydroxypyridin-3-yl)methoxy)-2-methylbenzofuran-3-carboxamide |
| Cpd 364 | 6-fluoro-N-(4-(hydroxymethyl)tetrahydro-2H-pyran-4-yl)-5-((2-methoxypyridin-3-yl)methoxy)-2-methylbenzofuran-3-carboxamide |
| Cpd 365 | 7-fluoro-N-(1-(2-hydroxyethyl)-2-oxopyrrolidin-3-yl)-2-methyl-5-((4-methylthiazol-5-yl)methoxy)benzofuran-3-carboxamide |
| Cpd 366 | 7-fluoro-N-(1-(hydroxymethyl)cyclopropyl)-2-methyl-5-((4-methylthiazol-5-yl)methoxy)benzofuran-3-carboxamide |

| | -continued |
|---|---|
| Cpd 367 | 7-fluoro-N-(3-(hydroxymethyl)oxetan-3-yl)-2-methyl-5-((4-methylthiazol-5-yl)methoxy)benzofuran-3-carboxamide |
| Cpd 368 | 7-fluoro-N-(4-(hydroxymethyl)tetrahydro-2H-pyran-4-yl)-5-((2-hydroxypyridin-3-yl)methoxy)-2-methylbenzofuran-3-carboxamide |
| Cpd 369 | 7-fluoro-N-(4-(hydroxymethyl)tetrahydro-2H-pyran-4-yl)-5-((2-methoxypyridin-3-yl)methoxy)-2-methylbenzofuran-3-carboxamide |
| Cpd 370 | N-((1-cyanocyclopropyl)methyl)-2-methyl-5-((2-methylthiazol-5-yl)methoxy)benzofuran-3-carboxamide |
| Cpd 371 | N-((1-cyanocyclopropyl)methyl)-2-methyl-5-((4-methylthiazol-5-yl)methoxy)benzofuran-3-carboxamide |
| Cpd 372 | N-((1-fluorocyclopropyl)methyl)-2-methyl-5-((2-methylthiazol-5-yl)methoxy)benzofuran-3-carboxamide |
| Cpd 373 | N-((1-fluorocyclopropyl)methyl)-2-methyl-5-((4-methylthiazol-5-yl)methoxy)benzofuran-3-carboxamide |
| Cpd 374 | N-((1H-pyrazol-3-yl)methyl)-2-methyl-5-((4-methylthiazol-5-yl)methoxy)benzofuran-3-carboxamide |
| Cpd 375 | N-((2S,3R)-1-amino-3-hydroxy-1-oxobutan-2-yl)-2-methyl-5-((2-methyloxazol-5-yl)methoxy)benzofuran-3-carboxamide |
| Cpd 376 | N-((2S,3R)-1-amino-3-hydroxy-1-oxobutan-2-yl)-2-methyl-5-((2-methylpyridin-3-yl)methoxy)benzofuran-3-carboxamide |
| Cpd 377 | N-((2S,3R)-1-amino-3-hydroxy-1-oxobutan-2-yl)-2-methyl-5-((2-methylthiazol-5-yl)methoxy)benzofuran-3-carboxamide |
| Cpd 378 | N-((2S,3R)-1-amino-3-hydroxy-1-oxobutan-2-yl)-2-methyl-5-((4-methylthiazol-5-yl)methoxy)benzofuran-3-carboxamide |
| Cpd 379 | N-((2S,3R)-1-amino-3-hydroxy-1-oxobutan-2-yl)-2-methyl-5-((4-methylthiazol-5-yl)methoxy)benzofuran-3-carboxamide |
| Cpd 380 | N-((2S,3R)-1-amino-3-hydroxy-1-oxobutan-2-yl)-2-methyl-5-((6-methylpyridin-3-yl)methoxy)benzofuran-3-carboxamide |
| Cpd 381 | N-((2S,3R)-1-amino-3-hydroxy-1-oxobutan-2-yl)-5-((1-(2,2-difluoroethyl)-1H-pyrazol-5-yl)methoxy)-2-methylbenzofuran-3-carboxamide |
| Cpd 382 | N-((2S,3R)-1-amino-3-hydroxy-1-oxobutan-2-yl)-5-((2,4-dimethylthiazol-5-yl)methoxy)-2-methylbenzofuran-3-carboxamide |
| Cpd 383 | N-((2S,3R)-1-amino-3-hydroxy-1-oxobutan-2-yl)-5-((4-fluoro-1-methyl-1H-pyrazol-5-yl)methoxy)-2-methylbenzofuran-3-carboxamide |
| Cpd 384 | N-((3-fluorooxetan-3-yl)methyl)-2-methyl-5-((2-methylthiazol-5-yl)methoxy)benzofuran-3-carboxamide |
| Cpd 385 | N-((3-fluorooxetan-3-yl)methyl)-2-methyl-5-((4-methylthiazol-5-yl)methoxy)benzofuran-3-carboxamide |
| Cpd 386 | N-(cis-4-hydroxytetrahydrofuran-3-yl)-2-methyl-5-((2-methylthiazol-5-yl)methoxy)benzofuran-3-carboxamide |
| Cpd 387 | N-(cis-4-hydroxytetrahydrofuran-3-yl)-2-methyl-5-(pyridin-2-ylmethoxy)benzofuran-3-carboxamide |
| Cpd 388 | N-(trans-4-hydroxytetrahydrofuran-3-yl)-2-methyl-5-((2-methylthiazol-5-yl)methoxy)benzofuran-3-carboxamide |
| Cpd 389 | N-(trans-4-hydroxytetrahydrofuran-3-yl)-2-methyl-5-(pyridin-2-ylmethoxy)benzofuran-3-carboxamide |
| Cpd 390 | N-((3S,4R)-4-hydroxy-2-oxopyrrolidin-3-yl)-2-methyl-5-((2-(trifluoromethyl)pyridin-3-yl)methoxy)benzofuran-3-carboxamide |
| Cpd 391 | N-((3S,4R)-4-hydroxy-2-oxopyrrolidin-3-yl)-2-methyl-5-((2-methylthiazol-5-yl)methoxy)benzofuran-3-carboxamide |
| Cpd 392 | N-((3S,4R)-4-hydroxy-2-oxopyrrolidin-3-yl)-2-methyl-5-((4-methylthiazol-5-yl)methoxy)benzofuran-3-carboxamide |
| Cpd 393 | N-((4-fluorotetrahydro-2H-pyran-4-yl)methyl)-2-methyl-5-((2-methylthiazol-5-yl)methoxy)benzofuran-3-carboxamide |
| Cpd 394 | N-((4-fluorotetrahydro-2H-pyran-4-yl)methyl)-2-methyl-5-((4-methylthiazol-5-yl)methoxy)benzofuran-3-carboxamide |
| Cpd 395 | N-((S)-1-amino-3-hydroxy-1-oxopropan-2-yl)-2-methyl-5-(1-(2-methylthiazol-5-yl)ethoxy)benzofuran-3-carboxamide |
| Cpd 396 | N-(1-((2-hydroxyethyl)(methyl)amino)-1-oxopropan-2-yl)-2-methyl-5-((4-methylthiazol-5-yl)methoxy)benzofuran-3-carboxamide |
| Cpd 397 | N-(1-((2-hydroxyethyl)amino)-1-oxopropan-2-yl)-2-methyl-5-((4-methylthiazol-5-yl)methoxy)benzofuran-3-carboxamide |
| Cpd 398 | N-(1-((2-hydroxyethyl)amino)-2-methyl-1-oxopropan-2-yl)-2-methyl-5-((4-methylthiazol-5-yl)methoxy)benzofuran-3-carboxamide |
| Cpd 399 | N-(1-((difluoromethoxy)methyl)cyclopropyl)-2-methyl-5-((2-methylthiazol-5-yl)methoxy)benzofuran-3-carboxamide |
| Cpd 400 | N-(1-((difluoromethoxy)methyl)cyclopropyl)-2-methyl-5-((4-methylthiazol-5-yl)methoxy)benzofuran-3-carboxamide |
| Cpd 401 | N-(1-(1H-benzo[d]imidazol-2-yl)-2-hydroxyethyl)-2-methyl-5-((2-methylthiazol-5-yl)methoxy)benzofuran-3-carboxamide |
| Cpd 402 | N-(1-(2-(2-hydroxyethoxy)ethyl)-2-oxopyrrolidin-3-yl)-2-methyl-5-((4-methylthiazol-5-yl)methoxy)benzofuran-3-carboxamide |
| Cpd 403 | N-(1-(2-hydroxyethyl)-2-oxopyrrolidin-3-yl)-2-methyl-5-((1-methyl-1H-imidazol-2-yl)methoxy)benzofuran-3-carboxamide |
| Cpd 404 | N-(1-(2-hydroxyethyl)-2-oxopyrrolidin-3-yl)-2-methyl-5-((1-methyl-1H-pyrazol-5-yl)methoxy)benzofuran-3-carboxamide |
| Cpd 405 | N-(1-(2-hydroxyethyl)-2-oxopyrrolidin-3-yl)-2-methyl-5-((1-methyl-2-oxo-1,2-dihydropyridin-3-yl)methoxy)benzofuran-3-carboxamide |

| | |
|---|---|
| Cpd 406 | N-(1-(2-hydroxyethyl)-2-oxopyrrolidin-3-yl)-2-methyl-5-(pyridin-2-ylmethoxy)benzofuran-3-carboxamide |
| Cpd 407 | N-(1-(2-hydroxyethyl)-2-oxopyrrolidin-3-yl)-2-methyl-5-(thiazol-2-ylmethoxy)benzofuran-3-carboxamide |
| Cpd 408 | N-(1-(2-hydroxyethyl)-2-oxopyrrolidin-3-yl)-5-((2-hydroxypyridin-3-yl)methoxy)-2-methylbenzofuran-3-carboxamide |
| Cpd 409 | N-(1-(2-hydroxyethyl)-2-oxopyrrolidin-3-yl)-5-((2-methoxypyridin-3-yl)methoxy)-2-methylbenzofuran-3-carboxamide |
| Cpd 410 | N-(1-(2-hydroxyethyl)-3-methyl-2-oxopyrrolidin-3-yl)-2-methyl-5-((4-methylthiazol-5-yl)methoxy)benzofuran-3-carboxamide |
| Cpd 411 | N-(1-(dimethylamino)-3-hydroxy-1-oxopropan-2-yl)-2-methyl-5-((4-methylthiazol-5-yl)methoxy)benzofuran-3-carboxamide |
| Cpd 412 | N-(1-(dimethylamino)-3-hydroxypropan-2-yl)-2-methyl-5-((2-methylthiazol-5-yl)methoxy)benzofuran-3-carboxamide |
| Cpd 413 | N-(1-(dimethylamino)-3-hydroxypropan-2-yl)-2-methyl-5-((4-methylthiazol-5-yl)methoxy)benzofuran-3-carboxamide |
| Cpd 414 | N-(1-(hydroxymethyl)cyclobutyl)-2-methyl-5-((2-methylthiazol-5-yl)methoxy)benzofuran-3-carboxamide |
| Cpd 415 | N-(1-(hydroxymethyl)cyclobutyl)-2-methyl-5-(pyridin-2-ylmethoxy)benzofuran-3-carboxamide |
| Cpd 416 | N-(1-(hydroxymethyl)cyclobutyl)-5-((2-hydroxypyridin-3-yl)methoxy)-2-methylbenzofuran-3-carboxamide |
| Cpd 417 | N-(1-(hydroxymethyl)cyclobutyl)-5-((2-methoxypyridin-3-yl)methoxy)-2-methylbenzofuran-3-carboxamide |
| Cpd 418 | N-(1-(hydroxymethyl)cyclopropyl)-2-methyl-5-((2-methylthiazol-5-yl)methoxy)benzofuran-3-carboxamide |
| Cpd 419 | N-(1-(hydroxymethyl)cyclopropyl)-2-methyl-5-(pyridin-2-ylmethoxy)benzofuran-3-carboxamide |
| Cpd 420 | N-(1-(hydroxymethyl)cyclopropyl)-5-((2-hydroxypyridin-3-yl)methoxy)-2-methylbenzofuran-3-carboxamide |
| Cpd 421 | N-(1-(hydroxymethyl)cyclopropyl)-5-((2-methoxypyridin-3-yl)methoxy)-2-methylbenzofuran-3-carboxamide |
| Cpd 422 | N-(1,3-dihydroxy-2-methylpropan-2-yl)-2-methyl-5-((1-methyl-1H-imidazol-2-yl)methoxy)benzofuran-3-carboxamide |
| Cpd 423 | N-(1,3-dihydroxy-2-methylpropan-2-yl)-2-methyl-5-((1-methyl-1H-pyrazol-5-yl)methoxy)benzofuran-3-carboxamide |
| Cpd 424 | N-(1,3-dihydroxy-2-methylpropan-2-yl)-2-methyl-5-((2-(trifluoromethyl)pyridin-3-yl)methoxy)benzofuran-3-carboxamide |
| Cpd 425 | N-(1,3-dihydroxy-2-methylpropan-2-yl)-2-methyl-5-((2-methylthiazol-5-yl)methoxy)benzofuran-3-carboxamide |
| Cpd 426 | N-(1,3-dihydroxy-2-methylpropan-2-yl)-2-methyl-5-((4-methylthiazol-5-yl)methoxy)benzofuran-3-carboxamide |
| Cpd 427 | N-(1,3-dihydroxy-2-methylpropan-2-yl)-2-methyl-5-(pyridazin-3-ylmethoxy)benzofuran-3-carboxamide |
| Cpd 428 | N-(1,3-dihydroxy-2-methylpropan-2-yl)-2-methyl-5-(pyridin-2-ylmethoxy)benzofuran-3-carboxamide |
| Cpd 429 | N-(1,3-dihydroxy-2-methylpropan-2-yl)-2-methyl-5-(pyrimidin-4-ylmethoxy)benzofuran-3-carboxamide |
| Cpd 430 | N-(1,3-dihydroxy-2-methylpropan-2-yl)-5-((2-hydroxypyridin-3-yl)methoxy)-2-methylbenzofuran-3-carboxamide |
| Cpd 431 | N-(1,3-dihydroxy-2-methylpropan-2-yl)-5-((2-methoxypyridin-3-yl)methoxy)-2-methylbenzofuran-3-carboxamide |
| Cpd 432 | N-(1-amino-1-oxo-3-(1H-1,2,4-triazol-1-yl)propan-2-yl)-2-methyl-5-((2-methylthiazol-5-yl)methoxy)benzofuran-3-carboxamide |
| Cpd 433 | N-(1-amino-1-oxopropan-2-yl)-2-methyl-5-((1-methyl-1H-pyrazol-5-yl)methoxy)benzofuran-3-carboxamide |
| Cpd 434 | N-(1-amino-1-oxopropan-2-yl)-2-methyl-5-((2-methylthiazol-5-yl)methoxy)benzofuran-3-carboxamide |
| Cpd 435 | N-(1-amino-1-oxopropan-2-yl)-2-methyl-5-(pyridin-2-ylmethoxy)benzofuran-3-carboxamide |
| Cpd 436 | N-(1-amino-1-oxopropan-2-yl)-5-((2-hydroxypyridin-3-yl)methoxy)-2-methylbenzofuran-3-carboxamide |
| Cpd 437 | N-(1-amino-1-oxopropan-2-yl)-5-((2-methoxypyridin-3-yl)methoxy)-2-methylbenzofuran-3-carboxamide |
| Cpd 438 | N-(1-amino-2-methyl-1-oxopropan-2-yl)-2-methyl-5-((1-methyl-1H-pyrazol-5-yl)methoxy)benzofuran-3-carboxamide |
| Cpd 439 | N-(1-amino-2-methyl-1-oxopropan-2-yl)-2-methyl-5-((2-methylthiazol-5-yl)methoxy)benzofuran-3-carboxamide |
| Cpd 440 | N-(1-amino-2-methyl-1-oxopropan-2-yl)-2-methyl-5-((4-methylthiazol-5-yl)methoxy)benzofuran-3-carboxamide |
| Cpd 441 | N-(1-amino-2-methyl-1-oxopropan-2-yl)-2-methyl-5-(pyridazin-3-ylmethoxy)benzofuran-3-carboxamide |
| Cpd 442 | N-(1-amino-2-methyl-1-oxopropan-2-yl)-2-methyl-5-(pyridin-2-ylmethoxy)benzofuran-3-carboxamide |
| Cpd 443 | N-(1-amino-2-methyl-1-oxopropan-2-yl)-5-((2-hydroxypyridin-3-yl)methoxy)-2-methylbenzofuran-3-carboxamide |
| Cpd 444 | N-(1-amino-2-methyl-1-oxopropan-2-yl)-5-((2-methoxypyridin-3-yl)methoxy)-2-methylbenzofuran-3-carboxamide |
| Cpd 445 | N-(1-amino-3-(cyclopropyl(methyl)amino)-1-oxopropan-2-yl)-2-methyl-5-((2-methylthiazol-5-yl)methoxy)benzofuran-3-carboxamide |
| Cpd 446 | N-(1-amino-3-(cyclopropyl(methyl)amino)-1-oxopropan-2-yl)-2-methyl-5-((4-methylthiazol-5-yl)methoxy)benzofuran-3-carboxamide |

-continued

| | |
|---|---|
| Cpd 447 | N-(1-amino-3-(difluoromethoxy)-1-oxopropan-2-yl)-2-methyl-5-((2-methylthiazol-5-yl)methoxy)benzofuran-3-carboxamide |
| Cpd 448 | N-(1-amino-3-(difluoromethoxy)-1-oxopropan-2-yl)-2-methyl-5-((4-methylthiazol-5-yl)methoxy)benzofuran-3-carboxamide |
| Cpd 449 | N-(1-amino-3-(dimethylamino)-1-oxopropan-2-yl)-2-methyl-5-((2-methylthiazol-5-yl)methoxy)benzofuran-3-carboxamide |
| Cpd 450 | N-(1-amino-3-(dimethylamino)-1-oxopropan-2-yl)-2-methyl-5-((4-methylthiazol-5-yl)methoxy)benzofuran-3-carboxamide |
| Cpd 451 | N-(1-amino-3-hydroxy-1-oxopropan-2-yl)-2-methyl-5-((1-methyl-1H-imidazol-2-yl)methoxy)benzofuran-3-carboxamide |
| Cpd 452 | N-(1-amino-3-hydroxy-1-oxopropan-2-yl)-2-methyl-5-((1-methyl-1H-pyrazol-5-yl)methoxy)benzofuran-3-carboxamide |
| Cpd 453 | N-(1-amino-3-hydroxy-1-oxopropan-2-yl)-2-methyl-5-((2-methylthiazol-5-yl)methoxy)benzofuran-3-carboxamide |
| Cpd 454 | N-(1-amino-3-hydroxy-1-oxopropan-2-yl)-2-methyl-5-((4-methylthiazol-5-yl)methoxy)benzofuran-3-carboxamide |
| Cpd 455 | N-(1-amino-3-hydroxy-1-oxopropan-2-yl)-2-methyl-5-(pyridin-2-ylmethoxy)benzofuran-3-carboxamide |
| Cpd 456 | N-(1-amino-3-hydroxy-1-oxopropan-2-yl)-5-((1-(2,2-difluoroethyl)-1H-pyrazol-5-yl)methoxy)-2-methylbenzofuran-3-carboxamide |
| Cpd 457 | N-(1-amino-3-hydroxy-1-oxopropan-2-yl)-5-((2-(difluoromethyl)pyridin-3-yl)methoxy)-2-methylbenzofuran-3-carboxamide |
| Cpd 458 | N-(1-amino-3-hydroxy-1-oxopropan-2-yl)-5-((2,4-dimethylthiazol-5-yl)methoxy)-2-methylbenzofuran-3-carboxamide |
| Cpd 459 | N-(1-amino-3-hydroxy-1-oxopropan-2-yl)-5-((2-hydroxypyridin-3-yl)methoxy)-2-methylbenzofuran-3-carboxamide |
| Cpd 460 | N-(1-amino-3-hydroxy-1-oxopropan-2-yl)-5-((4-fluoro-1-methyl-1H-pyrazol-5-yl)methoxy)-2-methylbenzofuran-3-carboxamide |
| Cpd 461 | N-(1-amino-3-hydroxy-2-methyl-1-oxopropan-2-yl)-2-methyl-5-((2-methylpyridin-3-yl)methoxy)benzofuran-3-carboxamide |
| Cpd 462 | N-(1-amino-3-hydroxy-2-methyl-1-oxopropan-2-yl)-2-methyl-5-((2-methylthiazol-5-yl)methoxy)benzofuran-3-carboxamide |
| Cpd 463 | N-(1-amino-3-hydroxy-2-methyl-1-oxopropan-2-yl)-2-methyl-5-((4-methylthiazol-5-yl)methoxy)benzofuran-3-carboxamide |
| Cpd 464 | N-(1-amino-3-hydroxy-2-methyl-1-oxopropan-2-yl)-2-methyl-5-((6-methylpyridin-3-yl)methoxy)benzofuran-3-carboxamide |
| Cpd 465 | N-(1-amino-3-hydroxy-2-methyl-1-oxopropan-2-yl)-5-((1-(2,2-difluoroethyl)-1H-pyrazol-5-yl)methoxy)-2-methylbenzofuran-3-carboxamide |
| Cpd 466 | N-(1-amino-3-hydroxy-2-methyl-1-oxopropan-2-yl)-5-((4-fluoro-1-methyl-1H-pyrazol-5-yl)methoxy)-2-methylbenzofuran-3-carboxamide |
| Cpd 467 | N-(1-amino-3-methoxy-1-oxopropan-2-yl)-2-methyl-5-((4-methylthiazol-5-yl)methoxy)benzofuran-3-carboxamide |
| Cpd 468 | N-(1-amino-3-methoxy-2-methyl-1-oxopropan-2-yl)-2-methyl-5-((4-methylthiazol-5-yl)methoxy)benzofuran-3-carboxamide |
| Cpd 469 | N-(1-amino-4-hydroxy-1-oxobutan-2-yl)-2-methyl-5-((4-methylthiazol-5-yl)methoxy)benzofuran-3-carboxamide |
| Cpd 470 | N-(1-carbamoyl-3,3-difluorocyclobutyl)-2-methyl-5-((4-methylthiazol-5-yl)methoxy)benzofuran-3-carboxamide |
| Cpd 471 | N-(1-carbamoylcyclobutyl)-2-methyl-5-((2-methylthiazol-5-yl)methoxy)benzofuran-3-carboxamide |
| Cpd 472 | N-(1-carbamoylcyclobutyl)-2-methyl-5-(pyridin-2-ylmethoxy)benzofuran-3-carboxamide |
| Cpd 473 | N-(1-carbamoylcyclobutyl)-5-((2-hydroxypyridin-3-yl)methoxy)-2-methylbenzofuran-3-carboxamide |
| Cpd 474 | N-(1-carbamoylcyclobutyl)-5-((2-methoxypyridin-3-yl)methoxy)-2-methylbenzofuran-3-carboxamide |
| Cpd 475 | N-(1-carbamoylcyclopropyl)-2-methyl-5-((2-(trifluoromethyl)pyridin-3-yl)methoxy)benzofuran-3-carboxamide |
| Cpd 476 | N-(1-carbamoylcyclopropyl)-2-methyl-5-((2-methylthiazol-5-yl)methoxy)benzofuran-3-carboxamide |
| Cpd 477 | N-(1-carbamoylcyclopropyl)-2-methyl-5-((4-methylthiazol-5-yl)methoxy)benzofuran-3-carboxamide |
| Cpd 478 | N-(1-carbamoylcyclopropyl)-2-methyl-5-(pyridin-2-ylmethoxy)benzofuran-3-carboxamide |
| Cpd 479 | N-(1-carbamoylcyclopropyl)-5-((2-hydroxypyridin-3-yl)methoxy)-2-methylbenzofuran-3-carboxamide |
| Cpd 480 | N-(1-carbamoylcyclopropyl)-5-((2-methoxypyridin-3-yl)methoxy)-2-methylbenzofuran-3-carboxamide |
| Cpd 481 | N-(1-hydroxy-2-methylpropan-2-yl)-2-methyl-5-((1-methyl-1H-imidazol-2-yl)methoxy)benzofuran-3-carboxamide |
| Cpd 482 | N-(1-hydroxy-2-methylpropan-2-yl)-2-methyl-5-((1-methyl-1H-pyrazol-5-yl)methoxy)benzofuran-3-carboxamide |
| Cpd 483 | N-(1-hydroxy-2-methylpropan-2-yl)-2-methyl-5-((2-methylthiazol-5-yl)methoxy)benzofuran-3-carboxamide |
| Cpd 484 | N-(1-hydroxy-2-methylpropan-2-yl)-2-methyl-5-(pyridin-2-ylmethoxy)benzofuran-3-carboxamide |
| Cpd 485 | N-(1-hydroxy-2-methylpropan-2-yl)-5-((2-hydroxypyridin-3-yl)methoxy)-2-methylbenzofuran-3-carboxamide |
| Cpd 486 | N-(1-hydroxy-2-methylpropan-2-yl)-5-((2-methoxypyridin-3-yl)methoxy)-2-methylbenzofuran-3-carboxamide |
| Cpd 487 | N-(1-hydroxy-3-morpholinopropan-2-yl)-2-methyl-5-((2-methylthiazol-5-yl)methoxy)benzofuran-3-carboxamide |

| | |
|---|---|
| Cpd 488 | N-(1-hydroxy-3-morpholinopropan-2-yl)-2-methyl-5-((4-methylthiazol-5-yl)methoxy)benzofuran-3-carboxamide |
| Cpd 489 | N-(1-hydroxypropan-2-yl)-2-methyl-5-((2-(trifluoromethyl)pyridin-3-yl)methoxy)benzofuran-3-carboxamide |
| Cpd 490 | N-(1-hydroxypropan-2-yl)-2-methyl-5-((2-methylthiazol-5-yl)methoxy)benzofuran-3-carboxamide |
| Cpd 491 | N-(1-hydroxypropan-2-yl)-2-methyl-5-((4-methylthiazol-5-yl)methoxy)benzofuran-3-carboxamide |
| Cpd 492 | (S)-N-(1-hydroxypropan-2-yl)-2-methyl-5-(pyridin-2-ylmethoxy)benzofuran-3-carboxamide |
| Cpd 493 | (R)-N-(1-hydroxypropan-2-yl)-2-methyl-5-(pyridin-2-ylmethoxy)benzofuran-3-carboxamide |
| Cpd 494 | (S)-N-(1-hydroxypropan-2-yl)-5-((2-hydroxypyridin-3-yl)methoxy)-2-methylbenzofuran-3-carboxamide |
| Cpd 495 | (R)-N-(1-hydroxypropan-2-yl)-5-((2-hydroxypyridin-3-yl)methoxy)-2-methylbenzofuran-3-carboxamide |
| Cpd 496 | (S)-N-(1-hydroxypropan-2-yl)-5-((2-methoxypyridin-3-yl)methoxy)-2-methylbenzofuran-3-carboxamide |
| Cpd 497 | (R)-N-(1-hydroxypropan-2-yl)-5-((2-methoxypyridin-3-yl)methoxy)-2-methylbenzofuran-3-carboxamide |
| Cpd 498 | N-(2,2-difluoroethyl)-2-methyl-5-((4-methylthiazol-5-yl)methoxy)benzofuran-3-carboxamide |
| Cpd 499 | N-(2,2-difluoropropyl)-2-methyl-5-((2-methylthiazol-5-yl)methoxy)benzofuran-3-carboxamide |
| Cpd 500 | N-(2,2-difluoropropyl)-2-methyl-5-((4-methylthiazol-5-yl)methoxy)benzofuran-3-carboxamide |
| Cpd 501 | N-(2-acetamidoethyl)-2-methyl-5-((4-methylthiazol-5-yl)methoxy)benzofuran-3-carboxamide |
| Cpd 502 | N-(2-amino-1-cyano-2-oxoethyl)-2-methyl-5-((4-methylthiazol-5-yl)methoxy)benzofuran-3-carboxamide |
| Cpd 503 | N-(2-amino-2-oxoethyl)-2-methyl-5-((4-methylthiazol-5-yl)methoxy)benzofuran-3-carboxamide |
| Cpd 504 | N-(2-fluoro-2-methylpropyl)-2-methyl-5-((2-methylthiazol-5-yl)methoxy)benzofuran-3-carboxamide |
| Cpd 505 | N-(2-fluoro-2-methylpropyl)-2-methyl-5-((4-methylthiazol-5-yl)methoxy)benzofuran-3-carboxamide |
| Cpd 506 | N-(2-hydroxy-2-methylpropyl)-2-methyl-5-((4-methylthiazol-5-yl)methoxy)benzofuran-3-carboxamide |
| Cpd 507 | N-(3-(aminomethyl)oxetan-3-yl)-2-methyl-5-((4-methylthiazol-5-yl)methoxy)benzofuran-3-carboxamide |
| Cpd 508 | N-(3-(dimethylamino)oxetane-3-carbonyl)-2-methyl-5-((4-methylthiazol-5-yl)methoxy)benzofuran-3-carboxamide |
| Cpd 509 | N-(3-(dimethylcarbamoyl)oxetan-3-yl)-2-methyl-5-((4-methylthiazol-5-yl)methoxy)benzofuran-3-carboxamide |
| Cpd 510 | N-(3-(hydroxymethyl)-2-oxopiperidin-3-yl)-2-methyl-5-((2-(trifluoromethyl)pyridin-3-yl)methoxy)benzofuran-3-carboxamide |
| Cpd 511 | N-(3-(hydroxymethyl)-2-oxopiperidin-3-yl)-2-methyl-5-((2-methyloxazol-5-yl)methoxy)benzofuran-3-carboxamide |
| Cpd 512 | N-(3-(hydroxymethyl)-2-oxopiperidin-3-yl)-2-methyl-5-((2-methylpyridin-3-yl)methoxy)benzofuran-3-carboxamide |
| Cpd 513 | N-(3-(hydroxymethyl)-2-oxopiperidin-3-yl)-2-methyl-5-((4-methylthiazol-5-yl)methoxy)benzofuran-3-carboxamide |
| Cpd 514 | N-(3-(hydroxymethyl)-2-oxopiperidin-3-yl)-2-methyl-5-((6-methylpyridin-3-yl)methoxy)benzofuran-3-carboxamide |
| Cpd 515 | N-(3-(hydroxymethyl)-2-oxopyrrolidin-3-yl)-2-methyl-5-((2-methyloxazol-5-yl)methoxy)benzofuran-3-carboxamide |
| Cpd 516 | N-(3-(hydroxymethyl)-2-oxopyrrolidin-3-yl)-2-methyl-5-((2-methylpyridin-3-yl)methoxy)benzofuran-3-carboxamide |
| Cpd 517 | N-(3-(hydroxymethyl)-2-oxopyrrolidin-3-yl)-2-methyl-5-((2-methylthiazol-5-yl)methoxy)benzofuran-3-carboxamide |
| Cpd 518 | N-(3-(hydroxymethyl)-2-oxopyrrolidin-3-yl)-2-methyl-5-((4-methylthiazol-5-yl)methoxy)benzofuran-3-carboxamide |
| Cpd 519 | N-(3-(hydroxymethyl)-2-oxopyrrolidin-3-yl)-2-methyl-5-((6-methylpyridin-3-yl)methoxy)benzofuran-3-carboxamide |
| Cpd 520 | N-(3-(hydroxymethyl)-2-oxopyrrolidin-3-yl)-2-methyl-5-(pyridin-2-ylmethoxy)benzofuran-3-carboxamide |
| Cpd 521 | N-(3-(hydroxymethyl)-2-oxopyrrolidin-3-yl)-5-((2-hydroxypyridin-3-yl)methoxy)-2-methylbenzofuran-3-carboxamide |
| Cpd 522 | N-(3-(hydroxymethyl)-2-oxopyrrolidin-3-yl)-5-((2-methoxypyridin-3-yl)methoxy)-2-methylbenzofuran-3-carboxamide |
| Cpd 523 | N-(3-(hydroxymethyl)oxetan-3-yl)-2-methyl-5-((1-methyl-1H-imidazol-2-yl)methoxy)benzofuran-3-carboxamide |
| Cpd 524 | N-(3-(hydroxymethyl)oxetan-3-yl)-2-methyl-5-((1-methyl-1H-pyrazol-5-yl)methoxy)benzofuran-3-carboxamide |
| Cpd 525 | N-(3-(hydroxymethyl)oxetan-3-yl)-2-methyl-5-((2-methylthiazol-5-yl)methoxy)benzofuran-3-carboxamide |
| Cpd 526 | N-(3-(hydroxymethyl)oxetan-3-yl)-2-methyl-5-(pyridin-2-ylmethoxy)benzofuran-3-carboxamide |
| Cpd 527 | N-(3-(hydroxymethyl)oxetan-3-yl)-2-methyl-5-(thiazol-2-ylmethoxy)benzofuran-3-carboxamide |
| Cpd 528 | N-(3-(hydroxymethyl)oxetan-3-yl)-5-((2-methoxypyridin-3-yl)methoxy)-2-methylbenzofuran-3-carboxamide |
| Cpd 529 | N-(3-(hydroxymethyl)oxetan-3-yl)-N,2-dimethyl-5-((4-methylthiazol-5-yl)methoxy)benzofuran-3-carboxamide |
| Cpd 530 | N-(3-(hydroxymethyl)pyrrolidin-3-yl)-2-methyl-5-((2-methylthiazol-5-yl)methoxy)benzofuran-3-carboxamide |
| Cpd 531 | N-(3-(hydroxymethyl)tetrahydro-2H-pyran-3-yl)-2-methyl-5-((2-(trifluoromethyl)pyridin-3-yl)methoxy)benzofuran-3-carboxamide |
| Cpd 532 | N-(3-(hydroxymethyl)tetrahydro-2H-pyran-3-yl)-2-methyl-5-((4-methylthiazol-5-yl)methoxy)benzofuran-3-carboxamide |

-continued

| | |
|---|---|
| Cpd 533 | N-(3-(hydroxymethyl)tetrahydrofuran-3-yl)-2-methyl-5-((2-methylthiazol-5-yl)methoxy)benzofuran-3-carboxamide |
| Cpd 534 | N-(3-(hydroxymethyl)tetrahydrofuran-3-yl)-2-methyl-5-(pyridin-2-ylmethoxy)benzofuran-3-carboxamide |
| Cpd 535 | N-(3-(hydroxymethyl)tetrahydrofuran-3-yl)-5-((2-hydroxypyridin-3-yl)methoxy)-2-methylbenzofuran-3-carboxamide |
| Cpd 536 | N-(3-(hydroxymethyl)tetrahydrofuran-3-yl)-5-((2-methoxypyridin-3-yl)methoxy)-2-methylbenzofuran-3-carboxamide |
| Cpd 537 | N-(3,3-difluoro-1-(hydroxymethyl)cyclobutyl)-2-methyl-5-((4-methylthiazol-5-yl)methoxy)benzofuran-3-carboxamide |
| Cpd 538 | N-(3,3-difluoropiperidin-4-yl)-2,4-dimethyl-5-((2-(trifluoromethyl)pyridin-3-yl)methoxy)benzofuran-3-carboxamide |
| Cpd 539 | N-(3,3-difluoropiperidin-4-yl)-2-methyl-5-(((2-(trifluoromethyl)pyridin-3-yl)oxy)methyl)benzofuran-3-carboxamide |
| Cpd 540 | N-(3,3-difluoropiperidin-4-yl)-2-methyl-5-((1-methyl-1H-1,2,3-triazol-4-yl)methoxy)benzofuran-3-carboxamide |
| Cpd 541 | N-(3,3-difluoropiperidin-4-yl)-2-methyl-5-((1-methyl-1H-1,2,3-triazol-5-yl)methoxy)benzofuran-3-carboxamide |
| Cpd 542 | N-(3,3-difluoropiperidin-4-yl)-2-methyl-5-((1-methyl-1H-1,2,4-triazol-3-yl)methoxy)benzofuran-3-carboxamide |
| Cpd 543 | N-(3,3-difluoropiperidin-4-yl)-2-methyl-5-((1-methyl-1H-pyrazol-5-yl)methoxy)benzofuran-3-carboxamide |
| Cpd 544 | N-(3,3-difluoropiperidin-4-yl)-2-methyl-5-((1-methyl-2-oxo-1,2-dihydropyridin-3-yl)methoxy)benzofuran-3-carboxamide |
| Cpd 545 | N-(3,3-difluoropiperidin-4-yl)-2-methyl-5-((1-methyl-6-oxo-1,6-dihydropyridin-2-yl)methoxy)benzofuran-3-carboxamide |
| Cpd 546 | N-(3,3-difluoropiperidin-4-yl)-2-methyl-5-((2-(trifluoromethyl)pyridin-3-yl)methoxy)benzofuran-3-carboxamide |
| Cpd 547 | N-(3,3-difluoropiperidin-4-yl)-2-methyl-5-((2-methylpyridin-3-yl)methoxy)benzofuran-3-carboxamide |
| Cpd 548 | N-(3,3-difluoropiperidin-4-yl)-2-methyl-5-((2-methylpyrimidin-4-yl)methoxy)benzofuran-3-carboxamide |
| Cpd 549 | N-(3,3-difluoropiperidin-4-yl)-2-methyl-5-((2-methylthiazol-5-yl)methoxy)benzofuran-3-carboxamide |
| Cpd 550 | N-(3,3-difluoropiperidin-4-yl)-2-methyl-5-((3-methyloxetan-3-yl)methoxy)benzofuran-3-carboxamide |
| Cpd 551 | N-(3,3-difluoropiperidin-4-yl)-2-methyl-5-((4-methyloxazol-2-yl)methoxy)benzofuran-3-carboxamide |
| Cpd 552 | N-(3,3-difluoropiperidin-4-yl)-2-methyl-5-((4-methylthiazol-2-yl)methoxy)benzofuran-3-carboxamide |
| Cpd 553 | N-(3,3-difluoropiperidin-4-yl)-2-methyl-5-((5-methylisoxazol-3-yl)methoxy)benzofuran-3-carboxamide |
| Cpd 554 | N-(3,3-difluoropiperidin-4-yl)-2-methyl-5-((5-methylpyrazin-2-yl)methoxy)benzofuran-3-carboxamide |
| Cpd 555 | N-(3,3-difluoropiperidin-4-yl)-2-methyl-5-((5-methylthiazol-2-yl)methoxy)benzofuran-3-carboxamide |
| Cpd 556 | N-(3,3-difluoropiperidin-4-yl)-2-methyl-5-((6-methylpyridazin-3-yl)methoxy)benzofuran-3-carboxamide |
| Cpd 557 | N-(3,3-difluoropiperidin-4-yl)-2-methyl-5-(pyridazin-3-ylmethoxy)benzofuran-3-carboxamide |
| Cpd 558 | N-(3,3-difluoropiperidin-4-yl)-2-methyl-5-(pyridin-3-ylmethoxy)benzofuran-3-carboxamide |
| Cpd 559 | N-(3,3-difluoropiperidin-4-yl)-2-methyl-5-(pyrimidin-2-ylmethoxy)benzofuran-3-carboxamide |
| Cpd 560 | N-(3,3-difluoropiperidin-4-yl)-2-methyl-5-(thiazol-2-ylmethoxy)benzofuran-3-carboxamide |
| Cpd 561 | N-(3,3-difluoropiperidin-4-yl)-2-methyl-5-(thiazol-5-ylmethoxy)benzofuran-3-carboxamide |
| Cpd 562 | N-(3,3-difluoropiperidin-4-yl)-4-fluoro-2-methyl-5-((4-methylthiazol-5-yl)methoxy)benzofuran-3-carboxamide |
| Cpd 563 | N-(3,3-difluoropiperidin-4-yl)-5-((2,4-dimethylthiazol-5-yl)methoxy)-2-methylbenzofuran-3-carboxamide |
| Cpd 564 | N-(3,3-difluoropiperidin-4-yl)-5-((2-hydroxypyridin-3-yl)methoxy)-2-methylbenzofuran-3-carboxamide |
| Cpd 565 | N-(3,3-difluoropiperidin-4-yl)-5-((2-methoxypyridin-3-yl)methoxy)-2-methylbenzofuran-3-carboxamide |
| Cpd 566 | N-(3,3-difluoropiperidin-4-yl)-5-((3-fluoropyridin-2-yl)methoxy)-2-methylbenzofuran-3-carboxamide |
| Cpd 567 | N-(3,3-difluoropiperidin-4-yl)-5-((5-(2-hydroxyethoxy)pyridin-2-yl)methoxy)-2-methylbenzofuran-3-carboxamide |
| Cpd 568 | N-(3,3-difluoropiperidin-4-yl)-5-((5-fluoropyridin-2-yl)methoxy)-2-methylbenzofuran-3-carboxamide |
| Cpd 569 | N-(3,3-difluoropiperidin-4-yl)-5-((6-hydroxypyridin-2-yl)methoxy)-2-methylbenzofuran-3-carboxamide |
| Cpd 570 | N-(3,3-difluoropiperidin-4-yl)-5-((6-methoxypyridin-2-yl)methoxy)-2-methylbenzofuran-3-carboxamide |
| Cpd 571 | N-(3,3-difluoropiperidin-4-yl)-5-(imidazo[1,2-a]pyridin-6-ylmethoxy)-2-methylbenzofuran-3-carboxamide |
| Cpd 572 | N-(3,3-difluoropiperidin-4-yl)-6-fluoro-2-methyl-5-((4-methylthiazol-5-yl)methoxy)benzofuran-3-carboxamide |
| Cpd 573 | N-(3,3-difluoropiperidin-4-yl)-7-fluoro-2-methyl-5-((4-methylthiazol-5-yl)methoxy)benzofuran-3-carboxamide |

-continued

| | |
|---|---|
| Cpd 574 | N-(3,3-difluoropropyl)-2-methyl-5-((4-methylthiazol-5-yl)methoxy)benzofuran-3-carboxamide |
| Cpd 575 | N-(3-amino-2-(dimethylamino)-3-oxopropyl)-2-methyl-5-((4-methylthiazol-5-yl)methoxy)benzofuran-3-carboxamide |
| Cpd 576 | N-(3-amino-2,2-dimethyl-3-oxopropyl)-2-methyl-5-((4-methylthiazol-5-yl)methoxy)benzofuran-3-carboxamide |
| Cpd 577 | N-(3-carbamoyloxetan-3-yl)-2-(difluoromethyl)-5-((4-methylthiazol-5-yl)methoxy)benzofuran-3-carboxamide |
| Cpd 578 | N-(3-carbamoyloxetan-3-yl)-2-methyl-5-((1-methyl-1H-imidazol-2-yl)methoxy)benzofuran-3-carboxamide |
| Cpd 579 | N-(3-carbamoyloxetan-3-yl)-2-methyl-5-((1-methyl-1H-pyrazol-5-yl)methoxy)benzofuran-3-carboxamide |
| Cpd 580 | N-(3-carbamoyloxetan-3-yl)-2-methyl-5-((2-methylthiazol-5-yl)methoxy)benzofuran-3-carboxamide |
| Cpd 581 | N-(3-carbamoyloxetan-3-yl)-2-methyl-5-(pyridin-2-ylmethoxy)benzofuran-3-carboxamide |
| Cpd 582 | N-(3-carbamoyloxetan-3-yl)-2-methyl-5-(thiazol-2-ylmethoxy)benzofuran-3-carboxamide |
| Cpd 583 | N-(3-carbamoyloxetan-3-yl)-4-fluoro-2-methyl-5-((4-methylthiazol-5-yl)methoxy)benzofuran-3-carboxamide |
| Cpd 584 | N-(3-carbamoyloxetan-3-yl)-5-((2-(difluoromethyl)pyridin-3-yl)methoxy)-2-methylbenzofuran-3-carboxamide |
| Cpd 585 | N-(3-carbamoyloxetan-3-yl)-5-((2-hydroxypyridin-3-yl)methoxy)-2-methylbenzofuran-3-carboxamide |
| Cpd 586 | N-(3-carbamoyloxetan-3-yl)-5-((2-methoxypyridin-3-yl)methoxy)-2-methylbenzofuran-3-carboxamide |
| Cpd 587 | N-(3-carbamoyloxetan-3-yl)-6-fluoro-2-methyl-5-((4-methylthiazol-5-yl)methoxy)benzofuran-3-carboxamide |
| Cpd 588 | N-(3-carbamoyloxetan-3-yl)-7-fluoro-2-methyl-5-((4-methylthiazol-5-yl)methoxy)benzofuran-3-carboxamide |
| Cpd 589 | N-(3-carbamoyloxetan-3-yl)-N,2-dimethyl-5-((4-methylthiazol-5-yl)methoxy)benzofuran-3-carboxamide |
| Cpd 590 | N-(3-carbamoyltetrahydro-2H-pyran-3-yl)-2-methyl-5-((2-methylthiazol-5-yl)methoxy)benzofuran-3-carboxamide |
| Cpd 591 | N-(3-carbamoyltetrahydrofuran-3-yl)-2-methyl-5-((2-methylpyridin-3-yl)methoxy)benzofuran-3-carboxamide |
| Cpd 592 | N-(3-carbamoyltetrahydrofuran-3-yl)-2-methyl-5-((2-methylthiazol-5-yl)methoxy)benzofuran-3-carboxamide |
| Cpd 593 | N-(3-carbamoyltetrahydrofuran-3-yl)-2-methyl-5-((4-methylthiazol-5-yl)methoxy)benzofuran-3-carboxamide |
| Cpd 594 | N-(3-carbamoyltetrahydrofuran-3-yl)-2-methyl-5-((6-methylpyridin-3-yl)methoxy)benzofuran-3-carboxamide |
| Cpd 595 | N-(3-carbamoyltetrahydrofuran-3-yl)-2-methyl-5-(pyridin-2-ylmethoxy)benzofuran-3-carboxamide |
| Cpd 596 | N-(3-carbamoyltetrahydrofuran-3-yl)-5-((2-hydroxypyridin-3-yl)methoxy)-2-methylbenzofuran-3-carboxamide |
| Cpd 597 | N-(3-carbamoyltetrahydrofuran-3-yl)-5-((2-methoxypyridin-3-yl)methoxy)-2-methylbenzofuran-3-carboxamide |
| Cpd 598 | N-(3-carbamoyltetrahydrofuran-3-yl)-5-((4-fluoro-1-methyl-1H-pyrazol-5-yl)methoxy)-2-methylbenzofuran-3-carboxamide |
| Cpd 599 | N-(3-cyanooxetan-3-yl)-N,2-dimethyl-5-((4-methylthiazol-5-yl)methoxy)benzofuran-3-carboxamide |
| Cpd 600 | N-(3-hydroxy-1-(methylamino)-1-oxopropan-2-yl)-2-methyl-5-((4-methylthiazol-5-yl)methoxy)benzofuran-3-carboxamide |
| Cpd 601 | N-(3-hydroxy-1-(methylamino)-1-oxopropan-2-yl)-2-methyl-5-(pyridin-2-ylmethoxy)benzofuran-3-carboxamide |
| Cpd 602 | N-(3-hydroxy-2,2-dimethylpropyl)-2-methyl-5-((4-methylthiazol-5-yl)methoxy)benzofuran-3-carboxamide |
| Cpd 603 | N-(4-(hydroxymethyl)tetrahydro-2H-pyran-4-yl)-2,4-dimethyl-5-((4-methylthiazol-5-yl)methoxy)benzofuran-3-carboxamide |
| Cpd 604 | N-(4-(hydroxymethyl)tetrahydro-2H-pyran-4-yl)-2-methyl-5-((1-methyl-1H-1,2,3-triazol-4-yl)methoxy)benzofuran-3-carboxamide |
| Cpd 605 | N-(4-(hydroxymethyl)tetrahydro-2H-pyran-4-yl)-2-methyl-5-((1-methyl-1H-1,2,3-triazol-5-yl)methoxy)benzofuran-3-carboxamide |
| Cpd 606 | N-(4-(hydroxymethyl)tetrahydro-2H-pyran-4-yl)-2-methyl-5-((1-methyl-1H-1,2,4-triazol-3-yl)methoxy)benzofuran-3-carboxamide |
| Cpd 607 | N-(4-(hydroxymethyl)tetrahydro-2H-pyran-4-yl)-2-methyl-5-((1-methyl-1H-imidazol-5-yl)methoxy)benzofuran-3-carboxamide |
| Cpd 608 | N-(4-(hydroxymethyl)tetrahydro-2H-pyran-4-yl)-2-methyl-5-((1-methyl-1H-pyrazol-5-yl)methoxy)benzofuran-3-carboxamide |
| Cpd 609 | N-(4-(hydroxymethyl)tetrahydro-2H-pyran-4-yl)-2-methyl-5-((1-methyl-2-oxo-1,2-dihydropyridin-3-yl)methoxy)benzofuran-3-carboxamide |
| Cpd 610 | N-(4-(hydroxymethyl)tetrahydro-2H-pyran-4-yl)-2-methyl-5-((1-methyl-6-oxo-1,6-dihydropyridin-2-yl)methoxy)benzofuran-3-carboxamide |
| Cpd 611 | N-(4-(hydroxymethyl)tetrahydro-2H-pyran-4-yl)-2-methyl-5-((2-methylpyridin-3-yl)methoxy)benzofuran-3-carboxamide |
| Cpd 612 | N-(4-(hydroxymethyl)tetrahydro-2H-pyran-4-yl)-2-methyl-5-((2-methylpyrimidin-4-yl)methoxy)benzofuran-3-carboxamide |
| Cpd 613 | N-(4-(hydroxymethyl)tetrahydro-2H-pyran-4-yl)-2-methyl-5-((2-methylthiazol-5-yl)methoxy)benzofuran-3-carboxamide |
| Cpd 614 | N-(4-(hydroxymethyl)tetrahydro-2H-pyran-4-yl)-2-methyl-5-((2-oxo-1,2-dihydropyridin-3-yl)methoxy)benzofuran-3-carboxamide |

| | -continued |
|---|---|
| Cpd 615 | N-(4-(hydroxymethyl)tetrahydro-2H-pyran-4-yl)-2-methyl-5-((3-(trifluoromethyl)-1H-pyrazol-4-yl)methoxy)benzofuran-3-carboxamide |
| Cpd 616 | N-(4-(hydroxymethyl)tetrahydro-2H-pyran-4-yl)-2-methyl-5-((4-methyloxazol-2-yl)methoxy)benzofuran-3-carboxamide |
| Cpd 617 | N-(4-(hydroxymethyl)tetrahydro-2H-pyran-4-yl)-2-methyl-5-((4-methylthiazol-2-yl)methoxy)benzofuran-3-carboxamide |
| Cpd 618 | N-(4-(hydroxymethyl)tetrahydro-2H-pyran-4-yl)-2-methyl-5-((5-methylisoxazol-3-yl)methoxy)benzofuran-3-carboxamide |
| Cpd 619 | N-(4-(hydroxymethyl)tetrahydro-2H-pyran-4-yl)-2-methyl-5-((5-methylpyrazin-2-yl)methoxy)benzofuran-3-carboxamide |
| Cpd 620 | N-(4-(hydroxymethyl)tetrahydro-2H-pyran-4-yl)-2-methyl-5-((5-methylthiazol-2-yl)methoxy)benzofuran-3-carboxamide |
| Cpd 621 | N-(4-(hydroxymethyl)tetrahydro-2H-pyran-4-yl)-2-methyl-5-((6-methylpyridazin-3-yl)methoxy)benzofuran-3-carboxamide |
| Cpd 622 | N-(4-(hydroxymethyl)tetrahydro-2H-pyran-4-yl)-2-methyl-5-((6-methylpyridin-3-yl)methoxy)benzofuran-3-carboxamide |
| Cpd 623 | N-(4-(hydroxymethyl)tetrahydro-2H-pyran-4-yl)-2-methyl-5-(1-(4-methylthiazol-5-yl)ethoxy)benzofuran-3-carboxamide |
| Cpd 624 | N-(4-(hydroxymethyl)tetrahydro-2H-pyran-4-yl)-2-methyl-5-(pyridazin-3-ylmethoxy)benzofuran-3-carboxamide |
| Cpd 625 | N-(4-(hydroxymethyl)tetrahydro-2H-pyran-4-yl)-2-methyl-5-(pyridin-3-ylmethoxy)benzofuran-3-carboxamide |
| Cpd 626 | N-(4-(hydroxymethyl)tetrahydro-2H-pyran-4-yl)-2-methyl-5-(pyrimidin-2-ylmethoxy)benzofuran-3-carboxamide |
| Cpd 627 | N-(4-(hydroxymethyl)tetrahydro-2H-pyran-4-yl)-2-methyl-5-(thiazol-5-ylmethoxy)benzofuran-3-carboxamide |
| Cpd 628 | N-(4-(hydroxymethyl)tetrahydro-2H-pyran-4-yl)-5-((2-hydroxypyridin-4-yl)methoxy)-2-methylbenzofuran-3-carboxamide |
| Cpd 629 | N-(4-(hydroxymethyl)tetrahydro-2H-pyran-4-yl)-5-((2-methoxypyridin-4-yl)methoxy)-2-methylbenzofuran-3-carboxamide |
| Cpd 630 | N-(4-(hydroxymethyl)tetrahydro-2H-pyran-4-yl)-5-((6-hydroxypyridin-2-yl)methoxy)-2-methylbenzofuran-3-carboxamide |
| Cpd 631 | N-(4-(hydroxymethyl)tetrahydro-2H-pyran-4-yl)-5-((6-hydroxypyridin-3-yl)methoxy)-2-methylbenzofuran-3-carboxamide |
| Cpd 632 | N-(4-(hydroxymethyl)tetrahydro-2H-pyran-4-yl)-5-((6-methoxypyridin-3-yl)methoxy)-2-methylbenzofuran-3-carboxamide |
| Cpd 633 | N-(4-(hydroxymethyl)tetrahydro-2H-pyran-4-yl)-5-(imidazo[1,2-a]pyridin-6-ylmethoxy)-2-methylbenzofuran-3-carboxamide |
| Cpd 634 | N-(4-(hydroxymethyl)tetrahydro-2H-pyran-4-yl)-N,2-dimethyl-5-((4-methylthiazol-5-yl)methoxy)benzofuran-3-carboxamide |
| Cpd 635 | N-(4,4-difluoropiperidin-3-yl)-2-methyl-5-((1-methyl-1H-imidazol-2-yl)methoxy)benzofuran-3-carboxamide |
| Cpd 636 | N-(4,4-difluoropiperidin-3-yl)-2-methyl-5-((1-methyl-1H-pyrazol-5-yl)methoxy)benzofuran-3-carboxamide |
| Cpd 637 | N-(4,4-difluoropiperidin-3-yl)-5-((2-hydroxypyridin-3-yl)methoxy)-2-methylbenzofuran-3-carboxamide |
| Cpd 638 | N-(4,4-difluoropyrrolidin-3-yl)-2-methyl-5-((1-methyl-1H-imidazol-2-yl)methoxy)benzofuran-3-carboxamide |
| Cpd 639 | N-(4,4-difluoropyrrolidin-3-yl)-2-methyl-5-((1-methyl-1H-pyrazol-5-yl)methoxy)benzofuran-3-carboxamide |
| Cpd 640 | N-(4,4-difluoropyrrolidin-3-yl)-5-((2-hydroxypyridin-3-yl)methoxy)-2-methylbenzofuran-3-carboxamide |
| Cpd 641 | N-(4,4-difluorotetrahydrofuran-3-yl)-2-methyl-5-((1-methyl-1H-imidazol-2-yl)methoxy)benzofuran-3-carboxamide |
| Cpd 642 | N-(4,4-difluorotetrahydrofuran-3-yl)-2-methyl-5-((1-methyl-1H-pyrazol-5-yl)methoxy)benzofuran-3-carboxamide |
| Cpd 643 | N-(4,4-difluorotetrahydrofuran-3-yl)-2-methyl-5-((2-methylthiazol-5-yl)methoxy)benzofuran-3-carboxamide |
| Cpd 646 | N-(4,4-difluorotetrahydrofuran-3-yl)-2-methyl-5-((4-methylthiazol-5-yl)methoxy)benzofuran-3-carboxamide |
| Cpd 647 | N-(4,4-difluorotetrahydrofuran-3-yl)-2-methyl-5-(pyridin-2-ylmethoxy)benzofuran-3-carboxamide |
| Cpd 648 | N-(4,4-difluorotetrahydrofuran-3-yl)-5-((2-hydroxypyridin-3-yl)methoxy)-2-methylbenzofuran-3-carboxamide |
| Cpd 649 | N-(4-amino-2-methyl-4-oxobutan-2-yl)-2-methyl-5-((4-methylthiazol-5-yl)methoxy)benzofuran-3-carboxamide |
| Cpd 650 | N-(4-carbamoyltetrahydro-2H-pyran-4-yl)-2-methyl-5-((4-methylthiazol-5-yl)methoxy)benzofuran-3-carboxamide |
| Cpd 651 | N-(4-hydroxy-2-methylbutan-2-yl)-2-methyl-5-((2-(trifluoromethyl)pyridin-3-yl)methoxy)benzofuran-3-carboxamide |
| Cpd 652 | N-(4-hydroxy-2-methylbutan-2-yl)-2-methyl-5-((4-methylthiazol-5-yl)methoxy)benzofuran-3-carboxamide |
| Cpd 653 | N-(cis-4-hydroxytetrahydrofuran-3-yl)-2-methyl-5-((1-methyl-1H-imidazol-2-yl)methoxy)benzofuran-3-carboxamide |
| Cpd 654 | N-(trans-4-hydroxytetrahydrofuran-3-yl)-2-methyl-5-((1-methyl-1H-imidazol-2-yl)methoxy)benzofuran-3-carboxamide |
| Cpd 655 | N-(cis-4-hydroxytetrahydrofuran-3-yl)-2-methyl-5-((1-methyl-1H-pyrazol-5-yl)methoxy)benzofuran-3-carboxamide |
| Cpd 656 | N-(trans-4-hydroxytetrahydrofuran-3-yl)-2-methyl-5-((1-methyl-1H-pyrazol-5-yl)methoxy)benzofuran-3-carboxamide |

-continued

| | |
|---|---|
| Cpd 657 | N3-(3,3-difluoropiperidin-4-yl)-5-((2-(trifluoromethyl)pyridin-3-yl)methoxy)benzofuran-2,3-dicarboxamide |
| Cpd 658 | N3-(4-(hydroxymethyl)tetrahydro-2H-pyran-4-yl)-5-((4-methylthiazol-5-yl)methoxy)benzofuran-2,3-dicarboxamide |
| Cpd 659 | N-cyclobutyl-N-(2-hydroxyethyl)-2-methyl-5-((2-(trifluoromethyl)pyridin-3-yl)methoxy)benzofuran-3-carboxamide |
| Cpd 660 | N-cyclobutyl-N-(2-hydroxyethyl)-2-methyl-5-((4-methylthiazol-5-yl)methoxy)benzofuran-3-carboxamide |
| Cpd 661 | 2-methyl-5-((4-methylthiazol-5-yl)methoxy)-N-(2-oxoazepan-3-yl)benzofuran-3-carboxamide |
| Cpd 662 | N-(1-amino-3-hydroxy-1-oxopropan-2-yl)-2-methyl-5-(pyridin-3-ylmethoxy)benzofuran-3-carboxamide |
| Cpd 663 | N-(4,4-difluoropyrrolidin-3-yl)-5-((2-methoxypyridin-3-yl)methoxy)-2-methylbenzofuran-3-carboxamide |
| Cpd 664 | N-(4,4-difluorotetrahydrofuran-3-yl)-2-methyl-5-((2-(trifluoromethyl)pyridin-3-yl)methoxy)benzofuran-3-carboxamide |
| Cpd 665 | N-(4,4-difluorotetrahydrofuran-3-yl)-5-((2-methoxypyridin-3-yl)methoxy)-2-methylbenzofuran-3-carboxamide |
| Cpd 666 | 2-methyl-5-((4-methylthiazol-5-yl)methoxy)-N-(2,2,2-trifluoroethyl)benzofuran-3-carboxamide |
| Cpd 667 | 5-((1,4-Dimethyl-1H-pyrazol-5-yl)methoxy)-2-methylbenzofuran-3-carboxylic acid |
| Cpd 668 | (S)-N-(1-Amino-3-hydroxy-1-oxopropan-2-yl)-5-(((1,4-dimethyl-1H-pyrazol-5-yl)methoxy)-2-methylbenzofuran-3-carboxamide |
| Cpd 669 | 5-((4-Chloro-1-methyl-1H-pyrazol-5-yl)methoxy)-2-methylbenzofuran-3-carboxylic acid |
| Cpd 670 | (S)-N-(1-Amino-3-hydroxy-1-oxopropan-2-yl)-5-((4-chloro-1-methyl-1H-pyrazol-5-yl)methoxy)-2-methylbenzofuran-3-carboxamide |
| Cpd 671 | 5-((4-chloro-1-isopropyl-1H-pyrazol-5-yl)methoxy)-2-methylbenzofuran-3-carboxylicacid |
| Cpd 672 | (S)-N-(1-amino-3-hydroxy-1-oxopropan-2-yl)-5-((4-chloro-1-isopropyl-1H-pyrazol-5-yl) methoxy)-2-methylbenzofuran-3-carboxamide |
| Cpd 673 | 2-Methyl-5-((3-methylisoxazol-5-yl)methoxy)benzofuran-3-carboxylic acid |
| Cpd 674 | (S)-N-(1-Amino-3-hydroxy-1-oxopropan-2-yl)-2-methyl-5-((3-methylisoxazol-5-yl)methyl)benzofuran-3-carboxamide |
| Cpd 675 | 5-((1-isopropyl-1H-pyrazol-5-yl)methoxy)-2-methylbenzofuran-3-carboxylic acid |
| Cpd 676 | (S)-N-(1-amino-3-hydroxy-1-oxopropan-2-yl)-5-((1-isopropyl-1H-pyrazol-5-yl)methoxy)-2-methylbenzofuran-3-carboxamide |
| Cpd 677 | 5-((2,4-Dimethyloxazol-5-yl)methoxy)-2-methylbenzofuran-3-carboxylic acid |
| Cpd 678 | (S)-N-(1-Amino-3-hydroxy-1-oxopropan-2-yl)-5-((2,4-dimethyloxazol-5-yl)methoxy)-2-methylbenzofuran-3-carboxamide |
| Cpd 679 | 2-Methyl-5-((4-methyloxazol-5-yl)methoxy)benzofuran-3-carboxylic acid |
| Cpd 680 | (S)-N-(1-Amino-3-hydroxy-1-oxopropan-2-yl)-2-methyl-5-((4-methyloxazol-5-yl)methoxy)benzofuran-3-carboxamide |
| Cpd 681 | 5-((2-Isopropylthiazol-5-yl)methoxy)-2-methylbenzofuran-3-carboxylic acid |
| Cpd 682 | (S)-N-(1-Amino-3-hydroxy-1-oxopropan-2-yl)-5-((2-isopropylthiazol-5-yl)methoxy)-2-methylbenzofuran-3-carboxamide |
| Cpd 683 | N-(1-(Difluoromethyl)cyclobutyl)-2-methyl-5-((2-methylthiazol-5-yl)methoxy)benzofuran-3-carboxamide |
| Cpd 684 | (S)-N-(1-Amino-3-hydroxy-1-oxopropan-2-yl)-2-methyl-5-((5-methylthiazol-2-yl)methoxy)benzofuran-3-carboxamide |
| Cpd 685 | N-((2S,3R)-1-amino-3-hydroxy-1-oxobutan-2-yl)-2-methyl-5-((3-(trifluoromethyl)-1H-pyrazol-4-yl)methoxy)benzofuran-3-carboxamide |
| Cpd 686 | (S)-N-(1-Amino-3-hydroxy-1-oxopropan-2-yl)-2-methyl-5-((1-methyl-1H-pyrazol-3-yl)methoxy)benzofuran-3-carboxamide |
| Cpd 687 | 2-Methyl-5-((1-(2,2,2-trifluoroethyl)-1H-pyrazol-5-yl)methoxy)benzofuran-3-carboxylic acid |
| Cpd 688 | (S)-N-(1-Amino-3-hydroxy-1-oxopropan-2-yl)-2-methyl-5-((1-(2,2,2-trifluoroethyl)-1H-pyrazol-5-yl)methoxy)benzofuran-3-carboxamide |
| Cpd 689 | 5-((1-(Cyclopropylmethyl)-1H-pyrazol-5-yl)methoxy)-2-methylbenzofuran-3-carboxylic acid |
| Cpd 690 | (S)-N-(1-amino-3-hydroxy-1-oxopropan-2-yl)-5-((1-(cyclopropylmethyl)-1H-pyrazol-5-yl)methoxy)-2-methylbenzofuran-3-carboxamide |
| Cpd 691 | 2-Methyl-5-((1-methyl-3-(trifluoromethyl)-1H-pyrazol-4-yl)methoxy)benzofuran-3-carboxylic acid |
| Cpd 692 | (S)-N-(1-Amino-3-hydroxy-1-oxopropan-2-yl)-2-methyl-5-((1-methyl-3-(trifluoromethyl)-1H-pyrazol-4-yl)methoxy)benzofuran-3-carboxamide |
| Cpd 693 | 2-Methyl-5-((4-(trifluoromethyl)thiazol-5-yl)methoxy)benzofuran-3-carboxylic acid |
| Cpd 694 | (S)-N-(1-Amino-3-hydroxy-1-oxopropan-2-yl)-2-methyl-5-((4-(trifluoromethyl)thiazol-5-yl)methoxy)benzofuran-3-carboxamide |
| Cpd 695 | (S)-N-(1-Amino-3-hydroxy-1-oxopropan-2-yl)-2-methyl-5-(thiazol-2-ylmethoxy)benzofuran-3-carboxamide |
| Cpd 696 | N-((2S,3R)-1-amino-3-hydroxy-1-oxobutan-2-yl)-5-((5-fluoropyridin-2-yl)methoxy)-2-methylbenzofuran-3-carboxamide |
| Cpd 697 | (S)-N-(1-Amino-3-hydroxy-1-oxopropan-2-yl)-2-methyl-5-(thiazol-5-ylmethoxy)benzofuran-3-carboxamide |
| Cpd 698 | (S)-N-(1-Amino-3-hydroxy-1-oxopropan-2-yl)-2-methyl-5-((1-methyl-1H-pyrazol-4-yl)methoxy)benzofuran-3-carboxamide |
| Cpd 699 | 2-Methyl-5-((5-methylpyridin-2-yl)methoxy)benzofuran-3-carboxylic acid |
| Cpd 700 | (S)-N-(1-Amino-3-hydroxy-1-oxopropan-2-yl)-2-methyl-5-((5-methylpyridin-2-yl)methoxy)benzofuran-3-carboxamide |
| Cpd 701 | 5-((2-cyclopropylpyridin-3-yl)methoxy)-2-methylbenzofuran-3-carboxylic acid |
| Cpd 702 | (S)-N-(1-Amino-3-hydroxy-1-oxopropan-2-yl)-5-((2-cyclopropylpyridin-3-yl)methoxy)-2-methylbenzofuran-3-carboxamide |
| Cpd 703 | 5-((3-Cyclopropylpyridin-2-yl)methoxy)-2-methylbenzofuran-3-carboxylic acid |
| Cpd 704 | (S)-N-(1-Amino-3-hydroxy-1-oxopropan-2-yl)-5-((3-cyclopropylpyridin-2-yl)methoxy)-2-methylbenzofuran-3-carboxamide; |

| | |
|---|---|
| Cpd 705 | 5-((3-cyclopropylpyridin-2-yl)methoxy)-N-(4-(hydroxymethyl)tetrahydro-2H-pyran-4-yl)-2-methylbenzofuran-3-carboxamide |
| Cpd 706 | (S)-N-(1-amino-3-hydroxy-1-oxopropan-2-yl)-5-((2-(azetidin-1-yl)pyridin-3-yl)methoxy)-2-methylbenzofuran-3-carboxamide |
| Cpd 707 | 2-Methyl-5-((2-methylpyrimidin-5-yl)methoxy)benzofuran-3-carboxylic acid |
| Cpd 708 | (S)-N-(1-Amino-3-hydroxy-1-oxopropan-2-yl)-2-methyl-5-((2-methylpyrimidin-5-yl)methoxy)benzofuran-3-carboxamide |
| Cpd 709 | 5-((2-Cyclopropoxypyridin-3-yl)methoxy)-2-methylbenzofuran-3-carboxylic acid |
| Cpd 710 | (S)-N-(1-amino-3-hydroxy-1-oxopropan-2-yl)-5-((2-cyclopropoxypyridin-3-yl)methoxy)-2-methylbenzofuran-3-carboxamide |
| Cpd 711 | 5-((2-cyclopropoxypyridin-3-yl)methoxy)-N-(4-(hydroxymethyl)tetrahydro-2H-pyran-4-yl)-2-methylbenzofuran-3-carboxamide |
| Cpd 712 | (S)-N-(1-Amino-3-hydroxy-1-oxopropan-2-yl)-2-methyl-5-(pyrimidin-2-ylmethoxy)benzofuran-3-carboxamide |
| Cpd 713 | 2-Methyl-5-(pyrazin-2-ylmethoxy)benzofuran-3-carboxylic acid |
| Cpd 714 | (S)-N-(1-Amino-3-hydroxy-1-oxopropan-2-yl)-2-methyl-5-(pyrazin-2-ylmethoxy)benzofuran-3-carboxamide |
| Cpd 715 | (S)-N-(1-amino-3-hydroxy-1-oxopropan-2-yl)-5-((2-methoxypyridin-3-yl)methoxy)-2-methylbenzofuran-3-carboxamide |
| Cpd 716 | (S)-N-(1-Amino-3-hydroxy-1-oxopropan-2-yl)-2-methyl-5-(pyridin-4-ylmethoxy)benzofuran-3-carboxamide |
| Cpd 717 | 5-((3-(Difluoromethyl)pyridin-2-yl)methoxy)-N-(3,3-difluoropiperidin-4-yl)-2-methylbenzofuran-3-carboxamide |
| Cpd 718 | N-((2S,3R)-1-amino-3-hydroxy-1-oxobutan-2-yl)-2-methyl-5-(pyridin-2-ylmethoxy)benzofuran-3-carboxamide |
| Cpd 719 | N-(3-(hydroxymethyl)-2-oxopiperidin-3-yl)-2-methyl-5-(pyridin-2-ylmethoxy)benzofuran-3-carboxamide |
| Cpd 720 | N-(1-amino-3-hydroxy-2-methyl-1-oxopropan-2-yl)-5-((2-methoxypyridin-3-yl)methoxy)-2-methylbenzofuran-3-carboxamide |
| Cpd 721 | N-(1-(Difluoromethyl)cyclobutyl)-2-methyl-5-((4-methylthiazol-5-yl)methoxy)benzofuran-3-carboxamide |
| Cpd 722 | N-(1-Amino-3-hydroxy-2-methyl-1-oxopropan-2-yl)-2-methyl-5-((2-methyloxazol-5-yl)methoxy)benzofuran-3-carboxamide |
| Cpd 723 | N-(3,3-difluorotetrahydro-2H-pyran-4-yl)-2-methyl-5-((4-methylthiazol-5-yl)methoxy)benzofuran-3-carboxamide |
| Cpd 724 | N-(3,3-Difluorotetrahydro-2H-pyran-4-yl)-2-methyl-5-((2-methylthiazol-5-yl)methoxy)benzofuran-3-carboxamide |
| Cpd 725 | N-(3-carbamoyltetrahydrofuran-3-yl)-2-methyl-5-((2-methyloxazol-5-yl)methoxy)benzofuran-3-carboxamide |
| Cpd 726 | N-(1-Amino-3-(methylsulfonyl)-1-oxopropan-2-yl)-2-methyl-5-((2-methylthiazol-5-yl)methoxy)benzofuran-3-carboxamide |
| Cpd 727 | N-(1-Imino-1-oxidotetrahydro-1H-1λ6-thiophen-3-yl)-2-methyl-5-((2-methylthiazol-5-yl)methoxy)benzofuran-3-carboxamide |
| Cpd 728 | N-(3-(hydroxymethyl)pyrrolidin-3-yl)-2-methyl-5-((4-methylthiazol-5-yl)methoxy)benzofuran-3-carboxamide |
| Cpd 729 | N-(1-Amino-1-oxo-3-(1H-1,2,4-triazol-1-yl)propan-2-yl)-2-methyl-5-((4-methylthiazol-5-yl)methoxy)benzofuran-3-carboxamide |
| Cpd 730 | N-(3-(Hydroxymethyl)-2-oxopyrrolidin-3-yl)-2-methyl-5-((3-(trifluoromethyl)-1H-pyrazol-4-yl)methoxy)benzofuran-3-carboxamide |
| Cpd 731 | N-(3-(hydroxymethyl)-2-oxopiperidin-3-yl)-2-methyl-5-((3-(trifluoromethyl)-1H-pyrazol-4-yl)methoxy)benzofuran-3-carboxamide |
| Cpd 732 | N-(3-(Hydroxymethyl)-2-oxopiperidin-3-yl)-2-methyl-5-((1-methyl-1H-pyrazol-5-yl)methoxy)benzofuran-3-carboxamide |
| Cpd 733 | N-(3-(Hydroxymethyl)-2-oxopyrrolidin-3-yl)-2-methyl-5-((1-methyl-1H-pyrazol-5-yl)methoxy)benzofuran-3-carboxamide |
| Cpd 734 | N-(3-(Hydroxymethyl)-2-oxopyrrolidin-3-yl)-2-methyl-5-(pyridazin-3-ylmethoxy)benzofuran-3-carboxamide |
| Cpd 735 | 5-((5-Fluoropyridin-2-yl)methoxy)-N-(3-(hydroxymethyl)-2-oxopyrrolidin-3-yl)-2-methylbenzofuran-3-carboxamide |
| Cpd 736 | 5-((2-(Difluoromethyl)pyridin-3-yl)methoxy)-N-(3-(hydroxymethyl)-2-oxopyrrolidin-3-yl)-2-methylbenzofuran-3-carboxamide |
| Cpd 737 | 5-((2-(Difluoromethyl)pyridin-3-yl)methoxy)-N-(3-(hydroxymethyl)-2-oxopiperidin-3-yl)-2-methylbenzofuran-3-carboxamide |
| Cpd 738 | N-(1-Amino-3-hydroxy-2-methyl-1-oxopropan-2-yl)-2-methyl-5-(pyridin-2-ylmethoxy)benzofuran-3-carboxamide |
| Cpd 739 | N-(1-Amino-3-hydroxy-2-methyl-1-oxopropan-2-yl)-5-((5-fluoropyridin-2-yl)methoxy)-2-methylbenzofuran-3-carboxamide |
| Cpd 740 | N-(3-carbamoyltetrahydrofuran-3-yl)-5-((1-(2,2-difluoroethyl)-1H-pyrazol-5-yl)methoxy)-2-methylbenzofuran-3-carboxamide |
| Cpd 741 | (S)-N-(1-Amino-3-hydroxy-1-oxopropan-2-yl)-5-((5-fluoropyridin-2-yl)methoxy)-2-methylbenzofuran-3-carboxamide |
| Cpd 742 | (S)-N-(1-amino-3-hydroxy-1-oxopropan-2-yl)-2-(difluoromethyl)-5-((4-methylthiazol-5-yl)methoxy)benzofuran-3-carboxamide |
| Cpd 743 | (S)-N-(1-Amino-3-hydroxy-1-oxopropan-2-yl)-2-(difluoromethyl)-5-((6-methylpyridin-3-yl)methoxy)benzofuran-3-carboxamide |
| Cpd 744 | (S)-N-(1-amino-3-hydroxy-1-oxopropan-2-yl)-2-(difluoromethyl)-5-(pyridin-2-ylmethoxy)benzofuran-3-carboxamide |
| Cpd 745 | (S)-N-(1-amino-3-hydroxy-1-oxopropan-2-yl)-2-(difluoromethyl)-5-((2-methylthiazol-5-yl)methoxy)benzofuran-3-carboxamide |

-continued

| | |
|---|---|
| Cpd 746 | (S)-N-(1-amino-3-hydroxy-1-oxopropan-2-yl)-2-(difluoromethyl)-5-((2-methyloxazol-5-yl)methoxy)benzofuran-3-carboxamide |
| Cpd 747 | (S)-N-(1-Amino-3-hydroxy-1-oxopropan-2-yl)-2-cyclopropyl-5-(pyridin-2-ylmethoxy)benzofuran-3-carboxamide |
| Cpd 748 | (S)-N-(1-Amino-3-hydroxy-1-oxopropan-2-yl)-2-cyclopropyl-5-((4-methylthiazol-5-yl)methoxy)benzofuran-3-carboxamide |
| Cpd 749 | (S)-N-(1-Amino-3-hydroxy-1-oxopropan-2-yl)-2-cyclopropyl-5-((2-methylthiazol-5-yl)methoxy)benzofuran-3-carboxamide |
| Cpd 750 | (S)-N-(1-Amino-3-hydroxy-1-oxopropan-2-yl)-2-cyclopropyl-5-((6-methylpyridin-3-yl)methoxy)benzofuran-3-carboxamide |
| Cpd 751 | (S)-N-(1-amino-3-hydroxy-1-oxopropan-2-yl)-2-cyclopropyl-5-((2-methyloxazol-5-yl)methoxy)benzofuran-3-carboxamide | and the physiologically acceptable salts thereof.

The benzofuran derivative according to the invention is for use in the treatment of pain which is preferably selected from nociceptive pain, inflammatory pain, and neuropathic pain. More preferably, the pain is post-operative pain.

Another aspect of the invention relates to a compound of formula (I),

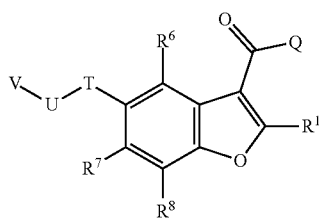
(I)

a stereo-isomeric form, a physiologically acceptable salt, solvate and/or polymorph thereof, as defined above; preferably wherein (a-1) Q represents —$OR^2$; and $R^1$ represents —$CH_2F$, —$CHF_2$, or —$CF_3$; and/or (a-2) Q represents —$OR^2$; and at least one of $R^5$ and $R^{5'}$ does not represent —H; and/or (a-3) Q represents —$OR^2$; and $R^6$ does not represent —H; and/or (a-3) Q represents —$OR^2$; and $R^8$ does not represent —H; or (b-1) Q represents —$NR^3R^4$; with the proviso that the following compounds and their salts are excluded

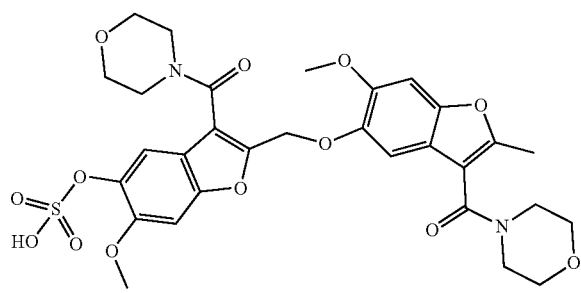

and/or (b-2) Q represents —$NR^3R^4$; and $R^1$ represents —$CH_2F$, —$CHF_2$, —$CF_3$, or -cyclopropyl; and/or (b-3) Q represents —$NR^3R^4$; and $R^1$ represents —$CH_2F$, —$CHF_2$, or —$CF_3$; and/or (b-4) Q represents —$NR^3R^4$; and at least one of $R^5$ and $R^{5'}$ does not represent —H; and/or (b-5) Q represents —$NR^3R^4$; and $R^3$ represents —H.

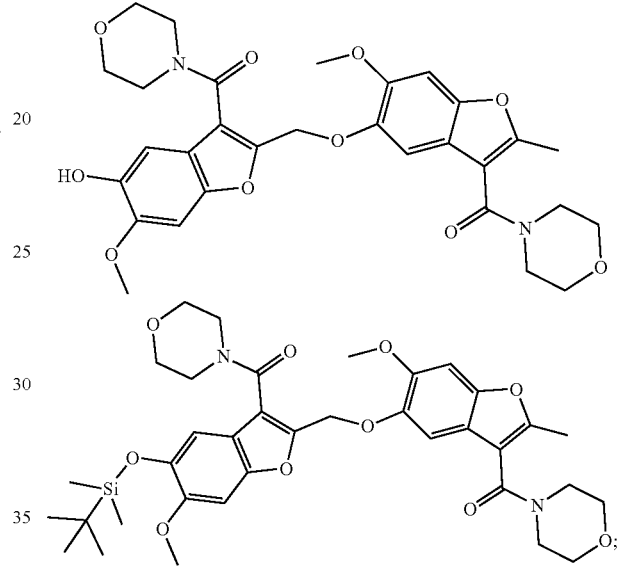

In preferred embodiments of the benzofuran derivatives according to the invention (a-1), (a-2), (a-3), (b-1), (b-2), (b-3), and (b-4) T represents —O— and U represents —$CR^5R^{5'}$— (i.e., the benzofuran derivatives is of formula (II)).

All definitions, preferred embodiments and preferred meanings of Q, T, U, V, $R^1$, $R^2$, $R^3$, $R^4$, $R^5$, $R^{5'}$, $R^6$, $R^7$, and $R^5$ including the preferred substituents also analogously apply the benzofuran derivatives according to the invention, including but not limited to (a-1), (a-2), (a-3), (b-1), (b-2), (b-3), and (b-4), which are not necessarily restricted for use in the treatment of pain. Thus, this aspect of the invention relates to the benzofuran derivatives as such, compositions comprising the benzofuran derivatives, medicaments comprising the benzofuran derivatives, and the benzofuran derivatives for use in the prevention and/or treatment of TRPM3 mediated disorders such as pain and/or inflammatory hypersensitivity; and/or for counteracting pain and/or inflammatory hypersensitivity. Preferably, the pain is selected from nociceptive pain, inflammatory pain, and neuropathic pain. More preferably, the pain is post-operative pain.

In preferred embodiments of the invention, the benzofuran derivative is selected from the group consisting of cpd 001 to cpd 207 as mentioned above and the physiologically acceptable salts thereof.

Another aspect of the invention relates to a pharmaceutical composition or a medicament comprising a compound according to the invention as described above.

Reference throughout this specification to "one embodiment" or "an embodiment" means that a particular feature, structure or characteristic described in connection with the embodiment is included in at least one embodiment of the invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Also, embodiments described for an aspect of the invention may be used for another aspect of the invention and can be combined. Where an indefinite or definite article is used when referring to a singular noun e.g., "a" or "an", "the", this includes a plural of that noun unless something else is specifically stated.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

The term "heteroatom(s)" as used herein means an atom selected from nitrogen, which can be quaternized; oxygen; and sulfur, including sulfoxide and sulfone.

The term "alkyl, saturated or unsaturated" as used herein encompasses saturated alkyl as well as unsaturated alkyl such as alkenyl, alkynyl, and the like. The term "alkyl" as used herein means normal, secondary, or tertiary, linear or branched hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The term "alkenyl" as used herein means normal, secondary or tertiary, linear or branched hydrocarbon with at least one site (usually 1 to 3, preferably 1) of unsaturation, namely a carbon-carbon, sp2 double bond. Examples include, but are not limited to: ethylene or vinyl ($-CH=CH_2$), allyl ($-CH_2CH=CH_2$), and 5-hexenyl ($-CH_2CH_2CH_2CH_2CH=CH_2$). The double bond may be in the cis or trans configuration. The term "alkynyl" as used herein means normal, secondary, tertiary, linear or branched hydrocarbon with at least one site (usually 1 to 3, preferably 1) of unsaturation, namely a carbon-carbon, sp triple bond. Examples include, but are not limited to: ethynyl ($-C\equiv CH$), and 1-propynyl (propargyl, $-CH_2C\equiv CH$).

The term "alkylene, saturated or unsaturated" as used herein encompasses saturated alkylene as well as unsaturated alkylene such as alkenylene, alkynylene, alkenynylene and the like. The term "alkylene" as used herein means saturated, linear or branched chain hydrocarbon radical having two monovalent radical centers derived by the removal of two hydrogen atoms from the same or two different carbon atoms of a parent alkane. Typical alkylene radicals include, but are not limited to: methylene ($-CH_2-$), 1,2-ethyl ($-CH_2CH_2-$), 1,3-propyl ($-CH_2CH_2CH_2-$), 1,4-butyl ($-CH_2CH_2CH_2CH_2-$), and the like. The term "alkenylene" as used herein means linear or branched chain hydrocarbon radical with at least one site (usually 1 to 3, preferably 1) of unsaturation, namely a carbon-carbon, sp2 double bond, and having two monovalent radical centers derived by the removal of two hydrogen atoms from the same or two different carbon atoms of a parent alkene. The term "alkynylene" as used herein means linear or branched chain hydrocarbon radical with at least one site (usually 1 to 3, preferably 1) of unsaturation, namely a carbon-carbon, sp triple bond, and having two monovalent radical centers derived by the removal of two hydrogen atoms from the same or two different carbon atoms of a parent alkyne.

The term "heteroalkyl, saturated or unsaturated" as used herein encompasses saturated heteroalkyl as well as unsaturated heteroalkyl such as heteroalkenyl, heteroalkynyl, heteroalkenynyl and the like. The term "heteroalkyl" as used herein means linear or branched chain alkyl wherein one or more carbon atoms (usually 1, 2 or 3) are replaced by a heteroatom, i.e., an oxygen, nitrogen or sulfur atom, with the proviso that said chain may not contain two adjacent O atoms or two adjacent S atoms. This means that one or more —CH$_3$ of said alkyl can be replaced by —NH$_2$ and/or that one or more —CH$_2$— of said alkyl can be replaced by —NH—, —O— or —S—. The S atoms in said chains may be optionally oxidized with one or two oxygen atoms, to afford sulfoxides and sulfones, respectively. Furthermore, the heteroalkyl groups in the benzofuran derivatives of the invention can contain an oxo or thio group at any carbon or heteroatom that will result in a stable compound. Exemplary heteroalkyl groups include, but are not limited to, alcohols, alkyl ethers (such as for example -methoxy, -ethoxy, -butoxy . . . ), primary, secondary, and tertiary alkyl amines, amides, ketones, esters, alkyl sulfides, and alkyl sulfones. The term "heteroalkenyl" means linear or branched chain alkenyl wherein one or more carbon atoms (usually 1, 2 or 3) are replaced by an oxygen, nitrogen or sulfur atom, with the proviso that said chain may not contain two adjacent O atoms or two adjacent S atoms. The term heteroalkenyl thus comprises imines, —O-alkenyl, —NH-alkenyl, —N(alkenyl)$_2$, —N(alkyl)(alkenyl), and —S-alkenyl. The term "heteroalkynyl" as used herein means linear or branched chain alkynyl wherein one or more carbon atoms (usually 1, 2 or 3) are replaced by an oxygen, nitrogen or sulfur atom, with the proviso that said chain may not contain two adjacent O atoms or two adjacent S atoms. The term heteroalkynyl thus comprises -cyano, —O-alkynyl, —NH-alkynyl, —N(alkynyl)$_2$, —N(alkyl)(alkynyl), —N(alkenyl)(alkynyl), and —S-alkynyl.

The term "heteroalkylene, saturated or unsaturated" as used herein encompasses saturated heteroalkylene as well as unsaturated heteroalkylene such as heteroalkenylene, heteroalkynylene, heteroalkenynylene and the like. The term "heteroalkylene" as used herein means linear or branched chain alkylene wherein one or more carbon atoms (usually 1, 2 or 3) are replaced by a heteroatom, i.e., an oxygen, nitrogen or sulfur atom, with the proviso that said chain may not contain two adjacent O atoms or two adjacent S atoms. The term "heteroalkenylene" as used herein means linear or branched chain alkenylene wherein one or more carbon atoms (usually 1, 2 or 3) are replaced by an oxygen, nitrogen or sulfur atom, with the proviso that said chain may not contain two adjacent O atoms or two adjacent S atoms. The term "heteroalkynylene" as used herein means linear or branched chain alkynylene wherein one or more carbon atoms (usually 1, 2 or 3) are replaced by an oxygen, nitrogen or sulfur atom, with the proviso that said chain may not contain two adjacent O atoms or two adjacent S atoms.

The term "cycloalkyl, saturated or unsaturated" as used herein encompasses saturated cycloalkyl as well as unsaturated cycloalkyl such as cycloalkenyl, cycloalkynyl and the like. The term "cycloalkyl" as used herein and unless otherwise stated means a saturated cyclic hydrocarbon radical, such as for instance cyclopropyl, cyclobutyl, cyclopentyl, cyclohexyl, cycloheptyl, cyclooctyl, norbornyl, fenchyl, decalinyl, adamantyl and the like. The term "cycloalkenyl" as used herein means a non-aromatic cyclic hydrocarbon radical with at least one site (usually 1 to 3, preferably 1) of unsaturation, namely a carbon-carbon, sp2 double bond. Examples include, but are not limited to cyclopentenyl and cyclohexenyl. The double bond may be in the cis or trans configuration. The term "cycloalkynyl" as used herein means a non-aromatic cyclic hydrocarbon radical with at least one site (usually 1 to 3, preferably 1) of unsaturation, namely a carbon-carbon, sp triple. An example is cyclohept-1-yne. Fused systems of a cycloalkyl ring with a heterocycloalkyl ring are considered as heterocycloalkyl irrespective of the ring that is bound to the core structure. Fused systems of a cycloalkyl ring with an aryl ring are considered as aryl irrespective of the ring that is bound to the core structure. Fused systems of a cycloalkyl ring with a heteroaryl ring are considered as heteroaryl irrespective of the ring that is bound to the core structure.

The term "heterocycloalkyl, saturated or unsaturated" as used herein encompasses saturated heterocycloalkyl as well as unsaturated non-aromatic heterocycloalkyl including at least one heteroatom, i.e., an N, O, or S as ring member. The term "heterocycloalkyl" as used herein and unless otherwise stated means "cycloalkyl" wherein one or more carbon atoms (usually 1, 2 or 3) are replaced by an oxygen, nitrogen or sulfur atom, with the proviso that said chain may not contain two adjacent O atoms or two adjacent S atoms. The term "heterocycloalkenyl" as used herein and unless otherwise stated means "cycloalkenyl" wherein one or more carbon atoms (usually 1, 2 or 3) are replaced by an oxygen, nitrogen or sulfur atom, with the proviso that said chain may not contain two adjacent O atoms or two adjacent S atoms. The term "heterocycloalkynyl" as used herein and unless otherwise stated means "cycloalkynyl" wherein one or more carbon atoms (usually 1, 2 or 3) are replaced by an oxygen, nitrogen or sulfur atom, with the proviso that said chain may not contain two adjacent O atoms or two adjacent S atoms. Examples of saturated and unsaturated heterocycloalkyl include but are not limited to azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin. Further heterocycloalkyls in the meaning of the invention are described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. When the heterocycloalkyl contains no nitrogen as ring member, it is typically bonded through carbon. When the heterocycloalkyl contains nitrogen as ring member, it may be bonded through nitrogen or carbon. Fused systems of heterocycloalkyl ring with a cycloalkyl ring are considered as heterocycloalkyl irrespective of the ring that is bound to the core structure. Fused systems of a heterocycloalkyl ring with an aryl ring are considered as heterocycloalkyl irrespective of the ring that is bound to the core structure. Fused systems of a heterocycloalkyl ring with a heteroaryl ring are considered as heteroaryl irrespective of the ring that is bound to the core structure.

The term "aryl" as used herein means an aromatic hydrocarbon. Typical aryl groups include, but are not limited to 1 ring, or 2 or 3 rings fused together, radicals derived from benzene, naphthalene, anthracene, biphenyl, and the like. Fused systems of an aryl ring with a cycloalkyl ring are considered as aryl irrespective of the ring that is bound to the core structure. Fused systems of an aryl ring with a heterocycloalkyl ring are considered as heterocycloalkyl irrespective of the ring that is bound to the core structure. Thus, indoline, dihydrobenzofuran, dihydrobenzothiophene and the like are considered as heterocycloalkyl according to the invention. Fused systems of an aryl ring with a heteroaryl ring are considered as heteroaryl irrespective of the ring that is bound to the core structure.

The term "heteroaryl" as used herein means an aromatic ring system including at least one heteroatom, i.e., N, O, or S as ring member of the aromatic ring system. Examples of heteroaryl include but are not limited to benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and [1,2,4]triazolo[4,3-a]pyrimidine.

By further way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

Preferred carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or ß-carboline. Preferred nitrogen bonded heterocycles include 1-aziridyl, 1-azetedyl, 1-pyrrolyl, 1-imidazolyl, 1-pyrazolyl, and 1-piperidinyl. Further heteroaryls in the meaning of the invention are described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566.

As used herein with respect to a substituting group, and unless otherwise stated, the terms "monosubstituted", "disubstituted", "trisubstituted", "polysubstituted" and the like means chemical structures defined herein, wherein the respective moiety is substituted with one or more substituents, meaning that one or more hydrogen atoms of said moiety are each independently replaced with a substituent. For example, —$C_{1-6}$-alkyl that may be polysubstituted with —F covers —$CH_2F$, —$CHF_2$, —$CF_3$, —$CH_2CF_3$, $CF_2CF_3$, and the like. Likewise, —$C_{1-6}$-alkyl that may be polysubstituted with substituents independently of one another selected from —F and —Cl covers —$CH_2F$, —$CHF_2$, —$CF_3$, —$CH_2CF_3$, $CF_2CF_3$, —$CH_2C_1$, —$CHCl_2$, —$CCl_3$, —$CH_2CCl_3$, $CCl_2CCl_3$, —$CHClF$, —$CClF_2$, —$CCl_2CF_3$, —$CF_2CCl_3$, —$CClFCCl_2F$, and the like. Any substituent designation that is found in more than one site in a compound of this invention shall be independently selected.

As used herein and unless otherwise stated, the term "solvate" includes any combination which may be formed by a derivative of this invention with a suitable inorganic solvent (e.g., hydrates) or organic solvent, such as but not limited to alcohols, ketones, esters, ethers, nitriles and the like.

The term "subject" as used herein, refers to an animal including humans, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease or disorder being treated.

The term "composition" as used herein is intended to encompass a product comprising the specified ingredients in the therapeutically effective amounts, as well as any product which results, directly or indirectly, from combinations of the specified ingredients in the specified amounts.

The term "antagonist" or "inhibitor" as used herein refers to a compound capable of producing, depending on the circumstance, a functional antagonism of the TRPM3 ion channel, including competitive antagonists, non-competitive antagonists, desensitizing agonists, and partial agonists.

For purposes of the invention, the term "TRPM3-modulated" is used to refer to the condition of being affected by the modulation of the TRPM3 ion channel, including the state of being mediated by the TRPM3 ion channel.

The term "TRPM3 mediated disorder" as used herein refers to disorders or diseases for which the use of an antagonist of TRPM3 would prevent, treat, (partially) alleviate or improve the symptoms and consist of pain and inflammatory hypersensitivity condition. According to the International Association for the Study of Pain and for the purpose of the invention, pain is an unpleasant sensory and emotional experience associated with actual or potential tissue damage, or described in terms of such damage. Preferably, the TRPM3 mediated disorder is pain which is preferably selected from nociceptive pain, inflammatory pain, and neuropathic pain. More preferably, the pain is post-operative pain. For the purpose of the invention, the term "inflammatory hypersensitivity" is used to refer to a condition that is characterized by one or more hallmarks of inflammation, including edema, erythema, hyperthermia and pain, and/or by an exaggerated physiologic or pathophysiologic response to one or more than one type of stimulation, including thermal, mechanical and/or chemical stimulation.

The benzofuran derivatives of the invention have been shown to be antagonists of TRPM3 and the invention therefore provides the compounds as such, the compounds for use as a medicine, more specifically for use as a medicine in the prevention or treatment of TRPM3 mediated disorders in a subject with a therapeutically effective amount of a benzofuran derivative of the invention.

In a preferred embodiment of the invention, the benzofuran derivative of the invention is the sole pharmacologically active compound to be administered for therapy. In another preferred embodiment of the invention, the benzofuran derivative of the invention may be employed in combination with other therapeutic agents for the treatment or prophylaxis of TRPM3 mediated disorders. The invention therefore also relates to the use of a composition comprising:
- one or more compounds of the formulae and embodiments herein, and
- one or more further therapeutic or preventive agents that are used for the prevention or treatment of TRPM3 mediated disorders as biologically active agents in the form of a combined preparation for simultaneous, separate or sequential use.

The pharmaceutical composition or combined preparation according to this invention may contain benzofuran derivatives of the invention over a broad content range depending on the contemplated use and the expected effect of the preparation. Generally, the content of the benzofuran derivatives of the invention of the combined preparation is within the range of 0.1 to 99.9% by weight, preferably from 1 to 99% by weight, more preferably from 5 to 95% by weight.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g., one of them may be in the form of an oral or parenteral formulation whereas the other is in the form of an ampoule for intravenous injection or an aerosol.

Those of skill in the art will also recognize that the benzofuran derivatives of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The benzofuran derivatives of the invention may bear multiple positive or negative charges. The net charge of the benzofuran derivatives of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise benzofuran derivatives of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The benzofuran derivatives of the invention also include physiologically acceptable salts thereof. Examples of physiologically acceptable salts of the benzofuran derivatives of the invention include salts derived from an appropriate base, such as an alkali metal (for example, sodium), an alkaline earth (for example, magnesium), ammonium and $NX4^+$ (wherein X is —$C_{1-6}$-alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX4^+$ (wherein X typically is independently selected from —H or a —$C_{1-4}$-alkyl group). However, salts of acids or bases which are not physiologically acceptable may also find use, for example, in the preparation or purification of a physiologically acceptable compound. All salts, whether or not derived form a physiologically acceptable acid or base, are within the scope of the invention.

As used herein and unless otherwise stated, the term "enantiomer" means each individual optically active form of a benzofuran derivative of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e., at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a benzofuran derivative of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compound. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthylisoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel® CA, OA, OB5, OC5, OD, OF, OG, OJ and OK, and Chiralpak® AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of the formulae described herein may easily be determined by those skilled in the art while using well-known methods such as, for example, X-ray diffraction.

When a compound is crystallized from a solution or slurry, it can be crystallized in a different arrangement lattice of spaces (this property is called "polymorphism") to form crystals with different crystalline forms, each of which is known as "polymorphs". The term "Polymorph" as used herein, therefore, refers to a crystal form of a compound of Formula (I), where the molecules are localized in the three-dimensional lattice sites. Different polymorphs of the compound of Formula (I) may be different from each other in one or more physical properties, such as solubility and dissolution rate, true specific gravity, crystal form, accumulation mode, flowability and/or solid state stability. etc.

Benzofuran derivatives of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intranasal, intravenous, intraarterial, intradermal, intrathecal and epidural). The preferred route of administration may vary with for example the condition of the recipient.

The therapeutically effective amount of the preparation of the compound(s), especially for the treatment of TRPM3 mediated disorders in humans and other mammals or in animals, preferably is a TRPM3 ion channel inhibiting amount of the compounds as defined herein and corresponds to an amount which ensures a plasma level of between 1 µg/ml and 100 mg/ml, optionally of 10 mg/ml.

Suitable dosages of the compounds or compositions of the invention should be used to treat or prevent the TRPM3 mediated disorders in a subject. Depending upon the pathologic condition to be treated and the patient's condition, the said effective amount may be divided into several sub-units per day or may be administered at more than one day intervals.

The invention further provides (pharmaceutical) compositions comprising one or more benzofuran derivatives of the invention, more in particular of all the Formula (I) and other formulas and embodiments described herein and the more particular aspects or embodiments thereof. Furthermore, the invention provides the compounds or (pharmaceutical) compositions of the invention, more in particular of all the Formula (I) and other formulas and embodiments described herein and the more particular aspects or embodiments thereof, for use as a medicine, more in particular for use in the treatment of pain. The TRPM3 mediated disorders are selected from pain and an inflammatory hypersensitivity condition.

The benzofuran derivatives of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986).

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e., the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the invention. They may also include additives such as wetting agents, dispersing agents, stickers, adhesives, emulsifying agents, surface-active agents, solvents, coatings, antibacterial and antifungal agents, isotonic agents and the like, provided the same are consistent with pharmaceutical practice, i.e., carriers and additives which do not create permanent damage to mammals. The pharmaceutical compositions of the invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

While it is possible for the benzofuran derivatives to be administered alone it is preferable to present them as pharmaceutical formulations. The formulations, both for veterinary and for human use, of the invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g., mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus, the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc.), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Benzofuran derivatives of the invention can be used to provide controlled release pharmaceutical formulations containing as active ingredient one or more benzofuran derivatives of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more benzofuran derivatives of the invention can be prepared according to conventional methods.

Another embodiment of this invention relates to various precursor or "prodrug" forms of the benzofuran derivatives of the invention. It may be desirable to formulate the benzofuran derivatives of the invention in the form of a chemical species which itself is not significantly biologically-active, but which when delivered to the animal, mammal or human will undergo a chemical reaction catalyzed by the normal function of the body, inter alia, enzymes present in the stomach or in blood serum, said chemical reaction having the effect of releasing a compound as defined herein. The term "prodrug" thus relates to these species which are converted in vivo into the active pharmaceutical ingredient.

The prodrugs of the benzofuran derivatives of the invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the invention the term "therapeutically suitable pro-drug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound such as represented by the structural formulae herein described, which undergoes spontaneous or enzymatic transformation within the body in order to release the pharmacologically active form of the compound. For a comprehensive review, reference is made to Rautio J. et al.

("Prodrugs: design and clinical applications" Nature Reviews Drug Discovery, 2008, doi: 10.1038/nrd2468).

Representative benzofuran derivatives of the invention can be synthesized in accordance with the general synthetic methods described below and illustrated in the schemes that follow. Since the schemes are an illustration, the invention should not be construed as being limited by the specific chemical reaction and specific conditions described in the schemes and examples. The various starting material used in the schemes are commercially available or may be prepared by methods well within the skill persons versed in the art. The variables are as defined herein and within the skill of persons verses in the art.

Preferred embodiments of the invention are summarized as Clauses 1 to 51 hereinafter:

1. A compound of formula (I), a stereo-isomeric form, a physiologically acceptable salt, solvate and/or polymorph thereof.

$$\text{(I)}$$

preferably, the compound of formula (I), a stereo-isomeric form, a physiologically acceptable salt, solvate and/or polymorph thereof, for use in the treatment of pain;

wherein $R^1$ represents —F, —Cl, —Br, —I, —CN, —$R^W$, —$OR^W$, —OC(=O)$R^W$, —$NR^WR^X$, —$NR^WC(=O)R^X$, —$SR^W$, —S(=O)$R^W$, —S(=O)$_2R^W$, —C(=O)$R^W$, —C(=O)O$R^W$, or —C(=O)$NR^WR^X$;

Q represents —$OR^2$ or —$NR^3R^4$;

$R^2$ represents —$R^Y$;

$R^3$ represents —OH or —$R^Y$;

$R^4$ represents —$R^Y$ or —S(=O)$_2R^Y$;

or $R^3$ and $R^4$ together form a 4, 5, 6, 7 or 8 membered heterocycle containing 1 to 3 heteroatoms selected from N, O and S, saturated or unsaturated, unsubstituted or mono- or polysubstituted;

T represents —O— and U represents —$CR^5R^{5'}$—; or T represents —$CR^5R^{5'}$— and U represents —O—;

$R^5$ and $R^{5'}$ independently of one another represent —$R^Y$;

$R^6$, $R^7$ and $R^8$ independently of one another represent —F, —Cl, —Br, —I, —CN, —$NO_2$, —$SF_5$, —$R^W$, —$OR^W$, —OC(=O)$R^W$, —$NR^WR^X$, —$NR^WC(=O)R^X$, —$SR^W$, —S(=O)$R^W$, —S(=O)$_2R^W$, —C(=O)$R^W$, —C(=O)O$R^W$, or —C(=O)$NR^WR^X$;

V represents 3-14-membered heterocycloalkyl, saturated or unsaturated; or 5-14-membered heteroaryl; in each case unsubstituted, mono- or polysubstituted with substituents independently of one another selected from —F, —Cl, —Br, —I, —CN, —NO, —$NO_2$, =O, =S, —$SF_5$, —$R^Y$, —$OR^Y$, —OC(=O)$R^Y$, —$NR^YR^Z$, —$NR^YC(=O)R^Z$, —$SR^Y$, —S(=O)$R^Y$, —S(=O)$_2R^Y$, —C(=O)$R^Y$, —C(=O)O$R^Y$, or —C(=O)$NR^YR^Z$;

wherein $R^W$ and $R^X$ independently of one another in each case independently represent
- —H;
- —$C_1$-$C_6$-alkyl, saturated or unsaturated, unsubstituted, mono- or polysubstituted;
- —$C_1$-$C_6$-heteroalkyl, saturated or unsaturated, unsubstituted, mono- or polysubstituted;
- 3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted; or
- 3-14-membered heterocycloalkyl, saturated or unsaturated, unsubstituted, mono- or polysubstituted;
- wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;

$R^Y$ and $R^Z$ independently of one another in each case independently represent
- —H;
- —$C_1$-$C_6$-alkyl, saturated or unsaturated, unsubstituted, mono- or polysubstituted;
- —$C_1$-$C_6$-heteroalkyl, saturated or unsaturated, unsubstituted, mono- or polysubstituted;
- 3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted;
- 3-14-membered heterocycloalkyl, saturated or unsaturated, unsubstituted, mono- or polysubstituted;
- wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;
- 6-14-membered aryl, unsubstituted, mono- or polysubstituted; wherein said 6-14-membered aryl is optionally connected through —$C_1$-$C_6$-alkylene- or —$C_1$-$C_6$-heteroalkylene-, in each case saturated or unsaturated, unsubstituted, mono- or polysubstituted; or
- 5-14-membered heteroaryl, unsubstituted, mono- or polysubstituted; wherein said 5-14-membered heteroaryl is optionally connected through —$C_1$-$C_6$-alkylene- or —$C_1$-$C_6$-heteroalkylene-, in each case saturated or unsaturated, unsubstituted, mono- or polysubstituted;

or $R^Y$ and $R^Z$ together form a 4, 5, 6, 7 or 8 membered heterocycle containing 1 to 3 heteroatoms selected from N, O and S, saturated or unsaturated, unsubstituted or mono- or polysubstituted;

and wherein "mono- or polysubstituted" in each case independently means substituted with one or more substituents independently of one another selected from —F, —Cl, —Br, —I, —CN, —$C_{1-6}$-alkyl, —$CF_3$, —$CF_2H$, —$CFH_2$, —$CF_2Cl$, —$CFCl_2$, —$C_{1-6}$-alkylene-$CF_3$, —$C_{1-6}$-alkylene-$CF_2H$, —$C_{1-6}$-alkylene-$CFH_2$, —$C_{1-6}$-alkylene-O—$CF_3$, —$C_{1-6}$-alkylene-O—$CF_2H$, —$C_{1-6}$-alkylene-O—$CFH_2$, —$C_{1-6}$-alkylene-NH—$C_{1-6}$-alkylene-$CF_3$, —$C_{1-6}$-alkylene-N($C_{1-6}$-alkyl)-$C_{1-6}$-alkylene-$CF_3$, —C(=O)—$C_{1-6}$-alkyl, —$C_{1-6}$-alkylene-C(=O)—$C_{1-6}$-alkyl, —C(=O)OH, —$C_{1-6}$-alkylene-C(=O)—OH, —C(=O)—O$C_{1-6}$-alkyl, —$C_{1-6}$-alkylene-C(=O)—O$C_{1-6}$-alkyl, —C(=O)O—$C_{1-6}$-alkylene-$CF_3$, —C(=O)—$NH_2$, —$C_{1-6}$-alkylene-C(=O)—$NH_2$, —C(=O)—NH($C_{1-6}$-alkyl), —$C_{1-6}$-alkylene-C(=O)—NH($C_{1-6}$-alkyl), —C(=O)—N($C_{1-6}$-alkyl)$_2$, —$C_{1-6}$-alkylene-C(=O)—N($C_{1-6}$-alkyl)$_2$, —C(=O)—NH(OH), —$C_{1-6}$-alkylene-C(=O)—NH(OH), —OH, —$C_{1-6}$-alkylene-OH, =O, —$OCF_3$, —$OCF_2H$, —$OCFH_2$, —$OCF_2Cl$, —$OCFCl_2$, —O—$C_{1-6}$-alkyl, —$C_{1-6}$-alkylene-O—$C_{1-6}$-alkyl, —O—$C_{1-6}$-alkylene-O—$C_{1-6}$-alkyl, —O—$C_{1-6}$-alkylene-$NH_2$, —O—$C_{1-6}$-alkylene-NH—$C_{1-6}$-alkyl, —O—$C_{1-6}$-alkylene-N($C_{1-6}$-alkyl)$_2$, —O—C(=O)—$C_{1-6}$-alkyl, —$C_{1-6}$-alkylene-O—C(=O)—$C_{1-6}$-alkyl, —O—C(=O)—O—$C_{1-6}$-alkyl, —$C_{1-6}$-alkylene-O—C(=O)—O—$C_{1-6}$-alkyl, —O—C(=O)—NH($C_{1-6}$-alkyl), —$C_{1-6}$-alkylene-O—C(=O)—NH($C_{1-6}$-alkyl), —O—C(=O)—N($C_{1-6}$-alkyl)$_2$, —$C_{1-6}$-alkylene-O—C(=O)—N($C_{1-6}$-alkyl)$_2$, —O—S(=O)$_2$—$NH_2$, —$C_{1-6}$-alkylene-O—S(=O)$_2$—$NH_2$, —O—S(=O)$_2$—NH($C_{1-6}$-alkyl), —$C_{1-6}$-alkylene-O—S(=O)$_2$—NH($C_{1-6}$-alkyl), —O—S(=O)$_2$—N($C_{1-6}$-alkyl)$_2$, —$C_{1-6}$-alkylene-O—S(=O)$_2$—N($C_{1-6}$-alkyl)$_2$, —$NH_2$, —NO, —$NO_2$, —$C_{1-6}$-alkylene-$NH_2$, —NH($C_{1-6}$-alkyl), —N(3-14-membered cycloalkyl)($C_{1-6}$-alkyl), —N($C_{1-6}$-alkyl)-$C_{1-6}$-alkylene-OH, —N(H)—$C_{1-6}$-alkylene-OH, —$C_{1-6}$-alkylene-NH($C_{1-6}$-alkyl), —N($C_{1-6}$-alkyl)$_2$, —$C_{1-6}$-alkylene-N($C_{1-6}$-alkyl)$_2$, —NH—C(=O)—$C_{1-6}$-alkyl, —$C_{1-6}$-alkylene-NH—C(=O)—$C_{1-6}$-alkyl, —NH—C(=O)—O—$C_{1-6}$-alkyl, —$C_{1-6}$-alkylene-NH—C(=O)—O—$C_{1-6}$-alkyl, —NH—C(=O)—$NH_2$, —$C_{1-6}$-alkylene-NH—C(=O)—$NH_2$, —NH—C(=O)—NH($C_{1-6}$-alkyl), —$C_{1-6}$-alkylene-NH—C(=O)—NH($C_{1-6}$-alkyl), —NH—C(=O)—N($C_{1-6}$-alkyl)$_2$, —$C_{1-6}$-alkylene-NH—C(=O)—N($C_{1-6}$-alkyl)$_2$, —N($C_{1-6}$-alkyl)-C(=O)—$C_{1-6}$-alkyl, —$C_{1-6}$-alkylene-N($C_{1-6}$-alkyl)-C(=O)—$C_{1-6}$-alkyl, —N($C_{1-6}$-alkyl)-C(=O)—O—$C_{1-6}$-alkyl, —$C_{1-6}$-alkylene-N($C_{1-6}$-alkyl)-C(=O)—O—$C_{1-6}$-alkyl, —N($C_{1-6}$-alkyl)-C(=O)—$NH_2$, —$C_{1-6}$-alkylene-N($C_{1-6}$-alkyl)-C(=O)—$NH_2$, —N($C_{1-6}$-alkyl)-C(=O)—NH($C_{1-6}$-alkyl), —$C_{1-6}$-alkylene-N($C_{1-6}$-alkyl)-C(=O)—NH($C_{1-6}$-alkyl), —N($C_{1-6}$-alkyl)-C(=O)—N($C_{1-6}$-alkyl)$_2$, —$C_{1-6}$-alkylene-N($C_{1-6}$-alkyl)-C(=O)—N($C_{1-6}$-alkyl)$_2$, —NH—S(=O)$_2$OH, —$C_{1-6}$-alkylene-NH—S(=O)$_2$OH, —NH—S(=O)$_2$—$C_{1-6}$-alkyl, —$C_{1-6}$-alkylene-NH—S(=O)$_2$—$C_{1-6}$-alkyl, —NH—S(=O)$_2$—O—$C_{1-6}$-alkyl, —$C_{1-6}$-alkylene-NH—S(=O)$_2$—O—$C_{1-6}$-alkyl, —NH—S(=O)$_2$—$NH_2$, —$C_{1-6}$-alkylene-NH—S(=O)$_2$—$NH_2$, —NH—S(=O)$_2$—NH($C_{1-6}$-alkyl), —$C_{1-6}$-alkylene-NH—S(=O)$_2$—NH($C_{1-6}$-alkyl), —NH—S(=O)$_2$N($C_{1-6}$-alkyl)$_2$, —$C_{1-6}$-alkylene-NH—S(=O)$_2$N($C_{1-6}$-alkyl)$_2$, —N($C_{1-6}$-alkyl)-S(=O)$_2$—OH, —$C_{1-6}$-alkylene-N($C_{1-6}$-alkyl)-S(=O)$_2$—OH, —N($C_{1-6}$-alkyl)-S(=O)$_2$—$C_{1-6}$-alkyl, —$C_{1-6}$-alkylene-N($C_{1-6}$-alkyl)-S(=O)$_2$—$C_{1-6}$-alkyl, —N($C_{1-6}$-alkyl)-S(=O)$_2$—O—$C_{1-6}$-alkyl, —$C_{1-6}$-alkylene-N($C_{1-6}$-alkyl)-S(=O)$_2$—O—$C_{1-6}$-alkyl, —N($C_{1-6}$-alkyl)-S(=O)$_2$—$NH_2$, —$C_{1-6}$-alkylene-N($C_{1-6}$-alkyl)-S(=O)$_2$—NH($C_{1-6}$-alkyl), —N($C_{1-6}$-alkyl)-S(=O)$_2$—NH($C_{1-6}$-alkyl), —$C_{1-6}$-alkylene-N($C_{1-6}$-alkyl)-S(=O)$_2$—N($C_{1-6}$-alkyl)$_2$, —N($C_{1-6}$-alkyl)-S(=O)$_2$—N($C_{1-6}$-alkyl)$_2$, —SH, =S, —$SF_5$, —$SCF_3$, —$SCF_2H$, —$SCFH_2$, —S—$C_{1-6}$-alkyl, —$C_{1-6}$-alkylene-S—$C_{1-6}$-alkyl, —S(=O)—$C_{1-6}$-alkyl, —$C_{1-6}$-alkylene-S(=O)—$C_{1-6}$-alkyl, —S(=O)$_2$—$C_{1-6}$-alkyl, —$C_{1-6}$-alkylene-S(=O)$_2$—$C_{1-6}$-alkyl, —S(=O)$_2$—OH, —$C_{1-6}$-alkylene-S(=O)$_2$—OH, —S(=O)$_2$—O—$C_{1-6}$-alkyl, —$C_{1-6}$-alkylene-S(=O)$_2$—O—$C_{1-6}$-alkyl, —S(=O)$_2$—$NH_2$, —$C_{1-6}$-alkylene-S(=O)$_2$—$NH_2$, —S(=O)$_2$—NH($C_{1-6}$-alkyl), —$C_{1-6}$-alkylene-S(=O)$_2$—NH($C_{1-6}$-alkyl), —S(=O)$_2$—N($C_{1-6}$-alkyl)$_2$, —$C_{1-6}$-alkylene-S(=O)$_2$—N($C_{1-6}$-alkyl)$_2$, 3-14-membered cycloalkyl, —$C_{1-6}$-alkylene-(3-14-membered cycloalkyl), 3 to 14-membered heterocycloalkyl, —$C_{1-6}$-alkylene-(3 to 14-membered heterocycloalkyl), -phenyl, —$C_{1-6}$-alkylene-phenyl, 5 to 14-membered heteroaryl, —$C_{1-6}$-alkylene-(5 to 14-membered heteroaryl), —O-(3-14-membered cycloalkyl), —O-(3 to 14-membered heterocycloalkyl), —O-phenyl, —O-(5 to 14-membered heteroaryl), —C(=O)-(3-14-membered cycloalkyl), —C(=O)-(3 to 14-membered heterocycloalkyl), —C(=O)-phenyl, —C(=O)-(5 to 14-membered heteroaryl), —S(=O)$_2$-(3-14-membered cycloalkyl), —S(=O)$_2$-(3 to 14-membered heterocycloalkyl), —S(=O)$_2$-phenyl, —S(=O)$_2$-(5 to 14-membered heteroaryl).

2. The compound per se, or for use according to Clause 1, wherein T represents —O— and U represents —$CR^5R^{5'}$—

3. The compound per se, or for use according to Clause 1, wherein T represents —$CR^5R^{5'}$— and U represents —O—.

4. The compound per se, or for use according to any one of Clauses 1 to 3, wherein Q represents —$NR^3R^4$.

5. The compound per se, or for use according to any one of Clauses 1 to 3, wherein Q represents —$OR^2$.

6. The compound per se, or for use according to any one of Clauses 1 to 5, wherein V represents 5-14-membered heteroaryl, unsubstituted, mono- or polysubstituted with substituents independently of one another selected from —F, —Cl, —Br, —I, —CN, —NO, —$NO_2$, =O, =S, —$SF_5$, —$R^Y$, —$OR^Y$, —OC(=O)$R^Y$, —$NR^YR^Z$, —$NR^YC(=O)R^Z$, —$SR^Y$, —S(=O)$R^Y$, —S(=O)$_2R^Y$, —C(=O)$R^Y$, —C(=O)$OR^Y$, or —C(=O)$NR^YR^Z$.

7. The compound per se, or for use according to Clause 6, wherein the 5-14-membered heteroaryl is not benzofuran.

8. The compound per se, or for use according to Clause 6 or 7, wherein the 5-14-membered heteroaryl is selected from benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and

[1,2,4]triazolo[4,3-a]pyrimidine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

9. The compound per se, or for use according to any one of Clauses 6 to 8, wherein the 5-14-membered heteroaryl is selected from the group consisting of furane, thiophene, imidazole, pyrazole, oxazole, isoxazole, thiazole, triazole, pyridine, isoquinoline, benzothiazole, pyridazine, pyrimidine, imidazopyridine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

10. The compound per se, or for use according to any one of Clauses 6 to 9, wherein the 5-14-membered heteroaryl is selected from the group consisting of furan-2-yl, furan-3-yl, thiophen-2-yl, thiophen-3-yl, pyrazol-5-yl, oxazol-5-yl, isoxazol-4-yl, thiazol-2-yl, thiazol-5-yl, 1,2,4-triazol-3-yl, 1,2,3-triazol-4-yl, pyridin-2-yl, pyridin-3-yl, pyridin-4-yl, isoquinolin-1-yl, isoquinolin-5-yl, benzo[d]thiazol-2-yl, pyridazin-3-yl, pyrimidin-5-yl, and imidazo[1,2-a]pyridin-6-yl; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

11. The compound per se, or for use according to any one of Clauses 1 to 5, wherein V represents 3-14-membered heterocycloalkyl, saturated or unsaturated, unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

12. The compound per se, or for use according to Clause 11, wherein the 3-14-membered heterocycloalkyl is selected from azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

13. The compound per se, or for use according to Clause 11 or 12, wherein the 3-14-membered heterocycloalkyl is tetrahydropyran or pyrrolidine; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

14. The compound per se, or for use according to any one of Clauses 11 to 13, wherein the 3-14-membered heterocycloalkyl is tetrahydropyran-4-yl or pyrrolidin-3-yl; in each case unsubstituted, mono- or polysubstituted with substituents independently of one another selected from —F, —Cl, —Br, —I, —CN, —NO, —NO$_2$, =O, =S, —SF$_5$, —R$^Y$, —OR$^Y$, —OC(=O)R$^Y$, —NR$^Y$R$^Z$, —NR$^Y$C(=O)R$^Z$, —SR$^Y$, —S(=O)R$^Y$, —S(=O)$_2$R$^Y$, —C(=O)R$^Y$, —C(=O)OR$^Y$, or —C(=O)NR$^Y$R$^Z$.

15. The compound per se, or for use according to any one of the preceding Clauses, wherein V is unsubstituted, mono- or polysubstituted with substituents independently of one another selected from —F, —Cl, —Br, —I, —CN, —C(=O)OH, —NH$_2$, —NO$_2$, —OH, =O, —SF$_5$;
—C$_{1-6}$-alkyl, saturated or unsaturated, unsubstituted, mono- or polysubstituted;
—C(=O)O—C$_{1-6}$-alkyl, saturated or unsaturated, unsubstituted, mono- or polysubstituted;
—NHC$_{1-6}$-alkyl, saturated or unsaturated, unsubstituted, mono- or polysubstituted;
—N(C$_{1-6}$-alkyl)$_2$, saturated or unsaturated, unsubstituted, mono- or poly substituted;
—O—C$_{1-6}$-alkyl, saturated or unsaturated, unsubstituted, mono- or polysubstituted;
—S(=O)$_2$—C$_{1-6}$-alkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —C$_1$-C$_6$-alkylene- or —C$_1$-C$_6$-heteroalkylene-, in each case saturated or unsaturated, unsubstituted, mono- or polysubstituted; or
3-14-membered heterocycloalkyl, saturated or unsaturated, unsubstituted, mono- or polysubstituted;
wherein said 3-14-membered heterocycloalkyl is optionally connected through —C$_1$-C$_6$-alkylene- or —C$_1$-C$_6$-heteroalkylene-, in each case saturated or unsaturated, unsubstituted, mono- or polysubstituted.

16. The compound per se, or for use according to any one of the preceding Clauses, wherein V is unsubstituted, mono- or polysubstituted with substituents independently of one another selected from
—OH, —F, —Cl, —Br, —I, —SH, —CF$_3$, —CHF$_2$, —CH$_2$F, —OCF$_3$, —OCHF$_2$, —OCH$_2$F, SF$_5$, —CN, —NO$_2$, —C(=O)OH, —NH$_2$, —N(CH$_3$)$_2$, -cyclopropyl, or —O-cyclopropyl; preferably selected from —OH, —F, —Cl, —Br, —I, —SH, —CF$_3$, —CHF$_2$, —CH$_2$F, —OCF$_3$, —OCHF$_2$, —OCH$_2$F, SF$_5$, —CN, —NO$_2$, —C(=O)OH, —NH$_2$, or —N(CH$_3$)$_2$;
—C$_{1-6}$-alkyl, saturated or unsaturated, unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, —C(=O)NH$_2$, and -cyclopropyl; preferably selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

—C$_{1-6}$-heteroalkyl, saturated or unsaturated, unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

—OC$_{1-6}$-alkyl, unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

—O(C=O)C$_{1-6}$-alkyl, unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

—C(=O)OC$_{1-6}$-alkyl, unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

3-14-membered cycloalkyl selected from the group consisting of cyclopropyl, cyclobutyl, cyclopentyl, cyclohexyl and cycloheptyl; in each case unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$;

3-14-membered heterocycloalkyl selected from the group consisting of azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin, in each case unsubstituted, mono- or polysubstituted with substituents independently of one another, selected from the group consisting of —F, —Cl, —Br, —I, —C$_{1-6}$-alkyl, C$_{2-6}$-alkenyl, —C$_{2-6}$-alkynyl, —OH, =O, —SH, =S, —CN, —CF$_3$, —CHF$_2$, —CH$_2$F, —OCF$_3$, —OCHF$_2$, —OCH$_2$F, SF$_5$, —NO$_2$, —C(=O)OH, —NH$_2$, C(=O)CHF$_2$, and —C(=O)NH$_2$.

17. The compound per se, or for use according to any one of the preceding Clauses, wherein V is unsubstituted, mono- or polysubstituted with substituents independently of one another selected from —F, —Cl, —CN, —OH, =O, —C$_{1-6}$-alkyl, —CHF$_2$, —CF$_3$, —C$_{1-6}$-alkylene-NH$_2$, —C$_{1-6}$-alkylene-NHC(=O)O—C$_{1-6}$-alkyl, —C$_{1-6}$-alkylene-OH, —C$_{1-6}$-alkylene-NHC(=O)—O—C$_{1-6}$-alkyl, —C(=O)O—C$_{1-6}$-alkyl, —N(C$_{1-6}$-alkyl)$_2$, —OC$_{1-6}$-alkyl, —OCF$_3$, —O—C$_{1-6}$-alkylene-N(C$_{1-6}$-alkyl)$_2$, —S(=O)$_2$—C$_{1-6}$-alkyl, -azetidine, —C$_{1-6}$-alkylene-O-tetrahydropyran, or -piperazine substituted with —C$_{1-6}$-alkyl; or represents oxetanyl, unsubstituted, mono- or polysubstituted.

18. The compound per se, or for use according to any one of the preceding Clauses, wherein V is
   (i) unsubstituted;
   (ii) monosubstituted;
   (iii) disubstituted;
   (iv) trisubstituted; or
   (v) tetrasubstituted.

19. The compound per se, or for use according to any one of the preceding Clauses, wherein R$^1$ represents
   —H, —F, —Cl, —Br, —I;
   —C$_{1-6}$-alkyl, saturated or unsaturated, unsubstituted, mono- or polysubstituted; —O—C$_{1-6}$-alkyl, saturated or unsaturated, unsubstituted, mono- or poly substituted;
   —C(=O)C$_{1-6}$-alkyl, saturated or unsaturated, unsubstituted, mono- or polysubstituted;
   —C(=O)OC$_{1-6}$-alkyl, saturated or unsaturated, unsubstituted, mono- or polysubstituted;
   —C(=O)NHC$_{1-6}$-alkyl, saturated or unsaturated, unsubstituted, mono- or polysubstituted;
   —C(=O)N(C$_{1-6}$-alkyl)$_2$, saturated or unsaturated, unsubstituted, mono- or polysubstituted;
   —S(=O)C$_{1-6}$-alkyl, saturated or unsaturated, unsubstituted, mono- or polysubstituted;
   —S(=O)$_2$—C$_{1-6}$-alkyl, saturated or unsaturated, unsubstituted, mono- or polysubstituted;
   —C$_1$-C$_6$-heteroalkyl, saturated or unsaturated, unsubstituted, mono- or polysubstituted; or
   3-14-membered cycloalkyl, saturated or unsaturated, unsubstituted, mono- or polysubstituted; wherein said 3-14-membered cycloalkyl is optionally connected through —C$_1$-C$_6$-alkylene- or —C$_1$-C$_6$-heteroalkylene-, in each case saturated or unsaturated, unsubstituted, mono- or polysubstituted.

20. The compound per se, or for use according to any one of the preceding Clauses, wherein R$^1$ represents —H, —F, —Cl, —Br, —I, —C$_{1-6}$-alkyl, —O—C$_{1-6}$-alkyl, —C$_{1-6}$-alkylene-O—C$_{1-6}$-alkyl, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, —C$_{1-6}$-alkylene-N(C$_{1-6}$-alkyl)-C$_{1-6}$-alkylene-CF$_3$, —C(=O)C$_{1-6}$-alkyl, —C(=O)OC$_{1-6}$-alkyl, —C(=O)NHC$_{1-6}$-alkyl, —C(=O)N(C$_{1-6}$-alkyl)$_2$, —S(=O)—

$C_{1-6}$-alkyl, —S(=O)$_2$—$C_{1-6}$-alkyl, —O—$C_{1-6}$-alkyl, -cyclopropyl unsubstituted, cyclobutyl unsubstituted, cyclopentyl unsubstituted or cyclohexyl unsubstituted.

21. The compound per se, or for use according to any one of the preceding Clauses, wherein $R^1$ represents —H, —$C_{1-6}$-alkyl, —$C_{1-6}$-alkylene-O—$C_{1-6}$-alkyl, —CH$_2$F, —CHF$_2$, —CF$_3$, -cyclopentyl, unsubstituted, or -cyclopropyl, unsubstituted; preferably wherein $R^1$ represents —H, —$C_{1-6}$-alkyl, —$C_{1-6}$-alkylene-O—$C_{1-6}$-alkyl, —CH$_2$F, —CHF$_2$, —CF$_3$, or -cyclopentyl, unsubstituted.

22. The compound per se, or for use according to any one of the preceding Clauses, wherein $R^1$ represents —CH$_2$F, —CHF$_2$, —CH$_3$, or -cyclopropyl, unsubstituted; preferably wherein $R^1$ represents —CH$_2$F, —CHF$_2$, or —CH$_3$.

23. The compound per se, or for use according to any one of the preceding Clauses, wherein $R^2$ represents
—H;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted; or
3-14-membered heterocycloalkyl, saturated or unsaturated, unsubstituted, mono- or polysubstituted;
wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted.

24. The compound per se, or for use according to any one of the preceding Clauses, wherein $R^2$ represents —H, —$C_{1-6}$-alkyl, —$C_{1-6}$-alkylene-O—$C_{1-6}$-alkyl, —$C_{1-6}$-alkylene-NH($C_{1-6}$-alkyl), —$C_{1-6}$-alkylene-N($C_{1-6}$-alkyl)$_2$, —CF$_3$, —CF$_2$H, —CFH$_2$, —CF$_2$Cl, —CFCl$_2$, —$C_{1-6}$-alkylene-CF$_3$, —$C_{1-6}$-alkylene-CF$_2$H, —$C_{1-6}$-alkylene-CFH$_2$, —$C_{1-6}$-alkylene-NH—$C_{1-6}$-alkylene-CF$_3$, or —$C_{1-6}$-alkylene-N($C_{1-6}$-alkyl)-$C_{1-6}$-alkylene-CF$_3$.

25. The compound per se, or for use according to any one of the preceding Clauses, wherein $R^2$ represents —H or —$C_{1-6}$-alkyl.

26. The compound per se, or for use according to any one of the preceding Clauses, wherein $R^3$ represents
—H;
—OH;
—$C_1$-$C_6$-alkyl, saturated or unsaturated, unsubstituted, mono- or polysubstituted; or
—$C_1$-$C_6$-heteroalkyl, saturated or unsaturated, unsubstituted, mono- or polysubstituted.

27. The compound per se, or for use according to any one of the preceding Clauses, wherein $R^3$ represents —H, —OH, —$C_{1-6}$-alkyl, —$C_{1-6}$-alkylene-OH, —$C_{1-6}$-alkylene-O—$C_{1-6}$-alkyl, —$C_{1-6}$-alkylene-NH$_2$, —$C_{1-6}$-alkylene-NH($C_{1-6}$-alkyl), —$C_{1-6}$-alkylene-N($C_{1-6}$-alkyl)$_2$, —CF$_3$, —CF$_2$H, —CFH$_2$, —CF$_2$Cl, —CFCl$_2$, —$C_{1-6}$-alkylene-CF$_3$, —$C_{1-6}$-alkylene-CF$_2$H, —$C_{1-6}$-alkylene-CFH$_2$, —$C_{1-6}$-alkylene-NH—$C_{1-6}$-alkylene-CF$_3$, or —$C_{1-6}$-alkylene-N($C_{1-6}$-alkyl)-$C_{1-6}$-alkylene-CF$_3$.

28. The compound per se, or for use according to any one of the preceding Clauses, wherein $R^3$ represents —H, —OH, or —$C_{1-6}$-alkyl, saturated, unsubstituted or monosubstituted with —OH.

29. The compound per se, or for use according to any one of the preceding Clauses, wherein $R^4$ represents
—H;
—S(=O)$C_{1-6}$-alkyl, saturated or unsaturated, unsubstituted, mono- or polysubstituted;
—S(=O)$_2$—$C_{1-6}$-alkyl, saturated or unsaturated, unsubstituted, mono- or polysubstituted;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted;
3-14-membered heterocycloalkyl, saturated or unsaturated, unsubstituted, mono- or polysubstituted;
wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;
6-14-membered aryl, unsubstituted, mono- or polysubstituted; wherein said 6-14-membered aryl is optionally connected through —$C_1$-$C_6$-alkylene- or —$C_1$-$C_6$-heteroalkylene-, in each case saturated or unsaturated, unsubstituted, mono- or poly substituted; or
5-14-membered heteroaryl, unsubstituted, mono- or polysubstituted; wherein said 5-14-membered heteroaryl is optionally connected through —$C_1$-$C_6$-alkylene- or —$C_1$-$C_6$-heteroalkylene-, in each case saturated or unsaturated, unsubstituted, mono- or poly substituted.

30. The compound per se, or for use according to any one of the preceding Clauses, wherein $R^4$ represents
—S(=O)$_2$$C_{1-6}$-alkyl, saturated or unsaturated, unsubstituted, mono- or polysubstituted with substituents independently of one another selected from the group consisting of —F, —Cl, —$C_{1-6}$-alkyl, —$C_{1-6}$-alkylene-CF$_3$, —OH, =O, —O$C_{1-6}$-alkyl, —$C_{1-6}$-alkylene-OH, —$C_{1-6}$-alkylene-O—$C_{1-6}$-alkyl, —NH$_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-NH$_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-CF$_3$, —C(=O)—$C_{1-6}$-alkyl, —C(=O)OH, —C(=O)O—$C_{1-6}$-alkyl, —C(=O)O—$C_{1-6}$-alkylene-CF$_3$, —C(=O)NH$_2$, —C(=O)NH($C_{1-6}$-alkyl), —C(=O)N($C_{1-6}$-alkyl)$_2$, —S(=O)$_2$$C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;
—S(=O)$_2$(3-14-membered cycloalkyl), wherein said 3-14-membered cycloalkyl is selected from the group consisting of cyclopropyl, cyclobutyl, cyclopentyl, cyclohexyl, and cycloheptyl, in each case saturated or unsaturated, unsubstituted, mono- or polysubstituted with substituents independently of one another selected from the group consisting of —F, —Cl, —$C_{1-6}$-alkyl, —$C_{1-6}$-alkylene-$CF_3$, —OH, =O, —O$C_{1-6}$-alkyl, —$C_{1-6}$-alkylene-OH, —$C_{1-6}$-alkylene-O—$C_{1-6}$-alkyl, —$NH_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —C(=O)N($C_{1-6}$-alkyl)$_2$, —S(=O)$_2$ $C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;

—$C_{1-6}$-alkyl, saturated or unsaturated, unsubstituted, mono- or polysubstituted with substituents independently of one another selected from the group consisting of —F, —Cl, —$C_{1-6}$-alkyl, —$C_{1-6}$-alkylene-$CF_3$, —OH, =O, —O$C_{1-6}$-alkyl, —$C_{1-6}$-alkylene-OH, —$C_{1-6}$-alkylene-O—$C_{1-6}$-alkyl, —$NH_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —C(=O)N($C_{1-6}$-alkyl)$_2$, —S(=O)$_2$$C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;

3-14-membered cycloalkyl or —$C_{1-6}$-alkylene-(3-14-membered cycloalkyl), wherein —$C_{1-6}$-alkylene- is unsubstituted or monosubstituted with —OH, wherein said 3-14-membered cycloalkyl is selected from the group consisting of cyclopropyl, cyclobutyl, cyclopentyl, cyclohexyl, and cycloheptyl, in each case saturated or unsaturated, in each case unsubstituted, mono- or polysubstituted with substituents independently of one another selected from the group consisting of —F, —Cl, —$C_{1-6}$-alkyl, —$C_{1-6}$-alkylene-$CF_3$, —OH, =O, —O$C_{1-6}$-alkyl, —$C_{1-6}$-alkylene-OH, —$C_{1-6}$-alkylene-O—$C_{1-6}$-alkyl, —$NH_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —C(=O)N($C_{1-6}$-alkyl)$_2$, —S(=O)$_2$$C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;

3-14-membered heterocycloalkyl or —$C_{1-6}$-alkylene-(3-14-membered heterocycloalkyl), wherein —$C_{1-6}$-alkylene- is unsubstituted or monosubstituted with —OH, wherein said 3-14-membered heterocycloalkyl in each case is selected from the group consisting of azepane, 1,4-oxazepane, azetane, azetidine, aziridine, azocane, diazepane, dioxane, dioxolane, dithiane, dithiolane, imidazolidine, isothiazolidine, isoxalidine, morpholine, oxazolidine, oxepane, oxetane, oxirane, piperazine, piperidine, pyrazolidine, pyrrolidine, quinuclidine, tetrahydrofuran, tetrahydropyran, tetrahydrothiopyran, thiazolidine, thietane, thiirane, thiolane, thiomorpholine, indoline, dihydrobenzofuran, dihydrobenzothiophene, 1,1-dioxothiacyclohexane, 2-azaspiro[3.3]heptane, 2-oxaspiro[3.3]heptane, 7-azaspiro[3.5]nonane, 8-azabicyclo[3.2.1]octane, 9-azabicyclo[3.3.1]nonane, hexahydro-1H-pyrrolizine, hexahydrocyclopenta[c]pyrrole, octahydrocyclopenta[c]pyrrole, and octahydropyrrolo[1,2-a]pyrazin; in each case unsubstituted, mono- or polysubstituted with substituents independently of one another selected from the group consisting of —F, —$C_1$, —$C_{1-6}$-alkyl, —$C_{1-6}$-alkylene-$CF_3$, —OH, =O, —O$C_{1-6}$-alkyl, —$C_{1-6}$-alkylene-OH, —$C_{1-6}$-alkylene-O—$C_{1-6}$-alkyl, —$NH_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkylene-$CF_3$, —C(=O)$NH_2$, —C(=O)NH($C_{1-6}$-alkyl), —C(=O)N($C_{1-6}$-alkyl)$_2$, —S(=O)$_2$$C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;

-phenyl unsubstituted, mono- or polysubstituted with substituents independently of one another selected from the group consisting of —F, —Cl, —CN, —$C_{1-6}$-alkyl, —$C_{1-6}$-alkylene-$CF_3$, —OH, =O, —O$C_{1-6}$-alkyl, —$C_{1-6}$-alkylene-OH, —$C_{1-6}$-alkylene-O—$C_{1-6}$-alkyl, —$NH_2$, —NH$C_{1-6}$-alkyl, —N($C_{1-6}$-alkyl)$_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl)$_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —C(=O)N($C_{1-6}$-alkyl)$_2$, —S(=O)$_2$$C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted;

5-14-membered heteroaryl or —$C_{1-6}$-alkylene-(5-14-membered heteroaryl), wherein —$C_{1-6}$-alkylene- is unsubstituted or monosubstituted with —OH, wherein said 5-14-membered heteroaryl in each case is selected from the group consisting of benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and [1,2,4]triazolo[4,3-a]pyrimidine; in each case unsubstituted, mono- or polysubstituted with substituents independently of one another selected from the group consisting of —F, —Cl, —CN, —$C_{1-6}$-alkyl, —$C_{1-6}$-alkylene-$CF_3$, —OH, =O, —$OC_{1-6}$-alkyl, —$C_{1-6}$-alkylene-OH, —$C_{1-6}$-alkylene-O—$C_{1-6}$-alkyl, —$NH_2$, —$NHC_{1-6}$-alkyl, —$N(C_{1-6}$-alkyl$)_2$, —NHC(=O)O—$C_{1-6}$-alkyl, —N($C_{1-6}$-alkyl)C(=O)O—$C_{1-6}$-alkyl, —$C_{1-6}$-alkylene-NHC(=O)O—$C_{1-6}$-alkyl, —$C_{1-6}$-alkylene-$NH_2$, —$C_{1-6}$-alkylene-NH—$C_{1-6}$-alkyl, —$C_{1-6}$-alkylene-N($C_{1-6}$-alkyl$)_2$, —$C_{1-6}$-alkylene-NH—$C_{1-6}$-alkylene-$CF_3$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —C(=O)N($C_{1-6}$-alkyl$)_2$, —S(=O)$_2C_{1-6}$-alkyl, -phenyl, —$C_{1-6}$-alkylene-phenyl, 3-14-membered heterocycloalkyl, saturated or unsaturated, unsubstituted; and 5-14-membered heteroaryl, unsubstituted.

31. The compound per se, or for use according to any one of the preceding Clauses, wherein $R^4$ represents
—H;
—S(=O)$_2C_{1-6}$-alkyl, saturated, unsubstituted, monosubstituted or polysubstituted with —F;
—S(=O)$_2$(3-14-membered cycloalkyl), saturated, unsubstituted;
—$C_{1-6}$-alkyl, saturated, unsubstituted, monosubstituted or disubstituted with substituents independently of one another selected from the group consisting of —OH, —$OC_{1-6}$-alkyl, —N($C_{1-6}$-alkyl$)_2$, —$C_{1-6}$-alkylene-$NH_2$, —$C_{1-6}$-alkylene-NH—$C_{1-6}$-alkyl, -phenyl unsubstituted;
3-14-membered cycloalkyl or —$C_{1-6}$-alkylene-(3-14-membered cycloalkyl), wherein —$C_{1-6}$-alkylene- is unsubstituted or monosubstituted with —OH, wherein said 3-14-membered cycloalkyl is saturated, unsubstituted, monosubstituted or disubstituted with substituents independently of one another selected from the group consisting of —$C_{1-6}$-alkyl, —$C_{1-6}$-alkylene-$NH_2$, —$C_{1-6}$-alkylene-NH—$C_{1-6}$-alkylene-$CF_3$, —$C_{1-6}$-alkylene-OH, —$C_{1-6}$-alkylene-NHC(=O)O—$C_{1-6}$-alkyl, —OH, —$OC_{1-6}$-alkyl, —$NH_2$, —N($C_{1-6}$-alkyl$)_2$, —NHC(=O)O—$C_{1-6}$-alkyl;
3-14-membered heterocycloalkyl or —$C_{1-6}$-alkylene-(3-14-membered heterocycloalkyl), wherein —$C_{1-6}$-alkylene- is unsubstituted or monosubstituted with —OH, wherein said 3-14-membered heterocycloalkyl in each case is selected from azetane, 1,4-oxazepane, pyrrolidine, piperidine, azepane, diazepane, tetrahydrofuran, tetrahydropyran, oxetane, morpholine, piperazine, hexahydrocyclopenta[c]pyrrole, octahydrocyclopenta[c]pyrrole, octahydropyrrolo[1,2-a]pyrazin, 8-azabicyclo[3.2.1]octane, 9-azabicyclo-[3.3.1]nonane, quinuclidine, hexahydro-1H-pyrrolizine, 2-oxaspiro[3.3]heptane, 2-azaspiro[3.3]heptane, 7-azaspiro[3.5]nonane, 1,1-dioxothiacyclohexane, in each case unsubstituted, mono- or polysubstituted with substituents independently of one another selected from the group consisting of —F, —OH, =O, —$C_{1-6}$-alkyl, —$C_{1-6}$-alkylene-$CF_3$, —$C_{1-6}$-alkylene-OH, —$C_{1-6}$-alkylene-O—$C_{1-6}$-alkyl, —$NH_2$, —N($C_{1-6}$-alkyl$)_2$, —$C_{1-6}$-alkylene-$NH_2$, —$C_{1-6}$-alkylene-N($C_{1-6}$-alkyl$)_2$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —S(=O)$_2C_{1-6}$-alkyl, oxetanyl, pyrimidinyl, —$C_{1-6}$-alkylene-phenyl;
-phenyl unsubstituted;
5-14-membered heteroaryl or —$C_{1-6}$-alkylene-(5-14-membered heteroaryl), wherein —$C_{1-6}$-alkylene- is unsubstituted or monosubstituted with —OH, wherein said 5-14-membered heteroaryl in each case is selected from the group consisting of pyridine, pyridazine, pyrazine, pyrazole, isoxazole, triazole, and [1,2,4]triazolo[4,3-a]pyrimidine, in each case unsubstituted, monosubstituted or disubstituted with substituents independently of one another selected from the group consisting of —$C_{1-6}$-alkyl, —OH.

32. The compound per se, or for use according to any one of the preceding Clauses, wherein $R^3$ and $R^4$ together form a 5- or 6-membered heterocycle containing 1 or 2 heteroatoms selected from N, O and S, saturated or unsaturated, unsubstituted or mono- or poly substituted.

33. The compound per se, or for use according to any one of the preceding Clauses, wherein $R^3$ and $R^4$ together form a heterocycle selected from the group consisting of pyrrolidine, piperidine, morpholine, and piperazine, in each case unsubstituted, mono- or polysubstituted with substituents independently of one another selected from the group consisting of —$C_{1-6}$-alkyl, —$NH_2$, —$NHCH_3$, —N($CH_3$)$_2$, —C(=O)NH—$C_{1-6}$-alkyl, —C(=O)N($C_{1-6}$-alkyl$)_2$, —C(=O)O—$C_{1-6}$-alkyl, —NHC(=O)O—$C_{1-6}$-alkyl, -pyridyl unsubstituted, and 1,2,4-oxadiazole unsubstituted or monosubstituted with —$C_{1-6}$-alkyl.

34. The compound per se, or for use according to any one of the preceding Clauses, wherein $R^3$ and $R^4$ together form a
pyrrolidine ring, unsubstituted or monosubstituted with —N($CH_3$)$_2$;
piperidine ring, unsubstituted or monosubstituted with a substituent selected from the group consisting of —$C_{1-6}$-alkyl, —$NH_2$, —N($CH_3$)$_2$, —C(=O)NH—$C_{1-6}$-alkyl, —C(=O)O—$C_{1-6}$-alkyl, —NHC(=O)O—$C_{1-6}$-alkyl, and 1,2,4-oxadiazole unsubstituted or monosubstituted with —$C_{1-6}$-alkyl;
morpholine ring, unsubstituted; or
piperazine ring, unsubstituted or N-substituted with a substituent selected from the group consisting of —$C_{1-6}$-alkyl and -pyridyl unsubstituted.

35. The compound per se, or for use according to one any one of the preceding Clauses, wherein $R^5$ and $R^{5'}$ independently of one another represent
—H;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or polysubstituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted.

36. The compound per se, or for use according to any one of the preceding Clauses, wherein $R^5$ and $R^{5'}$ independently of one another represent —H, —$C_1$-$C_6$-alkyl, or —$C_1$-$C_6$-alkylene-N($C_1$-$C_6$-alkyl$)_2$.

37. The compound per se, or for use according to any one of the preceding Clauses, wherein at least one of $R^5$ and $R^{5'}$ does not represent —H.

38. The compound per se, or for use according to any one of the preceding Clauses, wherein $R^6$, $R^7$ and $R^8$ independently of one another represent
    —H;
    —F, —Cl, —Br, —I, —OH, —SH, —SF$_5$, —CN, —NO$_2$, —C(═O)OH, —NH$_2$;
    —C$_{1-6}$-alkyl, saturated or unsaturated, unsubstituted, mono- or polysubstituted;
    —O—C$_{1-6}$-alkyl, saturated or unsaturated, unsubstituted, mono- or polysubstituted;
    —NHC$_{1-6}$-alkyl, saturated or unsaturated, unsubstituted, mono- or polysubstituted;
    —N(C$_{1-6}$-alkyl)$_2$, saturated or unsaturated, unsubstituted, mono- or poly substituted;
    —C(═O)OC$_{1-6}$-alkyl, saturated or unsaturated, unsubstituted, mono- or polysubstituted;
    —OC(═O)C$_{1-6}$-alkyl, saturated or unsaturated, unsubstituted, mono- or polysubstituted;
    —C$_{1-6}$-heteroalkyl, saturated or unsaturated, unsubstituted, mono- or poly substituted.

39. The compound per se, or for use according to any one of the preceding Clauses, wherein $R^6$, $R^7$ and $R^8$ independently of one another represent
    —H, —F, —Cl, —Br, —I, —OH, —SH, —SF$_5$, —CN, —NO$_2$, —C(═O)OH, —NH$_2$,
    —C$_{1-6}$-alkyl, —CF$_3$, —CHF$_2$, —CH$_2$F,
    —O—C$_{1-6}$-alkyl, —OCF$_3$, —OCHF$_2$, —OCH$_2$F,
    —NHC$_{1-6}$-alkyl unsubstituted or substituted with one or more substituents independently of one another selected from —OH, ═O, —F, —Cl, —Br, —I, —SH, ═S, —CN, —CF$_3$, —CHF$_2$, —CH$_2$F, —OCF$_3$, —OCHF$_2$, —OCH$_2$F, SF$_5$, —NO$_2$, —C(═O)OH, —NH$_2$, and —C(═O)NH$_2$;
    —N(C$_{1-6}$-alkyl)$_2$ unsubstituted or substituted with one or more substituents independently of one another selected from —OH, ═O, —F, —Cl, —Br, —I, —SH, ═S, —CN, —CF$_3$, —CHF$_2$, —CH$_2$F, —OCF$_3$, —OCHF$_2$, —OCH$_2$F, SF$_5$, —NO$_2$, —C(═O)OH, —NH$_2$, and —C(═O)NH$_2$;
    —C(═O)OC$_{1-6}$-alkyl unsubstituted or substituted with one or more substituents independently of one another selected from —OH, ═O, —F, —Cl, —Br, —I, —SH, ═S, —CN, —CF$_3$, —CHF$_2$, —CH$_2$F, —OCF$_3$, —OCHF$_2$, —OCH$_2$F, SF$_5$, —NO$_2$, —C(═O)OH, —NH$_2$, and —C(═O)NH$_2$;
    —OC(═O)C$_{1-6}$-alkyl unsubstituted or substituted with one or more substituents independently of one another selected from —OH, ═O, —F, —Cl, —Br, —I, —SH, ═S, —CN, —CF$_3$, —CHF$_2$, —CH$_2$F, —OCF$_3$, —OCHF$_2$, —OCH$_2$F, SF$_5$, —NO$_2$, —C(═O)OH, —NH$_2$, and —C(═O)NH$_2$; or
    —C$_{1-6}$-heteroalkyl unsubstituted or substituted with one or more substituents independently of one another selected from —OH, ═O, —F, —Cl, —Br, —I, —SH, ═S, —CN, —CF$_3$, —CHF$_2$, —CH$_2$F, —OCF$_3$, —OCHF$_2$, —OCH$_2$F, SF$_5$, —NO$_2$, —C(═O)OH, —NH$_2$, and —C(═O)NH$_2$.

40. The compound per se, or for use according to any one of the preceding Clauses, wherein $R^6$ represents —H, —F, —Cl, —CN, or —C$_1$-C$_6$-alkyl.

41. The compound per se, or for use according to any one of the preceding Clauses, wherein $R^6$ does not represent —H.

42. The compound per se, or for use according to any one of the preceding Clauses, wherein $R^7$ represents —H, —F, —Cl, —CN, or —C$_1$-C$_6$-alkyl.

43. The compound per se, or for use according to any one of the preceding Clauses, wherein $R^7$ does not represent —H.

44. The compound per se, or for use according to any one of the preceding Clauses, wherein $R^5$ represents —H, —F, —Cl, —CN, or —C$_1$-C$_6$-alkyl.

45. The compound per se, or for use according to any one of the preceding Clauses, wherein $R^8$ does not represent —H.

46. The compound per se, or for use according to any one of the preceding Clauses, wherein
    (i) $R^6$, $R^7$ and $R^8$ each represent —H; or
    (ii) two of $R^6$, $R^7$ and $R^8$ represent —H and the other of $R^6$, $R^7$ and $R^8$ represents —F, —Cl, —CN, or —CH$_3$; or
    (iii) one of $R^6$, $R^7$ and $R^8$ represents —H and the other of $R^6$, $R^7$ and $R^8$ independently of one another represent —F, —Cl, —CN, or —CH$_3$.

47. The compound per se, or for use according to any one of the preceding Clauses, which is selected from the group consisting of cpd 001 to cpd 207 as mentioned above and the physiologically acceptable salts thereof.

48. The compound per se, or for use according to any one of the preceding Clauses, wherein the pain is selected from nociceptive pain, inflammatory pain, and neuropathic pain.

49. The compound per se, or for use according to any one of the preceding Clauses, wherein the pain is postoperative pain.

50. A compound of formula (I), a stereo-isomeric form, a physiologically acceptable salt, solvate and/or polymorph thereof, as defined in any one of the preceding Clauses, wherein
    (a) Q represents —OR$^2$; and
        (a-1) $R^1$ represents —CH$_2$F, —CHF$_2$, or —CF$_3$; and/or
        (a-2) at least one of $R^5$ and $R^{5'}$ does not represent —H; and/or
        (a-3) $R^6$ does not represent —H; and/or
        (a-4) $R^5$ does not represent —H;
    or
    (b) Q represents —NR$^3$R$^4$; and
        (b-1) with the proviso that the following compounds and their salts are excluded

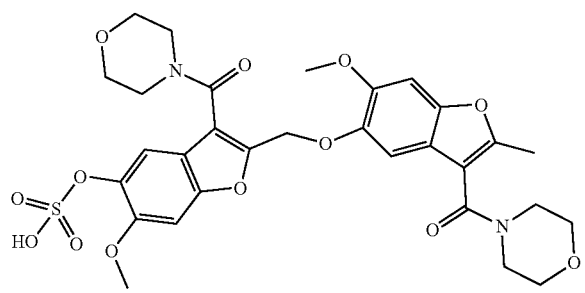

-continued

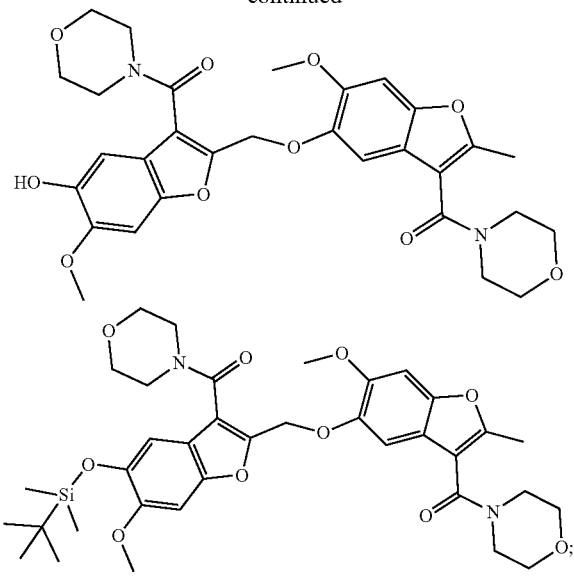

and/or
(b-2) $R^1$ represents —$CH_2F$, —$CHF_2$, or —$CF_3$, —CN, -propyl, or -cyclopropyl; and/or
(b-3) at least one of $R^5$ and $R^{5'}$ does not represent —H; and/or
(b-4) $R^3$ represents —H.

51. A pharmaceutical composition or a medicament comprising a compound according to any one of the preceding Clauses.

EXAMPLES

The following examples are provided for the purpose of illustrating the invention and by no means should be interpreted to limit the scope of the invention.

Representative compounds of the present invention can be synthesized in accordance with the general synthetic methods described below and illustrated in the schemes that follow. Since the schemes are an illustration, the invention should not be construed as being limited by the specific chemical reaction and specific conditions described in the schemes and examples. The various starting material used in the schemes are commercially available or may be prepared by methods well within the skill of persons versed in the art. The variables are as defined herein and within the skill of persons versed in the art.

Abbreviations used in the instant specification, particularly in the schemes and examples, are as follows: ACN—acetonitrile, AcOH—Acetic acid, ADDP—1,1'-(Azodicarbonyl)dipiperidide, aq.—Aqueous, AIBN—Azobisisobutyronitrile, CAN—Ceric ammonium nitrate, COMU—(1-Cyano-2-ethoxy-2-oxoethylidenaminooxy)dimethylamino-morpholino-carbenium, hexafluorophosphate, DABCO—1,4-diazabicyclo[2,2,2]octane, DAST—Diethylaminosulfur trifluoride, DBU—1,8-Diazabicyclo[5.4.0]undec-7-ene, DCC—N,N'-dicyclohexylcarbodiimide, DCM—Dichloromethane, DEAD—Diethyl azodicarboxylate, DIA—Diastereomer, DIAD—Diisopropyl azodicarboxylate, DEA—Diethylamine, DIPEA—Diisopropyl-ethyl amine, DME—1,2-Dimethoxyethane, DMF—N,N-Dimethylformamide, DMSO—Dimethylsulfoxide, DTBAD—tert-Butylazodicarboxylate, EDCI or EDC—1-Ethyl-3-(3-dimethylaminopropyl)carbodiimide, En—Enantiomer, Et2O—Diethyl ether, EtOH—Ethanol, EtOAc—Ethyl acetate, Eq.—Equivalent, FA—Formic acid, FCC—Flash column chromatography, h—Hour, HATU—O-(7-Azabenzotriazol-1-yl)-N,N,N',N'-tetramethyluronium hexafluorophosphate, HPLC—High performance liquid chromatography, IPA—isopropyl alcohol, LAH—Lithiumaluminiumhydrid, LG—Leaving group, MeOH—methanol, MgSO4—Magnesium sulfate, min.—Minute, Na2SO4—Sodium sulfate, NBS—N-Bromosuccinimide, NMP—1-Methyl-2-pyrrolidinone, Pd(PPh3)4—Tetrakis-(triphenylphosphine)-palladium(0), Pd2(dba)3—Tris(dibenzylideneacetone)dipalladium, Pet ether—Petroleum ether, PPh3—Triphenylphospine, PS-DIEA—Diisoprpropyl-ethyl amine supported on Poly-Styrene, PS—PPh3—Triphenylphospine supported on Poly-Styrene, PyBop—Benzotriazol-1-yl-oxytripyrrolidinophosphonium hexafluorophosphate, PTSA—p-Toluenesulfonic acid, RF: ratio of frontiers, RM—Reaction mixture, RP—Reverse phase, RT—Room temperature, sat.—Saturated, SEM—[2-(Trimethylsilyl)ethoxy]methyl acetal, SFC—Supercritical fluid chromatography, SPE—Solid Phase Extraction, TBDMS—Tert-Butyldimethylsilyl ether, TBAF—Tetrabutylammonium fluoride hydrate, TBAI—Tetrabutylammonium iodide, TEA—Triethylamine, THF—Tetrahydrofuran, TFA—Trifluoroacetic acid, TLC—thin layer chromatography, TPP—triphenyl phosphine, IPA—isopropyl alcohol, TMS—trimethyl silyl, T3P—Propylphosphonic anhydride, The compounds of interest having a structure according to the general formula (A) and all other formulas described herein and embodiments thereof can be prepared as outlined in the general chemical scheme 1.

Scheme 1: all R1, R2, R3, R4 and R5 are as described for the compounds of the present invention.

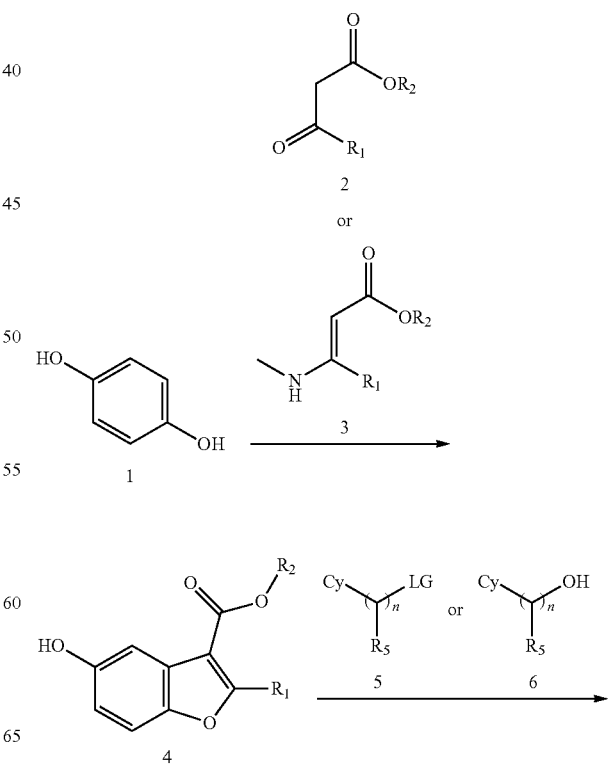

-continued

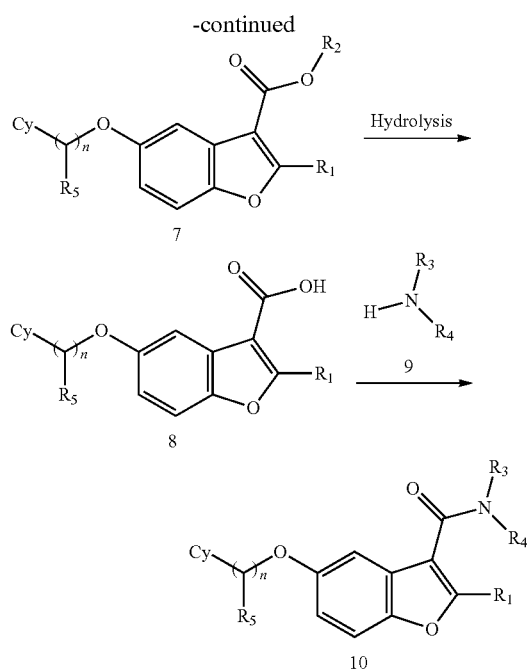

para-Benzoquinone of formula 1, may be condensed with a ketoester of formula 2 (commercially available or synthesized by procedures known to those skilled in the art), wherein $R_2$ is an ester protecting group (e.g. methyl, ethyl, t-Bu and the like), in the presence of a Lewis acid (e.g., Titanium(IV) chloride, zinc(II) chloride and the like) in a polar solvent (e.g., DCM, MeOH, EtOH, and the like) at a temperature ranging from 0 to 100° C. to provide intermediates of formula 4. More detailed information can be found in the following references (*Bioorg. Med. Chem.* 2012, 20, 4237-4244 and FR 1319594). Alternatively, para-benzoquinone of formula 1 may be reacted with an enamine of formula 3 (commercially available or synthesized by procedures known to those skilled in the art), in the presence of a protic acid (e.g., trifluoroacetic acid, para-toluenesulfonic acid, and the like) in a polar solvent (e.g., DCM, MeOH, EtOH, and the like) at a temperature ranging from 0 to 100° C. to provide intermediates of formula 4. More detailed information can be found in the following reference (*J. Heterocyclic Chem.* 2006, 43, 873). Intermediates of formula 4 may then be converted into the desired compounds of formula 7 via nucleophilic substitution using intermediates of formula 5 (commercially available or synthesized), wherein LG is a leaving group, in the presence of a base (e.g., DIPEA, DBU, triethylamine, $Cs_2CO_3$, and the like) in a polar solvent (e.g., acetonitrile, DMF, NMP, and the like), with or without a chelating agent (e.g., 18-crown-6, cis-anti-cis-dicyclohexano-18-crown-6, and the like) at a temperature ranging from 0 to 100° C. Alternatively, intermediates of formula 4 may also be reacted with intermediates of formula 6 (commercially available or synthesized) in the presence of an azodicarboxylate reagent (e.g., DEAD, DIAD, ADDP, and the like) and a phosphine (e.g., tributylphosphine, triphenylphosphine and the like) in a solvent (e.g., THF, toluene, and the like) at a temperature ranging from 0 to 100° C., to provide the desired compounds of formula 7. Ester derivatives 7 may then be converted into the desired compounds of formula 8 via standard saponification reactions. The desired compounds of formula 10 may be obtained from acid derivatives of formula 8 by reaction with amine derivatives of formula 9 (commercially available or synthesized by procedures known in the art or as set forth in the examples below) under standard peptide coupling conditions (e.g., DCC, EDCI, HATU, PyBop and the like) in a polar aprotic solvent (e.g., DCM, DMF and the like). Alternatively, carboxylic acid derivatives of formula 8, may be converted into acid chloride derivatives by procedures known to those skilled in the art or as set forth in the examples below, and then reacted with amines of formula 9 to obtain the desired compounds of formula 10 by procedures known to those skilled in the art or as set forth in the examples below.

In a more particular embodiment, the compounds of the present invention may be synthesized as depicted in scheme 2.

Scheme 2: all R1, R2, R3, R4 and R5 are as described for the compounds of the present invention.

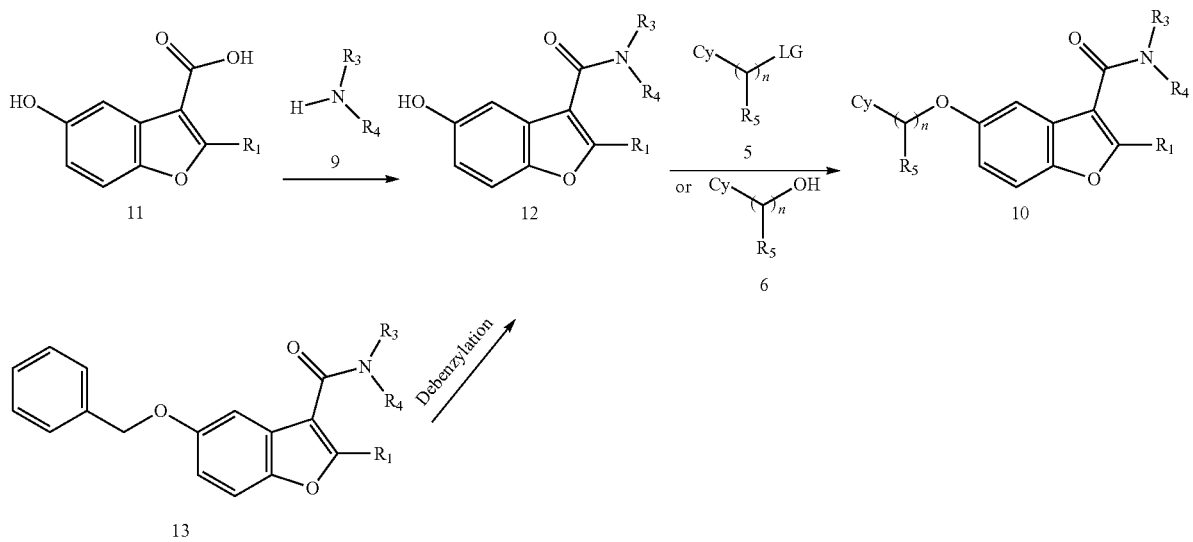

5-Hydroxy-benzofuran-3-carboxylic acid derivatives 11 (commercially available or synthesized by procedures known in the art or as set forth in the examples below) may be reacted with amine derivatives of formula 9 (commercially available or synthesized by procedures known in the art or as set forth in the examples below) under standard peptide coupling conditions (e.g. DCC, EDCI, HATU, PyBop and the like) in a polar aprotic solvent (e.g. DCM, DMF and the like) to provide intermediates of formula 12. Alternatively, compounds of formula 13 (synthetized as described in scheme 1) may be converted into intermediates of formula 12 via a hydrogenation reaction with a reducing agent (e.g., hydrogen gas, ammonium formate, cyclohexadiene and the like) using a catalyst (more preferably Pd or Pt) in a solvent (e.g., THF, EtOH, and the like). Intermediates of formula 12 may then be converted into the desired compounds of formula 10 via nucleophilic substitution using intermediates of formula 5 (commercially available or synthesized), wherein LG is a leaving group, in the presence of a base (e.g., DIPEA, DBU, triethylamine, $Cs_2CO_3$, and the like) in a polar solvent (e.g., acetonitrile, DMF, NMP, and the like), with or without a chelating agent (e.g., 18-crown-6, cis-anti-cis-dicyclohexano-18-crown-6, and the like) at a temperature ranging from 0 to 100° C. Alternatively, compounds of formula 12 may also be reacted with intermediates of formula 6 (commercially available or synthesized) in the presence of an azodicarboxylate reagent (e.g., DEAD, ADDP, DIAD, tert-butylazodicarboxylate, and the like) and a phosphine (e.g., tributylphosphine, triphenylphosphine and the like) in a solvent (e.g., THF, toluene, and the like) at a temperature ranging from 0 to 100° C., to provide the desired compounds of formula 10.

In a more particular embodiment, the compounds of the present invention may be synthesized as depicted in scheme 3.

Scheme 3: all R1, R2, R3, R4, R5, R7 and R8 are as described for the compounds of the present invention.

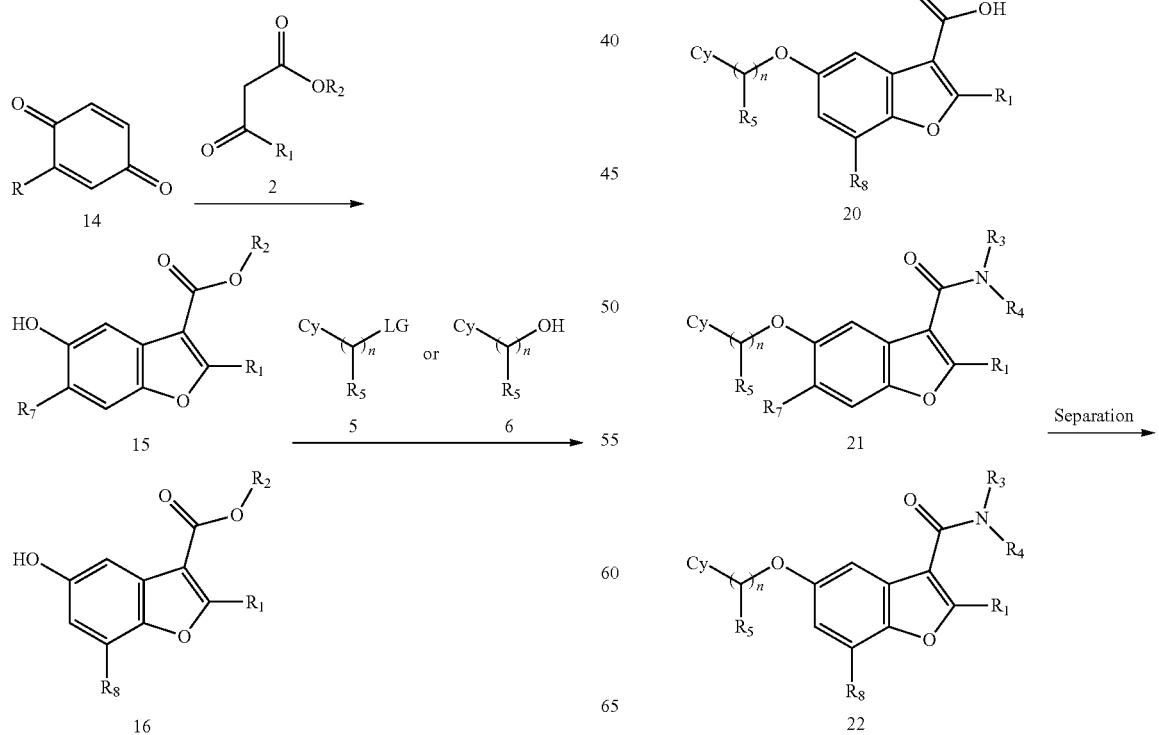

-continued

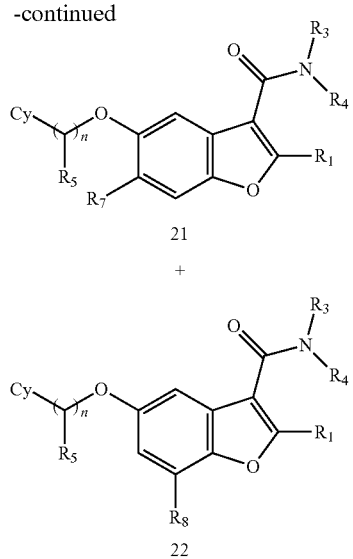

A substituted para-Benzoquinone derivatives of formula 14 may be condensed with a ketoester of formula 2 (commercially available or synthesized by procedures known to those skilled in the art), wherein $R_2$ is an ester protecting group (e.g. methyl, ethyl, t-Bu and the like), in the presence of a Lewis acid (e.g., Titanium(IV) chloride, zinc(II) chloride and the like) in a polar solvent (e.g., DCM, MeOH, EtOH, and the like) at a temperature ranging from 0 to 100° C. to provide a mixture of substituted intermediates of formula 15 and 16. More detailed information can be found in the following references (*Bioorg. Med. Chem.* 2012, 20, 4237-4244 and FR 1319594). Intermediates of formula 15 and/or 16 may then be converted into the desired compounds of formula 17 and/or 18 via nucleophilic substitution using intermediates of formula 5 (commercially available or synthesized), wherein LG is a leaving group, in the presence of a base (e.g., DIPEA, DBU, triethylamine, $Cs_2CO_3$, and the like) in a polar solvent (e.g., acetonitrile, DMF, NMP, and the like), with or without a chelating agent (e.g., 18-crown-6, cis-anti-cis-dicyclohexano-18-crown-6, and the like) at a temperature ranging from 0 to 100° C. Alternatively, intermediates of formula 15 and/or 16 may also be reacted with intermediates of formula 6 (commercially available or synthesized) in the presence of an azodicarboxylate reagent (e.g., DEAD, DIAD, ADDP, and the like) and a phosphine (e.g., tributylphosphine, triphenylphosphine and the like) in a solvent (e.g., THF, toluene, and the like) at a temperature ranging from 0 to 100° C., to provide the desired compounds of formula 17 and/or 18. Ester derivatives 17 and/or 18 may then be converted into the desired carboxylic acid of formula 19 and/or 20 via standard saponification reactions. The desired compounds of formula 21 and/or 22 may be obtained from acid derivatives of formula 19 and/or 20 by reaction with amine derivatives of formula 9 (commercially available or synthesized by procedures known in the art or as set forth in the examples below) under standard peptide coupling conditions (e.g., DCC, EDCI, HATU, PyBop and the like) in a polar aprotic solvent (e.g., DCM, DMF and the like). A mixture of compounds 21 and 22 may be separated (e.g., silica gel, HPLC, SFC or preparative CFC) to provide the desired compounds of formula 21 or 22.

In a more particular embodiment, the compounds of the present invention may be synthesized as depicted in scheme 4.

Scheme 4: all R1, R2, R3, R4, R5, R7 and R8 are as described for the compounds of the present invention.

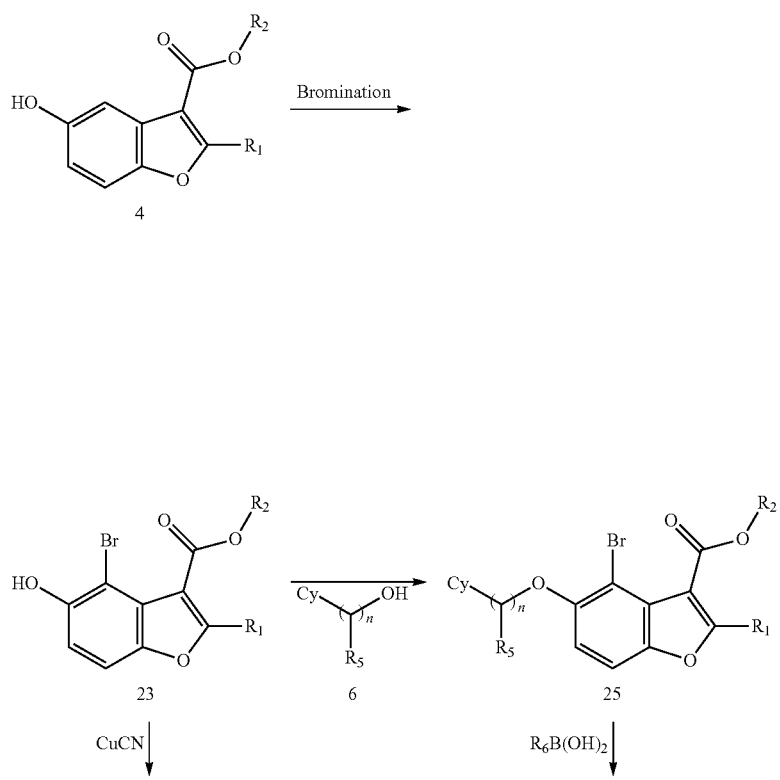

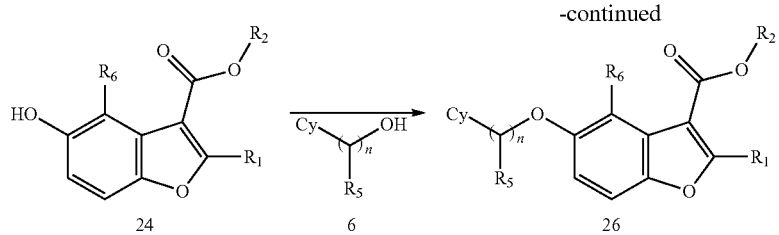

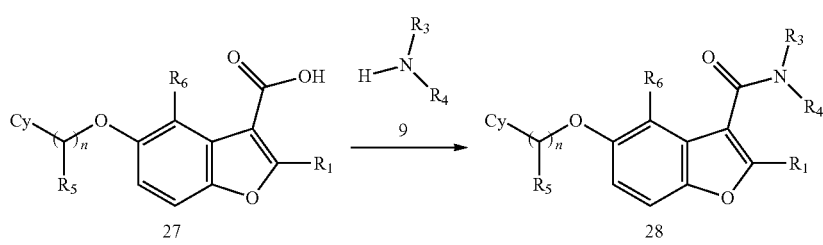

Intermediates of formula 4 may be halogenated with a suitable halogenating agent (e.g., Bromine, N-bromosuccinimide and the like) in a solvent (e.g., chloroform, water and the like) to provide the desired intermediates 23. The desired compounds of formula 26 may be obtained by an Ullmann type reaction with CuCN followed by a Mitsunobu type reaction with intermediates of formula 6 (commercially available or synthesized). Alternatively, the desired compounds of formula 26 may be obtained via a Mitsunobu type reaction with intermediates of formula 6 (commercially available or synthesized) followed by a Suzuki reaction. Ester derivatives 26 may then be converted into the desired compounds of formula 27 via standard saponification reactions. The desired compounds of formula 28 may be obtained from acid derivatives of formula 27 by reaction with amine derivatives of formula 9 (commercially available or synthesized by procedures known in the art or as set forth in the examples below) under standard peptide coupling conditions (e.g., DCC, EDCI, HATU, PyBop and the like) in a polar aprotic solvent (e.g., DCM, DMF and the like).

In a more particular embodiment, the compounds of the present invention may be synthesized as depicted in scheme 5.

Scheme 5: all R1, R2, R3 and are as described for the compounds of the present invention.

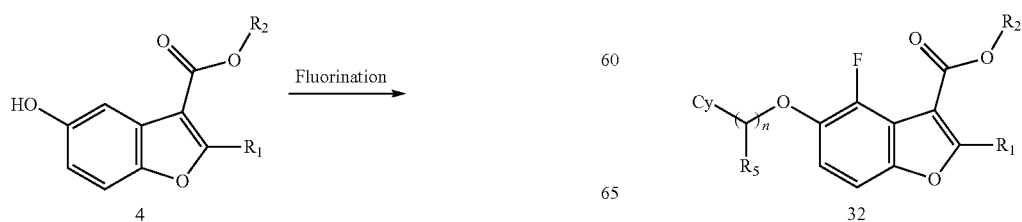

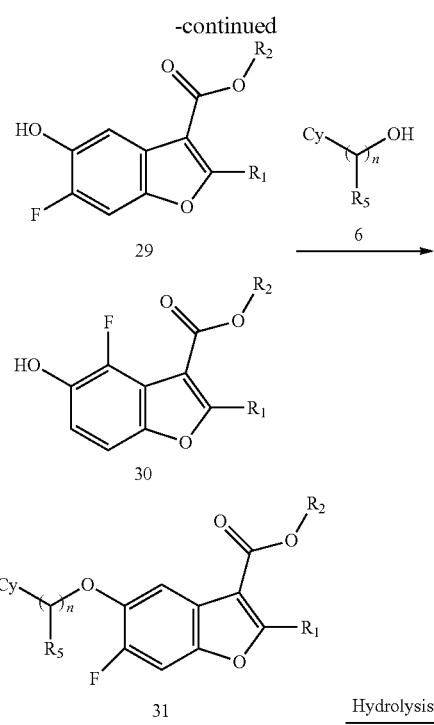

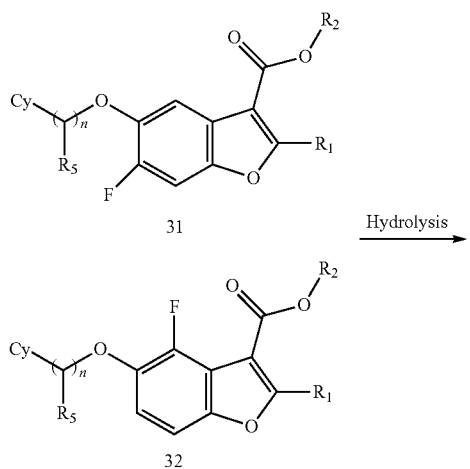

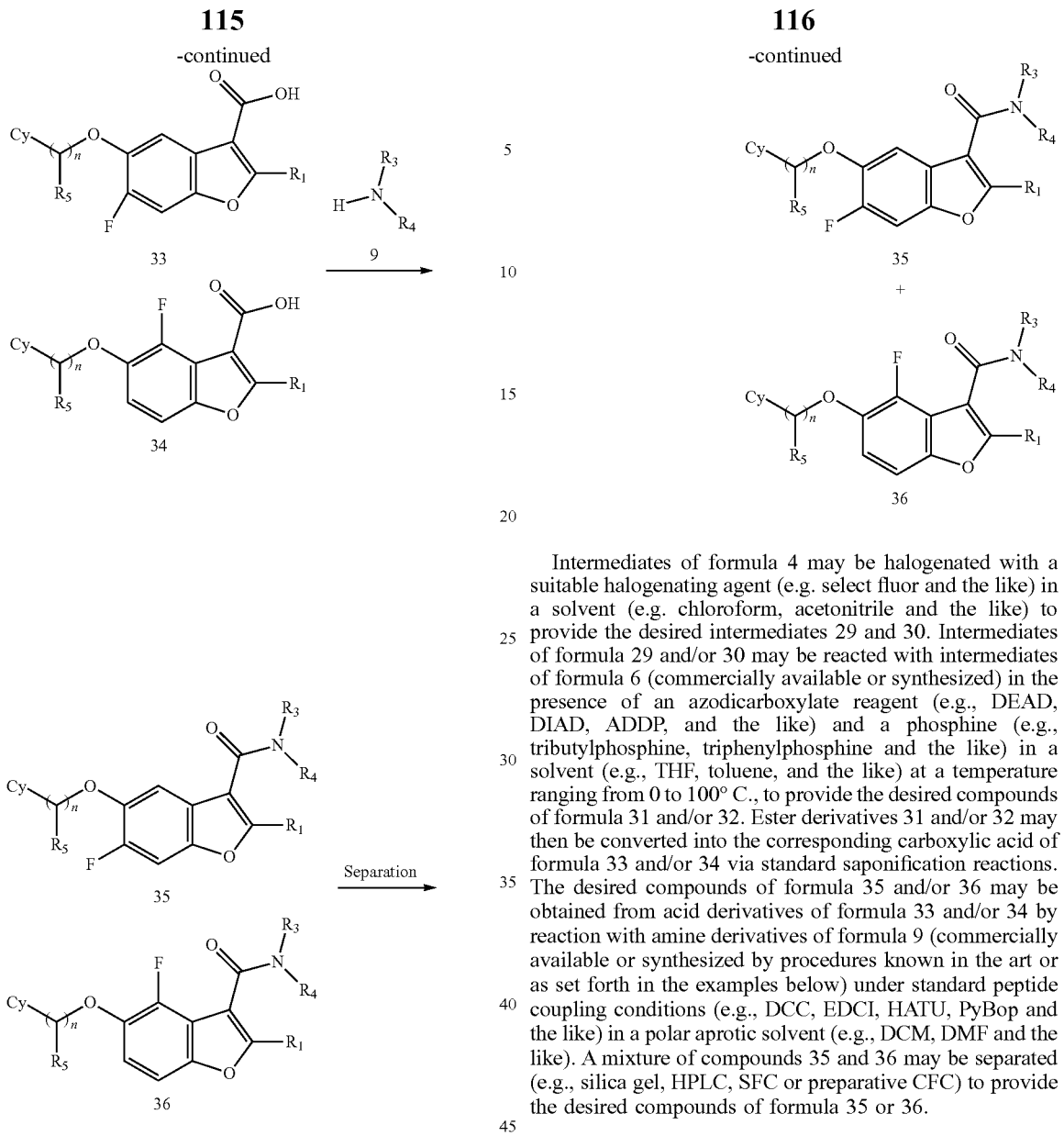

Intermediates of formula 4 may be halogenated with a suitable halogenating agent (e.g. select fluor and the like) in a solvent (e.g. chloroform, acetonitrile and the like) to provide the desired intermediates 29 and 30. Intermediates of formula 29 and/or 30 may be reacted with intermediates of formula 6 (commercially available or synthesized) in the presence of an azodicarboxylate reagent (e.g., DEAD, DIAD, ADDP, and the like) and a phosphine (e.g., tributylphosphine, triphenylphosphine and the like) in a solvent (e.g., THF, toluene, and the like) at a temperature ranging from 0 to 100° C., to provide the desired compounds of formula 31 and/or 32. Ester derivatives 31 and/or 32 may then be converted into the corresponding carboxylic acid of formula 33 and/or 34 via standard saponification reactions. The desired compounds of formula 35 and/or 36 may be obtained from acid derivatives of formula 33 and/or 34 by reaction with amine derivatives of formula 9 (commercially available or synthesized by procedures known in the art or as set forth in the examples below) under standard peptide coupling conditions (e.g., DCC, EDCI, HATU, PyBop and the like) in a polar aprotic solvent (e.g., DCM, DMF and the like). A mixture of compounds 35 and 36 may be separated (e.g., silica gel, HPLC, SFC or preparative CFC) to provide the desired compounds of formula 35 or 36.

EXAMPLES

| Structure/CODE |
| --- |
| 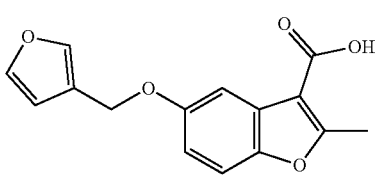 [SMILES: Cc1oc2ccc(OCc3ccoc3)cc2c1C(=O)O] cpd 001 |

-continued
| Structure/CODE | |
|---|---|
| 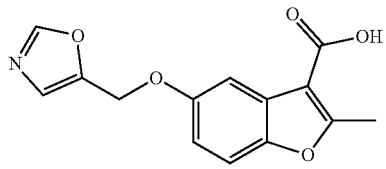 [SMILES: Cc1oc2ccc(OCc3cnco3)cc2c1C(=O)O] | cpd 002 |
| 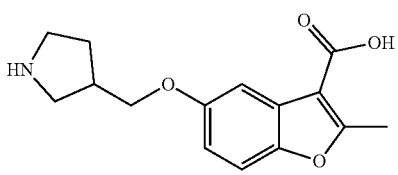 [SMILES: Cc1oc2ccc(OCC3CCNC3)cc2c1C(=O)O] | cpd 003 |
| 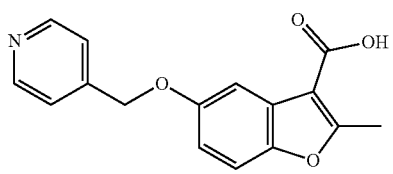 [SMILES: Cc1oc2ccc(OCc3ccncc3)cc2c1C(=O)O] | cpd 004 |
| 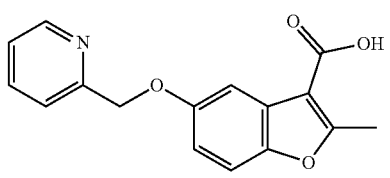 [SMILES: Cc1oc2ccc(OCc3ccccn3)cc2c1C(=O)O] | cpd 005 |
| 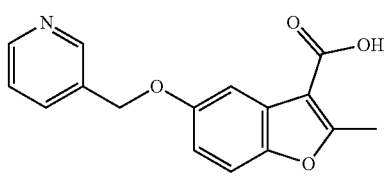 [SMILES: Cc1oc2ccc(OCc3cccnc3)cc2c1C(=O)O] | cpd 006 |
| 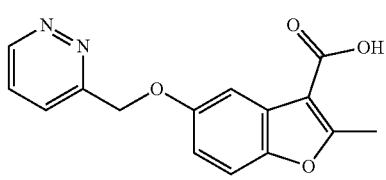 [SMILES: Cc1oc2ccc(OCc3cccnn3)cc2c1C(=O)O] | cpd 007 |
| 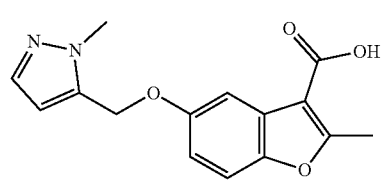 [SMILES: Cc1oc2ccc(OCc3ccnn3C)cc2c1C(=O)O] | cpd 008 |
| 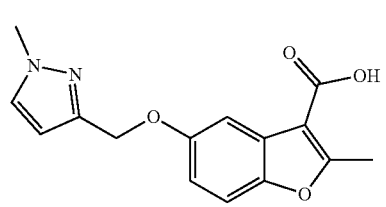 [SMILES: Cc1oc2ccc(OCc3ccn(C)n3)cc2c1C(=O)O] | cpd 009 |

-continued
| Structure/CODE | |
|---|---|
| 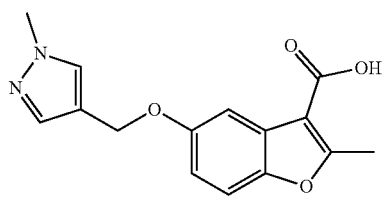 [SMILES: Cc1oc2ccc(OCc3cnn(C)c3)cc2c1C(=O)O] | cpd 010 |
| 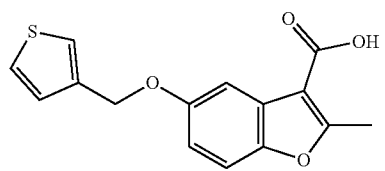 [SMILES: Cc1oc2ccc(OCc3ccsc3)cc2c1C(=O)O] | cpd 011 |
| 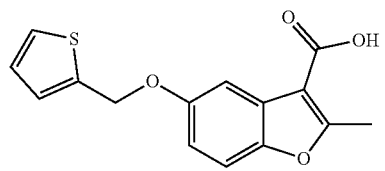 [SMILES: Cc1oc2ccc(OCc3cccs3)cc2c1C(=O)O] | cpd 012 |
| 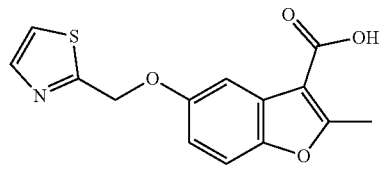 [SMILES: Cc1oc2ccc(OCc3nccs3)cc2c1C(=O)O] | cpd 013 |
| 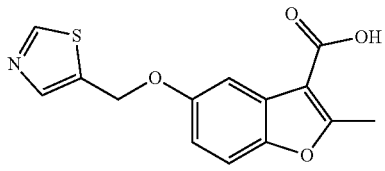 | cpd 014 |
| 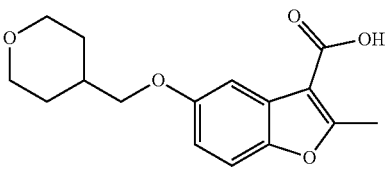 [SMILES: Cc1oc2ccc(OCC3CCOCC3)cc2c1C(=O)O] | cpd 015 |
| 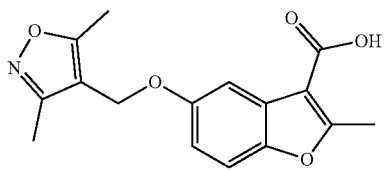 [SMILES: Cc1noc(C)c1COc1ccc2oc(C)c(C(=O)O)c2c1] | cpd 016 |
| 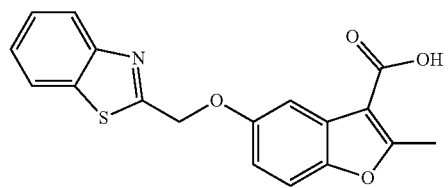 [SMILES: Cc1oc2ccc(OCc3nc4ccccc4s3)cc2c1C(=O)O] | cpd 017 |

-continued
| Structure/CODE | |
|---|---|
| 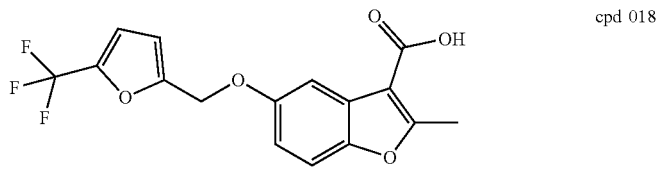 | cpd 018 |
| 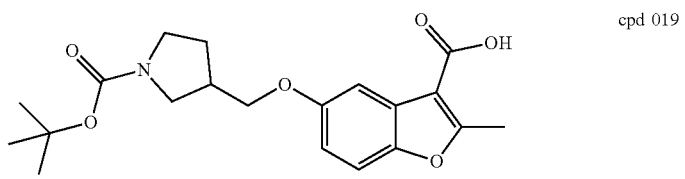 | cpd 019 |
| 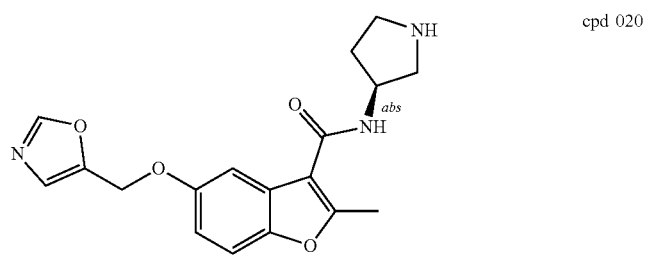 | cpd 020 |
| | cpd 021 |
| 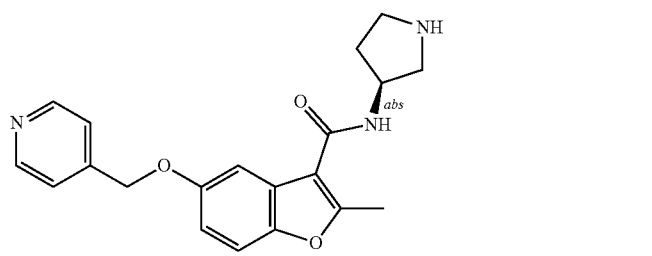 [SMILES: Cc1oc2ccc(OCc3ccncc3)cc2c1C(=O)N[C@H]1CCNC1] | |
| 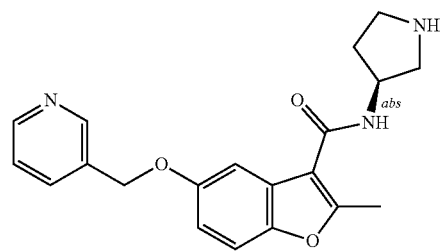 [SMILES: Cc1oc2ccc(OCc3cccnc3)cc2c1C(=O)N[C@H]1CCNC1] | cpd 022 |
| 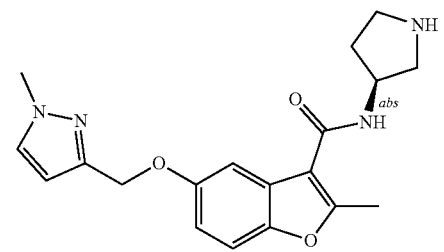 [SMILES: Cc1oc2ccc(OCc3ccn(C)n3)cc2c1C(=O)N[C@H]1CCNC1] | cpd 023 |

-continued
| Structure/CODE | |
|---|---|
| 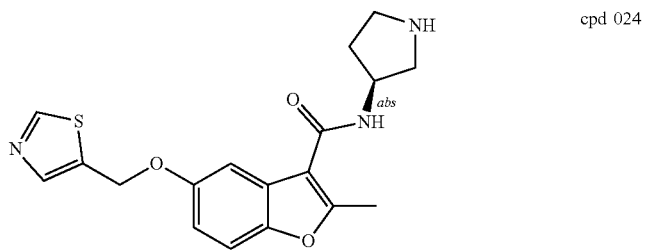 | cpd 024 |
| 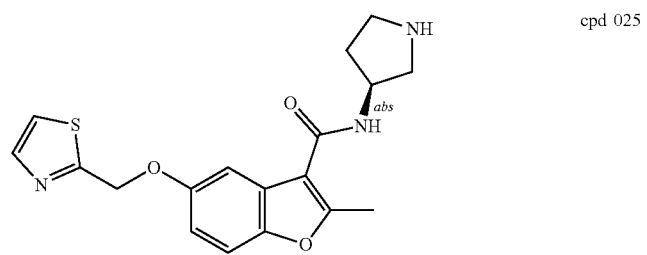 | cpd 025 |
| 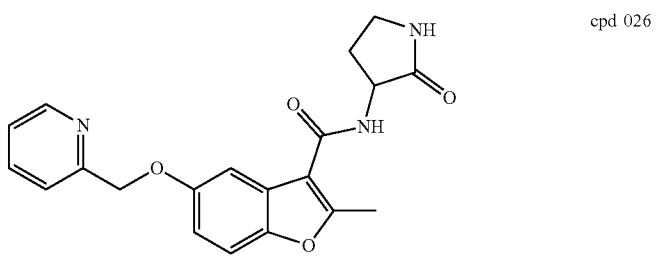 | cpd 026 |
| 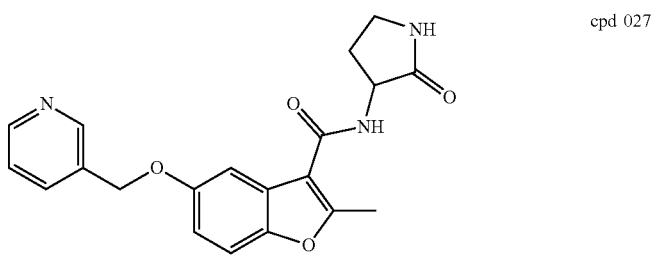 | cpd 027 |
| 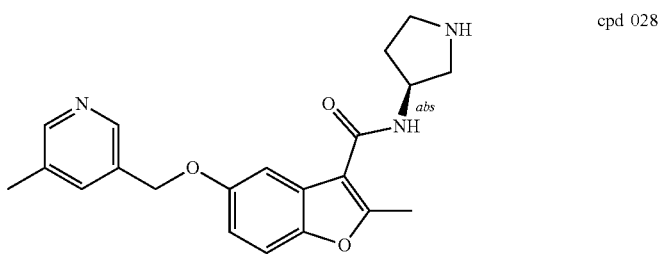 | cpd 028 |
| 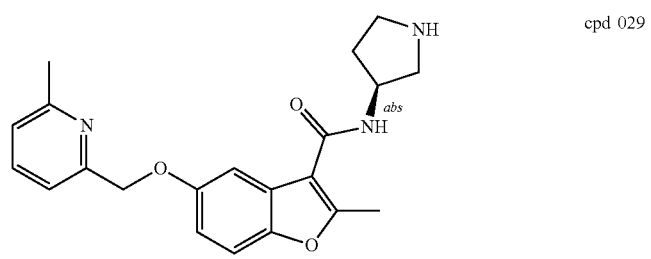 | cpd 029 |

| Structure/CODE | |
|---|---|
| 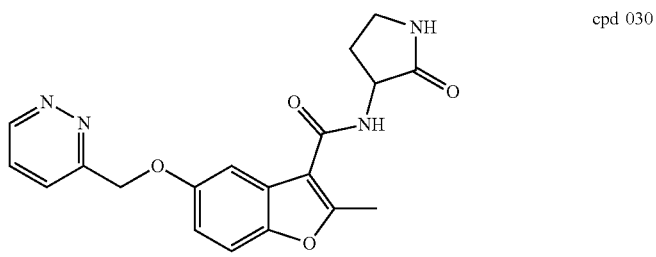 | cpd 030 |
| 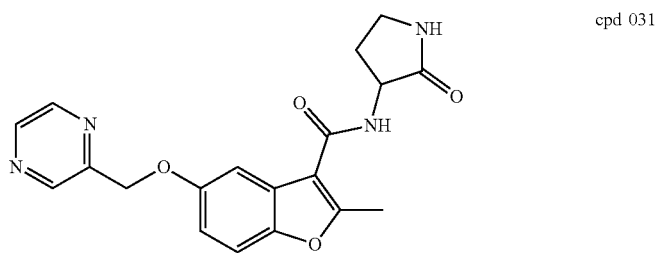 | cpd 031 |
| 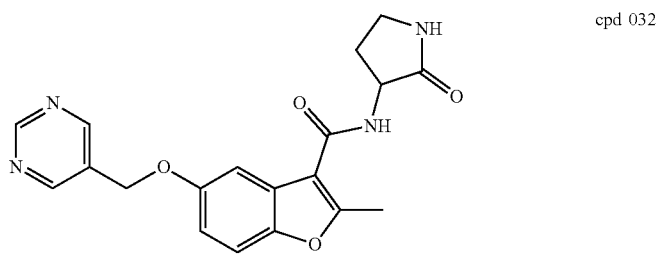 | cpd 032 |
| 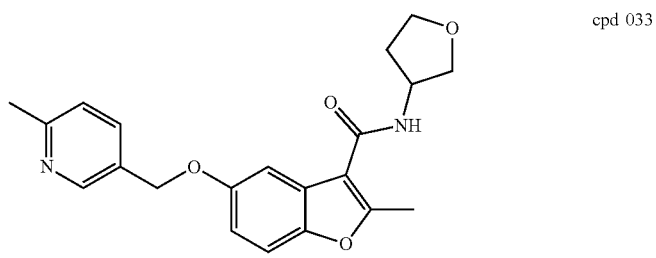 | cpd 033 |
| 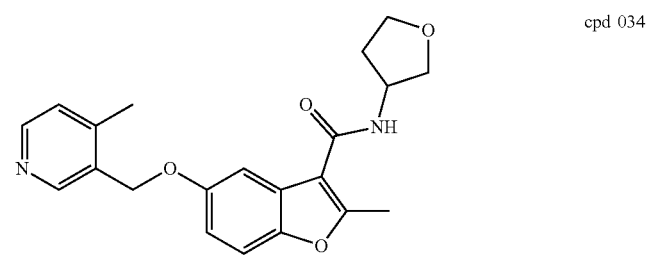 | cpd 034 |
| 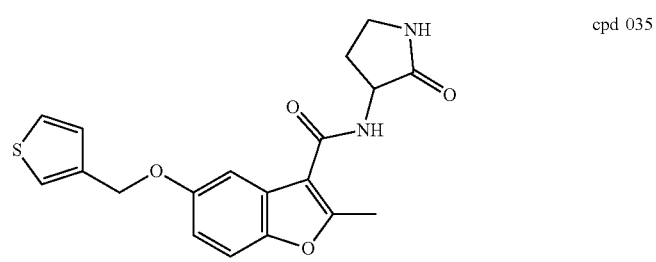 | cpd 035 |

-continued
| Structure/CODE | |
|---|---|
| 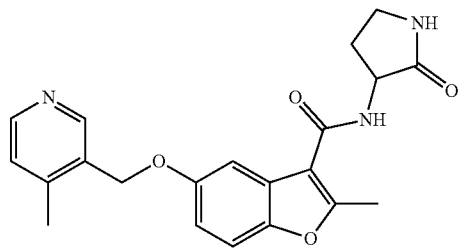 [SMILES: Cc1ccncc1COc1ccc2oc(C)c(C(=O)NC3CCNC3=O)c2c1] | cpd 037 |
| 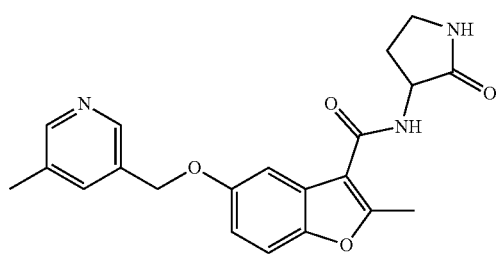 [SMILES: Cc1cncc(COc2ccc3oc(C)c(C(=O)NC4CCNC4=O)c3c2)c1] | cpd 038 |
| 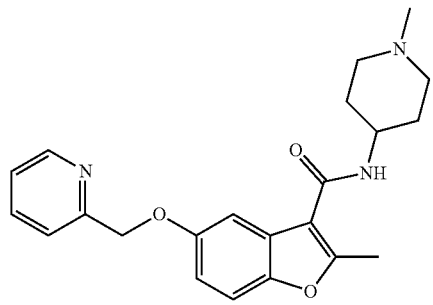 [SMILES: Cc1oc2ccc(OCc3ccccn3)cc2c1C(=O)NC1CCN(C)CC1] | cpd 039 |
| 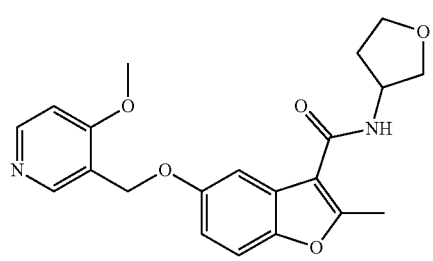 [SMILES: COc1ccncc1COc1ccc2oc(C)c(C(=O)NC3CCOC3)c2c1] | cpd 040 |
| 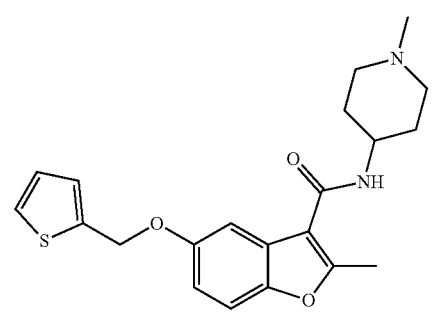 [SMILES: Cc1oc2ccc(OCc3cccs3)cc2c1C(=O)NC1CCN(C)CC1] | cpd 041 |

-continued
| Structure/CODE | |
|---|---|
| 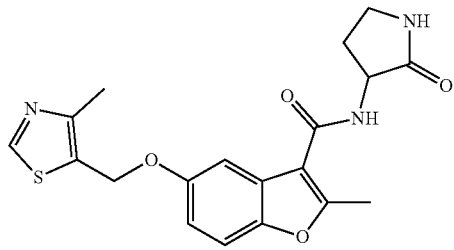 [SMILES: Cc1ncsc1COc1ccc2oc(C)c(C(=O)NC3CCNC3=O)c2c1] | cpd 042 |
| 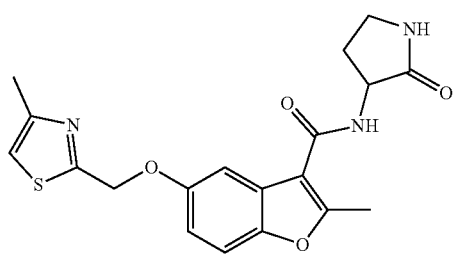 [SMILES: Cc1csc(COc2ccc3oc(C)c(C(=O)NC4CCNC4=O)c3c2)n1] | cpd 043 |
| 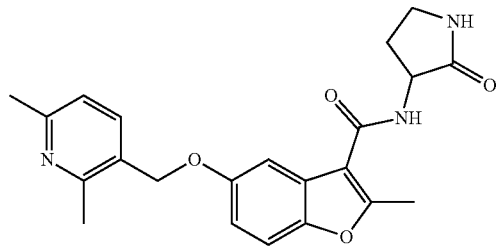 [SMILES: Cc1ccc(COc2ccc3oc(C)c(C(=O)NC4CCNC4=O)c3c2)c(C)n1] | cpd 044 |
| 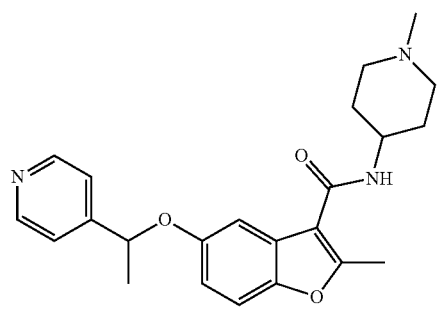 [SMILES: Cc1oc2ccc(OC(C)c3ccncc3)cc2c1C(=O)NC1CCN(C)CC1] | cpd 045 |
| 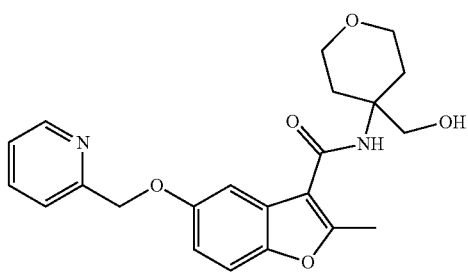 [SMILES: Cc1oc2ccc(OCc3ccccn3)cc2c1C(=O)NC1(CO)CCOCC1] | cpd 047 |

| Structure/CODE |
|---|
| 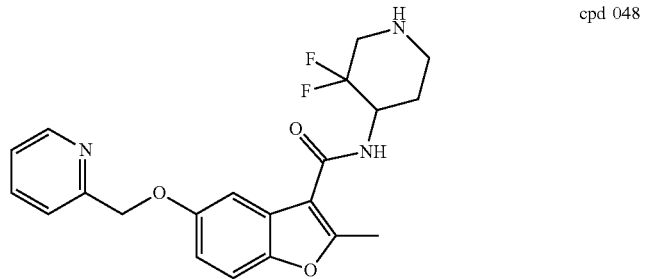 cpd 048 |
| 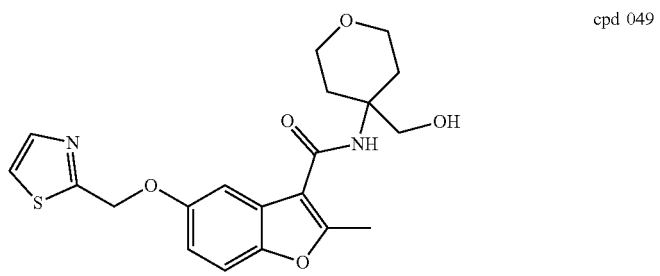 cpd 049 |
| 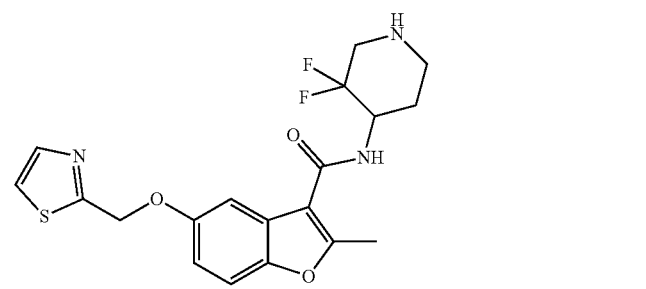 [SMILES: Cc1oc2ccc(OCc3nccs3)cc2c1C(=O)NC1CCNCC1(F)F] cpd 050 |
| 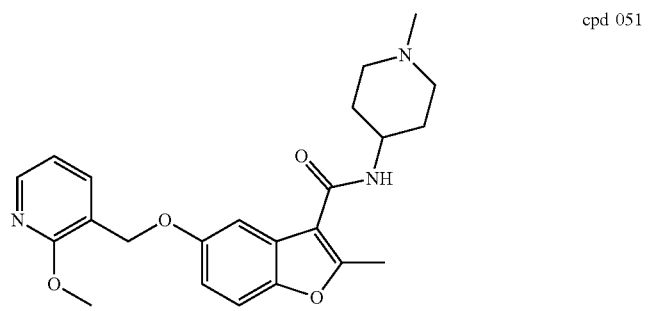 cpd 051 |
| 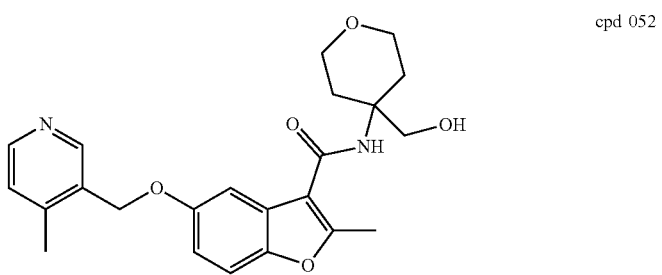 cpd 052 |

| Structure/CODE | |
|---|---|
| 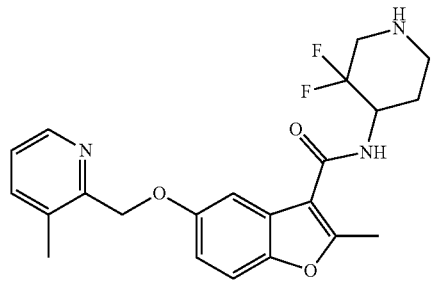 [SMILES: Cc1cccnc1COc1ccc2oc(C)c(C(=O)NC3CCNCC3(F)F)c2c1] | cpd 053 |
| 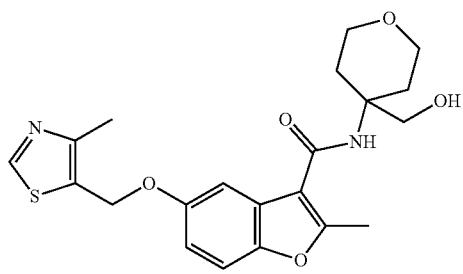 [SMILES: Cc1ncsc1COc1ccc2oc(C)c(C(=O)NC3(CO)CCOCC3)c2c1] | cpd 054 |
| 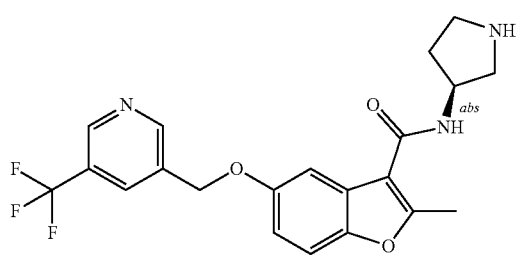 [SMILES: Cc1oc2ccc(OCc3cncc(C(F)(F)F)c3)cc2c1C(=O)N[C@H]1CCNC1] | cpd 055 |
| 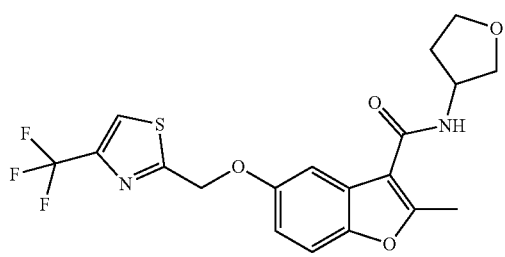 [SMILES: Cc1oc2ccc(OCc3nc(C(F)(F)F)cs3)cc2c1C(=O)NC1CCOC1] | cpd 057 |
| 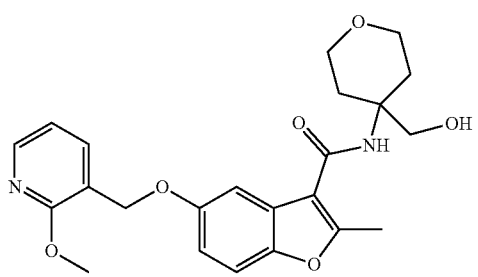 [SMILES: COc1ncccc1COc1ccc2oc(C)c(C(=O)NC3(CO)CCOCC3)c2c1] | cpd 058 |

| Structure/CODE |
|---|
| 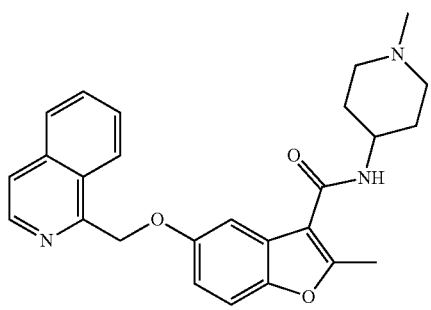 [SMILES: Cc1oc2ccc(OCc3nccc4ccccc34)cc2c1C(=O)NC1CCN(C)CC1] cpd 059 |
| 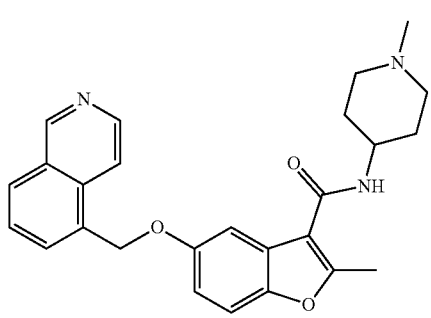 [SMILES: Cc1oc2ccc(OCc3cccc4cnccc34)cc2c1C(=O)NC1CCN(C)CC1] cpd 060 |
| 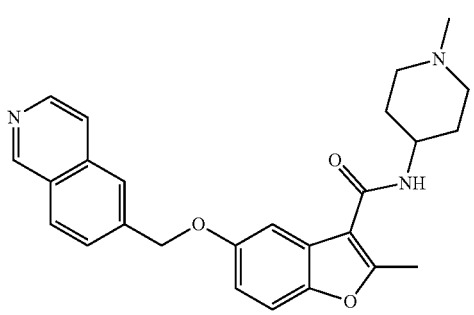 [SMILES: Cc1oc2ccc(OCc3ccc4cnccc4c3)cc2c1C(=O)NC1CCN(C)CC1] cpd 061 |
| 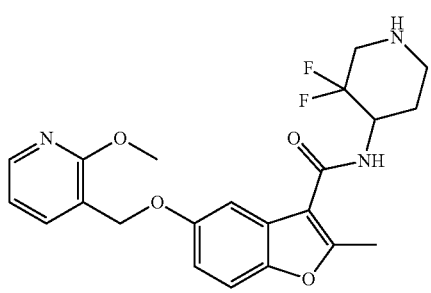 [SMILES: COc1ncccc1COc1ccc2oc(C)c(C(=O)NC3CCNCC3(F)F)c2c1] cpd 062 |
| 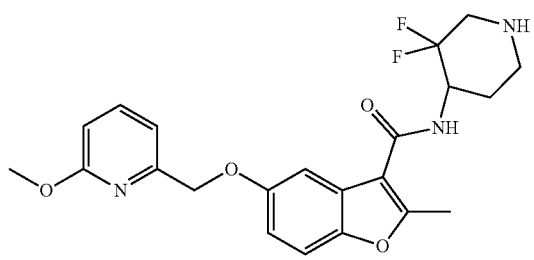 [SMILES: COc1cccc(COc2ccc3oc(C)c(C(=O)NC4CCNCC4(F)F)c3c2)n1] cpd 063 |

-continued
| Structure/CODE | |
|---|---|
| 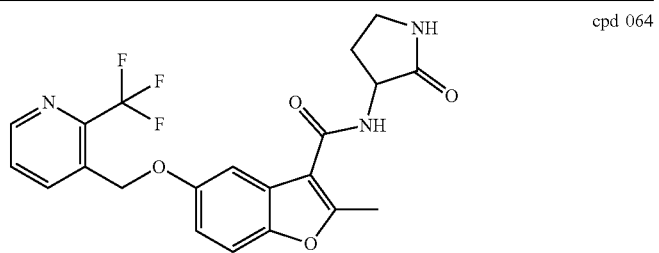 | cpd 064 |
| 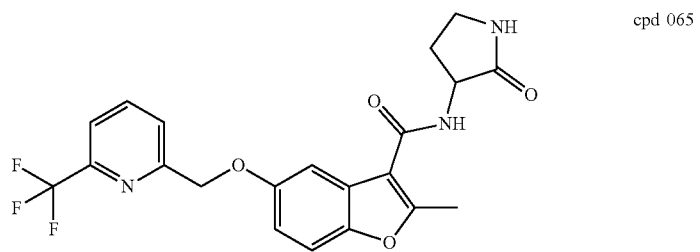 | cpd 065 |
| 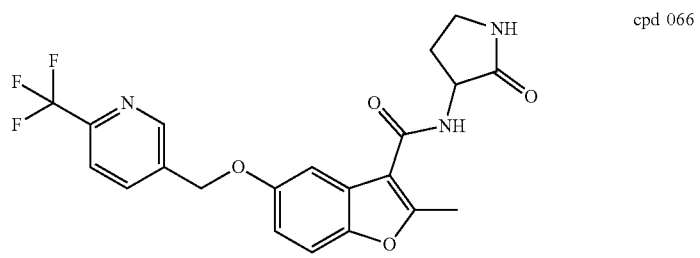 | cpd 066 |
| 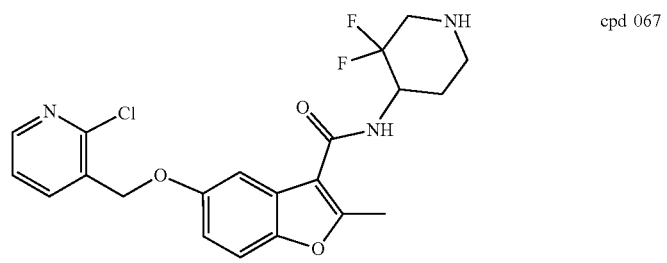 | cpd 067 |
| 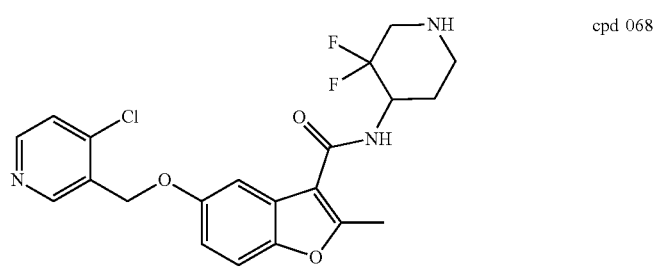 | cpd 068 |
| 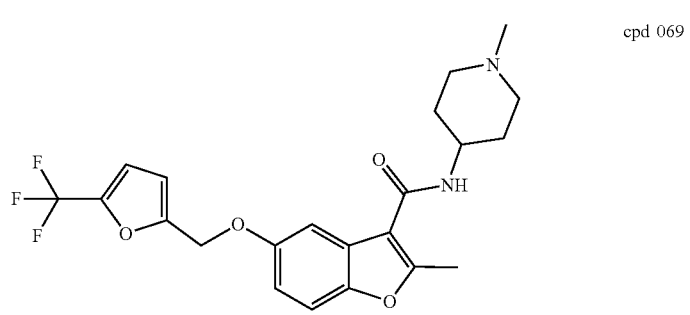 | cpd 069 |

| Structure/CODE |
|---|
| 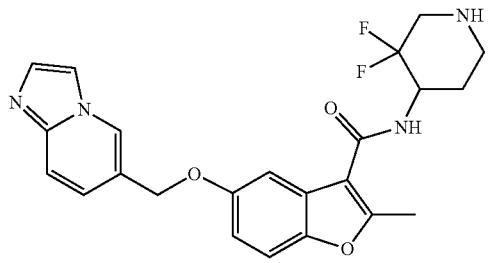 [SMILES: Cc1oc2ccc(OCc3ccc4nccn4c3)cc2c1C(=O)NC1CCNCC1(F)F] cpd 070 |
| 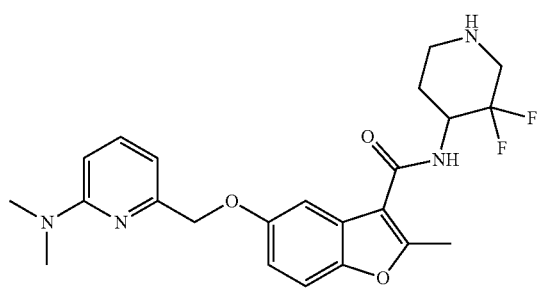 [SMILES: Cc1oc2ccc(OCc3cccc(N(C)C)n3)cc2c1C(=O)NC1CCNCC1(F)F] cpd 071 |
| 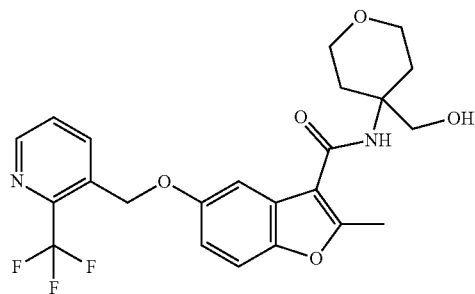 [SMILES: Cc1oc2ccc(OCc3cccnc3C(F)(F)F)cc2c1C(=O)NC1(CO)CCOCC1] cpd 072 |
| 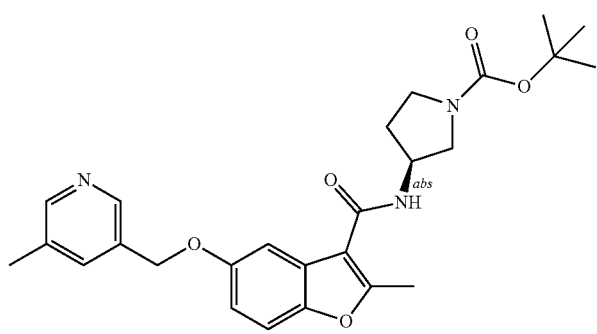 [SMILES: Cc1cncc(COc2ccc3oc(C)c(C(=O)N[C@H]4CCN(C(=O)OC(C)(C)C)C4)c3c2)c1] cpd 073 |
| 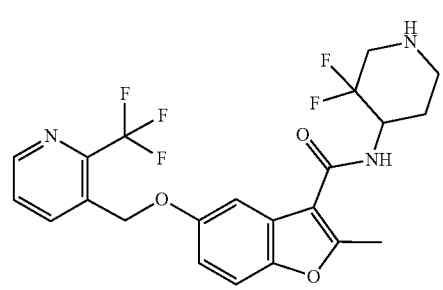 [SMILES: Cc1oc2ccc(OCc3cccnc3C(F)(F)F)cc2c1C(=O)NC1CCNCC1(F)F] cpd 074 |

-continued
Structure/CODE
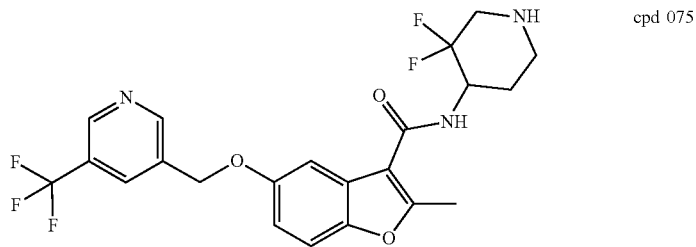
cpd 075
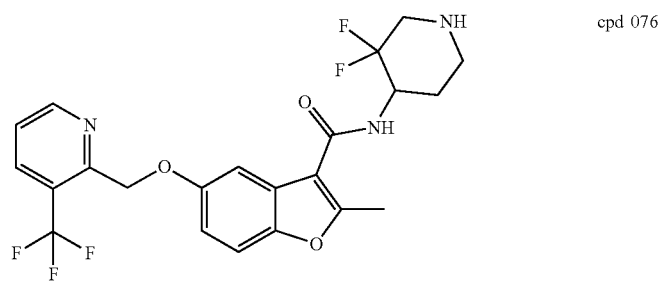
cpd 076
cpd 077
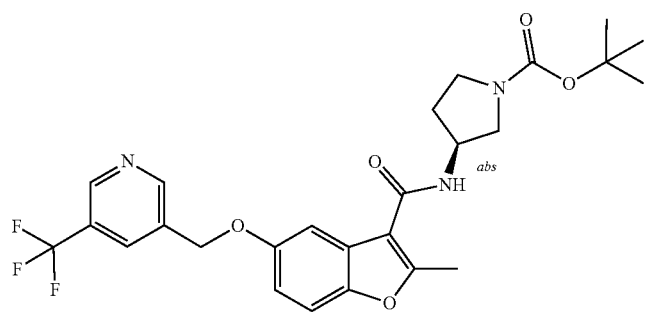 [SMILES: Cc1oc2ccc(OCc3cncc(C(F)(F)F)c3)cc2c1C(=O)N[C@H]1CCN(C(=O)OC(C)(C)C)C1]
cpd 078
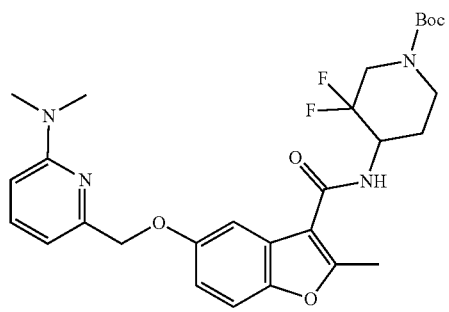 [SMILES: Cc1oc2ccc(OCc3cccc(N(C)C)n3)cc2c1C(=O)NC1CCN(C(=O)OC(C)(C)C)CC1(F)F]
cpd 079
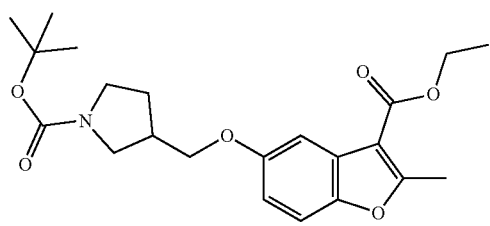 [SMILES: CCOC(=O)c1c(C)oc2ccc(OCC3CCN(C(=O)OC(C)(C)C)C3)cc12]

-continued
| Structure/CODE |
|---|
| 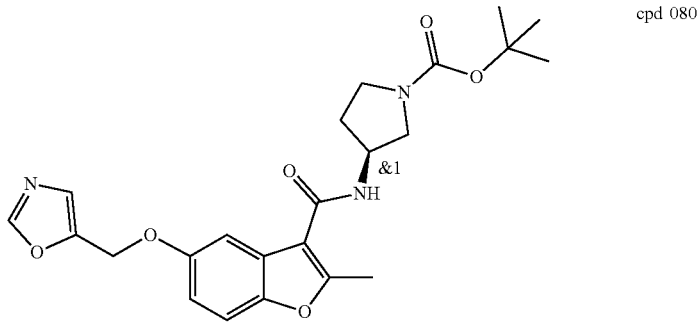 cpd 080 |
| 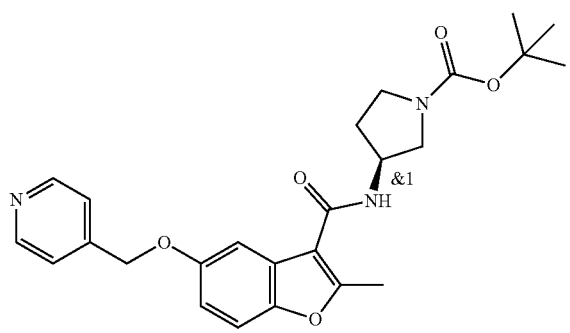 [SMILES: Cc1oc2ccc(OCc3ccncc3)cc2c1C(=O)N[C@H]1CCN(C(=O)OC(C)(C)C)C1] cpd 081 |
| 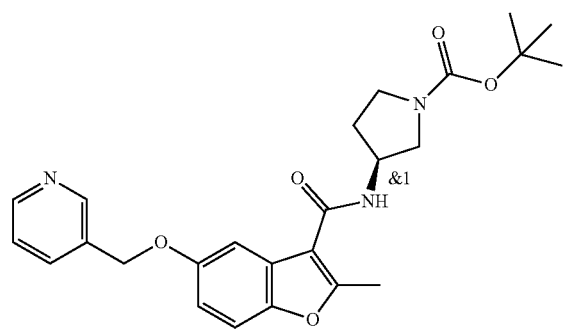 [SMILES: Cc1oc2ccc(OCc3cccnc3)cc2c1C(=O)N[C@H]1CCN(C(=O)OC(C)(C)C)C1] cpd 082 |
| 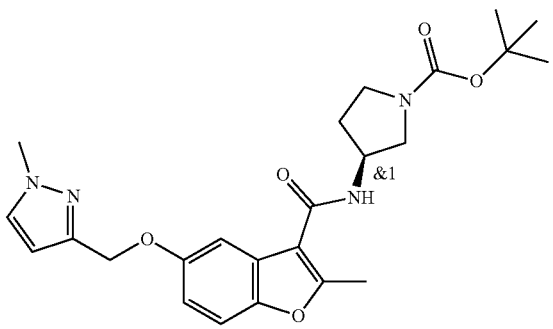 [SMILES: Cc1oc2ccc(OCc3ccn(C)n3)cc2c1C(=O)N[C@H]1CCN(C(=O)OC(C)(C)C)C1] cpd 083 |

-continued
| Structure/CODE |
|---|
| 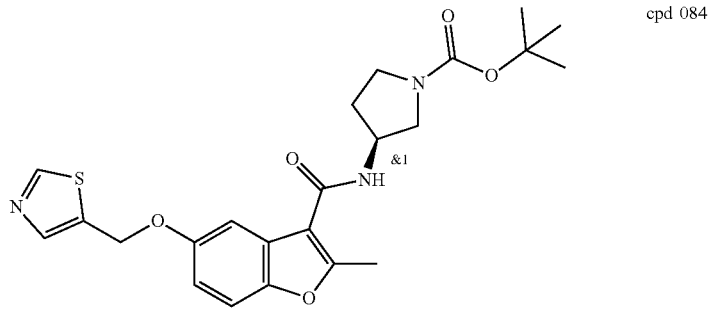 cpd 084 |
| 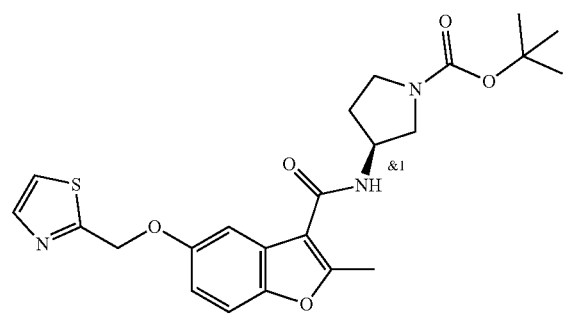 [SMILES: Cc1oc2ccc(OCc3nccs3)cc2c1C(=O)N[C@H]1CCN(C(=O)OC(C)(C)C)C1] cpd 085 |
| 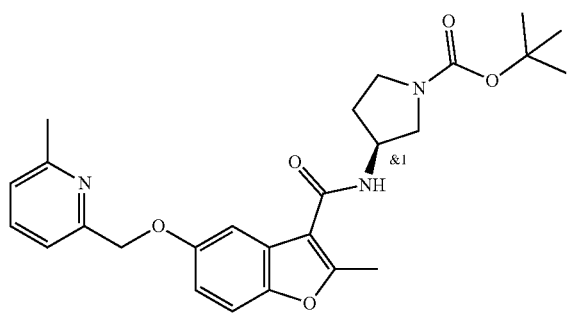 [SMILES: Cc1cccc(COc2ccc3oc(C)c(C(=O)N[C@H]4CCN(C(=O)OC(C)(C)C)C4)c3c2)n1] cpd 086 |
| 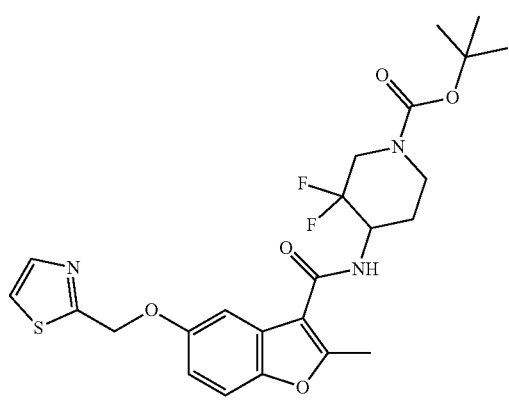 [SMILES: Cc1oc2ccc(OCc3nccs3)cc2c1C(=O)NC1CCN(C(=O)OC(C)(C)C)CC1(F)F] cpd 087 |

-continued
| Structure/CODE |
|---|
| 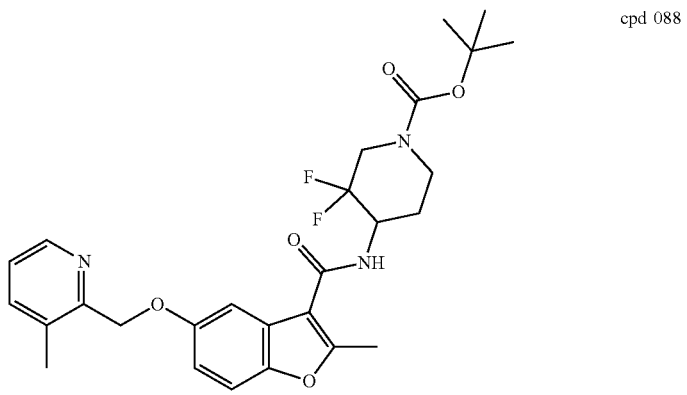 cpd 088 |
| 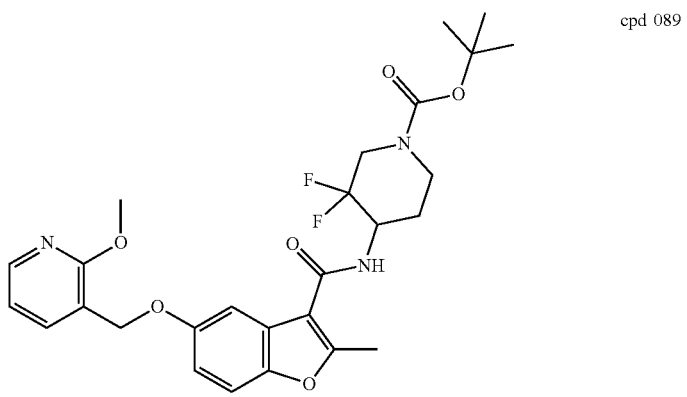 cpd 089 |
| 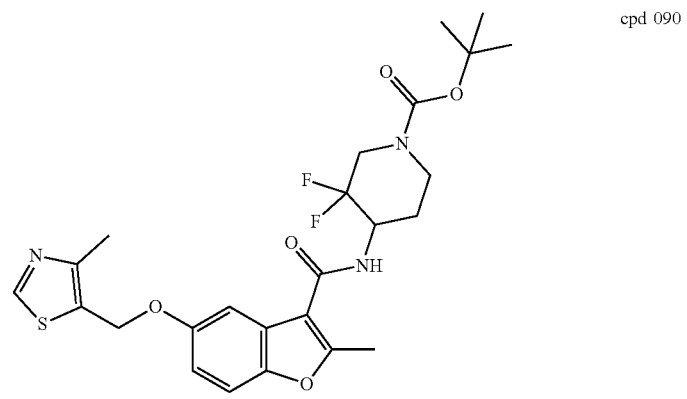 cpd 090 |
| 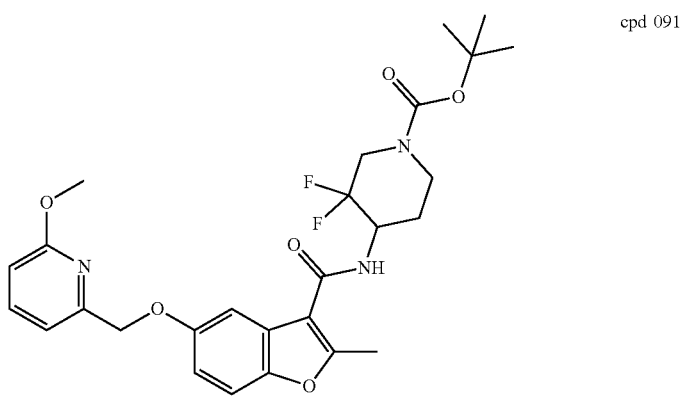 cpd 091 |

| Structure/CODE |
|---|
| 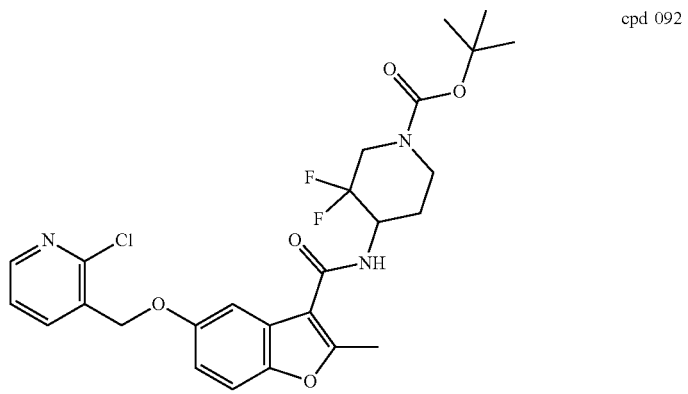 cpd 092 |
| 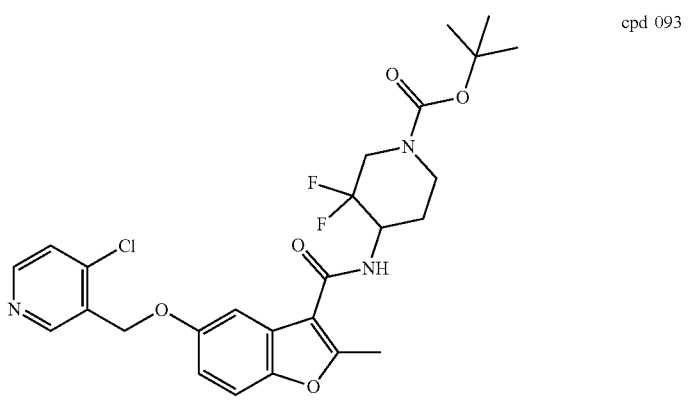 cpd 093 |
| 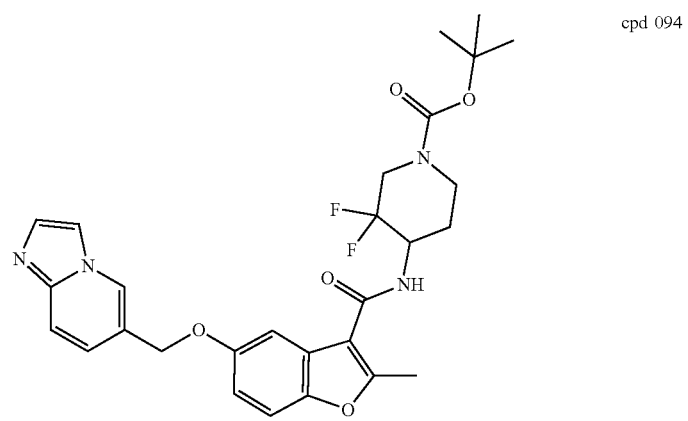 cpd 094 |
| 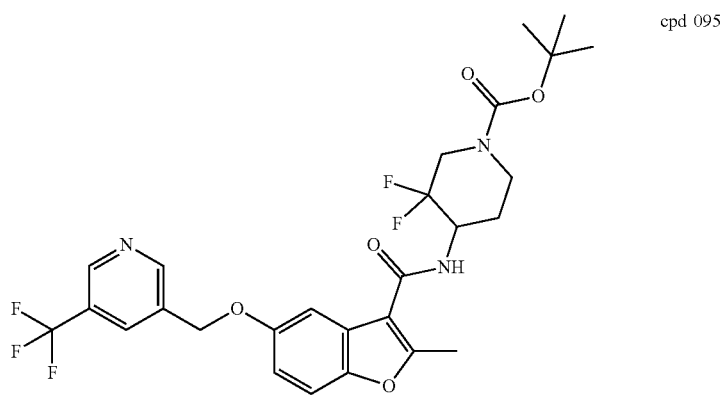 cpd 095 |

-continued
| Structure/CODE |
|---|
| 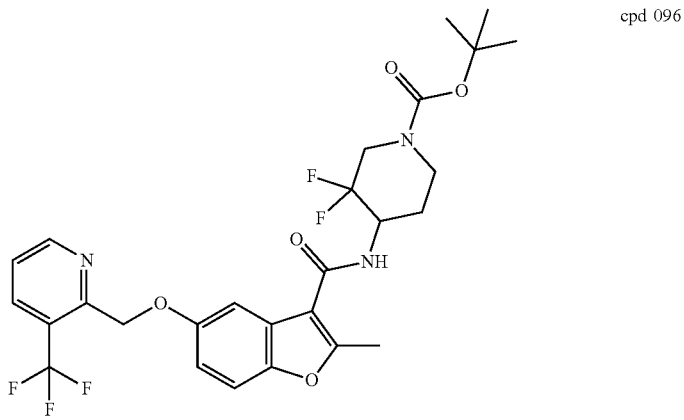 cpd 096 |
| 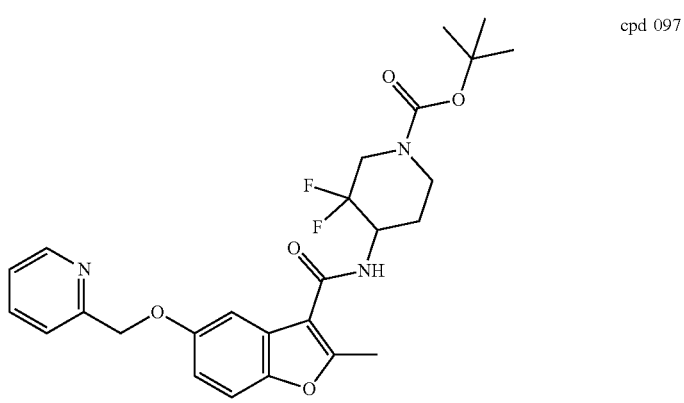 cpd 097 |
| 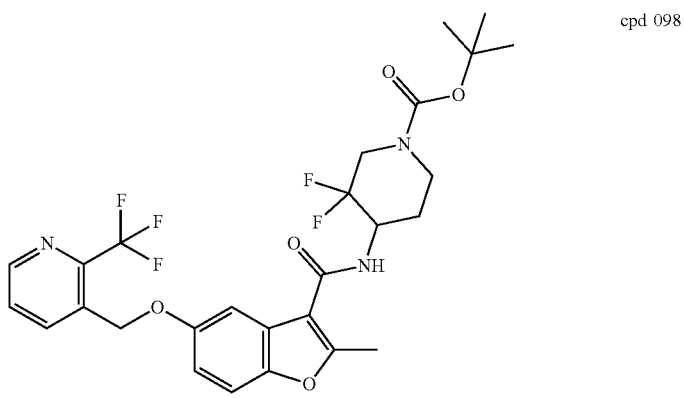 cpd 098 |
| 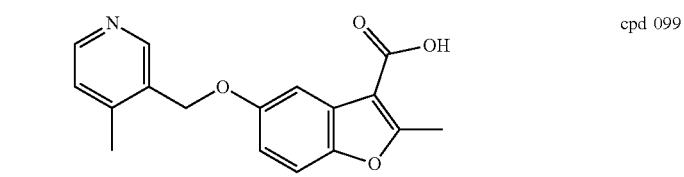 cpd 099 |
| 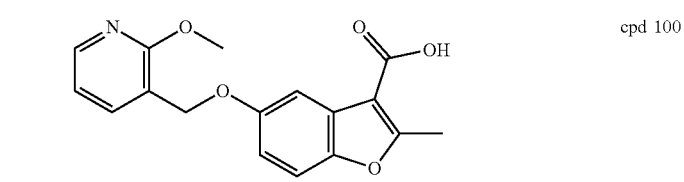 cpd 100 |

-continued
| Structure/CODE | |
|---|---|
| 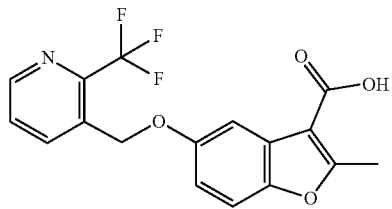 [SMILES: Cc1oc2ccc(OCc3cccnc3C(F)(F)F)cc2c1C(=O)O] | cpd 101 |
| 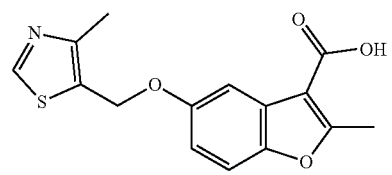 [SMILES: Cc1ncsc1COc1ccc2oc(C)c(C(=O)O)c2c1] | cpd 102 |
| 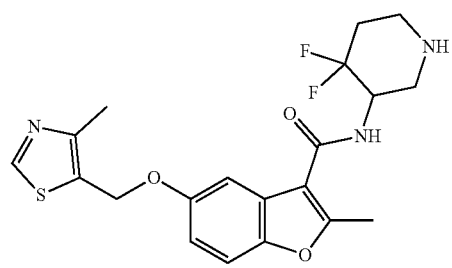 [SMILES: Cc1ncsc1COc1ccc2oc(C)c(C(=O)NC3CNCCC3(F)F)c2c1] | cpd 103 |
| 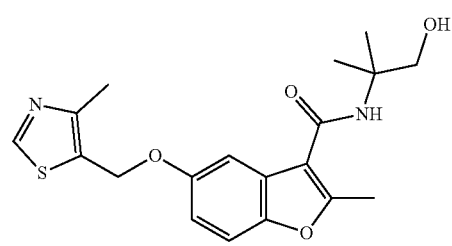 [SMILES: Cc1ncsc1COc1ccc2oc(C)c(C(=O)NC(C)(C)CO)c2c1] | cpd 104 |
| 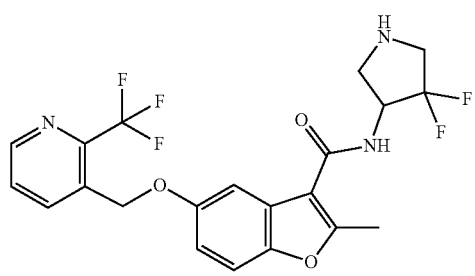 [SMILES: Cc1oc2ccc(OCc3cccnc3C(F)(F)F)cc2c1C(=O)NC1CNCC1(F)F] | cpd 105 |
| 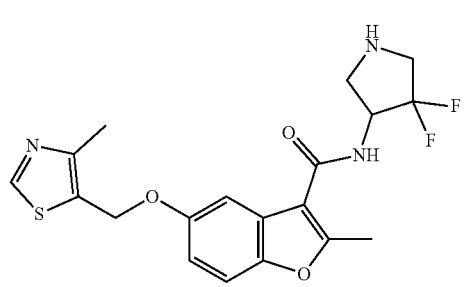 [SMILES: Cc1ncsc1COc1ccc2oc(C)c(C(=O)NC3CNCC3(F)F)c2c1] | cpd 106 |

| Structure/CODE | |
|---|---|
| 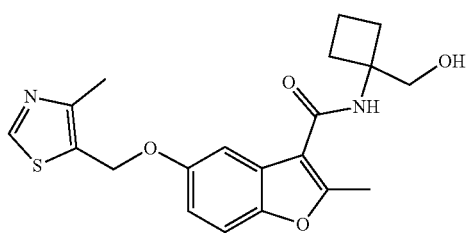 [SMILES: Cc1ncsc1COc1ccc2oc(C)c(C(=O)NC3(CO)CCC3)c2c1] | cpd 107 |
| 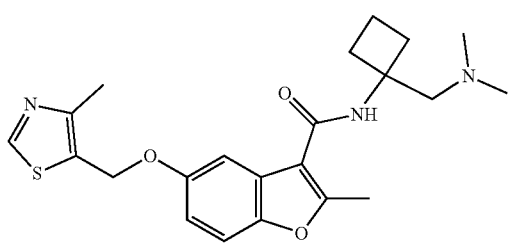 [SMILES: Cc1ncsc1COc1ccc2oc(C)c(C(=O)NC3(CN(C)C)CCC3)c2c1] | cpd 108 |
| 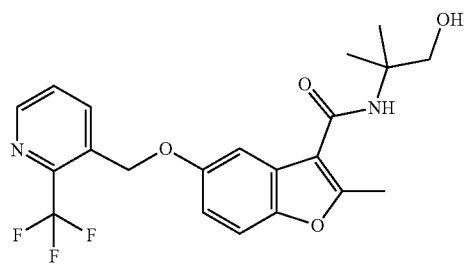 [SMILES: Cc1oc2ccc(OCc3cccnc3C(F)(F)F)cc2c1C(=O)NC(C)(C)CO] | cpd 109 |
| 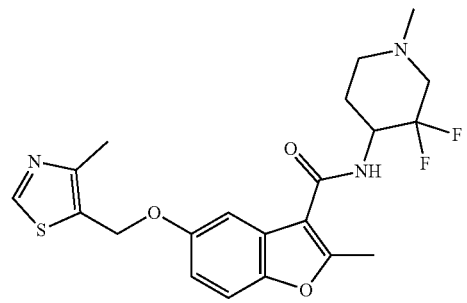 [SMILES: Cc1ncsc1COc1ccc2oc(C)c(C(=O)NC3CCN(C)CC3(F)F)c2c1] | cpd 110 |
| 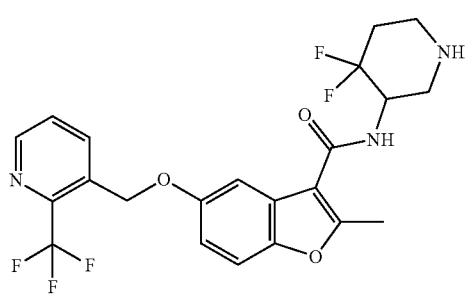 [SMILES: Cc1oc2ccc(OCc3cccnc3C(F)(F)F)cc2c1C(=O)NC1CNCCC1(F)F] | cpd 111 |

| Structure/CODE |
|---|
| -continued |
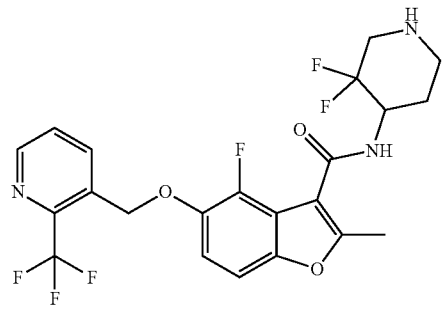 [SMILES: Cc1oc2ccc(OCc3cccnc3C(F)(F)F)c(F)c2c1C(=O)NC1CCNCC1(F)F]
cpd 112
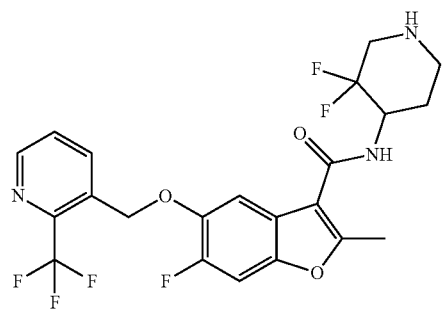 [SMILES: Cc1oc2cc(F)c(OCc3cccnc3C(F)(F)F)cc2c1C(=O)NC1CCNCC1(F)F]
cpd 113
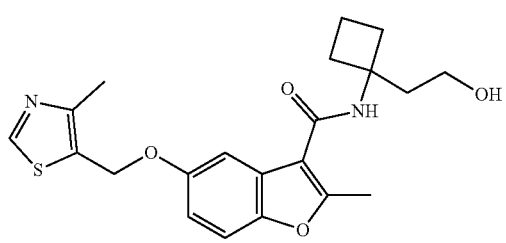 [SMILES: Cc1ncsc1COc1ccc2oc(C)c(C(=O)NC3(CCO)CCC3)c2c1]
cpd 114
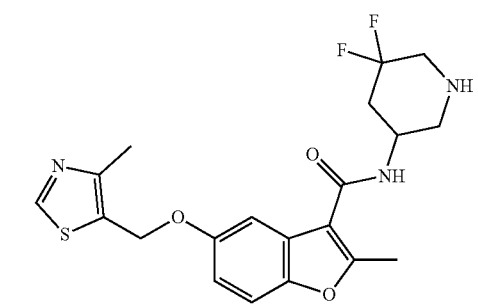 [SMILES: Cc1ncsc1COc1ccc2oc(C)c(C(=O)NC3CNCC(F)(F)C3)c2c1]
cpd 115
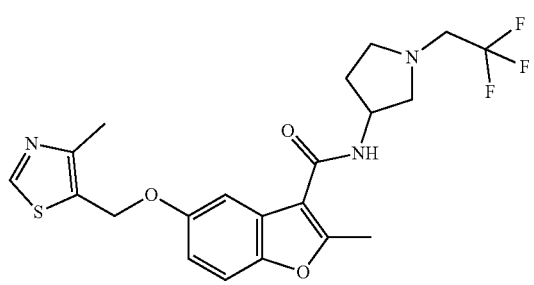 [SMILES: Cc1ncsc1COc1ccc2oc(C)c(C(=O)NC3CCN(CC(F)(F)F)C3)c2c1]
cpd 116

-continued
| Structure/CODE | |
|---|---|
| 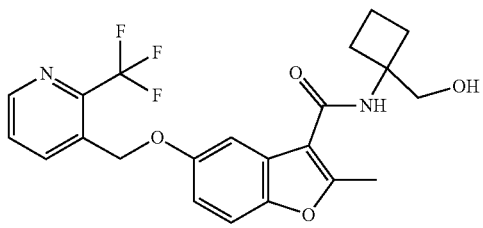 [SMILES: Cc1oc2ccc(OCc3cccnc3C(F)(F)F)cc2c1C(=O)NC1(CO)CCC1] | cpd 117 |
| 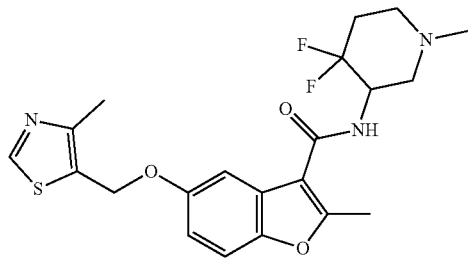 [SMILES: Cc1ncsc1COc1ccc2oc(C)c(C(=O)NC3CN(C)CCC3(F)F)c2c1] | cpd 118 |
| 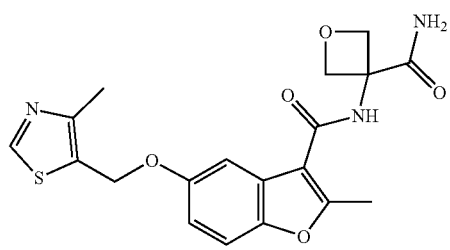 [SMILES: Cc1ncsc1COc1ccc2oc(C)c(C(=O)NC3(C(N)=O)COC3)c2c1] | cpd 119 |
| 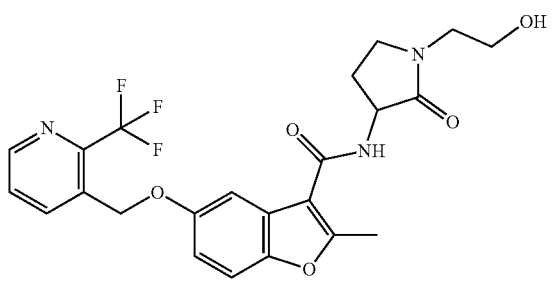 [SMILES: Cc1oc2ccc(OCc3cccnc3C(F)(F)F)cc2c1C(=O)NC1CCN(CCO)C1=O] | cpd 120 |
| 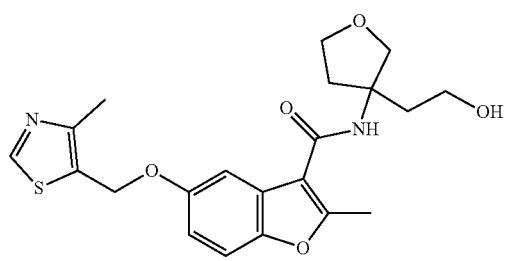 [SMILES: Cc1ncsc1COc1ccc2oc(C)c(C(=O)NC3(CCO)CCOC3)c2c1] | cpd 121 |
| 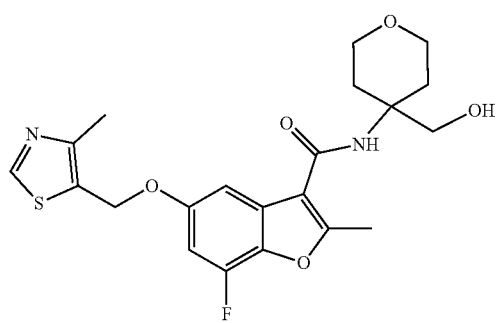 [SMILES: Cc1ncsc1COc1cc(F)c2oc(C)c(C(=O)NC3(CO)CCOCC3)c2c1] | cpd 122 |

-continued
Structure/CODE
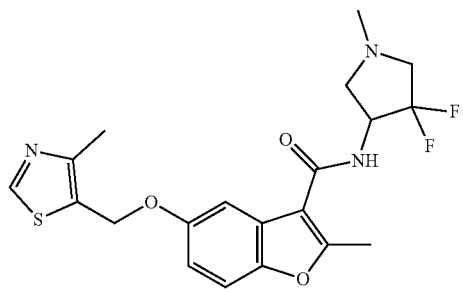 [SMILES: Cc1ncsc1COc1ccc2oc(C)c(C(=O)NC3CN(C)CC3(F)F)c2c1]
cpd 123
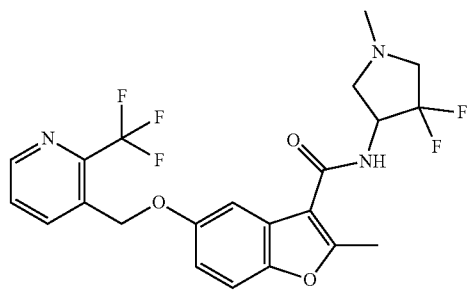 [SMILES: Cc1oc2ccc(OCc3cccnc3C(F)(F)F)cc2c1C(=O)NC1CN(C)CC1(F)F]
cpd 124
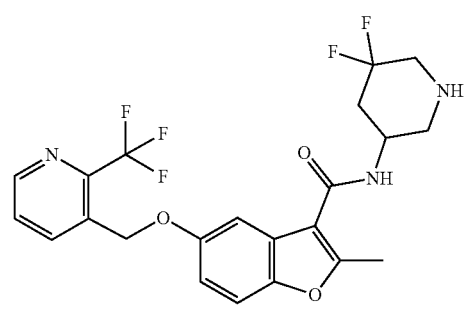 [SMILES: Cc1oc2ccc(OCc3cccnc3C(F)(F)F)cc2c1C(=O)NC1CNCC(F)(F)C1]
cpd 125
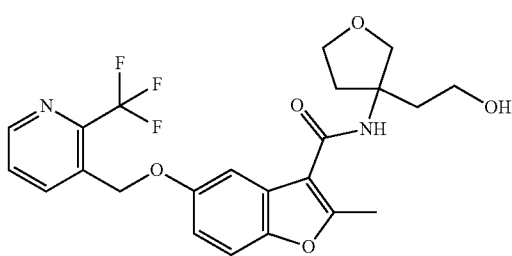 [SMILES: Cc1oc2ccc(OCc3cccnc3C(F)(F)F)cc2c1C(=O)NC1(CCO)CCOC1]
cpd 126
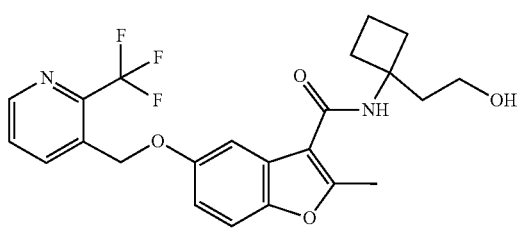 [SMILES: Cc1oc2ccc(OCc3cccnc3C(F)(F)F)cc2c1C(=O)NC1(CCO)CCC1]
cpd 127

-continued
| Structure/CODE | |
|---|---|
| 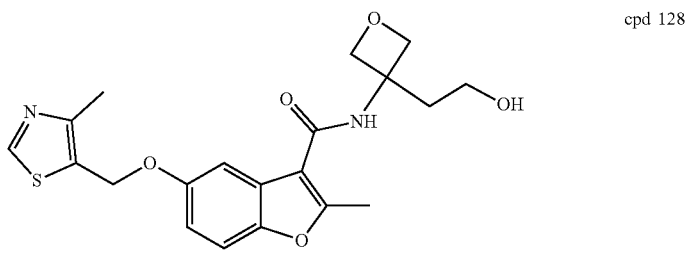 | cpd 128 |
| 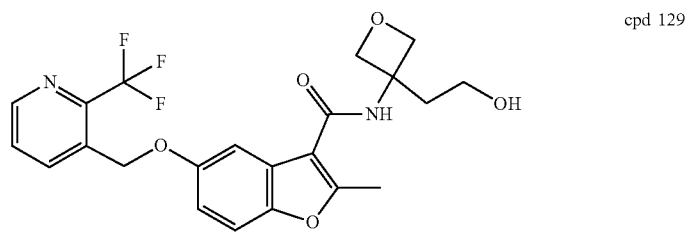 | cpd 129 |
| 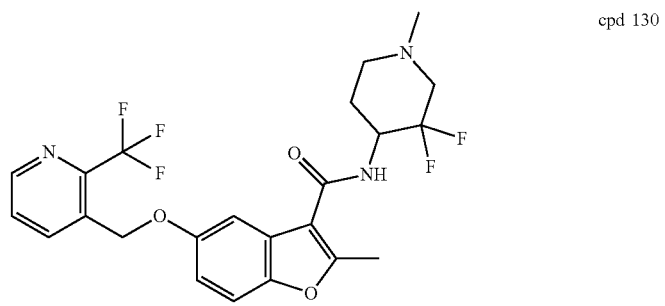 | cpd 130 |
| 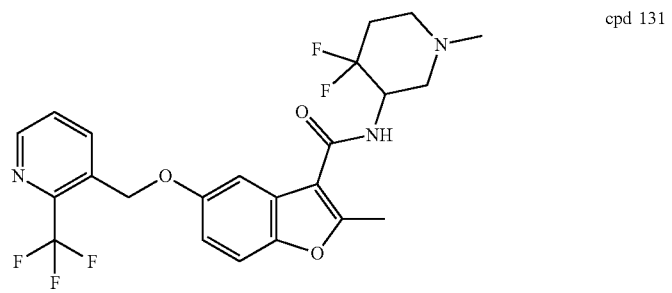 | cpd 131 |
| 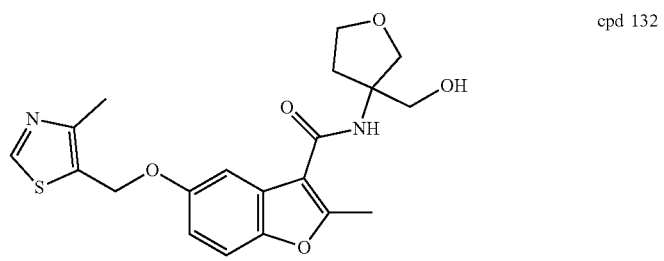 | cpd 132 |
| 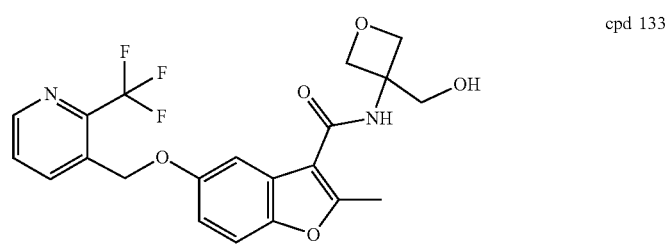 | cpd 133 |

| Structure/CODE | |
|---|---|
| 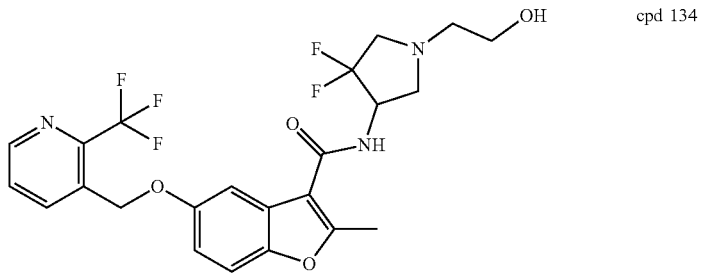 | cpd 134 |
| 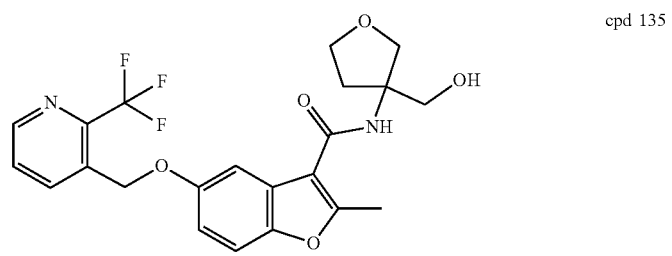 | cpd 135 |
| 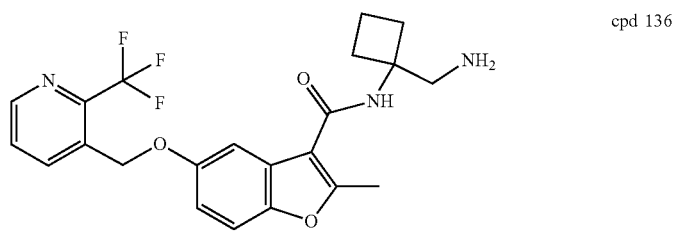 | cpd 136 |
| 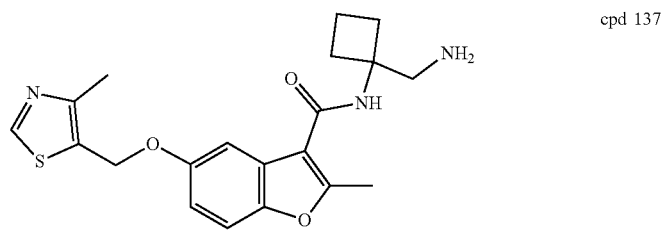 | cpd 137 |
| 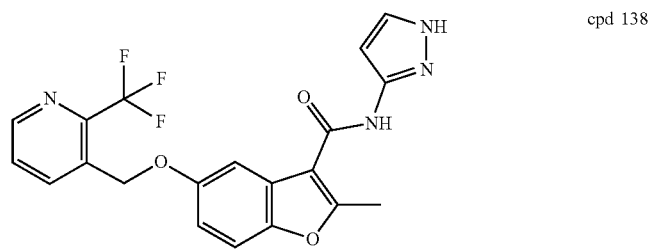 | cpd 138 |
| 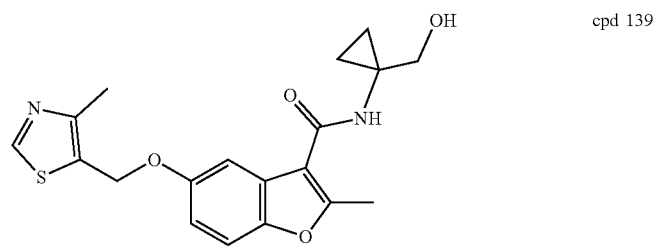 | cpd 139 |

-continued
| Structure/CODE | |
|---|---|
| 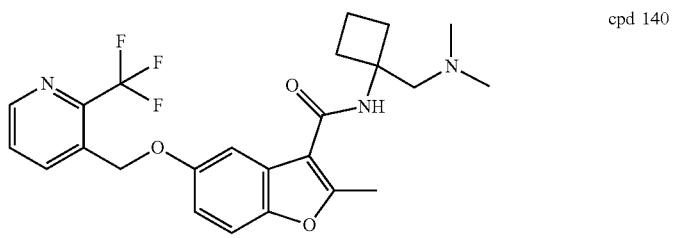 | cpd 140 |
| 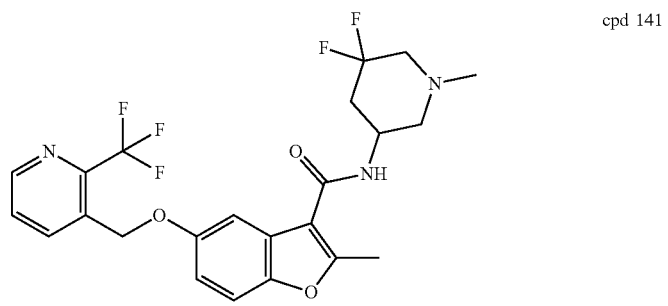 | cpd 141 |
| 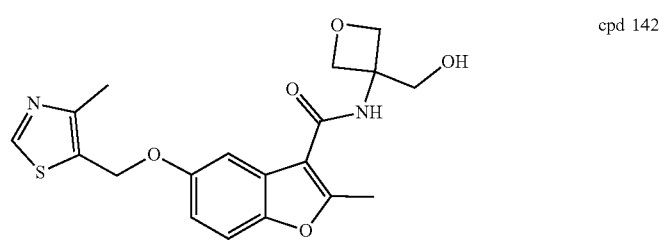 | cpd 142 |
| 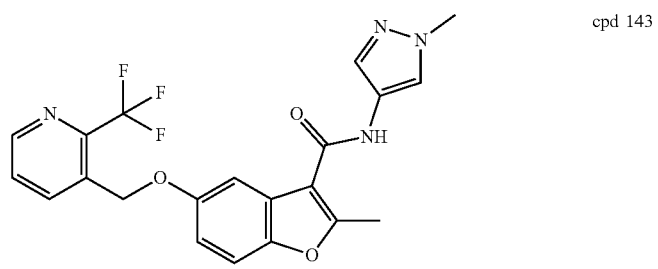 | cpd 143 |
| 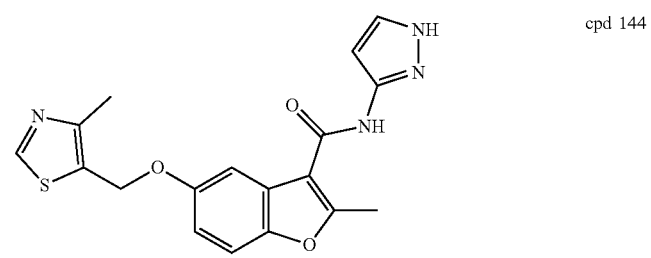 | cpd 144 |
| 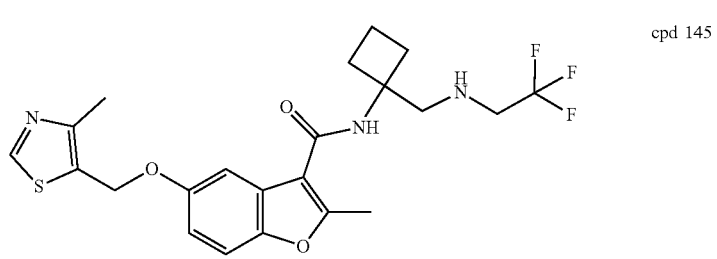 | cpd 145 |

-continued
| Structure/CODE | |
|---|---|
| 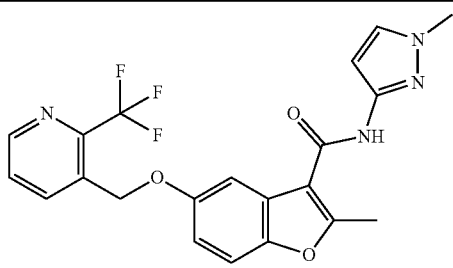 | cpd 146 |
| 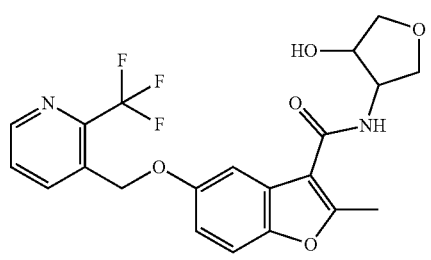 [SMILES: Cc1oc2ccc(OCc3cccnc3C(F)(F)F)cc2c1C(=O)NC1COCC1O] | cpd 147 |
| 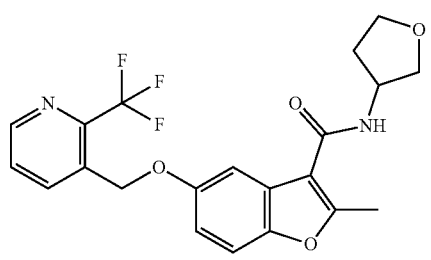 [SMILES: Cc1oc2ccc(OCc3cccnc3C(F)(F)F)cc2c1C(=O)NC1CCOC1] | cpd 148 |
| 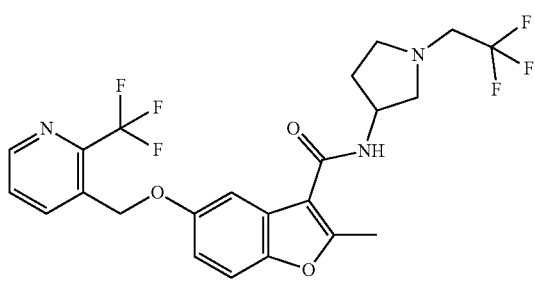 [SMILES: Cc1oc2ccc(OCc3cccnc3C(F)(F)F)cc2c1C(=O)NC1CCN(CC(F)(F)F)C1] | cpd 149 |
| 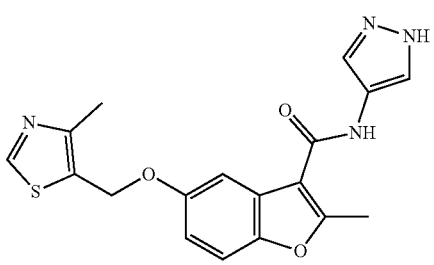 [SMILES: Cc1ncsc1COc1ccc2oc(C)c(C(=O)Nc3cn[nH]c3)c2c1] | cpd 150 |
| 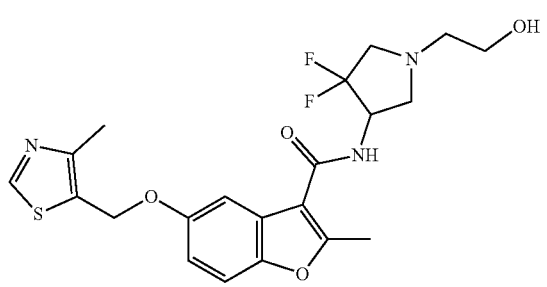 [SMILES: Cc1ncsc1COc1ccc2oc(C)c(C(=O)NC3CN(CCO)CC3(F)F)c2c1] | cpd 151 |

-continued
| Structure/CODE |
|---|
| 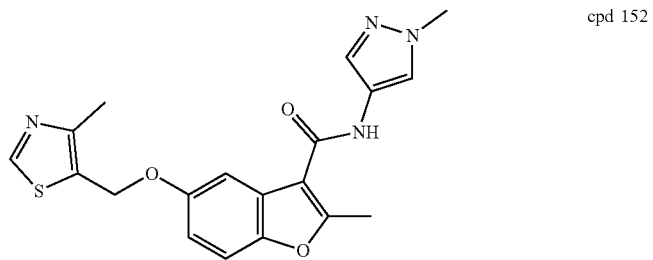 cpd 152 |
| 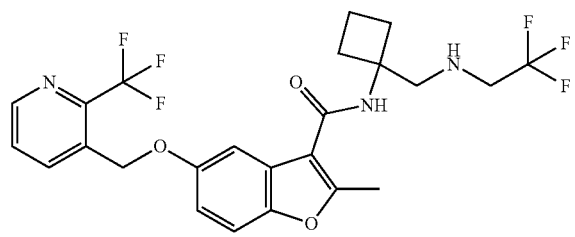 [SMILES: Cc1oc2ccc(OCc3cccnc3C(F)(F)F)cc2c1C(=O)NC1(CNCC(F)(F)F)CCC1] cpd 153 |
| 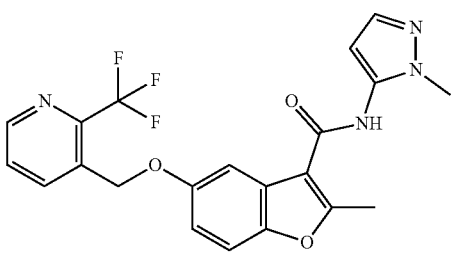 [SMILES: Cc1oc2ccc(OCc3cccnc3C(F)(F)F)cc2c1C(=O)Nc1ccnn1C] cpd 154 |
| 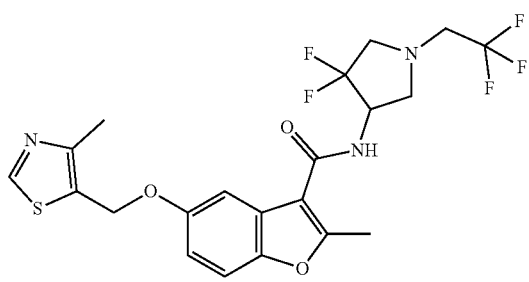 [SMILES: Cc1ncsc1COc1ccc2oc(C)c(C(=O)NC3CN(CC(F)(F)F)CC3(F)F)c2c1] cpd 155 |
| 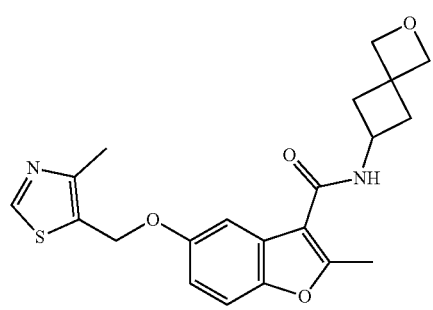 [SMILES: Cc1ncsc1COc1ccc2oc(C)c(C(=O)NC3CC4(COC4)C3)c2c1] cpd 156 |

US 12,404,266 B2
-continued
| Structure/CODE | |
|---|---|
| 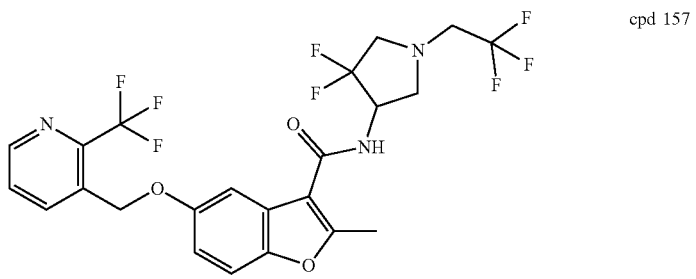 | cpd 157 |
| 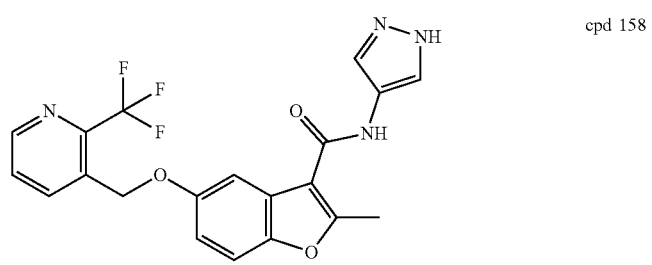 | cpd 158 |
| 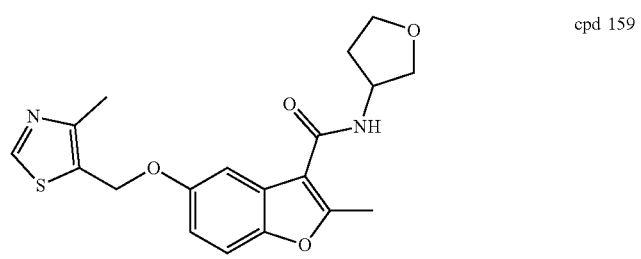 | cpd 159 |
| 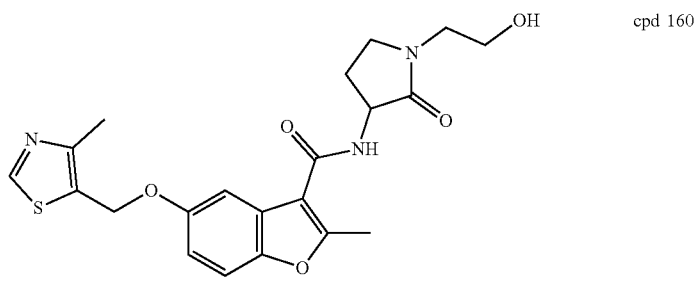 | cpd 160 |
| 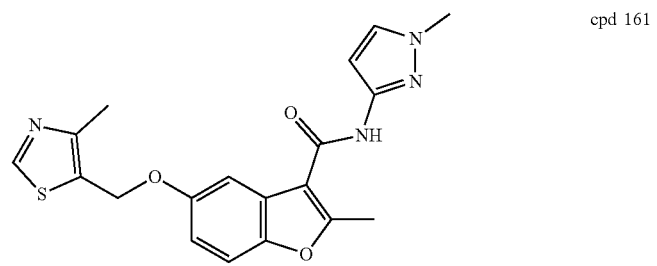 | cpd 161 |
| 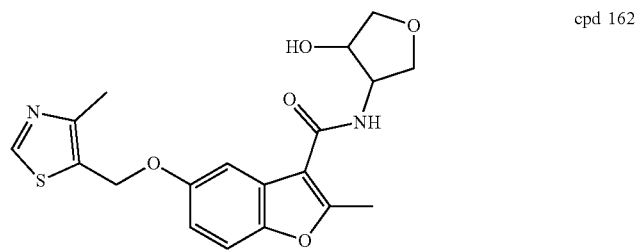 | cpd 162 |

| Structure/CODE |
|---|
| 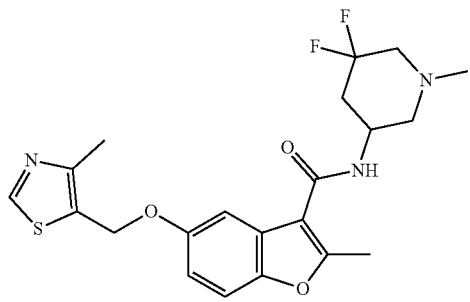 [SMILES: Cc1ncsc1COc1ccc2oc(C)c(C(=O)NC3CN(C)CC(F)(F)C3)c2c1] cpd 163 |
| 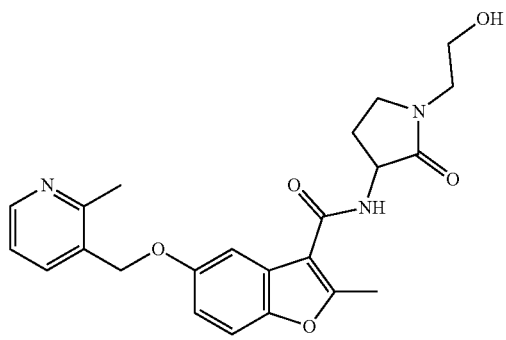 [SMILES: Cc1ncccc1COc1ccc2oc(C)c(C(=O)NC3CCN(CCO)C3=O)c2c1] cpd 164 |
| 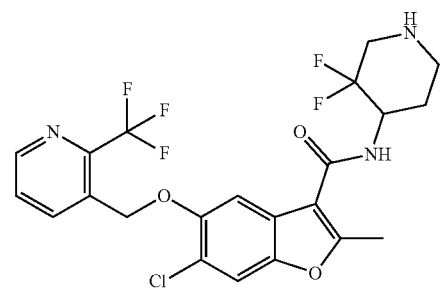 [SMILES: Cc1oc2cc(Cl)c(OCc3cccnc3C(F)(F)F)cc2c1C(=O)NC1CCNCC1(F)F] cpd 165 |
| 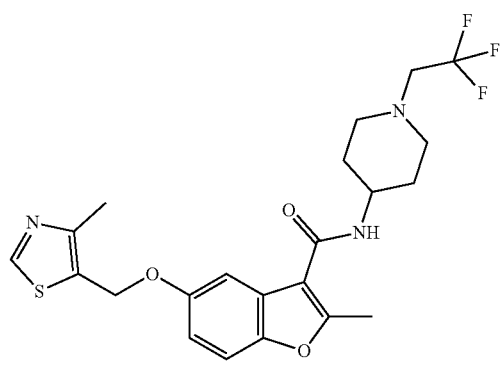 [SMILES: Cc1ncsc1COc1ccc2oc(C)c(C(=O)NC3CCN(CC(F)(F)F)CC3)c2c1] cpd 166 |

| Structure/CODE |
|---|
| 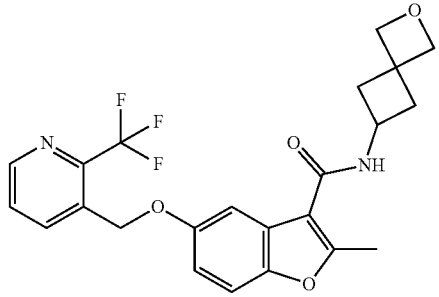 [SMILES: Cc1oc2ccc(OCc3cccnc3C(F)(F)F)cc2c1C(=O)NC1CC2(COC2)C1] cpd 167 |
| 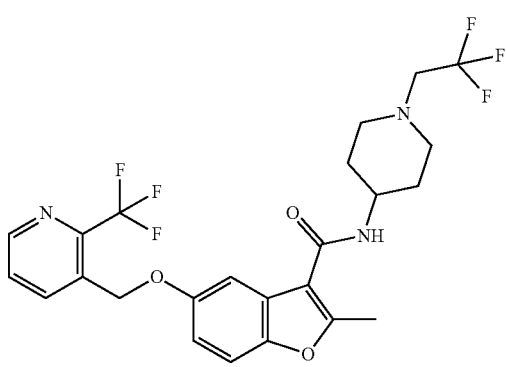 [SMILES: Cc1oc2ccc(OCc3cccnc3C(F)(F)F)cc2c1C(=O)NC1CCN(CC(F)(F)F)CC1] cpd 168 |
| 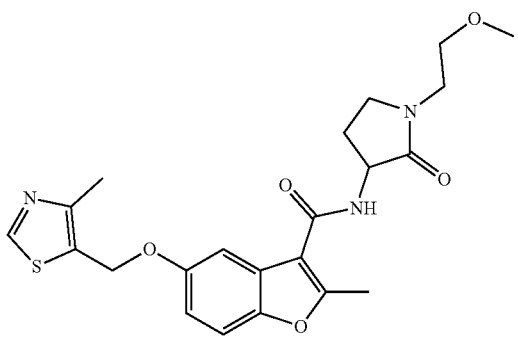 [SMILES: COCCN1CCC(NC(=O)c2c(C)oc3ccc(OCc4scnc4C)cc23)C1=O] cpd 169 |
| 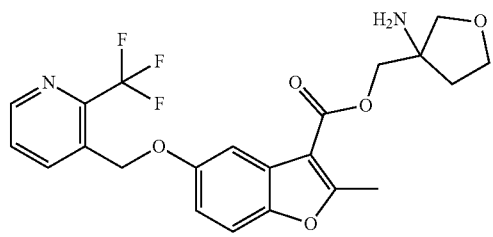 [SMILES: Cc1oc2ccc(OCc3cccnc3C(F)(F)F)cc2c1C(=O)OCC1(N)CCOC1] cpd 170 |
| 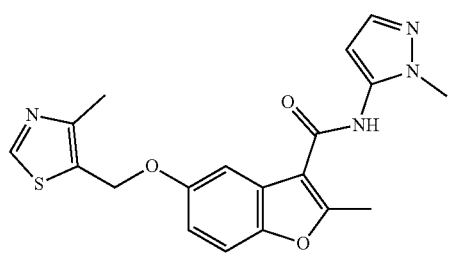 [SMILES: Cc1ncsc1COc1ccc2oc(C)c(C(=O)Nc3ccnn3C)c2c1] cpd 171 |

-continued
| Structure/CODE | |
|---|---|
| 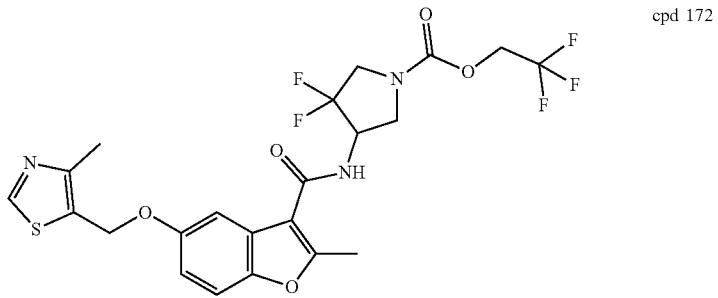 | cpd 172 |
| 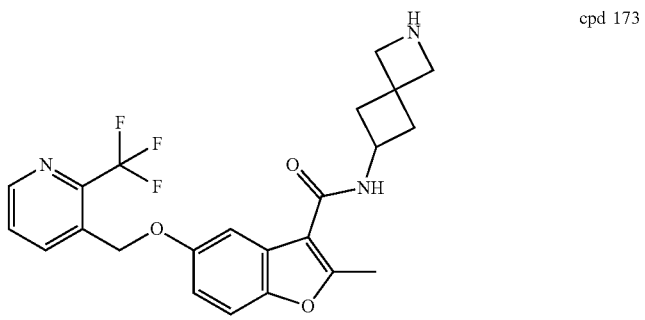 | cpd 173 |
| 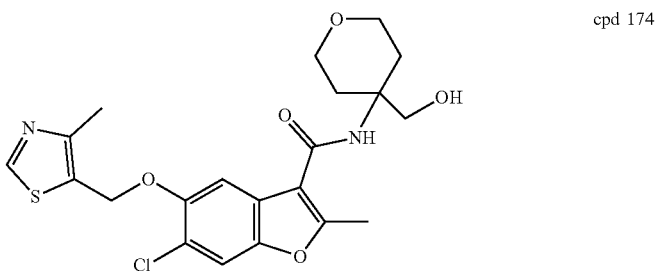 | cpd 174 |
| 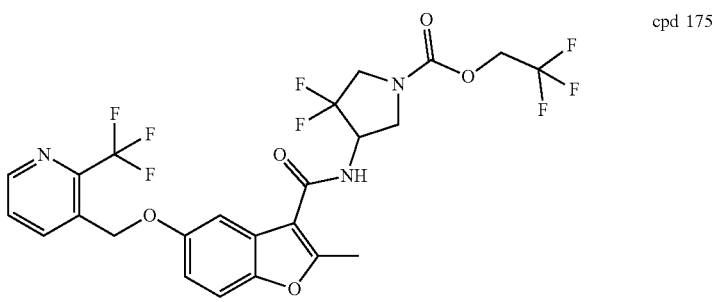 | cpd 175 |
| 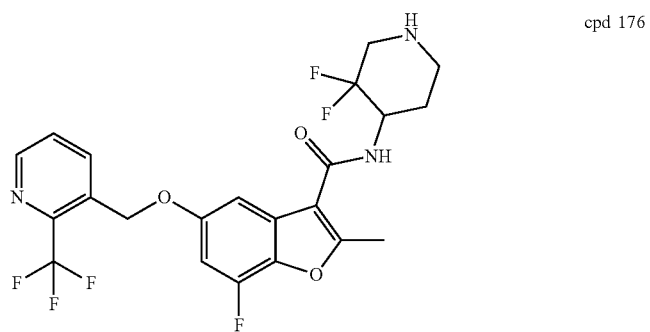 | cpd 176 |

-continued
| Structure/CODE | |
|---|---|
| 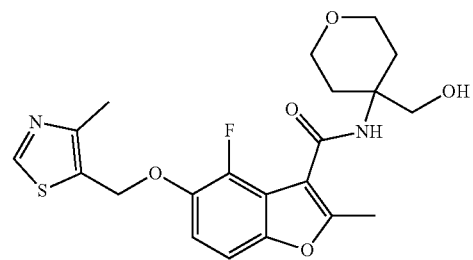 [SMILES: Cc1ncsc1COc1ccc2oc(C)c(C(=O)NC3(CO)CCOCC3)c2c1F] | cpd 177 |
| 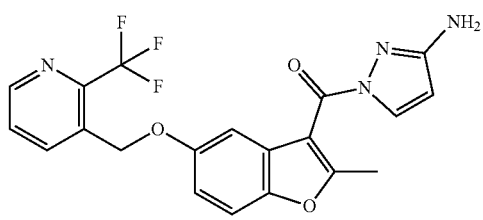 [SMILES: Cc1oc2ccc(OCc3cccnc3C(F)(F)F)cc2c1C(=O)n1ccc(N)n1] | cpd 178 |
| 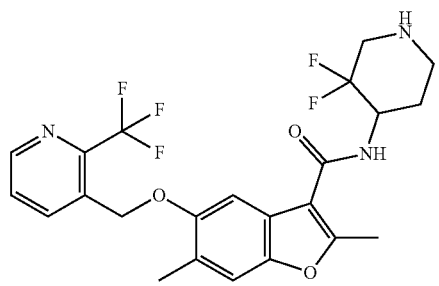 [SMILES: Cc1cc2oc(C)c(C(=O)NC3CCNCC3(F)F)c2cc1OCc1cccnc1C(F)(F)F] | cpd 179 |
| 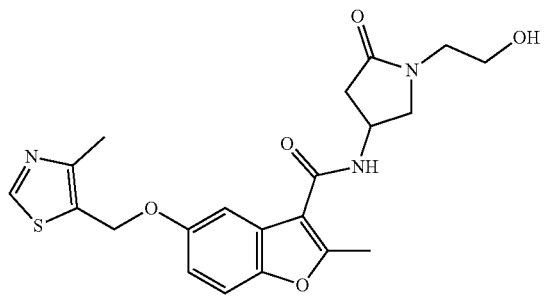 [SMILES: Cc1ncsc1COc1ccc2oc(C)c(C(=O)NC3CC(=O)N(CCO)C3)c2c1] | cpd 180 |
| 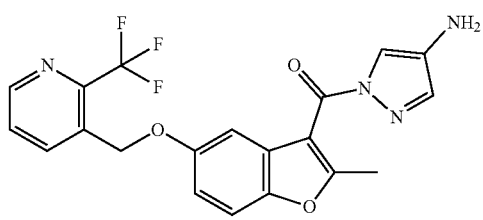 [SMILES: Cc1oc2ccc(OCc3cccnc3C(F)(F)F)cc2c1C(=O)n1cc(N)cn1] | cpd 181 |
| 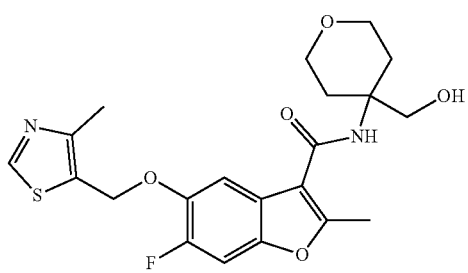 [SMILES: Cc1ncsc1COc1cc2c(C(=O)NC3(CO)CCOCC3)c(C)oc2cc1F] | cpd 182 |

-continued
| Structure/CODE | |
|---|---|
| 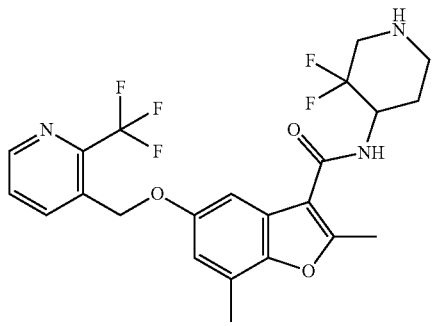 [SMILES: Cc1oc2c(C)cc(OCc3cccnc3C(F)(F)F)cc2c1C(=O)NC1CCNCC1(F)F] | cpd 183 |
| 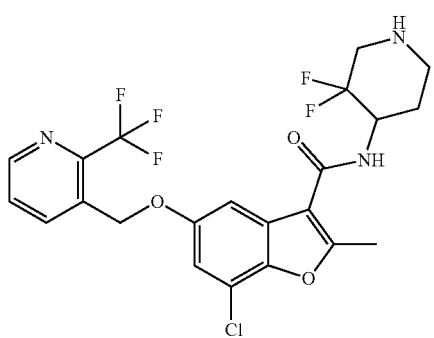 [SMILES: Cc1oc2c(Cl)cc(OCc3cccnc3C(F)(F)F)cc2c1C(=O)NC1CCNCC1(F)F] | cpd 184 |
| 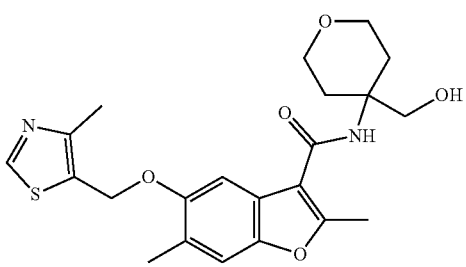 [SMILES: Cc1cc2oc(C)c(C(=O)NC3(CO)CCOCC3)c2cc1OCc1scnc1C] | cpd 185 |
| 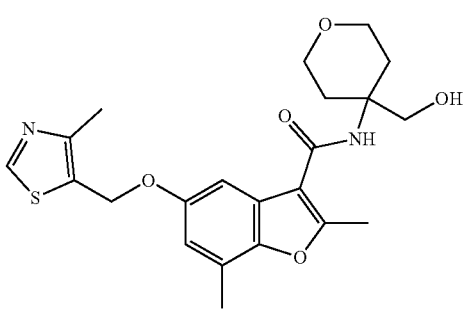 [SMILES: Cc1ncsc1COc1cc(C)c2oc(C)c(C(=O)NC3(CO)CCOCC3)c2c1] | cpd 186 |
| 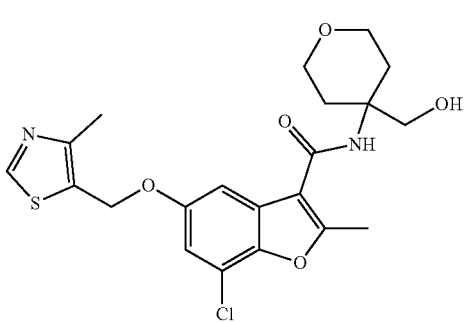 [SMILES: Cc1ncsc1COc1cc(Cl)c2oc(C)c(C(=O)NC3(CO)CCOCC3)c2c1] | cpd 187 |

| Structure/CODE | |
|---|---|
| 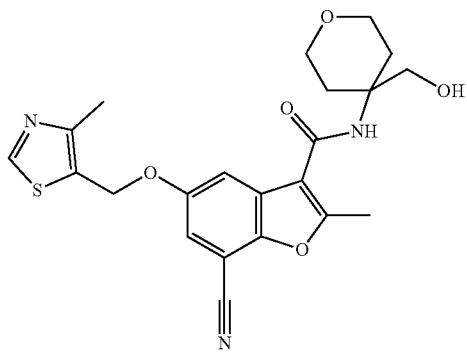 [SMILES: Cc1ncsc1COc1cc(C#N)c2oc(C)c(C(=O)NC3(CO)CCOCC3)c2c1] | cpd 188 |
| 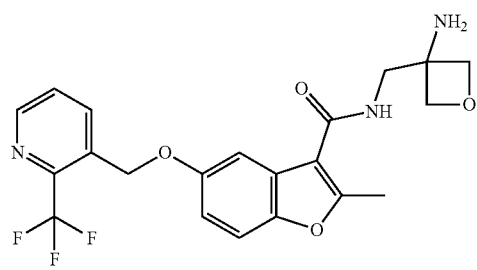 [SMILES: Cc1oc2ccc(OCc3cccnc3C(F)(F)F)cc2c1C(=O)NCC1(N)COC1] | cpd 189 |
| 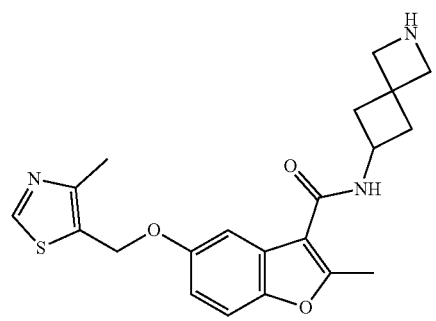 [SMILES: Cc1ncsc1COc1ccc2oc(C)c(C(=O)NC3CC4(CNC4)C3)c2c1] | cpd 190 |
| 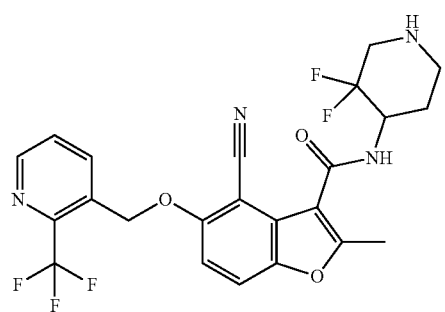 [SMILES: Cc1oc2ccc(OCc3cccnc3C(F)(F)F)c(C#N)c2c1C(=O)NC1CCNCC1(F)F] | cpd 191 |
| 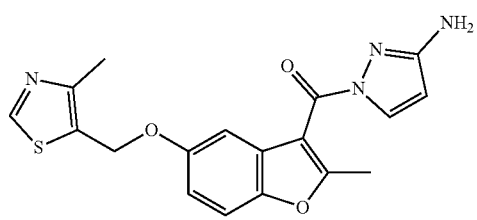 [SMILES: Cc1ncsc1COc1ccc2oc(C)c(C(=O)n3ccc(N)n3)c2c1] | cpd 192 |

-continued
| Structure/CODE | |
|---|---|
| 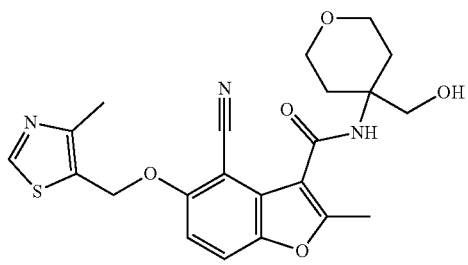 [SMILES: Cc1ncsc1COc1ccc2oc(C)c(C(=O)NC3(CO)CCOCC3)c2c1C#N] | cpd 193 |
| 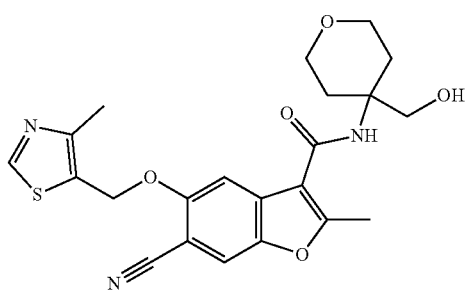 [SMILES: Cc1ncsc1COc1cc2c(C(=O)NC3(CO)CCOCC3)c(C)oc2cc1C#N] | cpd 194 |
| 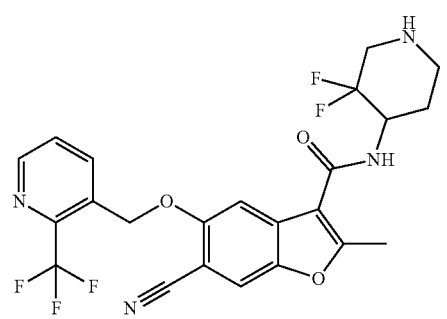 [SMILES: Cc1oc2cc(C#N)c(OCc3cccnc3C(F)(F)F)cc2c1C(=O)NC1CCNCC1(F)F] | cpd 195 |
| 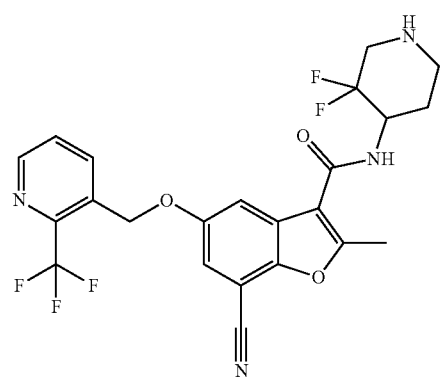 [SMILES: Cc1oc2c(C#N)cc(OCc3cccnc3C(F)(F)F)cc2c1C(=O)NC1CCNCC1(F)F] | cpd 196 |
| 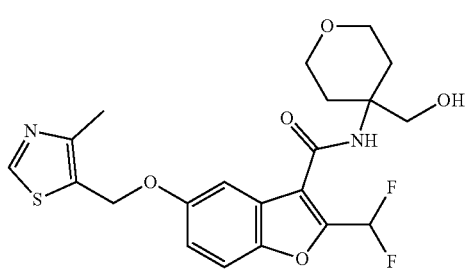 [SMILES: Cc1ncsc1COc1ccc2oc(C(F)F)c(C(=O)NC3(CO)CCOCC3)c2c1] | cpd 197 |

-continued
| Structure/CODE |
|---|
| 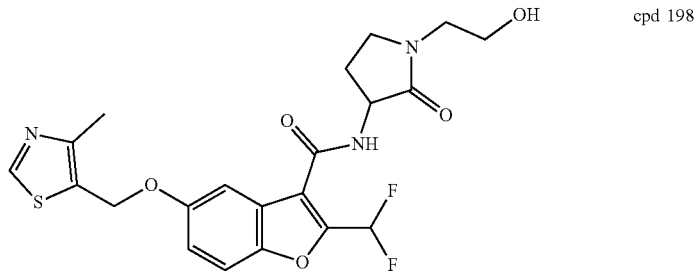 cpd 198 |
| 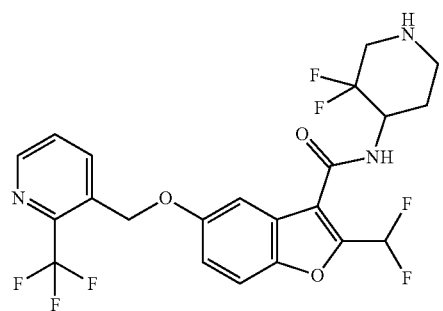 [SMILES: O=C(NC1CCNCC1(F)F)c1c(C(F)F)oc2ccc(OCc3cccnc3C(F)(F)F)cc12] cpd 199 |
| 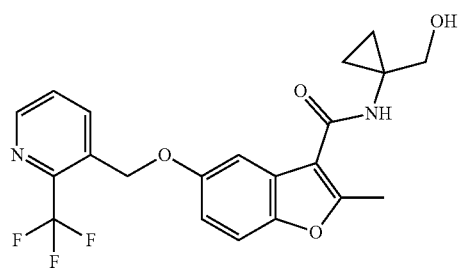 [SMILES: Cc1oc2ccc(OCc3cccnc3C(F)(F)F)cc2c1C(=O)NC1(CO)CC1] cpd 200 |
| 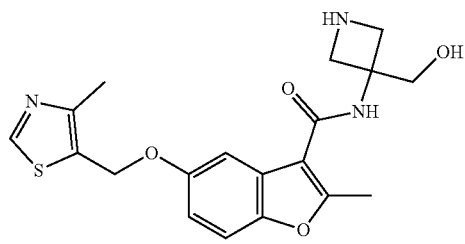 [SMILES: Cc1ncsc1COc1ccc2oc(C)c(C(=O)NC3(CO)CNC3)c2c1] cpd 201 |
| 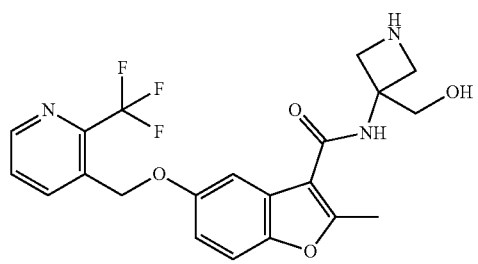 [SMILES: Cc1oc2ccc(OCc3cccnc3C(F)(F)F)cc2c1C(=O)NC1(CO)CNC1] cpd 202 |

-continued
| Structure/CODE |
|---|
| 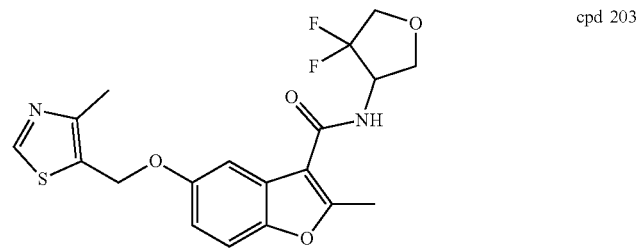 cpd 203 |
| 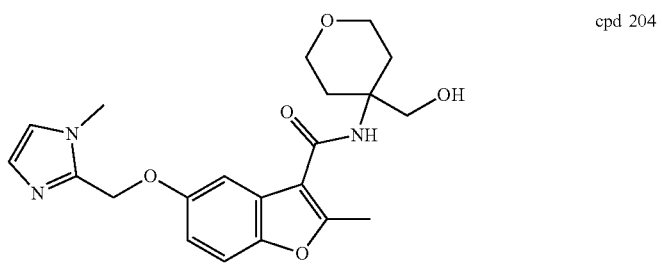 cpd 204 |
| 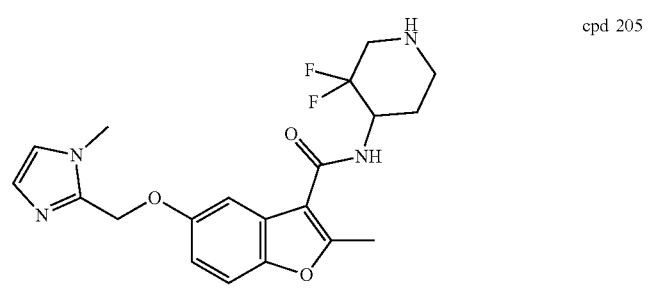 cpd 205 |
| 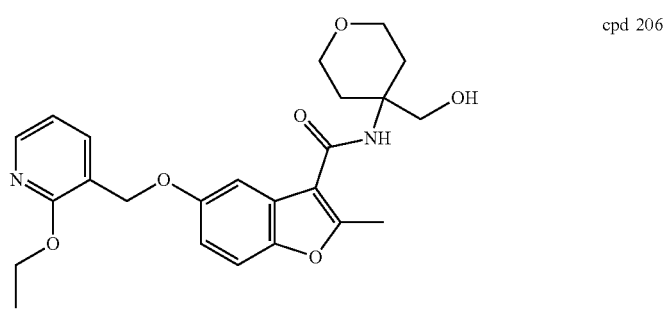 cpd 206 |
| 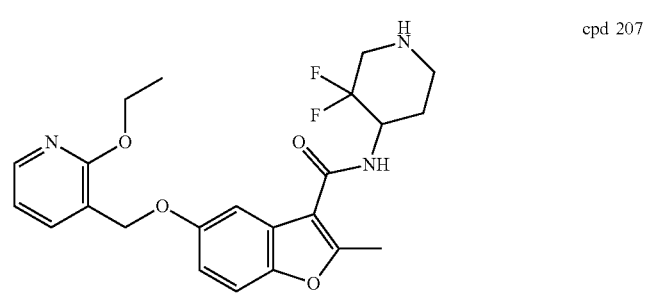 cpd 207 |
| 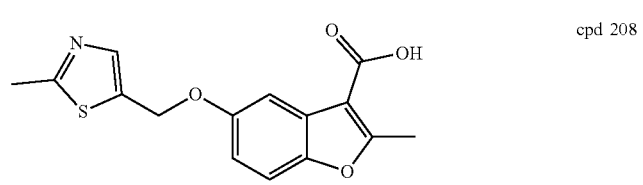 cpd 208 |

-continued
| Structure/CODE | |
|---|---|
| 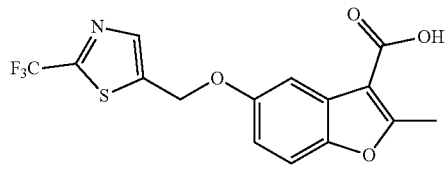 [SMILES: Cc1oc2ccc(OCc3cnc(C(F)(F)F)s3)cc2c1C(=O)O] | cpd 209 |
| 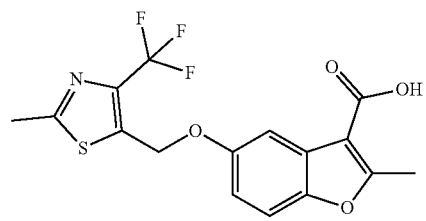 | cpd 210 |
| 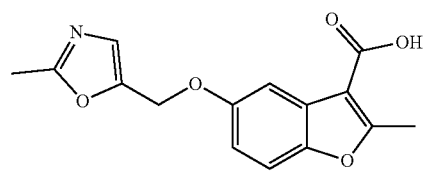 | cpd 211 |
| 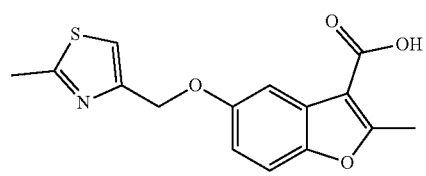 | cpd 212 |
| 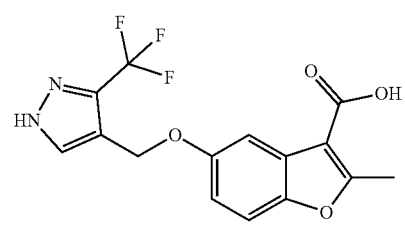 [SMILES: Cc1oc2ccc(OCc3c[nH]nc3C(F)(F)F)cc2c1C(=O)O] | cpd 213 |
| 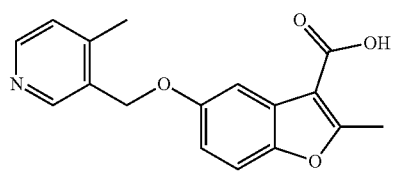 [SMILES: Cc1ccncc1COc1ccc2oc(C)c(C(=O)O)c2c1] | cpd 214 |
| 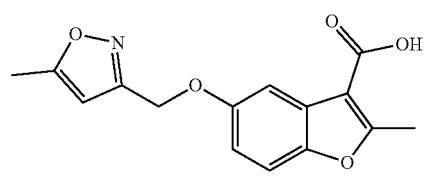 | cpd 215 |
| 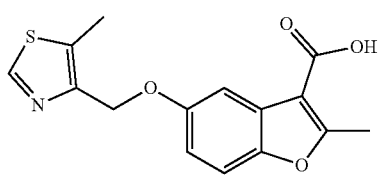 [SMILES: Cc1oc2ccc(OCc3ncsc3C)cc2c1C(=O)O] | cpd 216 |

| Structure/CODE | |
|---|---|
| 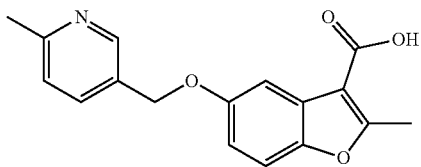 | cpd 217 |
| 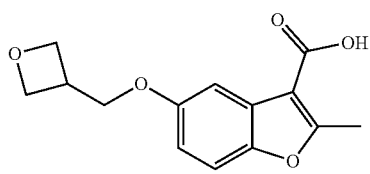 [SMILES: Cc1oc2ccc(OCC3COC3)cc2c1C(=O)O] | cpd 218 |
| 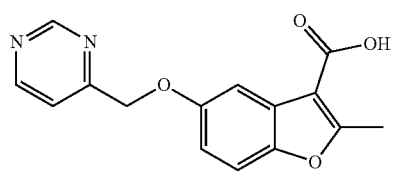 [SMILES: Cc1oc2ccc(OCc3ccncn3)cc2c1C(=O)O] | cpd 219 |
| 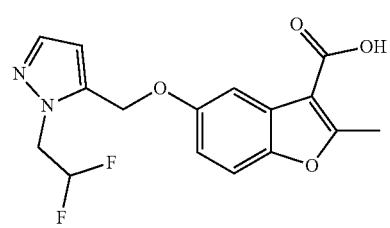 [SMILES: Cc1oc2ccc(OCc3ccnn3CC(F)F)cc2c1C(=O)O] | cpd 220 |
| 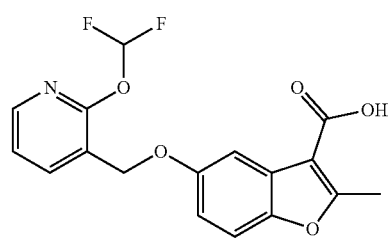 [SMILES: Cc1oc2ccc(OCc3cccnc3OC(F)F)cc2c1C(=O)O] | cpd 221 |
| 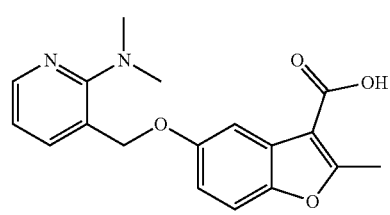 [SMILES: Cc1oc2ccc(OCc3cccnc3N(C)C)cc2c1C(=O)O] | cpd 222 |
| 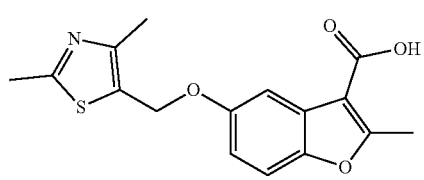 | cpd 223 |
| 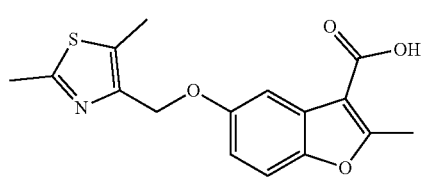 | cpd 224 |

| Structure/CODE | |
|---|---|
| 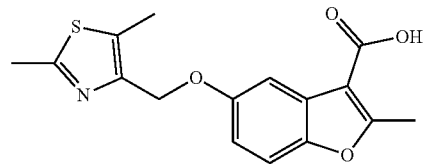 | cpd 225 |
| 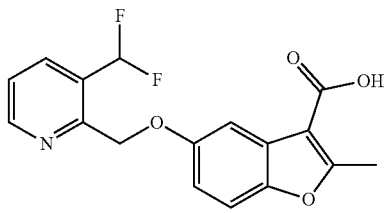 [SMILES: Cc1oc2ccc(OCc3ncccc3C(F)F)cc2c1C(=O)O] | cpd 226 |
| 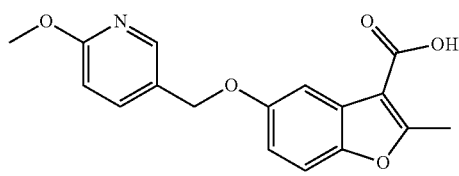 | cpd 227 |
| 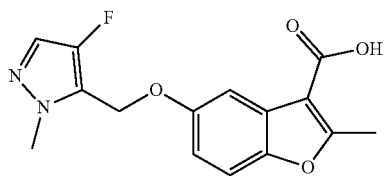 [SMILES: Cc1oc2ccc(OCc3c(F)cnn3C)cc2c1C(=O)O] | cpd 228 |
| 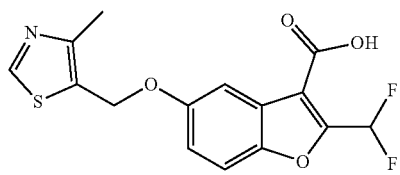 [SMILES: Cc1ncsc1COc1ccc2oc(C(F)F)c(C(=O)O)c2c1] | cpd 229 |
| 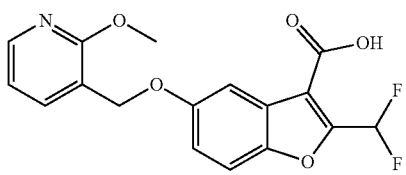 [SMILES: COc1ncccc1COc1ccc2oc(C(F)F)c(C(=O)O)c2c1] | cpd 230 |
| 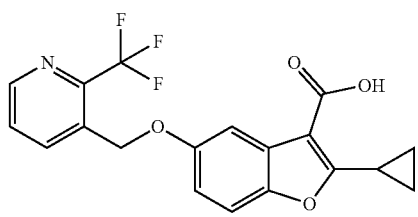 [SMILES: O=C(O)c1c(C2CC2)oc2ccc(OCc3cccnc3C(F)(F)F)cc12] | cpd 231 |
| 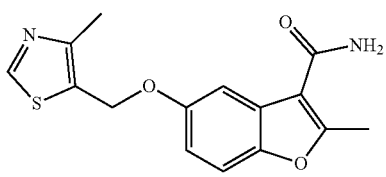 [SMILES: Cc1ncsc1COc1ccc2oc(C)c(C(N)=O)c2c1] | cpd 232 |

-continued
| Structure/CODE | |
|---|---|
| 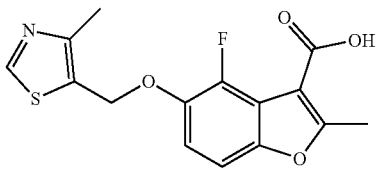 [SMILES: Cc1ncsc1COc1ccc2oc(C)c(C(=O)O)c2c1F] | cpd 233 |
| 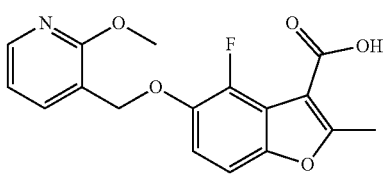 [SMILES: COc1ncccc1COc1ccc2oc(C)c(C(=O)O)c2c1F] | cpd 234 |
| 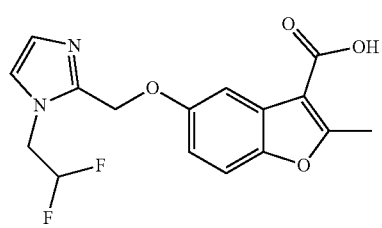 [SMILES: Cc1oc2ccc(OCc3nccn3CC(F)F)cc2c1C(=O)O] | cpd 235 |
| 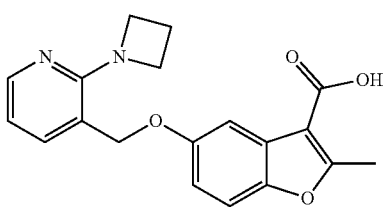 [SMILES: Cc1oc2ccc(OCc3cccnc3N3CCC3)cc2c1C(=O)O] | cpd 236 |
| 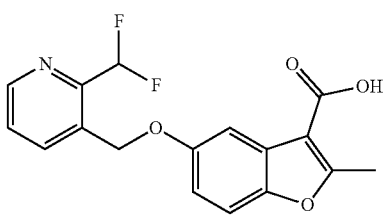 [SMILES: Cc1oc2ccc(OCc3cccnc3C(F)F)cc2c1C(=O)O] | cpd 237 |
| 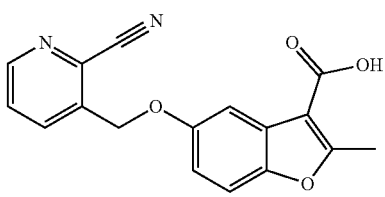 [SMILES: Cc1oc2ccc(OCc3cccnc3C#N)cc2c1C(=O)O] | cpd 238 |
| 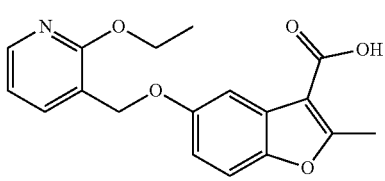 [SMILES: CCOc1ncccc1COc1ccc2oc(C)c(C(=O)O)c2c1] | cpd 239 |
| 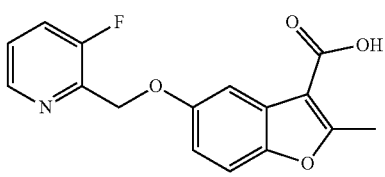 [SMILES: Cc1oc2ccc(OCc3ncccc3F)cc2c1C(=O)O] | cpd 240 |

-continued
| Structure/CODE | |
|---|---|
| 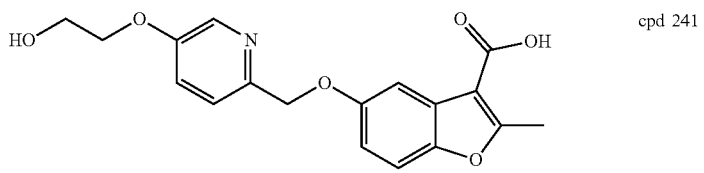 | cpd 241 |
| 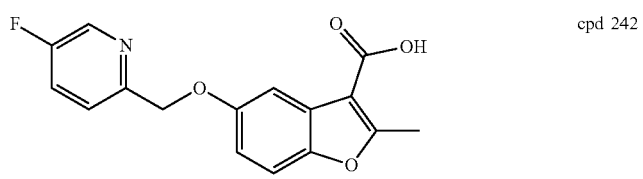 | cpd 242 |
| 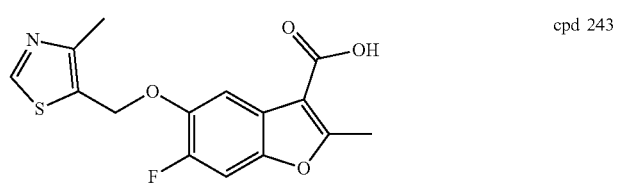 | cpd 243 |
| 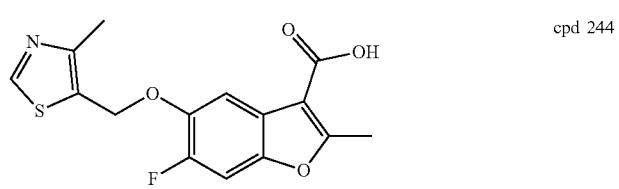 | cpd 244 |
| 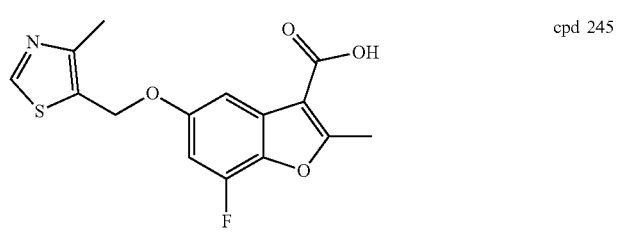 | cpd 245 |
| 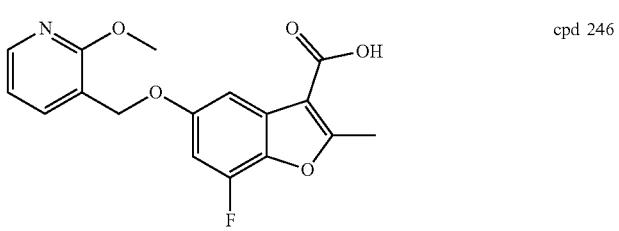 | cpd 246 |
| 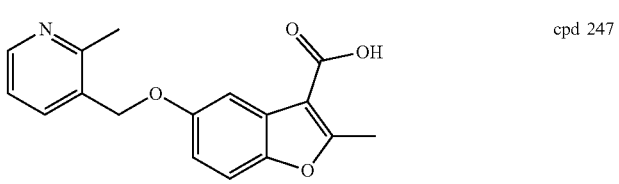 | cpd 247 |
| 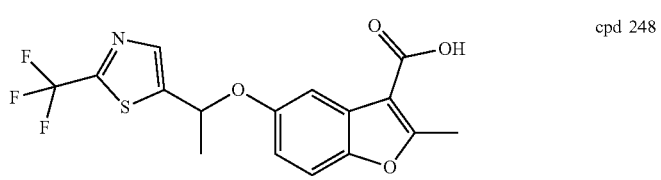 | cpd 248 |

-continued
| Structure/CODE | |
|---|---|
| 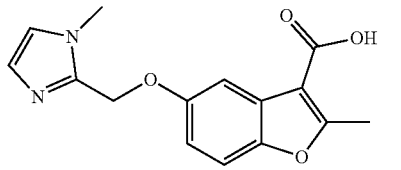 [SMILES: Cc1oc2ccc(OCc3nccn3C)cc2c1C(=O)O] | cpd 249 |
| 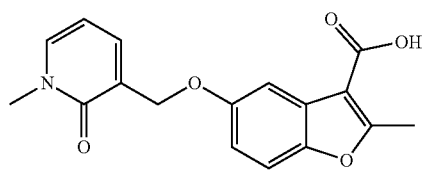 | cpd 250 |
| 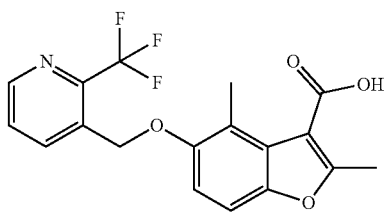 [SMILES: Cc1oc2ccc(OCc3cccnc3C(F)(F)F)c(C)c2c1C(=O)O] | cpd 251 |
| 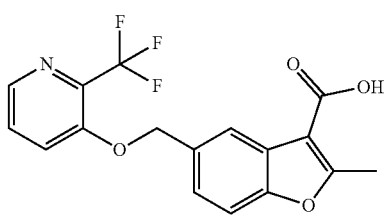 [SMILES: Cc1oc2ccc(COc3cccnc3C(F)(F)F)cc2c1C(=O)O] | cpd 252 |
| 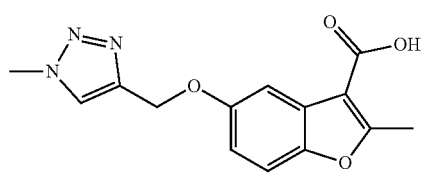 | cpd 253 |
| 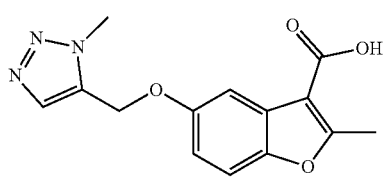 [SMILES: Cc1oc2ccc(OCc3cnnn3C)cc2c1C(=O)O] | cpd 254 |
| 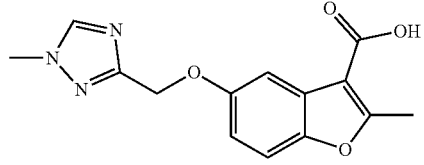 | cpd 255 |
| 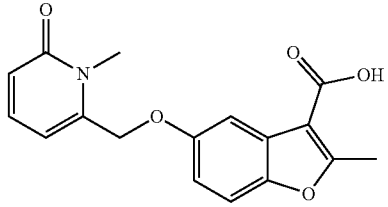 [SMILES: Cc1oc2ccc(OCc3cccc(=O)n3C)cc2c1C(=O)O] | cpd 256 |

-continued
| Structure/CODE | |
|---|---|
| 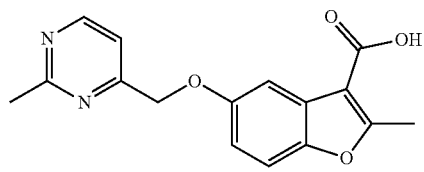 | cpd 257 |
| 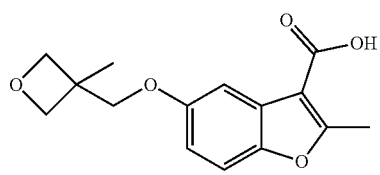 [SMILES: Cc1oc2ccc(OCC3(C)COC3)cc2c1C(=O)O] | cpd 258 |
| 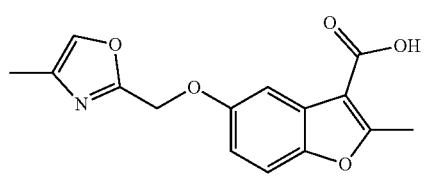 | cpd 259 |
| 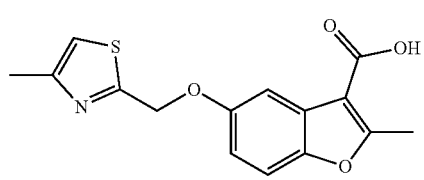 | cpd 260 |
| 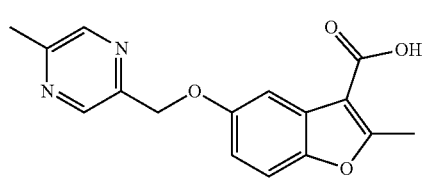 | cpd 261 |
| 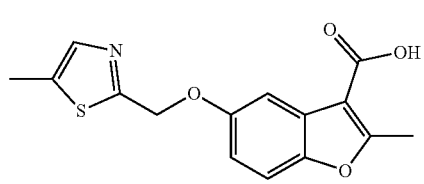 | cpd 262 |
| 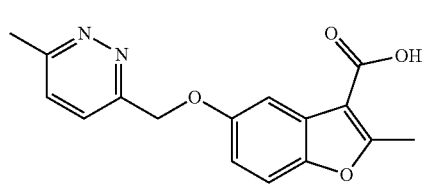 | cpd 263 |
| 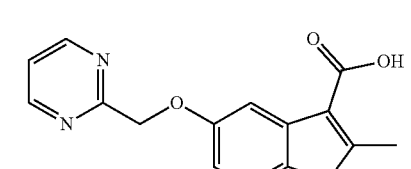 | cpd 264 |
| 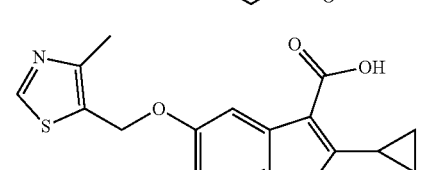 | cpd 265 |

-continued
| Structure/CODE | |
|---|---|
| 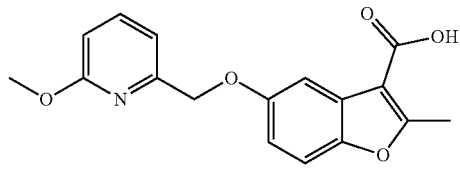 | cpd 266 |
| 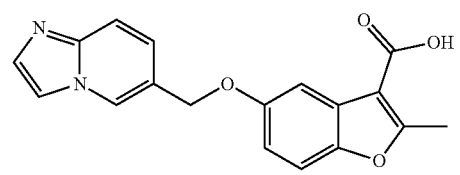 [SMILES: Cc1oc2ccc(OCc3ccc4nccn4c3)cc2c1C(=O)O] | cpd 267 |
| 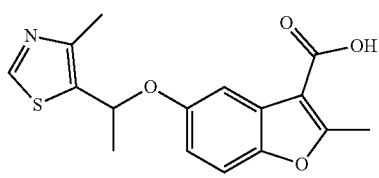 [SMILES: Cc1ncsc1C(C)Oc1ccc2oc(C)c(C(=O)O)c2c1] | cpd 268 |
| 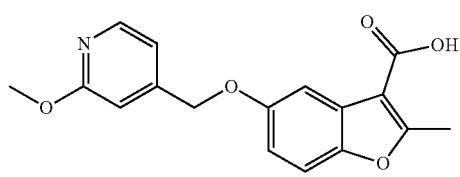 | cpd 269 |
| 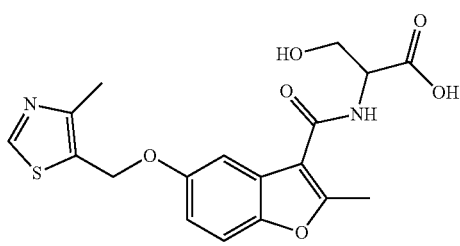 [SMILES: Cc1ncsc1COc1ccc2oc(C)c(C(=O)NC(CO)C(=O)O)c2c1] | cpd 270 |
| 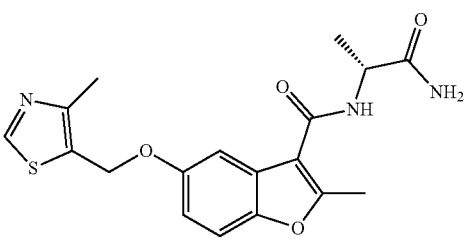 [SMILES: Cc1ncsc1COc1ccc2oc(C)c(C(=O)N[C@H](C)C(N)=O)c2c1] | cpd 271 |
| 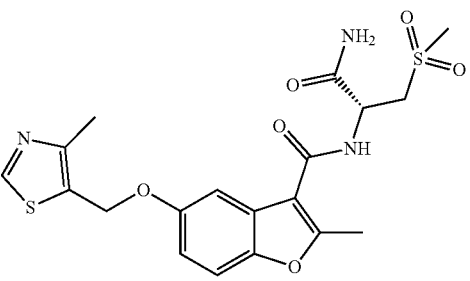 [SMILES: Cc1ncsc1COc1ccc2oc(C)c(C(=O)N[C@@H](CS(C)(=O)=O)C(N)=O)c2c1] | cpd 272 |

-continued
| Structure/CODE | |
|---|---|
| 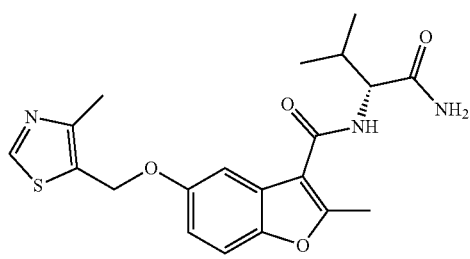 [SMILES: Cc1ncsc1COc1ccc2oc(C)c(C(=O)N[C@@H](C(N)=O)C(C)C)c2c1] | cpd 273 |
| 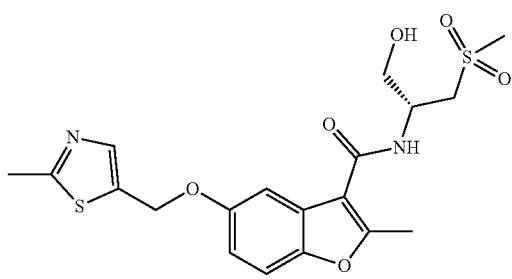 [SMILES: Cc1ncc(COc2ccc3oc(C)c(C(=O)N[C@H](CO)CS(C)(=O)=O)c3c2)s1] | cpd 274 |
| 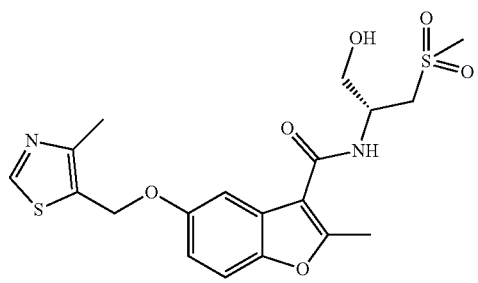 [SMILES: Cc1ncsc1COc1ccc2oc(C)c(C(=O)N[C@H](CO)CS(C)(=O)=O)c2c1] | cpd 275 |
| 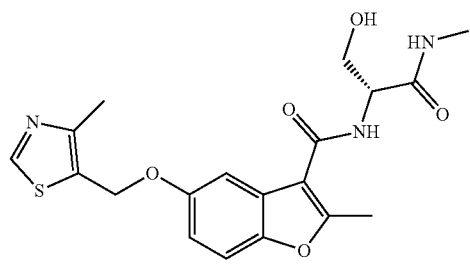 [SMILES: CNC(=O)[C@@H](CO)NC(=O)c1c(C)oc2ccc(OCc3scnc3C)cc12] | cpd 276 |
| 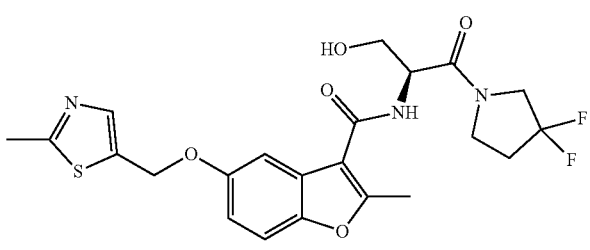 [SMILES: Cc1ncc(COc2ccc3oc(C)c(C(=O)N[C@@H](CO)C(=O)N4CCC(F)(F)C4)c3c2)s1] | cpd 277 |
| 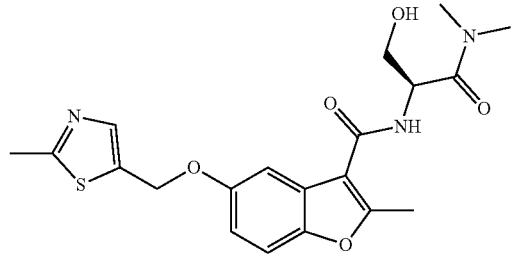 | cpd 278 |

-continued
| Structure/CODE |
|---|
| 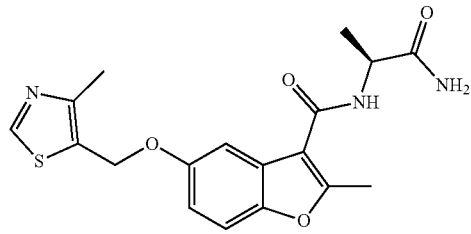 [SMILES: Cc1ncsc1COc1ccc2oc(C)c(C(=O)N[C@@H](C)C(N)=O)c2c1] cpd 279 |
| 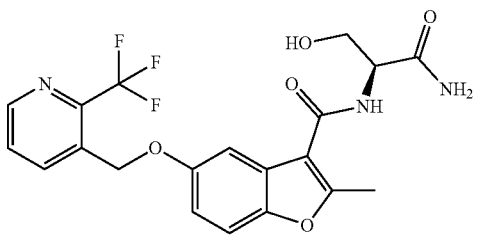 [SMILES: Cc1oc2ccc(OCc3cccnc3C(F)(F)F)cc2c1C(=O)N[C@@H](CO)C(N)=O] cpd 280 |
| 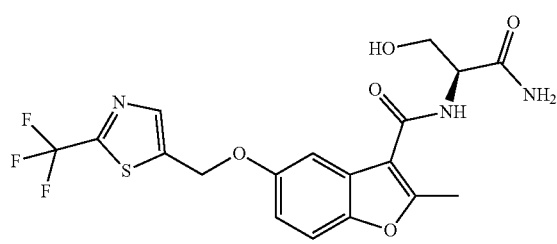 [SMILES: Cc1oc2ccc(OCc3cnc(C(F)(F)F)s3)cc2c1C(=O)N[C@@H](CO)C(N)=O] cpd 281 |
| 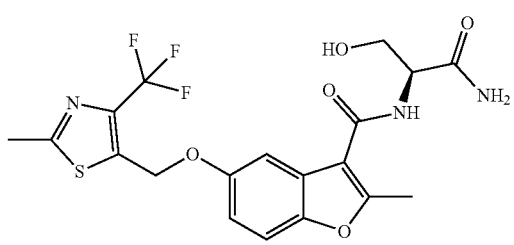 [SMILES: Cc1nc(C(F)(F)F)c(COc2ccc3oc(C)c(C(=O)N[C@@H](CO)C(N)=O)c3c2)s1] cpd 282 |
| 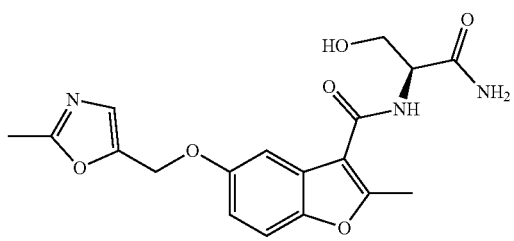 [SMILES: Cc1ncc(COc2ccc3oc(C)c(C(=O)N[C@@H](CO)C(N)=O)c3c2)o1] cpd 283 |
| 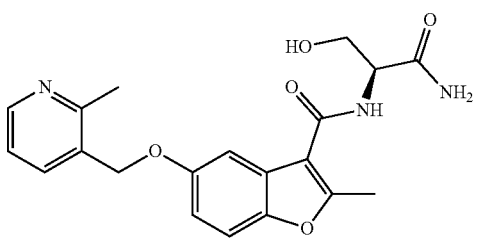 [SMILES: Cc1ncccc1COc1ccc2oc(C)c(C(=O)N[C@@H](CO)C(N)=O)c2c1] cpd 284 |

-continued
Structure/CODE
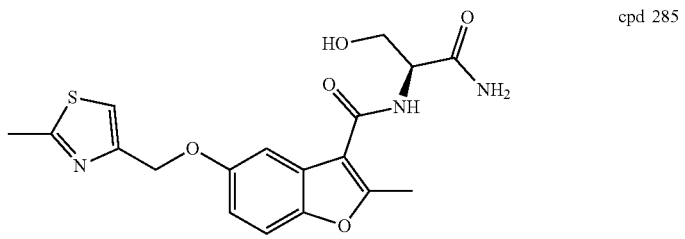
cpd 285
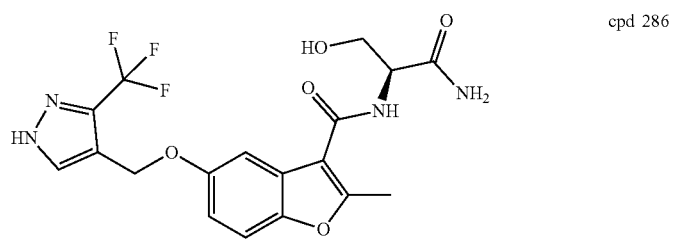
cpd 286
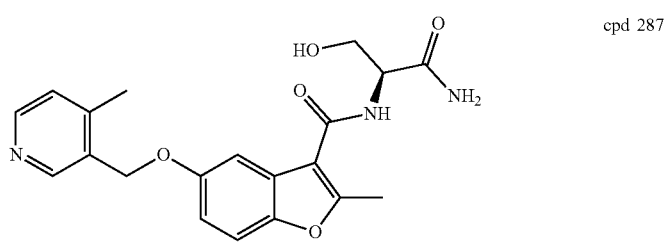
cpd 287
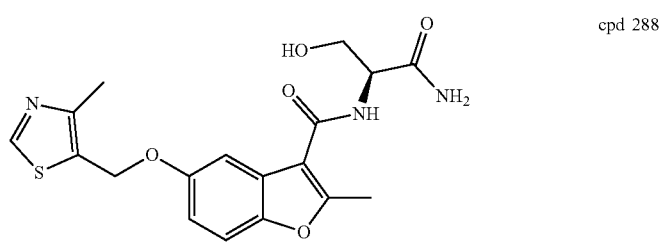
cpd 288
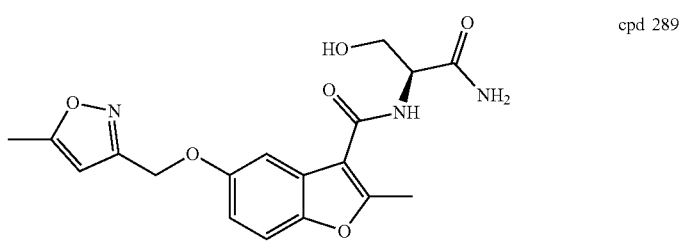
cpd 289
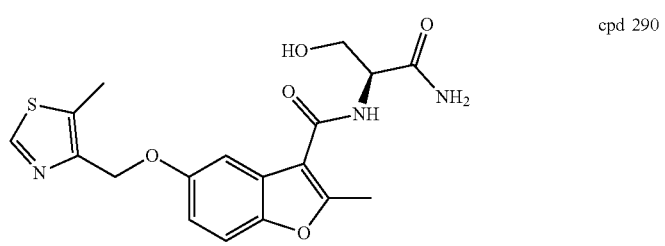
cpd 290

-continued
| Structure/CODE | |
|---|---|
| 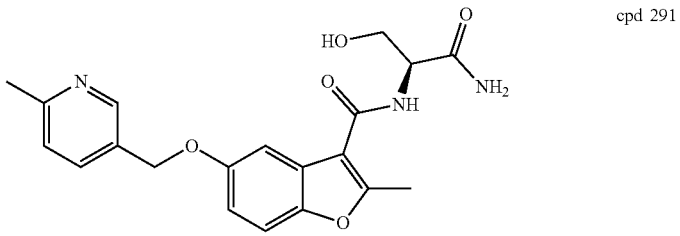 | cpd 291 |
| 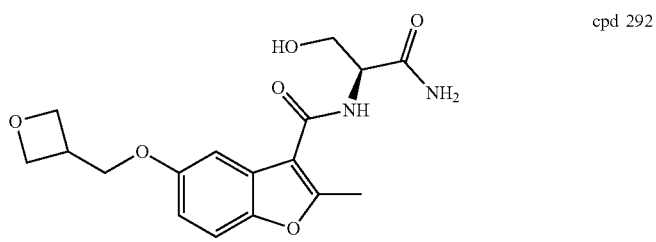 | cpd 292 |
| 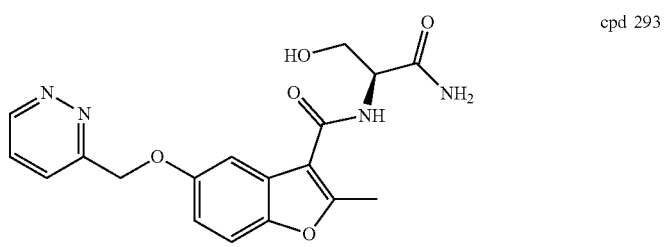 | cpd 293 |
| 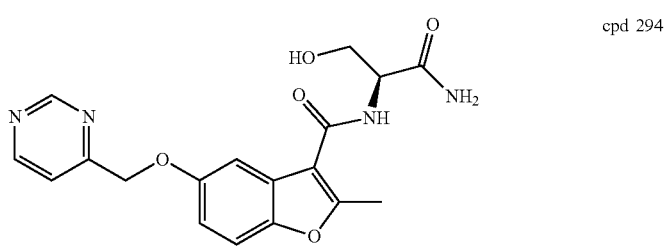 | cpd 294 |
| 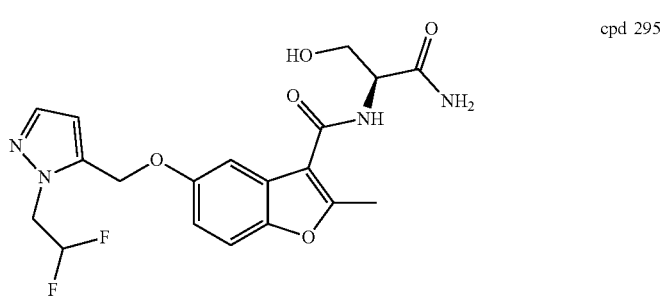 | cpd 295 |
| 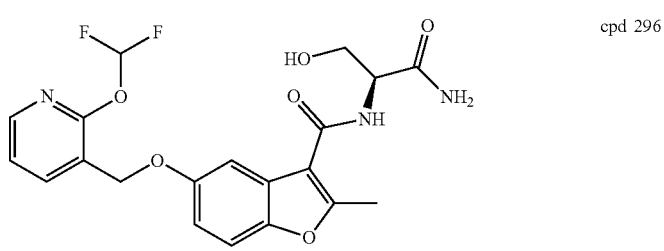 | cpd 296 |

-continued
| Structure/CODE | |
|---|---|
| 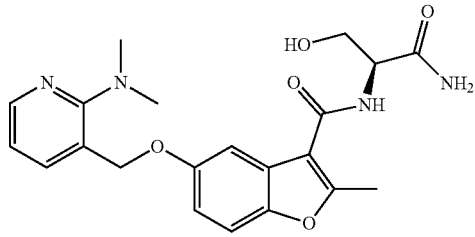 [SMILES: Cc1oc2ccc(OCc3cccnc3N(C)C)cc2c1C(=O)N[C@@H](CO)C(N)=O] | cpd 297 |
| 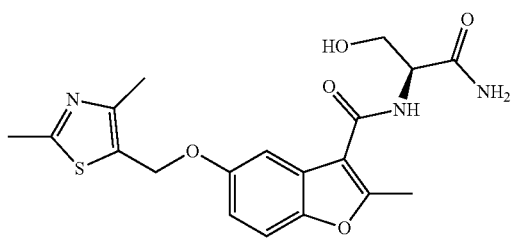 [SMILES: Cc1nc(C)c(COc2ccc3oc(C)c(C(=O)N[C@@H](CO)C(N)=O)c3c2)s1] | cpd 298 |
| 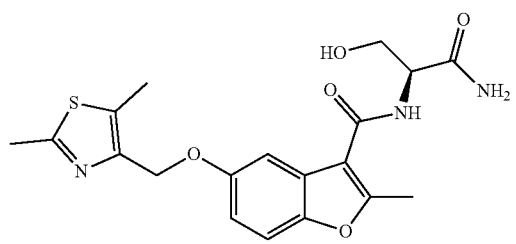 [SMILES: Cc1nc(COc2ccc3oc(C)c(C(=O)N[C@@H](CO)C(N)=O)c3c2)c(C)s1] | cpd 299 |
| 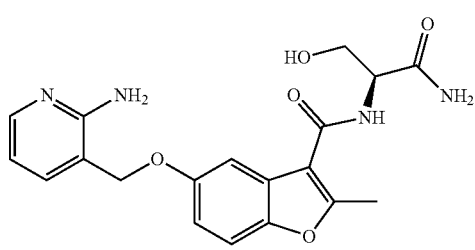 [SMILES: Cc1oc2ccc(OCc3cccnc3N)cc2c1C(=O)N[C@@H](CO)C(N)=O] | cpd 300 |
| 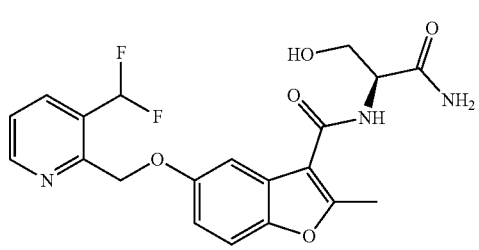 [SMILES: Cc1oc2ccc(OCc3ncccc3C(F)F)cc2c1C(=O)N[C@@H](CO)C(N)=O] | cpd 301 |
| 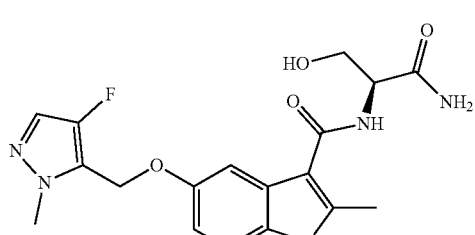 | cpd 302 |

-continued
Structure/CODE
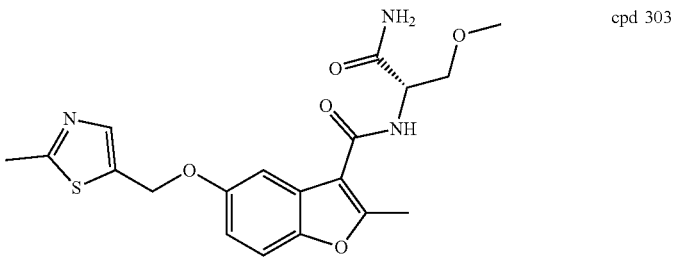
cpd 303
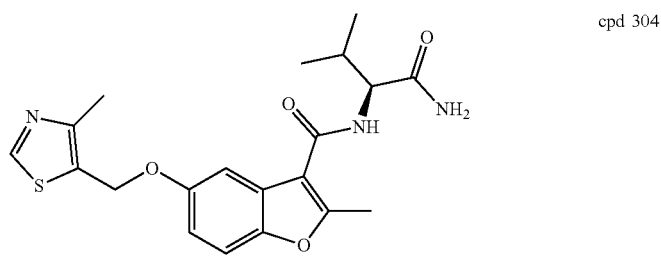
cpd 304
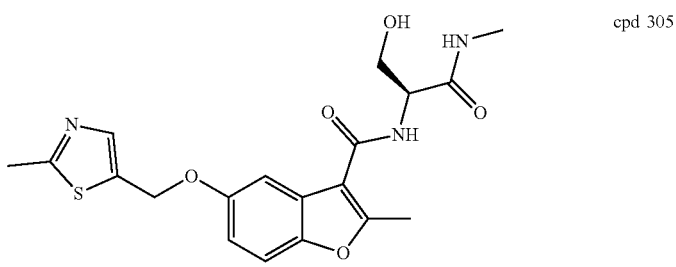
cpd 305
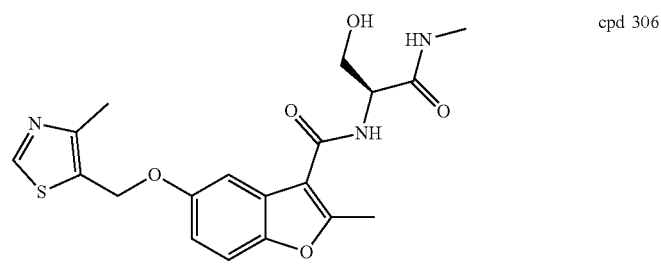
cpd 306
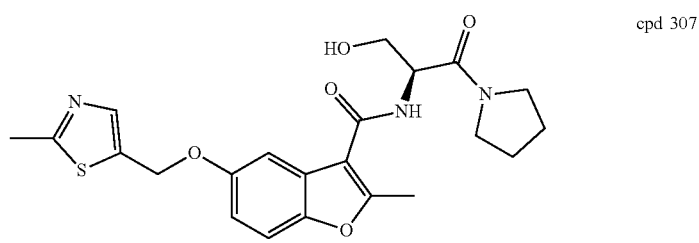
cpd 307
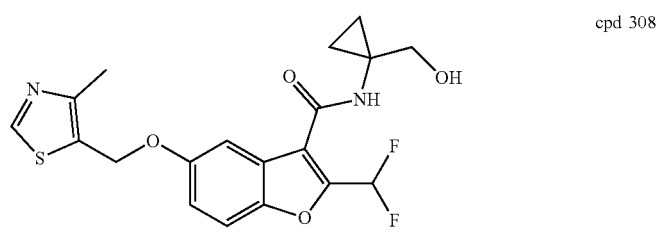
cpd 308

US 12,404,266 B2
221
222
-continued
| Structure/CODE | |
|---|---|
| 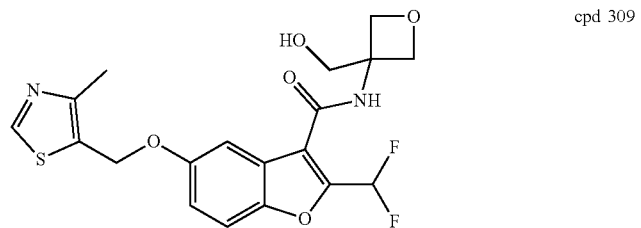 | cpd 309 |
| 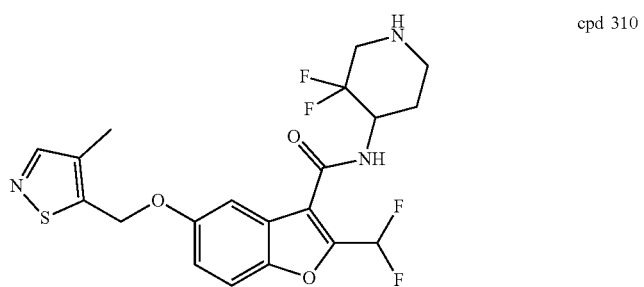 | cpd 310 |
| 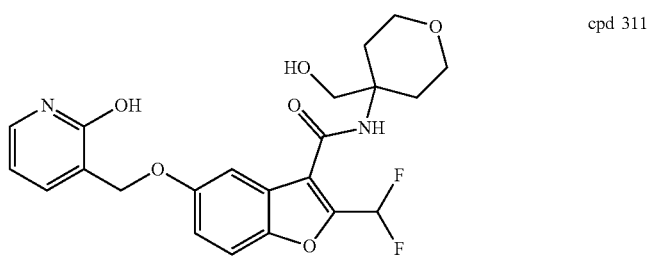 | cpd 311 |
| 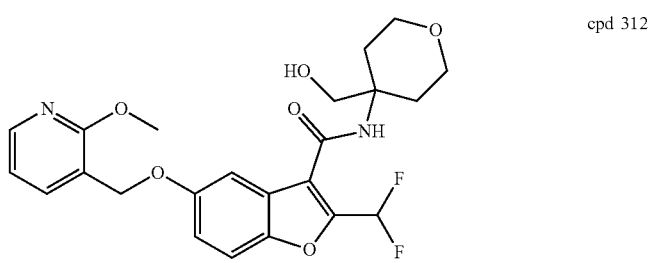 | cpd 312 |
| 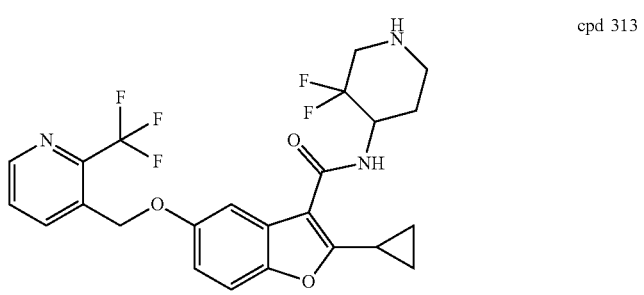 | cpd 313 |
| 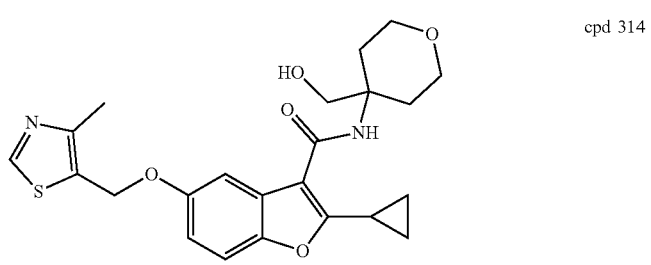 | cpd 314 |

-continued
| Structure/CODE | |
|---|---|
| 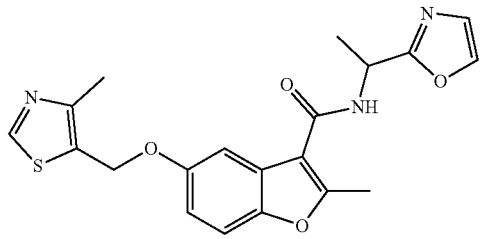 [SMILES: Cc1ncsc1COc1ccc2oc(C)c(C(=O)NC(C)c3ncco3)c2c1] | cpd 315 |
| 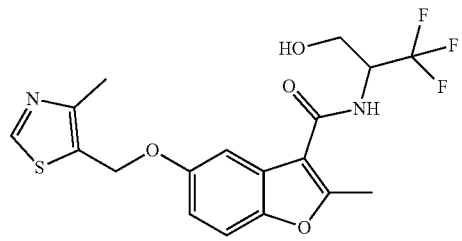 [SMILES: Cc1ncsc1COc1ccc2oc(C)c(C(=O)NC(CO)C(F)(F)F)c2c1] | cpd 316 |
| 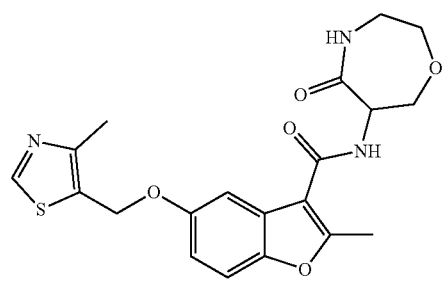 [SMILES: Cc1ncsc1COc1ccc2oc(C)c(C(=O)NC3COCCNC3=O)c2c1] | cpd 317 |
| 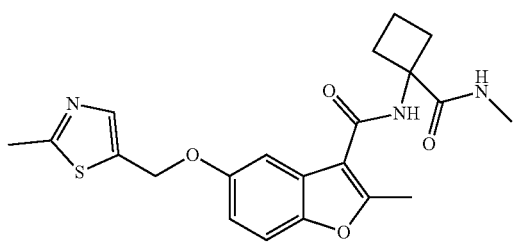 | cpd 318 |
| 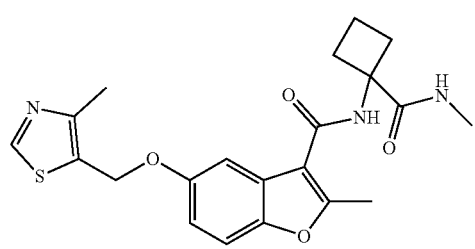 [SMILES: CNC(=O)C1(NC(=O)c2c(C)oc3ccc(OCc4scnc4C)cc23)CCC1] | cpd 319 |
| 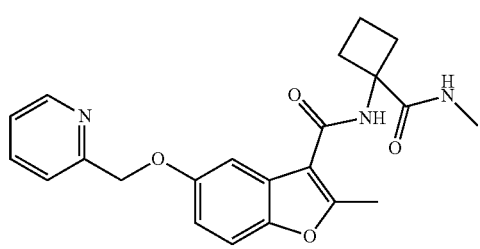 [SMILES: CNC(=O)C1(NC(=O)c2c(C)oc3ccc(OCc4ccccn4)cc23)CCC1] | cpd 320 |

-continued
| Structure/CODE | |
|---|---|
| 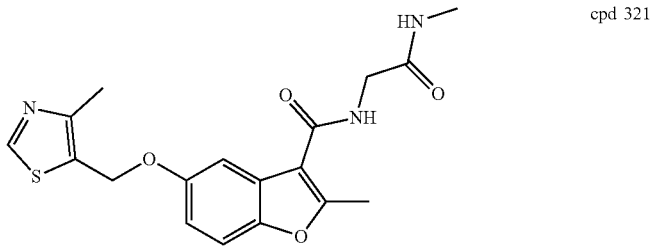 | cpd 321 |
| 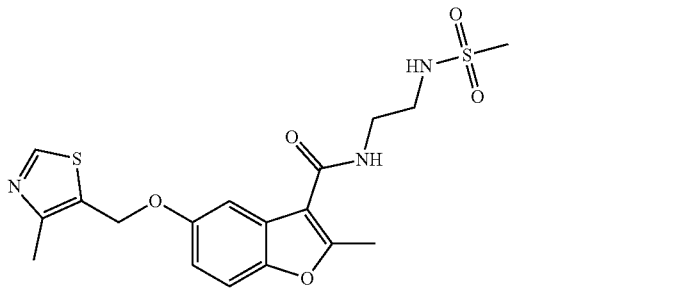 [SMILES: Cc1ncsc1COc1ccc2oc(C)c(C(=O)NCCNS(C)(=O)=O)c2c1] | cpd 322 |
| 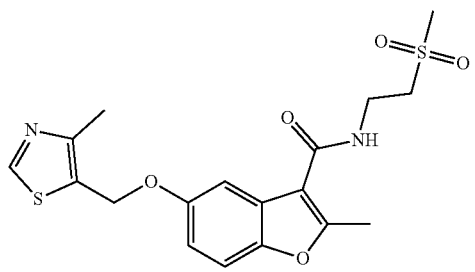 [SMILES: Cc1ncsc1COc1ccc2oc(C)c(C(=O)NCCS(C)(=O)=O)c2c1] | cpd 323 |
| 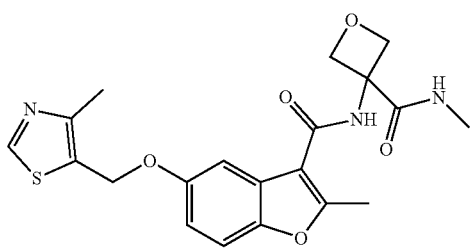 [SMILES: CNC(=O)C1(NC(=O)c2c(C)oc3ccc(OCc4scnc4C)cc23)COC1] | cpd 324 |
| 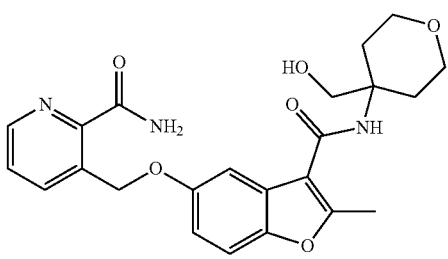 [SMILES: Cc1oc2ccc(OCc3cccnc3C(N)=O)cc2c1C(=O)NC1(CO)CCOCC1] | cpd 325 |

| Structure/CODE | |
|---|---|
| 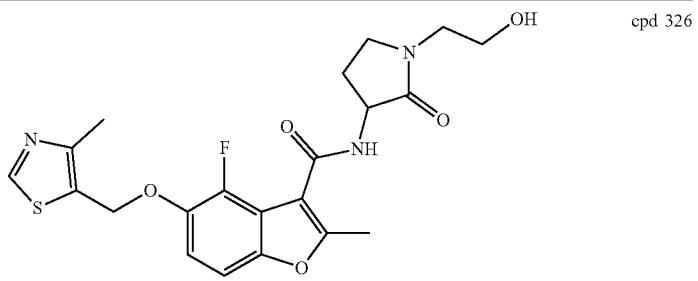 | cpd 326 |
| 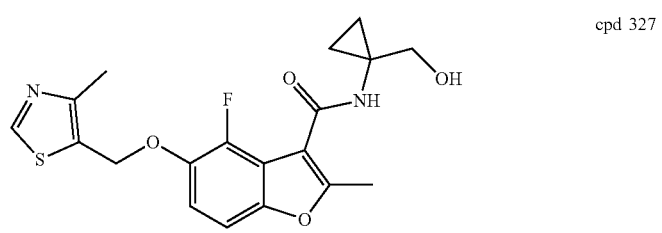 | cpd 327 |
| 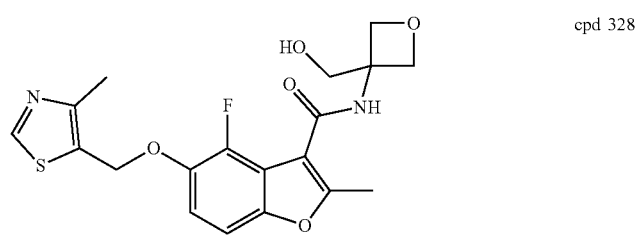 | cpd 328 |
| 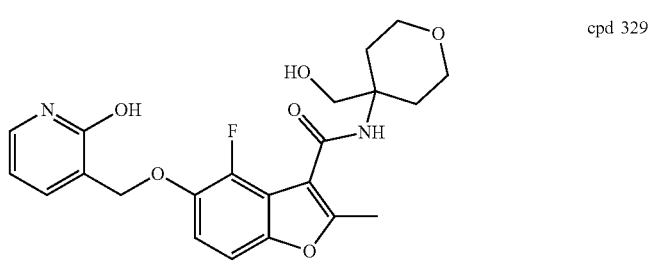 | cpd 329 |
| 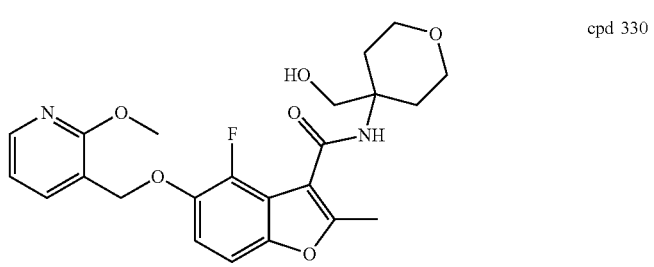 | cpd 330 |
| 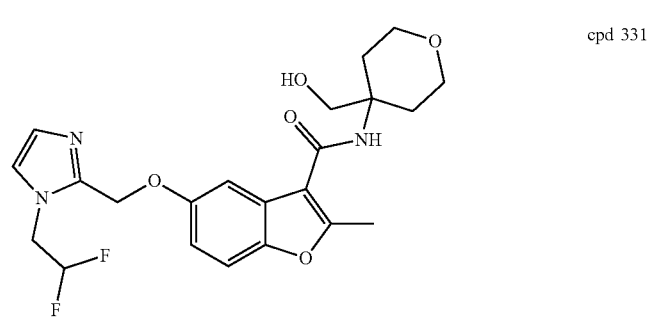 | cpd 331 |

| Structure/CODE | |
|---|---|
| 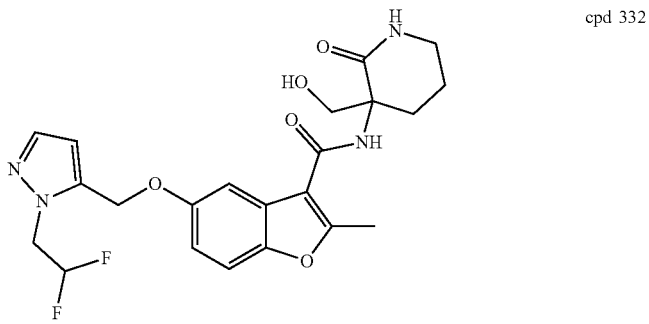 | cpd 332 |
| 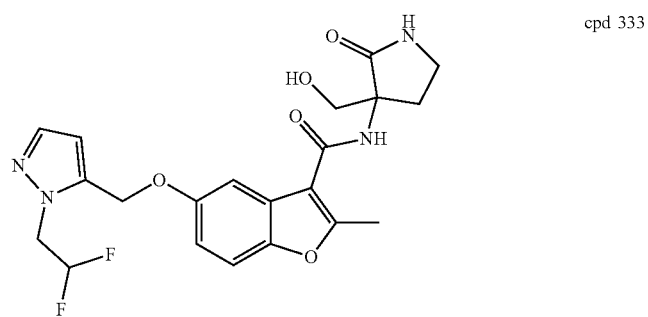 | cpd 333 |
| 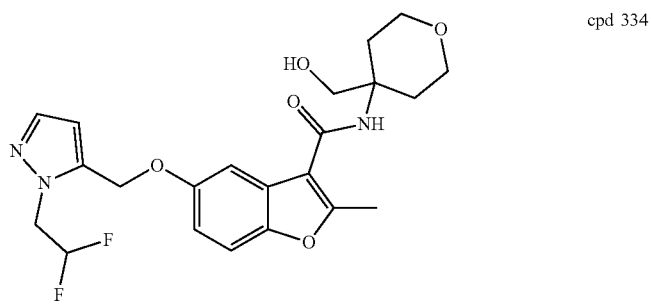 | cpd 334 |
| 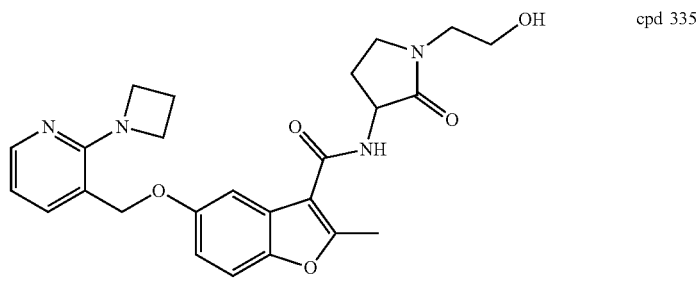 | cpd 335 |
| 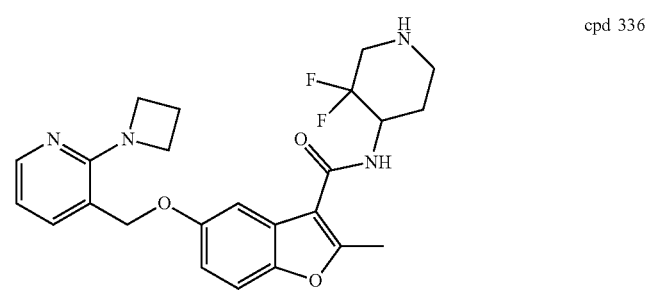 | cpd 336 |

| Structure/CODE | |
|---|---|
| 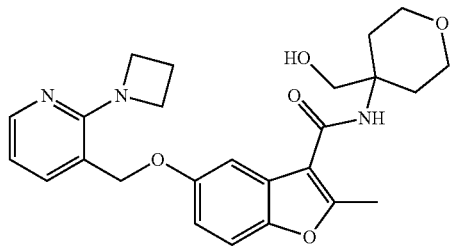 [SMILES: Cc1oc2ccc(OCc3cccnc3N3CCC3)cc2c1C(=O)NC1(CO)CCOCC1] | cpd 337 |
| 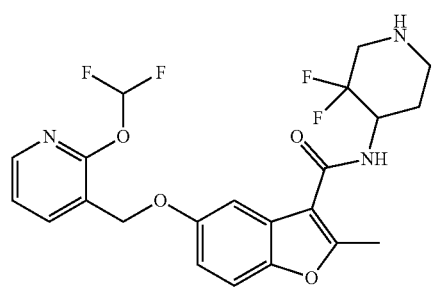 [SMILES: Cc1oc2ccc(OCc3cccnc3OC(F)F)cc2c1C(=O)NC1CCNCC1(F)F] | cpd 338 |
| 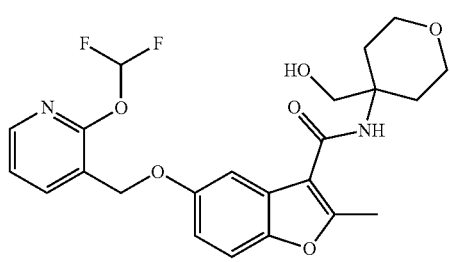 [SMILES: Cc1oc2ccc(OCc3cccnc3OC(F)F)cc2c1C(=O)NC1(CO)CCOCC1] | cpd 339 |
| 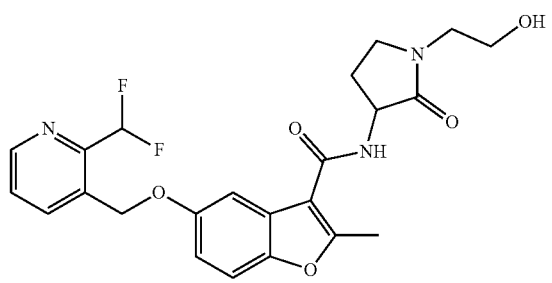 [SMILES: Cc1oc2ccc(OCc3cccnc3C(F)F)cc2c1C(=O)NC1CCN(CCO)C1=O] | cpd 340 |
| 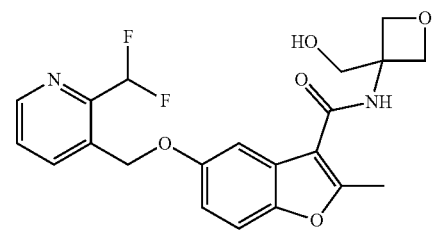 [SMILES: Cc1oc2ccc(OCc3cccnc3C(F)F)cc2c1C(=O)NC1(CO)COC1] | cpd 341 |
| 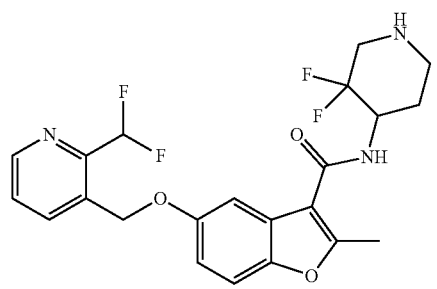 [SMILES: Cc1oc2ccc(OCc3cccnc3C(F)F)cc2c1C(=O)NC1CCNCC1(F)F] | cpd 342 |

| Structure/CODE | |
|---|---|
| 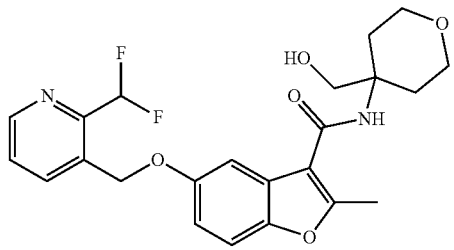 [SMILES: Cc1oc2ccc(OCc3cccnc3C(F)F)cc2c1C(=O)NC1(CO)CCOCC1] | cpd 343 |
| 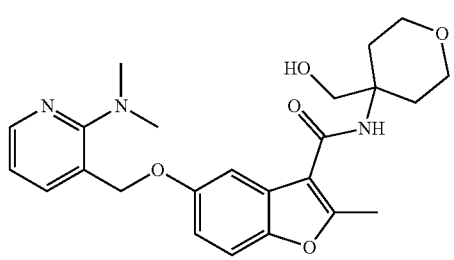 [SMILES: Cc1oc2ccc(OCc3cccnc3N(C)C)cc2c1C(=O)NC1(CO)CCOCC1] | cpd 344 |
| 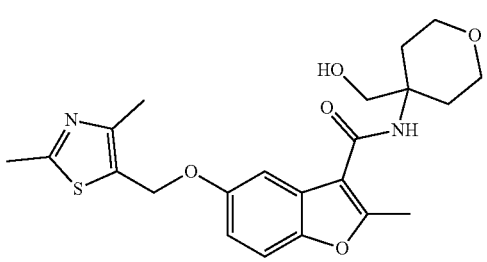 [SMILES: Cc1nc(C)c(COc2ccc3oc(C)c(C(=O)NC4(CO)CCOCC4)c3c2)s1] | cpd 345 |
| 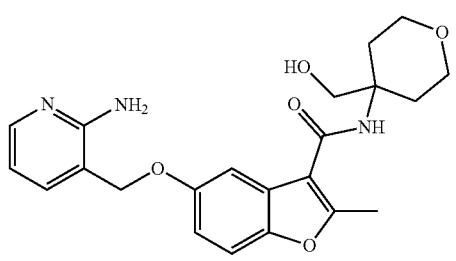 [SMILES: Cc1oc2ccc(OCc3cccnc3N)cc2c1C(=O)NC1(CO)CCOCC1] | cpd 346 |
| 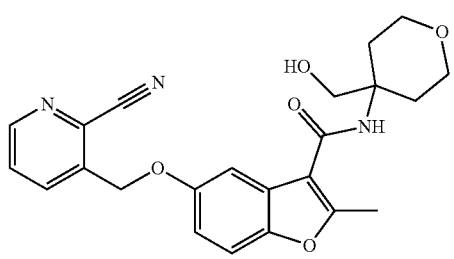 [SMILES: Cc1oc2ccc(OCc3cccnc3C#N)cc2c1C(=O)NC1(CO)CCOCC1] | cpd 347 |
| 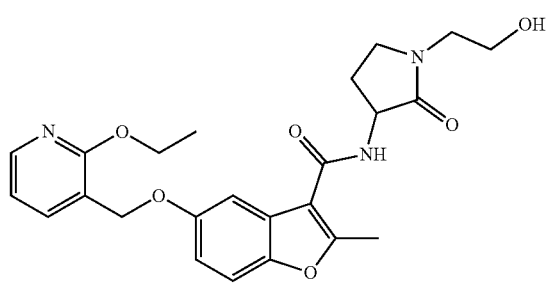 [SMILES: CCOc1ncccc1COc1ccc2oc(C)c(C(=O)NC3CCN(CCO)C3=O)c2c1] | cpd 348 |

-continued
| Structure/CODE | |
|---|---|
| 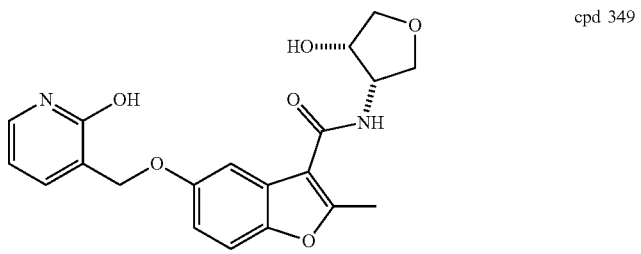 | cpd 349 |
| 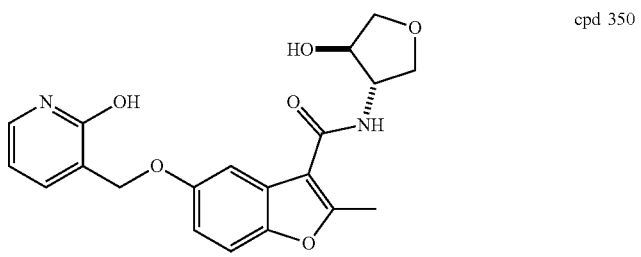 | cpd 350 |
| 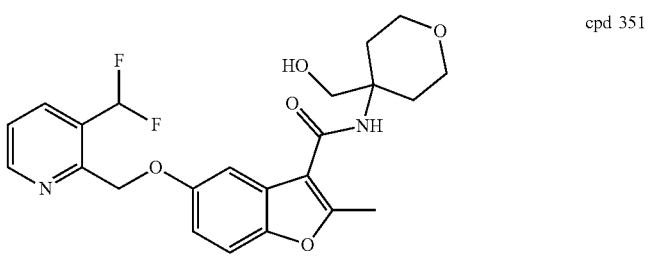 | cpd 351 |
| 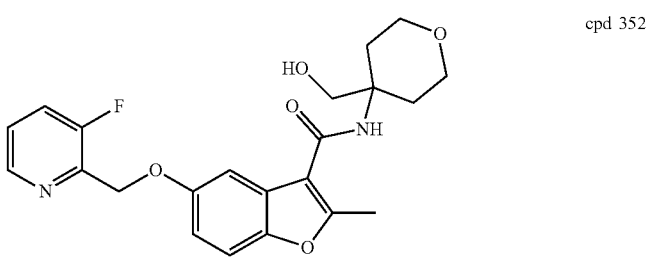 | cpd 352 |
| 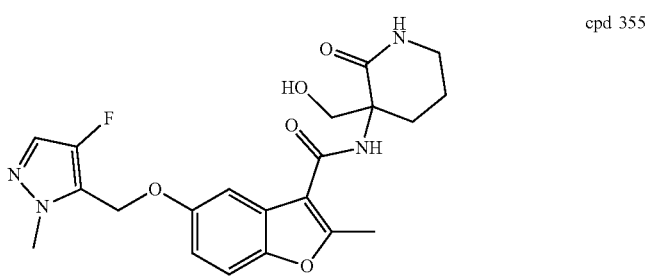 | cpd 355 |
| 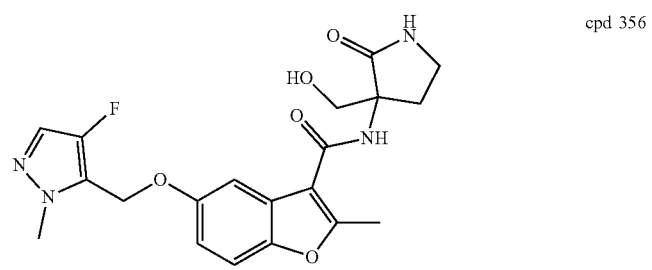 | cpd 356 |

-continued
| Structure/CODE |
|---|
| 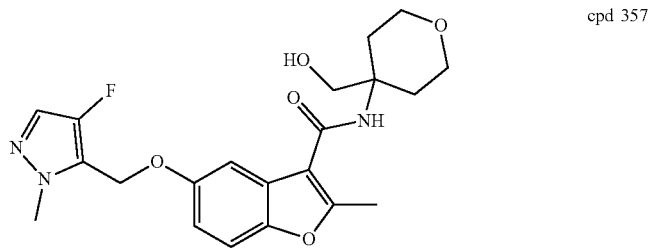 cpd 357 |
| 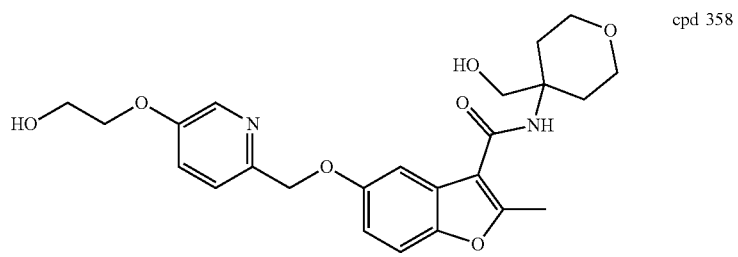 cpd 358 |
| 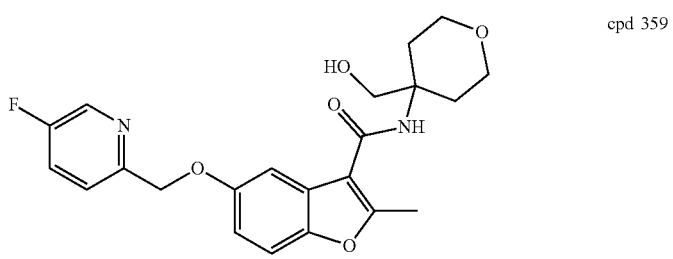 cpd 359 |
| 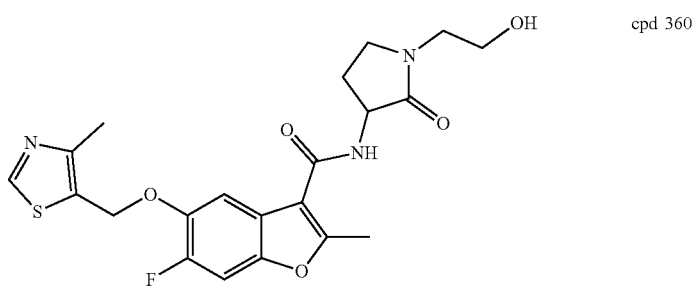 cpd 360 |
| 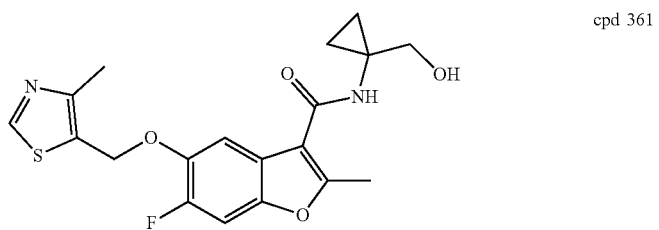 cpd 361 |
| 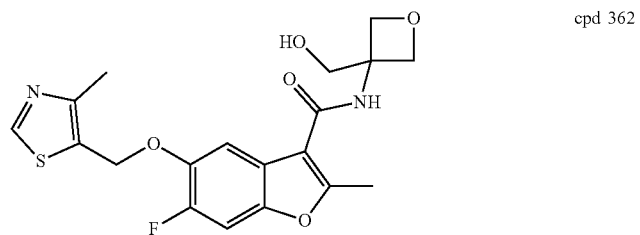 cpd 362 |

| Structure/CODE | |
|---|---|
| 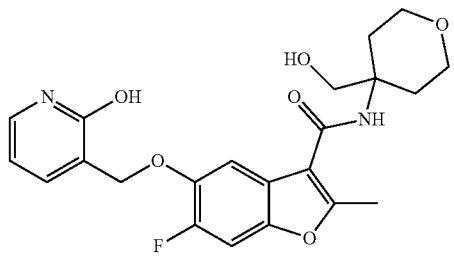 [SMILES: Cc1oc2cc(F)c(OCc3cccnc3O)cc2c1C(=O)NC1(CO)CCOCC1] | cpd 363 |
| 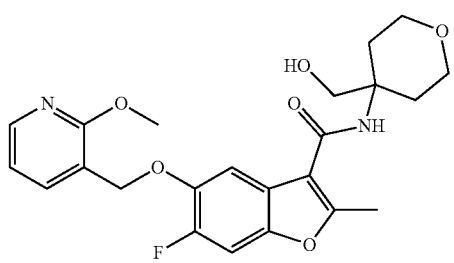 [SMILES: COc1ncccc1COc1cc2c(C(=O)NC3(CO)CCOCC3)c(C)oc2cc1F] | cpd 364 |
| 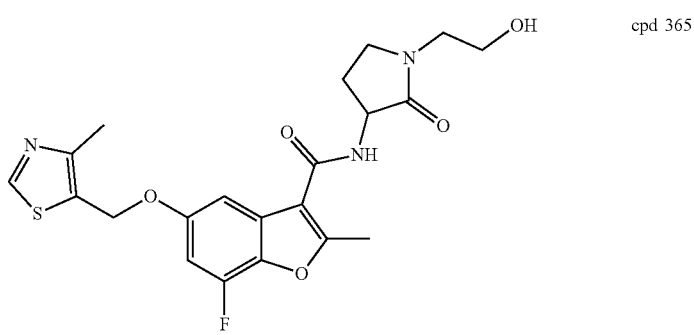 | cpd 365 |
| 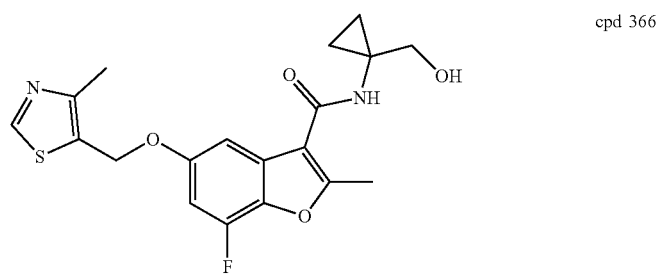 | cpd 366 |
| 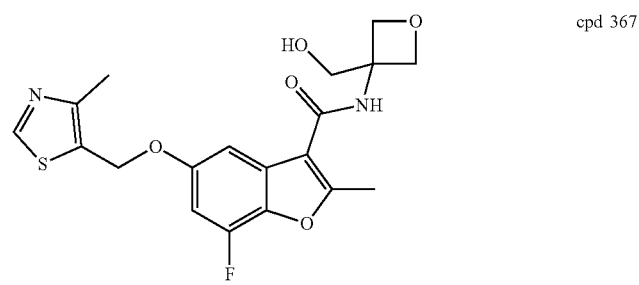 | cpd 367 |

-continued
| Structure/CODE |
|---|
| 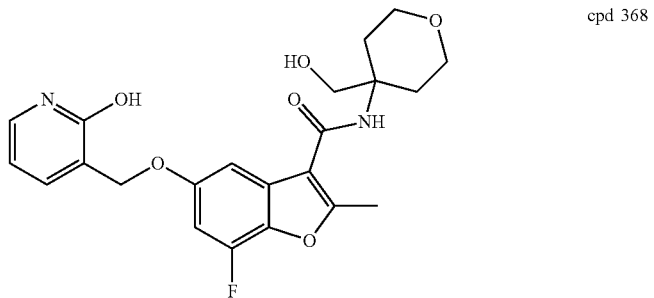 cpd 368 |
| 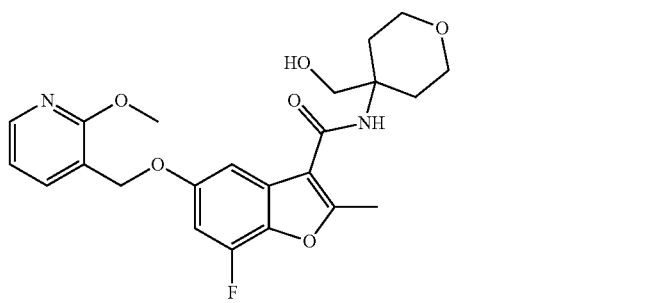 [SMILES: COc1ncccc1COc1cc(F)c2oc(C)c(C(=O)NC3(CO)CCOCC3)c2c1] cpd 369 |
| 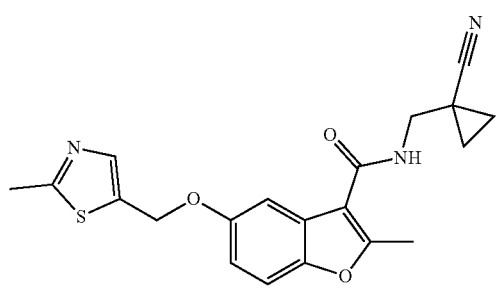 [SMILES: Cc1ncc(COc2ccc3oc(C)c(C(=O)NCC4(C#N)CC4)c3c2)s1] cpd 370 |
| 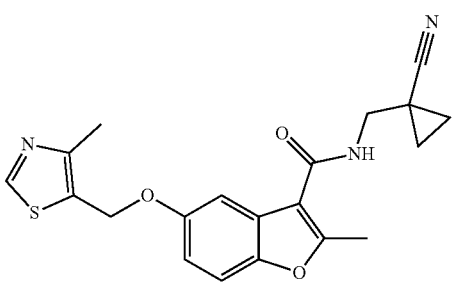 [SMILES: Cc1ncsc1COc1ccc2oc(C)c(C(=O)NCC3(C#N)CC3)c2c1] cpd 371 |
| 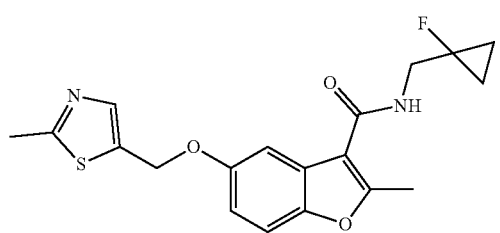 [SMILES: Cc1ncc(COc2ccc3oc(C)c(C(=O)NCC4(F)CC4)c3c2)s1] cpd 372 |

-continued
| Structure/CODE | |
|---|---|
| 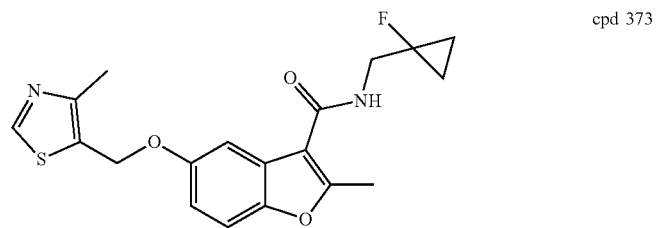 | cpd 373 |
| 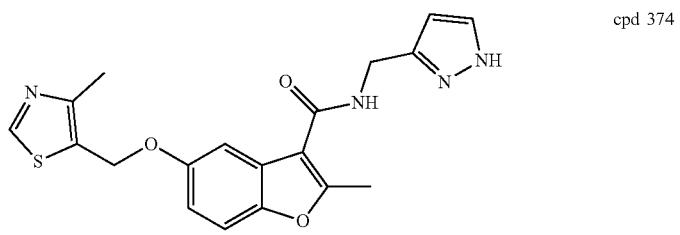 | cpd 374 |
| 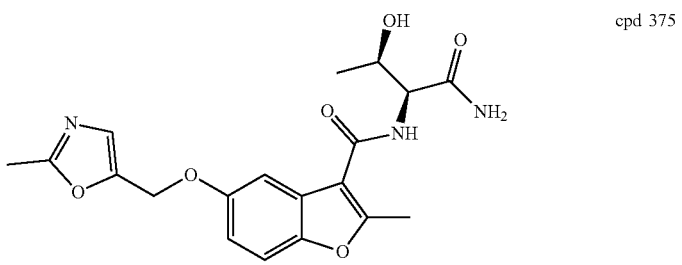 | cpd 375 |
| 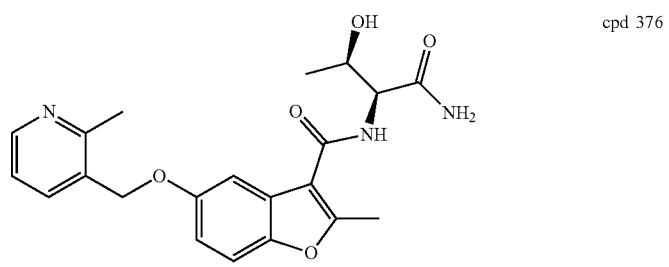 | cpd 376 |
| 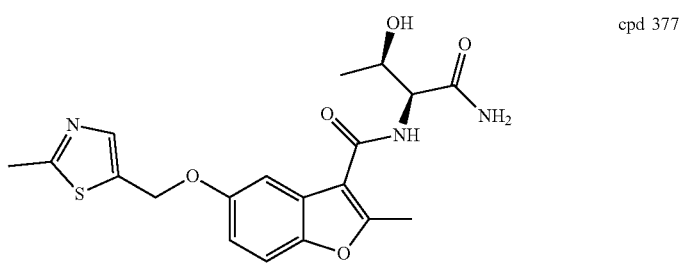 | cpd 377 |
| 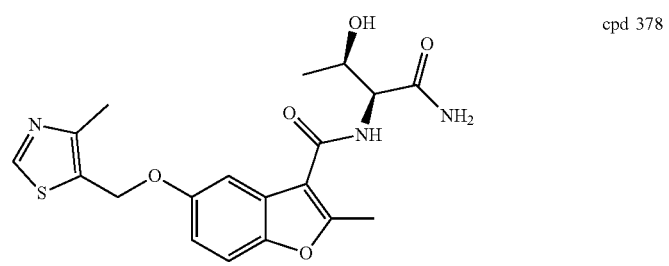 | cpd 378 |

-continued
| Structure/CODE | |
|---|---|
| 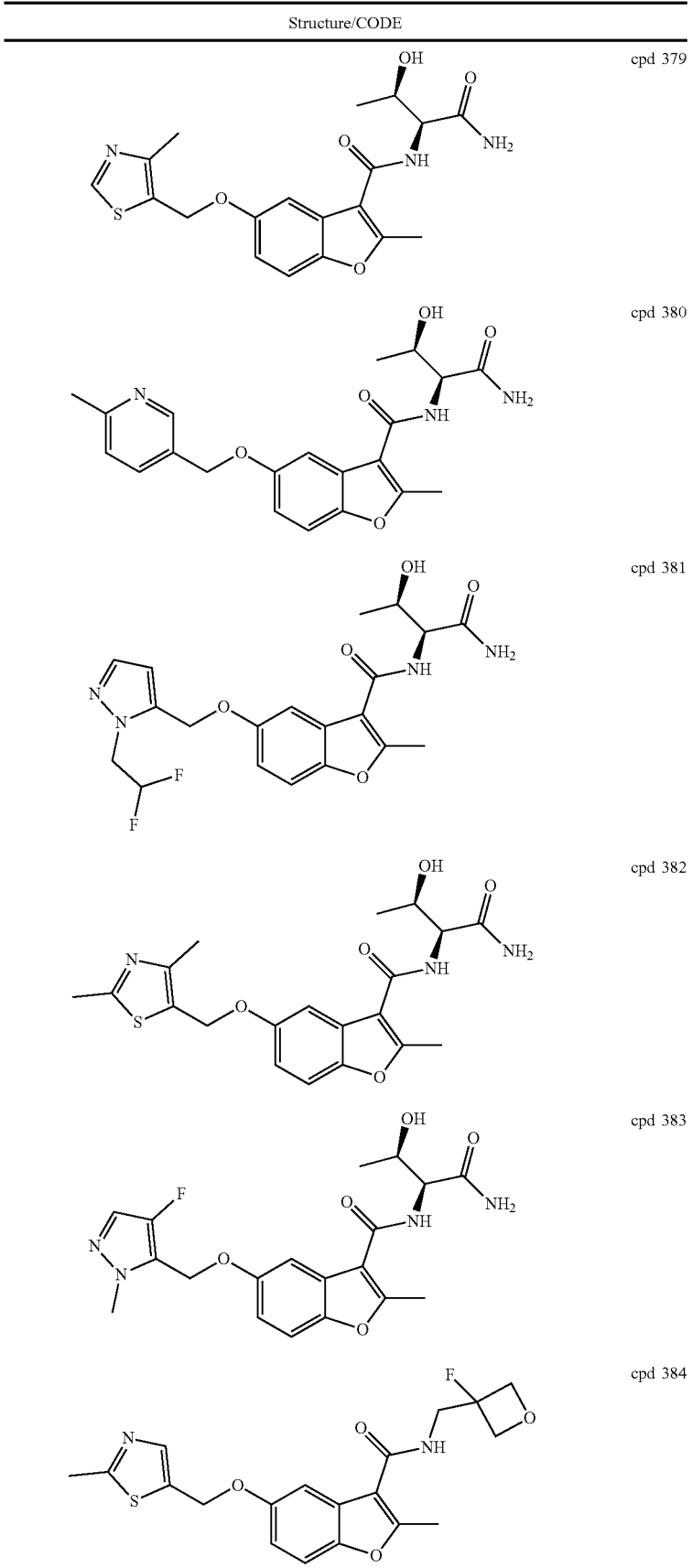 | cpd 379 |
| | cpd 380 |
| | cpd 381 |
| | cpd 382 |
| | cpd 383 |
| | cpd 384 |

| Structure/CODE | |
|---|---|
| 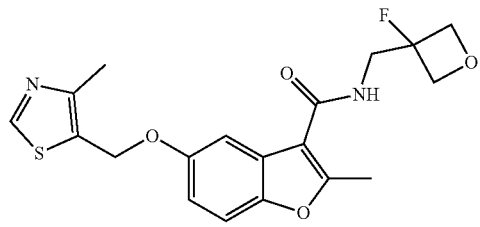 [SMILES: Cc1ncsc1COc1ccc2oc(C)c(C(=O)NCC3(F)COC3)c2c1] | cpd 385 |
| 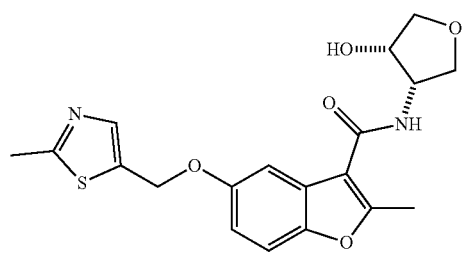 [SMILES: Cc1ncc(COc2ccc3oc(C)c(C(=O)N[C@H]4COC[C@H]4O)c3c2)s1] | cpd 386 |
| 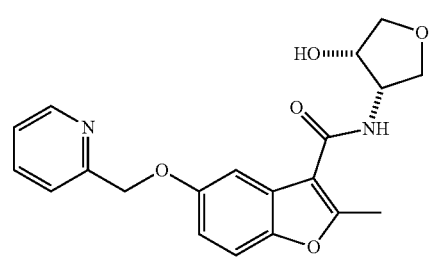 [SMILES: Cc1oc2ccc(OCc3ccccn3)cc2c1C(=O)N[C@H]1COC[C@H]1O] | cpd 387 |
| 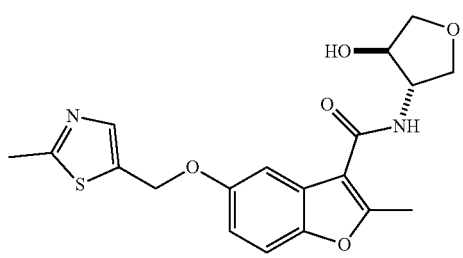 [SMILES: Cc1ncc(COc2ccc3oc(C)c(C(=O)N[C@H]4COC[C@@H]4O)c3c2)s1] | cpd 388 |
| 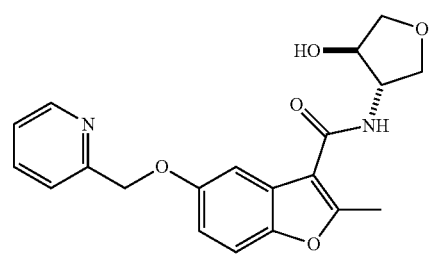 [SMILES: Cc1oc2ccc(OCc3ccccn3)cc2c1C(=O)N[C@H]1COC[C@@H]1O] | cpd 389 |
| 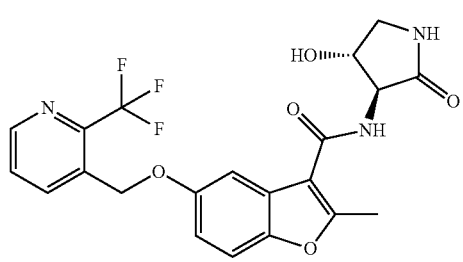 [SMILES: Cc1oc2ccc(OCc3cccnc3C(F)(F)F)cc2c1C(=O)N[C@@H]1C(=O)NC[C@H]1O] | cpd 390 |

| Structure/CODE | |
|---|---|
| 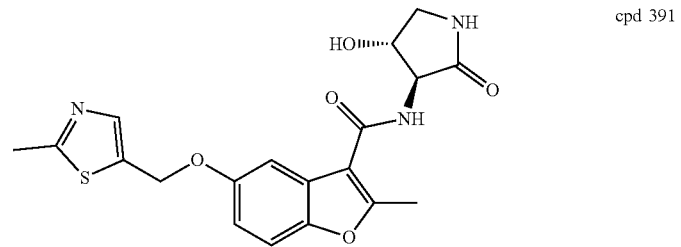 | cpd 391 |
| 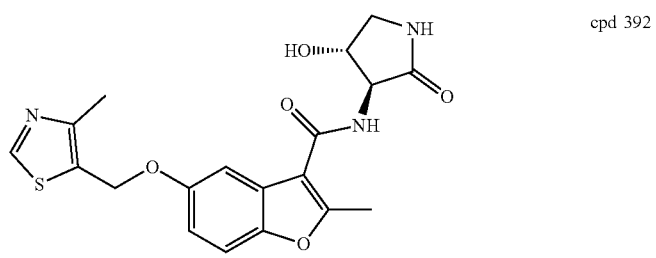 | cpd 392 |
| 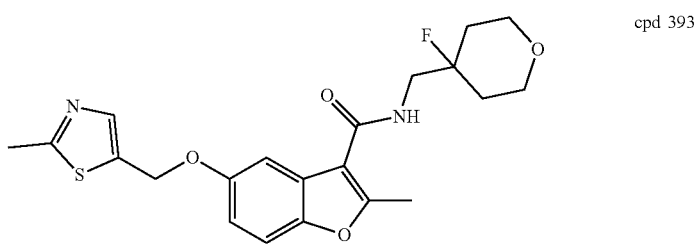 | cpd 393 |
| 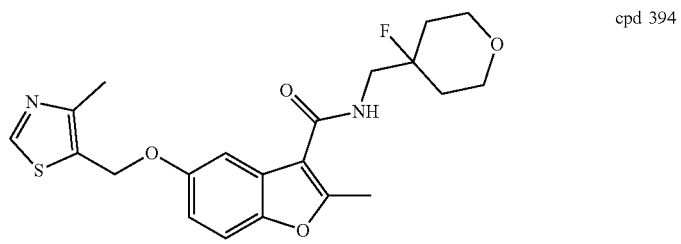 | cpd 394 |
| 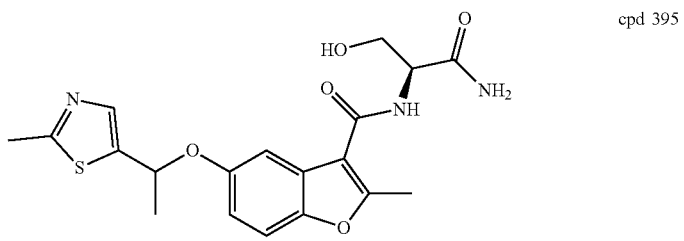 | cpd 395 |
| 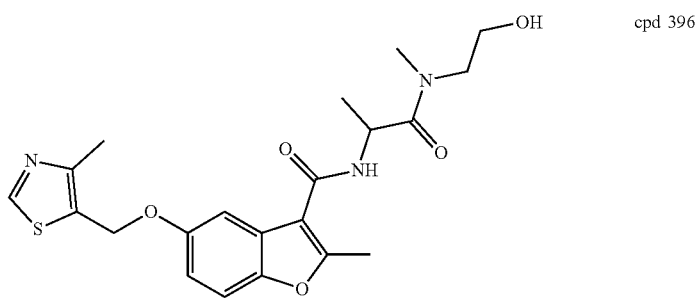 | cpd 396 |

-continued
| Structure/CODE |
|---|
| 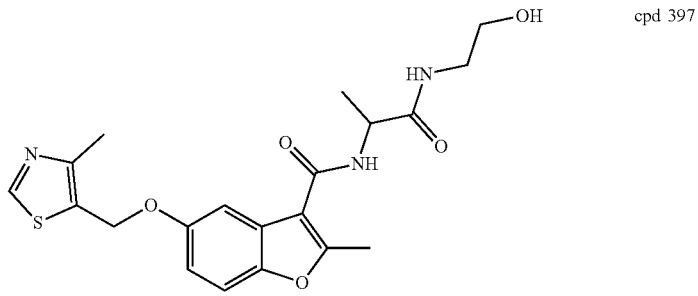 cpd 397 |
| 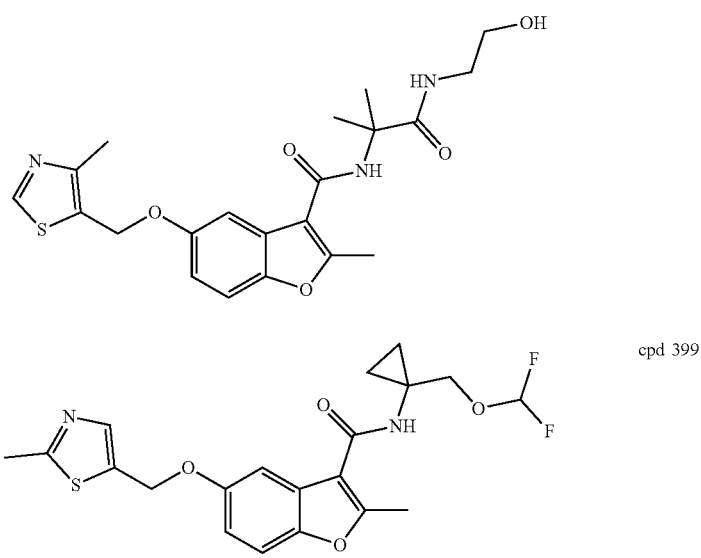 cpd 398<br><br>cpd 399<br><br>cpd 400 |
| 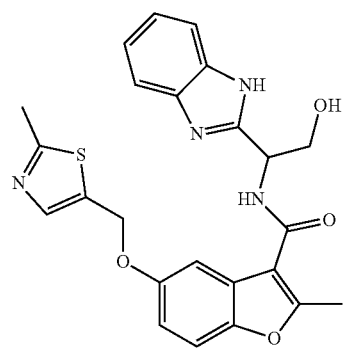 [SMILES: Cc1ncc(COc2ccc3oc(C)c(C(=O)NC(CO)c4nc5ccccc5[nH]4)c3c2)s1] cpd 401 |

-continued
| Structure/CODE | |
|---|---|
| 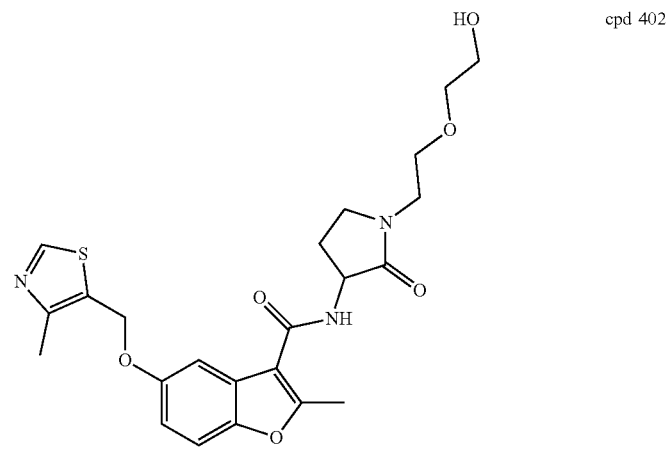 | cpd 402 |
| 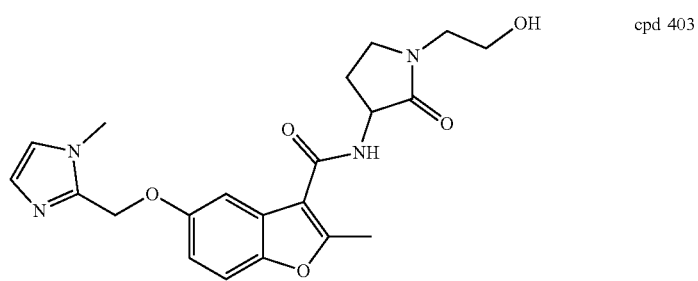 | cpd 403 |
| 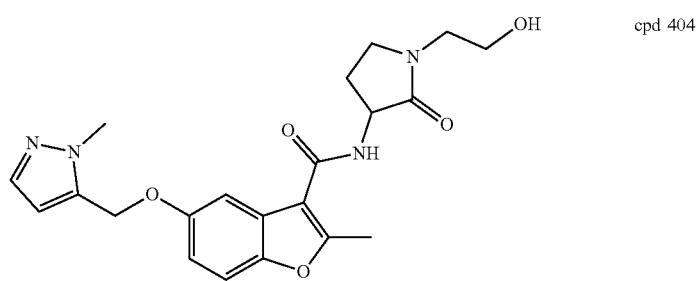 | cpd 404 |
| 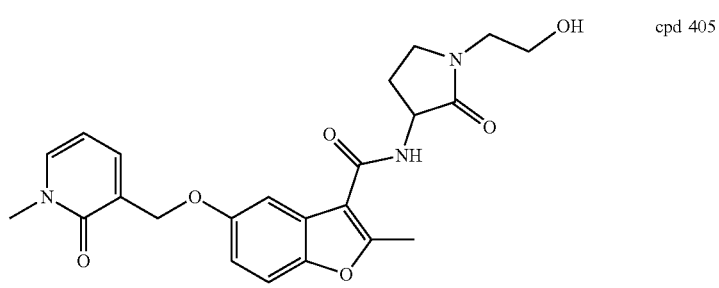 | cpd 405 |
| 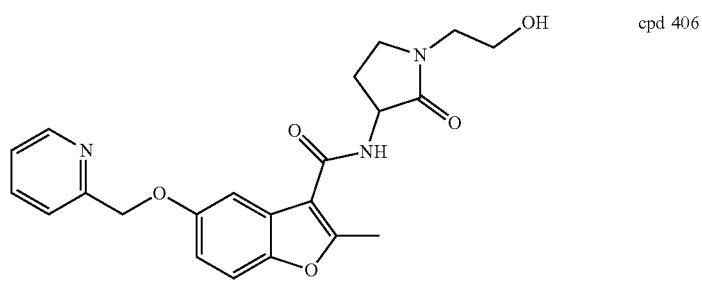 | cpd 406 |

-continued
| Structure/CODE |
|---|
| 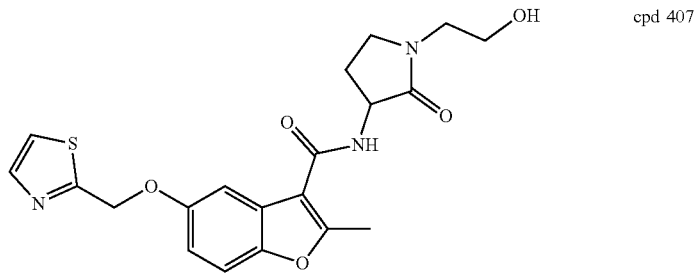 cpd 407 |
| 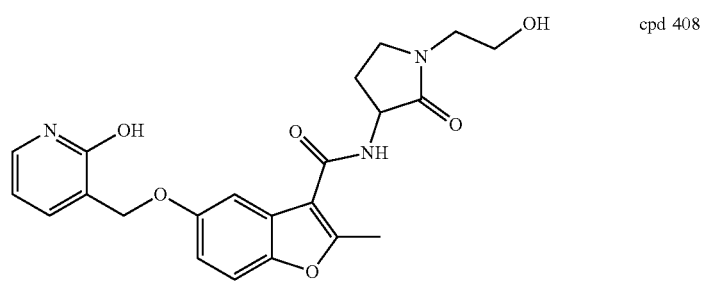 cpd 408 |
| 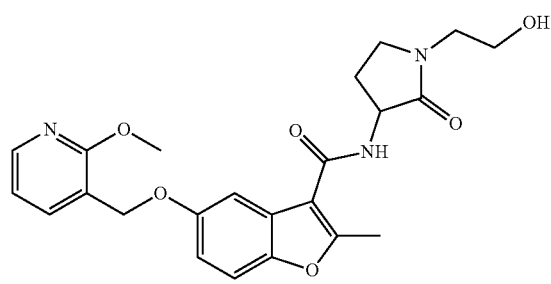 [SMILES: COc1ncccc1COc1ccc2oc(C)c(C(=O)NC3CCN(CCO)C3=O)c2c1] cpd 409 |
| 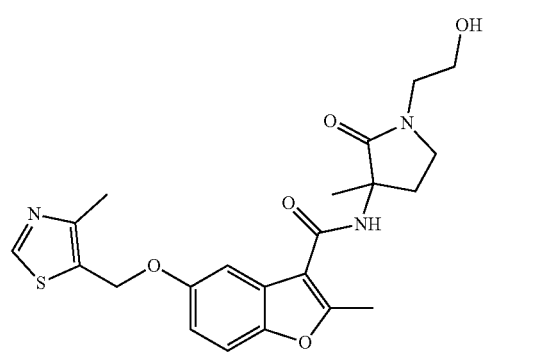 [SMILES: Cc1ncsc1COc1ccc2oc(C)c(C(=O)NC3(C)CCN(CCO)C3=O)c2c1] cpd 410 |
| 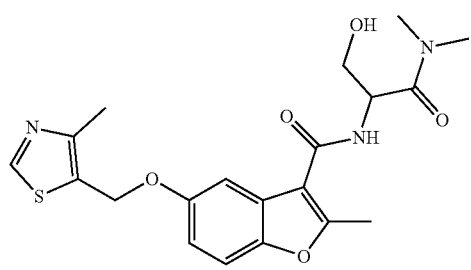 [SMILES: Cc1ncsc1COc1ccc2oc(C)c(C(=O)NC(CO)C(=O)N(C)C)c2c1] cpd 411 |

-continued
| Structure/CODE | |
|---|---|
| 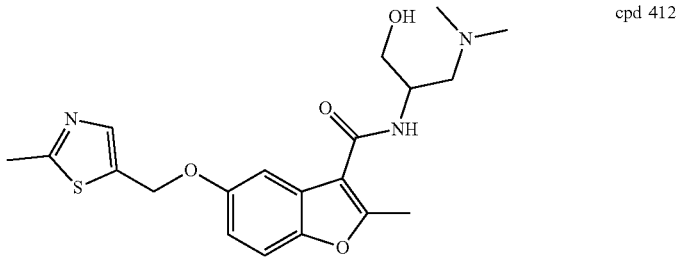 | cpd 412 |
| 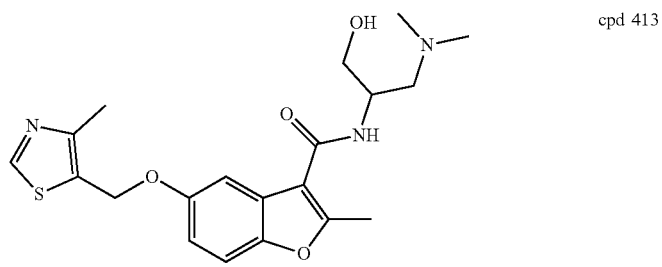 | cpd 413 |
| 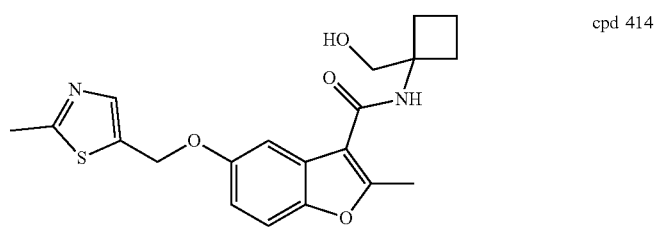 | cpd 414 |
| 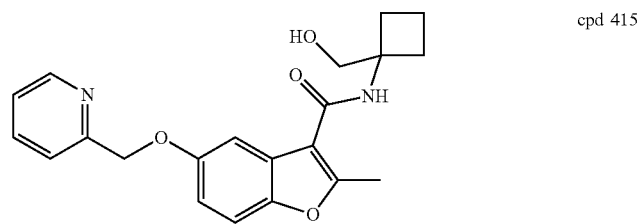 | cpd 415 |
| 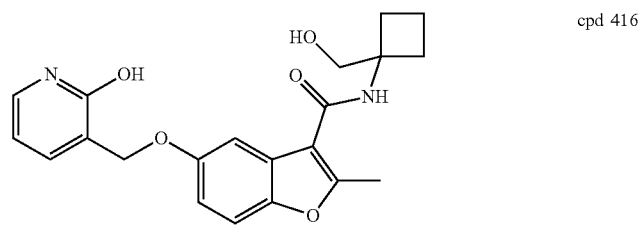 | cpd 416 |
| 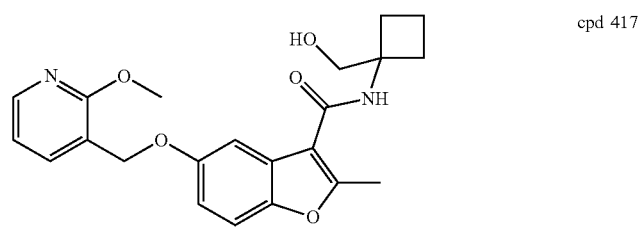 | cpd 417 |

-continued
| Structure/CODE | |
|---|---|
| 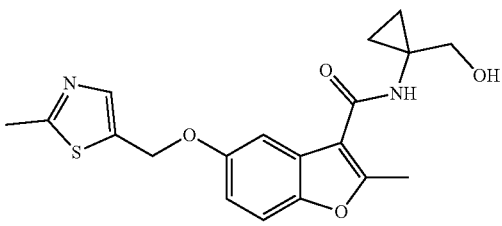 [SMILES: Cc1ncc(COc2ccc3oc(C)c(C(=O)NC4(CO)CC4)c3c2)s1] | cpd 418 |
| 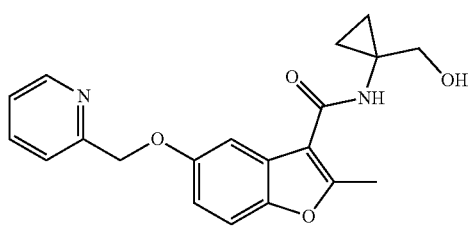 [SMILES: Cc1oc2ccc(OCc3ccccn3)cc2c1C(=O)NC1(CO)CC1] | cpd 419 |
| 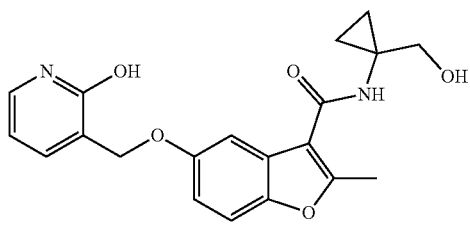 [SMILES: Cc1oc2ccc(OCc3cccnc3O)cc2c1C(=O)NC1(CO)CC1] | cpd 420 |
| 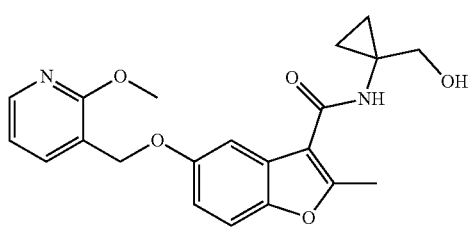 [SMILES: COc1ncccc1COc1ccc2oc(C)c(C(=O)NC3(CO)CC3)c2c1] | cpd 421 |
| 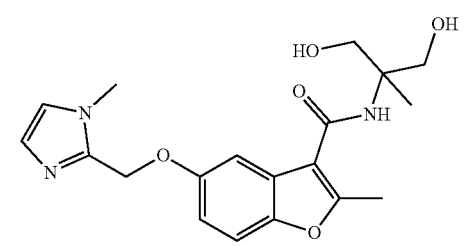 [SMILES: Cc1oc2ccc(OCc3nccn3C)cc2c1C(=O)NC(C)(CO)CO] | cpd 422 |
| 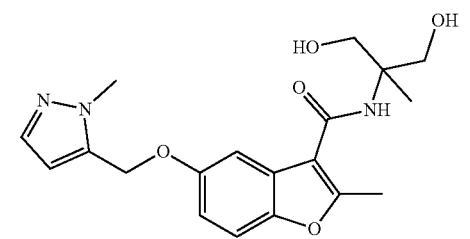 [SMILES: Cc1oc2ccc(OCc3ccnn3C)cc2c1C(=O)NC(C)(CO)CO] | cpd 423 |

-continued
| Structure/CODE | |
|---|---|
| 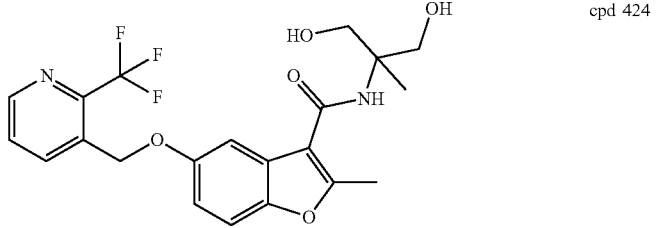 | cpd 424 |
| 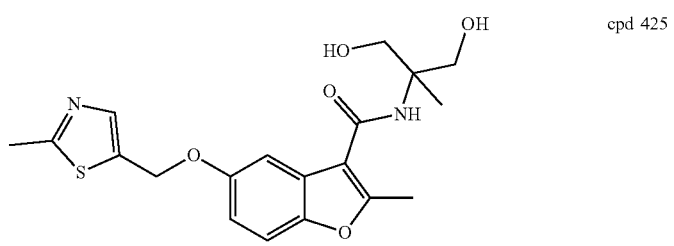 | cpd 425 |
| 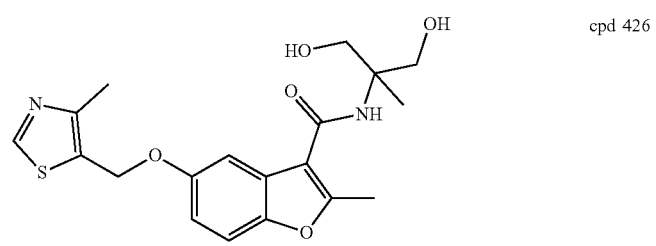 | cpd 426 |
| 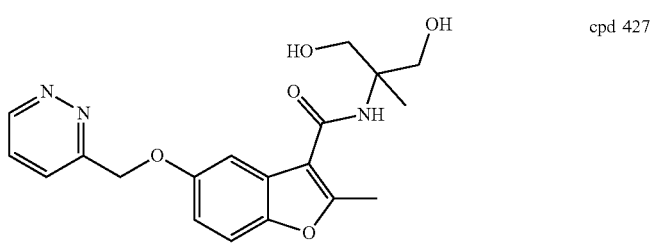 | cpd 427 |
| 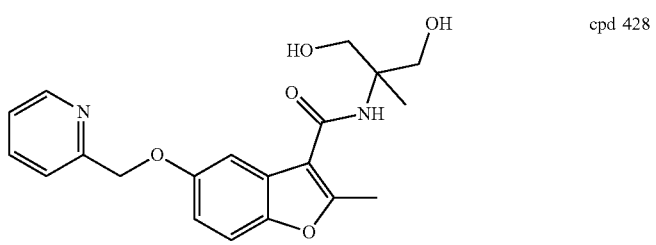 | cpd 428 |
| 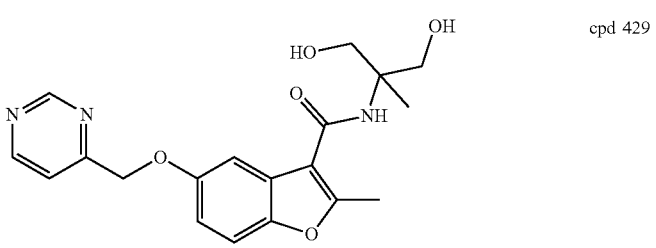 | cpd 429 |

-continued
| Structure/CODE | |
|---|---|
| 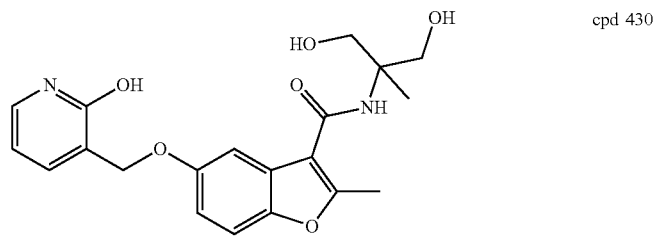 | cpd 430 |
| 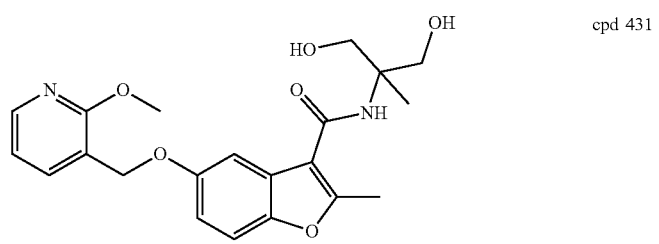 | cpd 431 |
| 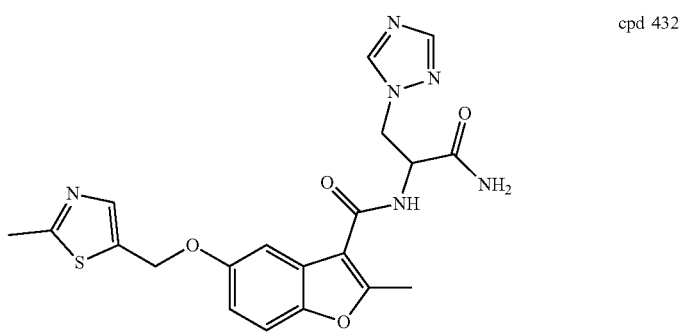 | cpd 432 |
| 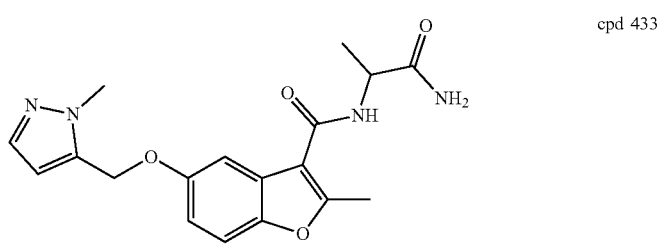 | cpd 433 |
| 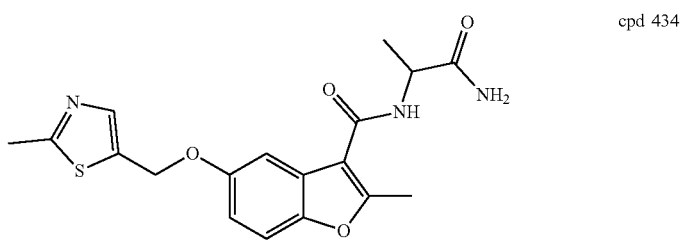 | cpd 434 |
| 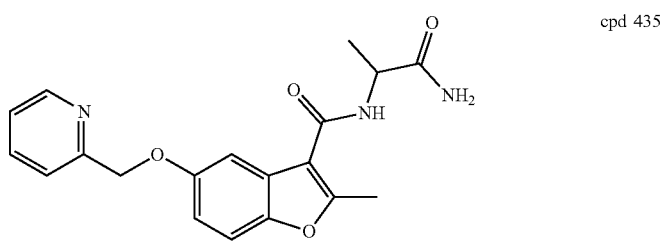 | cpd 435 |

-continued
| Structure/CODE | |
|---|---|
| 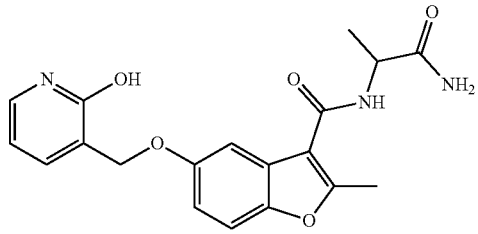 [SMILES: Cc1oc2ccc(OCc3cccnc3O)cc2c1C(=O)NC(C)C(N)=O] | cpd 436 |
| 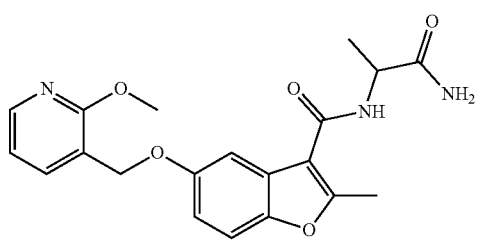 [SMILES: COc1ncccc1COc1ccc2oc(C)c(C(=O)NC(C)C(N)=O)c2c1] | cpd 437 |
| 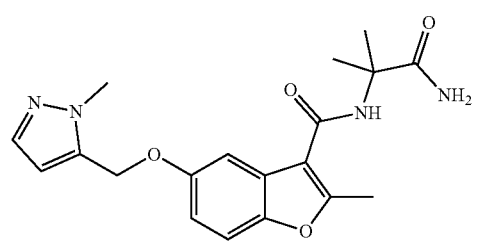 [SMILES: Cc1oc2ccc(OCc3ccnn3C)cc2c1C(=O)NC(C)(C)C(N)=O] | cpd 438 |
| 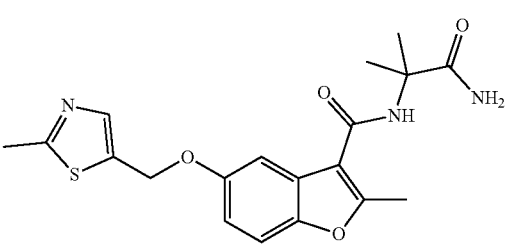 [SMILES: Cc1ncc(COc2ccc3oc(C)c(C(=O)NC(C)(C)C(N)=O)c3c2)s1] | cpd 439 |
| 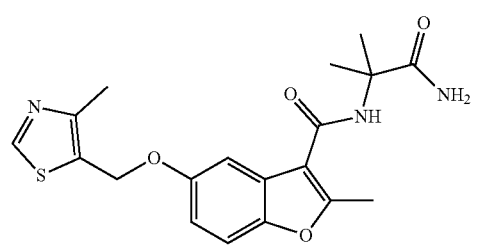 [SMILES: Cc1ncsc1COc1ccc2oc(C)c(C(=O)NC(C)(C)C(N)=O)c2c1] | cpd 440 |
| 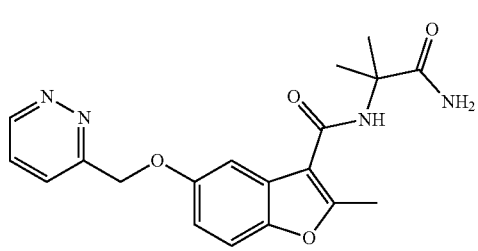 [SMILES: Cc1oc2ccc(OCc3cccnn3)cc2c1C(=O)NC(C)(C)C(N)=O] | cpd 441 |

|Structure/CODE| |
|---|---|
| 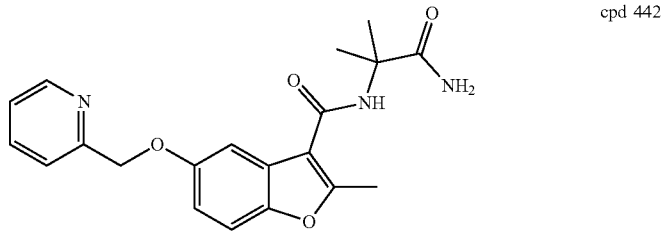 | cpd 442 |
| 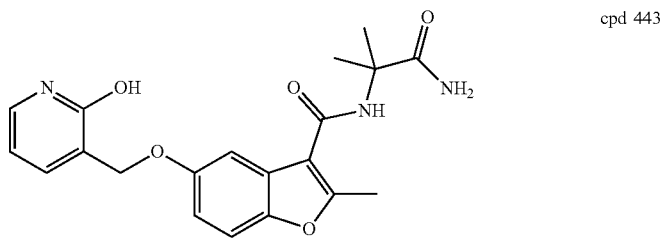 | cpd 443 |
| 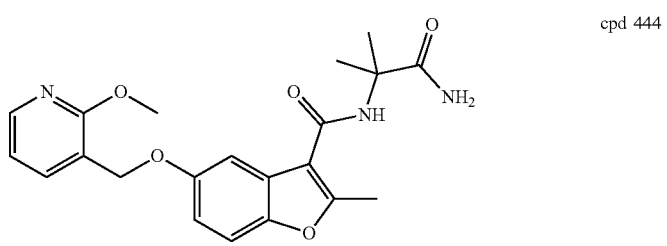 | cpd 444 |
| 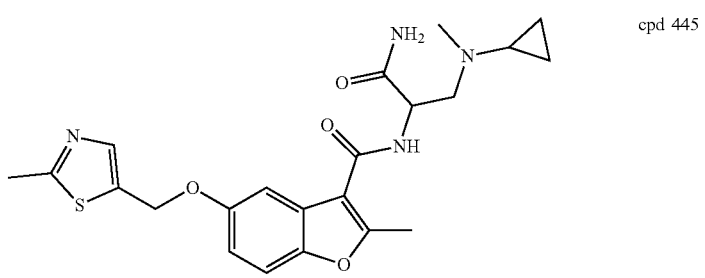 | cpd 445 |
| 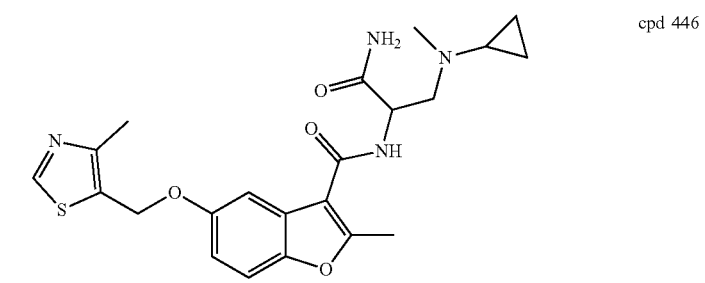 | cpd 446 |
| 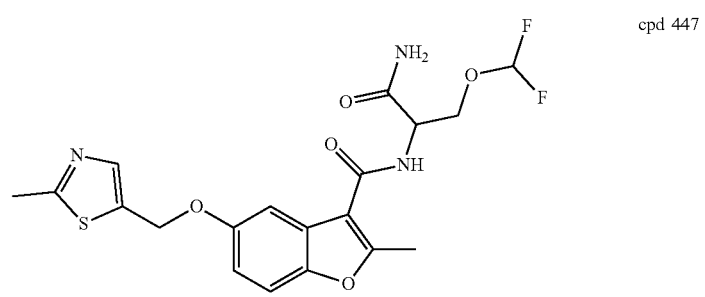 | cpd 447 |

-continued
| Structure/CODE | |
|---|---|
| 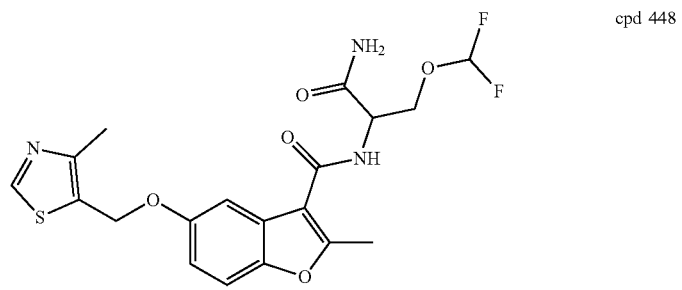 | cpd 448 |
| 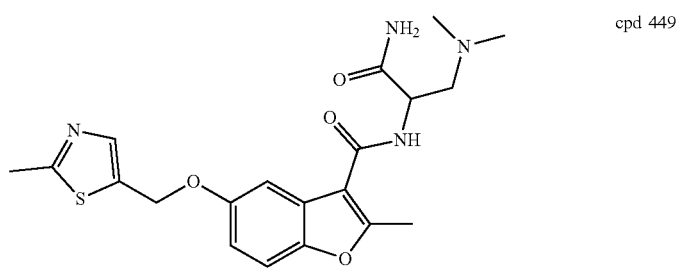 | cpd 449 |
| 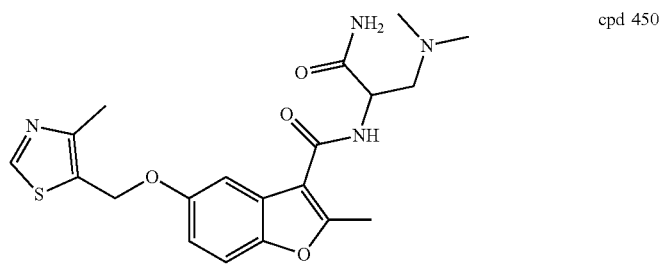 | cpd 450 |
| 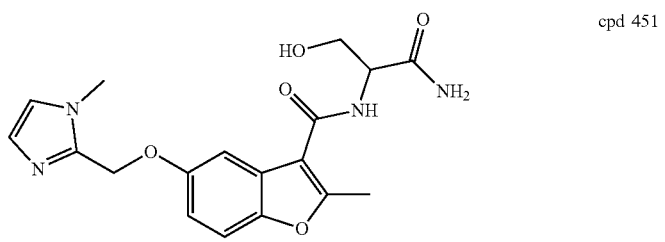 | cpd 451 |
| 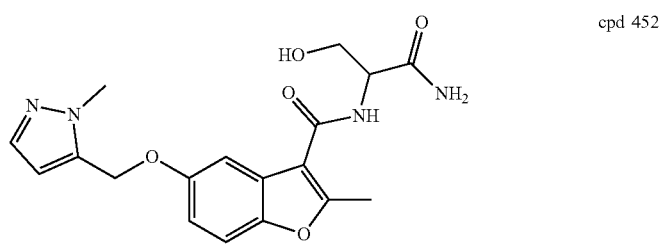 | cpd 452 |
| 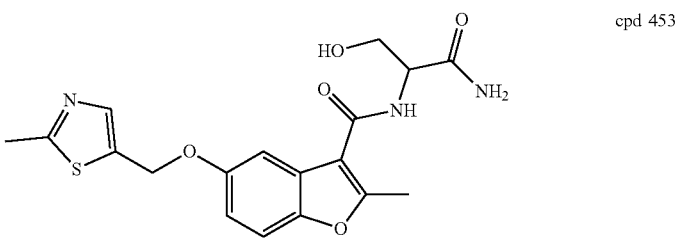 | cpd 453 |

-continued
| Structure/CODE | |
|---|---|
| 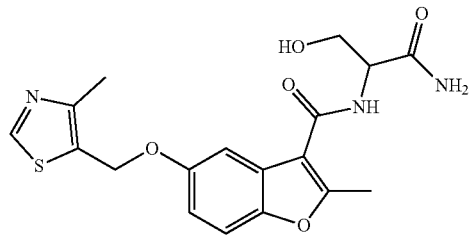 [SMILES: Cc1ncsc1COc1ccc2oc(C)c(C(=O)NC(CO)C(N)=O)c2c1] | cpd 454 |
| 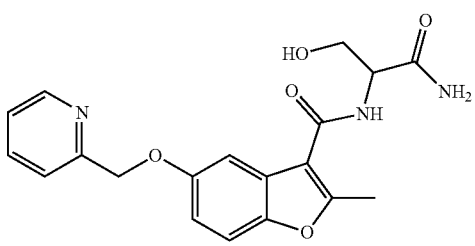 [SMILES: Cc1oc2ccc(OCc3ccccn3)cc2c1C(=O)NC(CO)C(N)=O] | cpd 455 |
| 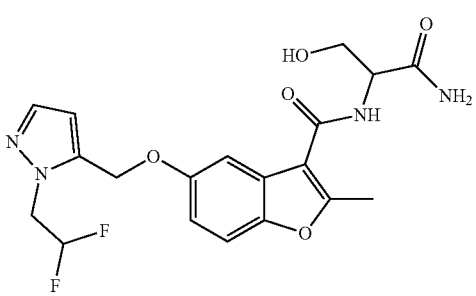 [SMILES: Cc1oc2ccc(OCc3ccnn3CC(F)F)cc2c1C(=O)NC(CO)C(N)=O] | cpd 456 |
| 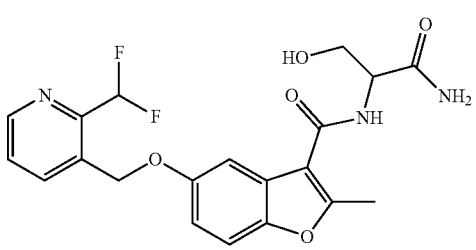 [SMILES: Cc1oc2ccc(OCc3cccnc3C(F)F)cc2c1C(=O)NC(CO)C(N)=O] | cpd 457 |
| 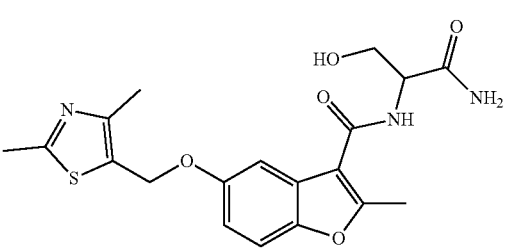 [SMILES: Cc1nc(C)c(COc2ccc3oc(C)c(C(=O)NC(CO)C(N)=O)c3c2)s1] | cpd 458 |
| 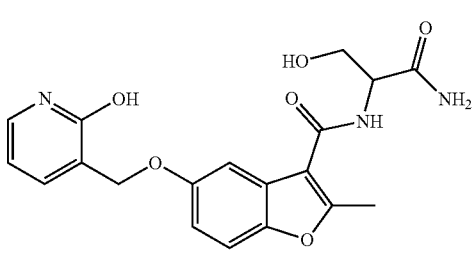 [SMILES: Cc1oc2ccc(OCc3cccnc3O)cc2c1C(=O)NC(CO)C(N)=O] | cpd 459 |

-continued
| Structure/CODE | |
|---|---|
| 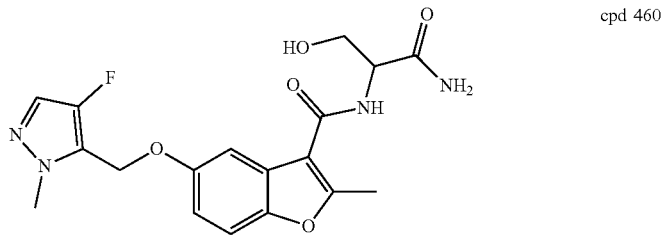 | cpd 460 |
| 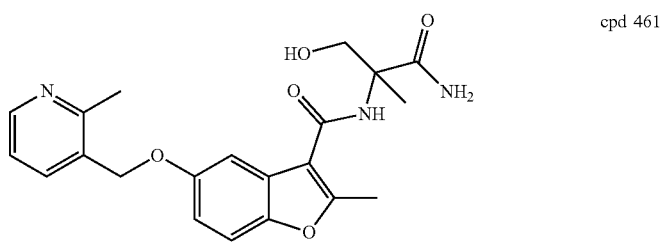 | cpd 461 |
| 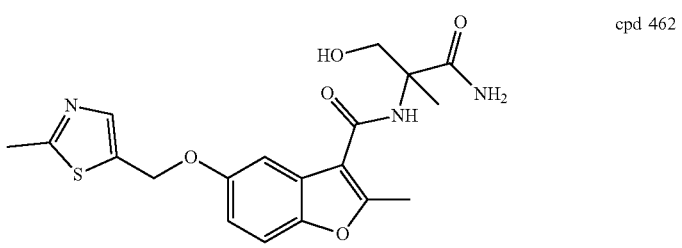 | cpd 462 |
| 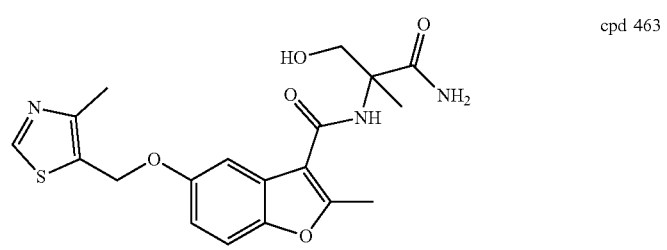 | cpd 463 |
| 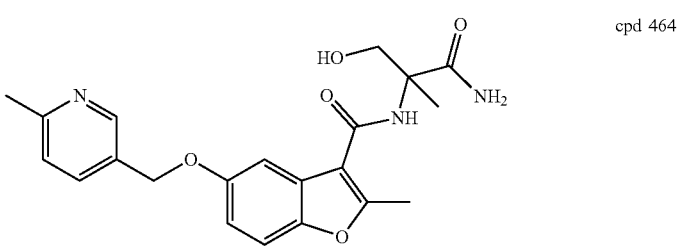 | cpd 464 |
| 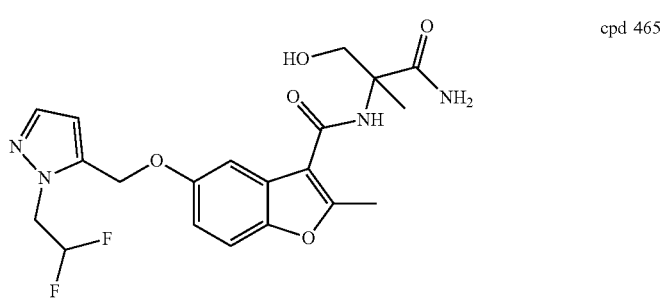 | cpd 465 |

| Structure/CODE | |
|---|---|
| 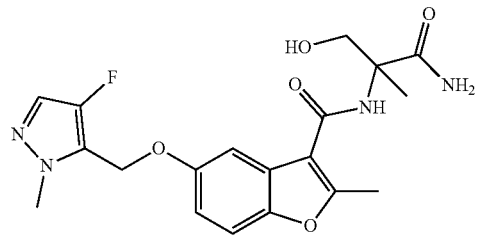 [SMILES: Cc1oc2ccc(OCc3c(F)cnn3C)cc2c1C(=O)NC(C)(CO)C(N)=O] | cpd 466 |
| 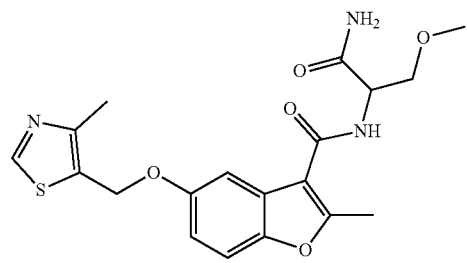 [SMILES: COCC(NC(=O)c1c(C)oc2ccc(OCc3scnc3C)cc12)C(N)=O] | cpd 467 |
| 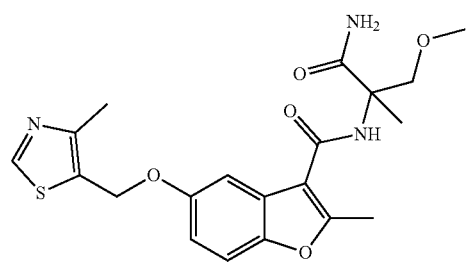 [SMILES: COCC(C)(NC(=O)c1c(C)oc2ccc(OCc3scnc3C)cc12)C(N)=O] | cpd 468 |
| 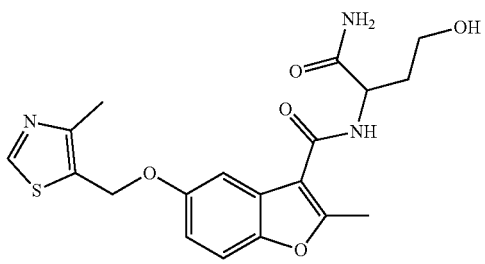 [SMILES: Cc1ncsc1COc1ccc2oc(C)c(C(=O)NC(CCO)C(N)=O)c2c1] | cpd 469 |
| 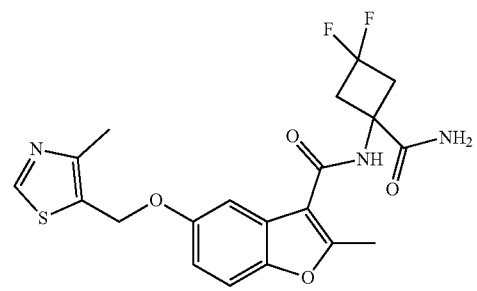 [SMILES: Cc1ncsc1COc1ccc2oc(C)c(C(=O)NC3(C(N)=O)CC(F)(F)C3)c2c1] | cpd 470 |
| 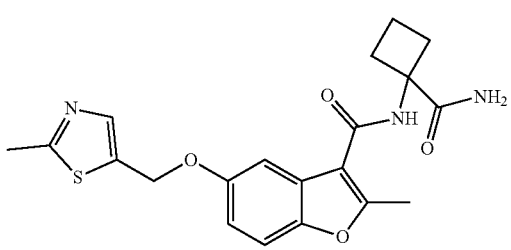 [SMILES: Cc1ncc(COc2ccc3oc(C)c(C(=O)NC4(C(N)=O)CCC4)c3c2)s1] | cpd 471 |

-continued
| Structure/CODE | |
|---|---|
| 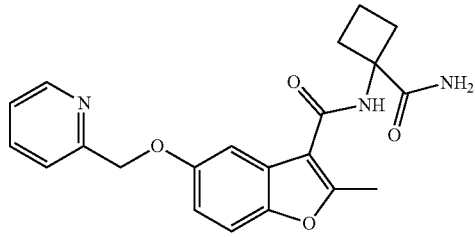 [SMILES: Cc1oc2ccc(OCc3ccccn3)cc2c1C(=O)NC1(C(N)=O)CCC1] | cpd 472 |
| 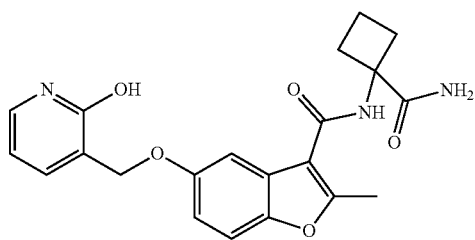 [SMILES: Cc1oc2ccc(OCc3cccnc3O)cc2c1C(=O)NC1(C(N)=O)CCC1] | cpd 473 |
| 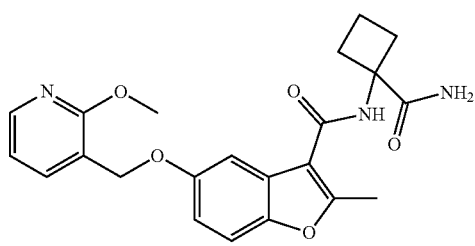 [SMILES: COc1ncccc1COc1ccc2oc(C)c(C(=O)NC3(C(N)=O)CCC3)c2c1] | cpd 474 |
| 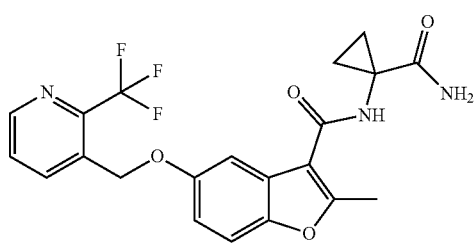 [SMILES: Cc1oc2ccc(OCc3cccnc3C(F)(F)F)cc2c1C(=O)NC1(C(N)=O)CC1] | cpd 475 |
| 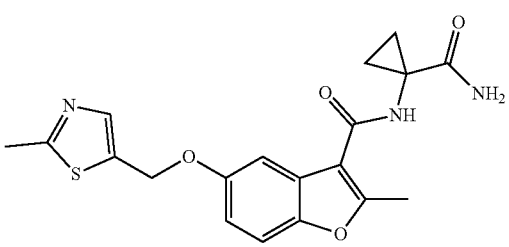 [SMILES: Cc1ncc(COc2ccc3oc(C)c(C(=O)NC4(C(N)=O)CC4)c3c2)s1] | cpd 476 |
| 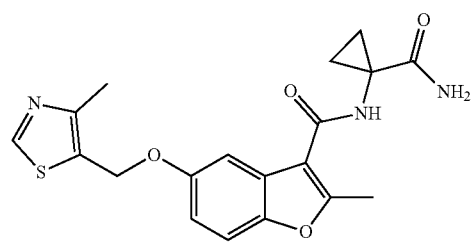 [SMILES: Cc1ncsc1COc1ccc2oc(C)c(C(=O)NC3(C(N)=O)CC3)c2c1] | cpd 477 |

| Structure/CODE | |
|---|---|
| 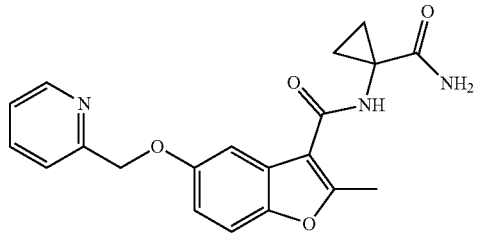 [SMILES: Cc1oc2ccc(OCc3ccccn3)cc2c1C(=O)NC1(C(N)=O)CC1] | cpd 478 |
| 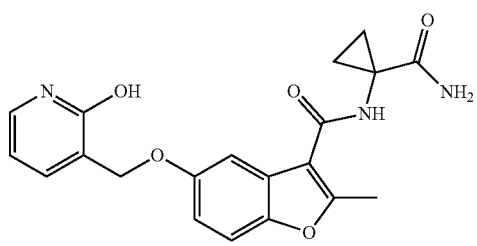 [SMILES: Cc1oc2ccc(OCc3cccnc3O)cc2c1C(=O)NC1(C(N)=O)CC1] | cpd 479 |
| 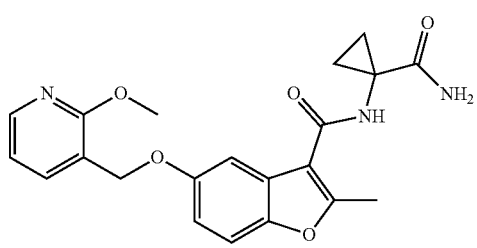 [SMILES: COc1ncccc1COc1ccc2oc(C)c(C(=O)NC3(C(N)=O)CC3)c2c1] | cpd 480 |
| 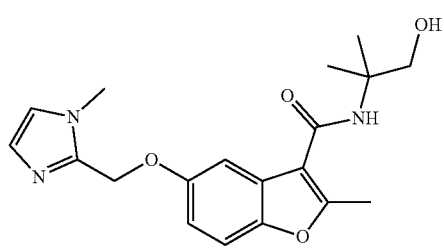 [SMILES: Cc1oc2ccc(OCc3nccn3C)cc2c1C(=O)NC(C)(C)CO] | cpd 481 |
| 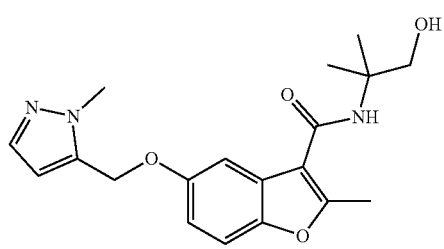 [SMILES: Cc1oc2ccc(OCc3ccnn3C)cc2c1C(=O)NC(C)(C)CO] | cpd 482 |
| 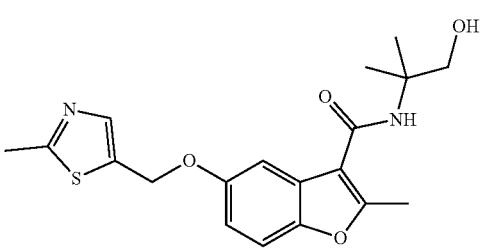 [SMILES: Cc1ncc(COc2ccc3oc(C)c(C(=O)NC(C)(C)CO)c3c2)s1] | cpd 483 |

| Structure/CODE | |
|---|---|
| 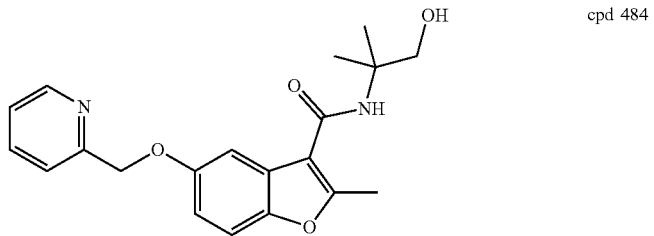 | cpd 484 |
| 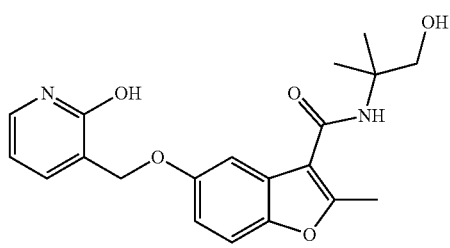 [SMILES: Cc1oc2ccc(OCc3cccnc3O)cc2c1C(=O)NC(C)(C)CO] | cpd 485 |
| 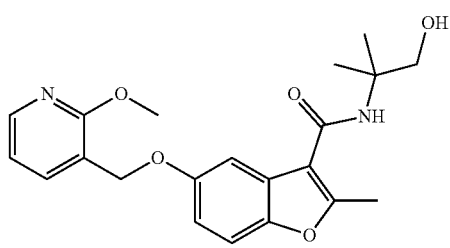 [SMILES: COc1ncccc1COc1ccc2oc(C)c(C(=O)NC(C)(C)CO)c2c1] | cpd 486 |
| 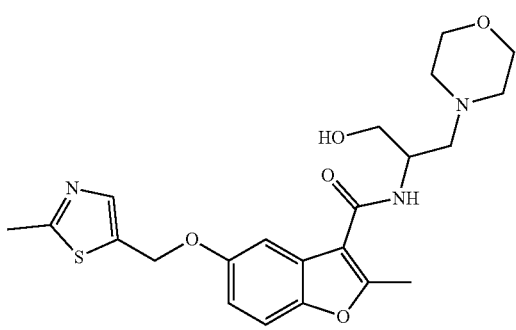 [SMILES: Cc1ncc(COc2ccc3oc(C)c(C(=O)NC(CO)CN4CCOCC4)c3c2)s1] | cpd 487 |
| 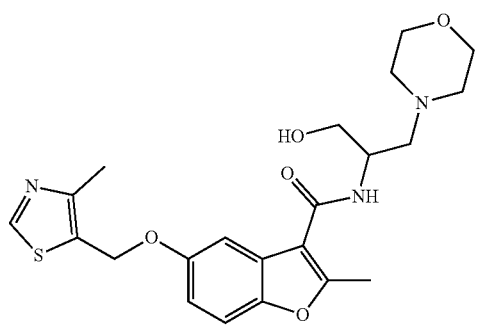 [SMILES: Cc1ncsc1COc1ccc2oc(C)c(C(=O)NC(CO)CN3CCOCC3)c2c1] | cpd 488 |

-continued
| Structure/CODE | |
|---|---|
| 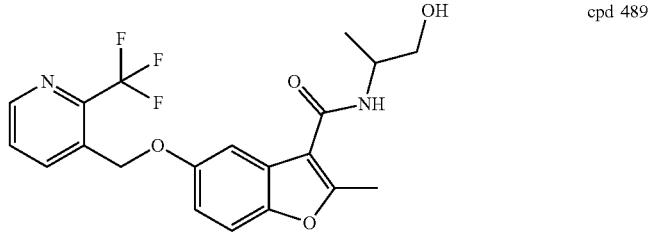 | cpd 489 |
| 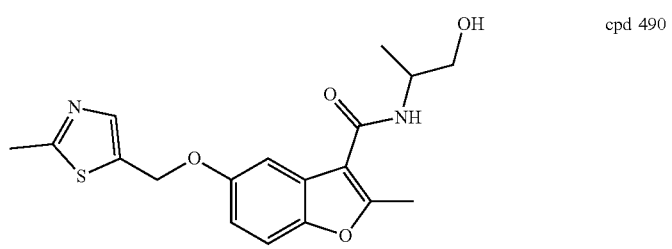 | cpd 490 |
| 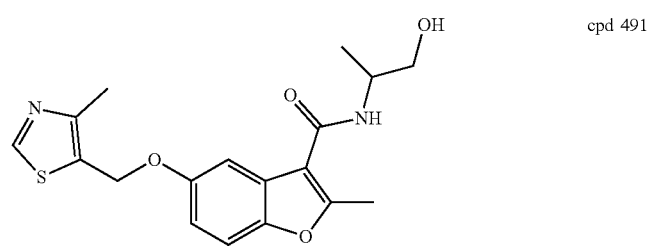 | cpd 491 |
| 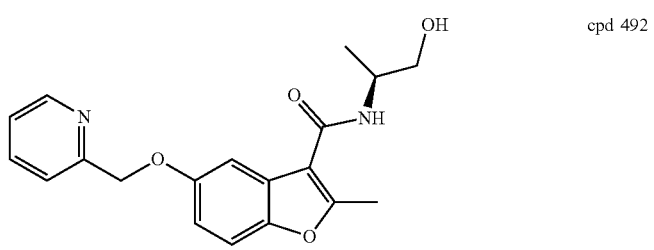 | cpd 492 |
| 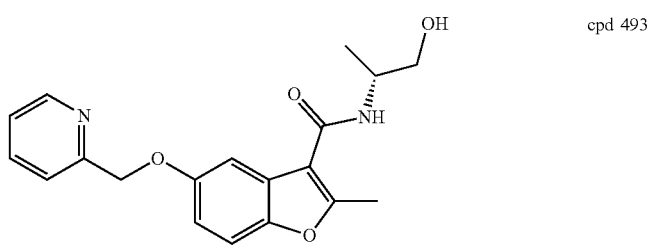 | cpd 493 |
| 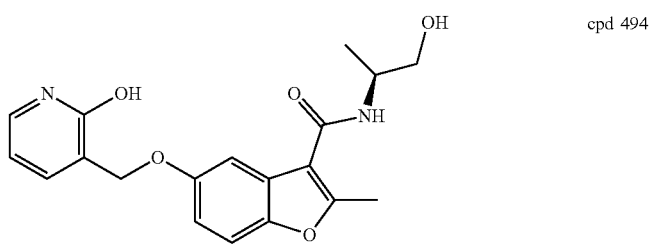 | cpd 494 |

-continued
| Structure/CODE | |
|---|---|
| 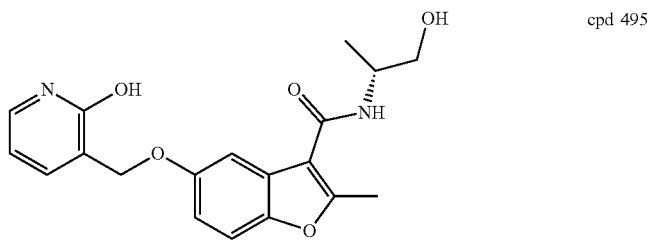 | cpd 495 |
| 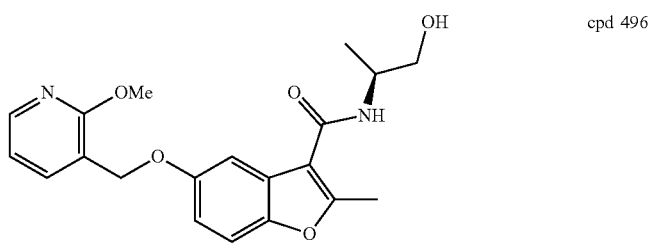 | cpd 496 |
| 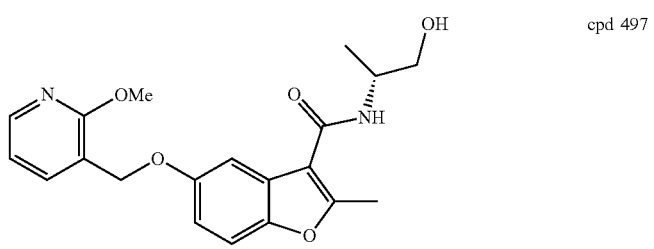 | cpd 497 |
| 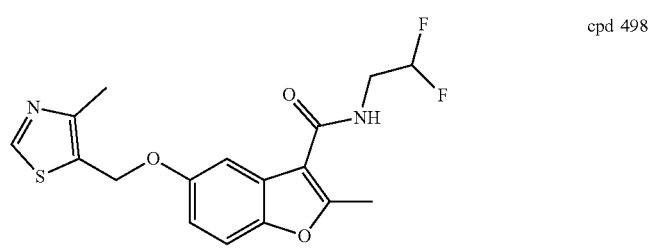 | cpd 498 |
| 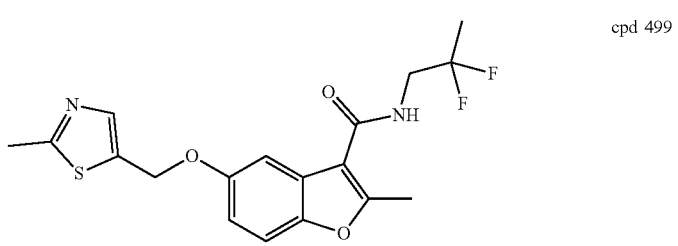 | cpd 499 |
| 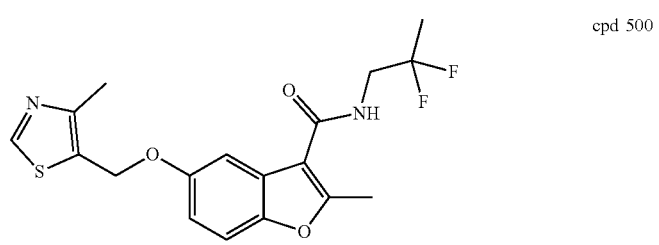 | cpd 500 |

-continued
| Structure/CODE | |
|---|---|
| 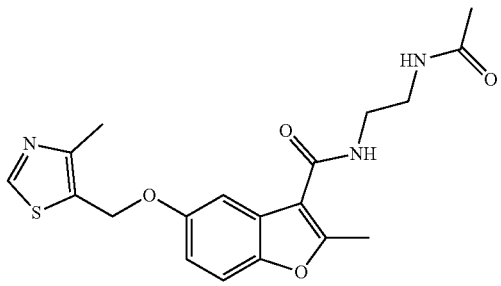 [SMILES: CC(=O)NCCNC(=O)c1c(C)oc2ccc(OCc3scnc3C)cc12] | cpd 501 |
| 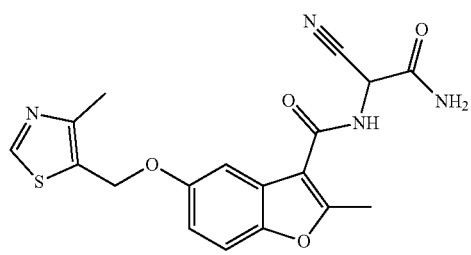 [SMILES: Cc1ncsc1COc1ccc2oc(C)c(C(=O)NC(C#N)C(N)=O)c2c1] | cpd 502 |
| 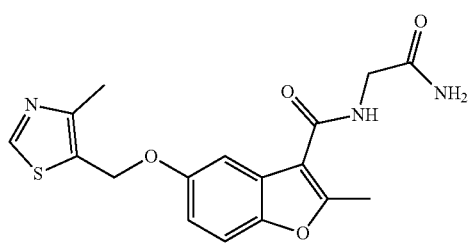 [SMILES: Cc1ncsc1COc1ccc2oc(C)c(C(=O)NCC(N)=O)c2c1] | cpd 503 |
| 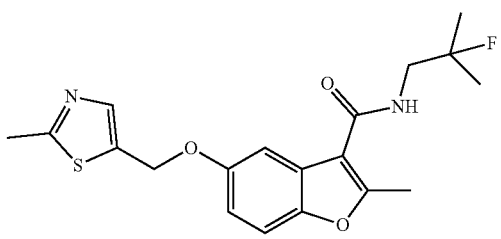 [SMILES: Cc1ncc(COc2ccc3oc(C)c(C(=O)NCC(C)(C)F)c3c2)s1] | cpd 504 |
| 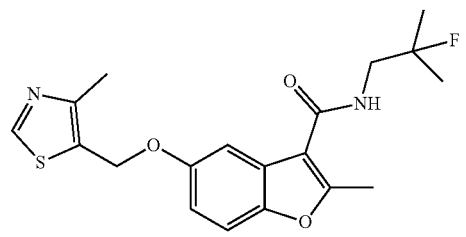 [SMILES: Cc1ncsc1COc1ccc2oc(C)c(C(=O)NCC(C)(C)F)c2c1] | cpd 505 |
| 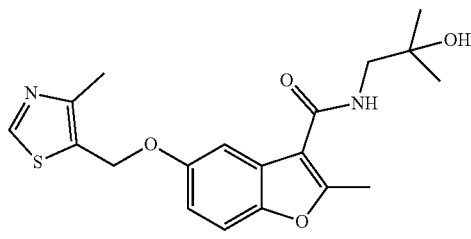 [SMILES: Cc1ncsc1COc1ccc2oc(C)c(C(=O)NCC(C)(C)O)c2c1] | cpd 506 |

-continued
| Structure/CODE |
|---|
| 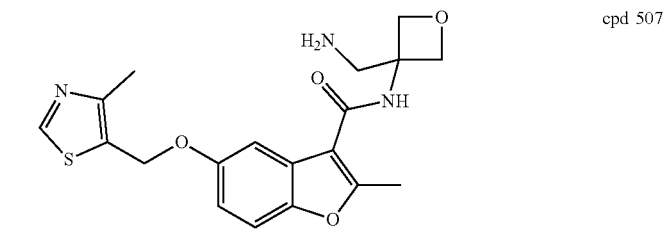 cpd 507 |
| 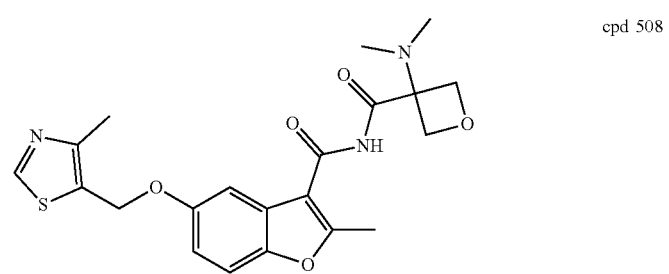 cpd 508 |
| 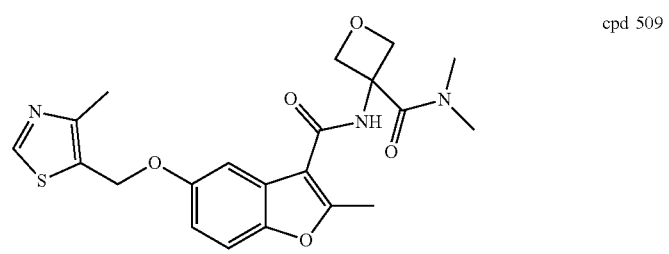 cpd 509 |
| 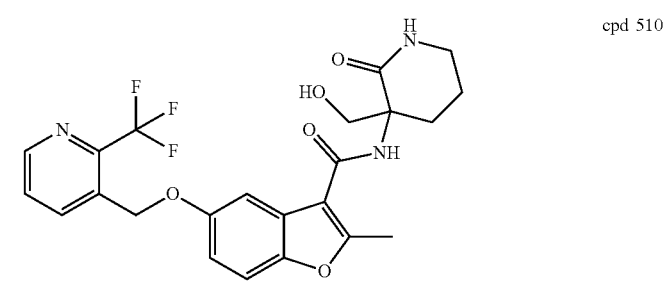 cpd 510 |
| 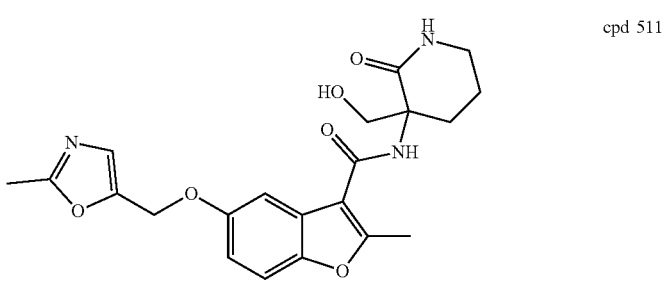 cpd 511 |
| 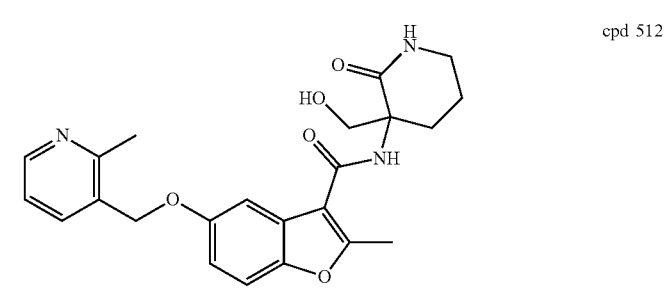 cpd 512 |

-continued
| Structure/CODE | |
|---|---|
| 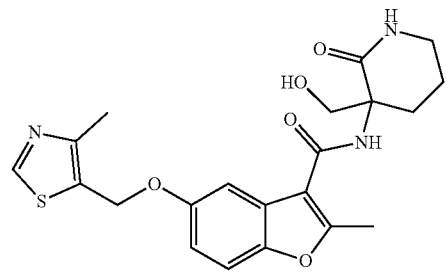 [SMILES: Cc1ncsc1COc1ccc2oc(C)c(C(=O)NC3(CO)CCCNC3=O)c2c1] | cpd 513 |
| 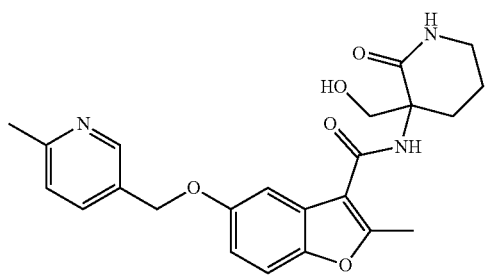 [SMILES: Cc1ccc(COc2ccc3oc(C)c(C(=O)NC4(CO)CCCNC4=O)c3c2)cn1] | cpd 514 |
| 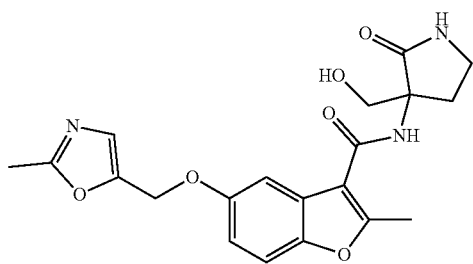 [SMILES: Cc1ncc(COc2ccc3oc(C)c(C(=O)NC4(CO)CCNC4=O)c3c2)o1] | cpd 515 |
| 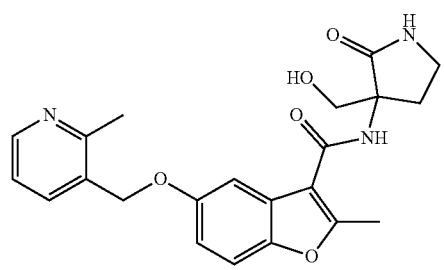 [SMILES: Cc1ncccc1COc1ccc2oc(C)c(C(=O)NC3(CO)CCNC3=O)c2c1] | cpd 516 |
| 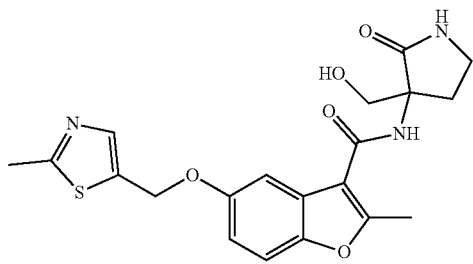 [SMILES: Cc1ncc(COc2ccc3oc(C)c(C(=O)NC4(CO)CCNC4=O)c3c2)s1] | cpd 517 |

| Structure/CODE | |
|---|---|
| 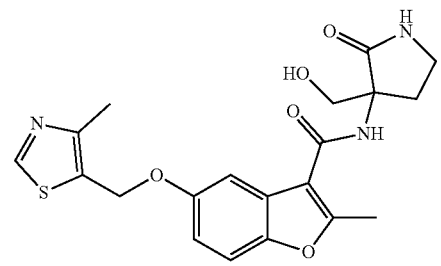 [SMILES: Cc1ncsc1COc1ccc2oc(C)c(C(=O)NC3(CO)CCNC3=O)c2c1] | cpd 518 |
| 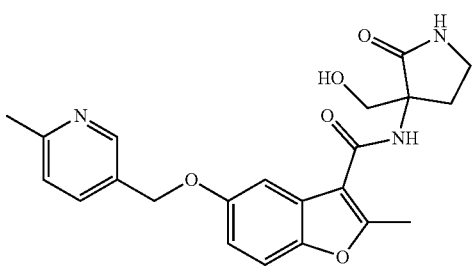 [SMILES: Cc1ccc(COc2ccc3oc(C)c(C(=O)NC4(CO)CCNC4=O)c3c2)cn1] | cpd 519 |
| 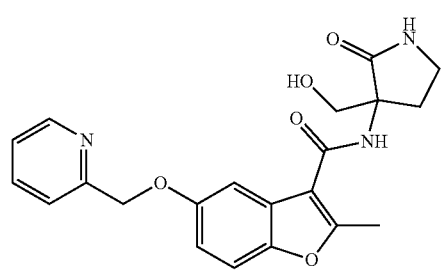 [SMILES: Cc1oc2ccc(OCc3ccccn3)cc2c1C(=O)NC1(CO)CCNC1=O] | cpd 520 |
| 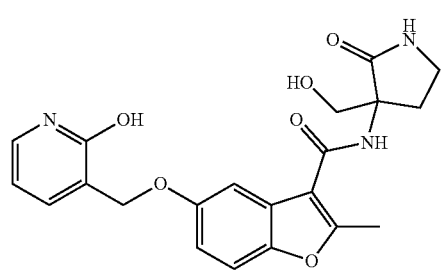 [SMILES: Cc1oc2ccc(OCc3cccnc3O)cc2c1C(=O)NC1(CO)CCNC1=O] | cpd 521 |
| 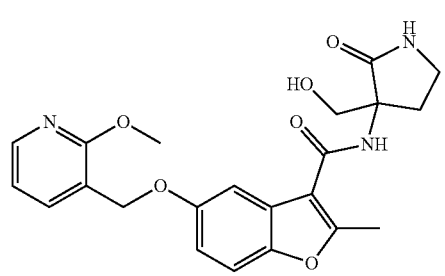 [SMILES: COc1ncccc1COc1ccc2oc(C)c(C(=O)NC3(CO)CCNC3=O)c2c1] | cpd 522 |
| 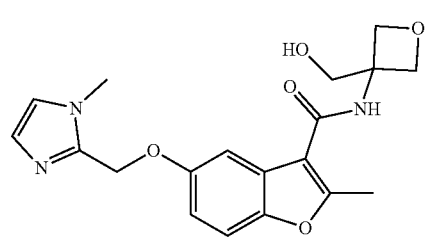 [SMILES: Cc1oc2ccc(OCc3nccn3C)cc2c1C(=O)NC1(CO)COC1] | cpd 523 |

-continued
| Structure/CODE | |
|---|---|
| 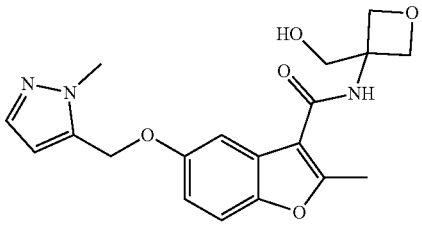 [SMILES: Cc1oc2ccc(OCc3ccnn3C)cc2c1C(=O)NC1(CO)COC1] | cpd 524 |
| 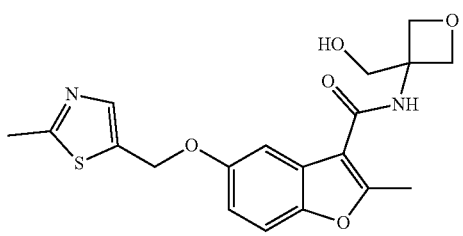 [SMILES: Cc1ncc(COc2ccc3oc(C)c(C(=O)NC4(CO)COC4)c3c2)s1] | cpd 525 |
| 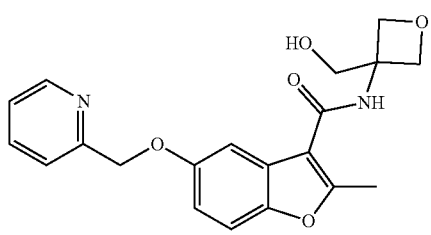 [SMILES: Cc1oc2ccc(OCc3ccccn3)cc2c1C(=O)NC1(CO)COC1] | cpd 526 |
| 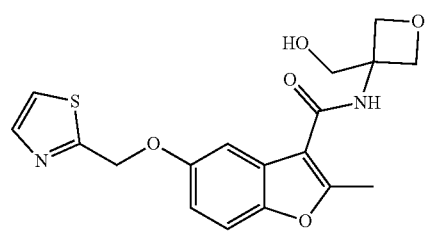 [SMILES: Cc1oc2ccc(OCc3nccs3)cc2c1C(=O)NC1(CO)COC1] | cpd 527 |
| 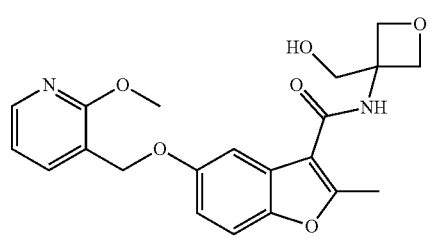 [SMILES: COc1ncccc1COc1ccc2oc(C)c(C(=O)NC3(CO)COC3)c2c1] | cpd 528 |
| 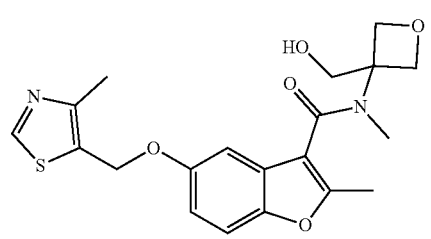 [SMILES: Cc1ncsc1COc1ccc2oc(C)c(C(=O)N(C)C3(CO)COC3)c2c1] | cpd 529 |

-continued
| Structure/CODE | |
|---|---|
| 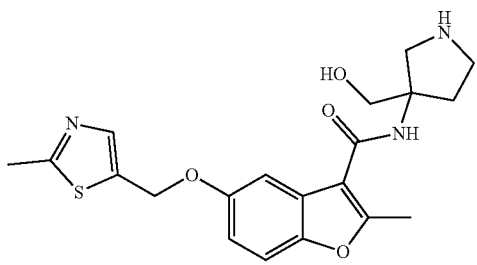 [SMILES: Cc1ncc(COc2ccc3oc(C)c(C(=O)NC4(CO)CCNC4)c3c2)s1] | cpd 530 |
| 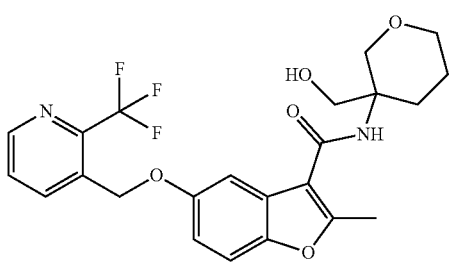 [SMILES: Cc1oc2ccc(OCc3cccnc3C(F)(F)F)cc2c1C(=O)NC1(CO)CCCOC1] | cpd 531 |
| 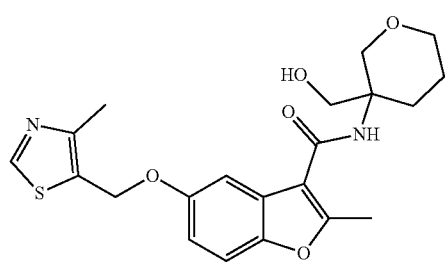 [SMILES: Cc1ncsc1COc1ccc2oc(C)c(C(=O)NC3(CO)CCCOC3)c2c1] | cpd 532 |
| 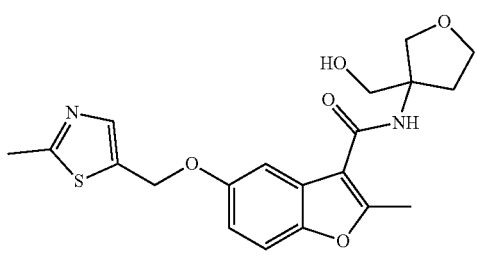 [SMILES: Cc1ncc(COc2ccc3oc(C)c(C(=O)NC4(CO)CCOC4)c3c2)s1] | cpd 533 |
| 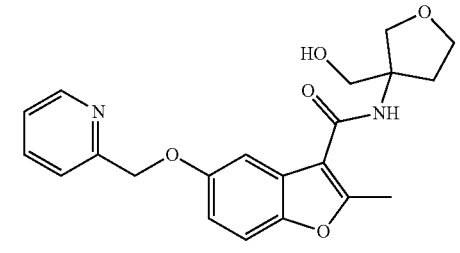 [SMILES: Cc1oc2ccc(OCc3ccccn3)cc2c1C(=O)NC1(CO)CCOC1] | cpd 534 |
| 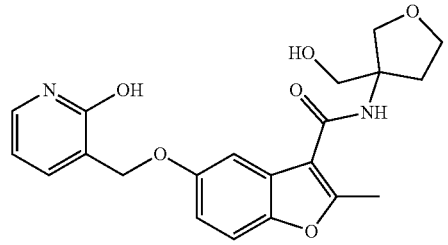 [SMILES: Cc1oc2ccc(OCc3cccnc3O)cc2c1C(=O)NC1(CO)CCOC1] | cpd 535 |

| Structure/CODE | |
|---|---|
| 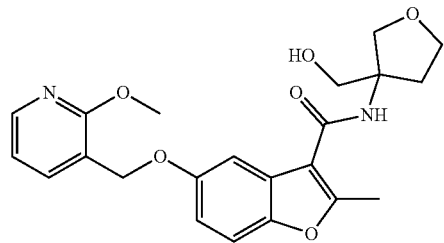 [SMILES: COc1ncccc1COc1ccc2oc(C)c(C(=O)NC3(CO)CCOC3)c2c1] | cpd 536 |
| 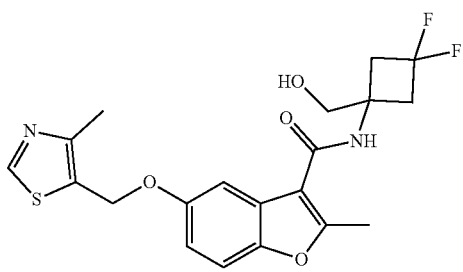 [SMILES: Cc1ncsc1COc1ccc2oc(C)c(C(=O)NC3(CO)CC(F)(F)C3)c2c1] | cpd 537 |
| 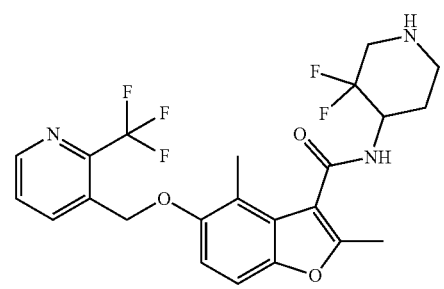 [SMILES: Cc1oc2ccc(OCc3cccnc3C(F)(F)F)c(C)c2c1C(=O)NC1CCNCC1(F)F] | cpd 538 |
| 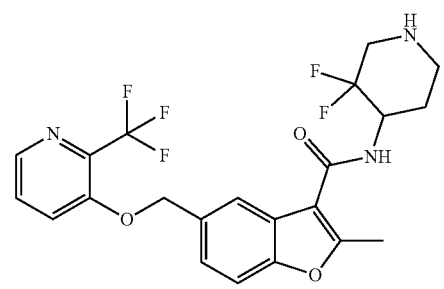 [SMILES: Cc1oc2ccc(COc3cccnc3C(F)(F)F)cc2c1C(=O)NC1CCNCC1(F)F] | cpd 539 |
| 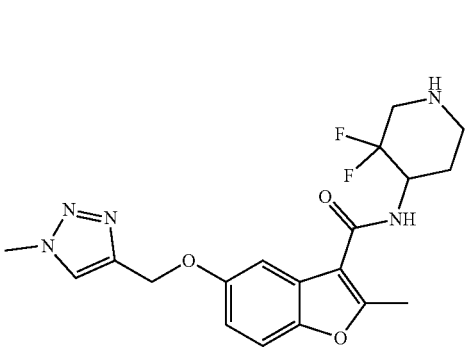 [SMILES: Cc1oc2ccc(OCc3cn(C)nn3)cc2c1C(=O)NC1CCNCC1(F)F] | cpd 540 |

| Structure/CODE | |
|---|---|
| 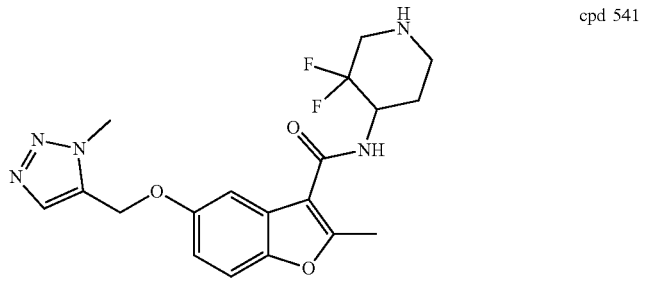 | cpd 541 |
| 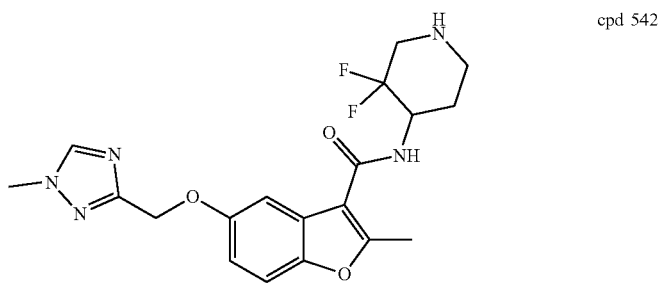 | cpd 542 |
| 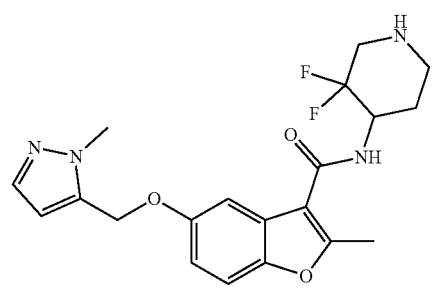 [SMILES: Cc1oc2ccc(OCc3ccnn3C)cc2c1C(=O)NC1CCNCC1(F)F] | cpd 543 |
| 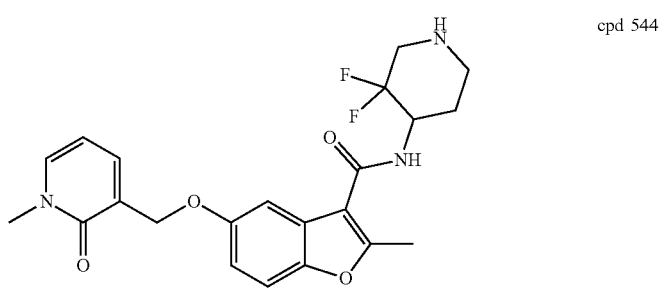 | cpd 544 |
| 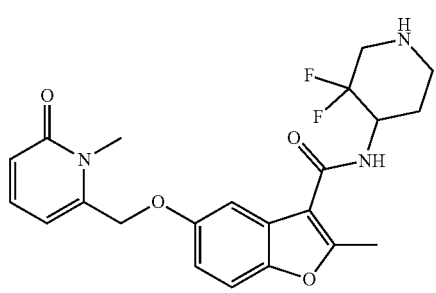 [SMILES: Cc1oc2ccc(OCc3cccc(=O)n3C)cc2c1C(=O)NC1CCNCC1(F)F] | cpd 545 |

-continued
| Structure/CODE |
|---|
| 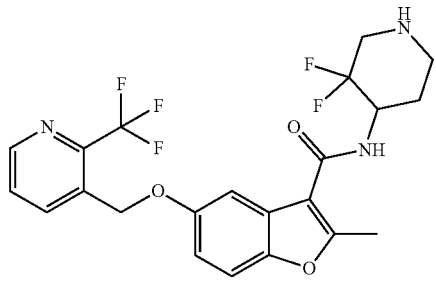 [SMILES: Cc1oc2ccc(OCc3cccnc3C(F)(F)F)cc2c1C(=O)NC1CCNCC1(F)F] cpd 546 |
| 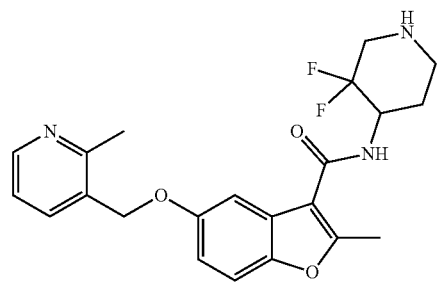 [SMILES: Cc1ncccc1COc1ccc2oc(C)c(C(=O)NC3CCNCC3(F)F)c2c1] cpd 547 |
| 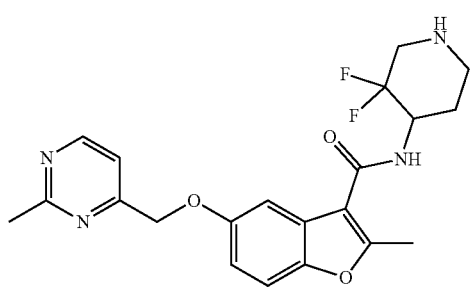 [SMILES: Cc1nccc(COc2ccc3oc(C)c(C(=O)NC4CCNCC4(F)F)c3c2)n1] cpd 548 |
| 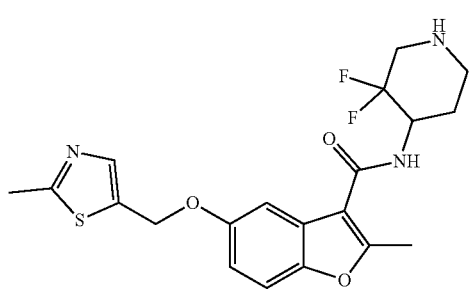 [SMILES: Cc1ncc(COc2ccc3oc(C)c(C(=O)NC4CCNCC4(F)F)c3c2)s1] cpd 549 |
| 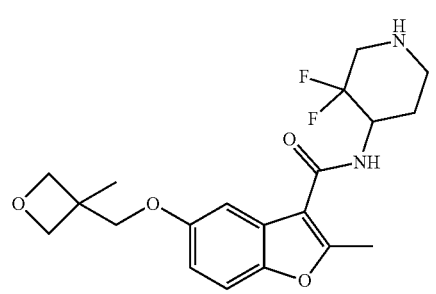 [SMILES: Cc1oc2ccc(OCC3(C)COC3)cc2c1C(=O)NC1CCNCC1(F)F] cpd 550 |

-continued
| Structure/CODE |
|---|
| 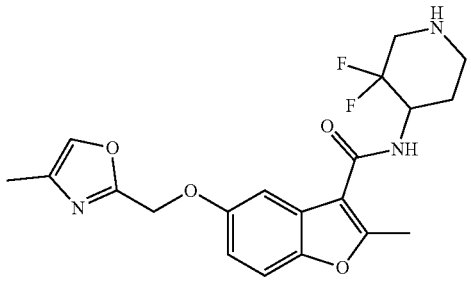 cpd 551 |
| 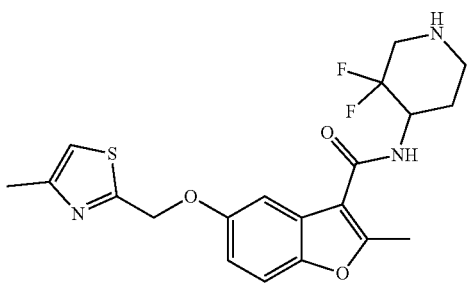 [SMILES: Cc1coc(COc2ccc3oc(C)c(C(=O)NC4CCNCC4(F)F)c3c2)n1] cpd 552 |
| 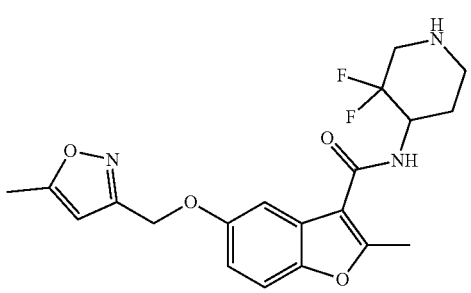 [SMILES: Cc1cc(COc2ccc3oc(C)c(C(=O)NC4CCNCC4(F)F)c3c2)no1] cpd 553 |
| 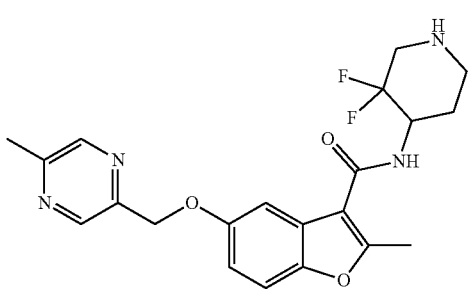 [SMILES: Cc1cnc(COc2ccc3oc(C)c(C(=O)NC4CCNCC4(F)F)c3c2)cn1] cpd 554 |
| 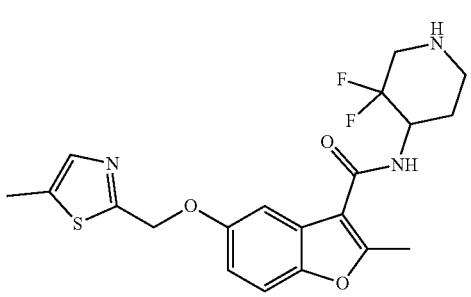 [SMILES: Cc1cnc(COc2ccc3oc(C)c(C(=O)NC4CCNCC4(F)F)c3c2)s1] cpd 555 |

-continued
| Structure/CODE | |
|---|---|
| 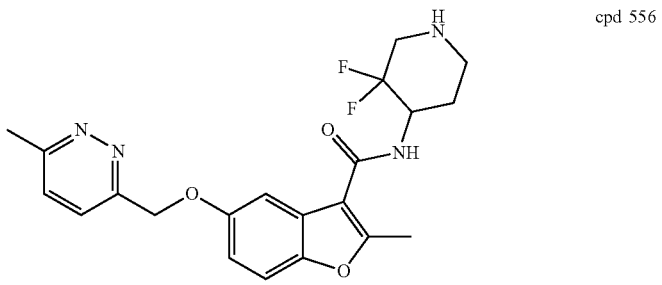 | cpd 556 |
| 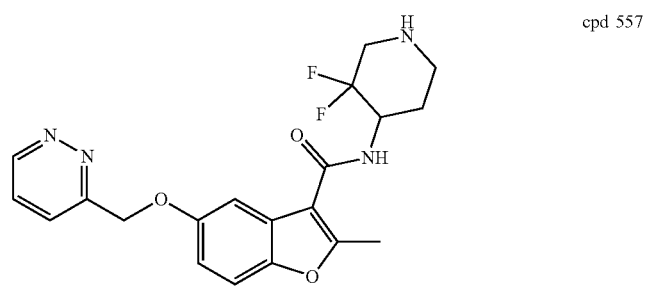 | cpd 557 |
| 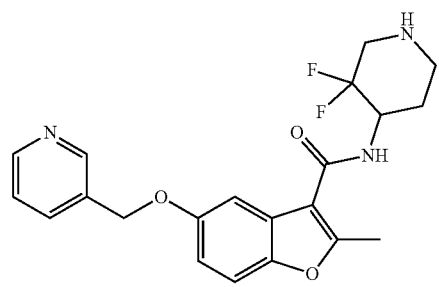 [SMILES: Cc1oc2ccc(OCc3cccnc3)cc2c1C(=O)NC1CCNCC1(F)F] | cpd 558 |
| 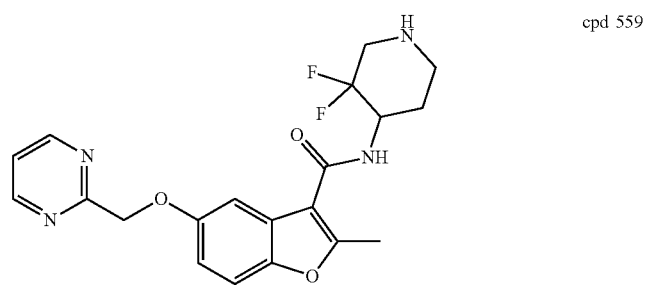 | cpd 559 |
| 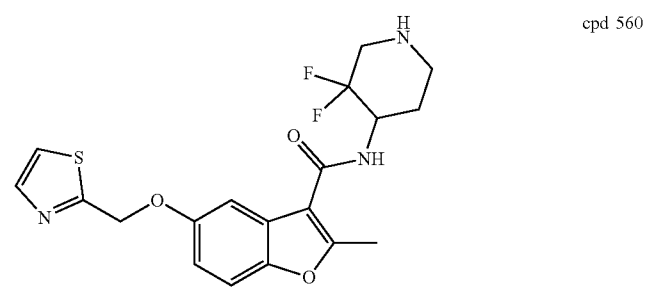 | cpd 560 |

| Structure/CODE | |
|---|---|
| 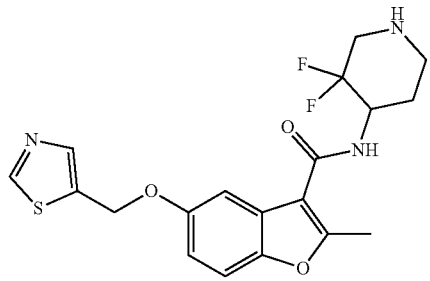 [SMILES: Cc1oc2ccc(OCc3cncs3)cc2c1C(=O)NC1CCNCC1(F)F] | cpd 561 |
| 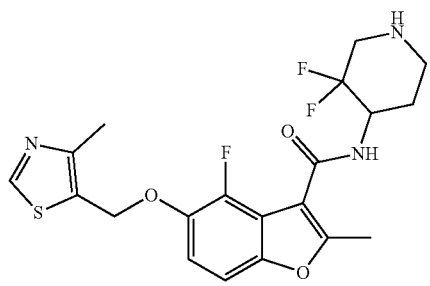 [SMILES: Cc1ncsc1COc1ccc2oc(C)c(C(=O)NC3CCNCC3(F)F)c2c1F] | cpd 562 |
| 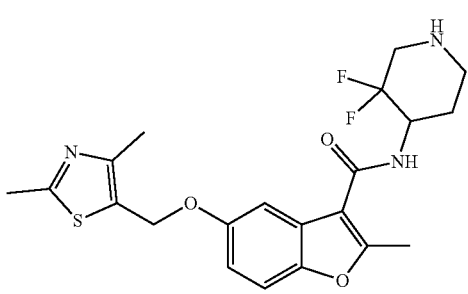 [SMILES: Cc1nc(C)c(COc2ccc3oc(C)c(C(=O)NC4CCNCC4(F)F)c3c2)s1] | cpd 563 |
| 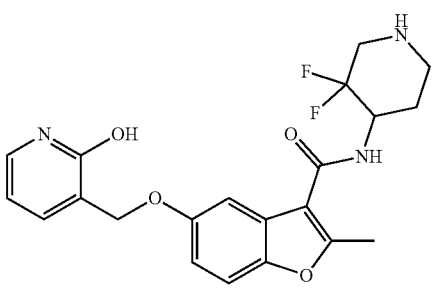 [SMILES: Cc1oc2ccc(OCc3cccnc3O)cc2c1C(=O)NC1CCNCC1(F)F] | cpd 564 |
| 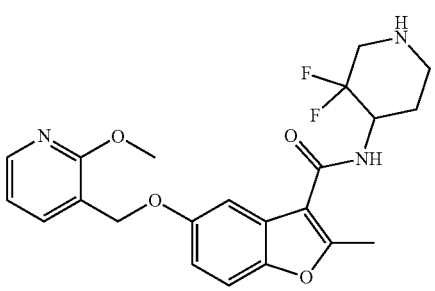 [SMILES: COc1ncccc1COc1ccc2oc(C)c(C(=O)NC3CCNCC3(F)F)c2c1] | cpd 565 |

| Structure/CODE | |
|---|---|
| 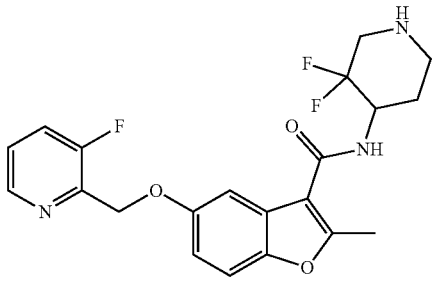 [SMILES: Cc1oc2ccc(OCc3ncccc3F)cc2c1C(=O)NC1CCNCC1(F)F] | cpd 566 |
| 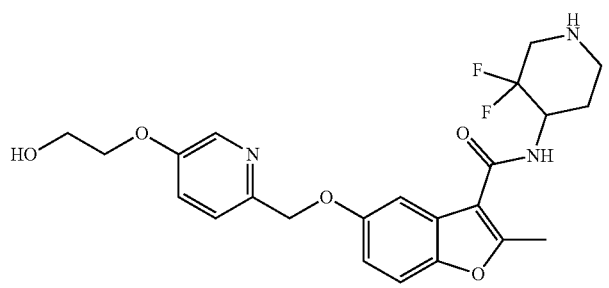 [SMILES: Cc1oc2ccc(OCc3ccc(OCCO)cn3)cc2c1C(=O)NC1CCNCC1(F)F] | cpd 567 |
| 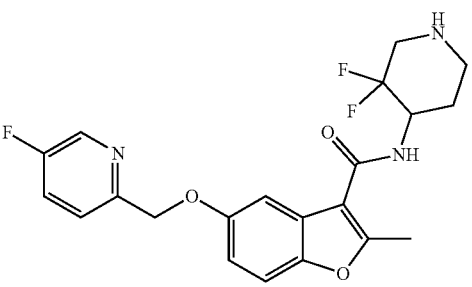 [SMILES: Cc1oc2ccc(OCc3ccc(F)cn3)cc2c1C(=O)NC1CCNCC1(F)F] | cpd 568 |
| 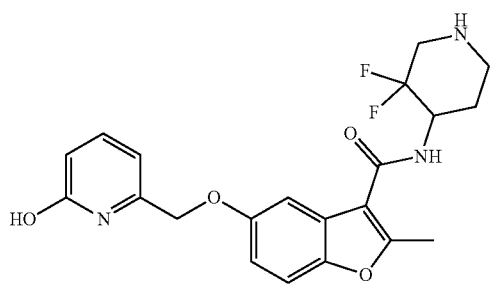 [SMILES: Cc1oc2ccc(OCc3cccc(O)n3)cc2c1C(=O)NC1CCNCC1(F)F] | cpd 569 |
| 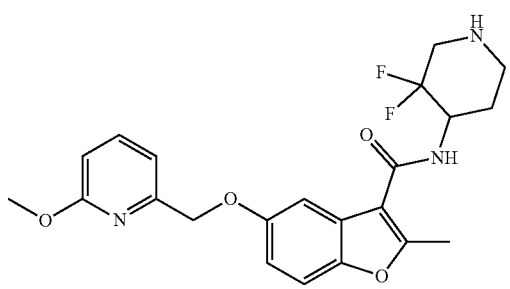 [SMILES: COc1cccc(COc2ccc3oc(C)c(C(=O)NC4CCNCC4(F)F)c3c2)n1] | cpd 570 |

-continued
Structure/CODE
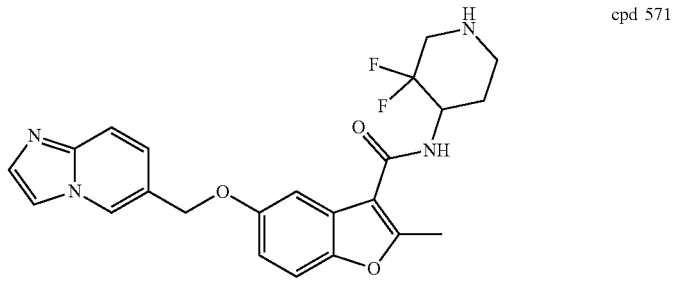
cpd 571
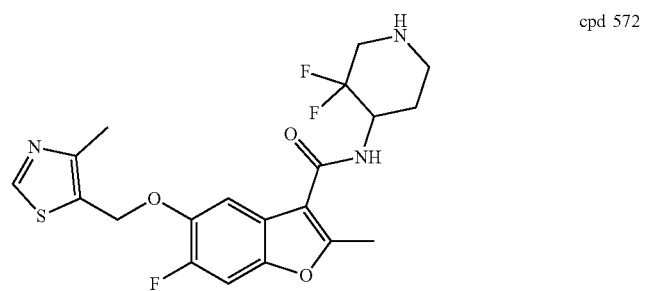
cpd 572
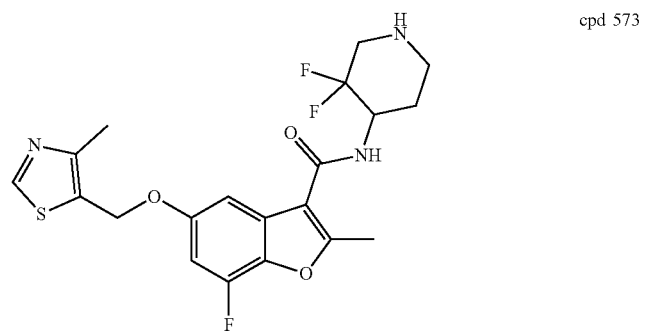
cpd 573
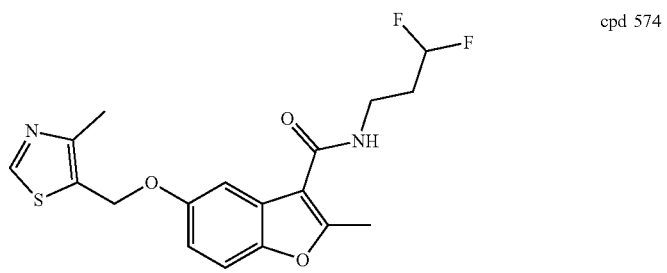
cpd 574
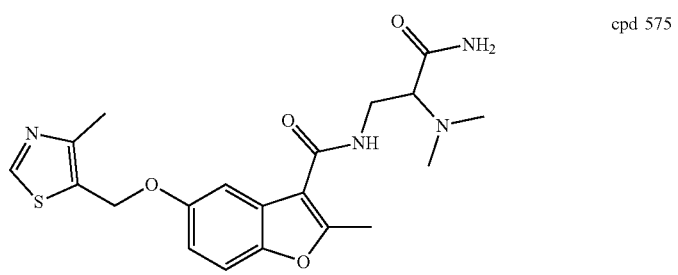
cpd 575

-continued
| Structure/CODE | |
|---|---|
| 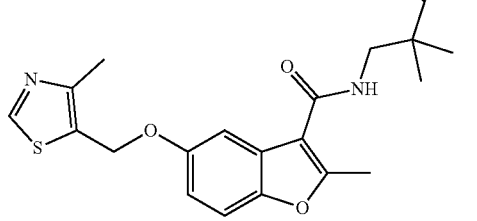 | cpd 576 |
| 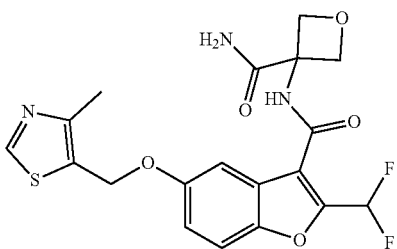 [SMILES: Cc1ncsc1COc1ccc2oc(C(F)F)c(C(=O)NC3(C(N)=O)COC3)c2c1] | cpd 577 |
| 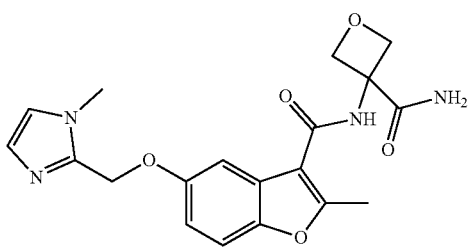 [SMILES: Cc1oc2ccc(OCc3nccn3C)cc2c1C(=O)NC1(C(N)=O)COC1] | cpd 578 |
| 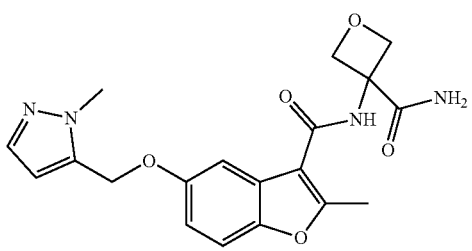 [SMILES: Cc1oc2ccc(OCc3ccnn3C)cc2c1C(=O)NC1(C(N)=O)COC1] | cpd 579 |
| 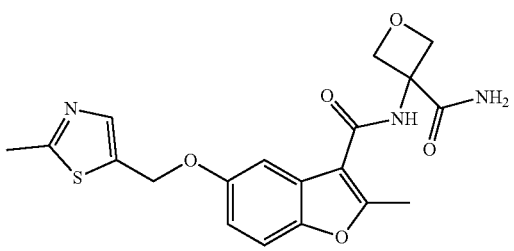 [SMILES: Cc1ncc(COc2ccc3oc(C)c(C(=O)NC4(C(N)=O)COC4)c3c2)s1] | cpd 580 |
| 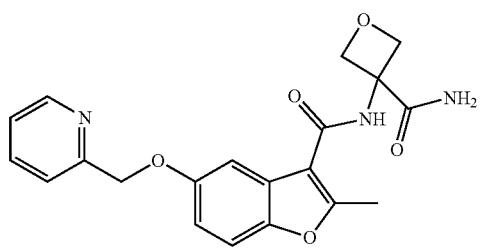 [SMILES: Cc1oc2ccc(OCc3ccccn3)cc2c1C(=O)NC1(C(N)=O)COC1] | cpd 581 |

| Structure/CODE | |
|---|---|
| 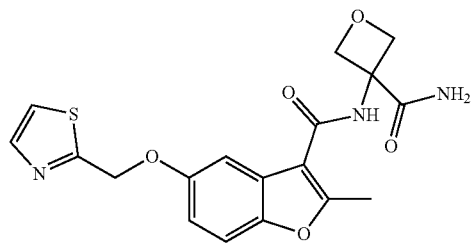 [SMILES: Cc1oc2ccc(OCc3nccs3)cc2c1C(=O)NC1(C(N)=O)COC1] | cpd 582 |
| 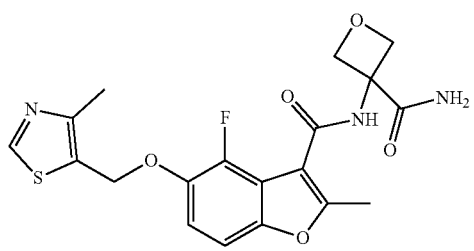 [SMILES: Cc1ncsc1COc1ccc2oc(C)c(C(=O)NC3(C(N)=O)COC3)c2c1F] | cpd 583 |
| 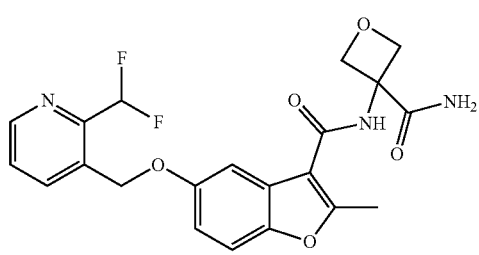 [SMILES: Cc1oc2ccc(OCc3cccnc3C(F)F)cc2c1C(=O)NC1(C(N)=O)COC1] | cpd 584 |
| 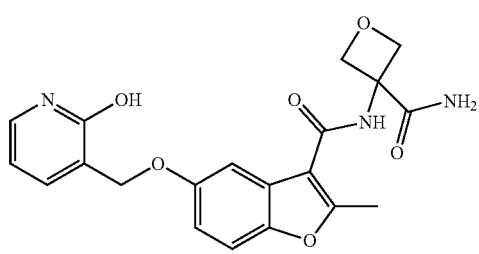 [SMILES: Cc1oc2ccc(OCc3cccnc3O)cc2c1C(=O)NC1(C(N)=O)COC1] | cpd 585 |
| 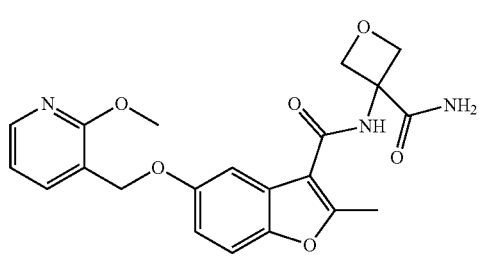 [SMILES: COc1ncccc1COc1ccc2oc(C)c(C(=O)NC3(C(N)=O)COC3)c2c1] | cpd 586 |
| 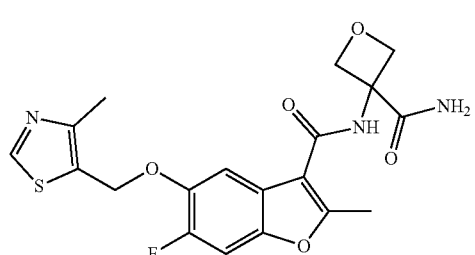 | cpd 587 |

-continued
| Structure/CODE | |
|---|---|
| 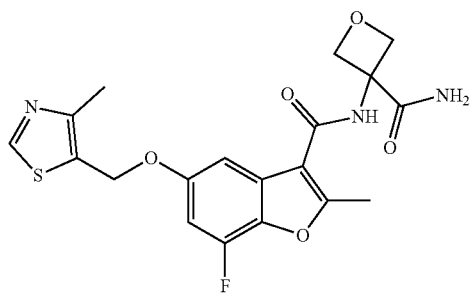 [SMILES: Cc1ncsc1COc1cc(F)c2oc(C)c(C(=O)NC3(C(N)=O)COC3)c2c1] | cpd 588 |
| 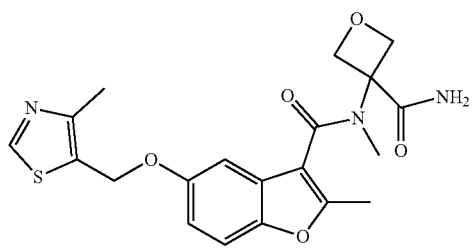 [SMILES: Cc1ncsc1COc1ccc2oc(C)c(C(=O)N(C)C3(C(N)=O)COC3)c2c1] | cpd 589 |
| 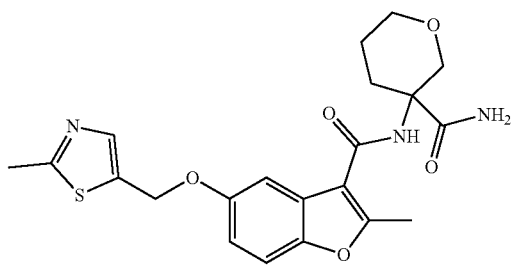 [SMILES: Cc1ncc(COc2ccc3oc(C)c(C(=O)NC4(C(N)=O)CCCOC4)c3c2)s1] | cpd 590 |
| 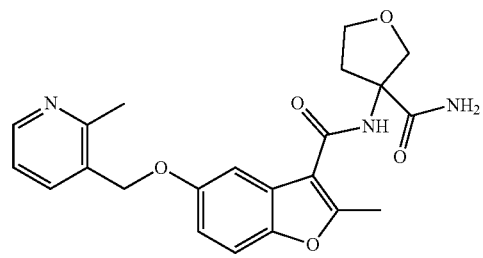 [SMILES: Cc1ncccc1COc1ccc2oc(C)c(C(=O)NC3(C(N)=O)CCOC3)c2c1] | cpd 591 |
| 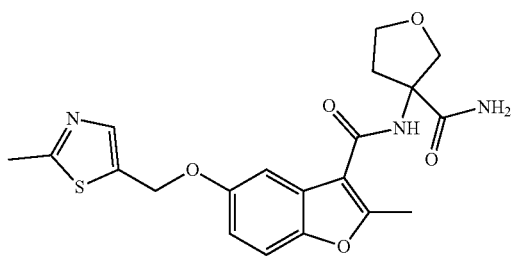 [SMILES: Cc1ncc(COc2ccc3oc(C)c(C(=O)NC4(C(N)=O)CCOC4)c3c2)s1] | cpd 592 |
| 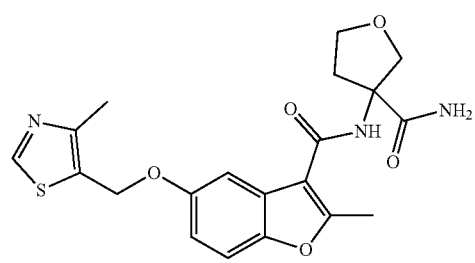 [SMILES: Cc1ncsc1COc1ccc2oc(C)c(C(=O)NC3(C(N)=O)CCOC3)c2c1] | cpd 593 |

| Structure/CODE | |
|---|---|
| 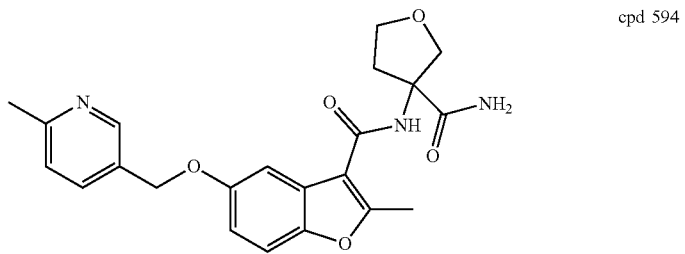 | cpd 594 |
| 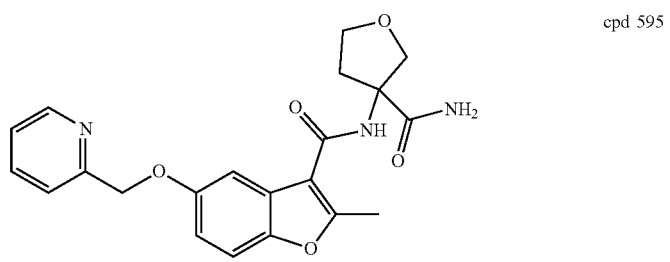 | cpd 595 |
| 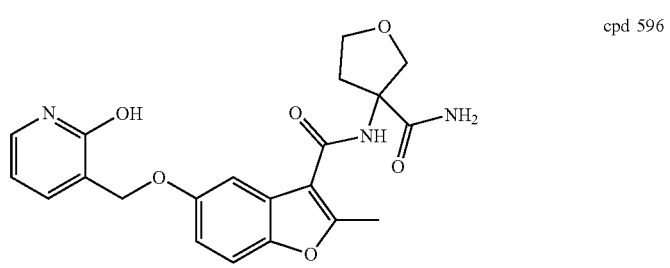 | cpd 596 |
| 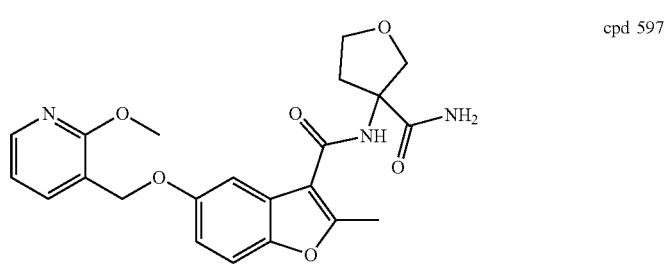 | cpd 597 |
| 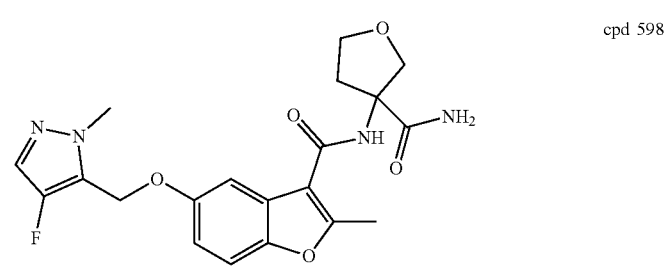 | cpd 598 |
| 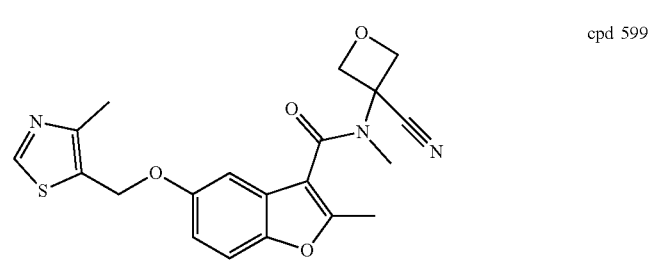 | cpd 599 |

-continued
| Structure/CODE | |
|---|---|
| 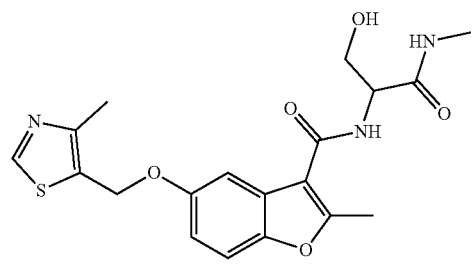 [SMILES: CNC(=O)C(CO)NC(=O)c1c(C)oc2ccc(OCc3scnc3C)cc12] | cpd 600 |
| 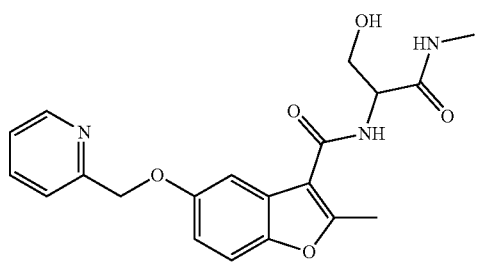 [SMILES: CNC(=O)C(CO)NC(=O)c1c(C)oc2ccc(OCc3ccccn3)cc12] | cpd 601 |
| 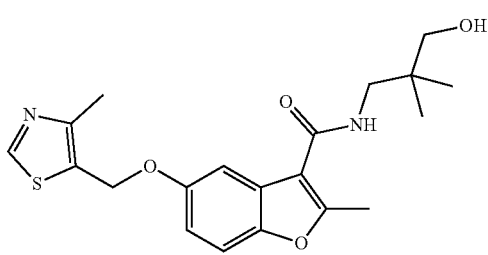 [SMILES: Cc1ncsc1COc1ccc2oc(C)c(C(=O)NCC(C)(C)CO)c2c1] | cpd 602 |
| 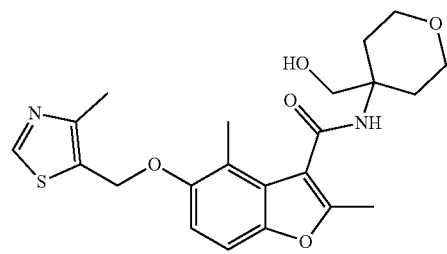 [SMILES: Cc1ncsc1COc1ccc2oc(C)c(C(=O)NC3(CO)CCOCC3)c2c1C] | cpd 603 |
| 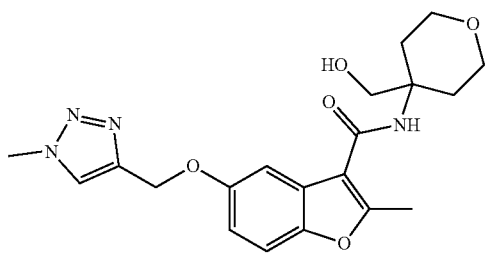 [SMILES: Cc1oc2ccc(OCc3cn(C)nn3)cc2c1C(=O)NC1(CO)CCOCC1] | cpd 604 |
| 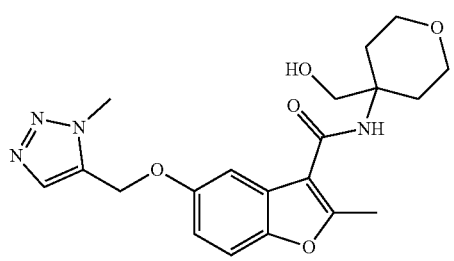 [SMILES: Cc1oc2ccc(OCc3cnnn3C)cc2c1C(=O)NC1(CO)CCOCC1] | cpd 605 |

-continued
| Structure/CODE | |
|---|---|
| 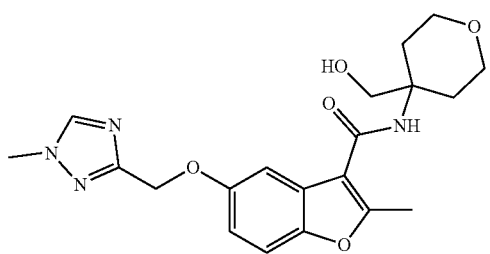 [SMILES: Cc1oc2ccc(OCc3ncn(C)n3)cc2c1C(=O)NC1(CO)CCOCC1] | cpd 606 |
| 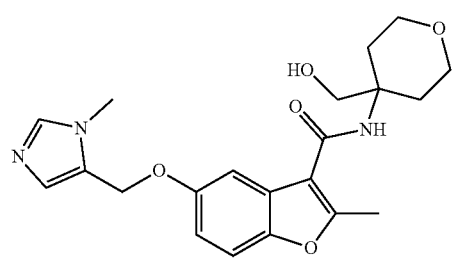 [SMILES: Cc1oc2ccc(OCc3cncn3C)cc2c1C(=O)NC1(CO)CCOCC1] | cpd 607 |
| 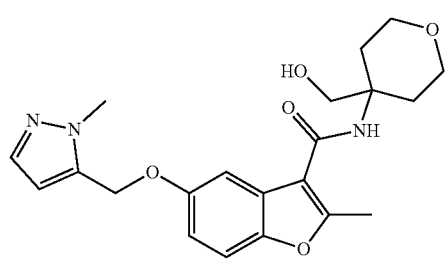 [SMILES: Cc1oc2ccc(OCc3ccnn3C)cc2c1C(=O)NC1(CO)CCOCC1] | cpd 608 |
| 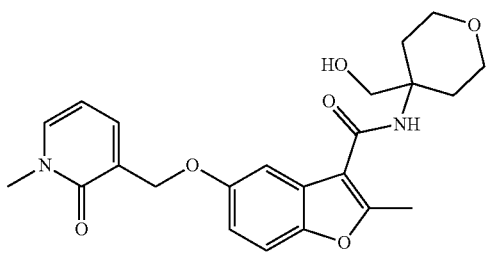 [SMILES: Cc1oc2ccc(OCc3cccn(C)c3=O)cc2c1C(=O)NC1(CO)CCOCC1] | cpd 609 |
| 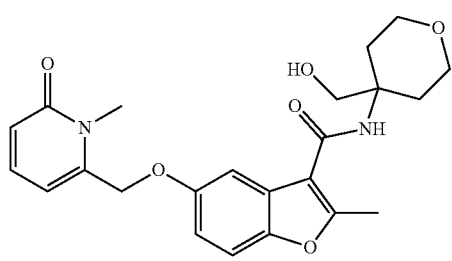 [SMILES: Cc1oc2ccc(OCc3cccc(=O)n3C)cc2c1C(=O)NC1(CO)CCOCC1] | cpd 610 |
| 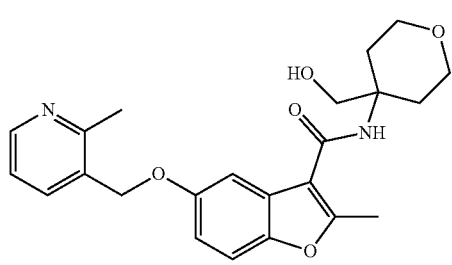 [SMILES: Cc1ncccc1COc1ccc2oc(C)c(C(=O)NC3(CO)CCOCC3)c2c1] | cpd 611 |

-continued
| Structure/CODE | |
|---|---|
| 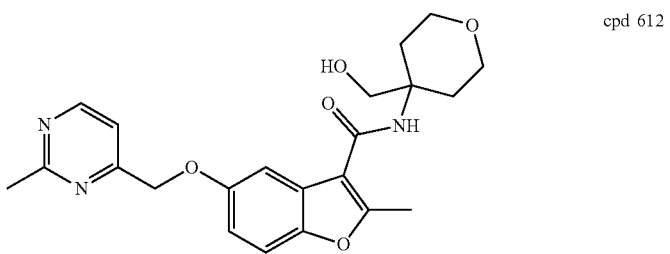 | cpd 612 |
| 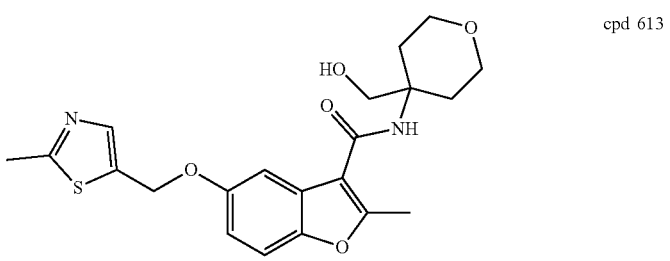 | cpd 613 |
| 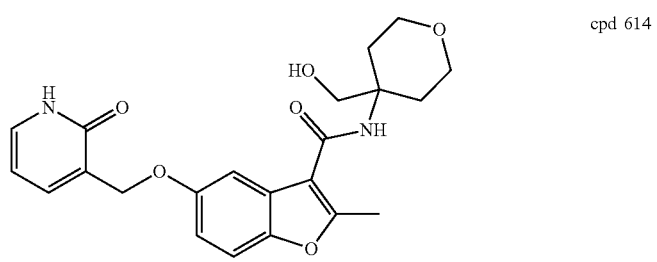 | cpd 614 |
| 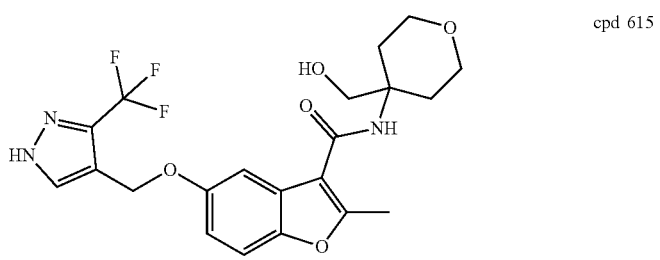 | cpd 615 |
| 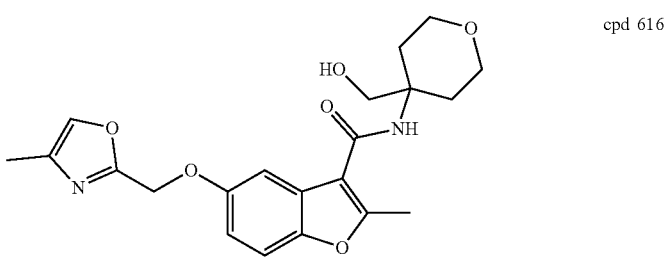 | cpd 616 |
| 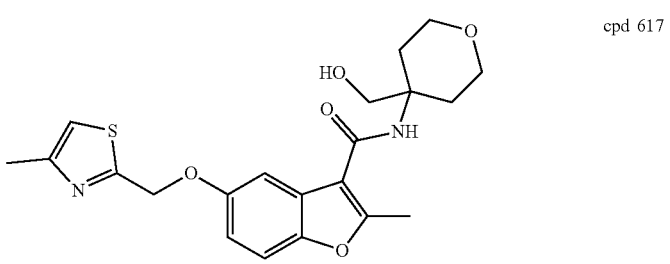 | cpd 617 |

-continued
| Structure/CODE | |
|---|---|
| 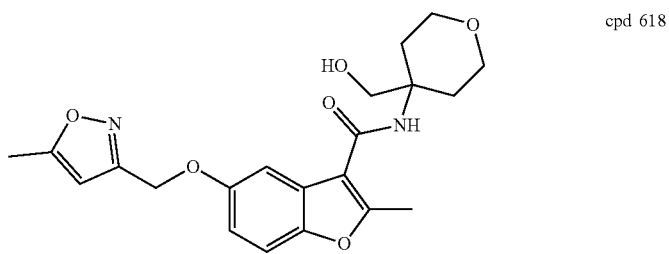 | cpd 618 |
| 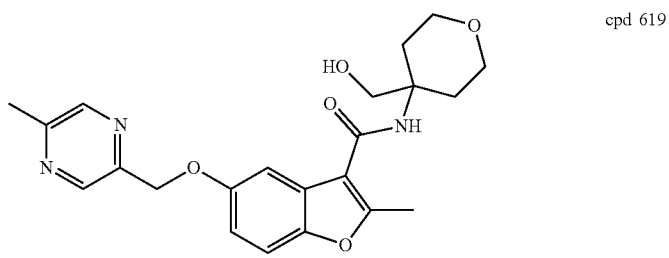 | cpd 619 |
| 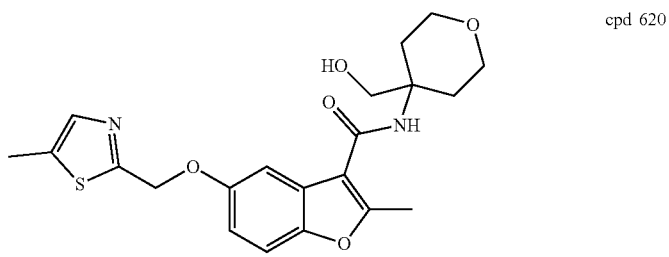 | cpd 620 |
| 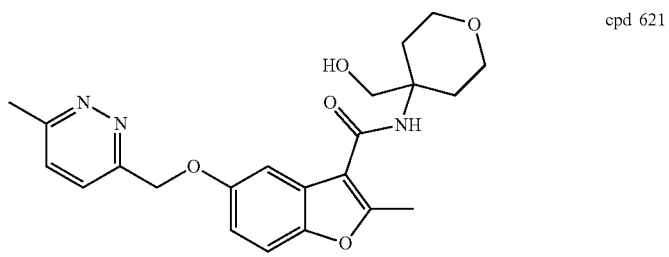 | cpd 621 |
| 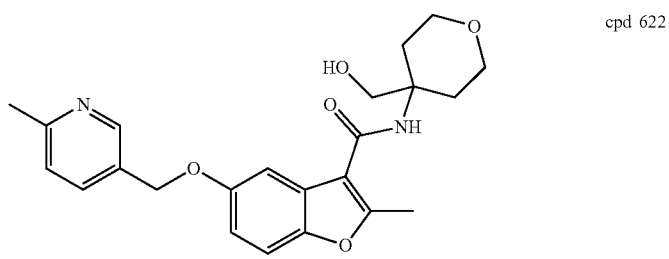 | cpd 622 |
| 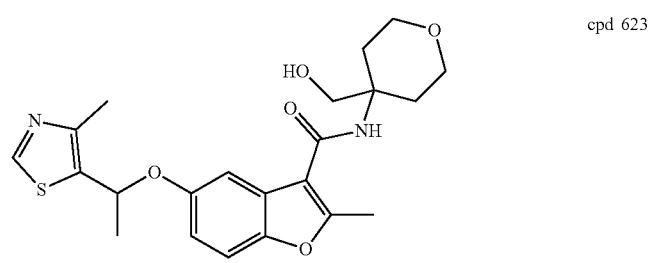 | cpd 623 |

| Structure/CODE | |
|---|---|
| 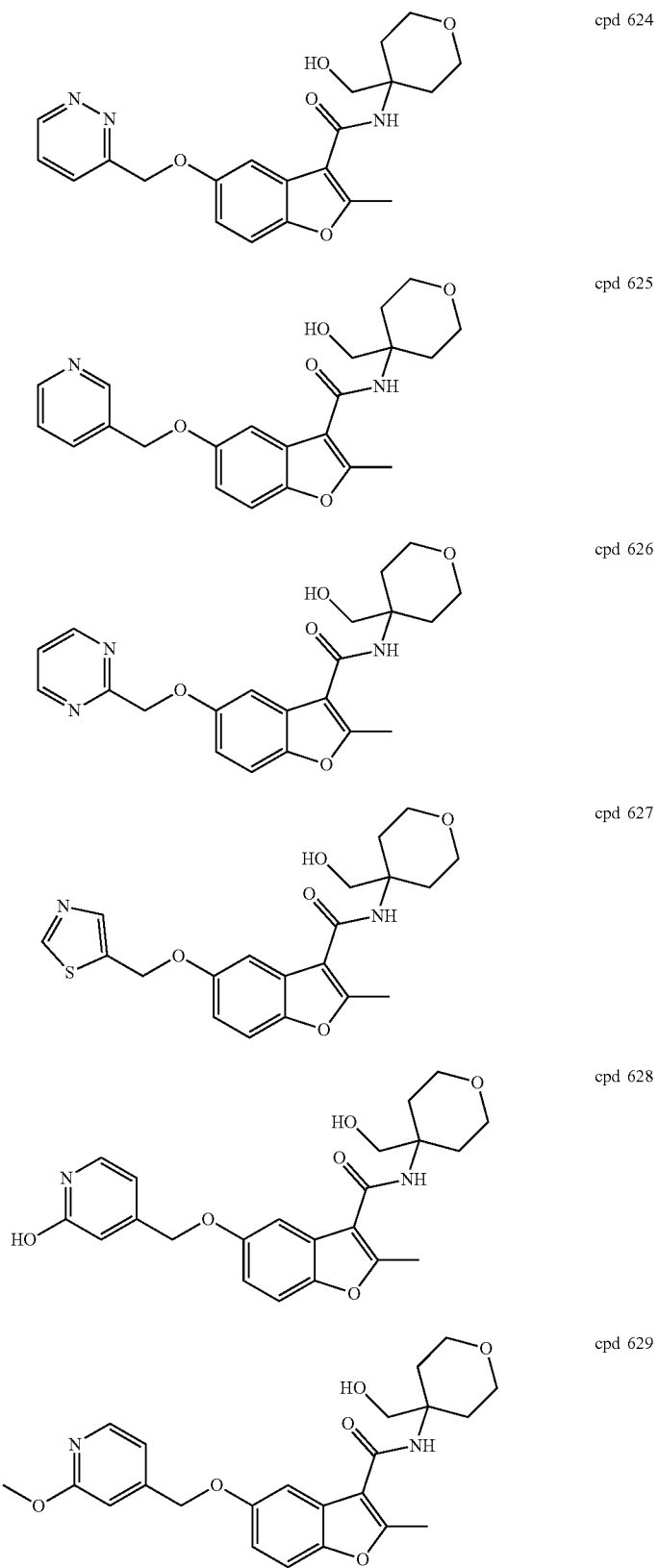 | cpd 624<br><br>cpd 625<br><br>cpd 626<br><br>cpd 627<br><br>cpd 628<br><br>cpd 629 |

333
-continued
| Structure/CODE |
|---|
| 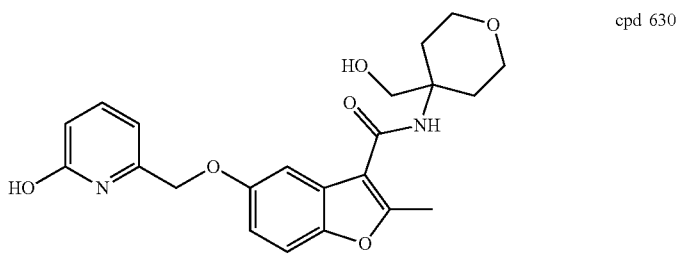 cpd 630 |
| 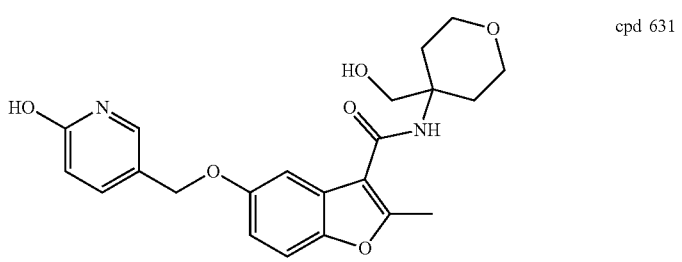 cpd 631 |
| 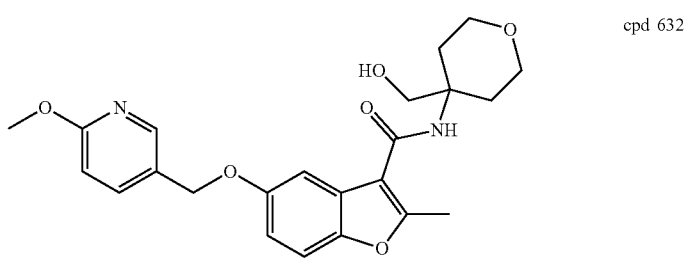 cpd 632 |
| 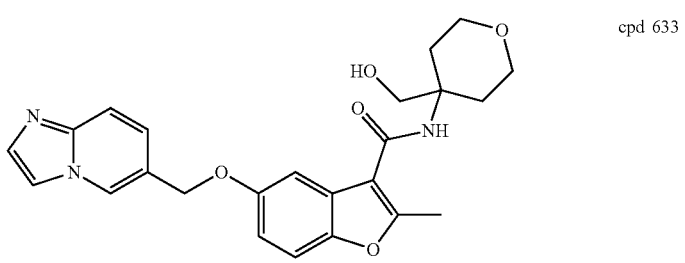 cpd 633 |
| 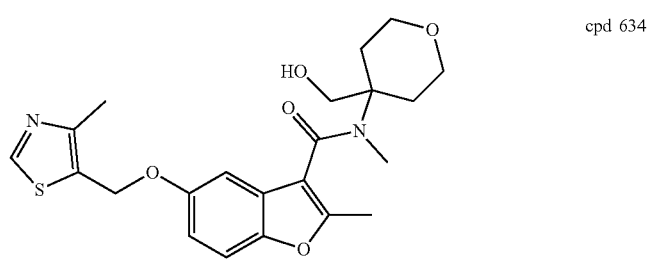 cpd 634 |
| 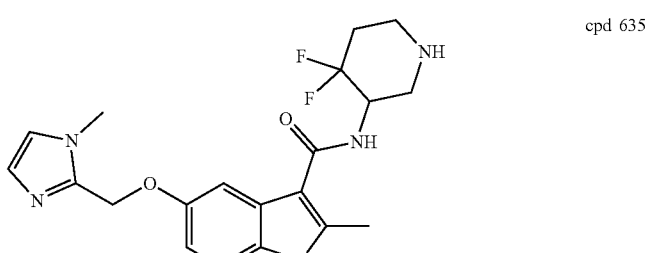 cpd 635 |

-continued
| Structure/CODE | |
|---|---|
| 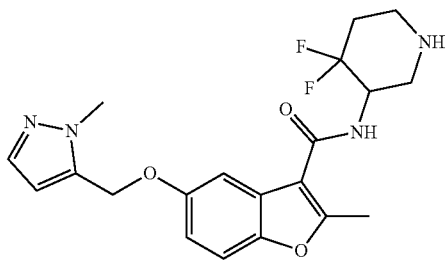 [SMILES: Cc1oc2ccc(OCc3ccnn3C)cc2c1C(=O)NC1CNCCC1(F)F] | cpd 636 |
| 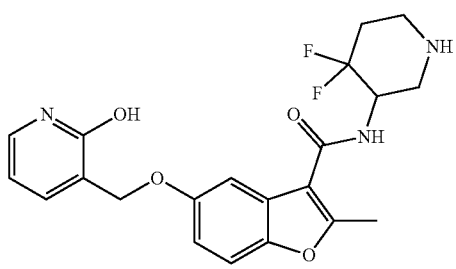 [SMILES: Cc1oc2ccc(OCc3cccnc3O)cc2c1C(=O)NC1CNCCC1(F)F] | cpd 637 |
| 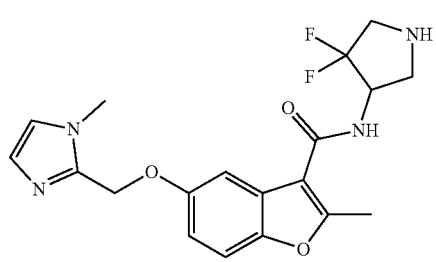 [SMILES: Cc1oc2ccc(OCc3nccn3C)cc2c1C(=O)NC1CNCC1(F)F] | cpd 638 |
| 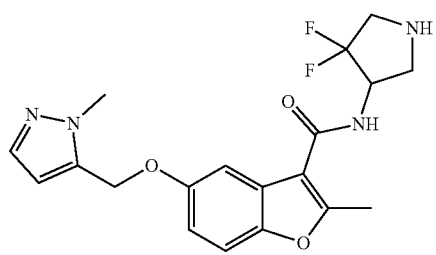 [SMILES: Cc1oc2ccc(OCc3ccnn3C)cc2c1C(=O)NC1CNCC1(F)F] | cpd 639 |
| 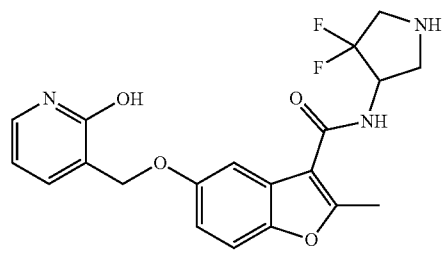 [SMILES: Cc1oc2ccc(OCc3cccnc3O)cc2c1C(=O)NC1CNCC1(F)F] | cpd 640 |
| 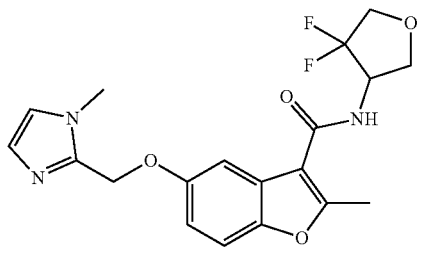 [SMILES: Cc1oc2ccc(OCc3nccn3C)cc2c1C(=O)NC1COCC1(F)F] | cpd 641 |

| Structure/CODE | |
|---|---|
| 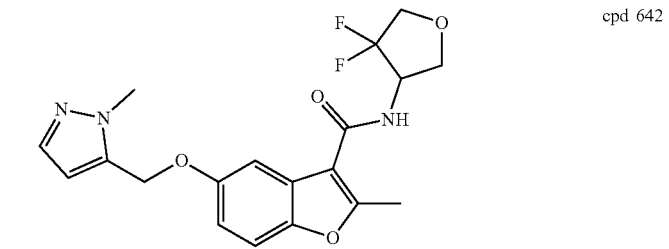 | cpd 642 |
| 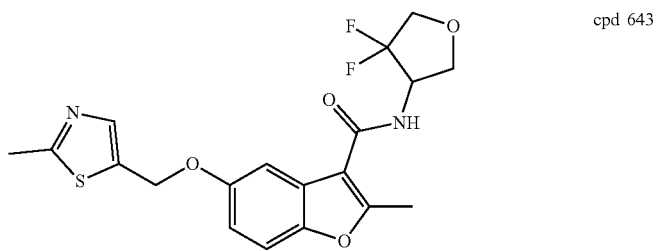 | cpd 643 |
| 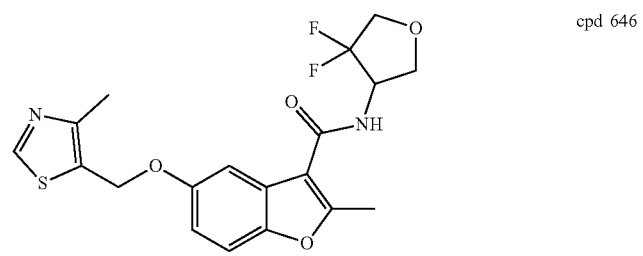 | cpd 646 |
| 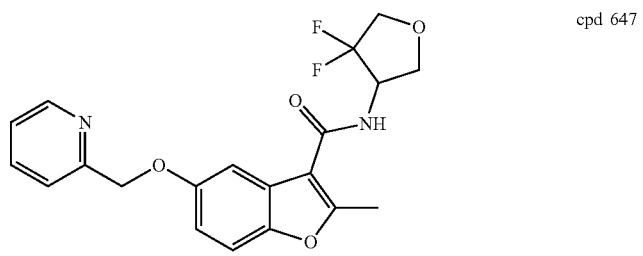 | cpd 647 |
| 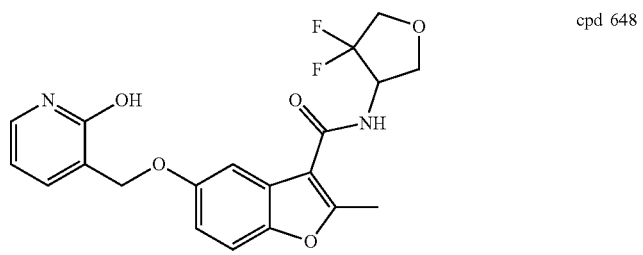 | cpd 648 |
| 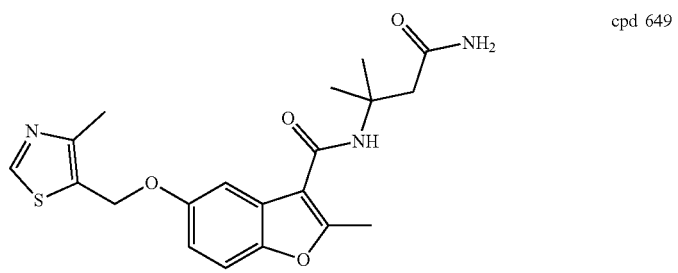 | cpd 649 |

| Structure/CODE | |
|---|---|
| 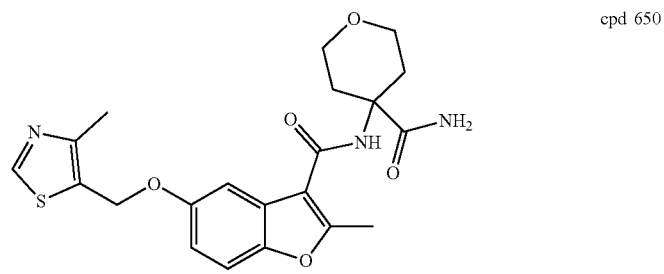 | cpd 650 |
| 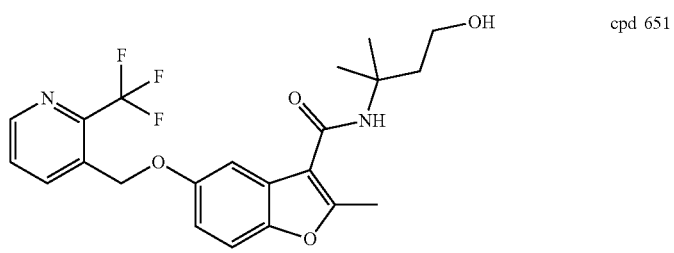 | cpd 651 |
| 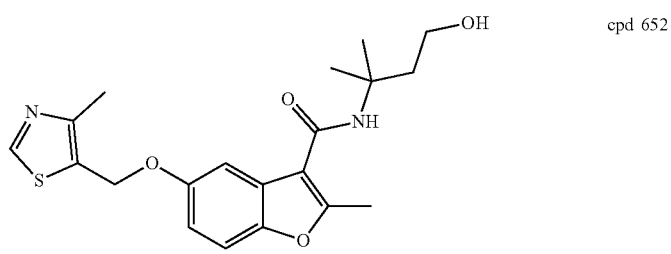 | cpd 652 |
| 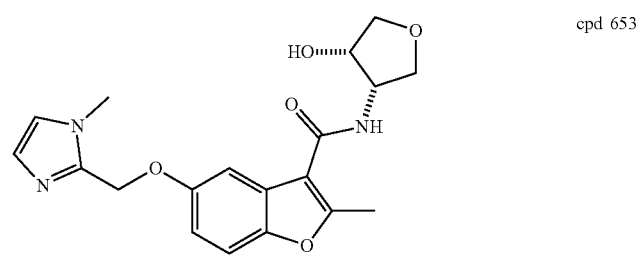 | cpd 653 |
| 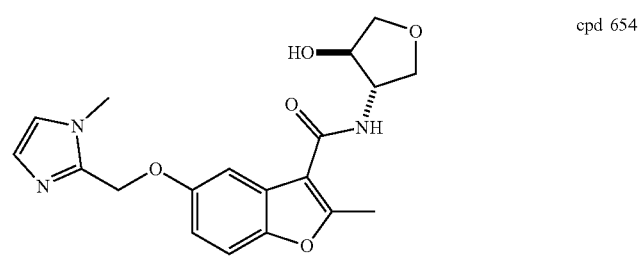 | cpd 654 |
| 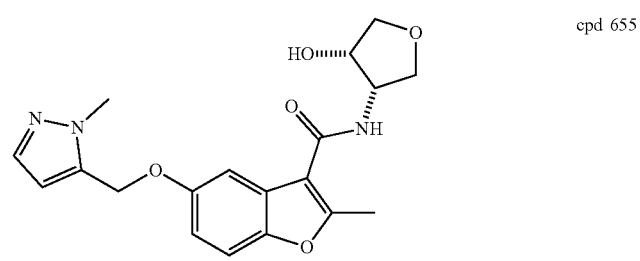 | cpd 655 |

| Structure/CODE | |
|---|---|
| 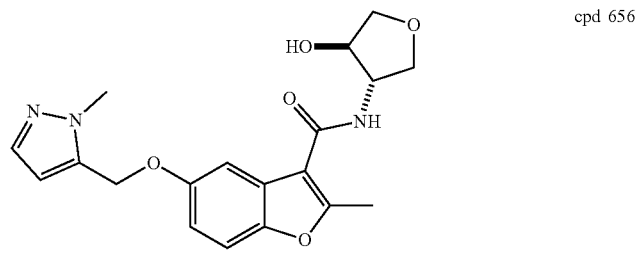 | cpd 656 |
| 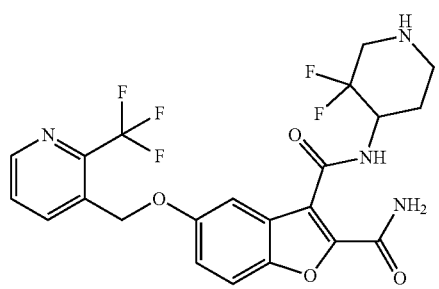 [SMILES: NC(=O)c1oc2ccc(OCc3cccnc3C(F)(F)F)cc2c1C(=O)NC1CCNCC1(F)F] | cpd 657 |
| 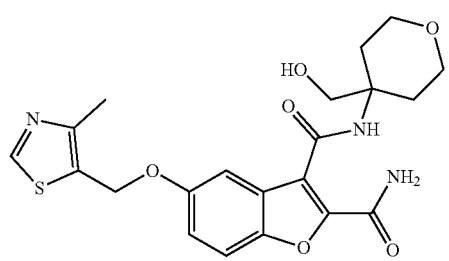 [SMILES: Cc1ncsc1COc1ccc2oc(C(N)=O)c(C(=O)NC3(CO)CCOCC3)c2c1] | cpd 658 |
| 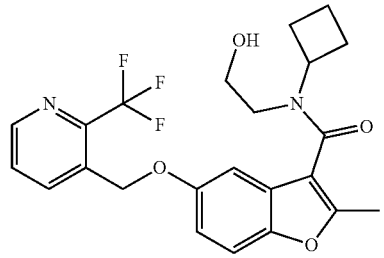 [SMILES: Cc1oc2ccc(OCc3cccnc3C(F)(F)F)cc2c1C(=O)N(CCO)C1CCC1] | cpd 659 |
| 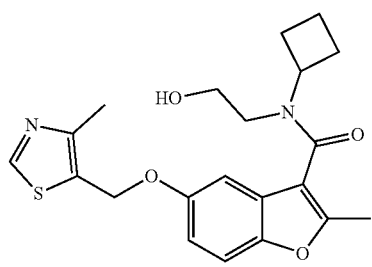 [SMILES: Cc1ncsc1COc1ccc2oc(C)c(C(=O)N(CCO)C3CCC3)c2c1] | cpd 660 |

-continued
| Structure/CODE | |
|---|---|
| 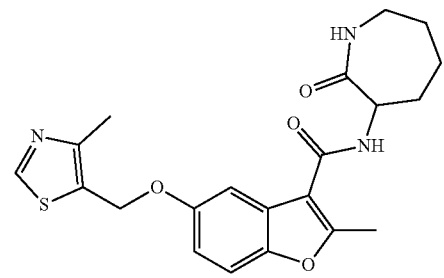 [SMILES: Cc1ncsc1COc1ccc2oc(C)c(C(=O)NC3CCCCNC3=O)c2c1] | cpd 661 |
| 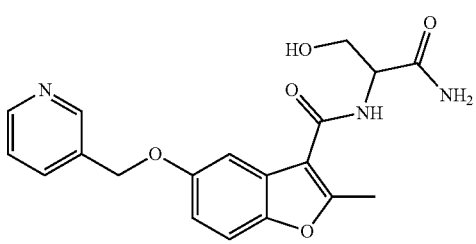 [SMILES: Cc1oc2ccc(OCc3cccnc3)cc2c1C(=O)NC(CO)C(N)=O] | cpd 662 |
| 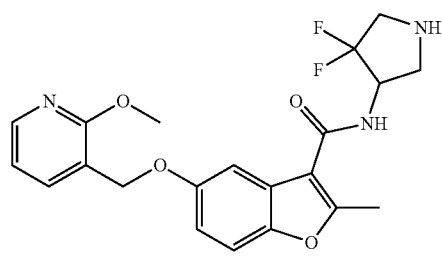 [SMILES: COc1ncccc1COc1ccc2oc(C)c(C(=O)NC3CNCC3(F)F)c2c1] | cpd 663 |
| 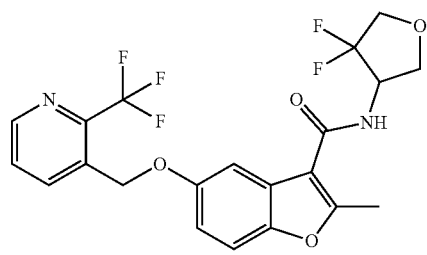 [SMILES: Cc1oc2ccc(OCc3cccnc3C(F)(F)F)cc2c1C(=O)NC1COCC1(F)F] | cpd 664 |
| 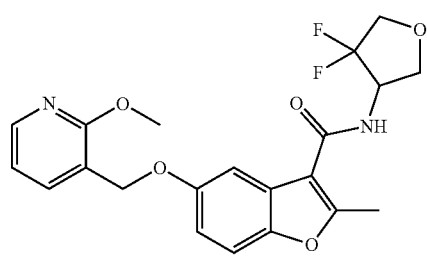 [SMILES: COc1ncccc1COc1ccc2oc(C)c(C(=O)NC3COCC3(F)F)c2c1] | cpd 665 |
| 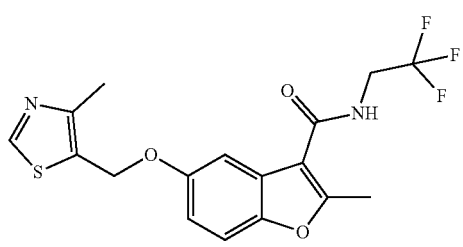 [SMILES: Cc1ncsc1COc1ccc2oc(C)c(C(=O)NCC(F)(F)F)c2c1] | cpd 666 |

| Structure/CODE | |
|---|---|
| 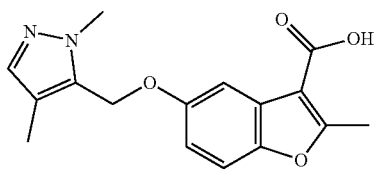 [SMILES: Cc1cnn(C)c1COc1ccc2oc(C)c(C(=O)O)c2c1] | cpd 667 |
| 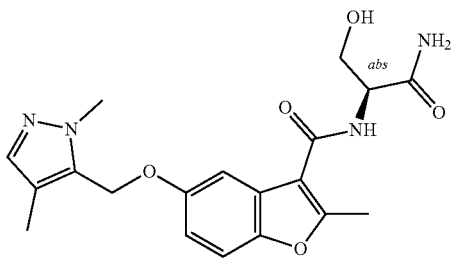 [SMILES: Cc1cnn(C)c1COc1ccc2oc(C)c(C(=O)N[C@@H](CO)C(N)=O)c2c1] | cpd 668 |
| 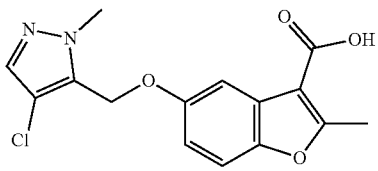 | cpd 669 |
| 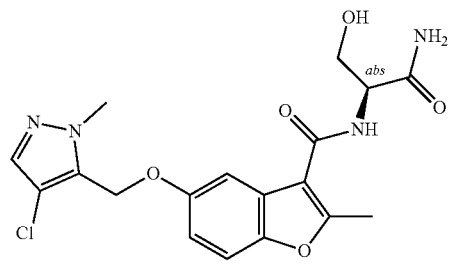 [SMILES: Cc1oc2ccc(OCc3c(Cl)cnn3C)cc2c1C(=O)N[C@@H](CO)C(N)=O] | cpd 670 |
| 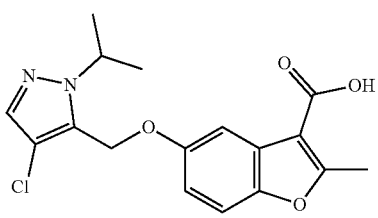 [SMILES: Cc1oc2ccc(OCc3c(Cl)cnn3C(C)C)cc2c1C(=O)O] | cpd 671 |
| 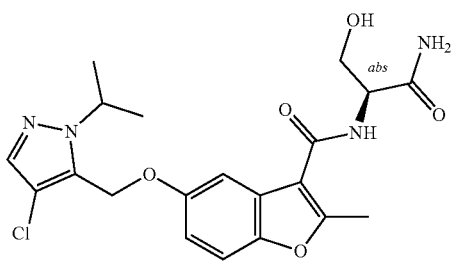 [SMILES: Cc1oc2ccc(OCc3c(Cl)cnn3C(C)C)cc2c1C(=O)N[C@@H](CO)C(N)=O] | cpd 672 |
| 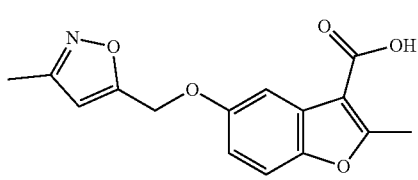 | cpd 673 |

-continued
| Structure/CODE | |
|---|---|
| 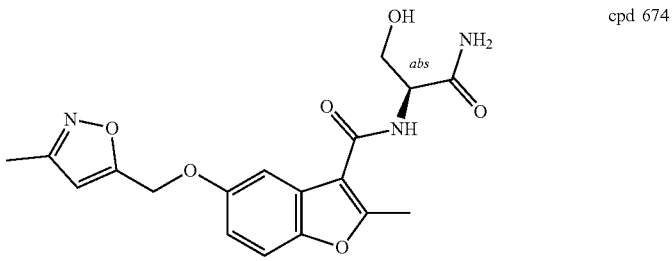 | cpd 674 |
| 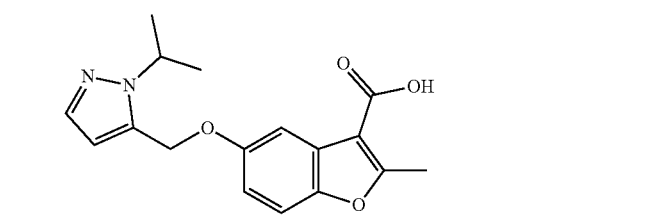 [SMILES: Cc1oc2ccc(OCc3ccnn3C(C)C)cc2c1C(=O)O] | cpd 675 |
| 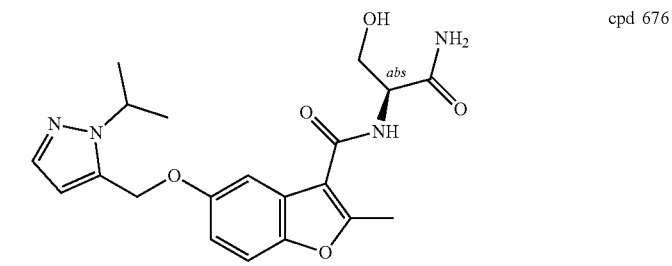 | cpd 676 |
| 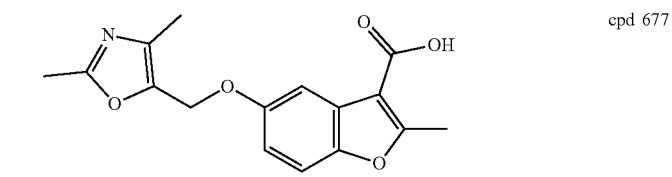 | cpd 677 |
| 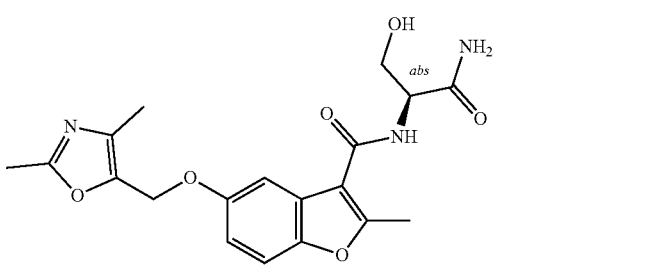 [SMILES: Cc1nc(C)c(COc2ccc3oc(C)c(C(=O)N[C@@H](CO)C(N)=O)c3c2)o1] | cpd 678 |
| 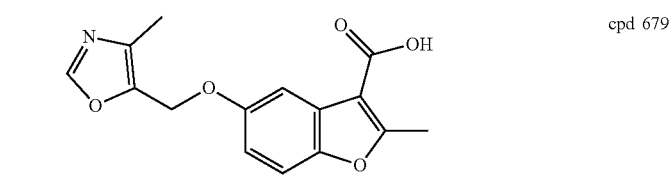 | cpd 679 |

-continued
| Structure/CODE | |
|---|---|
| 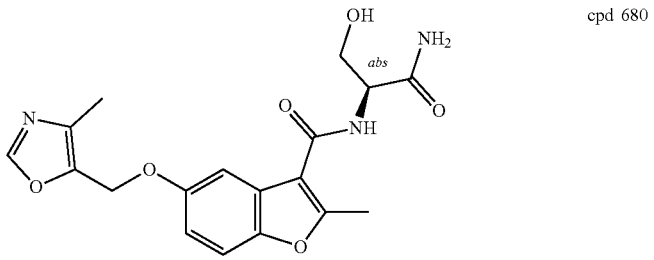 | cpd 680 |
| 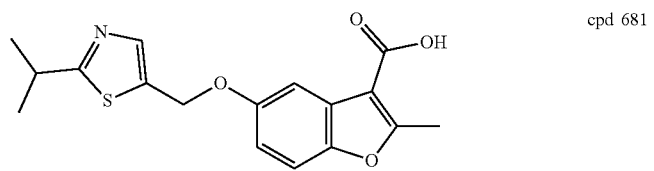 | cpd 681 |
| 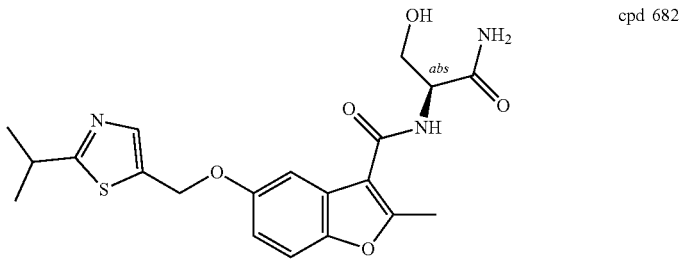 | cpd 682 |
| 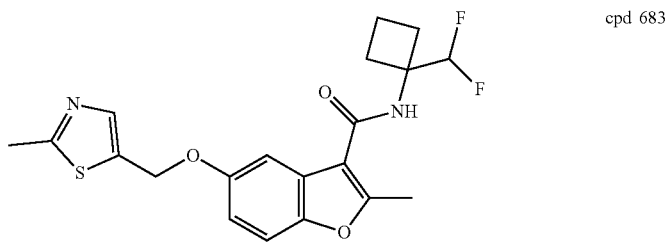 | cpd 683 |
| 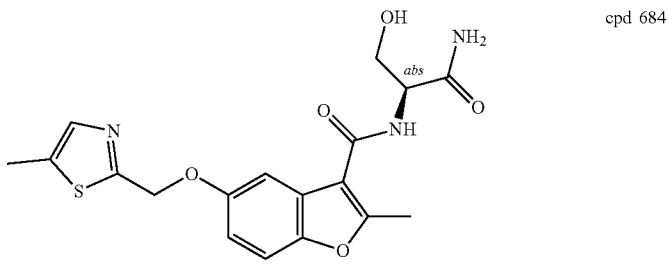 | cpd 684 |
| 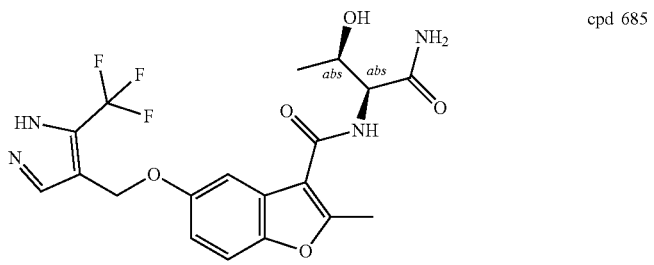 | cpd 685 |

-continued
| Structure/CODE | |
|---|---|
| 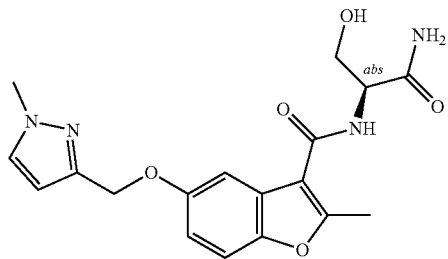 [SMILES: Cc1oc2ccc(OCc3ccn(C)n3)cc2c1C(=O)N[C@@H](CO)C(N)=O] | cpd 686 |
| 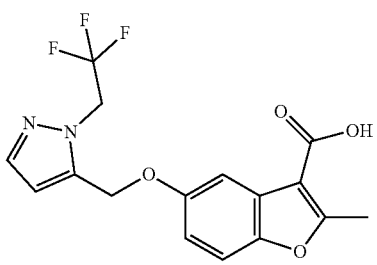 [SMILES: Cc1oc2ccc(OCc3ccnn3CC(F)(F)F)cc2c1C(=O)O] | cpd 687 |
| 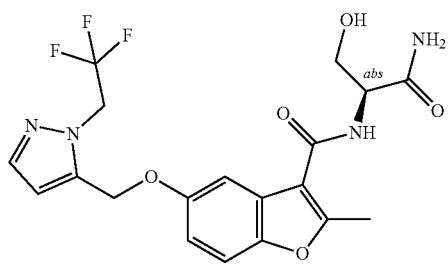 [SMILES: Cc1oc2ccc(OCc3ccnn3CC(F)(F)F)cc2c1C(=O)N[C@@H](CO)C(N)=O] | cpd 688 |
| 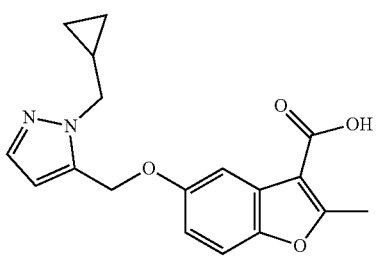 [SMILES: Cc1oc2ccc(OCc3ccnn3CC3CC3)cc2c1C(=O)O] | cpd 689 |
| 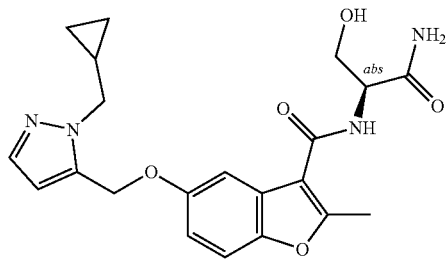 [SMILES: Cc1oc2ccc(OCc3ccnn3CC3CC3)cc2c1C(=O)N[C@@H](CO)C(N)=O] | cpd 690 |
| 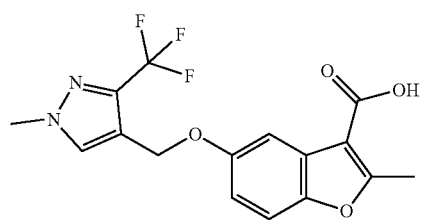 | cpd 691 |

| Structure/CODE | |
|---|---|
| 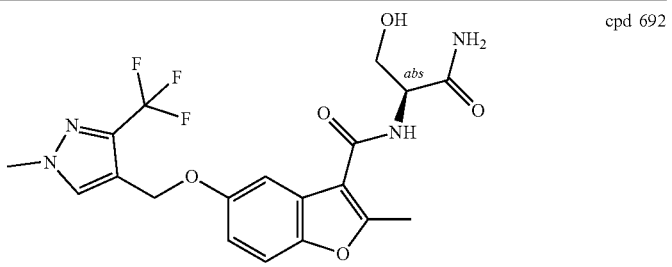 | cpd 692 |
| 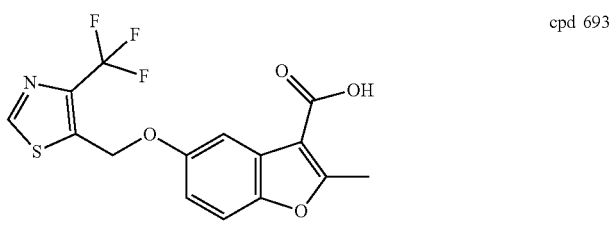 | cpd 693 |
| 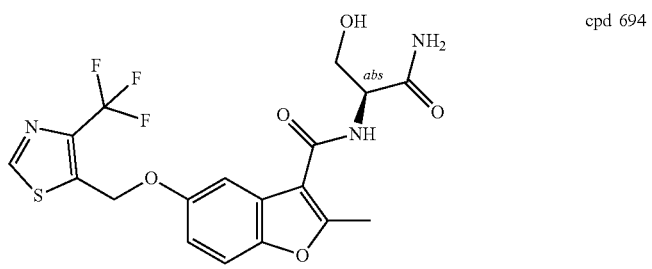 | cpd 694 |
| 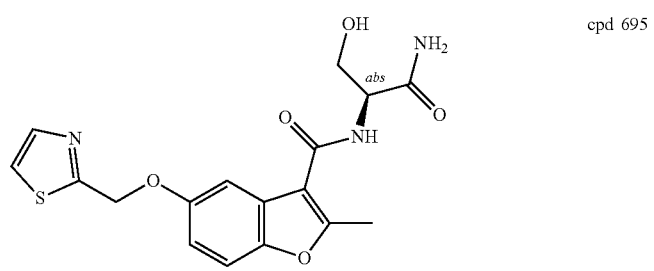 | cpd 695 |
| 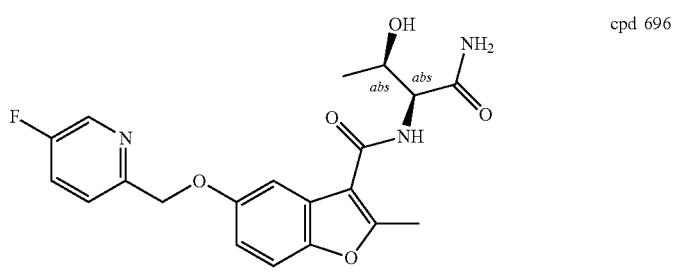 | cpd 696 |
| 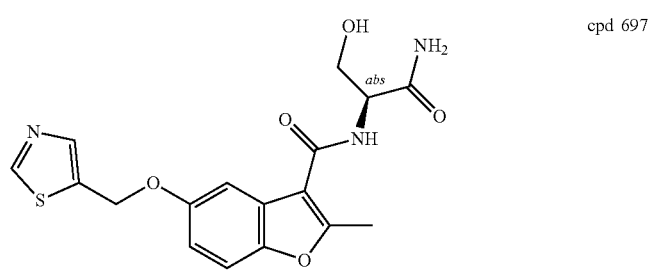 | cpd 697 |

-continued
| Structure/CODE | |
|---|---|
| 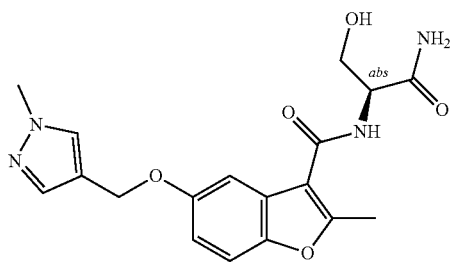 [SMILES: Cc1oc2ccc(OCc3cnn(C)c3)cc2c1C(=O)N[C@@H](CO)C(N)=O] | cpd 698 |
| 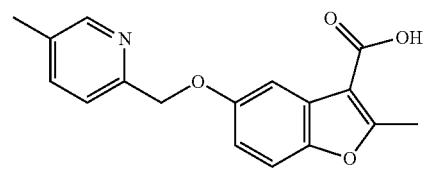 | cpd 699 |
| 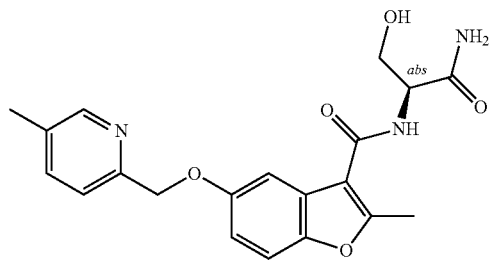 [SMILES: Cc1ccc(COc2ccc3oc(C)c(C(=O)N[C@@H](CO)C(N)=O)c3c2)nc1] | cpd 700 |
| 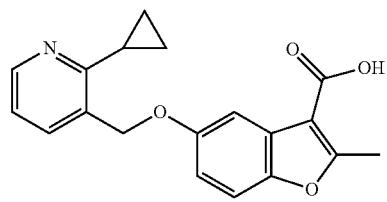 [SMILES: Cc1oc2ccc(OCc3cccnc3C3CC3)cc2c1C(=O)O] | cpd 701 |
| 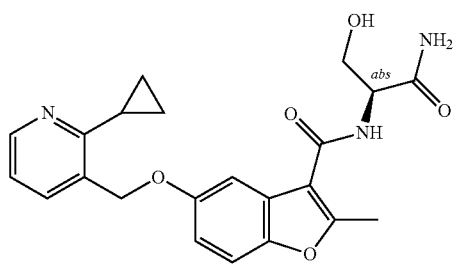 [SMILES: Cc1oc2ccc(OCc3cccnc3C3CC3)cc2c1C(=O)N[C@@H](CO)C(N)=O] | cpd 702 |
| 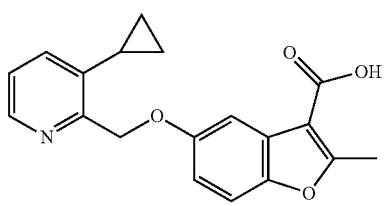 [SMILES: Cc1oc2ccc(OCc3ncccc3C3CC3)cc2c1C(=O)O] | cpd 703 |

| Structure/CODE | |
|---|---|
| 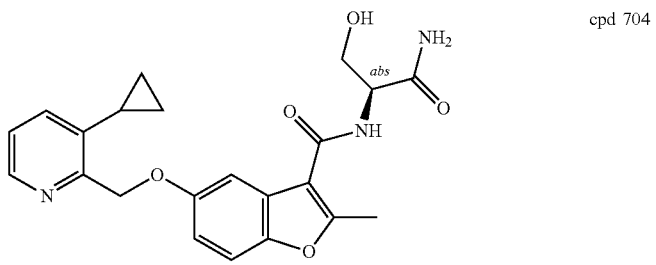 | cpd 704 |
| 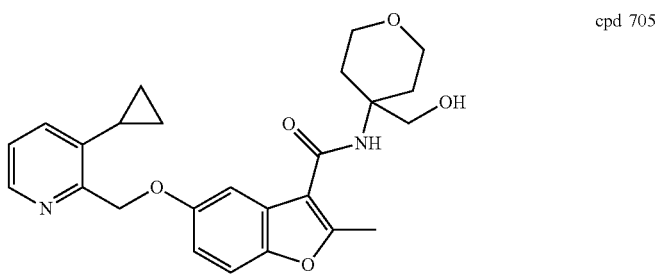 | cpd 705 |
| 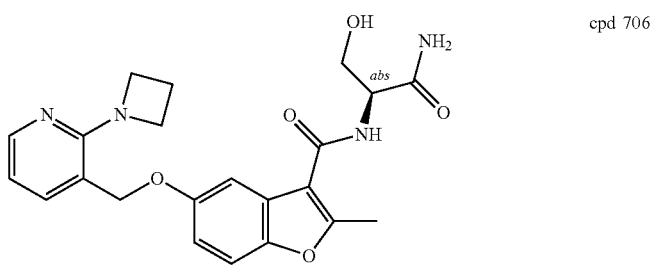 | cpd 706 |
| 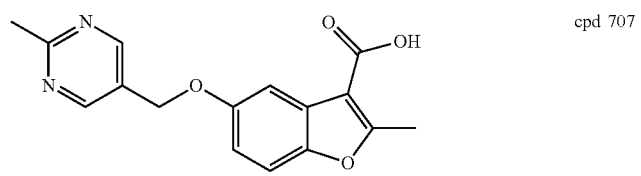 | cpd 707 |
| 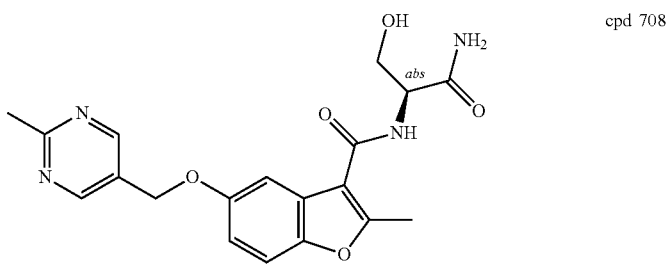 | cpd 708 |
| 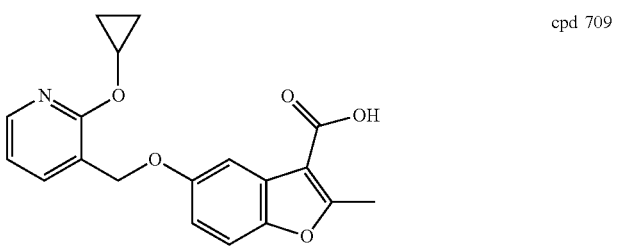 | cpd 709 |

| Structure/CODE | |
|---|---|
| 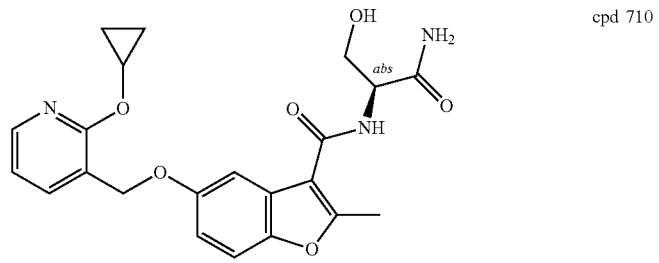 | cpd 710 |
| 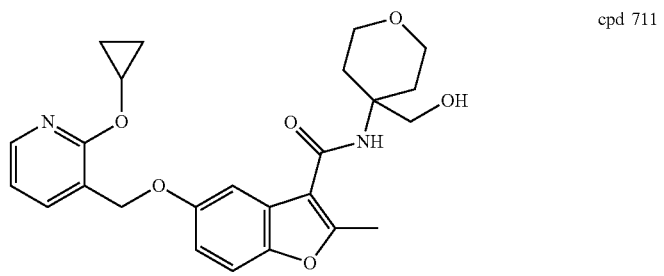 | cpd 711 |
| 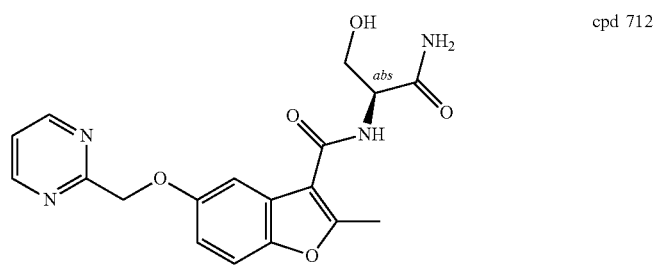 | cpd 712 |
| 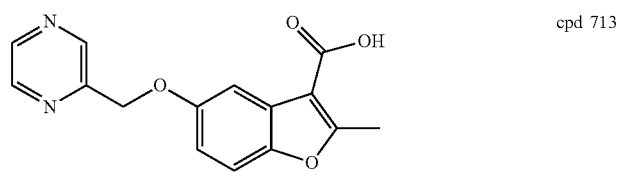 | cpd 713 |
| 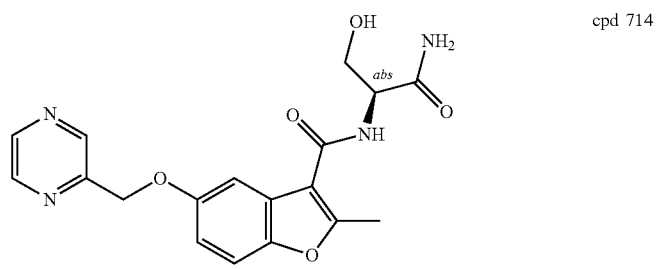 | cpd 714 |
| 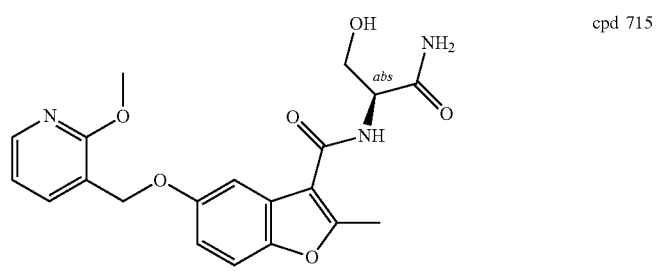 | cpd 715 |

-continued
| Structure/CODE | |
|---|---|
| 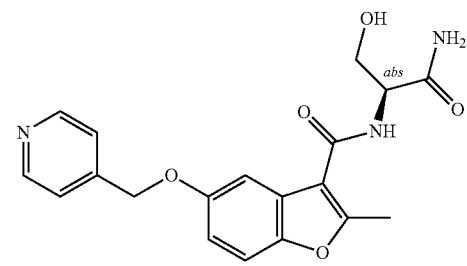 [SMILES: Cc1oc2ccc(OCc3ccncc3)cc2c1C(=O)N[C@@H](CO)C(N)=O] | cpd 716 |
| 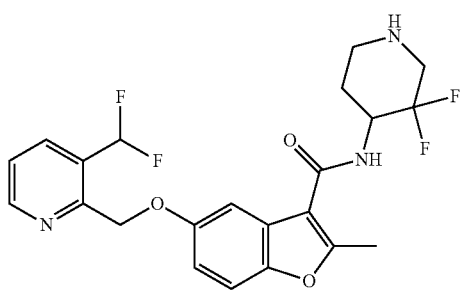 [SMILES: Cc1oc2ccc(OCc3ncccc3C(F)F)cc2c1C(=O)NC1CCNCC1(F)F] | cpd 717 |
| 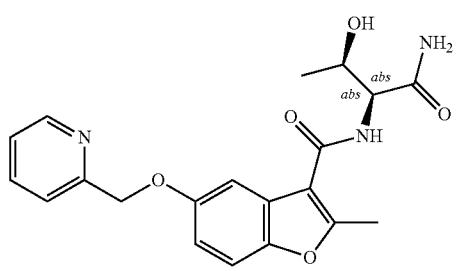 [SMILES: Cc1oc2ccc(OCc3ccccn3)cc2c1C(=O)N[C@H](C(N)=O)[C@@H](C)O] | cpd 718 |
| 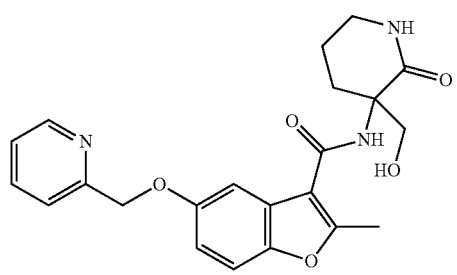 [SMILES: Cc1oc2ccc(OCc3ccccn3)cc2c1C(=O)NC1(CO)CCCNC1=O] | cpd 719 |
| 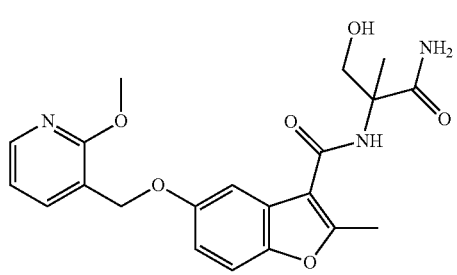 [SMILES: COc1ncccc1COc1ccc2oc(C)c(C(=O)NC(C)(CO)C(N)=O)c2c1] | cpd 720 |
| 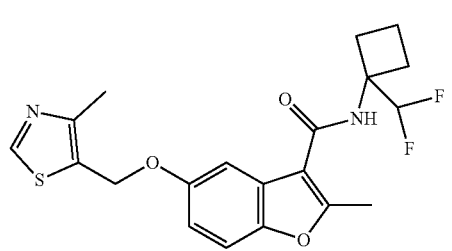 [SMILES: Cc1ncsc1COc1ccc2oc(C)c(C(=O)NC3(C(F)F)CCC3)c2c1] | cpd 721 |

| Structure/CODE |
|---|
| 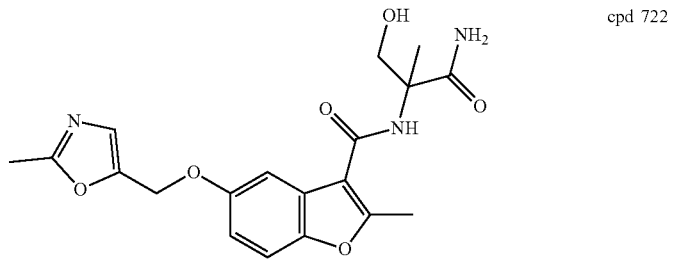 cpd 722 |
| 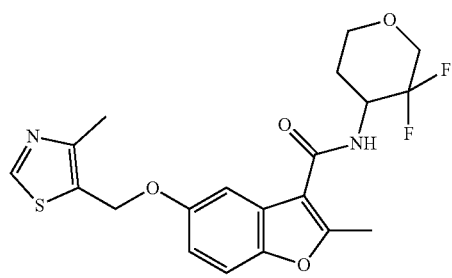 [SMILES: Cc1ncsc1COc1ccc2oc(C)c(C(=O)NC3CCOCC3(F)F)c2c1] cpd 723 |
| 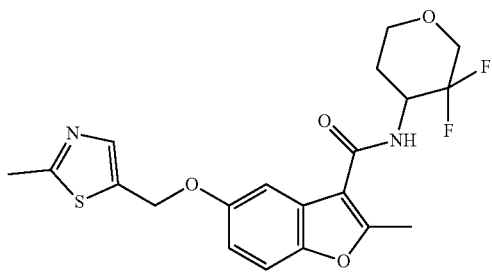 [SMILES: Cc1ncc(COc2ccc3oc(C)c(C(=O)NC4CCOCC4(F)F)c3c2)s1] cpd 724 |
| 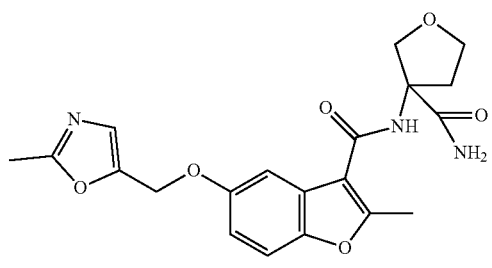 [SMILES: Cc1ncc(COc2ccc3oc(C)c(C(=O)NC4(C(N)=O)CCOC4)c3c2)o1] cpd 725 |
| 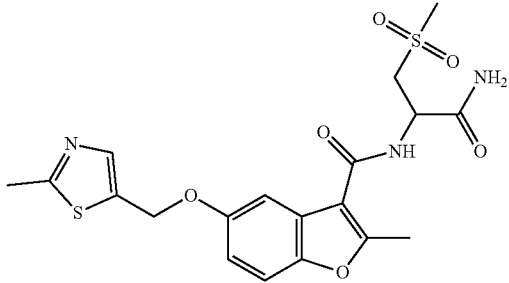 [SMILES: Cc1ncc(COc2ccc3oc(C)c(C(=O)NC(CS(C)(=O)=O)C(N)=O)c3c2)s1] cpd 726 |

| Structure/CODE |
|---|
| 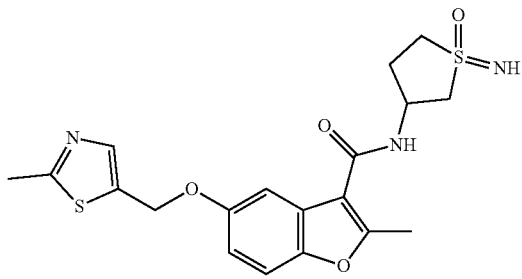 [SMILES: Cc1ncc(COc2ccc3oc(C)c(C(=O)NC4CCS(=N)(=O)C4)c3c2)s1] cpd 727 |
| 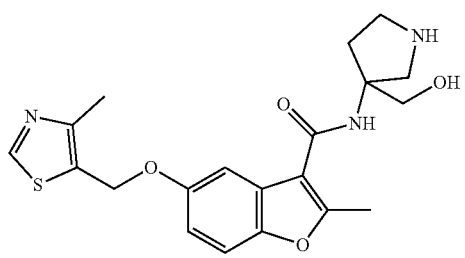 [SMILES: Cc1ncsc1COc1ccc2oc(C)c(C(=O)NC3(CO)CCNC3)c2c1] cpd 728 |
| 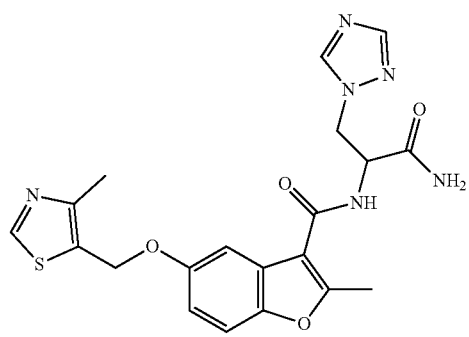 [SMILES: Cc1ncsc1COc1ccc2oc(C)c(C(=O)NC(Cn3cncn3)C(N)=O)c2c1] cpd 729 |
| 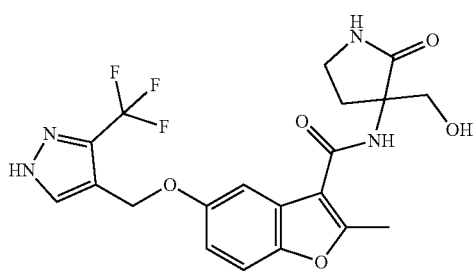 [SMILES: Cc1oc2ccc(OCc3c[nH]nc3C(F)(F)F)cc2c1C(=O)NC1(CO)CCNC1=O] cpd 730 |
| 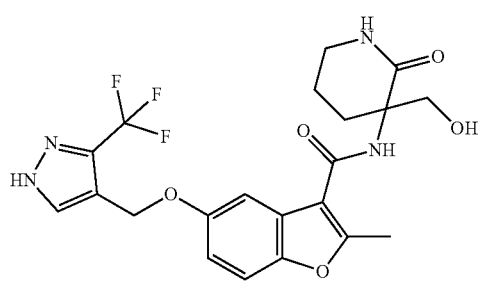 [SMILES: Cc1oc2ccc(OCc3c[nH]nc3C(F)(F)F)cc2c1C(=O)NC1(CO)CCCNC1=O] cpd 731 |

| Structure/CODE |
|---|
| 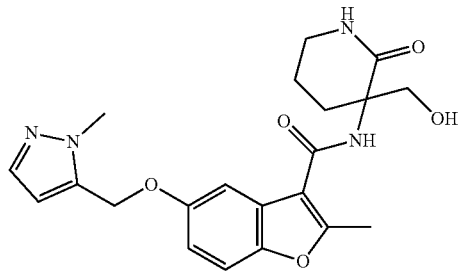 [SMILES: Cc1oc2ccc(OCc3ccnn3C)cc2c1C(=O)NC1(CO)CCCNC1=O] cpd 732 |
| 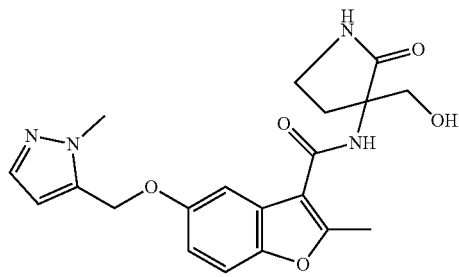 [SMILES: Cc1oc2ccc(OCc3ccnn3C)cc2c1C(=O)NC1(CO)CCNC1=O] cpd 733 |
| 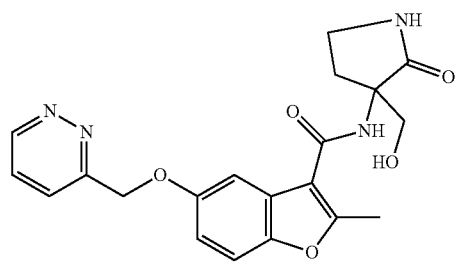 [SMILES: Cc1oc2ccc(OCc3cccnn3)cc2c1C(=O)NC1(CO)CCNC1=O] cpd 734 |
| 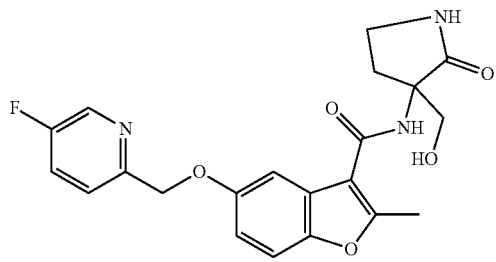 [SMILES: Cc1oc2ccc(OCc3ccc(F)cn3)cc2c1C(=O)NC1(CO)CCNC1=O] cpd 735 |
| 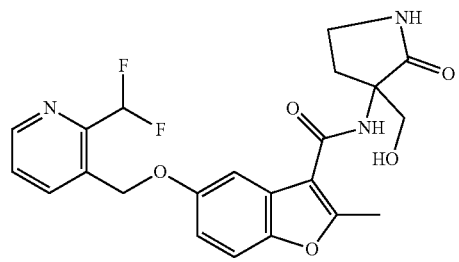 [SMILES: Cc1oc2ccc(OCc3cccnc3C(F)F)cc2c1C(=O)NC1(CO)CCNC1=O] cpd 736 |

-continued
| Structure/CODE | |
|---|---|
| 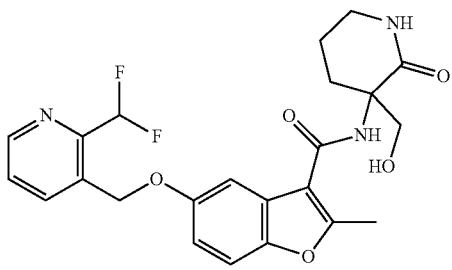 [SMILES: Cc1oc2ccc(OCc3cccnc3C(F)F)cc2c1C(=O)NC1(CO)CCCNC1=O] | cpd 737 |
| 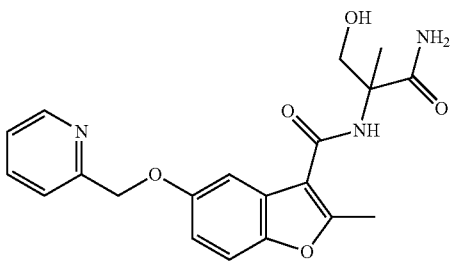 [SMILES: Cc1oc2ccc(OCc3ccccn3)cc2c1C(=O)NC(C)(CO)C(N)=O] | cpd 738 |
| 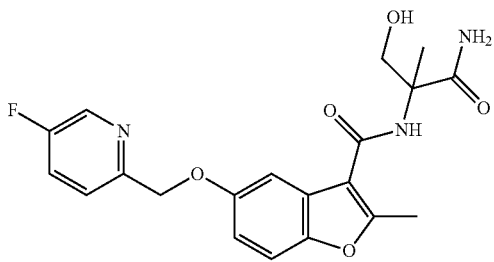 [SMILES: Cc1oc2ccc(OCc3ccc(F)cn3)cc2c1C(=O)NC(C)(CO)C(N)=O] | cpd 739 |
| 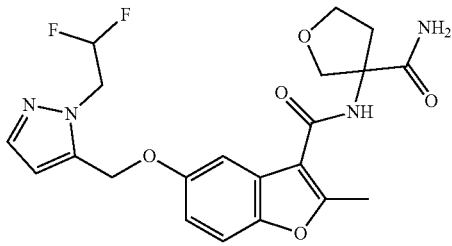 [SMILES: Cc1oc2ccc(OCc3ccnn3CC(F)F)cc2c1C(=O)NC1(C(N)=O)CCOC1] | cpd 740 |
| 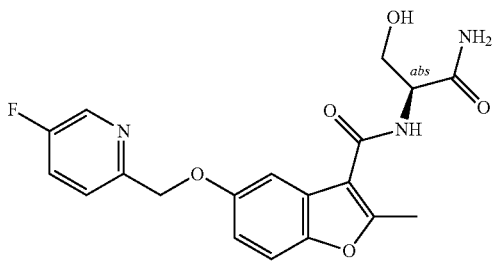 [SMILES: Cc1oc2ccc(OCc3ccc(F)cn3)cc2c1C(=O)N[C@@H](CO)C(N)=O] | cpd 741 |
| 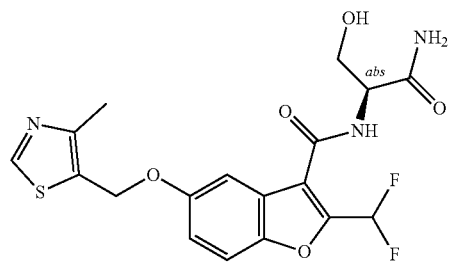 [SMILES: Cc1ncsc1COc1ccc2oc(C(F)F)c(C(=O)N[C@@H](CO)C(N)=O)c2c1] | cpd 742 |

| Structure/CODE | |
|---|---|
| 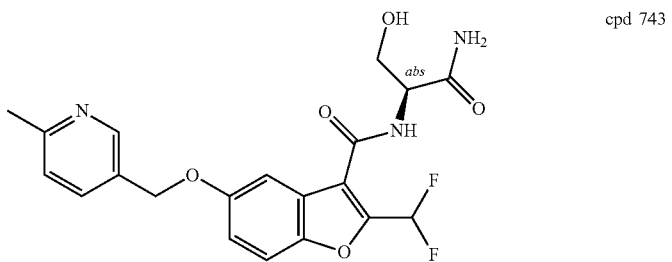 | cpd 743 |
| 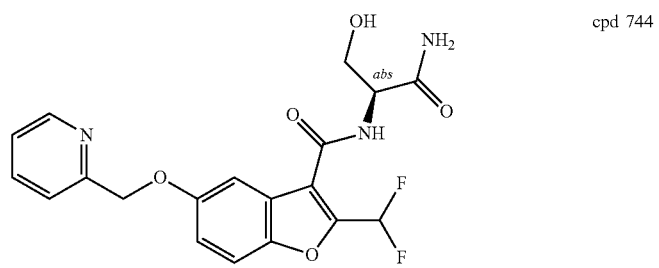 | cpd 744 |
| 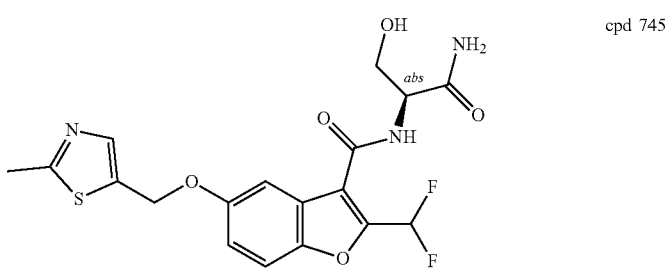 | cpd 745 |
| 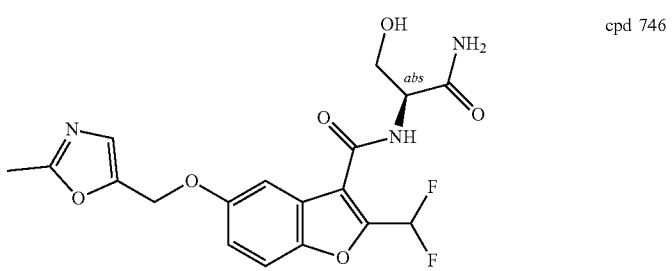 | cpd 746 |
| 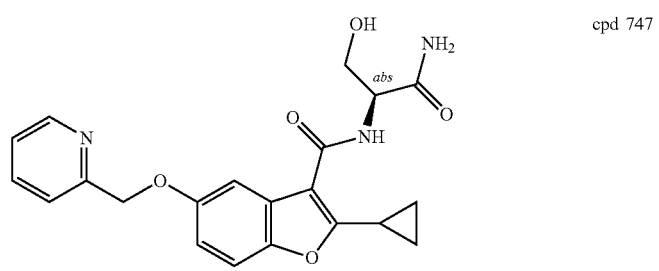 | cpd 747 |
| 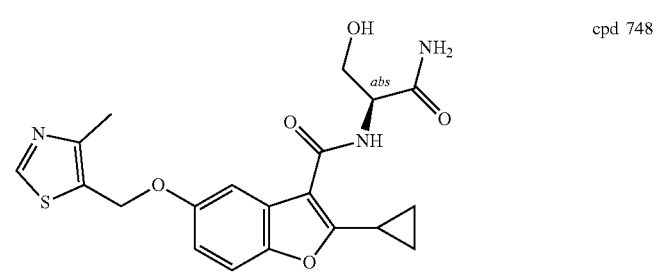 | cpd 748 |

| Structure/CODE |
|---|

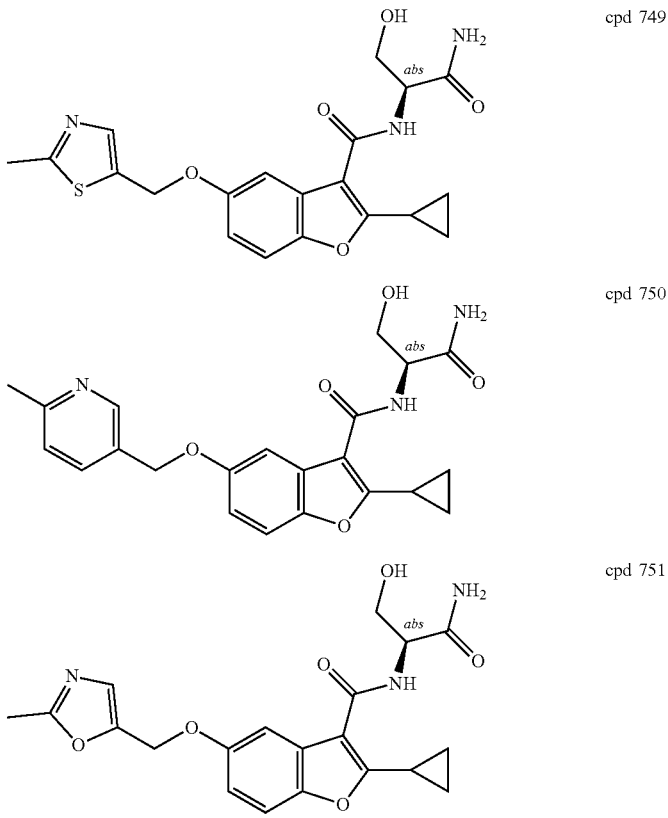

cpd 749 cpd 750 cpd 751

The following examples are provided for the purpose of illustrating the present invention and by no means should be interpreted to limit the scope of the present invention.

Part A represent the preparation of the compounds whereas Part B represents the pharmacological examples.

Part A

All starting materials which are not explicitly described were either commercially available (the details of suppliers such as for example Acros, Avocado, Aldrich, Fluka, FluoroChem, MatrixScientific, Maybridge, Merck, Sigma, etc. can be found in the SciFinder® Database for example) or the synthesis thereof has already been described precisely in the specialist literature (experimental guidelines canbe found in the Reaxys® Database or the SciFinder® Database respectively, for example) or can be prepared using the conventional methods known to the person skilled in the art.

The reactions were, if necessary, carried out under an inert atmosphere (mostly argon and $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

The indication "equivalents" ("eq." or "eq" or "equiv.") means molar equivalents, "RT" or "rt" means room temperature T (23±7° C.), "M" are indications of concentration in mol/l, "sol." means solution, "conc." means concentrated. The mixing ratios of solvents are usually stated in the volume/volume ratio.

Key analytical characterization was carried out by means of $^1$H-NMR spectroscopy and/or mass spectrometry (MS, m/z for $[M+H]^+$ and/or $[M-H]^-$) for all the exemplary compounds and selected intermediate products. In certain cases, where e.g., regioisomers and/or diastereomers could be/were formed during the reaction, additional analytics, such as, e.g., $^{13}$C NMR and NOE (nuclear overhauser effect) NMR experiments were in some cases performed.

Analytical instruments employed were e.g., for NMR analysis a BRUKER 400 MHz or a BRUKER 500 MHz machine (Software Topspin), alternatively a BRUKER AVANCE 300 MHz and 400 Mhz was employed. For LC/MS analysis e.g., an Agilent 1290 infinity, Mass: 6150 SQD (ESI/APCI) or an Agilent 1200 SERIES, Mass: 6130 SQD (ESI/APCI) (Software Chemistation) was employed. Analytical HPLCs were measured e.g., on Waters (Software Empower), an Agilent-1200-ELSD (Software Chemistation) or an Agilent-1260 (Software OpenLAB). Analytical SFC were performed e.g., on a PIC solution (Software: SFC PICLAB ONLINE), a WATERS-X5 (Software MASSLYNX) or a WATERS-UPC2 (Empower).

Preparative HPLC were performed e.g., on a Waters 2998 (Software Empower) or a YMC (Software K-Prep). Preparative SFC were performed e.g., on a Waters, SFC-200 (Software Chromscope or Super chrome), a Waters, SFC-80 (Super chrome) or a PIC,PIC-175 (Software S10-100).

Structures of example compounds that contain stereocentres are drawn and named with absolute stereochemistry, if known. In case of unknown absolute stereochemistry, the compounds can be either racemic, a mixture of diastereomers, a pure diastereomer of unknown stereochemistry, or a pure enantiomer of unknown stereochemistry. Dia 1 and Dia 2 means that diastereoisomers were separated but the stereochemistry is unknown. En 1 and En 2 means that both enantiomers were separated but the absolute configuration is unknown. No suffix given after the compound code means that a compound containing stereocentres was obtained as a racemic mixture or a mixture of diastereomers, respectively, unless the chemical name of the compound specifies the exact stereochemistry.

The LC/MS analysis mentioned in the experimental part were also performed on a Dionex Ultimate 3000 HPLC system (equipped with a PDA detector) connected to a mass spectrometer Brucker Esquire 6000 (equipped with a multimode source, ESI/APCI) (Method L in the table below). Or the LC/MS analysis mentioned in the experimental part were performed on a Waters system combining an Acquity UPLC H-Class equipped with a Acquity UPLC PDA Detector and an Acquity TQ Detector (ESI) (Method U in the table below).

Conditions used for the HPLC analysis in experimental part. The LC/MS analysis mentioned in the experimental part were performed on a Dionex Ultimate 3000 HPLC system (equipped with a PDA detector) connected to a mass spectrometer Brucker Esquire 6000 (equipped with a multimode source, ESI/APCI). The separations were performed with a SunFireC18, 3.5 µm 3.0×100 mm, column equipped with a SunFire C18, 3.5 µm, 3.0×20 mm Guard column or a X-Bridge C18 100×3.0 mm column equipped with a X-Bridge C18, 3.5 µm, 3.0×20 mm Guard column thermostated to 30° C. and the DAD acquisition wavelength was set in the range of 190-420 nm (Method L in the table below). Elutions were carried out with the methods described in the following tables. Solvent A: Formic Acid LC-MS grade 0.1% in milliQ water Solvent B: NH4OAc (LC-MS grade) 10 mMol in milliQ water, adjusted at pH10 with an aq. solution of NH3, LC-MS grade. Solvent C: Acetonitrile LC-MS grade.

| LC/MS Method | System | Time (min) | A (%) | B (%) | C (%) | Flow (mL/min) | Column |
|---|---|---|---|---|---|---|---|
| L1 | Dionex Ultimate 3000 HPLC | 0 | 80 | — | 20 | 1 | SunFire C18 |
| | | 0.2 | 80 | — | 20 | 1 | |
| | | 7 | 40 | — | 60 | 1 | |
| | | 8 | 10 | — | 90 | 1 | |
| | | 10.8 | 10 | — | 90 | 1 | |
| | | 11 | 80 | — | 20 | 1 | |
| | | 14 | 80 | — | 20 | 1 | |
| L2 | Dionex Ultimate 3000 HPLC | 0 | 50 | — | 50 | 1 | SunFire C18 |
| | | 0.2 | 50 | — | 50 | 1 | |
| | | 6 | 10 | — | 90 | 1 | |
| | | 10.8 | 10 | — | 90 | 1 | |
| | | 11 | 50 | — | 50 | 1 | |
| | | 14 | 50 | — | 50 | 1 | |
| L3 | Dionex Ultimate 3000 HPLC | 0 | — | 80 | 20 | 1 | X-Bridge C18 |
| | | 0.2 | — | 80 | 20 | 1 | |
| | | 7 | — | 40 | 60 | 1 | |
| | | 8 | — | 10 | 90 | 1 | |
| | | 10.8 | — | 10 | 90 | 1 | |
| | | 11 | — | 80 | 20 | 1 | |
| | | 14 | — | 80 | 20 | 1 | |
| L4 | Dionex Ultimate 3000 HPLC | 0 | — | 50 | 50 | 1 | X-Bridge C18 |
| | | 0.2 | — | 50 | 50 | 1 | |
| | | 6 | — | 10 | 90 | 1 | |
| | | 10.8 | — | 10 | 90 | 1 | |
| | | 11 | — | 50 | 50 | 1 | |
| | | 14 | — | 50 | 50 | 1 | |
| L5 | Dionex Ultimate 3000 HPLC | 0 | 95 | — | 5 | 1 | SunFire C18 |
| | | 1 | 95 | — | 5 | 1 | |
| | | 7 | 50 | — | 50 | 1 | |
| | | 8 | 10 | — | 90 | 1 | |
| | | 10.8 | 10 | — | 90 | 1 | |
| | | 11 | 95 | — | 5 | 1 | |
| | | 14 | 95 | — | 5 | 1 | |
| L6 | Dionex Ultimate 3000 HPLC | 0 | — | 95 | 5 | 1 | X-Bridge C18 |
| | | 1 | — | 95 | 5 | 1 | |
| | | 7 | — | 50 | 50 | 1 | |
| | | 8 | — | 10 | 90 | 1 | |
| | | 10.8 | — | 10 | 90 | 1 | |
| | | 11 | — | 95 | 5 | 1 | |
| | | 14 | — | 95 | 5 | 1 | |

Conditions used for the UPLC analysis in experimental part. The LC/MS analysis mentioned in the experimental part were performed on a Waters system combining an Acquity UPLC H-Class equipped with a Acquity UPLC PDA Detector and an Acquity TQ DetectorS (ES). The separations were performed with an Acquity UPLC HSS C18, 2.1×50 mm, 1.8 µM column equipped with a prefilter and thermostated at 40° C. or an Acquity UPLC BEH C18, 2.1×50 mm, 1.7 µM column equipped with a prefilter and thermostated at 40° C. and the PAD acquisition wavelength was set in the range of 210-420 nm (Method U in the table below). Elutions were carried out with the methods described in the following table. Solvent A: Formic Acid LC-MS grade 0.1% in milliQ water Solvent B: NH4OAc (LC-MS grade) 10 mMol in milliQ water, adjusted at pH10 with an aq. solution of NH3, LC-MS grade. Solvent C: Acetonitrile LC-MS grade.

| LC/MS Method | System | Time (min) | Solvents A (%) | B (%) | C (%) | Flow (mL/min) | Column |
|---|---|---|---|---|---|---|---|
| U1 | Waters UPLC | 0 | 95 | — | 5 | 0.5 | Acquity UPLC HSS C18 |
|  |  | 3.18 | 50 | — | 50 | 0.5 |  |
|  |  | 4 | 10 | — | 90 | 0.5 |  |
|  |  | 5 | 10 | — | 90 | 0.5 |  |
| U2 | Waters UPLC | 0 | 80 | — | 20 | 0.5 | Acquity UPLC HSS C18 |
|  |  | 3.4 | 40 | — | 60 | 0.5 |  |
|  |  | 4 | 10 | — | 90 | 0.5 |  |
|  |  | 5 | 10 | — | 90 | 0.5 |  |
| U3 | Waters UPLC | 0 | 50 | — | 50 | 0.5 | Acquity UPLC HSS C18 |
|  |  | 3.5 | 10 | — | 90 | 0.5 |  |
|  |  | 5 | 10 | — | 90 | 0.5 |  |
| U4 | Waters UPLC | 0 | — | 95 | 5 | 0.5 | Acquity UPLC BEH C18 |
|  |  | 3.18 | — | 50 | 50 | 0.5 |  |
|  |  | 4 | — | 10 | 90 | 0.5 |  |
|  |  | 5 | — | 10 | 90 | 0.5 |  |
| U5 | Waters UPLC | 0 | — | 80 | 20 | 0.5 | Acquity UPLC BEH C18 |
|  |  | 3.4 | — | 40 | 60 | 0.5 |  |
|  |  | 4 | — | 10 | 90 | 0.5 |  |
|  |  | 5 | — | 10 | 90 | 0.5 |  |
| U6 | Waters UPLC | 0 | — | 50 | 50 | 0.5 | Acquity UPLC BEH C18 |
|  |  | 3.5 | — | 10 | 90 | 0.5 |  |
|  |  | 5 | — | 10 | 90 | 0.5 |  |

Preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector. The separations were performed with a X-Bridge Prep C18 column, 100×19 mm, 5 µm column equipped with a X-Bridge C18, 19×10 mm, 5 µm Guard column or with a SunFire Prep C18 ODB column (5 µm; 19×100 mm) equipped with a SunFire C18 guard column (5 µm; 19×10 mm). Elutions were carried out with the methods described in the following tables, and detection wavelengths were fixed at 210 and 254 nm. Solvent A: Formic Acid LC-MS grade 0.1% in milliQ water Solvent B: NH4OAc (LC-MS grade) 10 mMol in milliQ water, adjusted at pH10 with an aq. solution of NH3, LC-MS grade. Solvent C: Acetonitrile LC-MS grade.

| HPLC Method | Time (min) | Solvent A (%) | B (%) | Flow (mL/min) | Column |
|---|---|---|---|---|---|
| H1 | 0 | 80 | 20 | 20 | X-Bridge Prep C18 |
|  | 2 | 80 | 20 | 20 |  |
|  | 8 | 10 | 90 | 20 |  |
|  | 10.8 | 10 | 90 | 20 |  |
|  | 11 | 80 | 20 | 20 |  |
|  | 16 | 80 | 20 | 20 |  |
| H2 | 0 | 95 | 5 | 20 | SunFire Prep C18 ODB |
|  | 2 | 95 | 5 | 20 |  |
|  | 8 | 50 | 50 | 20 |  |
|  | 9 | 10 | 90 | 20 |  |
|  | 13 | 10 | 90 | 20 |  |
|  | 14 | 95 | 5 | 20 |  |
|  | 16 | 95 | 5 | 20 |  |

Synthesis of 2-methyl-5-((5-(trifluoromethyl)furan-2-yl)methoxy)benzofuran-3-carboxylic acid (Cpd 018)

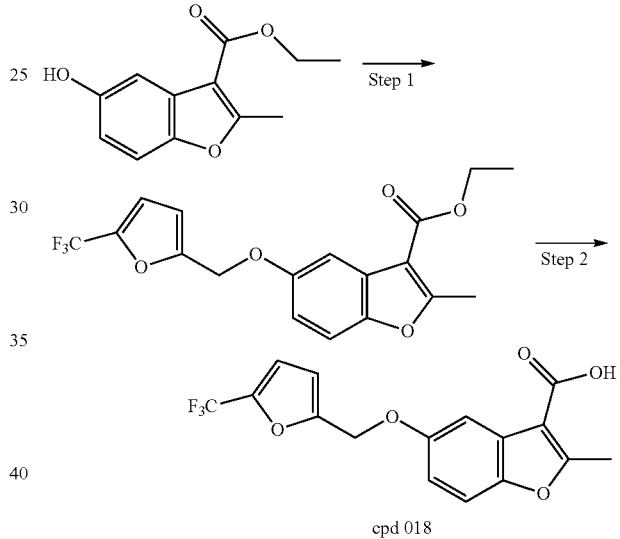

cpd 018

Step 1: To a solution of ethyl 5-hydroxy-2-methylbenzofuran-3-carboxylate (0.100 g; 0.45 mmol) in THF (10 mL) and NMP (1 mL) was added cesium carbonate (0.444 g; 1.36 mmol) and the RM was stirred at RT for 25 min. Then, 2-(bromomethyl)-5-(trifluoromethyl)furan (0.104 mg; 0.45 mmol) was added and the stirred solution was heated at 95° C. until the consumption of 5-hydroxy-2-methylbenzofuran-3-carboxylate. The mixture was cooled down to RT, poured in water and extracted twice with EtOAc. The combined organic layer was dried over sodium sulfate, filtered and concentrated under reduced pressure. The residue was purified by FC on silica gel using a gradient of EtOAc (0% to 80%) in heptane to afford 0.167 g (100%) of ethyl 2-methyl-5-((5-(trifluoromethyl)furan-2-yl)methoxy)benzofuran-3-carboxylate.

Step 2: To a solution of ethyl 2-methyl-5-((5-(trifluoromethyl)furan-2-yl)methoxy)benzofuran-3-carboxylate (0.167 g; 0.45 mmol) in a mixture of water-EtOH-MeOH-THF (6:3:3:1, 12 mL) was added sodium hydroxide (0.102 g; 1.8 mmol) and the RM was heated under reflux until the consumption of ethyl 5-(benzyloxy)-2-methylbenzofuran-3-carboxylate. After cooling, the volatiles were removed under reduced pressure and the remaining residue was dissolved in water and washed with DCM. The mixture was acidified with an aq. solution of hydrochloric acid (6 N) until pH~2 and extracted with EtOAc. The resulting organic layer was washed with water and brine, dried over magnesium sulfate and filtered to afford 147.6 mg (89%) of 2-methyl-5-((5-(trifluoromethyl)furan-2-yl)methoxy)benzofuran-3-carboxylic acid (cpd 018).

Cpd 016 and cpd 017 were prepared in a manner similar (use of appropriate reagents and purification methods known to those skilled in the art) to cpd 018.

Synthesis of 2-methyl-5-((2-(trifluoromethyl)benzyl)oxy)benzofuran-3-carboxylic acid (Cpd 101)

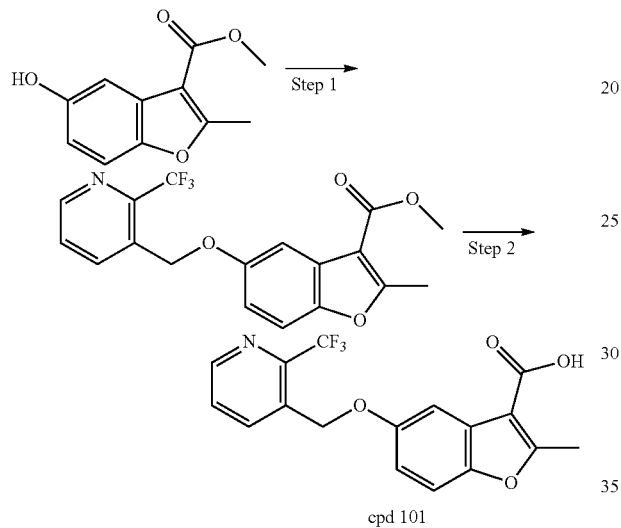

Step 1: Tributylphosphine (1.7 mL; 6.5 mmol) was added dropwise to a stirred mixture of methyl 5-hydroxy-2-methylbenzofuran-3-carboxylate (1 g; 4.6 mmol), 2-(trifluoromethyl)pyridin-3-yl)methanol (1.28 g; 6.9 mmol) and ADDP (1.66 g; 6.5 mmol) in dry THF (5 mL) under argon. The mixture was stirred for 2 h and was concentrated under reduced pressure. The residue was purified by FCC on silica gel using a gradient of EtOAc (0-20%) in heptane to afford 1.4 g (83%) of methyl 2-methyl-5-((2-(trifluoromethyl)pyridin-3-yl)methoxy)benzofuran-3-carboxylate. M/Z(+): 366 (M+H). M/Z(−): 364 (M−H).

Step 2: To a solution of methyl 2-methyl-5-((2-(trifluoromethyl)pyridin-3-yl)methoxy)benzofuran-3-carboxylate (1.40 g; 3.8 mmol) in a mixture of MeOH-THF (1:1, 40 mL) was added a solution of sodium hydroxide (2 N; 5 mL; 40 mmol) and the RM was heated at 75° C. overnight. After cooling, the volatiles were removed under reduced pressure and the remaining residue was dissolved in water. The mixture was acidified with a solution of HCl (6 N) until pH~5. The white precipitate was washed with water and dried under reduced pressure to afford 1.30 g (96%) of 2-methyl-5-((2-(trifluoromethyl)benzyl)oxy)benzofuran-3-carboxylic acid (cpd 101).

Cpd 099, cpd 100 and cpd 102 were prepared in a manner similar (use of appropriate reagents and purification methods known to those skilled in the art) to cpd 101.

The following compounds were prepared in a manner similar (use of appropriate reagents and purification methods known to the person skilled in the art) to cpd 101:

| Cpd. Nr. | [M + H]+ (m/z) | Cpd. Nr. | [M − H]− (m/z) |
|---|---|---|---|
| 208 | 304.0 | 261 | 297.0 |
| 210 | 372.1 | 263 | 297.0 |
| 211 | 288.1 | 679 | 288.1 |
| 212 | 304.1 | 681 | 332.1 |
| 214 | 298.1 | 713 | 285.1 |
| 216 | 304.1 | | |
| 217 | 298.1 | | |
| 218 | 263.1 | | |
| 219 | 285.0 | | |
| 220 | 337.1 | | |
| 223 | 318.0 | | |
| 224 | 318.1 | | |
| 227 | 314.2 | | |
| 228 | 303.1 | | |
| 235 | 337.0 | | |
| 239 | 328.1 | | |
| 240 | 302.1 | | |
| 242 | 302.1 | | |
| 248 | 318.1 | | |
| 249 | 287.1 | | |
| 257 | 299.1 | | |
| 260 | 304.0 | | |
| 262 | 304.0 | | |
| 264 | 285.0 | | |
| 268 | 318.1 | | |
| 269 | 314.1 | | |

Synthesis of 2-methyl-5-((1-methyl-1H-pyrazol-3-yl)methoxy)benzofuran-3-carboxylic acid (Cpd 008)

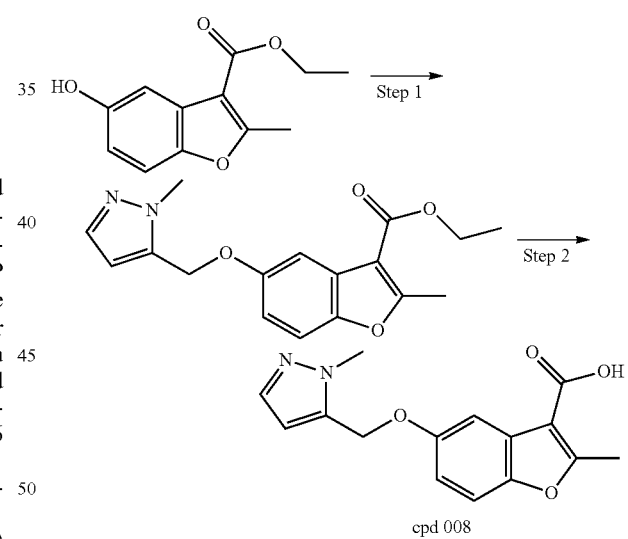

Step 1: Ethyl 5-hydroxy-2-methylbenzofuran-3-carboxylate (100 mg; 0.45 mmol), (1-methyl-1H-pyrazol-5-yl)methanol (0.075 g; 0.68 mmol) and PPh₃ (119 mg; 0.45 mmol) were dissolved in THF (5 mL) and cooled down to 0° C. Then DIAD (0.134 mL; 0.68 mmol) was added dropwise and the RM was stirred 36 h at RT. The volatiles were removed under reduced pressure and the residue was diluted with DCM and washed successively with an aq. solution of NaOH (1 N), water and brine. The organic layer was dried over magnesium sulfate, filtered and the solvent was removed under reduced pressure. The compound was purified by FCC on silica gel using a gradient of EtOAc (20 to 100%) in heptane to afford 0.071 g (50%) of the desired compound.

Step 2: An aq. solution of NaOH (2 N; 6 mL; 12 mmol) was added to a solution of ethyl 2-methyl-5-((1-methyl-1H-pyrazol-5-yl)methoxy)benzofuran-3-carboxylate (0.071 g; 0.25 mmol) in MeOH (4 mL) and ethanol (2 mL) and the mixture was stirred for 4 h at 80° C. After cooling, the mixture was diluted with water and washed with DCM. The aq. layer was acidified till pH=4 with an aq. solution of HCl (6 N). The solid formed was filtered and dried to afford 33 mg (51%) of 2-methyl-5-((1-methyl-1H-pyrazol-3-yl)methoxy)benzofuran-3-carboxylic acid (cpd 008).

The following compounds were prepared in a manner similar (use of appropriate reagents and purification methods known to the person skilled in the art) to cpd 008: Cpd 001, 002, 004, 005, 006, 007, 009, 010, 011, 012, 013 and 014.

The following compounds were prepared in a manner similar (use of appropriate reagents and purification methods known to the person skilled in the art) to cpd 008:

| Cpd. Nr. | [M + H]⁺ (m/z) |
|---|---|
| 255 | 288.1 |
| 266 | 328.1 |
| 267 | 323.1 |

Synthesis of 2-methyl-5-((5-methylisoxazol-3-yl)methoxy)benzofuran-3-carboxylic acid (Cpd 215)

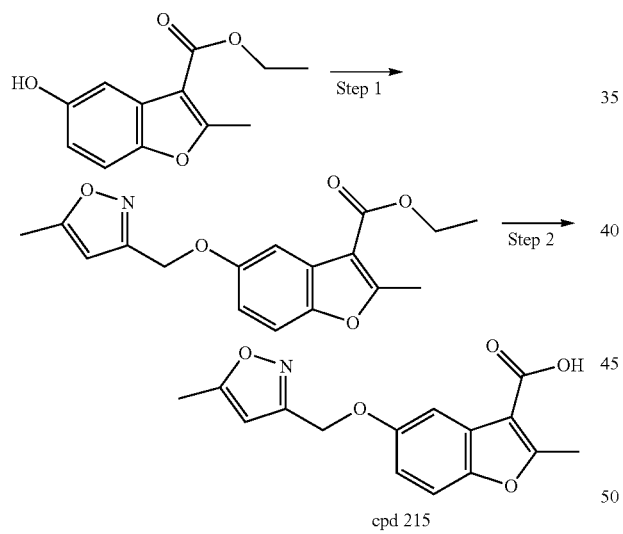

cpd 215

Step 1: To a stirred solution of ethyl 5-hydroxy-2-methylbenzofuran-3-carboxylate (0.4 g, 1.8 mmol) and (5-methylisoxazol-3-yl) methyl methanesulfonate (0.52 g, 2.7 mmol) in acetonitrile (25 mL) was added Cs₂CO₃ (1.18 g, 3.6 mmol) at RT. The reaction mixture was heated 70° C. and maintained at this temperature for 16 h. Reaction progress was monitored by TLC. The reaction mixture was filtered and concentrated under reduced pressure to give the crude compound. The crude was purified by 100-200 mesh silica-gel column chromatography using 5% ethyl acetate in pet ether as an eluent to afford ethyl 2-methyl-5-((5-methylisoxazol-3-yl)methoxy)benzofuran-3-carboxylate (0.4 g, 70%) as a pale yellow thick mass. TLC system: 30% Ethyl acetate in pet-ether; RF: 0.2.

Step 2: 2N aqueous NaOH (5 mL) was added to a stirred solution of ethyl 2-methyl-5-((5-methylisoxazol-3-yl)methoxy)benzofuran-3-carboxylate (0.4 g, 1.26 mmol) in methanol (5 mL) and THF (5 mL) at RT and the resulting reaction mixture was stirred at RT for 16 h. The reaction progress was monitored by TLC. The reaction mixture was diluted with water (10 mL) and acidified to pH ~2 with 1 N aq. HCl (10 mL), the precipitated solid was filtered and dried under vacuum to afford 2-methyl-5-((5-methylisoxazol-3-yl)methoxy)benzofuran-3-carboxylic acid (250 mg, 70%) as a white solid. TLC system: 50% Ethyl acetate in pet-ether; RF: 0.2. [M+H]⁺ (m/z): 288.1

The following compounds were prepared in a manner similar (use of appropriate reagents (including mesylates, chlorides and bromides) and purification methods known to the person skilled in the art) to cpd 215:

| Cpd. Nr. | [M + H]⁺ (m/z) | Cpd. Nr. | [M + H]⁺ (m/z) |
|---|---|---|---|
| 209 | 358.1 | 237 | 334.0 |
| 213 | 383.3 | 250 | 314.1 |
| 221 | 364.1 | 256 | 314.0 |
| 226 | 334.0 | 258 | 277.2 |
| 667 | 301.2 | 669 | 335.1 |
| 671 | 349.1 | 673 | 288.1 |
| 675 | 315.2 | 677 | 302.2 |
| 689 | 327.1 | 691 | 355.1 |
| 693 | 358.0 | 699 | 298.1 |
| 703 | 324.2 | 707 | 299.1 |

Synthesis of 5-((2-aminopyridin-3-yl)methoxy)-2-methylbenzofuran-3-carboxylic acid (Cpd 225)

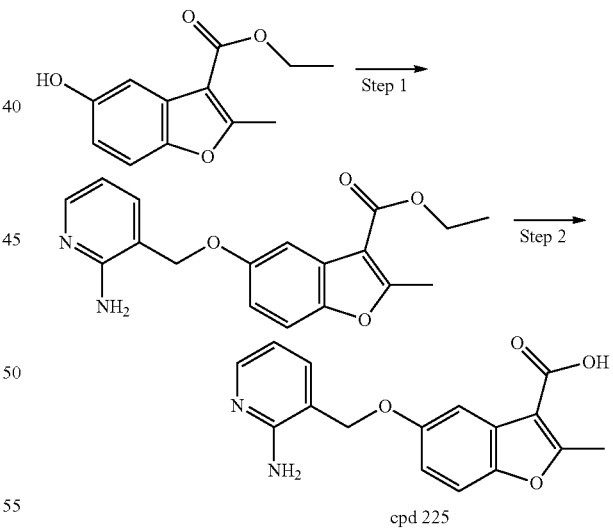

cpd 225

Step 1: To a pre-stirred solution of ethyl 5-hydroxy-2-methylbenzofuran-3-carboxylate (0.900 g, 4.09 mmol) in THF (30 ml), was added NaH (60%) (0.313 g, 8.18 mmol) lot wise at 0° C. under argon atmosphere, followed by the addition of 3-(chloro methyl) pyridin-2-amine (2239-1) (0.871 g, 6.13 mmol) at 0° C. under argon atmosphere. The reaction mixture was heated up to 60° C. for 18 h. The reaction progress was monitored by TLC. The reaction mixture was diluted with water (30 mL) and extracted with ethyl acetate (2×50 mL). The combined organic layer was washed with water (30 mL) and brine (30 mL), dried over anhydrous $Na_2SO_4$ and concentrated under reduced pressure to give the crude material. The crude was purified by column chromatography over silica gel (100-200 mesh) using 0-30% ethyl acetate in pet-ether as an eluent to afford ethyl 5-((2-aminopyridin-3-yl) methoxy)-2-methylbenzofuran-3-carboxylate (0.30 g, 23%) as a white solid. TLC system: 50% EtOAc in Pet ether; Rf: 0.3.

Step 2: To a pre-stirred solution of ethyl 5-((2-aminopyridin-3-yl) methoxy)-2-methylbenzofuran-3-carboxylate (0.30 g, 0.92 mmol), in $THF:MeOH:H_2O$ (1:1:1, 30 ml), was added NaOH (0.11 g, 2.76 mmol) at RT, then the reaction was heated to 50° C., and the reaction mixture was stirred for 6 h at 50° C. Reaction progress was monitored by TLC. The reaction mixture was concentrated to get the crude material, which was diluted with ice water and pH was adjusted to ~2 with 1 N aq. HCl solution to give a solid. The obtained solid was filtered and dried to afford 5-((2-aminopyridin-3-yl)methoxy)-2-methylbenzofuran-3-carboxylic acid (0.22 g, 80%) as an off-white solid. TLC system: 10% MeOH in $CH_2Cl_2$; Rf: 0.2. $[M+H]^+$ (m/z): 299.1

Synthesis of 2-methyl-5-((2-methylpyridin-3-yl) methoxy)benzofuran-3-carboxylic acid (Cpd 247)

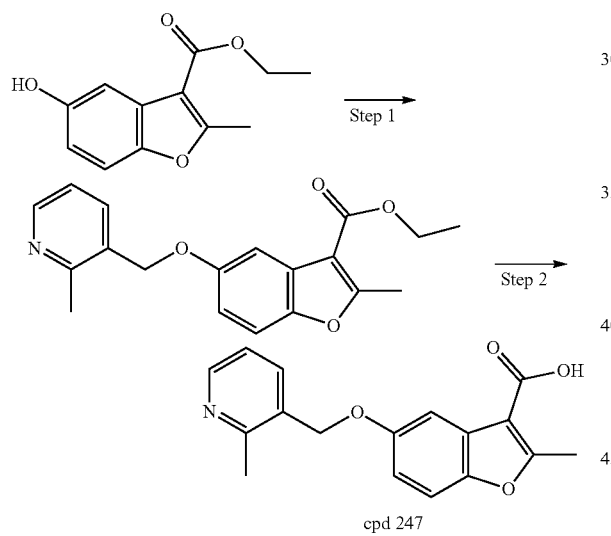

cpd 247

Step 1: To a solution of ethyl 5-hydroxy-2-methylbenzofuran-3-carboxylate (800 g, 3.636 mmol) and (2-methylpyridin-3-yl)methyl methanesulfonate (1.4 g 7.272 mmol) in DMF (5 mL) at 0° C. was added $K_2CO_3$ (1.5 g, 10.909 mmol). The reaction mixture was allowed to come to RT and was stirred for 12 h at the same temperature. Reaction progress was monitored by TLC. The reaction mixture was quenched with ice water (100 mL) and stirred for 30 minutes. The solid material was collected by filtration and dried to afford 1.2 g (92%) of ethyl 2-methyl-5-((2-methylpyridin-3-yl)methoxy)benzofuran-3-carboxylate as an off white solid. TLC system: 20% Ethyl acetate in pet-ether; RF: 0.20

Step 2: A solution of ethyl 2-methyl-5-((2-methylpyridin-3-yl)methoxy)benzofuran-3-carboxylate (1.2 g, 3.692 mmol), NaOH (295 mg, 7.384 mmol) in $EtOH:THF:H_2O$ (2:2:1, 5.0 mL) was stirred at 70° C. for 16 h. The reaction progress was monitored by TLC. The solvent was distilled off, then water was added (20 mL) to the crude residue and the aqueous phase was washed with diethyl ether (2×10 mL). The aqueous layer was acidified with 2N HCl, the resulting precipitated solid was collected by filtration, washed with water (10 mL) and dried under reduced pressure to afford 2-methyl-5-((2-methyl-4-(trifluoromethyl)thiazol-5-yl)methoxy)benzofuran-3-carboxylic acid (1.0 g, 91%) as an off-white solid. TLC system: 10% MeOH in dichloromethane; RF: 0.10. $[M+H]^+$ (m/z): 298.1

Synthesis of 5-((5-(2-hydroxyethoxy)pyridin-2-yl) methoxy)-2-methylbenzofuran-3-carboxylic acid (Cpd 241)

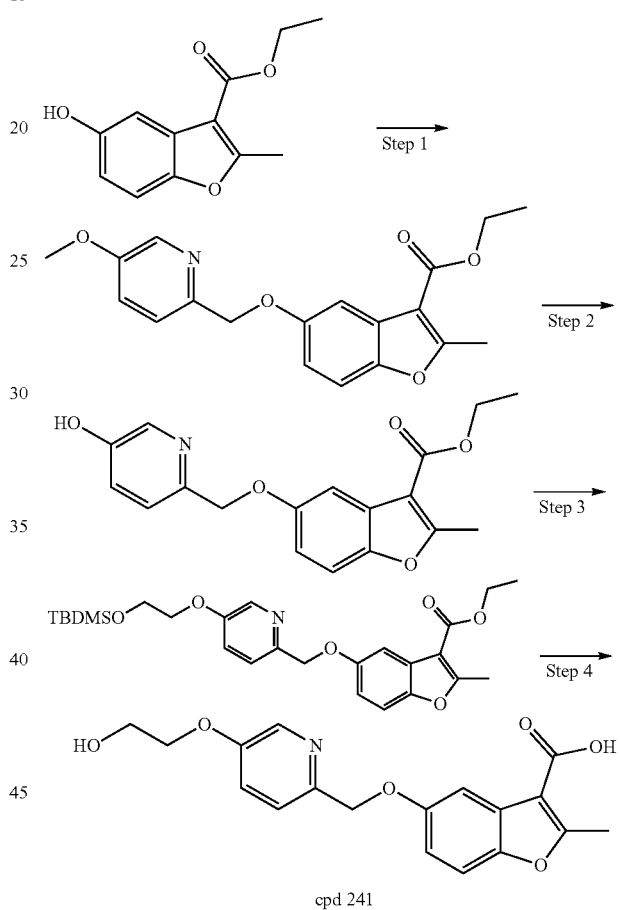

cpd 241

Step 1: To a stirred solution of ethyl 5-hydroxy-2-methylbenzofuran-3-carboxylate (5 g, 22.7 mmol), and (5-methoxypyridin-2-yl)methanol (3.79 g, 27.2 mmol) in THF (150 mL) was added ADDP (11.4 g, 46 mmol) followed by $Bu_3P$ (9.2 g, 46 mmol) at 0° C. The reaction mixture was stirred at RT for 16 hours and was then concentrated under reduced pressure. The residue was partitioned between water and ethyl acetate. After separation, the aqueous layer was extracted with ethyl acetate (150 mL×2). The combined organic extracts were concentrated under reduced pressure to give a residue. The residue was purified by flash chromatography (silica gel, 100-200 mesh size) using a gradient of ethyl acetate (5-40%) in hexane to afford ethyl 5-((5-methoxypyridin-2-yl)methoxy)-2-methylbenzofuran-3-carboxylate (3 g, 8.7 mmol, 38%) as a pale yellow solid. TLC system: 30% EtOAc in Pet ether; RF: 0.35.

Step 2: To a stirred solution of ethyl 5-((5-methoxypyridin-2-yl)methoxy)-2-methylbenzofuran-3-carboxylate (500 mg, 1.4 mmol) in CH$_2$Cl$_2$ (20 mL) was added portion wise AlCl$_3$ (390 mg, 2.9 mmol) at 0° C., the reaction mixture was then stirred at 50° C. for 2 hours. Reaction progress was monitored by LCMS. After completion of the reaction, the reaction mass was concentrated under reduced pressure to give a residue. The residue was treated with sat. NaHCO$_3$ solution (pH ~7) and was partitioned between water and dichloromethane. After separation, the aqueous layer was extracted with dichloromethane (50 mL×2). The combined organic extracts were concentrated under reduced pressure to afford ethyl 5-((5-hydroxypyridin-2-yl)methoxy)-2-methylbenzofuran-3-carboxylate (180 mg, 5 mmol) as a pale yellow solid. TLC system: 50% EtOAc in pet ether; RF: 0.3

Step 3: To a stirred solution of ethyl 5-((5-hydroxypyridin-2-yl)methoxy)-2-methylbenzofuran-3-carboxylate (600 mg, 1.8 mmol) in DMF (20 mL) was added (2-bromoethoxy)(tert-butyl)dimethylsilane (657 mg, 2.7 mmol) at 0° C., the reaction mixture was then stirred at 60° C. for 6 hours. Reaction progress was monitored by LCMS. After completion of the reaction, the reaction mass was partitioned between water and ethyl acetate. After separation, the aqueous layer was extracted with ethyl acetate (50 mL×2). Combined organic extracts were concentrated under reduced pressure to afford ethyl 5-((5-(2-((tert-butyldimethylsilyl)oxy)ethoxy)pyridin-2-yl)methoxy)-2-methylbenzofuran-3-carboxylate (600 mg, 1.2 mmol) as a pale yellow solid. TLC system: 30% EtOAc in Pet ether; RF: 0.7.

Step 4: To a stirred solution of ethyl 5-((5-(2-((tert-butyldimethylsilyl)oxy)ethoxy)pyridin-2-yl)methoxy)-2-methylbenzofuran-3-carboxylate (600 mg, 1.2 mmol) in THF (20 mL) was added NaOH (148 mg, 3 mmol) in water (3 ml), and MeOH (3 ml) at 0° C., the reaction mixture was then stirred at RT for 16 hours. Reaction progress was monitored by LCMS. After completion of the reaction, the reaction mass was concentrated under reduced pressure. The residue was stirred in 1 N HCl (pH ~2) for 30 min and was then partitioned between water and dichloromethane. After separation, the aqueous layer was extracted with dichloromethane (50 mL×2). Combined organic extracts were concentrated under reduced pressure to afford 5-((5-(2-hydroxyethoxy)pyridin-2-yl)methoxy)-2-methylbenzofuran-3-carboxylic acid (300 mg, 8 mmol) as an off-white solid. TLC system: 5% MeOH in dichloromethane; RF: 0.4. [M+H]$^+$ (m/z): 344.0

Synthesis of 5-((2-(dimethylamino)pyridin-3-yl)methoxy)-2-methylbenzofuran-3-carboxylic acid (Cpd 222)

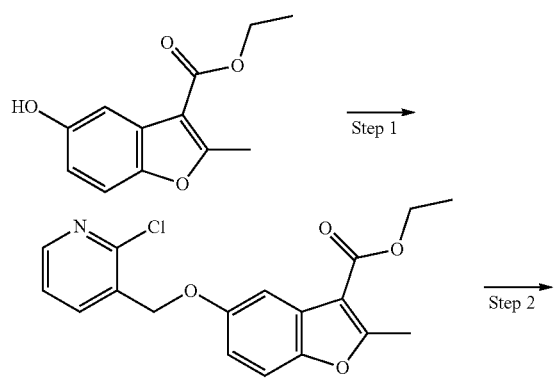

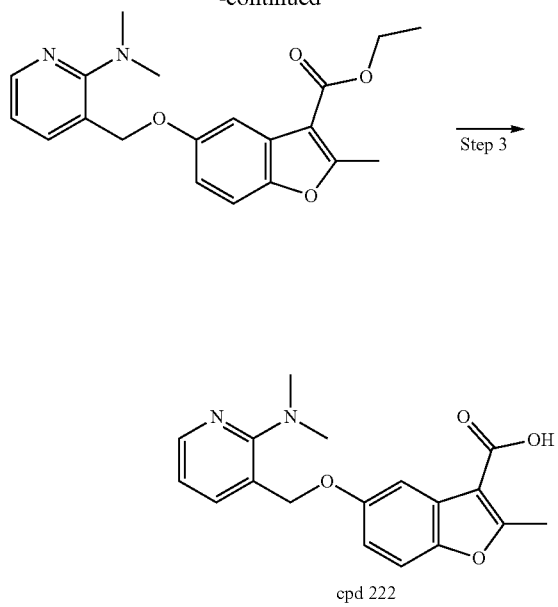

cpd 222

Step 1: To a pre-stirred solution of ethyl 5-hydroxy-2-methylbenzofuran-3-carboxylate (2.5 g, 0.011 mmol) in acetonitrile (50 mL) was added Cs$_2$CO$_3$ (7.3 g 0.022 mmol), 2-chloro-3-(chloromethyl) pyridine (2.1 g, 0.0132 mmol) under argon atmosphere at RT. The reaction mixture was heated to 80° C. for 16 h. The reaction progress was monitored by TLC. The reaction mixture was filtered and the filter cake was washed with acetonitrile (50 mL), and the filtrate was concentrated under reduced pressure to give the crude material. The crude material was purified by grace chromatography using 0-20% ethyl acetate in pet-ether as an eluent to afford ethyl 5-((2-chloropyridin-3-yl)methoxy)-2-methylbenzofuran-3-carboxylate (2.0 g, 63%) as an off-white solid. TLC system: 30% EtOAc in Pet ether; RF: 0.6.

Step 2: A solution of ethyl 5-((2-chloropyridin-3-yl)methoxy)-2-methylbenzofuran-3-carboxylate (500 mg, 1.44 mmol) and N,N-dimethyl amine solution in ethanol (10 mL, 5 M) was heated to 150° C. in a microwave for 2 h. The reaction progress was monitored by TLC. The reaction mixture was concentrated under reduced pressure to give the crude material. The crude material was purified by Grace flash chromatography using 0-5% ethyl acetate in pet-ether as an eluent to afford ethyl 5-((2-(dimethylamino)pyridin-3-yl)methoxy)-2-methylbenzofuran-3-carboxylate (180 mg, 39%) as an off-white solid. TLC system: 30% EtOAc in Pet ether; RF: 0.5.

Step 3: To a stirred solution of ethyl 5-((2-(dimethylamino) pyridin-3-yl) methoxy)-2-methylbenzofuran-3-carboxylate (300 mg, 0.847 mmol), in THF:MeOH:H$_2$O (1:1:0.5, 25 ml) was added NaOH (170 mg, 4.27 mmol) at RT and the mixture was heated to 50° C. The reaction mixture was stirred for 4 h at 50° C. and reaction progress was monitored by TLC. The reaction mixture was concentrated under vacuum and diluted with ice water, the pH was adjusted to ~2 with 1 N aq. HCl solution to give a solid which was filtered and dried to afford 5-((2-(dimethylamino)pyridin-3-yl)methoxy)-2-methylbenzofuran-3-carboxylic acid (170 mg, 61%) as a white solid. TLC system: 30% EtOAc in Pet ether; RF: 0.1. [M+H]$^+$ (m/z): 327.2.

Synthesis of 5-((2-cyclopropylpyridin-3-yl)methoxy)-2-methylbenzofuran-3-carboxylic acid (Cpd 701)

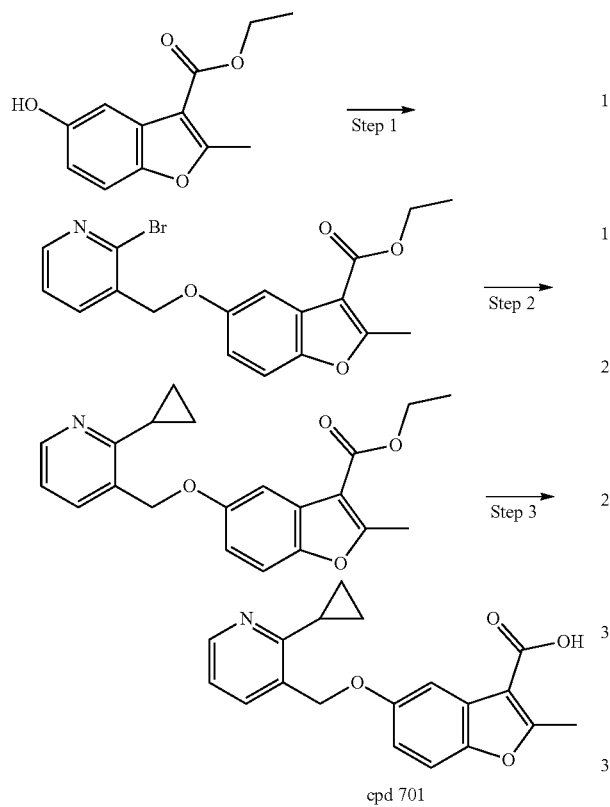

cpd 701

Step 1: To a pre-stirred solution of ethyl 5-hydroxy-2-methylbenzofuran-3-carboxylate (500 mg, 2.283 mmol) and (2-bromopyridin-3-yl)methanol (643.4 mg, 3.42 mmol) in THF (10 mL) was added ADDP (806.08 mg, 3.196 mmol) and n-Bu₃P (646.5 mg, 3.196 mmol) at RT. The RM was stirred for 16 h at RT. The reaction progress was monitored by TLC. The RM was diluted with water (100 mL) and extracted with ethyl acetate (2×50 mL). Combined organic layers were washed with brine (50 mL), dried over anhydrous Na₂SO₄ and evaporated under vacuum. The crude was purified by flash column chromatography using 0.1% formic acid in water and acetonitrile in water as an eluent to afford ethyl 5-((2-bromopyridin-3-yl)methoxy)-2-methylbenzofuran-3-carboxylate (520 mg, crude) as yellow solid. Proceeded to next step without purification.

Step 2: Pd(PPh₂)₂Cl₂ (45.04 mg, 0.06 mmol) was added to a stirred solution of ethyl 5-((2-bromopyridin-3-yl)methoxy)-2-methylbenzofuran-3-carboxylate (250 mg, 0.6426 mmol), cyclopropylboronic acid (83.38 mg, 0.9640 mmol), K3PO4 (409.15 mg, 1.9278 mmol) in 1,4-dioxane (10 mL) and water (4 mL) at RT. Reaction mixture was degassed with Ar gas for 15 minutes at RT. The reaction mixture was heated to 100° C. and stirred for 16 hours at 100° C. The reaction progress monitored by TLC. Reaction mass was filtered over celite bed, filtrate was diluted with water (20 mL) and extracted with ethyl acetate (2×50 mL). Combined organic layers were concentrated under reduced pressure to get crude. Crude was purified by Grace flash column chromatography using 0.1% formic acid in water and acetonitrile as an eluent to afford ethyl 5-((2-cyclopropylpyridin-3-yl)methoxy)-2-methylbenzofuran-3-carboxylate 150 mg, crude) as a brown solid. Proceeded to next step without purification. TLC system: 100% Ethyl acetate, RF: 0.4.

Step 3: A solution of NaOH (91.4 mg, 2.285 mmol) in water (8 mL) was added to a stirred solution of ethyl 5-((2-cyclopropylpyridin-3-yl)methoxy)-2-methylbenzofuran-3-carboxylate (80 mg, 0.228 mmol) in methanol (2 mL) and THF (2 mL) at RT. The resulting reaction mixture was stirred for 16 h at RT. The reaction progress was monitored by TLC. The reaction mixture was concentrated under reduced pressure and diluted with water (15 mL), pH was adjusted to ~5 with 1 N HCl solution. The precipitated solid was extracted with ethyl acetate (2×50 mL). Combined organic layers were dried over Na2SO4 and concentrated under reduced pressure to afford 5-((2-cyclopropylpyridin-3-yl)methoxy)-2-methylbenzofuran-3-carboxylic acid (6) (100 mg, crude) as a brown gummy liquid. Proceeded to next step without purification. TLC system: 10% MeOH in dichloromethane; RF: 0.2.

Synthesis of 5-((2-aminopyridin-3-yl)methoxy)-2-methylbenzofuran-3-carboxylic acid (Cpd 230)

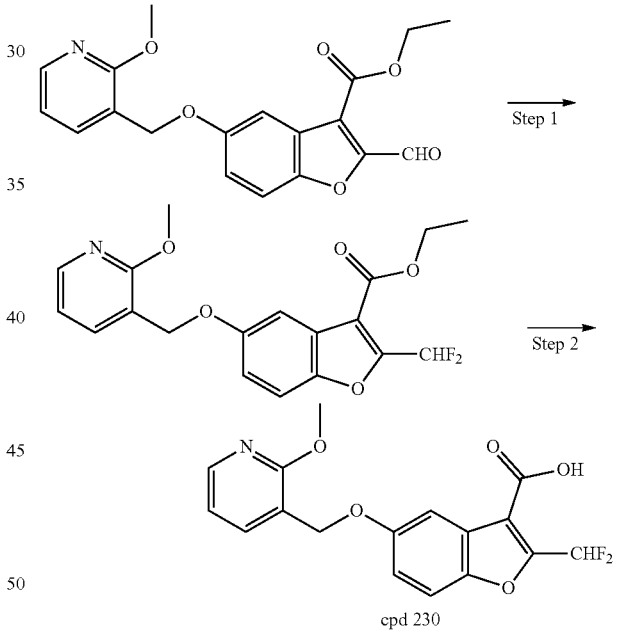

cpd 230

Step 1: To a stirred solution of ethyl 2-formyl-5-((2-methoxypyridin-3-yl)methoxy)benzofuran-3-carboxylate (1.5 g, 13.8 mmol) in CH₂Cl₂ (100 ml) was added DAST (4.47 g, 28 mmol) at 0° C. and the reaction mixture was stirred for 16 h at RT, the reaction progress was monitored by TLC. Ice cold water was added to the reaction mixture and aq. NaHCO₃ solution was added to get to pH ~7, followed by extraction with ethyl acetate (3×100 mL). The combined extracts were washed with brine (150 mL), dried over anhydrous Na₂SO₄ and concentrated under reduced pressure to get the material crude (1.4 g). The crude was purified by column chromatography using silica gel (100-200 mesh) and 20% ethyl acetate in pet ether as eluent to afford ethyl 2-(difluoromethyl)-5-((2-methoxypyridin-3-yl)

methoxy)benzofuran-3-carboxylate (1 g) as a white solid. TLC system: 20% Ethyl acetate in pet-ether; Rf: 0.6.

Step 2: To a stirred solution of ethyl 2-(difluoromethyl)-5-((2-methoxypyridin-3-yl)methoxy)benzofuran-3-carboxylate (1 g, 1.4 mmol), was added LiOH·H$_2$O (110 mg, 2.8 mmol) in THF:H$_2$O:MeOH (3:1:1) (25 mL) at RT under an argon atmosphere. The reaction mixture was stirred for 2 h at RT. The reaction progress was monitored by TLC. The solvents were removed and the reaction mixture was treated with citric acid to adjust the pH to ~1 and the resulting precipitate was filtered. The solid was dried under vacuum to afford 2-(difluoromethyl)-5-((2-methoxypyridin-3-yl)methoxy)benzofuran-3-carboxylic acid (1 g, 68%) as an off-white solid. TLC system: 5% MeOH in CH$_2$Cl$_2$; Rf: 0.2. [M+H]$^+$ (m/z): 350.0.

Synthesis of 5-((2-(azetidin-1-yl)pyridin-3-yl)methoxy)-2-methylbenzofuran-3-carboxylic acid (Cpd 236)

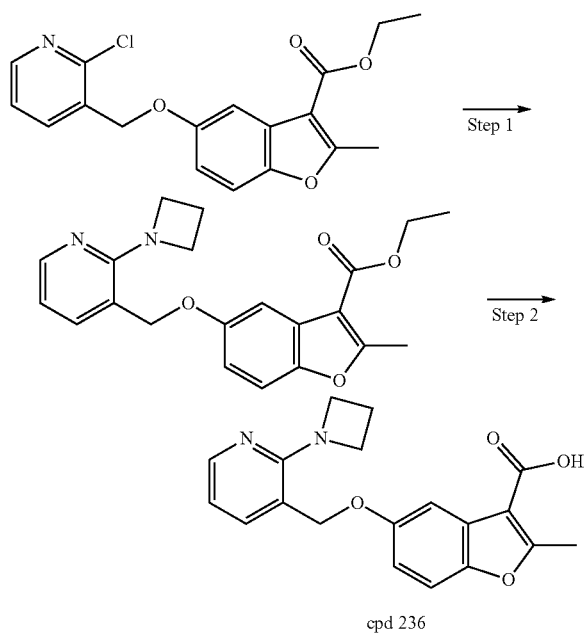

cpd 236

Step 1: To a stirred solution of ethyl 5-((2-chloropyridin-3-yl)methoxy)-2-methylbenzofuran-3-carboxylate (4.0 g, 11.59 mmol, 1.0 eq) in DMSO (40 ml), at 0° C. was added K$_2$CO$_3$ (15.99 g, 115.90 mmol, 10 eq) at 0° C. and the mixture was stirred for 5 min. Azetidine (5.39 g, 57.97 mmol, 5 eq) was added to the reaction and the mixture was stirred for 18 h at 120° C. Reaction progress was monitored by TLC. The reaction mixture was diluted with ice water (50 ml), the product was extracted with EtOAc (300 ml). The ethyl acetate layer was washed with ice water (50 ml) and brine (25 ml) and was then dried over anhydrous Na$_2$SO$_4$, filtered and concentrated to get the crude product, which was purified by Grace flash column chromatography using 20% EtOAc-pet ether as eluent to afford ethyl 5-((2-(azetidin-1-yl)pyridin-3-yl)methoxy)-2-methylbenzofuran-3-carboxylate (0.380 g, 9%, Off-white solid). TLC system: 30% Ethyl acetate in pet-ether; Rf: 0.3.

Step 2: To a stirred solution of ethyl 5-((2-(azetidin-1-yl)pyridin-3-yl)methoxy)-2-methylbenzofuran-3-carboxylate (0.700 g, 1.91 mmol, 1.0 eq), in THF:MeOH:H$_2$O (1:1:1) (60 ml), was added NaOH (0.29 g, 5.73 mmol, 3.0 eq) at RT, the mixture was then heated up to 50° C. The reaction mixture was stirred for 18 h at 50° C. and reaction progress was monitored by TLC. The reaction mixture was concentrated to get the crude material which was diluted with ice water and the pH was adjusted to 2 with 1 N HCl solution causing precipitation. The contents were further stirred for 30 min, the solids were then filtered off and dried to afford 5-((2-(azetidin-1-yl)pyridin-3-yl)methoxy)-2-methylbenzofuran-3-carboxylic acid (0.400 g, 61% white solid). TLC system: 100% Ethyl acetate; Rf: 0.2. [M+H]$^+$ (m/z): 339.0.

Synthesis of 5-((2-cyanopyridin-3-yl)methoxy)-2-methylbenzofuran-3-carboxylic acid (Cpd 238)

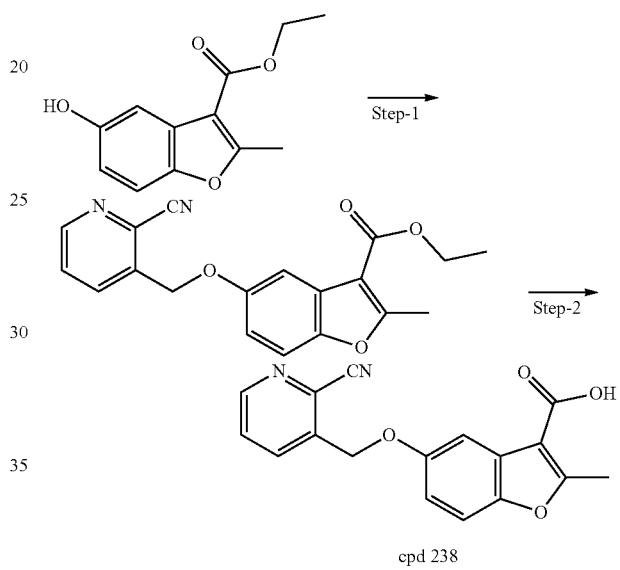

cpd 238

Step 1: To a stirred solution of ethyl 5-hydroxy-2-methylbenzofuran-3-carboxylate (0.8 g, 3.63 mmol, 1.0 eq) in ACN (10 ml) at 0° C. was added Cs$_2$CO$_3$ (3.55 g, 10.89 mmol, 3 eq) and the mixture was stirred for 5 minutes followed by the addition of 3-(bromomethyl)picolinonitrile (0.85 g, 4.36 mmol, 1.2 eq) at 0° C. The reaction mixture was stirred for 18 h at RT, monitored by TLC. The reaction mixture was diluted with ice water (100 ml) and extracted with EtOAc (300 ml). The organic layer was washed with ice water (100 ml) and brine (50 ml), dried over anhydrous Na$_2$SO$_4$, filtered and concentrated to get the crude product, which was purified by Grace flash column chromatography using eluent 20% EtOAc in pet ether to afford ethyl 5-((2-cyanopyridin-3-yl)methoxy)-2-methylbenzofuran-3-carboxylate (1.0 g, 81%, off-white solid). TLC system: 20% EtOAc-pet ether; 2:8; Rf: 0.3.

Step 2: To ethyl 5-((2-cyanopyridin-3-yl)methoxy)-2-methylbenzofuran-3-carboxylate (1.0 g, 2.97 mmol, 1.0 eq), in THF:MeOH:H$_2$O (1:1:1) (120 ml) was added NaOH (0.35 g, 8.92 mmol, 3.0 eq) at RT, the reaction mixture was then heated to 50° C. for 18 h, the reaction progress was monitored by TLC. The reaction mixture was concentrated and diluted with ice water, the pH was adjusted to ~2 with 1 N HCl solution to give a precipitate while stirring for 30 min. The precipitate was filtered off and dried under vacuum to afford a mixture of 5-((2-cyanopyridin-3-yl)methoxy)-2-methylbenzofuran-3-carboxylic acid (cpd 238) and 5-((2- carbamoylpyridin-3-yl)methoxy)-2-methylbenzofuran-3-carboxylic acid (0.75 g, crude). [M+H]+ (m/z): 309.0, TLC system: 50% EtOAc-pet ether; Rf: 0.1.

The following compounds were prepared in a manner similar (use of appropriate reagents and purification methods known to the person skilled in the art) to cpd 238:

| Cpd. Nr. | [M + H]+ (m/z) |
|---|---|
| 259 | 288.1 |
| 687 | 355.1 |
| 709 | 340.2 |

Synthesis of 2-methyl-5-(((2-(trifluoromethyl)pyridin-3-yl)oxy)methyl)benzofuran-3-carboxylic acid (Cpd 252)

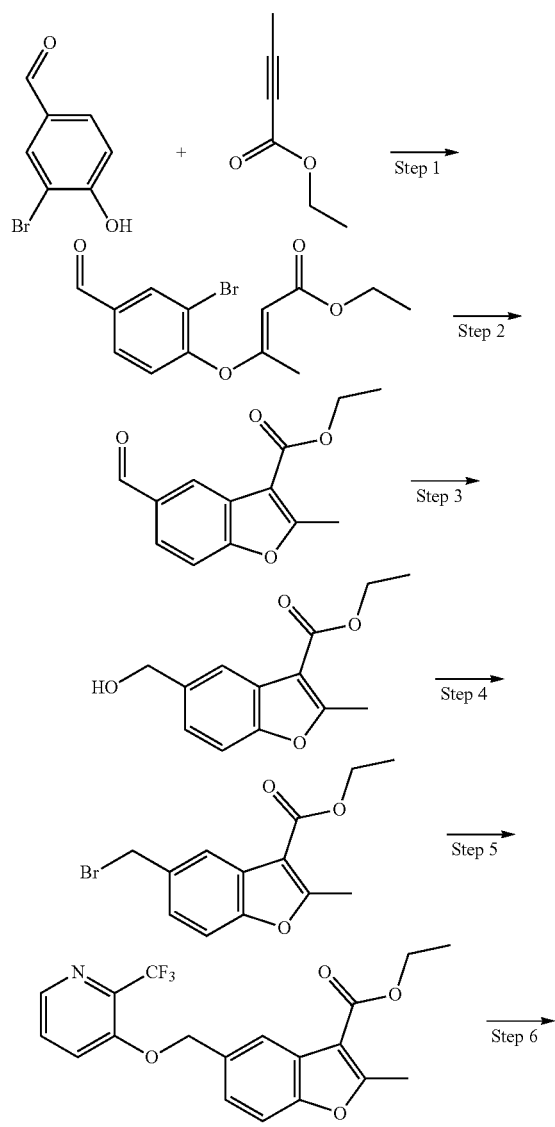

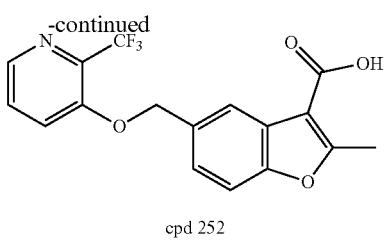

cpd 252

Step 1. DABCO (2.78 g, 24.75 mmol) was added to a stirred mixture of 3-bromo-4-hydroxybenzaldehyde (5.0 g, 24.75 mmol) and ethyl but-2-ynoate (3.32 g, 29.70 mmol) in acetonitrile (100 mL) at room temperature and the resulting reaction mixture was then heated to reflux for 4 h. The solvent was distilled off under reduced pressure, the residue was diluted with ethyl acetate (300 mL) and the resulting solution was sequentially washed with 1 N HCl (100 mL), aq. 1 N NaOH (2×75 mL), water (100 mL), brine (150 mL) and was then dried over anhydrous Na$_2$SO$_4$ and concentrated under reduced pressure. The crude compound was purified by column chromatography over silica-gel (100-200 mesh) using 10% ethyl acetate in pet-ether as an eluent to afford ethyl 3-(2-bromo-4-formylphenoxy)but-2-enoate (1.5 g, 29%) as an off-white solid. TLC system: 20% Ethyl acetate in pet-ether; Rf: 0.7.

Step 2: A solution mixture of ethyl 3-(2-bromo-4-formylphenoxy)but-2-enoate (1.2 g, 3.821 mmol) and TEA (0.21 mL, 1.528 mmol) in acetonitrile (25.0 mL) was degassed with argon for 5 min and then was added bis(tri-tert-butylphosphine)palladium(0)] (195 mg, 0.382 mmol). The resulting reaction mixture was heated to reflux for 2 h. The reaction progress was monitored by TLC. (Note: Another batch on 250 mg scale using the same procedure was combined with this reaction mixture for work-up). The reaction mixture was directly concentrated under reduced pressure. The crude was partitioned between water (100 mL) and ethyl acetate (2×100 mL). The combined organic layers were washed with brine (150 mL), dried over anhydrous Na$_2$SO$_4$ and concentrated under reduced pressure to afford ethyl 5-formyl-2-methylbenzofuran-3-carboxylate (1.0 g, 90%) as an off white crystalline solid. TLC system: 10% Ethyl acetate in pet-ether; Rf: 0.7.

Step 3: NaBH$_4$ (398 mg, 10.775 mmol) was added portionwise to a solution mixture of ethyl 5-formyl-2-methylbenzofuran-3-carboxylate (1.0 g, 4.310 mmol) in EtOH:THF (1:1) (40.0 mL) at 0° C. and the resulting reaction mixture was stirred for 30 min. The reaction mixture was then quenched with water (5.0 mL) and was concentrated under reduced pressure. The crude compound was diluted with ethyl acetate (50 mL), washed with water (2×50 mL), brine (100 mL), dried over anhydrous Na$_2$SO$_4$ and concentrated under reduced pressure to afford ethyl 5-(hydroxymethyl)-2-methylbenzofuran-3-carboxylate (900 mg, crude) as a colorless oil. TLC system: 20% Ethyl acetate in pet-ether; Rf: 0.4.

Step 4: A mixture of ethyl 5-(hydroxymethyl)-2-methylbenzofuran-3-carboxylate (700 mg, 2.991 mmol), TPP (1.17 g, 4.487 mmol) and CBr$_4$ (1.48 g, 4.487 mmol) in THF (40.0 mL) was stirred at 0° C. was then warmed to ambient temperature for 2 h. The reaction progress was monitored by TLC. The reaction mixture was diluted with ethyl acetate (100 mL), washed with NaHCO$_3$ solution (50 mL), water (50 mL), brine (50 mL), dried over anhydrous Na$_2$SO$_4$ and concentrated under reduced pressure to afford ethyl 5-(bromomethyl)-2-methylbenzofuran-3-carboxylate (1.25 g, crude) as a pale yellow thick gummy mass. TLC system: 10% Ethyl acetate in pet-ether; Rf: 0.6.

Step 5: To a suspension of 2-(trifluoromethyl)pyridin-3-ol (600 mg, 3.680 mmol) and $K_2CO_3$ (1.26 g, 9.20 mmol) in acetonitrile (30 mL) was added ethyl 5-(bromomethyl)-2-methylbenzofuran-3-carboxylate (1.32 g, 4.41 mmol) and the resulting reaction mixture was maintained at 90° C. for 1 h. The reaction progress was monitored by TLC. The reaction mixture was diluted with ethyl acetate (100 mL) and was filtered. The filtrate was washed with water (100 mL), brine (50 mL), dried over anhydrous $Na_2SO_4$ and concentrated under reduced pressure. The crude compound was purified by column chromatography over silica-gel (100-200 mesh) using 20% ethyl acetate in pet-ether as an eluent to afford ethyl 2-methyl-5-(((2-(trifluoromethyl)pyridin-3-yl)oxy)methyl)benzofuran-3-carboxylate (800 mg, 58%) as a red solid. TLC system: 20% Ethyl acetate in pet-ether; Rf: 0.5.

Step 6: To a stirred solution of ethyl 2-methyl-5-(((2-(trifluoromethyl)pyridin-3-yl)oxy)methyl)benzofuran-3-carboxylate) (800 mg, 2.110 mmol) in ethanol:THF (1:1) (40 mL) was added a solution of NaOH (253 mg, 6.332 mmol) dissolved in water (10 mL) and the resulting reaction mixture was maintained under stirring at 60° C. for 1 h. The reaction progress was monitored by TLC. The reaction mixture was cooled to room temperature and poured into ice cold water (100 mL), acidified with 1 N HCl to pH~5.0 and extracted with ethyl acetate (2×100 mL). The combined organic layer was washed with water (100 mL) followed by brine (100 mL), dried over anhydrous $Na_2SO_4$ and concentrated under reduced pressure to afford 2-methyl-5-(((2-(trifluoromethyl)pyridin-3-yl)oxy)methyl)benzofuran-3-carboxylic acid (800 mg, crude) as a red solid. TLC system: 10% MeOH in dichloromethane; Rf: 0.4. $[M+H]^+$ (m/z): 352.0.

Synthesis of 2,4-dimethyl-5-((2-(trifluoromethyl) pyridin-3-yl)methoxy)benzofuran-3-carboxylic acid (Cpd 251)

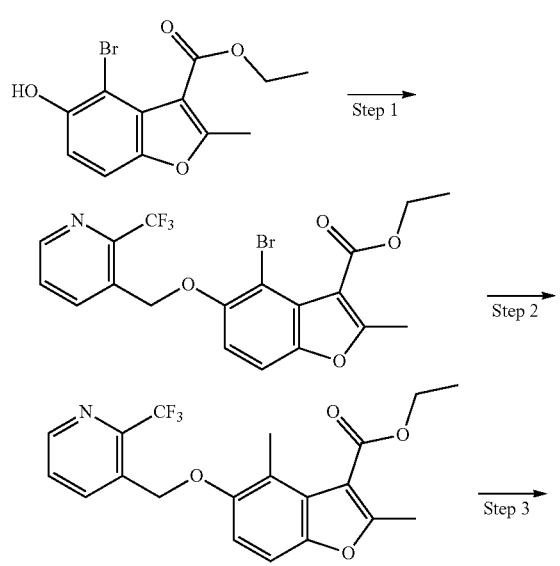

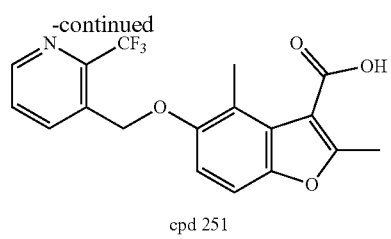

cpd 251

Step 1: 2-(Trifluoromethyl)pyridin-3-yl)methanol (0.887 mg, 5.01 mmol), ADDP (0.946 mg, 4.67 mmol) and tri-N-butylphosphine (1.18 g, 4.67 mmol) were added sequentially to a pre-stirred solution of ethyl 4-bromo-5-hydroxy-2-methylbenzofuran-3-carboxylate (1.0 g, 3.34 mmol) in THF (50 mL) at 0° C. under an argon atmosphere. The reaction mixture was warmed to room temperature and the stirred for 2 h. The reaction progress was monitored by TLC. The reaction mixture was poured into water (80 mL) followed by extraction with ethyl acetate (2×60 mL). The combined organic layers were sequentially washed with water (30 mL), brine (30 mL), were then dried over anhydrous $Na_2SO_4$ and concentrated under reduced pressure. The crude product was purified by column chromatography over silica gel (100-200 mesh) using 0-20% ethyl acetate in pet-ether as an eluent to afford ethyl 4-bromo-2-methyl-5-((2-(trifluoromethyl)pyridin-3-yl)methoxy)benzofuran-3-carboxylate (0.600 g, crude) as a pale yellow liquid. TLC system: 20% Ethyl acetate in pet-ether; Rf: 0.6.

Step 2: A suspension of ethyl 4-bromo-2-methyl-5-((2-(trifluoromethyl)pyridin-3-yl)methoxy)benzofuran-3-carboxylate (0.6 g, 1.31 mmol), methylboronic acid (0.157 g, 2.62 mmol) and $K_2CO_3$ (0.542 g, 3.93 mmol) in 1,4-dioxane:water (9:1) (10 mL) in a sealed tube was degassed with argon for 10 min and then $Pd(PPh_3)_4$ (0.151 g, 0.13 mmol) was added. The resulting reaction mixture was again degassed for 10 minutes and was then heated to 120° C. for 16 h. The reaction progress was monitored by LC-MS. The reaction mixture was cooled to room temperature and filtered through a celite pad, the celite pad was washed with ethyl acetate (2×30 mL). The combined filtrate was dried over anhydrous $Na_2SO_4$ and evaporated in vacuo. The crude product was purified by flash column chromatography over silica gel (100-200 mesh) using 0-20% ethyl acetate in pet-ether as an eluent to afford ethyl 2,4-dimethyl-5-((2-(trifluoromethyl)pyridin-3-yl)methoxy)benzofuran-3-carboxylate (0.5 g, 71%) as a colorless liquid. TLC system: 20% Ethyl acetate in pet-ether; Rf: 0.7.

Step 3: A solution of NaOH (0.203 g, 5.08 mmol) in water (4 mL) was added to a pre-stirred solution ethyl 2,4-dimethyl-5-((2-(trifluoromethyl)pyridin-3-yl)methoxy)benzofuran-3-carboxylate (0.5 g, 1.27 mmol) in a mixture of methanol:THF (1:1) (14 mL) and the resulting reaction mixture was heated to 60° C. for 4 h. The reaction progress was monitored by TLC. The reaction mixture was cooled and poured into ice cold water (30 mL) and was acidified with 1 N HCl to pH~2. The crude product was extracted with ethyl acetate (2×50 mL). The combined organic layer was washed with water (30 mL), brine (30 mL), dried over anhydrous $Na_2SO_4$ and concentrated under reduced pressure to afford 2,4-dimethyl-5-((2-(trifluoromethyl)pyridin-3-yl)methoxy)benzofuran-3-carboxylic acid (0.350 g, 65%) as an off-white solid. This crude product was used for next step without any further purification. TLC system: 50% Ethyl acetate in pet-ether; Rf: 0.3. $[M+H]^+$ (m/z): 366.1

Synthesis of 2-cyclopropyl-5-((4-methylthiazol-5-yl)methoxy)benzofuran-3-carboxylic acid (Cpd 265)

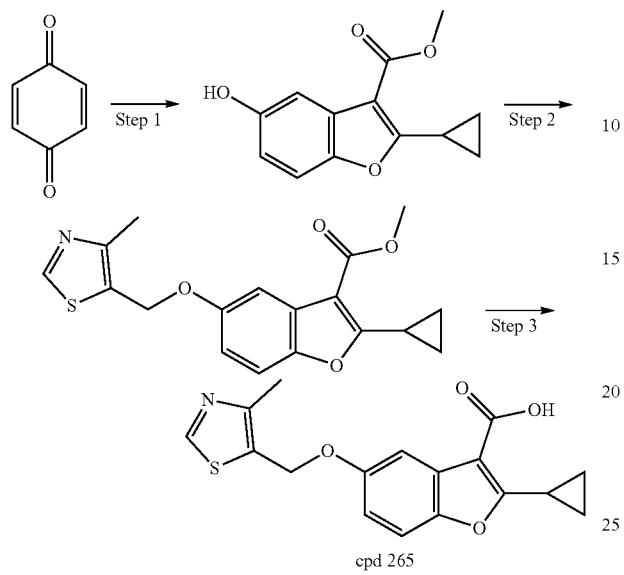

cpd 265

Step 1: To a stirred solution of benzoquinone (1.5 g, 13.8 mmol) in IPA (50 ml) was added $ZnCl_2$ (9.4 g, 69.44 mmol) followed by the addition of methyl 3-cyclopropyl-3-oxopropanoate (7.8 g, 55.55 mmol) at RT. The reaction mixture was stirred for 6 h at reflux, the reaction progress was monitored by TLC. Ice cold water was added to the reaction mixture and the mixture was then extracted with ethyl acetate (2×300 mL). The combined extracts were washed with brine (100 mL), dried over anhydrous $Na_2SO_4$ and concentrated under reduced pressure to get the crude material (3 g). The crude material was purified by column chromatography using silica gel (100-200 mesh) and 20% ethyl acetate in pet ether as an eluent to afford methyl 2-cyclopropyl-5-hydroxybenzofuran-3-carboxylate (800 mg, 74%) as a brown solid. TLC system: 50% ethyl acetate in pet-ether; RF: 0.63.

Step 2: To a stirred solution of methyl 2-cyclopropyl-5-hydroxybenzofuran-3-carboxylate (300 mg, 1.29 mmol) in $CH_3CN$ (25 mL) was added $Cs_2CO_3$ (1.2 g, 3.87 mmol) followed by the addition of (4-methylthiazol-5-yl) methyl methanesulfonate (370 mg, 1.93 mmol) at 0° C. under an argon atmosphere. The reaction mixture was stirred for 16 h at 50° C. The reaction progress was monitored by TLC. Solvents were removed, ice cold water was added to the reaction mixture and the mixture was extracted with ethyl acetate (2×100 mL). The combined extracts were washed with brine (50 mL), dried over anhydrous $Na_2SO_4$ and concentrated under reduced pressure to get the crude material (400 mg). The crude was purified by column chromatography using silica gel (100-200 mesh) and 25% ethyl acetate in pet ether as an eluent to afford methyl 2-cyclopropyl-5-((4-methylthiazol-5-yl) methoxy) benzofuran-3-carboxylate (200 mg, 45%) as a brown solid. TLC system: 50% ethyl acetate in pet-ether; RF: 0.42.

Step 3: To a stirred solution of methyl 2-cyclopropyl-5-((4-methylthiazol-5-yl) methoxy) benzofuran-3-carboxylate (200 mg, 0.583 mmol) in MeOH & THF (1:1, 10 ml) was added 2N NaOH (4 ml) at 0° C., then the reaction mixture was stirred for 4 h at 50° C. Reaction progress was monitored by TLC. The reaction mixture was concentrated, acidified to pH ~2 with 1 N aq HCl and extracted with ethyl acetate (3×50 mL). The combined extracts were washed with brine (20 ml), dried over anhydrous $Na_2SO_4$, filtered, and concentrated under reduced pressure to get crude 2-cyclopropyl-5-((4-methylthiazol-5-yl) methoxy) benzofuran-3-carboxylic acid (120 mg, crude) as an off-white solid. $[M+H]^+$ (m/z): 330.1

The following compounds were prepared in a manner similar (use of appropriate reagents and purification methods known to the person skilled in the art) to cpd 265:

| Cpd. Nr. | $[M + H]^+$ (m/z) |
|---|---|
| 231 | 378.1 |

Synthesis of tert-butyl 3-(((3-(ethoxycarbonyl)-2-methylbenzofuran-5-yl)oxy)methyl)pyrrolidine-1-carboxylate (cpd 079), 5-((1-(tert-butoxycarbonyl)pyrrolidin-3-yl)methoxy)-2-methylbenzofuran-3-carboxylic acid (Cpd 019) and 2-methyl-5-(pyrrolidin-3-ylmethoxy)benzofuran-3-carboxylic acid (Cpd 003)

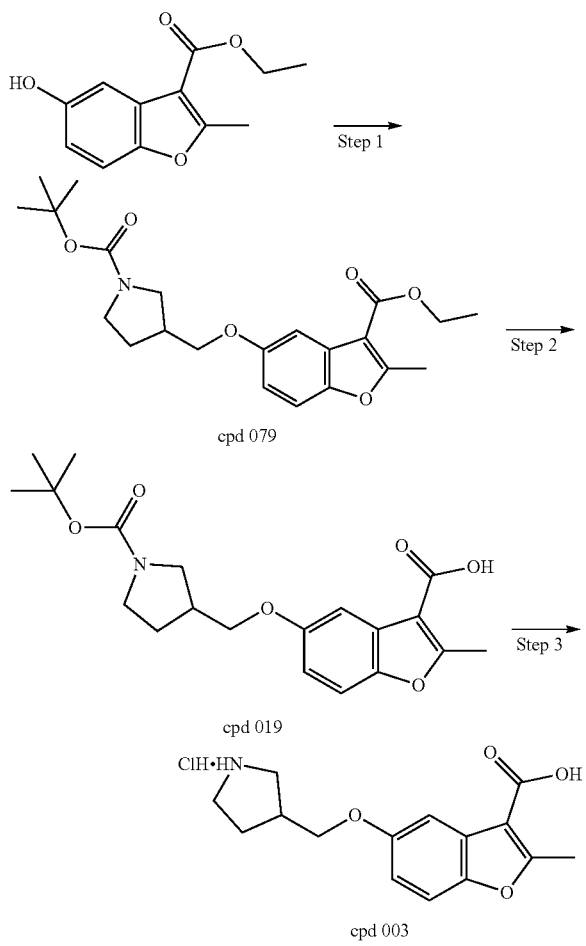

cpd 079 cpd 019 cpd 003

Step 1: To a cold solution of ethyl 5-hydroxy-2-methylbenzofuran-3-carboxylate (0.110 g; 0.5 mmol), tert-butyl 3-(hydroxymethyl)pyrrolidine-1-carboxylate (0.148 g; 0.75 mmol) and PS—PPh₃ (loading ~1.83 mmol/g; 0.546 g; 1 mmol) in THF (4 mL by mmol of ethyl 5-hydroxy-2-methylbenzofuran-3-carboxylate) was slowly added a solution of DIAD (0.148 mL; 0.75 mmol) in THF (0.4 mL). The RM was stirred at RT for 18 h and the volatiles were removed under reduced pressure. The crude material was purified by FCC on silica gel using a gradient of DCM (0% to 100%) in heptane to furnish 0.057 g (28%) of tert-butyl 3-(((3-(ethoxycarbonyl)-2-methylbenzofuran-5-yl)oxy)methyl)pyrrolidine-1-carboxylate (cpd 079).

Step 2: To a solution of tert-butyl 3-(((3-(ethoxycarbonyl)-2-methylbenzofuran-5-yl)oxy)methyl)pyrrolidine-1-carboxylate (cpd 079) (0.057 g; 0.141 mmol) in a mixture of MeOH-EtOH (2:1; 4.2 mL) was added an aq. solution of NaOH (1 N; 4.2 mL; 4.2 mmol) and the RM was heated under reflux for 18 h. After cooling, the volatiles were removed under reduced pressure and the remaining residue was solubilized in water. The mixture was acidified with an aq. solution of HCl (6 N) until pH~2. The white precipitate was washed with water and dried under high vacuum to furnish 0.052 g (98%) of 5-((1-(tert-butoxycarbonyl)pyrrolidin-3-yl)methoxy)-2-methylbenzofuran-3-carboxylic acid (cpd 019).

Step 3: To a solution of 5-((1-(tert-butoxycarbonyl)pyrrolidin-3-yl)methoxy)-2-methylbenzofuran-3-carboxylic acid (cpd 019) (0.050 g; 0.133 mmol) in THF (1 mL) was added a solution of HCl (4 N in dioxane; 1 mL) and the RM was stirred for 18 h. The volatiles were removed under reduced pressure and the remaining residue was dried under high vacuum to furnish 0.029 g (70%) of 3-(((3-carboxy-2-methylbenzofuran-5-yl)oxy)methyl)pyrrolidin-1-ium chloride (cpd 003).

Cpd 015 was prepared in a manner similar (use of appropriate reagents and purification methods known to the person skilled in the art) to cpd 019.

Synthesis of 2-methyl-N-(1-methylpiperidin-4-yl)-5-((5-(trifluoromethyl)furan-2-yl)methoxy)benzofuran-3-carboxamide (Cpd 069)

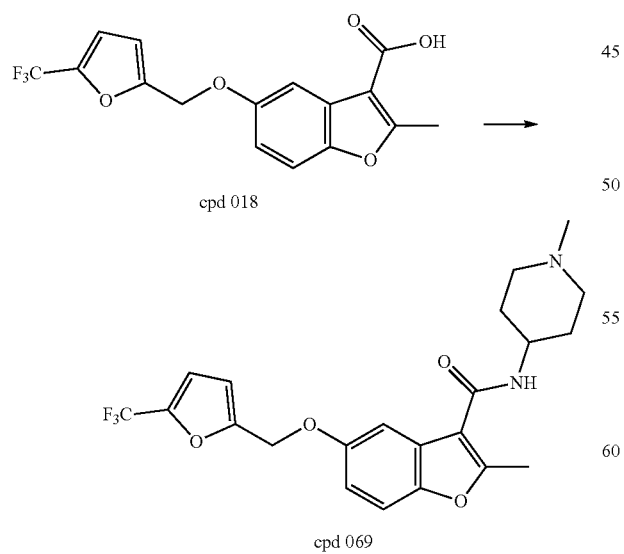

Step 1: HATU (235 mg; 0.62 mmol) was added to a solution of 2-methyl-5-((5-(trifluoromethyl)furan-2-yl)methoxy)benzofuran-3-carboxylic acid (cpd 018) (140 mg; 0.41 mmol) and DIPEA (0.21 mL; 1.2 mmol) in DCM (5 mL). After 4 h at RT, 1-methylpiperidin-4-amine (I-7) (59 mg; 0.51 mmol) was added and the RM was stirred overnight. The RM was then diluted with DCM and washed successively with a sat. solution of sodium hydrogen carbonate and brine. The organic layer was dried over magnesium sulfate and filtered. The volatiles were removed under reduced pressure and the crude material was purified by FCC on silica gel using a gradient of MeOH (0% to 20%) in DCM to afford 128 mg (71%) of 2-methyl-N-(1-methylpiperidin-4-yl)-5-((5-(trifluoromethyl)furan-2-yl)methoxy)benzofuran-3-carboxamide (cpd 069).

The following compounds were prepared in a manner similar (use of appropriate reagents and purification methods (including chiral HPLC or chiral SFC) known to the person skilled in the art) to cpd 069:

Cpd 037, 039, 047, 049, 052, 054, 058, 059, 060, 061, 072, 078, 097, 098, 104, 107, 109, 117, 119, 128, 129, 132-En1, 132-En2, 133, 135-En1, 135-En 1, 139, 142, 143, 146, 148-En1, 148-En2, 150, 152, 154, 156, 158, 159-En1, 159-En2, 161, 167, racemic 170, 171, 178, 181, 192, 200, racemic 203, 204, 206, 270-En 1, 270-En 2, 274, 275, 308, 309, 312, 314, 315-En 1, 315-En 2, 316-En 1, 316-En 2, 317-En 1, 317-En 2, 322, 323, 331, 334, 337, 339, 341, 343, 344, 345, 346, 351, 352, 357, 358, 359, 370, 371, 372, 373, 374, 384, 385, 390, 391, 392, 393, 394, 399, 400, 401-En 1, 401-En 2, 414, 415, 416, 417, 418, 419, 420, 421, 422, 423, 424, 425, 426, 427, 428, 429, 430, 431, 481, 482, 483, 484, 485, 486, 489-En 1, 489-En 2, 490-En 1, 490-En 2, 491-En 1, 491-En 2, 492, 493, 494, 495, 496, 497, 498, 499, 500, 501, 504, 505, 506, 507, 523, 524, 525, 526, 527, 528, 529, 531-En 1, 531-En 2, 532-En 1, 532-En 2, 533-En 1, 533-En 2, 534-En 1, 534-En 2, 535-En 1, 535-En 2, 536-En 1, 536-En 2, 537, 574, 576, 602, 603, 606, 607, 608, 609, 610, 611, 612, 613, 614, 615, 616, 617, 618, 619, 620, 621, 622, Cpd 623-En 1, Cpd 623-En 2, 624, 625, 626, 627, 628, 629, 630, 631, 632, 633, 634, 641-En1, 641-En2, 642-En1, 642-En2, 643-En1, 643-En2, 646-En1, 646-En 2, 647-En 1, 647-En 2, 648-En 1, 648-En 2, 649, 651, 652, 659, 660, 661-En 1, 661-En 2, 664, 665, 666, 668, 670, 672, 674, 676, 678, 680, 682, 683, 684, 685, 686, 688, 690, 692, 694, 695, 696, 697, 698, 700, 702, 704, 705, 706, 708, 710, 711, 712, 714, 715, 716, 718, 721, 722-En 1, 722-En 2, 723-En 1, 723-En 2, 724-En 1, 724-En 2, 726-En 1, 726-En 2, 727-En 1, 727-En 2, 727-En 3, 727-En 4, 738-En 1, 738-En 2, 739-En1, 739-En2, 741

Synthesis of 2-methyl-N-(2-oxopyrrolidin-3-yl)-5-(thiophen-3-ylmethoxy)benzofuran-3-carboxamide (Cpd 035)

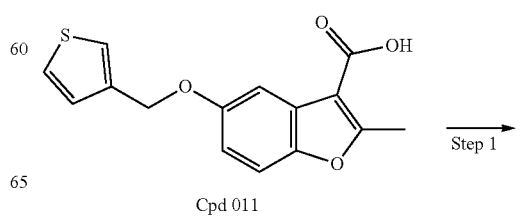

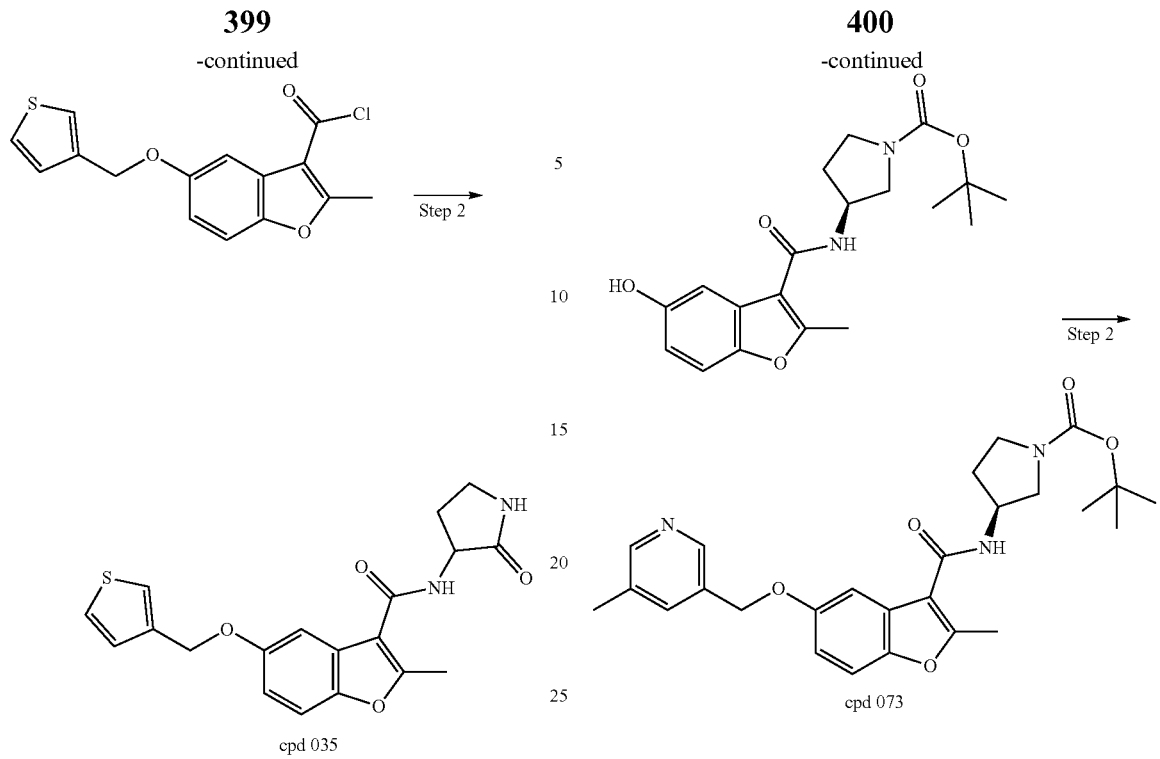

cpd 035

Step 1: Oxalyl chloride (0.300 mL; 2.96 mmol) and DMF (2 drops) were added to a mixture of 2-methyl-5-(thiophen-3-ylmethoxy)benzofuran-3-carboxylic acid (Cpd 011) (100 mg; 0.35 mmol) in DCM (5 mL). The resulting mixture was stirred for 4 h. The RM was concentrated under reduced pressure to afford 2-methyl-5-(thiophen-3-ylmethoxy)benzofuran-3-carbonyl chloride.

Step 2: A solution of 2-methyl-5-(thiophen-3-ylmethoxy)benzofuran-3-carbonyl chloride dissolved in DCM (3 mL) was added to a mixture of 3-aminopyrrolidin-2-one (0.052 g; 0.520 mmol) and DIPEA (0.121 mL; 0.520 mmol). The RM was stirred at RT for 18 h. The solid formed was filtered off and purified by FCC on silica gel using a gradient of MeOH (0% to 20%) in DCM to afford 0.023 g (18%) 2-methyl-N-(2-oxopyrrolidin-3-yl)-5-(thiophen-3-ylmethoxy)benzofuran-3-carboxamide (cpd 035).

The following compounds were prepared in a manner similar (use of appropriate reagents and purification methods known to the person skilled in the art) to cpd 035:

Cpd 036, 080, 081, 082, 083, 084 and 085.

Synthesis of tert-butyl (S)-3-(2-methyl-5-((5-methylpyridin-3-yl)methoxy)benzofuran-3-carboxamido)-pyrrolidine-1-carboxylate (Cpd 073)

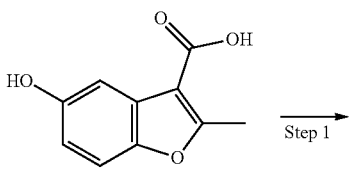

Step 1: Tert-butyl (S)-3-aminopyrrolidine-1-carboxylate (1.1 g; 5.7 mmol) was added to a solution of 5-hydroxy-2-methylbenzofuran-3-carboxylic acid (1 g; 5.2 mmol), HATU (1.98 g; 5.2 mmol) and DIPEA (2.7 mL; 15.6 mmol) in DMF (10 mL). After 60 h, the reaction was concentrated under reduced pressure. The residue was partitioned between water and EtOAc. After separation, the aq. layer was extracted twice with EtOAc. Combined EtOAc extracts were dried over magnesium sulphate, filtered, and concentrated under reduced pressure. The residue was purified by FCC on silica gel using a gradient of MeOH (0 to 6%) in DCM to afford 0.94 g (50%) of tert-butyl-(S)-3-(5-hydroxy-2-methylbenzofuran-3-carboxamido)pyrrolidine-1-carboxylate. M/Z(+): 361 (M+H). M/Z(−): 359 (M−H). $^1$H NMR (DMSO-d$_6$, 300 MHz) δ ppm: 9.26 (s, 1H), 8.17 (d, J=6.4 Hz, 1H), 7.32 (d, J=9.0 Hz, 1H), 6.99 (d, J=1.88 Hz, 1H), 6.70 (dd, J=8.9, 2.1 Hz, 1H), 4.35-4.50 (m, 1H), 3.51-3.3.65 (m, 1H), 3.35-3.49 (m, 1H), 3.15-3.31 (m, 1H), 2.53 (s., 3H), 2.02-2.19 (m, 1H), 1.84-1.99 (m, 1H), 1.41 (s, 9H).

Step 2: Tributylphosphine (0.155 mL; 0.583 mmol) was added dropwise to a stirred mixture of tert-butyl-(S)-3-(5-hydroxy-2-methylbenzofuran-3-carboxamido)pyrrolidine-1-carboxylate (0.150 g; 0.416 mmol), (5-methylpyridin-3-yl)methanol (0.081 g; 0.624 mmol) and ADDP (0.150 g; 0.583 mmol) in dry THF (5 mL) under argon. The mixture was stirred for 2 h and then the reaction was concentrated under reduced pressure. The residue was purified twice by FCC on silica gel using a gradient of MeOH (0-6%) in DCM for the first time and a gradient of MeOH (0-4%) in EtOAc for the second time to afford 0.113 g (58%) of tert-butyl (S)-3-(2-methyl-5-((5-methylpyridin-3-yl)methoxy)benzofuran-3-carboxamido)pyrrolidine-1-carboxylate (cpd 073).

The following compounds were prepared in a manner similar (use of appropriate reagents and purification methods known to the person skilled in the art) to cpd 073:

Cpd 026, 027, 030, 031, 032, 033, 034, 038, 040, 042, 043, 044, 046, 051, 057, 064, 065, 066, 077, 078; 086; 087; 088; 089; 090; 091; 092; 093; 094; 095 and 096.

401

(S)-2-methyl-5-((5-methylpyridin-3-yl)methoxy)-N-(pyrrolidin-3-yl)benzofuran-3-carboxamide (Cpd 028)

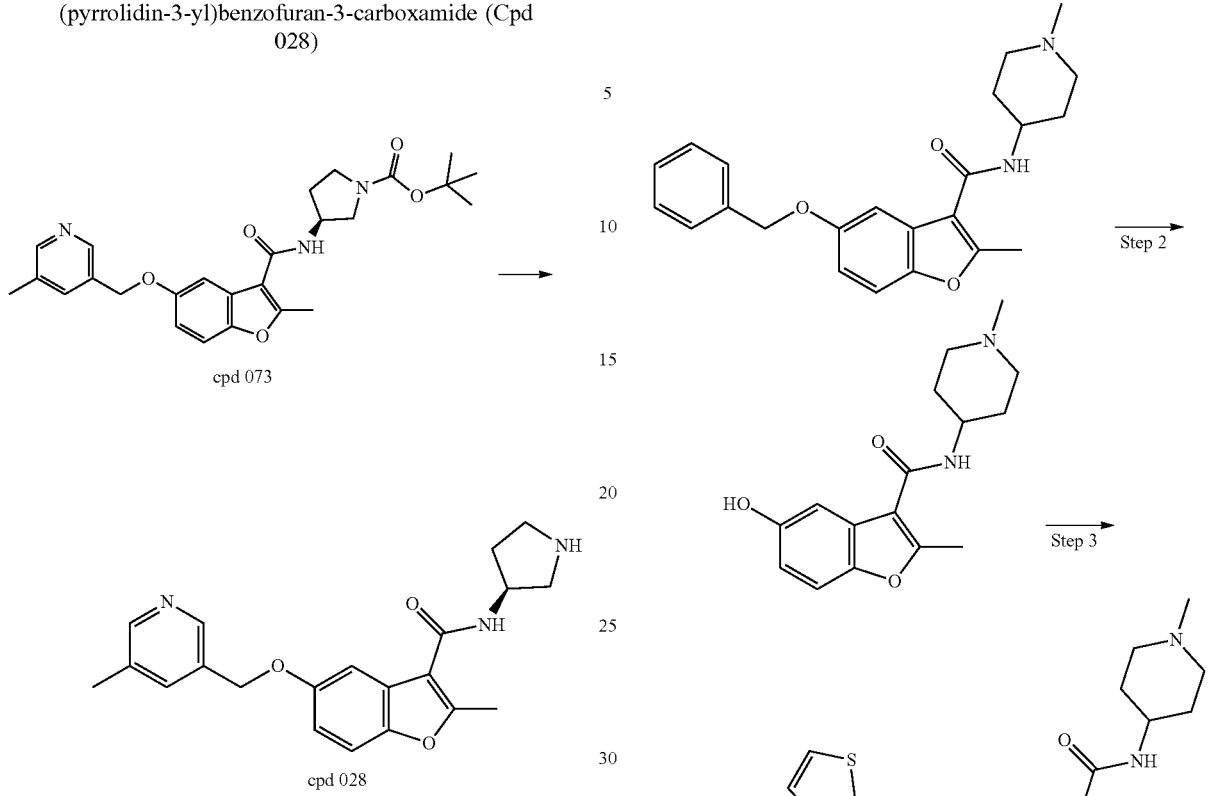

cpd 073 cpd 028

A solution of hydrogen chloride in 1,4-dioxane (4 M; 4 mL; 16 mmol) was added to a solution of tert-butyl (S)-3-(2-methyl-5-((5-methylpyridin-3-yl)methoxy)benzofuran-3-carboxamido)pyrrolidine-1-carboxylate (cpd 073) (0.105 g; 0.22 mmol) in DCM (3 mL). The mixture was stirred overnight at RT and was concentrated under reduced pressure. The residue was then purified by column of supported SiliaBond-PropylSulfonic Acid using a gradient of a solution of 3N ammonia in MeOH (0-100%) in DCM to afford 78 mg (95%) of (S)-2-methyl-5-((5-methylpyridin-3-yl)methoxy)-N-(pyrrolidin-3-yl)benzofuran-3-carboxamide (cpd 028).

The following compounds were prepared in a manner similar (use of appropriate reagents and purification methods known to the person skilled in the art) to cpd 028:

Cpd 020, 021, 022, 023, 034, 025, 029, 048, 050, 053, 055, 056, 062, 063, 067, 068, 070, 071, 074, 075 and 076.

Synthesis of 2-methyl-N-(1-methylpiperidin-4-yl)-5-(thiophen-2-ylmethoxy)benzofuran-3-carboxamide (Cpd 041)

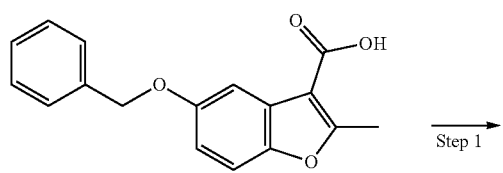

402

-continued

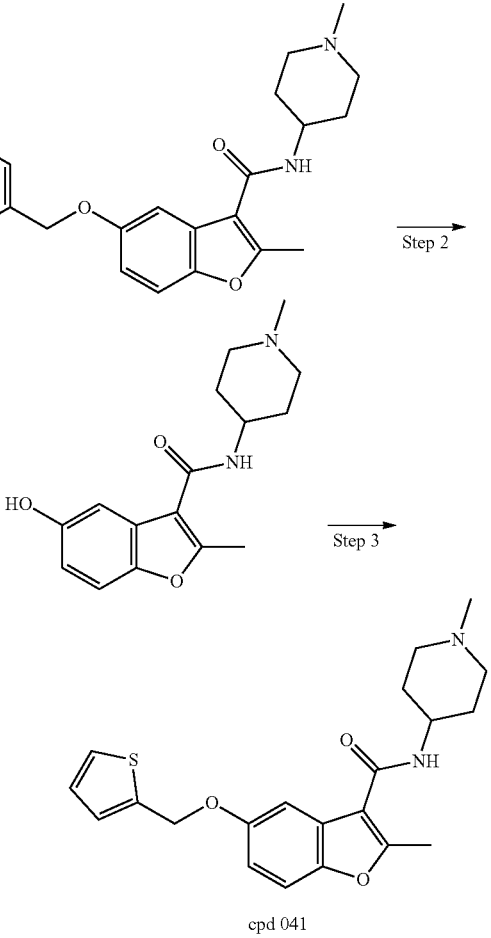

cpd 041

Step 1: 5-(Benzyloxy)-2-methylbenzofuran-3-carboxylic acid (2.6 g; 9.2 mmol), HATU (5.2 g; 13.8 mmol; 1.5) and DIPEA (4.8 mL; 27.6 mmol) were dissolved in DCM (50 mL). After 4 h of stirring at RT, 1-methylpiperidin-4-amine (1.2 mL; 9.7 mmol) was added and the RM was stirred at RT overnight. The RM was diluted in 80 mL of DCM and washed with a sat. solution of sodium hydrogen carbonate and brine. The solvent was removed under reduced pressure. The residue was purified by FCC on silica gel using a gradient of MeOH (0-20%) in DCM to afford 1.4 g (48%) of 5-(benzyloxy)-2-methyl-N-(1-methylpiperidin-4-yl)benzofuran-3-carboxamide. H NMR (DMSO $d_6$, 300 MHz) δ ppm 7.89 (d, 1H); 7.50-7.29 (m, 6H); 7.22 (d, 1H); 6.96 (dd, 1H); 5.13 (s, 2H); 3.85-3.65 (m, 1H); 2.75 (br d, 2H); 2.56 (s, 3H); 2.16 (s, 3H); 1.98 (ddd, 2H); 1.85-1.74 (m, 2H); 1.67-1.51 (m, 2H).

Step 2: A suspension of 5-(benzyloxy)-2-methyl-N-(1-methylpiperidin-4-yl)benzofuran-3-carboxamide (500 mg; 1.32 mmol) and Pd/C (70 mg, 0.065 mmol) in THF (13 mL) was stirred at RT under an atmospheric pressure of hydrogen until disappearance of the starting material. The RM was then filtered through a pad of Celite and the filtrate was evaporated under reduced pressure to afford 350 mg (92%) of 5-hydroxy-2-methyl-N-(1-methylpiperidin-4-yl)benzofuran-3-carboxamide, which was used without further purification. $^1$H NMR (DMSO $d_6$, 300 MHz) δ (ppm): 9.25 (s, 1H); 7.84 (d, 1H); 7.31 (d, 1H); 6.99 (d, 1H); 6.69 (dd, 1H); 3.80-3.65 (m, 1H); 2.80-2.70 (m, 2H); 2.52 (s, 3H); 2.16 (s, 3H); 2.04-1.89 (m, 2H); 1.84-1.74 (m, 2H); 1.58 (ddd, 2H).

Step 3: To a cold solution of 5-hydroxy-2-methyl-N-(1-methylpiperidin-4-yl)benzofuran-3-carboxamide (75 mg, 0.26 mmol), thiophen-2-ylmethanol (45 mg; 0.39 mmol) and PS—PPh₃ (1.8 mmol/g; 289 mg; 0.52 mmol) in THF (3 mL) was slowly added a solution of DIAD (75 μL; 0.39 mmol) in THF (0.8 mL). The RM was stirred at RT for 18 h and the volatiles were removed under reduced pressure. The crude material was purified by preparative HPLC (method H1) to furnish 8 mg (8%) of 2-methyl-N-(1-methylpiperidin-4-yl)-5-(thiophen-2-ylmethoxy)benzofuran-3-carboxamide (cpd 041).

Cpd 045 was prepared in a manner similar (use of appropriate reagents and purification methods known to the person skilled in the art) to cpd 041.

Synthesis of N-(4,4-difluoropyrrolidin-3-yl)-2-methyl-5-((2-(trifluoromethyl)pyridin-3-yl)methoxy)benzofuran-3-carboxamide (Cpd 105)

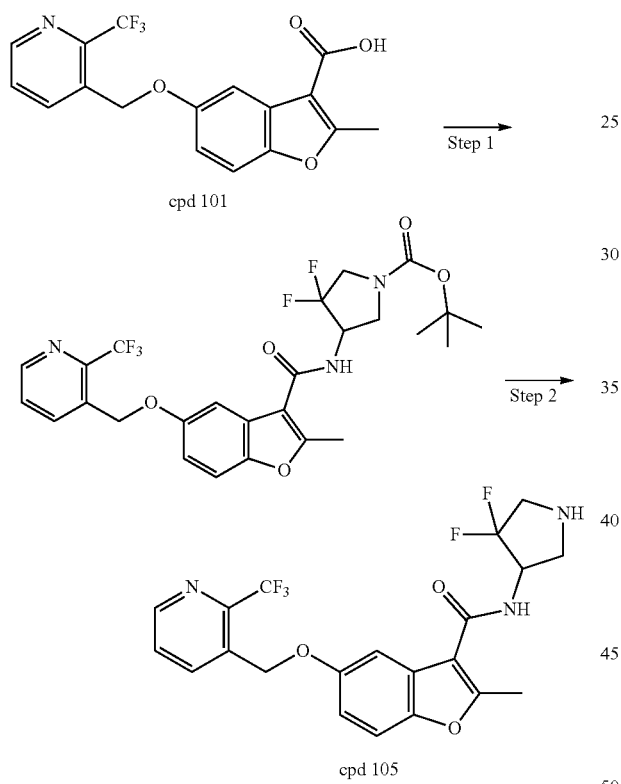

Step 1: To a stirred solution cpd 101 (250 mg, 0.71 mmol) in DCM (50 mL), DIPEA (0.3 mL, 1.78 mmol), HATU (297 mg, 0.78 mmol) and tert-butyl 4-amino-3,3-difluoropyrrolidine-1-carboxylate (237 mg, 1.07 mmol) in DCM (1 mL) were added at RT. The RM was stirred for 18 h. Reaction progress was monitored by TLC. After completion of the reaction, the RM was diluted with DCM (300 mL), washed with sat. NaHCO₃ (50 mL), water (2×50 mL) and brine solution (50 mL), dried over anhydrous Na₂SO₄, filtered and concentrated. The residue was purified by Grace FCC using eluent 50% EtOAc-Pet ether to afford tert-butyl 3,3-difluoro-4-(2-methyl-5-((2-(trifluoromethyl)pyridin-3-yl)methoxy)benzofuran-3-carboxamido)pyrrolidine-1-carboxylate (350 mg, 88%).

Step 2: To a stirred solution of tert-butyl 3,3-difluoro-4-(2-methyl-5-((2-(trifluoromethyl)pyridin-3-yl)methoxy) benzofuran-3-carboxamido)pyrrolidine-1-carboxylate (350 mg, 0.63 mmol) in DCM (20 ml), TFA (1 mL) was added at 0° C. The RM was stirred for 18 h at RT. Reaction progress was monitored by TLC. The RM was concentrated and diluted with DCM (300 mL), washed with sat. NaHCO₃ (2×50 mL) and brine solution (50 mL), dried over anhydrous Na₂SO₄, filtered and concentrated. The residue was triturated with Et₂O (10 mL) to afford cpd 105 (250 mg, 77% over 2 steps). A preparative chiral SFC was performed to provide cpd 105-En 1 and cpd 105-En 2.

The following compounds were prepared in a manner similar (use of appropriate reagents and purification methods known to the person skilled in the art) to cpd 105:

Cpd 103-En1, 103-En2, 106-En1, 106-En2, 111-En1, 111-En2, 115-En1, 115-En2, 125-En1, 125-En2, 205-En1, 205-En2, 207-En1, 207-, En2, 173, 189, 190, 310-En 1, 310-En 2, 313-En 1, 313-En 2, 336-En 1, 336-En 2, 338-En 1, 338-En 2, 342-En 1, 342-En 2, 538-En 1, 539-En 1, 539-En 2, 540-En 1, 540-En 2, 541-En 1, 541-En 2, 542-En 1, 542-En 2, 543-En 1, 543-En 2, 544-En 1, 544-, En2, 545-, En1, 545-, En2, 546-, En1, 547-, En1, 547-, En2, 548-, En1, 548-, En2, 549-, En1, 549-En 2, 550-En 1, 550-En 2, 551-En 1, 551-En 2, 552-En 1, 552-En 2, 553-En 1, 553-En 2, 554-En 1, 554-En 2, 555-En 1, 555-En 2, 556-En 1, 556-En 2, 557-En 1, 557-En 2, 558-En 1, 558-En 2, 559-En 1, 559-En 2, 560-En 1, 560-En 2, 561-En 1, 561-En 2, 562-En 1, 562-En 2, 563-En 1, 563-En 2, 564-En 1, 564-En 2, 565-En 1, 565-En 2, 566-En 1, 566-En 2, 567-En 1, 567-En 2, 568-En 1, 568-En 2, 569-En 1, 569-En 2, 570-En 1, 570-En 2, 571-En 1, 571-En 2, 572-En 1, 572-En 2, 573-En 1, 573-En 2, 635-En 1, 635-En 2, 636-En 1, 636-En 2, 637-En 1, 637-En 2, 638-En 1, 638-En 2, 639-En 1, 639-En 2, 663, 717.

Synthesis of N-(1-((dimethylamino)methyl)cyclobutyl)-2-methyl-5-((4-methylthiazol-5-yl)methoxy)benzofuran-3-carboxamide (Cpd 108)

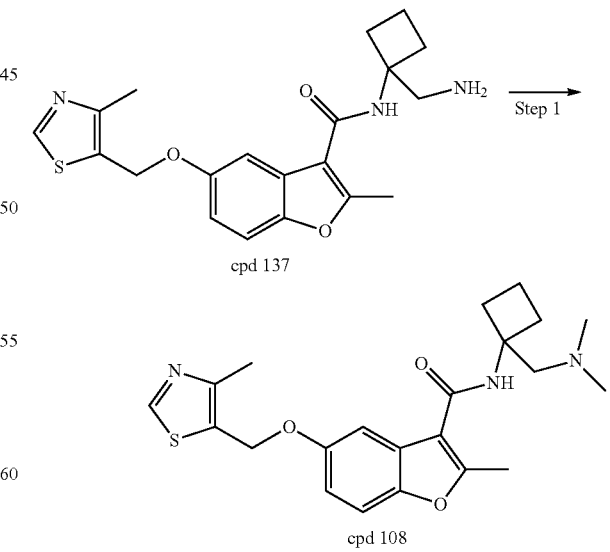

Step 1: 37% Formaldehyde in water (0.21 mL, 2.5 mmol) was added to a pre-stirred solution of cpd 137 (100 mg, 0.26 mmol) in MeOH (10 mL) at 0° C. under argon atmosphere.

Then, glacial acetic acid (2 drops) and NaCNBH$_3$ (32.6 mg, 0.51 mmol) were added to the reaction. The RM was allowed to attain RT and stirred for 16 h. The reaction progress was monitored by TLC. The RM was poured into water (25 mL) and extracted with EtOAc (3×25 mL). The combined organic layer was washed with sat. NaHCO$_3$ (25 mL), water (25 mL) and brine (25 mL), dried over Na$_2$SO$_4$ and excess solvent was removed under reduced pressure. The crude product was purified by flash chromatography using 0-50% acetonitrile in 0.1% FA as an eluent followed by reverse phase prep-HPLC to afford cpd 108 (55 mg, 51%).

Cpd 140 was prepared in a manner similar (use of appropriate reagents and purification methods known to the person skilled in the art) to cpd 108:

Synthesis of N-(3,3-difluoropiperidin-4-yl)-4-fluoro-2-methyl-5-((2-(trifluoromethyl)pyridin-3-yl)methoxy)-benzofuran-3-carboxamide (Cpd 112)

an eluent followed by reverse phase prep-HPLC to afford a mixture of ethyl 4-fluoro-2-methyl-5-((2-(trifluoromethyl)pyridin-3-yl)methoxy)benzofuran-3-carboxylate (300 mg, 8%) and ethyl 6-fluoro-2-methyl-5-((2-(trifluoromethyl)pyridin-3-yl)methoxy)benzofuran-3-carboxylate (400 mg, 11%).

Step 2: 2N NaOH (10 mL) was added to a solution of ethyl 4-fluoro-2-methyl-5-((2-(trifluoromethyl)pyridin-3-yl)methoxy)benzofuran-3-carboxylate (250 mg, 0.62 mmol) in a mixture of MeOH (15 mL) and THF (5 mL) at RT. The resulting RM was heated at 80° C. for 3 h. The reaction progress was monitored by TLC. The RM was cooled to RT, poured into ice cold water (50 mL) and acidified with 1 N HCl to pH~2. The crude product was extracted with EtOAc (3×50 mL), washed with water (100 mL), followed by brine (100 mL), dried over anhydrous Na$_2$SO$_4$ and concentrated under reduced pressure to afford 4-fluoro-2-methyl-5-((2-(trifluoromethyl)pyridin-3-yl)methoxy)benzofuran-3-carboxylic acid (220 mg, 95%). The crude product was used for next step without purification.

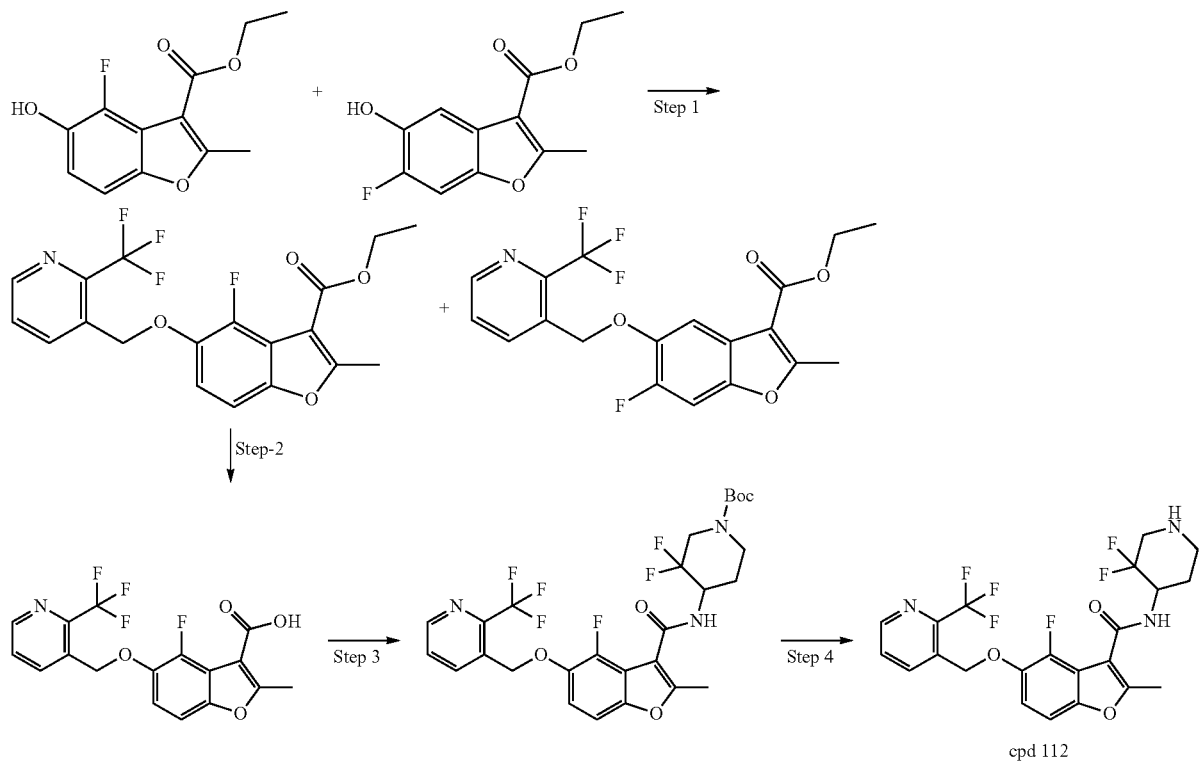

Step 1: 2-(Trifluoromethyl)pyridin-3-yl)methanol (2.23 g, 12.6 mmol), ADDP (2.96 g, 11.7 mmol) and tri-N-butylphosphine (2.37 g, 11.7 mmol) were added to a of mixture of ethyl 4-fluoro-5-hydroxy-2-methylbenzofuran-3-carboxylate and ethyl 6-fluoro-5-hydroxy-2-methylbenzofuran-3-carboxylate (2.0 g, 8.4 mmol) in THF (50 mL) at 0° C. under argon atmosphere. The RM was allowed to attain RT and was stirred for 3 h. The reaction progress was monitored by TLC. The RM was poured into water (100 mL) and extracted with EtOAc (3×100 mL). The combined organic layer was washed with brine (2×100 mL), dried over anhydrous Na$_2$SO$_4$ and concentrated under reduced pressure. The crude product was purified by column chromatography over silica gel using 10-20% EtOAc in pet-ether as Step 3: To a solution of a mixture of 4-fluoro-2-methyl-5-((2-(trifluoromethyl)pyridin-3-yl)methoxy)benzofuran-3-carboxylic acid (200 mg, 0.54 mmol) and tert-butyl 4-amino-3,3-difluoropiperidine-1-carboxylate (191 mg, 0.81 mmol) in DMF (15 mL) was added DIPEA (0.2 mL, 1.08 mmol) followed by HATU (412 mg, 1.08 mmol) at 0° C. under argon atmosphere. The RM was allowed to attain RT and stirred for 1 h. The reaction progress was monitored by TLC. The RM was diluted with ice cold water (50 mL) and filtered. The solid thus obtained was washed with water (50 mL) and dried under reduced pressure to afford tert-butyl 3,3-difluoro-4-(4-fluoro-2-methyl-5-((2-(trifluoromethyl)pyridin-3-yl)methoxy)benzofuran-3-carboxamido)piperidine-1-carboxylate (250 mg, 78%).

Step 4: 4M HCl in dioxane (5 mL) was added dropwise to a solution of tert-butyl 3,3-difluoro-4-(4-fluoro-2-methyl-5-((2-(trifluoromethyl)pyridin-3-yl)methoxy)benzofuran-3-carboxamido)piperidine-1-carboxylate (0.25 g, 0.42 mmol) in DCM (20 mL) at 0° C. under an argon atmosphere. The RM was warmed to RT and stirred for 5 h. The reaction progress was monitored by TLC. The excess solvents were evaporated in vacuo and the residue was cooled to 0° C., basified with sat. $NaHCO_3$ to pH ~9 and extracted with EtOAc (3×50 mL). The combined organic layer was washed with water (50 mL) and brine (50 mL), dried over anhydrous $Na_2SO_4$ and concentrated under reduced pressure to afford cpd 112 (200 mg, 96%). A preparative chiral SFC was performed on the racemic mixture of cpd 112 to afford cpd 112-En 1 and cpd 112-En 2.

Synthesis of N-(3,3-difluoropiperidin-4-yl)-6-fluoro-2-methyl-5-((2-(trifluoromethyl)pyridin-3-yl)methoxy)-benzofuran-3-carboxamide (Cpd 113) and N-(3,3-difluoropiperidin-4-yl)-7-fluoro-2-methyl-5-((2-(trifluoro-methyl)pyridin-3-yl)methoxy)benzo-furan-3-carboxamide (Cpd 176)

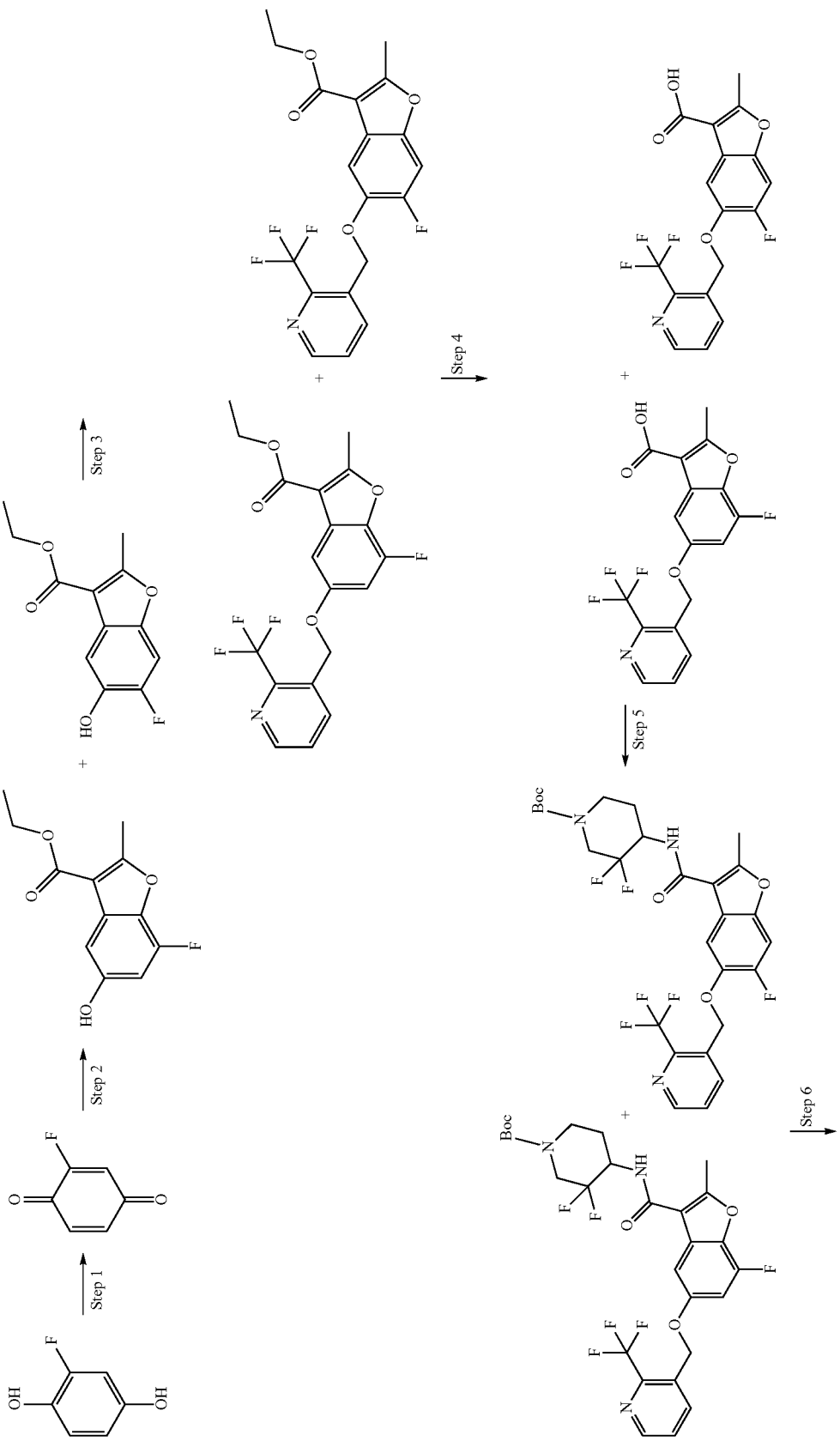

-continued
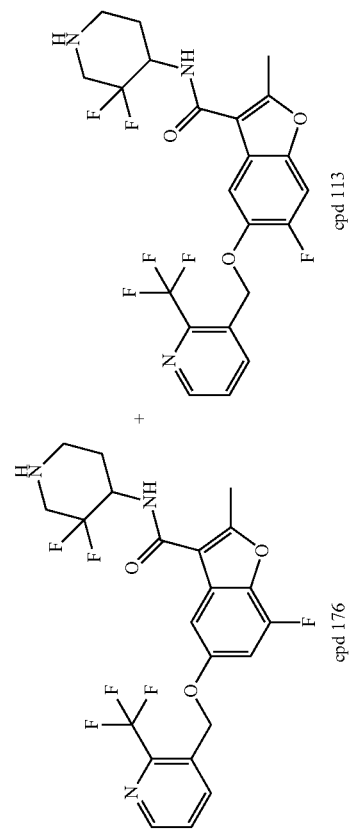

Step 1: To a pre-stirred solution of CAN (27.41 g, 50.00 mmol) in water (60 mL) was added 2-fluorobenzene-1,4-diol (3.0 g, 23.80 mmol) at 0° C. The resulting RM was stirred at RT for 4 h. The reaction progress was monitored by TLC. The organic compound was extracted with Et₂O (3×50 mL). The combined organic layer was washed with brine (50 mL), dried over anhydrous Na₂SO₄ and filtered. The clear filtrate was passed through a silica gel column, eluted with diethyl ether and the collected fractions were evaporated in vacuo to afford 2-fluorocyclohexa-2,5-diene-1,4-dione (2.5 g, 84%).

Step 2: To a pre-stirred solution of 2-fluorocyclohexa-2,5-diene-1,4-dione (2.5 g, 20.16 mmol) in toluene (30 mL) was added ethyl 3-oxobutanoate (7.86 g, 60.48 mmol) followed by anhydrous ZnCl₂ (3.29 g, 24.19 mmol) at RT under argon atmosphere. The resulting RM was heated to reflux and maintained at this temperature for 16 h using a Dean-Stark apparatus. The reaction progress was monitored by TLC. The RM was cooled to RT, filtered through a celite pad and the celite pad was washed with EtOAc (70 mL). The combined clear filtrate was concentrated under reduced pressure. The crude product was purified by FCC over silica gel using 0-10% EtOAc in pet-ether as an eluent to afford a mixture of ethyl 7-fluoro-5-hydroxy-2-methylbenzofuran-3-carboxylate and ethyl 6-fluoro-5-hydroxy-2-methylbenzofuran-3-carboxylate (0.8 g, 21%).

Step 3: (2-(Trifluoromethyl)pyridin-3-yl)methanol (1.11 g, 6.30 mmol), ADDP (1.48 g, 5.88 mmol) and tri-N-butylphosphine (1.38 mL, 5.88 mmol) were added sequentially to a pre-stirred solution of mixture of ethyl 6-fluoro-5-hydroxy-2-methylbenzofuran-3-carboxylate and ethyl 7-fluoro-5-hydroxy-2-methylbenzofuran-3-carboxylate (1.0 g, 4.20 mmol) in THF (30 mL) at RT under argon atmosphere. The RM was stirred for 2 h at the same temperature. The reaction progress was monitored by TLC. The RM was poured into water (100 mL) and extracted with EtOAc (2×100 mL). The combined organic layer was sequentially washed with water (50 mL) and brine (50 mL), dried over anhydrous Na₂SO₄ and concentrated under reduced pressure. The crude product was purified by column chromatography over silica gel using 0-20% EtOAc in pet-ether as an eluent to afford a mixture of ethyl 6-fluoro-2-methyl-5-((2-(trifluoromethyl)pyridin-3-yl)methoxy)benzofuran-3-carboxylate and ethyl 7-fluoro-2-methyl-5-((2-(trifluoromethyl)pyridin-3-yl)methoxy)benzofuran-3-carboxylate (1.1 g, 66%). The crude product was used for further step without purification.

Step 4: A solution of NaOH (0.44 g, 11.08 mmol) in water (8 mL) was added dropwise to a pre-stirred solution of a mixture of ethyl 6-fluoro-2-methyl-5-((2-(trifluoromethyl)pyridin-3-yl)methoxy)benzofuran-3-carboxylate and ethyl 7-fluoro-2-methyl-5-((2-(trifluoromethyl)pyridin-3-yl)methoxy)benzofuran-3-carboxylate (1.1 g, 2.77 mmol) in a mixture of MeOH (15 mL) and THF (7 mL) at RT. The resulting RM was heated to 60° C. and maintained for 4 h. The reaction progress was monitored by TLC. The RM was cooled to RT, poured into ice cold water (50 mL) and acidified with 1 N HCl to a pH~2. The crude product was extracted with EtOAc (2×50 mL). The combined organic layer was washed with water (50 mL) followed by brine (50 mL), dried over anhydrous Na₂SO₄ and concentrated under reduced pressure to afford a mixture of 6-fluoro-2-methyl-5-((2-(trifluoromethyl)pyridin-3-yl)methoxy)benzofuran-3-carboxylic acid and 7-fluoro-2-methyl-5-((2-(trifluoromethyl)pyridin-3-yl)methoxy)benzofuran-3-carboxylic acid (1.0 g, 99%). This crude product was used for next step without purification.

Step 5: To a pre-stirred solution of mixture of 6-fluoro-2-methyl-5-((2-(trifluoromethyl)pyridin-3-yl)methoxy)benzofuran-3-carboxylic acid and 7-fluoro-2-methyl-5-((2-(trifluoromethyl)pyridin-3-yl)methoxy)benzofuran-3-carboxylic acid (1.0 g, 2.71 mmol) and tert-butyl 4-amino-3,3-difluoropiperidine-1-carboxylate (0.74 g, 3.25 mmol) in DMF (20 mL) was added DIPEA (1.45 mL, 8.13 mmol) followed by HATU (2.05 g, 5.42 mmol) at 0° C. under an argon atmosphere. The RM was allowed to attain RT and stir for 16 h. The reaction progress was monitored by TLC. The RM was diluted with water (100 mL) and the organic compound was extracted with EtOAc (2×70 mL). The combined organic layer was washed with water (50 mL) and brine (50 mL), dried over anhydrous Na₂SO₄ and concentrated under reduced pressure. The crude product was purified by column chromatography over silica using 0-55% EtOAc and pet-ether as an eluent to afford a mixture of tert-butyl 3,3-difluoro-4-(6-fluoro-2-methyl-5-((2-(trifluoromethyl)pyridin-3-yl)methoxy)benzofuran-3-carboxamido)piperidine-1-carboxylate and tert-butyl 3,3-difluoro-4-(7-fluoro-2-methyl-5-((2-(trifluoromethyl)pyridin-3-yl)methoxy)benzofuran-3-carboxamido)piperidine-1-carboxylate (1.0 g, 62%).

Step 6: 4.0 M HCl in dioxane (13.62 mL, 13.62 mmol) was added dropwise to a pre-stirred solution of mixture of tert-butyl 4-(6-chloro-2-methyl-5-((2-(trifluoromethyl)pyridin-3-yl)methoxy)benzofuran-3-carboxamido)-3,3-difluoropiperidine-1-carboxylate and tert-butyl 4-(7-chloro-2-methyl-5-((2-(trifluoro-methyl)pyridin-3-yl)methoxy)benzofuran-3-carboxamido)-3,3-difluoropiperidine-1-carboxylate (1.0 g, 1.70 mmol) in DCM (15 mL) at 0° C. The RM was allowed to attain RT and stirred for 6 h. The reaction progress was monitored by TLC. The RM was concentrated under reduced pressure, the residue was basified with sat. NaHCO₃ (100 mL) and the organic compound was extracted with 10% MeOH in DCM (3×50 mL). The combined organic layer was washed with water (50 mL) and brine (50 mL), dried over anhydrous Na₂SO₄ and concentrated under reduced pressure. The crude product was purified by GRACE flash chromatography using 0-60% acetonitrile and 0.1% FA in water as an eluent to afford a mixture cpd 113 and cpd 176 (0.72 g, 87%). A preparative chiral SFC was performed on the mixture of racemic cpd 113 and racemic cpd 176 to provide cpd 113-En 1, cpd 113-En 2, cpd 176-En 1 and cpd 176-En 2.

The following compounds were prepared in a similar manner (use of appropriate reagents (chiral or racemic) and purification methods (including chiral HPLC or chiral SFC) known to the person skilled in the art) as described for the synthesis of cpd. 113 and cpd. 176: Cpd. 572-En 1, 572-En 2, 573-En 1, 573-En 2.

Synthesis of N-(1-(2-hydroxyethyl)cyclobutyl)-2-methyl-5-((4-methylthiazol-5-yl)methoxy)benzofuran-3-carboxamide (Cpd 114)

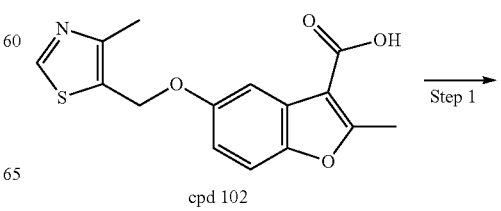

cpd 102

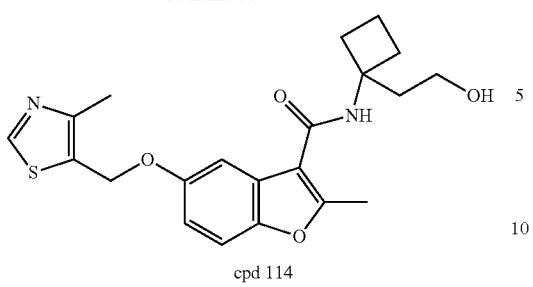

cpd 114

Step 1: To a pre-stirred solution of cpd 102 (0.3 g, 0.989 mmol) and 2-(1-aminocyclobutyl)ethan-1-ol (0.148 g, 1.285 mmol) in DMF (10 mL) was added DIPEA (0.675 mL, 3.959 mmol) followed by HATU (0.752 g, 1.978 mmol) at 0° C. under argon atmosphere. The RM was stirred for 1 h at same temperature. The reaction progress was monitored by LC-MS. The RM was diluted with sat. NaHCO$_3$ (80 mL) and then the crude product was extracted with EtOAc (2×50 mL). The combined organic layer was washed with water (30 mL) and brine (30 mL), dried over anhydrous Na$_2$SO$_4$ and concentrated under reduced pressure. The crude product was purified by reverse phase prep-HPLC to afford cpd 114 (0.18 g, 45%)

Synthesis of 2-methyl-5-((4-methylthiazol-5-yl)methoxy)-N-(1-(2,2,2-trifluoroethyl)pyrrolidin-3-yl)benzofuran-3-carboxamide (Cpd 116)

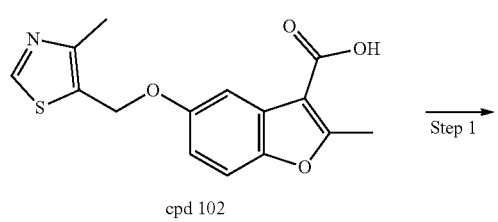

cpd 102

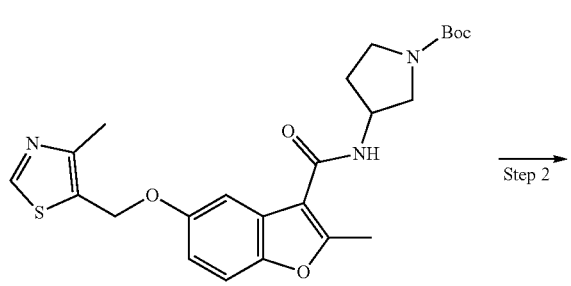

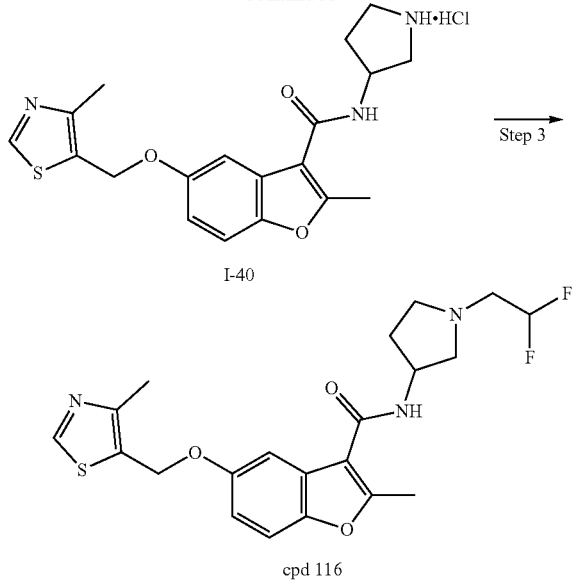

cpd 116

Step 1: To a solution of cpd 102 (600 mg, 1.98 mmol) in DCM (10 ml) at 0° C., DIPEA (1.77 ml, 9.90 mmol, 5 eq) was added dropwise at 0° C. and the RM stirred for 10 min. Tert-Butyl 3-aminopyrrolidine-1-carboxylate (552 mg, 2.97 mmol) and HATU (1.12 g, 2.97 mmol) were added to the RM. After completion of addition, the ice bath was removed and the RM was stirred at RT for 16 h. Reaction progress was monitored by TLC. The RM was extracted with DCM (2×100 ml), the combined organic layer was washed with water (100 mL) and brine (100 ml), dried over anhydrous Na$_2$SO$_4$, filtered, and concentrated to afford crude 2-methyl-5-((4-methylthiazol-5-yl)methoxy)benzofuran-3-carboxylic acid (1.03 g).

Step 2: To a solution of 2-methyl-5-((4-methylthiazol-5-yl)methoxy)benzofuran-3-carboxylic acid (1.0 g, 2.12 mmol) in DCM (15 ml) at 0° C., 4M aq. HCl (3 ml, 5.3 mmol) was added dropwise over 5 min at 0° C. and then the ice bath was removed. The RM was stirred at RT for 16 h. Reaction progress was monitored by TLC. The reaction was directly concentrated to get the crude product, which was washed with Et$_2$O (15 ml) to afford pure 2-methyl-5-((4-methylthiazol-5-yl)methoxy)-N-(pyrrolidin-3-yl)benzofuran-3-carboxamide hydrochloride (700 mg, 94%).

Step 3: To a stirred solution of 2-methyl-5-((4-methylthiazol-5-yl)methoxy)-N-(pyrrolidin-3-yl)benzofuran-3-carboxamide hydrochloride (700 mg, 1.71 mmol) in acetonitrile (20 ml), Cs$_2$CO$_3$ (328 mg, 5.13 mmol) and CF$_2$CH$_2$OTf (598 mg, 2.57 mmol) were added at RT. The resulting mixture was stirred for 3 h at RT. Reaction progress was monitored by TLC. After completion of the reaction, the RM was cooled to 0° C., quenched with ice-cold water (100 ml), and extracted with EtOAc (2×100 ml). The combined organic layer was washed with water (120 ml) and brine solution (120 ml), dried over anhydrous Na$_2$SO$_4$, and concentrated to afford a residue. This residue was purified by FCC using 80% EtOAc in pet ether as eluent to afford cpd 116 (280 mg, 74%). Cpd 116 was further purified by normal phase SFC-Prep to yield 190 mg (24%) of cpd 116. A preparative chiral SFC was performed on the racemic mixture of cpd 116 to afford cpd 116 En 1 and cpd 116 En 2.

417

Synthesis of N-(1-(2-hydroxyethyl)-2-oxopyrrolidin-3-yl)-2-methyl-5-((2(trifluoromethyl)pyridin-3-yl)methoxy)benzofuran-3-carboxamide (Cpd 120)

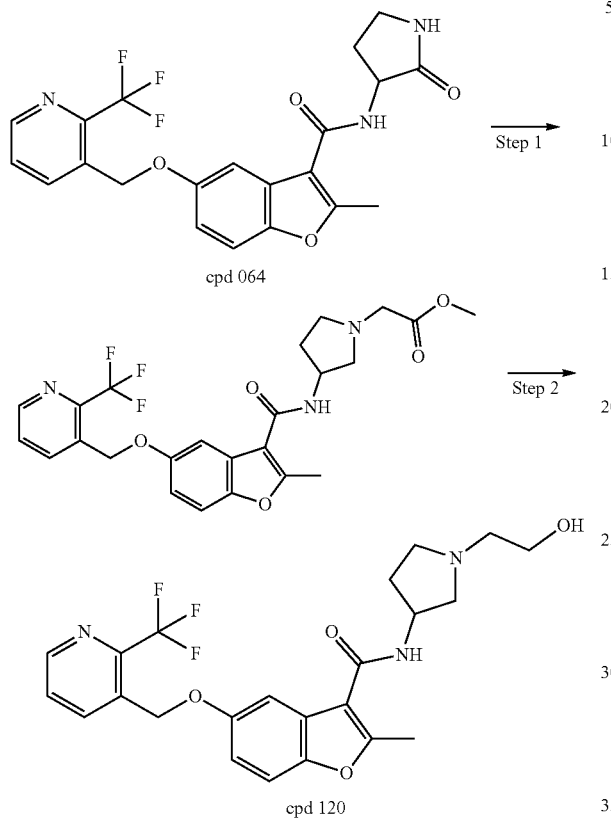

418

Synthesis of N-(3-(2-hydroxyethyl)tetrahydrofuran-3-yl)-2-methyl-5-((4-methylthiazol-5-yl)methoxy)benzo-furan-3-carboxamide (Cpd 121)

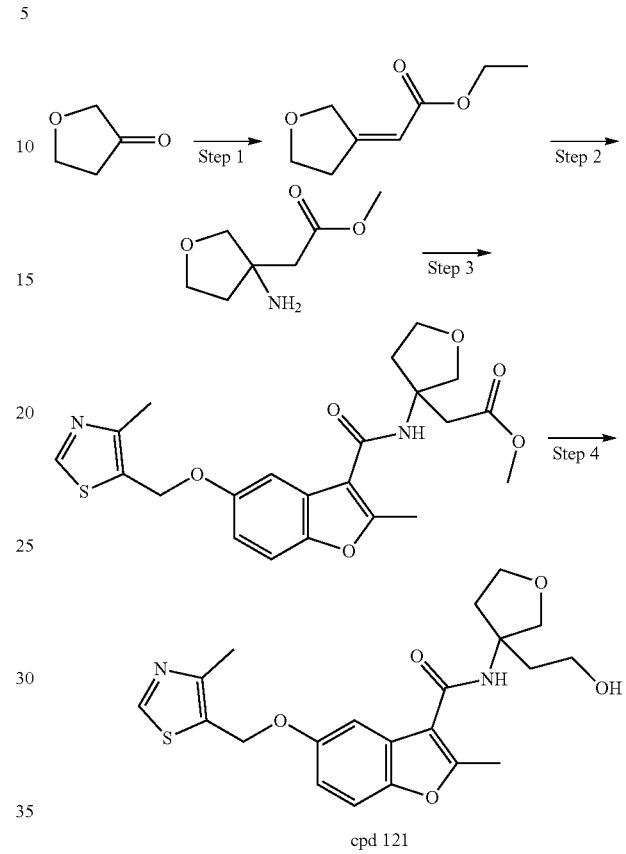

Step 1: To a suspension of 60% NaH (314 g, 7.852 mmol) in DMF (10 mL) under argon atmosphere at 0° C., cpd 064 (850 mg, 1.963 mmol) in DMF (5 mL) and methyl 2-bromoacetate (450.4 mg, 2.944 mmol) were added at 0° C. The RM was stirred at RT for 3 h. Reaction progress was monitored by TLC. After completion of the reaction, the RM was diluted with ice-water (150 mL), extracted with EtOAc (3×300 mL), and the combined organic layer was washed with brine (100 mL), dried over anhydrous $Na_2SO_4$, filtered and concentrated. The residue was purified by FCC to afford the crude product (650 mg).

Step 2: To a solution of methyl 2-(3-(2-methyl-5-((2-(trifluoromethyl)pyridin-3-yl)methoxy)benzofuran-3-carboxamido)pyrrolidin-1-yl)acetate (600 mg, 1.18 mmol) in MeOH (15 mL) under an argon atmosphere at 0° C., $NaBH_4$ (136.5 mg, 4.15 mmol) was added portionwise and then the solution was heated to 80° C. for 3 h. Reaction progress was monitored by TLC. After completion of the reaction, the RM was quenched with acetone (25 mL) and ice-water (150 mL), extracted with EtOAc (3×300 mL), and the combined organic layer was washed with brine solution (100 mL), dried over anhydrous $Na_2SO_4$, filtered and concentrated. The residue was purified by FCC to afford cpd 120 (280 mg, 30% over 2 steps). A preparative chiral SFC was performed on racemate cpd 120 to afford cpd 120-En 1 and cpd 120-En 2.

The following compounds were prepared in a manner similar (use of appropriate reagents and purification methods known to the person skilled in the art) to cpd 120-En 1 and cpd 120-En 2:

Cpd 134-En1, 134-En2, 151-En1 and 151-En2.

Step 1: To a stirred solution of dihydrofuran-3(2H)-one (5.0 g, 58.11 mmol) in toluene (60 ml), was added $Ph_3P=CHC(O)OCH_2CH_3$ (23.22 ml, 69.74 mmol), and then the RM was heated to 110° C. and stirred for 16 h. Reaction progress was monitored by TLC. After completion of the reaction, the RM was cooled to RT, and concentrated to yield the crude product, which was purified by Grace FCC using 20% EtOAc in Pet ether as eluent to afford ethyl (Z)-2-(dihydrofuran-3(2H)-ylidene)acetate (7.2 g, 80%).

Step 2: To a stirred solution of ethyl (Z)-2-(dihydrofuran-3(2H)-ylidene)acetate (5.0 g, 32.05 mmol) in toluene (60 ml), was added methanolic $NH_3$ (7M, 25 ml, 128.2 mmol), and then the RM was heated to 80° C. and stirred for 16 h in a steel bomb. The reaction progress was monitored by TLC. The RM was cooled to RT and concentrated to give the crude methyl 2-(3-aminotetrahydrofuran-3-yl)acetate (4.7 g, 92%).

Step 3: To a stirred solution of cpd 102 (800 mg, 2.64 mmol) in DCM (30 ml), were added DIPEA (1.89 ml, 10.56 mmol) and HATU (1.5 g, 3.96 mmol), followed by addition of methyl 2-(3-aminotetrahydrofuran-3-yl)acetate (629 mg, 3.96 mmol) at 0° C. and the RM was stirred for 2 h at RT. Reaction progress was monitored by TLC. After completion of the reaction, the RM was diluted with water (100 ml), and extracted with DCM (100 ml). The combined organic layer was washed with water (30 ml) and brine solution (25 ml), dried over anhydrous $Na_2SO_4$, filtered and concentrated to afford the crude product which was purified by Grace FCC using 3% MeOH in DCM as eluent to afford methyl 2-(3-(2-methyl-5-((4-methylthiazol-5-yl)methoxy)benzofuran-3-carboxamido)tetrahydrofuran-3-yl)acetate (650 mg, 55%).

Step 4: To a stirred solution of methyl 2-(3-(2-methyl-5-((4-methylthiazol-5-yl)methoxy)benzofuran-3-carboxamido)tetrahydrofuran-3-yl)acetate (650 mg, 1.463 mmol) in THF (20 ml) at −30° C., was added LAH powder (61.19 mg, 1.61 mmol) portionwise. The RM was slowly warmed to RT and stirred for 2 h at RT. Reaction progress was monitored by TLC. After completion of the reaction, the RM was quenched with sat. $Na_2SO_4$ solution (100 mL), and extracted with EtOAc (100 ml). The combined organic layer was washed with water (30 ml) and brine solution (25 ml), dried over anhydrous $Na_2SO_4$, filtered and concentrated to afford the crude product which was purified by Grace FCC using 6% MeOH in $CH_2Cl_2$ as eluent to afford cpd 121 (210 mg, 35%). A preparative chiral SFC was performed on racemic cpd 121 to provide cpd 121-En 1 and cpd 121-En 2.

Cpd 126-En 1 and cpd 126-En 2 was prepared in a manner similar (use of appropriate reagents and purification methods known to the person skilled in the art) to cpd 121-En 1 and cpd 121-En 2.

Synthesis of 7-fluoro-N-(4-(hydroxymethyl)tetrahydro-2H-pyran-4-yl)-2-methyl-5-((4-methylthiazol-5-yl)-methoxy)benzofuran-3-carboxamide (Cpd 122) and 6-fluoro-N-(4-(hydroxymethyl)tetrahydro-2H-pyran-4-yl)-2-methyl-5-((4-methylthiazol-5-yl)methoxy)benzofuran-3-carboxamide (Cpd 182)

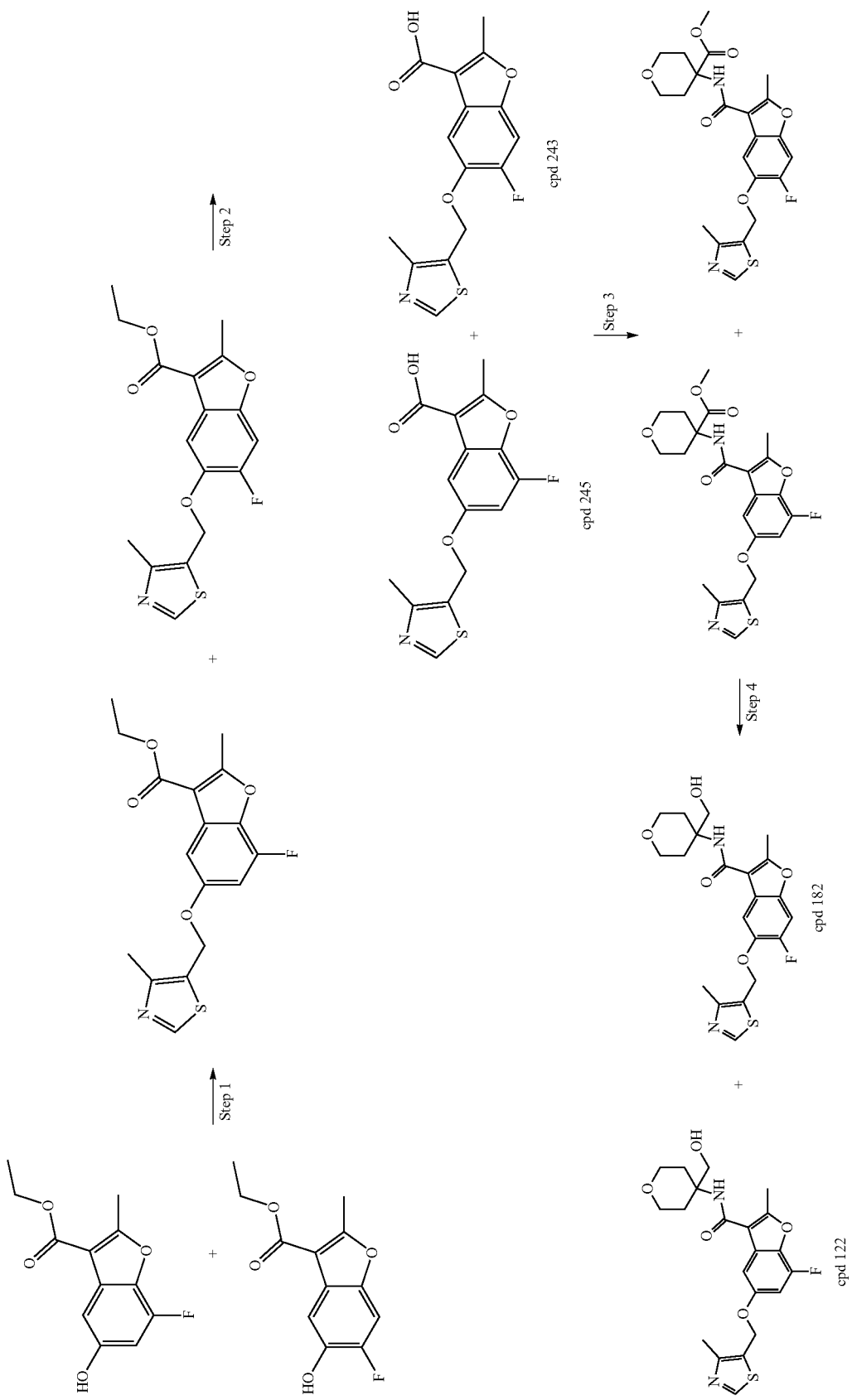

Step 1: (4-Methylthiazol-5-yl)methanol (0.65 g, 5.04 mmol), ADDP (1.18 g, 4.70 mmol) and tri-N-butylphosphine (1.15 mL, 4.70 mmol) were added sequentially to a pre-stirred solution of ethyl 7-fluoro-5-hydroxy-2-methyl-benzofuran-3-carboxylate and ethyl 6-fluoro-5-hydroxy-2-methylbenzofuran-3-carboxylate (0.8 g, 3.36 mmol) in THF (30 mL) at 0° C. under an argon atmosphere. The RM was allowed to attain RT and stirred for 2 h. The reaction progress was monitored by TLC. The RM was poured into water (50 mL) and extracted with EtOAc (2×50 mL). The combined organic layer was washed with water (50 mL) and brine (50 mL). The organic layer was dried over anhydrous Na₂SO₄ and concentrated under reduced pressure. The crude product was purified by FCC over silica gel using 0-20% EtOAc in pet-ether as an eluent to afford a mixture of ethyl 6-fluoro-2-methyl-5-((4-methylthiazol-5-yl)methoxy)benzofuran-3-carboxylate and ethyl 7-fluoro-2-methyl-5-((4-methylthiazol-5-yl)methoxy)benzofuran-3-carboxylate (0.7 g, 59%).

Step 2: A solution of NaOH (0.27 g, 6.87 mmol) in water (5 mL) was added to a pre-stirred solution of ethyl 6-fluoro-2-methyl-5-((4-methylthiazol-5-yl)methoxy)benzofuran-3-carboxylate compound and ethyl 7-fluoro-2-methyl-5-((4-methylthiazol-5-yl)methoxy)benzofuran-3-carboxylate (0.6 g, 1.71 mmol) in a mixture of MeOH (6 mL) and THF (3 mL) at RT. The resulting RM was heated to 60° C. and maintained at this temperature for 4 h. The reaction progress was monitored by TLC. The RM was cooled to RT, poured into ice cold water (50 mL), and acidified with 1 N HCl (pH~2). The crude product was extracted with EtOAc (2×50 mL). The combined organic layer was washed with water (2×50 mL), followed by brine (50 mL), dried over anhydrous Na₂SO₄ and concentrated under reduced pressure to afford a mixture of 6-fluoro-2-methyl-5-((4-methylthiazol-5-yl)methoxy)benzofuran-3-carboxylic acid (cpd 243) and 7-fluoro-2-methyl-5-((4-methylthiazol-5-yl)methoxy)benzofuran-3-carboxylic acid (cpd 245) (0.6 g, 92%).

Step 3: To a pre-stirred solution of a mixture of 6-fluoro-2-methyl-5-((4-methylthiazol-5-yl)methoxy)benzofuran-3-carboxylic acid and 7-fluoro-2-methyl-5-((4-methylthiazol-5-yl)methoxy)benzofuran-3-carboxylic acid (600 mg, 1.86 mmol), and methyl 4-aminotetrahydro-2H-pyran-4-carboxylate (0.356 g, 2.24 mmol) in DMF (10 mL) was added DIPEA (0.96 mL, 5.60 mmol) followed by HATU (1.41 g, 3.72 mmol) at 0° C. under an argon atmosphere. The RM was allowed to attain RT and stirred for 16 h. The reaction progress was monitored by TLC. The RM was diluted with water (50 mL) and then the organic compound was extracted with EtOAc (2×50 mL), and washed with water (50 mL) and brine (50 mL). The organic layer was dried over anhydrous Na₂SO₄ and concentrated under reduced pressure. The crude product was purified by column chromatography over silica gel using 0-55% EtOAc and pet ether as an eluent to afford a mixture of methyl 4-(6-fluoro-2-methyl-5-((4-methylthiazol-5-yl)methoxy)benzofuran-3-carboxamido) tetrahydro-2H-pyran-4-carboxylate and methyl 4-(7-fluoro-2-methyl-5-((4-methylthiazol-5-yl)methoxy)benzofuran-3-carboxamido)-tetrahydro-2H-pyran-4-carboxylate (0.5 g, 57%).

Step 4: NaBH₄ (1.02 g, 27.05 mmol) was added portionwise to a pre-stirred solution of a mixture of methyl 4-(6-fluoro-2-methyl-5-((4-methylthiazol-5-yl)methoxy)benzofuran-3-carboxamido) tetrahydro-2H-pyran-4-carboxylate and methyl 4-(7-fluoro-2-methyl-5-((4-methylthiazol-5-yl)methoxy)benzofuran-3-carboxamido)tetrahydro-2H-pyran-4-carboxylate (0.5 g, 1.08 mmol) in a mixture of MeOH (10 mL) and THF (5 mL) at 0° C. The RM was allowed to attain RT and stirred for 16 h. The reaction progress was monitored by TLC. The RM was diluted with water (50 mL) and the organic compound was extracted with EtOAc (2×50 mL). The combined organic layer was washed with water (50 mL) and brine (50 mL), dried over anhydrous Na₂SO₄ and concentrated under reduced pressure. The crude product was purified by GRACE flash chromatography using 0-60% acetonitrile and 0.1% FA in water as an eluent to afford a mixture of cpd 122 and cpd 182 (0.28 g, 59%). A preparative chiral SFC was performed on a mixture of cpd 111 and 182 to provide cpd 122 and cpd 182.

The following compounds were prepared in a similar manner (use of appropriate reagents (chiral or racemic) and purification methods (including chiral HPLC or chiral SFC) known to the person skilled in the art) as described in the synthesis of cpd. 112 and cpd. 182: Cpd. 360-En 1, 360-En 2, 361, 362, 364, 365-En 1, 365-En 2, 366, 367, 369, 587, 588.

The following compounds were prepared in a similar manner (use of appropriate reagents (chiral or racemic) and purification methods (including chiral HPLC or chiral SFC) known to the person skilled in the art) as described for step 3 in the synthesis of cpd. 243 and cpd. 245: Cpds. 244, 246.

Synthesis of N-(4,4-difluoro-1-methylpyrrolidin-3-yl)-2-methyl-5-((2-(trifluoromethyl)pyridin-3-yl)methoxy)-benzofuran-3-carboxamide (Cpd 124)

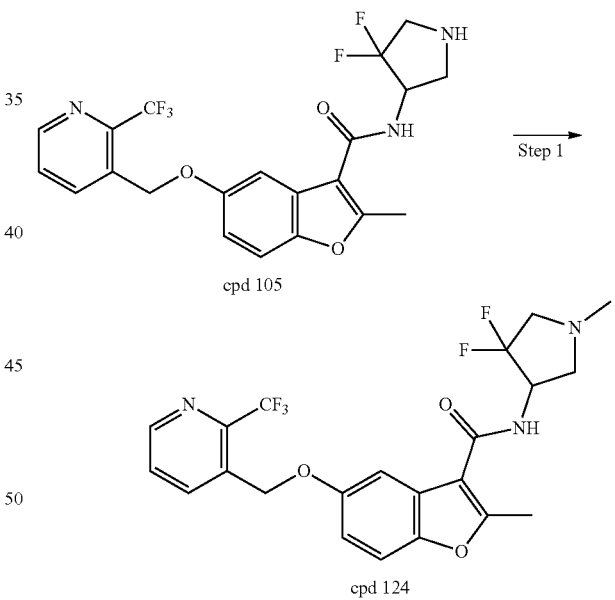

Step 1: To a stirred solution of cpd 105 (400 mg, 0.88 mmol) in MeOH (20 ml), 37% HCHO (0.5 mL) and acetic acid (0.1 mL) were added at 0° C. The RM was stirred for 30 min at 0° C. and then added NaCNBH₃ (109 mg, 1.76 mmol) at 0° C. The RM was stirred for 18 h at RT. Reaction progress was monitored by TLC. After completion of the reaction, the RM was quenched with water (50 mL). The product was extracted with EtOAc (3×100 mL), and the combined organic layer was washed with sat. NaHCO₃ (50 mL) and brine solution (50 mL), dried over anhydrous Na₂SO₄, filtered and concentrated. The residue was triturated with Et₂O (10 mL) to afford cpd 124 (370 mg, 90%).

A preparative chiral SFC was performed on the racemic mixture of cpd 124 to provide cpd 124-En 1 and cpd 124-En 2.

The following compounds were prepared in a manner similar (use of appropriate reagents and purification methods known to the person skilled in the art) to cpd 105:

Cpd 110-En1, 110-En2, 118-En1, 118-En2, 123-En1, 123-En2, 130-En1, 130-En2, 131-En1, 131-En2, 141-En1, 141-En2, 163-En1 and 163-En2.

Synthesis of N-(1-(2-hydroxyethyl)cyclobutyl)-2-methyl-5-((2-(trifluoromethyl)pyridin-3-yl)methoxy)benzo-furan-3-carboxamide (Cpd 127)

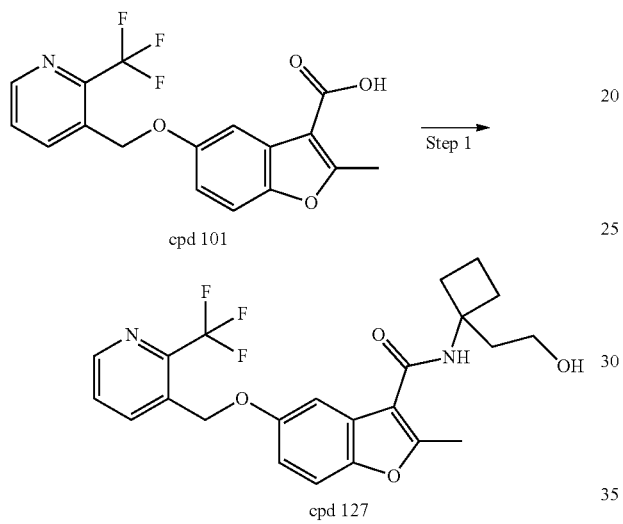

Step 1: To a pre-stirred solution of cpd 101 (0.52 g, 1.480 mmol) and 2-(1-aminocyclobutyl)ethan-1-ol (0.222 g, 1.924 mmol) in DMF (20 mL) was added DIPEA (1.01 mL, 5.920 mmol) followed by HATU (1.13 g, 2.96 mmol) at 0° C. under an argon atmosphere. The RM was stirred for 2 h at same temperature. The reaction progress was monitored by LC-MS. The RM was diluted with sat. NaHCO₃ (100 mL) and then the crude product was extracted with EtOAc (2×60 mL). The combined organic layer was washed with water (50 mL) and brine (50 mL), dried over anhydrous Na₂SO₄ and concentrated under reduced pressure. The crude product was purified by reverse phase prep-HPLC to afford cpd 127 (0.110 g, 16%).

Synthesis of N-(1-(aminomethyl)cyclobutyl)-2-methyl-5-((2-(trifluoromethyl)pyridin-3-yl)methoxy)benzo-furan-3-carboxamide (Cpd 136)

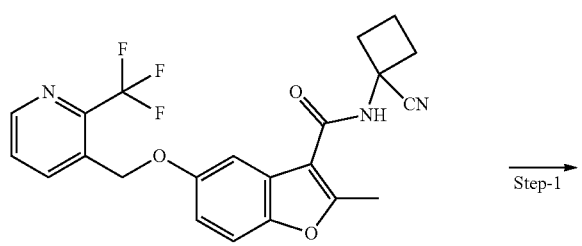

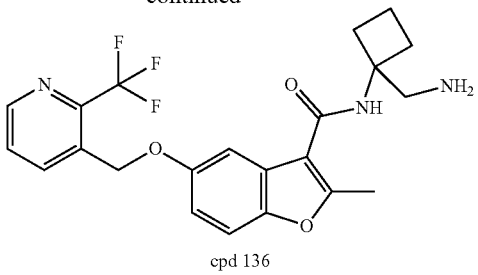

A solution of N-(1-cyanocyclobutyl)-2-methyl-5-((2-(trifluoromethyl)pyridin-3-yl)methoxy)benzofuran-3-carboxamide (450 mg, 1.048 mmol) in MeOH (10 mL) was added to a slurry of Raney-Ni (200 mg) in MeOH (10 mL), dropwise at RT. The RM was stirred under H₂ balloon pressure for 16 h. The RM was filtered through a celite pad and the celite pad was washed with MeOH (80 mL). The combined clear filtrate was concentrated under reduced pressure. The crude product was purified by reverse phase prep-HPLC to afford cpd 136 (0.3 g, 66%).

Synthesis of N-(1-(aminomethyl)cyclobutyl)-2-methyl-5-((4-methylthiazol-5-yl)methoxy)benzo-furan-3-carboxamide (Cpd 137)

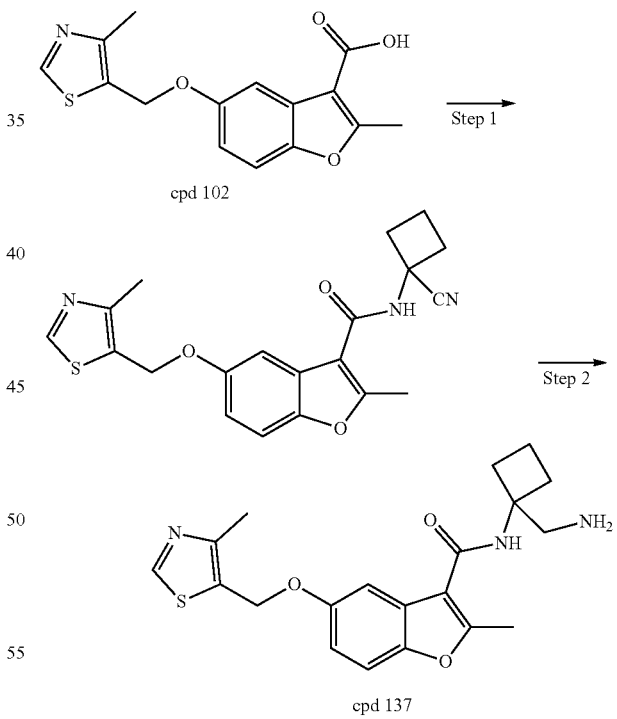

Step 1: To a solution of cpd 102 (2.0 g, 6.6 mmol) and 1-aminocyclobutane-1-carbonitrile (950 mg, 9.9 mmol) in DMF (20 mL) was added DIPEA (2.43 mL, 13.2 mmol) followed by HATU (5.0 g, 13.2 mmol) at 0° C. under argon atmosphere. The RM was allowed to attain RT and stirred for 1 h. The reaction progress was monitored by TLC. The RM was quenched with cold water (120 mL), the precipitated solid was filtered and dried under reduced pressure to afford N-(1-cyanocyclobutyl)-2-methyl-5-((4-methylthiazol-5-yl)methoxy)benzofuran-3-carboxamide (1.7 g, 68%).

Step 2: To a pre-stirred solution of N-(1-cyanocyclobutyl)-2-methyl-5-((4-methylthiazol-5-yl)methoxy) benzofuran-3-carboxamide (500 mg, 1.3 mmol) in a mixture of MeOH (10 mL) and THF (5 mL) was added $COCl_2 \cdot 6H_2O$ (468 mg, 1.96 mmol) followed by $NaBH_4$ (150 mg, 3.9 mmol) at 0° C. The RM was stirred for 30 min at same temperature. The reaction progress was monitored by LC-MS. The RM was poured into water (30 mL) and extracted with EtOAc (3×50 mL). The combined organic layer was washed with water (2×50 mL) and brine (50 mL), dried over anhydrous $Na_2SO_4$ and concentrated under reduced pressure. The crude product was purified by flash chromatography using 0-20% acetonitrile in 0.1% FA as an eluent, followed by reverse phase prep-HPLC to afford cpd 137 (80 mg, 16%).

Synthesis of 2-methyl-N-(1H-pyrazol-3-yl)-5-((2-(trifluoromethyl)pyridin-3-yl)methoxy)benzofuran-3-carboxamide (Cpd 138)

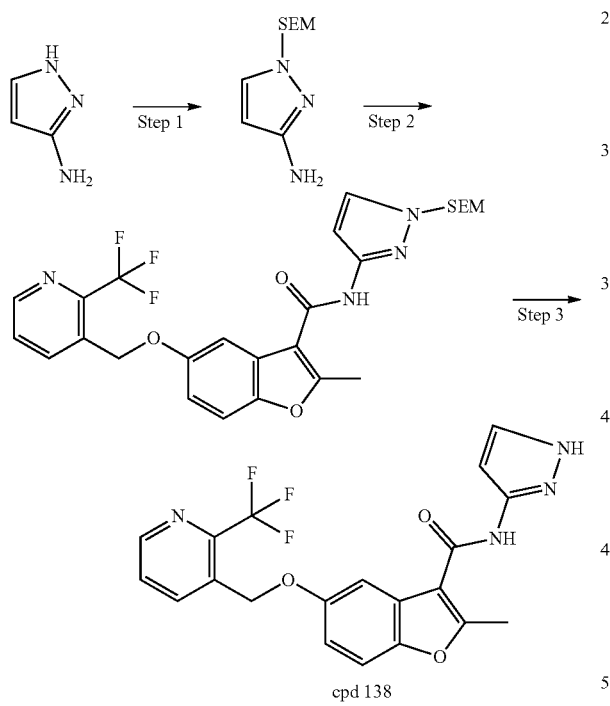

mmol), HATU (325 mg, 0.85 mmol) and 1-((2-(trimethylsilyl)ethoxy)methyl)-1H-pyrazol-3-amine (182 mg, 0.85 mmol) at RT. The RM was stirred for 18 h at RT. Reaction progress was monitored by TLC. After completion of the reaction, the RM was diluted with DCM (200 mL), the organic layer was washed with water (2×50 mL), sat. $NaHCO_3$ (50 mL) and brine (50 mL), dried over anhydrous $Na_2SO_4$, filtered and concentrated to give the crude product. The residue was purified by Grace FCC using 45% EtOAc in Pet ether as eluent to get 2-methyl-5-((2-(trifluoromethyl)pyridin-3-yl)methoxy)-N-(1-((2-(trimethylsilyl)ethoxy)methyl)-1H-pyrazol-3-yl)benzofuran-3-carboxamide (100 mg, 32%).

Step 3: To a stirred solution of 2-methyl-5-((2-(trifluoromethyl)pyridin-3-yl)methoxy)-N-(1-((2-(trimethylsilyl)ethoxy)methyl)-1H-pyrazol-3-yl)benzofuran-3-carboxamide (100 mg, 0.18 mmol) in DCM (10 mL), TFA (0.5 mL) was added at 0° C. The RM was stirred for 24 h at RT. Reaction progress was monitored by TLC. After completion of the reaction, the RM was poured into ice water (20 mL), basified to pH ~9 using sat. $NaHCO_3$ solution (20 mL), and the product was extracted with DCM (3×50 mL). The combined organic layer was washed with brine solution (50 mL), dried over anhydrous $Na_2SO_4$, filtered and concentrated to give the crude product. The residue was purified by Grace FCC using 100% EtOAc as eluent to afford cpd 138. The product was purified further by HPLC.

Synthesis of 2-methyl-5-((4-methylthiazol-5-yl)methoxy)-N-(1-(((2,2,2-trifluoroethyl)amino)methyl)cyclobutyl)-benzofuran-3-carboxamide (Cpd 145)

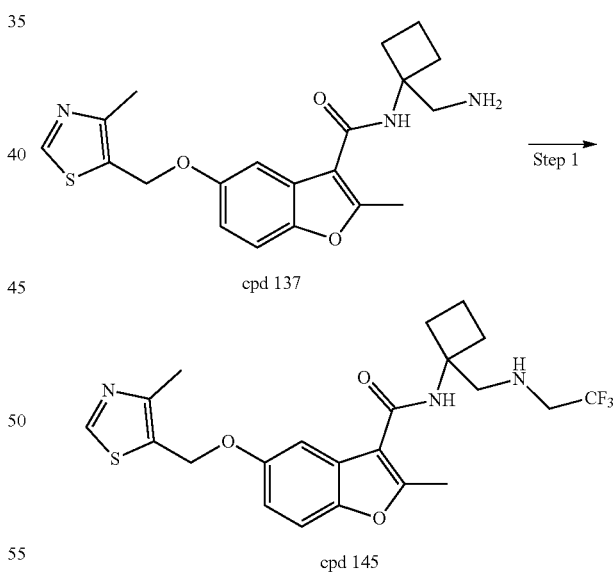

Step 1: To a stirred solution of 1H-pyrazol-3-amine (5 g, 60.24 mmol) in DMF (50 mL), was added NaH (60% in oil) (4.819 g, 120.48 mmol) at 0° C. The RM was stirred for 30 min at 0° C. and SEMCl (11.7 mL, 66.26 mmol) was added at 0° C. The RM was stirred for 1 h at RT. Reaction progress was monitored by TLC. After completion of the reaction, the RM was diluted with EtOAc (700 mL). The organic layer was washed with water (5×100 mL) and brine (100 mL), dried over anhydrous $Na_2SO_4$, filtered and concentrated to give the crude product. The crude product was purified by Grace FCC using 100% EtOAc as eluent to afford 1-((2-(trimethylsilyl)ethoxy)methyl)-1H-pyrazol-3-amine (2.3 g, 18%).

Step 2: To a stirred solution of cpd 101 (200 mg, 0.56 mmol) in DCM (10 mL), was added DIPEA (0.3 mL, 1.71

Step 1: 2,2,2-Trifluoroacetaldehyde monohydrate (77% in water, 0.85 mL, 5.1 mmol) was added to a solution of cpd 137 (200 mg, 0.51 mmol) in MeOH (15 mL) at 0° C. under an argon atmosphere. Then, glacial acetic acid (3 drops) and $NaCNBH_3$ (65 mg, 1.0 mmol) were added to the reaction. The resulting RM was heated at 80° C. for 16 h. The RM was cooled to RT, poured into water (50 mL) and extracted with EtOAc (2×50 mL). The combined organic layer was washed with sat. $NaHCO_3$ (25 mL), water (50 mL) and brine (50 mL), dried over $Na_2SO_4$ and excess solvent was removed

429 under reduced pressure. The crude product was purified by flash chromatography using 0-50% acetonitrile in 0.1% FA as an eluent followed by reverse phase prep-HPLC to afford cpd 145 (30 mg, 12%).

Cpd 153 was prepared in a manner similar (use of appropriate reagents and purification methods known to the person skilled in the art) to cpd 145.

Synthesis of N-(4-hydroxytetrahydrofuran-3-yl)-2-methyl-5-((2-(trifluoromethyl)pyridin-3-yl)methoxy)-benzofuran-3-carboxamide (Cpd 147)

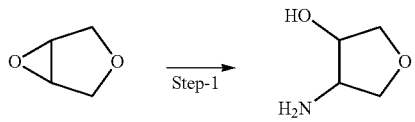 [SMILES: C1OCC2OC12 ; NC1COCC1O]

Step 1: To a stirred solution of 3,6-dioxabicyclo[3.1.0]hexane (0.2 g, 2.27 mmol) in EtOH (10 ml) in a 100 mL steel bomb was added aq. NH₄OH (5 ml), and the steel bomb was closed tightly. The RM was heated up to 80° C. for 18 h in the steel bomb. Reaction progress was monitored by TLC. After completion of the reaction, the RM was concentrated to give the crude product, and the crude product was co-distilled with toluene three times to give 4-aminotetrahydrofuran-3-ol (0.16 g, 65%).

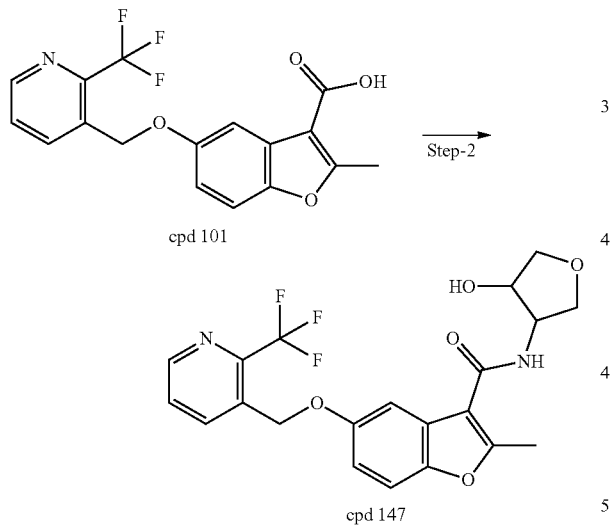

Step 2: To a solution of cpd 101 (0.35 g, 0.99 mmol) in DCM (20 ml), were added DIPEA (0.91 ml, 4.98 mmol) and HATU (0.568 g, 1.49 mmol), at 0° C., followed by a solution of 4-aminotetrahydrofuran-3-ol (0.151 g, 1.49 mmol) in DCM, dropwise at 0° C. Then the RM was stirred for 3 h at RT, and the reaction monitored by TLC. After completion of the reaction, the RM was diluted with water (20 ml), extracted with DCM (3×30 ml), and the combined organic layer was washed with water (50 ml) and brine solution (25 ml), dried over anhydrous Na₂SO₄, filtered and concentrated to yield the crude product. The crude product was purified by FCC using 60% EtOAc-pet ether as eluent to afford cpd 147 (0.30 g, 69%). A preparative chiral SFC was performed on racemic cpd 147 to afford cpd 147 Dia 1-En 1 and cpd 147 Dia 1-En 2.

430

Cpd 162-Dia 1-En 1, 162-Dia 1-En2, 386-En 1, 386-En 2, 387-En 1, 387-En 2, 388-En 1, 388-En 2, 389-En 1, 389-En 2,653-En 1, 653-En 2, 654-En 1, 654-En 2, 655-En 1, 655-En 2, 656-En 1, 656-En 2 were prepared in a manner similar (use of appropriate reagents and purification methods known to the person skilled in the art) to cpd 147-Dia 1-En 1 and cpd 147-Dia 1-En 2.

Synthesis of 2-methyl-N-(1-(2,2,2-trifluoroethyl)pyrrolidin-3-yl)-5-((2-(trifluoromethyl)pyridin-3-yl)methoxy)-benzofuran-3-carboxamide (Cpd 149)

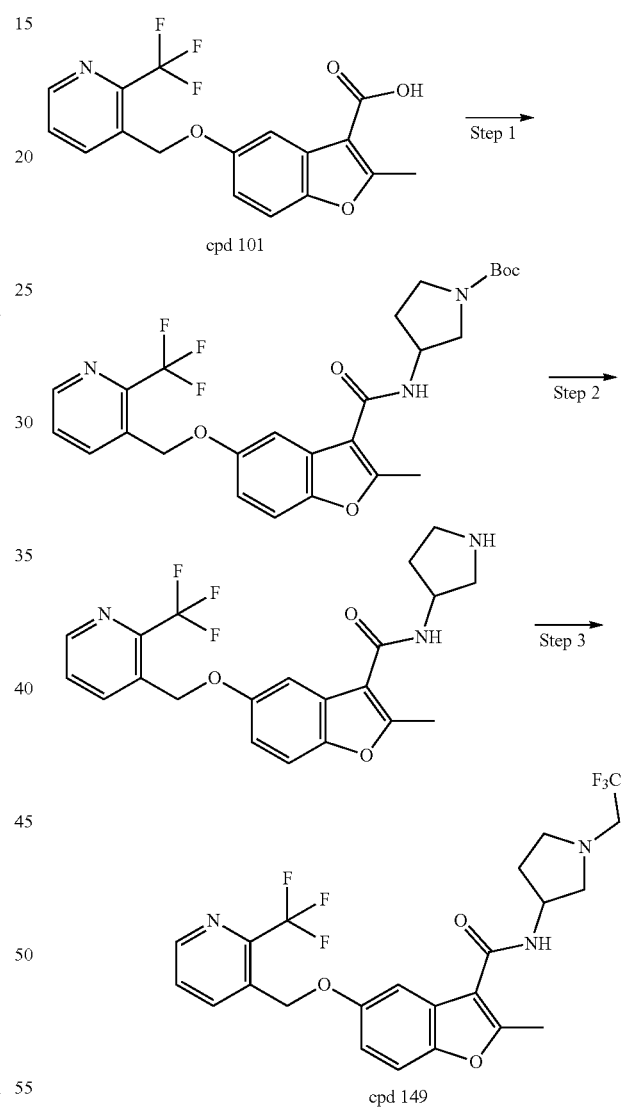

Step 1: To a stirred solution of cpd 101 (400 mg, 1.14 mmol) in DCM (15 mL), DIPEA (0.5 mL, 2.85 mmol) and HATU (476 mg, 1.25 mmol) were added at RT. The RM was stirred for 5 min at RT and tert-butyl 3-aminopyrrolidine-1-carboxylate (233 mg, 1.25 mmol) was added at RT. The RM was stirred for 18 h at RT. Reaction progress was monitored by TLC. After completion of the reaction, the RM was diluted with DCM (200 mL). The organic layer was washed with sat. NaHCO₃ solution (100 mL), water (100 mL) and brine (100 mL), dried over anhydrous Na₂SO₄, filtered and concentrated to give a residue. The residue was purified by Grace FCC using 45% EtOAc in Pet ether as eluent to afford tert-butyl 3-(2-methyl-5-((2-(trifluoromethyl)pyridin-3-yl)methoxy)benzofuran-3-carboxamido)pyrrolidine-1-carboxylate (450 mg, 76%).

Step 2: To a stirred solution of tert-butyl 3-(2-methyl-5-((2-(trifluoromethyl)pyridin-3-yl)methoxy)benzofuran-3-carboxamido)pyrrolidine-1-carboxylate (450 mg, 0.86 mmol) in DCM (10 ml), 4N HCl in dioxane (5 mL) was added at 0° C. The RM was stirred for 18 h at RT. Reaction progress was monitored by TLC. After completion of the reaction, the RM was concentrated and dried to afford 2-methyl-N-(pyrrolidin-3-yl)-5-((2-(trifluoromethyl)pyridin-3-yl)methoxy)benzofuran-3-carboxamide (520 mg, crude product).

Step 3: To a stirred solution of 2-methyl-N-(pyrrolidin-3-yl)-5-((2-(trifluoromethyl)pyridin-3-yl)methoxy)benzofuran-3-carboxamide (500 mg, 1.02 mmol) in CH$_3$CN (50 ml), Cs$_2$CO$_3$ (1.33 g, 4.07 mmol) and CF$_3$CH$_2$OTf (472 mg, 2.03 mmol) were added at RT. The RM was heated to 50° C. and stirred for 1 h at 50° C. Reaction progress was monitored by LCMS. After completion of the reaction, the RM was cooled to RT, diluted with EtOAc (250 mL), washed with water (2×50 mL) and brine solution (50 mL), dried over anhydrous Na$_2$SO$_4$, filtered and concentrated to give a residue. The residue was purified by RP-Prep HPLC to afford cpd 149 (280 mg, 64% over 2 steps). A preparative chiral SFC was performed on racemic cpd 149 to provide cpd 149-En 1 and cpd 149-En 2.

Synthesis of N-(4,4-difluoro-1-(2,2,2-trifluoroethyl)pyrrolidin-3-yl)-2-methyl-5-((4-methylthiazol-5-yl)methoxy)benzofuran-3-carboxamide (Cpd 155) and 2,2,2-trifluoroethyl 3,3-difluoro-4-(2-methyl-5-((4-methylthiazol-5-yl)methoxy)benzofuran-3-carboxamido)pyrrolidine-1-carboxylate (Cpd 172)

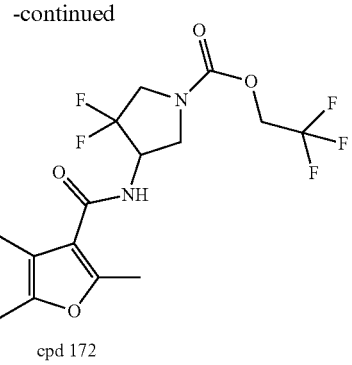

cpd 172

Step 1: To a solution of cpd 106 (400 mg, 0.982 mmol) in DMF (20 ml), Cs$_2$CO$_3$ (958 mg, 2.948 mmol) was added at RT. The RM was stirred for 5 min at RT and then CF$_3$CH$_2$OTf (342 mg, 1.474 mmol) was added at RT. The RM was stirred for 16 h at RT. Reaction progress was monitored by TLC. After completion of the reaction, the mixture was diluted with water (100 ml) and extracted with EtOAc (3×100 mL). The combined organic layer was washed with brine (50 mL), dried over anhydrous Na$_2$SO$_4$, filtered and concentrated. The residue was purified by RP-Prep HPLC to afford a mixture of cpd 155 and cpd 172 (320 mg, 45%). A preparative chiral SFC was performed on the mixture of racemic cpd 155 and racemic cpd 152 to afford cpd 155-En 1, cpd 155-En 2, cpd 172-En 1 and cpd 172-En 2.

Racemic Cpd 175 was prepared in a manner similar (use of appropriate reagents and purification methods known to the person skilled in the art) to cpd 155-En 1, cpd 155-En 2, cpd 172-En1 and cpd 172-En 2.

Synthesis of N-(4,4-difluoro-1-(2,2,2-trifluoroethyl)pyrrolidin-3-yl)-2-methyl-5-((2-(trifluoromethyl)pyridin-3-yl)methoxy)benzofuran-3-carboxamide (Cpd 157)

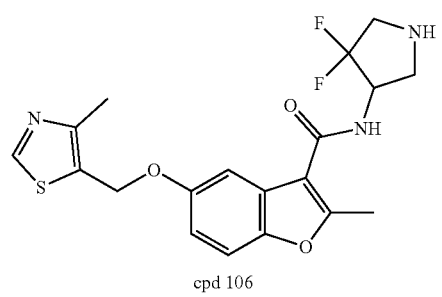

cpd 106

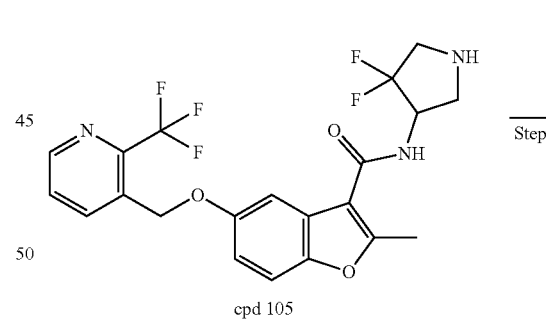

cpd 105

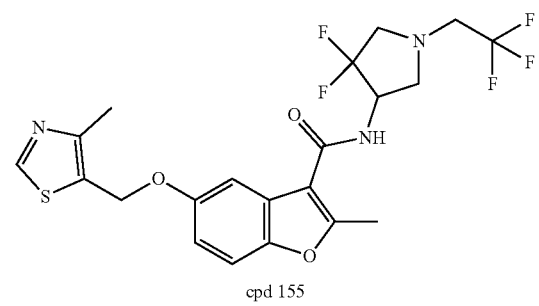

cpd 155

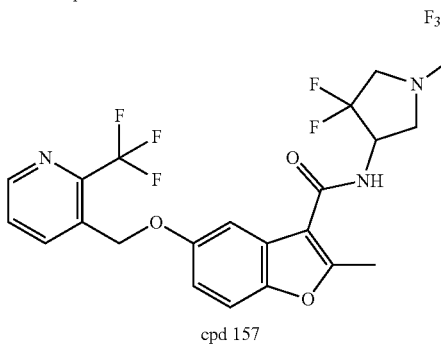

cpd 157

Step 1: To a stirred solution of cpd 105 (600 mg, 1.318 mmol) in DMF (20 ml), NaH (56.9 mg, 3.954 mmol) was added at 0° C. The RM was stirred for 5 min at 0° C. and then $CF_3CH_2OTf$ (609 mg, 2.637 mmol) was added at 0° C. The reaction was stirred for 18 h at RT. Reaction progress was monitored by TLC. After completion of the reaction, the mixture was diluted with ice water (50 mL) and extracted with EtOAc (3×100 mL). The combined organic layer was washed with brine (50 mL), dried over anhydrous $Na_2SO_4$, filtered and concentrated. The residue was purified by RP-Prep HPLC to afford cpd 157 (170 mg, 24%). A preparative chiral SFC was performed on racemic cpd 157 to afford cpd 157-En 1 and cpd 157-En 2.

Synthesis of N-(1-(2-hydroxyethyl)-2-oxopyrrolidin-3-yl)-2-methyl-5-((4-methylthiazol-5-yl)methoxy)benzo-furan-3-carboxamide (Cpd 160)

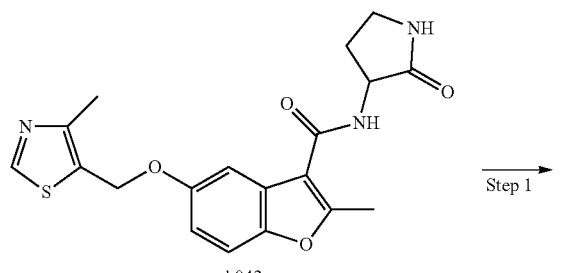

cpd 042

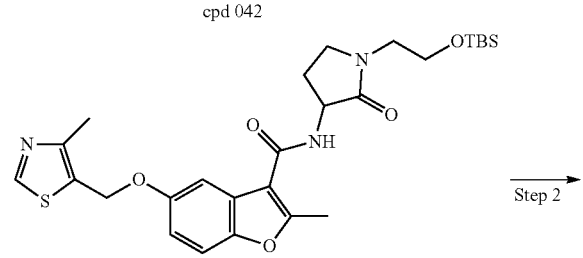

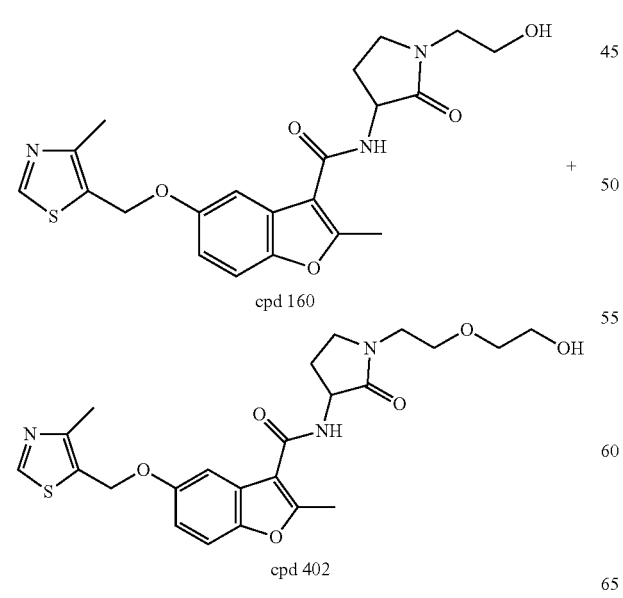

cpd 160 cpd 402

Step 1: To a suspension of 60% NaH (240 mg, 6.21 mmol) in DMF (5.0 ml), cpd 042 (800 mg, 2.07 mmol) in DMF (10 ml) and (2-bromoethoxy)(tert-butyl)dimethylsilane (980 mg, 4.14 mmol) was added at 0° C. and the RM was allowed to rise to RT and was stirred for 16 h. Reaction progress was monitored by TLC. The RM was extracted with DCM (2×100 ml), the combined organic layer was washed with water (50 mL) and brine solution (50 ml), and then dried over anhydrous $Na_2SO_4$, filtered, and concentrated to afford N-(1-(2-((tert-butyldimethylsilyl)oxy)ethyl)-2-oxopyrrolidin-3-yl)-2-methyl-5-((4-methylthiazol-5-yl)methoxy)benzofuran-3-carboxamide (850 mg, crude).

Step 2: To a solution of N-(1-(2-((tert-butyldimethylsilyl)oxy)ethyl)-2-oxopyrrolidin-3-yl)-2-methyl-5-((4-methylthiazol-5-yl)methoxy)benzofuran-3-carboxamide (850 mg, 1.63 mmol) in THF (15 ml) at 0° C., TBAF (2.45 ml, 2.45 mmol), was added dropwise at 0° C. and the RM was stirred at RT for 2 h. Reaction progress was monitored by TLC. The RM was extracted with EtOAc (2×100 ml), the combined organic layer was washed with water (150 mL) and brine solution (150 ml); dried over anhydrous $Na_2SO_4$, filtered, and concentrated to afford the crude product, which was purified by FCC to afford the desired product cpd 160 (190 mg). A preparative chiral SFC was performed on the racemic mixture of cpd 160 to provide cpd 160-En 1 and cpd 160-En 2. Cpd 402 was isolated as a byproduct that occurred during the synthetic sequence.

The following compounds were prepared in a similar manner (use of appropriate reagents (chiral or racemic) and purification methods (including chiral HPLC or chiral SFC) known to the person skilled in the art) as described for cpd 160: Cpds. 403-En 1, 403-En 2, 404-En 1, 404-En 2, 405-En 1, 405-En 2, 409-En 1, 409-En 2, 410-En 1, 410-En 2, Synthesis of N-(1-(2-hydroxyethyl)-2-oxopyrrolidin-3-yl)-2-methyl-5-((2-methylpyridin-3-yl)methoxy)benzo-furan-3-carboxamide (Cpd 164)

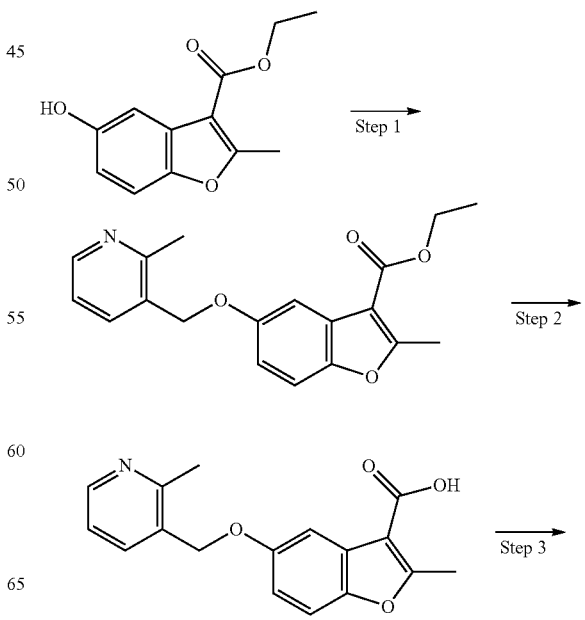

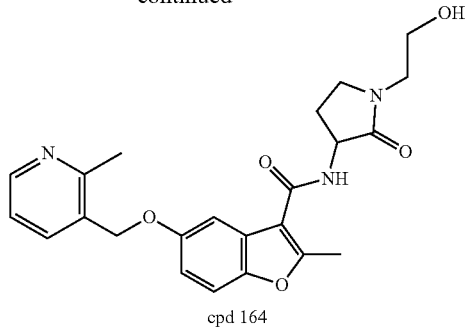

cpd 164

Step 1: (2-Methylpyridin-4-yl)methanol (1.8 g, 13.63 mmol), ADDP (3.2 g, 13.63 mmol) and tri-N-butyl phosphine (50% in EtOAc) (3.1 mL, 12.72 mmol) were added to a stirred solution of ethyl 5-hydroxy-2-methylbenzofuran-3-carboxylate (2.0 mg, 9.09 mmol) in THF (30 mL) at 0° C. under argon atmosphere. The resulting RM was stirred at rt for 24 h. The reaction progress was monitored by TLC. The RM was poured into water (100 mL) and extracted with EtOAc (2×100 mL). The combined organic layer was washed with brine (100 mL), dried over anhydrous $Na_2SO_4$ and concentrated under reduced pressure. The crude product was purified by flash chromatography using 0.1% FA and acetonitrile as eluent to afford ethyl 2-methyl-5-((2-methylpyridin-4-yl)methoxy)benzofuran-3-carboxylate (1.2 g, 40%).

Step 2: A solution of 2-methyl-5-((2-methylpyridin-4-yl)methoxy)benzofuran-3-carboxylate (1.2 g, 5.08 mmol) and 4 M NaOH (10 mL) solution in MeOH:THF (1:1) (24 mL) was heated to 80° C. and maintained for 2 h. The reaction progress was monitored by TLC. The RM was cooled to RT, poured into ice cold water (100 mL), acidified with 1 N HCl and extracted with EtOAc (2×100 mL). The combined organic layer was washed with brine (100 mL), dried over anhydrous $Na_2SO_4$ and concentrated under reduced pressure to afford 2-methyl-5-((2-methylpyridin-4-yl)methoxy)benzofuran-3-carboxylic acid (800 mg, 72%).

Step 3: To a stirred solution of 3-amino-1-(2-hydroxyethyl) pyrrolidin-2-one hydrochloride (0.362 g, 2.02 mmol) in DMF (10 mL) were added DIPEA (2.4 mL, 13.46 mmol) followed by 2-methyl-5-((2-methylpyridin-4-yl)methoxy) benzofuran-3-carboxylic acid (0.5 g, 1.68 mmol) and HATU (1.0 g, 3.36 mmol) sequentially at 0° C. under an argon atmosphere. The resulting RM was allowed warm to RT and stirred for 16 h. The reaction progress was monitored by TLC. The RM was diluted with ice cold water (100 mL) and extracted with 10% MeOH in DCM (2×50 mL). The combined organic layer was washed with brine (50 mL), dried over anhydrous $Na_2SO_4$ and concentrated under reduced pressure. The crude product was purified by flash chromatography using 0.1% FA and acetonitrile as eluent to afford cpd 164. A preparative chiral SFC was performed on racemic cpd 164 to afford cpd 164-En 1 and cpd 164-En 2.

The following compounds were prepared in a manner similar (use of appropriate reagents and purification methods known to the person skilled in the art) to cpd 164-En 1 and cpd 164-En 2: cpd 169-En 1, 169-En 2, 180-En 1 and 180-En 2.

The following compounds were prepared in a manner similar (use of appropriate reagents and purification methods known to the person skilled in the art) to step 3 in the preparation of cpd 164-En 1 and cpd 164-En 2 req: Cpd.

335-En1, 335-En2, 340-En1, 340-En2, 348-En1, 348-En2, 406-En1, 406-En2, 407-En 1, 407-En 2, 408-En 1, 408-En 2.

Synthesis of 2-methyl-5-((4-methylthiazol-5-yl)methoxy)-N-(1-(2,2,2-trifluoroethyl)piperidin-4-yl)benzofuran-3-carboxamide (Cpd 166)

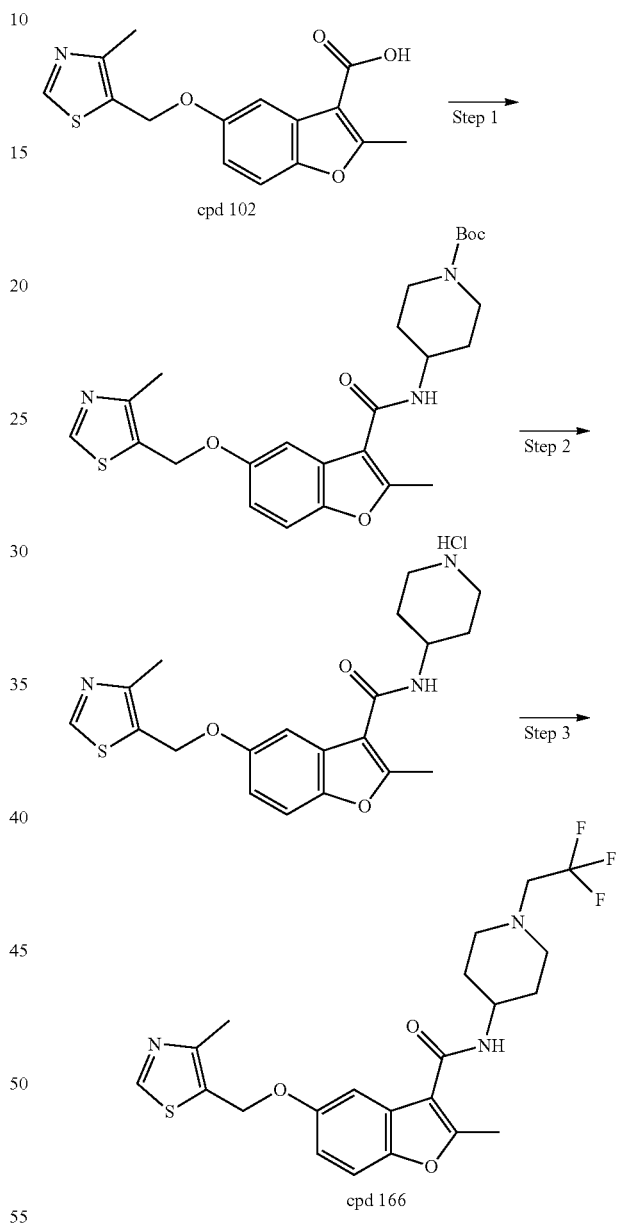

Step 1: To a stirred solution of cpd 102 (500 mg, 1.65 mmol) in DCM (50 ml), were added DIPEA (1.4 ml, 8.25 mmol) and HATU (940 mg, 2.47 mmol), followed by tert-butyl 4-aminopiperidine-1-carboxylate (495 mg, 2.47 mmol) and the RM was stirred for 2 h at RT. Reaction progress was monitored by TLC. The RM was diluted with water (100 ml), extracted with EtOAc (3×50 ml), washed with water (50 ml) and brine (30 ml), dried over anhydrous $Na_2SO_4$, filtered and concentrated to give the crude product. The crude product was purified by Grace FCC using 20% EtOAc in Pet ether as eluent to afford tert-butyl 4-(2-methyl- 5-((4-methylthiazol-5-yl)methoxy)benzofuran-3-carbox-amido)piperidine-1-carboxylate (600 mg, 75%).

Step 2: To a solution of tert-butyl 4-(2-methyl-5-((4-methylthiazol-5-yl)methoxy)benzofuran-3-carboxamido)piperidine-1-carboxylate (600 mg, 1.237 mmol) in DCM (80 ml) at 0° C., 4N HCl in dioxane (2.3 ml, 9.277 mmol) was added dropwise over 5 min at 0° C., and the ice bath was removed. The RM was stirred at RT for 16 h. Reaction progress was monitored by TLC. The RM was directly concentrated to afford the crude product, which was washed with Et$_2$O (15 ml) to afford 2-methyl-5-((4-methylthiazol-5-yl)methoxy)-N-(piperidin-4-yl)benzofuran-3-carboxamide hydrochloride (700 mg crude).

(120 ml) and brine (120 ml), dried over anhydrous Na$_2$SO$_4$, and concentrated to afford a residue, which was purified by Grace FCC using 80% EtOAc in pet ether as eluent to afford cpd 166 (150 mg, 14%).

Cpd 168 was prepared in a manner similar (use of appropriate reagents and purification methods known to the person skilled in the art) to cpd 166.

Synthesis of 4-fluoro-N-(4-(hydroxymethyl)tetra-hydro-2H-pyran-4-yl)-2-methyl-5-((4-methylthiazol-5-yl)-methoxy)benzofuran-3-carboxamide (Cpd 177)

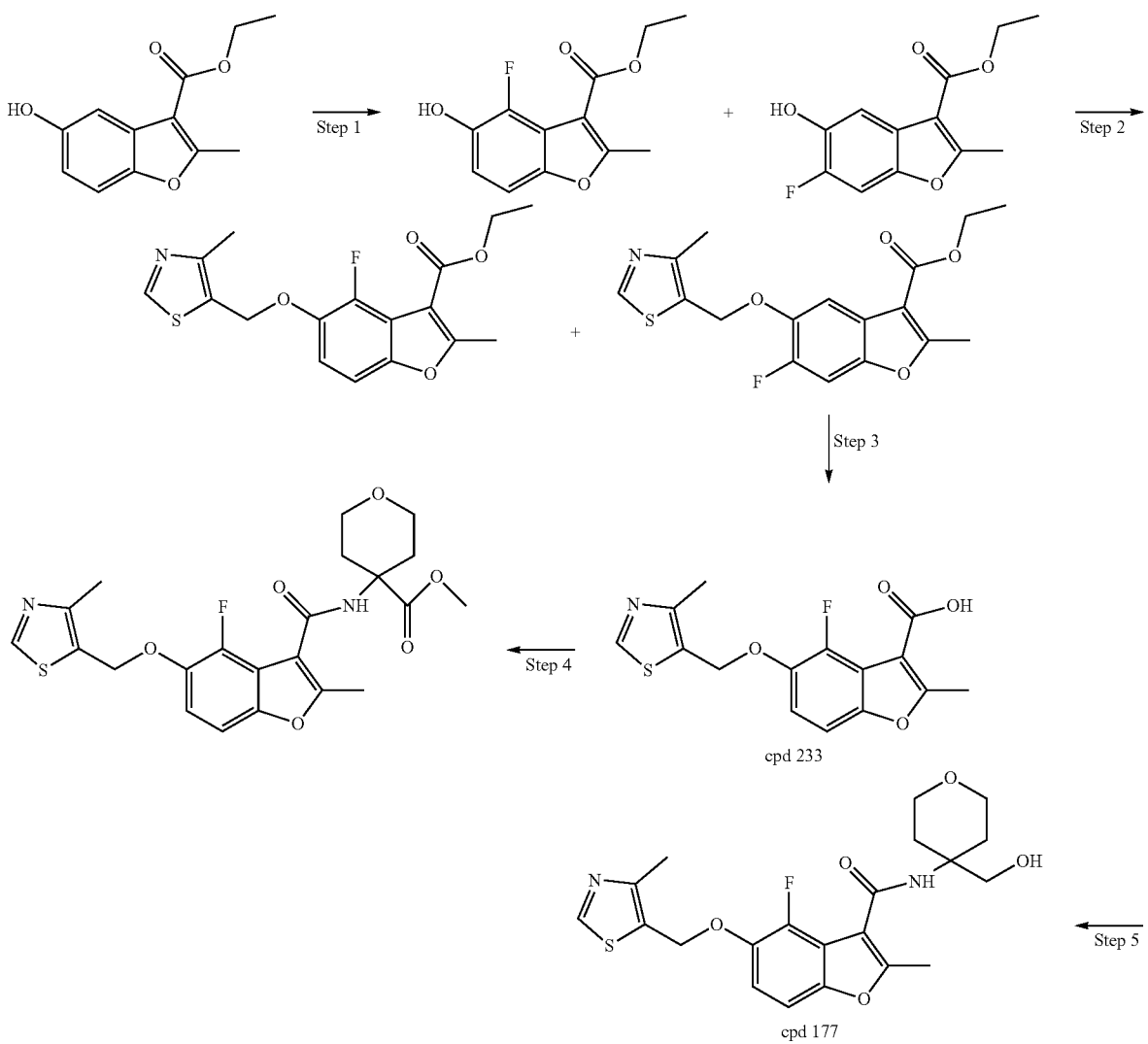

Step 3: To a stirred solution of 2-methyl-5-((4-methylthiazol-5-yl)methoxy)-N-(piperidin-4-yl)benzofuran-3-carboxamide (700 mg, 1.71 mmol) in acetonitrile (40 ml), Cs$_2$CO$_3$ (167 mg, 5.13 mmol) and CF$_3$CH$_2$OTf (595 mg, 2.57 mmol) were added at RT. The resulting RM was stirred for 4 h at RT. Reaction progress was monitored by TLC. After completion of the reaction, the RM was quenched with ice-cold water (100 ml), and extracted with EtOAc (2×100 ml). The combined organic layer was washed with water Step 1: To a solution of ethyl 5-hydroxy-2-methylbenzofuran-3-carboxylate (5.0 g, 22.7 mmol) in acetonitrile (300 mL) was added selectfluor (9.65 g, 27.2 mmol) at RT under argon atmosphere. The resulting RM was stirred for 16 h at same temperature. The reaction progress was monitored by TLC. The excess solvent was removed under reduced pressure and the crude compound was dissolved in EtOAc (500 mL). The above solution was washed with water (2×250 mL) and brine (250 mL), dried over anhydrous Na$_2$SO$_4$ and concentrated under reduced pressure. The crude product was purified by FCC over silica using 0-20% EtOAc in pet-ether as an eluent followed by a flash chromatography using 0-47% of acetonitrile in 0.1% FA in water as an eluent to afford a mixture of ethyl 4-fluoro-5-hydroxy-2-methylbenzofuran-3-carboxylate and ethyl 6-fluoro-5-hydroxy-2-methylbenzofuran-3-carboxylate (1.0 g, 19%).

Step 2: (4-Methylthiazol-5-yl)methanol (1.23 g, 9.5 mmol), ADDP (2.81 g, 11.1 mmol) and tri-N-butylphosphine (2.75 mL, 11.1 mmol) were added sequentially to a solution of a mixture of ethyl 4-fluoro-5-hydroxy-2-methylbenzofuran-3-carboxylate and ethyl 6-fluoro-5-hydroxy-2-methylbenzofuran-3-carboxylate (1.9 g, 7.98 mmol) in THF (100 mL) at 0° C. under an argon atmosphere. The RM was allowed to attain RT and stir for 1 h. The reaction progress was monitored by TLC. The RM was poured into water (200 mL) and extracted with EtOAc (2×250 mL). The combined organic layer was washed with water (200 mL) and brine (200 mL). The organic layer was dried over anhydrous $Na_2SO_4$ and concentrated under reduced pressure. The crude product was purified by FCC over silica using 0-30% EtOAc in pet-ether as an eluent to afford a mixture of ethyl 4-fluoro-2-methyl-5-((4-methylthiazol-5-yl)methoxy)benzofuran-3-carboxylate and ethyl 6-fluoro-2-methyl-5-((4-methylthiazol-5-yl)methoxy)benzofuran-3-carboxylate (1.5 g, 54%).

Step 3: 2N NaOH in water (20 mL) was added to a solution of a mixture of ethyl 4-fluoro-2-methyl-5-((4-methylthiazol-5-yl)methoxy)benzofuran-3-carboxylate and ethyl 6-fluoro-2-methyl-5-((4-methylthiazol-5-yl)methoxy)benzofuran-3-carboxylate (0.8 g, 2.29 mmol) in a mixture of MeOH (20 mL) and THF (5 mL) at RT. The resulting RM was heated to 80° C. for 3 h. The reaction progress was monitored by TLC. The RM was cooled to RT, poured into ice cold water (100 mL), and acidified with 1 N HCl (pH~2). The crude product was extracted with EtOAc (3×100 mL). The combined organic layer was washed with water (2×100 mL) followed by brine (100 mL), dried over anhydrous $Na_2SO_4$ and concentrated under reduced pressure. The crude product was purified by flash chromatography using 0-50% of acetonitrile in 0.1% FA in water as eluent to afford 4-fluoro-2-methyl-5-((4-methylthiazol-5-yl)methoxy)benzofuran-3-carboxylic acid (cpd 233) (280 mg, 38%). The corresponding undesired acid from was separately collected.

Step 4: To a pre-stirred solution of 4-fluoro-2-methyl-5-((4-methylthiazol-5-yl)methoxy)benzofuran-3-carboxylic acid (250 mg, 0.77 mmol) and methyl 4-aminotetrahydro-2H-pyran-4-carboxylate (185.7 mg, 1.10 mmol) in DMF (5 mL) was added DIPEA (0.28 mL, 1.55 mmol) followed by HATU (592 mg, 1.55 mmol) at 0° C. under argon atmosphere. The RM was allowed to attain RT and stirred for 1 h. The reaction progress was monitored by TLC. The RM was quenched with cold water (20 mL) and the solid was filtered and dried under reduced pressure to afford methyl 4-(4-fluoro-2-methyl-5-((4-methylthiazol-5-yl)methoxy)benzofuran-3-carboxamido)tetrahydro-2H-pyran-4-carboxylate (260 mg, 74%).

Step 4: $NaBH_4$ (507 mg, 13.5 mmol) was added portionwise to a pre-stirred solution of methyl 4-(4-fluoro-2-methyl-5-((4-methylthiazol-5-yl)methoxy)benzofuran-3-carboxamido)tetrahydro-2H-pyran-4-carboxylate (250 mg, 0.54 mmol) in a mixture of MeOH (10 mL) and THF (10 mL) at 0° C. The resulting RM was heated to 50° C. and maintained at this temperature for 16 h. The reaction progress was monitored by TLC. The RM was cooled to RT, diluted with water (50 mL) and the organic compound was extracted with EtOAc (2×50 mL). The combined organic layer was washed with water (50 mL) and brine (50 mL), dried over anhydrous $Na_2SO_4$ and concentrated under reduced pressure. The crude product was purified by GRACE flash chromatography using 0-50% acetonitrile and 0.1% FA in water as an eluent to afford cpd 177 (50 mg, 21%).

Synthesis of N-(3,3-difluoropiperidin-4-yl)-2,6-dimethyl-5-((2-(trifluoromethyl)pyridin-3-yl)methoxy) benzo-furan-3-carboxamide (Cpd 179) and N-(3,3-difluoropiperidin-4-yl)-2,7-dimethyl-5-((2-(trifluoromethyl)pyridin-3-yl)methoxy)benzofuran-3-carboxamide (Cpd 183)

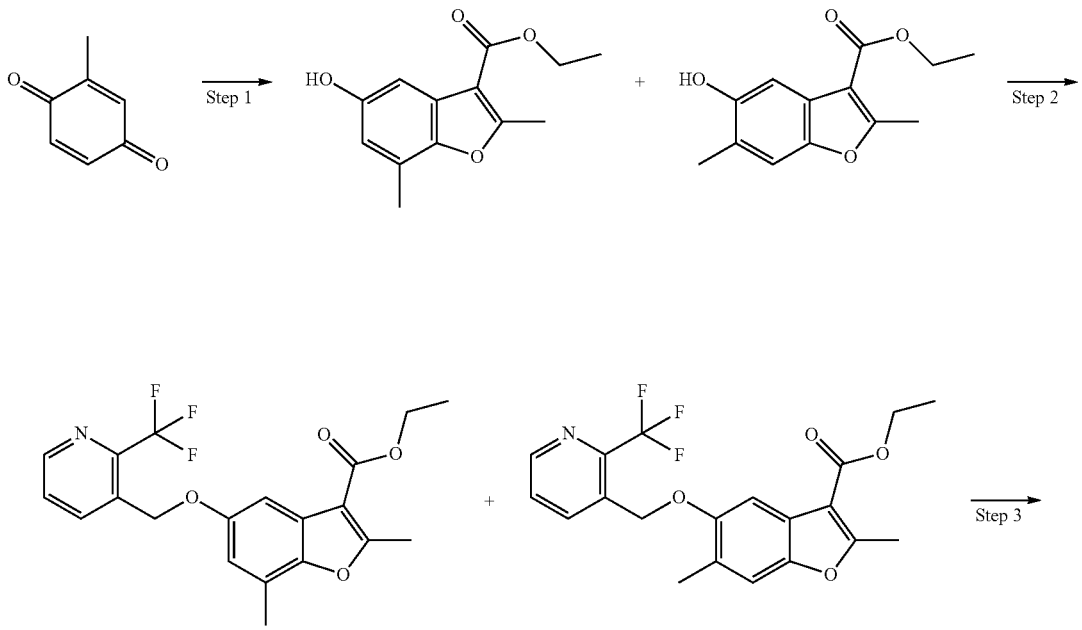

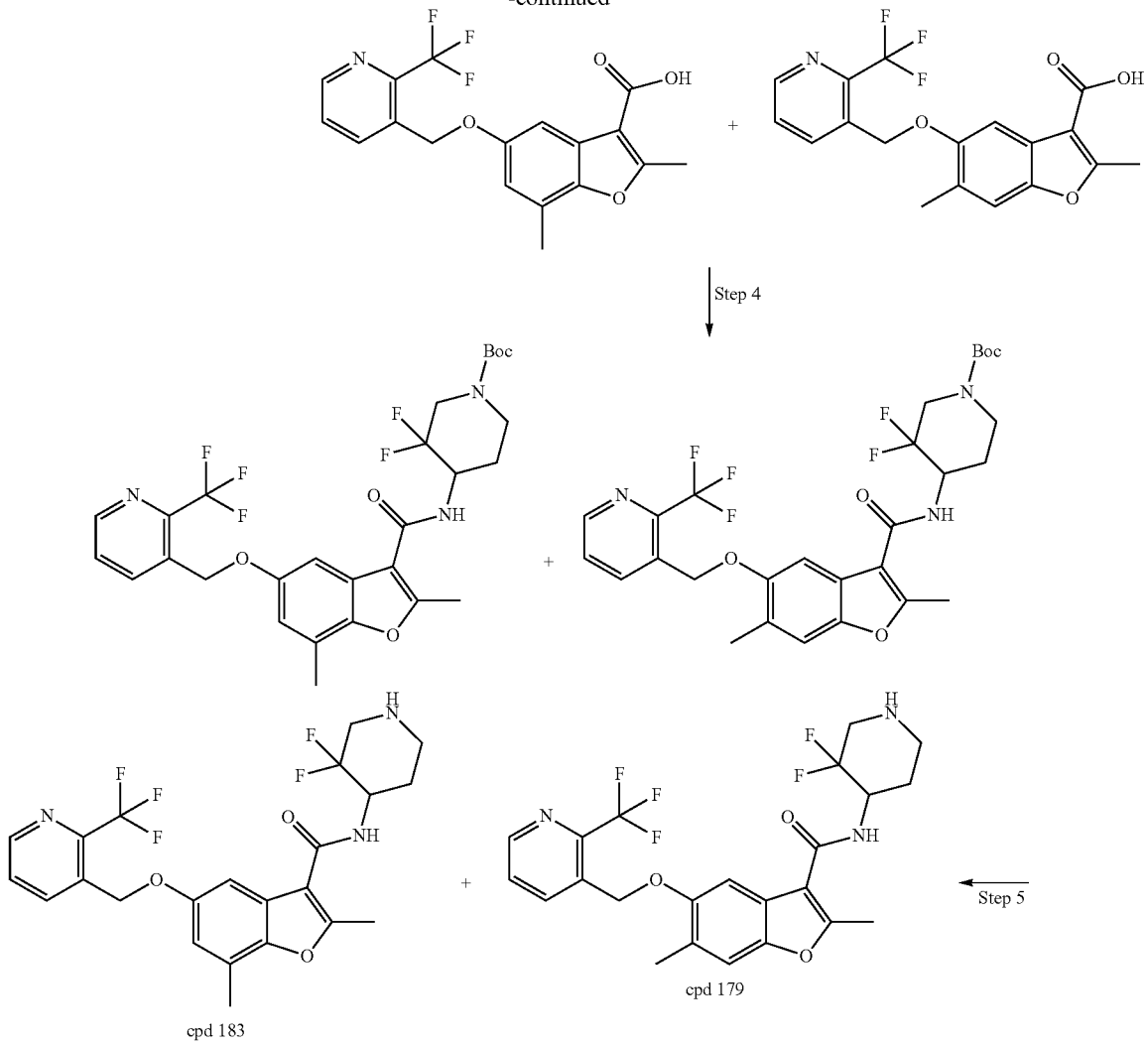

Step 1: To a solution of 2-methylcyclohexa-2,5-diene-1,4-dione (20.0 g, 163.93 mmol) in toluene (500 mL) was added ethyl 3-oxobutanoate (63.9 g, 491.79 mmol) and anhydrous ZnCl₂ (26.8 g, 196.71 mmol) at RT under argon atmosphere. The resulting RM was refluxed for 16 h using a Dean-Stark apparatus. The reaction progress was monitored by TLC. The RM was cooled to RT, filtered through a celite pad and the celite pad was washed with EtOAc (300 mL). The filtrate was concentrated under reduced pressure. The crude product was purified by FCC over silica using 0-10% EtOAc in pet-ether as an eluent to afford a mixture of ethyl 5-hydroxy-2,7-dimethylbenzofuran-3-carboxylate and ethyl 5-hydroxy-2,6-dimethylbenzofuran-3-carboxylate (20.0 g, 52%).

Step 2: (2-(Trifluoromethyl)pyridin-3-yl)methanol (11.35 g, 64.10 mmol), ADDP (15.0 g, 59.82 mmol) and tri-N-butylphosphine (14.75 mL, 59.82 mmol) were added sequentially to a solution of mixture of ethyl 5-hydroxy-2,7-dimethylbenzofuran-3-carboxylate and ethyl 5-hydroxy-2,6-dimethylbenzofuran-3-carboxylate (10.0 g, 42.73 mmol) in THF (200 mL) at 0° C. under argon atmosphere. The RM was allowed to attain RT and was stirred for 3 h. The reaction progress was monitored by TLC. The RM was poured into water (200 mL) and extracted with EtOAc (2×200 mL). The combined organic layer was washed with water (200 mL) and brine (200 mL). The organic layer was dried over anhydrous Na₂SO₄ and concentrated under reduced pressure. The crude product was purified by FCC over silica using 0-20% EtOAc in pet-ether as an eluent to afford a mixture of ethyl 2,6-dimethyl-5-((2-(trifluoromethyl)pyridin-3-yl)methoxy)benzofuran-3-carboxylate and ethyl 2,7-dimethyl-5-((2-(trifluoromethyl)pyridin-3-yl)methoxy)benzofuran-3-carboxylate (8.0 g, 47%).

Step 3: A solution of NaOH (2.03 g, 50.89 mmol) in water (50 mL) was added to a solution of mixture of ethyl 2,6-dimethyl-5-((2-(trifluoromethyl)pyridin-3-yl)methoxy)benzofuran-3-carboxylate and ethyl 2,7-dimethyl-5-((2-(trifluoromethyl)pyridin-3-yl)methoxy)benzofuran-3-carboxylate (5.0 g, 12.72 mmol) in a mixture of MeOH (50 mL) and THF (50 mL) at RT. The RM was heated to 60° C. for 3 h. The reaction progress was monitored by TLC. The RM was cooled to RT and poured into ice cold water (200 mL), then acidified with 1 N HCl (pH~2). The crude product was extracted with EtOAc (2×100 mL). The combined organic layer was washed with water (2×100 mL) followed by brine (100 mL), dried over anhydrous Na₂SO₄ and concentrated under reduced pressure to afford a mixture of 2,6-dimethyl-5-((2-(trifluoromethyl)pyridin-3-yl)methoxy)benzofuran-3- carboxylic acid and 2,7-dimethyl-5-((2-(trifluoromethyl)pyridin-3-yl)methoxy)benzofuran-3-carboxylic acid (3.5 g, 76%). The crude product thus obtained was used for next step without further purification.

Step 4: To a solution of a mixture of 2,6-dimethyl-5-((2-(trifluoromethyl)pyridin-3-yl)methoxy)-benzofuran-3-carboxylic acid and 2,7-dimethyl-5-((2-(trifluoromethyl)pyridin-3-yl)methoxy)benzofuran-3-carboxylic acid (2.0 g, 5.47 mmol) in DMF (50 mL) were added tert-butyl 4-amino-3,3-difluoropiperidine-1-carboxylate (1.5 g, 6.57 mmol), DIPEA (2.9 mL, 16.41 mmol) and HATU (4.1 g, 10.94 mmol) at 0° C. under argon atmosphere. The RM was allowed to attain RT for 3 h. The reaction progress was monitored by TLC. The RM was diluted with water (100 mL) and the crude product was extracted with EtOAc (2×100 mL). The combined organic layer was washed with water (100 mL) and brine (100 mL). The organic layer was dried over anhydrous Na₂SO₄ and concentrated under reduced pressure. The crude product was purified by column chromatography over silica using 0-55% EtOAc and pet-ether as an eluent to afford a mixture of tert-butyl 4-(2,6-dimethyl-5-((2-(trifluoromethyl)pyridin-3-yl)methoxy)benzofuran-3-carboxamido)-3,3-difluoropiperidine-1-carboxylate and tert-butyl 4-(2,7-dimethyl-5-((2-(trifluoromethyl)pyridin-3-yl)methoxy)benzofuran-3-carboxamido)-3,3-difluoro-piperidine-1-carboxylate (1.5 g, 48%).

Step 5: TFA (1.5 mL) was added dropwise to a pre-stirred solution of a mixture of tert-butyl 4-(2,6-dimethyl-5-((2-(trifluoromethyl)pyridin-3-yl)methoxy)benzofuran-3-carboxamido)-3,3-difluoropiperidine-1-carboxylate and tert-butyl 4-(2,7-dimethyl-5-((2-(trifluoromethyl)pyridin-3-yl)methoxy)benzofuran-3-carboxamido)-3,3-difluoropiperidine-1-carboxylate (1.0 g, 1.71 mmol) in DCM (10 mL) at 0° C. under an argon atmosphere. The RM was allowed to attain RT and stirred for 16 h. The reaction progress was monitored by TLC. The RM was concentrated under reduced pressure and basified with sat. NaHCO₃ solution (pH~8). The crude product was extracted with EtOAc (2×100 mL). The combined organic layer was washed with water (100 mL), followed by brine (100 mL). The organic layer was dried over anhydrous Na₂SO₄ and concentrated under reduced pressure. The crude product was purified by GRACE flash chromatography using 0-50% acetonitrile and 0.1% FA in water as an eluent to afford a mixture of cpd 179 and cpd 183 (450 mg, 84%). A preparative chiral SFC was performed on the racemate cpd 179 and the racemate cpd 183 to provide cpd 179-En 1, cpd 179-En 2, cpd 183-En 1 and cpd 183-En 2.

The following compounds were prepared in a manner similar (use of appropriate reagents and purification methods known to the person skilled in the art) to cpd 179-En 1, cpd 179-En 2, cpd 183-En 1 and cpd 183-En 2. Cpd: 165-En1, 165-En2, 184-En1, 184-En2, 174 and 187.

Synthesis of N-(4-(hydroxymethyl)tetrahydro-2H-pyran-4-yl)-2,6-dimethyl-5-((4-methylthiazol-5-yl)methoxy)-benzofuran-3-carboxamide (Cpd 185) and N-(4-(hydroxymethyl)tetrahydro-2H-pyran-4-yl)-2,7-dimethyl-5-((4-methylthiazol-5-yl)methoxy)benzofuran-3-carboxamide (Cpd 186)

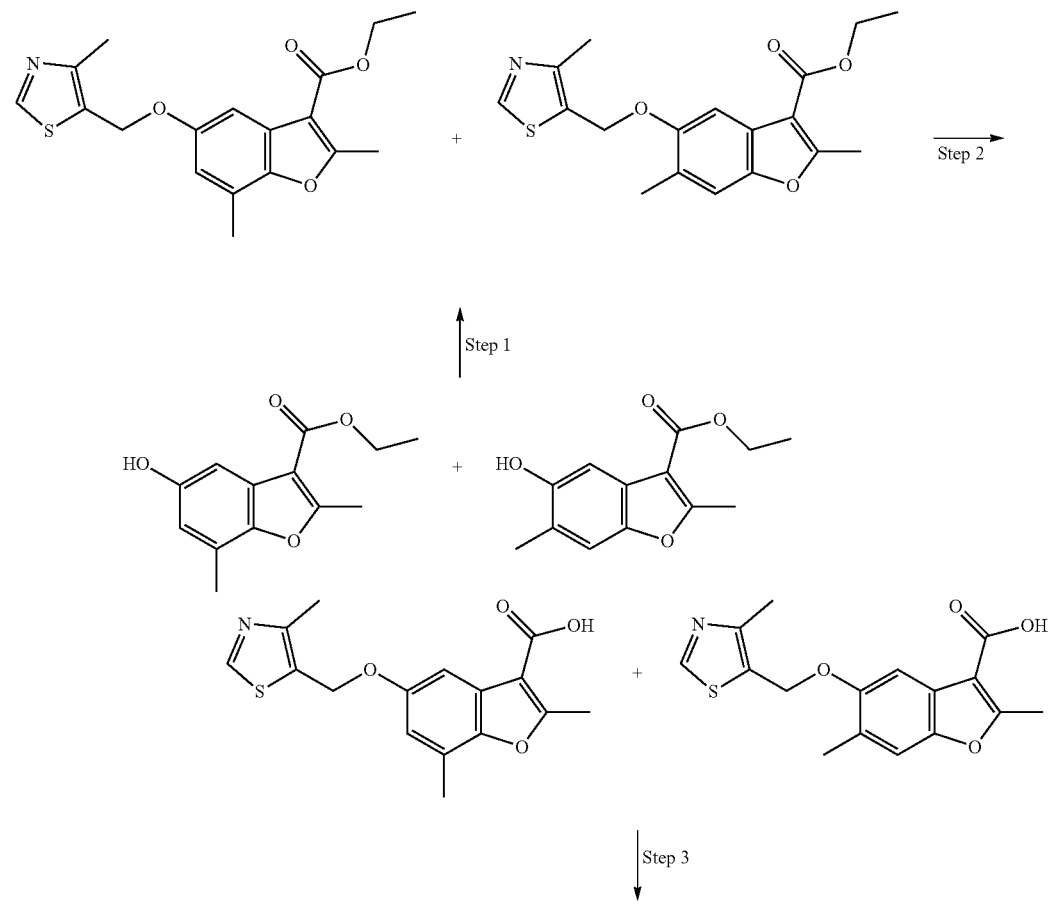

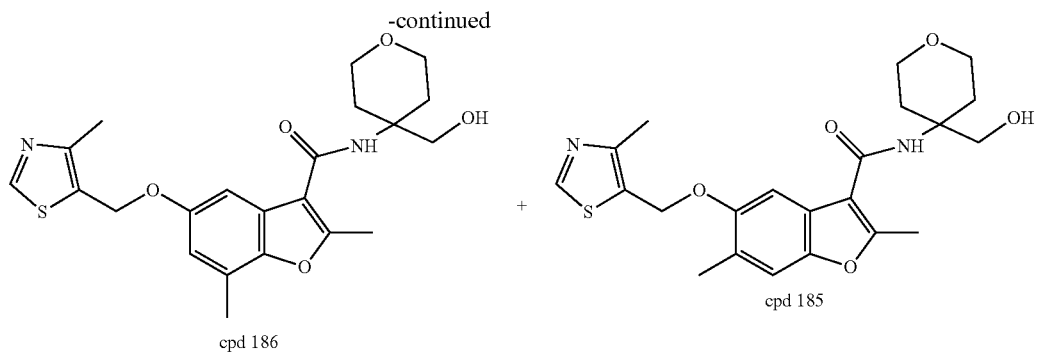

cpd 186 cpd 185

Step 1: (4-Methylthiazol-5-yl)methanol (8.26 g, 64.10 mmol), ADDP (15.0 g, 59.82 mmol) and tri-N-butylphosphine (14.75 mL, 59.82 mmol) were added sequentially to a pre-stirred solution of a mixture of ethyl 5-hydroxy-2,7-dimethylbenzofuran-3-carboxylate and ethyl 5-hydroxy-2,6-dimethylbenzofuran-3-carboxylate (10.0 g, 42.73 mmol) in THF (200 mL) at 0° C. under an argon atmosphere. The RM was allowed to attain RT and was stirred for 3 h. The reaction progress was monitored by TLC. The RM was poured into water (200 mL) and extracted with EtOAc (2×200 mL). The combined organic layer was washed with water (200 mL) and brine (200 mL). The organic layer was dried over anhydrous $Na_2SO_4$ and concentrated under reduced pressure. The crude product was purified by FCC over silica gel using 0-20% EtOAc in pet-ether as an eluent to afford a mixture of ethyl 2,7-dimethyl-5-((4-methylthiazol-5-yl)methoxy)benzofuran-3-carboxylate and ethyl 2,6-dimethyl-5-((4-methylthiazol-5-yl)methoxy)benzofuran-3-carboxylate (8.0 g, 57%).

Step 2: A solution of NaOH (0.927 g, 23.18 mmol) in water (14 mL) was added to a pre-stirred solution of a mixture of ethyl 2,7-dimethyl-5-((4-methylthiazol-5-yl)methoxy)benzofuran-3-carboxylate and ethyl 2,6-dimethyl-5-((4-methylthiazol-5-yl)methoxy)benzofuran-3-carboxylate (2.0 g, 5.79 mmol) in a mixture of MeOH (20 mL) and THF (20 mL) at RT. The resulting RM was heated to 60° C. and maintained for 3 h. The reaction progress was monitored by TLC. The RM was cooled to RT, poured into ice cold water (100 mL) and acidified with 1 N HCl (pH~2). The crude product was extracted with EtOAc (2×100 mL). The combined organic layer was washed with water (2×100 mL), followed by brine (100 mL), dried over anhydrous $Na_2SO_4$ and concentrated under reduced pressure to afford a mixture of 2,7-dimethyl-5-((4-methylthiazol-5-yl)methoxy)benzofuran-3-carboxylic acid and 2,6-dimethyl-5-((4-methylthiazol-5-yl)methoxy)benzofuran-3-carboxylic acid (1.6 g, 89%). The crude product thus obtained was used for next step without further purification.

Step 3: To a pre-stirred solution of a mixture of 2,7-dimethyl-5-((4-methylthiazol-5-yl)methoxy)benzofuran-3- and 2,6-dimethyl-5-((4-methylthiazol-5-yl)methoxy)benzofuran-3-carboxylic acid (1.0 g, 3.15 mmol) and (4-aminotetrahydro-2H-pyran-4-yl)methanol (0.619 g, 4.73 mmol) in DMF (10 mL) was added DIPEA (1.69 mL, 9.45 mmol), followed by HATU (2.39 g, 6.30 mmol) at 0° C. under an argon atmosphere. The RM was allowed to attain RT and stirred for 3 h. The reaction progress was monitored by TLC. The RM was diluted with water (100 mL), and the crude product was extracted with EtOAc (2×100 mL). The combined organic layer was washed with water (100 mL) and brine (100 mL). The organic layer was dried over anhydrous $Na_2SO_4$ and concentrated under reduced pressure. The crude product was purified by column chromatography over silica gel using 0-55% EtOAc and pet-ether as an eluent to afford a mixture of cpd 186 and cpd 185 (0.5 g, 57%). A preparative chiral SFC was performed on a mixture of cpd 186 and 185 to provide cpd 186 and cpd 185.

Synthesis of 7-cyano-N-(4-(hydroxymethyl)tetrahydro-2H-pyran-4-yl)-2-methyl-5-((4-methylthiazol-5-yl)methoxy)benzofuran-3-carboxamide (Cpd 188)

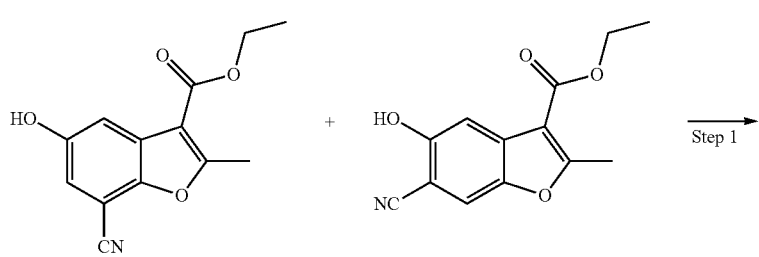

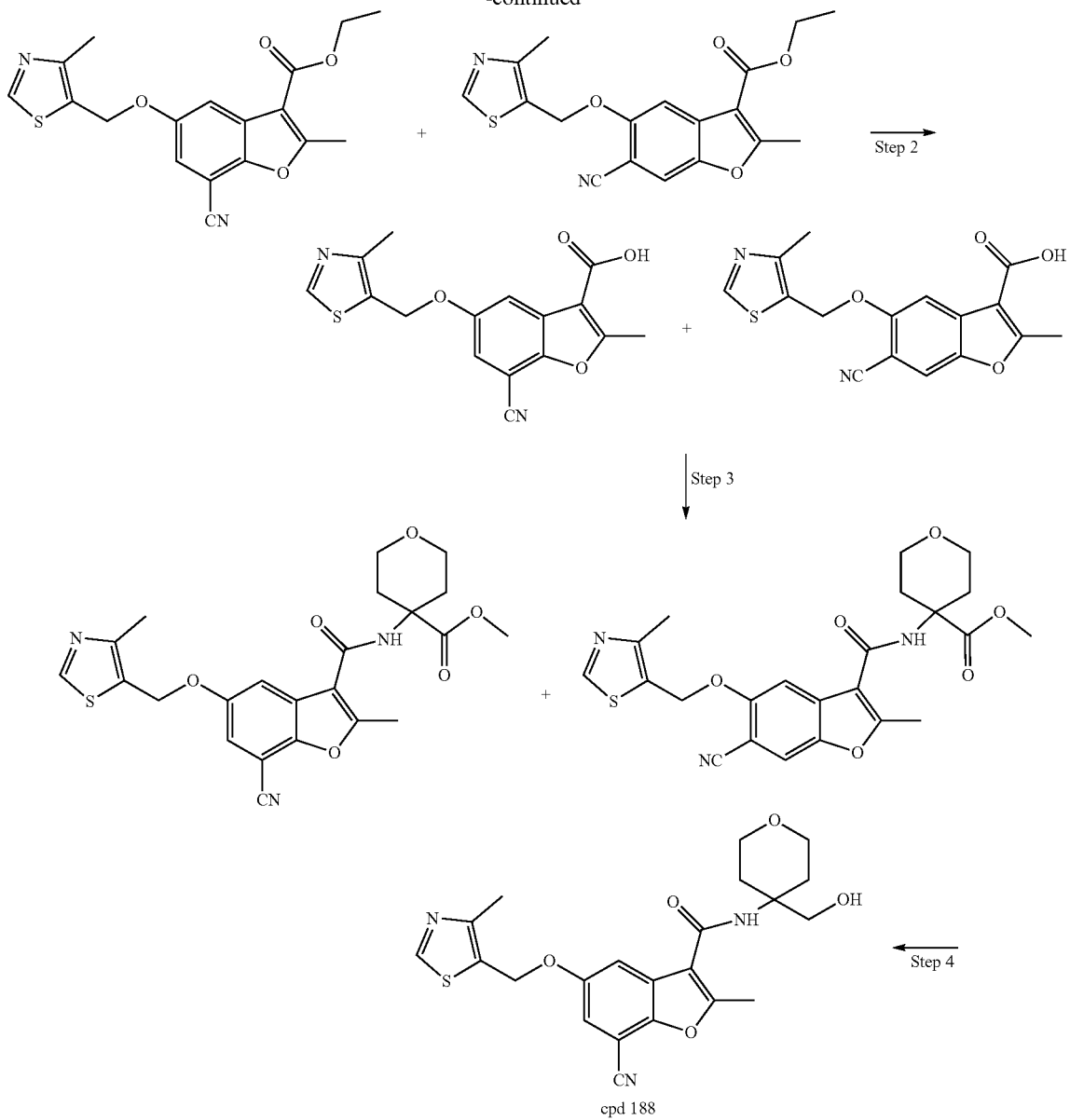

Step 1: (4-Methylthiazol-5-yl)methanol (0.47 g, 3.67 mmol), ADDP (0.64 g, 3.42 mmol) and tri-N-butylphosphine (0.80 mL, 3.42 mmol) were added sequentially to a pre-stirred solution of ethyl 6-cyano-5-hydroxy-2-methyl-benzofuran-3-carboxylate and ethyl 7-cyano-5-hydroxy-2-methylbenzofuran-3-carboxylate (0.6 g, 2.44 mmol) in THF (30 mL) at 0° C. under argon atmosphere. The RM was allowed to attain RT and stirred for 2 h. The reaction progress was monitored by TLC. The RM was poured into water (100 mL) and extracted with EtOAc (2×100 mL). The combined organic layer was washed with water (50 mL) and brine (50 mL). The organic layer was dried over anhydrous $Na_2SO_4$ and concentrated under reduced pressure. The crude product was purified by column chromatography over silica gel using 0-20% EtOAc in pet-ether as an eluent to afford a mixture of ethyl 6-cyano-2-methyl-5-((4-methylthiazol-5-yl)methoxy)benzofuran-3-carboxylate and ethyl 7-cyano-2-methyl-5-((4-methylthiazol-5-yl)methoxy)benzofuran-3-carboxylate (0.6 g, 68%).

Step 2: A solution of NaOH (0.26 g, 6.74 mmol) in water (8 mL) was added dropwise to a solution of ethyl 6-cyano-2-methyl-5-((4-methylthiazol-5-yl)methoxy)benzofuran-3-carboxylate and ethyl 7-cyano-2-methyl-5-((4-methylthiazol-5-yl)methoxy)benzofuran-3-carboxylate (0.6 g, 1.68 mmol) in a mixture of MeOH (10 mL) and THF (5 mL) at RT. The resulting RM was heated to 60° C. and maintained at this temperature for 4 h. The reaction progress was monitored by TLC. The RM was cooled to RT, poured into ice cold water (50 mL) and acidified with 1 N HCl (pH~2). The crude product was extracted with EtOAc (2×50 mL). The combined organic layer was washed with water (50 mL) followed by brine (50 mL), dried over anhydrous $Na_2SO_4$ and concentrated under reduced pressure to afford a mixture of 6-cyano-2-methyl-5-((4-methylthiazol-5-yl)methoxy)benzofuran-3-carboxylic acid and 7-cyano-2-methyl-5-((4-methylthiazol-5-yl)methoxy)benzofuran-3-carboxylic acid (0.55 g, 99%).

Step 3: To a solution of a mixture of 6-cyano-2-methyl-5-((4-methylthiazol-5-yl)methoxy)benzofuran-3-carboxylic acid and 7-cyano-2-methyl-5-((4-methylthiazol-5-yl)methoxy)benzofuran-3-carboxylic acid (0.55 g, 1.67 mmol), and methyl 4-aminotetrahydro-2H-pyran-4-carboxylate (0.31 g, 2.01 mmol) in DMF (10 mL) was added DIPEA (0.86 mL, 5.03 mmol) followed by HATU (1.27 g, 3.35 mmol) at 0° C. under an argon atmosphere. The RM was allowed to attain RT and stirred for 16 h. The reaction progress was monitored by TLC. The RM was diluted with water (50 mL) and the organic compound was extracted with EtOAc (2×50 mL). The organic layer was washed with water (50 mL) and brine (50 mL), dried over anhydrous Na₂SO₄ and concentrated under reduced pressure. The crude product was purified by column chromatography over silica gel using 0-55% EtOAc in pet ether as an eluent to afford a mixture of methyl 4-(6-cyano-2-methyl-5-((4-methylthiazol-5-yl)methoxy)benzofuran-3-carboxamido)tetrahydro-2H-pyran-4-carboxylate and methyl 4-(7-cyano-2-methyl-5-((4-methylthiazol-5-yl)methoxy)benzofuran-3-carboxamido)tetrahydro-2H-pyran-4-carboxylate (0.5 g, 63%). Step 4: NaBH₄ (1.01 g, 26.65 mmol) was added portionwise to a pre-stirred solution of a mixture of methyl 4-(6-chloro-2-methyl-5-((4-methylthiazol-5-yl)methoxy)benzofuran-3-carboxamido)tetrahydro-2H-pyran-4-carboxylate and methyl 4-(7-chloro-2-methyl-5-((4-methylthiazol-5-yl)methoxy)benzofuran-3-carboxamido)-tetrahydro-2H-pyran-4-carboxylate (0.5 g, 1.06 mmol) in a mixture of MeOH (10 mL) and THF (5 mL) at 0° C. The RM was allowed to attain RT and stirred for 16 h. The reaction progress was monitored by TLC. The RM was diluted with water (50 mL) and then the crude product was extracted with EtOAc (2×50 mL). The combined organic layer was washed with water (50 mL) and brine (50 mL), dried over anhydrous Na₂SO₄ and concentrated under reduced pressure. The crude product was purified by GRACE flash chromatography using 0-60% acetonitrile and 0.1% FA in water as an eluent followed by RP prep-HPLC to afford cpd 188 (25 mg, 5%).

Synthesis of 4-cyano-N-(3,3-difluoropiperidin-4-yl)-2-methyl-5-((2-(trifluoromethyl)pyridin-3-yl)methoxy)-benzofuran-3-carboxamide (Cpd 191)

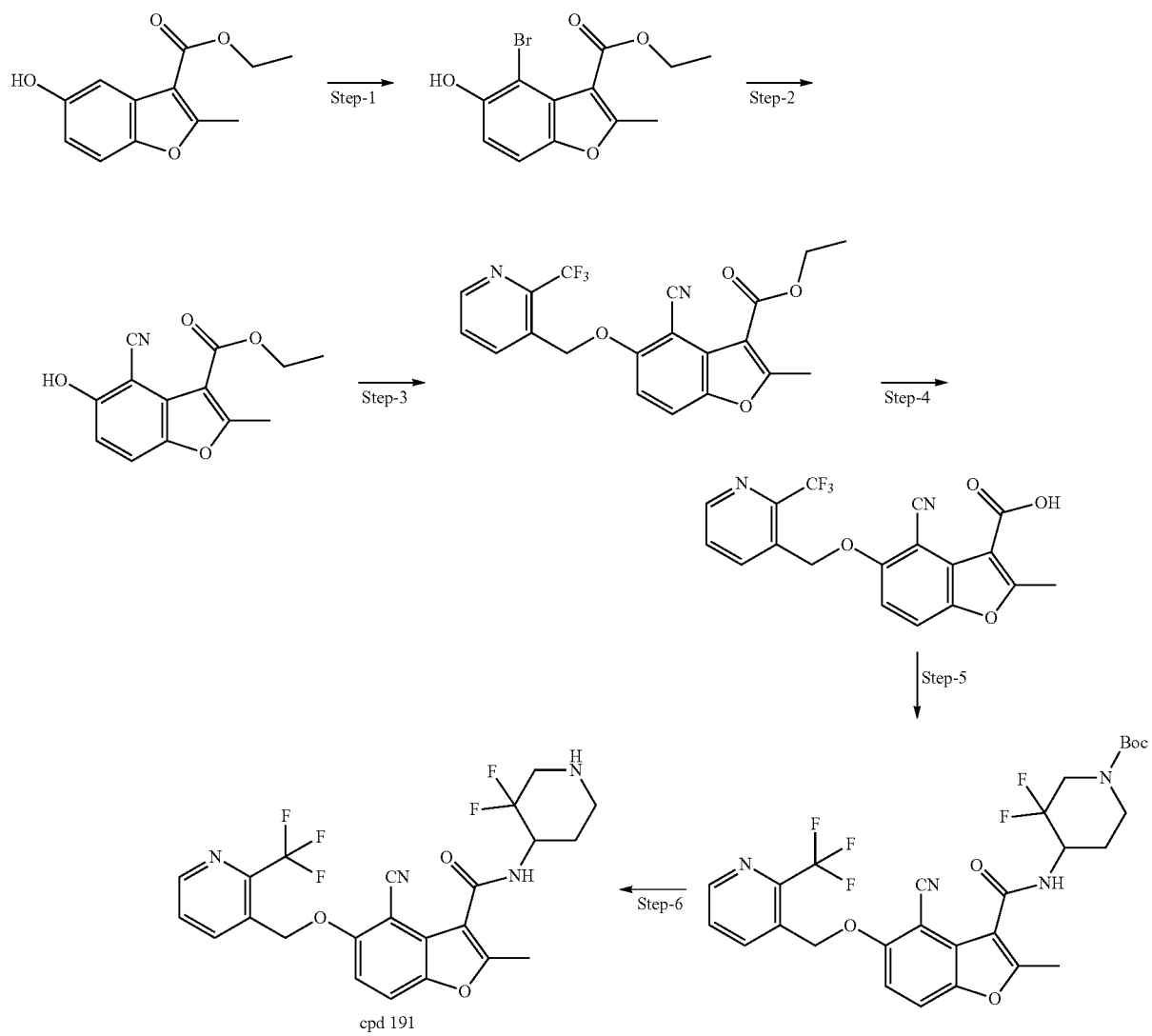

cpd 191

Step 1: NBS (24.2 g, 136.22 mmol) was added to a solution of ethyl 5-hydroxy-2-methylbenzofuran-3-carboxylate (20.0 g, 90.81 mmol) in acetonitrile (600 mL) at RT under an argon atmosphere. The RM was stirred for 16 h at same temperature. The reaction progress was monitored by TLC. The RM was diluted with water (300 mL) and acidified with 1N-HCl to pH~2. The crude product was extracted with EtOAc (2×300 mL). The combined organic layer was washed with water (200 mL) followed by brine (200 mL). The organic layer was dried over anhydrous $Na_2SO_4$ and concentrated under reduced pressure. The crude product was purified by column chromatography over silica gel using 0-20% EtOAc and pet-ether as an eluent to afford ethyl 4-bromo-5-hydroxy-2-methylbenzofuran-3-carboxylate (5.0 g, 19%).

Step 2: CuCN (0.74 g, 8.36 mmol) was added to a solution of ethyl 4-bromo-5-hydroxy-2-methylbenzofuran-3-carboxylate (1.0 g, 3.44 mmol) in N,N-dimethylformamide (25 mL) at RT under an argon atmosphere. The resulting mixture was heated to 160° C. and maintained for 3 h. The reaction progress was monitored by TLC. The RM was cooled to RT, poured into water (100 mL) and extracted with EtOAc (2×100 mL). The combined organic layer was washed with water (2×50 mL) followed by brine (50 mL). The organic layer was dried over anhydrous $Na_2SO_4$ and concentrated under reduced pressure. The crude product was purified by column chromatography over silica gel using 0-20% EtOAc in pet-ether as an eluent to afford ethyl 4-cyano-5-hydroxy-2-methylbenzofuran-3-carboxylate (0.45 g, 55%).

Step 3: (2-(Trifluoromethyl)pyridin-3-yl)methanol (0.65 g, 3.67 mmol), ADDP (0.861 g, 3.41 mmol) and tri-N-butylphosphine (0.84 mL, 3.41 mmol) were added sequentially to a pre-stirred solution of ethyl 4-cyano-5-hydroxy-2-methylbenzofuran-3-carboxylate (0.6 g, 2.44 mmol) in THF (20 mL) at 0° C. under an argon atmosphere. The RM was allowed to attain RT and stirred for 3 h. The reaction progress was monitored by TLC. The RM was poured into water (50 mL) and extracted with EtOAc (2×50 mL). The combined organic layer was washed with water (50 mL) and brine (50 mL). The organic layer was dried over anhydrous $Na_2SO_4$ and concentrated under reduced pressure. The crude product was purified by FCC over silica gel using 0-20% EtOAc in pet-ether as an eluent to afford ethyl 4-cyano-5-((2-(trifluoromethyl)pyridin-3-yl)methoxy)benzofuran-3-carboxylate (0.45 g, crude). The crude product thus obtained was used for next step without further purification.

Step 4: A solution of NaOH (0.178 g, 4.45 mmol) in water (5.0 mL) was added to a solution of ethyl 5-(benzyloxy)-4-cyano-2-methylbenzofuran-3-carboxylate (0.450 g, 1.11 mmol) in a mixture of MeOH (10 mL) and THF (10 mL) at RT. The resulting RM was heated to 60° C. and maintained for 3 h. The reaction progress was monitored by TLC. The RM was cooled to RT, poured into ice cold water (50 mL) and acidified with 1 N HCl (pH~2). The crude product was extracted with EtOAc (2×50 mL). The combined organic layer was washed with water (2×50 mL) followed by brine (50 mL), dried over anhydrous $Na_2SO_4$ and concentrated under reduced pressure to afford 4-cyano-2-methyl-5-((2-(trifluoromethyl)pyridin-3-yl)methoxy)benzofuran-3-carboxylic acid (0.4 g, crude). The crude product thus obtained was used for next step without further purification.

Step 5: To a solution of a mixture of 4-cyano-2-methyl-5-((2-(trifluoromethyl)pyridin-3-yl)methoxy)benzofuran-3-carboxylic acid (0.4 g, 1.06 mmol) and tert-butyl 4-amino-3,3-difluoropiperidine-1-carboxylate (0.376 g, 1.59 mmol) in DMF (10 mL) was added DIPEA (0.50 mL, 3.18 mmol) followed by HATU (0.805 g, 2.12 mmol) at 0° C. under argon atmosphere. The RM was allowed to attain RT and stirred for 3 h. The reaction progress was monitored by TLC. The RM was diluted with water (50 mL), and the crude product was extracted with EtOAc (2×50 mL). The combined organic layer was washed with water (50 mL), brine (50 mL), dried over anhydrous $Na_2SO_4$ and concentrated under reduced pressure. The crude product was purified by column chromatography over silica gel using 0-55% EtOAc and pet-ether as an eluent to afford tert-butyl 4-(4-cyano-2-methyl-5-((2-(trifluoromethyl)pyridin-3-yl)methoxy)benzofuran-3-carboxamido)-3,3-difluoropiperidine-1-carboxylate (0.3 g, crude).

Step 6: To a solution of tert-butyl 4-(4-cyano-2-methyl-5-((2-(trifluoromethyl)pyridin-3-yl)methoxy)benzofuran-3-carboxamido)-3,3-difluoropiperidine-1-carboxylate (0.3 g, 0.50 mmol) in DCM (2.5 mL) was added TFA (2.5 mL) dropwise at 0° C. under an argon atmosphere. The RM was allowed to attain RT and stirred for 16 h. The reaction progress was monitored by TLC. The RM was concentrated under reduced pressure, and the residue was basified with $NaHCO_3$ (pH~8). The crude product was extracted with EtOAc (2×50 mL). The combined organic layer was washed with water (50 mL) followed by brine (50 mL), dried over anhydrous $Na_2SO_4$ and concentrated under reduced pressure. The crude product was purified by flash chromatography using 0-50% acetonitrile in 0.1% FA in water as an eluent to afford racemic cpd 191 (0.21 g, 89%). A preparative chiral SFC was performed on the racemic mixture of cpd 191 to afford cpd 191-En 1 and cpd 191-En 2.

Synthesis of 4-cyano-N-(4-(hydroxymethyl)tetrahydro-2H-pyran-4-yl)-2-methyl-5-((4-methylthiazol-5-yl)-methoxy)benzofuran-3-carboxamide (Cpd 193)

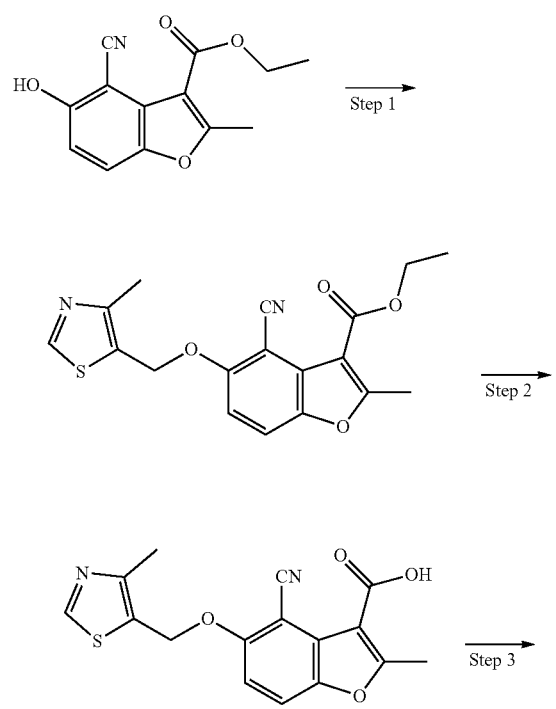

-continued

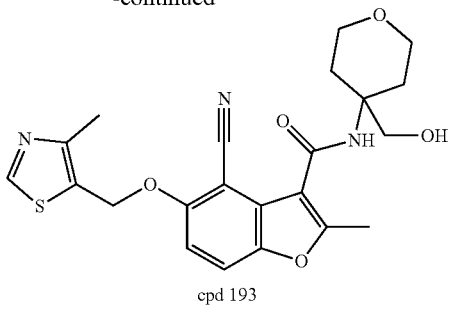

cpd 193

Step 1: (4-Methylthiazol-5-yl)methanol (0.31 g, 2.44 mmol), ADDP (0.57 g, 2.28 mmol) and tri-N-butylphosphine (0.56 mL, 2.28 mmol) were added sequentially to a pre-stirred solution of ethyl 4-cyano-5-hydroxy-2-methyl-benzofuran-3-carboxylate (0.4 g, 1.63 mmol) in THF (20 mL) at 0° C. under an argon atmosphere. The RM was allowed to warm to RT and stirred for 3 h. The reaction progress was monitored by TLC. The RM was poured into water (50 mL) and extracted with EtOAc (2×50 mL). The combined organic layer was washed with water (50 mL) and brine (50 mL), dried over anhydrous $Na_2SO_4$ and concentrated under reduced pressure. The crude product was purified by FCC over silica using 0-20% EtOAc in pet-ether as an eluent to afford ethyl 4-cyano-2-methyl-5-((4-methylthiazol-5-yl)methoxy)benzofuran-3-carboxylate (0.300 g, 52%). The crude product thus obtained was used for next step without further purification.

Step 2: A solution of NaOH (0.13 g, 3.38 mmol) in water (5.0 mL) was added to a pre-stirred solution of ethyl 5-(benzyloxy)-4-cyano-2-methylbenzofuran-3-carboxylate (0.30 g, 0.84 mmol) in MeOH (10 mL) and THF (10 mL) at RT. The resulting RM was heated to 60° C. and maintained at this temperature for 3 h. The reaction progress was monitored by TLC. The RM was cooled to RT, poured into ice cold water (50 mL), acidified with 1 N HCl (pH~2.0) and extracted with EtOAc (2×50 mL). The combined organic layer was washed with water (2×50 mL) and brine (50 mL), dried over anhydrous $Na_2SO_4$ and concentrated under reduced pressure to afford 4-cyano-2-methyl-5-((4-methylthiazol-5-yl)methoxy)benzofuran-3-carboxylic acid (0.20 g, crude). The crude product thus obtained was used for next step without further purification.

Step 3: To a pre-stirred solution of 4-cyano-2-methyl-5-((4-methylthiazol-5-yl)methoxy)benzofuran-3-carboxylic acid (0.20 g, 0.61 mmol) and (4-aminotetrahydro-2H-pyran-4-yl)methanol (0.12 g, 092 mmol) in DMF (5 mL) were added DIPEA (0.29 mL, 1.83 mmol) followed by HATU (0.46 g, 1.22 mmol) at 0° C. under an argon atmosphere. The RM was stirred at room temperature for 3 h. The reaction progress was monitored by TLC. The RM was diluted with water (50 mL) and extracted with EtOAc (2×50 mL). The combined organic layer was washed with water (50 mL) and brine (50 mL), dried over anhydrous $Na_2SO_4$ and concentrated under reduced pressure. The crude product was purified by RP-HPLC to afford cpd 193 (0.90 g, 60%).

Synthesis of 6-cyano-N-(4-(hydroxymethyl)tetra-hydro-2H-pyran-4-yl)-2-methyl-5-((4-methylthiazol-5-yl)-methoxy)benzofuran-3-carboxamide (Cpd 194)

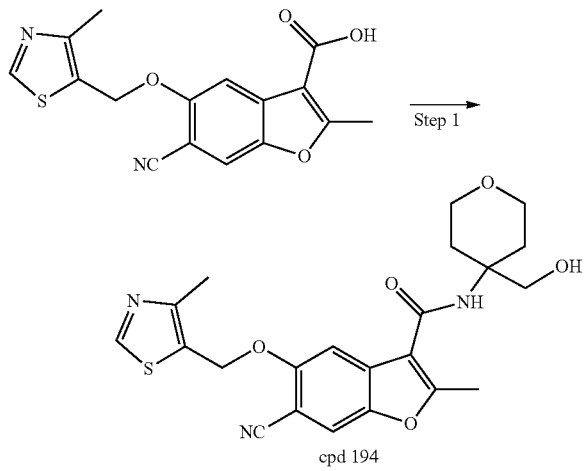

cpd 194

Step 1: To a solution of a mixture of 6-cyano-2-methyl-5-((4-methylthiazol-5-yl)methoxy)benzofuran-3-carboxylic acid (0.2 g, 0.60 mmol) and (4-aminotetrahydro-2H-pyran-4-yl)methanol (0.15 g, 1.21 mmol) in DMF (5 mL) was added DIPEA (0.32 mL, 1.82 mmol) followed by HATU (0.46 g, 1.21 mmol) at 0° C. under an argon atmosphere. The resulting RM was stirred at RT for 16 h. The reaction progress was monitored by TLC. The RM was diluted with water (30 mL) and extracted with EtOAc (2×30 mL). The combined organic layer was washed with water (30 mL) and brine (30 mL), dried over anhydrous $Na_2SO_4$ and concentrated under reduced pressure. The crude product was purified by GRACE flash chromatography using 0.1% FA in water and acetonitrile as an eluent to afford cpd 194 (85 mg, 32%).

Synthesis of 6-cyano-N-(3,3-difluoropiperidin-4-yl)-2-methyl-5-((2-(trifluoromethyl)pyridin-3-yl) methoxy)-benzofuran-3-carboxamide (Cpd 195) and 7-cyano-N-(3,3-difluoropiperidin-4-yl)-2-methyl-5-((2-(trifluoro-methyl)pyridin-3-yl)methoxy)benzo-furan-3-carboxamide (Cpd 196)

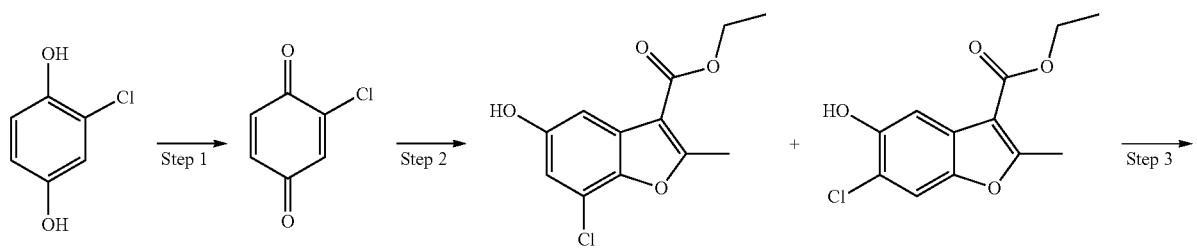

455 456
-continued
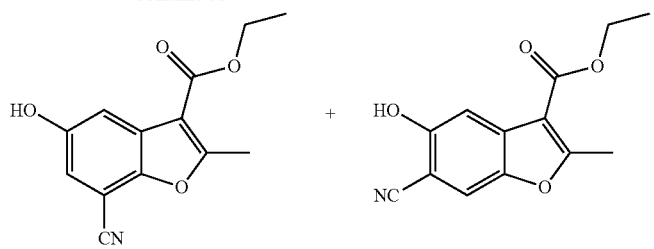
Step 4
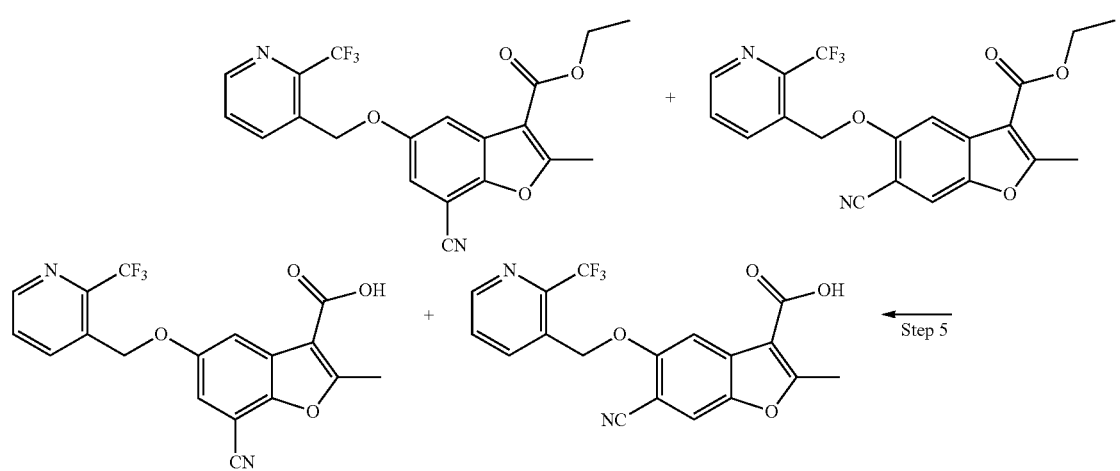
Step 5
Step 6
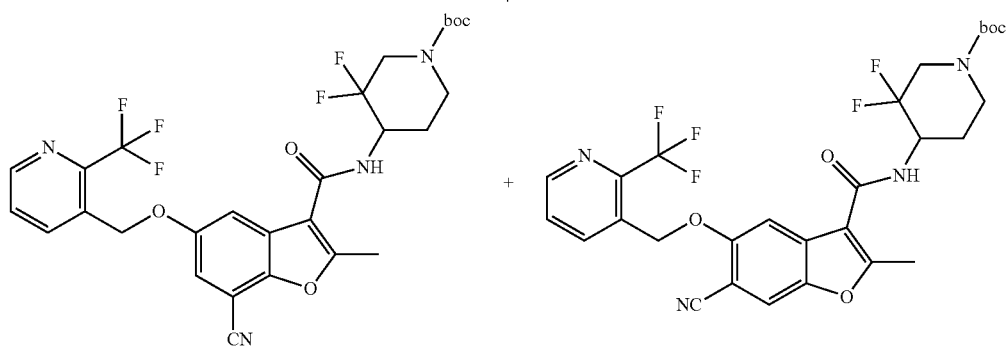
Step 7
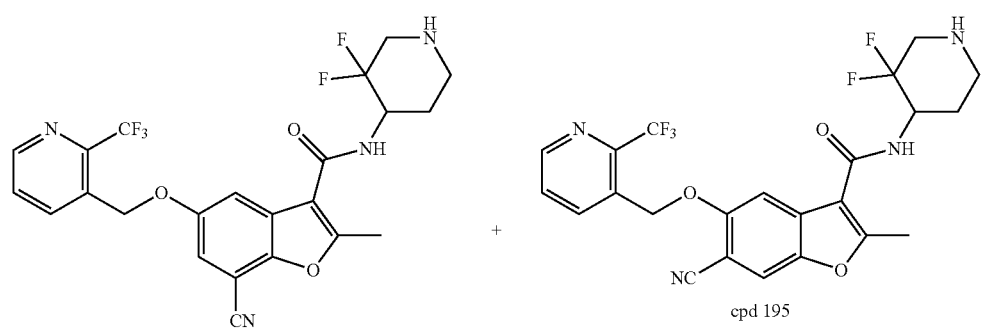
cpd 196           cpd 195

Step 1: To a pre-stirred solution of CAN (199.18 g, 363.32 mmol) in water (500 mL) was added 2-chlorobenzene-1,4-diol (25.0 g, 173.01 mmol) at 0° C. The resulting RM was stirred at RT for 4 h. The reaction progress was monitored by TLC. The organic compound was extracted with $Et_2O$ (3×200 mL). The combined organic layer was washed with brine (50 mL) and dried over anhydrous $Na_2SO_4$. The dried organic layer was passed through a silica gel column using diethyl ether as eluant and thus collected fractions were concentrated under reduced pressure to afford 2-chlorocyclohexa-2,5-diene-1,4-dione (20 g, 83%).

Step 2: To a pre-stirred solution of 2-chlorocyclohexa-2,5-diene-1,4-dione (20 g, 140.84 mmol) in toluene (300 mL) was added ethyl 3-oxobutanoate (54.92 g, 422.53 mmol) followed by anhydrous $ZnCl_2$ (23.0 g, 169.0 mmol) at RT under argon atmosphere. The resulting RM was heated to reflux and maintained for 16 h using Dean-Stark apparatus. The reaction progress was monitored by TLC. The RM was cooled to RT, filtered through a celite pad and the celite pad was washed with EtOAc (500 mL). The combined clear filtrate was concentrated under reduced pressure. The crude product was purified by FCC over silica gel using 0-10% EtOAc in pet-ether as an eluent to afford a mixture of ethyl 6-chloro-5-hydroxy-2-methylbenzofuran-3-carboxylate and ethyl 7-chloro-5-hydroxy-2-methylbenzofuran-3-carboxylate (7.0 g, 20%).

Step 3: A solution of a mixture of ethyl 6-chloro-5-hydroxy-2-methylbenzofuran-3-carboxylate and ethyl 7-chloro-5-hydroxy-2-methylbenzofuran-3-carboxylate (1.0 g, 3.93 mmol) and $Zn(CN)_2$ (2.01 g, 17.71 mmol) in dimethylacetamide (12 mL) was degassed with argon for 10 min. To the above RM, $Pd(P(t-Bu)_3)_2$ (0.60 g, 1.18 mmol) was added in one portion and it was then degassed for 5 min. The resulting mixture was heated to 160° C. and maintained at this temperature for 2 h under microwave heating. The reaction progress was monitored by TLC. The RM was poured into water (100 mL) and extracted with EtOAc (2×100 mL). The combined organic layer was washed with water (2×50 mL) and brine (50 mL). The organic layer was dried over anhydrous $Na_2SO_4$ and concentrated under reduced pressure. The crude product was purified by column chromatography over silica gel using 0-20% EtOAc in pet-ether as an eluent to afford a mixture of ethyl 6-cyano-5-hydroxy-2-methylbenzofuran-3-carboxylate and ethyl 7-cyano-5-hydroxy-2-methylbenzofuran-3-carboxylate (0.6 g, 62.5%).

Step 4: (2-(Trifluoromethyl)pyridin-3-yl)methanol (1.30 g, 7.34 mmol), ADDP (1.72 g, 6.85 mmol) and tri-N-butylphosphine (1.60 mL, 6.85 mmol) were added to a solution of a mixture of ethyl 6-cyano-5-hydroxy-2-methylbenzofuran-3-carboxylate and ethyl 7-cyano-5-hydroxy-2-methylbenzofuran-3-carboxylate (1.2 g, 4.89 mmol) in THF (30 mL) at RT under an argon atmosphere. The RM was stirred for 2 h at same temperature. The reaction progress was monitored by TLC. The RM was poured into water (100 mL) and extracted with EtOAc (2×100 mL). The combined organic layer was sequentially washed with water (50 mL) and brine (50 mL), dried over anhydrous $Na_2SO_4$ and concentrated under reduced pressure. The crude product was purified by column chromatography over silica gel using 0-20% EtOAc in pet-ether as an eluent to afford a regioisomeric mixture of ethyl 6-cyano-2-methyl-5-((2-(trifluoromethyl)pyridin-3-yl)methoxy)benzofuran-3-carboxylate and ethyl 7-cyano-2-methyl-5-((2-(trifluoromethyl)pyridin-3-yl)methoxy)benzofuran-3-carboxylate (1.2 g, 60%).

Step 5: A solution of NaOH (0.47 g, 11.88 mmol) in water (8 mL) was added dropwise to a solution of a mixture of ethyl 6-cyano-2-methyl-5-((2-(trifluoromethyl)pyridin-3-yl)methoxy)benzofuran-3-carboxylate and ethyl 7-cyano-2-methyl-5-((2-(trifluoromethyl)pyridin-3-yl)methoxy)benzofuran-3-carboxylate (1.2 g, 2.97 mmol) in a mixture of MeOH:THF (2:1) (23 mL) at RT. The resulting RM was heated to 60° C. for 4 h. The reaction progress was monitored by TLC. The RM was cooled to RT and poured into ice cold water (50 mL), and acidified with 1 N HCl to a pH~2. The crude product was extracted with EtOAc (2×50 mL). The combined organic layer was washed with water (50 mL) and brine (50 mL), dried over anhydrous $Na_2SO_4$ and concentrated under reduced pressure to afford a regioisomeric mixture of 6-cyano-2-methyl-5-((2-(trifluoromethyl)pyridin-3-yl)methoxy)benzofuran-3-carboxylic acid and 7-cyano-2-methyl-5-((2-(trifluoromethyl)pyridin-3-yl)methoxy)-benzofuran-3-carboxylic acid (1.0 g, 90%). This crude regioisomeric mixture was used in the next step without any separation.

Step 6: To a pre-stirred solution of a mixture of 6-cyano-2-methyl-5-((2-(trifluoromethyl)pyridin-3-yl)methoxy)benzofuran-3-carboxylic acid and 7-cyano-2-methyl-5-((2-(trifluoromethyl)pyridin-3-yl)methoxy)-benzofuran-3-carboxylic acid (1.0 g, 2.65 mmol), and tert-butyl 4-amino-3,3-difluoropiperidine-1-carboxylate (0.90 g, 3.97 mmol) in DMF (20 mL) was added DIPEA (1.36 mL, 7.95 mmol) followed by HATU (2.02 g, 5.31 mmol) at 0° C. under an argon atmosphere. The RM was allowed to attain RT and stirred for 16 h. The reaction progress was monitored by TLC. The RM was diluted with water (100 mL) and the organic compound was extracted with EtOAc (2×70 mL). The combined organic layer was washed with water (50 mL) and brine (50 mL), dried over anhydrous $Na_2SO_4$ and concentrated under reduced pressure. The crude product was purified by column chromatography over silica using a gradient mixture of 0-55% EtOAc in pet-ether as an eluent to afford a regioisomeric mixture of tert-butyl 4-(6-cyano-2-methyl-5-((2-(trifluoromethyl)pyridin-3-yl)methoxy)-benzofuran-3-carboxamido)-3,3-difluoropiperidine-1-carboxylate and tert-butyl 4-(7-cyano-2-methyl-5-((2-(trifluoromethyl)pyridin-3-yl)methoxy)benzofuran-3-carboxamido)-3,3-difluoropiperidine-1-carboxylate (1.0 g, 63%).

Step 7: 4.0 M HCl in dioxane (10.0 mL) was added dropwise to a solution of a mixture of tert-butyl 4-(6-cyano-2-methyl-5-((2-(trifluoromethyl)pyridin-3-yl)methoxy)benzofuran-3-carboxamido)-3,3-difluoro-piperidine-1-carboxylate and tert-butyl 4-(7-cyano-2-methyl-5-((2-(trifluoromethyl)pyridin-3-yl)methoxy)-benzofuran-3-carboxamido)-3,3-difluoropiperidine-1-carboxylate (1.0 g, 1.68 mmol) in DCM (15 mL) at 0° C. The RM was allowed to attain RT and was stirred for 5 h. The reaction progress was monitored by TLC. The RM was concentrated under reduced pressure. The residue was basified with sat. $NaHCO_3$ (100 mL) and the organic compound was extracted with 10% MeOH in DCM (3×50 mL). The combined organic layer was washed with water (50 mL) and brine (50 mL), dried over anhydrous $Na_2SO_4$ and concentrated under reduced pressure. The crude product was purified by flash chromatography using 0.1% FA in water and acetonitrile as an eluent to afford an isomeric mixtures of racemic cpd 195 and racemic cpd 196 (0.60 g, 72%). A preparative chiral SFC was performed on the regioisomeric mixture of cpd 195 and cpd 196 to afford cpd 195-En 1, cpd 195-En 2, cpd 196-En 1 and cpd 196-En 2.

Synthesis of (S)—N-(1-amino-3-hydroxy-1-oxopropan-2-yl)-2-cyclopropyl-5-(pyridin-2-ylmethoxy)benzofuran-3-carboxamide (Cpd 747)

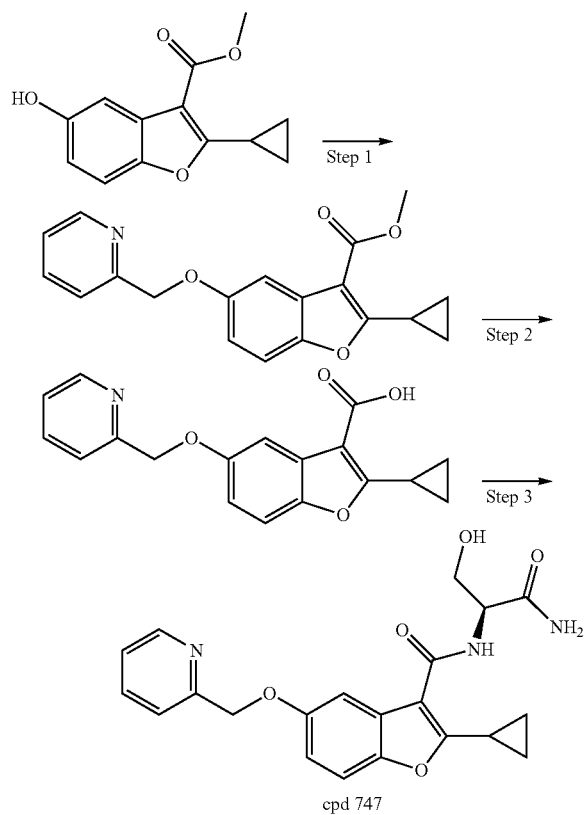

cpd 747

Step 1: To a stirred solution of methyl 2-cyclopropyl-5-hydroxybenzofuran-3-carboxylate (250 mg, 1.082 mmol) in THF (20 mL) was added ADDP (0.54 g, 2.164 mmol), n-Bu₃P (2.1 mL, 2.164 mmol) and followed by addition of pyridin-2-ylmethanol (140 mg, 1.298 mmol) at 0° C. The RM was stirred for 16 h at RT and the reaction progress was monitored by TLC. The RM was diluted with water (40 mL) and extracted with ethyl acetate (3×50 mL). Combined extracts were washed with water (20 mL), brine (20 mL), dried over anhydrous $Na_2SO_4$ and concentrated under reduced pressure to get crude. Crude was purified by column chromatography over silica gel (100-200 mesh) using 5% ethyl acetate in pet-ether as an eluent to afford methyl-2-cyclopropyl-5-(pyridin-2-ylmethoxy)benzofuran-3-carboxylate (3) (150 mg, 43%) as an off-white solid. TLC system: 20% ethyl acetate in pet ether; RF: 0.42.

Step 2: To a stirred solution of 2-cyclopropyl-5-(pyridin-2-ylmethoxy)benzofuran-3-carboxylate (150 mg, 0.464 mmol) in MeOH:THF (1:1, 20 mL) was added 2N aqueous NaOH (4 mL) at RT. The RM was stirred for 16 h at RT and the reaction progress was monitored by TLC. The RM was concentrated, acidified to pH ~2 with 1 N HCl. The precipitated solid was filtered and dried under vacuum to afford 2-cyclopropyl-5-(pyridin-2-ylmethoxy)benzofuran-3-carboxylic acid (120 mg) as an off-white solid. Crude used in the next step without purification. TLC system: 70% ethyl acetate in Pet ether; RF: 0.30.

Step 3: To a stirred solution of 2-cyclopropyl-5-(pyridin-2-ylmethoxy)benzofuran-3-carboxylic acid (0.120 mg, 0.388 mmol) in DMF (5 mL) was added DIPEA (0.2 mL, 1.553 mmol), HATU (0.295 g, 0.776 mmol) at RT and followed by addition of (S)-2-amino-3-hydroxypropanamide-HCl (0.081 mg, 0.582 mmol). The RM was stirred for 16 h at RT. Reaction progress was monitored by TLC. The RM was diluted with water (50 mL), extracted with ethyl acetate (3×50 mL). The combined extracts were washed with water (20 mL), brine (20 mL), dried over anhydrous $Na_2SO_4$ and concentrated under reduced pressure to get crude. The crude was purified by GRACE flash column chromatography using 0.1% aqueous formic acid and acetonitrile as an eluent to afford (S)—N-(1-amino-3-hydroxy-1-oxopropan-2-yl)-2-cyclopropyl-5-(pyridin-2-ylmethoxy)benzofuran-3-carboxamide (cpd 747) (35 mg, 19% over 2 steps).

The following compounds were prepared in a similar manner (use of appropriate reagents (chiral or racemic) and purification methods (including chiral HPLC or chiral SFC) known to the person skilled in the art) as described for cpd 747: Cpds: 748, 749, 750, 751.

Synthesis of 2-(difluoromethyl)-N-(1-(2-hydroxyethyl)-2-oxopyrrolidin-3-yl)-5-((4-methylthiazol-5-yl)-methoxy)benzofuran-3-carboxamide (Cpd 198)

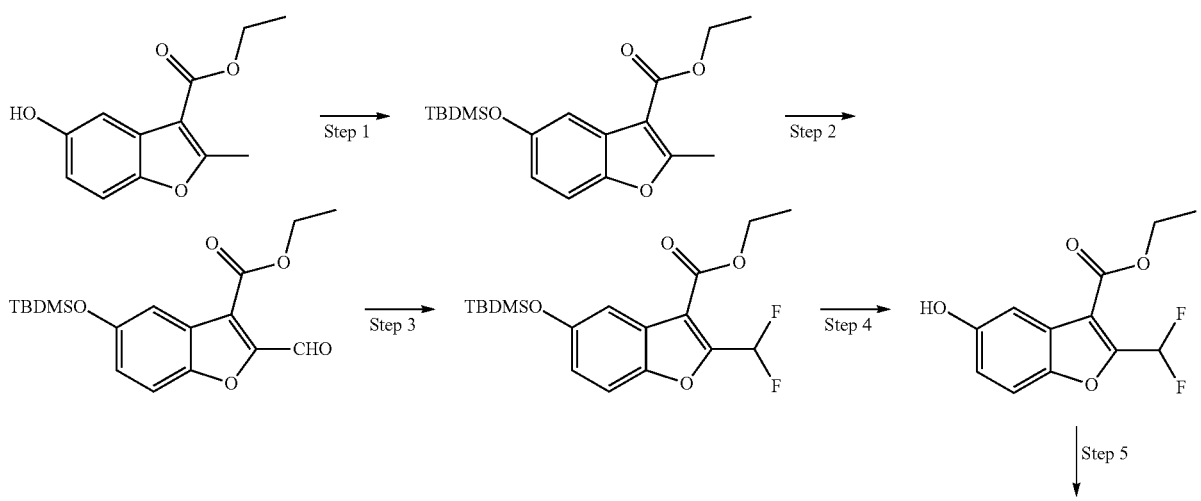

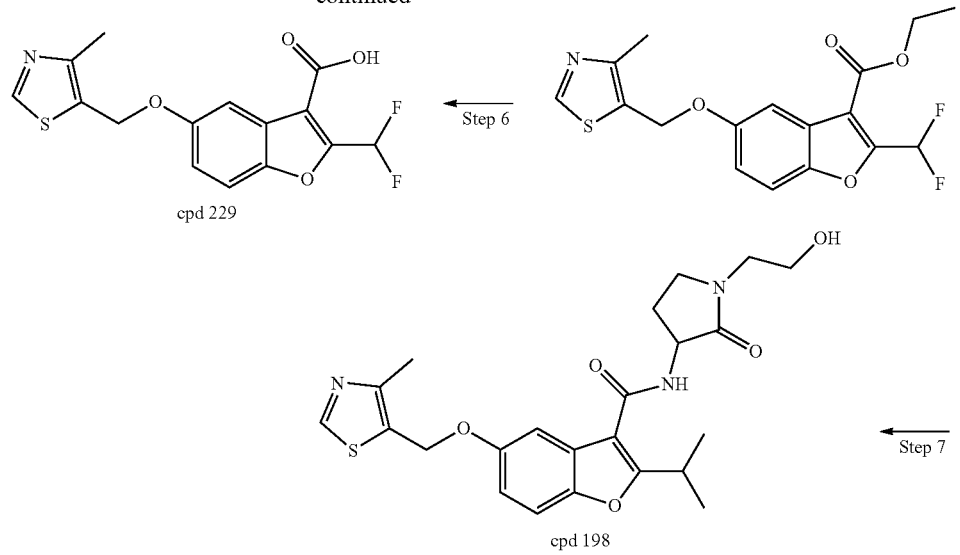

Step 1: To a solution of ethyl 5-hydroxy-2-methylbenzofuran-3-carboxylate (5.0 g, 22.7 mmol) in DCM (100 mL) was added imidazole (3.09 g, 45.4 mmol) followed by TBDMS-Cl (4.10 g, 27.2 mmol) at 0° C. under argon atmosphere. The RM was warmed to RT and stirred for 16 h. The reaction progress was monitored by TLC. The RM was poured into water (100 mL) and extracted with DCM (3×100 mL). The combined organic layer was washed with water (2×100 mL) followed by brine (200 mL), dried over anhydrous $Na_2SO_4$ and concentrated under reduced pressure. The crude product was purified by FCC over silica-gel using 5% EtOAc in pet-ether as an eluent to obtain ethyl 5-((tert-butyldimethylsilyl)oxy)-2-methylbenzofuran-3-carboxylate (5.1 g, 68%).

Step 2: To a solution of ethyl 5-((tert-butyldimethylsilyl)oxy)-2-methylbenzofuran-3-carboxylate (6.0 g, 17.9 mmol) in 1,4-dioxane (250 mL) was added $SeO_2$ (39.8 g, 358 mmol) at RT under argon atmosphere. The resulting RM was heated to 120° C. for 48 h. The reaction progress was monitored by TLC. The RM was cooled to RT and filtered. The filtrate was concentrated under reduced pressure. The crude product was purified by FCC over silica gel using 2% EtOAc in pet-ether as an eluent to afford ethyl 5-((tert-butyldimethylsilyl)oxy)-2-formylbenzofuran-3-carboxylate (2.6 g, 42%).

Step 3: To a solution of ethyl 5-((tert-butyldimethylsilyl)oxy)-2-formylbenzofuran-3-carboxylate (2.6 g, 7.7 mmol) in DCM (100 mL) was added DAST (3.0 mL, 23.3 mmol) at 0° C. under argon atmosphere. The RM was allowed to warm to RT and stirred for 3 h. The reaction progress was monitored by TLC. The RM was diluted with DCM (100 mL), washed with sat. $NaHCO_3$ solution (100 mL), water (100 mL), and brine (100 mL), dried over anhydrous $Na_2SO_4$ and concentrated under reduced pressure to afford ethyl 5-((tert-butyldimethylsilyl)oxy)-2-(difluoromethyl)benzofuran-3-carboxylate (2.4 g, crude product).

Step 4: To a solution of ethyl 5-((tert-butyldimethylsilyl)oxy)-2-(difluoromethyl)benzofuran-3-carboxylate (2.4 g, 6.48 mmol) in THF (50 mL) was added TBAF (1 M in THF) (12.9 mL, 12.9 mmol) at 0° C. under argon atmosphere. The RM was allowed to warm to RT and stirred for 1 h. The reaction progress was monitored by TLC. The RM was poured into water (100 mL) and extracted with EtOAc (3×100 mL). The combined organic layer was washed with water (100 mL) and brine (200 mL), dried over anhydrous $Na_2SO_4$ and concentrated under reduced pressure to afford ethyl 2-(difluoromethyl)-5-hydroxybenzofuran-3-carboxylate (1.8 g, crude). This crude product was used for next step without further purification.

Step 5: (4-Methylthiazol-5-yl)methanol (1.36 g, 10.5 mmol), ADDP (2.48 g, 9.8 mmol) and tri-N-butylphosphine (1.99 g, 9.8 mmol) were added sequentially to a solution of ethyl 2-(difluoromethyl)-5-hydroxybenzofuran-3-carboxylate (1.8 g, 7.0 mmol) in THF (150 mL) at 0° C. under an argon atmosphere. The resulting RM was stirred at RT for 3 h. The reaction progress was monitored by TLC. The RM was poured into water (200 mL) and extracted with EtOAc (3×100 mL). The combined organic layer was washed with water (100 mL) and brine (100 mL), dried over anhydrous $Na_2SO_4$ and concentrated under reduced pressure. The crude product was purified by column chromatography over silica gel using 0-20% EtOAc in pet-ether as an eluent to afford ethyl 2-(difluoromethyl)-5-((4-methylthiazol-5-yl)methoxy)benzofuran-3-carboxylate (1.5 g, 55% for 3 steps).

Step 6: 2 M NaOH (20 mL) solution was added to a solution of ethyl 2-(difluoromethyl)-5-((4-methylthiazol-5-yl)methoxy)benzofuran-3-carboxylate (800 mg, 2.17 mmol) in MeOH (25 mL) and THF (10 mL) at RT. The resulting RM was heated to 60° C. for 3 h. The reaction progress was monitored by TLC. The RM was cooled to RT and poured into ice cold water (100 mL) and acidified with 1 N HCl. The crude product was extracted with EtOAc (2×100 mL). The combined organic layer was washed with water (2×100 mL) and brine (100 mL), dried over anhydrous $Na_2SO_4$ and concentrated under reduced pressure to afford 2-(difluoromethyl)-5-((4-methylthiazol-5-yl)methoxy)benzofuran-3-carboxylic acid (cpd 229) (400 mg, 55%).

Step 7: To a solution mixture of 2-(difluoromethyl)-5-((4-methylthiazol-5-yl)methoxy)benzofuran-3-carboxylic acid (0.4 g, 1.17 mmol) and 3-amino-1-(2-hydroxyethyl)pyrrolidin-2-one hydrochloride (255 mg, 1.41 mmol) in DMF (25 mL) were added DIPEA (0.43 mL, 2.35 mmol) followed by HATU (0.897 g, 2.35 mmol) at 0° C. under an argon atmosphere. The resulting RM was stirred at RT for 1 h. The reaction progress was monitored by TLC. The RM was diluted with water (100 mL) and extracted with EtOAc (2×100 mL). The combined organic layer was washed with water (100 mL) and brine (100 mL), dried over anhydrous $Na_2SO_4$ and concentrated under reduced pressure. The crude product was purified by flash chromatography using 0.1% FA in water and acetonitrile as an eluent to afford cpd 198

(190 mg, 35%). A preparative chiral SFC was performed on the racemic mixture of cpd 198 to afford cpd 198-En 1 and cpd 198-En 2.

Cpd 197 was prepared in a manner similar (use of appropriate reagents and purification methods known to the person skilled in the art) to cpd 198-En 1 and cpd 198-En 2

The following compounds were prepared in a similar manner (use of appropriate reagents (chiral or racemic) and purification methods (including chiral HPLC or chiral SFC) known to the person skilled in the art) as described for cpd 198: Cpds 742, 743, 744, 745, 746.

Synthesis of 2-(difluoromethyl)-N-(3,3-difluoropiperidin-4-yl)-5-((2-(trifluoromethyl)pyridin-3-yl)methoxy)-benzofuran-3-carboxamide (Cpd 199)

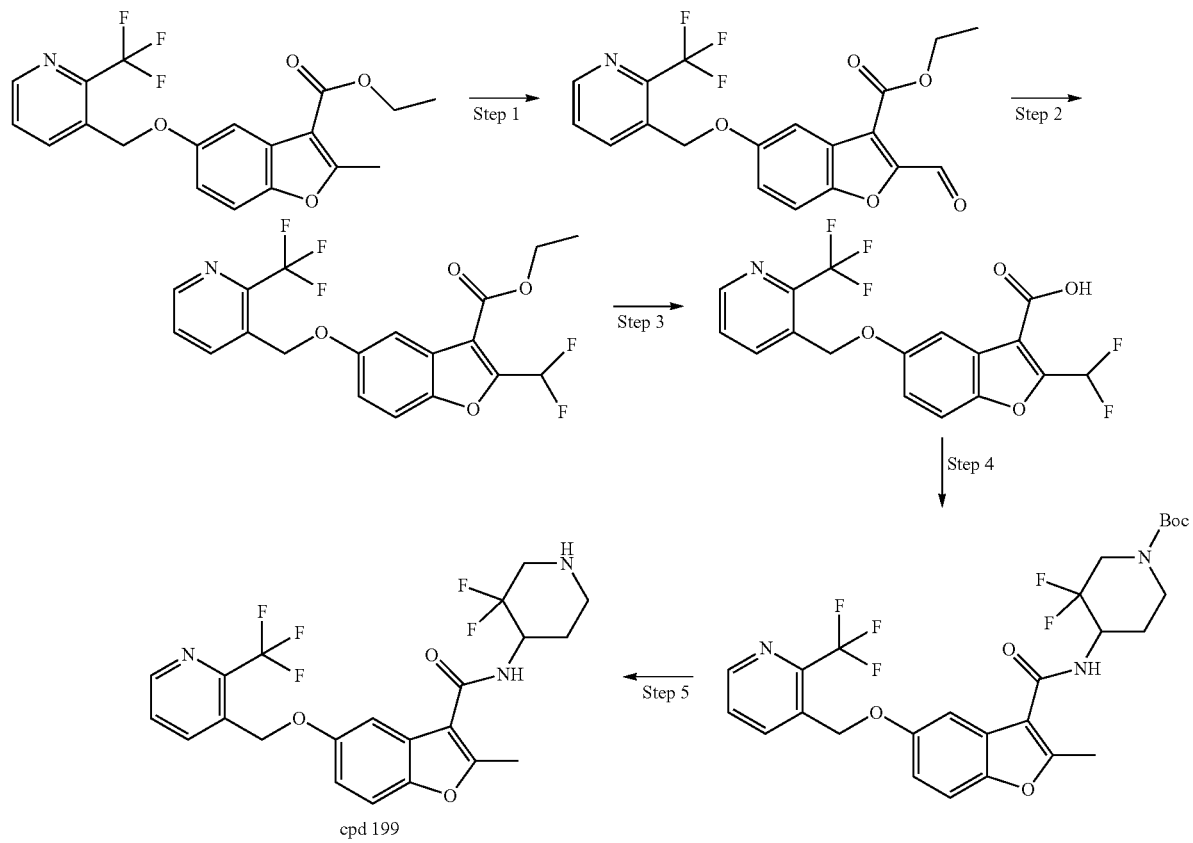

cpd 199

Step 1: To a pre-stirred solution of ethyl 2-methyl-5-((2-(trifluoromethyl)pyridin-3-yl)methoxy)benzofuran-3-carboxylate (2.0 g, 5.27 mmol) in 1,4-dioxane (150 mL) was added $SeO_2$ (3.51 g, 31.6 mmol) at RT under argon atmosphere. The resulting RM was heated to 120° C. and maintained under stirring for 16 h. Additional amount of $SeO_2$ (5.8 g, 52.7 mmol) was added and the reaction was continued for another 24 h. The reaction progress was monitored by TLC. The RM was cooled to RT, filtered and the filtrate was concentrated under reduced pressure. The crude product was purified by FCC with silica gel using 10% EtOAc in pet-ether as an eluent to afford ethyl 2-formyl-5-((2-(trifluoromethyl)pyridin-3-yl)methoxy)benzofuran-3-carboxylate (900 mg, 43%).

Step 2: To a solution of ethyl 2-formyl-5-((2-(trifluoromethyl)pyridin-3-yl)methoxy)benzofuran-3-carboxylate (0.8 g, 2.03 mmol) in DCM (25 mL) was added DAST (0.53 mL, 4.07 mmol) at 0° C. under argon atmosphere. The RM was allowed to cool to RT and was stirred for 2 h. The reaction progress was monitored by TLC. The RM was diluted with DCM (100 mL), washed with sat. $NaHCO_3$ solution (100 mL), water (50 mL), brine (50 mL), dried over anhydrous $Na_2SO_4$ and concentrated under reduced pressure to afford ethyl 2-(difluoromethyl)-5-((2-(trifluoromethyl)pyridin-3-yl)methoxy)benzofuran-3-carboxylate (800 mg). This crude product was used for next step without further purification.

Step 3: An aq. NaOH (2M solution) (25 mL) was added to a solution of ethyl 2-(difluoromethyl)-5-((2-(trifluoromethyl)pyridin-3-yl)methoxy)benzofuran-3-carboxylate (700 mg, 1.68 mmol) in MeOH (15 mL) and THF (5 mL) at RT. The resulting RM was heated to 60° C. for 3 h. The reaction progress was monitored by TLC. The RM was cooled to RT and poured into ice cold water (100 mL), acidified with 1 N HCl and extracted with EtOAc (2×100 mL). The combined organic layer was washed with water (2×100 mL), brine (100 mL), dried over anhydrous Na$_2$SO$_4$ and concentrated under reduced pressure to afford 2-(difluoromethyl)-5-((2-(trifluoromethyl)pyridin-3-yl)methoxy)benzofuran-3-carboxylic acid (600 mg, crude product).

Step 4: To a pre-stirred solution of mixture of 2-(difluoromethyl)-5-((2-(trifluoromethyl)pyridin-3-yl)methoxy)benzofuran-3-carboxylic acid (0.5 g, 1.29 mmol) and tert-butyl 4-amino-3,3-difluoropiperidine-1-carboxylate (0.365 g, 1.55 mmol) in DMF (25 mL) was added DIPEA (0.47 mL, 2.58 mmol) followed by HATU (0.982 g, 2.58 mmol) at 0° C. under argon atmosphere. The RM was allowed to attain RT and was stirred for 1 h. The reaction progress was monitored by TLC. The RM was diluted with water (100 mL), and extracted with EtOAc (2×100 mL). The combined organic layer was washed with water (100 mL) and brine (100 mL), dried over anhydrous Na$_2$SO$_4$ and concentrated under reduced pressure. The crude product was purified by column chromatography over silica gel using a gradient mixture of 0-25% EtOAc in pet-ether as an eluent to afford tert-butyl 4-(2-(difluoromethyl)-5-((2-(trifluoromethyl)pyridin-3-yl)methoxy)benzofuran-3-carboxamido)-3,3-difluoropiperidine-1-carboxylate (0.6 g, 55% over 3 steps).

Step 5: HCl (4M in dioxane) (15 mL) was added dropwise to a solution of 2-(difluoromethyl)-N-(3,3-difluoropiperidin-4-yl)-5-((2-(trifluoromethyl)pyridin-3-yl)methoxy)benzofuran-3-carboxamide (0.6 g, 0.99 mmol) in DCM (50 mL) at 0° C. under an argon atmosphere. The RM was warmed to RT and stirred for 4 h. The reaction progress was monitored by TLC. The solvents were evaporated in vacuo. The resulting crude residue was partitioned between sat. NaHCO$_3$ (pH~9) and EtOAc (3×50 mL). The combined organic layer was washed with water (100 mL) and brine (100 mL), dried over anhydrous Na$_2$SO$_4$ and concentrated under reduced pressure to afford 2-(difluoromethyl)-N-(3,3-difluoropiperidin-4-yl)-5-((2-(trifluoromethyl)pyridin-3-yl)methoxy)benzo-furan-3-carboxamide (0.4 g, 80%). A preparative chiral SFC was performed on the racemic mixture of cpd 199 to afford cpd 199-En 1 and cpd 199-En 2.

Synthesis of N-(3-(hydroxymethyl)azetidin-3-yl)-2-methyl-5-((4-methylthiazol-5-yl)methoxy)benzofuran-3-carboxamide (Cpd 201)

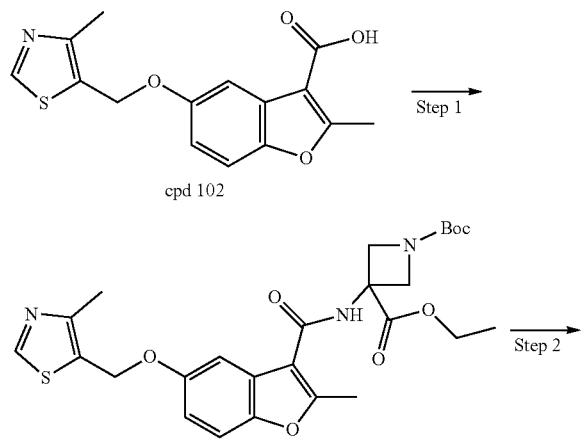

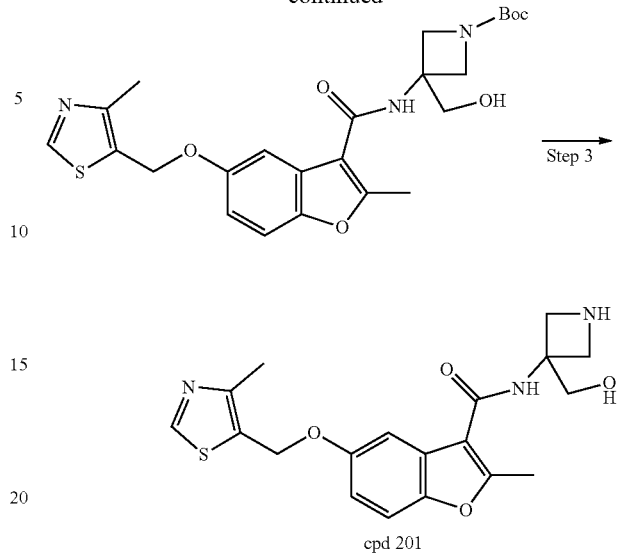

cpd 201

Step 1: To a pre-stirred solution of 1-(tert-butyl) 3-ethyl 3-aminoazetidine-1,3-dicarboxylate (0.483 g, 1.98 mmol) in DMF (10 mL) was added DIPEA (3.5 mL, 19.80 mmol) followed by cpd 102 (0.6 g, 1.98 mmol) and HATU (1.5 g, 3.96 mmol) sequentially at 0° C. under an argon atmosphere. The RM was heated to 55° C. and stirred for 2 h. The reaction progress was monitored by TLC. The RM was diluted with ice cold water (100 mL) and extracted with EtOAc (150 mL). The combined organic layer was washed with brine (50 mL), dried over anhydrous Na$_2$SO$_4$ and concentrated under reduced pressure. The crude product was purified by GRACE flash chromatography using 0.1% FA in water and acetonitrile as an eluent to afford 1-(tert-butyl) 3-ethyl 3-(2-methyl-5-((4-methylthiazol-5-yl)methoxy)benzofuran-3-carboxamido)azetidine-1,3-dicarboxylate (0.45 g, 42%).

Step 2: NaBH$_4$ (0.113 g, 2.97 mmol) was added in small portions to a solution of 1-(tert-butyl) 3-ethyl 3-(2-methyl-5-((4-methylthiazol-5-yl).methoxy)benzofuran-3-carboxamido)azetidine-1,3-dicarboxylate (0.45 g, 0.85 mmol) in MeOH (10 mL) at 0° C. and the resulting RM was stirred at RT for 2 h. The reaction progress was monitored by TLC. The RM was cooled to 0° C., diluted with water (30 mL) and extracted with 10% MeOH in DCM (2×50 mL). The combined organic layer was washed with brine (50 mL), dried over anhydrous Na$_2$SO$_4$ and concentrated under reduced pressure to afford tert-butyl 3-(hydroxymethyl)-3-(2-methyl-5-((4-methylthiazol-5-yl)methoxy)benzofuran-3-carboxamido)azetidine-1-carboxylate (0.4 g, crude). This crude product was used for next step without further purification.

Step 3: To a pre-stirred solution of tert-butyl 3-(hydroxymethyl)-3-(2-methyl-5-((4-methylthiazol-5-yl)methoxy)benzofuran-3-carboxamido)azetidine-1-carboxylate (0.4 g, crude) in DCM (5.0 mL) was added TFA (1.0 mL) dropwise at 0° C. under an argon atmosphere. The RM was allowed to warm to room temperature and stirred for 5 h. The reaction progress was monitored by LC-MS. The RM was concentrated under reduced pressure. The crude product was purified by RP prep-HPLC to afford cpd 201 (75 mg, 25%).

Synthesis of N-(3-(hydroxymethyl)azetidin-3-yl)-2-methyl-5-((2-(trifluoromethyl)pyridin-3-yl)methoxy)benzo-furan-3-carboxamide (Cpd 202)

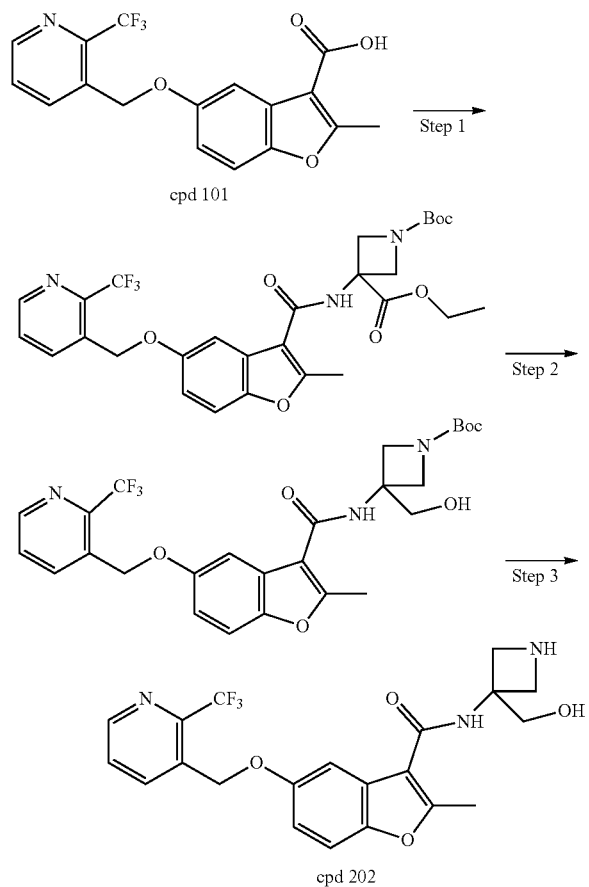

Step 1: To a solution of 1-(tert-butyl) 3-ethyl 3-amino-azetidine-1,3-dicarboxylate (0.417 g, 1.709 mmol) in DMF (10 mL) were added DIPEA (3.0 mL, 17.094 mmol), cpd 101 (0.6 g, 1.709 mmol) and HATU (1.2 g, 3.418 mmol) sequentially at 0° C. under an argon atmosphere. The resulting RM was heated to 55° C. for 2 h. The reaction progress was monitored by TLC. The RM was diluted with ice cold water (100 mL) and extracted with EtOAc (150 mL). The combined organic layer was washed with brine (50 mL), dried over anhydrous Na$_2$SO$_4$ and concentrated under reduced pressure. The crude product was purified by flash chromatography using a gradient mixture of 30-50% of EtOAc in pet ether as an eluent to afford 1-(tert-butyl) 3-ethyl 3-(2-methyl-5-((2-(trifluoromethyl)pyridin-3-yl)methoxy)benzofuran-3-carboxamido)azetidine-1,3-dicarboxylate (0.45 g, 42%).

Step 2: NaBH$_4$ (0.074. g, 1.94 mmol) was added in small portions to a solution of 1-(tert-butyl) 3-ethyl 3-(2-methyl-5-((4-methylthiazol-5-yl).methoxy)benzofuran-3-carbox-amido)azetidine-1,3-dicarboxylate (0.45 g, 0.779 mmol) in MeOH (10 mL) at 0° C. and the resulting RM was stirred at RT for 2 h. The reaction progress was monitored by TLC. The RM was cooled to 0° C., diluted with water (30 mL) and extracted with 10% MeOH in DCM (2×50 mL). The combined organic layer was washed with brine (50 mL), dried over anhydrous Na$_2$SO$_4$ and concentrated under reduced pressure to afford tert-butyl 3-(hydroxymethyl)-3-(2-methyl-5-((2-(trifluoromethyl)pyridin-3-yl)methoxy)benzo-furan-3-carboxamido)azetidine-1-carboxylate (0.4 g, crude). This crude product was used for next step without further purification.

Step 3: To a solution of tert-butyl 3-(hydroxymethyl)-3-(2-methyl-5-((2-(trifluoromethyl)pyridin-3-yl)methoxy) benzofuran-3-carboxamido)azetidine-1-carboxylate (0.4 g, crude) in MeOH (15.0 mL) was added acetyl chloride (2.6 mL) dropwise at 0° C. under an argon atmosphere. The RM was allowed to attain RT and was stirred for 24 h. The reaction progress was monitored by LC-MS. The RM was concentrated under reduced pressure. The crude product was purified by reverse phase prep-HPLC to afford cpd 202 (100 mg, 30%).

Synthesis of 2-methyl-5-((4-methylthiazol-5-yl)methoxy)benzofuran-3-carboxamide (Cpd 232)

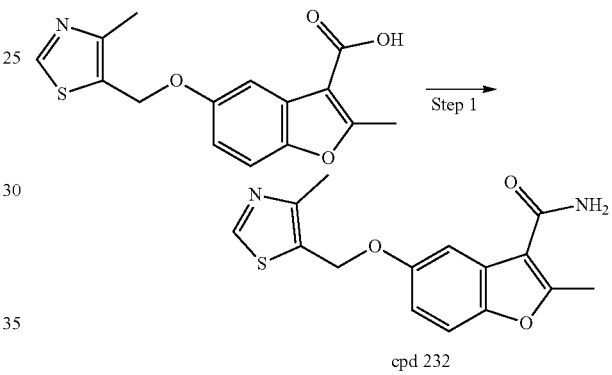

Step 1: To a pre-stirred solution mixture of 2-methyl-5-((4-methylthiazol-5-yl)methoxy)benzofuran-3-carboxylic acid (0.2 g, 0.66 mmol), HATU (0.501 g, 1.32 mmol) and DIPEA (0.24 mL, 1.32 mmol) in DMF (10 mL) was added ammonium chloride (0.176 g, 3.3 mmol) at 0° C. and the resulting reaction mixture was stirred at room temperature for 2 h. The reaction progress was monitored by TLC. The reaction mixture was diluted with ice cold water (50 mL) and the precipitated solid was collected by filtration and dried under vacuum. The solid was washed with diethyl ether (20 mL) and dried to afford 2-methyl-5-((4-methylthi-azol-5-yl)methoxy)benzofuran-3-carboxamide (130 mg, 65%) as an off white solid. TLC system: 100% Ethyl acetate; Rf: 0.15.

Synthesis of (S)—N-(1-amino-1-oxopropan-2-yl)-2-methyl-5-((4-methylthiazol-5-yl)methoxy)benzo-furan-3-carboxamide (Cpd 279)

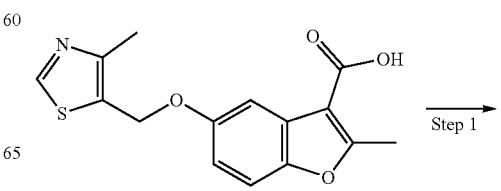

-continued

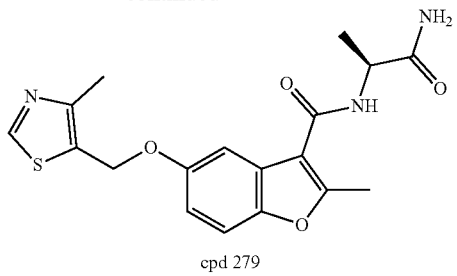

cpd 279

Step 1: To a stirred solution of 2-methyl-5-((4-methylthiazol-5-yl)methoxy)benzofuran-3-carboxylic acid (150 mg, 0.495 mmol), HATU (376.2 mg, 0.99 mmol) and DIPEA (0.36 mL, 1.98 mmol) in DMF (10 mL) was added L-alaninamide hydrochloride (61.6 mg, 0.495 mmol) at 0° C. and the resulting reaction mixture was warmed to room temperature and stirred for 1 h. The reaction mass was diluted with water (20 mL) and extracted with ethyl acetate (2×20 mL). The combined organic layer was washed with water (2×20 mL), dried over anhydrous sodium sulfate and concentrated under reduced pressure. The resulting compound was washed with n-pentane (2×10 mL) and was then filtered off to afford (S)—N-(1-amino-1-oxopropan-2-yl)-2-methyl-5-((4-methylthiazol-5-yl)methoxy)benzofuran-3-carboxamide (79 mg, 44%) as an off white solid. TLC: 10% Methanol in dichloromethane; $R_f$: 0.4.

The following compounds were prepared in a similar manner (use of appropriate reagents (chiral or racemic) and purification methods (including chiral HPLC or chiral SFC) known to the person skilled in the art) as described for cpd 279: Cpds. 271, 272, 273, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 318, 319, 320, 321, 324, 375, 376, 377, 378, 379, 380, 381, 382, 383, 395-Dia 1, 395-Dia 2, 396-En 1, 396-En 2, 397-En 1, 397-En 2, 398, 411-En 1, 411-En 2, 432-En 1, 432-En 2, 433-En 1, 433-En 2, 434-En 1, 434-En 2, 435-En 1, 435-En 2, 437-En 1, 437-En 2, 438, 439, 440, 441, 442, 443, 444, 445-En 1, 445-En 2, 446-En 1, 446-En 2, 447-En 1, 447-En 2, 448-En 1, 448-En 2, 449-En 1, 449-En 2, 450-En 1, 450-En 2, 451-En1, 451-En2, 452-En1, 452-En2, 453-En1, 453-En2, 454, 455-En1, 455-En2, 456-En1, 456-En 2, 457-En 1, 457-En 2, 458-En 1, 458-En 2, 459-En 1, 459-En 2, 460-En 1, 460-En 2, 461-En 1, 461-En 2, 462-En 1, 462-En 2, 463-En 1, 463-En 2, 464-En 1, 464-En 2, 465-En 1, 465-En 2, 466-En 1, 466-En 2, 467-En 1, 467-En 2, 468-En 1, 468-En 2, 469-En 1, 469-En 2, 470, 471, 472, 473, 474, 475, 476, 477, 478, 479, 480, 502, 503, 509, 577, 578, 579, 580, 581, 582, 584, 586, 590-En 1, 590-En2, 591-En1, 591-En2, 592-En1, 592-En2, 593-En1, 593-En2, 594-En1, 594-En2, 595-En1, 595-En 2, 596-En 1, 596-En 2, 597-En 1, 597-En 2, 598-En 1, 598-En 2, 600-En 1, 600-En 2, 601-En 1, 601-En 2, 650, 662.

Synthesis of 2-(difluoromethyl)-N-(4-(hydroxymethyl)tetrahydro-2H-pyran-4-yl)-5-((2-oxo-1,2-dihydropyridin-3-yl)methoxy)benzofuran-3-carboxamide (Cpd 311)

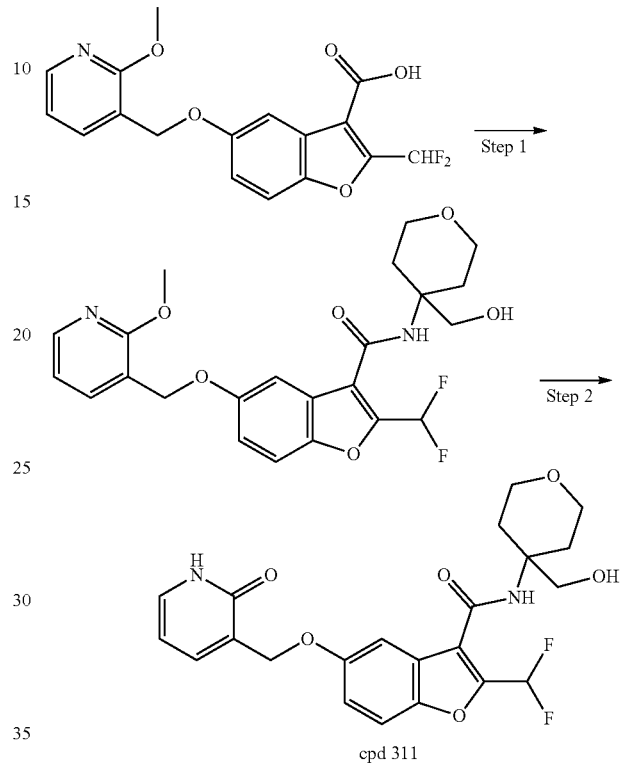

cpd 311

Step 1: To a stirred solution of 2-(difluoromethyl)-5-((2-methoxypyridin-3-yl)methoxy)benzofuran-3-carboxylic acid (0.5 g, 9 mmol) in $CH_2Cl_2$ (30 ml) were added DIPEA (0.23 g, 1.8 mmol) and HATU (0.69 g, 1.8 mmol) at 0° C. followed by the addition of tert-butyl 4-amino-3,3-difluoropiperidine-1-carboxylate (273 mg, 1.1 mmol). The reaction mixture was stirred for 16 h at RT, the reaction progress was monitored by TLC. The reaction mixture was diluted with water (150 mL) and extracted with $CH_2Cl_2$ (3×100 mL). The combined extracts were washed with brine (150 mL), dried over anhydrous $Na_2SO_4$ and concentrated under reduced pressure to get the crude material (0.7 g). The crude compound was purified by silica gel (100-200 mesh) column chromatography to afford 2-(difluoromethyl)-N-(4-(hydroxymethyl)tetrahydro-2H-pyran-4-yl)-5-((2-methoxypyridin-3-yl)methoxy)benzofuran-3-carboxamide (0.35 g) as a white solid. TLC system: 5% MeOH in $CH_2Cl_2$; Rf: 0.3.

Step 2: To a stirred solution of tert-butyl 3,3-difluoro-4-(5-((2-methoxypyridin-3-yl)methoxy)-2-methylbenzofuran-3-carboxamido)piperidine-1-carboxylate (0.25 g, 1.5 mmol) in acetonitrile (15 ml), was added TMSCl (0.26 g, 2.4 mmol) followed by NaI (0.350 g, 2.4 mmol) at 0° C. and the reaction mixture was stirred for 3 h at 70° C. The reaction progress was monitored by TLC. The reaction mixture was diluted with water (150 mL) and extracted with EtOAc (2×20 mL). The combined extracts were washed with brine (50 mL), dried over anhydrous $Na_2SO_4$ and concentrated under reduced pressure to get the crude material (500 mg, LCMS: 45%) as an off-white solid. The crude material was purified by reverse phase prep-HPLC purification to afford 2-(difluoromethyl)-N-(4-(hydroxymethyl)tetrahydro-2H-pyran-4-yl)-5-((2-oxo-1,2-dihydropyridin-3-yl)methoxy)benzofuran-3-carboxamide (130 mg) as an off-white solid. TLC system: 10% Methanol in Dichloromethane; Rf: 0.3.

The following compounds were prepared in a similar manner (use of appropriate reagents (chiral or racemic) and purification methods (including chiral HPLC or chiral SFC) known to the person skilled in the art) as described for cpd 311: Cpds. 349-En 1, 349-En 2, 350-En 1, 350-En 2, 408-En 1, 408-En 2, 420, 430, 436-En 1, 436-En 2, 443, 459-En 1, 459-En 2, 479, 485, 494, 495, 521-En 1, 521-En 2, 535-En 1, 535-En 2, 585, 596-En 1, 596-En 2, 614, 628, 630, 648-En 1, 648-En 2.

Synthesis of 2-methyl-N-(1-(methylcarbamoyl)cyclobutyl)-5-((2-methylthiazol-5-yl)methoxy)benzofuran-3-carboxamide (Cpd 318)

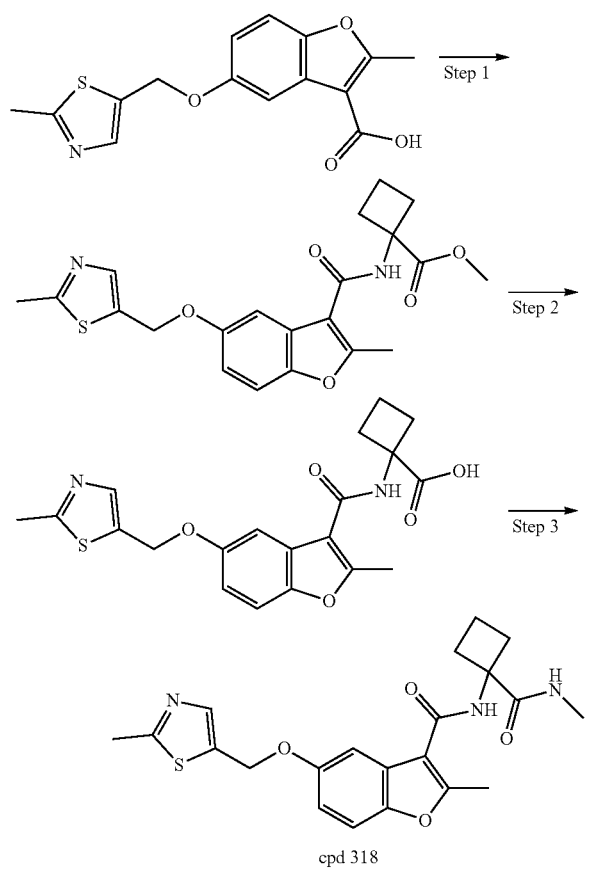

cpd 318

Step 1: To a pre-stirred solution of 2-methyl-5-(pyridin-2-ylmethoxy)benzofuran-3-carboxylic acid (400 mg, 1.320 mmol) in $CH_2Cl_2$ (30 mL) were added DIPEA (0.9 mL, 5.280 mmol) and methyl 1-aminocyclobutane-1-carboxylate hydrochloride (304 mg, 1.848 mmol) followed by HATU (702 mg, 1.848 mmol) at 0° C. under an argon atmosphere. The reaction mixture was stirred at room temperature for 16 h. The reaction progress was monitored by TLC. The reaction mixture was diluted with water (30 mL) and extracted with EtOAc (3×50 mL). The combined organic layers were washed with water (1×20 mL) and brine (1×20 mL), dried over anhydrous $Na_2SO_4$ and concentrated under reduced pressure to give the crude material, which was purified by flash chromatography with silica gel (100-200 mesh) using 30% ethyl acetate in pet ether as an eluent to afford methyl 1-(2-methyl-5-((2-methylthiazol-5-yl)methoxy) benzofuran-3-carboxamido) cyclobutane-1-carboxylate (300 mg, 55%) as an off-white solid. TLC system: 80% EtOAc in Pet ether; RF: 0.66

Step 2: To a pre-stirred solution of methyl 1-(2-methyl-5-((2-methylthiazol-5-yl) methoxy) benzofuran-3-carboxamido) cyclobutane-1-carboxylate (300 mg, 0.724 mmol), in THF:MeOH (1:1, 20 ml), was added 2N NaOH (3.5 ml) at RT, then the reaction mixture was heated to 60° C. The reaction mixture was stirred at this temperature for 3 h, and the reaction progress was monitored by TLC. The reaction mixture was concentrated, diluted with ice water, the pH was adjusted to ~2 with 1 N aq. HCl solution to give a solid. The solid was filtered off and dried under reduced pressure to afford 1-(2-methyl-5-((2-methylthiazol-5-yl) methoxy) benzofuran-3-carboxamido) cyclobutane-1-carboxylic acid (300 mg, crude) as an off-white solid. TLC system: 80% EtOAc in Pet ether; RF: 0.24.

Step 3: To a pre-stirred solution of 1-(2-methyl-5-((2-methylthiazol-5-yl) methoxy) benzofuran-3-carboxamido) cyclobutane-1-carboxylic acid (300 mg, 0.750 mmol) in $CH_2C_2$ (30 mL) were added DIPEA (0.5 mL, 3.00 mmol) and methyl amine (2M in THF) (2.1 ml, 1.05 mmol) followed by HATU (399 mg, 1.05 mmol) at 0° C. under an argon atmosphere. The reaction mixture was stirred at room temperature for 2 h. The reaction progress was monitored by TLC. The reaction mixture was diluted with water (30 mL) and extracted with EtOAc (2×40 mL). The combined organic layers were washed with water (1×20 mL) and brine (1×30 mL), dried over anhydrous $Na_2SO_4$ and concentrated under reduced pressure to afford the crude material, which was purified by flash chromatography with silica gel (100-200 mesh) using 20% ethyl acetate in pet ether as eluent to afford 2-methyl-N-(1-(methylcarbamoyl) cyclobutyl)-5-((2-methylthiazol-5-yl) methoxy) benzofuran-3-carboxamide (cpd 318) (85 mg, 28% over two steps) as a white solid. TLC system: 50% EtOAc in Pet ether; RF: 0.54.

The following compounds were prepared in a similar manner (use of appropriate reagents (chiral or racemic) and purification methods known to the person skilled in the art) as described for cpd 318: cpds. 319, 320, 324, 725-En 1, 725-En 2, 740-En 1, 740-En 2.

Synthesis of 5-((2-cyanopyridin-3-yl)methoxy)-N-(4-(hydroxymethyl)tetrahydro-2H-pyran-4-yl)-2-methylbenzofuran-3-carboxamide (Cpd 325) and 3-(((3-((4-(hydroxymethyl)tetrahydro-2H-pyran-4-yl)carbamoyl)-2-methylbenzofuran-5-yl)oxy)methyl) picolinamide (Cpd 347)

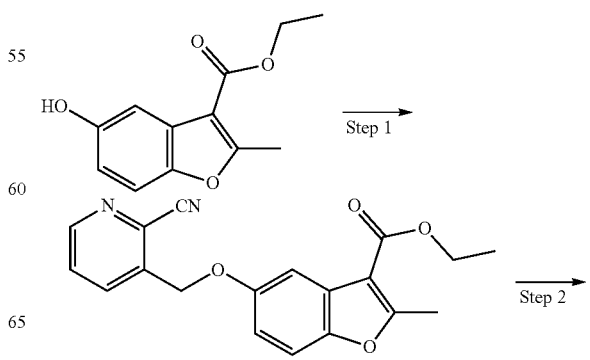

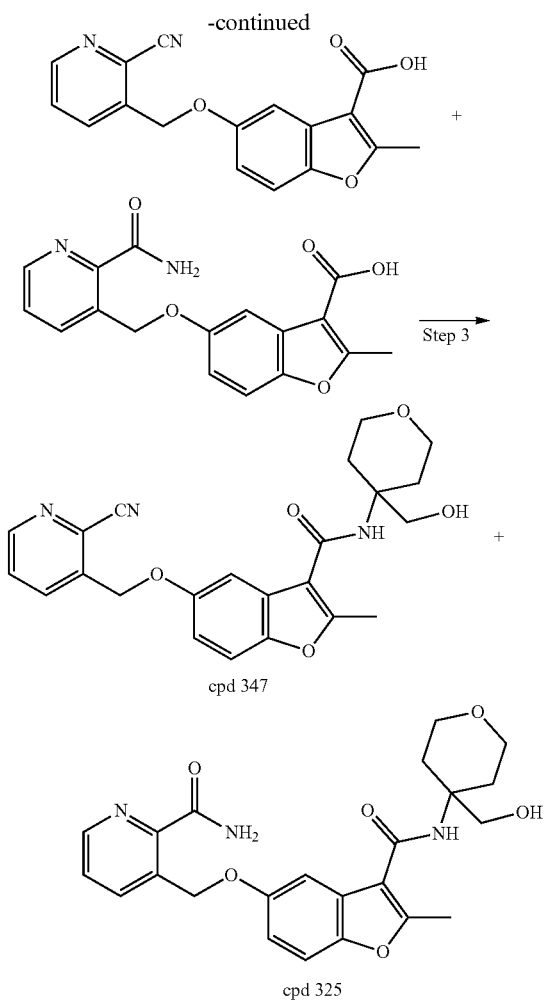

oylpyridin-3-yl)methoxy)-2-methylbenzofuran-3-carboxylic acid (0.75 g, crude). TLC system: 50% EtOAc-pet ether; Rf: 0.1.

Step 3: To a pre-stirred solution of a mixture of 5-((2-cyanopyridin-3-yl)methoxy)-2-methylbenzofuran-3-carboxylic acid, 5-((2-carbamoylpyridin-3-yl)methoxy)-2-methylbenzofuran-3-carboxylic acid (0.70 g, 2.27 mmol, 1 eq) and (4-aminotetrahydro-2H-pyran-4-yl)methanol (0.35 g, 2.72 mmol, 1.2 eq) in $CH_2Cl_2$ (100 mL) was added DIPEA (2.0 mL, 11.35 mmol, 5 eq) followed by HATU (1.29 g, 3.40 mmol, 1.5 eq) at 0° C. under an argon atmosphere. The reaction mixture was stirred at room temperature for 3 h and the reaction progress was monitored by TLC. The reaction mixture was diluted with water (100 mL) and extracted with $CH_2CL_2$ (2×100 mL). The combined organic layers were washed with water (100 mL) and brine (50 mL), dried over anhydrous $Na_2SO_4$ and concentrated under reduced pressure to afford the crude material, which was purified by column chromatography/prep HPLC to afford 3-(((3-((4-(hydroxymethyl)tetrahydro-2H-pyran-4-yl)carbamoyl)-2-methylbenzofuran-5-yl)oxy)methyl)picolinamide (cpd 325) (0.110 g, 8% over 2 steps) and 5-((2-cyanopyridin-3-yl)methoxy)-N-(4-(hydroxymethyl)tetrahydro-2H-pyran-4-yl)-2-methylbenzofuran-3-carboxamide (cpd 347) (0.130 g, 10% over 2 steps) as white solids.

Synthesis of 4-fluoro-N-(3-(hydroxymethyl)oxetan-3-yl)-2-methyl-5-((4-methylthiazol-5-yl)methoxy)benzofuran-3-carboxamide (Cpd 328) and 6-fluoro-N-(3-(hydroxymethyl)oxetan-3-yl)-2-methyl-5-((4-methylthiazol-5-yl)methoxy)benzofuran-3-carboxamide (Cpd 362)

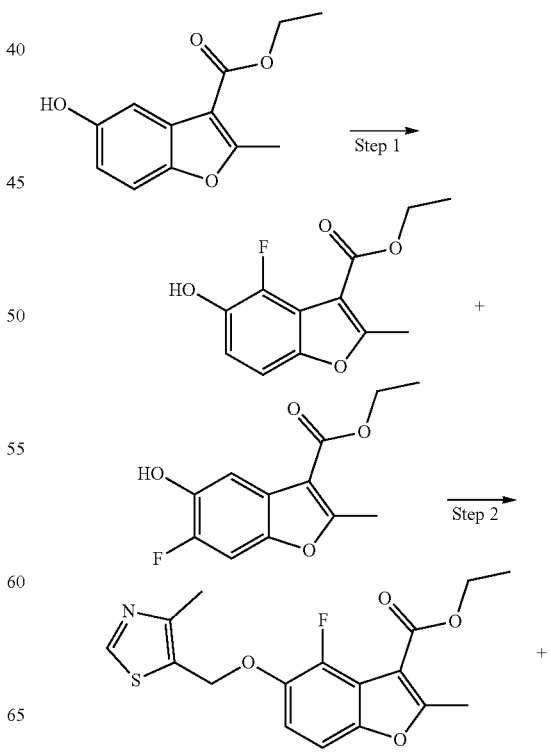

Step 1: To a stirred solution of ethyl 5-hydroxy-2-methylbenzofuran-3-carboxylate (0.8 g, 3.63 mmol, 1.0 eq) in ACN (10 ml) at 0° C. was added $Cs_2CO_3$ (3.55 g, 10.89 mmol, 3 eq) and the mixture was stirred for 5 minutes, followed by the addition of 3-(bromomethyl)picolinonitrile (0.85 g, 4.36 mmol, 1.2 eq) at 0° C. The reaction mixture was stirred for 18 h at RT, monitored by TLC. The reaction mixture was diluted with ice water (100 ml) and extracted with EtOAc (300 ml). The organic layer was washed with ice water (100 ml) and brine (50 ml), dried over anhydrous $Na_2SO_4$, filtered and concentrated to get the crude product, which was purified by Grace flash column chromatography using eluent 20% EtOAc in pet ether to afford ethyl 5-((2-cyanopyridin-3-yl)methoxy)-2-methylbenzofuran-3-carboxylate (1.0 g, 81%, off-white solid). TLC system: 20% EtOAc-pet ether; 2:8; Rf: 0.3.

Step 2: To ethyl 5-((2-cyanopyridin-3-yl)methoxy)-2-methylbenzofuran-3-carboxylate (1.0 g, 2.97 mmol, 1.0 eq), in THF:MeOH:$H_2O$ (1:1:1) (120 ml) was added NaOH (0.35 g, 8.92 mmol, 3.0 eq) at RT, the reaction mixture was then heated to 50° C. for 18 h, the reaction progress was monitored by TLC. The reaction mixture was concentrated and diluted with ice water, the pH was adjusted to ~2 with 1 N HCl solution to give a precipitate while stirring for 30 min. The precipitate was filtered off and was dried under vacuum to afford a mixture of 5-((2-cyanopyridin-3-yl)methoxy)-2-methylbenzofuran-3-carboxylic acid and 5-((2-carbam-

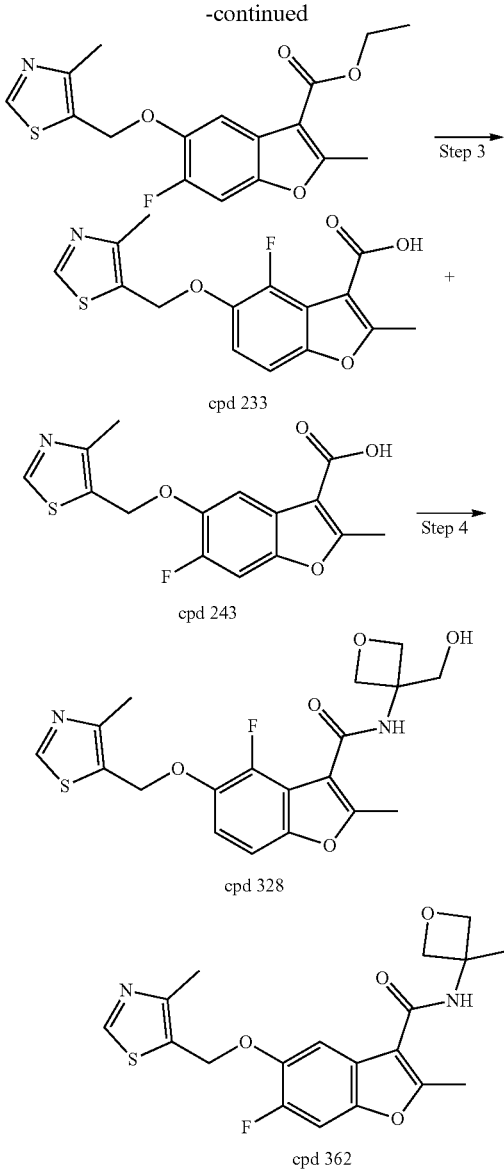

cpd 233 cpd 243 cpd 328 cpd 362

Step 1: To a pre-stirred solution of ethyl 5-hydroxy-2-methylbenzofuran-3-carboxylate (15 g, 68.18 mmol) in acetonitrile (500 mL) was added selectfluor (28.72 g, 81.13 mmol) at RT under an argon atmosphere. The reaction mixture was stirred at room temperature for 16 h. The reaction progress was monitored by TLC. The solvent was removed under reduced pressure to give a residue. The residue was dissolved in ethyl acetate (1000 mL), washed with water (500 mL) and brine (250 mL), dried over anhydrous $Na_2SO_4$ and concentrated under reduced pressure to give the crude material. The crude product was purified by column chromatography over silica gel (100-200 mesh) using 0-20% ethyl acetate in pet-ether as an eluent to afford mixture of ethyl 4-fluoro-5-hydroxy-2-methylbenzofuran-3-carboxylate and ethyl 6-fluoro-5-hydroxy-2-methylbenzofuran-3-carboxylate (3.0 g, 18%) as a yellow solid. TLC system: 30% Ethyl acetate in pet-ether; Rf: 0.5.

Step 2: (4-Methylthiazol-5-yl)methanol (4.06 g, 31.51 mmol), ADDP (10.58 g 42.01 mmol) and tri-N-butyl phosphine (10.60 ml 42.01 mmol) were added sequentially to a pre-stirred solution of a mixture of ethyl 4-fluoro-5-hydroxy-2-methylbenzofuran-3-carboxylate and ethyl 6-fluoro-5-hydroxy-2-methylbenzofuran-3-carboxylate (5.0 g, 21.00 mmol) in THF (500 mL) at 0° C. under an argon atmosphere. The reaction mixture was stirred at room temperature for 1 h. The reaction progress was monitored by TLC. The reaction mixture was diluted with water (500 mL) and extracted with ethyl acetate (2×500 mL). The combined organic layers were washed with water (250 mL) and brine (250 mL), dried over anhydrous $Na_2SO_4$ and concentrated under reduced pressure to give the crude material. The crude material was purified by column chromatography over silica gel (100-200 mesh) using 0-30% ethyl acetate in pet-ether as eluent to afford a mixture of ethyl 4-fluoro-2-methyl-5-((4-methylthiazol-5-yl)methoxy)benzofuran-3-carboxylate and ethyl 6-fluoro-2-methyl-5-((4-methylthiazol-5-yl)methoxy) benzofuran-3-carboxylate (6.0 g, 81%) as white solid. TLC system: 50% Ethyl acetate in pet-ether; Rf: 0.4.

Step 3: 2N NaOH in water (40 mL) was added to a pre-stirred solution of mixture of ethyl 4-fluoro-2-methyl-5-((4-methylthiazol-5-yl)methoxy)benzofuran-3-carboxylate and ethyl 6-fluoro-2-methyl-5-((4-methylthiazol-5-yl) methoxy)benzofuran-3-carboxylate (6.0 g, 17.19 mmol) in a mixture of methanol (40 mL) and THF (10 mL) at RT. The reaction mixture was heated to 80° C. for 3 h. The reaction progress was monitored by TLC. The reaction mixture was cooled to RT and then concentrated under reduced pressure to get the crude material. The crude material was poured into ice water (100 mL), acidified to pH~2 with 1 N HCl, the obtained white solid was filtered off and was washed with water (20 mL) to afford a mixture of 4-fluoro-2-methyl-5-((4-methylthiazol-5-yl)methoxy)benzofuran-3-carboxylic acid (cpd 233) and 6-fluoro-2-methyl-5-((4-methylthiazol-5-yl)methoxy)benzofuran-3-carboxylic acid (cpd 243) (4.5 g, 81%) as white solid. TLC system: 80% Ethyl acetate in pet-ether; Rf: 0.2.

Step 4: To a stirred solution of a mixture of 4-fluoro-2-methyl-5-((4-methylthiazol-5-yl)methoxy)benzofuran-3-carboxylic acid compound and 6-fluoro-2-methyl-5-((4-methylthiazol-5-yl)methoxy)benzofuran-3-carboxylic acid (1:1) (550 mg, 1.71 mmol) in DMF (10 ml), were added DIPEA (1.2 ml, 6.84 mmol), HATU (970 mg, 2.57 mmol) and (3-(methylamino)oxetan-3-yl)methanol (260 mg, 2.57 mmol) at 0° C. and the reaction mixture was stirred for 2 h at RT. The reaction progress was monitored by TLC. After completion of the reaction, the reaction mixture was diluted with water (150 mL) and extracted with ethyl acetate (3×100 mL). The combined organic layers were washed with brine (150 mL), dried over anhydrous $Na_2SO_4$ and concentrated under reduced pressure to get the crude compound (715 mg, LCMS: 37% & 23% ratio). The crude compound was purified by reverse phase prep-HPLC purification (column: INERTSIL-ODS 2 (250*19 mm), 5 μm, mobile phase: A: 10 mM Ammonium Bi Carbonate in $H_2O$, B: MeCN, Gradient: 0/30, 8/55, 9/55, 9.1/98, 11/98, 11.1/30, 14/30; flow rate: 18 mL/min; diluent: MeCN+H2O+THF) to afford cpd. 328 (325 mg) and cpd. 362 (170.9 mg) as an off-white solid.

The following compounds were prepared in a similar manner (use of appropriate reagents and purification methods (including chiral HPLC or chiral SFC) known to the person skilled in the art) as described for cpds 328 and 362: Cpd. 326-En 1, 326-En 2, 327, 330, 360-En 1, 360-En 2, 361, 364, 572-En 1, 572-En 2, 583, 587.

The following compounds were prepared in a similar manner (use of appropriate reagents and purification methods (including chiral HPLC or chiral SFC) known to the person skilled in the art) as described for cpds 233: Cpd 234.

Synthesis of 4-fluoro-N-(4-(hydroxymethyl)tetrahydro-2H-pyran-4-yl)-2-methyl-5-((2-oxo-1,2-dihydropyridin-3-yl)methoxy)benzofuran-3-carboxamide (Cpd 329) and 6-fluoro-N-(4-(hydroxymethyl)tetrahydro-2H-pyran-4-yl)-2-methyl-5-((2-oxo-1,2-dihydropyridin-3-yl)methoxy)benzofuran-3-carboxamide (Cpd 363)

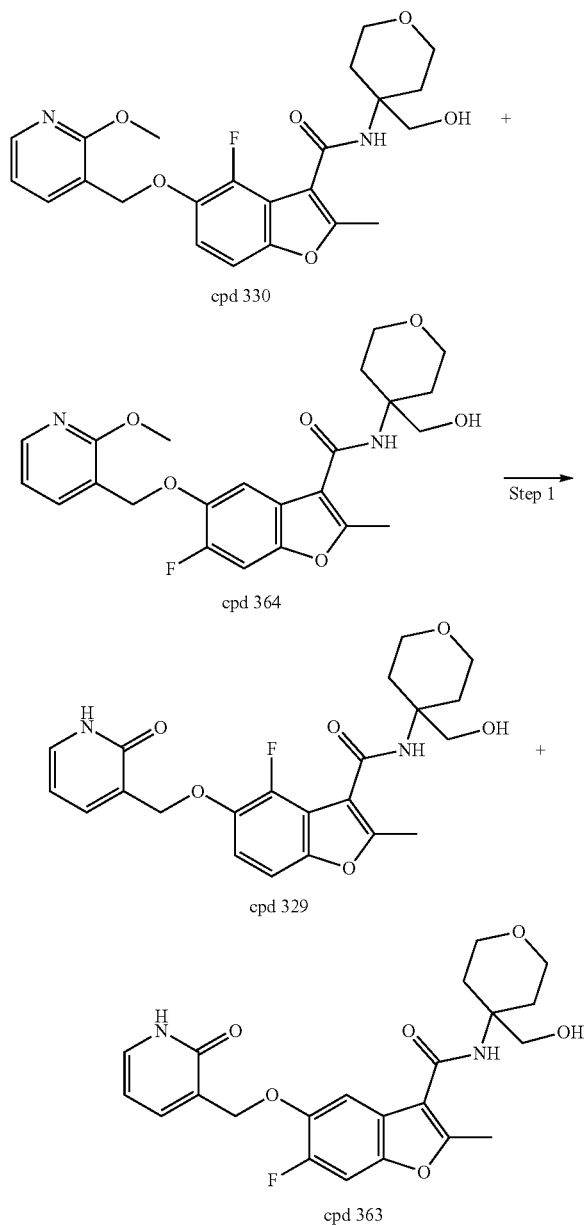 [SMILES: COc1ncccc1COc1ccc2oc(C)c(C(=O)NC3(CO)CCOCC3)c2c1F ; COc1ncccc1COc1cc2c(C(=O)NC3(CO)CCOCC3)c(C)oc2cc1F ; Cc1oc2ccc(OCc3ccc[nH]c3=O)c(F)c2c1C(=O)NC1(CO)CCOCC1 ; Cc1oc2cc(F)c(OCc3ccc[nH]c3=O)cc2c1C(=O)NC1(CO)CCOCC1]

Step 1: To a pre-stirred solution of a mixture of 4-fluoro-N-(4-(hydroxymethyl)tetrahydro-2H-pyran-4-yl)-5-((2-methoxypyridin-3-yl)methoxy)-2-methylbenzofuran-3-carboxamide (cpd 330) and 6-fluoro-N-(4-(hydroxymethyl)tetrahydro-2H-pyran-4-yl)-5-((2-methoxypyridin-3-yl)methoxy)-2-methylbenzofuran-3-carboxamide (cpd 364) (1.5 g, 3.37 mmol) in acetonitrile (100 mL) was added NaI (0.99 g, 6.75 mmol) at 0° C. followed by the dropwise addition of TMSCl (0.91 mL, 6.75 mmol) at 0° C. under an argon atmosphere. The reaction mixture was heated to 40° C. for 24 h. The reaction progress was monitored by TLC. The reaction mixture was diluted with water (100 mL) and extracted with 10% Methanol in CH$_2$CL$_2$ (2×100 mL). The combined organic layers were washed with water (100 mL) and brine (50 mL), dried over anhydrous Na$_2$SO$_4$ and concentrated under reduced pressure to afford the crude product, which was purified by prep-HPLC purification to afford 4-fluoro-N-(4-(hydroxymethyl)tetrahydro-2H-pyran-4-yl)-2-methyl-5-((2-oxo-1,2-dihydropyridin-3-yl)methoxy)benzofuran-3-carboxamide (cpd 329) (135 mg) as an off-white solid and 6-fluoro-N-(4-(hydroxymethyl)tetrahydro-2H-pyran-4-yl)-2-methyl-5-((2-oxo-1,2-dihydropyridin-3-yl)methoxy)benzofuran-3-carboxamide (cpd 363) (30 mg) as a white solid.

The following compounds were prepared in a similar manner (use of appropriate reagents (chiral or racemic) and purification methods known to the person skilled in the art) as described for cpds 329 and 363: Cpd. 368.

Synthesis of 5-((1-(2,2-difluoroethyl)-1H-pyrazol-5-yl)methoxy)-N-(3-(hydroxymethyl)-2-oxopiperidin-3-yl)-2-methylbenzofuran-3-carboxamide (Cpd 332)

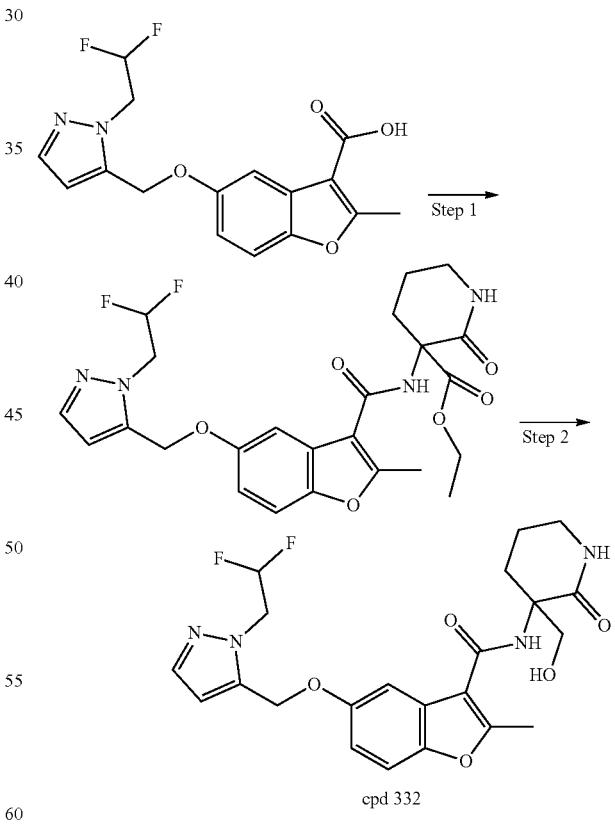

Step 1: To a stirred solution of 5-((1-(2,2-difluoroethyl)-1H-pyrazol-5-yl)methoxy)-2-methylbenzofuran-3-carboxylic acid (500 mg, 1.48 mmol) in DMF (20 mL) were added DIPEA (1.0 mL, 5.95 mmol), HATU (787 mg, 2.07 mmol) and ethyl 3-amino-2-oxopiperidine-3-carboxylate (385 mg, 2.07 mmol) at 0° C. The reaction mixture was stirred for 16 h at RT, and the reaction progress was monitored by TLC. The reaction mixture was diluted with water (50 mL) and extracted with ethyl acetate (2×100 mL). The combined organic layers were washed with water (40 mL) and brine (20 mL), dried over anhydrous Na₂SO₄, filtered and concentrated to get the crude material. The crude material was purified by Grace chromatography using 35% EtOAc in pet ether as an eluent to afford ethyl 3-(5-((1-(2,2-difluoroethyl)-1H-pyrazol-5-yl) methoxy)-2-methylbenzofuran-3-carboxamido)-2-oxopiperidine-3-carboxylate (350 mg, 46%) as a brown solid. TLC system: 60% Ethyl acetate in per ether; RF: 0.48.

Step 2: To a stirred solution of ethyl 3-(5-((1-(2,2-difluoroethyl)-1H-pyrazol-5-yl) methoxy)-2-methylbenzofuran-3-carboxamido)-2-oxopiperidine-3-carboxylate (350 mg, 0.69 mmol) in MeOH (40 mL) was added NaBH₄ (131 mg, 3.47 mmol) at 0° C. The reaction mixture was stirred for 16 h at RT. The reaction progress was monitored by TLC. The reaction mixture was concentrated under reduced pressure, diluted with water (100 mL), and extracted with ethyl acetate (2×100 mL). The combined extracts were washed with brine (50 mL), dried over anhydrous Na₂SO₄, filtered and concentrated under reduced pressure to get the crude material which was purified by GRACE flash chromatography using 0.1% aqueous formic acid in acetonitrile as an eluent to afford 5-((1-(2,2-difluoroethyl)-1H-pyrazol-5-yl) methoxy)-N-(3-(hydroxymethyl)-2-oxopiperidin-3-yl)-2-methylbenzofuran-3-carboxamide (250 mg, 78%) as an off-white solid. TLC system: 100% EtOAc; RF: 0.24.

A preparative chiral SFC was performed on the racemic mixture of cpd 332 to afford cpd 332-En 1 and cpd 332-En 2.

The following compounds were prepared in a similar manner (use of appropriate reagents and purification methods (including chiral HPLC or chiral SFC) known to the person skilled in the art) as described for cpd 332: Cpds. 333-En 1,333-En 2,355-En 1,355-En 2,356-En 1,356-En 2,510-En 1,510-En 2, 511-En 1,511-En 2, 512-En 1,512-En 2,513-En 1,513-En 2,514-En 1, 514-En 2,515-En 1, 515-En 2,516-En 1,516-En 2, 517-En 1, 517-En 2, 518-En 1, 518-En 2, 519-En 1, 519-En 2, 520-En 1, 520-En 2, 521-En 1, 521-En 2, 522-En 1, 522-En 2, 719-En 1, 719-En 2, 732-En 1, 732-En 2, 733-En 1, 733-En 2, 734-En 1, 734-En 2, 735-En 1, 735-En 2, 736-En 1, 736-En 2, 737-En 1, 737-En 2.

Synthesis of N-(1-((difluoromethoxy)methyl)cyclopropyl)-2-methyl-5-((2-methylthiazol-5-yl)methoxy) benzofuran-3-carboxamide (Cpd 399)

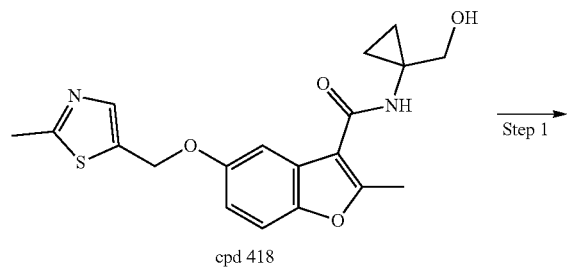

cpd 418

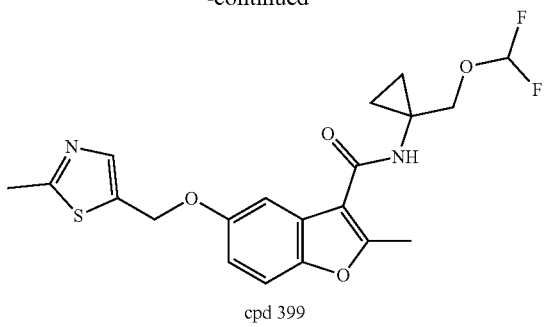

cpd 399

Step 1: To a suspension of N-(1-(hydroxymethyl)cyclopropyl)-2-methyl-5-((2-methylthiazol-5-yl)methoxy)benzofuran-3-carboxamide (cpd 418) (300 mg, 0.866 mmol) and CuI (30.6 mg, 0.168 mmol) in acetonitrile (20 mL) was added a solution of 2,2-difluoro-2-(fluorosulfonyl)acetic acid (215 mg, 1.209 mmol) in acetonitrile (3 mL) at room temperature and the resulting reaction mixture was heated to 50° C.-55° C. for 1 h. The reaction progress was monitored by TLC. The reaction mixture was cooled to room temperature and filtered. The filtrate was evaporated under reduced pressure to give the crude material which was purified by GRACE flash chromatography using 0.1% of formic acid in water and acetonitrile as an eluent to afford N-(1-((difluoromethoxy)methyl)cyclopropyl)-2-methyl-5-((4-methylthiazol-5-yl)methoxy)benzofuran-3-carboxamide (cpd 399) (40 mg, 12%) as a white solid. TLC system: 50% Ethyl acetate in pet-ether; Rf: 0.8

The following compounds were prepared in a similar manner (use of appropriate reagents and purification methods known to the person skilled in the art) as described for cpd 399: cpd 400.

Synthesis of (R)—N-(1-(1H-benzo[d]imidazol-2-yl)-2-hydroxyethyl)-2-methyl-5-((2-methylthiazol-5-yl)methoxy)benzofuran-3-carboxamide (Cpd 401-En 1)

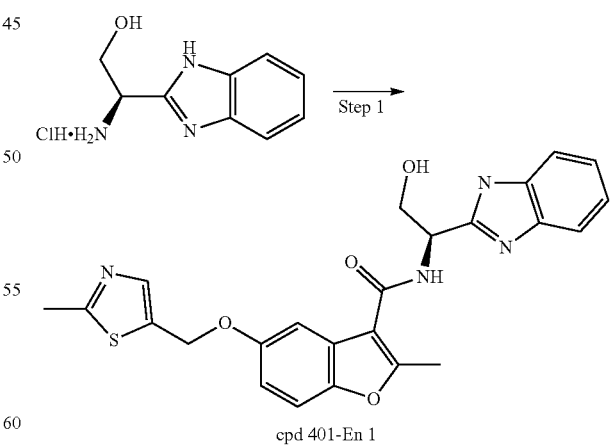

cpd 401-En 1

Step 1: EDC·HCl (0.378 g, 1.9801 mmol), HOBt (267 mg, 1.9801 mmol) and DIPEA (510 mg, 3.960 mmol) were added sequentially to a stirred solution of (S)-2-amino-2-(1H-benzo[d]imidazol-2-yl)ethan-1-ol hydrochloride (400 mg, 1.3201 mmol) in DMF (5.0 mL) at room temperature.

The resulting reaction mixture was stirred at room temperature for 2 h. The reaction progress was monitored by TLC. The reaction mixture was diluted with ice cold water (50 mL) and the precipitated solid was filtered and dried under vacuum to afford (S)—N-(1-(1H-benzo[d]imidazol-2-yl)-2-hydroxyethyl)-2-methyl-5-((2-methylthiazol-5-yl)methoxy)benzofuran-3-carboxamide (cpd 401-En 1) (140 mg) as a white solid. TLC system: 100% Ethyl acetate; Rf: 0.2.

The following compounds were prepared in a similar manner (use of appropriate reagents and purification methods known to the person skilled in the art) as described for cpd 401-En 1: cpd 401-En 2.

Synthesis of N-(1-(dimethylamino)-3-hydroxypropan-2-yl)-2-methyl-5-((4-methylthiazol-5-yl)methoxy)benzofuran-3-carboxamide (Cpd 413)

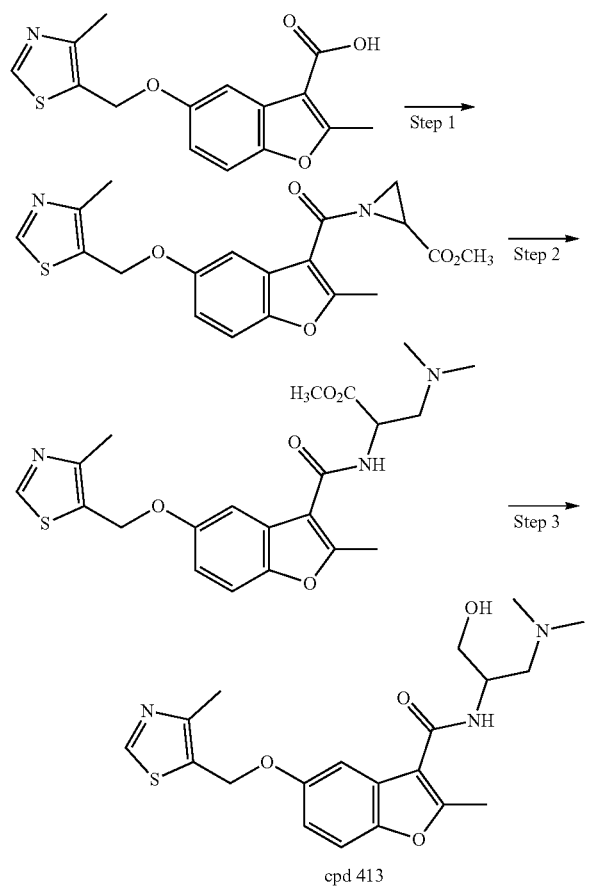

cpd 413

Step 1: To a stirred solution of 2-methyl-5-((4-methylthiazol-5-yl)methoxy)benzofuran-3-carboxylic acid (1.0 g, 3.3 mmol) in DMF (10 mL) was added DIPEA (1.7 mL, 9.9 mmol), HATU (2.5 g, 6.6 mmol) at 0° C. followed by addition of methyl aziridine-2-carboxylate (0.45 g, 4.95 mmol). The reaction mixture was then warmed to room temperature and stirred for 16 h at the same temperature. The reaction progress was monitored by TLC. The reaction mixture was diluted with water (20 mL) and extracted with EtOAc (2×20 mL). The combined extracts were washed with water (3×20 mL) and brine (20 mL), dried over anhydrous $Na_2SO_4$ and concentrated under reduced pressure to afford methyl 1-(2-methyl-5-((4-methylthiazol-5-yl)methoxy)benzofuran-3-carbonyl)aziridine-2-carboxylate (1.0 g, crude) as a pale green gum. TLC system: 10% MeOH in dichloromethane; RF: 0.6.

Step 2: To a stirred solution of methyl 1-(2-methyl-5-((4-methylthiazol-5-yl)methoxy)benzofuran-3-carbonyl)aziridine-2-carboxylate (1.0 g, 2.591 mmol) in dimethylamine (69.5 mmol, 5.8 g of dimethylamine HCl was therefore treated with TEA (10 mL) in $CHCl_3$ (10 mL)) at RT was added boron trifluoride diethyl etherate (0.3 mL, 2.59 mmol) at 0° C., then the reaction mixture was stirred for 16 h at RT. The reaction progress was monitored by TLC. The reaction mixture was diluted with water (30 mL) and extracted with dichloromethane (2×30 mL). The combined extracts were washed with brine (2×20 mL), dried over anhydrous $Na_2SO_4$ and concentrated under reduced pressure to get the crude compound, which was purified by GRACE flash chromatography using 0.1% aqueous formic acid in acetonitrile to afford methyl 3-(dimethylamino)-2-(2-methyl-5-((4-methylthiazol-5-yl)methoxy)benzofuran-3-carboxamido)propanoate (650 mg, 59%) as a pale yellow gum. TLC system: 80% EtOAc in pet-ether; Rf: 0.3.

Step 3: To a stirred solution of methyl 3-(dimethylamino)-2-(2-methyl-5-((4-methylthiazol-5-yl)methoxy)benzofuran-3-carboxamido)propanoate (300 mg, 0.694 mmol) in MeOH (10 mL) was added $NaBH_4$ (131.8 mg, 3.47 mmol) at 0° C. The reaction mixture was stirred for 16 h at RT and the reaction progress was monitored by TLC. Then the reaction mixture was evaporated under reduced pressure, diluted with water (20 mL) and extracted with ethyl acetate (2×20 mL). The combined organic layers were dried over anhydrous $Na_2SO_4$ and concentrated to get the crude material which was purified by GRACE flash chromatography using 0.1% aqueous formic acid in acetonitrile as an eluent to afford N-(1-(dimethylamino)-3-hydroxypropan-2-yl)-2-methyl-5-((4-methylthiazol-5-yl)methoxy)benzofuran-3-carboxamide (cpd 413) (130 mg, 46%) as an off-white gum. TLC system: 10% Methanol in dichloromethane; RF: 0.4

A preparative chiral SFC was performed on the racemic mixture of cpd 413 to afford cpd 413-En 1 and cpd 413-En2.

The following compounds were prepared in a similar manner (use of appropriate reagents (chiral or racemic) and purification methods (including chiral HPLC or chiral SFC) known to the person skilled in the art) as described for cpd 413: 412-En 1, 412-En 2, 446-En 1, 446-En 2, 449-En 1, 449-En 2, 450-En 1, 450-En 2, 487-En 1, 487-En 2, 488-En 1, 488-En 2, 575-En 1, 575-En 2.

Synthesis of N-(1-amino-1-oxo-3-(1H-1,2,4-triazol-1-yl)propan-2-yl)-2-methyl-5-((2-methylthiazol-5-yl)methoxy)benzofuran-3-carboxamide (Cpd 432)

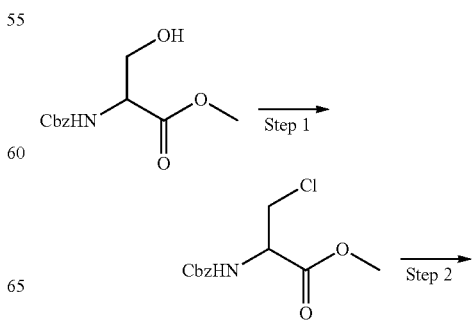

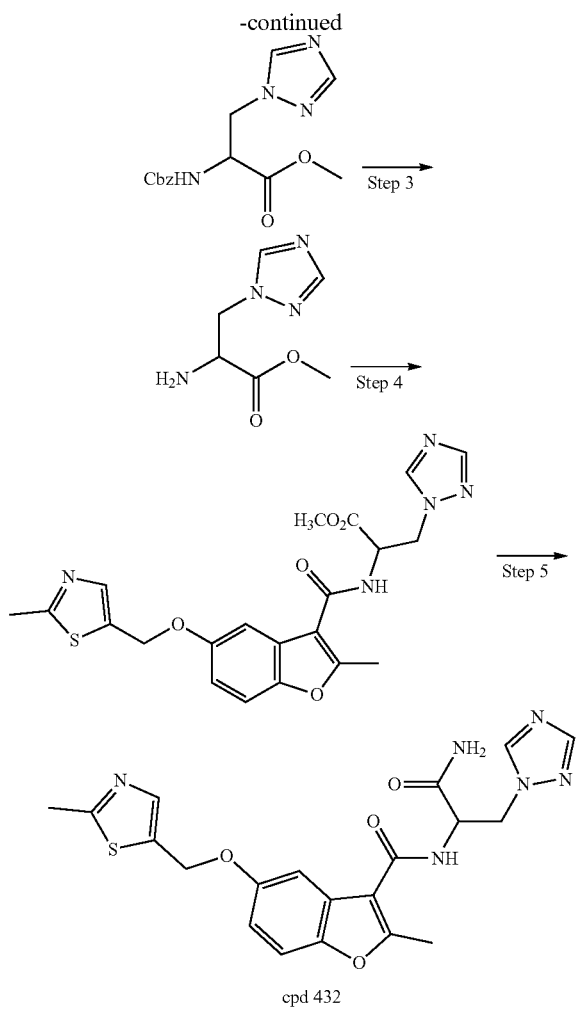

cpd 432

Step 1: To a stirred solution of methyl ((benzyloxy)carbonyl)serinate (1.0 g, 3.95 mmol) in chloroform (10 mL) was added PCl₅ (0.4 mL, 4.34 mmol) at 0° C. The reaction mixture was stirred for 16 h at RT. The reaction progress was monitored by TLC. The reaction mixture was diluted with water (50 mL) and extracted with dichloromethane (2×20 mL). The combined extracts were washed with sat. NaHCO₃ solution (2×20 mL) and brine (2×20 mL), dried over anhydrous Na₂SO₄ and concentrated under reduced pressure to get the crude compound, which was purified by column chromatography using silica gel (100-200) and 10% ethyl acetate in pet ether as an eluent to afford methyl 2-(((benzyloxy)carbonyl)amino)-3-chloropropanoate (500 mg, 47%) as an off-white solid. TLC system: 30% EtOAc in Pet ether; RF: 0.6.

Step 2: To a stirred solution of 1H-1,2,4-triazole (200 mg, 2.89 mmol) in chloroform (10 mL) was added methyl 2-(((benzyloxy)carbonyl)amino)-3-chloropropanoate (946 mg, 3.47 mmol) at RT. To the reaction mixture was added DBU (878 mg, 5.78 mmol) at 0° C. then the reaction mixture was stirred for 16 h at 60° C. The reaction progress was monitored by TLC. The reaction mixture was diluted with water (50 mL) and extracted with dichloromethane (3×30 mL). The combined extracts were washed with brine (2×20 mL), dried over anhydrous Na₂SO₄ and concentrated under reduced pressure to get the crude compound, which was purified by GRACE flash chromatography using 0.1% aqueous formic acid in acetonitrile as an eluent to afford methyl 2-(((benzyloxy)carbonyl)amino)-3-(1H-1,2,4-triazol-1-yl)propanoate (500 mg, 57%) as a pale yellow gum. TLC system: 50% EtOAC in Pet ether; RF: 0.6.

Step 3: To a stirred solution of methyl 2-(((benzyloxy)carbonyl)amino)-3-(1H-1,2,4-triazol-1-yl)propanoate (400 mg, 1.31 mmol) in MeOH (10 mL) was added 10% Pd/C (170 mg) at RT. The reaction mixture was stirred for 2 h at RT under H₂ (balloon atmosphere). The reaction progress was monitored by TLC. The reaction mixture was diluted with MeOH (10 mL), filtered through a celite bed and the celite bed was washed with MeOH (2×10 mL). The filtrate was concentered under reduced pressure to afford methyl 2-amino-3-(1H-1,2,4-triazol-1-yl)propanoate (200 mg, 42%) as a pale yellow gum. TLC system: 5% MeOH in dichloromethane; RF: 0.4.

Step 4: To a stirred solution of 2-methyl-5-((2-methylthiazol-5-yl)methoxy)benzofuran-3-carboxylic acid (300 mg, 0.99 mmol) and methyl 2-amino-3-(1H-1,2,4-triazol-1-yl)propanoate (175 mg, 1.48 mmol) in DMF (10 mL) were added DIPEA (0.5 mL, 2.97 mmol) and HATU (752 mg, 1.98 mmol) at 0° C. under an argon atmosphere. The reaction mixture was stirred at room temperature for 2 h. The reaction progress was monitored by TLC, the reaction mixture was diluted with cold water (25 mL) and extracted with ethyl acetate (2×40 mL). The combined organic layers were washed with water (15 mL) and brine (15 mL), dried over anhydrous Na₂SO₄ and concentrated under reduced pressure to afford the crude product which was purified by GRACE flash chromatography using 0.1% aqueous formic acid in acetonitrile as an eluent to afford methyl 2-(2-methyl-5-((2-methylthiazol-5-yl)methoxy)benzofuran-3-carboxamido)-3-(1H-1,2,4-triazol-1-yl)propanoate (200 mg, 44%) as an off-white gum. TLC system: 10% MeOH in dichloromethane; RF: 0.3

Step 5: A stirred solution of methyl 2-(2-methyl-5-((2-methylthiazol-5-yl)methoxy)benzofuran-3-carboxamido)-3-(1H-1,2,4-triazol-1-yl)propanoate (200 mg, 0.439 mmol) in 7.0 M NH₃ in methanol (20 mL) was stirred for 16 h at RT and the reaction progress was monitored by TLC. Then the reaction mixture was evaporated under reduced pressure to get the crude compound, which was purified by GRACE flash chromatography using 0.1% aqueous formic acid in acetonitrile as an eluent to afford (120 mg, 62%) of N-(1-amino-1-oxo-3-(1H-1,2,4-triazol-1-yl)propan-2-yl)-2-methyl-5-((2-methylthiazol-5-yl)methoxy)benzofuran-3-carboxamide (cpd 432) as an off-white gum. TLC system: 10% MeOH in dichloromethane; RF: 0.2

A preparative chiral SFC was performed on the racemic mixture of cpd 432 to afford cpd 432-En 1 and cpd 432-En 2.

The following compounds were prepared in a similar manner (use of appropriate reagents (chiral or racemic) and purification methods (including chiral HPLC or chiral SFC) known to the person skilled in the art) as described for cpd 432: 729-En 1, 729-En 2.

Synthesis of N-(1-amino-3-(difluoromethoxy)-1-oxopropan-2-yl)-2-methyl-5-((2-methylthiazol-5-yl)methoxy)benzofuran-3-carboxamide (Cpd 447)

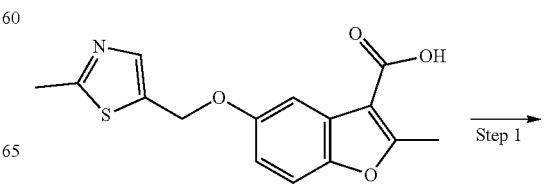

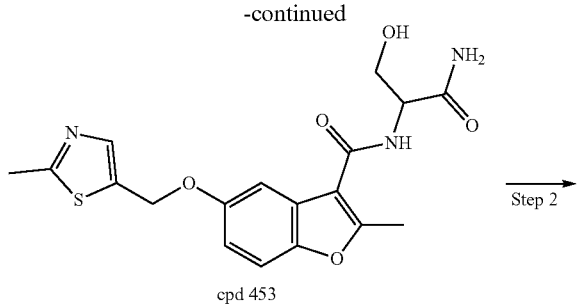

cpd 453

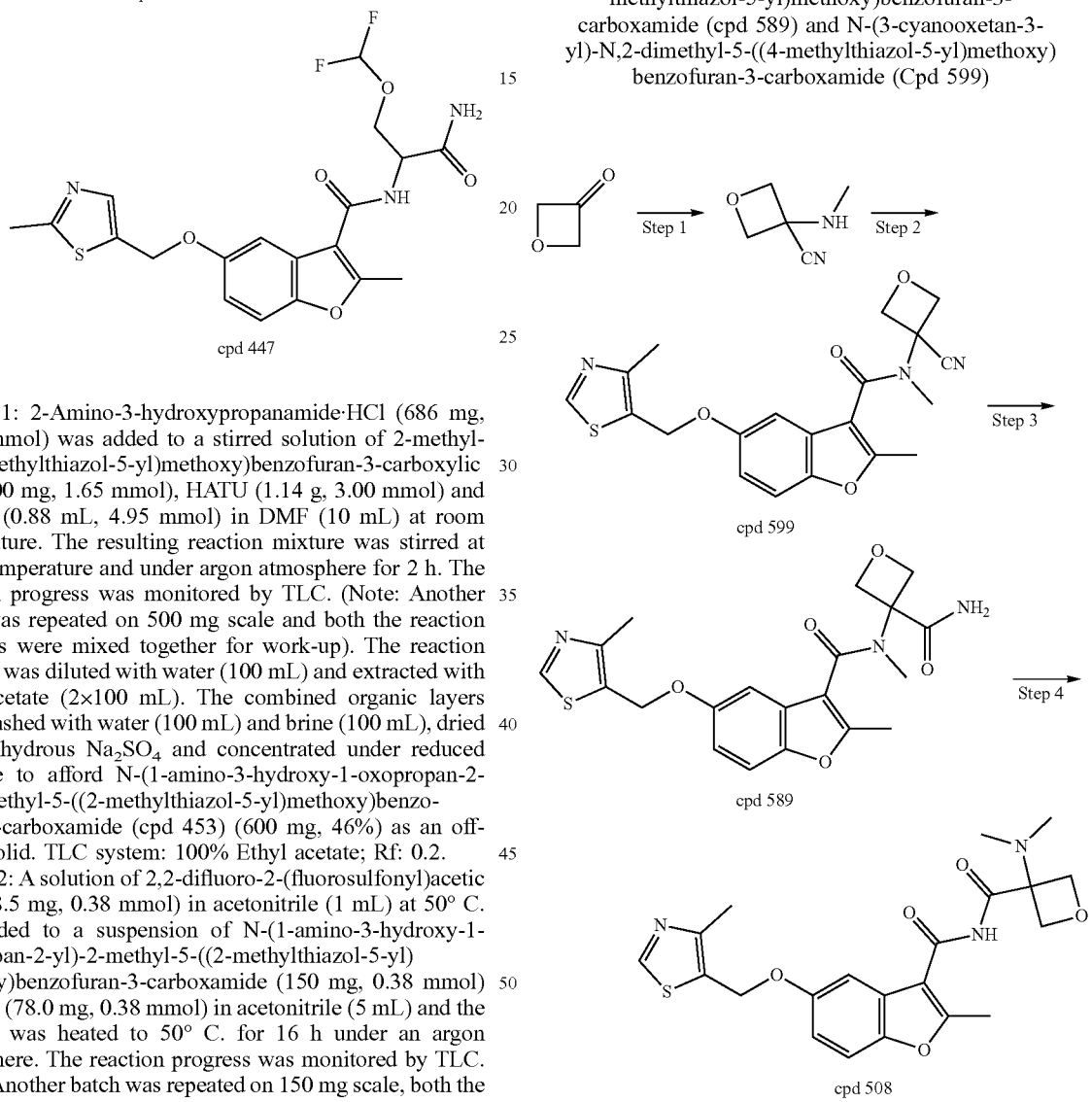

cpd 447

Step 1: 2-Amino-3-hydroxypropanamide·HCl (686 mg, 6.600 mmol) was added to a stirred solution of 2-methyl-5-((2-methylthiazol-5-yl)methoxy)benzofuran-3-carboxylic acid (500 mg, 1.65 mmol), HATU (1.14 g, 3.00 mmol) and DIPEA (0.88 mL, 4.95 mmol) in DMF (10 mL) at room temperature. The resulting reaction mixture was stirred at room temperature and under argon atmosphere for 2 h. The reaction progress was monitored by TLC. (Note: Another batch was repeated on 500 mg scale and both the reaction mixtures were mixed together for work-up). The reaction mixture was diluted with water (100 mL) and extracted with ethyl acetate (2×100 mL). The combined organic layers were washed with water (100 mL) and brine (100 mL), dried over anhydrous Na$_2$SO$_4$ and concentrated under reduced pressure to afford N-(1-amino-3-hydroxy-1-oxopropan-2-yl)-2-methyl-5-((2-methylthiazol-5-yl)methoxy)benzofuran-3-carboxamide (cpd 453) (600 mg, 46%) as an off-white solid. TLC system: 100% Ethyl acetate; Rf: 0.2.

Step 2: A solution of 2,2-difluoro-2-(fluorosulfonyl)acetic acid (68.5 mg, 0.38 mmol) in acetonitrile (1 mL) at 50° C. was added to a suspension of N-(1-amino-3-hydroxy-1-oxopropan-2-yl)-2-methyl-5-((2-methylthiazol-5-yl)methoxy)benzofuran-3-carboxamide (150 mg, 0.38 mmol) and CuI (78.0 mg, 0.38 mmol) in acetonitrile (5 mL) and the mixture was heated to 50° C. for 16 h under an argon atmosphere. The reaction progress was monitored by TLC. (Note: Another batch was repeated on 150 mg scale, both the reaction mixtures were mixed together for work-up). The reaction mixture was cooled to room temperature and filtered. The filtrate was evaporated under reduced pressure. The crude compound was purified by GRACE flash chromatography using 0.1% of formic acid in water and acetonitrile as an eluent to afford N-(1-amino-3-(difluoromethoxy)-1-oxopropan-2-yl)-2-methyl-5-((2-methylthiazol-5-yl)methoxy)benzofuran-3-carboxamide (cpd 447) (120 mg, 35%) as a white solid. TLC system: 100% Ethyl acetate; Rf: 0.4.

A preparative chiral SFC was performed on the racemic mixture of cpd 447 to afford cpd 447-En 1 and cpd 447-En 2.

The following compounds were prepared in a similar manner (use of appropriate reagents (chiral or racemic) and purification methods (including chiral HPLC or chiral SFC) known to the person skilled in the art) as described for cpd 447: 448-En 1, 448-En 2.

Synthesis of N-(3-(dimethylamino)oxetane-3-carbonyl)-2-methyl-5-((4-methylthiazol-5-yl)methoxy) benzofuran-3-carboxamide (Cpd 508), N-(3-carbamoyloxetan-3-yl)-N,2-dimethyl-5-((4-methylthiazol-5-yl)methoxy)benzofuran-3-carboxamide (cpd 589) and N-(3-cyanooxetan-3-yl)-N,2-dimethyl-5-((4-methylthiazol-5-yl)methoxy) benzofuran-3-carboxamide (Cpd 599)

Step 1: To a solution of 3-Oxetanone (3 g, 41.66 mmol) in CH$_2$Cl$_2$ (50 mL) was added 33% methyl amine in ethanol (39 mL, 416.6 mmol) and the solution was cooled to 0° C. TMSCN (8.3 mL, 66.66 mmol) was added slowly dropwise for 15 min to the reaction mixture and stirring was continued for 48 h at RT. The reaction mixture was diluted with dichloromethane (100 mL), washed with water (2×50 mL) and brine (50 mL), dried over anhydrous Na$_2$SO$_4$, filtered and the filtrate was concentrated under reduced pressure to give the crude material, which was purified by grace column chromatography using 2% methanol in dichloromethane as an eluent to afford 3-(methylamino)oxetane-3-carbonitrile (350 mg) as a light brown liquid. TLC system: 5% Methanol in dichloromethane; Rf: 0.4.

Step 2: To a stirred solution of 2-methyl-5-((4-methylthiazol-5-yl)methoxy)benzofuran-3-carboxylic acid (500 mg, 1.65 mmol) in dichloromethane (30 ml), was added thionyl chloride (0.24 mL, 3.30 mmol) at 0° C. and the mixture was then heated to 40° C. for 2 h. The reaction progress was monitored by TLC. After completion of the reaction volatiles were removed under reduced pressure. To this was added an already prepared mixture of 3-(methylamino)oxetane-3-carbonitrile (369 mg, 3.30 mmol) in dichloromethane (20 ml), the mixture was cooled to 0° C. followed by the addition of triethyl amine (1.15 mL, 8.25 mmol). The reaction mixture was stirred for 16 h at RT, reaction progress was monitored by TLC. The reaction mixture was diluted with water (50 mL) and extracted with dichloromethane (2×50 mL). The combined extracts were washed with brine (50 mL), dried over anhydrous $Na_2SO_4$ and concentrated under reduced pressure to get the crude material (0.6 g) which was purified by grace column chromatography to afford cpd 599 (300 mg) as an off-white solid. TLC system: 5% Methanol in dichloromethane; Rf: 0.6.

Step 3: To a solution of N-(3-cyanooxetan-3-yl)-N,2-dimethyl-5-((4-methylthiazol-5-yl)methoxy)benzofuran-3-carboxamide (1 g, 2.51 mmol) in THF (50 mL) was added NaOH (201 mg, 5.03 mmol) at 0° C. 30% $H_2O_2$ in water (0.2 mL, 2.51 mmol) was added slowly (dropwise) over 5 min to the reaction mixture and the mixture was then stirred for 1 h at RT. The reaction progress was monitored by TLC. The reaction mixture was diluted with dichloromethane (100 mL). The organic layer was washed with water (2×50 mL) and brine (50 mL), dried over anhydrous $Na_2SO_4$ and concentrated under reduced pressure to give the crude material which was purified by grace chromatography using 3% Methanol in dichloromethane as an eluent to afford N-(3-carbamoyloxetan-3-yl)-N,2-dimethyl-5-((4-methylthiazol-5-yl)methoxy)benzofuran-3-carboxamide (cpd 589) (530 mg) as an off-white solid. TLC system: 5% Methanol in Dichloromethane; Rf: 0.2.

Step 4: To a solution of N-(3-carbamoyloxetan-3-yl)-N,2-dimethyl-5-((4-methylthiazol-5-yl)methoxy)benzofuran-3-carboxamide (500 mg, 1.20 mmol) in THF (50 mL) was added 60% NaH (72.2 mg, 1.80 mmol) at 0° C., and the mixture was stirred for 15 min. MeI (0.082 mL, 1.32 mmol) was added slowly (dropwise) over 5 min to the reaction mixture and the mixture was stirred for 2 h at 0° C. The reaction progress was monitored by TLC. The reaction mixture was diluted with dichloromethane (100 mL). The organic layer was washed with water (2×50 mL) and brine (50 mL), dried over anhydrous $Na_2SO_4$ and concentrated under reduced pressure to give the crude material, which was purified by prep-HPLC to afford N-(3-(dimethylamino)oxetane-3-carbonyl)-2-methyl-5-((4-methylthiazol-5-yl)methoxy)benzofuran-3-carboxamide (cpd 508) (60 mg) as an off-white solid. TLC system: 5% Methanol in Dichloromethane; Rf: 0.5.

Synthesis of N-(3-(hydroxymethyl)pyrrolidin-3-yl)-2-methyl-5-((2-methylthiazol-5-yl)methoxy)benzofuran-3-carboxamide (Cpd 530)

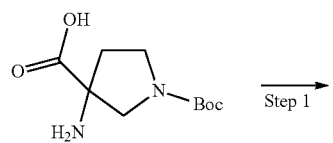

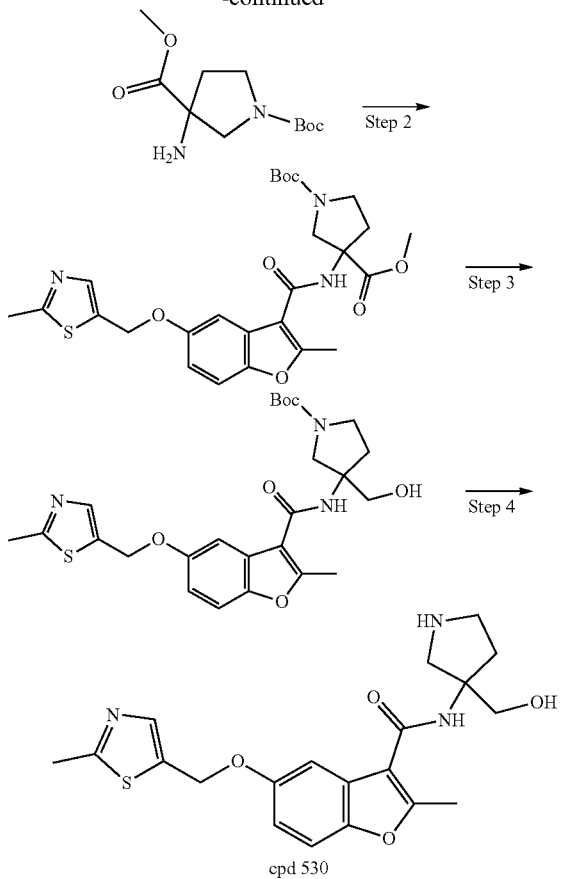

cpd 530

Step 1: To a stirred solution of 3-amino-1-(tert-butoxycarbonyl)pyrrolidine-3-carboxylic acid (0.6 g, 2.606 mmol) in dichloromethane (10 mL) and MeOH (5 mL) was added a 0.6 M TMS-diazomethane solution in n-Hexane (8.6 mL, 5.212 mmo) at 0° C. The reaction mixture was stirred for 16 h at RT. Reaction progress was monitored by TLC. The reaction mixture was diluted with water (20 mL) and extracted with dichloromethane (2×20 mL). The combined extracts were washed with brine (2×20 mL), dried over anhydrous $Na_2SO_4$ and concentrated under reduced pressure to afford the crude product of 1-(tert-butyl) 3-methyl 3-aminopyrrolidine-1,3-dicarboxylate (0.6 g) as a pale yellow gum. TLC system: 5% MeOH in dichloromethane; RF: 0.3.

Step 2: To a stirred solution of 2-methyl-5-((4-methylthiazol-5-yl)methoxy)benzofuran-3-carboxylic acid (300 mg, 0.99 mmol) in DMF (10 mL) were added DIPEA (0.53 mL, 2.97 mmol), HATU (564.3 mg, 1.485 mmol) and 1-(tert-butyl) 3-methyl 3-aminopyrrolidine-1,3-dicarboxylate (0.45 g, 4.95 mmol) at 0° C. The reaction mixture was stirred at room temperature for 16 h. The reaction progress was monitored by TLC. The reaction mixture was diluted with water (30 mL) and extracted with EtOAc (2×30 mL). The combined extracts were washed with water (3×20 mL) and brine (20 mL), dried over anhydrous $Na_2SO_4$ and concentrated under reduced pressure to get the crude material, which was purified by column chromatography over silica gel (100-200 mesh) using 40% ethyl acetate in pet-ether as an eluent to afford 1-(tert-butyl) 3-methyl 3-(2-methyl-5-((2-methylthiazol-5-yl)methoxy)benzofuran-3-carboxamido)pyrrolidine-1,3-dicarboxylate (330 mg, 62%) as a pale green gum. TLC system: 10% MeOH in dichloromethane; RF: 0.5.

Step 3: To a stirred solution of 1-(tert-butyl) 3-methyl 3-(2-methyl-5-((2-methylthiazol-5-yl)methoxy)benzofuran-3-carboxamido)pyrrolidine-1,3-dicarboxylate (300 mg, 0.566 mmol) in MeOH (15 mL) was added NaBH$_4$ (107.8 mg, 2.834 mmol) at 0° C. The reaction mixture was stirred for 16 h at RT and the reaction progress was monitored by TLC. The reaction mixture was evaporated under reduced pressure, diluted with water (20 mL), and extracted with ethyl acetate (2×20 mL). The combined organic layers were dried over anhydrous Na$_2$SO$_4$ and concentrated under reduced pressure to afford (250 mg, 85%) of tert-butyl 3-(hydroxymethyl)-3-(2-methyl-5-((2-methylthiazol-5-yl)methoxy)benzofuran-3-carboxamido)pyrrolidine-1-carboxylate as an off-white gum. TLC system: 10% Methanol in dichloromethane; RF: 0.2

Step 4: To a stirred solution of tert-butyl 3-(hydroxymethyl)-3-(2-methyl-5-((2-methylthiazol-5-yl)methoxy)benzofuran-3-carboxamido)pyrrolidine-1-carboxylate (250 mg, 0.498 mmol) in dichloromethane (10 mL) was added TFA (0.4 mL) at 0° C. The reaction mixture was stirred for 6 h at RT and the reaction progress was monitored by TLC. The reaction mixture was diluted with dichloromethane (50 mL). The organic layer was washed with saturated NaHCO$_3$ solution (2×20 mL) and brine (20 mL), dried over anhydrous Na$_2$SO$_4$ and concentrated to get the crude material which was purified by GRACE flash chromatography using 0.1% aqueous formic acid in acetonitrile as an eluent to afford N-(3-(hydroxymethyl)pyrrolidin-3-yl)-2-methyl-5-((2-methylthiazol-5-yl)methoxy)benzofuran-3-carboxamide (100 mg, 50%) as an off-white gum. TLC system: 10% Methanol in dichloromethane; RF: 0.1.

A preparative chiral SFC was performed on the racemic mixture of cpd 530 to afford cpd 530-En 1 and cpd 530-En2.

The following compounds were prepared in a similar manner (use of appropriate reagents (chiral or racemic) and purification methods (including chiral HPLC or chiral SFC) known to the person skilled in the art) as described for cpd 530-En 1 & cpd 530-En 2: Cpds. 728-En 1, 728-En 2.

Synthesis of N-(3-(hydroxymethyl)-2-oxopyrrolidin-3-yl)-2-methyl-5-((3-(trifluoromethyl)-1H-pyrazol-4-yl)methoxy)benzofuran-3-carboxamide (Cpd 730)

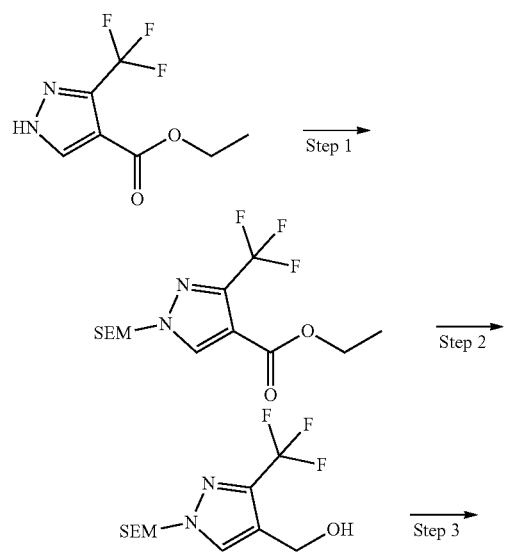

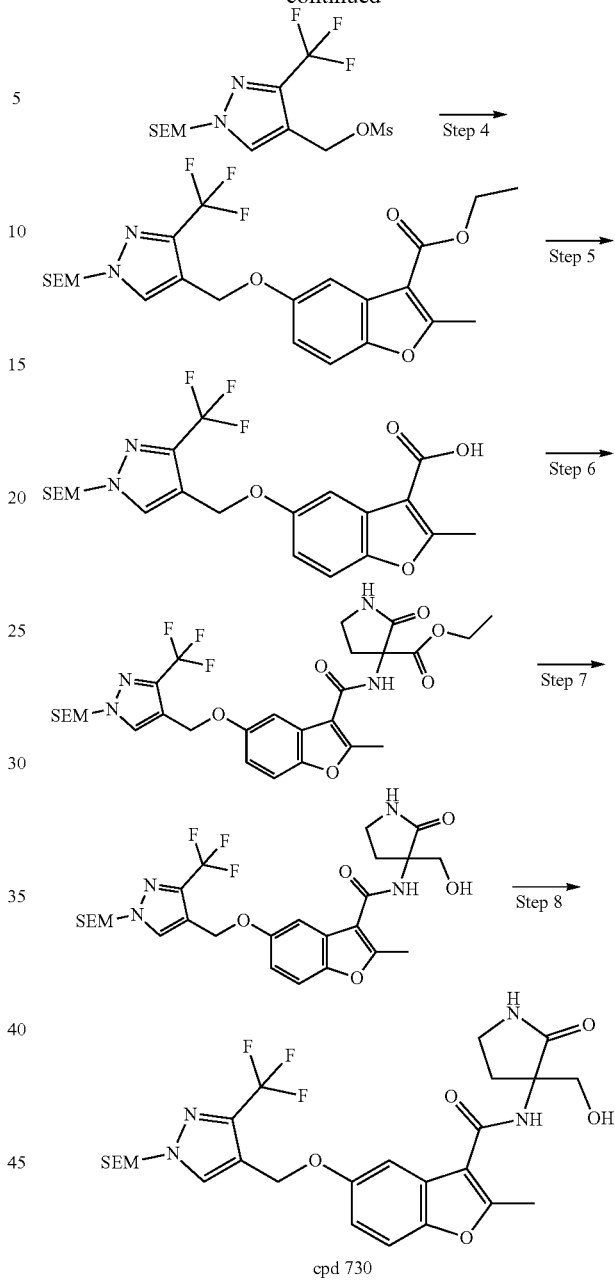

cpd 730

Step 1: To a stirred solution of ethyl 3-(trifluoromethyl)-1H-pyrazole-4-carboxylate (3.0 g, 14.42 mmol) in DMF (50 mL) was added K$_2$CO$_3$ (3.98 g, 28.84 mmol) at RT. The RM was cooled to 0° C., and added SEM-C$_1$ (3.0 mL, 17.30 mmol). The RM was stirred at 0° C. for 1 h and reaction progress was monitored by TLC. The reaction mixture was diluted with water (100 mL), and extracted with ethyl acetate (2×100 mL). Combined organic layers were washed with water (3×100 mL), dried over anhydrous Na$_2$SO$_4$ and concentrated under reduced pressure to get a crude. Crude was purified by column chromatography using silica gel (100-200 mesh) and 10% ethyl acetate in pet ether as an eluent to afford ethyl 3-(trifluoromethyl)-1-((2-(trimethylsilyl)ethoxy)methyl)-1H-pyrazole-4-carboxylate (2.8 g, 58%) as a solid. TLC system: 10% ethyl acetate in pet ether; Rf: 0.6.

Step 2: To a stirred solution of ethyl 3-(trifluoromethyl)-1-((2-(trimethylsilyl)ethoxy)methyl)-1H-pyrazole-4-carboxylate (2.8 g, 8.28 mmol) in THF (50 mL) was added 1M LAH solution in THF (12.4 mL, 12.42 mmol) at 0° C. The RM was stirred at 0° C. for 2 h and the reaction progress was monitored by TLC. Reaction mixture was quenched with aq. sat. sodium sulphate solution at 0° C., diluted with ethyl acetate (50 mL), filtered through celite bed, and celite bed was washed with ethyl acetate (50 mL). Combined filtrate was dried over anhydrous $Na_2SO_4$ and concentrated under reduced pressure to afford (3-(trifluoromethyl)-1-((2-(trimethylsilyl)ethoxy)methyl)-1H-pyrazol-4-yl)methanol (2.5 g). TL C system: 10% ethyl acetate in pet ether; RF: 0.23.

Step 3: To a stirred solution of (3-(trifluoromethyl)-1-((2-(trimethylsilyl)ethoxy)methyl)-1H-pyrazol-4-yl)methanol (1.5 g, 5.06 mmol) in DCM (50 mL) was added triethylamine (1.4 mL, 10.13 mmol) and followed by addition of Mesyl Chloride (0.58 mL, 7.60 mmol) at 0° C. The RM was stirred for 16 h at RT and the reaction progress was monitored by TLC. The RM was diluted with water (40 mL) and extracted with DCM (3×50 mL). Combined extracts were washed with brine (20 mL), dried over anhydrous $Na_2SO_4$ and concentrated under reduced pressure to afford (3-(trifluoromethyl)-1-((2-(trimethylsilyl)ethoxy)methyl)-1H-pyrazol-4-yl) methyl methanesulfonate (1.7 g) as a brown liquid. Proceeded to next step without further purification; TLC system: 10% ethyl acetate in pet ether; RF: 0.7.

Step 4: To a stirred solution of ethyl 5-hydroxy-2-methylbenzofuran-3-carboxylate (1.5 g, 6.81 mmol) in acetonitrile (100 mL) was added $Cs_2CO_3$ (6.6 g, 20.45 mmol) and followed by addition of (3-(trifluoromethyl)-1-((2-(trimethylsilyl)ethoxy)methyl)-1H-pyrazol-4-yl)methyl methane sulfonate (2.7 g, 7.49 mmol) at 0° C. The RM was stirred for 6 h at 80° C. and the reaction progress was monitored by TLC. The RM was filtered and washed the filter bed with ethyl acetate (100 mL). Filtrate was concentrated under reduced pressure to get crude. Crude was purified by column chromatography over silica gel (100-200 mesh) using 10% ethyl acetate in pet-ether as an eluent to afford ethyl 2-methyl-5-((3-(trifluoromethyl)-1-((2-(trimethylsilyl)ethoxy)methyl)-1H-pyrazol-4-yl)methoxy)benzofuran-3-carboxylate (1.3 g, 59% over 3 steps) as an off-white solid. TLC system: 20% ethyl acetate in pet ether; RF: 0.7.

Step 5: To a stirred solution of ethyl 2-methyl-5-((3-(trifluoromethyl)-1-((2-(trimethylsilyl)ethoxy)methyl)-1H-pyrazol-4-yl)methoxy)benzofuran-3-carboxylate (1.3 g, 2.61 mmol) in MeOH:THF:H2O (1:1:0.5, 50 mL) was added NaOH (1.0 g, 26.10 mmol) at RT. The RM was stirred for 4 h at 50° C. and the reaction progress was monitored by TLC. The RM was concentrated, acidified to pH ~2 with aq. 1 N HCl solution, and stirred for 20 minutes. The precipitated solid was filtered, washed with water (10 mL) and dried under vacuum to afford 2-methyl-5-((3-(trifluoromethyl)-1-((2-(trimethylsilyl)ethoxy)methyl)-1H-pyrazol-4-yl)methoxy)benzofuran-3-carboxylic acid (1.0 g) as an off-white solid. TLC system: 20% ethyl acetate in pet ether; RF: 0.1

Step 6: To a stirred solution of 2-methyl-5-((3-(trifluoromethyl)-1-((2-(trimethylsilyl)ethoxy)methyl)-1H-pyrazol-4-yl)methoxy)benzofuran-3-carboxylic acid (1.0 g, 2.12 mmol) in DMF (20 mL) was added HATU (1.21 g, 3.19 mmol), DIPEA (1.5 mL, 8.51 mmol) at 0° C. and followed by addition of ethyl 3-amino-2-oxopyrrolidine-3-carboxylate (548 mg, 3.19 mmol). The RM was stirred for 16 h at RT and reaction progress was monitored by TLC. The RM was diluted with water (100 mL), and extracted with ethyl acetate (2×100 mL). Combined organic layers were washed with water (3×100 mL), brine (100 mL), dried over anhydrous $Na_2SO_4$ and concentrated under reduced pressure to afford ethyl 3-(2-methyl-5-((3-(trifluoromethyl)-1-((2-(trimethylsilyl)ethoxy)methyl)-1H-pyrazol-4-yl)methoxy)benzofuran-3-carboxamido)-2-oxopyrrolidine-3-carboxylate (1.0 g) as a brown residue. TLC system: 60% ethyl acetate in pet ether; RF: 0.2.

Step 7: To a stirred solution of ethyl 3-(2-methyl-5-((3-(trifluoromethyl)-1-((2-(trimethylsilyl)ethoxy)methyl)-1H-pyrazol-4-yl)methoxy)benzofuran-3-carboxamido)-2-oxopyrrolidine-3-carboxylate (1.0 g, 1.60 mmol) in MeOH (20 mL) was added $NaBH_4$ (608 mg, 16.02 mmol) at 0° C. The RM was stirred for 16 h at RT and reaction progress was monitored by TLC. The RM was concentrated, diluted with water (50 mL), and extracted with ethyl acetate (2×100 mL). Combined organic layers were dried over anhydrous $Na_2SO_4$ and concentrated under reduced pressure to get N-(3-(hydroxymethyl)-2-oxopyrrolidin-3-yl)-2-methyl-5-((3-(trifluoromethyl)-1-((2-(trimethylsilyl)ethoxy)methyl)-1H-pyrazol-4-yl)methoxy)benzofuran-3-carboxamide (800 mg, crude) as a thick residue. TLC system: 60% ethyl acetate in pet-ether; RF: 0.2.

Step 8: To a stirred solution of N-(3-(hydroxymethyl)-2-oxopyrrolidin-3-yl)-2-methyl-5-((3-(trifluoromethyl)-1-((2-(trimethylsilyl)ethoxy)methyl)-1H-pyrazol-4-yl)methoxy)benzofuran-3-carboxamide (800 mg, 1.37 mmol) in DCM (30 mL) was added TFA (5 mL) at 0° C. The RM was stirred for 6 h at RT and the reaction progress was monitored by TLC. The reaction mixture was concentrated, basified to pH ~8 with aq. sat $NaHCO_3$ solution and extracted with ethyl acetate (2×100 mL). Combined organic layers were dried over anhydrous $Na_2SO_4$ and concentrated under reduced pressure to get crude. Crude was purified by Grace flash chromatography using 0.1% formic acid in acetonitrile as an eluent to afford N-(3-(hydroxymethyl)-2-oxopyrrolidin-3-yl)-2-methyl-5-((3-(trifluoromethyl)-1H-pyrazol-4-yl)methoxy)benzofuran-3-carboxamide (Cpd 730) (500 mg, 34% for 4 steps).

A preparative chiral SFC was performed on the racemic mixture of cpd 730 to afford cpd 730-En 1 and cpd 730-En 2.

The following compounds were prepared in a similar manner (use of appropriate reagents (chiral or racemic) and purification methods (including chiral HPLC or chiral SFC) known to the person skilled in the art) as described for cpd 730-En 1 and cpd 730-En 2: Cpds. 731-En 1, 731-En 2.

Synthesis of N-(3,3-difluoropiperidin-4-yl)-2-methyl-5-((6-oxo-1,6-dihydropyridin-2-yl)methoxy)benzofuran-3-carboxamide (Cpd 569)

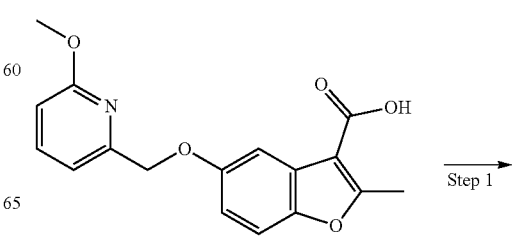

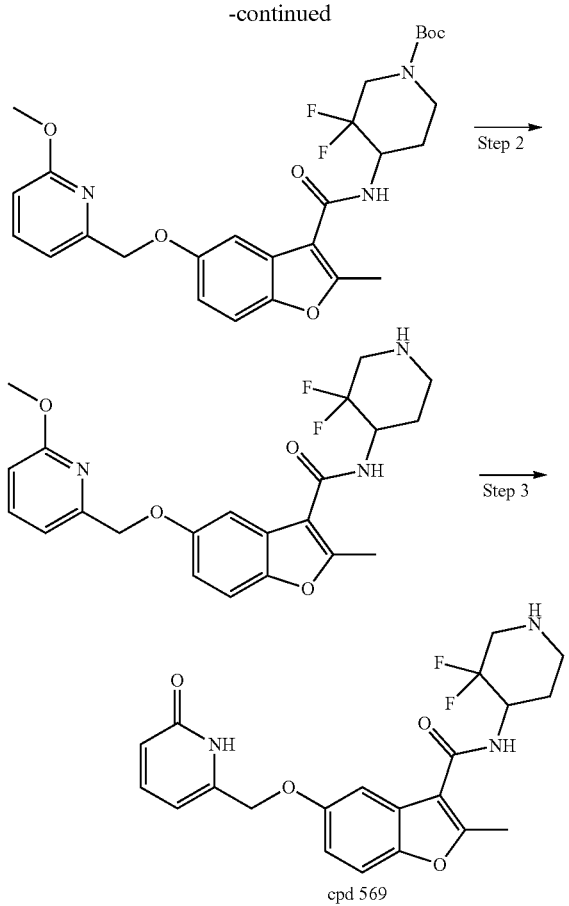

cpd 569

Step 1: To a pre-stirred solution mixture of 5-((6-methoxypyridin-2-yl)methoxy)-2-methylbenzofuran-3-carboxylic acid (1.0 g, 3.19 mmol), HATU (1.8 g, 4.79 mmol) and DIPEA (3.4 mL, 6.38 mmol) in DMF (20.0 mL) was added tert-butyl 4-amino-3,3-difluoropiperidine-1-carboxylate (0.904 g, 3.83 mmol) at 0° C. and the resulting reaction mixture was stirred at room temperature for 2 h. The reaction progress was monitored by TLC. (Note: Another 1.0 g of 5-((6-methoxypyridin-2-yl)methoxy)-2-methylbenzofuran-3-carboxylic acid was similarly reacted using the same procedure and was combined with the reaction described in detail for work-up). The combined reaction mixture was diluted with ice cold water (100 mL) and extracted with ethyl acetate (2×100 mL). The combined organic layers were washed with water (2×100 mL) and brine (100 mL), dried over anhydrous $Na_2SO_4$ and concentrated under reduced pressure. The crude product was purified by GRACE flash chromatography using 0.1% formic acid in water and acetonitrile as an eluent to afford tert-butyl 3,3-difluoro-4-(5-((6-methoxypyridin-2-yl)methoxy)-2-methylbenzofuran-3-carboxamido)piperidine-1-carboxylate (1.2 g, 36%) as an off-white solid. TLC system: 50% Ethyl acetate in pet ether; Rf: 0.4.

Step 2: HCl (4.0 M in dioxane) (10 mL) was added dropwise to a pre-stirred solution of tert-butyl 3,3-difluoro-4-(5-((6-methoxypyridin-2-yl)methoxy)-2-methylbenzofuran-3-carboxamido)piperidine-1-carboxylate (600 mg, 1.12 mmol) in dichloromethane (5 mL) at 0° C. under an argon atmosphere. The resulting reaction mixture was allowed to attain room temperature and was stirred for 5 h. The reaction progress was monitored by TLC. (Note: 600 mg of tert-butyl 3,3-difluoro-4-(5-((6-methoxypyridin-2-yl)methoxy)-2-methylbenzofuran-3-carboxamido)piperidine-1-carboxylate was similarly treated following the same procedure and was combined with the reaction mixture for work-up). The combined reaction mixture was concentrated under reduced pressure, the residue was basified with saturated $NaHCO_3$ (80 mL) solution and the organic compound was extracted with 10% methanol in dichloromethane (3×50 mL). The combined organic layers were washed with water (50 mL) and brine (50 mL), dried over anhydrous $Na_2SO_4$ and concentrated under reduced pressure. The crude product was purified by GRACE flash chromatography using 0.1% formic acid in water and acetonitrile as an eluent to afford N-(3,3-difluoropiperidin-4-yl)-5-((6-methoxypyridin-2-yl)methoxy)-2-methylbenzofuran-3-carboxamide (900 mg, 92%) as an off-white solid. TLC system: 5% Methanol in dichloromethane; Rf: 0.2.

Step 3: TMS-C$_l$ (189 mg, 1.740 mmol) was slowly added to a pre-stirred mixture of N-(3,3-difluoropiperidin-4-yl)-5-((6-methoxypyridin-2-yl)methoxy)-2-methylbenzofuran-3-carboxamide (500 mg, 1.156 mmol) and NaI (347 mg, 2.32 mmol) in acetonitrile (10 mL) at room temperature and the resulting reaction mixture was heated to 60° C. for 24 h. The reaction progress was monitored by TLC. (Note: 400 mg of N-(3,3-difluoropiperidin-4-yl)-5-((6-methoxypyridin-2-yl)methoxy)-2-methylbenzofuran-3-carboxamide was similarly reacted following the same procedure and was combined with the reaction mixture for work-up). The combined reaction mixture was cooled to room temperature, quenched with brine solution (50 mL) and extracted with ethyl acetate (3×50 mL). The combined organic layers were dried over anhydrous $Na_2SO_4$ and concentrated under reduced pressure. The crude product was purified by GRACE flash chromatography using 0.1% formic acid in water and acetonitrile as an eluent to afford N-(3,3-difluoropiperidin-4-yl)-2-methyl-5-((6-oxo-1,6-dihydropyridin-2-yl)methoxy)benzofuran-3-carboxamide (340 mg, 33%) as an off white solid. TLC system: 5% MeOH in dichloromethane; Rf: 0.3.

A preparative chiral SFC was performed on the racemic mixture of cpd 569 to afford cpd 569-En 1 and cpd 569-En 2.

The following compounds were prepared in a similar manner (use of appropriate reagents (chiral or racemic) and purification methods (including chiral HPLC or chiral SFC) known to the person skilled in the art) as described for cpd 569: Cpds. 564-En 1, 564-En 2, 569-En 1, 569-En 2, 637-En 1, 637-En 2, 640-En 1, 640-En 2.

Synthesis of 4-(((3-((4-(hydroxymethyl)tetrahydro-2H-pyran-4-yl)carbamoyl)-2-methylbenzofuran-5-yl)oxy)methyl)-1-methylene-1H-1,2,3-triazol-1-ium (Cpd 604) and N-(4-(hydroxymethyl)tetrahydro-2H-pyran-4-yl)-2-methyl-5-((1-methyl-1H-1,2,3-triazol-5-yl)methoxy)benzofuran-3-carboxamide (Cpd 605)

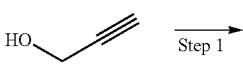

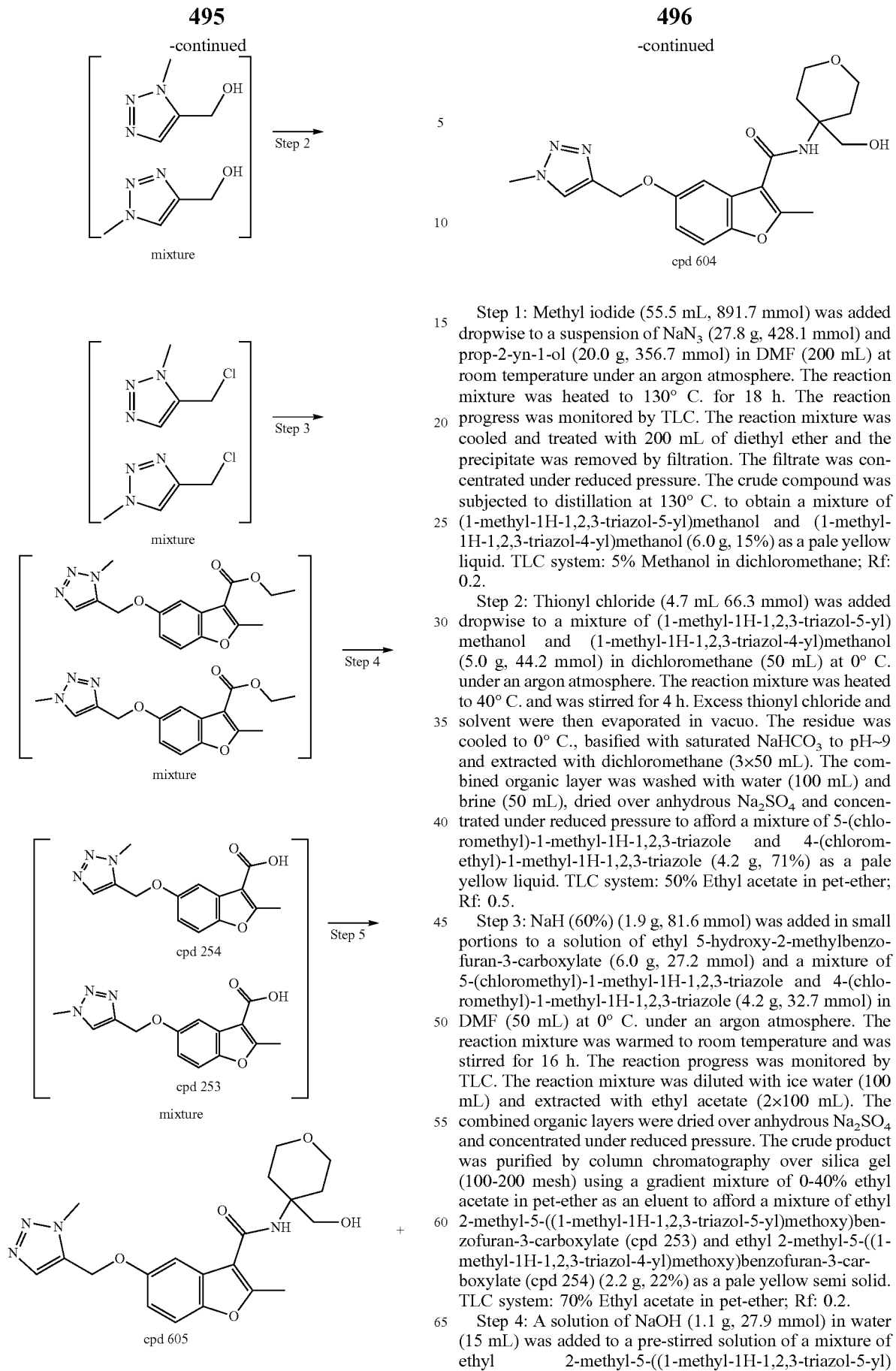

Step 1: Methyl iodide (55.5 mL, 891.7 mmol) was added dropwise to a suspension of NaN₃ (27.8 g, 428.1 mmol) and prop-2-yn-1-ol (20.0 g, 356.7 mmol) in DMF (200 mL) at room temperature under an argon atmosphere. The reaction mixture was heated to 130° C. for 18 h. The reaction progress was monitored by TLC. The reaction mixture was cooled and treated with 200 mL of diethyl ether and the precipitate was removed by filtration. The filtrate was concentrated under reduced pressure. The crude compound was subjected to distillation at 130° C. to obtain a mixture of (1-methyl-1H-1,2,3-triazol-5-yl)methanol and (1-methyl-1H-1,2,3-triazol-4-yl)methanol (6.0 g, 15%) as a pale yellow liquid. TLC system: 5% Methanol in dichloromethane; Rf: 0.2.

Step 2: Thionyl chloride (4.7 mL 66.3 mmol) was added dropwise to a mixture of (1-methyl-1H-1,2,3-triazol-5-yl)methanol and (1-methyl-1H-1,2,3-triazol-4-yl)methanol (5.0 g, 44.2 mmol) in dichloromethane (50 mL) at 0° C. under an argon atmosphere. The reaction mixture was heated to 40° C. and was stirred for 4 h. Excess thionyl chloride and solvent were then evaporated in vacuo. The residue was cooled to 0° C., basified with saturated NaHCO₃ to pH~9 and extracted with dichloromethane (3×50 mL). The combined organic layer was washed with water (100 mL) and brine (50 mL), dried over anhydrous Na₂SO₄ and concentrated under reduced pressure to afford a mixture of 5-(chloromethyl)-1-methyl-1H-1,2,3-triazole and 4-(chloromethyl)-1-methyl-1H-1,2,3-triazole (4.2 g, 71%) as a pale yellow liquid. TLC system: 50% Ethyl acetate in pet-ether; Rf: 0.5.

Step 3: NaH (60%) (1.9 g, 81.6 mmol) was added in small portions to a solution of ethyl 5-hydroxy-2-methylbenzofuran-3-carboxylate (6.0 g, 27.2 mmol) and a mixture of 5-(chloromethyl)-1-methyl-1H-1,2,3-triazole and 4-(chloromethyl)-1-methyl-1H-1,2,3-triazole (4.2 g, 32.7 mmol) in DMF (50 mL) at 0° C. under an argon atmosphere. The reaction mixture was warmed to room temperature and was stirred for 16 h. The reaction progress was monitored by TLC. The reaction mixture was diluted with ice water (100 mL) and extracted with ethyl acetate (2×100 mL). The combined organic layers were dried over anhydrous Na₂SO₄ and concentrated under reduced pressure. The crude product was purified by column chromatography over silica gel (100-200 mesh) using a gradient mixture of 0-40% ethyl acetate in pet-ether as an eluent to afford a mixture of ethyl 2-methyl-5-((1-methyl-1H-1,2,3-triazol-5-yl)methoxy)benzofuran-3-carboxylate (cpd 253) and ethyl 2-methyl-5-((1-methyl-1H-1,2,3-triazol-4-yl)methoxy)benzofuran-3-carboxylate (cpd 254) (2.2 g, 22%) as a pale yellow semi solid. TLC system: 70% Ethyl acetate in pet-ether; Rf: 0.2.

Step 4: A solution of NaOH (1.1 g, 27.9 mmol) in water (15 mL) was added to a pre-stirred solution of a mixture of ethyl 2-methyl-5-((1-methyl-1H-1,2,3-triazol-5-yl)

methoxy)benzofuran-3-carboxylate and ethyl 2-methyl-5-((1-methyl-1H-1,2,3-triazol-4-yl)methoxy)benzofuran-3-carboxylate (2.2 g, 6.98 mmol) in methanol:THF (1:1) (40 mL) at room temperature and the resulting reaction mixture was heated to 60° C. for 3 h. The reaction progress was monitored by TLC. The reaction mixture was cooled to room temperature and poured into ice cold water (100 mL), acidified with 1 N HCl to pH~2.0 and extracted with ethyl acetate (2×100 mL). The combined organic layers were washed with water (100 mL) followed by brine (100 mL), dried over anhydrous $Na_2SO_4$ and concentrated under reduced pressure to afford a mixture of 2-methyl-5-((1-methyl-1H-1,2,3-triazol-5-yl)methoxy)benzofuran-3-carboxylic acid and 2-methyl-5-((1-methyl-1H-1,2,3-triazol-4-yl)methoxy)benzofuran-3-carboxylic acid (1.7 g, 85%) as an pale yellow solid. TLC system: 5% Methanol in dichloromethane; Rf: 0.2.

Step 5: (4-Aminotetrahydro-2H-pyran-4-yl)methanol (164.3 mg, 1.25 mmol) was added to a stirred solution of a mixture of 2-methyl-5-((1-methyl-1H-1,2,3-triazol-5-yl)methoxy)benzofuran-3-carboxylic acid and 2-methyl-5-((1-methyl-1H-1,2,3-triazol-4-yl)methoxy)benzofuran-3-carboxylic acid (300 mg, 1.04 mmol), HATU (790.8 mg, 2.08 mmol) and DIPEA (0.56 mL, 3.12 mmol) in DMF (10 mL). The resulting reaction mixture was stirred at room temperature for 2 h. The reaction progress was monitored by TLC. The reaction mixture was diluted with ice water (20 mL) and extracted with ethyl acetate (2×30 mL). The combined organic layers were dried over anhydrous $Na_2SO_4$ and concentrated under reduced pressure. The crude product was purified by GRACE flash chromatography using 0.1% formic acid in water and acetonitrile as an eluent followed by chiral-SFC to afford N-(4-(hydroxymethyl)tetrahydro-2H-pyran-4-yl)-2-methyl-5-((1-methyl-1H-1,2,3-triazol-5-yl)methoxy)benzofuran-3-carboxamide (cpd 605) (90 mg) and N-(4-(hydroxymethyl)tetrahydro-2H-pyran-4-yl)-2-methyl-5-((1-methyl-1H-1,2,3-triazol-4-yl)methoxy)benzofuran-3-carboxamide (cpd 604) (50 mg) as off-white solids. TLC system: 70% Ethyl acetate in pet-ether; Rf: 0.4.

Synthesis of N3-(3,3-difluoropiperidin-4-yl)-5-((2-(trifluoromethyl)pyridin-3-yl)methoxy)benzofuran-2,3-dicarboxamide (Cpd 657)

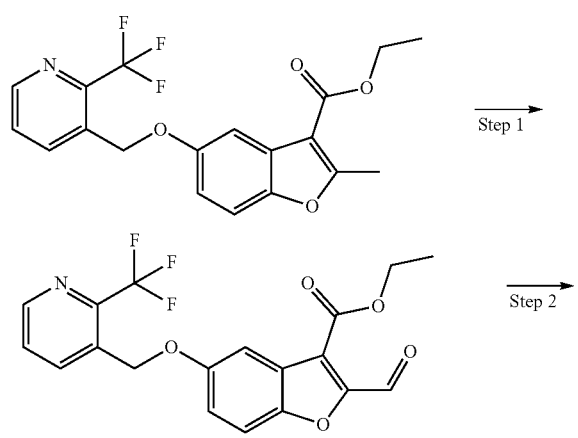

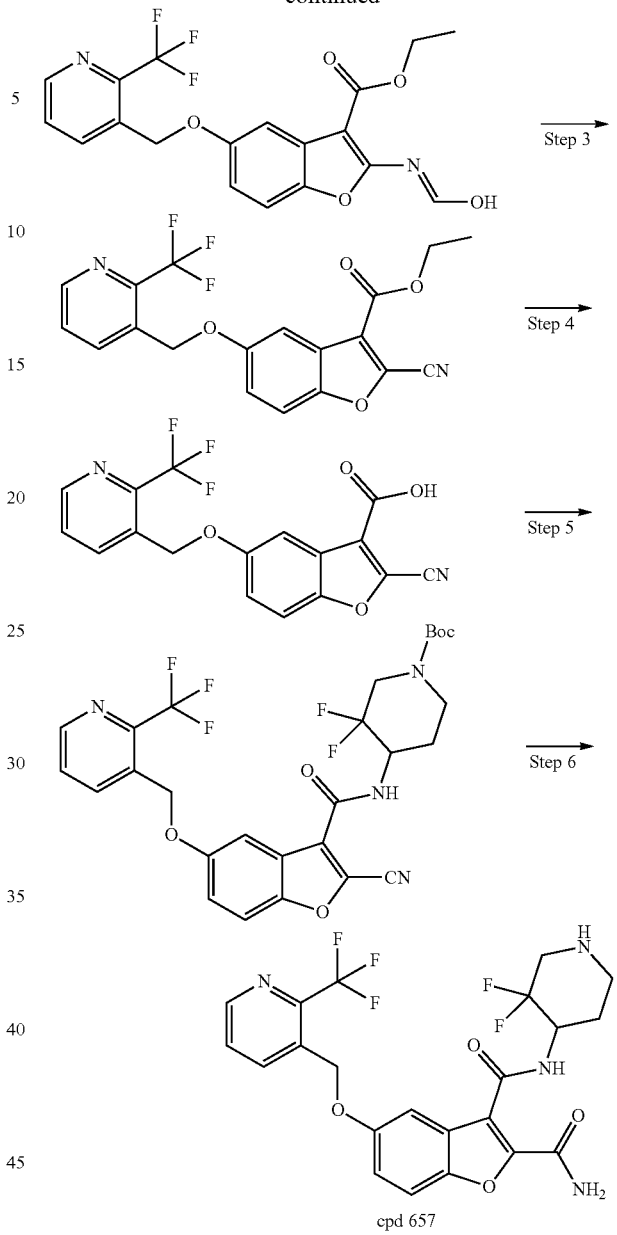

cpd 657

Step 1: To a stirred solution of ethyl 2-methyl-5-((2-(trifluoromethyl)pyridin-3-yl)methoxy)benzofuran-3-carboxylate (4 g, 10.5 mmol) in 1,4-dioxane (50 ml) was added $SeO_2$ (24 g, 21.1 mmol) at RT and the reaction mixture was stirred for 48 h at 120° C., the reaction progress was monitored by TLC. The reaction mixture was filtered through a celite pad and the filtrate was evaporated under reduced pressure to get the crude material (6 g), which was purified by silica gel (100-200 mesh) column chromatography to afford (1 g, 24%) as a pale yellow solid. TLC system: 30% Ethyl acetate in pet-ether; Rf: 0.4

Step 2: To a stirred solution of ethyl 2-formyl-5-((2-(trifluoromethyl)pyridin-3-yl)methoxy)benzofuran-3-carboxylate (1 g, 2.54 mmol) in ethanol (50 ml) was added $NH_2OH \cdot HCl$ (880 mg, 12.8 mmol) and pyridine (405 mg, 4.1 mmol) at RT and the resulting reaction mixture was then heated to 80° C. for 6 h. Ice cold water was added to the reaction mixture and the mixture was then extracted with EtOAc (2×10 mL). The combined organic layers were washed with water (50 mL) and brine (20 mL), dried over anhydrous Na$_2$SO$_4$, filtered and evaporated under reduced pressure to get the crude material which was used in the next step without further purification. TLC system: 100% Ethyl acetate in pet-ether; Rf: 0.2

Step 3: To a stirred solution of (E)-N-(3-(ethoxycarbonyl)-5-((2-(trifluoromethyl)pyridin-3-yl)methoxy)benzofuran-2-yl)formimidic acid (1 g, 2.4 mmol) in THF (50 ml) were added DIPEA (0.722 g, 3 mmol) and T$_3$P (2.64 g, 3 mmol) at 0° C. and the resulting reaction mixture was stirred at RT for 16 h. Ice cold water was added to the reaction mixture and the mixture was extracted with EtOAc (2×10 mL). The combined organic layers were washed with water (50 mL) and brine (20 mL), dried over anhydrous Na$_2$SO$_4$, filtered and evaporated under reduced pressure to get the crude material which was purified by flash column chromatography over neutral alumina using 20% ethyl acetate in pet-ether as an eluent to afford ethyl 2-cyano-5-((2-(trifluoromethyl)pyridin-3-yl)methoxy)benzofuran-3-carboxylate (0.5 g, 52%) as an off-white solid. TLC system: 50% Ethyl acetate in pet-ether; Rf: 0.7

Step 4: To ethyl 2-cyano-5-((2-(trifluoromethyl)pyridin-3-yl)methoxy)benzofuran-3-carboxylate (550 mg, 1.4 mmol) was added LiOH·H$_2$O (110 mg, 2.8 mmol) in THF:H$_2$O (20 mL) at RT under an argon atmosphere. The reaction mixture was stirred for 2 h at RT. The reaction progress was monitored by TL C. The reaction mixture was acidified to pH ~1 with citric acid and the resulting precipitate was filtered off. The solid obtained was dried under vacuum to afford 2-cyano-5-((2-(trifluoromethyl)pyridin-3-yl) methoxy)benzofuran-3-carboxylic acid (0.35 g, 68%) as an off-white solid. TLC system: 5% MeOH in CH$_2$Cl$_2$; Rf: 0.2.

Step 5: To a stirred solution of 2-cyano-5-((2-(trifluoromethyl)pyridin-3-yl)methoxy)benzofuran-3-carboxylic acid (0.35 g, 9 mmol) in CH$_2$Cl$_2$ (30 ml) were added DIPEA (0.23 g, 1.8 mmol) and HATU (0.69 g, 1.8 mmol) at 0° C. followed by the addition of tert-butyl 4-amino-3,3-difluoropiperidine-1-carboxylate (273 mg, 1.1 mmol), then the reaction mixture was stirred for 6 h at RT, and the reaction progress was monitored by TLC. The reaction mixture was diluted with water (150 mL), and extracted with CH$_2$Cl$_2$ (3×100 mL). The combined organic extracts were washed with brine (150 mL), dried over anhydrous Na$_2$SO$_4$ and concentrated under reduced pressure to get the crude compound (0.5 g) which was used without further purification in the next step.

Step 6: To a stirred solution of tert-butyl 4-(2-cyano-5-((2-(trifluoromethyl)pyridin-3-yl)methoxy)benzofuran-3-carboxamido)-3,3-difluoropiperidine-1-carboxylate (25 mg, 0.043 mmol) in 1,4-dioxane (10 ml), were added 4 M HCl in 1,4-dioxane (5 ml) at 0° C. and the mixture was stirred for 2 h at RT, the reaction progress was monitored by TLC. The reaction mixture was concentrated under reduced pressure to get the crude compound (30 mg, LCMS: 88%). The crude compound was purified by prep-SFC to afford of (12 mg) as an off-white solid. TLC system: 10% Methanol in Dichloromethane; Rf: 0.3.

Cpd 657 canbe obtained in enantiomerically pure form as cpd 657-En 1 and cpd 657-En 2 using a chiral SFC separation of the product obtained after step 5. Both obtained enantiomers are then forwarded independently to obtain cpd 657-En 1 and cpd 657-En 2.

Synthesis of N3-(4-(hydroxymethyl)tetrahydro-2H-pyran-4-yl)-5-((4-methylthiazol-5-yl)methoxy)benzofuran-2,3-dicarboxamide (Cpd 658)

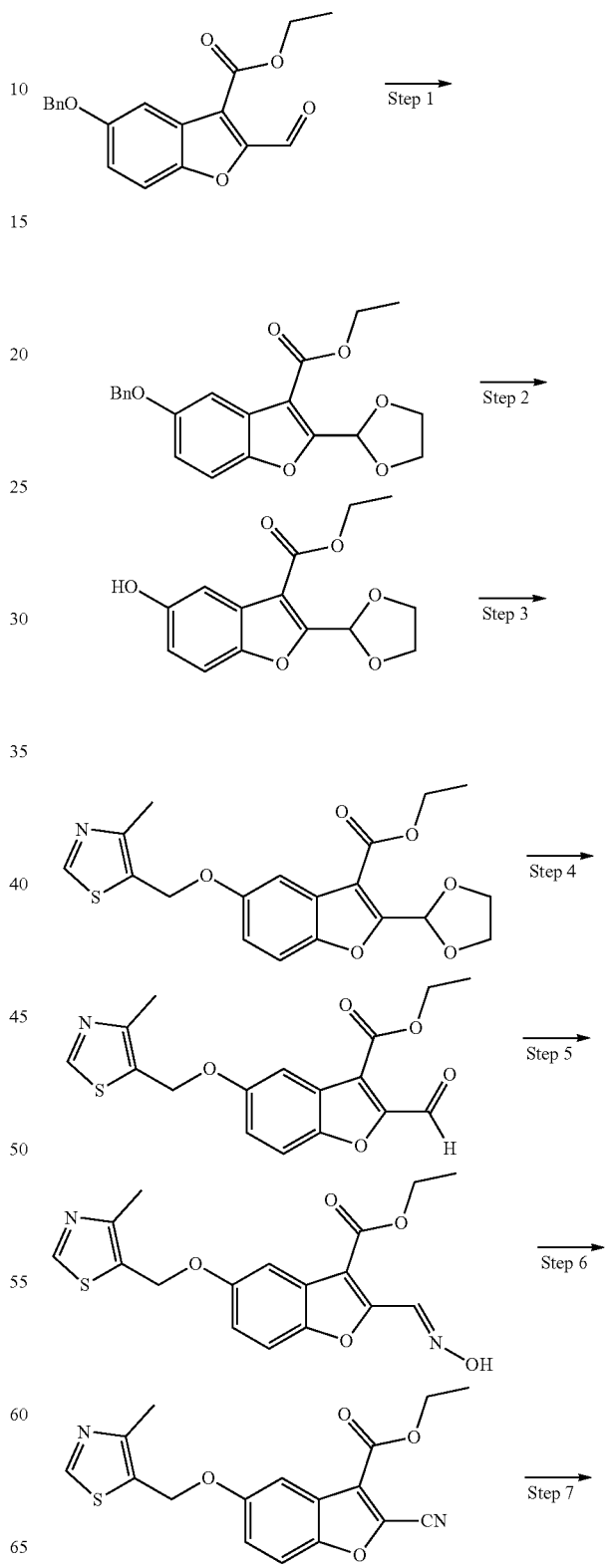

-continued

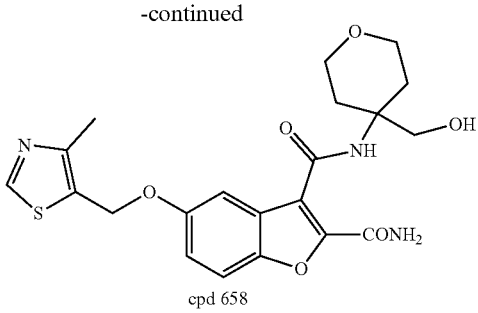

cpd 658

Step 1: PTSA (0.051 g, 0.3 mmol) was added to a stirred solution of ethyl 5-(benzyloxy)-2-formylbenzofuran-3-carboxylate (1 g, 3 mmol) and ethylene glycol (0.925 g, 15.4 mmol) in toluene (20 mL) at RT. The resulting reaction mixture was stirred at 120° C. for 12 h using a Dean-stark apparatus. The reaction mixture was evaporated under reduced pressure to get a residue. The residue obtained was dissolved in ethyl acetate (20 ml) and washed with sat. NaHCO$_3$ solution (100 mL). The organic layer was dried over anhydrous Na$_2$SO$_4$, filtered, and evaporated under reduced pressure to get the crude material which was purified by neutral alumina column chromatography using 20% ethyl acetate in pet ether to afford ethyl 5-(benzyloxy)-2-(1,3-dioxolan-2-yl)benzofuran-3-carboxylate (900 mg, 81%) as an off-white solid. TLC system: 20% EtOAc in Hexane; Rf: 0.4.

Step 2: To a stirred solution of ethyl 5-(benzyloxy)-2-(1,3-dioxolan-2-yl)benzofuran-3-carboxylate (0.9 g, 2.4 mmol) in ethanol (20 ml) was added 10% Pd/C (150 mg, 10 mol %), and then the reaction mixture was stirred for 6 h under H$_2$ atm pressure (60 psi) at RT, the reaction progress was monitored by TLC. The reaction mixture was filtered through a celite pad and the filtrate was evaporated under reduced pressure to get the crude material (1 g) as a colorless oil, which was used in the next step without further purification. TLC system: 40% Ethyl acetate in pet-ether; Rf: 0.5.

Step 3: (4-Methylthiazol-5-yl)methanol (2044-6) (0.229 g, 1.7 mmol), ADDP (0.604 g, 2.4 mmol) and tri-N-butylphosphine (0.484 g, 2.4 mmol) were added sequentially to a pre-stirred solution of ethyl 2-(1,3-dioxolan-2-yl)-5-hydroxybenzofuran-3-carboxylate (0.45 g, 1.6 mmol) in THF (15 mL) at RT under an argon atmosphere. The reaction mixture was stirred for 18 h at RT and the reaction progress was monitored by TLC. The reaction mixture was filtered and washed with diethyl ether (300 mL), the filtrate was concentrated under reduced pressure to give the crude material which was purified by flash column chromatography over neutral alumina using 10% ethyl acetate in pet-ether as an eluent to afford ethyl 2-(1,3-dioxolan-2-yl)-5-((4-methylthiazol-5-yl)methoxy)benzofuran-3-carboxylate (0.2 g, 30%) as an off-white solid. TLC system: 30% Ethyl acetate in pet-ether; Rf: 0.35

Step 4: To a stirred solution of ethyl 2-(1,3-dioxolan-2-yl)-5-((4-methylthiazol-5-yl)methoxy)benzofuran-3-carboxylate (100 mg, 2.57 mmol) in CH$_2$Cl$_2$ (10 ml) was added TFA (58 mg, 5.14 mmol) at 0° C. and the resulting reaction mixture was stirred at rt for 16 h. After completion of the reaction, ice-cold water was added to the reaction mixture and the mixture was extracted with CH$_2$Cl$_2$ (2×10 mL). The combined organic layers were washed with sat. NaHCO$_3$ solution (50 mL), dried over anhydrous Na$_2$SO$_4$, filtered and evaporated under reduced pressure to get the crude material, which was used in the next step without further purification. TLC system: 50% Ethyl acetate in pet-ether; Rf: 0.3

Step 5: To a stirred solution of ethyl 2-formyl-5-((4-methylthiazol-5-yl)methoxy)benzofuran-3-carboxylate (50 mg, 0.14 mmol) in ethanol (10 ml) were added NH$_2$OH·HCl (39 mg, 5 mmol) and pyridine (22 mg, 2.8 mmol) at RT and the resulting mixture was stirred at 90° C. for 6 h. After completion of the reaction ice-cold water was added to the reaction mixture and the mixture was extracted with CH$_2$Cl$_2$ (2×10 mL). The combined organic layers were washed with sat. NaHCO$_3$ solution (50 mL), dried over anhydrous Na$_2$SO$_4$, filtered and evaporated under reduced pressure to get the crude material, which was used in the next step without further purification. TLC system: 100% Ethyl acetate in pet-ether; Rf: 0.2.

Step 6: To a stirred solution of (E)-ethyl 2-((hydroxyimino)methyl)-5-((4-methylthiazol-5-yl)methoxy)benzofuran-3-carboxylate (1 g, 2.8 mmol) in THF (50 ml) were added DIPEA (0.722 g, 3 mmol) and T$_3$P (2.64 g, 3 mmol) at 0° C. and the resulting reaction mixture was then stirred at RT for 16 h. Ice cold water was added to the reaction mixture and the mixture was extracted with EtOAc (2×10 mL). The combined organic layers were washed with brine (20 mL), dried over anhydrous Na$_2$SO$_4$, filtered and evaporated under reduced pressure to get the crude material which was purified by flash column chromatography over neutral alumina using 20% ethyl acetate in pet-ether as an eluent to afford ethyl 2-cyano-5-((4-methylthiazol-5-yl)methoxy)benzofuran-3-carboxylate (0.3 g, 31%) as an off-white solid. TLC system: 50% Ethyl acetate in pet-ether; Rf: 0.6.

Step 7: To a stirred solution of ethyl 2-cyano-5-((4-methylthiazol-5-yl)methoxy)benzofuran-3-carboxylate (0.15 g, 4 mmol) in THF (50 ml) were added (4-aminotetrahydro-2H-pyran-4-yl)methanol (0.068 g, 5.2 mmol) and 2,3,4,6,7,8-hexahydro-1H-pyrimido[1,2-a]pyrimidine (0.108 g, 7.8 mmol) at RT and the resulting reaction mixture was heated to 80° C. for 40 min. Ice cold water was added to the reaction mixture and the mixture was extracted with EtOAc (2×10 mL). The combined organic layers were washed with brine (20 mL), dried over anhydrous Na$_2$SO$_4$, filtered and evaporated under reduced pressure to get the crude compound, which was purified by reverse phase prep-HPLC purification to afford 13 mg of cpf 658 as an off-white solid. TLC system: 50% Ethyl acetate in pet-ether; Rf: 0.2.

Synthesis of Small Synthetic Intermediates Used for the Synthesis of Cpds. 001-666

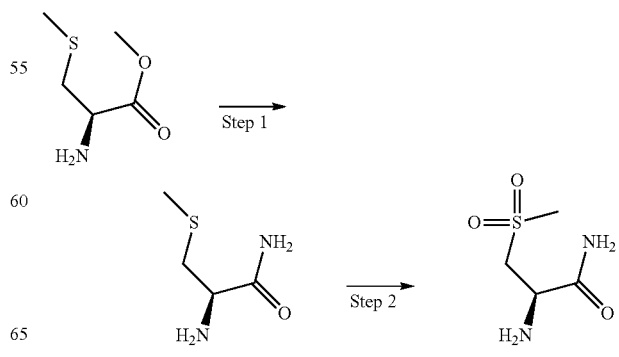

Step 1: A solution of methyl S-methyl-L-cysteinate (1) (2.0 g, 0.013 mmol) and 7 M NH₃ solution in methanol (20 mL) in a sealed tube was heated to 90° C. and stirred for 16 h at the same temperature. The reaction progress was monitored by TLC. The reaction mixture was concentrated under reduced pressure, and was then co-distilled with EtOAc (2×20 mL). To the reaction mixture was added EtOAc (30 mL), the reaction mixture was then stirred for 2 h, and the solid was filtered off and dried to afford (R)-2-amino-3-(methylthio)propanamide (1.6 g, 88%) as a brown solid. TLC system: 5% Methanol in dichloromethane; RF: 0.1

Step 2: To a stirred solution of (R)-2-amino-3-(methylthio) propanamide (1.0 g, 0.007 mmol) in methanol and water (2:1), was added oxone (5.0 g, 0.008 mmol) at RT. The reaction mixture was stirred for 16 h at RT. The reaction mixture was concentrated under reduced pressure, and was then co-distilled with methanol (2×20 mL) to afford (R)-2-amino-3-(methylsulfonyl)propanamide (6.0 g crude) as a white solid which was used without any further purification.

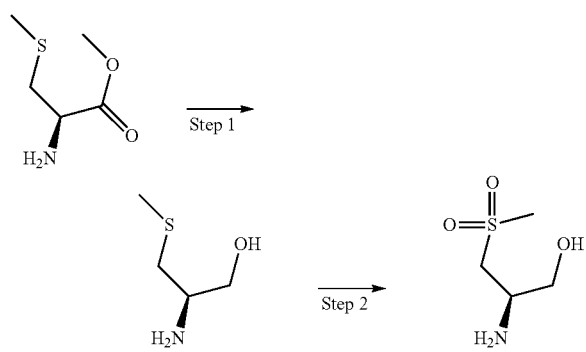

Step 1: To a stirred solution of methyl S-methyl-L-cysteinate (1.0 g, 6.71 mmol) and THF (20 mL) was added 1 M LAH solution in THF (8 mL, 8.0 mmol) at 0° C. The reaction mixture was stirred for 1 h at 0° C. The reaction progress was monitored by TLC. Then the reaction mixture was quenched with saturated Na₂SO₄ solution and was filtered. The filtrate was concentrated under reduced pressure to afford (R)-2-amino-3-(methylthio)propan-1-ol (800 mg, crude) as a thick residue. TLC system: 10% Methanol in dichloromethane; RF: 0.1

Step 2: To a stirred solution of (R)-2-amino-3-(methylthio)propan-1-ol (800 mg, 6.61 mmol) in methanol and water (2:1) was added oxone (4.4 g, 7.27 mmol) at RT. The reaction mixture was stirred for 16 h at RT. The reaction mixture was concentrated under reduced pressure, and was then co-distilled with methanol (2×20 mL) to afford (R)-2-amino-3-(methylsulfonyl)propan-1-ol (5.1 g crude) as a white solid, which was used without any further purification.

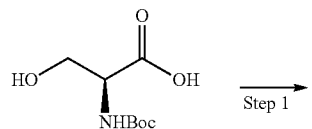

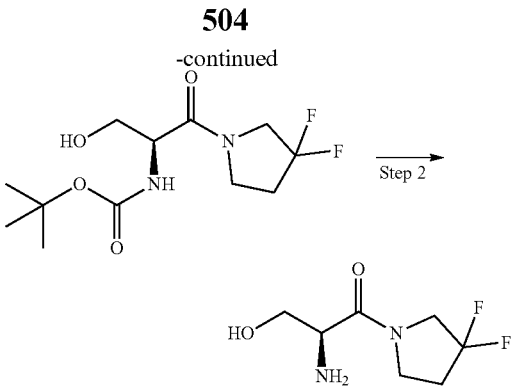

Step 1: EDC·HCl (1.3 g, 4.87 mmol), HOBt (0.98 g, 7.31 mmol), DIPEA (2.5 mL, 14.63 mmol) and 3,3-difluoropyrrolidine (0.837 g, 5.85 mmol) were added sequentially to a stirred solution of (tert-butoxycarbonyl)-L-serine (1.0 g, 4.87 mmol) at room temperature. The resulting reaction mixture was stirred at room temperature for 16 h. The reaction progress was monitored by TLC. The reaction mixture was diluted with ice cold water (100 mL) and the precipitated solid was filtered and dried under vacuum to afford t-butyl (S)-(1-(3,3-difluoropyrrolidin-1-yl)-3-hydroxy-1-oxopropan-2-yl)carbamate (650 mg, crude) as a yellow solid. TLC system: 30% Ethyl acetate in pet-ether; Rf: 0.5.

Step 2: 4M HCl in 1,4-dioxane (6.5 mL) was added to t-butyl (S)-(1-(3,3-difluoropyrrolidin-1-yl)-3-hydroxy-1-oxopropan-2-yl)carbamate (0.650 g, 2.210 mmol) at room temperature under an argon atmosphere. The resulting reaction mixture was stirred at room temperature for 30 min. The reaction progress was monitored by TLC. The reaction mixture was concentrated under reduced pressure to afford ((S)-2-amino-1-(3,3-difluoropyrrolidin-1-yl)-3-hydroxypropan-1-one (450 mg, crude) as an off-white solid. TLC system: 30% ethyl acetate in pet-ether; Rf: 0.3.

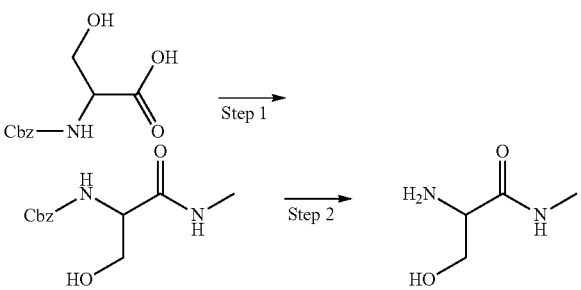

Step 1: To a stirred solution of 2-(benzyloxycarbonylamino)-3-hydroxypropanoic acid (2 g, 0.3 mmol) and methanamine hydrochloride (0.616 g, 9.2 mmol) in DCM (30 ml) was added DIPEA (0.077 g, 6 mmol) followed by HATU (0.228 g, 6 mmol) at 0° C. and the resulting mixture was stirred at RT for 18 h. Ice cold water was added to the reaction mixture and the mixture was extracted with DCM (2×50 mL). The combined organic layers were washed with water (50 mL) and brine (50 mL), dried over anhydrous Na₂SO₄, filtered and evaporated under reduced pressure to get the crude material, which was purified by neutral alumina column chromatography using 5% methanol in CHCl₃ as eluent. All appropriate fractions were combined and evaporated under reduced pressure to get benzyl 3-hydroxy- 1-(methylamino)-1-oxopropan-2-ylcarbamate (1 g) as pale yellow solid. TLC system: 20% Methanol in CHCl₃; Rf: 0.3

Step 2: To a stirred solution of benzyl 3-hydroxy-1-(methylamino)-1-oxopropan-2-ylcarbamate (1 g, 3.9 mmol) in methanol (50 mL) was added Pd/C (200 mg, 10 mol %) under a nitrogen atmosphere and the reaction mixture was stirred under H₂ pressure of 50 psi for 16 h at RT. The reaction mixture was then filtered through a pad of celite and the celite bed was washed with methanol (40 mL). The filtrate was evaporated under reduced pressure to afford crude 2-amino-3-hydroxy-N-ethylpropanamide (0.35 g) as a colorless semi-solid residue. The crude product thus obtained was used in the next step without further purification. TLC system: 20% Ethyl acetate in pet-ether; Rf: 0.1.

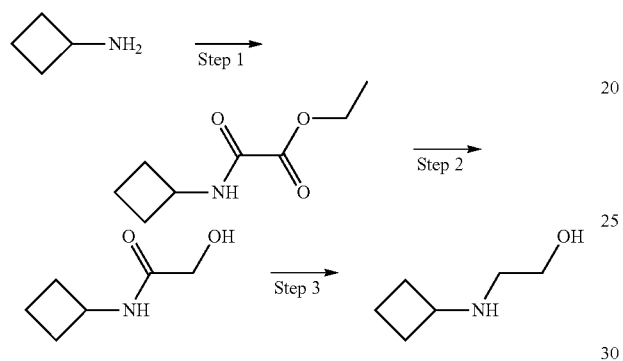

Step 1: At 0° C., ethyl 2-chloro-2-oxoacetate (3.6 mL, 30.985 mmol) was added drop-wise to a solution of cyclobutanamine (2.0 g, 28.169 mmol) and Et₃N (8.6 mL, 61.971 mmol) in diethyl ether (20 mL). The resulting reaction mixture was stirred at 0° C. to RT for 1 h. The reaction progress was monitored by TLC. The reaction mixture was filtered and the filtrate washed with diethyl ether (2×100 mL). The filtrate was concentrated under reduced pressure to afford ethyl 2-(cyclobutylamino)-2-oxoacetate (3.0 g, 62%) as a brown oil. This crude compound was used without further purification. TLC system: 10% MeOH in dichloromethane; Rf: 0.5.

Step 2: A solution of LAH (1 M in in THF, 35 mL, 35.08 mmol) was added to a suspension of ethyl 2-(cyclobutylamino)-2-oxoacetate (3.0 g, 17.54 mmol) in THF at 0° C. and the resulting reaction mixture was stirred at 0° C.-RT for 3 h. The reaction was monitored by TLC. The reaction mixture was quenched with aq. 1M NaOH solution (5 mL) at 0° C. under stirring. The solids were filtered off, and the filter cake was washed the with 10% MeOH in dichloromethane. The filtrate was concentrated under reduced pressure to afford N-cyclobutyl-2-hydroxyacetamide (1.8 g, 79%) as a pale yellow solid. This compound was used in the next step without any further purification. TLC system: 10% MeOH in dichloromethane; Rf: 0.3.

Step 3: LiAlH₄ (1M solution in THF) (16.7 mL, 16.74 mmol) was added to a suspension of N-cyclobutyl-2-hydroxyacetamide (1.8 g, 13.95 mmol) in THF at 0° C. and the resulting reaction mixture was heated to 70° C. for 16 h. The reaction was monitored by TLC. The reaction mixture was quenched with aq. 1M NaOH solution (5 mL) at 0° C. under stirring, the precipitated solids were filtered off, the filter cake was washed with 10% MeOH in dichloromethane. The combined filtrate was dried over anhyd. Na₂SO₄ and concentrated under reduced pressure to afford 2-(cyclobutylamino)ethan-1-ol (1.0 g, 62%) as a brown gummy solid. TLC system: 10% Methanol in dichloromethane; Rf: 0.2

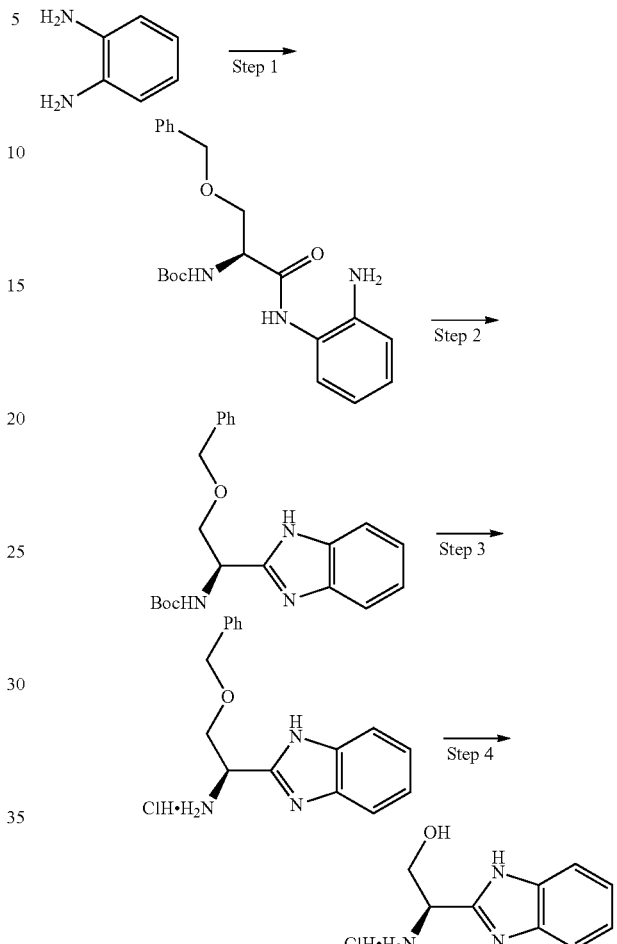

Step 1: To a pre-stirred mixture of benzene-1,2-diamine (1.0 g, 9.250 mmol), HATU (4.210 g, 11.10 mmol) and DIPEA (4.8 mL, 27.75 mmol) in DMF (10.0 mL) was added O-benzyl-N-(tert-butoxycarbonyl)-D-serine (3.0 g, 10.175 mmol) at 0° C. and the resulting reaction mixture was stirred at room temperature for 16 h. The reaction progress was monitored by TLC. The reaction mixture was diluted with water (75 mL) and extracted with ethyl acetate (2×80 mL). The combined extracts were washed with brine (50 mL), dried over anhydrous Na₂SO₄ and concentrated to give the crude material which was purified by column chromatography over silica-gel (100-200 mesh) eluting with 25% ethyl acetate in pet-ether as an eluent to afford tert-butyl (S)-(1-((2-aminophenyl)amino)-3-(benzyloxy)-1-oxopropan-2-yl)carbamate (1.1 g) as a yellow semi-solid. TLC system: 5% Methanol in dichloromethane; Rf: 0.1.

Step 2: A solution of tert-butyl (S)-(1-((2-aminophenyl)amino)-3-(benzyloxy)-1-oxopropan-2-yl)carbamate (500 mg, 1.298 mmol) and acetic acid (5.0 mL) was stirred at 80° C. for 1 h. The reaction progress was monitored by TLC. The reaction mixture was concentrated under reduced pressure to afford tert-butyl (R)-(1-(1H-benzo[d]imidazol-2-yl)-2-(benzyloxy)ethyl)carbamate (400 mg, crude) as a colorless semi solid. This crude compound was directly used in the next step. TLC system: 5% methanol in dichloromethane; Rf: 0.7.

Step 3: A solution of tert-butyl (R)-(1-(1H-benzo[d]imidazol-2-yl)-2-(benzyloxy)ethyl)carbamate (2.3 g, 6.259 mmol) and HCl (4 M in dioxane) (23.0 mL) was stirred at room temperature for 1 h. The reaction progress was monitored by TLC. The reaction mixture was concentrated under reduced pressure to afford (R)-1-(1H-benzo[d]imidazol-2-yl)-2-(benzyloxy)ethan-1-amine hydrochloride (1.8 g, crude) as a pale yellow semi-solid. This crude was directly used in the next step. TLC system: 5% Methanol in dichloromethane; Rf: 0.3.

Step 4: 10% Pd—C (230 mg) was added to a stirred solution of (R)-1-(1H-benzo[d]imidazol-2-yl)-2-(benzyloxy) ethan-1-amine hydrochloride (0.500 g, 1.872 mmol) in ethyl acetate (30 mL) and concentrated HCl (0.5 mL) at room temperature. The resulting reaction mixture was stirred at room temperature under hydrogen gas balloon pressure for 16 h. The reaction progress was monitored by TLC. The reaction mixture was filtered through a celite bed. The filtrate was concentrated under reduced pressure to afford (R)-2-amino-2-(1H-benzo[d]imidazol-2-yl)ethan-1-ol hydrochloride (400 mg, crude) as an off-white solid. TLC system: 30% ethyl acetate in pet-ether; Rf: 0.2.

(S)-2-amino-2-(1H-benzo[d]imidazol-2-yl)ethan-1-ol hydrochloride can be prepared using the same synthetic sequence starting from O-benzyl-N-(tert-butoxycarbonyl)-L-serine.

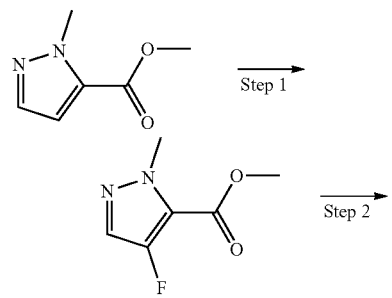

Step 1: To a pre-stirred solution of methyl 1-methyl-1H-pyrazole-5-carboxylate (5 g, 35.71 mmol) in acetonitrile (200 mL) was added selectfluor (28.72 g, 42.85 mmol) and acetic acid (5 mL) at 0° C. under an argon atmosphere. The reaction mixture was heated up to 120° C. for 24 h. The reaction progress was monitored by TLC. The excess solvent was removed under reduced pressure and the crude product was dissolved in ethyl acetate (500 mL). The ethyl acetate layer was washed with water (250 mL) and brine (150 mL), dried over anhydrous Na$_2$SO$_4$ and concentrated under reduced pressure to give the crude material, which was purified by silica gel (100-200 mesh) column chromatography using 0-20% ethyl acetate in pet-ether as an eluent to afford methyl 4-fluoro-1-methyl-1H-pyrazole-5-carboxylate (0.8 g, 14%) as an off-white solid. TLC system: 20% EtOAc in Pet ether; Rf: 0.4.

Step 2: To a stirred solution of methyl 4-fluoro-1-methyl-1H-pyrazole-5-carboxylate (0.8 g, 5.06 mmol 1 eq) in THF (30 mL) at 0° C., was added LAH (1M) (6 mL, 6.07 mmol, 1.2 eq) solution in THF drop wise at 0° C. under an argon atmosphere. The reaction mixture was stirred at room temperature for 2 h. The reaction progress was monitored by TLC. The reaction mixture was quenched with sat. Na$_2$SO$_4$ solution and extracted with 10% methanol in dichloromethane (2×50 mL). The combined organic layers were washed with water (20 mL) and brine (20 mL), dried over anhydrous Na$_2$SO$_4$ and concentrated under reduced pressure to give the crude material, which was purified by column chromatography over silica gel (100-200 mesh) using 0-20% ethyl acetate in pet-ether as an eluent to afford (4-fluoro-1-methyl-1H-pyrazol-5-yl)methanol (0.45 g, 69%) as a colorless liquid. TLC system: 20% EtOAc in Pet ether; Rf: 0.3.

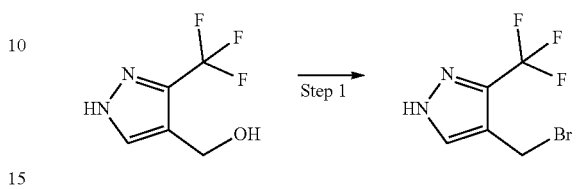

Step 1: To a stirred solution of (3-(trifluoromethyl)-1H-pyrazol-4-yl)methanol (600 mg, 3.61 mmol, 1.0 eq) and dichloromethane (50 mL) was added phosphorous tribromide (0.51 mL, 5.42 mmol, 1.5 eq) at 0° C. under an argon atmosphere. The reaction mixture was stirred for 2 h at 0° C. The reaction progress was monitored by TLC. The reaction mixture was diluted with ice water (100 mL) and extracted with dichloromethane (2×50 mL). The combined organic layers were washed with water (50 mL) and brine (50 mL), dried over anhydrous Na$_2$SO$_4$ and concentrated under reduced pressure to afford 4-(bromomethyl)-3-(trifluoromethyl)-1H-pyrazole (430 mg, 52%) as a thick residue. TLC system: 5% methanol in dichloromethane; Rf: 0.7.

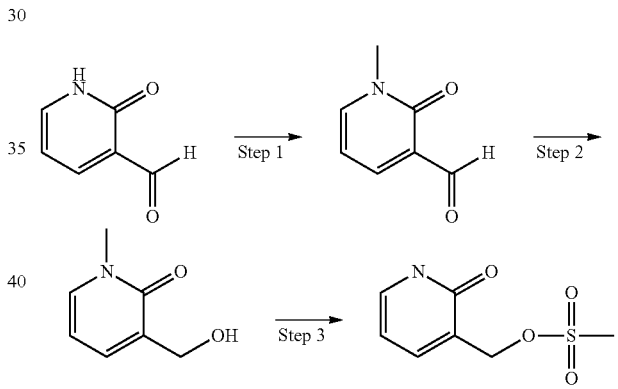

Step 1: To a stirred solution of 2-oxo-1,2-dihydropyridine-3-carbaldehyde (10 g, 81.3 mmol, 1.0 eq) in DMF (10 ml) was added Cs$_2$CO$_3$ (31.7 g, 97.56 mmol, 1.2 eq) followed by MeI (6.07 ml, 97.56 mmol, 1.2 eq) at 0° C. The reaction mixture was stirred for 3 h at RT and the reaction progress was monitored by TLC. After completion of the reaction, the mixture was diluted with water (30 ml) and extracted with EtOAc (3×50 ml). The combined organic layers were washed with water (20 ml) and brine (20 ml), dried over anhydrous Na$_2$SO$_4$, filtered and concentrated to afford 1-methyl-2-oxo-1,2-dihydropyridine-3-carbaldehyde (6.8 g, 61%, of-white solid). TLC system: 40% EtOAc/Pet ether; RF: 0.4.

Step 2: To a stirred solution of 1-methyl-2-oxo-1,2-dihydropyridine-3-carbaldehyde (6.8 g, mmol, 1.0 eq) in methanol (10 ml) was added NaBH$_4$ (208.6 mg, 6.347 mmol, 1.2 eq) at 0° C. The reaction mixture was stirred for 3 h at RT and the reaction progress was monitored by TLC. After completion of the reaction, the reaction mixture was diluted with water (30 ml) and extracted with EtOAc (3×50 ml). The combined organic layers were washed with water (20 ml) and brine (20 ml), dried over anhydrous Na$_2$SO$_4$, filtered and concentrated to get the crude material which was purified by Grace flash column chromatography to afford 3-(hydroxymethyl)-1-methylpyridin-2(1H)-one (3.5 g, 52%, off-white solid). TLC system: 40% EtOAc/Pet ether; RF: 0.4.

Step 3: To a stirred solution of 3-(hydroxymethyl)-1-methylpyridin-2(1H)-one (600 g, 4.37 mmol, 1.0 eq) in CH₂Cl₂ (15 ml) was added Et₃N (1.5 ml, 10.86 mmol, 2.5 eq) followed by methanesulfonyl chloride (0.5 ml, 6.52 mmol, 1.5 eq) at 0° C. The reaction mixture was stirred for 3 h at RT and the reaction progress was monitored by TLC. After completion of the reaction, the reaction mixture was diluted with water (30 ml) and extracted with EtOAc (3×50 ml). The combined organic layers were washed with water (20 ml) and brine (20 ml), dried over anhydrous Na₂SO₄, filtered and concentrated to get (1-methyl-2-oxo-1,2-dihydropyridin-3-yl)methyl methanesulfonate (365 mg crude, yellow color liquid). TLC system: 40% EtOAc/Pet ether; RF: 0.75. Note: (1-Methyl-2-oxo-1,2-dihydropyridin-3-yl) methyl methanesulfonate was unstable even in work up and distillation at RT under vacuum. Crude was directly taken to next step.

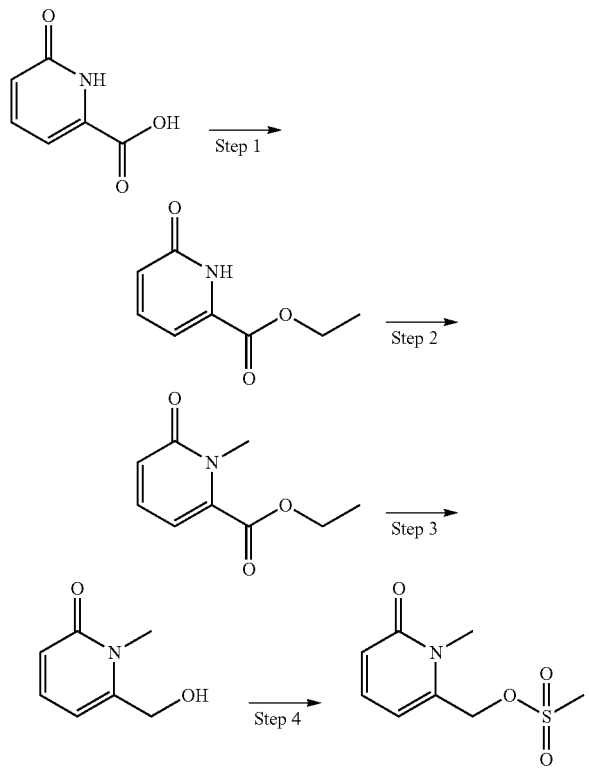

Step 1: Thionyl chloride (5 mL) was added dropwise to a solution of 6-oxo-1,6-dihydropyridine-2-carboxylic acid (12.0 g, 86.26 mmol) in ethanol (300 mL) at 0° C. under an argon atmosphere. The reaction mixture was warmed to room temperature and stirred for 16 h. The excess of thionyl chloride and solvent was evaporated in vacuo and the residue was cooled to 0° C., the remains were basified with saturated NaHCO₃ to pH ~9 and the resulting mixture was extracted with ethyl acetate (3×200 mL). The combined organic layer was washed with water (200 mL) and brine (200 mL), dried over anhydrous Na₂SO₄ and concentrated under reduced pressure to afford ethyl 6-oxo-1,6-dihydropyridine-2-carboxylate (8.0 g, 57%) as an off-white solid. TLC system: 50% Ethyl acetate in pet-ether; Rf: 0.5.

Step 2: Methyl iodide (8.1 g, 57.48 mmol) was added to a suspension of ethyl 6-oxo-1,6-dihydropyridine-2-carboxylate (8.0 g, 47.90 mmol) and Cs₂CO₃ (46.7 g, 143.71 mmol) in DMF (100 mL) at 0° C. under an argon atmosphere. The reaction mixture was warmed to room temperature and was stirred for 5 h. The reaction progress was monitored by TLC. The reaction mixture was diluted with ice cold water (200 mL) and extracted with ethyl acetate (3×100 mL). The combined organic layers were dried over anhydrous Na₂SO₄ and concentrated under reduced pressure. The crude product was purified by column chromatography over silica-gel (100-200 mesh) using a solvent gradient mixture of 0-30% ethyl acetate in pet-ether to obtain ethyl 1-methyl-6-oxo-1,6-dihydropyridine-2-carboxylate (2.0 g) & ethyl 6-methoxypicolinate (2.5 g, 52%) as pale yellow solid.

Step 3: NaBH₄ (1.25 g, 33.14 mmol) was added in small portions to a solution of ethyl 1-methyl-6-oxo-1,6-dihydropyridine-2-carboxylate (2.0 g, 11.04 mmol) in t-butanol (50 mL) at room temperature. The reaction mixture was heated to 60° C., and was then stirred for 1 h before being rapidly cooled to room temperature. Methanol (2.5 mL) was added dropwise to the reaction mixture was then heated to 60° C. for 3 h. The reaction progress was monitored by TLC. The reaction mixture was cooled to 0° C. and was diluted with water (100 mL). The mixture was extracted with 10% methanol in dichloromethane (2×100 mL). The combined organic layers were washed with brine (100 mL), dried over anhydrous Na₂SO₄ and concentrated under reduced pressure to afford 6-(hydroxymethyl)-1-methylpyridin-2(1H)-one (1.2 g 80%) as a pale yellow thick mass. TLC system: 100% Ethyl acetate; Rf: 0.2.

Step 4: Methanesulfonyl chloride (1.2 mL) was added dropwise to a solution mixture of 6-(hydroxymethyl)-1-methylpyridin-2(1H)-one (1.2 g, 8.63 mmol) and TEA (3.5 mL, 25.89 mmol) in dichloromethane (30 mL) at 0° C. under an argon atmosphere. The reaction mixture was warmed to room temperature and was stirred for 3 h. The reaction progress was monitored by TLC. The solvents were evaporated in vacuo and the residue was cooled to 0° C., basified with saturated NaHCO₃ to a pH ~8 and extracted with ethyl acetate (3×50 mL). The combined organic layers were washed with water (50 mL) and brine (50 mL), dried over anhydrous Na₂SO₄ and concentrated under reduced pressure to afford (1-methyl-6-oxo-1,6-dihydropyridin-2-yl)methyl methanesulfonate (2.4 g, crude) as a pale yellow thick mass. The resulting crude product was used for next step without further purification. TLC system: 30% Ethyl acetate in pet-ether; Rf: 0.5

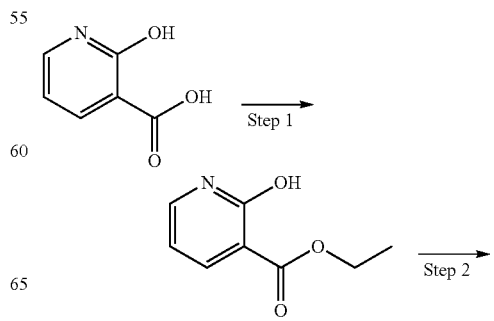

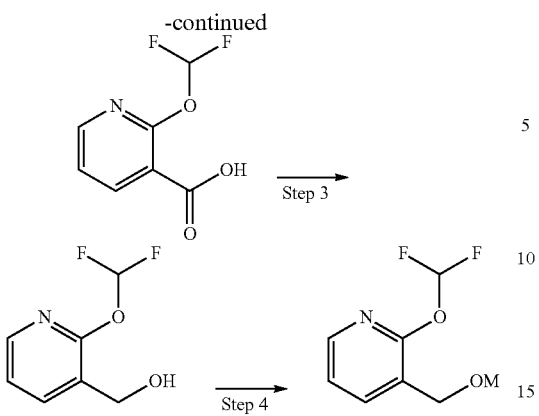

Step 1: To a stirred solution of 2-hydroxynicotinic acid (3.0 g, 21.58 mmol) in ethanol (50 mL) was added SOCl$_2$ (21 mL) at room temperature, and reaction mixture was heated to 90° C. for 8 h. The reaction progress was monitored by TLC. The mixture was cooled to RT, the volatiles were evaporated under reduced pressure and ice-cold water (400 ml) was added to the reaction mixture. The pH was adjusted to ~7-8 with NaHCO$_3$ powder and the mixture was then extracted with chloroform (3×500 mL). The combined extracts were washed with brine (50 mL), dried over anhydrous Na$_2$SO$_4$ and concentrated under reduced pressure to get ethyl 2-hydroxynicotinate (1.0 g, 27%, crude) as an off-white solid. TLC system: 100% Ethyl acetate; RF: 0.43. The material was used in the next step without further purification.

Step 2: To a stirred solution of ethyl 2-hydroxynicotinate (500 mg, 2.99 mmol) in acetonitrile (10 mL) was added 6M KOH (6 mL) followed by the addition of difluoromethyl trifluoromethanesulfonate (1.7 g, 8.98 mmol) at 0° C. under an argon atmosphere. The reaction mixture was stirred for 16 h at RT. The reaction progress was monitored by TLC. Solvents were removed under vacuum and ice cold water was added to the reaction mixture. The mixture was then extracted with ethyl acetate (2×100 mL). The combined extracts were washed with brine (50 mL), dried over anhydrous Na$_2$SO$_4$ and concentrated under reduced pressure to afford crude 2-(difluoromethoxy) nicotinic (500 mg) as a yellow solid, which was used in the next step without further purification. TLC system: 10% MeOH in CH$_2$Cl$_2$; RF: 0.38.

Step 3: To a stirred solution of 2-(difluoromethoxy) nicotinic acidoxylate (500 mg, 2.64 mmol) in THF (15 mL) was added NaBH$_4$ (201 mg, 5.29 mmol) followed by the addition of BF$_3$ etherate (0.7 mL, 5.29 mmol) at 0° C. The reaction mixture was heated to 80° C. for 16 h. The reaction progress was monitored by TLC. The reaction mixture was concentrated, diluted with H$_2$O (50 mL) and extracted with ethyl acetate (3×50 mL). The combined extracts were washed with brine (20 mL), dried over anhydrous Na$_2$SO$_4$, filtered and concentrated under vacuum to get the crude material, which was purified by flash chromatography to afford (2-(difluoromethoxy) pyridin-3-yl) methanol (100 mg, 19% over 2 steps) as a colorless liquid. TLC system: 80% Ethyl acetate in pet ether; RF: 0.56.

Step 4: To a stirred solution of (2-(difluoromethoxy) pyridin-3-yl) methanol (100 mg, 0.57 mmol) in dichloromethane (10 mL) was added Et$_3$N (0.1 ml, 0.85 mmol) followed by the addition of MsCl (98 mg, 0.85 mmol) at 0° C. The reaction mixture was stirred for 16 h at RT and the reaction progress was monitored by TLC. The reaction mixture was diluted with water (50 mL) and extracted with ethyl acetate (3×50 mL). The combined extracts were washed with brine (20 mL), dried over anhydrous Na$_2$SO$_4$ and concentrated under reduced pressure to afford crude (2-(difluoromethoxy) pyridin-3-yl) methyl methanesulfonate (150 mg) as a brown solid. TLC system: 50% EtOAc in pet-ether; RF: 0.62. Crude was used in the next step without further purification and analytical data.

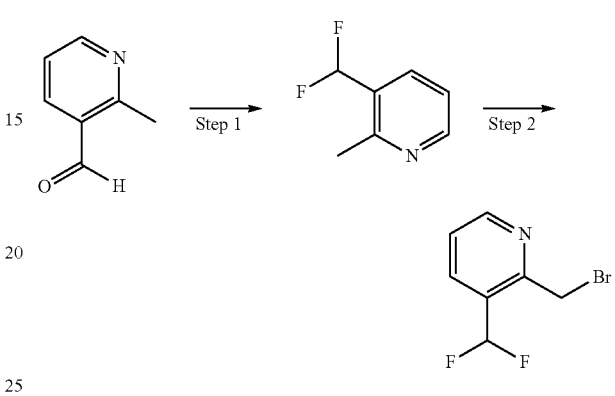

Step 1: To a stirred solution of 2-methylnicotinaldehyde (1.0 g, 8.26 mmol) in dichloromethane (50 mL) was added DAST (1.63 mL, 12.3 mmol) at 0° C. and reaction mixture was stirred for 2 h at RT. The reaction progress was monitored by TLC, reaction mass was diluted with dichloromethane (100 mL) and washed with water (2×50 mL) followed by brine (50 mL), dried over anhydrous Na$_2$SO$_4$ and concentrated under reduced pressure to get the crude material, which was purified by Grace flash chromatography using 20% ethyl acetate in pet ether as an eluent to afford 3-(difluoromethyl)-2-methylpyridine (500 mg, 42%) as a thick colorless liquid. TLC system: 30% Ethyl acetate in pet-ether; RF: 0.3.

Step 2: To a stirred solution of 3-(difluoromethyl)-2-methylpyridine (500 mg, 3.49 mmol) in carbon tetra chloride (30 mL) were added NBS (742 mg, 4.19 mmol) and AIBN (58 mg, 0.349 mmol) at 0° C. under an argon atmosphere. The reaction mixture was stirred for 16 h at 80° C. The reaction progress was monitored by TLC. The reaction mass was diluted with dichloromethane (100 mL) and was washed with water (2×50 mL) followed by brine (50 mL), dried over anhydrous Na$_2$SO$_4$ and concentrated under reduced pressure to get the crude material, which was purified by Grace flash chromatography using 15% ethyl acetate in pet ether as an eluent to afford 2-(bromomethyl)-3-(difluoromethyl)pyridine (150 mg, 20%). TLC system: 30% Ethyl acetate in pet-ether; RF: 0.6

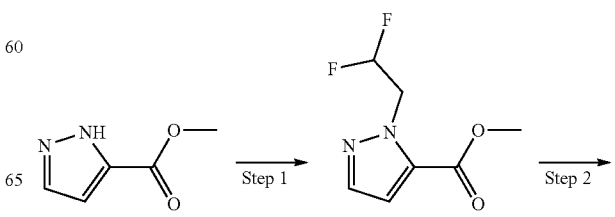

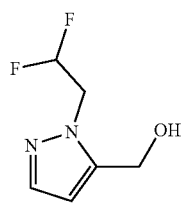

Step 1: To a stirred solution of methyl 1H-pyrazole-5-carboxylate (1.5 g, 11.90 mmol) in CH₃CN (50 ml) was added Cs₂CO₃ (11.6 g, 35.712 mmol) followed by the addition of 2,2-difluoroethyl trifluoromethanesulfonate (3.8 g, 17.857 mmol) at RT and the reaction mixture was then heated to 70° C. for 2 h. The reaction progress was monitored by TLC. The reaction mixture was diluted with water (100 mL) and was extracted with ethyl acetate (3×100 mL). The combined extracts were washed with brine (30 ml), dried over anhydrous Na₂SO₄, filtered and concentrated under reduced pressure to get the crude material, which was purified by flash chromatography using 10% ethyl acetate in pet ether as eluent to afford methyl 1-(2,2-difluoroethyl)-1H-pyrazole-5-carboxylate (1 g) as a colorless liquid. (TLC: 40% Ethyl acetate in pet ether: Rf=0.68)

Step 2: To a stirred solution of methyl 1-(2,2-difluoroethyl)-1H-pyrazole-5-carboxylate (1 g, 5.263 mmol) in MeOH (30 ml), was added NaBH₄ (600 mg, 15.789 mmol) at 0° C. and the reaction mixture was stirred at reflux for 16 h. The reaction progress was monitored by TLC. The reaction mixture was concentrated, diluted with water (120 mL) and extracted with ethyl acetate (3×100 mL). The combined extracts were washed with brine (20 ml), dried over anhydrous Na₂SO₄, filtered and concentrated under reduced pressure to afford (1-(2,2-difluoroethyl)-1H-pyrazol-5-yl) methanol (900 mg, crude) as a colorless liquid. The obtained crude material was used in the next step without further purification. (TLC: 100% Ethyl acetate: Rf=0.2).

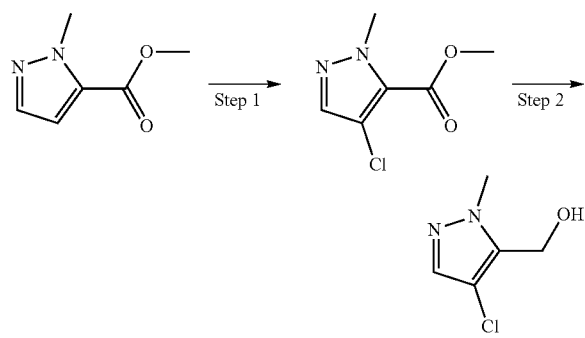

Step 1: To a stirred solution of methyl 1-methyl-1H-pyrazole-5-carboxylate (700 mg, 5.00 mmol) in Acetic acid (15 mL) was added NaOCl (2.2 g, 30.00 mmol) at 0° C. The RM was stirred for 2 h at RT and the reaction progress was monitored by TLC. The RM was concentrated under reduced pressure, diluted with water (50 mL) and extracted with ethyl acetate (3×50 mL). Combined extracts were washed with brine (20 mL), dried over anhydrous Na₂SO₄ and concentrated under reduced pressure. The residue was purified by column chromatography by using 5% ethyl acetate in pet ether as eluents.

Step 2: To a stirred solution of methyl 4-fluoro-1-methyl-1H-pyrazole-5-carboxylate (0.8 g, 5.06 mmol 1 eq) in THF (30 mL) at 0° C., was added LAH (1M) (6 mL, 6.07 mmol, 1.2 eq) solution in THF drop wise at 0° C. under an argon atmosphere. The RM was stirred at RT for 2 h. The reaction progress was monitored by TLC. The reaction mixture was quenched with sat. Na₂SO₄ solution and extracted with 10% methanol in dichloromethane (2×50 mL). The combined organic layers were washed with water (20 mL) and brine (20 mL), dried over anhydrous Na₂SO₄ and concentrated under reduced pressure to give the crude material, which was purified by column chromatography over silica gel (100-200 mesh) using 0-20% ethyl acetate in pet-ether as an eluent to afford (4-fluoro-1-methyl-1H-pyrazol-5-yl)methanol (0.45 g, 69%) as a colorless liquid. TLC system: 20% EtOAc in Pet ether; Rf: 0.3.

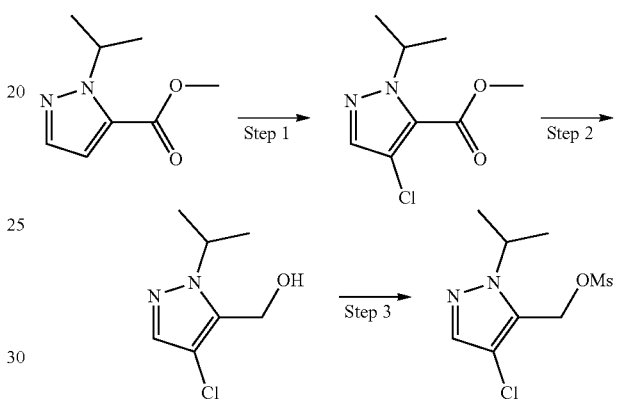

Step 1: To a stirred solution of ethyl 1-isopropyl-1H-pyrazole-5-carboxylate (1.5 g, 8.287 mmol) in Acetic acid (15 mL) was added NaOCl (3.3 mL, 49.723 mmol) at 0° C. The RM was stirred for 6 h at RT, and the reaction progress was monitored by TLC. The RM was diluted with water (50 mL) and extracted with ethyl acetate (3×50 mL). Combined extracts were washed with water (20 mL), brine (20 mL), dried over anhydrous Na₂SO₄ and concentrated under reduced pressure. The residue was purified by column chromatography over silica gel (100-200 mesh) using 15% ethyl acetate in pet-ether as an eluent to afford ethyl 4-chloro-1-isopropyl-1H-pyrazole-5-carboxylate (500 mg, 28%). TLC system: 30% ethyl acetate in pet ether; RF: 0.68

Step 2: To a stirred solution of methyl 4-fluoro-1-methyl-1H-pyrazole-5-carboxylate (0.8 g, 5.06 mmol 1 eq) in THF (30 mL) at 0° C., was added LAH (1M) (6 mL, 6.07 mmol, 1.2 eq) solution in THF drop wise at 0° C. under an argon atmosphere. The RM was stirred at RT for 2 h. The reaction progress was monitored by TLC. The RM was quenched with sat. Na₂SO₄ solution and extracted with 10% methanol in dichloromethane (2×50 mL). The combined organic layers were washed with water (20 mL) and brine (20 mL), dried over anhydrous Na₂SO₄ and concentrated under reduced pressure. The residue was purified by column chromatography over silica gel (100-200 mesh) using 0-20% ethyl acetate in pet-ether as an eluent to afford (4-fluoro-1-methyl-1H-pyrazol-5-yl)methanol (0.45 g, 69%) as a colorless liquid. TLC system: 20% EtOAc in Pet ether; Rf: 0.3.

Step 3: To a pre-stirred solution of (4-chloro-1-isopropyl-1H-pyrazol-5-yl) methanol (350 mg, 2.011 mmol) in dichloromethane (15 mL) was added triethylamine (0.5 mL, 4.02 mmol) and mesyl chloride (0.2 ml, 3.016 mmol) at 0° C. and the RM was stirred at RT for 16 h. The reaction progress was monitored by TLC. The RM was diluted with water (50 mL)

and extracted with dichloromethane (2×30 mL). Combined organic layers were dried over anhydrous Na₂SO₄ and concentrated under reduced pressure to afford (4-chloro-1-isopropyl-1H-pyrazol-5-yl) methyl methanesulfonate (450 mg, crude) as a color less liquid. Crude was used in the next without further purification. TLC system: 20% ethyl acetate in pet ether; RF: 0.75.

organic layers were dried over anhydrous Na₂SO₄ and evaporated under reduced pressure to afford 5-(bromomethyl)-1-(2,2,2-trifluoroethyl)-1H-pyrazole (2355-3) (500 mg, crude) as an off-white solid. Proceeded to next step without further purification and based on TLC. TLC system: 30% ethyl acetate in pet ether; RF: 0.3.

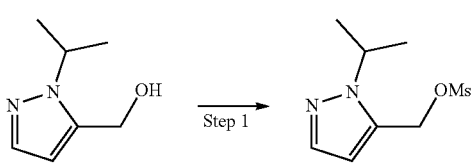

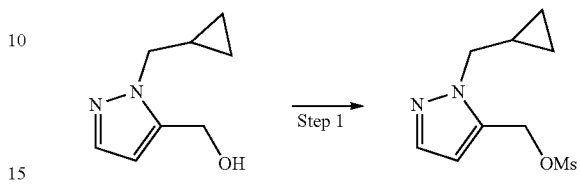

Step 1: To a pre-stirred solution of (1-isopropyl-1H-pyrazol-5-yl) methanol (500 mg, 3.571 mmol) in dichloromethane (15 mL) was added triethylamine (1 mL, 7.142 mmol) and mesyl chloride (0.4 ml, 5.357 mmol) at 0° C. The RM was stirred at RT for 16 h. The reaction progress was monitored by TLC. The RM was diluted with water (50 mL) and extracted with dichloromethane (2×30 mL). Combined organic layers were dried over anhydrous Na₂SO₄ and concentrated under reduced pressure to afford ((1-isopropyl-1H-pyrazol-5-yl) methyl methanesulfonate (550 mg, crude) as a color less liquid. Crude was used in next without further purification. TLC system: 50% ethyl acetate in pet ether; RF: 0.65.

Step 1: To a stirred solution of (1-(cyclopropylmethyl)-1H-pyrazol-5-yl)methanol (1.0 6.570 mmol) in dichloromethane (20 mL) was added Et₃N (2.7 mL, 19.71 mmol) and followed by addition of mesyl chloride (1.12 g, 9.855 mmol) at 0° C. The RM was stirred at RT for 2 h and the reaction progress was monitored by TLC. The RM was diluted with water (30 mL) and extracted with dichloromethane (2×30 mL). Combined organic layers were dried over anhydrous Na₂SO₄ and evaporated under reduced pressure to afford (1-(cyclopropylmethyl)-1H-pyrazol-5-yl)methyl methanesulfonate (1.4 g, crude) as a pale brown liquid. Crude was used in the next step without purification and based on TLC. TLC system: 40% Ethyl acetate in pet ether; RF: 0.5.

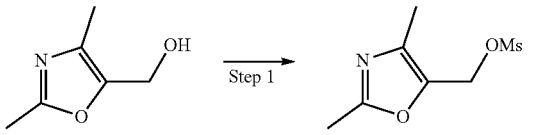

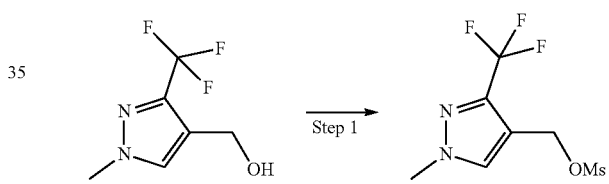

Step 1: To a pre-stirred solution of (2,4-dimethyloxazol-5-yl)methanol (500 mg, 3.937 mmol) in DCM (50 mL) was added triethylamine (1.6 mL, 11.811 mmol) and Mesyl chloride (676.1 mg, 5.905 mmol) at 0° C. and the RM was stirred at RT for 3 h. The RM was diluted with water (25 mL) and extracted with dichloromethane (2×25 mL). The combined organic layer was dried over anhydrous Na₂SO₄ and evaporated under vacuum at 35° C. to afford (2,4-dimethylthiazol-5-yl) methyl methanesulfonate (560 mg, crude) as a brown liquid. TLC system: 30% Ethyl acetate in Pet ether; RF: 0.6. Proceeded to next step without purification and based on TLC.

Step 1: To a stirred solution of (1-methyl-3-(trifluoromethyl)-1H-pyrazol-4-yl)methanol (400 mg, 2.222 mmol) in dichloromethane (20 mL) was added triethylamine (673 mg, 6.666 mmol) and followed by addition of methane sulfonyl chloride (379 mg, 3.333 mmol) at 0° C. The reaction mixture was stirred for 16 h at RT and the reaction progress was monitored by TLC. The reaction mixture was diluted with water (40 mL) and extracted with dichloromethane (3×50 mL). Combined extracts were washed with brine (20 mL), dried over anhydrous Na₂SO₄ and concentrated under reduced pressure to afford (1-methyl-3-(trifluoromethyl)-1H-pyrazol-4-yl)methyl methanesulfonate (3) (360 mg) as a pink solid. Crude was used in the next step without purification. TLC system: 20% Ethyl acetate in pet ether; RF: 0.54

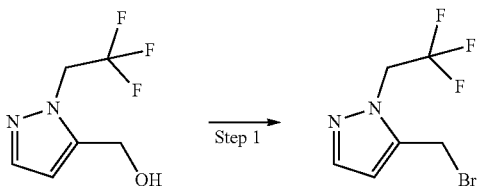 [SMILES: OCc1ccnn1CC(F)(F)F ; FC(F)(F)Cn1nccc1CBr]

Step 1: To a stirred solution of (1-(2,2,2-trifluoroethyl)-1H-pyrazol-5-yl)methanol (200 mg, 1.11 mmol) in DCM (10 ml), was added CBr4 (551 mg, 1.66 mmol) and followed by addition of TPP (582 ml, 262 mmol) at 0° C. The RM was stirred at RT for 3 h. The reaction progress was monitored by TLC. The RM was diluted with water (30 mL) and extracted with dichloromethane (2×40 mL). Combined

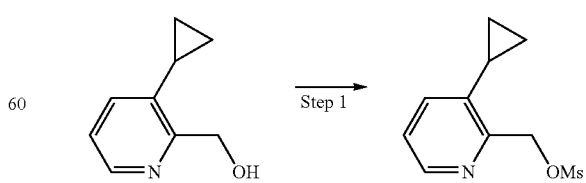

Step 1: To a stirred solution of (3-cyclopropylpyridin-2-yl) methanol (500 mg, 3.355 mmol) in DCM (25 mL) was added triethylamine (1 mL, 6.711 mmol) and mesyl chloride (0.4 ml, 5.032 mmol) at 0° C. and the resulting reaction mixture was stirred at room temperature for 16 h. The reaction progress was monitored by TLC. The reaction mixture was diluted with water (50 mL) and extracted with dichloromethane (2×50 mL). Combined organic layer were dried over anhydrous $Na_2SO_4$ and concentrated under reduced pressure to afford (3-cyclopropylpyridin-2-yl) methyl methanesulfonate (650 mg, crude) as a brown liquid. Crude was used in the next without further purification. TLC system: 50% Ethyl acetate in pet ether; RF: 0.68.

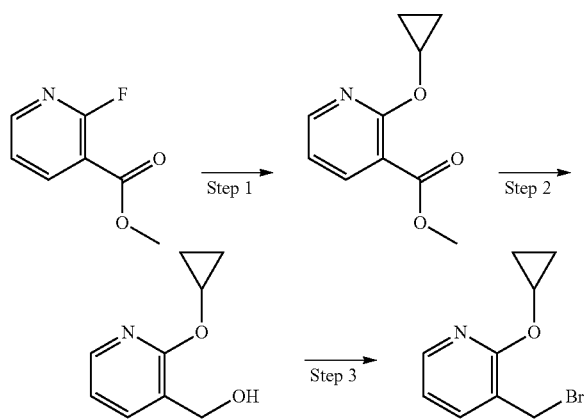

Step 1: To a stirred solution of methyl 2-fluoronicotinate (2 g, 12.90 mmol) in DMF (50 mL) was added $Cs_2CO_3$ (6.2 g, 19.354 mmol) and followed by addition of cyclopropanol (1.1 g, 19.354 mmol) at RT. The reaction mixture was stirred for 16 h at 80° C., and the reaction progress was monitored by TLC. The reaction mixture was diluted with water (50 mL) and extracted with ethyl acetate (3×40 mL). Combined organic layers were washed with water (40 mL), brine (40 mL), dried over anhydrous $Na_2SO_4$ and concentrated under reduced pressure to give crude. Crude was purified by column chromatography using silica gel (100-200 mesh size) and 20% ethyl acetate in pet ether as an eluent to afford methyl 2-cyclopropoxynicotinate (1.0 g, 40%) as a brown liquid. TLC system: 40% Ethyl acetate in Pet ether; RF: 0.62.

Step 2: To a stirred solution of methyl 2-cyclopropoxynicotinate (1.0 g, 5.181 mmol) in THF (15 mL) was added 1M LAH (5 mL, 5.181 mmol) at 0° C. The reaction mixture was stirred for 6 h at RT, and the reaction progress was monitored by TLC. The reaction mixture was quenched with Aq $Na_2SO_4$ and stirred for 10 min, solid was filtered and the filtrate was dried under vacuum to afford (2-cyclopropoxypyridin-3-yl) methanol (600 mg, crude) as a brown liquid. TLC system: 50% Ethyl acetate; RF: 0.20.

Step 3: To a stirred solution of (2-cyclopropoxypyridin-3-yl) methanol (500 mg, 3.030 mmol) in $CCl_4$ (20 mL) was added $PPh_3$ (1.58 g, 6.060 mmol) and followed by addition of $CBr_4$ (2.0 g, 6.060 mmol) at 0° C. The reaction mixture was stirred for 16 h at RT, and the reaction progress was monitored by TLC. The reaction mixture was diluted with water (50 mL), and extracted with ethyl acetate (3×40 mL). Combined organic layers were washed with water (20 mL), brine (20 mL), dried over anhydrous $Na_2SO_4$ and concentrated under reduced pressure to afford crude. Crude was purified by column chromatography using silica gel (100-200 mesh size) and 15% ethyl acetate in pet ether as an eluent to afford 3-(bromomethyl)-2-cyclopropoxypyridine (800 mg) as a brown liquid. TLC system: 40% Ethyl acetate in Pet ether; RF: 0.71.

Analytical Data

| Cpd | [M + H]+ (m/z): | [M − H]− (m/z): | LC/MS Method | RT (min.) | 1H NMR (δ ppm) |
|---|---|---|---|---|---|
| 001 | — | 271 | L1 | 7.6 | (300 MHz, DMSO-d6): 12.94 (1H, s); 7.78 (1H, s); 7.68 (1H, s), 7.45-7.53 (2H, m), 6.96 (1H, dd), 6.60 (1H, br s), 4.99 (2H, s), 2.71 (3H, s) |
| 002 | 274 | 272 | L1 | 6.2 | — |
| 003 | 276 | 274 | L5 | 5.1 | — |
| 004 | 284 | 282 | L5 | 6.1 | (300 MHz, DMSO-d6): 8.58 (d, 2H); 7.43-7.56 (4H, m); 7.02 (1H, dd); 5.22 (2H, s); 2.71 (3H, s) |
| 005 | 284 | 282 | L5 | 7.8 | (300 MHz, DMSO-d6): 8.51-8.65 (1H, m); 7.96 (1H, s); 7.83 (1H, td); 7.72 (1H, d); 7.53 (1H, d); 7.19-7.39 (2H, m); 6.77-6.97 (1H, m); 5.16 (2H, s); 2.66 (3H, s) |
| 006 | 284 | 282 | L1 | 3.5 | (300 MHz, DMSO-d6): 8.70 (1H, s); 8.55 (1H, d); 7.91 (1H, d); 7.33-7.61 (3H, m); 6.99-7.16 (1H, m); 5.19 (2H, s); 2.71 (3H, s) |
| 007 | 285 | 283 | L5 | 7.6 | (300 MHz, DMSO-d6): 12.96 (1H, br. s.); 9.22 (1H, dd); 7.82-7.92 (1H, m); 7.67-7.80 (1H, m); 7.45-7.54 (2H, m); 7.05 (1H, dd); 5.27-5.63 (2H, m); 2.71 (3H, s) |
| 008 | 287 | 285 | L1 | 6.6 | (300 MHz, DMSO-d6): 7.48-7.73 (2H, m); 7.37 (1H, d); 6.92-7.08 (1H, m); 6.37 (1H, d); 5.20 (2H, s); 3.85-3.98 (3H, m); 2.71 (3H, s) |
| 009 | 287 | 285 | L1 | 6.5 | — |
| 010 | 287 | 285 | L1 | 6.0 | — |
| 011 | — | 287 | L1 | 9.2 | (300 MHz, DMSO-d6): 12.04 (1H, br s); 7.53-7.63 (2H, m); 7.42-7.51 (2H, m); 7.21 (1H, dd); 6.97 (1H, dd); 5.11 (2H, s); 2.71 (3H, s) |
| 012 | — | 287 | L1 | 8.9 | — |
| 013 | 290 | 288 | L1 | 7.0 | (300 MHz, DMSO-d6): 12.96 (1H, br s); 7.85 (1H, d); 7.78 (1H, d); 7.39-7.60 (2H, m); 7.04 (1H, dd); 5.48 (2H, s); 2.71 (3H, s) |
| 014 | 290 | 288 | L1 | 6.7 | — |
| 015 | 0 | 289 | L1 | 7.3 | — |
| 016 | 302 | 300 | L1 | 8.4 | — |
| 017 | 340 | 338 | L2 | 4.8 | — |
| 018 | — | 339 | L1 | 8.8 | — |

-continued

| Cpd | [M + H]+ (m/z): | [M − H]− (m/z): | LC/MS Method | RT (min.) | 1H NMR (δ ppm) |
|---|---|---|---|---|---|
| 019 | — | 374 | L1 | 9.1 | — |
| 020 | 342 | — | L6 | 6.80 | — |
| 021 | 352 | 350 | L3 | 4.30 | (DMSO d6, 300 MHz): 8.87 (2 H, d); 8.12 (2 H, d); 7.51 (1 H, d); 7.34 (1 H, br s); 7.08-7.03 (1 H, m); 5.51 (2 H, s); 4.60-4.50 (1 H, m); 3.01-3.55 (4 H, m); 2.59 (3 H, s); 2.30-2.19 (1 H, m); 1.92-2.10 (1 H, m) |
| 022 | 352 | 350 | L3 | 4.90 | (DMSO d6-D2O, 300 MHz): 8.93 (1H, s); 8.79 (1H, d); 8.58 (1H, d); 7.01 (1H, dd); 7.53 (1H, d); 7.34 (1H, d); 7.08 (1H, dd); 5.36 (1H, s); 4.51-4.69 (1H, m); 3.22-3.62 (2H, m); 2.61 (1H, s); 2.20-2.43 (1H, m); 1.91-2.16 (1H, m) |
| 023 | 355 | — | L3 | 4.40 | — |
| 024 | 358 | 356 | L6 | 7.20 | — |
| 025 | 358 | — | L3 | 4.70 | (DMSO d6-D2O, 300 MHz): 7.86 (1 H, d); 7.76 (1 H, d); 7.52 (1 H, d); 7.32 (1 H, d); 6.98-7.12 (1 H, m); 5.49 (2 H, s); 4.6-4.5 (1 H, m); 3.6-3.2 (4 H, m); 2.61 (3 H, s); 2.40-2.2 (1 H, m); 2.18-1.97 (1 H, m) |
| 026 | 366 | 364 | U5 | 1.8 | (300 MHz, DMSO-d6): 8.43-8.73 (1 H, m); 8.01-8.25 (1 H, m); 7.70-7.96 (2 H, m); 7.20-7.65 (4 H, m); 7.05-6.95 (1 H, m); 5.08-5.30 (2 H, s) 4.35-4.76 (1 H, m) 3.51-3.54 (1 H, m) 2.94-3.27 (4 H, m) 2.61 (3 H, s) 1.92-2.17 (1 H, m) |
| 027 | 366 | — | U5 | 1.6 | — |
| 028 | 366 | 364 | U5 | 2.24 | (DMSO d6, 300 MHz): 8.52 (br. s., 1H), 8.42 (br. s., 1H), 8.27 (d, 1H), 7.73 (br. s., 1H), 7.49 (d, 1H), 7.31 (br. s., 1H), 7.00 (d, , 1H), 5.18 (br. s., 2H), 4.48 (br. s., 1H), 3.06-3.30 (m, 2H), 2.87-3.03 (m, 2H), 2.61 (s., 3H), 2.34 (s, 3H), 2.00-2.21 (m, 1H), 1.74-1.96 (m, 1H). |
| 029 | 366 | — | U5 | 2.20 | (CDCl3, 300 MHz): 7.61 (1 H, t); 7.29-7.42 (2 H, m); 7.22-7.43 (1 H, m); 7.27 (1 H, s); 7.16 (1 H, m); 7.03-7.13 (1 H, m); 6.95 (1 H, dd); 6.18-6.30 (1 H, m); 5.22 (2 H, s); 4.40-4.82 (1 H, m); 3.06-3.39 (2 H, m); 2.90-3.10 (2 H, m); 2.68 (3 H, s); 2.58 (3 H, s); 2.08-2.38 (1 H, m); 1.59-1.98 (1 H, m) |
| 030 | 397 | — | U4 | 2.4 | — |
| 031 | 366 | 364 | U4 | 2.5 | — |
| 032 | 367 | 365 | U5 | 1.3 | — |
| 033 | 367 | 365 | U5 | 2.4 | — |
| 034 | 367 | — | U5 | 2.3 | — |
| 035 | 371 | — | U3 | 0.6 | — |
| 036 | 372 | 370 | U2 | 2.01 | (300 MHz, DMSO-d6): 8.15 (1H, d); 7.89 (1H, s); 7.85 (1H, d); 7.79 (1H, d); 7.50 (1H, d); 7.41 (1H, d); 7.03 (1H, dd); 5.47 (2H, s); 4.59 (1H, m); 3.25 (3H, dd); 2.62 (3H, s); 1.80-2.19 (m, 1H) |
| 037 | 380 | — | U5 | 2.05 | — |
| 038 | 380 | — | U5 | 2.2 | (300 MHz, CDCl3): 8.52 (1 H, s); 8.41 (1 H, s); 7.64 (1 H, s); 7.35-7.39 (1 H, m); 7.34 (1 H, s); 6.82-7.01 (1 H, m); 6.38-6.56 (1 H, m); 5.72-6.00 (1 H, m); 5.11 (2 H, s); 4.54 (1 H, d); 3.48 (2 H, dd); 2.83-3.08 (1 H, m); 2.58-2.77 (3 H, m); 2.37 (3 H, s); 1.86-2.23 (1 H, m) |
| 039 | 380 | 378 | L3 | 4.50 | — |
| 040 | 383 | 381 | U5 | 2.0 | (300 MHz, DMSO-d6): 8.42-8.53 (m, 2H), 8.23 (d, 1H), 7.46 (d, 1H), 7.23 (d, 1H), 7.12 (d, 1H), 6.96 (dd, 1H), 5.09 (s, 2H), 4.41-4.57 (m, 1H), 3.91 (s, 3H), 3.80-3.89 (m, 2H), 3.69-3.78 (m, 1H), 3.61 (dd, 1H), 2.57 (s, 3H), 2.08-2.23 (m, 1H), 1.85-2.02 (m, 1H). |
| 041 | 385 | — | L3 | 6.5 | — |
| 042 | 386 | — | U5 | 1.8 | — |
| 043 | 386 | 384 | U5 | 2.0 | (400 MHz, DMSO-d6): 8.14 (1 H, d); 7.88 (1 H, s); 7.46-7.54 (1 H, m); 7.41 (1 H, d); 7.30 (1 H, s); 6.86-7.09 (1 H, m); 5.41 (2 H, s); 4.53-4.67 (1 H, m); 3.14-3.27 (2 H, m); 2.62 (3 H, s); 2.30-2.45 (4 H, m) 1.97-2.17 (1 H, m) |
| 044 | 394 | 392 | U5 | 2.1 | — |
| 045 | 394 | — | L3 | 4.8 | — |
| 046 | 396 | 394 | U5 | 2.4 | (300 MHz, DMSO-d6): 8.12-8.22 (m, 2H), 7.89 (s, 1H), 7.84 (d, 1H), 7.47 (d, , 1H), 7.37 (d, 1H), 7.04 (dd, 1H), 6.97 (dd, , 1H), 5.08 (s, 2H), 4.51-4.65 (m, 1H), 3.93 (s, 3H), 3.20-3.31 (m, 2H), 2.62 (s, 3H), 2.30-2.44 (m, 1H), 1.93-2.11 (m, 1H). |
| 047 | 397 | 395 | U4 | 3.15 | (DMSO d6, 400 MHz): 8.58 (1H, m); 7.84 (1H, td) 7.54 (1H, d); 7.48-7.42 (2H, m); 7.34 (1H, ddd); 7.26 (1H, d); 6.99 (1H, dd); 5.21 (2H, s); 4.92 (1H, t); 3.72-3.58 (6H, m); 2.60 (3H, s); 2.20 (1H, m); 2.16 (1H, m); 1.63 (2H, ddd). |
| 048 | 402 | — | U4 | 2.38 | (DMSO d6, 300 MHz): 8.58 (1H, d); 8.22 (1H, d); 7.82 (1H, td); 7.54 (1H, d); 7.48 (1H, d); 7.00 (1H, dd); 5.19 (2H, s); 4.57-4.38 (1H, m); 3.11-3.07 (1H, m); 2.95-2.76 (2H, m); 2.66-2.57 (4H, m); 1.79-1.65 (2H, m). |

| Cpd | [M + H]+ (m/z): | [M − H]− (m/z): | LC/MS Method | RT (min.) | 1H NMR (δ ppm) |
|---|---|---|---|---|---|
| 049 | 403 | 401 | U5 | 1.95 | — |
| 050 | 408 | — | U5 | 1.10 | (CDCl3, 300 MHz): 7.81 (1 H, d); 7.33-7.43 (2 H, m); 7.27-730 (1 H, m); 6.89-7.08 (1 H, m); 6.05 (1 H, d); 5.43 (2 H, s); 3.30-3.40 (1 H, m); 3.17 (1 H, m); 2.73-3.07 (2 H, m); 2.71 (3 H, s); 2.20-2.25 (1 H, m) |
| 051 | 410 | 408 | U5 | 2.9 | (300MHz, CDCl3): 8.14 (1H, dd); 7.77 (1H, d); 7.34 (1H, d); 7.18 (1H, d); 6.97-6.90 (2H, m); 5.67 (1H, d); 5.10 (2H, m); 4.10-3.96 (4H, m); 2.83 (2H, d); 2.69 (3H; s); 2.32 (3H, s); 2.20 (2H, t); 2.09 (2H, m). |
| 052 | 411 | 409 | U4 | 3.18 | — |
| 053 | 416 | 414 | U4 | 3.41 | — |
| 054 | 417 | 415 | U5 | 2.24 | (CDCl3, 300 MHz): 8.72 (1 H, s); 7.38 (1 H, d); 7.12-7.31 (2 H, m); 6.95 (1 H, dd); 5.79 (1 H, s); 5.23 (2 H, s); 4.56 (1 H, br. s.); 3.68-3.98 (6 H, m); 2.71 (3 H, s); 2.49 (3 H, s); 1.85-2.12 (4 H, m) |
| 055 | 366 | 364 | U5 | 2.24 | — |
| 056 | 422 | 420 | U4 | 2.76 | (CDCl3, 300 MHz): 8.72 (1 H, s); 7.37 (1 H, d); 6.83-7.00 (1 H, m); 6.02 (1 H, d); 5.23 (2 H, s); 3.28-3.46 (1 H, m); 3.13-3.20 (1 H, m); 2.75-3.04 (2 H, m); 2.71 (3 H, s); 2.50 (3 H, s); 2.15-2.25 (1 H, m); 1.61-1.79 (1 H, m) 1.25 (2 H, s) |
| 057 | 427 | 425 | U5 | 3.3 | — |
| 058 | 427 | 425 | U5 | 2.56 | — |
| 059 | 430 | 428 | L3 | 6.00 | — |
| 060 | 430 | 428 | L6 | 7.70 | — |
| 061 | 430 | 428 | L6 | 7.70 | — |
| 062 | 432 | 430 | U5 | 2.98 | (CDCl3 300 MHz): 8.00-8.29 (1 H, m); 7.75 (1 H, d); 7.36 (1 H, d); 7.20-7.26 (1 H, m); 6.82-7.03 (2 H, m); 6.01 (1 H, d); 5.11 (2 H, s); 4.45-4.74 (1 H, m); 4.01 (3 H, s); 3.30-3.40 (1 H, m); 3.10-3.20 (1 H, m); 2.75-3.02 (2 H, m) 2.71 (3 H, s) 2.15-2.25 (1 H, m); 1.15-1.37 (1 H, m) |
| 063 | 432 | — | U5 | 3.17 | (CDCl3, 300 MHz): 7.58 (1 H, t); 7.35 (1 H, d); 7.27.21 (1 H, d); 7.08 (1 H, d); 6.98 (1 H, dd) 6.66 (1 H, d); 6.00 (1 H, d); 5.14 (2 H, s); 4.44-4.73 (1 H, m); 3.94 (3 H, s); 3.26-3.44 (1 H, m); 3.10-3.20 (1 H, m); 2.74-3.02 (2 H, m); 2.70 (3 H, s); 2.17 (1 H, d); 1.50-1.69 (1 H, m); 1.25 (1 H, s) |
| 064 | 434 | 432 | U5 | 2.5 | (300 MHz, DMSO-d6): 8.74 (d, 1H), 8.28 (d, 1H), 8.19 (d, 1H), 7.90 (s, 1H), 7.79 (dd, , 1H), 7.50 (d, 1H), 7.38 (d, 1H), 6.99 (dd, 1H), 5.33 (s, 2H), 4.59 (q, 1H), 3.19-3.31 (m, 2H), 2.62 (s, 3H); 2.31-2.42 (m, 1H), 1.93-2.11 (m, 1H). |
| 065 | 434 | 432 | U5 | 2.9 | — |
| 066 | 434 | 432 | U5 | 2.8 | — |
| 067 | 436 | 434 | U5 | 2.87 | (DMSO d6, 300 MHz): 8.42 (1 H, d); 8.26 (1 H, d); 8.06 (1 H, d); 7.41-7.60 (2 H, m); 7.24 (1 H, d); 7.02 (1 H, dd); 5.19 (2 H, s); 4.34-4.69 (1 H, m); 3.04-3.20 (1 H, m); 2.69-3.01 (3 H, m); 2.55-2.68 (5 H, m); 1.59-1.91 (2 H, m) |
| 068 | 436 | — | U5 | 2.69 | (CDCl3, 300 MHz): 8.77 (1 H, s); 8.50 (1 H); 7.32-7.48 (2 H, m); 7.22-7.32 (1 H, m); 6.91-7.08 (1 H, m); 6.08 (1 H, d); 5.05-5.34 (2 H, m); 4.43-4.79 (1 H, m); 3.25-3.40 (1 H, m); 3.05-3.23 (1 H, m); 2.76-3.04 (2 H, m); 2.55-2.75 (3 H, m); 2.20 (1 H, d); 1.94 (1 H, br. s.); 1.38-1.76 (1 H, m); 0.62-0.96 (1 H, m) |
| 069 | 437 | 435 | L3 | 7.20 | — |
| 070 | 441 | — | U5 | 2.33 | — |
| 071 | 445 | — | U5 | 3.37 | (DMSO d6, 300 MHz): 8.19 (1 H, d); 7.38-7.56 (2 H, m); 7.15-7.26 (1 H, m); 6.88-7.05 (1 H, m); 6.68 (1 H, d); 6.46-6.60 (1 H, m); 4.88-5.09 (2 H, m); 4.36-4.62 (1 H, m); 3.05-3.20 (1 H, m); 3.02 (6 H, s); 2.75-2.96 (2 H, m); 2.54-2.70 (4 H, m); 1.61-1.86 (2 H, m) |
| 072 | 465 | 463 | U4 | 3.76 | — |
| 073 | 361 | 359 | U5 | 3.5 | — |
| 074 | 470 | 468 | U5 | 3.10 | (CDCl3, 300 MHz): 8.66 (1 H, d); 8.19 (1 H, d); 7.50-7.72 (1 H, m); 7.38 (1 H, d); 7.21 (1 H, d); 6.89-7.02 (1 H, m); 6.02 (1 H, d); 5.35 (2 H, s); 3.20-3.50 (2H, m); 2.74-3.11 (2 H, m); 2.70 (3 H, s) 2.05-2.28 (1 H, m); 1.25 (3 H, s); 0.87 (1 H, d) |
| 075 | 470 | 468 | U5 | 3.18 | — |
| 076 | 470 | 468 | U4 | 3.78 | — |
| 077 | 520 | 518 | U5 | 1.5 | — |

| cpd | [M + H]+ (m/z) | 1H NMR (δ ppm) |
|---|---|---|
| 103 - En 1 | 422.1 | (DMSO-d6) δ = 1.85-1.96 (m, 1H), 2.04-2.13 (m, 1H), 2.41-2.45 (m, 4H), 2.57 (s, 3H), 2.62-2.69 (m, 2H), 2.89-2.99 (m, 2H), 4.30-4.41 (m, 1H), 5.30 (s, 2H), 6.97 (dd, 1H), 7.21 (d, 1H), 7.47 (d, 1H), 8.08 ( d, 1H), 8.98 (s, 1H). |
| 104 | 375.1 | (DMSO-d6) δ = 1.34 (s, 6H), 2.42 (s, 3H), 2.57 (s, 3H), 3.48 (d, , 2H), 5.04 (t, 1H), 5.31 (s, 2H), 6.95 (dd, 1H), 7.2 (s, 1H), 7.25 (s, 1H), 7.45 (d, 1H), 8.98 (s, 1H). |
| 105 - En 1 | 456.3 | (DMSO-d6) δ = 2.59 (s, 3H), 2.85-3.01 (m, 3H), 3.17-3.21 (m, 2H), 4.57-4.65 (m, 1H), 5.33 (s, 2H), 7.01 (dd, 1H), 7.25 (d, 1H), 7.52 (d, 1H), 7.77-7.80 (m, 1H), 8.20-8.33 (m, 2H), 8.73 (d, 1H). |
| 106 - En 1 | 408.1 | (DMSO-d6) δ = 2.32 (s, 3H), 2.59 (s, 3H), 2.83-3.06 (m, 3H), 3.21-3.27 (m, 2H), 4.57-4.66 (m, 1H), 5.32 (s, 2H), 6.98 (dd, 1H), 7.25 (d, 1H), 7.49 (d, 1H), 8.18 (br d, 1H), 8.98 (s, 1H). |
| 107 | 386.8 | (DMSO-d6): δ = 8.98 (s, 1H), 7.75 (s, 1H), 7.45 (d, 1H), 7.27 (d, 1H), 6.94 (dd, 1H), 5.31 (s, 2H), 4.90 (t, 1H), 3.66 (d, 2H), 2.58 (s, 3H), 2.42 (s, 3H), 2.38-2.29 (m, 2H), 2.15-2.09 (m, 2H), 1.90-1.81 (m, 1H), 1.80-1.70 (m, 1H). |
| 108 | 414.1 | (DMSO-d6): δ = 8.98 (s, 1H), 7.80 (s, 1H), 7.47 (d, 1H), 7.30 (d, 1H), 6.96 (dd, 1H), 5.31 (s, 2H), 2.70 (s, 2H), 2.65-2.55 (m, 5H), 2.42 (s, 3H), 2.24 (s, 6H), 2.10-2.00 (m, 2H), 1.99-1.86 (m, 1H), 1.79-1.70 (m, 1H). |
| 109 | 423.1 | (DMSO-d6) δ = 1.33 (s, 6H), 2.60 (s, 3H), 3.49-3.53 (m, 2H), 5.01-5.04 (m, 1H), 5.31 (s, 2H), 6.97 (d, 1H), 7.23 (d, 2H), 7.48 (d, 1H), 7.78 (s, 1H), 8.26 (d, 1H), 8.73 (d, 1H). |
| 110 - En 1 | 436.1 | (DMSO): δ = 1.86 (m, 2H), 2.15-2.21 (m, 1H), 2.25 (s, 3H), 2.34-2.44 (m, 5H), 2.569 (s, 3H), 2.77-2.80 (m, 1H), 3.04-3.11 (m, 1H), 4.31-4.41 (m, 1H), 5.30 (s, 2H), 6.95-6.98 (dd, 1H), 7.21 (s, 1H), 7.47 (d, 1H), 8.20 (d, 1H), 8.98 (s, 1H). |
| 111 - En 1 | 470.2 | (DMSO-d6) δ = 1.85-2.11 (m, 2H), 2.31-2.32 (m, 1H), 2.50-2.69 (m, 5H), 2.89-2.96 (m, 2H), 4.31-4.38 (m, 1H), 5.31 (s, 2H), 7.00 (dd, 1H), 7.22 (d, 1H), 7.50 (d, 1H), 7.77-7.80 (m, 1H), 8.10 (d, 1H), 8.25 (d, 1H), 8.73 (d, 1H). |
| 112 - En 1 | 488.1 | (DMSO-d6) δ = 8.74 (d, 1H), 8.42 (d, 1H), 8.25 (d, 1H), 7.82-7.79 (m, 1H), 7.39-7.36 (m, 1H), 7.24 (t, 1H), 5.36 (s, 2H), 4.50-4.37 (m, 1H), 3.12-3.04 (m, 1H), 2.95-2.72 (m, 2H), 2.70-2.52 (m, 1H), 2.52 (s, 3H), 2.45-2.35 (m, 1H), 1.82-1.75 (m, 1H), 1.68-1.55 (m, 1H). |
| 113 - En 1 | 488.2 | (DMSO-d6) δ = 8.75 (d, 1H), 8.30-8.24 (m, 2H), 7.82-7.79 (m, 1H), 7.67 (d, 1H), 7.37 (d, 1H), 5.37 (s, 2H), 4.52-4.42 (m, 1H), 3.14-3.07 (m, 1H), 2.94-2.72 (m, 2H), 2.60-2.56 (m, 4H), 2.49-2.39 (m, 1H), 1.82-1.68 (m, 2H). |
| 114 | 401.1 | (DMSO-d6): δ = 8.99 (s, 1H), 7.95 (s, 1H), 7.45 (d, 1H), 7.27 (d, 1H), 6.96-6.93 (m, 1H), 5.32 (s, 2H), 4.57 (t, 1H), 3.57-3.53 (m, 2H), 2.51 (s, 3H), 2.49-2.43 (m, 2H), 2.42 (s, 3H), 2.09-2.04 (m, 4H), 1.80-1.62 (m, 2H). |
| 115 - En 1 | 422.1 | (DMSO-d6) δ = 2.02-2.13 (m, 1H), 2.45-2.51 (m, 4H), 2.54 (s, 1H), 2.58-2.65 (m, 3H), 2.67- 2.73 (m, 2H), 2.98 (d, 2H), 4.11-4.13 (m, 1H), 5.32 (s, 2H), 6.95-6.98 (m, 1H), 7.26 (s, 1H), 7.47 ( d, 1H), 7.87 ( d, 1H), 8.98 (s, 1H) |
| 116 | 454.1 | (DMSO) δ = 1.80-1.84 (m, 1H), 2.12-2.19 (m, 1H), 2.43 (s, 3H), 2.56 (s, 3H), 2.68-2.75 (m, 2H), 2.84-2.89 (m, 1H), 3.02-3.05 (m, 1H), 3.26-3.30 (m, 2H), 4.39-4.43 (m, 1H), 5.31 (s, 2H), 6.94-6.96 (dd, 1H), 7.23 (s, 1H), 7.45 (d, 1H), 8.12 (m, 1H). |
| 117 | 435.1 | (DMSO) δ = 8.73 (d, 1H), 8.26 (d, 1H), 7.78 (t, 2H), 7.47 (d, 1H), 7.27 (d, 1H), 6.99-6.96 (m, 1H), 5.32 (s, 2H), 4.88 (t, 1H), 3.65 (d, 2H), 2.58 (s, 3H), 2.33-2.24 (m, 2H), 2.16-2.09 (m, 2H), 1.90-1.81 (m, 1H), 1.80-1.70 (m, 1H) |
| 118 - En 1 | 436.1 | (DMSO-d6) δ = 2.00-2.14 (m, 7H), 2.41 (s, 3H), 2.67-2.50 (m, 3H), 2.69-2.78 (m, 2H), 4.44-4.53 (m, 1H), 5.30 (s, 2H), 6.97 (dd, 1H), 7.25 (d, 1H), 7.47 (m, 1H), 8.15 (d, 1H), 8.98 (s, 1H). |
| 119 | 402.1 | (DMSO-d6) δ = 8.99 (s, 1H), 8.68 (s, 1H), 7.51-7.45 (m, 2H), 7.23-7.20 (m, 2H), 7.00-6.97 (m, 1H), 5.35 (s, 2H), 4.88-4.86 (m, 2H), 4.69-4.67 (m, 2H), 2.66 (s, 3H), 2.43 (s, 3H). |
| 120 - En 1 | 478.2 | (DMSO): δ = 1.96-2.01 (m, 1H), 2.32-2.38 (m, 1H), 2.61 (s, 3H), 3.13-3.19 (m, 1H), 3.36-3.47 (m, 3H), 3.52 (m, 2H), 4.65-4.72 (m, 2H), 5.32 (s, 2H), 6.97-7.005 (dd, 1H), 7.36 (s, 1H), 7.49 (d, 1H), 7.77-7.80 (m, 2H), 8.19-8.27 (dd, 1H), 8.735 (s, 1H). |
| 121 | 417.1 | (DMSO-d6) δ = 1.93-1.97 (m, 1H), 2.03-2.07 (m, 1H), 2.12-2.16 (m, 1H), 2.41-2.46 (s, 4H), 2.55 (s, 3H), 3.52-3.54 (m, 2H), 3.61 (d, 1H), 3.80-3.83 (m, 2H), 4.09 (d, 1H), 4.49 (s, 1H), 5.31 (s, 2H), 6.93-6.95 (dd, 1H), 7.2 (s, 1H), 7.45 (d, 1H), 7.86 (s, 1H), 8.98 (s, 1H). |
| 122 | 435.1 | (DMSO-d6): δ = 8.99 (s, 1H), 7.60 (d, 1H), 7.43-7.41 (m, 2H), 5.37 (s, 2H), 4.89 (br s, 1H), 3.73-3.56 (m, 6H), 2.59 (s, 3H), 2.41 (s, 3H), 2.16 (d, 2H), 1.65-1.59 (m, 2H). |
| 123 - En 1 | 422.1 | (DMSO-d6) δ = 2.29 (s, 3H), 2.42 (s, 3H), 2.51-2.58 (m, 1H), 2.61 (s, 3H), 2.68-2.71 (m, 1H), 3.17-3.25 (m, 2H), 4.68-4.76 (m, 1H), 5.31 (s, 2H), 6.98 (dd, 1H), 7.23 (d, 1H), 7.48 (d, 1H), 8.27 (br d, 1H), 8.98 (s, 1H). |
| 124 - En 1 | 470.1 | (DMSO-d6) δ = 2.29 (s, 3H), 2.45-2.49 (m, 1H), 2.56-2.62 (m, 3H), 2.66-2.69 (m, 1H), 3.17-3.25 (m, 2H), 4.67-4.75 (m, 1H), 5.33 (s, 2H), 6.99-7.02 (m, 1H,), 7.24 (d, 1H), 7.51 (d, 1H), 7.77-7.80 (m, 1H), 8.24-8.30 (m, 2H), 8.73 (d, 1H). |
| 125 - En 1 | 470.1 | (DMSO-d6) δ = 2.04-2.11 (m, 1H), 2.32-2.35 (m, 1H), 2.50 (br s, 1H), 2.58 (s, 3H), 2.67-2.82 (m, 2H), 2.98 (d, 2H), 4.06-4.12 (m, 1H), 5.33 (s, 2H), 7.00 (dd, 1H), 7.26 (d, 1H), 7.50 (d, 1H), 7.77-7.80 (m, 1H), 7.90 (d, 1H), 8.26 (d, 1H), 8.73 (d, 1H). |
| 126 - En 1 | 465.1 | (DMSO-d6) δ = 1.93 (td, 1H), 2.03 (td, 1H), 2.12-2.18 (m, 1H), 2.39-2.46 (m, 1H), 2.56 (s, 3H), 3.47-3.56 (m, 2H), 3.60 (d, 1H), 3.80 (dd, 2H), 4.08 (d, 1H), 4.47 (d, 1H), 5.31 (s, 2H), 6.99 (dd, 1H), 7.21 (d, 1H), 7.49 (d, 1H), 7.79 (dd, 1H), 7.88 (s, 1H), 8.26 (d, 1H), 8.72 (d, 1H). |
| 127 | 449.1 | (DMSO-d6): δ = 8.37 (d, 1H), 8.26 (d, 1H), 7.97 (s, 1H), 7.80-7.77 (m, 1H), 7.48 (d, 1H), 7.27 (d, 1H), 6.99-6.97 (m, 1H), 5.33 (s, 2H), 4.53 (t, 1H), 3.56-3.51 (m, 2H), 2.58 (s, 3H), 2.46-2.40 (m, 2H), 2.10-2.02 (m, 4H), 1.99-1.72 (m, 2H). |
| 128 | 403.1 | (DMSO-d6) δ = 8.98 (s, 1H), 8.37 (s, 1H), 7.47 (d, 1H), 7.31 (d, 1H), 6.97 (dd, 1H), 5.32 (s, 2H), 4.75-4.74 (m, 2H), 4.53-4.51 (m, 3H), 3.59-3.56 (m, 2H), 2.60 (s, 3H), 2.42 (s, 3H), 2.25 (t, 2H). |
| 129 | 451.1 | (DMSO-d6) δ = 8.74 (d, 1H), 8.39 (s, 1H), 8.26 (d, 1H), 7.80-7.77 (m, 1H), 7.51-7.49 (m, 1H), 7.31 (d, 1H), 7.00 (dd, 1H), 5.32 (s, 2H), 4.73 (d, 2H), 4.53-4.48 (m, 3H), 3.59-3.54 (m, 2H), 2.61 (s, 3H), 2.25 (t, 2H). |

-continued

| cpd | [M + H]+ (m/z) | 1H NMR (δ ppm) |
|---|---|---|
| 130 - En 1 | 484.1 | (DMSO): δ = 1.8-1.813 (m, 2H), 2.14-2.17 (m, 1H), 2.21 (s, 3H), 2.32-2.41 (m, 1H), 2.54 (s, 3H), 2.77-2.79 (m, 1H), 3.03-3.09 (m, 1H), 4.33-4.40 (m, 1H), 5.30 (s, 2H), 6.98-7.01 (dd, 1H), 7.221 (s, 1H), 7.50 (d, 1H), 7.76-7.80 (m, 1H), 8.21-8.21-8.26 (m, 2H), 8.73 (d, 1H). |
| 131 - En 1 | 484.2 | (DMSO-d6) δ = 2.07-2.33 (m, 7H), 2.57 (s, 3H), 2.61-2.77 (m, 2H), 4.43-4.53 (m, 1H), 5.31 (s, 2H), 7.00 (dd, 1H), 7.22 (d, 1H), 7.51 (d, 1H), 7.77-7.80 (m, 1H), 8.17 (d, 1H), 8.26 (d, 1H), 8.73 (d, 1H). |
| 132 - En 1 | 403.1 | (DMSO-d6) δ = 2.04-2.07 (m, 1H), 2.23-2.25 (m, 1H), 2.42 (s, 3H), 2.57 (s, 3H), 3.66-3.71 (m, 2H), 3.78-3.82 (m, 3H), 3.92 (d, 1H), 5.07 (s, 1H), 5.30 (s, 2H), 6.93-6.95 (dd, 1H), 7.25 (s, 1H), 7.47 (d, 1H), 7.84 (s, 1H), 8.98 (s, 1H). |
| 133 | 475.1 | (DMSO-d6) δ = 8.73 (d, 1H), 8.37 (s, 1H), 8.26 (d, 1H), 7.80-7.77 (m, 1H), 7.49 (d, 1H), 7.34-7.33 (m, 1H), 7.00-6.98 (m, 1H), 5.32 (s, 2H), 5.18 (t, 1H), 4.66 (d, 2H), 4.55 (d, 2H), 3.76 (d, 2H), 2.61 (s, 3H). |
| 134 - En 1 | 500.2 | (DMSO-d6): δ = 2.49-2.58 (m, 6H), 2.69-2.80 (m, 1H), 3.24-3.31 (m, 2H), 3.51 (s, 2H), 4.54 (s, 1H), 4.65-4.73 (m, 1H), 5.32 (s, 2H), 7.01 (dd, 1H), 7.24 (d, 1H), 7.51 (d, 1H), 7.77-7.80 (m, 1H), 8.26 (t, 2H), 8.73 (d, 1H). |
| 135 - En1 | 451.0 | (DMSO-d6) δ = 2.06 (td, 1H), 2.22 (td, 1H), 2.58 (s, 3H), 3.63-3.73 (m, 2H), 3.75-3.82 (m, 3H), 3.92 (d, 1H), 5.05 (t, 1H), 5.32 (s, 2H), 6.98 (dd, 1H), 7.25 (d, 1H), 7.48 (d, 1H), 7.78 (dd, 1H), 7.86 (s, 1H), 8.25 (d, 1H), 8.72 (d, 1H). |
| 136 | 434.1 | (DMSO-d6) δ = 8.73 (d, 1H), 8.26 (d, 1H), 7.82-7.76 (m, 1H), 7.75 (s, 1H), 7.48 (d, 1H), 7.30 (d, 1H), 6.98 (dd, 1H), 5.32 (s, 2H), 2.87 (s, 2H), 2.60 (s, 3H), 2.42-2.35 (m, 2H), 2.09-2.00 (m, 2H), 1.90-1.80 (m, 1H), 1.79-1.52 (m, 3H). |
| 137 | 468.1 | (DMSO-d6) δ = 8.98 (s, 1H), 7.79 (s, 1H), 7.45 (d, 1H), 7.26 (d, 1H), 6.94 (dd, 1H), 5.31 (s, 2H), 3.29-3.26 (m, 2H), 3.05 (d, 2H), 2.58 (s, 3H), 2.41 (s, 3H), 2.40-2.32 (m, 3H), 2.15-2.08 (m, 2H), 1.90-1.81 (m, 1H), 1.80-1.73 (m, 1H). |
| 138 | 383.1 | (DMSO-d6) δ = 2.41 (s, 3H), 2.69 (s, 3H), 3.75 (s, 3H), 5.34 (s, 2H), 6.31 (d, 1H), 6.98 (dd, 1H), 7.39-7.40 (m, 1H), 7.53 (d, 1H), 8.98 (s, 1H), 10.0 (s, 1H). |
| 139 | 373.1 | (DMSO-d6) δ = 0.75-0.78 (m, 4H), 2.42 (s, 3H), 2.56 (s, 3H), 3.55 (d, 2H), 4.77 (t, 1H), 5.32 (s, 2H), 6.93 (dd, 1H), 7.26 (s, 1H), 7.44 (d, 1H), 8.14 (s, 1H), 8.98 (s, 1H). |
| 140 | 462.2 | (DMSO-d6) δ = 8.73 (d, 1H), 8.26 (d, 1H), 7.83 (s, 1H), 7.82-7.78 (m, 1H), 7.50 (d, 1H), 7.28 (d, 1H), 6.99 (dd, 1H), 5.31 (s, 2H), 2.68 (s, 2H), 2.59 (s, 3H), 2.58-2.51 (m, 2H), 2.21 (s, 6H), 2.10-2.01 (m, 2H), 1.95-1.85 (m, 1H), 1.80-1.70 (m, 1H). |
| 141 - En 1 | 484.2 | (DMSO-d6) δ = 1.95-2.10 (m, 1H), 2.12-2.15 (m, 1H), 2.29-2.49 (m, 5H), 2.67 (s, 3H), 2.82-2.93 (m, 2H), 4.19-4.21 (m, 1H), 5.33 (s, 2H), 7.01 (dd, 1H), 7.25 (d, 1H), 7.51 (d, 1H), 7.77-7.80 (m, 1H), 7.84 (br d, 1H), 8.26 (d, 1H), 8.73 (d, 1H). |
| 142 | 388.8 | (DMSO-d6) δ = 8.98 (s, 1H), 8.33 (s, 1H), 7.47 (d, 1H), 7.33 (d, 1H), 6.96 (dd, 1H), 5.32 (s, 2H), 5.20 (t, 1H), 4.67 (d, 2H), 4.54 (d, 2H), 3.77 (d, 2H), 2.60 (s, 3H), 2.43 (s, 3H). |
| 143 | 431.1 | (DMSO) δ = 2.63 (s, 3H), 3.82 (s, 3H), 5.34 (s, 2H), 7.02 (br dd, 1H), 7.31 (d, 1H), 7.51-7.54 (m, 2H), 7.77-7.80 (m, 1H), 8.01 (s, 1H), 8.27 (d, 1H), 8.73 (d, 1H), 10.07 (s, 1H). |
| 144 | 369.1 | (DMSO-d6) δ = 2.41 (s, 3H), 2.62 (s, 3H), 5.32 (s, 2H), 6.63 (s, 1H), 6.94-6.97 (dd, 1H), 7.3 (s, 1H), 7.47 (d, 1H), 7.67 (s, 1H), 8.97 (s, 1H), 10.45 (s, 1H), 12.43 (s, 1H). |
| 145 | 468.1 | (DMSO-d6) δ = 8.98 (s, 1H), 7.79 (s, 1H), 7.45 (d, 1H), 7.26 (d, 1H), 6.94 (dd, 1H), 5.31 (s, 2H), 3.29-3.26 (m, 2H), 3.05 (d, 2H), 2.58 (s, 3H), 2.41 (s, 3H), 2.40-2.32 (m, 3H), 2.15-2.08 (m, 2H), 1.90-1.81 (m, 1H), 1.80-1.73 (m, 1H). |
| 146 | 431.1 | (DMSO) δ = 2.63 (s, 3H), 3.78 (s, 3H), 5.32 (s, 2H), 6.57 (s, 1H), 7.00 (dd, 1H), 7.30 (s, 1H), 7.51 (d, 1H), 7.61 (d, 1H), 7.77-7.79 (m, 1H), 8.27 (d, 1H), 8.73 (d, 1H), 10.46 (s, 1H). |
| 147 - Dia 1 - En 1 | 437.1 | (DMSO-d6) δ = 2.56 (s, 3H), 3.56 (dd, 1H), 3.65 (dd, 1H), 3.88-3.92 (m, 1H), 3.99-4.02 (m, 1H), 4.23 (s, 2H), 5.30 (t, 3H), 6.99 (dd, 1H), 7.23 (d, 1H), 7.50 (d, 1H), 7.77-7.80 (m, 1H), 8.17 (dd, 1H), 8.25 (d, 1H), 8.73 (t, 1H). |
| 148 | 421.1 | (DMSO) δ = 1.89-1.92 (m, 1H), 2.14-2.18 (m, 1H), 2.57 (s, 3H), 3.58-3.61 (m, 1H), 3.71-3.75 (m, 1H), 3.81-3.89 (m, 2H), 4.42-4.47 (m, 1H), 5.32 (s, 2H), 7.00 (dd, 1H), 7.23 (s, 1H), 7.50 (d, 1H), 7.77-7.80 (m, 1H), 8.20 (d, 2H), 8.26 (d, 2H), 8.73 (d, 1H). |
| 149 | 502.2 | (DMSO-d6): δ = 1.78-1.82 (m, 1H), 2.12-2.16 (m, 1H), 2.57 (s, 3H), 2.66-2.77 (m, 2H), 2.82-2.89 (m, 1H), 3.02-3.07 (m, 1H), 3.25-3.32 (m, 2H), 4.37-4.45 (m, 1H), 5.31 (s, 2H), 6.98-7.00 (m, 1H), 7.22 (d, 1H), 7.49 (d, 1H), 7.79 (dd, 1H), 8.15 (d, 1H), 8.26 (d, 1H), 8.73 (d, 1H). |
| 150 | 369.1 | (DMSO-d6) δ = 2.41 (s, 3H), 2.63 (s, 3H), 5.34(s, 2H), 6.97-6.99 (m, 1H), 7.32 (s, 1H), 7.50 (d, 1H), 7.67 (br s, 1H), 7.98 (br s, 1H), 8.98 (s, 1H), 10.0 (s, 1H). |
| 151 - En 1 | 452.2 | (DMSO-d6) δ = 2.41 (s, 3H), 2.53-2.61 (m, 6H), 2.73-2.78 (m, 1H), 3.25-3.28 (m, 1H), 3.50-3.51 (m, 2H), 4.54 (m, 1H), 4.65-4.75 (m, 1H), 5.31 (s, 2H), 6.96-6.98 (m, 1H), 7.23 (s, 1H), 7.48 (d, 1H), 8.25 (d, 1H), 8.98 (s, 1H). |
| 152 | 383.1 | (DMSO-d6) δ = 2.41 (s, 3H), 2.62 (s, 3H), 3.82 (s, 3H), 5.33 (s, 2H), 6.98 (dd, 1H), 7.30 (s, 1H), 7.49 (d, 1H), 7.56 (s, 1H), 8.01 (s, 1H), 8.98 (s, 1H), 10.04 (s, 1H). |
| 153 | 516.2 | (DMSO-d6) δ = 8.73 (d, 1H), 8.25 (d, 1H), 7.82-7.77 (m, 2H), 7.48 (d, 1H), 7.26 (d, 1H), 6.99 (dd, 1H), 5.32 (s, 2H), 3.29-3.25 (m, 2H). 3.04 (d, 2H), 2.58 (s, 3H), 2.38-2.28 (m, 3H), 2.13-2.08 (m, 2H), 1.91-1.72 (m, 2H). |
| 154 | 431.1 | (DMSO-d6): δ = 2.70 (s, 3H), 3.74 (s, 3H), 5.35 (s, 2H), 6.32 (s, 1H), 7.04 (dd, 1H), 7.37-7.41 (m, 2H), 7.56 (d, 1H), 7.76-7.79 (m, 1H), 8.27 (d, 1H), 8.74 (d, 1H), 10.04 (s, 1H). |
| 155 - En 1 | 490.1 | (DMSO-d6) δ = 2.42 (s, 3H), 2.58 (s, 3H), 2.88-2.92 (m, 1H), 3.04-3.07 (m, 1H), 3.38-3.44 (m, 4H), 4.74-4.82 (m, 1H), 5.31 (s, 2H), 6.96 (dd, 1H), 7.24 (d, 1H), 7.48 (d, 1H), 8.31 (d, 1H). 8.98 (s, 1H). |
| 156 | 398.8 | (DMSO-d6) δ = 8.99 (s, 1H), 8.14 (d, 1H), 7.46 (d, 1H), 7.24 (d, 1H), 6.96 (dd, 1H), 5.32 (s, 2H), 4.64 (s, 2H), 4.52 (s, 2H), 4.28-4.21 (m, 1H), 2.61-2.55 (m, 5H), 2.42 (s, 3H), 2.30-2.23 (m, 2H). |

| cpd | [M + H]+ (m/z) | 1H NMR (δ ppm) |
|---|---|---|
| 157 - En 1 | 538.1 | (DMSO-d6): δ = 2.60 (s, 3H), 2.85-2.90 (m, 1H), 3.02- 3.13 (m, 1H), 3.38-3.39 (m, 4H), 4.73-4.81 (m, 1H), 5.32 (s, 2H), 7.01 (dd, 1H), 7.24 (d, 1H), 7.52 (d, 1H), 7.77-7.80 (m, 1H), 8.26 (d, 1H), 8.35 (d, 1H), 8.73 (d, 1H). |
| 158 | 417.1 | (DMSO-d6): δ =2.64 (s, 3H), 5.34 (s, 2H), 7.02 (dd, 1H), 7.33 (s, 1H), 7.53 (d, 1H), 7.65 (br s, 1H), 7.76-7.79 (m, 1H), 7.99 (br s, 1H), 8.27 (d, 1H), 8.73 (d, 1H), 10.07 (s, 1H), 12.64 (br s, 1H). |
| 159 | 373.1 | (DMSO-d6) δ = 1.89-1.94 (m, 1H), 2.15-2.19 (m, 1H), 2.49 (m, 3H), 2.56 (s, 3H), 3.59-3.62 (m, 1H), 3.71-3.75 (m, 1H), 3.83-3.89 (m, 2H), 4.47-4.48 (m, 1H), 5.32 (s, 2H), 6.94-6.96 (dd, 1H), 7.22-7.23 (d, 1H), 7.45-7.46 (d, 1H), 8.18-8.19 (d, 1H), 8.98 (s, 1H) |
| 160 | 430.1 | (DMSO) δ = 1.94-2.00 (m, 1H), 2.32-2.37 (m, 1H), 2.42 (m, 3H), 2.61 (s, 3H), 3.14-3.19 (m, 1H), 3.31-3.45 (m, 3H), 3.50-3.54 (m, 2H), 4.65-4.73 (m, 1H), 5.32 (s, 2H), 6.95-6.98 (dd, 1H), 7.36 (s, 1H), 7.47 (d, 1H), 8.17 (d, 1H), 8.98 (s, 1H). |
| 161 | 383.1 | (DMSO-d6) δ = 2.41 (s, 3H), 2.61 (s, 3H), 3.76 (s, 3H), 5.32 (s, 2H), 6.58 (s, 1H), 6.96 (dd, 1H), 7.28 (s, 1H), 7.47 (d, 1H), 7.61 (s, 1H), 8.98 (s, 1H), 10.45 (s, 1H). |
| 162 - Dia1 - En 1 | 389.1 | (DMSO-d6) δ = 2.42 (s, 3H), 2.56 (s, 3H), 3.57 (dd, 1H), 3.67 (dd, 1H), 3.89-3.93 (m, 1H), 3.99-4.03 (m, 1H), 4.22-4.24 (m, 2H), 5.31 (s, 3H), 6.96 (dd, 1H), 7.22 (d, 1H), 7.47 (d, 1H), 8.14 (d, 1H), 8.98 (s, 1H). |
| 163 - En 1 | 436.2 | (DMSO-d6) δ = 1.9-2.17 (m, 1H), 2.30-2.33 (m, 1H), 2.34-2.37 (m, 3H), 2.39-2.42 (m, 2H), 2.49-2.51 (m, 3H), 2.58 (s, 3H), 2.84- 2.91 (m, 2H), 4.68-4.76 (m, 1H), 5.32 (s, 2H), 6.95-6.98 (m, 1H), 7.26 (s, 1H), 7.47 ( d, 1H), 7.87 ( d, 1H), 8.99 (s, 1H) |
| 164 - En 1 | 424.2 | (DMSO-d6) δ = 8.41 (d, 1H), 8.19 (d, 1H), 7.81 (d, 1H), 7.48 (d, 1H), 7.40 (d, 1H), 7.24 (t, 1H), 7.01 (dd, 1H), 5.16 (s, 2H), 4.73-4.65 (m, 2H), 3.52 (s, 2H), 3.48-3.37 (m, 3H), 3.21-3.14 (m, 1H), 2.63 (s, 3H), 2.53 (s, 3H), 2.40-2.30 (m, 1H), 2.01-1.90 (m, 1H). |
| 165 - En 1 | 504.1 | (DMSO-d6) δ = 8.75 (d, 1H), 8.31 (d, 2H), 7.84-7.81 (m, 2H), 7.37 (s, 1H), 5.39 (s, 2H), 4.49-4.42 (m, 1H), 3.14-3.07 (m, 1H), 2.93-2.72 (m, 2H), 2.60-2.56 (m, 4H), 2.49-2.39 (m, 1H), 1.82-1.68 (m, 2H). |
| 166 | 468.1 | (DMSO) δ = 1.58-1.65 (m, 2H), 1.81-1.83 (m, 2H), 2.42-2.49 (m, 5H), 2.56 (s, 3H), 2.92-2.94 (m, 2H), 3.13-3.20 (m, 2H), 3.78-3.80 (m, 1H), 5.32 (s, 2H), 6.96 (dd, 1H), 7.23 (brs, 1H), 7.45 (d, 1H), 7.86 (brd, 1H), 8.98 (s, 1H). |
| 167 | 447.1 | (DMSO-d6) δ = 8.73 (d, 1H), 8.25 (d, 1H), 8.17 (d, 1H), 7.80-7.77 (m, 1H), 7.49 (d, 1H), 7.23-7.23 (d, 1H), 7.00-6.98 (m, 1H), 5.34 (s, 2H), 4.63 (s, 2H), 4.51 (s, 2H), 4.26-4.21 (m, 1H), 2.60-2.54 (m, 5H), 2.26-2.22 (m, 2H). |
| 168 | 516.1 | (DMSO-d6) δ = 1.55-1.60 (m, 2H), 1.79-1.84 (m, 2H), 2.41-2.48 (m, 2H), 2.57 (s, 3H), 2.92 (br d, 2H), 3.10-3.16 (m, 2H), 3.74-3.81 (m, 1H), 5.33 (s, 2H), 6.99 (dd, 1H), 7.23 (d, 1H), 7.49 (d, 1H), 7.76-7.80 (m, 1H), 7.89 (d, 1H), 8.26 (d, 1H), 8.73 (d, 1H). |
| 169 - En 1 | 444.2 | (DMSO-d6) δ = 8.99 (s, 1H), 8.36 (d, 1H), 7.47 (d, 1H), 7.27 (d, 1H), 6.96 (dd, 1H), 5.32 (s, 2H), 4.72 (t, 1H), 4.62-4.52 (m, 1H), 3.85-3.77 (m, 1H), 3.53-3.48 (m, 2H), 3.42-3.33 (m, 1H), 3.28-3.23 (m, 2H), 2.70-2.62 (m, 1H), 2.58 (s, 3H), 2.43-2.35 (m, 4H). |
| 170 | 451.1 | (DMSO-d6) δ = 2.08 (td, 1H), 2.26 (br s, 1H), 2.76 (s, 3H), 3.80-3.91 (m, 3H), 3.95-4.02 (m, 1H), 4.57 (br d, 2H), 5.35 (br s, 2H), 7.08 (br dd, 1H), 7.46 (br d, 1H), 7.60 (br d, 1H), 7.80 (br dd, 1H), 8.20-8.31 (m, 3H), 8.75 (br d, 1H) |
| 171 | 383.1 | (DMSO-d6) δ = 2.41 (s, 3H), 2.69 (s, 3H), 3.75 (s, 3H), 5.34 (s, 2H), 6.31 (d, 1H), 6.98 (dd, 1H), 7.39-7.40 (m, 2H), 7.53 (d, 1H), 8.98 (s, 1H), 10.0 (s, 1H). |
| 172 - En 1 | 534.1 | (DMSO-d6) δ = 2.41 (s, 3H), 2.59 (s, 3H), 3.50-3.58 (m, 1H), 3.86-3.96 (m, 3H), 4.71-4.77 (m, 2H), 5.08-5.12 (m, 1H), 5.31 (s, 2H), 6.96 (dd, 1H), 7.24 (d, 1H), 7.49 (d, 1H), 8.51 (t, 1H). 8.98 (s, 1H). |
| 173 | 446.2 | (CDCl3) δ = 8.66 (d, 1H), 8.17 (d, 1H), 7.56-7.53 (m, 1H), 7.36 (d, 1H), 7.13 (s, 1H), 6.94 (d, 1H), 5.78 (d, 1H), 5.36 (s, 2H), 4.48-4.42 (m, 1H), 3.72 (s, 2H), 3.61 (s, 2H), 2.74-2.68 (m, 6H), 2.04 (t, 2H). |
| 174 | 451.1 | (DMSO-d6): δ = 8.99 (s, 1H), 7.76 (s, 1H), 7.47-7.43 (m, 2H), 5.39 (s, 2H), 4.91 (t, 1H), 3.73-3.56 (m, 6H), 2.61 (s, 3H), 2.42 (s, 3H), 2.20-2.15 (m, 2H), 1.68-1.59 (m, 2H). |
| 175 | 582.1 | (DMSO-d6): δ = 2.59 (s, 3H), 3.50-3.56 (m, 1H), 3.82- 3.96 (m, 3H), 4.70-4.77 (m, 2H), 5.05-5.15 (m, 1H), 5.32 (s, 2H), 7.02 (dd, 1H), 7.24 (d, 1H), 7.53 (d, 1H), 7.77-7.80 (m, 1H), 8.25 (d, 1H), 8.54 (t, 1H), 8.73 (d, 1H). |
| 176 - En 1 | 488.1 | (DMSO-d6) δ = 8.74 (d, 1H), 8.35 (d, 1H), 8.26 (d, 1H), 7.80-7.77 (m, 1H), 7.06-7.03 (m, 2H), 5.32 (s, 2H), 4.51-4.40 (m, 1H), 3.13-3.07 (m, 1H), 2.93-2.78 (m, 2H), 2.65-2.59 (m, 4H), 2.49-2.44 (m, 1H), 1.80-1.65 (m, 2H). |
| 177 | 435.2 | (DMSO-d6): δ 8.98 (s, 1H), 7.72 (s, 1H), 7.34 (d, 1H), 7.23 (t, 1H), 5.37 (s, 2H), 4.81 (t, 1H), 3.71-3.55 (m, 6H), 2.52 (s, 3H), 2.39 (s, 3H), 2.10 (d, 2H), 1.66-1.58 (m, 2H). |
| 178 | 417.1 | (DMSO-d6): — = 2.54 (s, 3H), 5.29 (s, 2H), 5.65 (s, 2H), 6.02 (d, 1H), 6.99-7.01 (m, 1H), 7.16 (d, 1H), 7.53 (d, 1H), 7.75-7.78 (m, 1H), 8.16 (d, 1H), 8.23 (d, 1H), 8.71-8.72 (m, 1H). |
| 179 - En 1 | 484.2 | (DMSO-d6) δ = 8.74 (d, 1H), 8.29 (d, 1H), 8.20 (d, 1H), 7.82-7.79 (m, 1H), 7.41 (s, 1H), 7.20 (s, 1H), 5.30 (s, 2H), 4.50-4.43 (m, 1H), 3.18-3.05 (m, 1H), 2.95-2.72 (m, 2H), 2.63-2.40 (m, 5H), 2.28 (s, 3H), 1.71-1.64 (m, 2H). |
| 180 - En 1 | 430.1 | (DMSO-d6) δ = 8.99 (s, 1H), 8.36 (d, 1H), 7.47 (d, 1H), 7.27 (d, 1H), 6.96 (dd, 1H), 5.32 (s, 2H), 4.72 (t, 1H), 4.62-4.52 (m, 1H), 3.85-3.77 (m, 1H), 3.53-3.48 (m, 2H), 3.42-3.33 (m, 1H), 3.28-3.23 (m, 2H), 2.70-2.62 (m, 1H), 2.58 (s, 3H), 2.43-2.35 (m, 4H). |
| 181 | 417.1 | (DMSO-d6): δ = 2.52 (s, 3H), 4.72 (s, 2H), 5.27 (s, 2H), 7.00-7.03 (m, 1H), 7.10 (s, 1H), 7.47 (s, 1H), 7.54 (d, 1H), 7.60 (s, 1H), 7.76-7.78 (m, 1H), 8.22 (d, 1H), 8.72 (d, 1H). |
| 182 | 435.1 | (DMSO-d6): δ = 8.99 (s, 1H), 7.51 (s, 1H), 7.07 (d, 1H), 7.00-6.97 (m, 1H), 5.33 (s, 2H), 4.89 (t, 1H), 3.73-3.57 (m, 6H), 2.62 (s, 3H), 2.42 (s, 3H), 2.16 (d, 2H), 1.65-1.59 (m, 2H). |
| 183 - En 1 | 484.2 | (DMSO-d6) δ = 8.73 (d, 1H), 8.24 (d, 1H), 8.18 (d, 1H), 7.79-7.76 (m, 1H), 7.04 (d, 1H), 6.86 (d, 1H), 5.28 (s, 2H), 4.49-4.40 (m, 1H), 3.13-3.06 (m, 1H), 2.92-2.77 (m, 2H), 2.63-2.56 (m, 4H), 2.49-2.29 (m, 4H), 1.79-1.70 (m, 2H). |

| cpd | [M + H]+ (m/z) | 1H NMR (δ ppm) |
|---|---|---|
| 184 - En 1 | 504.1 | (DMSO-d6) δ = 8.74 (d, 1H), 8.35 (d, 1H), 8.26 (d, 1H), 7.80-7.77 (m, 1H), 7.19 (dd, 2H), 5.33 (s, 2H), 4.51-4.40 (m, 1H), 3.14-3.07 (m, 1H), 2.93-2.27 (m, 2H), 2.65-2.59 (m, 4H), 2.50-2.44 (m, 1H), 1.80-1.67 (m, 2H). |
| 185 | 431.1 | (DMSO-d6): δ = 8.97 (s, 1H), 7.36 (s, 1H), 7.32 (s, 1H), 7.28 (s, 1H), 5.33 (s, 2H), 4.88 (t, 1H), 3.73-3.59 (m, 6H), 2.59 (s, 3H), 2.42 (s, 3H), 2.23 (s, 3H), 2.22-2.16 (m, 2H), 1.68-1.60 (m, 2H). |
| 186 | 431.1 | (DMSO-d6): δ = 8.97 (s, 1H), 7.32 (s, 1H), 7.08 (d, 1H), 6.81 (d, 1H), 5.28 (s, 2H), 4.88 (t, 1H), 3.72-3.58 (m, 6H), 2.60 (s, 3H), 2.41 (s, 6H), 2.18-2.16 (m, 2H), 1.66-1.60 (m, 2H). |
| 187 | 451.1 | (DMSO-d6) δ = 8.99 (s, 1H), 7.76 (s, 1H), 7.47-7.43 (m, 2H), 5.39 (s, 2H), 4.91 (t, 1H), 3.73-3.56 (m, 6H), 2.61 (s, 3H), 2.42 (s, 3H), 2.20-2.15 (m, 2H), 1.68-1.59 (m, 2H). |
| 188 | 442.2 | (DMSO-d6) δ = 9.01 (s, 1H), 7.63 (s, 1H), 7.58 (d, 1H), 7.56 (d, 1H), 5.39 (s, 2H), 4.91 (t, 1H), 3.73-3.56 (m, 6H), 2.67 (s, 3H), 2.43 (s, 3H), 2.17 (d, 2H), 1.65-1.58 (m, 2H). |
| 189 | 436.2 | (DMSO-d6) δ = 8.73 (d, 1H), 8.26 (d, 1H), 7.80-7.76 (m, 1H), 7.56 (d, 1H), 7.45 (d, 1H), 6.95 (dd, 1H), 6.52-6.13 (br s, 1H), 5.31 (s, 2H), 4.57 (br s, 2H), 3.49-3.38 (m, 6H), 2.64 (s, 3H). |
| 190 | 398.2 | (CDCl3) δ = 8.72 (d, 1H), 7.35 (d, 1H), 7.20 (d, 1H), 6.92 (dd, 1H), 5.81 (d, 1H), 5.23 (s, 2H), 4.50-4.43 (m, 1H), 3.73 (s, 2H), 3.61 (s, 2H), 2.78-2.71 (m, 2H), 2.68 (s, 3H), 2.50 (s, 3H), 2.11-2.05 (m, 2H). |
| 191 - En 1 | 495.1 | (DMSO-d6) δ = 8.78-8.74 (m, 2H), 8.30 (d, 1H), 7.92 (m, 1H), 7.86-7.83 (m, 1H), 7.30 (d, 1H), 5.49 (s, 2H), 4.52-4.40 (m, 1H), 3.18-3.07 (m, 1H), 2.93-2.77 (m, 2H), 2.63-2.51 (m, 2H), 2.52 (s, 3H), 1.90-1.84 (m, 1H), 1.70-1.61 (m, 1H). |
| 192 | 369.1 | (DMSO-d6) δ = 2.38 (s, 3H), 2.54 (s, 3H), 5.28 (s, 2H), 5.67 (s, 2H), 6.032 (s, 1H), 6.96 (dd, 1H), 7.16 (s, 1H), 7.5 (d, 1H), 8.17 (s, 1H), 8.97 (s, 1H). |
| 193 | 442.1 | (DMSO-d6): δ = 9.00 (s, 1H), 7.93 (s, 1H), 7.88 (d, 1H), 7.33 (d, 1H), 5.52 (s, 2H), 4.77 (t, 1H), 3.70-3.55 (m, 6H), 2.56 (s, 3H), 2.44 (s, 3H), 2.11-2.07 (m, 2H), 1.69-1.65 (m, 2H). |
| 194 | 442.2 | (DMSO-d6) δ = 9.01 (s, 1H), 8.09 (s, 1H), 7.56 (d, 1H), 7.48 (s, 1H), 5.49 (s, 2H), 4.91 (t, 1H), 3.73-3.56 (m, 6H), 2.65 (s, 3H), 2.45 (s, 3H), 2.19-2.15 (m, 2H), 1.67-1.58 (m, 2H). |
| 195 - En 1 | 495.1 | (DMSO-d6) δ = 8.77-8.75 (m, 1H), 8.43 (d, 1H), 8.30 (d, 1H), 8.17 (s, 1H), 7.86-7.83 (m, 1H), 7.39 (s, 1H), 5.46 (s, 2H), 4.52-4.41 (m, 1H), 3.15-3.07 (m, 1H), 2.93-2.80 (m, 2H), 2.63-2.48 (m, 5H), 1.85-1.75 (m, 1H), 1.73-1.65 (m, 1H). |
| 196 - En 1 | 495.1 | (DMSO-d6) δ = 8.74 (m, 1H), 8.44 (d, 1H), 8.27 (d, 1H), 7.82-7.77 (m, 1H), 7.65 (d, 1H), 7.53 (d, 1H), 5.37 (s, 2H), 4.53-4.40 (m, 1H), 3.15-3.06 (m, 1H), 2.93-2.75 (m, 2H), 2.65-2.55 (m, 4H), 2.49-1.82-1.78 (m, 1H), 1.72-1.65 (m, 2H). |
| 197 | 453.1 | (DMSO-d6) δ = 9.00 (s, 1H), 8.00 (s, 1H), 7.70 (d, 1H), 7.45-7.15 (m, 3H), 5.36 (s, 2H), 4.93 (t, 1H), 3.75-3.56 (m, 6H), 2.42 (s, 3H), 2.21-2.14 (m, 2H), 1.67-1.54 (m, 2H). |
| 198 - En 1 | 466.1 | (DMSO-d6) δ = 9.00 (s, 1H), 8.75 (d, 1H), 7.73 (d, 1H), 7.51 (d, 1H), 7.41 (t, 1H), 7.23 (dd, 1H), 5.37 (s, 2H), 4.75-4.68 (m, 2H), 3.58-3.50 (m, 2H), 3.48-3.38 (m, 3H), 3.22-3.14 (m, 1H), 2.43 (s, 3H), 2.42-2.32 (m, 1H), 2.08-1.95 (m, 1H). |
| 199 - En 1 | 506.1 | (DMSO-d6) δ = 8.86 (d, 1H), 8.74 (d, 1H), 8.26 (d, 1H), 7.81-7.73 (m, 2H), 7.41-7.14 (m, 3H), 5.35 (s, 2H), 4.58-4.39 (m, 1H), 3.16-3.05 (m, 1H), 2.95-2.78 (m, 2H), 2.68-2.55 (m, 1H), 2.50-2.40 (m, 1H), 1.85-1.76 (m, 1H), 1.75-1.60 (m, 1H). |
| 200 | 421.1 | (DMSO-d6) δ = 0.71-0.79 (m, 4H), 2.56 (s, 3H), 3.55 (s, 2H), 4.76 (t, 1H), 5.32 (s, 2H), 6.96 (dd, 1H), 7.26 (d, 1H), 7.47 (d, 1H), 7.77-7.80 (m, 1H), 8.18 (s, 1H), 8.26 (d, 1H), 8.73 (d, 1H). |
| 201 | 388.1 | (DMSO-d6): δ 8.98 (s, 1H), 8.04 (s, 1H), 7.45 (d, 1H), 7.30 (d, 1H), 6.95 (dd, 1H), 5.31 (s, 2H), 4.97 (s, 1H), 3.78 (s, 2H), 3.67 (d, 2H), 3.43 (d, 2H), 2.59 (s, 3H), 2.42 (s, 3H). |
| 202 | 436.1 | (DMSO-d6) δ = 8.73 (d, 1H), 8.26 (d, 1H), 8.07 (s, 1H), 7.79 (dd, 1H), 7.47 (d, 1H), 7.31 (d, 1H), 6.97 (dd, 1H), 5.31 (s, 2H), 4.95 (s, 1H), 3.78 (s, 2H), 3.64 (d, 2H), 3.41 (d, 2H), 2.59 (s, 3H). |
| 203 | 409.1 | (DMSO) δ = 2.42 (s, 3H), 2.59 (s, 3H), 3.83-3.94 (m, 2H), 4.09-4.16 (m, 1H), 4.31-4.34 (m, 1H), 4.82-4.88 (m, 1H), 5.32 (s, 2H), 6.98 (dd, 1H), 7.25 (s, 1H), 7.49 (d, 1H), 8.39 (d, 1H), 8.98 (s, 1H). |
| 204 | 400.1 | (DMSO) δ = 1.59-1.67 (m, 2H), 2.25 (d, 2H), 2.59 (s, 3H), 3.64-3.71 (m, 9H), 4.95 (t, 1H), 5.14 (s, 2H), 6.86 (d, 1H), 7.00 (dd, 1H), 7.18 (d, 1H), 7.33 (d, 1H), 7.36 (s, 1H), 7.46 (d, 1H). |
| 205 - En 1 | 405.1 | (DMSO) δ = 1.74-1.87 (m, 2H), 2.41-2.49 (m, 1H), 2.57-2.59 (m, 4H), 2.78-2.98 (m, 2H), 3.11-3.19 (m, 1H), 3.68 (s, 3H), 4.42-4.53 (m, 1H), 5.12 (s, 2H), 6.86 (d, 1H), 7.02 (dd, 1H), 7.18 (d, 1H), 7.26 (d, 1H), 7.48 (d, 1H), 8.19 (d, 1H). |
| 206 | 441.2 | (DMSO-d6) δ = 1.31-1.34 (m, 3H), 1.59-1.66 (m, 2H), 2.15 (d, 2H), 2.59 (s, 3H), 3.56-3.72 (m, 6H), 4.36-4.41 (m, 2H), 4.86 (t, 1H), 5.06 (s, 2H), 6.94-7.01 (m, 2H), 7.23 (d, 1H), 7.40 (s, 1H), 7.46 (d, 1H), 7.78 (m, 1H), 8.11-8.13 (m, 1H). |
| 207 - En 1 | 446.1 | (DMSO-d6) δ = 1.32 (t, 3H), 1.68-1.80 (m, 2H), 2.44-2.49 (m, 1H), 2.56-2.63 (m, 4H), 2.77-2.93 (m, 2H), 3.07-3.14 (m, 1H), 4.35-4.52 (m, 3H), 5.05 (s, 2H), 6.95-7.01 (m, 2H), 7.19-7.22 (m, 1H), 7.47 (d, 1H), 7.78-7.81 (m, 1H), 8.11-8.13 (m, 1H), 8.22 (d, 1H). |

| cpd Nr | NMR Data |
|---|---|
| 232 | 1H NMR (400 MHz, DMSO) δ = 8.99 (s, 1H), 7.45 (d, 1H), 7.38 (d, 1H), 6.93 (dd, 1H), 5.33 (s, 2H), 2.62 (s, 3H), 2.43 (s, 3H). |
| 270 - En 1 | 1H NMR (400 MHz, DMSO) δ = 8.98 (s, 1H), 7.79 (d, 1H), 7.52-7.42 (m, 2H), 6.98 (dd, 1H), 5.32 (s, 2H), 4.30 (d, 1H), 3.80 (dd, 1H), 3.68 (dd, 1H), 2.64 (s, 3H), 2.42 (s, 3H). |
| 271 | 1H NMR (500 MHz, DMSO) δ = 8.98 (s, 1H), 7.88 (d, 1H), 7.47 (s, 1H), 7.47 (d, 1H), 7.36 (d, 1H), 7.09 (s, 1H), 6.96 (dd, 1H), 5.32 (d, 2H), 4.48 (p, 1H), 2.62 (s, 3H), 2.42 (s, 3H), 1.36 (d, 3H). |

| cpd Nr | NMR Data |
|---|---|
| 272 | 1H NMR (500 MHz, DMSO) δ = 8.99 (s, 1H), 7.59 (s, 1H), 7.52 (d, 1H), 7.48 (d, 1H), 7.35 (s, 1H), 6.97 (dd, 1H), 5.36-5.25 (m, 2H), 4.94 (td, 1H), 3.73 (dd, 1H), 3.66 (dd, 1H), 3.07 (s, 3H), 2.63 (s, 3H), 2.42 (s, 3H). |
| 273 | 1H NMR (400 MHz, DMSO) δ = 8.98 (s, 1H), 7.62 (d, 1H), 7.57-7.52 (m, 1H), 7.48 (d, 1H), 7.30 (d, 1H), 7.16 (s, 1H), 6.97 (dd, 1H), 5.32 (s, 2H), 4.37 (dd, 1H), 2.61 (s, 3H), 2.41 (s, 3H), 2.17-2.04 (m, 1H), 0.95 (dd, 6H). |
| 274 | 1H NMR (500 MHz, DMSO) δ = 7.95 (d, 1H), 7.70 (s, 1H), 7.46 (d, 1H), 7.38 (d, 1H), 6.95 (dd, 1H), 5.31 (d, 2H), 5.16 (t, 1H), 4.57-4.51 (m, 1H), 3.60 (dt, 1H), 3.53-3.40 (m, 3H), 3.04 (s, 3H), 2.63 (s, 3H), 2.60 (s, 3H). |
| 275 | 1H NMR (500 MHz, DMSO) δ = 8.99 (s, 1H), 7.96 (d, 1H), 7.47 (d, 1H), 7.41 (d, 1H), 6.96 (dd, 1H), 5.36-5.26 (m, 2H), 5.15 (s, 1H), 4.54 (d, 1H), 3.60 (dd, 1H), 3.53-3.43 (m, 3H), 3.04 (s, 3H), 2.60 (s, 3H), 2.42 (s, 3H). |
| 276 | 1H NMR (500 MHz, DMSO) δ = 8.99 (s, 1H), 7.94 (d, 1H), 7.68 (d, 1H), 7.49 (d, 1H), 7.39 (d, 1H), 6.98 (dd, 1H), 5.32 (s, 2H), 5.02 (t, 1H), 4.49 (dt, 1H), 3.72 (t, 2H), 2.63 (d, 6H), 2.42 (s, 3H). |
| 277 | 1H NMR (500 MHz, DMSO) δ = 8.01 (s, 1H), 7.71 (s, 1H), 7.47 (d, 1H), 7.30 (d, 1H), 6.97 (dd, 1H), 5.32 (s, 2H), 5.08 (q, 1H), 4.79 (dq, 1H), 4.14 (dt, 1H), 3.93 (q, 1H), 3.89-3.66 (m, 3H), 3.72-3.51 (m, 1H), 2.62 (d, 6H), 2.42 (dq, 1H). |
| 278 | 1H NMR (500 MHz, DMSO) δ = 7.86 (d, 1H), 7.72 (s, 1H), 7.47 (d, 1H), 7.33 (d, 1H), 6.96 (dd, 1H), 5.33 (s, 2H), 5.04 (dt, 1H), 4.99 (t, 1H), 3.71 (dt, 1H), 3.65 (dt, 1H), 3.13 (s, 3H), 2.89 (s, 3H), 2.62 (d, 6H). |
| 279 | 1H NMR (500 MHz, DMSO) δ = 8.98 (s, 1H), 7.88 (d, 1H), 7.47 (s, 1H), 7.47 (d, 1H), 7.36 (d, 1H), 7.09 (s, 1H), 6.96 (dd, 1H), 5.32 (d, 2H), 4.48 (p, 1H), 2.62 (s, 3H), 2.42 (s, 3H), 1.36 (d, 3H). |
| 280 | 1H NMR (500 MHz, DMSO) δ = 8.74 (dd, 1H), 8.27 (dd, 1H), 7.79 (dd, 1H), 7.64 (d, 1H), 7.54-7.45 (m, 2H), 7.43 (d, 1H), 7.18 (s, 1H), 7.00 (dd, 1H), 5.32 (s, 2H), 5.00 (t, 1H), 4.48 (dt, 1H), 3.74 (t, 2H), 2.65 (s, 3H). |
| 281 | 1H NMR (400 MHz, DMSO) δ = 8.27-8.22 (m, 1H), 7.64 (d, 1H), 7.55-7.47 (m, 2H), 7.45 (d, 1H), 7.20 (s, 1H), 7.02 (dd, 1H), 5.53 (s, 2H), 5.02 (t, 1H), 4.49 (dt, 1H), 3.75 (t, 2H), 2.64 (s, 3H). |
| 282 | 1H NMR (500 MHz, DMSO) δ = 7.65 (d, 1H), 7.51 (d, 1H), 7.47 (s, 1H), 7.40 (d, 1H), 7.18 (s, 1H), 6.99 (dd, 1H), 5.45 (d, 2H), 5.01 (t, 1H), 4.47 (dt, 1H), 3.74 (t, 2H), 2.66 (d, 6H). |
| 283 | 1H NMR (400 MHz, DMSO) δ = 7.64 (d, 1H), 7.49 (d, 2H), 7.42 (d, 1H), 7.19 (d, 2H), 6.98 (dd, 1H), 5.13 (s, 2H), 5.07 (t, 1H), 4.49 (dt, 1H), 3.75 (q, 2H), 2.64 (s, 3H), 2.42 (s, 3H). |
| 284 | 1H NMR (500 MHz, DMSO) δ = 8.41 (dd, 1H), 7.83 (dd, 1H), 7.65 (d, 1H), 7.50 (d, 2H), 7.46 (d, 1H), 7.24 (dd, 1H), 7.19 (s, 1H), 7.01 (dd, 1H), 5.16 (s, 2H), 5.05 (s, 1H), 4.48 (dt, 1H), 3.75 (d, 2H), 2.65 (s, 3H), 2.54 (s, 3H). |
| 285 | 1H NMR (500 MHz, DMSO) δ = 7.61 (d, 1H), 7.58 (s, 1H), 7.48 (d, 2H), 7.43 (d, 1H), 7.20 (s, 1H), 6.99 (dd, 1H), 5.13 (s, 2H), 5.03 (t, 1H), 4.49 (dt, 1H), 3.81-3.70 (m, 2H), 2.65 (d, 6H). |
| 286 | 1H NMR (500 MHz, DMSO) δ = 13.70 (s, 1H), 8.13 (s, 1H), 7.65 (d, 1H), 7.52-7.44 (m, 2H), 7.40 (d, 1H), 7.19 (s, 1H), 6.93 (dd, 1H), 5.06 (s, 2H), 5.04 (s, 1H), 4.48 (dt, 1H), 3.78-3.72 (m, 2H), 2.64 (s, 3H). |
| 287 | 1H NMR (500 MHz, DMSO) δ = 8.57 (s, 1H), 8.42 (d, 1H), 7.64 (d, 1H), 7.53-7.44 (m, 3H), 7.28 (d, 1H), 7.19 (s, 1H), 7.01 (dd, 1H), 5.17 (s, 2H), 5.02 (t, 1H), 4.48 (dt, 1H), 3.78-3.71 (m, 2H), 2.65 (s, 3H), 2.38 (s, 3H). |
| 288 | 1H NMR (500 MHz, DMSO) δ = 8.98 (s, 1H), 7.63 (d, 1H), 7.49 (d, 1H), 7.47 (s, 1H), 7.42 (d, 1H), 7.21-7.17 (m, 1H), 6.98 (dd, 1H), 5.32 (s, 2H), 5.01 (t, 1H), 4.48 (dt, 1H), 3.74 (tt, 2H), 2.64 (s, 3H), 2.42 (s, 3H). |
| 289 | 1H NMR (400 MHz, DMSO) δ = 7.62 (d, 1H), 7.53-7.45 (m, 2H), 7.42 (d, 1H), 7.19 (s, 1H), 6.99 (dd, 1H), 6.36 (d, 1H), 5.16 (s, 2H), 5.01 (t, 1H), 4.48 (dt, 1H), 3.74 (tt, 2H), 2.64 (s, 3H), 2.41 (d, 3H). |
| 290 | 1H NMR (500 MHz, DMSO) δ = 8.88 (s, 1H), 7.62 (d, 1H), 7.51-7.42 (m, 3H), 7.19 (s, 1H), 6.99 (dd, 1H), 5.15 (s, 2H), 5.02 (t, 1H), 4.48 (dt, 1H), 3.75 (tt, 2H), 2.64 (s, 3H), 2.53-2.49 (m, 3H). |
| 291 | 1H NMR (500 MHz, DMSO) δ = 8.55 (d, 1H), 7.78 (dd, 1H), 7.62 (d, 1H), 7.48 (s, 1H), 7.48 (d, 1H), 7.42 (d, 1H), 7.28 (d, 1H), 7.19 (s, 1H), 6.98 (dd, 1H), 5.13 (s, 2H), 5.02 (t, 1H), 4.48 (dt, 1H), 3.81-3.69 (m, 2H), 2.64 (s, 3H), 2.47 (s, 3H). |
| 292 | 1H NMR (600 MHz, DMSO) δ = 7.60 (d, 1H), 7.47 (d, 2H), 7.35 (d, 1H), 7.16 (s, 1H), 6.94 (dd, 1H), 5.07-4.99 (m, 1H), 4.73 (dd, 2H), 4.49 (d, 1H), 4.45 (t, 2H), 4.24 (d, 2H), 3.76 (h, 2H), 3.47-3.39 (m, 1H), 2.64 (s, 3H). |
| 293 | 1H NMR (500 MHz, DMSO) δ = 9.22 (dd, 1H), 7.87 (dd, 1H), 7.76 (dd, 1H), 7.64 (d, 1H), 7.52-7.45 (m, 3H), 7.21-7.17 (m, 1H), 7.04 (dd, 1H), 5.43 (s, 2H), 5.02 (t, 1H), 4.48 (dt, 1H), 3.75 (td, 2H), 2.64 (s, 3H). |
| 294 | 1H NMR (600 MHz, DMSO) δ = 9.18 (d, 1H), 8.83 (d, 1H), 7.67 (dd, 1H), 7.61 (d, 1H), 7.50 (d, 1H), 7.46 (s, 1H), 7.43 (d, 1H), 7.16 (s, 1H), 7.03 (dd, 1H), 5.24 (s, 2H), 4.48 (dt, 1H), 3.79-3.71 (m, 2H), 2.64 (s, 3H). |
| 295 | 1H NMR (500 MHz, DMSO) δ = 7.63 (d, 1H), 7.55-7.47 (m, 3H), 7.45 (d, 1H), 7.20 (s, 1H), 7.00 (dd, 1H), 6.54-6.24 (m, 2H), 5.24 (s, 2H), 5.02 (t, 1H), 4.67 (td, 2H), 4.49 (dt, 1H), 3.75 (tt, 2H), 2.64 (s, 3H). |
| 296 | 1H NMR (500 MHz, DMSO) δ = 8.26 (dd, 1H), 8.06 (dd, 1H), 7.98-7.57 (m, 2H), 7.48 (s, 1H), 7.57-7.24 (m, 3H), 7.24-7.09 (m, 1H), 7.00 (dd, 1H), 5.13 (s, 2H), 5.00 (t, 1H), 4.48 (dt, 1H), 3.87-3.62 (m, 2H), 2.65 (s, 3H). |
| 297 | 1H NMR (500 MHz, DMSO) δ = 8.19 (dd, 1H), 7.77 (dd, 1H), 7.63 (d, 1H), 7.53-7.45 (m, 2H), 7.42 (d, 1H), 7.18 (s, 1H), 6.94 (ddd, 2H), 5.08 (s, 2H), 5.00 (t, 1H), 4.48 (dt, 1H), 3.75 (td, 2H), 2.86 (s, 6H), 2.64 (s, 3H). |
| 298 | 1H NMR (500 MHz, DMSO) δ = 7.62 (d, 1H), 7.48 (d, 2H), 7.39 (d, 1H), 7.19 (s, 1H), 6.96 (dd, 1H), 5.23 (s, 2H), 5.01 (t, 1H), 4.48 (dt, 1H), 3.80-3.70 (m, 2H), 2.64 (s, 3H), 2.57 (s, 3H), 2.32 (s, 3H). |
| 299 | 1H NMR (500 MHz, DMSO) δ = 7.62 (d, 1H), 7.51-7.45 (m, 2H), 7.42 (d, 1H), 7.18 (s, 1H), 6.97 (dd, 1H), 5.08-4.99 (m, 3H), 4.48 (dt, 1H), 3.81-3.69 (m, 2H), 2.64 (s, 3H), 2.58 (s, 3H), 2.42 (s, 3H). |

| cpd Nr | NMR Data |
|---|---|
| 300 | 1H NMR (500 MHz, DMSO) δ = 7.92 (dd, 1H), 7.61 (d, 1H), 7.55 (dd, 1H), 7.51-7.46 (m, 2H), 7.44 (d, 1H), 7.21-7.17 (m, 1H), 6.99 (dd, 1H), 6.57 (dd, 1H), 5.86 (s, 2H), 5.05-4.96 (m, 3H), 4.49 (dt, 1H), 3.81-3.70 (m, 2H), 2.64 (s, 3H). |
| 301 | 1H NMR (500 MHz, DMSO) δ = 8.85-8.64 (m, 1H), 8.22-8.01 (m, 1H), 7.74-7.16 (m, 6H), 7.29-7.09 (m, 1H), 6.99 (dd, 1H), 5.35 (s, 2H), 5.01 (t, 1H), 4.48 (dt, 1H), 3.75 (td, 2H), 2.64 (s, 3H). |
| 302 | 1H NMR (500 MHz, DMSO) δ = 7.65 (d, 1H), 7.51 (d, 1H), 7.46 (dd, 3H), 7.21-7.16 (m, 1H), 7.01 (dd, 1H), 5.18 (s, 2H), 5.01 (t, 1H), 4.48 (dt, 1H), 3.83 (s, 3H), 3.75 (td, 2H), 2.64 (s, 3H). |
| 303 | 1H NMR (500 MHz, DMSO) δ = 7.79 (d, 1H), 7.71 (s, 1H), 7.56 (s, 1H), 7.48 (d, 1H), 7.35 (d, 1H), 7.24 (s, 1H), 6.96 (dd, 1H), 5.33 (s, 2H), 4.66 (ddd, 1H), 3.73-3.61 (m, 2H), 3.30 (s, 3H), 2.62 (d, 6H). |
| 304 | 1H NMR (400 MHz, DMSO) δ = 8.98 (s, 1H), 7.62 (d, 1H), 7.58-7.52 (m, 1H), 7.48 (d, 1H), 7.30 (d, 1H), 7.16 (s, 1H), 6.97 (dd, 1H), 5.32 (s, 2H), 4.37 (d, 1H), 2.61 (s, 3H), 2.41 (s, 3H), 2.11 (h, 1H), 0.95 (dd, 6H). |
| 305 | 1H NMR (500 MHz, DMSO) δ = 7.99-7.93 (m, 1H), 7.72 (s, 1H), 7.67 (d, 1H), 7.48 (d, 1H), 7.38 (d, 1H), 6.98 (dd, 1H), 5.33 (s, 2H), 5.07 (s, 1H), 4.49 (dt, 1H), 3.77-3.67 (m, 2H), 2.67-2.57 (m, 9H). |
| 306 | 1H NMR (500 MHz, DMSO) δ = 8.99 (s, 1H), 7.95 (q, 1H), 7.69 (d, 1H), 7.49 (d, 1H), 7.39 (d, 1H), 6.98 (dd, 1H), 5.32 (s, 2H), 5.05 (s, 1H), 4.49 (dt, 1H), 3.72 (d, 2H), 2.63 (d, 6H), 2.42 (s, 3H). |
| 307 | 1H NMR (400 MHz, DMSO) δ = 7.88 (d, 1H), 7.72 (s, 1H), 7.47 (d, 1H), 7.33 (d, 1H), 6.96 (dd, 1H), 5.33 (s, 2H), 5.02 (s, 1H), 4.83 (q, 1H), 3.76-3.56 (m, 3H), 3.44-3.30 (m, 1H), 2.62 (d, 6H), 1.91 (p, 2H), 1.80 (p, 2H). |
| 308 | 1H NMR (400 MHz, DMSO) δ = 9.01 (s, 1H), 8.71 (s, 1H), 7.69 (d, 1H), 7.58-7.06 (m, 3H), 5.37 (s, 2H), 4.82 (t, 1H), 3.57 (d, 2H), 2.44 (s, 3H), 0.80 (dt, 4H). |
| 309 | 1H NMR (400 MHz, DMSO) δ = 9.01 (s, 1H), 8.95 (s, 1H), 7.72 (d, 1H), 7.78-7.09 (m, 3H), 5.38 (s, 2H), 5.28 (s, 1H), 4.72 (d, 2H), 4.54 (d, 1H), 3.81 (s, 2H), 2.44 (s, 3H). |
| 310 - En 1 | 1H NMR (400 MHz, DMSO) δ = 9.00 (s, 1H), 8.84 (d, 1H), 7.73 (d, 1H), 7.52-7.02 (m, 3H), 5.36 (s, 2H), 4.62-4.37 (m, 1H), 3.13 (s, 1H), 3.03-2.73 (m, 2H), 2.60 (d, 1H), 2.42 (s, 4H), 1.97-1.55 (m, 2H). |
| 311 | 1H NMR (500 MHz, DMSO) δ = 11.77 (s, 1H), 8.00 (s, 1H), 7.80-7.48 (m, 2H), 7.48-7.04 (m, 4H), 6.22 (t, 1H), 4.94 (s, 2H), 4.92 (s, 1H), 3.81-3.46 (m, 6H), 2.17 (d, 2H), 1.60 (ddd, 2H). |
| 312 | 1H NMR (500 MHz, DMSO) δ = 8.17 (dd, 1H), 8.01 (s, 1H), 7.91-7.60 (m, 2H), 7.51-7.12 (m, 3H), 7.03 (dd, 1H), 5.12 (s, 2H), 4.91 (t, 1H), 3.93 (s, 3H), 3.81-3.54 (m, 4H), 3.56 (td, 2H), 2.16 (d, 2H), 1.72-1.47 (m, 2H). |
| 313 - En 1 | 1H NMR (500 MHz, DMSO) δ = 8.73 (dd, 1H), 8.30-8.20 (m, 2H), 7.78 (dd, 1H), 7.44 (d, 1H), 7.19 (d, 1H), 6.96 (dd, 1H), 5.31 (s, 2H), 4.55-4.43 (m, 1H), 3.19-3.04 (m, 1H), 2.97-2.77 (m, 2H), 2.67-2.50 (m, 2H), 1.78 (s, 2H), 1.21-0.98 (m, 4H). |
| 314 | 1H NMR (500 MHz, DMSO) δ = 8.98 (s, 1H), 7.43-7.37 (m, 2H), 7.25 (d, 1H), 6.92 (dd, 1H), 5.30 (s, 2H), 4.91 (t, 1H), 3.75-3.58 (m, 6H), 2.60-2.50 (m, 1H), 2.41 (s, 3H), 2.20 (d, 2H), 1.65 (ddd, 2H), 1.10 (dt, 2H), 1.11-1.02 (m, 2H). |
| 315 - En 1 | 1H NMR (400 MHz, DMSO) δ = 8.98 (s, 1H), 8.59 (d, 1H), 8.08 (d, 1H), 7.47 (d, 1H), 7.33 (d, 1H), 7.19 (d, 1H), 6.97 (dd, 1H), 5.40-5.28 (m, 1H), 5.32 (s, 2H), 2.61 (s, 3H), 2.42 (s, 3H), 1.58 (d, 3H). |
| 316 - En 1 | 1H NMR (400 MHz, DMSO) δ = 8.98 (s, 1H), 8.44 (s, 1H), 7.50 (d, 1H), 7.24 (d, 1H), 6.99 (dd, 1H), 5.31 (s, 2H), 5.24 (t, 1H), 4.81 (t, 1H), 3.77 (dp, 2H), 2.59 (s, 3H), 2.42 (s, 3H). |
| 317 - En 1 | 1H NMR (500 MHz, DMSO) δ = 8.99 (s, 1H), 8.26 (dd, 1H), 7.69 (d, 1H), 7.53-7.45 (m, 2H), 6.99 (dd, 1H), 5.38-5.28 (m, 2H), 4.86 (ddd, 1H), 3.92 (td, 2H), 3.55 (ddd, 1H), 3.47 (dd, 1H), 3.38-3.32 (m, 1H), 3.10 (ddd, 1H), 2.66 (s, 3H), 2.42 (s, 3H). |
| 318 | 1H NMR (500 MHz, DMSO) δ = 8.24 (s, 1H), 7.70 (s, 1H), 7.50-7.43 (m, 2H), 7.37 (d, 1H), 6.97 (dd, 1H), 5.34 (s, 2H), 2.63 (d, 6H), 2.62 (d, 3H), 2.55 (dd, 1H), 2.26 (ddd, 2H), 2.00-1.80 (m, 2H). |
| 319 | 1H NMR (500 MHz, DMSO) δ = 8.99 (s, 1H), 8.24 (s, 1H), 7.50-7.42 (m, 2H), 7.37 (d, 1H), 6.97 (dd, 1H), 5.34 (s, 2H), 2.66-2.57 (m, 6H), 2.61-2.51 (m, 2H), 2.43 (s, 3H), 2.26 (tdt, 2H), 2.00-1.79 (m, 2H). |
| 320 | 1H NMR (500 MHz, DMSO) δ = 8.58 (d, 1H), 8.24 (s, 1H), 7.84 (t, 1H), 7.56 (d, 1H), 7.46 (dd, 2H), 7.36 (dd, 2H), 7.01 (d, 1H), 5.23 (s, 2H), 2.65-2.59 (m, 5H), 2.24 (q, 2H), 1.93 (s, 1H), 1.86 (d, 1H). |
| 321 | 1H NMR (500 MHz, DMSO) δ = 8.99 (s, 1H), 7.99 (t, 1H), 7.87 (d, 1H), 7.51-7.42 (m, 2H), 6.97 (dd, 1H), 5.33 (s, 2H), 3.88 (d, 2H), 2.67-2.60 (m, 6H), 2.43 (s, 3H). |
| 322 | 1H NMR (600 MHz, DMSO) δ = 8.99 (s, 1H), 7.92 (s, 1H), 7.47 (d, 1H), 7.38 (d, 1H), 7.15 (t, 1H), 6.96 (dd, 1H), 5.33 (s, 2H), 3.42 (q, 1H), 3.17 (q, 2H), 2.93 (s, 3H), 2.62 (s, 3H), 2.43 (s, 3H). |
| 323 | 1H NMR (600 MHz, DMSO) δ = 8.99 (s, 1H), 8.08 (t, 1H), 7.48 (d, 1H), 7.43 (d, 1H), 6.97 (dd, 1H), 5.33 (s, 2H), 3.74 (td, 2H), 3.44 (t, 2H), 3.07 (s, 3H), 2.63 (s, 3H), 2.43 (s, 3H). |
| 324 | 1H NMR (400 MHz, DMSO) δ = 8.99 (s, 1H), 8.67 (s, 1H), 7.72 (d, 1H), 7.54-7.43 (m, 2H), 6.99 (dd, 1H), 5.35 (s, 2H), 4.86 (d, 2H), 4.68 (d, 2H), 2.70-2.61 (m, 6H), 2.43 (s, 3H). |
| 325 | 1H NMR (400 MHz, DMSO) δ = 8.58 (dd, 1H), 8.15 (dd, 2H), 7.68-7.57 (m, 2H), 7.48 (d, 1H), 7.39 (s, 1H), 7.22 (d, 1H), 6.97 (dd, 1H), 5.59 (s, 2H), 4.86 (s, 1H), 3.74-3.50 (m, 6H), 2.61 (s, 3H), 2.14 (d, 2H), 1.62 (ddd, 2H). |
| 326 - En 1 | 1H NMR (400 MHz, DMSO) δ = 8.99 (s, 1H), 8.43 (d, 1H), 7.35 (dd, 1H), 7.24 (dd, 1H), 5.36 (s, 2H), 4.72 (s, 1H), 4.64 (dt, 1H), 3.56-3.32 (m, 5H), 3.18 (dt, 1H), 2.55 (s, 3H), 2.39 (s, 3H), 2.44-2.31 (m, 1H), 1.89 (dq, 1H). |
| 327 | 1H NMR (500 MHz, DMSO) δ = 8.99 (s, 1H), 8.42 (s, 1H), 7.33 (d, 1H), 7.22 (t, 1H), 5.36 (s, 2H), 4.73 (s, 1H), 3.55 (d, 2H), 2.39 (s, 3H), 0.83-0.75 (m, 2H), 0.71-0.65 (m, 2H). |
| 328 | 1H NMR (400 MHz, DMSO) δ = 8.99 (s, 1H), 8.65 (s, 1H), 7.36 (dd, 1H), 7.25 (dd, 1H), 5.37 (s, 2H), 5.18 (t, 1H), 4.65-4.53 (m, 4H), 3.73 (d, 2H), 2.53 (s, 3H), 2.39 (s, 3H). |
| 329 | 1H NMR (400 MHz, DMSO) δ = 11.75 (s, 1H), 7.72 (s, 1H), 7.62-7.54 (m, 1H), 7.39 (dd, 1H), 7.32 (dd, 1H), 7.25-7.15 (m, 1H), 6.23 (t, 1H), 4.95 (s, 2H), 4.81 (t, 1H), 3.72-3.55 (m, 6H), 2.52 (s, 3H), 2.15-2.05 (m, 2H), 1.70-1.57 (m, 1H). |
| 330 | 1H NMR (500 MHz, DMSO) δ = 8.17 (dd, 1H), 7.81 (dd, 1H), 7.73 (s, 1H), 7.33 (d, 1H), 7.20 (t, 1H), 7.03 (dd, 1H), 5.13 (s, 2H), 4.81 (t, 1H), 3.91 (s, 3H), 3.72-3.56 (m, 6H), 2.52 (s, 3H), 2.14-2.06 (m, 2H), 1.63 (ddd, 2H). |

| cpd Nr | NMR Data |
|---|---|
| 331 | 1H NMR (500 MHz, DMSO) δ = 7.47 (d, 1H), 7.37 (s, 1H), 7.32 (d, 1H), 7.26 (d, 1H), 7.10-6.85 (m, 2H), 6.55-6.13 (m, 1H), 5.18 (s, 2H), 4.91 (t, 1H), 4.58 (td, 2H), 3.82-3.52 (m, 6H), 2.60 (s, 3H), 2.20 (d, 2H), 1.76-1.51 (m, 2H). |
| 332 - En 1 | 1H NMR (500 MHz, DMSO) δ = 7.69-7.30 (m, 4H), 7.31 (s, 1H), 6.99 (d, 1H), 6.58-6.16 (m, 2H), 5.23 (s, 3H), 4.67 (td, 2H), 3.74 (d, 1H), 3.64 (d, 1H), 3.38-3.20 (m, 1H), 3.20-3.02 (m, 1H), 2.61 (s, 3H), 2.20 (dt, 2H), 1.79 (q, 2H). |
| 333 - En 1 | 1H NMR (500 MHz, DMSO) δ = 7.79 (s, 1H), 7.71-7.39 (m, 3H), 7.29 (d, 1H), 6.99 (dd, 1H), 6.59-6.16 (m, 2H), 5.23 (s, 3H), 4.68 (td, 2H), 3.61 (q, 2H), 3.41-3.08 (m, 2H), 2.60 (s, 3H), 2.63-2.28 (m, 2H). |
| 334 | 1H NMR (400 MHz, DMSO) δ = 7.52 (d, 1H), 7.47 (d, 1H), 7.40 (s, 1H), 7.28 (d, 1H), 6.98 (dd, 1H), 6.65-6.11 (m, 2H), 5.23 (s, 2H), 4.89 (t, 1H), 4.67 (td, 2H), 3.84-3.47 (m, 6H), 2.61 (s, 3H), 2.18 (d, 2H), 1.67 (d, 0H), 1.64 (s, 1H). |
| 335 - En 1 | 1H NMR (400 MHz, DMSO) δ = 8.18 (d, 1H), 8.09 (dd, 1H), 7.60 (dd, 1H), 7.47 (d, 1H), 7.36 (d, 1H), 6.97 (dd, 1H), 6.69 (dd, 1H), 4.95 (s, 2H), 4.70 (dt, 2H), 4.08 (t, 4H), 3.52 (d, 2H), 3.49-3.36 (m, 3H), 3.17 (dt, 1H), 2.62 (s, 3H), 2.23 (p, 2H), 2.05-1.89 (m, 1H). |
| 336 - En 1 | 1H NMR (400 MHz, DMSO) δ = 8.22 (d, 1H), 8.09 (dd, 1H), 7.58 (dd, 1H), 7.47 (d, 1H), 7.21 (d, 1H), 6.97 (dd, 1H), 6.69 (dd, 1H), 4.93 (s, 2H), 4.46 (dd, 1H), 4.07 (t, 4H), 3.20-3.04 (m, 1H), 2.98-2.74 (m, 2H), 2.62 (d, 1H), 2.57 (s, 3H), 2.43 (s, 1H), 2.23 (p, 2H), 1.83-1.62 (m, 2H). |
| 337 | 1H NMR (400 MHz, DMSO) δ = 8.08 (dd, 1H), 7.59 (dd, 1H), 7.46 (d, 1H), 7.41 (s, 1H), 7.25 (d, 1H), 6.96 (dd, 1H), 6.69 (dd, 1H), 4.94 (s, 2H), 4.89 (t, 1H), 4.08 (t, 4H), 3.75-3.66 (m, 2H), 3.71-3.56 (m, 4H), 2.60 (s, 3H), 2.29-2.13 (m, 4H), 1.70-1.57 (m, 2H). |
| 338 - En 1 | 1H NMR (500 MHz, DMSO) δ = 8.36-8.14 (m, 2H), 8.04 (dd, 1H), 7.77 (t, 1H), 7.49 (d, 1H), 7.40-7.12 (m, 2H), 7.00 (dd, 1H), 5.24-5.00 (m, 2H), 4.47 (dt, 1H), 3.26-3.00 (m, 1H), 3.00-2.70 (m, 2H), 2.58 (d, 1H), 2.57 (s, 3H), 2.42 (s, 1H), 1.90-1.57 (m, 2H). |
| 339 | 1H NMR (500 MHz, DMSO) δ = 8.25 (dd, 1H), 8.04 (dd, 1H), 7.76 (t, 1H), 7.55-7.16 (m, 4H), 6.98 (dd, 1H), 5.13 (s, 2H), 4.88 (s, 1H), 3.80-3.47 (m, 6H), 2.60 (s, 3H), 2.16 (d, 2H), 1.62 (ddd, 2H). |
| 340 - En 1 | 1H NMR (500 MHz, DMSO) δ = 8.67 (dd, 1H), 8.20 (d, 1H), 8.13 (d, 1H), 7.75-6.87 (m, 5H), 5.36 (s, 2H), 4.69 (dt, 1H), 3.53 (t, 2H), 3.48-3.35 (m, 3H), 3.25-3.05 (m, 1H), 2.62 (s, 3H), 2.48-2.23 (m, 1H), 1.96 (dq, 1H). |
| 341 | 1H NMR (400 MHz, DMSO) δ = 8.67 (dd, 1H), 8.36 (s, 1H), 8.13 (dd, 1H), 7.78-7.36 (m, 2H), 7.48-6.86 (m, 3H), 5.36 (s, 2H), 5.28-5.06 (m, 1H), 4.67 (d, 2H), 4.55 (d, 2H), 3.77 (d, 2H), 2.61 (s, 3H). |
| 342 - En 1 | 1H NMR (400 MHz, DMSO) δ = 8.66 (dd, 1H), 8.22 (d, 1H), 8.12 (d, 1H), 7.77-7.37 (m, 2H), 7.37-6.86 (m, 3H), 5.34 (s, 2H), 4.73-4.20 (m, 1H), 3.11 (s, 1H), 3.02-2.65 (m, 2H), 2.57 (s, 3H), 2.42 (s, 1H), 1.93-1.53 (m, 2H). |
| 343 | 1H NMR (400 MHz, DMSO) δ = 8.67 (dd, 1H), 8.26-8.00 (m, 1H), 7.78-7.29 (m, 3H), 7.44-6.85 (m, 3H), 5.35 (s, 2H), 4.88 (t, 1H), 3.84-3.46 (m, 6H), 2.61 (s, 3H), 2.16 (d, 2H), 1.87-1.47 (m, 2H). |
| 344 | 1H NMR (500 MHz, DMSO) δ = 8.18 (dd, 1H), 7.76 (dd, 1H), 7.48-7.39 (m, 2H), 7.23 (d, 1H), 6.97-6.90 (m, 2H), 5.08 (s, 2H), 4.88 (s, 1H), 3.74-3.67 (m, 2H), 3.67-3.57 (m, 4H), 2.85 (s, 6H), 2.59 (s, 3H), 2.17 (d, 2H), 1.68-1.58 (m, 2H). |
| 345 | 1H NMR (400 MHz, DMSO) δ = 7.45 (d, 1H), 7.40 (s, 1H), 7.23 (d, 1H), 6.93 (dd, 1H), 5.22 (s, 2H), 4.89 (t, 1H), 3.75-3.56 (m, 6H), 2.60 (s, 3H), 2.57 (s, 3H), 2.32 (s, 3H), 2.17 (d, 2H), 1.63 (ddd, 2H). |
| 346 | 1H NMR (500 MHz, DMSO) δ = 7.92 (dd, 1H), 7.51 (dd, 1H), 7.46 (d, 1H), 7.37 (s, 1H), 7.27 (d, 1H), 6.97 (dd, 1H), 6.56 (dd, 1H), 5.85 (s, 2H), 4.97 (s, 2H), 4.90 (s, 1H), 3.70 (dt, 2H), 3.66 (s, 2H), 3.61 (td, 2H), 2.61 (s, 3H), 2.17 (d, 2H), 1.64 (ddd, 2H). |
| 347 | 1H NMR (400 MHz, DMSO) δ = 8.75 (dd, 1H), 8.22 (dd, 1H), 7.80 (dd, 1H), 7.50 (d, 1H), 7.43 (s, 1H), 7.30 (d, 1H), 7.01 (dd, 1H), 5.33 (s, 2H), 4.88 (s, 1H), 3.74-3.55 (m, 6H), 2.61 (s, 3H), 2.17 (d, 2H), 1.70-1.57 (m, 2H). |
| 348 - En 1 | 1H NMR (400 MHz, DMSO) δ = 8.20 (d, 1H), 8.13 (dd, 1H), 7.82 (dd, 1H), 7.47 (d, 1H), 7.35 (d, 1H), 6.99 (ddd, 2H), 5.07 (s, 2H), 4.77-4.61 (m, 1H), 4.39 (q, 2H), 3.52 (q, 2H), 3.49-3.36 (m, 3H), 3.17 (dt, 1H), 2.61 (s, 3H), 2.41-2.31 (m, 1H), 1.96 (p, 1H), 1.33 (t, 3H), 1.23 (s, 1H). |
| 349 - En 1 | 1H NMR (400 MHz, DMSO) δ = 11.76 (s, 1H), 7.61-7.54 (m, 1H), 7.48 (dd, 2H), 7.42-7.31 (m, 2H), 6.95 (dd, 1H), 6.22 (t, 1H), 5.65 (s, 1H), 4.89 (s, 2H), 4.45-4.34 (m, 2H), 4.31 (ddd, 1H), 4.02-3.90 (m, 2H), 3.63 (dd, 1H), 3.58 (t, 1H), 2.63 (s, 3H). |
| 350 - En 1 | 1H NMR (500 MHz, DMSO) δ = 8.15 (d, 1H), 7.54 (dd, 1H), 7.47-7.38 (m, 2H), 7.34 (s, 1H), 6.92 (dd, 1H), 6.20 (t, 1H), 4.96-4.86 (m, 2H), 4.33 (dt, 1H), 4.19 (tt, 1H), 4.05 (dd, 1H), 3.91 (dd, 1H), 3.63 (dd, 1H), 3.54 (dd, 1H), 2.57 (s, 3H). |
| 351 | 1H NMR (500 MHz, DMSO) δ = 8.73 (d, 1H), 8.11 (d, 1H), 7.69-7.16 (m, 5H), 6.96 (dd, 1H), 5.36 (s, 2H), 4.88 (t, 1H), 3.71 (d, 2H), 3.75-3.52 (m, 4H), 2.59 (s, 3H), 2.17 (d, 2H), 1.64 (s, 2H). |
| 352 | 1H NMR (500 MHz, DMSO) δ = 8.45 (dt, 1H), 7.79 (ddd, 1H), 7.53 (dt, 1H), 7.45 (d, 1H), 7.40 (s, 1H), 7.30 (d, 1H), 6.96 (dd, 1H), 5.25 (s, 2H), 4.88 (t, 1H), 3.74-3.58 (m, 6H), 2.59 (s, 3H), 2.18 (d, 2H), 1.63 (ddd, 2H). |
| 355 - En 1 | 1H NMR (500 MHz, DMSO) δ = 7.58 (d, 1H), 7.55-7.45 (m, 3H), 7.31 (d, 1H), 7.00 (dd, 1H), 5.22 (t, 1H), 5.17 (s, 2H), 3.83 (s, 3H), 3.73 (dd, 1H), 3.64 (dd, 1H), 3.27 (dt, 1H), 3.16-3.09 (m, 1H), 2.60 (s, 3H), 2.27-2.14 (m, 2H), 1.85-1.73 (m, 1H). |
| 356 - En 1 | 1H NMR (500 MHz, DMSO) δ = 7.78 (s, 1H), 7.54-7.45 (m, 3H), 7.29 (d, 1H), 6.99 (dd, 1H), 5.19 (d, 3H), 3.83 (s, 3H), 3.60 (qd, 2H), 3.20 (q, 1H), 2.60 (s, 3H), 2.49-2.35 (m, 2H). |
| 357 | 1H NMR (400 MHz, DMSO) δ = 7.51-7.44 (m, 2H), 7.41 (s, 1H), 7.29 (d, 1H), 6.97 (dd, 1H), 5.17 (s, 2H), 4.89 (s, 1H), 3.83 (d, 3H), 3.76-3.56 (m, 6H), 2.60 (s, 3H), 2.18 (d, 2H), 1.64 (ddd, 2H). |
| 358 | 1H NMR (500 MHz, DMSO) δ = 8.28 (dd, 1H), 7.50-7.40 (m, 3H), 7.39 (s, 1H), 7.24 (d, 1H), 6.96 (dd, 1H), 5.12 (s, 2H), 4.90 (s, 2H), 4.07 (dd, 2H), 3.74-3.57 (m, 8H), 2.59 (s, 3H), 2.21-2.13 (m, 2H), 1.63 (ddd, 2H). |
| 359 | 1H NMR (400 MHz, DMSO) δ = 8.58 (d, 1H), 7.77 (td, 1H), 7.62 (dd, 1H), 7.46 (d, 1H), 7.39 (s, 1H), 7.24 (d, 1H), 6.98 (dd, 1H), 5.20 (s, 2H), 4.88 (t, 1H), 3.74-3.54 (m, 6H), 2.59 (s, 3H), 2.16 (d, 2H), 1.69-1.56 (m, 2H). |

| cpd Nr | NMR Data |
|---|---|
| 360 - En 1 | 1H NMR (400 MHz, DMSO) δ = 9.00 (s, 1H), 8.24 (d, 1H), 7.62 (d, 1H), 7.56 (d, 1H), 5.40 (s, 2H), 4.69 (dt, 1H), 3.53 (s, 2H), 3.51-3.36 (m, 3H), 3.18 (dt, 1H), 2.61 (s, 3H), 2.42 (s, 3H), 2.38 (dd, 1H), 1.97 (dq, 1H). |
| 361 | 1H NMR (400 MHz, DMSO) δ = 9.00 (s, 1H), 8.20 (s, 1H), 7.59 (d, 1H), 7.46 (d, 1H), 5.39 (s, 2H), 4.79 (s, 1H), 3.57 (s, 2H), 2.55 (s, 3H), 2.42 (s, 3H), 0.77 (dt, 4H). |
| 362 | 1H NMR (400 MHz, DMSO) δ = 9.00 (s, 1H), 8.39 (s, 1H), 7.62 (d, 1H), 7.51 (d, 1H), 5.40 (s, 2H), 5.22 (s, 1H), 4.68 (d, 2H), 4.56 (d, 2H), 3.79 (d, 2H), 2.60 (s, 3H), 2.42 (s, 3H). |
| 363 | 1H NMR (500 MHz, DMSO) δ = 7.70 (dd, 2H), 7.55 (d, 1H), 7.40 (d, 1H), 6.23 (t, 1H), 4.97 (s, 2H), 4.08 (s, 2H), 3.72 (t, 2H), 3.62 (d, 2H), 2.74 (s, 3H), 1.75-1.64 (m, 2H), 1.33 (d, 2H). |
| 364 | 1H NMR (500 MHz, DMSO) δ = 8.17 (dd, 1H), 7.81 (dd, 1H), 7.62 (d, 1H), 7.44 (s, 1H), 7.39 (d, 1H), 7.04 (dd, 1H), 5.14 (s, 2H), 4.88 (t, 1H), 3.93 (s, 3H), 3.74-3.62 (m, 4H), 3.58 (td, 2H), 2.60 (s, 3H), 2.15 (d, 2H), 1.62 (ddd, 2H). |
| 365 - En 1 | 1H NMR (500 MHz, DMSO) δ = 9.00 (s, 1H), 8.29 (d, 1H), 7.20 (d, 1H), 7.02 (dd, 1H), 5.34 (s, 2H), 4.68 (dt, 1H), 3.52 (t, 2H), 3.47-3.37 (m, 3H), 3.22-3.13 (m, 1H), 2.64 (s, 3H), 2.43 (s, 3H), 2.35 (s, 1H), 1.96 (dq, 1H). |
| 366 | 1H NMR (500 MHz, DMSO) δ = 9.00 (s, 1H), 8.25 (s, 1H), 7.10 (d, 1H), 6.98 (dd, 1H), 5.34 (s, 2H), 4.78 (d, 1H), 3.55 (d, 2H), 2.58 (s, 3H), 2.43 (s, 3H), 0.76 (dt, 4H). |
| 367 | 1H NMR (500 MHz, DMSO) δ = 9.00 (s, 1H), 8.44 (s, 1H), 7.16 (d, 1H), 7.02 (dd, 1H), 5.34 (s, 2H), 5.20 (t, 1H), 4.67 (d, 2H), 4.54 (d, 2H), 3.78 (d, 2H), 2.63 (s, 3H), 2.43 (s, 3H). |
| 368 | 1H NMR (400 MHz, DMSO) δ = 11.77 (s, 1H), 7.58 (dd, 1H), 7.51 (s, 1H), 7.39 (d, 1H), 7.05 (d, 1H), 6.96 (dd, 1H), 6.22 (t, 1H), 4.89 (d, 3H), 3.74-3.53 (m, 6H), 2.62 (s, 3H), 2.16 (d, 2H), 1.68-1.55 (m, 2H). |
| 369 | 1H NMR (400 MHz, DMSO) δ = 8.16 (dd, 1H), 7.82 (dd, 1H), 7.52 (s, 1H), 7.07 (d, 1H), 7.07-6.94 (m, 2H), 5.08 (s, 2H), 4.88 (t, 1H), 3.92 (s, 3H), 3.75-3.52 (m, 6H), 2.62 (s, 3H), 2.15 (d, 2H), 1.62 (ddd, 2H). |
| 370 | 1H NMR (500 MHz, DMSO) δ = 8.43 (t, 1H), 7.69 (s, 1H), 7.48 (d, 1H), 7.34 (d, 1H), 6.97 (dd, 1H), 5.32 (s, 2H), 3.44 (d, 2H), 2.62 (d, 6H), 1.29-1.20 (m, 2H), 1.20-1.11 (m, 2H). |
| 371 | 1H NMR (500 MHz, DMSO) δ = 8.99 (s, 1H), 8.45 (t, 1H), 7.49 (d, 1H), 7.36 (d, 1H), 6.98 (dd, 1H), 5.32 (s, 2H), 3.44 (d, 2H), 2.62 (s, 3H), 2.41 (s, 3H), 1.26 (q, 2H), 1.15 (q, 2H). |
| 372 | 1H NMR (500 MHz, DMSO) δ = 8.29 (t, 1H), 7.69 (s, 1H), 7.47 (d, 1H), 7.28 (d, 1H), 6.96 (dd, 1H), 5.32 (s, 2H), 3.72 (dd, 2H), 2.61 (d, 6H), 1.10-0.92 (m, 2H), 0.92-0.76 (m, 1H). |
| 373 | 1H NMR (500 MHz, DMSO) δ = 8.98 (s, 1H), 8.30 (t, 1H), 7.48 (d, 1H), 7.29 (d, 1H), 6.97 (dd, 1H), 5.32 (s, 2H), 3.72 (dd, 2H), 2.60 (s, 3H), 2.42 (s, 3H), 1.13-0.91 (m, 2H), 0.98-0.77 (m, 2H). |
| 374 | 1H NMR (600 MHz, CDCl3) δ = 8.72 (s, 1H), 7.57 (d, 1H), 7.37 (d, 1H), 7.32 (d, 1H), 6.94 (dd, 1H), 6.57 (s, 1H), 6.33 (d, 1H), 5.25 (s, 2H), 4.73 (d, 2H), 2.74 (s, 3H), 2.50 (s, 3H). |
| 375 | 1H NMR (500 MHz, DMSO) δ = 7.51 (d, 1H), 7.48-7.42 (m, 2H), 7.37 (d, 1H), 7.18 (d, 2H), 6.99 (dd, 1H), 5.12 (s, 2H), 5.07 (d, 1H), 4.39 (dd, 1H), 4.14 (td, 1H), 2.65 (s, 3H), 2.41 (s, 3H), 1.14 (d, 3H). |
| 376 | 1H NMR (500 MHz, DMSO) δ = 8.41 (dd, 1H), 7.82 (dd, 1H), 7.54-7.47 (m, 2H), 7.46 (s, 1H), 7.40 (d, 1H), 7.24 (dd, 1H), 7.19-7.15 (m, 1H), 7.03 (dd, 1H), 5.16 (s, 2H), 5.08 (d, 1H), 4.37 (dd, 1H), 4.14 (td, 1H), 2.65 (s, 3H), 2.53 (s, 3H), 1.14 (d, 3H). |
| 377 | 1H NMR (500 MHz, DMSO) δ = 7.72 (s, 1H), 7.50 (d, 1H), 7.48-7.41 (m, 2H), 7.36 (d, 1H), 7.18 (s, 1H), 6.98 (dd, 1H), 5.33 (s, 2H), 5.07 (d, 1H), 4.38 (dd, 1H), 4.14 (td, 1H), 2.65 (s, 3H), 2.63 (s, 3H), 1.14 (d, 3H). |
| 378 | 1H NMR (500 MHz, DMSO) δ = 8.98 (s, 1H), 7.50 (d, 1H), 7.44 (d, 2H), 7.38 (d, 1H), 7.16 (s, 1H), 6.99 (dd, 1H), 5.32 (s, 2H), 5.06 (d, 1H), 4.37 (dd, 1H), 4.19-4.09 (m, 1H), 2.65 (s, 3H), 2.42 (s, 3H), 1.14 (d, 3H). |
| 379 | 1H NMR (600 MHz, DMSO) δ = 8.98 (s, 1H), 7.51 (d, 1H), 7.48-7.40 (m, 2H), 7.37 (d, 1H), 7.14 (s, 1H), 7.00 (dd, 1H), 5.32 (s, 2H), 5.05 (d, 1H), 4.38 (dd, 1H), 4.15 (t, 1H), 2.66 (s, 3H), 2.42 (s, 3H), 1.15 (d, 3H). |
| 380 | 1H NMR (500 MHz, DMSO) δ = 8.54 (d, 1H), 7.78 (dd, 1H), 7.50 (d, 1H), 7.46 (s, 1H), 7.45 (d, 1H), 7.38 (d, 1H), 7.27 (d, 1H), 7.19-7.15 (m, 1H), 6.99 (dd, 1H), 5.13 (s, 2H), 5.09 (s, 1H), 4.37 (dd, 1H), 4.18-4.10 (m, 1H), 2.65 (s, 3H), 2.47 (s, 3H), 1.14 (d, 3H). |
| 381 | 1H NMR (500 MHz, DMSO) δ = 7.62-7.28 (m, 5H), 7.28-6.90 (m, 2H), 6.59-6.16 (m, 2H), 5.24 (s, 2H), 5.07 (s, 1H), 4.67 (td, 2H), 4.38 (dd, 1H), 4.14 (q, 1H), 2.66 (s, 3H), 1.14 (d, 3H). |
| 382 | 1H NMR (500 MHz, DMSO) δ = 7.50 (d, 1H), 7.46-7.40 (m, 2H), 7.38 (d, 1H), 7.17 (s, 1H), 6.97 (dd, 1H), 5.23 (s, 2H), 5.06 (d, 1H), 4.37 (dd, 1H), 4.18-4.09 (m, 1H), 2.65 (s, 3H), 2.57 (s, 3H), 2.32 (s, 3H), 1.14 (d, 3H). |
| 383 | 1H NMR (500 MHz, DMSO) δ = 7.52 (d, 1H), 7.50-7.43 (m, 3H), 7.41 (d, 1H), 7.17 (s, 1H), 7.02 (dd, 1H), 5.17 (s, 2H), 5.06 (d, 1H), 4.37 (dd, 1H), 4.14 (s, 1H), 3.83 (s, 3H), 2.66 (s, 3H), 1.14 (d, 3H). |
| 384 | 1H NMR (500 MHz, DMSO) δ = 8.35 (t, 1H), 7.69 (s, 1H), 7.48 (d, 1H), 7.27 (d, 1H), 6.97 (dd, 1H), 5.32 (s, 2H), 4.79-4.60 (m, 4H), 3.82 (dd, 2H), 2.61 (d, 6H). |
| 385 | 1H NMR (500 MHz, DMSO) δ = 8.99 (s, 1H), 8.36 (t, 1H), 7.48 (d, 1H), 7.29 (d, 1H), 6.97 (dd, 1H), 5.31 (s, 2H), 4.79-4.60 (m, 4H), 3.82 (dd, 2H), 2.59 (s, 3H), 2.42 (s, 3H). |
| 386 - En 1 | 1H NMR (500 MHz, DMSO) δ = 7.70 (s, 1H), 7.48 (dd, 2H), 7.34 (d, 1H), 6.97 (dd, 1H), 5.61 (s, 1H), 5.31 (s, 2H), 4.45-4.36 (m, 1H), 4.31 (td, 1H), 4.00-3.91 (m, 2H), 3.64 (dd, 1H), 3.58 (t, 1H), 2.63 (d, 6H). |
| 387 - En 1 | 1H NMR (400 MHz, DMSO) δ = 8.59 (ddd, 1H), 7.84 (td, 1H), 7.60-7.53 (m, 1H), 7.48 (dd, 2H), 7.40-7.31 (m, 2H), 7.00 (dd, 1H), 5.60 (s, 1H), 5.19 (s, 2H), 4.46-4.30 (m, 1H), 4.30 (s, 1H), 4.01-3.90 (m, 2H), 3.64 (dd, 1H), 3.58 (t, 1H), 2.63 (s, 3H). |
| 388 - En 1 | 1H NMR (500 MHz, DMSO) δ = 8.13 (d, 1H), 7.69 (s, 1H), 7.46 (d, 1H), 7.21 (d, 1H), 6.95 (dd, 1H), 5.32 (s, 3H), 4.23 (ddq, 2H), 4.01 (dd, 1H), 3.92 (dd, 1H), 3.66 (dd, 1H), 3.56 (dd, 1H), 2.63 (s, 3H), 2.56 (s, 3H). |
| 389 - En 1 | 1H NMR (400 MHz, DMSO) δ = 8.58 (ddd, 1H), 8.13 (d, 1H), 7.84 (td, 1H), 7.54 (d, 1H), 7.47 (d, 1H), 7.35 (ddd, 1H), 7.21 (d, 1H), 6.99 (dd, 1H), 5.31 (s, 1H), 5.20 (s, 2H), 4.23 (s, 2H), 4.01 (dd, 1H), 3.91 (dd, 1H), 3.65 (dd, 1H), 3.56 (dd, 1H), 2.56 (s, 3H). |

| cpd Nr | NMR Data |
|---|---|
| 390 | 1H NMR (500 MHz, DMSO) δ = 8.74 (dd, 1H), 8.28 (d, 1H), 8.18 (d, 1H), 7.83-7.76 (m, 2H), 7.50 (d, 1H), 7.42 (d, 1H), 6.99 (dd, 1H), 5.57 (s, 1H), 5.32 (s, 2H), 4.45-4.35 (m, 2H), 3.48-3.40 (m, 1H), 3.02-2.94 (m, 1H), 2.63 (s, 3H). |
| 391 | 1H NMR (500 MHz, DMSO) δ = 8.17-8.11 (m, 1H), 7.81 (d, 1H), 7.71 (s, 1H), 7.47 (d, 1H), 7.39 (d, 1H), 6.96 (dd, 1H), 5.58 (s, 1H), 5.32 (s, 2H), 4.40 (dd, 2H), 3.44 (td, 1H), 3.02-2.94 (m, 1H), 2.63 (d, 6H). |
| 392 | 1H NMR (500 MHz, DMSO) δ = 8.99 (s, 1H), 8.15 (d, 1H), 7.80 (d, 1H), 7.48 (d, 1H), 7.41 (d, 1H), 6.97 (dd, 1H), 5.57 (s, 1H), 5.32 (s, 2H), 4.46-4.35 (m, 2H), 3.44 (ddd, 1H), 2.98 (dd, 1H), 2.63 (s, 3H), 2.43 (s, 3H). |
| 393 | 1H NMR (400 MHz, DMSO) δ = 8.19 (t, 1H), 7.68 (s, 1H), 7.47 (d, 1H), 7.26 (d, 1H), 6.96 (dd, 1H), 5.32 (s, 2H), 3.75 (dt, 2H), 3.66-3.47 (m, 4H), 2.61 (d, 6H), 1.91-1.66 (m, 4H). |
| 394 | 1H NMR (400 MHz, DMSO) δ = 8.98 (s, 1H), 8.19 (t, 1H), 7.47 (d, 1H), 7.27 (d, 1H), 6.97 (dd, 1H), 5.31 (s, 2H), 3.75 (dt, 2H), 3.57 (dq, 4H), 2.59 (s, 3H), 2.41 (s, 3H), 1.92-1.66 (m, 4H). |
| 395 - Dia 1 | 1H NMR (500 MHz, DMSO) δ = 7.64 (s, 1H), 7.57 (d, 1H), 7.50 (s, 1H), 7.44 (d, 1H), 7.37 (d, 1H), 7.21 (s, 1H), 6.94 (dd, 1H), 5.82 (q, 1H), 5.05 (t, 1H), 4.47 (dt, 1H), 3.76 (hept, 2H), 2.62 (s, 3H), 2.58 (s, 3H), 1.65 (d, 3H). |
| 395 - Dia 2 | 1H NMR (500 MHz, DMSO) δ = 7.65 (s, 1H), 7.56 (d, 1H), 7.51 (s, 1H), 7.44 (d, 1H), 7.39 (d, 1H), 7.23 (s, 1H), 6.93 (dd, 1H), 5.82 (q, 1H), 5.02 (t, 1H), 4.49 (dt, 1H), 3.75 (hept, 2H), 2.62 (s, 3H), 2.57 (s, 3H), 1.65 (d, 3H). |
| 396 - En 1 | 1H NMR (500 MHz, DMSO) δ = 8.99 (s, 1H), 8.04 (dd, 1H), 7.48 (dd, 1H), 7.33 (dd, 1H), 6.97 (dd, 1H), 5.33 (t, 2H), 4.99 (dp, 1H), 4.88 (t, 1H), 4.67 (t, 1H), 3.65-3.59 (m, 1H), 3.59-3.41 (m, 2H), 3.01 (d, 3H), 2.62 (d, 3H), 2.43 (d, 3H), 1.33 (t, 3H). |
| 397 - En 1 | 1H NMR (400 MHz, DMSO) δ = 8.98 (s, 1H), 8.04-7.92 (m, 2H), 7.47 (d, 1H), 7.34 (d, 1H), 6.96 (dd, 1H), 5.32 (s, 2H), 4.68 (t, 1H), 4.53 (p, 1H), 3.42 (q, 2H), 3.17 (q, 2H), 2.61 (s, 3H), 2.42 (s, 3H), 1.34 (d, 3H). |
| 398 | 1H NMR (400 MHz, DMSO) δ = 8.99 (s, 1H), 7.89 (s, 1H), 7.66 (t, 1H), 7.48 (d, 1H), 7.35 (d, 1H), 6.98 (dd, 1H), 5.33 (s, 2H), 4.58 (t, 1H), 3.41 (q, 2H), 3.18 (q, 2H), 2.62 (s, 3H), 2.43 (s, 3H), 1.52 (s, 6H). |
| 399 | 1H NMR (400 MHz, DMSO) δ = 8.34 (s, 1H), 7.69 (s, 1H), 7.57-7.10 (m, 2H), 6.94 (dd, 1H), 6.73 (t, 1H), 5.31 (s, 2H), 4.01 (s, 2H), 2.63 (s, 3H), 2.54 (s, 3H), 0.89 (d, 4H). |
| 400 | 1H NMR (500 MHz, DMSO) δ = 8.99 (s, 1H), 8.34 (s, 1H), 7.45 (d, 1H), 7.23 (d, 1H), 6.94 (dd, 1H), 6.73 (t, 1H), 5.31 (s, 2H), 4.02 (s, 2H), 2.55 (s, 3H), 2.42 (s, 3H), 0.89 (dt, 4H). |
| 401 - En 1 | 1H NMR (400 MHz, DMSO) δ = 12.35 (s, 1H), 8.20 (d, 1H), 7.71 (s, 1H), 7.55-7.46 (m, 3H), 7.50 (s, 1H), 7.18-7.11 (m, 2H), 6.97 (dd, 1H), 5.39 (d, 1H), 5.36 (s, 2H), 5.21 (s, 1H), 4.04-3.90 (m, 2H), 2.64 (d, 6H). |
| 402 - En 1 | 1H NMR (400 MHz, DMSO) δ = 8.99 (s, 1H), 8.20 (d, 1H), 7.47 (d, 1H), 7.37 (d, 1H), 6.97 (dd, 1H), 5.32 (s, 2H), 4.72-4.62 (m, 1H), 4.59 (t, 1H), 3.59-3.43 (m, 4H), 3.47-3.38 (m, 4H), 2.61 (s, 3H), 2.43 (s, 3H), 2.41-2.31 (m, 1H), 1.98 (dq, 1H). |
| 403 - En 1 | 1H NMR (400 MHz, DMSO) δ = 8.16 (d, 1H), 7.48 (d, 1H), 7.41 (d, 1H), 7.20 (d, 1H), 7.02 (dd, 1H), 6.88 (d, 1H), 5.15 (s, 2H), 4.76-4.64 (m, 2H), 3.70 (s, 3H), 3.52 (q, 2H), 3.48-3.35 (m, 3H), 3.23-3.12 (m, 1H), 2.62 (s, 3H), 2.36 (s, 1H), 2.07-1.91 (m, 1H). |
| 404 - En 1 | 1H NMR (400 MHz, DMSO) δ = 8.18 (d, 1H), 7.48 (d, 1H), 7.38 (dd, 2H), 6.99 (dd, 1H), 6.39 (d, 1H), 5.20 (s, 2H), 4.73 (d, 1H), 4.73-4.63 (m, 1H), 3.85 (s, 3H), 3.53 (q, 2H), 3.49-3.37 (m, 3H), 3.18 (dt, 1H), 2.61 (s, 3H), 2.42-2.32 (m, 1H), 2.05-1.90 (m, 1H). |
| 405 | 1H NMR (400 MHz, DMSO) δ = 8.18 (d, 1H), 7.72 (dd, 1H), 7.61-7.53 (m, 1H), 7.46 (d, 1H), 7.33 (d, 1H), 6.95 (dd, 1H), 6.26 (t, 1H), 4.93 (s, 2H), 4.68 (dt, 1H), 3.53 (t, 2H), 3.48 (s, 3H), 3.48-3.35 (m, 3H), 3.17 (dt, 1H), 2.61 (s, 3H), 2.42-2.32 (m, 1H), 1.98 (dq, 1H). |
| 406 - En 1 | 1H NMR (400 MHz, DMSO) δ = 8.58 (ddd, 1H), 8.18 (m, 1H), 7.84 (td, 1H), 7.56 (dt, 1H), 7.47 (d, 1H), 7.40-7.31 (m, 2H), 7.00 (dd, 1H), 5.21 (s, 2H), 4.76-4.63 (m, 2H), 3.53 (q, 2H), 3.49-3.35 (m, 3H), 3.17 (dt, 1H), 2.61 (s, 3H), 2.36 (s, 1H), 2.05-1.89 (m, 1H). |
| 407 - En 1 | 1H NMR (400 MHz, DMSO) δ = 8.18 (d, 1H), 7.85 (d, 1H), 7.78 (d, 1H), 7.50 (d, 1H), 7.40 (d, 1H), 7.03 (dd, 1H), 5.47 (s, 2H), 4.76-4.63 (m, 1H), 3.53 (q, 1H), 3.48-3.35 (m, 3H), 3.23-3.12 (m, 1H), 2.62 (s, 3H), 2.36 (s, 1H), 1.98 (dq, 1H). |
| 408 - En 1 | 1H NMR (400 MHz, DMSO) δ = 8.19 (d, 1H), 7.57 (dd, 1H), 7.46 (d, 1H), 7.42-7.33 (m, 2H), 6.95 (dd, 1H), 6.22 (t, 1H), 4.90 (s, 2H), 4.75-4.63 (m, 1H), 3.53 (t, 2H), 3.42 (dt, 3H), 3.19 (dt, 1H), 2.61 (s, 3H), 2.42-2.32 (m, 1H), 2.07-1.92 (m, 1H). |
| 409 - En 1 | 1H NMR (500 MHz, DMSO) δ = 8.22-8.13 (m, 2H), 7.83 (dd, 1H), 7.47 (d, 1H), 7.35 (d, 1H), 7.03 (dd, 1H), 6.97 (dd, 1H), 5.08 (s, 2H), 4.75-4.63 (m, 2H), 3.93 (s, 3H), 3.53 (q, 2H), 3.47-3.35 (m, 3H), 3.22-3.13 (m, 1H), 2.61 (s, 3H), 2.35 (q, 1H), 1.97 (dq, 1H). |
| 410 - En 1 | 1H NMR (400 MHz, DMSO) δ = 8.98 (s, 1H), 7.92 (s, 1H), 7.47 (d, 1H), 7.22 (d, 1H), 6.96 (dd, 1H), 5.32 (s, 2H), 4.68 (s, 1H), 3.53 (t, 2H), 3.49-3.35 (m, 3H), 3.22-3.13 (m, 1H), 2.58 (s, 3H), 2.43 (s, 3H), 2.03 (ddd, 1H), 1.35 (s, 3H). |
| 411 - En 1 | 1H NMR (400 MHz, DMSO) δ = 8.98 (s, 1H), 7.89 (d, 1H), 7.48 (d, 1H), 7.34 (d, 1H), 6.97 (dd, 1H), 5.32 (s, 2H), 5.04 (dt, 1H), 4.99 (s, 1H), 3.68 (dd, 1H), 3.13 (s, 3H), 2.89 (s, 3H), 2.61 (s, 3H), 2.42 (s, 3H). |
| 412 - En 1 | 1H NMR (400 MHz, DMSO) δ = 7.70 (d, 1H), 7.51 (d, 1H), 7.46 (d, 1H), 7.33 (d, 1H), 6.94 (dd, 1H), 5.31 (s, 2H), 4.79 (s, 1H), 4.10 (q, 1H), 3.55-3.48 (m, 2H), 2.61 (d, 6H), 2.50-2.42 (m, 1H), 2.39 (dd, 1H), 2.20 (s, 6H). |
| 413 - En 1 | 1H NMR (500 MHz, DMSO) δ = 8.99 (s, 1H), 7.52 (d, 1H), 7.46 (d, 1H), 7.34 (d, 1H), 6.95 (dd, 1H), 5.31 (d, 2H), 4.78 (s, 1H), 4.10 (d, 0H), 3.52 (tt, 2H), 2.59 (s, 3H), 2.48-2.43 (m, 1H), 2.42 (s, 3H), 2.39 (dd, 1H), 2.20 (s, 6H). |
| 414 | 1H NMR (400 MHz, DMSO) δ = 7.74 (s, 1H), 7.69 (s, 1H), 7.45 (d, 1H), 7.27 (d, 1H), 6.94 (dd, 1H), 5.31 (s, 2H), 4.91 (t, 1H), 3.66 (d, 2H), 2.63 (s, 3H), 2.58 (s, 3H), 2.33 (q, 1H), 2.18-2.05 (m, 3H), 1.86 (dd, 1H), 1.81-1.69 (m, 1H). |

| cpd Nr | NMR Data |
| --- | --- |
| 415 | 1H NMR (400 MHz, DMSO) δ = 8.58 (ddd, 1H), 7.84 (td, 1H), 7.74 (s, 1H), 7.55 (dt, 1H), 7.45 (d, 1H), 7.35 (ddd, 1H), 7.28 (d, 1H), 6.98 (dd, 1H), 5.20 (s, 2H), 4.89 (d, 1H), 3.65 (d, 2H), 2.58 (s, 3H), 2.31 (q, 2H), 2.19-2.07 (m, 1H), 1.92-1.69 (m, 2H). |
| 416 | 1H NMR (400 MHz, DMSO) δ = 11.76 (s, 1H), 7.76 (s, 1H), 7.61-7.54 (m, 1H), 7.44 (d, 1H), 7.38 (dd, 1H), 7.24 (d, 1H), 6.93 (dd, 1H), 6.22 (t, 1H), 4.90 (t, 1H), 4.89 (s, 2H), 3.66 (d, 2H), 2.58 (s, 3H), 2.38-2.25 (m, 2H), 2.13 (s, 2H), 1.94-1.66 (m, 2H). |
| 417 | 1H NMR (400 MHz, DMSO) δ = 8.16 (dd, 1H), 7.82 (dd, 1H), 7.76 (s, 1H), 7.45 (d, 1H), 7.26 (d, 1H), 7.03 (dd, 1H), 6.95 (dd, 1H), 5.07 (s, 2H), 4.89 (t, 1H), 3.93 (s, 3H), 3.65 (d, 2H), 2.58 (s, 3H), 2.37-2.23 (m, 2H), 2.13 (ddd, 1H), 1.93-1.66 (m, 2H). |
| 418 | 1H NMR (400 MHz, DMSO) δ = 8.14 (s, 1H), 7.69 (s, 1H), 7.44 (d, 1H), 7.26 (d, 1H), 6.93 (dd, 1H), 5.32 (s, 2H), 4.77 (t, 1H), 3.56 (d, 2H), 2.64 (s, 3H), 2.56 (s, 3H), 0.83 (s, 1H), 0.82-0.71 (m, 3H). |
| 419 | 1H NMR (400 MHz, DMSO) δ = 8.58 (ddd, 1H), 8.14 (s, 1H), 7.84 (td, 1H), 7.55 (d, 1H), 7.44 (d, 1H), 7.35 (ddd, 1H), 7.26 (d, 1H), 6.97 (dd, 1H), 5.21 (s, 2H), 4.76 (t, 1H), 3.55 (d, 2H), 2.56 (s, 3H), 0.83-0.70 (m, 4H). |
| 420 | 1H NMR (400 MHz, DMSO) δ = 11.76 (s, 1H), 8.16 (s, 1H), 7.57 (ddd, 1H), 7.43 (d, 1H), 7.38 (dd, 1H), 7.24 (d, 1H), 6.93 (dd, 1H), 6.23 (t, 1H), 4.90 (s, 2H), 4.76 (s, 1H), 3.56 (s, 2H), 2.56 (s, 3H), 0.76 (dt, 4H). |
| 421 | 1H NMR (400 MHz, DMSO) δ = 8.20-8.12 (m, 2H), 7.83 (dd, 1H), 7.44 (d, 1H), 7.25 (d, 1H), 7.03 (dd, 1H), 6.95 (dd, 1H), 5.07 (s, 2H), 4.76 (t, 1H), 3.93 (s, 3H), 3.55 (s, 2H), 2.56 (s, 3H), 0.76 (dt, 4H). |
| 422 | 1H NMR (400 MHz, DMSO) δ = 7.48 (d, 1H), 7.37 (d, 1H), 7.19 (d, 1H), 7.04-6.96 (m, 2H), 6.88 (d, 1H), 5.18-5.08 (m, 4H), 3.68 (d, 5H), 3.56 (dd, 2H), 2.60 (s, 3H), 1.33 (s, 3H). |
| 423 | 1H NMR (400 MHz, DMSO) δ = 7.48 (d, 1H), 7.37 (d, 1H), 7.33 (d, 1H), 7.05 (s, 1H), 6.98 (dd, 1H), 6.39 (d, 1H), 5.18 (s, 2H), 4.98 (t, 2H), 3.85 (s, 3H), 3.65 (dd, 2H), 3.55 (dd, 2H), 2.60 (s, 3H), 1.32 (s, 3H). |
| 424 | 1H NMR (400 MHz, DMSO) δ = 8.74 (d, 1H), 8.27 (d, 1H), 7.79 (dd, 1H), 7.49 (d, 1H), 7.31 (d, 1H), 7.07 (s, 1H), 6.98 (dd, 1H), 5.31 (s, 2H), 4.94 (t, 2H), 3.64 (dd, 2H), 3.55 (dd, 2H), 2.60 (s, 3H), 1.31 (s, 3H). |
| 425 | 1H NMR (400 MHz, DMSO) δ = 7.70 (s, 1H), 7.47 (d, 1H), 7.29 (d, 1H), 7.03 (s, 1H), 6.95 (dd, 1H), 5.31 (s, 2H), 4.98 (t, 2H), 3.65 (dd, 2H), 3.55 (dd, 2H), 2.61 (d, 6H), 1.32 (s, 3H). |
| 426 | 1H NMR (400 MHz, DMSO) δ = 8.99 (s, 1H), 7.47 (d, 1H), 7.30 (d, 1H), 7.05 (s, 1H), 6.96 (dd, 1H), 5.30 (s, 2H), 4.96 (t, 2H), 3.65 (dd, 2H), 3.55 (dd, 2H), 2.60 (s, 3H), 2.42 (s, 3H), 1.32 (s, 3H). |
| 427 | 1H NMR (600 MHz, DMSO) δ = 9.22 (dd, 1H), 7.86 (dd, 1H), 7.76 (dd, 1H), 7.49 (d, 1H), 7.35 (d, 1H), 7.06-7.00 (m, 2H), 5.43 (s, 2H), 4.96 (tq, 2H), 3.66 (dd, 2H), 3.56 (dd, 2H), 2.60 (s, 3H), 1.32 (s, 3H). |
| 428 | 1H NMR (500 MHz, DMSO) δ = 8.58 (ddd, 1H), 7.84 (td, 1H), 7.59-7.53 (m, 1H), 7.47 (d, 1H), 7.35 (ddd, 1H), 7.30 (d, 1H), 7.03 (s, 1H), 6.99 (dd, 1H), 5.19 (s, 2H), 4.96 (t, 2H), 3.64 (dd, 2H), 3.55 (dd, 2H), 2.59 (s, 3H), 1.31 (s, 3H). |
| 429 | 1H NMR (600 MHz, DMSO) δ = 9.18 (d, 1H), 8.86-8.79 (m, 1H), 7.67 (dd, 1H), 7.49 (d, 1H), 7.30 (d, 1H), 7.05-7.00 (m, 2H), 5.24 (s, 2H), 4.98-4.92 (m, 2H), 3.64 (dd, 2H), 3.55 (dd, 2H), 2.60 (s, 3H), 1.31 (s, 3H). |
| 430 | 1H NMR (500 MHz, DMSO) δ = 11.77 (s, 1H), 7.58 (ddd, 1H), 7.46 (d, 1H), 7.41-7.35 (m, 1H), 7.26 (d, 1H), 7.04 (s, 1H), 6.94 (dd, 1H), 6.22 (t, 1H), 4.95 (t, 2H), 4.88 (s, 2H), 3.64 (dd, 2H), 3.55 (dd, 2H), 2.59 (s, 3H), 1.31 (s, 3H). |
| 431 | 1H NMR (500 MHz, DMSO) δ = 8.16 (dd, 1H), 7.83 (dd, 1H), 7.46 (d, 1H), 7.29 (d, 1H), 7.07-6.99 (m, 2H), 6.96 (dd, 1H), 5.06 (s, 2H), 4.94 (t, 2H), 3.93 (s, 3H), 3.64 (dd, 2H), 3.55 (dd, 2H), 2.60 (s, 3H), 1.31 (s, 3H). |
| 432 - En 1 | 1H NMR (500 MHz, DMSO) δ = 8.46 (s, 1H), 8.03 (d, 1H), 7.98 (s, 1H), 7.72 (d, 2H), 7.46 (d, 1H), 7.37 (s, 1H), 7.29 (d, 1H), 6.95 (dd, 1H), 5.32 (s, 2H), 4.94 (td, 1H), 4.65 (dd, 1H), 4.60 (dd, 1H), 2.64 (s, 3H), 2.52 (s, 3H). |
| 433 - En 1 | 1H NMR (400 MHz, DMSO) δ = 7.88 (d, 1H), 7.48 (d, 2H), 7.38 (dd, 2H), 7.11 (s, 1H), 6.98 (dd, 1H), 6.39 (d, 1H), 5.20 (s, 2H), 4.48 (p, 1H), 3.85 (s, 3H), 2.62 (s, 3H), 1.36 (d, 3H). |
| 434 - En 1 | 1H NMR (400 MHz, DMSO) δ = 7.87 (d, 1H), 7.71 (s, 1H), 7.52-7.43 (m, 2H), 7.36 (d, 1H), 7.11 (s, 1H), 6.95 (dd, 1H), 5.33 (s, 2H), 4.48 (p, 1H), 2.62 (s, 6H), 1.36 (d, 3H). |
| 435 - En 1 | 1H NMR (400 MHz, DMSO) δ = 8.58 (ddd, 1H), 7.91-7.79 (m, 2H), 7.56 (dt, 1H), 7.51-7.44 (m, 2H), 7.40-7.31 (m, 2H), 7.10 (s, 1H), 7.00 (dd, 1H), 5.21 (s, 2H), 4.47 (p, 1H), 2.62 (s, 3H), 1.36 (d, 3H). |
| 436 - En 1 | 1H NMR (400 MHz, DMSO) δ = 11.74 (s, 1H), 7.89 (d, 1H), 7.58 (d, 1H), 7.52-7.42 (m, 2H), 7.36 (dd, 2H), 7.07 (s, 1H), 6.95 (dd, 1H), 6.22 (t, 1H), 4.90 (s, 2H), 4.46 (q, 1H), 2.62 (s, 3H), 1.36 (d, 3H). |
| 437 - En 1 | 1H NMR (400 MHz, DMSO) δ = 8.16 (dd, 1H), 7.83 (dd, 1H), 7.47 (s, 1H), 7.47 (d, 1H), 7.35 (d, 1H), 7.08 (s, 1H), 7.03 (dd, 1H), 6.97 (dd, 1H), 5.08 (s, 2H), 4.47 (p, 1H), 3.93 (s, 3H), 2.62 (s, 3H), 1.35 (d, 3H). |
| 438 | 1H NMR (400 MHz, DMSO) δ = 7.83 (s, 1H), 7.49 (d, 1H), 7.44 (d, 1H), 7.37 (d, 2H), 7.19 (s, 1H), 7.00 (dd, 1H), 6.39 (d, 1H), 5.21 (s, 2H), 3.86 (s, 3H), 2.64 (s, 3H), 1.57 (s, 6H). |
| 439 | 1H NMR (400 MHz, DMSO) δ = 7.81 (s, 1H), 7.48 (d, 1H), 7.39 (d, 1H), 7.37 (s, 1H), 7.19 (s, 1H), 6.97 (dd, 1H), 5.34 (s, 2H), 2.63 (d, 6H), 1.56 (s, 6H). |
| 440 | 1H NMR (400 MHz, DMSO) δ = 8.99 (s, 1H), 7.82 (s, 1H), 7.48 (d, 1H), 7.40 (d, 1H), 7.16 (s, 1H), 6.98 (dd, 1H), 5.33 (s, 2H), 2.64 (s, 3H), 2.42 (s, 3H), 1.56 (s, 6H). |
| 441 | 1H NMR (600 MHz, DMSO) δ = 7.86 (d, 2H), 7.50 (d, 1H), 7.47-7.42 (m, 1H), 7.11 (s, 1H), 5.45 (s, 2H), 2.64 (s, 3H), 1.56 (s, 6H). |
| 442 | 1H NMR (400 MHz, DMSO) δ = 8.58 (ddd, 1H), 7.89-7.79 (m, 2H), 7.57 (dt, 1H), 7.49 (d, 1H), 7.41 (d, 1H), 7.39-7.31 (m, 1H), 7.34 (s, 1H), 7.16 (s, 1H), 7.01 (dd, 1H), 5.21 (s, 2H), 2.63 (s, 3H), 1.55 (s, 6H). |
| 443 | 1H NMR (400 MHz, DMSO) δ = 11.75 (s, 1H), 7.82 (s, 1H), 7.63-7.55 (m, 1H), 7.47 (d, 1H), 7.42-7.31 (m, 3H), 7.12 (s, 1H), 6.95 (dd, 1H), 6.22 (t, 1H), 4.90 (s, 2H), 2.63 (s, 3H), 1.55 (s, 6H). |

| cpd Nr | NMR Data |
|---|---|
| 444 | 1H NMR (400 MHz, DMSO) δ = 8.16 (dd, 1H), 7.87-7.80 (m, 1H), 7.82 (s, 1H), 7.48 (d, 1H), 7.39 (d, 1H), 7.34 (s, 1H), 7.14 (s, 1H), 7.00 (ddd, 2H), 5.08 (s, 2H), 3.93 (s, 3H), 2.64 (s, 3H), 1.55 (s, 6H). |
| 445 - En 1 | 1H NMR (500 MHz, DMSO) δ = 7.69 (d, 2H), 7.51-7.44 (m, 2H), 7.32 (d, 1H), 7.13-7.09 (m, 1H), 6.97 (dd, 1H), 5.31 (s, 2H), 4.56 (td, 1H), 2.88 (dd, 1H), 2.82 (dd, 1H), 2.62 (d, 6H), 2.34 (s, 3H), 1.75 (ddd, 1H), 0.48-0.37 (m, 3H), 0.32 (dt, 1H). |
| 446 - En 1 | 1H NMR (500 MHz, DMSO) δ = 8.99 (s, 1H), 7.70 (d, 1H), 7.51-7.45 (m, 2H), 7.33 (d, 1H), 7.10 (s, 1H), 6.98 (dd, 1H), 5.31 (d, 2H), 4.55 (td, 1H), 2.88 (dd, 1H), 2.81 (dd, 1H), 2.60 (s, 3H), 2.42 (s, 3H), 2.33 (s, 3H), 1.75 (dq, 1H), 0.45-0.37 (m, 3H), 0.40-0.29 (m, 1H). |
| 447 - En 1 | 1H NMR (500 MHz, DMSO) δ = 7.97 (d, 1H), 7.79-7.25 (m, 4H), 7.08-6.47 (m, 2H), 5.32 (s, 2H), 4.87-4.64 (m, 1H), 4.19 (qd, 2H), 3.33 (s, 2H), 2.63 (d, 5H). |
| 448 - En 1 | 1H NMR (500 MHz, DMSO) δ = 8.98 (s, 1H), 7.98 (d, 1H), 7.66 (s, 1H), 7.58-7.26 (m, 2H), 7.37 (s, 1H), 6.98 (dd, 1H), 6.72 (t, 1H), 5.31 (s, 2H), 4.75 (td, 1H), 4.19 (qd, 2H), 2.62 (s, 3H), 2.42 (s, 3H). |
| 449 - En 1 | 1H NMR (500 MHz, DMSO) δ = 7.77-7.69 (m, 2H), 7.59 (s, 1H), 7.47 (d, 1H), 7.41 (d, 1H), 7.14 (s, 1H), 6.95 (dd, 1H), 5.32 (s, 2H), 4.52 (q, 1H), 2.63 (d, 7H), 2.55 (dd, 1H), 2.24 (s, 6H). |
| 450 - En 1 | 1H NMR (500 MHz, DMSO) δ = 8.99 (s, 1H), 7.76 (s, 1H), 7.58 (s, 1H), 7.48 (d, 1H), 7.15-7.11 (m, 1H), 6.97 (dd, 1H), 5.32 (d, 2H), 4.51 (td, 1H), 2.66 (dd, 1H), 2.62 (s, 3H), 2.55 (dd, 1H), 2.42 (s, 3H), 2.24 (s, 6H). |
| 451 - En 1 | 1H NMR (400 MHz, DMSO) δ = 7.63 (d, 1H), 7.53-7.43 (m, 3H), 7.19 (t, 2H), 7.02 (dd, 1H), 6.87 (d, 1H), 5.22 (s, 1H), 5.16 (s, 2H), 4.48 (dt, 1H), 3.77 (q, 2H), 3.70 (s, 3H), 2.64 (s, 3H). |
| 452 - En 1 | 1H NMR (400 MHz, DMSO) δ = 7.64 (d, 1H), 7.49 (s, 1H), 7.53-7.42 (m, 2H), 7.37 (d, 1H), 7.20 (s, 1H), 7.00 (dd, 1H), 6.40 (d, 1H), 5.20 (s, 2H), 5.07 (s, 1H), 4.53-4.44 (m, 1H), 3.85 (s, 3H), 3.81-3.69 (m, 2H), 2.64 (s, 3H). |
| 453 - En 1 | 1H NMR (400 MHz, DMSO) δ = 7.72 (s, 1H), 7.62 (d, 1H), 7.52-7.45 (m, 2H), 7.41 (d, 1H), 7.20 (s, 1H), 6.97 (dd, 1H), 5.33 (s, 2H), 5.04 (s, 1H), 4.48 (dt, 1H), 3.78-3.72 (m, 2H), 2.63 (m, 6H). |
| 454 | 1H NMR (400 MHz, DMSO) δ = 8.98 (s, 1H), 7.63 (d, 1H), 7.49 (d, 2H), 7.42 (d, 1H), 7.19 (s, 1H), 6.98 (dd, 1H), 5.32 (s, 2H), 5.02 (s, 1H), 4.48 (dt, 1H), 3.75 (s, 2H), 2.64 (s, 3H), 2.42 (s, 3H). |
| 455 - En 1 | 1H NMR (400 MHz, DMSO) δ = 8.58 (ddd, 1H), 7.84 (td, 1H), 7.62 (d, 1H), 7.57 (dt, 1H), 7.49 (d, 2H), 7.43 (d, 1H), 7.35 (ddd, 1H), 7.19 (s, 1H), 7.01 (dd, 1H), 5.20 (s, 2H), 5.02 (t, 1H), 4.48 (dt, 1H), 3.75 (td, 2H), 2.64 (s, 3H). |
| 456 - En 1 | 1H NMR (500 MHz, DMSO) δ = 7.65 (d, 1H), 7.56-7.47 (m, 3H), 7.45 (d, 1H), 7.20 (s, 1H), 6.99 (dd, 1H), 6.55-6.23 (m, 2H), 5.24 (s, 2H), 5.05 (s, 1H), 4.67 (td, 2H), 4.49 (dt, 1H), 3.75 (dd, 2H), 2.64 (s, 3H). |
| 457 - En 1 | 1H NMR (500 MHz, DMSO) δ = 8.67 (dd, 1H), 8.24-8.03 (m, 1H), 7.75-7.34 (m, 5H), 7.44-6.89 (m, 3H), 5.35 (s, 2H), 5.01 (s, 1H), 4.48 (dt, 1H), 3.74 (d, 2H), 2.65 (s, 3H). |
| 458 - En 1 | 1H NMR (500 MHz, DMSO) δ = 7.62 (d, 1H), 7.48 (d, 2H), 7.39 (d, 1H), 7.18 (s, 1H), 6.96 (dd, 1H), 5.23 (s, 2H), 5.01 (t, 1H), 4.48 (dt, 1H), 3.74 (td, 2H), 2.64 (s, 3H), 2.57 (s, 3H), 2.32 (s, 3H). |
| 459 - En 1 | 1H NMR (400 MHz, DMSO) δ = 11.75 (s, 1H), 7.66-7.56 (m, 2H), 7.51-7.44 (m, 2H), 7.38 (dd, 2H), 7.17 (s, 1H), 6.96 (dd, 1H), 6.22 (t, 1H), 5.04 (s, 1H), 4.90 (s, 2H), 4.47 (dt, 1H), 3.78-3.72 (m, 2H), 2.64 (s, 3H). |
| 460 - En 1 | 1H NMR (500 MHz, DMSO) δ = 7.65 (d, 1H), 7.51 (d, 1H), 7.46 (dd, 3H), 7.21-7.16 (m, 1H), 7.01 (dd, 1H), 5.18 (s, 2H), 5.01 (t, 1H), 4.48 (dt, 1H), 3.83 (s, 3H), 3.75 (td, 2H), 2.64 (s, 3H). |
| 461 - En 1 | 1H NMR (400 MHz, DMSO) δ = 8.41 (dd, 1H), 7.83 (dd, 1H), 7.65 (s, 1H), 7.54-7.47 (m, 2H), 7.45 (s, 1H), 7.30 (s, 1H), 7.24 (dd, 1H), 7.02 (dd, 1H), 5.17 (s, 2H), 3.97 (d, 1H), 3.77 (d, 1H), 2.66 (s, 3H), 2.54 (s, 3H), 1.53 (s, 3H). |
| 462 - En 1 | 1H NMR (500 MHz, DMSO) δ = 7.72 (s, 1H), 7.63 (s, 1H), 7.52-7.44 (m, 3H), 7.31 (s, 1H), 6.97 (dd, 1H), 5.33 (s, 2H), 5.14 (s, 1H), 3.97 (d, 1H), 3.77 (d, 1H), 2.64 (d, 6H), 1.53 (s, 3H). |
| 463 - En 1 | 1H NMR (400 MHz, DMSO) δ = 8.99 (s, 1H), 7.63 (s, 1H), 7.53-7.40 (m, 2H), 7.44 (s, 1H), 7.28 (s, 1H), 6.98 (dd, 1H), 5.32 (s, 2H), 5.16 (s, 1H), 3.96 (d, 1H), 3.76 (d, 1H), 2.65 (s, 3H), 2.42 (s, 3H), 1.53 (s, 3H). |
| 464 - En 1 | 1H NMR (400 MHz, DMSO) δ = 8.55 (d, 1H), 7.78 (dd, 1H), 7.64 (s, 1H), 7.52-7.45 (m, 2H), 7.45 (s, 1H), 7.33-7.24 (m, 2H), 6.98 (dd, 1H), 5.13 (s, 2H), 3.97 (d, 1H), 3.77 (d, 1H), 2.65 (s, 3H), 2.47 (s, 3H), 1.53 (s, 3H). |
| 465 - En 1 | 1H NMR (500 MHz, DMSO) δ = 7.74-7.38 (m, 5H), 7.30 (s, 1H), 7.00 (dd, 1H), 6.59-6.16 (m, 2H), 5.25 (s, 2H), 5.15 (s, 1H), 4.68 (td, 2H), 3.97 (d, 1H), 3.77 (d, 1H), 2.66 (s, 3H), 1.53 (s, 3H). |
| 466 - En 1 | 1H NMR (500 MHz, DMSO) δ = 7.64 (s, 1H), 7.54-7.45 (m, 3H), 7.43 (s, 1H), 7.28 (s, 1H), 7.02 (dd, 1H), 5.18 (s, 2H), 5.12 (s, 1H), 3.96 (d, 1H), 3.83 (s, 3H), 3.77 (d, 1H), 2.66 (s, 3H), 1.53 (s, 3H). |
| 467 - En 1 | 1H NMR (400 MHz, DMSO) δ = 8.98 (s, 1H), 7.81 (d, 1H), 7.57-7.52 (m, 1H), 7.48 (d, 1H), 7.35 (d, 1H), 7.25-7.20 (m, 1H), 5.32 (s, 2H), 4.66 (ddd, 1H), 3.73-3.60 (m, 2H), 3.30 (s, 3H), 2.62 (s, 3H), 2.42 (s, 3H). |
| 468 - En 1 | 1H NMR (400 MHz, DMSO) δ = 8.99 (s, 1H), 7.71 (s, 1H), 7.50 (d, 2H), 7.43 (d, 1H), 7.37 (s, 1H), 6.99 (dd, 1H), 5.33 (s, 2H), 4.00 (d, 1H), 3.75 (d, 1H), 3.26 (s, 3H), 2.65 (s, 3H), 2.42 (s, 3H), 1.55 (s, 3H). |
| 469 - En 1 | 1H NMR (400 MHz, DMSO) δ = 8.98 (s, 1H), 7.93 (d, 1H), 7.51-7.42 (m, 2H), 7.39 (d, 1H), 7.08 (s, 1H), 6.96 (dd, 1H), 5.31 (s, 2H), 4.75 (t, 1H), 4.51 (td, 1H), 3.56 (dt, 2H), 2.63 (s, 3H), 2.42 (s, 3H), 2.03-1.81 (m, 2H). |
| 470 | 1H NMR (400 MHz, DMSO) δ = 8.99 (s, 1H), 8.62 (s, 1H), 7.49 (d, 1H), 7.38 (d, 1H), 7.27 (s, 1H), 7.20 (s, 1H), 6.99 (dd, 1H), 5.32 (s, 2H), 2.99-2.87 (m, 3H), 2.63 (s, 3H), 2.42 (s, 3H). |
| 471 | 1H NMR (400 MHz, DMSO) δ = 8.24 (s, 1H), 7.70 (s, 1H), 7.47 (d, 1H), 7.36 (d, 1H), 7.02-6.93 (m, 2H), 6.88 (s, 1H), 5.34 (s, 2H), 2.63 (s, 6H), 2.59-2.53 (m, 2H), 2.26 (q, 2H), 2.00-1.80 (m, 2H). |
| 472 | 1H NMR (400 MHz, DMSO) δ = 8.58 (d, 1H), 8.25 (s, 1H), 7.84 (t, 1H), 7.56 (d, 1H), 7.48 (d, 1H), 7.40-7.31 (m, 2H), 7.05-6.95 (m, 2H), 6.88 (s, 1H), 5.23 (s, 2H), 2.62 (s, 3H), 2.24 (q, 2H), 1.93 (s, 2H), 1.88 (dd, 2H). |
| 473 | 1H NMR (500 MHz, DMSO-d6): δ 8.16 (dd, 1H), 7.82 (dd, 1H), 7.46 (d, 1H) 7.29-7.26 (m, 2H), 7.06-7.00 (m, 1H), 6.96 (dd, 1H), 5.06 (s, 2H), 5.04 (t, 1H), 3.92 (s, 3H), 3.50 (d, 2H), 3.58 (s, 3H), 1.33 (s, 6H). |

| cpd Nr | NMR Data |
|---|---|
| 474 | 1H NMR (500 MHz, DMSO-d6): δ 8.98 (s, 1H), 7.58 (d, 1H), 7.46 (d, 1H), 7.33 (d, 1H), 6.97 (dd, 1H), 5.31 (s, 2H), 4.78 (s, 1H), 4.14-4.18 (m, 1H), 3.50-3.58 (m, 6H), 2.60 (s, 3H), 2.40-2.50 (m, 4H), 2.34-2.37 (m, 5H). |
| 475 | 1H NMR (400 MHz, DMSO) δ = 8.78-8.70 (m, 1H), 8.27 (d, 1H), 7.79 (dd, 1H), 7.48 (d, 1H), 7.36 (d, 1H), 7.20 (s, 1H), 7.05 (s, 1H), 6.98 (dd, 1H), 5.33 (s, 2H), 2.61 (s, 3H), 1.35 (q, 2H), 1.01 (q, 2H). |
| 476 | 1H NMR (400 MHz, DMSO) δ = 8.29 (s, 1H), 7.70 (s, 1H), 7.45 (d, 1H), 7.35 (d, 1H), 7.19 (s, 1H), 7.05 (s, 1H), 6.94 (dd, 1H), 5.33 (s, 2H), 2.62 (d, 6H), 1.35 (q, 2H), 1.03 (q, 2H). |
| 477 | 1H NMR (400 MHz, DMSO) δ = 8.99 (s, 1H), 8.29 (s, 1H), 7.45 (d, 1H), 7.36 (d, 1H), 7.05 (s, 1H), 6.95 (dd, 1H), 5.33 (s, 2H), 2.60 (s, 3H), 2.42 (s, 3H), 1.35 (q, 2H), 1.04 (q, 2H). |
| 478 | 1H NMR (400 MHz, DMSO) δ = 8.58 (ddd, 1H), 8.30 (s, 1H), 7.84 (td, 1H), 7.55 (d, 1H), 7.45 (d, 1H), 7.39-7.31 (m, 2H), 7.18 (s, 1H), 7.05 (s, 1H), 6.98 (dd, 1H), 5.23 (s, 2H), 2.60 (s, 3H), 1.35 (q, 2H), 1.02 (q, 2H). |
| 479 | 1H NMR (400 MHz, DMSO) δ = 11.76 (s, 1H), 8.32 (s, 1H), 7.62-7.54 (m, 1H), 7.44 (d, 1H), 7.41-7.30 (m, 2H), 7.20 (s, 1H), 7.04 (s, 1H), 6.94 (dd, 1H), 6.23 (t, 1H), 4.92 (s, 2H), 2.60 (s, 3H), 1.34 (q, 2H), 1.03 (g, 2H). |
| 480 | 1H NMR (400 MHz, DMSO) δ = 8.32 (s, 1H), 8.16 (dd, 1H), 7.83 (dd, 1H), 7.45 (d, 1H), 7.35 (d, 1H), 7.20 (s, 1H), 7.03 (dd, 2H), 6.96 (dd, 1H), 5.09 (s, 2H), 3.93 (s, 3H), 2.60 (s, 3H), 1.34 (q, 2H), 1.01 (g, 2H). |
| 481 | 1H NMR (400 MHz, DMSO) δ = 7.46 (d, 1H), 7.34 (d, 1H), 7.19 (d, 1H), 7.15 (s, 1H), 6.99 (dd, 1H), 6.87 (d, 1H), 5.25 (t, 1H), 5.16 (s, 2H), 3.69 (s, 3H), 3.52 (d, 2H), 2.58 (s, 3H), 1.36 (s, 6H). |
| 482 | 1H NMR (500 MHz, DMSO) δ = 7.46 (d, 1H), 7.37 (d, 1H), 7.29 (d, 1H), 7.20 (s, 1H), 6.97 (dd, 1H), 6.38 (d, 1H), 5.18 (s, 2H), 5.07 (t, 1H), 3.85 (s, 3H), 3.51 (d, 2H), 2.58 (s, 3H), 1.35 (s, 6H). |
| 483 | 1H NMR (400 MHz, DMSO) δ = 7.70 (s, 1H), 7.46 (d, 1H), 7.25 (d, 1H), 7.19 (s, 1H), 6.95 (dd, 1H), 5.32 (s, 2H), 5.08 (t, 1H), 3.51 (d, 2H), 2.64 (s, 3H), 2.58 (s, 3H), 1.35 (s, 6H). |
| 484 | 1H NMR (500 MHz, DMSO) δ = 8.58 (dt, 1H), 7.84 (td, 1H), 7.55 (d, 1H), 7.46 (d, 1H), 7.35 (ddd, 1H), 7.25 (d, 1H), 7.18 (s, 1H), 6.98 (dd, 1H), 5.20 (s, 2H), 5.05 (t, 1H), 3.50 (d, 2H), 2.57 (s, 3H), 1.34 (s, 6H). |
| 485 | 1H NMR (400 MHz, DMSO) δ = 11.76 (s, 1H), 7.61-7.54 (m, 1H), 7.45 (d, 1H), 7.41-7.34 (m, 1H), 7.25-7.17 (m, 2H), 6.94 (dd, 1H), 6.22 (t, 1H), 5.03 (t, 1H), 4.89 (s, 2H), 3.50 (d, 2H), 2.57 (s, 3H), 1.34 (s, 6H). |
| 486 | 1H NMR (400 MHz, DMSO) δ = 8.16 (dd, 1H), 7.82 (dd, 1H), 7.45 (d, 1H), 7.27-7.17 (m, 2H), 7.03 (dd, 1H), 6.95 (dd, 1H), 5.10-4.99 (m, 3H), 3.93 (s, 3H), 3.50 (d, 2H), 2.57 (s, 3H), 1.33 (s, 6H). |
| 487 - En 1 | 1H NMR (400 MHz, DMSO) δ = 7.69 (s, 1H), 7.57 (d, 1H), 7.46 (d, 1H), 7.32 (d, 1H), 6.97 (dd, 1H), 5.31 (s, 2H), 4.80 (s, 1H), 4.19-4.13 (m, 1H), 3.55 (t, 7H), 2.62 (d, 7H), 2.40 (s, 3H). |
| 488 - En 1 | 1H NMR (500 MHz, DMSO) δ = 8.98 (s, 1H), 7.58 (d, 1H), 7.47 (d, 1H), 7.34 (d, 1H), 6.98 (dd, 1H), 5.31 (s, 2H), 4.79 (s, 1H), 4.16 (s, 1H), 3.64-3.46 (m, 7H), 2.60 (s, 3H), 2.48 (d, 1H), 2.42 (s, 3H). |
| 489 - En 1 | 1H NMR (400 MHz, DMSO) δ = 8.73 (dd, 1H), 8.29-8.22 (m, 1H), 7.79 (dd, 1H), 7.67 (d, 1H), 7.48 (d, 1H), 7.27 (d, 1H), 6.98 (dd, 1H), 5.32 (d, 2H), 4.76 (t, 1H), 4.08-3.97 (m, 1H), 3.48 (dt, 1H), 3.43-3.33 (m, 1H), 2.58 (s, 3H), 1.14 (d, 3H). |
| 490 - En 1 | 1H NMR (400 MHz, DMSO) δ = 7.69 (s, 1H), 7.63 (d, 1H), 7.45 (d, 1H), 7.26 (d, 1H), 6.95 (dd, 1H), 5.32 (s, 2H), 4.80 (s, 1H), 4.04 (dt, 1H), 3.49 (dd, 1H), 3.39 (dd, 1H), 2.60 (d, 6H), 1.15 (d, 3H). |
| 491 - En 1 | 1H NMR (400 MHz, DMSO) δ = 8.98 (s, 1H), 7.65 (d, 1H), 7.46 (d, 1H), 7.27 (d, 1H), 6.95 (dd, 1H), 5.32 (s, 2H), 4.78 (t, 1H), 4.11-3.98 (m, 1H), 3.49 (dt, 1H), 3.44-3.35 (m, 1H), 2.58 (s, 3H), 2.42 (s, 3H), 1.16 (d, 3H). |
| 492 | 1H NMR (400 MHz, DMSO) δ = 8.58 (ddd, 1H), 7.84 (td, 1H), 7.63 (d, 1H), 7.55 (d, 1H), 7.46 (d, 1H), 7.35 (ddd, 1H), 7.26 (d, 1H), 6.99 (dd, 1H), 5.20 (s, 2H), 4.78 (t, 1H), 4.09-3.97 (m, 1H), 3.48 (dt, 1H), 3.43-3.34 (m, 1H), 2.57 (s, 3H), 1.15 (d, 3H). |
| 493 | 1H NMR (400 MHz, DMSO) δ = 8.58 (ddd, 1H), 7.84 (td, 1H), 7.63 (d, 1H), 7.55 (d, 1H), 7.46 (d, 1H), 7.35 (ddd, 1H), 7.27 (d, 1H), 6.99 (dd, 1H), 5.20 (s, 2H), 4.78 (t, 1H), 4.03 (dt, 1H), 3.54-3.43 (m, 1H), 3.38 (dt, 1H), 2.57 (s, 3H), 1.15 (d, 3H). |
| 494 | 1H NMR (400 MHz, DMSO) δ = 11.76 (s, 1H), 7.64 (d, 1H), 7.57 (ddd, 1H), 7.45 (d, 1H), 7.38 (dd, 1H), 7.25 (d, 1H), 6.94 (dd, 1H), 6.22 (t, 1H), 4.90 (s, 2H), 4.79 (s, 1H), 4.03 (p, 1H), 3.49 (dd, 1H), 3.39 (dd, 1H), 2.58 (s, 3H), 1.15 (d, 3H). |
| 495 | 1H NMR (400 MHz, DMSO) δ = 11.76 (s, 1H), 7.64 (d, 1H), 7.61-7.53 (m, 1H), 7.45 (d, 1H), 7.38 (dd, 1H), 7.25 (d, 1H), 6.94 (dd, 1H), 6.22 (t, 1H), 4.90 (s, 2H), 4.79 (s, 1H), 4.03 (p, 1H), 3.49 (dd, 1H), 3.39 (dd, 1H), 2.58 (s, 3H), 1.15 (d, 3H). |
| 496 | 1H NMR (400 MHz, DMSO) δ = 8.16 (dd, 1H), 7.82 (dd, 1H), 7.66 (d, 1H), 7.45 (d, 1H), 7.25 (d, 1H), 7.03 (dd, 1H), 6.96 (dd, 1H), 5.07 (s, 2H), 4.77 (s, 1H), 4.03 (p, 1H), 3.93 (s, 3H), 3.48 (t, 1H), 3.40 (s, 1H), 2.58 (s, 3H), 1.15 (d, 3H). |
| 497 | 1H NMR (400 MHz, DMSO) δ = 8.16 (dd, 1H), 7.82 (dd, 1H), 7.65 (d, 1H), 7.45 (d, 1H), 7.25 (d, 1H), 7.03 (dd, 1H), 6.96 (dd, 1H), 5.07 (s, 2H), 4.77 (t, 1H), 4.03 (p, 1H), 3.93 (s, 3H), 3.48 (dt, 1H), 3.43-3.34 (m, 1H), 2.58 (s, 3H), 1.15 (d, 3H). |
| 498 | 1H NMR (600 MHz, DMSO) δ = 8.98 (s, 1H), 8.25 (t, 1H), 7.49 (d, 1H), 7.34 (d, 1H), 6.99 (dd, 1H), 6.18 (tt, 1H), 5.33 (s, 2H), 3.72 (tdd, 2H), 2.62 (s, 3H), 2.43 (s, 3H). |
| 499 | 1H NMR (500 MHz, DMSO) δ = 8.35 (t, 1H), 7.69 (s, 1H), 7.48 (d, 1H), 7.27 (d, 1H), 6.97 (dd, 1H), 5.32 (s, 2H), 3.75 (td, 2H), 2.61 (d, 6H), 1.66 (t, 3H). |
| 500 | 1H NMR (500 MHz, DMSO) δ = 8.98 (s, 1H), 8.36 (t, 1H), 7.48 (d, 1H), 7.28 (d, 1H), 6.98 (dd, 1H), 5.32 (s, 2H), 3.75 (td, 2H), 2.60 (s, 3H), 2.42 (s, 3H), 1.66 (t, 3H). |
| 501 | 1H NMR (600 MHz, CDCl3) δ = 8.73 (s, 1H), 7.45 (d, 1H), 7.36 (d, 1H), 6.94 (dd, 1H), 6.78 (s, 1H), 6.14 (s, 1H), 5.34 (s, 2H), 3.69-3.61 (m, 2H), 3.61-3.55 (m, 2H), 2.75 (s, 3H), 2.53 (s, 3H), 2.02 (s, 3H). |
| 502 | 1H NMR (400 MHz, DMSO) δ = 8.99 (s, 1H), 8.87 (d, 1H), 7.85 (s, 1H), 7.50 (d, 1H), 7.45 (d, 1H), 7.00 (dd, 1H), 5.65 (d, 1H), 5.33 (s, 2H), 2.67 (s, 3H), 2.43 (s, 3H). |
| 503 | 1H NMR (400 MHz, DMSO) δ = 8.99 (s, 1H), 7.94 (t, 1H), 7.52-7.41 (m, 2H), 7.42 (s, 1H), 7.07 (s, 1H), 6.97 (dd, 1H), 5.33 (s, 2H), 3.87 (d, 2H), 2.64 (s, 3H), 2.42 (s, 3H). |

| cpd Nr | NMR Data |
|---|---|
| 504 | 1H NMR (500 MHz, DMSO) δ = 8.17 (t, 1H), 7.68 (s, 1H), 7.47 (d, 1H), 7.26 (d, 1H), 6.96 (dd, 1H), 5.32 (s, 2H), 3.50 (dd, 2H), 2.61 (d, 6H), 1.37 (d, 6H). |
| 505 | 1H NMR (500 MHz, DMSO) δ = 8.98 (s, 1H), 8.17 (t, 1H), 7.47 (d, 1H), 7.27 (d, 1H), 6.97 (dd, 1H), 5.31 (s, 2H), 3.50 (dd, 2H), 2.60 (s, 3H), 2.41 (s, 3H), 1.37 (d, 6H). |
| 506 | 1H NMR (400 MHz, DMSO) δ = 8.98 (s, 1H), 7.74 (t, 1H), 7.47 (d, 1H), 7.32 (d, 1H), 6.97 (dd, 1H), 5.31 (s, 2H), 4.61 (s, 1H), 3.28 (d, 2H), 2.61 (s, 3H), 2.41 (s, 3H), 1.15 (s, 6H). |
| 507 | 1H NMR (600 MHz, DMSO) δ = 8.97 (s, 1H), 7.52 (d, 1H), 7.47 (d, 1H), 6.98 (dd, 1H), 5.34 (s, 2H), 4.27 (q, 3H), 3.55 (d, 1H), 2.76 (d, 1H), 2.69 (d, 1H), 2.68 (s, 3H), 2.46 (s, 3H). |
| 508 | 1H NMR (400 MHz, DMSO) δ = 10.65 (s, 1H), 9.00 (s, 1H), 7.54 (d, 1H), 7.37 (s, 1H), 7.02 (dd, 1H), 5.33 (s, 2H), 4.70 (t, 4H), 2.67 (s, 3H), 2.42 (s, 3H), 2.35 (s, 6H). |
| 509 | 1H NMR (400 MHz, DMSO) δ = 9.14 (s, 1H), 8.99 (s, 1H), 7.49 (d, 1H), 7.25 (d, 1H), 6.99 (dd, 1H), 5.33 (s, 2H), 5.02 (d, 2H), 4.78 (d, 2H), 2.85 (s, 6H), 2.60 (s, 3H), 2.41 (s, 3H). |
| 510 - En 1 | 1H NMR (400 MHz, DMSO) δ = 8.77-8.71 (m, 1H), 8.31-8.24 (m, 1H), 7.79 (dd, 1H), 7.57 (d, 1H), 7.55-7.47 (m, 2H), 7.29 (d, 1H), 6.99 (dd, 1H), 5.31 (s, 2H), 5.18 (s, 1H), 3.73 (d, 1H), 3.62 (d, 1H), 3.30-3.21 (m, 1H), 3.17-3.09 (m, 1H), 2.60 (s, 3H), 2.23 (s, 0H), 2.18 (s, 3H), 1.79 (q, 2H). |
| 511 - En 1 | 1H NMR (500 MHz, DMSO) δ = 7.59 (d, 1H), 7.53-7.45 (m, 2H), 7.27 (d, 1H), 7.17 (s, 1H), 6.97 (dd, 1H), 5.25 (s, 1H), 5.12 (s, 2H), 3.74 (d, 1H), 3.64 (d, 1H), 3.26 (dd, 1H), 3.16-3.10 (m, 1H), 2.60 (s, 3H), 2.42 (s, 3H), 2.28-2.14 (m, 2H), 1.85-1.72 (m, 2H). |
| 512 - En 1 | 1H NMR (400 MHz, DMSO) δ = 8.41 (dd, 1H), 7.83 (dd, 1H), 7.62-7.56 (m, 1H), 7.54-7.46 (m, 2H), 7.32 (d, 1H), 7.25 (dd, 1H), 7.01 (dd, 1H), 5.24 (s, 1H), 5.15 (s, 2H), 3.74 (d, 1H), 3.63 (d, 1H), 3.26 (dd, 1H), 3.17-3.08 (m, 1H), 2.57 (d, 6H), 2.29-2.13 (m, 2H), 1.86-1.73 (m, 2H). |
| 513 - En 1 | 1H NMR (400 MHz, DMSO) δ = 8.98 (s, 1H), 7.58 (s, 1H), 7.53-7.45 (m, 2H), 7.27 (d, 1H), 6.97 (dd, 1H), 5.31 (s, 2H), 5.21 (t, 1H), 3.74 (dd, 1H), 3.63 (dd, 1H), 3.12 (d, 1H), 2.60 (s, 3H), 2.42 (s, 3H), 2.21 (d, 2H), 1.78 (s, 2H), 1.24 (s, 1H). |
| 514 - En 1 | 1H NMR (500 MHz, DMSO) δ = 8.55 (d, 1H), 7.78 (dd, 1H), 7.58 (d, 1H), 7.51 (s, 1H), 7.48 (d, 1H), 7.31-7.24 (m, 2H), 6.98 (dd, 1H), 5.28 (s, 1H), 5.12 (s, 2H), 3.74 (d, 1H), 3.64 (d, 1H), 3.26 (dd, 1H), 3.13 (dd, 1H), 2.60 (s, 3H), 2.47 (s, 3H), 2.27-2.14 (m, 1H), 1.85-1.73 (m, 1H). |
| 515 - En 1 | 1H NMR (500 MHz, DMSO) δ = 7.80 (s, 1H), 7.51-7.45 (m, 2H), 7.25 (d, 1H), 7.17 (s, 1H), 6.97 (dd, 1H), 5.22 (t, 1H), 5.12 (s, 2H), 3.67-3.55 (m, 2H), 3.29 (s, 0H), 3.21 (q, 1H), 2.59 (s, 3H), 2.49-2.36 (m, 2H), 2.42 (s, 3H). |
| 516 - En 1 | 1H NMR (400 MHz, DMSO) δ = 8.41 (dd, 1H), 7.86-7.77 (m, 2H), 7.53-7.45 (m, 2H), 7.30 (d, 1H), 7.25 (dd, 1H), 7.01 (dd, 1H), 5.22 (s, 1H), 5.15 (s, 2H), 3.67-3.55 (m, 2H), 3.31-3.14 (m, 2H), 2.57 (d, 6H), 2.50-2.37 (m, 1H). |
| 517 - En 1 | 1H NMR (500 MHz, DMSO) δ = 7.79 (s, 1H), 7.71 (s, 1H), 7.51 (s, 1H), 7.47 (d, 1H), 7.24 (d, 1H), 6.96 (dd, 1H), 5.32 (s, 2H), 3.63 (d, 1H), 3.58 (d, 1H), 3.30 (d, 1H), 3.21 (q, 1H), 2.61 (d, 6H), 2.48-2.35 (m, 1H). |
| 518 - En 1 | 1H NMR (400 MHz, DMSO) δ = 8.98 (s, 1H), 7.78 (s, 1H), 7.53-7.44 (m, 2H), 7.25 (d, 1H), 6.97 (dd, 1H), 5.31 (s, 2H), 5.21 (t, 1H), 3.62 (td, 2H), 3.20 (d, 1H), 2.59 (s, 3H), 2.49-2.34 (m, 1H), 2.42 (s, 3H). |
| 519 - En 1 | 1H NMR (400 MHz, DMSO) δ = 8.55 (d, 1H), 7.81-7.74 (m, 2H), 7.51-7.44 (m, 2H), 7.31-7.22 (m, 2H), 6.97 (dd, 1H), 5.23 (s, 1H), 5.12 (s, 2H), 3.67-3.54 (m, 2H), 3.21 (q, 1H), 2.59 (s, 3H), 2.47 (s, 3H), 2.45 (d, 0H), 2.44-2.34 (m, 1H). |
| 520 - En 1 | 1H NMR (500 MHz, DMSO) δ = 8.58 (d, 1H), 7.88-7.80 (m, 1H), 7.78 (s, 1H), 7.56 (d, 1H), 7.52-7.45 (m, 2H), 7.35 (dd, 1H), 7.27 (d, 1H), 7.00 (dd, 1H), 5.25 (t, 1H), 5.19 (s, 2H), 3.60 (qd, 2H), 3.20 (q, 1H), 2.59 (s, 3H), 2.49-2.37 (m, 3H). |
| 521 - En 1 | 1H NMR (500 MHz, DMSO) δ = 11.77 (s, 1H), 7.78 (s, 1H), 7.59 (dd, 1H), 7.51 (s, 1H), 7.47 (d, 1H), 7.38 (dd, 1H), 7.26-7.22 (m, 1H), 6.95 (dd, 1H), 6.23 (t, 1H), 5.24 (s, 1H), 4.88 (s, 2H), 3.63 (d, 1H), 3.58 (d, 1H), 3.24-3.14 (m, 1H), 2.59 (s, 3H), 2.49-2.36 (m, 1H). |
| 522 - En 1 | 1H NMR (500 MHz, DMSO) δ = 8.16 (dd, 1H), 7.84 (dd, 1H), 7.78 (s, 1H), 7.51 (s, 1H), 7.47 (d, 1H), 7.25 (d, 1H), 7.03 (dd, 1H), 6.97 (dd, 1H), 5.21 (s, 1H), 5.07 (s, 2H), 3.93 (s, 3H), 3.60 (q, 2H), 3.20 (q, 1H), 2.59 (s, 3H), 2.48-2.37 (m, 1H). |
| 523 | 1H NMR (400 MHz, DMSO) δ = 8.31 (s, 1H), 7.47 (d, 1H), 7.41 (s, 1H), 7.19 (s, 1H), 7.00 (d, 1H), 6.87 (s, 1H), 5.26 (t, 1H), 5.16 (s, 2H), 4.70 (d, 2H), 4.55 (d, 2H), 3.79 (d, 2H), 3.69 (s, 3H), 2.60 (s, 3H). |
| 524 | 1H NMR (400 MHz, DMSO) δ = 8.34 (s, 1H), 7.48 (d, 1H), 7.37 (dd, 2H), 6.99 (dd, 1H), 6.38 (d, 1H), 5.20 (d, 3H), 4.68 (d, 2H), 4.55 (d, 2H), 3.85 (s, 3H), 3.78 (s, 2H), 2.61 (s, 3H). |
| 525 | 1H NMR (400 MHz, DMSO-d6): δ 8.35 (s, 1H), 7.69 (s, 1H), 7.46 (d, 1H), 7.32 (s, 1H), 7.95 (s, 1H), 5.32 (s, 2H), 5.19 (t, 1H), 4.67 (d, 2H), 4.54 (d, 2H), 3.77 (d, 2H), 2.63 (s, 3H), 2.60 (s, 3H). |
| 526 | 1H NMR (400 MHz, DMSO) δ = 8.62-8.55 (m, 1H), 8.33 (s, 1H), 7.84 (td, 1H), 7.56 (d, 1H), 7.47 (d, 1H), 7.39-7.31 (m, 2H), 7.00 (dd, 1H), 5.21 (s, 2H), 5.19 (d, 1H), 4.67 (d, 2H), 4.55 (d, 2H), 3.77 (d, 2H), 2.60 (s, 3H). |
| 527 | 1H NMR (400 MHz, DMSO) δ = 8.33 (s, 1H), 7.85 (d, 1H), 7.79 (d, 1H), 7.49 (d, 1H), 7.38 (d, 1H), 7.03 (dd, 1H), 5.48 (s, 2H), 5.20 (t, 1H), 4.68 (d, 2H), 4.55 (d, 2H), 3.78 (d, 2H), 2.61 (s, 3H). |
| 528 | 1H NMR (400 MHz, DMSO) δ = 8.35 (s, 1H), 8.16 (dd, 1H), 7.88-7.79 (m, 1H), 7.47 (d, 1H), 7.33 (d, 1H), 7.03 (dd, 1H), 6.97 (dd, 1H), 5.19 (t, 1H), 5.08 (s, 2H), 4.67 (d, 2H), 4.55 (d, 2H), 3.93 (s, 3H), 3.77 (d, 2H), 2.61 (s, 3H). |
| 529 | 1H NMR (400 MHz, DMSO) δ = 8.99 (s, 1H), 7.48 (dd, 1H), 7.08 (d, 1H), 6.96 (dd, 1H), 5.35 (s, 2H), 5.35-5.24 (m, 1H), 4.77 (d, 2H), 4.47-4.39 (m, 2H), 4.00 (d, 2H), 2.87 (s, 3H), 2.45 (d, 6H). |
| 530 - En 1 | 1H NMR (500 MHz, DMSO) δ = 7.70 (s, 1H), 7.54 (s, 1H), 7.45 (d, 1H), 7.25 (d, 1H), 6.93 (dd, 1H), 5.31 (s, 2H), 5.08 (s, 1H), 3.66 (dd, 2H), 3.00 (d, 1H), 2.95-2.85 (m, 1H), 2.79 (ddd, 1H), 2.63 (s, 3H), 2.56 (d, 4H), 2.06 (ddd, 1H), 1.79 (dt, 2H). |
| 531 - En 1 | 1H NMR (400 MHz, DMSO) δ = 8.74 (dd, 1H), 8.27 (d, 1H), 7.79 (dd, 1H), 7.49 (d, 1H), 7.31 (d, 1H), 7.24 (s, 1H), 6.98 (dd, 1H), 5.31 (s, 2H), 4.88 (t, 1H), 4.00 (d, 1H), 3.76-3.60 (m, 3H), 3.47 (dd, 2H), 2.60 (s, 3H), 2.29 (dd, 1H), 1.70 (dt, 2H), 1.51 (d, 1H). |
| 532 - En 1 | 1H NMR (400 MHz, DMSO) δ = 8.98 (s, 1H), 7.46 (d, 1H), 7.31 (d, 1H), 7.21 (s, 1H), 6.95 (dd, 1H), 5.30 (s, 2H), 4.90 (t, 1H), 4.05-3.96 (m, 1H), 3.76-3.61 (m, 3H), 3.51 (d, 1H), 3.46 (s, 1H), 2.60 (s, 3H), 2.42 (s, 3H), 2.31 (d, 1H), 1.75-1.65 (m, 2H), 1.52 (d, 1H). |

| cpd Nr | NMR Data |
|---|---|
| 533 - En 1 | 1H NMR (500 MHz, DMSO) δ = 7.84 (s, 1H), 7.69 (s, 1H), 7.45 (d, 1H), 7.24 (d, 1H), 6.94 (dd, 1H), 5.31 (s, 2H), 5.11-5.05 (m, 1H), 3.92 (d, 1H), 3.86-3.75 (m, 3H), 3.72 (dd, 1H), 3.66 (dd, 1H), 2.63 (s, 3H), 2.57 (s, 3H), 2.25 (ddd, 1H), 2.06 (dt, 1H). |
| 534 - En 1 | 1H NMR (400 MHz, DMSO) δ = 8.58 (ddd, 1H), 7.88-7.79 (m, 2H), 7.55 (d, 1H), 7.46 (d, 1H), 7.35 (ddd, 1H), 7.25 (d, 1H), 6.98 (dd, 1H), 5.20 (s, 2H), 5.08 (d, 1H), 3.92 (d, 1H), 3.87-3.74 (m, 3H), 3.71 (dd, 1H), 3.65 (dd, 1H), 2.57 (s, 3H), 2.23 (ddd, 1H), 2.06 (dt, 1H). |
| 535 - En 1 | 1H NMR (400 MHz, DMSO) δ = 11.77 (s, 1H), 7.85 (s, 1H), 7.61-7.54 (m, 1H), 7.45 (d, 1H), 7.41-7.34 (m, 1H), 7.22 (d, 1H), 6.94 (dd, 1H), 6.22 (t, 1H), 5.08 (s, 1H), 4.88 (s, 2H), 3.92 (d, 1H), 3.80 (dt, 3H), 3.75-3.62 (m, 2H), 2.57 (s, 3H), 2.24 (dt, 1H), 2.06 (dt, 1H). |
| 536 - En 1 | 1H NMR (400 MHz, DMSO) δ = 8.16 (dd, 1H), 7.88-7.79 (m, 2H), 7.45 (d, 1H), 7.24 (d, 1H), 7.03 (dd, 1H), 6.95 (dd, 1H), 5.06 (d, 3H), 3.92 (d, 4H), 3.80 (d, 2H), 3.78 (d, 1H), 3.68 (qd, 2H), 2.57 (s, 3H), 2.23 (dt, 1H), 2.05 (dt, 1H). |
| 537 | 1H NMR (500 MHz, DMSO) δ = 8.99 (s, 1H), 8.24 (s, 1H), 7.47 (d, 1H), 7.27 (d, 1H), 6.96 (dd, 1H), 5.31 (s, 2H), 5.22 (t, 1H), 3.65 (d, 2H), 2.87 (dd, 4H), 2.58 (s, 3H), 2.42 (s, 3H). |
| 538 - En 1 | 1H NMR (400 MHz, DMSO) δ = 8.78-8.65 (m, 2H), 8.31-8.20 (m, 1H), 7.79 (dd, 1H), 7.33 (dd, 1H), 7.03 (d, 1H), 5.33-5.24 (m, 2H), 4.47 (d, 1H), 3.09 (s, 1H), 2.97-2.72 (m, 2H), 2.69-2.55 (m, 1H), 2.42 (s, 3H), 2.26 (s, 3H), 1.79 (d, 1H), 1.72-1.55 (m, 1H), 1.24 (s, 1H). |
| 539 - En 1 | 1H NMR (400 MHz, DMSO) δ = 8.33-8.21 (m, 2H), 7.91 (d, 1H), 7.79-7.64 (m, 2H), 7.60 (dd, 1H), 7.39 (dd, 1H), 5.41 (s, 2H), 4.49 (s, 1H), 3.20-3.04 (m, 1H), 2.98-2.75 (m, 2H), 2.70-2.54 (m, 1H), 2.59 (s, 3H), 1.86-1.60 (m, 2H). |
| 540 - En 1 | 1H NMR (500 MHz, DMSO) δ = 8.20 (d, 1H), 8.15 (s, 1H), 7.47 (d, 1H), 7.23 (d, 1H), 6.97 (dd, 1H), 5.14 (d, 2H), 4.54-4.42 (m, 1H), 4.05 (s, 2H), 3.30 (s, 1H), 3.11 (q, 1H), 2.92 (d, 1H), 2.84 (dd, 1H), 2.62 (d, 1H), 2.57 (s, 3H), 2.44 (s, 1H), 1.73 (ddd, 2H). |
| 541 - En 1 | 1H NMR (400 MHz, DMSO) δ = 8.23 (d, 1H), 7.79 (s, 1H), 7.49 (d, 1H), 7.25 (d, 1H), 7.00 (dd, 1H), 5.30 (s, 2H), 4.55-4.40 (m, 1H), 4.06 (s, 3H), 3.13 (t, 1H), 2.99-2.74 (m, 2H), 2.63 (d, 1H), 2.57 (s, 3H), 1.83-1.63 (m, 2H). |
| 542 - En 1 | 1H NMR (400 MHz, DMSO) δ = 8.46 (s, 1H), 8.18 (d, 1H), 7.46 (d, 1H), 7.23 (d, 1H), 6.97 (dd, 1H), 5.05 (d, 2H), 4.47 (s, 1H), 3.86 (s, 3H), 3.20-3.04 (m, 1H), 2.98-2.74 (m, 2H), 2.62 (d, 1H), 2.57 (s, 3H), 2.43 (s, 1H), 1.78 (s, 1H), 1.86-1.63 (m, 1H). |
| 543 - En 1 | 1H NMR (400 MHz, DMSO) δ = 8.21 (d, 1H), 7.48 (d, 1H), 7.37 (d, 1H), 7.24 (d, 1H), 6.99 (dd, 1H), 6.36 (d, 1H), 5.18 (s, 2H), 4.47 (dd, 1H), 3.85 (s, 3H), 3.21-3.04 (m, 1H), 2.98-2.74 (m, 2H), 2.57 (s, 3H), 2.43 (s, 1H), 1.78 (s, 2H), 1.86-1.62 (m, 1H). |
| 544 - En 1 | 1H NMR (500 MHz, DMSO) δ = 8.20 (d, 1H), 7.71 (d, 1H), 7.55 (d, 1H), 7.46 (d, 1H), 7.18 (s, 1H), 6.95 (d, 1H), 6.26 (t, 1H), 4.92 (t, 2H), 4.47 (s, 1H), 3.48 (s, 3H), 3.39 (s, 2H), 3.11 (s, 1H), 2.97-2.75 (m, 2H), 2.59 (d, 3H), 1.78 (s, 1H), 1.71 (d, 1H). |
| 545 - En 1 | 1H NMR (400 MHz, DMSO) δ = 8.22 (d, 1H), 7.50 (d, 1H), 7.39 (dd, 1H), 7.24 (d, 1H), 7.03 (dd, 1H), 6.48-6.36 (m, 2H), 5.14 (s, 2H), 3.49 (s, 3H), 3.20-3.04 (m, 1H), 2.98-2.74 (m, 2H), 2.62 (d, 1H), 2.58 (s, 3H), 2.43 (s, 1H), 1.86-1.61 (m, 2H). |
| 546 - En 1 | 1H NMR (DMSO-d6) δ = 8.73 (d, 1H), 8.25 (t, 2H), 7.79 (dd, 1H), 7.50 (d, 1H), 7.22 (d, 1H), 7.00 (dd, 1H), 5.31 (s, 2H), 4.37-4.58 (m, 1H), 3.04-3.17 (m, 1H), 2.74-2.96 (m, 2H), 2.59-2.72 (m, 1H), 2.58 (s, 3H), 1.63-1.85 (m, 2H). |
| 547 - En 1 | 1H NMR (500 MHz, DMSO) δ = 8.41 (dd, 1H), 8.22 (d, 1H), 7.80 (dd, 1H), 7.48 (d, 1H), 7.29-7.19 (m, 2H), 7.00 (dd, 1H), 5.14 (s, 2H), 4.47 (dd, 1H), 3.12 (s, 0H), 2.92 (d, 1H), 2.84 (dd, 1H), 2.55 (d, 7H), 2.44 (s, 1H), 1.82-1.64 (m, 2H). |
| 548 - En 1 | 1H NMR (400 MHz, DMSO) δ = 8.70 (d, 1H), 8.20 (d, 1H), 7.49 (d, 1H), 7.41 (d, 1H), 7.19 (d, 1H), 7.02 (dd, 1H), 5.18 (s, 2H), 4.46 (d, 1H), 3.19-3.03 (m, 1H), 2.98-2.73 (m, 2H), 2.60 (d, 7H), 1.76 (s, 1H), 1.80-1.62 (m, 1H). |
| 549 - En 1 | 1H NMR (400 MHz, DMSO) δ = 8.20 (d, 1H), 7.68 (s, 1H), 7.47 (d, 1H), 7.20 (d, 1H), 6.96 (dd, 1H), 5.31 (s, 2H), 4.48 (s, 1H), 3.12 (s, 1H), 2.92 (d, 2H), 2.80 (d, 1H), 2.60 (s, 1H), 2.60 (d, 6H), 1.77 (s, 2H), 1.78-1.66 (m, 0H). |
| 550 - En 1 | 1H NMR (400 MHz, DMSO) δ = 8.22 (d, 1H), 7.46 (dd, 1H), 7.17 (d, 1H), 6.94 (dt, 1H), 4.50 (d, 2H), 4.45 (s, 1H), 4.32 (d, 2H), 4.06 (d, 2H), 3.22-3.04 (m, 1H), 2.99-2.74 (m, 2H), 2.59 (d, 1H), 2.57 (s, 3H), 1.78 (s, 2H), 1.81-1.63 (m, 1H), 1.38 (s, 3H). |
| 551 - En 1 | 1H NMR (400 MHz, DMSO) δ = 8.20 (d, 1H), 7.83 (q, 1H), 7.48 (d, 1H), 7.22 (d, 1H), 6.98 (dd, 1H), 5.16 (s, 2H), 4.47 (s, 1H), 3.20-3.04 (m, 1H), 2.98-2.74 (m, 2H), 2.63 (d, 1H), 2.57 (s, 3H), 2.43 (s, 1H), 2.09 (d, 3H), 1.74 (dtd, 2H). |
| 552 - En 1 | 1H NMR (400 MHz, DMSO) δ = 8.21 (d, 1H), 7.49 (d, 1H), 7.29 (d, 1H), 7.24 (d, 1H), 7.01 (dd, 1H), 5.38 (s, 2H), 4.46 (dd, 1H), 3.22-3.04 (m, 0H), 3.12 (s, 1H), 2.99-2.74 (m, 2H), 2.61 (s, 1H), 2.57 (s, 3H), 2.37 (s, 4H), 1.74 (ddt, 2H). |
| 553 - En 1 | 1H NMR (400 MHz, DMSO) δ = 8.20 (d, 1H), 7.48 (d, 1H), 7.21 (d, 1H), 6.97 (dd, 1H), 6.34 (d, 1H), 5.14 (s, 2H), 4.47 (s, 1H), 3.20-3.04 (m, 1H), 2.98-2.74 (m, 2H), 2.62 (d, 1H), 2.57 (s, 3H), 2.41 (d, 3H), 1.78 (s, 1H), 1.80-1.62 (m, 1H). |
| 554 - En 1 | 1H NMR (400 MHz, DMSO) δ = 8.67 (d, 1H), 8.56 (d, 1H), 8.20 (d, 1H), 7.48 (d, 1H), 7.23 (d, 1H), 7.01 (dd, 1H), 5.22 (s, 2H), 4.53-4.40 (m, 1H), 3.13 (s, 1H), 2.93 (s, 2H), 2.57 (s, 3H), 1.80 (s, 1H), 1.71 (d, 1H). |
| 555 - En 1 | 1H NMR (400 MHz, DMSO) δ = 8.20 (d, 1H), 7.54-7.43 (m, 2H), 7.23 (d, 1H), 7.00 (dd, 1H), 5.35 (s, 2H), 4.45 (s, 1H), 3.12 (s, 1H), 2.99-2.74 (m, 2H), 2.63 (d, 1H), 2.57 (s, 3H), 2.44 (d, 3H), 1.82-1.62 (m, 2H). |
| 556 - En 1 | 1H NMR (400MHz, DMSO) δ = 8.19 (d, 1H), 7.71 (d, 1H), 7.60 (d, 1H), 7.47 (d, 1H), 7.23 (d, 1H), 6.99 (dd, 1H), 5.36 (s, 2H), 4.41-4.5 (m, 1H), 3.09-3.14 (t, 1H), 2.70-2.93 (m, 2H), 2.57-2.78 (m, 7H), 2.50 (bs, 1H), 1.72-1.78 (m, 2H). |
| 557 - En 1 | 1H NMR (400 MHz, DMSO) δ = 9.22 (dd, 1H), 8.21 (d, 1H), 7.85 (dd, 1H), 7.76 (dd, 1H), 7.49 (d, 1H), 7.25 (d, 1H), 7.03 (dd, 1H), 5.42 (s, 2H), 4.47 (d, 1H), 3.11 (q, 1H), 2.98-2.73 (m, 2H), 2.62 (d, 1H), 2.57 (s, 3H), 1.85-1.63 (m, 2H). |

| cpd Nr | NMR Data |
|---|---|
| 558 - En 1 | 1H NMR (400 MHz, DMSO) δ = 8.68 (d, 1H), 8.55 (dd, 1H), 8.21 (d, 1H), 7.88 (dt, 1H), 7.53-7.37 (m, 2H), 7.23 (d, 1H), 6.99 (dd, 1H), 5.17 (s, 2H), 4.55-4.40 (m, 1H), 3.19-3.04 (m, 1H), 2.98-2.74 (m, 2H), 2.62 (d, 1H), 2.57 (s, 3H), 1.72 (ddd, 2H). |
| 559 - En 1 | 1H NMR (400 MHz, DMSO) δ = 8.83 (d, 2H), 8.16 (d, 1H), 7.52-7.39 (m, 2H), 7.15 (d, 1H), 6.95 (dd, 1H), 5.28 (s, 2H), 3.10 (s, 1H), 2.98-2.72 (m, 2H), 2.56 (s, 4H), 2.42 (s, 1H), 1.81-1.60 (m, 2H). |
| 560 - En 1 | 1H NMR (400 MHz, DMSO) δ = 8.21 (d, 1H), 7.84 (d, 1H), 7.78 (d, 1H), 7.49 (d, 1H), 7.25 (d, 1H), 7.03 (dd, 1H), 5.45 (s, 2H), 3.20-3.04 (m, 1H), 2.99-2.74 (m, 2H), 2.63 (d, 1H), 2.57 (s, 3H), 2.44 (s, 1H), 1.78 (s, 1H), 1.86-1.62 (m, 1H). |
| 561 - En 1 | 1H NMR (400 MHz, DMSO) δ = 9.11 (d, 1H), 8.21 (d, 1H), 7.99 (d, 1H), 7.48 (d, 1H), 7.22 (d, 1H), 6.98 (dd, 1H), 5.40 (s, 2H), 4.45 (s, 0H), 3.20-3.04 (m, 1H), 2.98-2.74 (m, 2H), 2.61 (t, 1H), 2.57 (s, 3H), 1.74 (dtt, 2H). |
| 562 - En 1 | 1H NMR (400 MHz, DMSO) δ = 8.99 (s, 1H), 8.40 (d, 1H), 7.36 (dd, 1H), 7.24 (dd, 1H), 5.37 (s, 2H), 3.08 (q, 1H), 2.96-2.72 (m, 2H), 2.59 (d, 2H), 2.51 (s, 3H), 2.39 (s, 3H), 1.79 (dt, 1H), 1.63 (qd, 1H) |
| 563 - En 1 | 1H NMR (500 MHz, DMSO) δ = 8.20 (d, 1H), 7.46 (d, 1H), 7.20 (d, 1H), 6.94 (dd, 1H), 5.22 (s, 2H), 4.47 (s, 1H), 3.12 (s, 1H), 2.87 (dt, 2H), 2.62 (d, 1H), 2.57 (s, 6H), 2.32 (s, 3H), 1.84-1.64 (m, 2H). |
| 564 - En 1 | 1H NMR (400 MHz, DMSO) δ = 11.75 (s, 1H), 8.20 (d, 1H), 7.56 (dd, 1H), 7.46 (d, 1H), 7.38 (dd, 1H), 7.18 (d, 1H), 6.95 (dd, 1H), 6.22 (t, 1H), 4.96-4.80 (m, 2H), 4.48 (d, 1H), 3.12 (t, 1H), 2.92 (d, 1H), 2.80 (s, 1H), 2.57 (s, 3H), 2.42 (s, 1H), 1.83-1.66 (m, 2H). |
| 565 - En 1 | 1H NMR (400 MHz, DMSO) δ = 8.22 (d, 1H), 8.15 (dd, 1H), 7.81 (dd, 1H), 7.47 (d, 1H), 7.20 (d, 1H), 7.00 (ddd, 2H), 5.06 (s, 2H), 4.47 (dt, 1H), 3.92 (s, 3H), 3.11 (s, 1H), 2.98-2.73 (m, 2H), 2.60 (s, 1H), 2.57 (s, 3H), 2.43 (s, 1H), 1.85-1.61 (m, 2H). |
| 566 - En 1 | 1H NMR (500 MHz, DMSO) δ = 8.45 (dt, 1H), 8.20 (d, 1H), 7.79 (ddd, 1H), 7.53 (dt, 1H), 7.47 (d, 1H), 7.24 (d, 1H), 6.98 (dd, 1H), 5.29-5.17 (m, 2H), 3.18-3.06 (m, 1H), 2.88 (s, 1H), 2.97-2.75 (m, 1H), 2.61 (s, 1H), 2.57 (s, 3H), 2.42 (s, 1H), 1.84-1.64 (m, 2H). |
| 567 - En 1 | 1H NMR (400 MHz, DMSO) δ = 8.28 (d, 1H), 8.19 (d, 1H), 7.44 (qd, 3H), 7.21 (d, 1H), 6.97 (dd, 1H), 5.10 (s, 2H), 4.91 (t, 1H), 4.48 (d, 1H), 4.07 (dd, 2H), 3.73 (q, 2H), 3.11 (d, 1H), 2.98-2.74 (m, 2H), 2.69-2.53 (m, 1H), 2.57 (s, 3H), 1.78 (s, 2H), 1.24 (s, 1H). |
| 568 - En 1 | 1H NMR (500 MHz, DMSO) δ = 8.58 (d, 1H), 8.19 (d, 1H), 7.77 (td, 1H), 7.63 (dd, 1H), 7.48 (d, 1H), 7.21 (d, 1H), 6.99 (dd, 1H), 5.19 (s, 2H), 4.55-4.41 (m, 1H), 3.12 (t, 1H), 2.86 (dt, 2H), 2.57 (s, 4H), 2.47-2.39 (m, 1H), 1.82-1.74 (m, 1H), 1.71 (qd, 1H). |
| 569 - En 1 | 1H NMR (400 MHz, DMSO) δ = 11.68 (s, 1H), 8.21 (d, 1H), 7.45 (dd, 2H), 7.18 (d, 1H), 6.97 (dd, 1H), 6.35-6.24 (m, 2H), 4.91 (s, 2H), 4.45 (s, 1H), 3.10 (d, 1H), 2.98-2.74 (m, 2H), 2.61 (s, 1H), 2.57 (s, 3H), 1.78 (s, 1H), 1.79-1.62 (m, 1H). |
| 570 - En 1 | 1H NMR (400 MHz, DMSO) δ = 8.20 (d, 1H), 7.72 (dd, 1H), 7.47 (d, 1H), 7.23 (d, 1H), 7.10 (dd, 1H), 6.99 (dd, 1H), 6.75 (dd, 1H), 5.11 (s, 2H), 3.86 (s, 3H), 3.19-3.03 (m, 1H), 2.98-2.73 (m, 2H), 2.62 (d, 1H), 2.57 (s, 3H), 2.43 (s, 1H), 1.76 (s, 1H), 1.84-1.61 (m, 1H). |
| 571 - En 1 | 1H NMR (400 MHz, DMSO) δ = 8.72-8.63 (m, 1H), 8.19 (dd, 1H), 7.96 (dt, 1H), 7.64-7.53 (m, 2H), 7.48 (dd, 1H), 7.38-7.20 (m, 2H), 6.99 (ddd, 1H), 5.13 (s, 2H), 4.43 (s, 2H), 4.11 (d, 1H), 3.12 (s, 1H), 2.88 (dd, 1H), 2.57 (d, 3H), 1.82-1.61 (m, 2H). |
| 572 - En 1 | 1H NMR (400 MHz, DMSO) δ = 8.99 (s, 1H), 8.26 (d, 1H), 7.62 (d, 1H), 7.40 (d, 1H), 5.38 (s, 2H), 4.48 (dt, 1H), 3.19-3.04 (m, 1H), 2.99-2.74 (m, 2H), 2.61 (s, 1H), 2.56 (s, 3H), 2.44 (s, 1H), 2.41 (s, 3H), 1.86-1.61 (m, 2H). |
| 573 - En 1 | 1H NMR (400 MHz, DMSO) δ = 8.99 (s, 1H), 8.33 (d, 1H), 7.09-6.95 (m, 2H), 5.33 (s, 2H), 4.47 (d, 1H), 3.11 (s, 1H), 2.98-2.73 (m, 2H), 2.59 (s, 3H), 2.43 (d, 1H), 2.42 (s, 3H), 1.72 (ddd, 2H), 1.23 (s, 1H). |
| 574 | 1H NMR (500 MHz, DMSO) δ = 8.21 (dd, 2H), 8.06 (s, 1H), 7.95 (t, 1H), 7.57 (d, 1H), 4.24 (t, 1H), 3.74 (d, 1H), 3.21-3.11 (m, 3H), 2.55 (d, 3H), 2.17 (d, 1H), 2.11-1.96 (m, 1H), 1.99 (s, 1H), 1.74 (d, 1H), 1.56 (s, 3H), 1.43 (d, 1H), 1.01 (d, 6H), 0.86 (s, 0H). |
| 575 - En 1 | 1H NMR (500 MHz, DMSO) δ = 8.99 (s, 1H), 7.78 (t, 1H), 7.46 (d, 2H), 7.40 (d, 1H), 7.16 (s, 1H), 6.95 (dd, 1H), 5.32 (s, 2H), 3.56 (dt, 1H), 3.46 (ddd, 1H), 3.23 (t, 1H), 2.60 (s, 3H), 2.42 (s, 3H), 2.30 (s, 6H). |
| 576 | 1H NMR (400 MHz, DMSO) δ = 8.98 (s, 1H), 7.47 (d, 1H), 7.36 (d, 1H), 7.28 (s, 1H), 7.00 (s, 1H), 6.95 (dd, 1H), 5.33 (s, 2H), 3.40 (d, 2H), 2.61 (s, 3H), 2.42 (s, 3H), 1.16 (s, 6H). |
| 577 | 1H NMR (400 MHz, DMSO) δ = 9.30 (s, 1H), 9.02 (s, 1H), 7.75 (dd, 1H), 7.64-7.54 (m, 1H), 7.42 (d, 1H), 7.28 (s, 1H), 7.33-7.22 (m, 1H), 5.42 (s, 2H), 4.89 (d, 2H), 4.74 (d, 2H), 2.45 (s, 3H). |
| 578 | 1H NMR (500 MHz, DMSO) δ = 8.70 (s, 1H), 7.56 (d, 1H), 7.49 (d, 1H), 7.23 (d, 1H), 7.19 (d, 1H), 7.02 (dd, 1H), 6.87 (d, 1H), 5.19 (s, 2H), 4.88 (d, 2H), 4.71 (d, 2H), 3.70 (s, 3H), 2.65 (s, 3H). |
| 579 | 1H NMR (400 MHz, DMSO) δ = 8.69 (s, 1H), 7.54-7.46 (m, 2H), 7.38 (d, 1H), 7.22 (d, 2H), 7.01 (dd, 1H), 6.38 (d, 1H), 5.21 (s, 2H), 4.88 (d, 2H), 4.68 (d, 2H), 3.86 (s, 3H), 2.67 (s, 3H). |
| 580 | 1H-NMR (400 MHz, DMSO-d6): δ 8.67 (s, 1H), 7.70 (s, 1H), 7.51-7.44 (m, 2H), 7.24-7.19 (m, 2H), 6.98 (dd, 1H), 5.34 (s, 2H), 4.87 (d, 2H), 4.68 (d, 2H), 2.65 (s, 3H), 2.63 (s, 3H). |
| 581 | 1H NMR (400 MHz, DMSO) δ = 8.70 (s, 1H), 8.59 (ddd, 1H), 7.85 (td, 1H), 7.57 (dt, 1H), 7.53-7.45 (m, 2H), 7.35 (ddd, 1H), 7.21 (d, 2H), 7.02 (dd, 1H), 5.24 (s, 2H), 4.88 (d, 2H), 4.68 (d, 2H), 2.65 (s, 3H). |
| 582 | 1H NMR (400 MHz, DMSO) δ = 8.70 (s, 1H), 7.85 (d, 1H), 7.79 (d, 1H), 7.55-7.47 (m, 2H), 7.22 (d, 2H), 7.05 (dd, 1H), 5.50 (s, 2H), 4.88 (d, 2H), 4.69 (d, 2H), 2.66 (s, 3H). |
| 583 | 1H NMR (400 MHz, DMSO) δ = 9.11-9.05 (m, 1H), 9.00 (s, 1H), 7.40 (dd, 1H), 7.34-7.24 (m, 2H), 7.03 (s, 1H), 5.39 (s, 2H), 4.87 (d, 2H), 4.60 (d, 2H), 2.57 (s, 3H), 2.40 (s, 3H). |
| 584 | 1H NMR (500 MHz, DMSO) δ = 8.74 (s, 1H), 8.67 (dd, 1H), 8.14 (d, 1H), 7.75-7.39 (m, 3H), 7.36-6.91 (m, 4H), 5.37 (s, 2H), 4.88 (d, 2H), 4.67 (d, 2H), 2.67 (s, 3H). |
| 585 | 1H NMR (500 MHz, DMSO) δ = 11.78 (s, 1H), 8.78 (s, 1H), 7.61 (dd, 1H), 7.51-7.43 (m, 2H), 7.39 (dd, 1H), 7.28 (d, 1H), 7.17 (s, 1H), 6.97 (dd, 1H), 6.23 (t, 1H), 4.93 (s, 2H), 4.87 (d, 2H), 4.68 (d, 2H), 2.65 (s, 3H). |
| 586 | 1H NMR (500 MHz, DMSO) δ = 8.70 (s, 1H), 8.16 (dd, 1H), 7.85 (dd, 1H), 7.52-7.43 (m, 2H), 7.23 (s, 1H), 7.20 (s, 1H), 7.02 (ddd, 2H), 5.10 (s, 2H), 4.87 (d, 2H), 4.67 (d, 2H), 3.92 (s, 3H), 2.67 (s, 3H |
| 587 | 1H NMR (400 MHz, DMSO) δ = 9.00 (s, 1H), 8.72 (s, 1H), 7.68-7.60 (m, 2H), 7.25 (d, 2H), 5.42 (s, 2H), 4.88 (d, 2H), 4.69 (d, 2H), 2.67 (s, 3H), 2.42 (s, 3H). |

| cpd Nr | NMR Data |
| --- | --- |
| 588 | 1H NMR (500 MHz, DMSO) δ = 9.00 (s, 1H), 8.78 (s, 1H), 7.29 (d, 1H), 7.22 (s, 1H), 7.05 (dd, 1H), 5.36 (s, 2H), 4.87 (d, 2H), 4.68 (d, 2H), 2.69 (s, 3H), 2.43 (s, 3H). |
| 589 | 1H NMR (400 MHz, DMSO) δ = 8.98 (s, 1H), 7.49 (d, 1H), 7.44 (s, 2H), 7.13 (d, 1H), 6.97 (dd, 1H), 5.35 (s, 2H), 4.84 (d, 2H), 4.76 (d, 2H), 2.90 (s, 3H), 2.47 (s, 3H), 2.43 (s, 3H). |
| 590 - En 1 | 1H NMR (500 MHz, DMSO) δ = 7.69 (s, 1H), 7.59 (s, 1H), 7.49 (d, 1H), 7.34 (d, 1H), 7.08 (d, 2H), 6.98 (dd, 1H), 5.32 (s, 2H), 4.08 (dd, 1H), 3.83 (d, 1H), 3.65 (d, 1H), 3.43 (td, 1H), 2.63 (d, 6H), 2.34 (d, 1H), 1.95 (td, 1H), 1.76 (d, 1H). |
| 591 - En 1 | 1H NMR (500 MHz, DMSO) δ = 8.41 (dd, 1H), 8.24 (s, 1H), 7.81 (dd, 1H), 7.49 (d, 1H), 7.25 (dd, 1H), 7.13 (s, 1H), 7.09 (s, 1H), 7.02 (dd, 1H), 5.16 (s, 2H), 4.18 (d, 1H), 3.94 (d, 1H), 3.90-3.79 (m, 2H), 2.62 (s, 3H), 2.53 (s, 3H), 2.41-2.28 (m, 2H). |
| 592 - En 1 | 1H NMR (500 MHz, DMSO) δ = 8.22 (s, 1H), 7.70 (s, 1H), 7.47 (d, 1H), 7.31 (d, 1H), 7.12 (s, 1H), 7.08 (s, 1H), 5.33 (s, 2H), 4.18 (d, 1H), 3.94 (d, 1H), 3.86 (dd, 2H), 2.62 (d, 6H), 2.36 (hept, 2H). |
| 593 - En 1 | 1H NMR (500 MHz, DMSO) δ = 8.99 (s, 1H), 7.48 (d, 1H), 7.33 (d, 1H), 7.14 (s, 1H), 7.08 (s, 1H), 6.98 (dd, 1H), 5.33 (s, 2H), 4.19 (d, 1H), 3.94 (d, 1H), 3.85 (dd, 2H), 2.62 (s, 3H), 2.42 (s, 3H), 2.41-2.28 (m, 2H). |
| 594 - En 1 | 1H NMR (500 MHz, DMSO) δ = 8.54 (d, 1H), 8.24 (s, 1H), 7.77 (dd, 1H), 7.47 (d, 1H), 7.28 (d, 1H), 7.13 (s, 1H), 7.08 (s, 1H), 6.98 (dd, 1H), 5.13 (s, 2H), 4.18 (d, 1H), 3.94 (d, 1H), 3.85 (dd, 2H), 2.62 (s, 3H), 2.47 (s, 3H), 2.41-2.28 (m, 2H). |
| 595 - En 1 | 1H NMR (400 MHz, DMSO) δ = 8.58 (ddd, 1H), 8.22 (s, 1H), 7.84 (td, 1H), 7.59-7.45 (m, 2H), 7.39-7.30 (m, 2H), 7.10 (d, 2H), 7.01 (dd, 1H), 5.22 (s, 2H), 4.19 (d, 1H), 3.93 (d, 1H), 3.89-3.79 (m, 2H), 2.61 (s, 3H), 2.42-2.26 (m, 2H), 1.25 (dd, 0H). |
| 596 - En 1 | 1H NMR (500 MHz, DMSO) δ = 8.26 (s, 1H), 7.58 (dd, 1H), 7.46 (d, 1H), 7.38 (dd, 1H), 7.32 (d, 1H), 7.17 (s, 1H), 7.05 (s, 1H), 6.95 (dd, 1H), 6.22 (t, 1H), 4.91 (s, 2H), 4.20 (d, 1H), 3.93 (d, 1H), 3.84 (t, 2H), 2.61 (s, 3H), 2.37-2.31 (m, 1H). |
| 597 - En 1 | 1H NMR (500 MHz, DMSO) δ = 8.25 (s, 1H), 8.16 (dd, 1H), 7.83 (dd, 1H), 7.48 (d, 1H), 7.13 (s, 1H), 7.08 (s, 1H), 7.03 (dd, 1H), 6.98 (dd, 1H), 5.08 (s, 2H), 4.18 (d, 1H), 3.93 (d, 1H), 3.93 (s, 3H), 3.90-3.78 (m, 2H), 2.62 (s, 3H), 2.38-2.27 (m, 2H). |
| 598 - En 1 | 1H NMR (500 MHz, DMSO) δ = 8.27 (s, 1H), 7.53-7.45 (m, 2H), 7.36 (d, 1H), 7.13 (s, 1H), 7.08 (s, 1H), 7.00 (dd, 1H), 5.19 (s, 2H), 4.20 (d, 1H), 3.94 (d, 1H), 3.85 (dd, 2H), 3.83 (s, 3H), 2.62 (s, 3H), 2.41-2.29 (m, 2H). |
| 599 | 1H NMR (500 MHz, DMSO) δ = 8.99 (s, 1H), 7.53 (d, 1H), 7.18 (d, 1H), 7.00 (dd, 1H), 5.37 (s, 2H), 4.98-4.92 (m, 2H), 4.91-4.85 (m, 2H), 2.93 (s, 3H), 2.54 (s, 3H), 2.43 (s, 3H). |
| 600 - En 1 | 1H NMR (400 MHz, DMSO) δ = 8.99 (s, 1H), 7.95 (d, 1H), 7.68 (d, 1H), 7.49 (d, 1H), 7.39 (d, 1H), 6.98 (dd, 1H), 5.32 (s, 2H), 5.04 (s, 1H), 4.49 (dt, 1H), 3.72 (d, 2H), 2.63 (d, 6H), 2.42 (s, 3H). |
| 601 - En 1 | 1H NMR (500 MHz, DMSO) δ = 8.58 (dt, 1H), 7.94 (d, 1H), 7.84 (td, 1H), 7.67 (d, 1H), 7.57 (d, 1H), 7.49 (d, 1H), 7.40 (d, 1H), 7.35 (ddd, 1H), 7.01 (dd, 1H), 5.20 (s, 2H), 5.03 (t, 1H), 4.48 (dt, 1H), 3.72 (t, 2H), 2.63 (d, 6H). |
| 602 | 1H NMR (400 MHz, DMSO) δ = 8.98 (s, 1H), 7.93 (t, 1H), 7.48 (d, 1H), 7.30 (d, 1H), 6.97 (dd, 1H), 5.31 (s, 2H), 4.75 (t, 1H), 3.21 (t, 4H), 2.61 (s, 3H), 2.41 (s, 3H), 0.88 (s, 6H). |
| 603 | 1H NMR (400 MHz, DMSO) δ = 8.96 (s, 1H), 7.93 (s, 1H), 7.30 (d, 1H), 7.08 (d, 1H), 5.28 (s, 2H), 4.83 (t, 1H), 3.74-3.51 (m, 6H), 2.49 (s, 2H), 2.38 (s, 3H), 2.25 (s, 3H), 2.12 (d, 2H), 1.68-1.55 (m, 2H). |
| 604 | 1H NMR (500 MHz, DMSO) δ = 8.16 (s, 1H), 7.45 (d, 1H), 7.39 (s, 1H), 7.28 (d, 1H), 6.95 (dd, 1H), 5.15 (s, 2H), 4.90 (s, 1H), 4.05 (s, 3H), 3.70 (dt, 2H), 3.67-3.58 (m, 4H), 2.59 (s, 3H), 2.19 (d, 2H), 1.63 (ddd, 2H). |
| 605 | 1H NMR (500 MHz, DMSO) δ = 7.80 (s, 1H), 7.47 (d, 1H), 7.41 (s, 1H), 7.29 (d, 1H), 6.99 (dd, 1H), 5.30 (s, 2H), 4.93-4.87 (m, 1H), 4.06 (s, 3H), 3.66 (dddd, 6H), 2.61 (s, 3H), 2.18 (d, 2H), 1.63 (ddd, 2H). |
| 606 | 1H NMR (400 MHz, DMSO) δ = 8.46 (s, 1H), 7.44 (d, 1H), 7.37 (s, 1H), 7.29 (d, 1H), 6.95 (dd, 1H), 5.07 (s, 2H), 4.88 (t, 1H), 3.86 (s, 3H), 3.74-3.63 (m, 4H), 3.67-3.58 (m, 2H), 2.59 (s, 3H), 2.19 (d, 2H), 1.63 (ddd, 2H). |
| 607 | 1H NMR (500 MHz, DMSO) δ = 7.64 (s, 1H), 7.45 (d, 1H), 7.40 (s, 1H), 7.27 (d, 1H), 7.00 (d, 1H), 6.96 (dd, 1H), 5.10 (s, 2H), 4.90 (t, 1H), 3.74-3.68 (m, 2H), 3.68-3.58 (m, 7H), 2.60 (s, 3H), 2.18 (d, 2H), 1.68-1.58 (m, 2H). |
| 608 | 1H NMR (400 MHz, DMSO) δ = 7.46 (d, 1H), 7.40 (s, 1H), 7.37 (d, 1H), 7.28 (d, 1H), 6.97 (dd, 1H), 6.37 (d, 1H), 5.18 (s, 2H), 4.90 (t, 1H), 3.85 (s, 3H), 3.76-3.56 (m, 6H), 2.60 (s, 3H), 2.18 (d, 2H), 1.70-1.57 (m, 2H). |
| 609 | 1H NMR (400 MHz, DMSO) δ = 7.71 (dd, 1H), 7.53 (dd, 1H), 7.49-7.38 (m, 2H), 7.21 (d, 1H), 6.94 (dd, 1H), 6.25 (t, 1H), 4.92 (s, 2H), 4.87 (t, 1H), 3.73-3.52 (m, 6H), 3.48 (s, 3H), 2.60 (s, 3H), 2.16 (d, 2H), 1.68-1.55 (m, 2H). |
| 610 | 1H NMR (400 MHz, DMSO) δ = 7.49 (d, 1H), 7.44-7.35 (m, 2H), 7.29 (d, 1H), 7.02 (dd, 1H), 6.47-6.38 (m, 2H), 5.14 (s, 2H), 4.90 (t, 1H), 3.75-3.55 (m, 6H), 3.49 (s, 3H), 2.61 (s, 3H), 2.18 (d, 2H), 1.63 (ddd, 2H). |
| 611 | 1H NMR (500 MHz, DMSO) δ = 8.41 (dd, 1H), 7.81 (dd, 1H), 7.47 (d, 1H), 7.40 (s, 1H), 7.29 (d, 1H), 7.24 (dd, 1H), 6.99 (dd, 1H), 5.15 (s, 2H), 4.89 (s, 1H), 3.74-3.56 (m, 6H), 2.60 (s, 3H), 2.53 (s, 3H), 2.17 (d, 2H), 1.63 (ddd, 2H). |
| 612 | 1H NMR (400 MHz, DMSO) δ = 8.70 (d, 1H), 7.48 (d, 1H), 7.43-7.37 (m, 2H), 7.21 (d, 1H), 7.00 (dd, 1H), 5.19 (s, 2H), 4.87 (t, 1H), 3.73-3.61 (m, 4H), 3.56 (td, 2H), 2.61 (d, 6H), 2.15 (d, 2H), 1.62 (ddd, 2H). |
| 613 | 1H NMR (400 MHz, DMSO) δ = 7.68 (s, 1H), 7.45 (d, 1H), 7.40 (s, 1H), 7.24 (d, 1H), 6.94 (dd, 1H), 5.31 (s, 2H), 4.89 (t, 1H), 3.75-3.56 (m, 6H), 2.61 (d, 6H), 2.18 (d, 2H), 1.63 (ddd, 1H). |
| 614 | 1H NMR (400 MHz, DMSO) δ = 11.75 (s, 1H), 7.56 (dd, 1H), 7.45 (d, 1H), 7.42-7.34 (m, 2H), 7.22 (d, 1H), 6.94 (dd, 1H), 6.22 (t, 1H), 4.88 (s, 3H), 3.75-3.54 (m, 6H), 2.60 (s, 3H), 2.17 (d, 2H), 1.62 (ddd, 2H). |
| 615 | 1H NMR (500 MHz, DMSO) δ = 13.66 (s, 1H), 8.10 (s, 1H), 7.47-7.40 (m, 2H), 7.23 (d, 1H), 6.91 (dd, 1H), 5.04 (s, 2H), 4.89 (s, 1H), 3.70 (dt, 2H), 3.67-3.57 (m, 4H), 2.60 (s, 3H), 2.17 (d, 2H), 1.63 (ddd, 2H). |

| cpd Nr | NMR Data |
|---|---|
| 616 | 1HNMR (400 MHz, DMSO-d6): δ 7.82-7.83 (m, 1H), 7.46 (d, 1H), 7.38 (s, 1H), 7.26 (d, 1H), 6.95 (dd, 1H), 5.17 (s, 2H), 4.88 (bs, 1H), 3.63-3.71 (m, 6H), 2.59 (s, 3H), 2.08 (d, 2H), 1.86 (s, 3H), 1.63-1.65 (m, 2H). |
| 617 | 1H NMR (400 MHz, DMSO) δ = 7.48 (d, 1H), 7.40 (s, 1H), 7.32-7.25 (m, 2H), 6.99 (dd, 1H), 5.39 (s, 2H), 4.88 (t, 1H), 3.71 (dt, 2H), 3.68-3.56 (m, 4H), 2.60 (s, 3H), 2.37 (d, 3H), 2.17 (d, 2H), 1.63 (ddd, 2H). |
| 618 | 1H NMR (400 MHz, DMSO) δ = 7.46 (d, 1H), 7.38 (s, 1H), 7.25 (d, 1H), 6.96 (dd, 1H), 6.34 (d, 1H), 5.15 (s, 2H), 4.88 (t, 1H), 3.75-3.56 (m, 6H), 2.60 (s, 3H), 2.40 (d, 3H), 2.18 (d, 2H), 1.69-1.57 (m, 2H). |
| 619 | 1H NMR (400 MHz, DMSO) δ = 8.67 (d, 1H), 8.55 (d, 1H), 7.47 (d, 1H), 7.40 (s, 1H), 7.26 (d, 1H), 6.99 (dd, 1H), 5.23 (s, 2H), 4.89 (s, 1H), 3.74-3.54 (m, 7H), 2.59 (s, 3H), 2.17 (d, 2H), 1.63 (ddd, 2H). |
| 620 | 1H NMR (400 MHz, DMSO) δ = 7.52-7.43 (m, 2H), 7.38 (s, 1H), 7.27 (d, 1H), 6.98 (dd, 1H), 5.36 (s, 2H), 4.88 (t, 1H), 3.75-3.68 (m, 1H), 3.64 (qd, 5H), 2.59 (s, 3H), 2.44 (d, 3H), 2.17 (d, 2H), 1.63 (ddd, 2H). |
| 621 | 1HNMR (400 MHz, DMSO-d6): δ 7.74 (d, 1H), 7.62 (d, 1H), 7.45 (b, 1H), 7.38 (s, 1H), 7.27 (d , 1H), 6.98 (dd, 1H), 5.37 (s, 2H), 4.88 (t, 1H), 3.57-3.71 (m, 6H), 2.62 (s, 3H), 2.59 (s, 3H), 2.07 (d, 2H), 1.6-1.66 (t, 2H). |
| 622 | 1H NMR (500 MHz, DMSO) δ = 8.53 (d, 1H), 7.76 (dd, 1H), 7.45 (d, 1H), 7.39 (s, 1H), 7.31-7.23 (m, 2H), 6.95 (dd, 1H), 5.11 (s, 2H), 4.89 (t, 1H), 3.70 (dt, 2H), 3.67-3.56 (m, 4H), 2.60 (s, 3H), 2.47 (s, 3H), 2.17 (d, 2H), 1.63 (ddd, 2H). |
| 623 - En 1 | 1H NMR (400 MHz, DMSO) δ = 8.88 (s, 1H), 7.43-7.36 (m, 2H), 7.13 (d, 1H), 6.87 (dd, 1H), 5.81 (q, 1H), 4.88 (t, 1H), 3.71 (d, 2H), 3.65 (q, 1H), 3.62 (s, 1H), 3.58 (s, 1H), 2.57 (s, 3H), 2.37 (s, 3H), 2.14 (d, 2H), 1.63 (t, 5H). |
| 624 | 1H NMR (400 MHz, DMSO) δ = 9.22 (d, 1H), 7.85 (dd, 1H), 7.76 (dd, 1H), 7.48 (d, 1H), 7.39 (s, 1H), 7.29 (d, 1H), 7.01 (dd, 1H), 5.43 (s, 2H), 4.89 (s, 1H), 3.75-3.55 (m, 6H), 2.60 (s, 3H), 2.17 (d, 2H), 1.63 (s, 1H). |
| 625 | 1H NMR (400 MHz, DMSO) δ = 8.68 (d, 1H), 8.58-8.51 (m, 1H), 7.89 (dt, 1H), 7.50-7.37 (m, 3H), 7.27 (d, 1H), 6.97 (dd, 1H), 5.17 (s, 2H), 4.90 (t, 1H), 3.75-3.55 (m, 6H), 2.60 (s, 3H), 2.17 (d, 2H), 1.63 (ddd, 2H). |
| 626 | 1H NMR (400 MHz, DMSO) δ = 8.83 (d, 2H), 7.50-7.40 (m, 2H), 7.36 (s, 1H), 7.18 (d, 1H), 6.94 (dd, 1H), 5.29 (s, 2H), 4.86 (t, 1H), 3.73-3.51 (m, 6H), 2.57 (s, 3H), 2.14 (d, 2H), 1.62 (ddd, 2H). |
| 627 | 1H NMR (400 MHz, DMSO) δ = 9.11 (d, 1H), 7.99 (d, 1H), 7.46 (d, 1H), 7.40 (s, 1H), 7.26 (d, 1H), 6.96 (dd, 1H), 5.40 (d, 2H), 4.89 (t, 1H), 3.75-3.68 (m, 2H), 3.68-3.56 (m, 4H), 2.60 (s, 3H), 2.18 (d, 2H), 1.69-1.57 (m, 2H). |
| 628 | 1H NMR (500 MHz, DMSO) δ = 11.46 (s, 1H), 7.47 (d, 1H), 7.41-7.33 (m, 2H), 7.21 (d, 1H), 6.95 (dd, 1H), 6.36 (d, 1H), 6.21 (dd, 1H), 4.99 (d, 2H), 4.89 (s, 1H), 3.70 (dt, 2H), 3.65 (s, 2H), 3.60 (td, 2H), 2.60 (s, 3H), 2.16 (d, 2H), 1.63 (ddd, 2H). |
| 629 | 1H NMR (400 MHz, DMSO) δ = 8.16 (dd, 1H), 7.46 (d, 1H), 7.38 (s, 1H), 7.22 (d, 1H), 7.05 (dd, 1H), 6.97 (dd, 1H), 6.89-6.83 (m, 1H), 5.16 (s, 2H), 4.90 (s, 1H), 3.84 (s, 3H), 3.75-3.63 (m, 4H), 3.59 (td, 2H), 2.59 (s, 3H), 2.16 (d, 2H), 1.62 (ddd, 2H). |
| 630 | 1H NMR (400 MHz, DMSO) δ = 11.71 (s, 1H), 7.45 (dd, 2H), 7.40 (s, 1H), 7.22 (d, 1H), 6.95 (dd, 1H), 6.30 (d, 1H), 4.90 (d, 3H), 3.76-3.55 (m, 6H), 2.61 (s, 3H), 2.17 (d, 2H), 1.63 (ddd, 2H), 1.23 (s, 0H). |
| 631 | 1H NMR (400 MHz, DMSO) δ = 11.59 (s, 1H), 7.57-7.48 (m, 2H), 7.48-7.37 (m, 2H), 7.22 (d, 1H), 6.92 (dd, 1H), 6.35 (d, 1H), 4.89 (t, 1H), 4.82 (s, 2H), 3.75-3.56 (m, 6H), 2.60 (s, 3H), 2.18 (d, 2H), 1.69-1.57 (m, 2H). |
| 632 | 1H NMR (500 MHz, DMSO) δ = 8.26 (d, 1H), 7.80 (dd, 1H), 7.45 (d, 1H), 7.40 (s, 1H), 7.25 (d, 1H), 6.94 (dd, 1H), 6.85 (d, 1H), 5.06 (s, 2H), 4.89 (t, 1H), 3.85 (s, 3H), 3.74-3.57 (m, 6H), 2.60 (s, 3H), 2.17 (d, 2H), 1.63 (ddd, 2H). |
| 633 | 1H NMR (400 MHz, DMSO) δ = 8.68 (dd, 1H), 7.95 (t, 1H), 7.62-7.55 (m, 2H), 7.47 (d, 1H), 7.41 (s, 1H), 7.36-7.26 (m, 2H), 6.98 (dd, 1H), 5.13 (s, 2H), 4.90 (t, 1H), 3.74-3.55 (m, 5H), 2.60 (s, 3H), 2.17 (d, 2H), 1.69-1.57 (m, 2H). |
| 634 | 1H NMR (400 MHz, DMSO) δ = 8.99 (s, 1H), 7.58-7.50 (m, 2H), 7.01 (dd, 1H), 5.33 (s, 2H), 4.26 (s, 2H), 3.75-3.63 (m, 2H), 3.58 (dt, 2H), 2.75 (s, 3H), 2.42 (s, 3H), 2.27 (s, 3H), 1.65 (d, 3H), 1.53 (d, 2H). |
| 635 - En 1 | 1H NMR (400 MHz, DMSO) δ = 8.06 (d, 1H), 7.48 (d, 1H), 7.27 (d, 1H), 7.18 (d, 1H), 7.02 (dd, 1H), 6.86 (d, 1H), 5.13 (s, 2H), 4.36 (ddd, 1H), 3.69 (s, 3H), 3.02-2.85 (m, 1H), 2.66 (td, 3H), 2.58 (s, 3H), 2.16-2.03 (m, 1H), 1.94 (s, 1H). |
| 636 - En 1 | 1H NMR (500 MHz, DMSO) δ = 8.09 (d, 1H), 7.48 (d, 1H), 7.37 (d, 1H), 7.24 (d, 1H), 6.99 (dd, 1H), 6.36 (d, 1H), 5.18 (s, 2H), 3.85 (s, 3H), 2.93 (t, 2H), 2.66 (dt, 2H), 2.58 (s, 3H), 2.09 (q, 1H), 1.91 (d, 1H). |
| 637 - En 1 | 1H NMR (400 MHz, DMSO) δ = 11.75 (s, 1H), 8.07 (d, 1H), 7.55 (dd, 1H), 7.47 (d, 1H), 7.37 (dd, 1H), 7.18 (d, 1H), 6.95 (dd, 1H), 6.22 (t, 1H), 4.96-4.80 (m, 2H), 4.35 (dd, 1H), 2.93 (s, 2H), 2.92 (d, 1H), 2.67 (q, 2H), 2.57 (s, 3H), 2.41 (s, 1H), 2.13-1.98 (m, 1H), 1.90 (d, 1H). |
| 638 - En 1 | 1H NMR (400 MHz, DMSO) δ = 8.15 (d, 1H), 7.49 (d, 1H), 7.31 (d, 1H), 7.19 (d, 1H), 7.02 (dd, 1H), 6.86 (d, 1H), 5.14 (s, 2H), 4.62 (dt, 1H), 3.69 (s, 3H), 3.13-2.97 (m, 1H), 2.90 (t, 2H), 2.59 (s, 3H). |
| 639 - En 1 | 1H NMR (400 MHz, DMSO) δ = 8.19 (d, 1H), 7.49 (d, 1H), 7.37 (d, 1H), 7.27 (d, 1H), 7.00 (dd, 1H), 6.36 (d, 1H), 5.19 (s, 2H), 4.63 (dt, 1H), 3.85 (s, 3H), 3.30-3.18 (m, 1H), 3.12-2.80 (m, 2H), 2.59 (s, 3H). |
| 640 - En 1 | 1H NMR (500 MHz, DMSO) δ = 11.75 (s, 1H), 8.18 (d, 1H), 7.60-7.52 (m, 1H), 7.47 (d, 1H), 7.38 (d, 1H), 7.23 (s, 1H), 6.96 (d, 1H), 6.22 (t, 1H), 4.90 (s, 2H), 4.62 (s, 1H), 3.58 (s, 1H), 3.03 (s, 1H), 2.88 (s, 2H), 2.59 (s, 3H), 1.24 (s, 0H). |
| 641 - En 1 | 1H NMR (500 MHz, DMSO) δ = 8.38 (d, 1H), 7.49 (d, 1H), 7.31 (d, 1H), 7.19 (s, 1H), 7.03 (dd, 1H), 6.86 (s, 1H), 5.15 (s, 2H), 4.86 (dt, 1H), 4.34 (t, 1H), 4.13 (q, 1H), 4.00-3.83 (m, 2H), 3.69 (s, 3H), 2.60 (s, 3H). |

| cpd Nr | NMR Data |
|---|---|
| 642 - En 1 | 1H NMR (400 MHz, DMSO) δ = 8.41 (d, 1H), 7.50 (d, 1H), 7.37 (d, 1H), 7.27 (d, 1H), 7.01 (dd, 1H), 6.37 (d, 1H), 5.19 (s, 2H), 4.85 (dq, 1H), 4.33 (t, 1H), 4.13 (q, 1H), 3.90 (ddd, 2H), 3.85 (s, 3H), 2.60 (s, 3H). |
| 643 - En 1 | 1H NMR (400 MHz, DMSO) δ = 8.39 (d, 1H), 7.69 (s, 1H), 7.49 (d, 1H), 7.24 (d, 1H), 6.98 (dd, 1H), 5.32 (s, 2H), 4.85 (dq, 1H), 4.33 (dd, 1H), 4.13 (q, 1H), 4.01-3.79 (m, 2H), 2.61 (d, 6H). |
| 646 - En 1 | 1H NMR (500 MHz, DMSO) δ = 8.99 (s, 1H), 8.40 (d, 1H), 7.49 (d, 1H), 7.25 (d, 1H), 6.99 (dd, 1H), 5.32 (s, 2H), 4.85 (dp, 1H), 4.33 (dd, 1H), 4.13 (q, 1H), 3.98-3.80 (m, 2H), 2.60 (s, 3H), 2.42 (s, 3H) |
| 647 - En 1 | 1H NMR (400 MHz, DMSO) δ = 8.58 (ddd, 1H), 8.39 (d, 1H), 7.84 (td, 1H), 7.60-7.44 (m, 2H), 7.35 (ddd, 1H), 7.25 (d, 1H), 7.02 (dd, 1H), 5.21 (s, 2H), 4.84 (dq, 1H), 4.39-4.26 (m, 1H), 4.13 (q, 1H), 4.00-3.78 (m, 2H), 2.59 (s, 3H). |
| 648 - En 1 | 1H NMR (500 MHz, DMSO) δ = 11.76 (s, 1H), 8.39 (d, 1H), 7.56 (dd, 1H), 7.48 (d, 1H), 7.42-7.34 (m, 1H), 7.22 (d, 1H), 6.97 (dd, 1H), 6.22 (t, 1H), 4.90 (s, 2H), 4.96-4.77 (m, 1H), 4.33 (t, 1H), 4.12 (q, 1H), 3.98-3.80 (m, 2H), 2.59 (s, 3H). |
| 649 | 1H NMR (400 MHz, DMSO) δ = 8.98 (s, 1H), 8.07 (s, 1H), 7.65-7.52 (m, 2H), 7.45 (d, 1H), 7.16-7.07 (m, 1H), 6.92 (dd, 1H), 5.35 (s, 2H), 2.63 (s, 3H), 2.46 (s, 2H), 2.42 (s, 3H), 1.50 (s, 6H). |
| 650 | 1H NMR (400 MHz, DMSO) δ = 8.98 (s, 1H), 7.82 (s, 1H), 7.49 (d, 1H), 7.04 (s, 1H), 6.99 (dd, 1H), 6.96 (s, 1H), 5.32 (s, 2H), 3.80-3.70 (m, 2H), 3.64 (td, 2H), 2.64 (s, 3H), 2.41 (s, 3H), 2.13-1.94 (m, 4H). |
| 651 | 1H NMR (400 MHz, DMSO) δ = 8.73 (dd, 1H), 8.30-8.22 (m, 1H), 7.79 (dd, 1H), 7.70 (s, 1H), 7.48 (d, 1H), 7.28 (d, 1H), 6.98 (dd, 1H), 5.36-5.30 (m, 2H), 4.75 (s, 1H), 3.61 (t, 2H), 2.58 (s, 3H), 1.87 (t, 2H), 1.42 (s, 6H). |
| 652 | 1H NMR (400 MHz, DMSO) δ = 8.98 (s, 1H), 7.69 (s, 1H), 7.45 (d, 1H), 7.28 (d, 1H), 6.93 (dd, 1H), 5.31 (s, 2H), 4.78 (s, 1H), 3.62 (d, 2H), 2.57 (s, 3H), 2.42 (s, 3H), 1.88 (t, 2H), 1.43 (s, 6H). |
| 653 - En 1 | 1H NMR (400 MHz, DMSO) δ = 7.53-7.43 (m, 3H), 7.20 (d, 1H), 7.00 (dd, 1H), 6.89 (d, 1H), 5.97 (s, 1H), 5.22-5.10 (m, 2H), 4.42 (qd, 1H), 4.36-4.31 (m, 1H), 4.02-3.91 (m, 2H), 3.69 (s, 3H), 3.65 (dd, 1H), 3.59 (t, 1H), 2.63 (s, 3H). |
| 654 - En 1 | 1H NMR (400 MHz, DMSO) δ = 8.12 (d, 1H), 7.46 (d, 1H), 7.30 (d, 1H), 7.18 (d, 1H), 7.00 (dd, 1H), 6.86 (d, 1H), 5.37-5.32 (m, 1H), 5.15 (s, 2H), 4.25 (ddt, 2H), 4.02 (dd, 1H), 3.94 (dd, 1H), 3.69 (s, 3H), 3.71-3.63 (m, 1H), 3.56 (dd, 1H), 2.56 (s, 3H). |
| 655 - En 1 | 1H NMR (400 MHz, DMSO) δ = 7.49 (d, 2H), 7.38 (dd, 2H), 7.00 (dd, 1H), 6.39 (d, 1H), 5.61 (d, 1H), 5.18 (s, 2H), 4.41 (qd, 1H), 4.35-4.26 (m, 1H), 4.02-3.90 (m, 2H), 3.85 (s, 3H), 3.64 (dd, 1H), 3.59 (t, 1H), 2.64 (s, 3H). |
| 656 - En 1 | 1H NMR (400 MHz, DMSO) δ = 8.14 (d, 1H), 7.47 (d, 1H), 7.37 (d, 1H), 7.25 (d, 1H), 6.98 (dd, 1H), 6.37 (d, 1H), 5.31 (d, 1H), 5.19 (s, 2H), 4.24 (s, 1H), 4.02 (dd, 1H), 3.92 (dd, 1H), 3.66 (dd, 1H), 3.56 (dd, 1H), 2.56 (s, 3H). |
| 657 - En 1 | 1H NMR (400 MHz, DMSO) δ = 11.25 (d, 1H), 8.75 (d, 2H), 8.47 (s, 1H), 8.28 (d, 1H), 7.99 (d, 1H), 7.80 (dd, 1H), 7.63 (d, 1H), 7.27 (dd, 1H), 5.36 (s, 2H), 2.96 (d, 2H), 2.72 (d, 1H), 2.38-2.27 (m, 2H), 1.93 (s, 1H), 1.61 (d, 1H), 1.24 (s, 1H). |
| 658 | 1H NMR (400 MHz, DMSO) δ = 8.99 (s, 1H), 8.68 (s, 1H), 8.39 (s, 1H), 7.97 (d, 1H), 7.57 (d, 1H), 7.24-7.14 (m, 1H), 5.35 (s, 2H), 4.77 (s, 1H), 3.76-3.54 (m, 6H), 2.45 (s, 3H), 2.08 (d, 2H), 1.71-1.58 (m, 2H). |
| 659 | 1H NMR (400 MHz, DMSO) δ = 8.72 (dd, 1H), 8.23 (dd, 1H), 7.77 (dd, 1H), 7.50 (d, 1H), 6.99 (dd, 1H), 6.90 (d, 1H), 5.32 (s, 2H), 4.75 (s, 1H), 4.27-4.17 (m, 1H), 3.43 (s, 3H), 2.40 (s, 3H), 2.11 (s, 3H), 1.98 (s, 2H), 1.59 (s, 1H), 1.47 (s, 1H). |
| 660 | 1H NMR (400 MHz, DMSO) δ = 8.98 (s, 1H), 7.50-7.42 (m, 1H), 6.99-6.90 (m, 2H), 5.31 (s, 2H), 4.75 (s, 1H), 4.24 (s, 1H), 3.46 (s, 4H), 2.40 (d, 6H), 2.14 (h, 2H), 2.00 (s, 2H), 1.60 (s, 1H), 1.50 (s, 1H). |
| 661 - En 1 | 1H NMR (400 MHz, DMSO) δ = 8.98 (s, 1H), 8.01 (t, 1H), 7.82 (d, 1H), 7.50 (d, 1H), 7.44 (d, 1H), 6.99 (dd, 1H), 5.33 (d, 2H), 4.69-4.59 (m, 1H), 3.29-3.21 (m, 1H), 3.15-3.06 (m, 1H), 2.66 (s, 3H), 2.42 (s, 3H), 2.04-1.90 (m, 2H), 1.84-1.69 (m, 2H), 1.52 (q, 1H), 1.25 (q, 1H). |
| 662 | 1H NMR (500 MHz, DMSO) δ = 8.70 (s, 1H), 8.55 (d, 1H), 7.90 (d, 1H), 7.63 (d, 1H), 7.49 (d, 2H), 7.43 (dd, 2H), 7.19 (s, 1H), 7.00 (dd, 1H), 5.18 (s, 2H), 5.03 (t, 1H), 4.48 (dd, 1H), 3.74 (dt, 2H), 2.64 (s, 3H). |
| 663 | 1H NMR (500 MHz, DMSO) δ = 8.23-8.12 (m, 2H), 7.81 (dd, 1H), 7.48 (d, 1H), 7.23 (d, 1H), 7.00 (ddd, 2H), 5.08 (s, 2H), 4.61 (dt, 1H), 3.93 (s, 3H), 3.26 (dd, 1H), 3.00 (dt, 1H), 2.85 (dd, 1H), 2.59 (s, 3H). |
| 664 | 1H NMR (400 MHz, DMSO) δ = 8.73 (dd, 1H), 8.43 (d, 1H), 8.26 (d, 1H), 7.79 (dd, 1H), 7.52 (d, 1H), 7.25 (d, 1H), 7.02 (dd, 1H), 5.33 (s, 2H), 4.85 (dt, 1H), 4.32 (t, 1H), 4.13 (q, 1H), 3.98-3.77 (m, 2H), 2.60 (s, 3H). |
| 665 | 1H NMR (500 MHz, DMSO) δ = 8.41 (d, 1H), 8.16 (dd, 1H), 7.81 (dd, 1H), 7.49 (d, 1H), 7.24 (d, 1H), 7.01 (ddd, 2H), 5.08 (s, 2H), 4.85 (dp, 1H), 4.32 (dd, 1H), 4.13 (q, 1H), 3.93 (s, 3H), 3.97-3.79 (m, 2H), 2.60 (s, 3H). |
| 666 | 1H NMR (400 MHz, DMSO) δ = 8.99 (s, 1H), 8.57 (t, 1H), 7.50 (d, 1H), 7.29 (d, 1H), 7.00 (dd, 1H), 5.33 (s, 2H), 4.19-4.03 (m, 2H), 2.61 (s, 3H), 2.42 (s, 3H). |
| 668 | 1H NMR (400 MHz, DMSO) δ = 7.66 (d, 1H), 7.57 (bs, 1H), 7.51 (d, 1H), 7.45 (d, 2H), 7.18 (bs, 1H), 7.02 (dd, 1H), 5.16 (s, 2H), 5.01 (t, 1H), 4.48-4.46 (m, 1H), 3.88 (s, 3H), 3.76-3.73 (m, 2H), 2.64 (s, 3H). |
| 670 | 1H NMR (400 MHz, DMSO) δ = 7.65 (d, 1H), 7.62 (s, 1H), 7.55 (d, 2H), 7.18 (bs, 1H), 7.01-6.96 (m, 1H), 5.17 (s, 2H), 5.02 (t, 1H), 4.69-4.63 (m, 1H), 4.52-4.40 (m, 1H), 3.77-3.73 (m, 2H), 2.64 (s, 3H), 1.40 (d, 6H), |
| 672 | 1H NMR (400 MHz, DMSO) δ = 7.65 (d, 1H), 7.62 (s, 1H), 7.55 (d, 2H), 7.18 (bs, 1H), 7.01-6.96 (m, 1H), 5.17 (s, 2H), 5.02 (t, 1H), 4.69-4.63 (m, 1H), 4.52-4.40 (m, 1H), 3.77-3.73 (m, 2H), 2.64 (s, 3H), 1.40 (d, 6H). |
| 674 | 1H NMR (500 MHz, DMSO) δ = 7.63 (d, 1H), 7.52-7.48 (m, 2H), 7.42 (d, 1H), 7.19 (bs, 1H), 6.99 (dd, 1H), 6.51 (s, 1H), 5.25 (s, 2H), 5.03 (t, 1H), 4.50-4.45 (m, 1H), 3.76-3.73 (m, 2H), 2.63 (s, 3H), 2.23 (s, 3H). |

| cpd Nr | NMR Data |
|---|---|
| 676 | 1H NMR (500 MHz, DMSO δ = 7.61 (d, 1H), 7.52-7.40 (m, 4H), 7.19 (s, 1H), 7.00-6.94 (m, 1H), 6.37 (d, 1 H), 5.20 (m, 2H), 5.02 (t, 1H), 4.65-4.58 (m, 1H), 4.52-4.44 (m, 2 H), 3.80-3.70 (m, 2H), 2.64 (s, 3H), 1.40 (d, 6H). |
| 678 | 1H NMR (500 MHz, DMSO): δ 7.62 (d, 1H), 7.50-7.46 (m, 2H), 7.40 (d, 1H), 7.18 (s, 1H), 6.96 (dd, 1H), 5.07 (s, 2H), 5.01 (t, 1H), 4.50-4.45 (m, 1H), 3.79-3.70 (m, 2H), 2.64 (s, 3H), 2.36 (s, 3H), 2.09 (s, 3H). |
| 680 | 1H NMR (400 MHz, DMSO): δ 8.28 (s, 1H), 7.62 (d, 1H), 7.49-7.46 (m, 2H), 7.41 (d, 1H), 7.18 (s, 1H), 6.97 (dd, 1H), 5.15 (s, 2H), 5.01 (t, 1H), 4.49-4.45 (m, 1H), 3.76-3.72 (m, 2H), 2.64 (s, 3H), 2.16 (s, 3H). |
| 682 | 1H NMR (500 MHz, DMSO): δ 7.76 (s, 1H), 7.61 (d, 1H), 7.50-7.47 (m, 2H), 7.42 (d, 1H), 7.19 (s, 1H), 6.98 (dd, 1H), 5.33 (s, 2H), 5.02 (t, 1H), 4.51-4.45 (m, 1H), 3.79-3.70 (m, 2H), 3.29-3.21 (m, 1H), 2.63 (s, 3H), 1.31 (d, 6H). |
| 683 | 1H NMR (500 MHz, DMSO): δ 8.48 (s, 1H), 7.68 (s, 1H), 7.47 (d, 1H), 7.22 (d, 1H), 6.96 (dd, 1H), 6.34 (t, 1H), 5.32 (s, 2H), 2.63 (s, 3H), 2.58 (s, 3H), 2.49-2.39 (m, 2H), 2.37-2.28 (m, 2H), 2.05-1.97 (m, 1H), 1.90-1.80 (m, 1H). |
| 684 | 1H NMR (500 MHz, DMSO): δ 7.62 (d, 1H), 7.54-7.46 (m, 3H), 7.42 (d, 1H), 7.19 (s, 1H), 7.01 (dd, 1H), 5.38 (s, 2H), 5.01 (t, 1H), 4.50-4.45 (m, 1H), 3.78-3.70 (m, 2H), 2.64 (s, 3H), 2.44 (s, 3H). |
| 685 | 1H NMR (400 MHz, DMSO-d6): δ 7.88 (bs, 1H), 7.52-7.36 (m, 4H), 7.15 (bs, 1H), 6.94-6.90 (m, 1H), 5.44 (s, 1H), 5.07-5.01 (m, 2H), 4.40-4.35 (m, 1H), 4.17-4.12 (m, 1H), 2.65 (s, 3H), 1.15 (d, 3H). |
| 686 | 1H NMR (500 MHz, DMSO): δ 7.65 (d, 1H), 7.47 (d, 1H), 7.40 (d, 1H), 6.96 (dd, 1H), 6.33 (d, 1H), 5.01 (s, 2H), 4.48 (t, 1H), 3.82 (s, 3H), 3.77-3.73 (m, 2H), 2.63 (s, 3H). |
| 688 | 1H NMR (400 MHz, DMSO): δ 7.62 (d, 1H), 7.57 (d, 1H), 7.50-7.49 (m, 2H), 7.42 (d, 1H), 7.19 (bs, 1H), 6.99-6.96 (dd, 1H), 6.53 (d, 1H), 5.25 (s, 2H), 5.19-5.12 (m, 2H), 5.02 (bs, 1H), 4.50-4.46 (m, 1H), 3.74 (d, 2H), 2.64 (s, 2H). |
| 690 | 1H NMR (500 MHz, DMSO): δ 7.63 (d, 1H), 7.51-7.43 (m, 3H), 7.40 (d, 1H), 7.20 (bs, 1H), 6.98 (dd, 1H), 6.41 (s, 1H), 5.19 (s, 2H), 5.02 (t, 1H), 4.51-4.45 (m, 1H), 4.01 (d, 2H), 3.77-3.72 (m, 2H), 2.64 (s, 3H), 1.30-1.25 (m, 1H), 0.50-0.45 (m, 2H), 0.38-0.33 (m, 2H). |
| 692 | 1H NMR (500 MHz, DMSO): δ 8.10 (s, 1H), 7.62 (d, 1H), 7.50 (s, 1H), 7.47 (d, 1H), 7.39 (d, 1H), 7.21 (s, 1H), 6.92 (dd, 1H), 5.05-5.00 (m, 3H), 4.51-4.47 (m, 1H), 3.91 (s, 3H), 3.78-3.73 (m, 2H), 2.63 (s, 3H). |
| 694 | 1H NMR (500 MHz, DMSO): δ 9.24 (s, 1H), 7.67 (d, 1H), 7.52-7.41 (m, 3H), 7.17 (s, 1H), 7.02 (dd, 1H), 5.53 (s, 2H), 5.01 (s, 1H), 4.49-4.45 (m, 1H), 3.77-3.72 (m, 2H), 2.64 (s, 3H). |
| 695 | 1H NMR (500 MHz, DMSO): δ 7.85 (d, 1H), 7.78 (d, 1H), 7.64 (d, 1H), 7.53-7.43 (m, 3H), 7.19 (bs, 1H), 7.05-7.02 (dd, 1H), 5.46 (s, 2H), 5.01 (t, 1H), 4.50-4.45 (m, 1H), 3.76-3.73 (m, 2H), 2.64 (s, 3H). |
| 696 | 1H-NMR (500 MHz, DMSO): δ 8.58 (d, 1H), 7.80-7.65 (m, 1H), 7.67-7.62 (m, 1H), 7.50-7.43 (m, 1H), 7.39 (d, 1H), 7.17 (s, 1H), 7.01 (dd, 1H), 5.19 (s, 2H), 5.09-5.06 (m, 1H), 4.39-4.34 (m, 1H), 4.16-4.11 (m, 1H), 2.64 (s, 3H), 1.13 (d, 3H). |
| 697 | 1H NMR (500 MHz, DMSO): δ 9.11 (s, 1H), 8.02 (s, 1H), 7.62 (d, 1H), 7.51-7.47 (m, 2H), 7.43 (d, 1H), 7.20 (bs, 1H), 6.99 (dd, 1H), 5.42 (s, 2H), 5.02 (t, 1H), 4.50-4.46 (m, 1H), 3.77-3.72 (m, 2H), 2.63 (s, 3H) |
| 698 | 1H NMR (400 MHz, DMSO): δ 7.81 (s, 1H), 7.59 (d, 1H), 7.54 (bs, 2H), 7.46 (d, 1H), 7.39 (d, 1H), 7.20 (bs, 1H), 6.92 (dd, 1H), 5.04 (bs, 1H), 4.97 (s, 2H), 4.52-4.45 (m, 1H), 3.81 (s, 3H), 3.77-3.73 (m, 2H), 2.63 (s, 3H). |
| 700 | 1H NMR (500 MHz, DMSO): δ 8.41 (d, 1H), 7.65-7.58 (m, 2H), 7.49-7.40 (m, 4H), 7.18 (s, 1H), 6.98 (dd, 1H), 5.15 (s, 2H), 5.01 (t, 1H), 4.49-4.45 (m, 1H), 3.76-3.73 (m, 2H), 2.64 (s, 3H), 2.30 (s, 3H). |
| 702 | 1H NMR (500 MHz, DMSO): δ 8.38 (dd, 1H), 7.79 (dd, 1H), 7.64 (d, 1H), 7.52-7.46 (d, 3H), 7.19-7.13 (m, 2H), 7.02 (dd, 1H), 5.28 (s, 2H), 5.03 (t, 1H), 4.50-4.61 (m, 1H), 3.76-3.73 (m, 2H), 2.64 (s, 3H), 2.28-2.22 (m, 1H), 1.02-0.95 (m, 4H). |
| 704 | 1H NMR (500 MHz, DMSO): δ 8.37 (d, 1H), 7.65 (d, 1H), 7.48-7.41 (m, 4H), 7.31-7.28 (m, 1H), 7.18 (bs, 1H), 7.00 (dd, 1H), 5.32 (s, 1H), 5.07 (bs, 1H), 4.47 (d, 1H), 3.76 (bs, 2H), 2.66 (s, 3H), 2.15 (t, 1H), 0.96 (d, 2H), 0.74 (d, 2H). |
| 705 | 1H NMR (500 MHz, DMSO): δ 8.36 (d, 1H), 7.47-7.38 (m, 3H), 7.32-7.25 (m, 2H), 7.0-6.90 (m, 1H), 5.32 (s, 2H), 4.92 (bs, 1H), 3.73-3.59 (m, 6H), 2.58 (s, 3H), 2.20-2.10 (m, 3H), 1.68-1.58 (m, 2H), 1.00-0.96 (m, 2 H), 0.72-0.70 (m, 2H). |
| 706 | 1H NMR (500 MHz, DMSO): δ 8.10-8.07 (m, 1H), 7.64-7.57 (m, 2H), 7.50-7.47 (m, 2H), 7.42 (d, 1H), 7.19 (s, 1H), 6.98 (dd, 1H), 6.69-6.67 (m, 1H), 5.01 (t, 1H), 4.94 (s, 2H), 4.50-4.45 (m, 1H), 4.07 (t, 4H), 3.77-3.73 (m, 2H), 2.64 (s, 3H), 2.26-2.18 (m, 2H). |
| 708 | 1H NMR (500 MHz, DMSO): δ 8.80 (s, 2H), 7.64 (d, 1H), 7.51-7.47 (d, 2H), 7.43 (d, 1H), 7.19 (brs, 1H), 7.01 (dd, 1H), 5.20 (s, 2H), 5.03 (t, 1H), 4.49-4.46 (m, 1H), 3.78-3.71 (m, 2H), 2.64 (s, 3H), 2.62 (s, 3H). |
| 710 | 1H NMR (400 MHz, DMSO): δ 8.18 (dd, 1H), 7.82 (dd, 1H), 7.61 (d, 1H), 7.47 (d, 2H), 7.38 (d, 1H), 7.16 (bs, 1H), 7.07-7.02 (m, 1H), 6.97-6.92 (m, 1H), 4.99 (t, 3H), 4.51- 4.44 (m, 1H), 4.36-4.31 (m, 1H), 3.74 (t, 2H), 2.64 (s, 3H), 0.76-0.62 (m, 4H). |
| 711 | 1H NMR (400 MHz, DMSO): δ 8.17 (dd, 1H), 7.80 (dd, 1H), 7.45 (d, 2H), 7.37 (bs, 1H), 7.20 (d, 1H), 7.07-7.02 (m, 1H), 6.94 (dd, 1H), 5.00 (s, 2H), 4.85 (s, 1H), 3.72-3.56 (m, 6H), 2.59 (s, 3H), 2.16 (d, 2H), 1.68-1.58 (m, 2H), 0.78-0.64 (m, 4H). |
| 712 | 1H NMR (500 MHz, DMSO): δ 8.83 (d, 2H), 7.60 (d, 1H), 7.48-7.46 (m, 3H), 7.38 (d, 1H), 7.17 (brs, 1H), 6.96 (dd, 1H), 5.28 (s, 2H), 5.00 (t, 1H), 4.48-4.44 (m, 1H), 3.74-3.72 (m, 2H), 2.63 (s, 3H). |
| 714 | 1H NMR (500 MHz, DMSO): δ 8.84 (d, 1H), 8.67 (d, 1H), 8.63 (d, 1H), 7.61 (d, 1H), 7.50 (d, 1H), 7.47-7.44 (m, 2H), 7.15 (bs, 1H), 7.04 (dd, 1H), 5.28 (s, 2H), 4.99 (t, 1H), 4.49-4.46 (m, 1H), 3.76-3.72 (m, 2H), 2.64 (s, 3H). |
| 715 | 1H NMR (500 MHz, DMSO): δ 8.15 (dd, 1H), 7.86-7.81 (m, 1H), 7.63 (d, 1H), 7.50-7.45 (m, 2H), 7.40 (d, 1H), 7.18 (s, 1H), 7.05-6.95 (m, 2H), 5.07 (s, 2H), 5.00 (t, 1H), 4.50-4.46 (m, 1H), 3.92 (s, 3H), 3.76-3.71 (m, 2H), 2.64 (s, 3H). |
| 716 | 1H NMR (500 MHz, DMSO): δ 8.58 (dd, 2H), 7.62 (d, 1H), 7.50-7.47 (m, 4H), 7.41 (d, 1H), 7.19 (s, 1H), 7.00 (dd, 1H), 5.21 (s, 2H), 5.02 (t, 1H), 4.49-4.45 (m, 1H), 3.75-3.74 (m, 2H), 2.63 (s, 3H). |
| 717 | 1H NMR (500 MHz, DMSO): δ 9.87 (bs, 1H), 9.31 (bs, 1H), 8.74 (d, 1H), 8.47 (d, 1H), 8.12 (d, 1H), 7.61-7.57 (m, 1H), 7.50-7.22 (m, 3H), 7.02-6.97 (m, 1H), 5.35 (s, 2H), 4.88-4.80 (m, 1H), 3.87-3.79 (m, 2H), 3.36-3.30 (m, 1H), 3.26-3.15 (m, 1H), 2.63 (s, 3H), 2.10-2.00 (m, 2H). |

| cpd Nr | NMR Data |
|---|---|
| 718 | 1H NMR (500 MHz, DMSO): δ 8.59-8.57 (m, 1H), 7.83 (td, 1H), 7.56 (d, 1H), 7.50 (d, 1H), 7.45-7.42 (m, 2H), 7.40-7.33 (m, 2H), 7.17 (s, 1H), 7.02 (dd, 1H), 5.19 (s, 2H), 5.06 (d, 1H), 4.36 (dd, 1H), 4.18-4.10 (m, 1H), 2.64 (s, 3H), 1.13 (d, 3H). |
| 719 - En 1 | 1H NMR (400 MHz, DMSO): δ 8.57 (dd, 1H), 7.83 (t, 1H), 7.57-7.47 (m, 4H), 7.35 (t, 1H), 7.27 (d, 1H), 7.00 (dd, 1H), 5.24 (s, 1H), 5.19 (s, 1H), 3.74-3.62 (m, 2H), 3.31 (s, 1H), 3.11 (d, 1H), 2.59 (s, 3H), 2.21-2.15 (m, 2H), 1.83-1.74 (m, 2H). |
| 720 - En 1 | 1H NMR (500 MHz, DMSO): δ 8.17 (dd, 1H), 7.86-7.82 (m, 1H), 7.64 (s, 1H), 7.50-7.42 (m, 3H), 7.28 (s, 1H), 7.05-7.01 (m, 1H), 6.97 (dd, 1H), 5.13-5.05 (m, 3H), 4.00-3.92 (m, 4H), 3.78-3.72 (m, 1H), 2.65 (s, 3H), 1.52 (s, 3H). |
| 721 | 1H NMR (500 MHz, DMSO): δ 8.98 (s, 1H), 8.49 (s, 1H), 7.47 (d, 1H), 7.23 (d, 1H), 6.96 (dd, 1H), 6.34 (t, 1H), 5.32 (s, 2H), 2.58 (s, 3H), 2.47-2.41 (m, 5H), 2.39-2.30 (m, 2H), 2.05-1.95 (m, 1H), 1.90-1.82 (m, 1H). |
| 722 - En 1 | 1H NMR (500 MHz, DMSO): δ 7.63 (s, 1H), 7.49 (d, 1H), 7.48-7.43 (m, 2H), 7.30 (s, 1H), 7.18 (s, 1H), 6.97 (dd, 1H), 5.14-5.10 (m, 3H), 4.00-3.93 (m, 1H), 3.80-3.73 (m, 1H), 2.65 (s, 3H), 2.49 (s, 3H), 1.53. |
| 723 - En 1 | 1H NMR (500 MHz, DMSO): δ 8.98 (s, 1H), 8.29 (d, 1H), 7.48 (d, 1H), 7.22 (d, 1H), 6.97 (dd, 1H), 5.31 (s, 2H), 4.73-4.62 (m, 1H), 4.00-3.88 (m, 2H), 3.75-3.59 (m, 2H), 2.58 (s, 3H), 2.41 (s, 3H), 1.95-1.86 (m, 2H). |
| 724 - En 1 | 1H NMR (500 MHz, DMSO): δ 8.28 (d, 1H), 7.68 (s, 1H), 7.47 (d, 1H), 7.21 (d, 1H), 6.97 (dd, 1H), 5.31 (s, 2H), 4.75-4.62 (m, 1H), 4.00-3.88 (m, 2H), 3.74-3.58 (m, 2H), 2.63 (s, 3H), 2.57 (s, 3H), 1.95-1.88 (m, 2H). |
| 725 - En 1 | 1H NMR (500 MHz, DMSO): δ 8.23 (s, 1H), 7.47 (d, 1H), 7.32 (d, 1H), 7.16-7.06 (m, 3H), 6.97 (dd, 1H), 5.13 (s, 2H), 4.18 (d, 1H), 3.94 (d, 1H), 3.85 (t, 2H), 2.61 (s, 3H), 2.41 (s, 3H), 2.38-2.31 (m, 2H). |
| 726 - En 1 | 1H NMR (500 MHz, DMSO) δ = 8.20 (d, 1H), 7.70 (s, 1H), 7.59 (bs, 1H), 7.49-7.46 (m, 2H), 7.35 (bs, 1H), 6.95 (dd, 1H), 5.34-5.28 (m, 2H), 4.97-4.93 (m, 1H), 3.74-3.63 (m, 2H), 3.07 (s, 3H), 2.63 (s, 3H), 2.62 (s, 3H). |
| 727 - En 1 | 1H-NMR (500 MHz, DMSO): δ 8.26 (d, 1H), 7.70 (s, 1H), 7.47 (d, 1H), 7.35 (d, 1H), 6.95 (dd, 1H), 5.33 (s, 2H), 4.78-4.74 (m, 1H), 4.17 (s, 1H), 3.44-3.40 (m, 1H), 3.30-3.27 (m, 1H), 3.17-3.12 (m, 2H), 2.63 (s, 3H), 2.60 (s, 3H), 2.49-2.46 (s, 1H), 2.27-2.23 (m, 1H). |
| 727 - En 3 | 1H-NMR (400 MHz, DMSO): δ 8.26 (d, 1H), 7.69 (s, 1H), 7.47 (d, 1H), 7.30 (d, 1H), 6.95 (dd, 1H), 5.32 (s, 2H), 4.70-4.64 (m, 1H), 4.07 (s, 1H), 3.45-3.40 (m, 1H), 3.30-3.27 (m, 1H), 3.18-3.10 (m, 2H), 2.63 (s, 3H), 2.59 (s, 3H), 2.46-2.41 (m, 1H), 2.33-2.26 (m, 1H). |
| 727 - En 4 | 1H-NMR (400 MHz, DMSO): δ 8.26 (d, 1H), 7.69 (s, 1H), 7.47 (d, 1H), 7.30 (d, 1H), 6.95 (dd, 1H), 5.32 (s, 2H), 4.70-4.66 (m, 1H), 4.07 (s, 1H), 3.45-3.40 (m, 1H), 3.30-3.26 (m, 1H), 3.15-3.10 (m, 2H), 2.63 (s, 3H), 2.59 (s, 3H), 2.46-2.41 (m, 1H), 2.33-2.27 (m, 1H). |
| 728 - En 1 | 1H NMR (500 MHz, DMSO): δ 8.98 (s, 1H), 7.55 (s, 1H), 7.44 (d, 1H), 7.26-7.20 (m, 1H), 6.93 (dd, 1H), 5.30 (s, 2H), 5.12-4.93 (m, 1H), 3.70-3.62 (m, 3H), 3.02-2.75 (m, 3H), 2.59-2.52 (m, 4H), 2.49 (s, 3H), 2.10-2.01 (m, 1H), 1.84-1.77 (m, 1H), |
| 729 - En 1 | 1H NMR (500 MHz, DMSO): δ 8.99 ( s, 1H), 8.47 (s, 1H), 8.06 (d, 1H), 7.97 (s, 1H), 7.73 (s, 1H), 7.46 (d, 1H), 7.36 (s, 1H), 7.27 (d, 1H), 6.97 (dd, 1H), 5.34-5.28 (s, 2H), 4.97-4.90 (m, 1H), 4.68-4.57 (m, 2H), 2.52 (s, 3H), 2.43 (s, 3H). |
| 730 - En 1 | 1H NMR (400 MHz, DMSO): δ 8.08 (s, 1H), 7.78 (s, 1H), 7.51 (s, 1H), 7.45 (d, 1H), 7.23 (d, 1H), 6.91 (dd, 1H), 5.04 (s, 3H), 3.65-3.55 (m, 2H), 3.24-3.16 (m, 2H), 2.58 (s, 3H), 2.48-2.38 (m, 2H). |
| 731 - En 1 | 1H NMR (400 MHz, DMSO): δ 8.12 (s, 1H), 7.58 (bs, 1H), 7.52 (s, 1H), 7.46 (d, 1H), 7.25 (d, 1H), 6.92 (dd, 1H), 5.05 (s, 2H), 3.73 (d, 1H), 3.63 (d, 1H), 3.29-3.24 (m, 1H), 3.15- 3.10 (d, 1H), 2.59 (s, 3H), 2.27-2.14 (m, 2H), 1.87-1.75 (m, 2H). |
| 732 - En 1 | 1H NMR (400 MHz, DMSO): δ 7.59 (brs, 1H), 7.51-7.47 (m, 2H), 7.37 (d, 1H), 7.31 (d, 1H), 7.00 (dd, 1H), 6.39 (d, 1H), 5.23 (brs, 1H), 5.18 (s, 2H), 3.85 (s, 3H), 3.75-3.72 (m, 1H), 3.65-3.62 (m, 1H), 3.28-3.25 (m, 1H), 3.15-3.12 (m, 1H), 2.60 (s, 3H), 2.23-2.2.17 (m, 2H), 1.85-1.73 (m, 2H). |
| 733 - En 1 | 1H NMR (400 MHz, DMSO): δ 7.79 (brs, 1H), 7.51-7.47 (m, 2H), 7.37 (d, 1H), 7.29 (d, 1H), 7.00 (dd, 1H), 6.39 (d, 1H), 5.22 (brs, 1H), 5.18 (s, 2H), 3.85 (s, 3H), 3.62-3.60 (m, 2H), 3.21-3.19 (m, 2H), 2.59 (s, 3H), 2.49-2.39 (m, 2H). |
| 734 - En 1 | 1H NMR (400 MHz, DMSO): δ 9.23-9.20 (m, 1H), 7.89-7.86 (m, 1H), 7.78-7.74 (m, 2H), 7.52-7.48 (m, 2H), 7.30 (d, 1H), 7.04 (dd, 1H), 5.42 (s, 2H), 5.25 (brs, 1H), 3.65-3.55 (m, 2H), 3.29-3.25 (m, 1H), 3.24-3.17 (m, 1H), 2.59 (s, 3H), 2.49-2.39 (m, 2H). |
| 735 - En 1 | 1H NMR (400 MHz, DMSO): δ 8.60-7.57 (m, 1H), 7.79-7.72 (m, 2H), 7.67-7.62 (m, 1H), 7.50-7.44 (m, 2H), 7.28-7.23 (m, 1H), 7.00 (dd, 1H), 5.25-5.16 (m, 3H), 3.64-3.55 (m, 2H), 3.30-3.26 (m, 1H), 3.25-3.16 (m, 1H), 2.58 (s, 3H), 2.46-2.38 (m, 2H). |
| 736 - En 1 | 1H NMR (400 MHz, DMSO): δ 8.67 (d, 1H), 8.13 (d, 1H), 7.78 (brs, 1H), 7.66-7.61 (m, 1H), 7.54-7.46 (m, 2H), 7.30-6.96 (m, 3H), 5.34 (s, 2H), 5.21 (brs, 1H), 3.64-3.55 (m, 2H), 3.21-3.15 (m, 2H), 2.62 (s, 3H), 2.45-2.36 (m, 2H). |
| 737 - En 1 | 1H NMR (400 MHz, DMSO): δ 8.66 (d, 1H), 8.13 (d, 1H), 7.66-7.46 (m, 4H), 7.31-6.96 (m, 3H), 5.34 (s, 2H), 5.23 (brs, 1H), 3.75-3.70 (m, 1H), 3.65-3.60 (m, 1H), 3.25-3.20 (m, 1H), 3.18-3.10 (m, 1H), 2.60 (s, 3H), 2.25-2.12 (m, 2H), 1.90-1.70 (m, 2H). |
| 738 - En 1 | 1H-NMR (400 MHz, DMSO): δ 8.58 (d, 1H), 7.84 (td, 1H), 7.63 (s, 1H), 7.58 (d, 1H), 7.51-7.46 (m, 2H), 7.43 (s, 1H), 7.36-7.33 (m, 1H), 7.29 (s, 1H), 7.02 (dd, 1H), 5.20 (s, 2H), 5.12 (t, 1H), 3.98-3.95 (m, 1H), 3.78-3.74 (m, 1H), 2.65 (s, 3H), 1.52 (s, 3H). |
| 739 - En 1 | 1H-NMR (400 MHz, DMSO): δ 8.58 (d, 1H), 7.80-7.75 (m, 1H), 7.67-7.63 (m, 2H), 7.51-7.47 (m, 2H), 7.43 (s, 1H), 7.29 (s, 1H), 7.00 (dd, 1H), 5.19 (s, 2H), 5.12 (s, 1H), 3.96 (d, 1H), 3.76 (d, 1H), 2.65 (s, 3H), 1.52 (s, 3H). |
| 740 - En 1 | 1HNMR (500 MHz, DMSO): δ 8.25 (s, 1H), 7.53-7.45 (m, 2H), 7.34 (d, 1H), 7.13(bs, 1H), 7.08 (bs, 1H), 7.00 (dd, 1H), 6.50-6.26 (m, 2H), 5.24 (s, 2H), 4.72-4.63 (m, 2H), 4.18 (d, 1H), 3.94 (d, 1H), 3.89-3.83 (m, 2H), 2.62 (s, 3H), 2.40-2.35 (m, 2H). |
| 741 | 1H NMR (500 MHz, DMSO): δ 8.59 (d, 1H), 7.80-7.76 (m, 1H), 7.67-7.62 (m, 2H), 7.50-7.47 (m, 2H), 7.43 (d, 1H), 7.20 (bs, 1H), 7.00 (dd, 1H), 5.20 (s, 2H), 5.03 (t, 1H), 4.49-4.45 (m, 1H), 3.76-3.73 (m, 2H), 2.63 (s, 3H). |

| cpd Nr | NMR Data |
|---|---|
| 742 | 1H NMR (500 MHz, DMSO): δ 9.00 (s, 1H), 8.35 (d, 1H), 7.73 (d, 1H), 7.54-7.31 (m, 3H), 7.26-7.21 (m, 2H), 5.36 (s, 2H), 5.05 (t, 1H), 4.53-4.47 (m, 1H), 3.80-3.73 (m, 2H), 2.43 (s, 3H). |
| 743 | 1H NMR (500 MHz, DMSO): δ 8.56 (d, 1H), 8.35 (d, 1H), 7.80 (d, 1H), 7.73 (d, 1H), 7.53-7.28 (m, 3H), 7.28 (d, 1H), 7.24-7.22 (m, 2H), 5.17 (s, 2H), 5.08 (bs, 1H), 3.77 (bs, 2H), 2.47 (s, 3H). |
| 744 | 1H NMR (500 MHz, DMSO): δ 8.59 (d, 1H), 8.35 (bs, 1H), 7.86 (t, 1H), 7.73 (d, 1H), 7.68-7.03 (m, 7H), 5.24 (s, 2H), 5.10 (bs, 1H), 4.49 (bs, 1H), 3.81-3.75 (m, 2H). |
| 745 | 1H NMR (500 MHz, DMSO): δ 8.32 (d, 1H), 7.75-7.70 (m, 2H), 7.55-7.32 (m, 3H), 7.24-7.21 (m, 2H), 5.37 (s, 2H), 5.07 (t, 2H), 4.53-4.49 (m, 1H), 3.80-3.74 (m, 2H), 2.63 (s, 3H). |
| 746 | 1HNMR (500 MHz, DMSO): δ 8.31 (d, 1H), 7.73 (d, 1H), 7.56-7.30 (m, 3H), 7.21 (d, 3H), 5.18 (s, 2H), 5.07 (s, 1H), 4.55-4.45 (m, 1H), 3.77 (bs, 2H), 2.41 (s, 3H). |
| 747 | 1H NMR (500 MHz, DMSO): δ 8.58 (s, 1H), 7.86-7.81 (m, 1H), 7.61-7.56 (m, 2H), 7.50 (s, 1H), 7.44-7.41 (m, 2H), 7.36-7.34 (m, 1H), 7.20 (s, 1H), 6.98 (dd, 1H), 5.19 (s, 2H), 5.04 (t, 1H), 4.51-4.47 (m, 1H), 3.80-3.71 (m, 2H), 2.77-2.70 (m, 1H), 1.16-1.07 (m, 4H). |
| 748 | 1H NMR (500 MHz, DMSO): δ 8.98 (s, 1H), 7.60 (d, 1H), 7.49 (s, 1H), 7.44-7.40 (m, 2H), 7.19 (s, 1H), 6.95 (dd, 1H), 5.31 (s, 2H), 5.03 (t, 1H), 4.52-4.46 (m, 1H), 3.80-3.71 (m, 2H), 2.76-2.70 (m, 1H), 2.41 (s, 3H), 1.16-1.06 (m, 4H). |
| 749 | 1HNMR (500 MHz, DMSO): δ 7.71 (s, 1H), 7.59 (d, 1H), 7.52 (s, 1H), 7.43-7.40 (m, 2H), 7.22 (s, 1H), 6.94 (dd, 1H), 5.32 (s, 2H), 5.05 (t, 1H), 4.51-4.46 (m, 1H), 3.82-3.70 (m, 2H), 2.78-2.69 (m, 1H), 2.62 (s, 3H), 1.16-1.05 (m, 4H). |
| 750 | 1HNMR (500 MHz, DMSO): δ 8.54 (d, 1H), 7.78 (dd, 1H), 7.59 (d, 1H), 7.51 (s, 1H), 7.44-7.40 (m, 2H), 7.27 (d, 1H), 7.21 (s, 1H), 6.94 (dd, 1H), 5.12 (s, 2H), 5.04 (t, 1H), 4.51-4.47 (m, 1H), 3.80-3.72 (m, 2H), 2.76-2.71 (m, 1H), 2.46 (s, 3H), 1.15-1.07 (m, 4H). |
| 751 | 1HNMR (500 MHz, DMSO): δ 7.59 (d, 1H), 7.51 (bs, 1H), 7.43-7.41 (m, 2H), 7.20-7.18 (m, 2H), 6.96-6.92 (dd, 1H), 5.12 (s, 1H), 5.04 (t, 1H), 4.52-4.48 (m, 2H), 3.81-3.72 (m, 2H), 2.77-2.73 (m, 1H), 2.41 (s, 3H), 1.14-1.09 (m, 4H) |

In all above cases the analytical LCMS and $^1$H NMR data collected for En2 matched the data for En1.

Chiral Analytical Data

| | Chiral SFC analysis | | | | | |
|---|---|---|---|---|---|---|
| Code | Column Name | co-solvent | co-solvent % | Flow [g/min] | RT [min] | Purity [%] |
| cpd 103-En 1 | (1) | MeOH | 40 | 4 | 3.23 | 99.0 |
| cpd 103-En 2 | (1) | MeOH | 40 | 4 | 1.32 | 100.0 |
| cpd 105-En 1 | (2) | 0.5% DEA in MeOH | 25 | 3 | 3.76 | 99.5 |
| cpd 105-En 2 | (2) | 0.5% DEA in MeOH | 25 | 3 | 2.49 | 99.1 |
| cpd 106-En 1 | (3) | MeOH | 35 | 3 | 7.81 | 99.2 |
| cpd 106-En 2 | (3) | MeOH | 35 | 3 | 3.75 | 99.6 |
| cpd 110-En 1 | (4) | MeOH | 40 | 3 | 2.74 | 99.9 |
| cpd 110-En 2 | (4) | MeOH | 40 | 3 | 1.66 | 99.9 |
| cpd 111-En 1 | (5) | MeOH | 40 | 3 | 2.85 | 99.8 |
| cpd 111-En 2 | (5) | MeOH | 40 | 3 | 1.16 | 99.9 |
| cpd 112-En 1 | (5) | 0.5% DEA in MeOH | 40 | 3 | 1.35 | 95.2 |
| cpd 112-En 2 | (5) | 0.5% DEA in MeOH | 40 | 3 | 2.03 | 99.1 |
| cpd 113-En 1 | (6) | 0.5% DEA in EtOH | 20 | 3 | 4.59 | 99.9 |
| cpd 113-En 2 | (6) | 0.5% DEA in EtOH | 20 | 3 | 3.34 | 99.8 |
| cpd 115-En 1 | (6) | 0.5% DEA in MeOH | 40 | 3 | 6.14 | 99.6 |
| cpd 115-En 2 | (6) | 0.5% DEA in MeOH | 40 | 3 | 3.98 | 99.7 |
| cpd 116-En 1 | (4) | MeOH | 20 | 3 | 3.58 | 99.1 |
| cpd 116-En 2 | (4) | MeOH | 20 | 3 | 3.07 | 99.3 |
| cpd 118-En 1 | (7) | MeOH | 15 | 3 | 3.90 | 99.9 |
| cpd 118-En 2 | (7) | MeOH | 15 | 3 | 2.50 | 99.9 |
| cpd 120-En 1 | (6) | MeOH | 40 | 3 | 6.10 | 99.5 |
| cpd 120-En 2 | (6) | MeOH | 40 | 3 | 4.52 | 99.9 |
| cpd 121-En 1 | (5) | IPA | 20 | 3 | 11.20 | 96.9 |
| cpd 121-En 2 | (5) | IPA | 20 | 3 | 9.36 | 99.7 |
| cpd 123-En 1 | (4) | MeOH | 30 | 3 | 1.61 | 99.9 |
| cpd 123-En 2 | (4) | MeOH | 30 | 3 | 2.22 | 99.7 |
| cpd 124-En 1 | (8) | MeOH | 25 | 3 | 5.77 | 99.9 |
| cpd 124-En 2 | (8) | MeOH | 25 | 3 | 4.48 | 99.9 |
| cpd 125-En 1 | (6) | 0.5% DEA in MeOH | 30 | 3 | 3.48 | 99.5 |
| cpd 125-En 2 | (6) | 0.5% DEA in MeOH | 30 | 3 | 2.59 | 99.6 |
| cpd 126-En 1 | (9) | IPA | 30 | 3 | 3.57 | 95.1 |
| cpd 126-En 2 | (9) | IPA | 30 | 3 | 2.69 | 98.7 |
| cpd 130-En 1 | (4) | MeOH | 30 | 3 | 1.85 | 99.9 |
| cpd 130-En 2 | (4) | MeOH | 30 | 3 | 1.29 | 99.9 |
| cpd 131-En 1 | (7) | MeOH | 10 | 3 | 3.04 | 99.0 |
| cpd 131-En 2 | (7) | MeOH | 10 | 3 | 2.43 | 98.0 |
| cpd 132-En 1 | (1) | MeOH | 30 | 3 | 4.50 | 99.3 |
| cpd 132-En 2 | (1) | MeOH | 30 | 3 | 2.98 | 99.7 |

| | | Chiral SFC analysis | | | | |
|---|---|---|---|---|---|---|
| Code | Column Name | co-solvent | co-solvent % | Flow [g/min] | RT [min] | Purity [%] |
| cpd 134-En 1 | (4) | MeOH | 25 | 3 | 3.20 | 99.2 |
| cpd 134-En 2 | (4) | MeOH | 25 | 3 | 1.48 | 99.5 |
| cpd 135-En 1 | (1) | MeOH | 25 | 3 | 2.19 | 99.8 |
| cpd 135-En 2 | (1) | MeOH | 25 | 3 | 3.33 | 99.9 |
| cpd 141-En 1 | (6) | MeOH | 15 | 3 | 4.48 | 99.8 |
| cpd 141-En 2 | (6) | MeOH | 15 | 3 | 5.61 | 99.9 |
| cpd 147-Dia 1-En 1 | (9) | IPA | 25 | 3 | 3.24 | 99.6 |
| cpd 147-Dia 1-En 2 | (9) | IPA | 25 | 3 | 6.21 | 98.3 |
| cpd 148-En 1 | (10) | MeOH | 30 | 3 | 5.02 | 99.3 |
| cpd 148-En 2 | (10) | MeOH | 30 | 3 | 4.22 | 99.8 |
| cpd 151-En 1 | (3) | MeOH | 30 | 3 | 6.04 | 98.5 |
| cpd 151-En 2 | (3) | MeOH | 30 | 3 | 9.85 | 97.9 |
| cpd 155-En 1 | (11) | MeOH | 10 | 3 | 8.77 | 95.3 |
| cpd 155-En 2 | (11) | MeOH | 10 | 3 | 9.41 | 100.0 |
| cpd 157-En 1 | (2) | MeOH | 10 | 3 | 8.08 | 99.7 |
| cpd 157-En 2 | (2) | MeOH | 10 | 3 | 5.55 | 98.9 |
| cpd 159-En 1 | (1) | MeOH | 30 | 3 | 3.21 | 99.9 |
| cpd 159-En 2 | (1) | MeOH | 30 | 3 | 4.08 | 99.8 |
| cpd 160-En 1 | (9) | MeOH | 40 | 4 | 6.91 | 99.9 |
| cpd 160-En 2 | (9) | MeOH | 40 | 4 | 9.94 | 99.6 |
| cpd 162-Dia 1-En1 | (5) | MeOH | 40 | 3 | 2.01 | 99.7 |
| cpd 162-Dia 1-En2 | (5) | MeOH | 40 | 3 | 2.53 | 99.5 |
| cpd 163-En 1 | (3) | MeOH | 35 | 3 | 5.40 | 96.0 |
| cpd 163-En 2 | (3) | MeOH | 35 | 3 | 3.30 | 98.3 |
| cpd 164-En 1 | (9) | MeOH | 40 | 3 | 5.39 | 99.0 |
| cpd 164-En 2 | (9) | MeOH | 40 | 3 | 8.72 | 97.6 |
| cpd 165-En 1 | (6) | 0.5% DEA in MeOH | 30 | 3 | 6.35 | 96.4 |
| cpd 165-En 2 | (6) | 0.5% DEA in MeOH | 30 | 3 | 4.51 | 97.4 |
| cpd 169-En 1 | (7) | MeOH | 20 | 3 | 3.68 | 94.7 |
| cpd 169-En 2 | (7) | MeOH | 20 | 3 | 3.10 | 99.6 |
| cpd 172-En 1 | (11) | MeOH | 10 | 3 | 13.12 | 97.6 |
| cpd 172-En 2 | (11) | MeOH | 10 | 3 | 16.13 | 99.9 |
| cpd 176-En 1 | (6) | 0.5% DEA in EtOH | 20 | 3 | 2.69 | 99.6 |
| cpd 176-En 2 | (6) | 0.5% DEA in EtOH | 20 | 3 | 3.87 | 99.5 |
| cpd 179-En 1 | (6) | 0.5% DEA in EtOH | 30 | 3 | 5.15 | 98.8 |
| cpd 179-En 2 | (6) | 0.5% DEA in EtOH | 30 | 3 | 3.42 | 99.3 |
| cpd 180-En 1 | (12) | MeOH | 40 | 3 | 4.23 | 99.0 |
| cpd 180-En 2 | (12) | MeOH | 40 | 3 | 6.03 | 97.7 |
| cpd 183-En 1 | (6) | 0.5% DEA in EtOH | 20 | 3 | 6.70 | 99.3 |
| cpd 183-En 2 | (6) | 0.5% DEA in EtOH | 20 | 3 | 3.73 | 97.1 |
| cpd 184-En 1 | (6) | 0.5% DEA in MeOH | 30 | 3 | 5.84 | 96.7 |
| cpd 184-En 2 | (6) | 0.5% DEA in MeOH | 30 | 3 | 3.89 | 99.9 |
| cpd 191-En 1 | (4) | MeOH | 40 | 3 | 2.24 | 99.8 |
| cpd 191-En 2 | (4) | MeOH | 40 | 3 | 0.83 | 99.9 |
| cpd 195-En 1 | (6) | 0.5% DEA in MeOH | 30 | 3 | 1.79 | 99.6 |
| cpd 195-En 2 | (6) | 0.5% DEA in MeOH | 30 | 3 | 1.54 | 99.8 |
| cpd 196-En 1 | (9) | 0.5% DEA in MeOH | 40 | 3 | 1.81 | 95.6 |
| cpd 196-En 2 | (9) | 0.5% DEA in MeOH | 40 | 3 | 1.47 | 99.9 |
| cpd 198-En 1 | (4) | 0.5% DEA in MeOH | 40 | 3 | 2.58 | 99.7 |
| cpd 198-En 2 | (4) | 0.5% DEA in MeOH | 40 | 3 | 2.00 | 99.9 |
| cpd 199-En 1 | (5) | MeOH | 20 | 3 | 2.27 | 99.9 |
| cpd 199-En 2 | (5) | MeOH | 20 | 3 | 1.80 | 99.4 |
| cpd 205-En 1 | (7) | MeOH | 20 | 3 | 3.59 | 99.7 |
| cpd 205-En 2 | (7) | MeOH | 20 | 3 | 2.17 | 99.7 |
| cpd 207-En 1 | (5) | 0.5% DEA in MeOH | 30 | 3 | 2.55 | 97.2 |
| cpd 207-En 2 | (5) | 0.5% DEA in MeOH | 30 | 3 | 1.92 | 98.1 |
| Cpd 270-En 1 | (8) | 30 mM Ammonia in MeOH | 25 | 3 | 10.80 | 91.0 |
| Cpd 270-En 2 | (8) | 30 mM Ammonia in MeOH | 25 | 3 | 7.55 | 99.5 |
| Cpd 313-En 1 | (6) | 0.5% DEA in MeOH | 30 | 3 | 7.02 | 99.3 |
| Cpd 313-En 2 | (6) | 0.5% DEA in MeOH | 30 | 3 | 3.69 | 99.2 |
| Cpd 315-En 1 | (9) | IPA | 40 | 3 | 4.60 | 99.6 |
| Cpd 315-En 2 | (9) | IPA | 40 | 3 | 3.62 | 99.9 |
| Cpd 316-En 1 | (6) | MeOH | 40 | 3 | 1.22 | 97.6 |
| Cpd 316-En 2 | (6) | MeOH | 40 | 3 | 1.48 | 95.6 |
| Cpd 317-En 1 | (13) | MeOH | 40 | 3 | 5.18 | 99.8 |
| Cpd 317-En 2 | (13) | MeOH | 40 | 3 | 3.11 | 99.9 |
| Cpd 326-En 1 | (3) | MeOH | 40 | 3 | 7.76 | 100.0 |
| Cpd 326-En 2 | (3) | MeOH | 40 | 3 | 9.84 | 99.6 |
| Cpd 332-En 1 | (5) | MeOH | 30 | 3 | 2.82 | 100.0 |
| Cpd 332-En 2 | (5) | MeOH | 30 | 3 | 3.66 | 99.6 |
| Cpd 333-En 1 | (11) | MeOH | 40 | 3 | 2.32 | 100.0 |

-continued

| Chiral SFC analysis | | | | | | |
|---|---|---|---|---|---|---|
| Code | Column Name | co-solvent | co-solvent % | Flow [g/min] | RT [min] | Purity [%] |
| Cpd 333-En 2 | (11) | MeOH | 40 | 3 | 3.30 | 98.2 |
| Cpd 336-En 1 | (1) | MeOH | 40 | 3 | 2.88 | 99.4 |
| Cpd 336-En 2 | (1) | MeOH | 40 | 3 | 4.59 | 98.7 |
| Cpd 342-En 1 | (6) | MeOH | 40 | 3 | 5.69 | 99.8 |
| Cpd 342-En 2 | (6) | MeOH | 40 | 3 | 2.70 | 99.9 |
| Cpd 348-En 1 | (9) | MeOH | 40 | 3 | 5.84 | 96.7 |
| Cpd 348-En 2 | (9) | MeOH | 40 | 3 | 3.57 | 99.2 |
| Cpd 349-En 1 | (9) | MeOH | 40 | 3 | 3.63 | 96.9 |
| Cpd 349-En 2 | (9) | MeOH | 40 | 3 | 2.99 | 99.2 |
| Cpd 350-En 1 | (9) | MeOH | 40 | 3 | 4.43 | 97.6 |
| Cpd 350-En 2 | (9) | MeOH | 40 | 3 | 3.44 | 99.2 |
| Cpd 355-En 1 | (5) | MeOH | 30 | 3 | 3.58 | 99.8 |
| Cpd 355-En 2 | (5) | MeOH | 30 | 3 | 4.65 | 99.0 |
| Cpd 356-En 1 | (11) | MeOH | 40 | 3 | 3.30 | 99.9 |
| Cpd 356-En 2 | (11) | MeOH | 40 | 3 | 4.70 | 96.8 |
| Cpd 360-En 1 | (11) | MeOH | 40 | 4 | 12.59 | 99.2 |
| Cpd 360-En 2 | (11) | MeOH | 40 | 4 | 9.56 | 100.0 |
| Cpd 365-En 1 | (4) | MeOH | 40 | 3 | 3.18 | 99.9 |
| Cpd 365-En 2 | (4) | MeOH | 40 | 3 | 4.57 | 99.8 |
| Cpd 386-En 1 | (4) | 0.5% DEA in MeOH | 40 | 3 | 4.48 | 99.9 |
| Cpd 386-En 2 | (4) | 0.5% DEA in MeOH | 40 | 3 | 7.10 | 99.9 |
| Cpd 387-En 1 | (3) | MeOH | 50 | 4 | 4.32 | 99.2 |
| Cpd 387-En 2 | (3) | MeOH | 50 | 4 | 9.59 | 99.7 |
| Cpd 388-En 1 | (1) | MeOH | 40 | 3 | 2.04 | 100.0 |
| Cpd 388-En 2 | (1) | MeOH | 40 | 3 | 2.86 | 99.9 |
| Cpd 389-En 1 | (3) | MeOH | 40 | 4 | 6.07 | 99.6 |
| Cpd 389-En 2 | (3) | MeOH | 40 | 4 | 9.29 | 99.8 |
| Cpd 395-Dia 1 | (4) | IPA | 20 | 3 | 5.94 | 96.5 |
| Cpd 395-Dia 2 | (4) | IPA | 20 | 3 | 4.25 | 99.5 |
| Cpd 396-En 1 | (1) | 0.5% DEA in MeOH | 40 | 3 | 1.86 | 92.2 |
| Cpd 396-En 2 | (3) | MeOH | 40 | 3 | 5.59 | 96.3 |
| Cpd 397-En 1 | (1) | 0.5% DEA in MeOH | 40 | 3 | 2.79 | 97.4 |
| Cpd 397-En 2 | (4) | 0.5% DEA in MeOH | 30 | 3 | 3.77 | 97.6 |
| Cpd 401-En 1 | (13) | 0.5% DEA in MeOH | 40 | 3 | 2.90 | 99.9 |
| Cpd 401-En 2 | (13) | 0.5% DEA in MeOH | 40 | 3 | 2.19 | 99.7 |
| Cpd 402-En 1 | (2) | MeOH | 25 | 3 | 5.92 | 99.8 |
| Cpd 403-En 1 | (9) | 0.5% DEA in MeOH | 40 | 3 | 7.35 | 100.0 |
| Cpd 403-En 2 | (9) | 0.5% DEA in MeOH | 40 | 3 | 5.07 | 100.0 |
| Cpd 404-En 1 | (9) | MeOH | 35 | 3 | 12.13 | 96.1 |
| Cpd 404-En 2 | (9) | MeOH | 35 | 3 | 9.74 | 99.8 |
| Cpd 406-En 1 | (4) | EtOH | 40 | 3 | 5.69 | 99.7 |
| Cpd 406-En 2 | (4) | EtOH | 40 | 3 | 7.65 | 99.1 |
| Cpd 407-En 1 | (3) | MeOH | 40 | 4 | 7.98 | 99.8 |
| Cpd 407-En 2 | (3) | MeOH | 40 | 4 | 13.25 | 99.6 |
| Cpd 408-En 1 | (3) | MeOH | 50 | 4 | 11.11 | 99.1 |
| Cpd 408-En 2 | (3) | MeOH | 50 | 4 | 6.04 | 99.9 |
| Cpd 409-En 1 | (9) | MeOH | 40 | 3 | 6.82 | 99.9 |
| Cpd 409-En 2 | (9) | MeOH | 40 | 3 | 4.46 | 100.0 |
| Cpd 410-En 1 | (4) | MeOH | 40 | 3 | 3.93 | 99.9 |
| Cpd 410-En 2 | (4) | MeOH | 40 | 3 | 1.65 | 99.7 |
| Cpd 411-En 1 | (4) | MeOH | 40 | 3 | 6.88 | 96.5 |
| Cpd 411-En 2 | (4) | MeOH | 40 | 3 | 2.97 | 98.2 |
| Cpd 412-En 1 | (4) | IPA | 25 | 3 | 3.30 | 98.8 |
| Cpd 412-En 2 | (4) | IPA | 25 | 3 | 2.48 | 99.3 |
| Cpd 413-En 1 | (6) | 0.5% DEA in MeOH | 40 | 3 | 2.56 | 99.5 |
| Cpd 413-En 2 | (6) | 0.5% DEA in MeOH | 40 | 3 | 3.51 | 95.1 |
| Cpd 432-En 1 | (7) | MeOH | 40 | 3 | 1.86 | 99.1 |
| Cpd 432-En 2 | (7) | MeOH | 40 | 3 | 3.67 | 99.9 |
| Cpd 433-En 1 | (1) | MeOH | 30 | 3 | 5.13 | 99.9 |
| Cpd 433-En 2 | (1) | MeOH | 30 | 3 | 2.46 | 99.4 |
| Cpd 434-En 1 | (8) | MeOH | 40 | 3 | 7.31 | 100.0 |
| Cpd 434-En 2 | (8) | MeOH | 40 | 3 | 2.97 | 100.0 |
| Cpd 435-En 1 | (9) | 0.5% DEA in MeOH | 40 | 3 | 3.14 | 99.9 |
| Cpd 435-En 2 | (9) | 0.5% DEA in MeOH | 40 | 3 | 6.33 | 99.9 |
| Cpd 436-En 1 | (9) | MeOH | 40 | 3 | 10.57 | 99.9 |
| Cpd 436-En 2 | (9) | MeOH | 40 | 3 | 5.48 | 99.9 |
| Cpd 437-En 1 | (5) | 0.5% DEA in MeOH | 40 | 3 | 1.84 | 99.7 |
| Cpd 437-En 2 | (5) | 0.5% DEA in MeOH | 40 | 3 | 5.23 | 99.8 |
| Cpd 445-En 1 | (9) | 0.5% DEA in MeOH | 40 | 3 | 5.65 | 98.7 |
| Cpd 445-En 2 | (9) | 0.5% DEA in MeOH | 40 | 3 | 9.32 | 98.2 |
| Cpd 446-En 1 | (4) | MeOH | 40 | 3 | 3.08 | 99.3 |
| Cpd 446-En 2 | (4) | MeOH | 40 | 3 | 2.08 | 99.7 |
| Cpd 447-En 1 | (4) | MeOH | 35 | 3 | 6.58 | 99.9 |

Chiral SFC analysis

| Code | Column Name | co-solvent | co-solvent % | Flow [g/min] | RT [min] | Purity [%] |
|---|---|---|---|---|---|---|
| Cpd 447-En 2 | (4) | MeOH | 35 | 3 | 2.35 | 99.7 |
| Cpd 448-En 1 | (9) | MeOH | 30 | 3 | 3.26 | 98.9 |
| Cpd 448-En 2 | (9) | MeOH | 30 | 3 | 4.80 | 99.1 |
| Cpd 449-En 1 | (9) | 0.5% DEA in MeOH | 40 | 3 | 4.71 | 99.9 |
| Cpd 449-En 2 | (9) | 0.5% DEA in MeOH | 40 | 3 | 8.69 | 99.5 |
| Cpd 450-En 1 | (5) | 0.5% DEA in MeOH | 30 | 3 | 4.32 | 99.9 |
| Cpd 450-En 2 | (5) | 0.5% DEA in MeOH | 30 | 3 | 6.95 | 99.6 |
| Cpd 451-En 1 | (9) | 0.5% DEA in MeOH | 40 | 3 | 3.49 | 99.9 |
| Cpd 451-En 2 | (9) | 0.5% DEA in MeOH | 40 | 3 | 5.14 | 99.9 |
| Cpd 452-En 1 | (4) | MeOH | 40 | 3 | 4.12 | 97.3 |
| Cpd 452-En 2 | (4) | MeOH | 40 | 3 | 3.42 | 99.2 |
| Cpd 455-En 1 | (9) | MeOH | 40 | 3 | 3.10 | 99.9 |
| Cpd 455-En 2 | (9) | MeOH | 40 | 3 | 4.74 | 99.8 |
| Cpd 456-En 1 | (4) | MeOH | 35 | 3 | 3.92 | 99.5 |
| Cpd 456-En 2 | (4) | MeOH | 35 | 3 | 2.54 | 99.9 |
| Cpd 457-En 1 | (5) | MeOH | 40 | 3 | 2.05 | 99.9 |
| Cpd 457-En 2 | (5) | MeOH | 40 | 3 | 3.79 | 99.0 |
| Cpd 458-En 1 | (9) | MeOH | 40 | 3 | 2.84 | 99.5 |
| Cpd 458-En 2 | (9) | MeOH | 40 | 3 | 4.36 | 97.3 |
| Cpd 459-En 1 | (9) | 0.5% DEA in MeOH | 40 | 4 | 9.06 | 98.8 |
| Cpd 459-En 2 | (9) | 0.5% DEA in MeOH | 40 | 4 | 6.34 | 94.1 |
| Cpd 460-En 1 | (4) | MeOH | 35 | 3 | 4.26 | 100.0 |
| Cpd 460-En 2 | (4) | MeOH | 35 | 3 | 2.18 | 100.0 |
| Cpd 461-En 1 | (4) | MeOH | 40 | 3 | 2.58 | 99.8 |
| Cpd 461-En 2 | (4) | MeOH | 40 | 3 | 4.69 | 98.4 |
| Cpd 462-En 1 | (1) | 0.5% IP Amine in IPA | 40 | 3 | 1.71 | 99.9 |
| Cpd 462-En 2 | (1) | 0.5% IP Amine in IPA | 40 | 3 | 2.23 | 98.8 |
| Cpd 463-En 1 | (14) | EtOH | 30 | 3 | 5.45 | 99.4 |
| Cpd 463-En 2 | (14) | EtOH | 30 | 3 | 4.01 | 96.6 |
| Cpd 464-En 1 | (4) | MeOH | 30 | 3 | 6.03 | 99.1 |
| Cpd 464-En 2 | (4) | MeOH | 30 | 3 | 5.62 | 95.4 |
| Cpd 465-En 1 | (4) | MeOH | 30 | 3 | 2.84 | 99.5 |
| Cpd 465-En 2 | (4) | MeOH | 30 | 3 | 4.27 | 99.2 |
| Cpd 466-En 1 | (15) | 0.5% IP Amine in IPA | 30 | 3 | 3.47 | 98.9 |
| Cpd 466-En 2 | (15) | 0.5% IP Amine in IPA | 30 | 3 | 2.58 | 99.1 |
| Cpd 467-En 1 | (3) | MeOH | 40 | 4 | 3.40 | 99.9 |
| Cpd 467-En 2 | (3) | MeOH | 40 | 4 | 5.24 | 99.7 |
| Cpd 468-En 1 | (8) | MeOH | 40 | 4 | 13.80 | 99.8 |
| Cpd 468-En 2 | (8) | MeOH | 40 | 4 | 17.00 | 97.3 |
| Cpd 469-En 1 | (4) | MeOH | 40 | 3 | 3.03 | 99.7 |
| Cpd 469-En 2 | (4) | MeOH | 40 | 3 | 2.04 | 97.5 |
| Cpd 487-En 1 | (6) | MeOH | 40 | 3 | 7.18 | 99.9 |
| Cpd 487-En 2 | (6) | MeOH | 40 | 3 | 12.10 | 99.6 |
| Cpd 488-En 1 | (4) | MeOH | 20 | 3 | 5.99 | 99.9 |
| Cpd 488-En 2 | (4) | MeOH | 20 | 3 | 8.52 | 97.9 |
| Cpd 489-En 1 | (6) | MeOH | 30 | 3 | 1.82 | 99.3 |
| Cpd 489-En 2 | (6) | MeOH | 30 | 3 | 2.58 | 100.0 |
| Cpd 491-En 1 | (4) | IPA | 30 | 3 | 1.66 | 99.5 |
| Cpd 491-En 2 | (4) | IPA | 30 | 3 | 2.73 | 99.7 |
| Cpd 510-En 1 | (3) | EtOH | 40 | 4 | 6.45 | 100.0 |
| Cpd 510-En 2 | (3) | EtOH | 40 | 4 | 13.34 | 99.9 |
| Cpd 511-En 1 | (5) | MeOH | 35 | 3 | 3.15 | 99.9 |
| Cpd 511-En 2 | (5) | MeOH | 35 | 3 | 4.04 | 99.8 |
| Cpd 512-En 1 | (5) | MeOH | 30 | 3 | 7.00 | 99.9 |
| Cpd 512-En 2 | (5) | MeOH | 30 | 3 | 9.01 | 99.8 |
| Cpd 513-En 1 | (13) | MeOH | 30 | 3 | 2.86 | 99.8 |
| Cpd 513-En 2 | (13) | MeOH | 30 | 3 | 3.54 | 99.3 |
| Cpd 514-En 1 | (13) | MeOH | 35 | 3 | 5.70 | 99.7 |
| Cpd 514-En 2 | (13) | MeOH | 35 | 3 | 7.10 | 99.3 |
| Cpd 515-En 1 | (11) | MeOH | 35 | 3 | 6.52 | 99.8 |
| Cpd 515-En 2 | (11) | MeOH | 35 | 3 | 10.07 | 97.9 |
| Cpd 516-En 1 | (13) | 0.5% DEA in MeOH | 35 | 3 | 2.25 | 99.8 |
| Cpd 516-En 2 | (13) | 0.5% DEA in MeOH | 35 | 3 | 2.62 | 98.3 |
| Cpd 517-En 1 | (3) | MeOH | 50 | 4 | 18.69 | 99.9 |
| Cpd 518-En 1 | (11) | MeOH | 50 | 4 | 5.46 | 99.9 |
| Cpd 518-En 2 | (11) | MeOH | 50 | 4 | 8.69 | 97.9 |
| Cpd 519-En 1 | (11) | MeOH | 40 | 3 | 8.75 | 99.1 |
| Cpd 519-En 2 | (11) | MeOH | 40 | 3 | 14.26 | 97.8 |
| Cpd 520-En 1 | (11) | MeOH | 50 | 4 | 6.38 | 99.1 |
| Cpd 520-En 2 | (11) | MeOH | 50 | 4 | 10.10 | 95.3 |
| Cpd 521-En 1 | (9) | 0.5% DEA in MeOH | 40 | 3 | 5.78 | 97.7 |
| Cpd 521-En 2 | (9) | 0.5% DEA in MeOH | 40 | 3 | 6.56 | 96.7 |
| Cpd 522-En 1 | (13) | MeOH | 30 | 3 | 2.53 | 99.7 |

-continued

Chiral SFC analysis

| Code | Column Name | co-solvent | co-solvent % | Flow [g/min] | RT [min] | Purity [%] |
|---|---|---|---|---|---|---|
| Cpd 522-En 2 | (13) | MeOH | 30 | 3 | 3.00 | 98.3 |
| Cpd 530-En 1 | (4) | 0.5% DEA in MeOH | 40 | 3 | 1.36 | 99.7 |
| Cpd 530-En 2 | (4) | 0.5% DEA in MeOH | 40 | 3 | 3.41 | 99.4 |
| Cpd 531-En 1 | (2) | MeOH | 35 | 3 | 2.28 | 99.9 |
| Cpd 531-En 2 | (2) | MeOH | 35 | 3 | 3.15 | 99.9 |
| Cpd 532-En 1 | (2) | MeOH | 25 | 3 | 4.46 | 99.7 |
| Cpd 532-En 2 | (2) | MeOH | 25 | 3 | 6.30 | 97.1 |
| Cpd 533-En 1 | (16) | MeOH | 35 | 3 | 4.06 | 99.7 |
| Cpd 533-En 2 | (16) | MeOH | 35 | 3 | 5.13 | 99.5 |
| Cpd 534-En 1 | (4) | MeOH | 40 | 3 | 4.12 | 99.9 |
| Cpd 534-En 2 | (4) | MeOH | 40 | 3 | 2.95 | 99.5 |
| Cpd 535-En 1 | (16) | 0.5% DEA in MeOH | 40 | 4 | 4.12 | 97.2 |
| Cpd 535-En 2 | (16) | 0.5% DEA in MeOH | 40 | 4 | 3.49 | 98.8 |
| Cpd 536-En 1 | (1) | MeOH | 30 | 3 | 2.43 | 99.3 |
| Cpd 536-En 2 | (1) | MeOH | 30 | 3 | 3.49 | 99.9 |
| Cpd 538-En 1 | (5) | MeOH | 30 | 3 | 1.68 | 99.5 |
| Cpd 539-En 1 | (5) | 0.5% DEA in MeOH | 20 | 3 | 1.45 | 99.8 |
| Cpd 539-En 2 | (5) | 0.5% DEA in MeOH | 20 | 3 | 2.08 | 99.8 |
| Cpd 540-En 1 | (6) | 0.5% DEA in EtOH | 40 | 3 | 8.33 | 97.2 |
| Cpd 540-En 2 | (6) | 0.5% DEA in EtOH | 40 | 3 | 7.01 | 98.9 |
| Cpd 541-En 1 | (6) | 0.5% DEA in EtOH | 40 | 3 | 5.65 | 99.1 |
| Cpd 541-En 2 | (6) | 0.5% DEA in EtOH | 40 | 3 | 4.02 | 98.6 |
| Cpd 542-En 1 | (8) | 0.5% DEA in MeOH | 40 | 4 | 9.68 | 98.4 |
| Cpd 542-En 2 | (8) | 0.5% DEA in MeOH | 40 | 4 | 12.98 | 97.0 |
| Cpd 543-En 1 | (4) | EtOH | 40 | 3 | 4.58 | 99.2 |
| Cpd 543-En 2 | (4) | EtOH | 40 | 3 | 2.34 | 98.8 |
| Cpd 544-En 1 | (7) | 0.5% DEA in MeOH | 30 | 3 | 1.72 | 99.4 |
| Cpd 544-En 2 | (7) | 0.5% DEA in MeOH | 30 | 3 | 2.43 | 98.7 |
| Cpd 545-En 1 | (4) | 0.5% DEA in MeOH | 40 | 3 | 2.65 | 97.7 |
| Cpd 545-En 2 | (4) | 0.5% DEA in MeOH | 40 | 3 | 3.57 | 95.0 |
| Cpd 547-En 1 | (4) | EtOH | 40 | 3 | 7.20 | 99.8 |
| Cpd 547-En 2 | (4) | EtOH | 40 | 3 | 2.19 | 99.4 |
| Cpd 548-En 1 | (5) | MeOH | 40 | 3 | 1.59 | 99.9 |
| Cpd 548-En 2 | (5) | MeOH | 40 | 3 | 2.44 | 99.0 |
| Cpd 549-En 1 | (7) | MeOH | 30 | 3 | 1.46 | 99.9 |
| Cpd 549-En 2 | (7) | MeOH | 30 | 3 | 2.18 | 99.7 |
| Cpd 550-En 1 | (4) | 0.5% DEA in MeOH | 25 | 3 | 4.63 | 95.6 |
| Cpd 550-En 2 | (4) | 0.5% DEA in MeOH | 25 | 3 | 3.28 | 99.5 |
| Cpd 551-En 1 | (2) | MeOH | 25 | 3 | 2.69 | 99.2 |
| Cpd 551-En 2 | (2) | MeOH | 25 | 3 | 4.40 | 98.4 |
| Cpd 552-En 1 | (5) | MeOH | 30 | 3 | 2.27 | 99.5 |
| Cpd 552-En 2 | (5) | MeOH | 30 | 3 | 2.96 | 99.6 |
| Cpd 553-En 1 | (7) | MeOH | 25 | 3 | 1.40 | 98.9 |
| Cpd 553-En 2 | (7) | MeOH | 25 | 3 | 2.03 | 98.1 |
| Cpd 554-En 1 | (5) | MeOH | 30 | 3 | 2.51 | 99.0 |
| Cpd 554-En 2 | (5) | MeOH | 30 | 3 | 3.10 | 99.8 |
| Cpd 555-En 1 | (7) | IPA | 40 | 3 | 1.13 | 99.9 |
| Cpd 555-En 2 | (7) | IPA | 40 | 3 | 1.92 | 99.4 |
| Cpd 556-En 1 | (5) | 0.5% DEA in MeOH | 30 | 3 | 3.91 | 97.8 |
| Cpd 556-En 2 | (5) | 0.5% DEA in MeOH | 30 | 3 | 4.83 | 98.8 |
| Cpd 557-En 1 | (17) | MeOH | 40 | 4 | 6.63 | 99.2 |
| Cpd 557-En 2 | (17) | MeOH | 40 | 4 | 9.10 | 98.3 |
| Cpd 558-En 1 | (16) | MeOH | 30 | 3 | 6.15 | 98.8 |
| Cpd 558-En 2 | (16) | MeOH | 30 | 3 | 7.89 | 99.4 |
| Cpd 559-En 1 | (4) | 0.5% DEA in MeOH | 40 | 3 | 4.26 | 97.3 |
| Cpd 559-En 2 | (4) | 0.5% DEA in MeOH | 40 | 3 | 2.54 | 97.7 |
| Cpd 561-En 1 | (7) | MeOH | 40 | 3 | 1.23 | 98.8 |
| Cpd 561-En 2 | (7) | MeOH | 40 | 3 | 1.63 | 99.6 |
| Cpd 562-En 1 | (5) | MeOH | 40 | 3 | 2.14 | 99.6 |
| Cpd 562-En 2 | (5) | MeOH | 40 | 3 | 3.30 | 97.1 |
| Cpd 563-En 1 | (8) | MeOH | 40 | 4 | 11.84 | 99.6 |
| Cpd 563-En 2 | (8) | MeOH | 40 | 4 | 5.84 | 99.9 |
| Cpd 564-En 1 | (2) | MeOH | 25 | 3 | 4.83 | 99.3 |
| Cpd 564-En 2 | (2) | MeOH | 25 | 3 | 8.28 | 97.3 |
| Cpd 566-En 1 | (2) | MeOH | 30 | 3 | 2.60 | 99.4 |
| Cpd 566-En 2 | (2) | MeOH | 30 | 3 | 3.85 | 97.0 |
| Cpd 567-En 1 | (5) | 0.5% DEA in MeOH | 30 | 3 | 4.17 | 99.0 |
| Cpd 567-En 2 | (5) | 0.5% DEA in MeOH | 30 | 3 | 5.60 | 96.2 |
| Cpd 568-En 1 | (6) | 0.5% DEA in MeOH | 40 | 3 | 6.17 | 99.9 |
| Cpd 568-En 2 | (6) | 0.5% DEA in MeOH | 40 | 3 | 11.11 | 99.8 |
| Cpd 569-En 1 | (3) | 0.5% DEA in MeOH | 40 | 4 | 11.89 | 97.8 |
| Cpd 569-En 2 | (3) | 0.5% DEA in MeOH | 40 | 4 | 7.67 | 96.2 |
| Cpd 570-En 1 | (6) | 0.5% DEA in EtOH | 30 | 3 | 4.64 | 96.6 |

-continued

| | | Chiral SFC analysis | | | | |
|---|---|---|---|---|---|---|
| Code | Column Name | co-solvent | co-solvent % | Flow [g/min] | RT [min] | Purity [%] |
| Cpd 570-En 2 | (6) | 0.5% DEA in EtOH | 30 | 3 | 3.96 | 97.2 |
| Cpd 571-En 1 | (4) | 0.5% DEA in MeOH | 40 | 3 | 7.15 | 99.8 |
| Cpd 571-En 2 | (4) | 0.5% DEA in MeOH | 40 | 3 | 3.90 | 99.2 |
| Cpd 572-En 1 | (6) | MeOH | 40 | 3 | 4.63 | 99.4 |
| Cpd 572-En 2 | (6) | MeOH | 40 | 3 | 2.94 | 100.0 |
| Cpd 573-En 1 | (6) | 0.5% DEA in MeOH | 40 | 3 | 3.87 | 93.9 |
| Cpd 573-En 2 | (6) | 0.5% DEA in MeOH | 40 | 3 | 2.76 | 97.1 |
| Cpd 575-En 1 | (13) | 0.5% DEA in MeOH | 20 | 3 | 6.59 | 99.5 |
| Cpd 575-En 2 | (13) | 0.5% DEA in MeOH | 20 | 3 | 7.57 | 99.6 |
| Cpd 590-En 1 | (4) | IPA | 35 | 3 | 4.05 | 96.6 |
| Cpd 590-En 2 | (4) | IPA | 35 | 3 | 2.96 | 99.4 |
| Cpd 591-En 1 | (17) | MeOH | 40 | 3 | 4.20 | 99.9 |
| Cpd 591-En 2 | (17) | MeOH | 40 | 3 | 6.10 | 99.6 |
| Cpd 592-En 1 | (3) | MeOH | 50 | 4 | 9.41 | 98.7 |
| Cpd 592-En 2 | (3) | MeOH | 50 | 4 | 4.05 | 99.2 |
| Cpd 593-En 1 | (3) | MeOH | 30 | 3 | 13.39 | 99.6 |
| Cpd 593-En 2 | (3) | MeOH | 30 | 3 | 10.89 | 99.9 |
| Cpd 594-En 1 | (4) | MeOH | 40 | 3 | 12.23 | 99.8 |
| Cpd 594-En 2 | (4) | MeOH | 40 | 3 | 5.43 | 99.4 |
| Cpd 595-En 1 | (4) | MeOH | 40 | 3 | 4.72 | 100.0 |
| Cpd 595-En 2 | (4) | MeOH | 40 | 3 | 7.39 | 99.8 |
| Cpd 597-En 1 | (17) | MeOH | 40 | 4 | 8.05 | 99.8 |
| Cpd 597-En 2 | (17) | MeOH | 40 | 4 | 4.95 | 99.9 |
| Cpd 598-En 1 | (3) | MeOH | 30 | 3 | 7.79 | 99.7 |
| Cpd 598-En 2 | (3) | MeOH | 30 | 3 | 10.31 | 98.2 |
| Cpd 600-En 1 | (4) | MeOH | 40 | 3 | 4.15 | 96.5 |
| Cpd 600-En 2 | (4) | MeOH | 40 | 3 | 2.49 | 98.8 |
| Cpd 601-En 1 | (9) | MeOH | 40 | 3 | 3.22 | 99.7 |
| Cpd 601-En 2 | (9) | MeOH | 40 | 3 | 4.69 | 99.3 |
| Cpd 623-En 1 | (12) | MeOH | 20 | 3 | 5.96 | 99.7 |
| Cpd 623-En 2 | (12) | MeOH | 20 | 3 | 9.51 | 99.2 |
| Cpd 635-En 1 | (5) | 0.5% DEA in MeOH | 20 | 3 | 3.51 | 98.9 |
| Cpd 635-En 2 | (5) | 0.5% DEA in MeOH | 20 | 3 | 2.24 | 99.0 |
| Cpd 636-En 1 | (10) | MeOH | 40 | 4 | 2.78 | 98.4 |
| Cpd 636-En 2 | (10) | MeOH | 40 | 4 | 4.44 | 97.7 |
| Cpd 637-En 1 | (1) | MeOH | 40 | 3 | 2.71 | 98.8 |
| Cpd 637-En 2 | (1) | MeOH | 40 | 3 | 3.93 | 99.9 |
| Cpd 638-En 1 | (9) | 0.5% DEA in MeOH | 40 | 3 | 2.17 | 99.9 |
| Cpd 638-En 2 | (9) | 0.5% DEA in MeOH | 40 | 3 | 1.70 | 99.8 |
| Cpd 639-En 1 | (6) | 0.5% DEA in MeOH | 40 | 3 | 4.09 | 97.8 |
| Cpd 639-En 2 | (6) | 0.5% DEA in MeOH | 40 | 3 | 2.82 | 99.7 |
| Cpd 640-En 1 | (4) | MeOH | 40 | 3 | 8.41 | 98.4 |
| Cpd 640-En 2 | (4) | MeOH | 40 | 3 | 3.13 | 99.4 |
| Cpd 641-En 1 | (4) | EtOH | 40 | 3 | 2.13 | 99.3 |
| Cpd 641-En 2 | (4) | EtOH | 40 | 3 | 3.53 | 99.4 |
| Cpd 642-En 1 | (9) | MeOH | 15 | 3 | 3.43 | 99.9 |
| Cpd 642-En 2 | (9) | MeOH | 15 | 3 | 4.41 | 98.9 |
| Cpd 643-En 1 | (9) | MeOH | 30 | 3 | 3.59 | 99.9 |
| Cpd 643-En 2 | (9) | MeOH | 30 | 3 | 2.52 | 100.0 |
| Cpd 646-En 1 | (8) | MeOH | 45 | 3 | 5.57 | 99.9 |
| Cpd 646-En 2 | (8) | MeOH | 45 | 3 | 7.23 | 99.4 |
| Cpd 647-En 1 | (6) | MeOH | 40 | 3 | 3.26 | 99.4 |
| Cpd 647-En 2 | (6) | MeOH | 40 | 3 | 4.85 | 100.0 |
| Cpd 648-En 1 | (6) | EtOH | 40 | 3 | 2.04 | 98.6 |
| Cpd 648-En 2 | (6) | EtOH | 40 | 3 | 3.16 | 97.1 |
| Cpd 653-En 1 | (9) | MeOH | 4 | 3 | 3.26 | 99.1 |
| Cpd 653-En 2 | (9) | MeOH | 4 | 3 | 2.60 | 99.3 |
| Cpd 654-En 1 | (9) | MeOH | 4 | 3 | 3.00 | 99.4 |
| Cpd 654-En 2 | (9) | MeOH | 4 | 3 | 2.47 | 99.4 |
| Cpd 655-En 1 | (6) | MeOH | 40 | 3 | 4.72 | 98.4 |
| Cpd 655-En 2 | (6) | MeOH | 40 | 3 | 7.67 | 97.1 |
| Cpd 656-En 1 | (9) | MeOH | 35 | 3 | 3.1. | 99.6 |
| Cpd 656-En 2 | (9) | MeOH | 35 | 3 | 2.48 | 99.9 |
| Cpd 657-En 1 | (9) | MeOH | 25 | 3 | 15.35 | 99.3 |
| Cpd 657-En 2 | (9) | MeOH | 25 | 3 | 11.72 | 99.1 |
| Cpd 661-En 1 | (3) | MeOH | 40 | 4 | 9.70 | 98.6 |
| Cpd 661-En 2 | (3) | MeOH | 40 | 4 | 6.77 | 99.7 |
| Cpd 719-En 1 | (15) | MeOH | 40 | 3 | 4.31 | 99.91 |
| Cpd 719-En 2 | (15) | MeOH | 40 | 3 | 5.49 | 99.79 |
| Cpd 720-En 1 | (3) | 0.5% DEA in EtOH | 40 | 3 | 2.19 | 98.40 |
| Cpd 720-En 2 | (3) | 0.5% DEA in EtOH | 40 | 3 | 2.70 | 96.48 |
| Cpd 723-En 1 | (7) | MeOH | 20 | 3 | 1.94 | 99.52 |
| Cpd 723-En 2 | (7) | MeOH | 20 | 3 | 3.21 | 98.87 |

-continued

| | | Chiral SFC analysis | | | | |
|---|---|---|---|---|---|---|
| Code | Column Name | co-solvent | co-solvent % | Flow [g/min] | RT [min] | Purity [%] |
| Cpd 724-En 1 | (7) | MeOH | 15 | 3 | 2.51 | 99.76 |
| Cpd 724-En 2 | (7) | MeOH | 15 | 3 | 5.19 | 99.54 |
| Cpd 725-En 1 | (4) | MeOH | 40 | 3 | 2.33 | 99.90 |
| Cpd 725-En 2 | (4) | MeOH | 40 | 3 | 3.78 | 99.18 |
| Cpd 726-En 1 | (3) | MeOH | 50 | 4 | 7.04 | 99.74 |
| Cpd 726-En 2 | (3) | MeOH | 50 | 4 | 13.63 | 99.03 |
| Cpd 727-En 1 | (9) | 0.5% DEA in MeOH | 40 | 3 | 7.45 | 99.88 |
| Cpd 727-En 2 | (9) | 0.5% DEA in MeOH | 40 | 3 | 9.55 | 99.41 |
| Cpd 727-En 3 | (9) | MeOH | 40 | 3 | 7.24 | 99.95 |
| Cpd 727-En 4 | (9) | MeOH | 40 | 3 | 8.81 | 98.96 |
| Cpd 728-En 1 | (6) | 0.5% DEA in MeOH | 40 | 3 | 2.68 | 98.62 |
| Cpd 728-En 2 | (6) | 0.5% DEA in MeOH | 40 | 3 | 4.26 | 91.00 |
| Cpd 730-En 1 | (4) | MeOH | 35 | 3 | 2.38 | 99.98 |
| Cpd 730-En 2 | (4) | MeOH | 35 | 3 | 4.47 | 99.89 |
| Cpd 731-En 1 | (4) | MeOH | 35 | 3 | 2.91 | 99.73 |
| Cpd 731-En 2 | (4) | MeOH | 35 | 3 | 7.73 | 99.87 |
| Cpd 732-En 1 | (11) | MeOH | 40 | 3 | 6.38 | 99.59 |
| Cpd 732-En 2 | (11) | MeOH | 40 | 3 | 11.44 | 99.00 |
| Cpd 733-En 1 | (11) | MeOH | 35 | 3 | 6.49 | 99.96 |
| Cpd 733-En 2 | (11) | MeOH | 35 | 3 | 9.83 | 96.78 |
| Cpd 734-En 1 | (4) | 0.5% IP Amine in IPA | 40 | 3 | 1.80 | 99.73 |
| Cpd 734-En 2 | (4) | 0.5% IP Amine in IPA | 40 | 3 | 3.15 | 99.10 |
| Cpd 735-En 1 | (11) | MeOH | 40 | 3 | 5.11 | 99.88 |
| Cpd 735-En 2 | (11) | MeOH | 40 | 3 | 7.47 | 96.72 |
| Cpd 736-En 1 | (11) | MeOH | 40 | 3 | 3.76 | 99.15 |
| Cpd 736-En 2 | (11) | MeOH | 40 | 3 | 5.26 | 97.35 |
| Cpd 737-En 1 | (5) | MeOH | 30 | 3 | 4.52 | 95.25 |
| Cpd 737-En 2 | (5) | MeOH | 30 | 3 | 6.07 | 95.40 |
| Cpd 738-En 1 | (4) | EtOH | 40 | 3 | 4.42 | 98.28 |
| Cpd 738-En 2 | (4) | EtOH | 40 | 3 | 6.48 | 97.26 |
| Cpd 739-En 1 | (4) | MeOH | 40 | 3 | 4.49 | 98.44 |
| Cpd 739-En 2 | (4) | MeOH | 40 | 3 | 5.55 | 94.15 |
| Cpd 740-En 1 | (11) | MeOH | 35 | 3 | 2.83 | 99.41 |
| Cpd 740-En 2 | (11) | MeOH | 35 | 3 | 3.47 | 96.41 |

CHIRALCEL OZ-3 (4.6*150 mm) 3 µm = (1); CHIRACEL OD-H (250 mm × 4.6), 5 µm = (2); CHIRALPAK AD-H (4.6 × 250 mm), 5 µm = (3); CHIRALPAK AD-3 (4.6*150 mm) 3 µm = (4); CHIRALCEL OX-3 (4.6*150 mm) 3 µm = (5); Chiralpak IG-3 (4.6 × 150 mm), 3 µm = (6); CHIRALCEL OD-3 (4.6*150 mm) 3 µm = (7); CHIRALPAK IG-3 (4.6*250 mm) 5 µm = (8); CHIRALPAK IC-3 (4.6*150 mm) 3 µm = (9); Lux Cellulose-3 (4.6 × 250) mm, 5 µm = (10); CHIRALPAK IE-3 (4.6*150 mm) 3 µm = (11); Lux-Amylose-2 (4.6 × 250) mm, 5 µm = (12); (R,R) WHELK-01 (4.6*150 mm) 3.5 µm = (13); CHIRLPAK AD-H (4.6*150 mm) 3 µm = (14); Lux Cellulose-2 (4.6 × 150 mm) 3 µm = (15); CHIRALCEL OX-H (4.6*250) mm, 5 µm = (16); CHIRALPAK IF-3 (4.6*150 mm), 3 µm = (17)

| | | Chiral HPLC analysis | | | | |
|---|---|---|---|---|---|---|
| Cpd | Column Name | Phase A/B | Ratio A/B | Flow [mL/min] | RT [min] | Purity [%] |
| Cpd 729-En 1 | CHIRALCEL ODH (250 × 4.6 mm): 5µ | n-Hex/EtOH | 3/7 | 1 | 5.44 | 96.50 |
| Cpd 729-En 2 | CHIRALCEL ODH (250 × 4.6 mm): 5µ | n-Hex/EtOH | 3/7 | 1 | 9.58 | 99.89 |

Part B
Monitoring the TRPM3 Ion Channel Driven $Ca^{2+}$ Uptake.

In order to monitor the inhibition of the mouse TRPM3α2 (mTRPM3) ion channel by the compounds of the invention, a cellular system making use of an mTRPM3 alpha2 or hTRPM3 overexpressing cell line (flip-in HEK293) was used. The TRPM3 channel was stimulated/opened with Pregnenolone sulfate (PS) (50 µM) which results in $Ca^{2+}$ influx.

For mTRPM3, the intracellular $Ca^{2+}$ was measured with a Calcium responsive dye, Fluor-4 AM ester (Invitrogen). Cells were cultured until a confluence of 80-90%, washed with Versene (Invitrogen) and detached from the surface by a short incubation with 0.05% Trypsin (Invitrogen). The trypsination process was stopped by the addition of complete cell culture medium (DMEM, glutamax, 10% FCS, NEAA, Pen-Strep). Cells were collected and resuspended in Krebs buffer without Calcium at RT.

Prior the cell seeding (+2000 cells/well into a black, 384 well plate (Greiner)) the diluted compound was added in the assay plate, together with the PS dissolved in Krebs buffer containing Calcium. This resulted in a 2.4 mM $Ca^{2+}$ assay solution. Directly after cell addition the plates were read on an Envision fluorescence reader (Perkin Elmer) by an Excitation of 485 nM and emission at 535 nM.

Channel inhibition was calculated compared to a non-PS stimulated control versus a condition stimulated with PS (50 µM) with vehicle. The ability of the compounds of the invention to inhibit this activity was determined as: Percentage inhibition=[1−((RFU determined for sample with test compound present−RFU determined for sample with positive control inhibitor) divided by (RFU determined in the presence of vehicle−RFU determined for sample with positive control inhibitor))]*100.

The activities of the Example compounds cpd 001-199 tested are depicted in the table below. The activity ranges A, B and C refer to IC50 values in the Fluo-4 AM assay as follows: "A": $IC_{50} < 1$ μM; "B": $1\ \mu M \leq IC_{50} \leq 20\ \mu M$ and "C": $IC_{50} > 20$ μM

| cpd | $IC_{50}$ |
|---|---|
| 001 | B |
| 002 | C |
| 003 | C |
| 004 | C |
| 005 | B |
| 006 | B |
| 007 | B |
| 008 | C |
| 009 | B |
| 010 | B |
| 011 | B |
| 012 | B |
| 013 | B |
| 014 | B |
| 015 | C |
| 016 | C |
| 017 | C |
| 018 | B |
| 019 | C |
| 020 | B |
| 021 | B |
| 022 | A |
| 023 | B |
| 024 | A |
| 025 | A |
| 026 | A |
| 027 | A |
| 028 | A |
| 029 | A |
| 030 | A |
| 031 | B |
| 032 | B |
| 033 | C |
| 034 | B |
| 035 | A |
| 036 | A |
| 037 | B |
| 038 | A |
| 039 | B |
| 040 | C |
| 041 | A |
| 042 | A |
| 043 | A |
| 044 | B |
| 045 | B |
| 046 | A |
| 047 | A |
| 048 | A |
| 049 | A |
| 050 | A |
| 051 | A |
| 052 | B |
| 053 | B |
| 054 | A |
| 055 | C |
| 056 | A |
| 057 | C |
| 058 | A |
| 059 | B |
| 060 | B |
| 061 | C |
| 062 | A |
| 063 | A |
| 064 | A |
| 065 | B |
| 066 | B |
| 067 | A |
| 068 | A |
| 069 | B |
| 070 | A |
| 071 | A |
| 072 | A |
| 073 | B |
| 074 | A |
| 075 | C |
| 076 | B |
| 077 | C |
| 078 | B |
| 079 | B |
| 080 | B |
| 081 | B |
| 082 | B |
| 083 | B |
| 084 | B |
| 085 | B |
| 086 | B |
| 087 | B |
| 088 | B |
| 089 | B |
| 090 | B |
| 091 | B |
| 092 | B |
| 093 | B |
| 094 | B |
| 095 | B |
| 096 | B |
| 097 | B |
| 098 | B |
| 099 | B |
| 100 | B |
| 101 | B |
| 102 | B |
| 103-En 1 | A |
| 103-En 2 | A |
| 104 | A |
| 105-En 1 | A |
| 105-En 2 | A |
| 106-En 1 | A |
| 106-En 2 | A |
| 107 | A |
| 108 | A |
| 109 | A |
| 110-En 1 | A |
| 110-En 2 | A |
| 111-En 1 | A |
| 111-En 2 | A |
| 112-En 1 | A |
| 112-En 2 | A |
| 114 | A |
| 115-En 1 | A |
| 115-En 2 | A |
| 116-En 1 | A |
| 116-En 2 | A |
| 117 | A |
| 118-En 1 | A |
| 118-En 2 | A |
| 119 | A |
| 120-En 1 | A |
| 120-En 2 | A |
| 121-En 1 | A |
| 121-En 2 | A |
| 122 | B |
| 123-En 1 | A |
| 123-En 2 | A |
| 124-En 1 | A |
| 124-En 2 | A |
| 125-En 1 | A |
| 125-En 2 | A |
| 126-En 1 | A |
| 126-En 2 | A |
| 127 | A |

| cpd | IC$_{50}$ |
|---|---|
| 128 | A |
| 129 | A |
| 130-En 1 | A |
| 130-En 2 | A |
| 131-En 1 | A |
| 131-En 2 | A |
| 132-En 1 | A |
| 132-En 2 | A |
| 133 | A |
| 134-En 1 | B |
| 134-En 2 | A |
| 135-En 1 | A |
| 135-En 2 | A |
| 136 | A |
| 137 | A |
| 138 | A |
| 139 | A |
| 140 | A |
| 141-En 1 | A |
| 141-En 2 | A |
| 142 | A |
| 143 | A |
| 144 | A |
| 145 | A |
| 146 | A |
| 147-Dia 1-En 1 | A |
| 147-Dia 1-En 2 | A |
| 148-En 1 | A |
| 148-En 2 | A |
| 149-En 1 | A |
| 149-En 2 | A |
| 150 | A |
| 151-En 1 | A |
| 151-En 2 | A |
| 152 | A |
| 153 | A |
| 154 | A |
| 155-En 1 | A |
| 155-En 2 | A |
| 156 | A |
| 157-En 1 | A |
| 157-En 2 | A |
| 158 | A |
| 159-En 1 | A |
| 159-En 2 | A |
| 160-En 1 | A |
| 160-En 2 | A |
| 161 | A |
| cpd 162-Dia 1-En2 | A |
| cpd 162-Dia 1-En1 | A |
| 163-En 1 | A |
| 163-En 2 | A |
| 164-En 1 | A |
| 164-En 2 | A |
| 165-En 1 | A |
| 165-En 2 | B |
| 166 | A |
| 167 | A |
| 168 | A |
| 169-En 1 | A |
| 169-En 2 | A |
| 170 | A |
| 171 | A |
| 172-En 1 | A |
| 172-En 2 | A |
| 173 | A |
| 174 | A |
| 175 | A |
| 176-En 1 | B |
| 176-En 2 | A |
| 177 | A |
| 178 | B |
| 179-En 1 | B |
| 179-En 2 | C |
| 180-En 1 | B |
| 180-En 2 | B |
| 181 | B |
| 182 | A |
| 183-En 1 | B |
| 183-En 2 | C |
| 184-En 1 | B |
| 184-En 2 | C |
| 185 | B |
| 186 | B |
| 187 | B |
| 188 | B |
| 189 | B |
| 190 | B |
| 191-En 1 | C |
| 191-En 2 | C |
| 192 | C |
| 193 | C |
| 194 | C |
| 195-En 1 | C |
| 195-En 2 | C |
| 196-En 1 | C |
| 196-En 2 | B |
| 197 | B |
| 198-En 1 | B |
| 198-En 2 | B |
| 199-En 1 | A |
| 199-En 2 | A |

The activities of the Example compounds (cpds 200-299) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM.

| cpd | IC$_{50}$ |
|---|---|
| 200 | A |
| 201 | B |
| 202 | B |
| 203 | A |
| 204 | A |
| 205 - En 1 | B |
| 205 - En 2 | A |
| 206 | A |
| 207 - En 1 | A |
| 207 - En 2 | A |
| 232 | A |
| 270 - En 1 | C |
| 270 - En 2 | C |
| 271 | A |
| 272 | A |
| 273 | A |
| 274 | A |
| 275 | A |
| 276 | A |
| 277 | B |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |

| cpd | IC$_{50}$ |
| --- | --- |
| 298 | A |
| 299 | A |

The activities of the Example compounds (cpds. 300-399) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM

| cpd | IC$_{50}$ |
| --- | --- |
| 300 | A |
| 301 | A |
| 302 | A |
| 303 | A |
| 304 | A |
| 305 | A |
| 306 | A |
| 307 | B |
| 308 | B |
| 309 | B |
| 310-En 1 | A |
| 310-En 2 | A |
| 311 | A |
| 312 | B |
| 313-En 1 | A |
| 313-En 2 | B |
| 314 | A |
| 315-En 1 | A |
| 315-En 2 | A |
| 316-En 1 | A |
| 316-En 2 | A |
| 317-En 1 | A |
| 317-En 2 | A |
| 318 | A |
| 319 | A |
| 320 | A |
| 321 | A |
| 322 | A |
| 323 | A |
| 324 | A |
| 325 | B |
| 326-En 1 | A |
| 326-En 2 | B |
| 327 | B |
| 328 | A |
| 329 | B |
| 330 | A |
| 331 | B |
| 332-En 1 | A |
| 332-En 2 | A |
| 333-En 1 | A |
| 333-En 2 | A |
| 334 | A |
| 335-En 1 | A |
| 335-En 2 | A |
| 336-En 1 | A |
| 336-En 2 | A |
| 337 | A |
| 338-En 1 | A |
| 338-En 2 | A |
| 339 | A |
| 340-En 1 | A |
| 340-En 2 | A |
| 341 | A |
| 342-En 1 | A |
| 342-En 2 | A |
| 343 | A |
| 344 | A |
| 345 | A |
| 346 | A |
| 347 | A |
| 348-En 1 | A |
| 348-En 2 | A |
| 349-En 1 | A |
| 349-En 2 | A |
| 350-En 1 | A |
| 350-En 2 | A |
| 351 | B |
| 352 | A |
| 355-En 1 | A |
| 355-En 2 | A |
| 356-En 1 | A |
| 356-En 2 | A |
| 357 | A |
| 358 | C |
| 359 | A |
| 360-En 1 | A |
| 360-En 2 | A |
| 361 | A |
| 362 | A |
| 363 | A |
| 364 | A |
| 365-En 1 | C |
| 365-En 2 | C |
| 366 | B |
| 367 | A |
| 368 | B |
| 369 | B |
| 370 | A |
| 371 | A |
| 372 | A |
| 373 | A |
| 374 | A |
| 375 | A |
| 376 | A |
| 377 | A |
| 378 | A |
| 379 | A |
| 380 | A |
| 381 | A |
| 382 | A |
| 383 | A |
| 384 | A |
| 385 | A |
| 386-En 1 | A |
| 386-En 2 | B |
| 387-En 1 | A |
| 387-En 2 | A |
| 388-En 1 | A |
| 388-En 2 | B |
| 389-En 1 | A |
| 389-En 2 | A |
| 390 | A |
| 391 | A |
| 392 | A |
| 393 | A |
| 394 | A |
| 395-Dia 1 | A |
| 395-Dia 2 | A |
| 396-En 1 | A |
| 396-En 2 | A |
| 397-En 1 | A |
| 397-En 2 | A |
| 398 | A |
| 399 | A |

The activities of the Example compounds (cpds. 400-499) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM

| cpd | IC$_{50}$ |
| --- | --- |
| 400 | A |
| 401-En 1 | A |
| 401-En 2 | B |

| cpd | IC$_{50}$ |
| --- | --- |
| 402-En 1 | B |
| 403-En 1 | B |
| 403-En 2 | C |
| 404-En 1 | B |
| 404-En 2 | B |
| 405 | C |
| 406-En 1 | A |
| 406-En 2 | A |
| 407-En 1 | A |
| 407-En 2 | B |
| 408-En 1 | A |
| 408-En 2 | A |
| 409-En 1 | A |
| 409-En 2 | A |
| 410-En 1 | A |
| 410-En 2 | B |
| 411-En 1 | A |
| 411-En 2 | A |
| 412-En 1 | A |
| 412-En 2 | A |
| 413-En 1 | A |
| 413-En 2 | A |
| 414 | A |
| 415 | A |
| 416 | A |
| 417 | A |
| 418 | A |
| 419 | A |
| 420 | A |
| 421 | A |
| 422 | A |
| 423 | A |
| 424 | A |
| 425 | A |
| 426 | A |
| 427 | A |
| 428 | A |
| 429 | A |
| 429 | A |
| 430 | A |
| 431 | A |
| 432-En 1 | B |
| 432-En 2 | A |
| 433-En 1 | A |
| 433-En 2 | A |
| 434-En 1 | A |
| 434-En 2 | A |
| 435-En 1 | A |
| 435-En 2 | A |
| 436-En 1 | A |
| 436-En 2 | A |
| 437-En 1 | A |
| 437-En 2 | A |
| 438 | A |
| 439 | A |
| 440 | A |
| 441 | A |
| 442 | A |
| 443 | A |
| 444 | A |
| 445-En 1 | A |
| 445-En 2 | B |
| 446-En 1 | A |
| 446-En 2 | B |
| 447-En 1 | A |
| 447-En 2 | A |
| 448-En 1 | A |
| 448-En 1 | A |
| 449-En 1 | A |
| 449-En 2 | A |
| 450-En 1 | A |
| 450-En 2 | A |
| 451-En 1 | A |
| 451-En 2 | B |
| 452-En 1 | A |
| 452-En 2 | A |
| 453-En 1 | A |
| 453-En 2 | A |
| 454 | A |
| 455-En 2 | A |
| 456-En 1 | A |
| 456-En 2 | A |
| 457-En 1 | A |
| 457-En 2 | A |
| 458-En 1 | A |
| 458-En 2 | A |
| 459-En 1 | A |
| 459-En 2 | A |
| 460-En 1 | A |
| 460-En 2 | A |
| 461-En 1 | A |
| 461-En 2 | A |
| 462-En 1 | A |
| 462-En 2 | A |
| 463-En 1 | A |
| 463-En 2 | A |
| 464-En 1 | A |
| 464-En 2 | A |
| 465-En 1 | A |
| 465-En 2 | A |
| 466-En 1 | A |
| 466-En 2 | A |
| 467-En 1 | A |
| 467-En 2 | A |
| 468-En 1 | A |
| 468-En 2 | A |
| 469-En 1 | A |
| 469-En 2 | A |
| 470 | A |
| 471 | A |
| 472 | A |
| 473 | A |
| 474 | A |
| 475 | A |
| 476 | A |
| 477 | A |
| 478 | A |
| 479 | B |
| 480 | A |
| 481 | A |
| 482 | A |
| 483 | A |
| 484 | A |
| 485 | A |
| 486 | A |
| 487-En 1 | B |
| 487-En 2 | B |
| 488-En 1 | A |
| 488-En 2 | B |
| 489-En 1 | A |
| 489-En 2 | A |
| 490-En 1 | A |
| 490-En 2 | A |
| 491-En 1 | A |
| 491-En 2 | A |
| 492 | A |
| 493 | A |
| 494 | A |
| 495 | A |
| 496 | A |
| 497 | A |
| 498 | A |
| 499 | A |

The activities of the Example compounds (cpds. 500-599) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM

| cpd | IC$_{50}$ |
|---|---|
| 500 | A |
| 501 | A |
| 502 | A |
| 503 | A |
| 504 | A |
| 505 | A |
| 506 | A |
| 507 | B |
| 508 | A |
| 509 | A |
| 510-En 1 | A |
| 510-En 2 | A |
| 511-En 1 | A |
| 511-En 2 | B |
| 512-En 1 | A |
| 512-En 2 | A |
| 513-En 1 | A |
| 513-En 2 | A |
| 514-En 1 | A |
| 514-En 2 | A |
| 515-En 1 | A |
| 515-En 1 | B |
| 516-En 1 | A |
| 516-En 2 | A |
| 517-En 1 | A |
| 517-En 2 | A |
| 518-En 1 | A |
| 518-En 2 | A |
| 519-En 1 | A |
| 519-En 2 | A |
| 520-En 1 | A |
| 520-En 2 | A |
| 521-En 1 | A |
| 521-En 2 | B |
| 522-En 1 | A |
| 522-En 2 | A |
| 523 | B |
| 524 | A |
| 525 | A |
| 526 | A |
| 527 | A |
| 528 | A |
| 529 | A |
| 530-En 1 | B |
| 530-En 2 | A |
| 531-En 1 | A |
| 531-En 2 | A |
| 532-En 1 | A |
| 532-En 2 | A |
| 533-En 1 | A |
| 533-En 2 | A |
| 534-En 1 | A |
| 534-En 2 | A |
| 535-En 1 | A |
| 535-En 2 | A |
| 536-En 1 | A |
| 536-En 2 | A |
| 537 | A |
| 538-En 1 | B |
| 539-En 1 | B |
| 539-En 2 | A |
| 540-En 1 | B |
| 540-En 2 | C |
| 541-En 1 | B |
| 541-En 2 | C |
| 542-En 1 | B |
| 542-En 2 | C |
| 543-En 1 | A |
| 543-En 2 | A |
| 544-En 1 | B |
| 544-En 2 | B |
| 545-En 1 | B |
| 545-En 2 | B |
| 546-En 1 | A |
| 547-En 1 | A |
| 547-En 2 | A |
| 548-En 1 | B |
| 548-En 2 | C |
| 549-En 1 | A |
| 549-En 2 | B |
| 550-En 1 | B |
| 550-En 2 | B |
| 551-En 1 | A |
| 551-En 2 | B |
| 552-En 1 | A |
| 552-En 2 | B |
| 553-En 1 | A |
| 553-En 2 | B |
| 554-En 1 | A |
| 554-En 2 | C |
| 555-En 1 | A |
| 555-En 2 | B |
| 556-En 1 | B |
| 556-En 2 | C |
| 557-En 1 | A |
| 557-En 2 | A |
| 558-En 1 | A |
| 558-En 2 | A |
| 559-En 1 | B |
| 559-En 2 | C |
| 560-En 1 | A |
| 560-En 2 | A |
| 561-En 1 | A |
| 561-En 2 | A |
| 562-En 1 | A |
| 562-En 2 | A |
| 563-En 1 | A |
| 563-En 2 | A |
| 564-En 1 | A |
| 564-En 2 | A |
| 565-En 1 | A |
| 565-En 2 | A |
| 566-En 1 | A |
| 566-En 2 | B |
| 567-En 1 | C |
| 567-En 2 | C |
| 568-En 1 | A |
| 568-En 2 | B |
| 569-En 1 | B |
| 569-En 2 | C |
| 570-En 1 | A |
| 570-En 2 | B |
| 571-En 1 | B |
| 571-En 2 | B |
| 572-En 1 | A |
| 572-En 2 | A |
| 573-En 1 | A |
| 573-En 2 | B |
| 574 | A |
| 575-En 1 | A |
| 575-En 1 | A |
| 576 | A |
| 577 | A |
| 578 | B |
| 579 | A |
| 580 | A |
| 581 | A |
| 582 | A |
| 583 | A |
| 584 | A |
| 585 | A |
| 586 | A |
| 587 | A |
| 588 | A |
| 589 | B |
| 590-En 1 | A |
| 590-En 2 | A |
| 591-En 1 | A |
| 591-En 2 | A |
| 592-En 1 | A |
| 592-En 2 | A |
| 593-En 1 | A |
| 593-En 2 | A |
| 594-En 1 | A |
| 594-En 2 | A |
| 595-En 1 | A |

| cpd | IC$_{50}$ |
|---|---|
| 595-En 2 | A |
| 596-En 1 | A |
| 596-En 2 | A |
| 597-En 1 | A |
| 597-En 2 | A |
| 598-En 1 | A |
| 598-En 2 | A |
| 599 | B |

The activities of the Example compounds (cpds. 600-666) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM

| cpd | IC$_{50}$ |
|---|---|
| 600-En 1 | A |
| 600-En 2 | A |
| 601-En 1 | A |
| 601-En 2 | A |
| 602 | A |
| 603 | B |
| 604 | C |
| 605 | C |
| 606 | B |
| 607 | B |
| 608 | A |
| 609 | B |
| 610 | B |
| 611 | A |
| 612 | B |
| 613 | A |
| 614 | A |
| 615 | A |
| 616 | B |
| 617 | B |
| 618 | A |
| 619 | B |
| 620 | A |
| 621 | C |
| 622 | B |
| 623-En 1 | A |
| 623-En 2 | A |
| 624 | A |
| 625 | A |
| 626 | B |
| 627 | A |
| 628 | B |
| 629 | A |
| 630 | C |
| 631 | C |
| 632 | B |
| 633 | B |
| 634 | A |
| 635-En 1 | A |
| 635-En 2 | B |
| 636-En 1 | A |
| 636-En 2 | A |
| 637-En 1 | A |
| 637-En 2 | A |
| 638-En 1 | A |
| 638-En 2 | B |
| 639-En 1 | A |
| 639-En 2 | A |
| 640-En 1 | A |
| 640-En 2 | A |
| 641-En 1 | B |
| 641-En 2 | B |
| 642-En 1 | A |
| 642-En 2 | A |
| 643-En 1 | A |
| 643-En 2 | A |
| 646-En 1 | A |
| 646-En 2 | A |
| 647-En 1 | A |
| 647-En 2 | A |
| 648-En 1 | A |
| 648-En 2 | A |
| 649 | A |
| 650 | A |
| 651 | A |
| 652 | A |
| 653-En 1 | B |
| 654-En 1 | B |
| 653-En 2 | B |
| 654-En 2 | B |
| 655-En 1 | A |
| 655-En 2 | A |
| 656-En 1 | B |
| 656-En 2 | B |
| 657-En 1 | C |
| 657-En 1 | C |
| 658 | C |
| 659 | B |
| 660 | C |
| 661-En 1 | A |
| 661-En 1 | A |
| 662 | A |
| 663 | A |
| 664 | A |
| 665 | A |
| 666 | A |

The activities of the Example compounds (cpds. 667-5751) tested are depicted in the table below. The activity ranges A, B and C refer to IC50 values in the Fluo-4 AM assay as follows: "A": IC$_{50}$<1 µM; "B": 1 µM≤IC$_{50}$≤20 µM and "C": IC$_{50}$>20 µM

| cpd | IC$_{50}$ |
|---|---|
| 667 |  |
| 668 | A |
| 669 |  |
| 670 | A |
| 671 |  |
| 672 | A |
| 673 |  |
| 674 | A |
| 675 |  |
| 676 | A |
| 677 |  |
| 678 | A |
| 679 |  |
| 680 | A |
| 681 |  |
| 682 | A |
| 683 | A |
| 684 | A |
| 685 | A |
| 686 | A |
| 687 |  |
| 688 | A |
| 689 |  |
| 690 | A |
| 691 |  |
| 692 | A |
| 693 |  |
| 694 | A |
| 695 | A |
| 696 | A |
| 697 | A |
| 698 | A |
| 699 |  |
| 700 | A |
| 701 |  |
| 702 | A |

-continued

| cpd | IC$_{50}$ |
|---|---|
| 703 | |
| 704 | A |
| 705 | B |
| 706 | A |
| 707 | |
| 708 | A |
| 709 | |
| 710 | A |
| 711 | A |
| 712 | A |
| 713 | |
| 714 | A |
| 715 | A |
| 716 | A |
| 717 | A |
| 718 | A |
| 719 - En 1 | A |
| 719 - En 2 | A |
| 720 - En 1 | A |
| 720 - En 2 | A |
| 721 | A |
| 722 - En 1 | A |
| 722 - En 2 | A |
| 723 - En 1 | A |
| 723 - En 2 | A |
| 724 - En 1 | A |
| 724 - En 2 | B |
| 725 - En 1 | A |
| 725 - En 2 | A |
| 726 - En 1 | A |
| 726 - En 2 | A |
| 727 - En 1 | B |
| 727 - En 2 | B |
| 727 - En 3 | B |
| 727 - En 4 | B |
| 728 - En 1 | B |
| 728 - En 2 | A |
| 729 - En 1 | A |
| 729 - En 2 | A |
| 730 - En 1 | A |
| 730 - En 2 | A |
| 731 - En 1 | A |
| 731 - En 2 | A |
| 732 - En 1 | A |
| 732 - En 2 | A |
| 733 - En 1 | A |
| 733 - En 2 | A |
| 734 - En 1 | A |
| 734 - En 2 | B |
| 735 - En 1 | A |
| 735 - En 2 | A |
| 736 - En 1 | A |
| 736 - En 2 | A |
| 737 - En 1 | A |
| 737 - En 2 | A |
| 738 - En 1 | A |
| 738 - En 2 | A |
| 739 - En 1 | A |
| 739 - En 2 | A |
| 740 - En 1 | A |
| 740 - En 2 | A |
| 741 | A |
| 742 | A |
| 743 | A |
| 744 | A |
| 745 | A |
| 746 | A |
| 747 | A |
| 748 | A |
| 749 | A |
| 750 | A |
| 751 | A |

The invention claimed is:

1. A compound of formula (I), a stereo-isomeric form, a physiologically acceptable salt, solvate and/or polymorph thereof

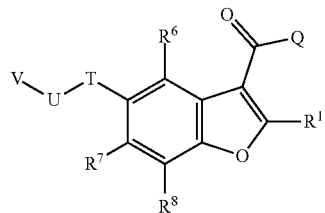

(I)

wherein $R^1$ represents —F, —Cl, —Br, —I, —CN, —$R^W$, —$OR^W$, —OC(=O)$R^W$, —$NR^WR^X$, —$NR^WC(=O)R^X$, —$SR^W$, —S(=O)$R^W$, —S(=O)$_2R^W$, —C(=O)$R^W$, —C(=O)$OR^W$, or —C(=O)$NR^WR^X$;

Q represents —$NR^3R^4$;

$R^3$ represents —OH or —$R^Y$;

$R^4$ represents —$R^Y$ or —S(=O)$_2R^Y$;

or $R^3$ and $R^4$ together form a 4, 5, 6, 7 or 8 membered heterocycle containing 1 to 3 heteroatoms selected from N, O and S, saturated or unsaturated, unsubstituted or mono- or polysubstituted;

T represents —O— and U represents —$CR^5R^{5'}$—; or T represents —$CR^5R^{5'}$—and U represents —O—;

$R^5$ and $R^{5'}$ independently of one another represent —$R^Y$;

$R^6$, $R^7$ and $R^8$ independently of one another represent —F, —Cl, —Br, —I, —CN, —$NO_2$, —$SF_5$, —$R^W$, —$OR^W$, —OC(=O)$R^W$, —$NR^WR^X$, —$NR^WC(=O)R^X$, —$SR^W$, —S(=O)$R^W$, —S(=O)$_2R^W$, —C(=O)$R^W$, —C(=O)$OR^W$, or —C(=O)$NR^WR^X$;

V represents 3-14-membered heterocycloalkyl, saturated or unsaturated; or 5-14-membered heteroaryl; in each case unsubstituted, mono- or polysubstituted with substituents independently of one another selected from —F, —Cl, —Br, —I, —CN, —NO, —$NO_2$, =O, =S, —$SF_5$, —$R^Y$, —$OR^Y$, —OC(=O)$R^Y$, —$NR^YR^Z$, —$NR^YC(=O)R^Z$, —$SR^Y$, —S(=O)$R^Y$, —S(=O)$_2R^Y$, —C(=O)$R^Y$, —C(=O)$OR^Y$, or —C(=O)$NR^YR^Z$;

wherein $R^W$ and $R^X$ independently of one another in each case independently represent
—H;
—$C_1$-$C_6$-alkyl, saturated or unsaturated, unsubstituted, mono- or polysubstituted;
—$C_1$-$C_6$-heteroalkyl, saturated or unsaturated, unsubstituted, mono- or poly substituted;
3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted; or
3-14-membered heterocycloalkyl, saturated or unsaturated, unsubstituted, mono- or polysubstituted;
wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;

$R^Y$ and $R^Z$ independently of one another in each case independently represent
—H;
—$C_1$-$C_6$-alkyl, saturated or unsaturated, unsubstituted, mono- or polysubstituted;

—$C_1$-$C_6$-heteroalkyl, saturated or unsaturated, unsubstituted, mono- or polysubstituted;

3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted;

3-14-membered heterocycloalkyl, saturated or unsaturated, unsubstituted, mono- or polysubstituted; wherein said 3-14-membered heterocycloalkyl is optionally connected through —$C_1$-$C_6$-alkylene- or —$C_1$-$C_6$-heteroalkylene-, in each case saturated or unsaturated, unsubstituted, mono- or polysubstituted;

6-14-membered aryl, unsubstituted, mono- or polysubstituted; wherein said 6-14-membered aryl is optionally connected through —$C_1$-$C_6$-alkylene- or —$C_1$-$C_6$-heteroalkylene-, in each case saturated or unsaturated, unsubstituted, mono- or polysubstituted; or 5-14-membered heteroaryl, unsubstituted, mono- or polysubstituted; wherein said 5-14-membered heteroaryl is optionally connected through —$C_1$-$C_6$-alkylene- or —$C_1$-$C_6$-heteroalkylene-, in each case saturated or unsaturated, unsubstituted, mono- or polysubstituted;

or $R^Y$ and $R^Z$ together form a 4, 5, 6, 7 or 8 membered heterocycle containing 1 to 3 heteroatoms selected from N, O and S, saturated or unsaturated, unsubstituted or mono- or polysubstituted;

and wherein "mono- or polysubstituted" in each case independently means substituted with one or more substituents independently of one another selected from —F, —Cl, —Br, —I, —CN, —$C_{1-6}$-alkyl, —$CF_3$, —$CF_2H$, —$CFH_2$, —$CF_2Cl$, —$CFCl_2$, —$C_{1-6}$-alkylene-$CF_3$, —$C_{1-6}$-alkylene-$CF_2H$, —$C_{1-6}$-alkylene-$CFH_2$, —$C_{1-6}$-alkylene-O—$CF_3$, —$C_{1-6}$-alkylene-O—$CF_2H$, —$C_{1-6}$-alkylene-O—$CFH_2$, —$C_{1-6}$-alkylene-NH—$C_{1-6}$-alkylene-$CF_3$, —$C_{1-6}$-alkylene-N($C_{1-6}$-alkyl)-$C_{1-6}$-alkylene-$CF_3$, —C(=O)—$C_{1-6}$-alkyl, —$C_{1-6}$-alkylene-C(=O)—$C_{1-6}$-alkyl, —C(=O)OH, —$C_{1-6}$-alkylene-C(=O)—OH, —C(=O)—O$C_{1-6}$-alkyl, —$C_{1-6}$-alkylene-C(=O)—O$C_{1-6}$-alkyl, —C(=O)O—$C_{1-6}$-alkylene-$CF_3$, —C(=O)—$NH_2$, —$C_{1-6}$-alkylene-C(=O)—$NH_2$, —C(=O)—NH($C_{1-6}$-alkyl), —$C_{1-6}$-alkylene-C(=O)—NH($C_{1-6}$-alkyl), —C(=O)—N($C_{1-6}$-alkyl)$_2$, —$C_{1-6}$-alkylene-C(=O)—N($C_{1-6}$-alkyl)$_2$, —C(=O)—NH(OH), —$C_{1-6}$-alkylene-C(=O)—NH(OH), —OH, —$C_{1-6}$-alkylene-OH, =O, —$OCF_3$, —$OCF_2H$, —$OCFH_2$, —$OCF_2Cl$, —$OCFCl_2$, —O—$C_{1-6}$-alkyl, —$C_{1-6}$-alkylene-O—$C_{1-6}$-alkyl, —O—$C_{1-6}$-alkylene-O—$C_{1-6}$-alkyl, —O—$C_{1-6}$-allylene-$NH_2$, —O—$C_{1-6}$-alkylene-NH—$C_{1-6}$-alkyl, —O—$C_{1-6}$-alkylene-N($C_{1-6}$-alkyl)$_2$, —O—C(=O)—$C_{1-6}$-alkyl, —$C_{1-6}$-alkylene-O—C(=O)—$C_{1-6}$-alkyl, —O—C(=O)—O—$C_{1-6}$-alkyl, —$C_{1-6}$-alkylene-O—C(=O)—O—$C_{1-6}$-alkyl, —O—C(=O)—NH($C_{1-6}$-alkyl), —$C_{1-6}$-alkylene-O—C(=O)—NH($C_{1-6}$-alkyl), —O—C(=O)—N($C_{1-6}$-alkyl)$_2$, —$C_{1-6}$-alkylene-O—C(=O)—N($C_{1-6}$-alkyl)$_2$, —O—S(=O)$_2$—$NH_2$, —$C_{1-6}$-alkylene-O—S(=O)$_2$—$NH_2$, —O—S(=O)$_2$—NH($C_{1-6}$-alkyl), —$C_{1-6}$-alkylene-O—S(=O)$_2$—NH($C_{1-6}$-alkyl), —O—S(=O)$_2$—N($C_{1-6}$-alkyl)$_2$, —$C_{1-6}$-alkylene-O—S(=O)$_2$—N($C_{1-6}$-alkyl)$_2$, —$NH_2$, —NO, —$NO_2$, —$C_{1-6}$-alkylene-$NH_2$, —NH($C_{1-6}$-alkyl), —N(3-14-membered cycloalkyl)($C_{1-6}$-alkyl), —N($C_{1-6}$-alkyl)-$C_{1-6}$-alkylene-OH, —N(H)—$C_{1-6}$-alkylene-OH, —$C_{1-6}$-alkylene-NH($C_{1-6}$-alkyl), —N($C_{1-6}$-alkyl)$_2$, —$C_{1-6}$-alkylene-N($C_{1-6}$-alkyl)$_2$, —NH—C(=O)—$C_{1-6}$-alkyl, —$C_{1-6}$-alkylene-NH—C(=O)—$C_{1-6}$-alkyl, —NH—C(=O)—O—$C_{1-6}$-alkyl, —$C_{1-6}$-alkylene-NH—C(=O)—O—$C_{1-6}$-alkyl, —NH—C(=O)—$NH_2$, —$C_{1-6}$-alkylene-NH—C(=O)—$NH_2$, —NH—C(=O)—NH($C_{1-6}$-alkyl), —$C_{1-6}$-alkylene-NH—C(=O)—NH($C_{1-6}$-alkyl), —NH—C(=O)—N($C_{1-6}$-alkyl)$_2$, —$C_{1-6}$-alkylene-NH—C(=O)—N($C_{1-6}$-alkyl)$_2$, —N($C_{1-6}$-alkyl)-C(=O)—$C_{1-6}$-alkyl, —$C_{1-6}$-alkylene-N($C_{1-6}$-alkyl)-C(=O)—$C_{1-6}$-alkyl, —N($C_{1-6}$-alkyl)-C(=O)—O—$C_{1-6}$-alkyl, —$C_{1-6}$-alkylene-N($C_{1-6}$-alkyl)-C(=O)—O—$C_{1-6}$-alkyl, —N($C_{1-6}$-alkyl)-C(=O)—$NH_2$, —$C_{1-6}$-alkylene-N($C_{1-6}$-alkyl)-C(=O)—$NH_2$, —N($C_{1-6}$-alkyl)-C(=O)—NH($C_{1-6}$-alkyl), —$C_{1-6}$-alkylene-N($C_{1-6}$-alkyl)-C(=O)—NH($C_{1-6}$-alkyl), —N($C_{1-6}$-alkyl)-C(=O)—N($C_{1-6}$-alkyl)$_2$, —$C_{1-6}$-alkylene-N($C_{1-6}$-alkyl)-C(=O)—N($C_{1-6}$-alkyl)$_2$, —NH—S(=O)$_2$OH, —$C_{1-6}$-alkylene-NH—S(=O)$_2$OH, —NH—S(=O)$_2$—$C_{1-6}$-alkyl, —$C_{1-6}$-alkylene-NH—S(=O)$_2$—$C_{1-6}$-alkyl, —NH—S(=O)$_2$—O—$C_{1-6}$-alkyl, —$C_{1-6}$-alkylene-NH—S(=O)$_2$—O—$C_{1-6}$-alkyl, —NH—S(=O)$_2$—$NH_2$, —$C_{1-6}$-alkylene-NH—S(=O)$_2$—$NH_2$, —NH—S(=O)$_2$—NH($C_{1-6}$-alkyl), —$C_{1-6}$-alkylene-NH—S(=O)$_2$—NH($C_{1-6}$-alkyl), —NH—S(=O)$_2$N($C_{1-6}$-alkyl)$_2$, —$C_{1-6}$-alkylene-NH—S(=O)$_2$N($C_{1-6}$-alkyl)$_2$, —N($C_{1-6}$-alkyl)-S(=O)$_2$—OH, —$C_{1-6}$-alkylene-N($C_{1-6}$-alkyl)-S(=O)$_2$—OH, —N($C_{1-6}$-alkyl)-S(=O)$_2$—$C_{1-6}$-alkyl, —$C_{1-6}$-alkylene-N($C_{1-6}$-alkyl)-S(=O)$_2$—$C_{1-6}$-alkyl, —N($C_{1-6}$-alkyl)-S(=O)$_2$—O—$C_{1-6}$-alkyl, —$C_{1-6}$-alkylene-N($C_{1-6}$-alkyl)-S(=O)$_2$—O—$C_{1-6}$-alkyl, —N($C_{1-6}$-alkyl)-S(=O)$_2$—$NH_2$, —$C_{1-6}$-alkylene-N($C_{1-6}$-alkyl)-S(=O)$_2$—$NH_2$, —N($C_{1-6}$-alkyl)-S(=O)$_2$—NH($C_{1-6}$-alkyl), —$C_{1-6}$-alkylene-N($C_{1-6}$-alkyl)-S(=O)$_2$—NH($C_{1-6}$-alkyl), —N($C_{1-6}$-alkyl)-S(=O)$_2$—N($C_{1-6}$-alkyl)$_2$, —$C_{1-6}$-alkylene-N($C_{1-6}$-alkyl)-S(=O)$_2$—N($C_{1-6}$-alkyl)$_2$, —SH, =S, —$SF_5$, —$SCF_3$, —$SCF_2H$, —$SCFH_2$, —S—$C_{1-6}$-alkyl, —$C_{1-6}$-alkylene-S—$C_{1-6}$-alkyl, —S(=O)—$C_{1-6}$-alkyl, —$C_{1-6}$-alkylene-S(=O)—$C_{1-6}$-alkyl, —S(=O)$_2$—$C_{1-6}$-alkyl, —$C_{1-6}$-alkylene-S(=O)$_2$—$C_{1-6}$-alkyl, —S(=O)$_2$—OH, —$C_{1-6}$-alkylene-S(=O)$_2$—OH, —S(=O)$_2$—O—$C_{1-6}$-alkyl, —$C_{1-6}$-alkylene-S(=O)$_2$—O—$C_{1-6}$-alkyl, —S(=O)$_2$—$NH_2$, —$C_{1-6}$-alkylene-S(=O)$_2$—$NH_2$, —S(=O)$_2$—NH($C_{1-6}$-alkyl), —$C_{1-6}$-alkylene-S(=O)$_2$—NH($C_{1-6}$-alkyl), —S(=O)$_2$—N($C_{1-6}$-alkyl)$_2$, —$C_{1-6}$-alkylene-S(=O)$_2$—N($C_{1-6}$-alkyl)$_2$, 3-14-membered cycloalkyl, —$C_{1-6}$-alkylene-(3-14-membered cycloalkyl), 3 to 14-membered heterocycloalkyl, —$C_{1-6}$-alkylene-(3 to 14-membered heterocycloalkyl), -phenyl, —$C_{1-6}$-alkylene-phenyl, 5 to 14-membered heteroaryl, —$C_{1-6}$-alkylene-(5 to 14-membered heteroaryl), —O-(3-14-membered cycloalkyl), —O-(3 to 14-membered heterocycloalkyl), —O-phenyl, —O-(5 to 14-membered heteroaryl), —C(=O)-(3-14-membered cycloalkyl), —C(=O)-(3 to 14-membered hetero-cycloalkyl), —C(=O)-phenyl, —C(=O)-(5 to 14-membered heteroaryl), —S(=O)$_2$-(3-14-membered cycloalkyl), —S(=O)$_2$-(3 to 14-membered heterocycloalkyl), —S(=O)$_2$-phenyl, —S(=O)$_2$-(5 to 14-membered heteroaryl);

with the proviso that the following compounds and their salts are excluded

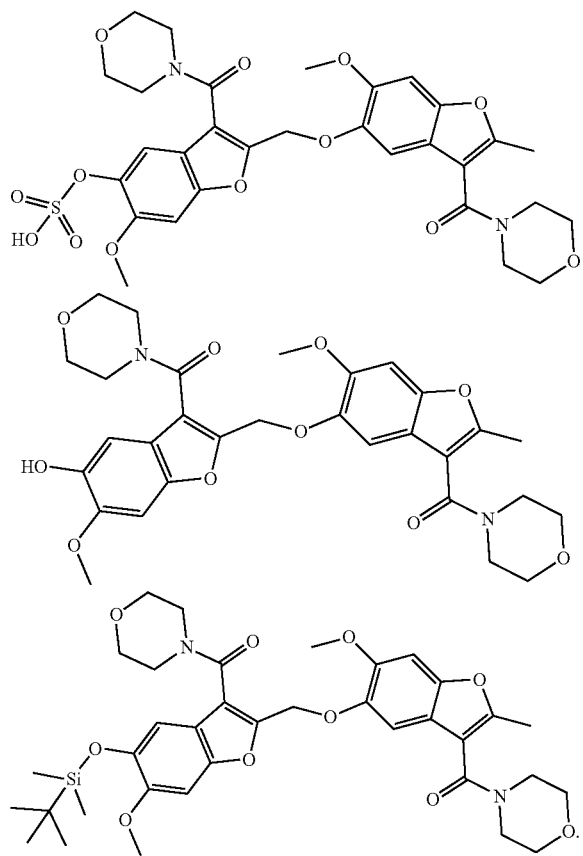

2. A compound of formula (I), a stereo-isomeric form, a physiologically acceptable salt, solvate and/or polymorph thereof, as defined in claim 1, wherein $R^3$ represents —H.

3. A compound of formula (I), a stereo-isomeric form, a physiologically acceptable salt, solvate and/or polymorph thereof, as defined in claim 1, wherein $R^1$ represents —CH$_2$F, —CHF$_2$, or —CF$_3$.

4. The compound according to claim 1, wherein T represents —O— and U represents —CR$^5$R$^{5\prime}$—.

5. The compound according to claim 1, wherein V represents (i) 5-14-membered heteroaryl selected from benzimidazole, benzisoxazole, benzoazole, benzodioxole, benzofuran, benzothiadiazole, benzothiazole, benzothiophene, carbazole, cinnoline, dibenzofuran, furane, furazane, imidazole, imidazopyridine, indazole, indole, indolizine, isobenzofuran, isoindole, isoquinoline, isothiazole, isoxazole, naphthyridine, oxadiazole, oxazole, oxindole, phthalazine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and [1,2,4]triazolo[4,3-a]pyrimidine; in each case unsubstituted, mono- or polysubstituted with substituents independently of one another selected from —F, —Cl, —CN, —OH, =O, —C$_{1-6}$-alkyl, —CHF$_2$, —CF$_3$, —C$_{1-6}$-alkylene-NH$_2$, —C$_{1-6}$-alkylene-NHC(=O)O—C$_{1-6}$-alkyl, —C$_{1-6}$-alkylene-OH, —C$_{1-6}$-alkylene-CHF$_2$, —C$_{1-6}$-alkylene-CF$_3$, —C$_{1-6}$-alkylene-cyclopropyl, -cyclopropyl, —O-cyclopropyl, —C$_{1-6}$-alkylene-NHC(=O)—O—C$_{1-6}$-alkyl, —C(=O)O—C$_{1-6}$-alkyl, —N(C$_{1-6}$-alkyl)$_2$, —OC$_{1-6}$-alkyl, —OCF$_3$, —O—C$_{1-6}$-alkylene-N(C$_{1-6}$-alkyl)$_2$, —S(=O)$_2$—C$_{1-6}$-alkyl, -azetidine, —C$_{1-6}$-alkylene-O-tetrahydropyran, or -piperazine substituted with —C$_{1-6}$-alkyl; particularly in each case unsubstituted, mono- or polysubstituted with substituents independently of one another selected from —F, —Cl, —CN, —OH, =O, —C$_{1-6}$-alkyl, —CHF$_2$, —CF$_3$, —C$_{1-6}$-alkylene-NH$_2$, —C$_{1-6}$-alkylene-NHC(=O)O—C$_{1-6}$-alkyl, —C$_{1-6}$-alkylene-OH, —C$_{1-6}$-alkylene-NHC(=O)—O—C$_{1-6}$-alkyl, —C(=O)O—C$_{1-6}$-alkyl, —N(C$_{1-6}$-alkyl)$_2$, —OC$_{1-6}$-alkyl, —OCF$_3$, —O—C$_{1-6}$-alkylene-N(C$_{1-6}$-alkyl)$_2$, —S(=O)$_2$—C$_{1-6}$-alkyl, -azetidine, —C$_{1-6}$-alkylene-O-tetrahydropyran, or -piperazine substituted with —C$_{1-6}$-alkyl; or represents (ii) -oxetanyl, unsubstituted, mono- or polysubstituted.

6. The compound according to claim 1, wherein $R^1$ represents —H, —F, —Cl, —Br, —I, —C$_{1-6}$-alkyl, —O—C$_{1-6}$-alkyl, —C$_{1-6}$-alkylene-O—C$_{1-6}$-alkyl, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, —C$_{1-6}$-alkylene-N(C$_{1-6}$-alkyl)-C$_{1-6}$-alkylene-CF$_3$, —C(=O)C$_{1-6}$-alkyl, —C(=O)OC$_{1-6}$-alkyl, —C(=O)NH$_2$, —C(=O)NHC$_{1-6}$-alkyl, —C(=O)N(C$_{1-6}$-alkyl)$_2$, —S(=O)—C$_{1-6}$-alkyl, —S(=O)$_2$—C$_{1-6}$-alkyl, —O—C$_{1-6}$-alkyl, -cyclopropyl unsubstituted, cyclobutyl unsubstituted, cyclopentyl unsubstituted or cyclohexyl unsubstituted.

7. The compound according to claim 1, wherein $R^3$ represents —H, —OH, —C$_{1-6}$-alkyl, —C$_{1-6}$-alkylene-OH, —C$_{1-6}$-alkylene-O—C$_{1-6}$-alkyl, —C$_{1-6}$-alkylene-NH$_2$, —C$_{1-6}$-alkylene-NH(C$_{1-6}$-alkyl), —C$_{1-6}$-alkylene-N(C$_{1-6}$-alkyl)$_2$, —CF$_3$, —CF$_2$H, —CFH$_2$, —CF$_2$Cl, —CFCl$_2$, —C$_{1-6}$-alkylene-CF$_3$, —C$_{1-6}$-alkylene-CF$_2$H, —C$_{1-6}$-alkylene-CFH$_2$, —C$_{1-6}$-alkylene-NH—C$_{1-6}$-alkylene-CF$_3$, or —C$_{1-6}$-alkylene-N(C$_{1-6}$-alkyl)-C$_{1-6}$-alkylene-CF$_3$.

8. The compound according to claim 1, wherein $R^4$ represents
—H;
—S(=O)$_2$C$_{1-6}$-alkyl, saturated, unsubstituted, monosubstituted or polysubstituted with —F;
—S(=O)$_2$(3-14-membered cycloalkyl), saturated, unsubstituted;
—C$_{1-6}$-alkyl, saturated, unsubstituted, monosubstituted or disubstituted with substituents independently of one another selected from the group consisting of —OH, =O, —OC$_{1-6}$-alkyl, —NH$_2$, —NHC$_{1-6}$-alkyl, —N(C$_{1-6}$-alkyl)$_2$, —C$_{1-6}$-alkylene-NH$_2$, —C$_{1-6}$-alkylene-NH—C$_{1-6}$-alkyl, —C(=O)NH$_2$, —C(=O)—NH—C$_{1-3}$-alkyl, —C(=O)N(C$_{1-3}$-alkyl)$_2$, —phenyl unsubstituted;
3-14-membered cycloalkyl or —C$_{1-6}$-alkylene-(3-14-membered cycloalkyl), wherein —C$_{1-6}$-alkylene- is unsubstituted or monosubstituted with —OH, wherein said 3-14-membered cycloalkyl is saturated, unsubstituted, monosubstituted or disubstituted with substituents independently of one another selected from the group consisting of —C$_{1-6}$-alkyl, —C$_{1-6}$-alkylene-NH$_2$, —C$_{1-6}$-alkylene-NH—C$_{1-6}$-alkylene-CF$_3$, —C$_{1-6}$-alkylene-OH, —C$_{1-6}$-alkylene-NHC(=O)O—C$_{1-6}$-alkyl, —OH, —OC$_{1-6}$-alkyl, —NH$_2$, —N(C$_{1-6}$-alkyl)$_2$, —NHC(=O)O—C$_{1-6}$-alkyl;
3-14-membered heterocycloalkyl or —C$_{1-6}$-alkylene-(3-14-membered heterocycloalkyl), wherein —C$_{1-6}$-alkylene- is unsubstituted or monosubstituted with —OH, wherein said 3-14-membered heterocycloalkyl in each case is selected from azetane, 1,4-oxazepane, pyrrolidine, piperidine, azepane, diazepane, tetrahydrofuran, tetrahydropyran, oxetane, morpholine, piperazine, hexahydrocyclopenta[c]pyrrole, octahydro-cyclopenta[c]pyrrole, octahydropyrrolo[1,2-a]pyrazin, 8-azabicyclo[3.2.1]octane, 9-azabicyclo[3.3.1]nonane, quinuclidine, hexahydro-1H-pyrrolizine, 2-oxaspiro[3.3]heptane, 2-azaspiro[3.3]heptane, 7-azaspiro[3.5]nonane, 1,1-dioxothiacyclohexane, in each case unsubstituted, mono- or polysubstituted with substituents independently of one another selected from the group consisting of —F, —OH, =O, —$C_{1-6}$-alkyl, —$C_{1-6}$-alkylene-$CF_3$, —$C_{1-6}$-alkylene-OH, —$C_{1-6}$-alkylene-O—$C_{1-6}$-alkyl, —$NH_2$, —N($C_{1-6}$-alkyl)$_2$, —$C_{1-6}$-alkylene-$NH_2$, —$C_{1-6}$-alkylene-N($C_{1-6}$-alkyl)$_2$, —C(=O)—$C_{1-6}$-alkyl, —C(=O)OH, —C(=O)O—$C_{1-6}$-alkyl, —C(=O)O—$C_{1-6}$-alkylene-$CF_3$, —C(=O)$NH_2$, —C(=O)NH($C_{1-6}$-alkyl), —S(=O)$_2$$C_{1-6}$-alkyl, oxetanyl, pyrimidinyl, —$C_{1-6}$-alkylene-phenyl;

-phenyl unsubstituted;

5-14-membered heteroaryl or —$C_{1-6}$-alkylene-(5-14-membered heteroaryl), wherein —$C_{1-6}$-alkylene- is unsubstituted or monosubstituted with —OH, wherein said 5-14-membered heteroaryl in each case is selected from the group consisting of pyridine, pyridazine, pyrazine, pyrazole, isoxazole, triazole, and [1,2,4]triazolo[4,3-a]pyrimidine, in each case unsubstituted, monosubstituted or disubstituted with substituents independently of one another selected from the group consisting of —$C_{1-6}$-alkyl, —OH.

9. The compound according to claim 1, wherein $R^3$ and $R^4$ together form a heterocycle selected from the group consisting of pyrrolidine, piperidine, morpholine, and piperazine, in each case unsubstituted, mono- or polysubstituted with substituents independently of one another selected from the group consisting of —F, —$C_{1-6}$-alkyl, —$NH_2$, —$NHCH_3$, —N($CH_3$)$_2$, —C(=O)NH—$C_{1-6}$-alkyl, —C(=O)N($C_{1-6}$-alkyl)$_2$, —C(=O)O—$C_{1-6}$-alkyl, —NHC(=O)O—$C_{1-6}$-alkyl, -pyridyl unsubstituted, and 1,2,4-oxadiazole unsubstituted or monosubstituted with —$C_{1-6}$-alkyl.

10. The compound according to claim 1, wherein $R^5$ and $R^{5'}$ independently of one another represent

—H;

—$C_1$-$C_6$-alkyl, saturated or unsaturated, unsubstituted, mono- or poly substituted;

—$C_1$-$C_6$-heteroalkyl, saturated or unsaturated, unsubstituted, mono- or poly substituted;

3-14-membered cycloalkyl, saturated or unsaturated, unsubstituted, mono- or polysubstituted; wherein said 3-14-membered cycloalkyl is optionally connected through —$C_1$-$C_6$-alkylene- or —$C_1$-$C_6$-heteroalkylene-, in each case saturated or unsaturated, unsubstituted, mono- or polysubstituted.

11. The compound according to claim 1, wherein $R^6$, $R^7$ and $R^8$ independently of one another represent —H, —F, —Cl, —Br, —I, —OH, —SH, —$SF_5$, —CN, —$NO_2$, —C(=O)OH, —$NH_2$, —$C_{1-6}$-alkyl, —$CF_3$, —$CHF_2$, —$CH_2F$, —O—$C_{1-6}$-alkyl, —$OCF_3$, —$OCHF_2$, —$OCH_2F$, —$NHC_{1-6}$-alkyl unsubstituted or substituted with one or more substituents independently of one another selected from —OH, =O, —F, —Cl, —Br, —I, —SH, =S, —CN, —$CF_3$, —$CHF_2$, —$CH_2F$, —$OCF_3$, —$OCHF_2$, —$OCH_2F$, $SF_5$, —$NO_2$, —C(=O)OH, —$NH_2$, and —C(=O)$NH_2$;

—N($C_{1-6}$-alkyl)$_2$ unsubstituted or substituted with one or more substituents independently of one another selected from —OH, =O, —F, —Cl, —Br, —I, —SH, =S, —CN, —$CF_3$, —$CHF_2$, —$CH_2F$, —$OCF_3$, —$OCHF_2$, —$OCH_2F$, $SF_5$, —$NO_2$, —C(=O)OH, —$NH_2$, and —C(=O)$NH_2$;

—C(=O)O$C_{1-6}$-alkyl unsubstituted or substituted with one or more substituents independently of one another selected from —OH, =O, —F, —Cl, —Br, —I, —SH, =S, —CN, —$CF_3$, —$CHF_2$, —$CH_2F$, —$OCF_3$, —$OCHF_2$, —$OCH_2F$, $SF_5$, —$NO_2$, —C(=O)OH, —$NH_2$, and —C(=O)$NH_2$;

—OC(=O)$C_{1-6}$-alkyl unsubstituted or substituted with one or more substituents independently of one another selected from —OH, =O, —F, —Cl, —Br, —I, —SH, =S, —CN, —$CF_3$, —$CHF_2$, —$CH_2F$, —$OCF_3$, —$OCHF_2$, —$OCH_2F$, $SF_5$, —$NO_2$, —C(=O)OH, —$NH_2$, and —C(=O)$NH_2$; or —$C_{1-6}$-heteroalkyl unsubstituted or substituted with one or more substituents independently of one another selected from —OH, =O, —F, —Cl, —Br, —I, —SH, =S, —CN, —$CF_3$, —$CHF_2$, —$CH_2F$, —$OCF_3$, —$OCHF_2$, —$OCH_2F$, $SF_5$, —$NO_2$, —C(=O)OH, —$NH_2$, and —C(=O)$NH_2$.

12. The compound according to claim 1, which is selected from the group consisting of cpd 001 5-(furan-3-ylmethoxy)-2-methylbenzofuran-3-carboxylic acid cpd 002 2-methyl-5-(oxazol-5-ylmethoxy)benzofuran-3-carboxylic acid cpd 003 2-methyl-5-(pyrrolidin-3-ylmethoxy)benzofuran-3-carboxylic acid cpd 004 2-methyl-5-(pyridin-4-ylmethoxy)benzofuran-3-carboxylic acid cpd 005 2-methyl-5-(pyridin-2-ylmethoxy)benzofuran-3-carboxylic acid cpd 006 2-methyl-5-(pyridin-3-ylmethoxy)benzofuran-3-carboxylic acid cpd 007 2-methyl-5-(pyridazin-3-ylmethoxy)benzofuran-3-carboxylic acid cpd 008 2-methyl-5-((1-methyl-1H-pyrazol-5-yl)methoxy)benzofuran-3-carboxylic acid cpd 009 2-methyl-5-((1-methyl-1H-pyrazol-3-yl)methoxy)benzofuran-3-carboxylic acid cpd 010 2-methyl-5-((1-methyl-1H-pyrazol-4-yl)methoxy)benzofuran-3-carboxylic acid cpd 011 2-methyl-5-(thiophen-3-ylmethoxy)benzofuran-3-carboxylic acid cpd 012 2-methyl-5-(thiophen-2-ylmethoxy)benzofuran-3-carboxylic acid cpd 013 2-methyl-5-(thiazol-2-ylmethoxy)benzofuran-3-carboxylic acid cpd 014 2-methyl-5-(thiazol-5-ylmethoxy)benzofuran-3-carboxylic acid cpd 015 2-methyl-5-((tetrahydro-2H-pyran-4-yl)methoxy)benzofuran-3-carboxylic acid cpd 016 5-((3,5-dimethylisoxazol-4-yl)methoxy)-2-methylbenzofuran-3-carboxylic acid cpd 017 5-(benzo[d]thiazol-2-ylmethoxy)-2-methylbenzofuran-3-carboxylic acid cpd 018 2-methyl-5-((5-(trifluoromethyl)furan-2-yl)methoxy)benzofuran-3-carboxylic acid cpd 019 5-((1-(tert-butoxycarbonyl)pyrrolidin-3-yl)methoxy)-2-methylbenzofuran-3-carboxylic acid cpd 020 (S)-2-methyl-5-(oxazol-5-ylmethoxy)-N-(pyrrolidin-3-yl)benzofuran-3-carboxamide cpd 021 (S)-2-methyl-5-(pyridin-4-ylmethoxy)-N-(pyrrolidin-3-yl)benzofuran-3-carboxamide cpd 022 (S)-2-methyl-5-(pyridin-3-ylmethoxy)-N-(pyrrolidin-3-yl)benzofuran-3-carboxamide cpd 023 (S)-2-methyl-5-((1-methyl-1H-pyrazol-3-yl)methoxy)-N-(pyrrolidin-3-yl)benzofuran-3-carboxamide cpd 024 (S)-2-methyl-N-(pyrrolidin-3-yl)-5-(thiazol-5-yl-methoxy)benzofuran-3-carboxamide
cpd 025 (S)-2-methyl-N-(pyrrolidin-3-yl)-5-(thiazol-2-yl-methoxy)benzofuran-3-carboxamide
cpd 026 2-methyl-N-(2-oxopyrrolidin-3-yl)-5-(pyridin-2-ylmethoxy)benzofuran-3-carboxamide
cpd 027 2-methyl-N-(2-oxopyrrolidin-3-yl)-5-(pyridin-3-ylmethoxy)benzofuran-3-carboxamide
cpd 028 (S)-2-methyl-5-((5-methylpyridin-3-yl)methoxy)-N-(pyrrolidin-3-yl)benzofuran-3-carboxamide
cpd 029 (S)-2-methyl-5-((6-methylpyridin-2-yl)methoxy)-N-(pyrrolidin-3-yl)benzofuran-3-carboxamide
cpd 030 2-methyl-N-(2-oxopyrrolidin-3-yl)-5-(pyridazin-3-ylmethoxy)benzofuran-3-carboxamide
cpd 031 2-methyl-N-(2-oxopyrrolidin-3-yl)-5-(pyrazin-2-ylmethoxy)benzofuran-3-carboxamide
cpd 032 2-methyl-N-(2-oxopyrrolidin-3-yl)-5-(pyrimidin-5-ylmethoxy)benzofuran-3-carboxamide
cpd 033 2-methyl-5-((6-methylpyridin-3-yl)methoxy)-N-(tetrahydrofuran-3-yl)benzofuran-3-carboxamide
cpd 034 2-methyl-5-((4-methylpyridin-3-yl)methoxy)-N-(tetrahydrofuran-3-yl)benzofuran-3-carboxamide
cpd 035 2-methyl-N-(2-oxopyrrolidin-3-yl)-5-(thiophen-3-ylmethoxy)benzofuran-3-carboxamide
cpd 036 2-methyl-N-(2-oxopyrrolidin-3-yl)-5-(thiazol-2-ylmethoxy)benzofuran-3-carboxamide
cpd 037 2-methyl-5-((4-methylpyridin-3-yl)methoxy)-N-(2-oxopyrrolidin-3-yl)benzofuran-3-carboxamide
cpd 038 2-methyl-5-((5-methylpyridin-3-yl)methoxy)-N-(2-oxopyrrolidin-3-yl)benzofuran-3-carboxamide
cpd 039 2-methyl-N-(1-methylpiperidin-4-yl)-5-(pyridin-2-ylmethoxy)benzofuran-3-carboxamide
cpd 040 5-((4-methoxypyridin-3-yl)methoxy)-2-methyl-N-(tetrahydrofuran-3-yl)benzofuran-3-carboxamide
cpd 041 2-methyl-N-(1-methylpiperidin-4-yl)-5-(thiophen-2-ylmethoxy)benzofuran-3-carboxamide
cpd 042 2-methyl-5-((4-methylthiazol-5-yl)methoxy)-N-(2-oxopyrrolidin-3-yl)benzofuran-3-carboxamide
cpd 043 2-methyl-5-((4-methylthiazol-2-yl)methoxy)-N-(2-oxopyrrolidin-3-yl)benzofuran-3-carboxamide
cpd 044 5-((2,6-dimethylpyridin-3-yl)methoxy)-2-methyl-N-(2-oxopyrrolidin-3-yl)benzofuran-3-carboxamide
cpd 045 2-methyl-N-(1-methylpiperidin-4-yl)-5-(1-(pyridin-4-yl)ethoxy)benzofuran-3-carboxamide
cpd 046 5-((2-methoxypyridin-3-yl)methoxy)-2-methyl-N-(2-oxopyrrolidin-3-yl)benzofuran-3-carboxamide
cpd 047 N-(4-(hydroxymethyl)tetrahydro-2H-pyran-4-yl)-2-methyl-5-(pyridin-2-ylmethoxy)benzofuran-3-carboxamide
cpd 048 N-(3,3-difluoropiperidin-4-yl)-2-methyl-5-(pyridin-2-ylmethoxy)benzofuran-3-carboxamide
cpd 049 N-(4-(hydroxymethyl)tetrahydro-2H-pyran-4-yl)-2-methyl-5-(thiazol-2-ylmethoxy)benzofuran-3-carboxamide
cpd 050 N-(3,3-difluoropiperidin-4-yl)-2-methyl-5-(thiazol-2-ylmethoxy)benzofuran-3-carboxamide
cpd 051 5-((2-methoxypyridin-3-yl)methoxy)-2-methyl-N-(1-methylpiperidin-4-yl)benzofuran-3-carboxamide
cpd 052 N-(4-(hydroxymethyl)tetrahydro-2H-pyran-4-yl)-2-methyl-5-((4-methylpyridin-3-yl)methoxy)-benzofuran-3-carboxamide
cpd 053 N-(3,3-difluoropiperidin-4-yl)-2-methyl-5-((3-methylpyridin-2-yl)methoxy)benzofuran-3-carboxamide
cpd 054 N-(4-(hydroxymethyl)tetrahydro-2H-pyran-4-yl)-2-methyl-5-((4-methylthiazol-5-yl)methoxy)-benzofuran-3-carboxamide
cpd 055 (S)-2-methyl-N-(pyrrolidin-3-yl)-5-((5-(trifluoromethyl)pyridin-3-yl)methoxy)benzofuran-3-carboxamide
cpd 056 N-(3,3-difluoropiperidin-4-yl)-2-methyl-5-((4-methylthiazol-5-yl)methoxy)benzofuran-3-carboxamide
cpd 057 2-methyl-N-(tetrahydrofuran-3-yl)-5-((4-(trifluoromethyl)thiazol-2-yl)methoxy)benzofuran-3-carboxamide
cpd 058 N-(4-(hydroxymethyl)tetrahydro-2H-pyran-4-yl)-5-((2-methoxypyridin-3-yl)methoxy)-2-methyl-benzofuran-3-carboxamide
cpd 059 5-(isoquinolin-1-ylmethoxy)-2-methyl-N-(1-methylpiperidin-4-yl)benzofuran-3-carboxamide
cpd 060 5-(isoquinolin-5-ylmethoxy)-2-methyl-N-(1-methylpiperidin-4-yl)benzofuran-3-carboxamide
cpd 061 5-(isoquinolin-6-ylmethoxy)-2-methyl-N-(1-methylpiperidin-4-yl)benzofuran-3-carboxamide
cpd 062 N-(3,3-difluoropiperidin-4-yl)-5-((2-methoxypyridin-3-yl)methoxy)-2-methylbenzofuran-3-carboxamide
cpd 063 N-(3,3-difluoropiperidin-4-yl)-5-((6-methoxypyridin-2-yl)methoxy)-2-methylbenzofuran-3-carboxamide
cpd 064 2-methyl-N-(2-oxopyrrolidin-3-yl)-5-((2-(trifluoromethyl)pyridin-3-yl)methoxy)benzofuran-3-carboxamide
cpd 065 2-methyl-N-(2-oxopyrrolidin-3-yl)-5-((6-(trifluoromethyl)pyridin-2-yl)methoxy)benzofuran-3-carboxamide
cpd 066 2-methyl-N-(2-oxopyrrolidin-3-yl)-5-((6-(trifluoromethyl)pyridin-3-yl)methoxy)benzofuran-3-carboxamide
cpd 067 5-((2-chloropyridin-3-yl)methoxy)-N-(3,3-difluoropiperidin-4-yl)-2-methylbenzofuran-3-carboxamide
cpd 068 5-((4-chloropyridin-3-yl)methoxy)-N-(3,3-difluoropiperidin-4-yl)-2-methylbenzofuran-3-carboxamide
cpd 069 2-methyl-N-(1-methylpiperidin-4-yl)-5-((5-(trifluoromethyl)furan-2-yl)methoxy)benzofuran-3-carboxamide
cpd 070 N-(3,3-difluoropiperidin-4-yl)-5-(imidazo[1,2-a]pyridin-6-ylmethoxy)-2-methylbenzofuran-3-carboxamide
cpd 071 N-(3,3-difluoropiperidin-4-yl)-5-((6-(dimethylamino)pyridin-2-yl)methoxy)-2-methylbenzofuran-3-carboxamide
cpd 072 N-(4-(hydroxymethyl)tetrahydro-2H-pyran-4-yl)-2-methyl-5-((2-(trifluoromethyl)pyridin-3-yl)methoxy)benzofuran-3-carboxamide
cpd 073 tert-butyl (S)-3-(2-methyl-5-((5-methylpyridin-3-yl)methoxy)benzofuran-3-carboxamido)-pyrrolidine-1-carboxylate
cpd 074 N-(3,3-difluoropiperidin-4-yl)-2-methyl-5-((2-(trifluoromethyl)pyridin-3-yl)methoxy)benzofuran-3-carboxamide
cpd 075 N-(3,3-difluoropiperidin-4-yl)-2-methyl-5-((5-(trifluoromethyl)pyridin-3-yl)methoxy)benzofuran-3-carboxamide
cpd 076 N-(3,3-difluoropiperidin-4-yl)-2-methyl-5-((3-(trifluoromethyl)pyridin-2-yl)methoxy)benzofuran-3-carboxamide cpd 077 tert-butyl (S)-3-(2-methyl-5-((5-(trifluoromethyl)pyridin-3-yl)methoxy)benzofuran-3-carboxamido)pyrrolidine-1-carboxylate cpd 078 tert-butyl 4-(5-(((6-(dimethylamino)pyridin-2-yl)methoxy)-2-methylbenzofuran-3-carboxamido)-3,3-difluoropiperidine-1-carboxylate cpd 079 tert-butyl 3-(((3-(ethoxycarbonyl)-2-methylbenzofuran-5-yl)oxy)methyl)pyrrolidine-1-carboxylate cpd 080 tert-butyl (R)-3-(2-methyl-5-(oxazol-5-ylmethoxy)benzofuran-3-carboxamido)pyrrolidine-1-carboxylate cpd 081 tert-butyl (R)-3-(2-methyl-5-(pyridin-4-ylmethoxy)benzofuran-3-carboxamido)pyrrolidine-1-carboxylate cpd 082 tert-butyl (R)-3-(2-methyl-5-(pyridin-3-ylmethoxy)benzofuran-3-carboxamido)pyrrolidine-1-carboxylate cpd 083 tert-butyl (R)-3-(2-methyl-5-((1-methyl-1H-pyrazol-3-yl)methoxy)benzofuran-3-carboxamido)-pyrrolidine-1-carboxylate cpd 084 tert-butyl (R)-3-(2-methyl-5-(thiazol-5-ylmethoxy)benzofuran-3-carboxamido)pyrrolidine-1-carboxylate cpd 085 tert-butyl (R)-3-(2-methyl-5-(thiazol-2-ylmethoxy)benzofuran-3-carboxamido)pyrrolidine-1-carboxylate cpd 086 tert-butyl (R)-3-(2-methyl-5-((6-methylpyridin-2-yl)methoxy)benzofuran-3-carboxamido)-pyrrolidine-1-carboxylate cpd 087 tert-butyl 3,3-difluoro-4-(2-methyl-5-(thiazol-2-ylmethoxy)benzofuran-3-carboxamido)piperidine-1-carboxylate cpd 088 tert-butyl 3,3-difluoro-4-(2-methyl-5-((3-methylpyridin-2-yl)methoxy)benzofuran-3-carboxamido)piperidine-1-carboxylate cpd 089 tert-butyl 3,3-difluoro-4-(5-((2-methoxypyridin-3-yl)methoxy)-2-methylbenzofuran-3-carboxamido)piperidine-1-carboxylate cpd 090 tert-butyl 3,3-difluoro-4-(2-methyl-5-((4-methylthiazol-5-yl)methoxy)benzofuran-3-carboxamido)piperidine-1-carboxylate cpd 091 tert-butyl 3,3-difluoro-4-(5-((6-methoxypyridin-2-yl)methoxy)-2-methylbenzofuran-3-carboxamido)piperidine-1-carboxylate cpd 092 tert-butyl 4-(5-((2-chloropyridin-3-yl)methoxy)-2-methylbenzofuran-3-carboxamido)-3,3-difluoropiperidine-1-carboxylate cpd 093 tert-butyl 4-(5-((4-chloropyridin-3-yl)methoxy)-2-methylbenzofuran-3-carboxamido)-3,3-difluoropiperidine-1-carboxylate cpd 094 tert-butyl 3,3-difluoro-4-(5-(imidazo[1,2-a]pyridin-6-ylmethoxy)-2-methylbenzofuran-3-carboxamido)piperidine-1-carboxylate cpd 095 tert-butyl 3,3-difluoro-4-(2-methyl-5-((5-(trifluoromethyl)pyridin-3-yl)methoxy)benzofuran-3-carboxamido)piperidine-1-carboxylate cpd 096 tert-butyl 3,3-difluoro-4-(2-methyl-5-((3-(trifluoromethyl)pyridin-2-yl)methoxy)benzofuran-3-carboxamido)piperidine-1-carboxylate cpd 097 tert-butyl 3,3-difluoro-4-(2-methyl-5-(pyridin-2-ylmethoxy)benzofuran-3-carboxamido)piperidine-1-carboxylate cpd 098 tert-butyl 3,3-difluoro-4-(2-methyl-5-((2-(trifluoromethyl)pyridin-3-yl)methoxy)benzofuran-3-carboxamido)piperidine-1-carboxylate cpd 099 2-methyl-5-((4-methylpyridin-3-yl)methoxy)benzofuran-3-carboxylic acid cpd 100 5-((2-methoxypyridin-3-yl)methoxy)-2-methylbenzofuran-3-carboxylic acid cpd 101 2-methyl-5-((2-(trifluoromethyl)pyridin-3-yl)methoxy)benzofuran-3-carboxylic acid cpd 102 2-methyl-5-((4-methylthiazol-5-yl)methoxy)benzofuran-3-carboxylic acid cpd 103 N-(4,4-difluoropiperidin-3-yl)-2-methyl-5-((4-methylthiazol-5-yl)methoxy)benzofuran-3-carboxamide cpd 104 N-(1-hydroxy-2-methylpropan-2-yl)-2-methyl-5-((4-methylthiazol-5-yl)methoxy)benzofuran-3-carboxamide cpd 105 N-(4,4-difluoropyrrolidin-3-yl)-2-methyl-5-((2-(trifluoromethyl)pyridin-3-yl)methoxy)benzofuran-3-carboxamide cpd 106 N-(4,4-difluoropyrrolidin-3-yl)-2-methyl-5-((4-methylthiazol-5-yl)methoxy)benzofuran-3-carboxamide cpd 107 N-(1-(hydroxymethyl)cyclobutyl)-2-methyl-5-((4-methylthiazol-5-yl)methoxy)benzofuran-3-carboxamide cpd 108 N-(1-((dimethylamino)methyl)cyclobutyl)-2-methyl-5-((4-methylthiazol-5-yl)methoxy)benzofuran-3-carboxamide cpd 109 N-(1-hydroxy-2-methylpropan-2-yl)-2-methyl-5-((2-(trifluoromethyl)pyridin-3-yl)methoxy)-benzofuran-3-carboxamide cpd 110 N-(3,3-difluoro-1-methylpiperidin-4-yl)-2-methyl-5-((4-methylthiazol-5-yl)methoxy)benzofuran-3-carboxamide cpd 111 N-(4,4-difluoropiperidin-3-yl)-2-methyl-5-((2-(trifluoromethyl)pyridin-3-yl)methoxy)benzofuran-3-carboxamide cpd 112 N-(3,3-difluoropiperidin-4-yl)-4-fluoro-2-methyl-5-((2-(trifluoromethyl)pyridin-3-yl)methoxy)-benzofuran-3-carboxamide cpd 113 N-(3,3-difluoropiperidin-4-yl)-6-fluoro-2-methyl-5-((2-(trifluoromethyl)pyridin-3-yl)methoxy)-benzofuran-3-carboxamide cpd 114 N-(1-(2-hydroxyethyl)cyclobutyl)-2-methyl-5-((4-methylthiazol-5-yl)methoxy)benzofuran-3-carboxamide cpd 115 N-(5,5-difluoropiperidin-3-yl)-2-methyl-5-((4-methylthiazol-5-yl)methoxy)benzofuran-3-carboxamide cpd 116 2-methyl-5-((4-methylthiazol-5-yl)methoxy)-N-(1-(2,2,2-trifluoroethyl)pyrrolidin-3-yl)benzo-furan-3-carboxamide cpd 117 N-(1-(hydroxymethyl)cyclobutyl)-2-methyl-5-((2-(trifluoromethyl)pyridin-3-yl)methoxy)-benzofuran-3-carboxamide cpd 118 N-(4,4-difluoro-1-methylpiperidin-3-yl)-2-methyl-5-((4-methylthiazol-5-yl)methoxy)benzofuran-3-carboxamide cpd 119 N-(3-carbamoyloxetan-3-yl)-2-methyl-5-((4-methylthiazol-5-yl)methoxy)benzofuran-3-carboxamide cpd 120 N-(1-(2-hydroxyethyl)-2-oxopyrrolidin-3-yl)-2-methyl-5-((2-(trifluoromethyl)pyridin-3-yl)methoxy)benzofuran-3-carboxamide cpd 121 N-(3-(2-hydroxyethyl)tetrahydrofuran-3-yl)-2-methyl-5-((4-methylthiazol-5-yl)methoxy)-benzofuran-3-carboxamide cpd 122 7-fluoro-N-(4-(hydroxymethyl)tetrahydro-2H-pyran-4-yl)-2-methyl-5-((4-methylthiazol-5-yl)methoxy)benzofuran-3-carboxamide cpd 123 N-(4,4-difluoro-1-methylpyrrolidin-3-yl)-2-methyl-5-((4-methylthiazol-5-yl)methoxy)benzofuran-3-carboxamide
cpd 124 N-(4,4-difluoro-1-methylpyrrolidin-3-yl)-2-methyl-5-((2-(trifluoromethyl)pyridin-3-yl)-methoxy)benzofuran-3-carboxamide
cpd 125 N-(5,5-difluoropiperidin-3-yl)-2-methyl-5-((2-(trifluoromethyl)pyridin-3-yl)methoxy)benzofuran-3-carboxamide
cpd 126 N-(3-(2-hydroxyethyl)tetrahydrofuran-3-yl)-2-methyl-5-((2-(trifluoromethyl)pyridin-3-yl)-methoxy)benzofuran-3-carboxamide
cpd 127 N-(1-(2-hydroxyethyl)cyclobutyl)-2-methyl-5-((2-(trifluoromethyl)pyridin-3-yl)methoxy)-benzofuran-3-carboxamide
cpd 128 N-(3-(2-hydroxyethyl)oxetan-3-yl)-2-methyl-5-((4-methylthiazol-5-yl)methoxy)benzofuran-3-carboxamide
cpd 129 N-(3-(2-hydroxyethyl)oxetan-3-yl)-2-methyl-5-((2-(trifluoromethyl)pyridin-3-yl)methoxy)-benzofuran-3-carboxamide
cpd 130 N-(3,3-difluoro-1-methylpiperidin-4-yl)-2-methyl-5-((2-(trifluoromethyl)pyridin-3-yl)methoxy)-benzofuran-3-carboxamide
cpd 131 N-(4,4-difluoro-1-methylpiperidin-3-yl)-2-methyl-5-((2-(trifluoromethyl)pyridin-3-yl)methoxy)-benzofuran-3-carboxamide
cpd 132 N-(3-(hydroxymethyl)tetrahydrofuran-3-yl)-2-methyl-5-((4-methylthiazol-5-yl)methoxy)-benzofuran-3-carboxamide
cpd 133 N-(3-(hydroxymethyl)oxetan-3-yl)-2-methyl-5-((2-(trifluoromethyl)pyridin-3-yl)methoxy)-benzofuran-3-carboxamide
cpd 134 N-(4,4-difluoro-1-(2-hydroxyethyl)pyrrolidin-3-yl)-2-methyl-5-((2-(trifluoromethyl)pyridin-3-yl)methoxy)benzofuran-3-carboxamide
cpd 135 N-(3-(hydroxymethyl)tetrahydrofuran-3-yl)-2-methyl-5-((2-(trifluoromethyl)pyridin-3-yl)-methoxy)benzofuran-3-carboxamide
cpd 136 N-(1-(aminomethyl)cyclobutyl)-2-methyl-5-((2-(trifluoromethyl)pyridin-3-yl)methoxy)benzo-furan-3-carboxamide
cpd 137 N-(1-(aminomethyl)cyclobutyl)-2-methyl-5-((4-methylthiazol-5-yl)methoxy)benzofuran-3-carboxamide
cpd 138 2-methyl-N-(1H-pyrazol-3-yl)-5-((2-(trifluoromethyl)pyridin-3-yl)methoxy)benzofuran-3-carboxamide
cpd 139 N-(1-(hydroxymethyl)cyclopropyl)-2-methyl-5-((4-methylthiazol-5-yl)methoxy)benzofuran-3-carboxamide
cpd 140 N-(1-((dimethylamino)methyl)cyclobutyl)-2-methyl-5-((2-(trifluoromethyl)pyridin-3-yl)methoxy)-benzofuran-3-carboxamide
cpd 141 N-(5,5-difluoro-1-methylpiperidin-3-yl)-2-methyl-5-((2-(trifluoromethyl)pyridin-3-yl)methoxy)-benzofuran-3-carboxamide
cpd 142 N-(3-(hydroxymethyl)oxetan-3-yl)-2-methyl-5-((4-methylthiazol-5-yl)methoxy)benzofuran-3-carboxamide
cpd 143 2-methyl-N-(1-methyl-1H-pyrazol-4-yl)-5-((2-(trifluoromethyl)pyridin-3-yl)methoxy)benzofuran-3-carboxamide
cpd 144 2-methyl-5-((4-methylthiazol-5-yl)methoxy)-N-(1H-pyrazol-3-yl)benzofuran-3-carboxamide
cpd 145 2-methyl-5-((4-methylthiazol-5-yl)methoxy)-N-(1-(((2,2,2-trifluoroethyl)amino)methyl)-cyclobutyl)benzofuran-3-carboxamide
cpd 146 2-methyl-N-(1-methyl-1H-pyrazol-3-yl)-5-((2-(trifluoromethyl)pyridin-3-yl)methoxy)benzofuran-3-carboxamide
cpd 147 N-(4-hydroxytetrahydrofuran-3-yl)-2-methyl-5-((2-(trifluoromethyl)pyridin-3-yl)methoxy)-benzofuran-3-carboxamide
cpd 148 2-methyl-N-(tetrahydrofuran-3-yl)-5-((2-(trifluoromethyl)pyridin-3-yl)methoxy)benzofuran-3-carboxamide
cpd 149 2-methyl-N-(1-(2,2,2-trifluoroethyl)pyrrolidin-3-yl)-5-((2-(trifluoromethyl)pyridin-3-yl)methoxy)-benzofuran-3-carboxamide
cpd 150 2-methyl-5-((4-methylthiazol-5-yl)methoxy)-N-(1H-pyrazol-4-yl)benzofuran-3-carboxamide
cpd 151 N-(4,4-difluoro-1-(2-hydroxyethyl)pyrrolidin-3-yl)-2-methyl-5-((4-methylthiazol-5-yl)methoxy)-benzofuran-3-carboxamide
cpd 152 2-methyl-N-(1-methyl-1H-pyrazol-4-yl)-5-((4-methylthiazol-5-yl)methoxy)benzofuran-3-carboxamide
cpd 153 2-methyl-N-(1-(((2,2,2-trifluoroethyl)amino)methyl)cyclobutyl)-5-((2-(trifluoromethyl)pyridin-3-yl)methoxy)benzofuran-3-carboxamide
cpd 154 2-methyl-N-(1-methyl-1H-pyrazol-5-yl)-5-((2-(trifluoromethyl)pyridin-3-yl)methoxy)benzofuran-3-carboxamide
cpd 155 N-(4,4-difluoro-1-(2,2,2-trifluoroethyl)pyrrolidin-3-yl)-2-methyl-5-((4-methylthiazol-5-yl)methoxy)benzofuran-3-carboxamide
cpd 156 2-methyl-5-((4-methylthiazol-5-yl)methoxy)-N-(2-oxaspiro[3.3]heptan-6-yl)benzofuran-3-carboxamide
cpd 157 N-(4,4-difluoro-1-(2,2,2-trifluoroethyl)pyrrolidin-3-yl)-2-methyl-5-((2-(trifluoromethyl)pyridin-3-yl)methoxy)benzofuran-3-carboxamide
cpd 158 2-methyl-N-(1H-pyrazol-4-yl)-5-((2-(trifluoromethyl)pyridin-3-yl)methoxy)benzofuran-3-carboxamide
cpd 159 2-methyl-5-((4-methylthiazol-5-yl)methoxy)-N-(tetrahydrofuran-3-yl)benzofuran-3-carboxamide
cpd 160 N-(1-(2-hydroxyethyl)-2-oxopyrrolidin-3-yl)-2-methyl-5-((4-methylthiazol-5-yl)methoxy)-benzofuran-3-carboxamide
cpd 161 2-methyl-N-(1-methyl-1H-pyrazol-3-yl)-5-((4-methylthiazol-5-yl)methoxy)benzofuran-3-carboxamide
cpd 162 N-(4-hydroxytetrahydrofuran-3-yl)-2-methyl-5-((4-methylthiazol-5-yl)methoxy)benzofuran-3-carboxamide
cpd 163 N-(5,5-difluoro-1-methylpiperidin-3-yl)-2-methyl-5-((4-methylthiazol-5-yl)methoxy)benzofuran-3-carboxamide
cpd 164 N-(1-(2-hydroxyethyl)-2-oxopyrrolidin-3-yl)-2-methyl-5-((2-methylpyridin-3-yl)methoxy)-benzofuran-3-carboxamide
cpd 165 6-chloro-N-(3,3-difluoropiperidin-4-yl)-2-methyl-5-((2-(trifluoromethyl)pyridin-3-yl)methoxy)-benzofuran-3-carboxamide
cpd 166 2-methyl-5-((4-methylthiazol-5-yl)methoxy)-N-(1-(2,2,2-trifluoroethyl)piperidin-4-yl)benzofuran-3-carboxamide
cpd 167 2-methyl-N-(2-oxaspiro[3.3]heptan-6-yl)-5-((2-(trifluoromethyl)pyridin-3-yl)methoxy)-benzofuran-3-carboxamide cpd 168 2-methyl-N-(1-(2,2,2-trifluoroethyl)piperidin-4-yl)-5-((2-(trifluoromethyl)pyridin-3-yl)methoxy)-benzofuran-3-carboxamide cpd 169 N-(1-(2-methoxyethyl)-2-oxopyrrolidin-3-yl)-2-methyl-5-((4-methylthiazol-5-yl)methoxy)-benzofuran-3-carboxamide cpd 170 (3-aminotetrahydrofuran-3-yl)methyl 2-methyl-5-((2-(trifluoromethyl)pyridin-3-yl)methoxy)-benzofuran-3-carboxylate cpd 171 2-methyl-N-(1-methyl-1H-pyrazol-5-yl)-5-((4-methylthiazol-5-yl)methoxy)benzofuran-3-carboxamide cpd 172 2,2,2-trifluoroethyl 3,3-difluoro-4-(2-methyl-5-((4-methylthiazol-5-yl)methoxy)benzofuran-3-carboxamido)pyrrolidine-1-carboxylate cpd 173 2-methyl-N-(2-azaspiro[3.3]heptan-6-yl)-5-((2-(trifluoromethyl)pyridin-3-yl)methoxy)benzofuran-3-carboxamide cpd 174 6-chloro-N-(4-(hydroxymethyl)tetrahydro-2H-pyran-4-yl)-2-methyl-5-((4-methylthiazol-5-yl)methoxy)benzofuran-3-carboxamide cpd 175 2,2,2-trifluoroethyl (R)-3,3-difluoro-4-(2-methyl-5-((2-(trifluoromethyl)pyridin-3-yl)methoxy)-benzofuran-3-carboxamido)pyrrolidine-1-carboxylate cpd 176 N-(3,3-difluoropiperidin-4-yl)-7-fluoro-2-methyl-5-((2-(trifluoromethyl)pyridin-3-yl)-methoxy)benzofuran-3-carboxamide cpd 177 4-fluoro-N-(4-(hydroxymethyl)tetrahydro-2H-pyran-4-yl)-2-methyl-5-((4-methylthiazol-5-yl)-methoxy)benzofuran-3-carboxamide cpd 178 (3-amino-1H-pyrazol-1-yl)(2-methyl-5-((2-(trifluoromethyl)pyridin-3-yl)methoxy)benzofuran-3-yl)methanone cpd 179 N-(3,3-difluoropiperidin-4-yl)-2,6-dimethyl-5-((2-(trifluoromethyl)pyridin-3-yl)methoxy)-benzofuran-3-carboxamide cpd 180 N-(1-(2-hydroxyethyl)-5-oxopyrrolidin-3-yl)-2-methyl-5-((4-methylthiazol-5-yl)methoxy)-benzofuran-3-carboxamide cpd 181 (4-amino-1H-pyrazol-1-yl)(2-methyl-5-((2-(trifluoromethyl)pyridin-3-yl)methoxy)benzofuran-3-yl)methanone cpd 182 6-fluoro-N-(4-(hydroxymethyl)tetrahydro-2H-pyran-4-yl)-2-methyl-5-((4-methylthiazol-5-yl)-methoxy)benzofuran-3-carboxamide cpd 183 N-(3,3-difluoropiperidin-4-yl)-2,7-dimethyl-5-((2-(trifluoromethyl)pyridin-3-yl)methoxy)benzofuran-3-carboxamide cpd 184 7-chloro-N-(3,3-difluoropiperidin-4-yl)-2-methyl-5-((2-(trifluoromethyl)pyridin-3-yl)methoxy)-benzofuran-3-carboxamide cpd 185 N-(4-(hydroxymethyl)tetrahydro-2H-pyran-4-yl)-2,6-dimethyl-5-((4-methylthiazol-5-yl)methoxy)-benzofuran-3-carboxamide cpd 186 N-(4-(hydroxymethyl)tetrahydro-2H-pyran-4-yl)-2,7-dimethyl-5-((4-methylthiazol-5-yl)-methoxy)benzofuran-3-carboxamide cpd 187 7-chloro-N-(4-(hydroxymethyl)tetrahydro-2H-pyran-4-yl)-2-methyl-5-((4-methylthiazol-5-yl)methoxy)benzofuran-3-carboxamide cpd 188 7-cyano-N-(4-(hydroxymethyl)tetrahydro-2H-pyran-4-yl)-2-methyl-5-((4-methylthiazol-5-yl)methoxy)benzofuran-3-carboxamide cpd 189 N-((3-aminooxetan-3-yl)methyl)-2-methyl-5-((2-(trifluoromethyl)pyridin-3-yl)methoxy)-benzofuran-3-carboxamide cpd 190 2-methyl-5-((4-methylthiazol-5-yl)methoxy)-N-(2-azaspiro[3.3]heptan-6-yl)benzofuran-3-carboxamide cpd 191 4-cyano-N-(3,3-difluoropiperidin-4-yl)-2-methyl-5-((2-(trifluoromethyl)pyridin-3-yl)-methoxy)benzofuran-3-carboxamide cpd 192 (3-amino-1H-pyrazol-1-yl)(2-methyl-5-((4-methylthiazol-5-yl)methoxy)benzofuran-3-yl)-methanone cpd 193 4-cyano-N-(4-(hydroxymethyl)tetrahydro-2H-pyran-4-yl)-2-methyl-5-((4-methylthiazol-5-yl)methoxy)benzofuran-3-carboxamide cpd 194 6-cyano-N-(4-(hydroxymethyl)tetrahydro-2H-pyran-4-yl)-2-methyl-5-((4-methylthiazol-5-yl)methoxy)benzofuran-3-carboxamide cpd 195 6-cyano-N-(3,3-difluoropiperidin-4-yl)-2-methyl-5-((2-(trifluoromethyl)pyridin-3-yl)-methoxy)benzofuran-3-carboxamide cpd 196 7-cyano-N-(3,3-difluoropiperidin-4-yl)-2-methyl-5-((2-(trifluoromethyl)pyridin-3-yl)-methoxy)benzofuran-3-carboxamide cpd 197 2-(difluoromethyl)-N-(4-(hydroxymethyl)tetrahydro-2H-pyran-4-yl)-5-((4-methylthiazol-5-yl)-methoxy)benzofuran-3-carboxamide cpd 198 2-(difluoromethyl)-N-(1-(2-hydroxyethyl)-2-oxopyrrolidin-3-yl)-5-((4-methylthiazol-5-yl)-methoxy)benzofuran-3-carboxamide cpd 199 2-(difluoromethyl)-N-(3,3-difluoropiperidin-4-yl)-5-((2-(trifluoromethyl)pyridin-3-yl)methoxy)-benzofuran-3-carboxamide cpd 200 N-(1-(hydroxymethyl)cyclopropyl)-2-methyl-5-((2-(trifluoromethyl)pyridin-3-yl)methoxy)-benzofuran-3-carboxamide cpd 201 N-(3-(hydroxymethyl)azetidin-3-yl)-2-methyl-5-((4-methylthiazol-5-yl)methoxy)benzofuran-3-carboxamide cpd 202 N-(3-(hydroxymethyl)azetidin-3-yl)-2-methyl-5-((2-(trifluoromethyl)pyridin-3-yl)methoxy)-benzofuran-3-carboxamide cpd 203 N-(4,4-difluorotetrahydrofuran-3-yl)-2-methyl-5-((4-methylthiazol-5-yl)methoxy)benzofuran-3-carboxamide cpd 204 N-(4-(hydroxymethyl)tetrahydro-2H-pyran-4-yl)-2-methyl-5-((1-methyl-1H-imidazol-2-yl)-methoxy)benzofuran-3-carboxamide cpd 205 N-(3,3-difluoropiperidin-4-yl)-2-methyl-5-((1-methyl-1H-imidazol-2-yl)methoxy)benzofuran-3-carboxamide cpd 206 5-((2-ethoxypyridin-3-yl)methoxy)-N-(4-(hydroxymethyl)tetrahydro-2H-pyran-4-yl)-2-methyl-benzofuran-3-carboxamide cpd 207 N-(3,3-difluoropiperidin-4-yl)-5-((2-ethoxypyridin-3-yl)methoxy)-2-methylbenzofuran-3-carboxamide Cpd 208 2-methyl-5-((2-methylthiazol-5-yl)methoxy)benzofuran-3-carboxylic acid Cpd 209 2-methyl-5-((2-(trifluoromethyl)thiazol-5-yl)methoxy)benzofuran-3-carboxylic acid Cpd 210 2-methyl-5-((2-methyl-4-(trifluoromethyl)thiazol-5-yl)methoxy)benzofuran-3-carboxylic acid Cpd 211 2-methyl-5-((2-methyloxazol-5-yl)methoxy)benzofuran-3-carboxylic acid Cpd 212 2-methyl-5-((2-methylthiazol-4-yl)methoxy)benzofuran-3-carboxylic acid Cpd 213 2-methyl-5-((3-(trifluoromethyl)-1H-pyrazol-4-yl)methoxy)benzofuran-3-carboxylic acid Cpd 214 2-methyl-5-((4-methylpyridin-3-yl)methoxy)benzofuran-3-carboxylic acid
Cpd 215 2-methyl-5-((5-methylisoxazol-3-yl)methoxy)benzofuran-3-carboxylic acid
Cpd 216 2-methyl-5-((5-methylthiazol-4-yl)methoxy)benzofuran-3-carboxylic acid
Cpd 217 2-methyl-5-((6-methylpyridin-3-yl)methoxy)benzofuran-3-carboxylic acid
Cpd 218 2-methyl-5-(oxetan-3-ylmethoxy)benzofuran-3-carboxylic acid
Cpd 219 2-methyl-5-(pyrimidin-4-ylmethoxy)benzofuran-3-carboxylic acid
Cpd 220 5-((1-(2,2-difluoroethyl)-1H-pyrazol-5-yl)methoxy)-2-methylbenzofuran-3-carboxylic acid
Cpd 221 5-((2-(difluoromethoxy)pyridin-3-yl)methoxy)-2-methylbenzofuran-3-carboxylic acid
Cpd 222 5-((2-(dimethylamino)pyridin-3-yl)methoxy)-2-methylbenzofuran-3-carboxylic acid
Cpd 223 5-((2,4-dimethylthiazol-5-yl)methoxy)-2-methylbenzofuran-3-carboxylic acid
Cpd 224 5-((2,5-dimethylthiazol-4-yl)methoxy)-2-methylbenzofuran-3-carboxylic acid
Cpd 225 5-((2-aminopyridin-3-yl)methoxy)-2-methylbenzofuran-3-carboxylic acid
Cpd 226 5-((3-(difluoromethyl)pyridin-2-yl)methoxy)-2-methylbenzofuran-3-carboxylic acid
Cpd 227 5-((6-methoxypyridin-3-yl)methoxy)-2-methylbenzofuran-3-carboxylic acid
Cpd 228 5-((4-fluoro-1-methyl-1H-pyrazol-5-yl)methoxy)-2-methylbenzofuran-3-carboxylic acid
Cpd 229 2-(difluoromethyl)-5-((4-methylthiazol-5-yl)methoxy)benzofuran-3-carboxylic acid
Cpd 230 2-(difluoromethyl)-5-((2-methoxypyridin-3-yl)methoxy)benzofuran-3-carboxylic acid
Cpd 231 2-cyclopropyl-5-((2-(trifluoromethyl)pyridin-3-yl)methoxy)benzofuran-3-carboxylic acid
Cpd 232 2-methyl-5-((4-methylthiazol-5-yl)methoxy)benzofuran-3-carboxamide
Cpd 233 4-fluoro-2-methyl-5-((4-methylthiazol-5-yl)methoxy)benzofuran-3-carboxylic acid
Cpd 234 4-fluoro-5-((2-methoxypyridin-3-yl)methoxy)-2-methylbenzofuran-3-carboxylic acid
Cpd 235 5-((1-(2,2-difluoroethyl)-1H-imidazol-2-yl)methoxy)-2-methylbenzofuran-3-carboxylic acid
Cpd 236 5-((2-(azetidin-1-yl)pyridin-3-yl)methoxy)-2-methylbenzofuran-3-carboxylic acid
Cpd 237 5-((2-(difluoromethyl)pyridin-3-yl)methoxy)-2-methylbenzofuran-3-carboxylic acid
Cpd 238 5-((2-cyanopyridin-3-yl)methoxy)-2-methylbenzofuran-3-carboxylic acid
Cpd 239 5-((2-ethoxypyridin-3-yl)methoxy)-2-methylbenzofuran-3-carboxylic acid
Cpd 240 5-((3-fluoropyridin-2-yl)methoxy)-2-methylbenzofuran-3-carboxylic acid
Cpd 241 5-((5-(2-hydroxyethoxy)pyridin-2-yl)methoxy)-2-methylbenzofuran-3-carboxylic acid
Cpd 242 5-((5-fluoropyridin-2-yl)methoxy)-2-methylbenzofuran-3-carboxylic acid
Cpd 243 6-fluoro-2-methyl-5-((4-methylthiazol-5-yl)methoxy)benzofuran-3-carboxylic acid
Cpd 244 6-fluoro-5-((2-methoxypyridin-3-yl)methoxy)-2-methylbenzofuran-3-carboxylic acid
Cpd 245 7-fluoro-2-methyl-5-((4-methylthiazol-5-yl)methoxy)benzofuran-3-carboxylic acid
Cpd 246 7-fluoro-5-((2-methoxypyridin-3-yl)methoxy)-2-methylbenzofuran-3-carboxylic acid
Cpd 247 2-methyl-5-((2-methylpyridin-3-yl)methoxy)benzofuran-3-carboxylic acid
Cpd 248 2-methyl-5-(1-(2-(trifluoromethyl)thiazol-5-yl)ethoxy)benzofuran-3-carboxylic acid
Cpd 249 2-methyl-5-((1-methyl-1H-imidazol-2-yl)methoxy)benzofuran-3-carboxylic acid
Cpd 250 2-methyl-5-((1-methyl-2-oxo-1,2-dihydropyridin-3-yl)methoxy)benzofuran-3-carboxylic acid
Cpd 251 2,4-dimethyl-5-((2-(trifluoromethyl)pyridin-3-yl)methoxy)benzofuran-3-carboxylic acid
Cpd 252 2-methyl-5-(((2-(trifluoromethyl)pyridin-3-yl)oxy)methyl)benzofuran-3-carboxylic acid
Cpd 253 2-methyl-5-((1-methyl-1H-1,2,3-triazol-4-yl)methoxy)benzofuran-3-carboxylic acid
Cpd 254 2-methyl-5-((1-methyl-1H-1,2,3-triazol-5-yl)methoxy)benzofuran-3-carboxylic acid
Cpd 255 2-methyl-5-((1-methyl-1H-1,2,4-triazol-3-yl)methoxy)benzofuran-3-carboxylic acid
Cpd 256 2-methyl-5-((1-methyl-6-oxo-1,6-dihydropyridin-2-yl)methoxy)benzofuran-3-carboxylic acid
Cpd 257 2-methyl-5-((2-methylpyrimidin-4-yl)methoxy)benzofuran-3-carboxylic acid
Cpd 258 2-methyl-5-((3-methyloxetan-3-yl)methoxy)benzofuran-3-carboxylic acid
Cpd 259 2-methyl-5-((4-methyloxazol-2-yl)methoxy)benzofuran-3-carboxylic acid
Cpd 260 2-methyl-5-((4-methylthiazol-2-yl)methoxy)benzofuran-3-carboxylic acid
Cpd 261 2-methyl-5-((5-methylpyrazin-2-yl)methoxy)benzofuran-3-carboxylic acid
Cpd 262 2-methyl-5-((5-methylthiazol-2-yl)methoxy)benzofuran-3-carboxylic acid
Cpd 263 2-methyl-5-((6-methylpyridazin-3-yl)methoxy)benzofuran-3-carboxylic acid
Cpd 264 2-methyl-5-(pyrimidin-2-ylmethoxy)benzofuran-3-carboxylic acid
Cpd 265 2-cyclopropyl-5-((4-methylthiazol-5-yl)methoxy)benzofuran-3-carboxylic acid
Cpd 266 5-((6-methoxypyridin-2-yl)methoxy)-2-methylbenzofuran-3-carboxylic acid
Cpd 267 5-(imidazo[1,2-a]pyridin-6-ylmethoxy)-2-methylbenzofuran-3-carboxylic acid
Cpd 268 2-methyl-5-(1-(4-methylthiazol-5-yl)ethoxy)benzofuran-3-carboxylic acid
Cpd 269 5-((2-methoxypyridin-4-yl)methoxy)-2-methylbenzofuran-3-carboxylic acid
Cpd 270 (2-methyl-5-((4-methylthiazol-5-yl)methoxy)benzofuran-3-carbonyl)serine
Cpd 271 (R)—N-(1-amino-1-oxopropan-2-yl)-2-methyl-5-((4-methylthiazol-5-yl)methoxy)benzofuran-3-carboxamide
Cpd 272 (R)—N-(1-amino-3-(methylsulfonyl)-1-oxopropan-2-yl)-2-methyl-5-((4-methylthiazol-5-yl)methoxy)benzofuran-3-carboxamide
Cpd 273 (R)—N-(1-amino-3-methyl-1-oxobutan-2-yl)-2-methyl-5-((4-methylthiazol-5-yl)methoxy)benzofuran-3-carboxamide
Cpd 274 (R)—N-(1-hydroxy-3-(methylsulfonyl)propan-2-yl)-2-methyl-5-((2-methylthiazol-5-yl)methoxy)benzofuran-3-carboxamide
Cpd 275 (R)—N-(1-hydroxy-3-(methylsulfonyl)propan-2-yl)-2-methyl-5-((4-methylthiazol-5-yl)methoxy)benzofuran-3-carboxamide
Cpd 276 (R)—N-(3-hydroxy-1-(methylamino)-1-oxopropan-2-yl)-2-methyl-5-((4-methylthiazol-5-yl)methoxy)benzofuran-3-carboxamide Cpd 277 (S)—N-(1-(3,3-difluoropyrrolidin-1-yl)-3-hydroxy-1-oxopropan-2-yl)-2-methyl-5-((2-methylthiazol-5-yl)methoxy)benzofuran-3-carboxamide Cpd 278 (S)—N-(1-(dimethylamino)-3-hydroxy-1-oxopropan-2-yl)-2-methyl-5-((2-methylthiazol-5-yl)methoxy)benzofuran-3-carboxamide Cpd 279 (S)—N-(1-amino-1-oxopropan-2-yl)-2-methyl-5-((4-methylthiazol-5-yl)methoxy)benzofuran-3-carboxamide Cpd 280 (S)—N-(1-amino-3-hydroxy-1-oxopropan-2-yl)-2-methyl-5-((2-(trifluoromethyl)pyridin-3-yl)methoxy)benzofuran-3-carboxamide Cpd 281 (S)—N-(1-amino-3-hydroxy-1-oxopropan-2-yl)-2-methyl-5-((2-(trifluoromethyl)thiazol-5-yl)methoxy)benzofuran-3-carboxamide Cpd 282 (S)—N-(1-amino-3-hydroxy-1-oxopropan-2-yl)-2-methyl-5-((2-methyl-4-(trifluoromethyl)thiazol-5-yl)methoxy)benzofuran-3-carboxamide Cpd 283 (S)—N-(1-amino-3-hydroxy-1-oxopropan-2-yl)-2-methyl-5-((2-methyloxazol-5-yl)methoxy)benzofuran-3-carboxamide Cpd 284 (S)—N-(1-amino-3-hydroxy-1-oxopropan-2-yl)-2-methyl-5-((2-methylpyridin-3-yl)methoxy)benzofuran-3-carboxamide Cpd 285 (S)—N-(1-amino-3-hydroxy-1-oxopropan-2-yl)-2-methyl-5-((2-methylthiazol-4-yl)methoxy)benzofuran-3-carboxamide Cpd 286 (S)—N-(1-amino-3-hydroxy-1-oxopropan-2-yl)-2-methyl-5-((3-(trifluoromethyl)-1H-pyrazol-4-yl)methoxy)benzofuran-3-carboxamide Cpd 287 (S)—N-(1-amino-3-hydroxy-1-oxopropan-2-yl)-2-methyl-5-((4-methylpyridin-3-yl)methoxy)benzofuran-3-carboxamide Cpd 288 (S)—N-(1-amino-3-hydroxy-1-oxopropan-2-yl)-2-methyl-5-((4-methylthiazol-5-yl)methoxy)benzofuran-3-carboxamide Cpd 289 (S)—N-(1-amino-3-hydroxy-1-oxopropan-2-yl)-2-methyl-5-((5-methylisoxazol-3-yl)methoxy)benzofuran-3-carboxamide Cpd 290 (S)—N-(1-amino-3-hydroxy-1-oxopropan-2-yl)-2-methyl-5-((5-methylthiazol-4-yl)methoxy)benzofuran-3-carboxamide Cpd 291 (S)—N-(1-amino-3-hydroxy-1-oxopropan-2-yl)-2-methyl-5-((6-methylpyridin-3-yl)methoxy)benzofuran-3-carboxamide Cpd 292 (S)—N-(1-amino-3-hydroxy-1-oxopropan-2-yl)-2-methyl-5-(oxetan-3-ylmethoxy)benzofuran-3-carboxamide Cpd 293 (S)—N-(1-amino-3-hydroxy-1-oxopropan-2-yl)-2-methyl-5-(pyridazin-3-ylmethoxy)benzofuran-3-carboxamide Cpd 294 (S)—N-(1-amino-3-hydroxy-1-oxopropan-2-yl)-2-methyl-5-(pyrimidin-4-ylmethoxy)benzofuran-3-carboxamide Cpd 295 (S)—N-(1-amino-3-hydroxy-1-oxopropan-2-yl)-5-((1-(2,2-difluoroethyl)-1H-pyrazol-5-yl)methoxy)-2-methylbenzofuran-3-carboxamide Cpd 296 (S)—N-(1-amino-3-hydroxy-1-oxopropan-2-yl)-5-((2-(difluoromethoxy)pyridin-3-yl)methoxy)-2-methylbenzofuran-3-carboxamide Cpd 297 (S)—N-(1-amino-3-hydroxy-1-oxopropan-2-yl)-5-((2-(dimethylamino)pyridin-3-yl)methoxy)-2-methylbenzofuran-3-carboxamide Cpd 298 (S)—N-(1-amino-3-hydroxy-1-oxopropan-2-yl)-5-((2,4-dimethylthiazol-5-yl)methoxy)-2-methylbenzofuran-3-carboxamide Cpd 299 (S)—N-(1-amino-3-hydroxy-1-oxopropan-2-yl)-5-((2,5-dimethylthiazol-4-yl)methoxy)-2-methylbenzofuran-3-carboxamide Cpd 300 (S)—N-(1-amino-3-hydroxy-1-oxopropan-2-yl)-5-((2-aminopyridin-3-yl)methoxy)-2-methylbenzofuran-3-carboxamide Cpd 301 (S)—N-(1-amino-3-hydroxy-1-oxopropan-2-yl)-5-((3-(difluoromethyl)pyridin-2-yl)methoxy)-2-methylbenzofuran-3-carboxamide Cpd 302 (S)—N-(1-amino-3-hydroxy-1-oxopropan-2-yl)-5-((4-fluoro-1-methyl-1H-pyrazol-5-yl)methoxy)-2-methylbenzofuran-3-carboxamide Cpd 303 (S)—N-(1-amino-3-methoxy-1-oxopropan-2-yl)-2-methyl-5-((2-methylthiazol-5-yl)methoxy)benzofuran-3-carboxamide Cpd 304 (S)—N-(1-amino-3-methyl-1-oxobutan-2-yl)-2-methyl-5-((4-methylthiazol-5-yl)methoxy)benzofuran-3-carboxamide Cpd 305 (S)—N-(3-hydroxy-1-(methylamino)-1-oxopropan-2-yl)-2-methyl-5-((2-methylthiazol-5-yl)methoxy)benzofuran-3-carboxamide Cpd 306 (S)—N-(3-hydroxy-1-(methylamino)-1-oxopropan-2-yl)-2-methyl-5-((4-methylthiazol-5-yl)methoxy)benzofuran-3-carboxamide Cpd 307 (S)—N-(3-hydroxy-1-oxo-1-(pyrrolidin-1-yl)propan-2-yl)-2-methyl-5-((2-methylthiazol-5-yl)methoxy)benzofuran-3-carboxamide Cpd 308 2-(difluoromethyl)-N-(1-(hydroxymethyl)cyclopropyl)-5-((4-methylthiazol-5-yl)methoxy)benzofuran-3-carboxamide Cpd 309 2-(difluoromethyl)-N-(3-(hydroxymethyl)oxetan-3-yl)-5-((4-methylthiazol-5-yl)methoxy)benzofuran-3-carboxamide Cpd 310 2-(difluoromethyl)-N-(3,3-difluoropiperidin-4-yl)-5-((4-methylthiazol-5-yl)methoxy)benzofuran-3-carboxamide Cpd 311 2-(difluoromethyl)-N-(4-(hydroxymethyl)tetrahydro-2H-pyran-4-yl)-5-((2-hydroxypyridin-3-yl)methoxy)benzofuran-3-carboxamide Cpd 312 2-(difluoromethyl)-N-(4-(hydroxymethyl)tetrahydro-2H-pyran-4-yl)-5-((2-methoxypyridin-3-yl)methoxy)benzofuran-3-carboxamide Cpd 313 2-cyclopropyl-N-(3,3-difluoropiperidin-4-yl)-5-((2-(trifluoromethyl)pyridin-3-yl)methoxy)benzofuran-3-carboxamide Cpd 314 2-cyclopropyl-N-(4-(hydroxymethyl)tetrahydro-2H-pyran-4-yl)-5-((4-methylthiazol-5-yl)methoxy)benzofuran-3-carboxamide Cpd 315 2-methyl-5-((4-methylthiazol-5-yl)methoxy)-N-(1-(oxazol-2-yl)ethyl)benzofuran-3-carboxamide Cpd 316 2-methyl-5-((4-methylthiazol-5-yl)methoxy)-N-(1,1,1-trifluoro-3-hydroxypropan-2-yl)benzofuran-3-carboxamide Cpd 317 2-methyl-5-((4-methylthiazol-5-yl)methoxy)-N-(5-oxo-1,4-oxazepan-6-yl)benzofuran-3-carboxamide Cpd 318 2-methyl-N-(1-(methylcarbamoyl)cyclobutyl)-5-((2-methylthiazol-5-yl)methoxy)benzofuran-3-carboxamide Cpd 319 2-methyl-N-(1-(methylcarbamoyl)cyclobutyl)-5-((4-methylthiazol-5-yl)methoxy)benzofuran-3-carboxamide Cpd 320 2-methyl-N-(1-(methylcarbamoyl)cyclobutyl)-5-(pyridin-2-ylmethoxy)benzofuran-3-carboxamide Cpd 321 2-methyl-N-(2-(methylamino)-2-oxoethyl)-5-((4-methylthiazol-5-yl)methoxy)benzofuran-3-carboxamide Cpd 322 2-methyl-N-(2-(methylsulfonamido)ethyl)-5-((4-methylthiazol-5-yl)methoxy)benzofuran-3-carboxamide Cpd 323 2-methyl-N-(2-(methylsulfonyl)ethyl)-5-((4-methylthiazol-5-yl)methoxy)benzofuran-3-carboxamide Cpd 324 2-methyl-N-(3-(methylcarbamoyl)oxetan-3-yl)-5-((4-methylthiazol-5-yl)methoxy)benzofuran-3-carboxamide Cpd 325 3-(((3-((4-(hydroxymethyl)tetrahydro-2H-pyran-4-yl)carbamoyl)-2-methylbenzofuran-5-yl)oxy)methyl)picolinamide Cpd 326 4-fluoro-N-(1-(2-hydroxyethyl)-2-oxopyrrolidin-3-yl)-2-methyl-5-((4-methylthiazol-5-yl)methoxy)benzofuran-3-carboxamide Cpd 327 4-fluoro-N-(1-(hydroxymethyl)cyclopropyl)-2-methyl-5-((4-methylthiazol-5-yl)methoxy)benzofuran-3-carboxamide Cpd 328 4-fluoro-N-(3-(hydroxymethyl)oxetan-3-yl)-2-methyl-5-((4-methylthiazol-5-yl)methoxy)benzofuran-3-carboxamide Cpd 329 4-fluoro-N-(4-(hydroxymethyl)tetrahydro-2H-pyran-4-yl)-5-((2-hydroxypyridin-3-yl)methoxy)-2-methylbenzofuran-3-carboxamide Cpd 330 4-fluoro-N-(4-(hydroxymethyl)tetrahydro-2H-pyran-4-yl)-5-((2-methoxypyridin-3-yl)methoxy)-2-methylbenzofuran-3-carboxamide Cpd 331 5-((1-(2,2-difluoroethyl)-1H-imidazol-2-yl)methoxy)-N-(4-(hydroxymethyl)tetrahydro-2H-pyran-4-yl)-2-methylbenzofuran-3-carboxamide Cpd 332 5-((1-(2,2-difluoroethyl)-1H-pyrazol-5-yl)methoxy)-N-(3-(hydroxymethyl)-2-oxopiperidin-3-yl)-2-methylbenzofuran-3-carboxamide Cpd 333 5-((1-(2,2-difluoroethyl)-1H-pyrazol-5-yl)methoxy)-N-(3-(hydroxymethyl)-2-oxopyrrolidin-3-yl)-2-methylbenzofuran-3-carboxamide Cpd 334 5-((1-(2,2-difluoroethyl)-1H-pyrazol-5-yl)methoxy)-N-(4-(hydroxymethyl)tetrahydro-2H-pyran-4-yl)-2-methylbenzofuran-3-carboxamide Cpd 335 5-((2-(azetidin-1-yl)pyridin-3-yl)methoxy)-N-(1-(2-hydroxyethyl)-2-oxopyrrolidin-3-yl)-2-methylbenzofuran-3-carboxamide Cpd 336 5-((2-(azetidin-1-yl)pyridin-3-yl)methoxy)-N-(3,3-difluoropiperidin-4-yl)-2-methylbenzofuran-3-carboxamide Cpd 337 5-((2-(azetidin-1-yl)pyridin-3-yl)methoxy)-N-(4-(hydroxymethyl)tetrahydro-2H-pyran-4-yl)-2-methylbenzofuran-3-carboxamide Cpd 338 5-((2-(difluoromethoxy)pyridin-3-yl)methoxy)-N-(3,3-difluoropiperidin-4-yl)-2-methylbenzofuran-3-carboxamide Cpd 339 5-((2-(difluoromethoxy)pyridin-3-yl)methoxy)-N-(4-(hydroxymethyl)tetrahydro-2H-pyran-4-yl)-2-methylbenzofuran-3-carboxamide Cpd 340 5-((2-(difluoromethyl)pyridin-3-yl)methoxy)-N-(1-(2-hydroxyethyl)-2-oxopyrrolidin-3-yl)-2-methylbenzofuran-3-carboxamide Cpd 341 5-((2-(difluoromethyl)pyridin-3-yl)methoxy)-N-(3-(hydroxymethyl)oxetan-3-yl)-2-methylbenzofuran-3-carboxamide Cpd 342 5-((2-(difluoromethyl)pyridin-3-yl)methoxy)-N-(3,3-difluoropiperidin-4-yl)-2-methylbenzofuran-3-carboxamide Cpd 343 5-((2-(difluoromethyl)pyridin-3-yl)methoxy)-N-(4-(hydroxymethyl)tetrahydro-2H-pyran-4-yl)-2-methylbenzofuran-3-carboxamide Cpd 344 5-((2-(dimethylamino)pyridin-3-yl)methoxy)-N-(4-(hydroxymethyl)tetrahydro-2H-pyran-4-yl)-2-methylbenzofuran-3-carboxamide Cpd 345 5-((2,4-dimethylthiazol-5-yl)methoxy)-N-(4-(hydroxymethyl)tetrahydro-2H-pyran-4-yl)-2-methyl-benzofuran-3-carboxamide Cpd 346 5-((2-aminopyridin-3-yl)methoxy)-N-(4-(hydroxymethyl)tetrahydro-2H-pyran-4-yl)-2-methylbenzofuran-3-carboxamide Cpd 347 5-((2-cyanopyridin-3-yl)methoxy)-N-(4-(hydroxymethyl)tetrahydro-2H-pyran-4-yl)-2-methylbenzofuran-3-carboxamide Cpd 348 5-((2-ethoxypyridin-3-yl)methoxy)-N-(1-(2-hydroxyethyl)-2-oxopyrrolidin-3-yl)-2-methylbenzofuran-3-carboxamide Cpd 349 5-((2-hydroxypyridin-3-yl)methoxy)-N-(cis-4-hydroxytetrahydrofuran-3-yl)-2-methylbenzofuran-3-carboxamide Cpd 350 5-((2-hydroxypyridin-3-yl)methoxy)-N-(trans-4-hydroxytetrahydrofuran-3-yl)-2-methylbenzofuran-3-carboxamide Cpd 351 5-((3-(difluoromethyl)pyridin-2-yl)methoxy)-N-(4-(hydroxymethyl)tetrahydro-2H-pyran-4-yl)-2-methylbenzofuran-3-carboxamide Cpd 352 5-((3-fluoropyridin-2-yl)methoxy)-N-(4-(hydroxymethyl)tetrahydro-2H-pyran-4-yl)-2-methylbenzofuran-3-carboxamide Cpd 355 5-((4-fluoro-1-methyl-1H-pyrazol-5-yl)methoxy)-N-(3-(hydroxymethyl)-2-oxopiperidin-3-yl)-2-methylbenzofuran-3-carboxamide Cpd 356 5-((4-fluoro-1-methyl-1H-pyrazol-5-yl)methoxy)-N-(3-(hydroxymethyl)-2-oxopyrrolidin-3-yl)-2-methylbenzofuran-3-carboxamide Cpd 357 5-((4-fluoro-1-methyl-1H-pyrazol-5-yl)methoxy)-N-(4-(hydroxymethyl)tetrahydro-2H-pyran-4-yl)-2-methylbenzofuran-3-carboxamide Cpd 358 5-((5-(2-hydroxyethoxy)pyridin-2-yl)methoxy)-N-(4-(hydroxymethyl)tetrahydro-2H-pyran-4-yl)-2-methylbenzofuran-3-carboxamide Cpd 359 5-((5-fluoropyridin-2-yl)methoxy)-N-(4-(hydroxymethyl)tetrahydro-2H-pyran-4-yl)-2-methylbenzofuran-3-carboxamide Cpd 360 6-fluoro-N-(1-(2-hydroxyethyl)-2-oxopyrrolidin-3-yl)-2-methyl-5-((4-methylthiazol-5-yl)methoxy)benzofuran-3-carboxamide Cpd 361 6-fluoro-N-(1-(hydroxymethyl)cyclopropyl)-2-methyl-5-((4-methylthiazol-5-yl)methoxy)benzofuran-3-carboxamide Cpd 362 6-fluoro-N-(3-(hydroxymethyl)oxetan-3-yl)-2-methyl-5-((4-methylthiazol-5-yl)methoxy)benzofuran-3-carboxamide Cpd 363 6-fluoro-N-(4-(hydroxymethyl)tetrahydro-2H-pyran-4-yl)-5-((2-hydroxypyridin-3-yl)methoxy)-2-methylbenzofuran-3-carboxamide Cpd 364 6-fluoro-N-(4-(hydroxymethyl)tetrahydro-2H-pyran-4-yl)-5-((2-methoxypyridin-3-yl)methoxy)-2-methylbenzofuran-3-carboxamide Cpd 365 7-fluoro-N-(1-(2-hydroxyethyl)-2-oxopyrrolidin-3-yl)-2-methyl-5-((4-methylthiazol-5-yl)methoxy)benzofuran-3-carboxamide Cpd 366 7-fluoro-N-(1-(hydroxymethyl)cyclopropyl)-2-methyl-5-((4-methylthiazol-5-yl)methoxy)benzofuran-3-carboxamide Cpd 367 7-fluoro-N-(3-(hydroxymethyl)oxetan-3-yl)-2-methyl-5-((4-methylthiazol-5-yl)methoxy)benzofuran-3-carboxamide Cpd 368 7-fluoro-N-(4-(hydroxymethyl)tetrahydro-2H-pyran-4-yl)-5-((2-hydroxypyridin-3-yl)methoxy)-2-methylbenzofuran-3-carboxamide Cpd 369 7-fluoro-N-(4-(hydroxymethyl)tetrahydro-2H-pyran-4-yl)-5-((2-methoxypyridin-3-yl)methoxy)-2-methylbenzofuran-3-carboxamide Cpd 370 N-((1-cyanocyclopropyl)methyl)-2-methyl-5-((2-methylthiazol-5-yl)methoxy)benzofuran-3-carboxamide Cpd 371 N-((1-cyanocyclopropyl)methyl)-2-methyl-5-((4-methylthiazol-5-yl)methoxy)benzofuran-3-carboxamide Cpd 372 N-((1-fluorocyclopropyl)methyl)-2-methyl-5-((2-methylthiazol-5-yl)methoxy)benzofuran-3-carboxamide Cpd 373 N-((1-fluorocyclopropyl)methyl)-2-methyl-5-((4-methylthiazol-5-yl)methoxy)benzofuran-3-carboxamide Cpd 374 N-((1H-pyrazol-3-yl)methyl)-2-methyl-5-((4-methylthiazol-5-yl)methoxy)benzofuran-3-carboxamide Cpd 375 N-((2S,3R)-1-amino-3-hydroxy-1-oxobutan-2-yl)-2-methyl-5-((2-methyloxazol-5-yl)methoxy)benzofuran-3-carboxamide Cpd 376 N-((2S,3R)-1-amino-3-hydroxy-1-oxobutan-2-yl)-2-methyl-5-((2-methylpyridin-3-yl)methoxy)benzofuran-3-carboxamide Cpd 377 N-((2S,3R)-1-amino-3-hydroxy-1-oxobutan-2-yl)-2-methyl-5-((2-methylthiazol-5-yl)methoxy)benzofuran-3-carboxamide Cpd 378 N-((2S,3R)-1-amino-3-hydroxy-1-oxobutan-2-yl)-2-methyl-5-((4-methylthiazol-5-yl)methoxy)benzofuran-3-carboxamide Cpd 379 N-((2S,3R)-1-amino-3-hydroxy-1-oxobutan-2-yl)-2-methyl-5-((4-methylthiazol-5-yl)methoxy)benzofuran-3-carboxamide Cpd 380 N-((2S,3R)-1-amino-3-hydroxy-1-oxobutan-2-yl)-2-methyl-5-((6-methylpyridin-3-yl)methoxy)benzofuran-3-carboxamide Cpd 381 N-((2S,3R)-1-amino-3-hydroxy-1-oxobutan-2-yl)-5-((1-(2,2-difluoroethyl)-1H-pyrazol-5-yl)methoxy)-2-methylbenzofuran-3-carboxamide Cpd 382 N-((2S,3R)-1-amino-3-hydroxy-1-oxobutan-2-yl)-5-((2,4-dimethylthiazol-5-yl)methoxy)-2-methyl-benzofuran-3-carboxamide Cpd 383 N-((2S,3R)-1-amino-3-hydroxy-1-oxobutan-2-yl)-5-((4-fluoro-1-methyl-1H-pyrazol-5-yl)methoxy)-2-methylbenzofuran-3-carboxamide Cpd 384 N-((3-fluorooxetan-3-yl)methyl)-2-methyl-5-((2-methylthiazol-5-yl)methoxy)benzofuran-3-carboxamide Cpd 385 N-((3-fluorooxetan-3-yl)methyl)-2-methyl-5-((4-methylthiazol-5-yl)methoxy)benzofuran-3-carboxamide Cpd 386 N-(cis-4-hydroxytetrahydrofuran-3-yl)-2-methyl-5-((2-methylthiazol-5-yl)methoxy)benzofuran-3-carboxamide Cpd 387 N-(cis-4-hydroxytetrahydrofuran-3-yl)-2-methyl-5-(pyridin-2-ylmethoxy)benzofuran-3-carboxamide Cpd 388 N-(trans-4-hydroxytetrahydrofuran-3-yl)-2-methyl-5-((2-methylthiazol-5-yl)methoxy)benzofuran-3-carboxamide Cpd 389 N-(trans-4-hydroxytetrahydrofuran-3-yl)-2-methyl-5-(pyridin-2-ylmethoxy)benzofuran-3-carboxamide Cpd 390 N-((3S,4R)-4-hydroxy-2-oxopyrrolidin-3-yl)-2-methyl-5-((2-(trifluoromethyl)pyridin-3-yl)methoxy)benzofuran-3-carboxamide Cpd 391 N-((3S,4R)-4-hydroxy-2-oxopyrrolidin-3-yl)-2-methyl-5-((2-methylthiazol-5-yl)methoxy)benzofuran-3-carboxamide Cpd 392 N-((3S,4R)-4-hydroxy-2-oxopyrrolidin-3-yl)-2-methyl-5-((4-methylthiazol-5-yl)methoxy)benzofuran-3-carboxamide Cpd 393 N-((4-fluorotetrahydro-2H-pyran-4-yl)methyl)-2-methyl-5-((2-methylthiazol-5-yl)methoxy)benzofuran-3-carboxamide Cpd 394 N-((4-fluorotetrahydro-2H-pyran-4-yl)methyl)-2-methyl-5-((4-methylthiazol-5-yl)methoxy)benzofuran-3-carboxamide Cpd 395 N—((S)-1-amino-3-hydroxy-1-oxopropan-2-yl)-2-methyl-5-(1-(2-methylthiazol-5-yl)ethoxy)benzofuran-3-carboxamide Cpd 396 N-(1-((2-hydroxyethyl)(methyl)amino)-1-oxopropan-2-yl)-2-methyl-5-((4-methylthiazol-5-yl)methoxy)benzofuran-3-carboxamide Cpd 397 N-(1-((2-hydroxyethyl)amino)-1-oxopropan-2-yl)-2-methyl-5-((4-methylthiazol-5-yl)methoxy)benzofuran-3-carboxamide Cpd 398 N-(1-((2-hydroxyethyl)amino)-2-methyl-1-oxopropan-2-yl)-2-methyl-5-((4-methylthiazol-5-yl)methoxy)benzofuran-3-carboxamide Cpd 399 N-(1-((difluoromethoxy)methyl)cyclopropyl)-2-methyl-5-((2-methylthiazol-5-yl)methoxy)benzofuran-3-carboxamide Cpd 400 N-(1-((difluoromethoxy)methyl)cyclopropyl)-2-methyl-5-((4-methylthiazol-5-yl)methoxy)benzofuran-3-carboxamide Cpd 401 N-(1-(1H-benzo[d]imidazol-2-yl)-2-hydroxyethyl)-2-methyl-5-((2-methylthiazol-5-yl)methoxy)benzofuran-3-carboxamide Cpd 402 N-(1-(2-(2-hydroxyethoxy)ethyl)-2-oxopyrrolidin-3-yl)-2-methyl-5-((4-methylthiazol-5-yl)methoxy)benzofuran-3-carboxamide Cpd 403 N-(1-(2-hydroxyethyl)-2-oxopyrrolidin-3-yl)-2-methyl-5-((1-methyl-1H-imidazol-2-yl)methoxy)benzofuran-3-carboxamide Cpd 404 N-(1-(2-hydroxyethyl)-2-oxopyrrolidin-3-yl)-2-methyl-5-((1-methyl-1H-pyrazol-2-yl)methoxy)benzofuran-3-carboxamide Cpd 405 N-(1-(2-hydroxyethyl)-2-oxopyrrolidin-3-yl)-2-methyl-5-((1-methyl-2-oxo-1,2-dihydropyridin-3-yl)methoxy)benzofuran-3-carboxamide Cpd 406—N-(1-(2-hydroxyethyl)-2-oxopyrrolidin-3-yl)-2-methyl-5-(pyridin-2-ylmethoxy)benzofuran-3-carboxamide Cpd 407—N-(1-(2-hydroxyethyl)-2-oxopyrrolidin-3-yl)-2-methyl-5-(thiazol-2-ylmethoxy)benzofuran-3-carboxamide Cpd 408 N-(1-(2-hydroxyethyl)-2-oxopyrrolidin-3-yl)-5-((2-hydroxypyridin-3-yl)methoxy)-2-methylbenzofuran-3-carboxamide Cpd 409 N-(1-(2-hydroxyethyl)-2-oxopyrrolidin-3-yl)-5-((2-methoxypyridin-3-yl)methoxy)-2-methylbenzofuran-3-carboxamide Cpd 410 N-(1-(2-hydroxyethyl)-3-methyl-2-oxopyrrolidin-3-yl)-2-methyl-5-((4-methylthiazol-5-yl)methoxy)benzofuran-3-carboxamide Cpd 411 N-(1-(dimethylamino)-3-hydroxy-1-oxopropan-2-yl)-2-methyl-5-((4-methylthiazol-5-yl)methoxy)benzofuran-3-carboxamide Cpd 412 N-(1-(dimethylamino)-3-hydroxypropan-2-yl)-2-methyl-5-((2-methylthiazol-5-yl)methoxy)benzofuran-3-carboxamide
Cpd 413 N-(1-(dimethylamino)-3-hydroxypropan-2-yl)-2-methyl-5-((4-methylthiazol-5-yl)methoxy)benzofuran-3-carboxamide
Cpd 414 N-(1-(hydroxymethyl)cyclobutyl)-2-methyl-5-((2-methylthiazol-5-yl)methoxy)benzofuran-3-carboxamide
Cpd 415 N-(1-(hydroxymethyl)cyclobutyl)-2-methyl-5-(pyridin-2-ylmethoxy)benzofuran-3-carboxamide
Cpd 416 N-(1-(hydroxymethyl)cyclobutyl)-5-((2-hydroxypyridin-3-yl)methoxy)-2-methylbenzofuran-3-carboxamide
Cpd 417 N-(1-(hydroxymethyl)cyclobutyl)-5-((2-methoxypyridin-3-yl)methoxy)-2-methylbenzofuran-3-carboxamide
Cpd 418 N-(1-(hydroxymethyl)cyclopropyl)-2-methyl-5-((2-methylthiazol-5-yl)methoxy)benzofuran-3-carboxamide
Cpd 419 N-(1-(hydroxymethyl)cyclopropyl)-2-methyl-5-(pyridin-2-ylmethoxy)benzofuran-3-carboxamide
Cpd 420 N-(1-(hydroxymethyl)cyclopropyl)-5-((2-hydroxypyridin-3-yl)methoxy)-2-methylbenzofuran-3-carboxamide
Cpd 421 N-(1-(hydroxymethyl)cyclopropyl)-5-((2-methoxypyridin-3-yl)methoxy)-2-methylbenzofuran-3-carboxamide
Cpd 422 N-(1,3-dihydroxy-2-methylpropan-2-yl)-2-methyl-5-((1-methyl-1H-imidazol-2-yl)methoxy)benzofuran-3-carboxamide
Cpd 423 N-(1,3-dihydroxy-2-methylpropan-2-yl)-2-methyl-5-((1-methyl-1H-pyrazol-5-yl)methoxy)benzofuran-3-carboxamide
Cpd 424 N-(1,3-dihydroxy-2-methylpropan-2-yl)-2-methyl-5-((2-(trifluoromethyl)pyridin-3-yl)methoxy)benzofuran-3-carboxamide
Cpd 425 N-(1,3-dihydroxy-2-methylpropan-2-yl)-2-methyl-5-((2-methylthiazol-5-yl)methoxy)benzofuran-3-carboxamide
Cpd 426 N-(1,3-dihydroxy-2-methylpropan-2-yl)-2-methyl-5-((4-methylthiazol-5-yl)methoxy)benzofuran-3-carboxamide
Cpd 427 N-(1,3-dihydroxy-2-methylpropan-2-yl)-2-methyl-5-(pyridazin-3-ylmethoxy)benzofuran-3-carboxamide
Cpd 428 N-(1,3-dihydroxy-2-methylpropan-2-yl)-2-methyl-5-(pyridin-2-ylmethoxy)benzofuran-3-carboxamide
Cpd 429 N-(1,3-dihydroxy-2-methylpropan-2-yl)-2-methyl-5-(pyrimidin-4-ylmethoxy)benzofuran-3-carboxamide
Cpd 430 N-(1,3-dihydroxy-2-methylpropan-2-yl)-5-((2-hydroxypyridin-3-yl)methoxy)-2-methylbenzofuran-3-carboxamide
Cpd 431 N-(1,3-dihydroxy-2-methylpropan-2-yl)-5-((2-methoxypyridin-3-yl)methoxy)-2-methylbenzofuran-3-carboxamide
Cpd 432 N-(1-amino-1-oxo-3-(1H-1,2,4-triazol-1-yl)propan-2-yl)-2-methyl-5-((2-methylthiazol-5-yl)methoxy)benzofuran-3-carboxamide
Cpd 433—N-(1-amino-1-oxopropan-2-yl)-2-methyl-5-((1-methyl-1H-pyrazol-5-yl)methoxy)benzofuran-3-carboxamide
Cpd 434 N-(1-amino-1-oxopropan-2-yl)-2-methyl-5-((2-methylthiazol-5-yl)methoxy)benzofuran-3-carboxamide
Cpd 435 N-(1-amino-1-oxopropan-2-yl)-2-methyl-5-(pyridin-2-ylmethoxy)benzofuran-3-carboxamide
Cpd 436 N-(1-amino-1-oxopropan-2-yl)-5-((2-hydroxypyridin-3-yl)methoxy)-2-methylbenzofuran-3-carboxamide
Cpd 437 N-(1-amino-1-oxopropan-2-yl)-5-((2-methoxypyridin-3-yl)methoxy)-2-methylbenzofuran-3-carboxamide
Cpd 438 N-(1-amino-2-methyl-1-oxopropan-2-yl)-2-methyl-5-((1-methyl-1H-pyrazol-5-yl)methoxy)benzofuran-3-carboxamide
Cpd 439 N-(1-amino-2-methyl-1-oxopropan-2-yl)-2-methyl-5-((2-methylthiazol-5-yl)methoxy)benzofuran-3-carboxamide
Cpd 440 N-(1-amino-2-methyl-1-oxopropan-2-yl)-2-methyl-5-((4-methylthiazol-5-yl)methoxy)benzofuran-3-carboxamide
Cpd 441 N-(1-amino-2-methyl-1-oxopropan-2-yl)-2-methyl-5-(pyridazin-3-ylmethoxy)benzofuran-3-carboxamide
Cpd 442 N-(1-amino-2-methyl-1-oxopropan-2-yl)-2-methyl-5-(pyridin-2-ylmethoxy)benzofuran-3-carboxamide
Cpd 443 N-(1-amino-2-methyl-1-oxopropan-2-yl)-5-((2-hydroxypyridin-3-yl)methoxy)-2-methylbenzofuran-3-carboxamide
Cpd 444 N-(1-amino-2-methyl-1-oxopropan-2-yl)-5-((2-methoxypyridin-3-yl)methoxy)-2-methylbenzofuran-3-carboxamide
Cpd 445 N-(1-amino-3-(cyclopropyl(methyl)amino)-1-oxopropan-2-yl)-2-methyl-5-((2-methylthiazol-5-yl)methoxy)benzofuran-3-carboxamide
Cpd 446 N-(1-amino-3-(cyclopropyl(methyl)amino)-1-oxopropan-2-yl)-2-methyl-5-((4-methylthiazol-5-yl)methoxy)benzofuran-3-carboxamide
Cpd 447 N-(1-amino-3-(difluoromethoxy)-1-oxopropan-2-yl)-2-methyl-5-((2-methylthiazol-5-yl)methoxy)benzofuran-3-carboxamide
Cpd 448 N-(1-amino-3-(difluoromethoxy)-1-oxopropan-2-yl)-2-methyl-5-((4-methylthiazol-5-yl)methoxy)benzofuran-3-carboxamide
Cpd 449 N-(1-amino-3-(dimethylamino)-1-oxopropan-2-yl)-2-methyl-5-((2-methylthiazol-5-yl)methoxy)benzofuran-3-carboxamide
Cpd 450 N-(1-amino-3-(dimethylamino)-1-oxopropan-2-yl)-2-methyl-5-((4-methylthiazol-5-yl)methoxy)benzofuran-3-carboxamide
Cpd 451 N-(1-amino-3-hydroxy-1-oxopropan-2-yl)-2-methyl-5-((1-methyl-1H-imidazol-2-yl)methoxy)benzofuran-3-carboxamide
Cpd 452 N-(1-amino-3-hydroxy-1-oxopropan-2-yl)-2-methyl-5-((1-methyl-1H-pyrazol-5-yl)methoxy)benzofuran-3-carboxamide
Cpd 453 N-(1-amino-3-hydroxy-1-oxopropan-2-yl)-2-methyl-5-((2-methylthiazol-5-yl)methoxy)benzofuran-3-carboxamide
Cpd 454 N-(1-amino-3-hydroxy-1-oxopropan-2-yl)-2-methyl-5-((4-methylthiazol-5-yl)methoxy)benzofuran-3-carboxamide
Cpd 455 N-(1-amino-3-hydroxy-1-oxopropan-2-yl)-2-methyl-5-(pyridin-2-ylmethoxy)benzofuran-3-carboxamide
Cpd 456 N-(1-amino-3-hydroxy-1-oxopropan-2-yl)-5-((1-(2,2-difluoroethyl)-1H-pyrazol-5-yl)methoxy)-2-methylbenzofuran-3-carboxamide Cpd 457 N-(1-amino-3-hydroxy-1-oxopropan-2-yl)-5-((2-(difluoromethyl)pyridin-3-yl)methoxy)-2-methylbenzofuran-3-carboxamide
Cpd 458 N-(1-amino-3-hydroxy-1-oxopropan-2-yl)-5-((2,4-dimethylthiazol-5-yl)methoxy)-2-methylbenzofuran-3-carboxamide
Cpd 459 N-(1-amino-3-hydroxy-1-oxopropan-2-yl)-5-((2-hydroxypyridin-3-yl)methoxy)-2-methylbenzofuran-3-carboxamide
Cpd 460 N-(1-amino-3-hydroxy-1-oxopropan-2-yl)-5-((4-fluoro-1-methyl-1H-pyrazol-5-yl)methoxy)-2-methylbenzofuran-3-carboxamide
Cpd 461 N-(1-amino-3-hydroxy-2-methyl-1-oxopropan-2-yl)-2-methyl-5-((2-methylpyridin-3-yl)methoxy)benzofuran-3-carboxamide
Cpd 462 N-(1-amino-3-hydroxy-2-methyl-1-oxopropan-2-yl)-2-methyl-5-((2-methylthiazol-5-yl)methoxy)benzofuran-3-carboxamide
Cpd 463 N-(1-amino-3-hydroxy-2-methyl-1-oxopropan-2-yl)-2-methyl-5-((4-methylthiazol-5-yl)methoxy)benzofuran-3-carboxamide
Cpd 464 N-(1-amino-3-hydroxy-2-methyl-1-oxopropan-2-yl)-2-methyl-5-((6-methylpyridin-3-yl)methoxy)benzofuran-3-carboxamide
Cpd 465 N-(1-amino-3-hydroxy-2-methyl-1-oxopropan-2-yl)-5-((1-(2,2-difluoroethyl)-1H-pyrazol-5-yl)methoxy)-2-methylbenzofuran-3-carboxamide
Cpd 466 N-(1-amino-3-hydroxy-2-methyl-1-oxopropan-2-yl)-5-((4-fluoro-1-methyl-1H-pyrazol-5-yl)methoxy)-2-methylbenzofuran-3-carboxamide
Cpd 467 N-(1-amino-3-methoxy-1-oxopropan-2-yl)-2-methyl-5-((4-methylthiazol-5-yl)methoxy)benzofuran-3-carboxamide
Cpd 468 N-(1-amino-3-methoxy-2-methyl-1-oxopropan-2-yl)-2-methyl-5-((4-methylthiazol-5-yl)methoxy)benzofuran-3-carboxamide
Cpd 469 N-(1-amino-4-hydroxy-1-oxobutan-2-yl)-2-methyl-5-((4-methylthiazol-5-yl)methoxy)benzofuran-3-carboxamide
Cpd 470 N-(1-carbamoyl-3,3-difluorocyclobutyl)-2-methyl-5-((4-methylthiazol-5-yl)methoxy)benzofuran-3-carboxamide
Cpd 471 N-(1-carbamoylcyclobutyl)-2-methyl-5-((2-methylthiazol-5-yl)methoxy)benzofuran-3-carboxamide
Cpd 472 N-(1-carbamoylcyclobutyl)-2-methyl-5-(pyridin-2-ylmethoxy)benzofuran-3-carboxamide
Cpd 473 N-(1-carbamoylcyclobutyl)-5-((2-hydroxypyridin-3-yl)methoxy)-2-methylbenzofuran-3-carboxamide
Cpd 474 N-(1-carbamoylcyclobutyl)-5-((2-methoxypyridin-3-yl)methoxy)-2-methylbenzofuran-3-carboxamide
Cpd 475 N-(1-carbamoylcyclopropyl)-2-methyl-5-((2-(trifluoromethyl)pyridin-3-yl)methoxy)benzofuran-3-carboxamide
Cpd 476 N-(1-carbamoylcyclopropyl)-2-methyl-5-((2-methylthiazol-5-yl)methoxy)benzofuran-3-carboxamide
Cpd 477 N-(1-carbamoylcyclopropyl)-2-methyl-5-((4-methylthiazol-5-yl)methoxy)benzofuran-3-carboxamide
Cpd 478 N-(1-carbamoylcyclopropyl)-2-methyl-5-(pyridin-2-ylmethoxy)benzofuran-3-carboxamide
Cpd 479 N-(1-carbamoylcyclopropyl)-5-((2-hydroxypyridin-3-yl)methoxy)-2-methylbenzofuran-3-carboxamide
Cpd 480 N-(1-carbamoylcyclopropyl)-5-((2-methoxypyridin-3-yl)methoxy)-2-methylbenzofuran-3-carboxamide
Cpd 481 N-(1-hydroxy-2-methylpropan-2-yl)-2-methyl-5-((1-methyl-1H-imidazol-2-yl)methoxy)benzofuran-3-carboxamide
Cpd 482 N-(1-hydroxy-2-methylpropan-2-yl)-2-methyl-5-((1-methyl-1H-pyrazol-5-yl)methoxy)benzofuran-3-carboxamide
Cpd 483 N-(1-hydroxy-2-methylpropan-2-yl)-2-methyl-5-((2-methylthiazol-5-yl)methoxy)benzofuran-3-carboxamide
Cpd 484 N-(1-hydroxy-2-methylpropan-2-yl)-2-methyl-5-(pyridin-2-ylmethoxy)benzofuran-3-carboxamide
Cpd 485 N-(1-hydroxy-2-methylpropan-2-yl)-5-((2-hydroxypyridin-3-yl)methoxy)-2-methylbenzofuran-3-carboxamide
Cpd 486 N-(1-hydroxy-2-methylpropan-2-yl)-5-((2-methoxypyridin-3-yl)methoxy)-2-methylbenzofuran-3-carboxamide
Cpd 487 N-(1-hydroxy-3-morpholinopropan-2-yl)-2-methyl-5-((2-methylthiazol-5-yl)methoxy)benzofuran-3-carboxamide
Cpd 488 N-(1-hydroxy-3-morpholinopropan-2-yl)-2-methyl-5-((4-methylthiazol-5-yl)methoxy)benzofuran-3-carboxamide
Cpd 489 N-(1-hydroxypropan-2-yl)-2-methyl-5-((2-(trifluoromethyl)pyridin-3-yl)methoxy)benzofuran-3-carboxamide
Cpd 490 N-(1-hydroxypropan-2-yl)-2-methyl-5-((2-methylthiazol-5-yl)methoxy)benzofuran-3-carboxamide
Cpd 491 N-(1-hydroxypropan-2-yl)-2-methyl-5-((4-methylthiazol-5-yl)methoxy)benzofuran-3-carboxamide
Cpd 492 (S)—N-(1-hydroxypropan-2-yl)-2-methyl-5-(pyridin-2-ylmethoxy)benzofuran-3-carboxamide
Cpd 493 (R)—N-(1-hydroxypropan-2-yl)-2-methyl-5-(pyridin-2-ylmethoxy)benzofuran-3-carboxamide
Cpd 494 (S)—N-(1-hydroxypropan-2-yl)-5-((2-hydroxypyridin-3-yl)methoxy)-2-methylbenzofuran-3-carboxamide
Cpd 495 (R)—N-(1-hydroxypropan-2-yl)-5-((2-hydroxypyridin-3-yl)methoxy)-2-methylbenzofuran-3-carboxamide
Cpd 496 (S)—N-(1-hydroxypropan-2-yl)-5-((2-methoxypyridin-3-yl)methoxy)-2-methylbenzofuran-3-carboxamide
Cpd 497 (R)—N-(1-hydroxypropan-2-yl)-5-((2-methoxypyridin-3-yl)methoxy)-2-methylbenzofuran-3-carboxamide
Cpd 498 N-(2,2-difluoroethyl)-2-methyl-5-((4-methylthiazol-5-yl)methoxy)benzofuran-3-carboxamide
Cpd 499 N-(2,2-difluoropropyl)-2-methyl-5-((2-methylthiazol-5-yl)methoxy)benzofuran-3-carboxamide
Cpd 500 N-(2,2-difluoropropyl)-2-methyl-5-((4-methylthiazol-5-yl)methoxy)benzofuran-3-carboxamide
Cpd 501 N-(2-acetamidoethyl)-2-methyl-5-((4-methylthiazol-5-yl)methoxy)benzofuran-3-carboxamide
Cpd 502 N-(2-amino-1-cyano-2-oxoethyl)-2-methyl-5-((4-methylthiazol-5-yl)methoxy)benzofuran-3-carboxamide
Cpd 503 N-(2-amino-2-oxoethyl)-2-methyl-5-((4-methylthiazol-5-yl)methoxy)benzofuran-3-carboxamide
Cpd 504 N-(2-fluoro-2-methylpropyl)-2-methyl-5-((2-methylthiazol-5-yl)methoxy)benzofuran-3-carboxamide Cpd 505 N-(2-fluoro-2-methylpropyl)-2-methyl-5-((4-methylthiazol-5-yl)methoxy)benzofuran-3-carboxamide Cpd 506 N-(2-hydroxy-2-methylpropyl)-2-methyl-5-((4-methylthiazol-5-yl)methoxy)benzofuran-3-carboxamide Cpd 507 N-(3-(aminomethyl)oxetan-3-yl)-2-methyl-5-((4-methylthiazol-5-yl)methoxy)benzofuran-3-carboxamide Cpd 508 N-(3-(dimethylamino)oxetane-3-carbonyl)-2-methyl-5-((4-methylthiazol-5-yl)methoxy)benzofuran-3-carboxamide Cpd 509 N-(3-(dimethylcarbamoyl)oxetan-3-yl)-2-methyl-5-((4-methylthiazol-5-yl)methoxy)benzofuran-3-carboxamide Cpd 510 N-(3-(hydroxymethyl)-2-oxopiperidin-3-yl)-2-methyl-5-((2-(trifluoromethyl)pyridin-3-yl)methoxy)benzofuran-3-carboxamide Cpd 511 N-(3-(hydroxymethyl)-2-oxopiperidin-3-yl)-2-methyl-5-((2-methyloxazol-5-yl)methoxy)benzofuran-3-carboxamide Cpd 512 N-(3-(hydroxymethyl)-2-oxopiperidin-3-yl)-2-methyl-5-((2-methylpyridin-3-yl)methoxy)benzofuran-3-carboxamide Cpd 513 N-(3-(hydroxymethyl)-2-oxopiperidin-3-yl)-2-methyl-5-((4-methylthiazol-5-yl)methoxy)benzofuran-3-carboxamide Cpd 514 N-(3-(hydroxymethyl)-2-oxopiperidin-3-yl)-2-methyl-5-((6-methylpyridin-3-yl)methoxy)benzofuran-3-carboxamide Cpd 515 N-(3-(hydroxymethyl)-2-oxopyrrolidin-3-yl)-2-methyl-5-((2-methyloxazol-5-yl)methoxy)benzofuran-3-carboxamide Cpd 516 N-(3-(hydroxymethyl)-2-oxopyrrolidin-3-yl)-2-methyl-5-((2-methylpyridin-3-yl)methoxy)benzofuran-3-carboxamide Cpd 517 N-(3-(hydroxymethyl)-2-oxopyrrolidin-3-yl)-2-methyl-5-((2-methylthiazol-5-yl)methoxy)benzofuran-3-carboxamide Cpd 518 N-(3-(hydroxymethyl)-2-oxopyrrolidin-3-yl)-2-methyl-5-((4-methylthiazol-5-yl)methoxy)benzofuran-3-carboxamide Cpd 519 N-(3-(hydroxymethyl)-2-oxopyrrolidin-3-yl)-2-methyl-5-((6-methylpyridin-3-yl)methoxy)benzofuran-3-carboxamide Cpd 520 N-(3-(hydroxymethyl)-2-oxopyrrolidin-3-yl)-2-methyl-5-(pyridin-2-ylmethoxy)benzofuran-3-carboxamide Cpd 521 N-(3-(hydroxymethyl)-2-oxopyrrolidin-3-yl)-5-((2-hydroxypyridin-3-yl)methoxy)-2-methylbenzofuran-3-carboxamide Cpd 522 N-(3-(hydroxymethyl)-2-oxopyrrolidin-3-yl)-5-((2-methoxypyridin-3-yl)methoxy)-2-methylbenzofuran-3-carboxamide Cpd 523 N-(3-(hydroxymethyl)oxetan-3-yl)-2-methyl-5-((1-methyl-1H-imidazol-2-yl)methoxy)benzofuran-3-carboxamide Cpd 524 N-(3-(hydroxymethyl)oxetan-3-yl)-2-methyl-5-((1-methyl-1H-pyrazol-5-yl)methoxy)benzofuran-3-carboxamide Cpd 525 N-(3-(hydroxymethyl)oxetan-3-yl)-2-methyl-5-((2-methylthiazol-5-yl)methoxy)benzofuran-3-carboxamide Cpd 526 N-(3-(hydroxymethyl)oxetan-3-yl)-2-methyl-5-(pyridin-2-ylmethoxy)benzofuran-3-carboxamide Cpd 527 N-(3-(hydroxymethyl)oxetan-3-yl)-2-methyl-5-(thiazol-2-ylmethoxy)benzofuran-3-carboxamide Cpd 528 N-(3-(hydroxymethyl)oxetan-3-yl)-5-((2-methoxypyridin-3-yl)methoxy)-2-methylbenzofuran-3-carboxamide Cpd 529 N-(3-(hydroxymethyl)oxetan-3-yl)-N,2-dimethyl-5-((4-methylthiazol-5-yl)methoxy)benzofuran-3-carboxamide Cpd 530 N-(3-(hydroxymethyl)pyrrolidin-3-yl)-2-methyl-5-((2-methylthiazol-5-yl)methoxy)benzofuran-3-carboxamide Cpd 531 N-(3-(hydroxymethyl)tetrahydro-2H-pyran-3-yl)-2-methyl-5-((2-(trifluoromethyl)pyridin-3-yl)methoxy)benzofuran-3-carboxamide Cpd 532 N-(3-(hydroxymethyl)tetrahydro-2H-pyran-3-yl)-2-methyl-5-((4-methylthiazol-5-yl)methoxy)benzofuran-3-carboxamide Cpd 533 N-(3-(hydroxymethyl)tetrahydrofuran-3-yl)-2-methyl-5-((2-methylthiazol-5-yl)methoxy)benzofuran-3-carboxamide Cpd 534 N-(3-(hydroxymethyl)tetrahydrofuran-3-yl)-2-methyl-5-(pyridin-2-ylmethoxy)benzofuran-3-carboxamide Cpd 535 N-(3-(hydroxymethyl)tetrahydrofuran-3-yl)-5-((2-hydroxypyridin-3-yl)methoxy)-2-methylbenzofuran-3-carboxamide Cpd 536 N-(3-(hydroxymethyl)tetrahydrofuran-3-yl)-5-((2-methoxypyridin-3-yl)methoxy)-2-methylbenzofuran-3-carboxamide Cpd 537 N-(3,3-difluoro-1-(hydroxymethyl)cyclobutyl)-2-methyl-5-((4-methylthiazol-5-yl)methoxy)benzofuran-3-carboxamide Cpd 538 N-(3,3-difluoropiperidin-4-yl)-2,4-dimethyl-5-((2-(trifluoromethyl)pyridin-3-yl)methoxy)benzofuran-3-carboxamide Cpd 539 N-(3,3-difluoropiperidin-4-yl)-2-methyl-5-(((2-(trifluoromethyl)pyridin-3-yl)oxy)methyl)benzofuran-3-carboxamide Cpd 540 N-(3,3-difluoropiperidin-4-yl)-2-methyl-5-((1-methyl-1H-1,2,3-triazol-4-yl)methoxy)benzofuran-3-carboxamide Cpd 541 N-(3,3-difluoropiperidin-4-yl)-2-methyl-5-((1-methyl-1H-1,2,3-triazol-5-yl)methoxy)benzofuran-3-carboxamide Cpd 542 N-(3,3-difluoropiperidin-4-yl)-2-methyl-5-((1-methyl-1H-1,2,4-triazol-3-yl)methoxy)benzofuran-3-carboxamide Cpd 543 N-(3,3-difluoropiperidin-4-yl)-2-methyl-5-((1-methyl-1H-pyrazol-5-yl)methoxy)benzofuran-3-carboxamide Cpd 544 N-(3,3-difluoropiperidin-4-yl)-2-methyl-5-((1-methyl-2-oxo-1,2-dihydropyridin-3-yl)methoxy)benzofuran-3-carboxamide Cpd 545 N-(3,3-difluoropiperidin-4-yl)-2-methyl-5-((1-methyl-6-oxo-1,6-dihydropyridin-2-yl)methoxy)benzofuran-3-carboxamide Cpd 546 N-(3,3-difluoropiperidin-4-yl)-2-methyl-5-((2-(trifluoromethyl)pyridin-3-yl)methoxy)benzofuran-3-carboxamide Cpd 547 N-(3,3-difluoropiperidin-4-yl)-2-methyl-5-((2-methylpyridin-3-yl)methoxy)benzofuran-3-carboxamide Cpd 548 N-(3,3-difluoropiperidin-4-yl)-2-methyl-5-((2-methylpyrimidin-4-yl)methoxy)benzofuran-3-carboxamide Cpd 549 N-(3,3-difluoropiperidin-4-yl)-2-methyl-5-((2-methylthiazol-5-yl)methoxy)benzofuran-3-carboxamide Cpd 550 N-(3,3-difluoropiperidin-4-yl)-2-methyl-5-((3-methyloxetan-3-yl)methoxy)benzofuran-3-carboxamide Cpd 551 N-(3,3-difluoropiperidin-4-yl)-2-methyl-5-((4-methyloxazol-2-yl)methoxy)benzofuran-3-carboxamide Cpd 552 N-(3,3-difluoropiperidin-4-yl)-2-methyl-5-((4-methylthiazol-2-yl)methoxy)benzofuran-3-carboxamide Cpd 553 N-(3,3-difluoropiperidin-4-yl)-2-methyl-5-((5-methylisoxazol-3-yl)methoxy)benzofuran-3-carboxamide Cpd 554 N-(3,3-difluoropiperidin-4-yl)-2-methyl-5-((5-methylpyrazin-2-yl)methoxy)benzofuran-3-carboxamide Cpd 555 N-(3,3-difluoropiperidin-4-yl)-2-methyl-5-((5-methylthiazol-2-yl)methoxy)benzofuran-3-carboxamide Cpd 556 N-(3,3-difluoropiperidin-4-yl)-2-methyl-5-((6-methylpyridazin-3-yl)methoxy)benzofuran-3-carboxamide Cpd 557 N-(3,3-difluoropiperidin-4-yl)-2-methyl-5-(pyridazin-3-ylmethoxy)benzofuran-3-carboxamide Cpd 558 N-(3,3-difluoropiperidin-4-yl)-2-methyl-5-(pyridin-3-ylmethoxy)benzofuran-3-carboxamide Cpd 559 N-(3,3-difluoropiperidin-4-yl)-2-methyl-5-(pyrimidin-2-ylmethoxy)benzofuran-3-carboxamide Cpd 560 N-(3,3-difluoropiperidin-4-yl)-2-methyl-5-(thiazol-2-ylmethoxy)benzofuran-3-carboxamide Cpd 561 N-(3,3-difluoropiperidin-4-yl)-2-methyl-5-(thiazol-5-ylmethoxy)benzofuran-3-carboxamide Cpd 562 N-(3,3-difluoropiperidin-4-yl)-4-fluoro-2-methyl-5-((4-methylthiazol-5-yl)methoxy)benzofuran-3-carboxamide Cpd 563 N-(3,3-difluoropiperidin-4-yl)-5-((2,4-dimethylthiazol-5-yl)methoxy)-2-methylbenzofuran-3-carboxamide Cpd 564 N-(3,3-difluoropiperidin-4-yl)-5-((2-hydroxypyridin-3-yl)methoxy)-2-methylbenzofuran-3-carboxamide Cpd 565 N-(3,3-difluoropiperidin-4-yl)-5-((2-methoxypyridin-3-yl)methoxy)-2-methylbenzofuran-3-carboxamide Cpd 566 N-(3,3-difluoropiperidin-4-yl)-5-((3-fluoropyridin-2-yl)methoxy)-2-methylbenzofuran-3-carboxamide Cpd 567 N-(3,3-difluoropiperidin-4-yl)-5-((5-(2-hydroxyethoxy)pyridin-2-yl)methoxy)-2-methylbenzofuran-3-carboxamide Cpd 568 N-(3,3-difluoropiperidin-4-yl)-5-((5-fluoropyridin-2-yl)methoxy)-2-methylbenzofuran-3-carboxamide Cpd 569 N-(3,3-difluoropiperidin-4-yl)-5-((6-hydroxypyridin-2-yl)methoxy)-2-methylbenzofuran-3-carboxamide Cpd 570 N-(3,3-difluoropiperidin-4-yl)-5-((6-methoxypyridin-2-yl)methoxy)-2-methylbenzofuran-3-carboxamide Cpd 571 N-(3,3-difluoropiperidin-4-yl)-5-(imidazo[1,2-a]pyridin-6-ylmethoxy)-2-methylbenzofuran-3-carboxamide Cpd 572 N-(3,3-difluoropiperidin-4-yl)-6-fluoro-2-methyl-5-((4-methylthiazol-5-yl)methoxy)benzofuran-3-carboxamide Cpd 573 N-(3,3-difluoropiperidin-4-yl)-7-fluoro-2-methyl-5-((4-methylthiazol-5-yl)methoxy)benzofuran-3-carboxamide Cpd 574 N-(3,3-difluoropropyl)-2-methyl-5-((4-methylthiazol-5-yl)methoxy)benzofuran-3-carboxamide Cpd 575 N-(3-amino-2-(dimethylamino)-3-oxopropyl)-2-methyl-5-((4-methylthiazol-5-yl)methoxy)benzofuran-3-carboxamide Cpd 576 N-(3-amino-2,2-dimethyl-3-oxopropyl)-2-methyl-5-((4-methylthiazol-5-yl)methoxy)benzofuran-3-carboxamide Cpd 577 N-(3-carbamoyloxetan-3-yl)-2-(difluoromethyl)-5-((4-methylthiazol-5-yl)methoxy)benzofuran-3-carboxamide Cpd 578 N-(3-carbamoyloxetan-3-yl)-2-methyl-5-((1-methyl-1H-imidazol-2-yl)methoxy)benzofuran-3-carboxamide Cpd 579 N-(3-carbamoyloxetan-3-yl)-2-methyl-5-((1-methyl-1H-pyrazol-5-yl)methoxy)benzofuran-3-carboxamide Cpd 580 N-(3-carbamoyloxetan-3-yl)-2-methyl-5-((2-methylthiazol-5-yl)methoxy)benzofuran-3-carboxamide Cpd 581 N-(3-carbamoyloxetan-3-yl)-2-methyl-5-(pyridin-2-ylmethoxy)benzofuran-3-carboxamide Cpd 582 N-(3-carbamoyloxetan-3-yl)-2-methyl-5-(thiazol-2-ylmethoxy)benzofuran-3-carboxamide Cpd 583 N-(3-carbamoyloxetan-3-yl)-4-fluoro-2-methyl-5-((4-methylthiazol-5-yl)methoxy)benzofuran-3-carboxamide Cpd 584 N-(3-carbamoyloxetan-3-yl)-5-((2-(difluoromethyl)pyridin-3-yl)methoxy)-2-methylbenzofuran-3-carboxamide Cpd 585 N-(3-carbamoyloxetan-3-yl)-5-((2-hydroxypyridin-3-yl)methoxy)-2-methylbenzofuran-3-carboxamide Cpd 586 N-(3-carbamoyloxetan-3-yl)-5-((2-methoxypyridin-3-yl)methoxy)-2-methylbenzofuran-3-carboxamide Cpd 587 N-(3-carbamoyloxetan-3-yl)-6-fluoro-2-methyl-5-((4-methylthiazol-5-yl)methoxy)benzofuran-3-carboxamide Cpd 588 N-(3-carbamoyloxetan-3-yl)-7-fluoro-2-methyl-5-((4-methylthiazol-5-yl)methoxy)benzofuran-3-carboxamide Cpd 589 N-(3-carbamoyloxetan-3-yl)-N,2-dimethyl-5-((4-methylthiazol-5-yl)methoxy)benzofuran-3-carboxamide Cpd 590 N-(3-carbamoyltetrahydro-2H-pyran-3-yl)-2-methyl-5-((2-methylthiazol-5-yl)methoxy)benzofuran-3-carboxamide Cpd 591 N-(3-carbamoyltetrahydrofuran-3-yl)-2-methyl-5-((2-methylpyridin-3-yl)methoxy)benzofuran-3-carboxamide Cpd 592 N-(3-carbamoyltetrahydrofuran-3-yl)-2-methyl-5-((2-methylthiazol-5-yl)methoxy)benzofuran-3-carboxamide Cpd 593 N-(3-carbamoyltetrahydrofuran-3-yl)-2-methyl-5-((4-methylthiazol-5-yl)methoxy)benzofuran-3-carboxamide Cpd 594 N-(3-carbamoyltetrahydrofuran-3-yl)-2-methyl-5-((6-methylpyridin-3-yl)methoxy)benzofuran-3-carboxamide Cpd 595 N-(3-carbamoyltetrahydrofuran-3-yl)-2-methyl-5-(pyridin-2-ylmethoxy)benzofuran-3-carboxamide Cpd 596 N-(3-carbamoyltetrahydrofuran-3-yl)-5-((2-hydroxypyridin-3-yl)methoxy)-2-methylbenzofuran-3-carboxamide Cpd 597 N-(3-carbamoyltetrahydrofuran-3-yl)-5-((2-methoxypyridin-3-yl)methoxy)-2-methylbenzofuran-3-carboxamide Cpd 598 N-(3-carbamoyltetrahydrofuran-3-yl)-5-((4-fluoro-1-methyl-1H-pyrazol-5-yl)methoxy)-2-methylbenzofuran-3-carboxamide Cpd 599 N-(3-cyanooxetan-3-yl)-N,2-dimethyl-5-((4-methylthiazol-5-yl)methoxy)benzofuran-3-carboxamide Cpd 600 N-(3-hydroxy-1-(methylamino)-1-oxopropan-2-yl)-2-methyl-5-((4-methylthiazol-5-yl)methoxy)benzofuran-3-carboxamide Cpd 601 N-(3-hydroxy-1-(methylamino)-1-oxopropan-2-yl)-2-methyl-5-(pyridin-2-ylmethoxy)benzofuran-3-carboxamide Cpd 602 N-(3-hydroxy-2,2-dimethylpropyl)-2-methyl-5-((4-methylthiazol-5-yl)methoxy)benzofuran-3-carboxamide Cpd 603 N-(4-(hydroxymethyl)tetrahydro-2H-pyran-4-yl)-2,4-dimethyl-5-((4-methylthiazol-5-yl)methoxy)benzofuran-3-carboxamide Cpd 604 N-(4-(hydroxymethyl)tetrahydro-2H-pyran-4-yl)-2-methyl-5-((1-methyl-1H-1,2,3-triazol-4-yl)methoxy)benzofuran-3-carboxamide Cpd 605 N-(4-(hydroxymethyl)tetrahydro-2H-pyran-4-yl)-2-methyl-5-((1-methyl-1H-1,2,3-triazol-5-yl)methoxy)benzofuran-3-carboxamide Cpd 606 N-(4-(hydroxymethyl)tetrahydro-2H-pyran-4-yl)-2-methyl-5-((1-methyl-1H-1,2,4-triazol-3-yl)methoxy)benzofuran-3-carboxamide Cpd 607 N-(4-(hydroxymethyl)tetrahydro-2H-pyran-4-yl)-2-methyl-5-((1-methyl-1H-imidazol-5-yl)methoxy)benzofuran-3-carboxamide Cpd 608 N-(4-(hydroxymethyl)tetrahydro-2H-pyran-4-yl)-2-methyl-5-((1-methyl-1H-pyrazol-5-yl)methoxy)benzofuran-3-carboxamide Cpd 609 N-(4-(hydroxymethyl)tetrahydro-2H-pyran-4-yl)-2-methyl-5-((1-methyl-2-oxo-1,2-dihydropyridin-3-yl)methoxy)benzofuran-3-carboxamide Cpd 610 N-(4-(hydroxymethyl)tetrahydro-2H-pyran-4-yl)-2-methyl-5-((1-methyl-6-oxo-1,6-dihydropyridin-2-yl)methoxy)benzofuran-3-carboxamide Cpd 611 N-(4-(hydroxymethyl)tetrahydro-2H-pyran-4-yl)-2-methyl-5-((2-methylpyridin-3-yl)methoxy)benzofuran-3-carboxamide Cpd 612 N-(4-(hydroxymethyl)tetrahydro-2H-pyran-4-yl)-2-methyl-5-((2-methylpyrimidin-4-yl)methoxy)benzofuran-3-carboxamide Cpd 613 N-(4-(hydroxymethyl)tetrahydro-2H-pyran-4-yl)-2-methyl-5-((2-methylthiazol-5-yl)methoxy)benzofuran-3-carboxamide Cpd 614 N-(4-(hydroxymethyl)tetrahydro-2H-pyran-4-yl)-2-methyl-5-((2-oxo-1,2-dihydropyridin-3-yl)methoxy)benzofuran-3-carboxamide Cpd 615 N-(4-(hydroxymethyl)tetrahydro-2H-pyran-4-yl)-2-methyl-5-((3-(trifluoromethyl)-1H-pyrazol-4-yl)methoxy)benzofuran-3-carboxamide Cpd 616 N-(4-(hydroxymethyl)tetrahydro-2H-pyran-4-yl)-2-methyl-5-((4-methyloxazol-2-yl)methoxy)benzofuran-3-carboxamide Cpd 617 N-(4-(hydroxymethyl)tetrahydro-2H-pyran-4-yl)-2-methyl-5-((4-methylthiazol-2-yl)methoxy)benzofuran-3-carboxamide Cpd 618 N-(4-(hydroxymethyl)tetrahydro-2H-pyran-4-yl)-2-methyl-5-((5-methylisoxazol-3-yl)methoxy)benzofuran-3-carboxamide Cpd 619 N-(4-(hydroxymethyl)tetrahydro-2H-pyran-4-yl)-2-methyl-5-((5-methylpyrazin-2-yl)methoxy)benzofuran-3-carboxamide Cpd 620 N-(4-(hydroxymethyl)tetrahydro-2H-pyran-4-yl)-2-methyl-5-((5-methylthiazol-2-yl)methoxy)benzofuran-3-carboxamide Cpd 621 N-(4-(hydroxymethyl)tetrahydro-2H-pyran-4-yl)-2-methyl-5-((6-methylpyridazin-3-yl)methoxy)benzofuran-3-carboxamide Cpd 622 N-(4-(hydroxymethyl)tetrahydro-2H-pyran-4-yl)-2-methyl-5-((6-methylpyridin-3-yl)methoxy)benzofuran-3-carboxamide Cpd 623 N-(4-(hydroxymethyl)tetrahydro-2H-pyran-4-yl)-2-methyl-5-(1-(4-methylthiazol-5-yl)ethoxy)benzofuran-3-carboxamide Cpd 624 N-(4-(hydroxymethyl)tetrahydro-2H-pyran-4-yl)-2-methyl-5-(pyridazin-3-ylmethoxy)benzofuran-3-carboxamide Cpd 625 N-(4-(hydroxymethyl)tetrahydro-2H-pyran-4-yl)-2-methyl-5-(pyridin-3-ylmethoxy)benzofuran-3-carboxamide Cpd 626 N-(4-(hydroxymethyl)tetrahydro-2H-pyran-4-yl)-2-methyl-5-(pyrimidin-2-ylmethoxy)benzofuran-3-carboxamide Cpd 627 N-(4-(hydroxymethyl)tetrahydro-2H-pyran-4-yl)-2-methyl-5-(thiazol-5-ylmethoxy)benzofuran-3-carboxamide Cpd 628 N-(4-(hydroxymethyl)tetrahydro-2H-pyran-4-yl)-5-((2-hydroxypyridin-4-yl)methoxy)-2-methylbenzofuran-3-carboxamide Cpd 629 N-(4-(hydroxymethyl)tetrahydro-2H-pyran-4-yl)-5-((2-methoxypyridin-4-yl)methoxy)-2-methylbenzofuran-3-carboxamide Cpd 630 N-(4-(hydroxymethyl)tetrahydro-2H-pyran-4-yl)-5-((6-hydroxypyridin-2-yl)methoxy)-2-methylbenzofuran-3-carboxamide Cpd 631 N-(4-(hydroxymethyl)tetrahydro-2H-pyran-4-yl)-5-((6-hydroxypyridin-3-yl)methoxy)-2-methylbenzofuran-3-carboxamide Cpd 632 N-(4-(hydroxymethyl)tetrahydro-2H-pyran-4-yl)-5-((6-methoxypyridin-3-yl)methoxy)-2-methylbenzofuran-3-carboxamide Cpd 633 N-(4-(hydroxymethyl)tetrahydro-2H-pyran-4-yl)-5-(imidazo[1,2-a]pyridin-6-ylmethoxy)-2-methylbenzofuran-3-carboxamide Cpd 634 N-(4-(hydroxymethyl)tetrahydro-2H-pyran-4-yl)-N,2-dimethyl-5-((4-methylthiazol-5-yl)methoxy)benzofuran-3-carboxamide Cpd 635 N-(4,4-difluoropiperidin-3-yl)-2-methyl-5-((1-methyl-1H-imidazol-2-yl)methoxy)benzofuran-3-carboxamide Cpd 636 N-(4,4-difluoropiperidin-3-yl)-2-methyl-5-((1-methyl-1H-pyrazol-5-yl)methoxy)benzofuran-3-carboxamide Cpd 637 N-(4,4-difluoropiperidin-3-yl)-5-((2-hydroxypyridin-3-yl)methoxy)-2-methylbenzofuran-3-carboxamide Cpd 638 N-(4,4-difluoropyrrolidin-3-yl)-2-methyl-5-((1-methyl-1H-imidazol-2-yl)methoxy)benzofuran-3-carboxamide Cpd 639 N-(4,4-difluoropyrrolidin-3-yl)-2-methyl-5-((1-methyl-1H-pyrazol-5-yl)methoxy)benzofuran-3-carboxamide Cpd 640 N-(4,4-difluoropyrrolidin-3-yl)-5-((2-hydroxypyridin-3-yl)methoxy)-2-methylbenzofuran-3-carboxamide Cpd 641 N-(4,4-difluorotetrahydrofuran-3-yl)-2-methyl-5-((1-methyl-1H-imidazol-2-yl)methoxy)benzofuran-3-carboxamide
Cpd 642 N-(4,4-difluorotetrahydrofuran-3-yl)-2-methyl-5-((1-methyl-1H-pyrazol-5-yl)methoxy)benzofuran-3-carboxamide
Cpd 643 N-(4,4-difluorotetrahydrofuran-3-yl)-2-methyl-5-((2-methylthiazol-5-yl)methoxy)benzofuran-3-carboxamide
Cpd 646 N-(4,4-difluorotetrahydrofuran-3-yl)-2-methyl-5-((4-methylthiazol-5-yl)methoxy)benzofuran-3-carboxamide
Cpd 647 N-(4,4-difluorotetrahydrofuran-3-yl)-2-methyl-5-(pyridin-2-ylmethoxy)benzofuran-3-carboxamide
Cpd 648 N-(4,4-difluorotetrahydrofuran-3-yl)-5-((2-hydroxypyridin-3-yl)methoxy)-2-methylbenzofuran-3-carboxamide
Cpd 649 N-(4-amino-2-methyl-4-oxobutan-2-yl)-2-methyl-5-((4-methylthiazol-5-yl)methoxy)benzofuran-3-carboxamide
Cpd 650 N-(4-carbamoyltetrahydro-2H-pyran-4-yl)-2-methyl-5-((4-methylthiazol-5-yl)methoxy)benzofuran-3-carboxamide
Cpd 651 N-(4-hydroxy-2-methylbutan-2-yl)-2-methyl-5-((2-(trifluoromethyl)pyridin-3-yl)methoxy)benzofuran-3-carboxamide
Cpd 652 N-(4-hydroxy-2-methylbutan-2-yl)-2-methyl-5-((4-methylthiazol-5-yl)methoxy)benzofuran-3-carboxamide
Cpd 653 N-(cis-4-hydroxytetrahydrofuran-3-yl)-2-methyl-5-((1-methyl-1H-imidazol-2-yl)methoxy)benzofuran-3-carboxamide
Cpd 654 N-(trans-4-hydroxytetrahydrofuran-3-yl)-2-methyl-5-((1-methyl-1H-imidazol-2-yl)methoxy)benzofuran-3-carboxamide
Cpd 655 N-(cis-4-hydroxytetrahydrofuran-3-yl)-2-methyl-5-((1-methyl-1H-pyrazol-5-yl)methoxy)benzofuran-3-carboxamide
Cpd 656 N-(trans-4-hydroxytetrahydrofuran-3-yl)-2-methyl-5-((1-methyl-1H-pyrazol-5-yl)methoxy)benzofuran-3-carboxamide
Cpd 657 N3-(3,3-difluoropiperidin-4-yl)-5-((2-(trifluoromethyl)pyridin-3-yl)methoxy)benzofuran-2,3-dicarboxamide
Cpd 658 N3-(4-(hydroxymethyl)tetrahydro-2H-pyran-4-yl)-5-((4-methylthiazol-5-yl)methoxy)benzofuran-2,3-dicarboxamide
Cpd 659 N-cyclobutyl-N-(2-hydroxyethyl)-2-methyl-5-((2-(trifluoromethyl)pyridin-3-yl)methoxy)benzofuran-3-carboxamide
Cpd 660 N-cyclobutyl-N-(2-hydroxyethyl)-2-methyl-5-((4-methylthiazol-5-yl)methoxy)benzofuran-3-carboxamide
Cpd 661 2-methyl-5-((4-methylthiazol-5-yl)methoxy)-N-(2-oxoazepan-3-yl)benzofuran-3-carboxamide
Cpd 662 N-(1-amino-3-hydroxy-1-oxopropan-2-yl)-2-methyl-5-(pyridin-3-ylmethoxy)benzofuran-3-carboxamide
Cpd 663 N-(4,4-difluoropyrrolidin-3-yl)-5-((2-methoxypyridin-3-yl)methoxy)-2-methylbenzofuran-3-carboxamide
Cpd 664 N-(4,4-difluorotetrahydrofuran-3-yl)-2-methyl-5-((2-(trifluoromethyl)pyridin-3-yl)methoxy)benzofuran-3-carboxamide
Cpd 665 N-(4,4-difluorotetrahydrofuran-3-yl)-5-((2-methoxypyridin-3-yl)methoxy)-2-methylbenzofuran-3-carboxamide
Cpd 666 2-methyl-5-((4-methylthiazol-5-yl)methoxy)-N-(2,2,2-trifluoroethyl)benzofuran-3-carboxamide
Cpd 667 5-((1,4-Dimethyl-1H-pyrazol-5-yl)methoxy)-2-methylbenzofuran-3-carboxylic acid
Cpd 668 (S)—N-(1-Amino-3-hydroxy-1-oxopropan-2-yl)-5-((1,4-dimethyl-1H-pyrazol-5-yl)methoxy)-2-methylbenzofuran-3-carboxamide
Cpd 669 5-((4-Chloro-1-methyl-1H-pyrazol-5-yl)methoxy)-2-methylbenzofuran-3-carboxylic acid
Cpd 670 (S)—N-(1-Amino-3-hydroxy-1-oxopropan-2-yl)-5-((4-chloro-1-methyl-1H-pyrazol-5-yl)methoxy)-2-methylbenzofuran-3-carboxamide
Cpd 671 5-((4-chloro-1-isopropyl-1H-pyrazol-5-yl)methoxy)-2-methylbenzofuran-3-carboxylicacid
Cpd 672 (S)—N-(1-amino-3-hydroxy-1-oxopropan-2-yl)-5-((4-chloro-1-isopropyl-1H-pyrazol-5-yl)methoxy)-2-methylbenzofuran-3-carboxamide
Cpd 673 2-Methyl-5-((3-methylisoxazol-5-yl)methoxy)benzofuran-3-carboxylic acid
Cpd 674 (S)—N-(1-Amino-3-hydroxy-1-oxopropan-2-yl)-2-methyl-5-((3-methylisoxazol-5-yl)methyl)benzofuran-3-carboxamide
Cpd 675 5-((1-isopropyl-1H-pyrazol-5-yl) methoxy)-2-methylbenzofuran-3-carboxylic acid
Cpd 676 (S)—N-(1-amino-3-hydroxy-1-oxopropan-2-yl)-5-((1-isopropyl-1H-pyrazol-5-yl) methoxy)-2-methylbenzofuran-3-carboxamide
Cpd 677 5-((2, 4-Dimethyloxazol-5-yl) methoxy)-2-methylbenzofuran-3-carboxylic acid
Cpd 678 (S)—N-(1-Amino-3-hydroxy-1-oxopropan-2-yl)-5-((2, 4-dimethyloxazol-5-yl) methoxy)-2-methylbenzofuran-3-carboxamide
Cpd 679 2-Methyl-5-((4-methyloxazol-5-yl)methoxy)benzofuran-3-carboxylic acid
Cpd 680 (S)—N-(1-Amino-3-hydroxy-1-oxopropan-2-yl)-2-methyl-5-((4-methyloxazol-5-yl)methoxy)benzofuran-3-carboxamide
Cpd 681 5-((2-Isopropylthiazol-5-yl)methoxy)-2-methylbenzofuran-3-carboxylic acid
Cpd 682 (S)—N-(1-Amino-3-hydroxy-1-oxopropan-2-yl)-5-((2-isopropylthiazol-5-yl)methoxy)-2-methylbenzofuran-3-carboxamide
Cpd 683 N-(1-(Difluoromethyl) cyclobutyl)-2-methyl-5-((2-methylthiazol-5-yl) methoxy) benzofuran-3-carboxamide
Cpd 684 (S)—N-(1-Amino-3-hydroxy-1-oxopropan-2-yl)-2-methyl-5-((5-methylthiazol-2-yl)methoxy)benzofuran-3-carboxamide
Cpd 685 N-((2S,3R)-1-amino-3-hydroxy-1-oxobutan-2-yl)-2-methyl-5-((3-(trifluoromethyl)-1H-pyrazol-4-yl)methoxy)benzofuran-3-carboxamide
Cpd 686 (S)—N-(1-Amino-3-hydroxy-1-oxopropan-2-yl)-2-methyl-5-((1-methyl-1H-pyrazol-3-yl)methoxy)benzofuran-3-carboxamide
Cpd 687 2-Methyl-5-((1-(2,2,2-trifluoroethyl)-1H-pyrazol-5-yl)methoxy)benzofuran-3-carboxylic acid
Cpd 688 (S)—N-(1-Amino-3-hydroxy-1-oxopropan-2-yl)-2-methyl-5-((1-(2,2,2-trifluoroethyl)-1H-pyrazol-5-yl)methoxy)benzofuran-3-carboxamide
Cpd 689 5-((1-(Cyclopropylmethyl)-1H-pyrazol-5-yl)methoxy)-2-methylbenzofuran-3-carboxylic acid
Cpd 690 (S)—N-(1-amino-3-hydroxy-1-oxopropan-2-yl)-5-((1-(cyclopropylmethyl)-1H-pyrazol-5-yl)methoxy)-2-methylbenzofuran-3-carboxamide
Cpd 691 2-Methyl-5-((1-methyl-3-(trifluoromethyl)-1H-pyrazol-4-yl)methoxy)benzofuran-3-carboxylic acid Cpd 692 (S)—N-(1-Amino-3-hydroxy-1-oxopropan-2-yl)-2-methyl-5-((1-methyl-3-(trifluoromethyl)-1H-pyrazol-4-yl)methoxy)benzofuran-3-carboxamide Cpd 693 2-Methyl-5-((4-(trifluoromethyl)thiazol-5-yl)methoxy)benzofuran-3-carboxylic acid Cpd 694 (S)—N-(1-Amino-3-hydroxy-1-oxopropan-2-yl)-2-methyl-5-((4-(trifluoromethyl)thiazol-5-yl)methoxy)benzofuran-3-carboxamide Cpd 695 (S)—N-(1-Amino-3-hydroxy-1-oxopropan-2-yl)-2-methyl-5-(thiazol-2-ylmethoxy)benzofuran-3-carboxamide Cpd 696 N-((2S,3R)-1-amino-3-hydroxy-1-oxobutan-2-yl)-5-((5-fluoropyridin-2-yl)methoxy)-2-methylbenzofuran-3-carboxamide Cpd 697 (S)—N-(1-Amino-3-hydroxy-1-oxopropan-2-yl)-2-methyl-5-(thiazol-5-ylmethoxy)benzofuran-3-carboxamide Cpd 698 (S)—N-(1-Amino-3-hydroxy-1-oxopropan-2-yl)-2-methyl-5-((1-methyl-1H-pyrazol-4-yl)methoxy)benzofuran-3-carboxamide Cpd 699 2-Methyl-5-((5-methylpyridin-2-yl)methoxy)benzofuran-3-carboxylic acid Cpd 700 (S)—N-(1-Amino-3-hydroxy-1-oxopropan-2-yl)-2-methyl-5-((5-methylpyridin-2-yl)methoxy)benzofuran-3-carboxamide Cpd 701 5-((2-cyclopropylpyridin-3-yl)methoxy)-2-methylbenzofuran-3-carboxylic acid Cpd 702 (S)—N-(1-Amino-3-hydroxy-1-oxopropan-2-yl)-5-((2-cyclopropylpyridin-3-yl)methoxy)-2-methylbenzofuran-3-carboxamide Cpd 703 5-((3-Cyclopropylpyridin-2-yl) methoxy)-2-methylbenzofuran-3-carboxylic acid Cpd 704 (S)—N-(1-Amino-3-hydroxy-1-oxopropan-2-yl)-5-((3-cyclopropylpyridin-2-yl) methoxy)-2-methylbenzofuran-3-carboxamide;

Cpd 705 5-((3-cyclopropylpyridin-2-yl) methoxy)-N-(4-(hydroxymethyl) tetrahydro-2H-pyran-4-yl)-2-methylbenzofuran-3-carboxamide Cpd 706 (S)—N-(1-amino-3-hydroxy-1-oxopropan-2-yl)-5-((2-(azetidin-1-yl) pyridin-3-yl)methoxy)-2-methylbenzofuran-3-carboxamide Cpd 707 2-Methyl-5-((2-methylpyrimidin-5-yl)methoxy)benzofuran-3-carboxylic acid Cpd 708 (S)—N-(1-Amino-3-hydroxy-1-oxopropan-2-yl)-2-methyl-5-((2-methylpyrimidin-5-yl)methoxy)benzofuran-3-carboxamide Cpd 709 5-((2-Cyclopropoxypyridin-3-yl) methoxy)-2-methylbenzofuran-3-carboxylic acid Cpd 710 (S)—N-(1-amino-3-hydroxy-1-oxopropan-2-yl)-5-((2-cyclopropoxypyridin-3-yl) methoxy)-2-methylbenzofuran-3-carboxamide Cpd 711 5-((2-cyclopropoxypyridin-3-yl) methoxy)-N-(4-(hydroxymethyl) tetrahydro-2H-pyran-4-yl)-2-methylbenzofuran-3-carboxamide Cpd 712 (S)—N-(1-Amino-3-hydroxy-1-oxopropan-2-yl)-2-methyl-5-(pyrimidin-2-ylmethoxy)benzofuran-3-carboxamide Cpd 713 2-Methyl-5-(pyrazin-2-ylmethoxy)benzofuran-3-carboxylic acid Cpd 714 (S)—N-(1-Amino-3-hydroxy-1-oxopropan-2-yl)-2-methyl-5-(pyrazin-2-ylmethoxy)benzofuran-3-carboxamide Cpd 715 (S)—N-(1-amino-3-hydroxy-1-oxopropan-2-yl)-5-((2-methoxypyridin-3-yl)methoxy)-2-methylbenzofuran-3-carboxamide Cpd 716 (S)—N-(1-Amino-3-hydroxy-1-oxopropan-2-yl)-2-methyl-5-(pyridin-4-ylmethoxy)benzofuran-3-carboxamide Cpd 717 5-((3-(Difluoromethyl)pyridin-2-yl)methoxy)-N-(3,3-difluoropiperidin-4-yl)-2-methylbenzofuran-3-carboxamide Cpd 718 N-((2S,3R)-1-amino-3-hydroxy-1-oxobutan-2-yl)-2-methyl-5-(pyridin-2-ylmethoxy)benzofuran-3-carboxamide Cpd 719 N-(3-(hydroxymethyl)-2-oxopiperidin-3-yl)-2-methyl-5-(pyridin-2-ylmethoxy)benzofuran-3-carboxamide Cpd 720 N-(1-amino-3-hydroxy-2-methyl-1-oxopropan-2-yl)-5-((2-methoxypyridin-3-yl)methoxy)-2-methylbenzofuran-3-carboxamide Cpd 721 N-(1-(Difluoromethyl)cyclobutyl)-2-methyl-5-((4-methylthiazol-5-yl)methoxy)benzofuran-3-carboxamide Cpd 722 N-(1-Amino-3-hydroxy-2-methyl-1-oxopropan-2-yl)-2-methyl-5-((2-methyloxazol-5-yl)methoxy)benzofuran-3-carboxamide Cpd 723 N-(3,3-difluorotetrahydro-2H-pyran-4-yl)-2-methyl-5-((4-methylthiazol-5-yl)methoxy)benzofuran-3-carboxamide Cpd 724 N-(3,3-Difluorotetrahydro-2H-pyran-4-yl)-2-methyl-5-((2-methylthiazol-5-yl)methoxy)benzofuran-3-carboxamide Cpd 725 N-(3-carbamoyltetrahydrofuran-3-yl)-2-methyl-5-((2-methyloxazol-5-yl)methoxy)benzofuran-3-carboxamide Cpd 726 N-(1-Amino-3-(methylsulfonyl)-1-oxopropan-2-yl)-2-methyl-5-((2-methylthiazol-5-yl)methoxy)benzofuran-3-carboxamide Cpd 727 N-(1-Imino-1-oxidotetrahydro-1H-1l6-thiophen-3-yl)-2-methyl-5-((2-methylthiazol-5-yl)methoxy)benzofuran-3-carboxamide Cpd 728 N-(3-(hydroxymethyl)pyrrolidin-3-yl)-2-methyl-5-((4-methylthiazol-5-yl)methoxy)benzofuran-3-carboxamide Cpd 729 N-(1-Amino-1-oxo-3-(1H-1,2,4-triazol-1-yl)propan-2-yl)-2-methyl-5-((4-methylthiazol-5-yl)methoxy)benzofuran-3-carboxamide Cpd 730 N-(3-(Hydroxymethyl)-2-oxopyrrolidin-3-yl)-2-methyl-5-((3-(trifluoromethyl)-1H-pyrazol-4-yl)methoxy)benzofuran-3-carboxamide Cpd 731 N-(3-(hydroxymethyl)-2-oxopiperidin-3-yl)-2-methyl-5-((3-(trifluoromethyl)-1H-pyrazol-4-yl)methoxy)benzofuran-3-carboxamide Cpd 732 N-(3-(Hydroxymethyl)-2-oxopiperidin-3-yl)-2-methyl-5-((1-methyl-1H-pyrazol-5-yl)methoxy)benzofuran-3-carboxamide Cpd 733 N-(3-(Hydroxymethyl)-2-oxopyrrolidin-3-yl)-2-methyl-5-((1-methyl-1H-pyrazol-5-yl)methoxy)benzofuran-3-carboxamide Cpd 734 N-(3-(Hydroxymethyl)-2-oxopyrrolidin-3-yl)-2-methyl-5-(pyridazin-3-ylmethoxy)benzofuran-3-carboxamide Cpd 735 5-((5-Fluoropyridin-2-yl) methoxy)-N-(3-(hydroxymethyl)-2-oxopyrrolidin-3-yl)-2-methylbenzofuran-3-carboxamide Cpd 736 5-((2-(Difluoromethyl)pyridin-3-yl)methoxy)-N-(3-(hydroxymethyl)-2-oxopyrrolidin-3-yl)-2-methylbenzofuran-3-carboxamide Cpd 737 5-((2-(Difluoromethyl)pyridin-3-yl)methoxy)-N-(3-(hydroxymethyl)-2-oxopiperidin-3-yl)-2-methylbenzofuran-3-carboxamide Cpd 738 N-(1-Amino-3-hydroxy-2-methyl-1-oxopropan-2-yl)-2-methyl-5-(pyridin-2-ylmethoxy)benzofuran-3-carboxamide Cpd 739 N-(1-Amino-3-hydroxy-2-methyl-1-oxopropan-2-yl)-5-((5-fluoropyridin-2-yl)methoxy)-2-methylbenzofuran-3-carboxamide Cpd 740 N-(3-carbamoyltetrahydrofuran-3-yl)-5-((1-(2,2-difluoroethyl)-1H-pyrazol-5-yl) methoxy)-2-methyl-benzofuran-3-carboxamide Cpd 741 (S)—N-(1-Amino-3-hydroxy-1-oxopropan-2-yl)-5-((5-fluoropyridin-2-yl)methoxy)-2-methylbenzofuran-3-carboxamide Cpd 742 (S)—N-(1-amino-3-hydroxy-1-oxopropan-2-yl)-2-(difluoromethyl)-5-((4-methylthiazol-5-yl)methoxy)benzofuran-3-carboxamide Cpd 743 (S)—N-(1-Amino-3-hydroxy-1-oxopropan-2-yl)-2-(difluoromethyl)-5-((6-methylpyridin-3-yl)methoxy)benzofuran-3-carboxamide Cpd 744 (S)—N-(1-amino-3-hydroxy-1-oxopropan-2-yl)-2-(difluoromethyl)-5-(pyridin-2-ylmethoxy)benzofuran-3-carboxamide Cpd 745 (S)—N-(1-amino-3-hydroxy-1-oxopropan-2-yl)-2-(difluoromethyl)-5-((2-methylthiazol-5-yl)methoxy)benzofuran-3-carboxamide Cpd 746 (S)—N-(1-amino-3-hydroxy-1-oxopropan-2-yl)-2-(difluoromethyl)-5-((2-methyloxazol-5-yl)methoxy) benzofuran-3-carboxamide Cpd 747 (S)—N-(1-Amino-3-hydroxy-1-oxopropan-2-yl)-2-cyclopropyl-5-(pyridin-2-ylmethoxy)benzofuran-3-carboxamide Cpd 748 (S)—N-(1-Amino-3-hydroxy-1-oxopropan-2-yl)-2-cyclopropyl-5-((4-methylthiazol-5-yl)methoxy)benzofuran-3-carboxamide Cpd 749 (S)—N-(1-Amino-3-hydroxy-1-oxopropan-2-yl)-2-cyclopropyl-5-((2-methylthiazol-5-yl)methoxy)benzofuran-3-carboxamide Cpd 750 (S)—N-(1-Amino-3-hydroxy-1-oxopropan-2-yl)-2-cyclopropyl-5-((6-methylpyridin-3-yl)methoxy)benzofuran-3-carboxamide Cpd 751 (S)—N-(1-amino-3-hydroxy-1-oxopropan-2-yl)-2-cyclopropyl-5-((2-methyloxazol-5-yl) methoxy)benzofuran-3-carboxamide and the physiologically acceptable salts thereof.

13. A pharmaceutical composition comprising a compound according to claim 1 and a pharmaceutically acceptable carrier.

* * * * *